(12) United States Patent
Marzabadi et al.

(10) Patent No.: US 6,727,264 B1
(45) Date of Patent: Apr. 27, 2004

(54) SUBSTITUTED ANILINIC PIPERIDINES AS MCH SELECTIVE ANTAGONISTS

(75) Inventors: Mohammad R. Marzabadi, Ridgewood, NJ (US); John Wetzel, Fairlawn, NJ (US); John E. DeLeon, North Bergen, NJ (US); Yu Jiang, Jersey City, NJ (US); Chien-An Chen, Fresh Meadows, NY (US); Kai Lu, Elmwood Park, NJ (US)

(73) Assignee: Synaptic Pharmaceutical Corporation, Paramus, NJ (US)

( * ) Notice: Subject to any disclaimer, the term of this patent is extended or adjusted under 35 U.S.C. 154(b) by 0 days.

(21) Appl. No.: 10/188,434

(22) Filed: Jul. 3, 2002

Related U.S. Application Data

(60) Provisional application No. 60/346,997, filed on Jan. 9, 2002, and provisional application No. 60/303,091, filed on Jul. 5, 2001, now abandoned.

(51) Int. Cl.[7] ............... A61K 31/445; C07D 211/30; C07D 401/06
(52) U.S. Cl. ............... 514/323; 514/331; 546/200; 546/234
(58) Field of Search ............... 514/323, 331; 546/200, 234

(56) References Cited

U.S. PATENT DOCUMENTS

| | | | | |
|---|---|---|---|---|
| 5,459,151 | A | 10/1995 | Lombardo | 514/318 |
| 5,563,150 | A | 10/1996 | Curtis et al. | 514/300 |
| 6,365,602 | B1 * | 4/2002 | Bernstein et al. | 514/319 |
| 6,441,000 | B1 | 8/2002 | Gibson et al. | 514/322 |
| 2003/0077701 | A1 * | 4/2003 | Forray et al. | 435/69.1 |

FOREIGN PATENT DOCUMENTS

| | | |
|---|---|---|
| EP | 0639568 | 2/1995 |
| EP | 0659743 | 6/1995 |
| WO | WO9201672 | 2/1992 |
| WO | WO9222554 | 12/1992 |
| WO | WO9304684 | 3/1993 |
| WO | WO9533721 | 12/1995 |
| WO | WO9631508 | 10/1996 |
| WO | WO9634863 | 11/1996 |
| WO | WO9732835 | 9/1997 |
| WO | WO9741108 | 11/1997 |
| WO | WO 98/27081 * | 6/1998 |
| WO | WO9847885 | 10/1998 |
| WO | WO9959971 | 11/1999 |
| WO | WO0032582 | 6/2000 |
| WO | WO0121577 | 3/2001 |
| WO | WO0202744 | 1/2002 |

OTHER PUBLICATIONS

Chemical Abstracts CA 129:81756 (1998) Registry No. 209481–69–6.
Chemical Abstracts CA 129:330740 (1998) Registry No. 183810–20–0.
Chemical Abstracts CA 122:105695 (1995) Registry No. 160587–15–5.
Chemical Abstracts CA 118:254749 (1993) Registry No. 147539–58–0.

* cited by examiner

*Primary Examiner*—Ceila Chang
(74) *Attorney, Agent, or Firm*—John P. White; Cooper & Dunham LLP

(57) ABSTRACT

This invention is directed to compounds which are selective antagonists for melanin concentrating hormone-1 (MCH1) receptors. The invention provides a pharmaceutical composition comprising a therapeutically effective amount of the compound of the invention and a pharmaceutically acceptable carrier. This invention provides a pharmaceutical composition made by combining a therepeutically effective amount of the compound of this invention and a pharmaceutically acceptable carrier. This invention further provides a process for making a pharmaceutical composition comprising combining a therapeutically effective amount of the compound of the invention and a pharmaceutically acceptable carrier.

20 Claims, No Drawings

SUBSTITUTED ANILINIC PIPERIDINES AS MCH SELECTIVE ANTAGONISTS

This application claims the benefit of U.S. Provisional Appplication No. 60/346,997, filed Jan. 9, 2002 and of U.S. Provisional Application No. 60/303,091, filed Jul. 5, 2001 now abandoned, the contents both of which are hereby incorporated by reference into the subject application.

BACKGROUND OF THE INVENTION

Throughout this application, various publications are referenced in parentheses by author and year. Full citations for these references may be found at the end of the specification immediately preceding the sequence listings and the claims. The disclosure of these publications in their entireties are hereby incorporated by reference into this application to describe more fully the state of the art to which this invention pertains. Melanin-concentrating hormone (MCH) is a cyclic peptide originally isolated from salmonid (teleost fish) pituitaries (Kawauchi et al., 1983). In fish the 17 amino acid peptide causes aggregation of melanin within the melanophores and inhibits the release of ACTH, acting as a functional antagonist of α-MSH. Mammalian MCH (19 amino acids) is highly conserved between rat, mouse, and human, exhibiting 100% amino acid identity, but its physiological roles are less clear. MCH has been reported to participate in a variety of processes including feeding, water balance, energy metabolism, general arousal/attention state, memory and cognitive functions, and psychiatric disorders (for reviews, see Baker, 1991; Baker, 1994; Nahon, 1994; Knigge et al., 1996). Its role in feeding or body weight regulation is supported by a recent *Nature* publication (Qu et al., 1996) demonstrating that MCH is overexpressed in the hypothalamus of ob/ob mice compared with ob/+ mice, and that fasting further increased MCH mRNA in both obese and normal mice during fasting. MCH also stimulated feeding in normal rats when injected into the lateral ventricles (Rossi et al., 1997). MCH also has been reported to functionally antagonize the behavioral effects of α-MSH (Miller et al., 1993; Gonzalez et al, 1996; Sanchez et al., 1997); in addition, stress has been shown to increase POMC mRNA levels while decreasing the MCH precursor preproMCH (ppMCH) mRNA levels (Presse et al., 1992). Thus MCH may serve as an integrative neuropeptide involved in the reaction to stress, as well as in the regulation of feeding and sexual activity (Baker, 1991; Knigge et al., 1996).

Although the biological effects of MCH are believed to be mediated by specific receptors, binding sites for MCH have not been well described. A tritiated ligand ($[^3H]$-MCH) was reported to exhibit specific binding to brain membranes but was unusable for saturation analyses, so neither affinity nor $B_{max}$ were determined (Drozdz and Eberle, 1995). Radioiodination of the tyrosine at position thirteen resulted in a ligand with dramatically reduced biological activity (see Drozdz and Eberle, 1995). In contrast, the radioiodination of the MCH analogue [Phe$^{13}$, Tyr$^{19}$]-MCH was successful (Drozdz et al., 1995); the ligand retained biological activity and exhibited specific binding to a variety of cell lines including mouse melanoma (B16-F1, G4F, and G4F-7), PC12, and COS cells. In G4F-7 cells, the $K_D$=0.118 nM and the $B_{max}$ ~1100 sites/cell. Importantly, the binding was not inhibited by α-MSH but was weakly inhibited by rat ANF (Ki=116 nM vs. 12 nM for native MCH) (Drozdz et al., 1995). More recently specific MCH binding was reported in transformed keratinocytes (Burgaud et al., 1997) and melanoma cells (Drozdz et al., 1998), where photo-crosslinking studies suggest that the receptor is a membrane protein with an apparent molecular weight of 45–50 kDaltons, compatible with the molecular weight range of the GPCR superfamily of receptors. No radioautoradiographic studies of MCH receptor localization using this ligand have been reported as yet.

The localization and biological activities of MCH peptide suggest that the modulation of MCH receptor activity may be useful in a number of therapeutic applications. The role of MCH in feeding is the best characterized of its potential clinical uses. MCH is expressed in the lateral hypothalamus, a brain area implicated in the regulation of thirst and hunger (Grillon et al., 1997); recently orexins A and B, which are potent orexigenic agents, have been shown to have very similar localization to MCH in the lateral hypothalamus (Sakurai et al., 1998). MCH mRNA levels in this brain region are increased in rats after 24 hours of food-deprivation (Hervé and Fellman, 1997); after insulin injection, a significant increase in the abundance and staining intensity of MCH immunoreactive perikarya and fibres was observed concurrent with a significant increase in the level of MCH mRNA (Bahjaoui-Bouhaddi et al., 1994). Consistent with the ability of MCH to stimulate feeding in rats (Rossi et al., 1997) is the observation that MCH mRNA levels are upregulated in the hypothalami of obese ob/ob mice (Qu et al., 1996), and decreased in the hypothalami of rats treated with leptin, whose food intake and body weight gains are also decreased (Sahu, 1998). MCH appears to act as a functional antagonist of the melanocortin system in its effects on food intake and on hormone secretion within the HPA (hypothalamopituitary/adrenal axis) (Ludwig et al., 1998). Together these data suggest a role for endogenous MCH in the regulation of energy balance and response to stress, and provide a rationale for the development of specific compounds acting at MCH receptors for use in the treatment of obesity and stress-related disorders.

In all species studied to date, a major portion of the neurons of the MCH cell group occupies a rather constant location in those areas of the lateral hypothalamus and subthalamus where they lie and may be a part of some of the so-called "extrapyramidal" motor circuits. These involve substantial striato- and pallidofugal pathways involving the thalamus and cerebral cortex, hypothalamic areas, and reciprocal connections to subthalamic nucleus, substantia nigra, and mid-brain centers (Bittencourt et al., 1992). In their location, the MCH cell group may offer a bridge or mechanism for expressing hypothalamic visceral activity with appropriate and coordinated motor activity. Clinically it may be of some value to consider the involvement of this MCH system in movement disorders, such as Parkinson's disease and Huntingdon's Chorea in which extrapyramidal circuits are known to be involved.

Human genetic linkage studies have located authentic hMCH loci on chromosome 12 (12q23-24) and the variant hMCH loci on chromosome 5 (5q12-13) (Pedeutour et al., 1994). Locus 12q23-24 coincides with a locus to which autosomal dominant cerebellar ataxia type II (SCA2) has been mapped (Auburger et al., 1992; Twells et al., 1992). This disease comprises neurodegenerative disorders, including an olivopontocerebellar atrophy. Furthermore, the gene for Darier's disease, has been mapped to locus 12q23-24 (Craddock et al., 1993). Dariers' disease is characterized by abnormalities I keratinocyte adhesion and mental illnesses in some families. In view of the functional and neuroanatomical patterns of the MCH neural system in the rat and human brains, the MCH gene may represent a good candidate for SCA2 or Darier's disease. Interestingly, diseases with high social impact have been mapped to this locus. Indeed, the gene responsible for chronic or acute forms of spinal muscular atrophies has been assigned to chromosome 5q12-13 using genetic linkage analysis (Melki et al., 1990; Westbrook et al., 1992). Furthermore, independent lines of evidence support the assignment of a major schizophrenia locus to chromosome 5q11.2-13.3 (Sherrington et al., 1988; Bassett et al., 1988; Gilliam et al., 1989). The above studies suggest that MCH may play a role in neurodegenerative diseases and disorders of emotion.

Additional therapeutic applications for MCH-related compounds are suggested by the observed effects of MCH in other biological systems. For example, MCH may regulate reproductive functions in male and female rats. MCH transcripts and MCH peptide were found within germ cells in testes of adult rats, suggesting that MCH may participate in stem cell renewal and/or differentiation of early spermatocytes (Hervieu et al., 1996). MCH injected directly into the medial preoptic area (MPOA) or ventromedial nucleus (VMN) stimulated sexual activity in female rats (Gonzalez et al., 1996). In ovariectomized rats primed with estradiol, MCH stimulated luteinizing hormone (LH) release while anti-MCH antiserum inhibited LH release (Gonzalez et al., 1997). The zona incerta, which contains a large population of MCH cell bodies, has previously been identified as a regulatory site for the pre-ovulatory LH surge (MacKenzie et al., 1984). MCH has been reported to influence release of pituitary hormones including ACTH and oxytocin. MCH analogues may also be useful in treating epilepsy. In the PTZ seizure model, injection of MCH prior to seizure induction prevented seizure activity in both rats and guinea pigs, suggesting that MCH-containing neurons may participate in the neural circuitry underlying PTZ-induced seizure (Knigge and Wagner, 1997). MCH has also been observed to affect behavioral correlates of cognitive functions. MCH treatment hastened extinction of the passive avoidance response in rats (McBride et al., 1994), raising the possibility that MCH receptor antagonists may be beneficial for memory storage and/or retention. A possible role for MCH in the modulation or perception of pain is supported by the dense innervation of the periaqueductal grey (PAG) by MCH-positive fibers. Finally, MCH may participate in the regulation of fluid intake. ICV infusion of MCH in conscious sheep produced diuretic, natriuretic, and kaliuretic changes in response to increased plasma volume (Parkes, 1996). Together with anatomical data reporting the presence of MCH in fluid regulatory areas of the brain, the results indicate that MCH may be an important peptide involved in the central control of fluid homeostasis in mammals.

The identification of a G-protein coupled receptor for MCH has recently been published (Chambers et al., 1999; Saito et al., 1999). These groups identified MCH as the endogenous ligand for the human orphan G-protein coupled receptor SLC-1 (Lakaye et al., 1998). The rat homologue of this receptor (now called MCH-1) was reported to be localized in regions of the rat brain associated with feeding behavior (e.g. dorsomedial and ventromedial hypothalamus) The link between MCH-1 and the effects of MCH on feeding has been strengthened by recent reports on the phenotype of MCH-1 knockout mice. Two groups have shown independently (Marsh et al, 2002; Chen et al, 2002) that the targeted disruption of the MCH-1 receptor gene (MCH-1 knockout) in mice results in animals that are hyperphagic but are lean and have decreased body mass relative to wild-type littermates. The decrease in body mass is attributed to an increase in metabolism. Each group demonstrated that the MCH-1 knockout mice are resistant to diet-induced obesity, and generally exhibit weights similar to littermates maintained on regular chow.

Finally, synthetic antagonist molecules for the MCH-1 receptor have now been described in the literature. Bednarek et al. (2002) have reported on the synthesis of high affinity peptide antagonists of MCH-1. In addition, a small molecule antagonist of MCH-1 has been described by Takekawa et al. (Takekawa et al., 2002). This compound, T-226296, exhibits high affinity for the MCH-1 receptor (~5–9 nM for rat and human MCH-1), and was shown to inhibit food intake induced by the intracerebroventricular application of MCH. These data validate the strategy of using an MCH-1 receptor antagonist to treat obesity.

Furthermore, in our own studies, we have tested MCH1 antagonists in several animal models that are well known as predictive for the efficacy of compounds in humans (Borowsky, et al., in press; unpublished data). These experiments indicate that MCH1 antagonists are useful to treat obesity, depression, anxiety, as well as urinary disorders.

As used in this invention, the term "antagonist" refers to a compound which binds to, and decreases the activity of, a receptor in the presence of an agonist. In the case of a G-protein coupled receptor, activation may be measured using any appropriate second messenger system which is coupled to the receptor in a cell or tissue in which the receptor is expressed. Some specific, but by no means limiting, examples of well-known second messenger systems are adenylate cyclase, intracellular calcium mobilization, ion channel activation, guanylate cyclase and inositol phospholipid hydrolysis. Conversely, the term "agonist" refers to a compound which binds to, and increases activity of, a receptor as compared with the activity of the receptor in the absence of any agonist.

In one embodiment of this invention, the synthesis of novel compounds which bind selectively to the cloned human melanin-concentrating hormone-1 (MCH1) receptor, compared to other cloned G-protein coupled receptors, and inhibit the activation of the cloned receptors as measured in in vitro assays is disclosed. The in vitro receptor binding assays described hereinafter were performed using various cultured cell lines, each transfected with and expressing only a single cloned receptor.

Furthermore, the compounds of the present invention may also be used to treat abnormal conditions such as feeding disorders (obesity, bulimia and bulimia nervosa), sexual/reproductive disorders, depression, anxiety, depression and anxiety, epileptic seizure, hypertension, cerebral hemorrhage, congestive heart failure, sleep disturbances, or any condition in which antagonism of an MCH1 receptor may be beneficial. In addition, the compounds of the present invention may be used to reduce the body mass of a subject. Furthermore, the compounds of the present invention may be used to treat urinary disorders.

SUMMARY OF THE INVENTION

This invention provides a compound having the structure:

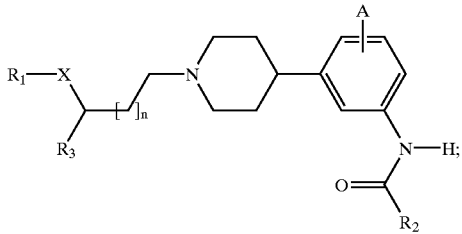

wherein $R_1$ is hydrogen, straight chained or branched $C_1$–$C_7$ alkyl, monofluoroalkyl or polyfluoroalkyl, aryl or heteroaryl, wherein the aryl or heteroaryl is optionally substituted with one or more —F, —Cl, —Br, —I, —CN, —NO$_2$—, —CH$_3$, —CF$_3$, —COR$_2$, —CO$_2$R$_2$, phenyl, phenoxy or straight chained or branched $C_1$–$C_7$ alkyl;

wherein $R_2$ is straight-chained or branched $C_3$–$C_4$ alkyl or cyclopropyl;

wherein $R_3$ is aryl or heteroaryl, wherein the aryl or heteroaryl is optionally substituted with one or more —F, —Cl, —Br, —I, —CN, —NO$_2$, straight chained or branched $C_1$–$C_7$ alkyl;

wherein A is —H, —F, —Cl, —Br, —CN, —NO$_2$, —COR$_3$, —CO$_2$R$_3$, straight chained or branched $C_1$–$C_7$ alkyl, monofluoroalkyl or polyfluoroalkyl;

wherein X is O or NH; and wherein n is an integer from 0 to 5 inclusive.

In one embodiment, $R_1$ is aryl optionally substituted with one or more —F, —Cl, —Br, —I, —CN, —NO$_2$, —COR$_2$, —CO$_2$R$_2$, straight chained or branched $C_1$–$C_7$ alkyl;

wherein $R_3$ is phenyl;

wherein A is H; and wherein X is O.

In one embodiment, $R_2$ is isopropyl.
In one embodiment, the compound has the structure:

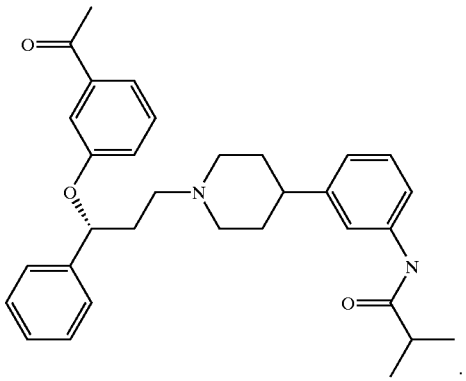

In one embodiment, compound has the structure:

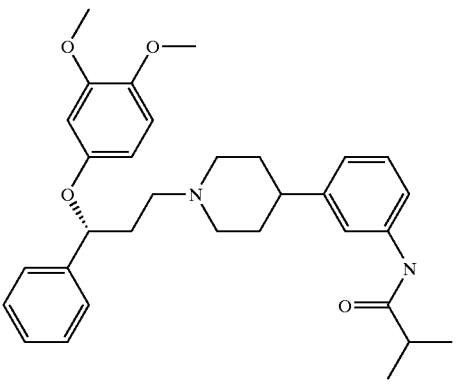

In one embodiment, $R_1$ is hydrogen, straight chained or branched $C_1$–$C_7$ alkyl; and wherein $R_3$ is aryl.

In one embodiment, $R_2$ is isopropyl; and A is hydrogen.
In one embodiment, the compound has the structure:

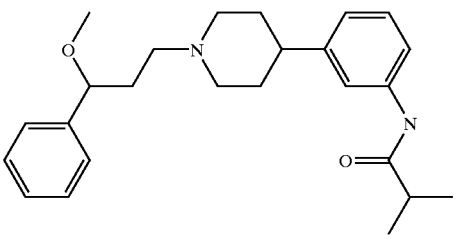

In one embodiment, the compound has the structure:

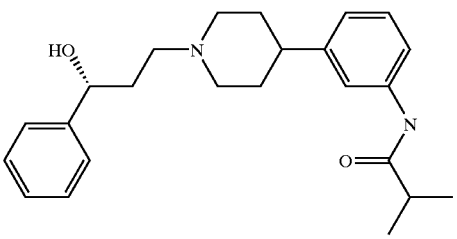

The present invention also provides a compound having the structure:

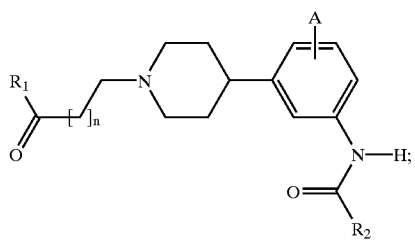

wherein $R_1$ is aryl or heteroaryl optionally substituted with one or more —F, —Cl, —Br, —I, —CN, —NO$_2$, —OCH$_3$, phenoxy, fused cyclopentanyl, straight chained or branched $C_1$–$C_7$ alkyl, monofluoroalkyl or polyfluoroalkyl;

wherein $R_2$ is straight-chained or branched $C_1$–$C_4$ alkyl or cyclopropyl;

wherein A is —H, —F, —Cl, —Br, —CN, —NO₂, straight chained or branched C₁–C₇ alkyl, monofluoroalkyl or polyfluoroalkyl; and wherein n is an integer from 1 to 5 inclusive.

In one embodiment, R₁ is aryl optionally substituted with one or more —F, —Cl, —Br, —I or straight chained or branched C₁–C₄ alkyl; and wherein A is H.

In one embodiment, R₂ is isopropyl; and wherein n is 2.

In one embodiment, the compound has the structure:

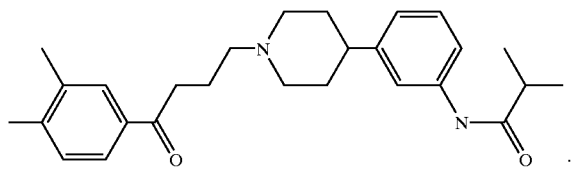

In one embodiment, the compound has the structure:

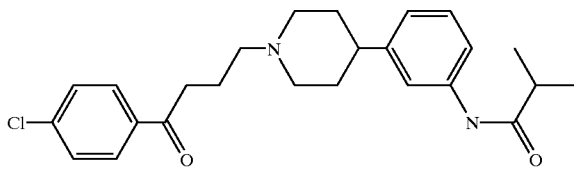

In one embodiment, the compound has the structure:

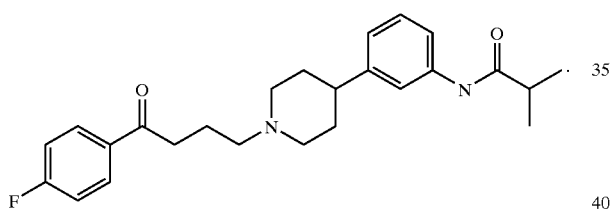

In one embodiment, R₁ is thienyl; and wherein A is H.
In one embodiment, R₂ is isopropyl.
In one embodiment, the compound has the structure:

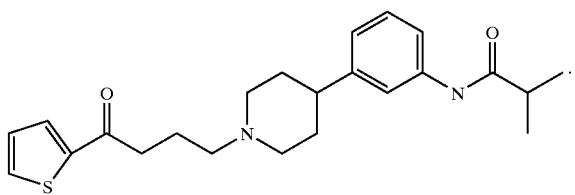

The invention provides a compound having the structure:

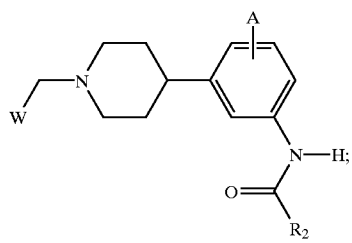

wherein W is

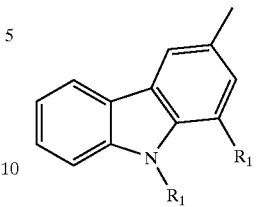 or 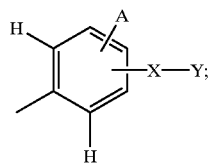

wherein each $R_1$ is independently hydrogen, methyl or ethyl;

wherein $R_2$ is straight-chained or branched $C_3$–$C_4$ alkyl or cyclopropyl;

wherein $R_3$ is hydrogen, aryl or heteroaryl, wherein the aryl or heteroaryl is optionally substituted with one or more —H, —F, —Cl, —Br, —I, —CN, —NO₂, straight chained or branched $C_1$–$C_7$ alkyl.

wherein each A is independently —H, —F, —Cl, —Br, —CN, —NO₂, —COR₃, —CO₂R₃, straight chained or branched $C_1$–$C_7$ alkyl, monofluoroalkyl or polyfluoroalkyl;

wherein X is O, NR₃, CO or may be absent; and wherein Y is hydrogen, aryl or heteroaryl, wherein the aryl or heteroaryl is optionally substituted with one or more —F, —Cl, —Br, —I, —CN, —NO₂, straight chained or branched $C_1$–$C_7$ alkyl.

In one embodiment, W is

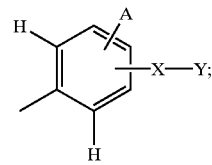

and wherein X is O or may be absent.

In one embodiment, R₂ is isopropyl.

In one embodiment, the compound has the structure:

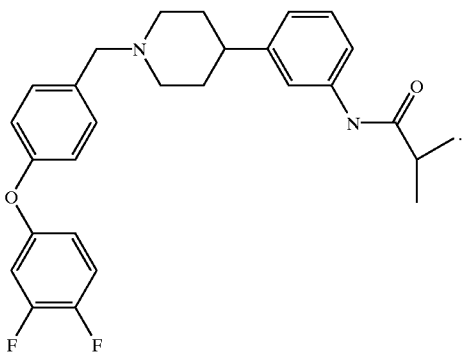

In one embodiment, the compound has the structure:

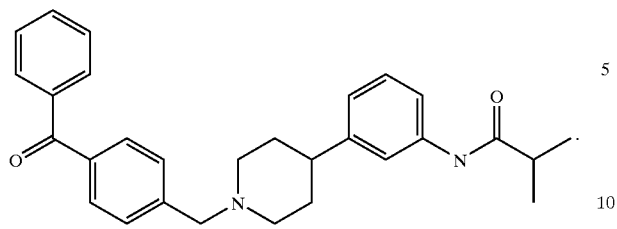

In one embodiment, W is

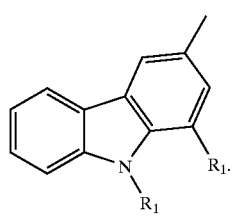

In one embodiment, A is —H, —F, —Cl, —Br.
In one embodiment, $R_2$ is isopropyl; and A is hydrogen.
In one embodiment, the compound has the structure:

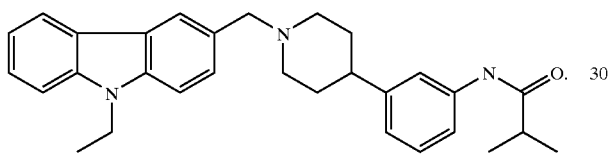

This invention provides a compound having the structure:

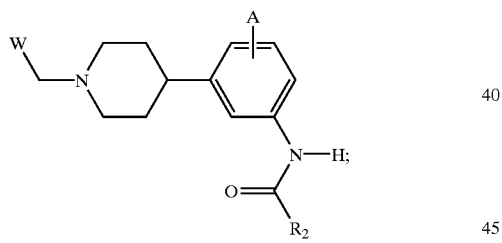

wherein W is

wherein $R_1$ is hydrogen, straight chained or branched $C_1$–$C_7$ alkyl, aryl or heteroaryl, wherein the aryl or heteroaryl is optionally substituted with one or more —F, —Cl, —Br, —CN, —NO$_2$, —OCH$_3$, —CO$_2$CH$_3$, —CF$_3$, phenyl, straight chained or branched $C_1$–$C_7$ alkyl;
wherein $R_2$ is straight-chained or branched $C_3$–$C_4$ alkyl or cyclopropyl;
wherein A is —H, —F, —Cl, —Br, —CN, —NO$_2$, —COR$_1$, —CO$_2$R$_1$, straight chained or branched $C_1$–$C_7$ alkyl, monofluoroalkyl or polyfluoroalkyl or phenyl.

wherein each B is independently —H, —F, —Cl, —Br, —I, —CN, —NO$_2$, —COR$_1$, —CO$_2$R$_1$, —OCH$_3$, —OCF$_3$, —CF$_3$, straight chained or branched $C_1$–$C_7$ alkyl, monofluoroalkyl or polyfluoroalkyl or aryl, phenoxy or benzyloxy, wherein the aryl, phenoxy or benzyloxy is optionally substituted with one or more —F, —Cl, —Br, —CN, —NO$_2$, —COR$_1$, —CO$_2$R$_1$, —OCH$_3$, —OCF$_3$, —CF$_3$ or straight chained or branched $C_1$–$C_3$ alkyl.

In one embodiment, W is

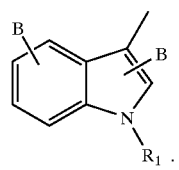

In one embodiment, $R_1$ is hydrogen or phenyl optionally substituted with one or more —F, —Cl, —Br, —CN, —NO$_2$, straight chained or branched $C_1$–$C_7$ alkyl.
In one embodiment, $R_2$ is isopropyl.
In one embodiment, the compound has the structure:

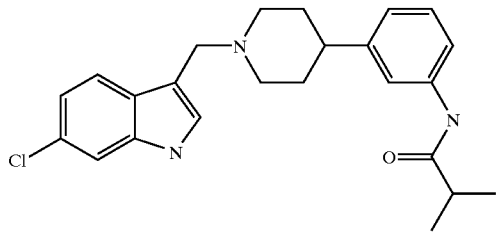

In one embodiment, the compound has the structure:

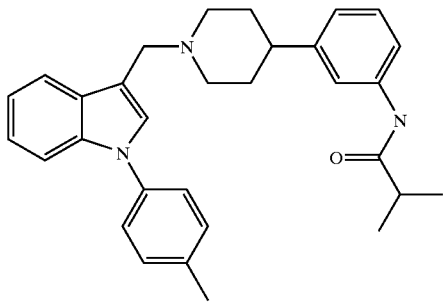

This invention provides a compound having the structure:

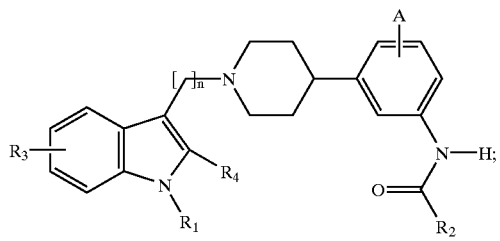

wherein R₁ is hydrogen, straight chained or branched $C_1$–$C_7$ alkyl, aryl or heteroaryl, wherein the aryl or heteroaryl is optionally substituted with one or more —F, —Cl, —Br, —CN, —NO₂, —CF₃, —OCH₃, straight chained or branched $C_1$–$C_3$ alkyl;

wherein R₂ is straight-chained or branched $C_3$–$C_4$ alkyl or cyclopropyl;

wherein R₃ is —H, —F, —Cl, —Br, —I, —CN, —NO₂, —CF₃, —OCH₃, or straight chained or branched $C_1$–$C_3$ alkyl, monofluoroalkyl or polyfluoroalkyl, or a phenyl ring fused to $C_6$ and $C_7$ of the indole moiety;

wherein R₄ is hydrogen or aryl optionally substituted with one or more —F, —Cl, —Br, —I, —CN, —NO₂, —CF₃, straight chained or branched $C_1$–$C_3$ alkyl;

wherein A is —H, —F, —Cl, —Br, —CN, —NO₂, straight chained or branched $C_1$–$C_7$ alkyl, monofluoroalkyl or polyfluoroalkyl; and wherein n is an integer from 2 to 4 inclusive.

In one embodiment, R₃ is —H, —F, —Cl, —Br, —I, —CN, —NO₂, —OCF₃ or —OCH₃; and wherein R₄ is hydrogen or phenyl optionally substituted with one or more —F, —Cl or —CF₃.

In one embodiment, R₁ is hydrogen or phenyl optionally substituted with one or more —F, —Cl, —Br, —CN, —NO₂, —CF₃, —OCH₃ or straight chained or branched $C_1$–$C_3$ alkyl;

In one embodiment, R₂ is isopropyl.

In one embodiment, the compound has the structure:

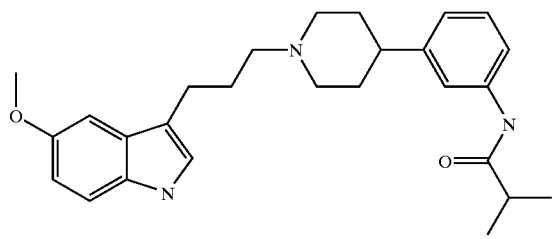

In one embodiment, the compound has the structure:

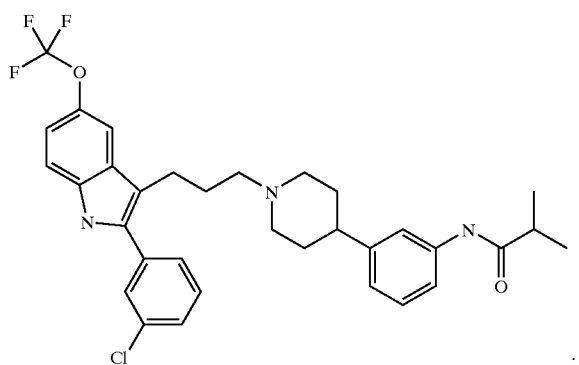

In one embodiment, the compound has the structure:

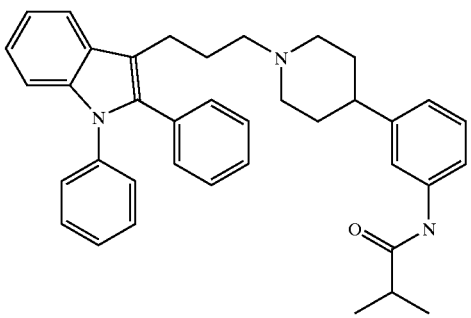

This invention provides a compound having the structure:

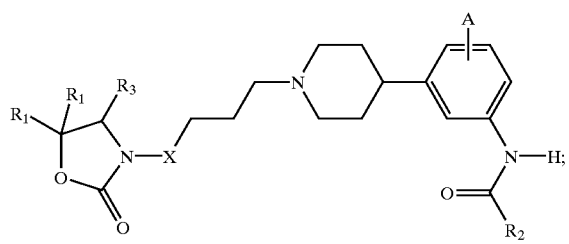

wherein each R₁ is independently hydrogen or CH₃;

wherein R₂ is straight-chained or branched $C_1$–$C_4$ alkyl or cyclopropyl;

wherein R₃ is benzyl or phenyl, wherein the benzyl or phenyl is optionally substituted with a methylenedioxy group or one or more —F or —Cl;

wherein A is —H, —F, —Cl, —Br, —CN, —NO₂, straight chained or branched $C_1$–$C_7$ alkyl, monofluoroalkyl or polyfluoroalkyl;

wherein X is (CH₂)₂, COCH₂ or CONH;

In one embodiment, R₃ is phenyl optionally substituted with one or more —F; and wherein A is hydrogen.

In one embodiment, X is CONH.

In one embodiment, R₂ is methyl.

In one embodiment, the compound has the structure:

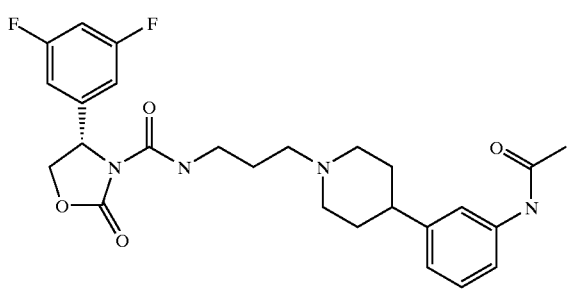

In one embodiment, the compound has the structure:

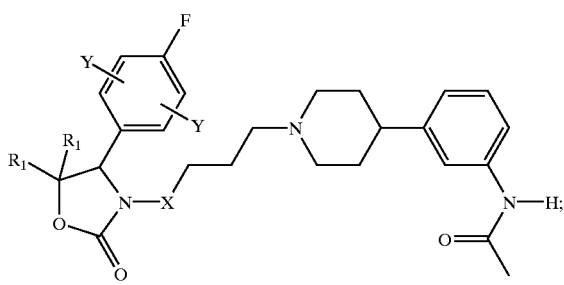

wherein each Y is independently hydrogen or —F.

In one embodiment, the compound has the structure:

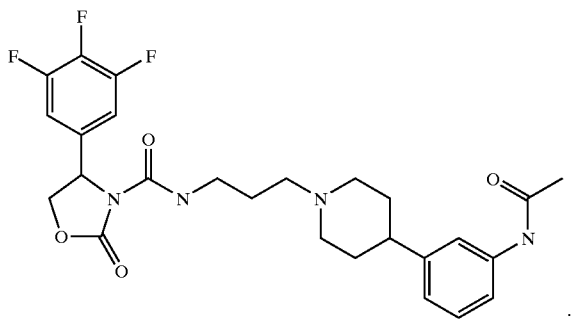

In one embodiment, the compound has the structure:

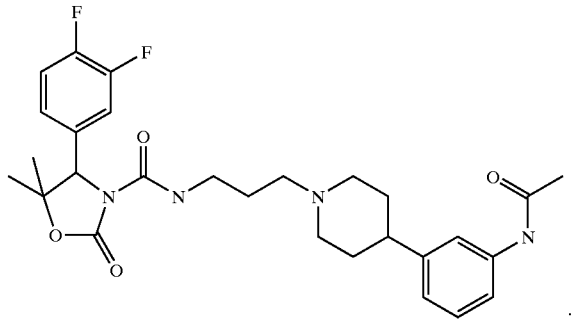

In one embodiment, $R_3$ is benzyl optionally substituted with a methylenedioxy group or one or more —F or —Cl.

In one embodiment, the compound has the structure:

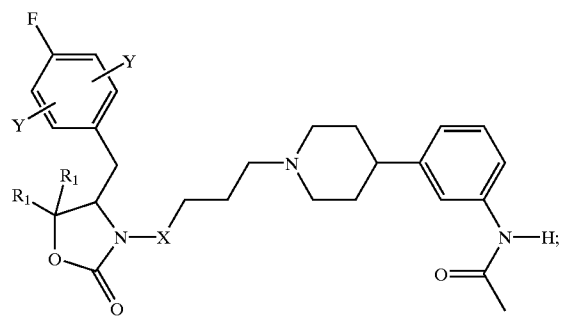

wherein each Y is independently hydrogen or —F.

In one embodiment, the compound has the structure:

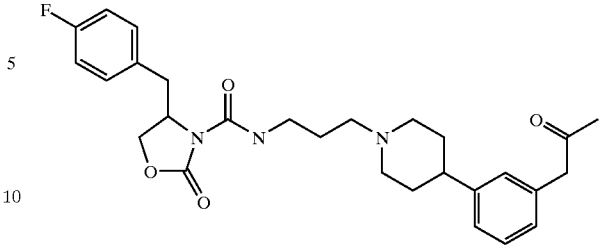

In one embodiment, the compound is enantiomerically pure.

In one embodiment, the compound is diastereomerically pure.

In one embodiment, the compound is enantiomerically and diastereomerically pure.

This invention also provides a pharmaceutical composition comprising a therapeutically amount of a compound of the invention and a pharmaceutically acceptable carrier.

In one embodiment, the amount of the compound is from about 0.01 mg to about 500 mg.

In one embodiment, the amount of the compound is from about 0.1 mg to about 60 mg.

In one embodiment, the amount of the compound is from about 1 mg to about 20 mg.

In one embodiment, the pharmaceutical composition consists of a carrier which is a liquid and the composition is a solution.

In one embodiment, the pharmaceutical composition consists of a carrier which is a solid and the composition is a tablet.

In one embodiment, the pharmaceutical composition consists of a carrier which is a gel and the composition is a suppository.

The invention also provides a process for making a pharmaceutical composition comprising admixing a therapeutically effective amount of the compound of any of the invention and a pharmaceutically acceptable carrier.

This invention also provides the method of treating a subject suffering from a disorder selected from the group consisting of depression, anxiety, urge incontinence, or obesity comprising administering to the subject a therapeutically effective amount of the compound of the invention.

In one embodiment, the therapeutically effective amount is between about 0.03 and about 1000 mg per day.

In one embodiment, the therapeutically effective amount is between about 0.30 and about 300 mg per day.

In one embodiment, the therapeutically effective amount is between about 1.0 and about 100 mg per day.

In one embodiment, the disorder is depression.

In one embodiment, the disorder is anxiety.

In one embodiment, the disorder is obesity.

In one embodiment, the disorder is urge incontinence.

The invention provides the method of reducing the body mass of a subject, which comprises administering to the subject an amount of a compound of the invention effective to reduce the body mass of the subject.

The invention provides the method of treating a subject suffering from depression, which comprises administering to the subject an amount of a compound of any of claims of the invention effective to treat the subject's depression.

The invention provides the method of treating a subject suffering from anxiety, which comprises administering to the subject an amount of a compound of the invention effective to treat the subject's anxiety.

The invention provides the method of alleviating urge urinary incontinence in a subject suffering from an overactive bladder, which comprises administering to the subject an amount of the compound of the invention effective to alleviate the subject's urge urinary incontinence.

The invention provides the method of managing obesity in a subject in need of weight loss, which comprises administering to the subject an amount of a compound of the invention effective to induce weight loss in the subject.

The invention provides the method of managing obesity in a subject who has experienced weight loss, which comprises administering to the subject an amount of a compound of the invention effective to maintain such weight loss in the subject.

The invention provides the method of treating overactive bladder in a subject, which comprises administering to the subject an amount of a compound of any of the invention effective to treat the subject's overactive bladder.

The invention provides the method of treating a disorder in a subject, wherein the symptoms of the subject can be alleviated by treatment with an MCH1 antagonist, wherein the MCH1 antagonist is the compound of the invention.

The invention provides the method of alleviating the symptoms of a disorder in a subject, which comprises administering to the subject an amount of an MCH1 antagonist effective to alleviate the symptoms, wherein the MCH1 antagonist is the compound of the invention.

DETAILED DESCRIPTION OF THE INVENTION

This invention provides a compound having the structure:

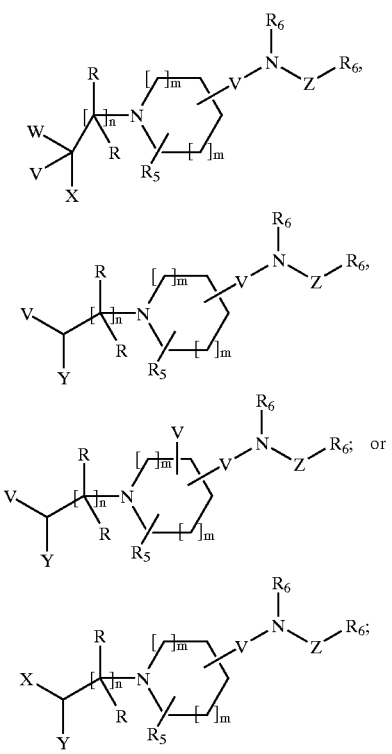

wherein each V is independently phthalimide, aryl, phenoxy or heteroaryl, wherein the aryl, phenoxy or heteroaryl is optionally substituted with one or more F; Cl; Br; I; $COR_5$; $CO_2R_5$; —$OCOR_5$; —$CON(R_5)_2$; —$N(R_5)COR_5$; CN; —$NO_2$; —$N(R_5)_2$; —$OR_5$; —$SR_5$; $(CH_2)_qOR_5$; $(CH_2)_qR_5$; $(CH_2)_qSR_5$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; aryl; phenoxy; $C_3$–$C_7$ cycloalkyl, monofluorocycloalkyl, polyfluorocycloalkyl or cycloalkenyl;

wherein each W is independently aryl or heteroaryl, wherein the aryl or heteroaryl is optionally substituted with one or more F; Cl; Br; I; $COR_3$; —$OCOR_3$; $CO_2R_3$; —$CON(R_3)_2$; —$N(R_3)COR_3$; CN; —$NO_2$; —$N(R_3)_2$; —$OR_3$; —$SR_3$; $(CH_2)_qOR_3$; $(CH_2)_qSR_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; aryl; phenoxy; $C_3$–$C_7$ cycloalkyl, monofluorocycloalkyl, polyfluorocycloalkyl or cycloalkenyl;

wherein X is hydrogen or —$OR_3$, provided that when X is —$OR_3$ the V geminal to X cannot be phthalimide;

wherein Y is hydrogen, =O (carbonyl oxygen), $OR_3$, OV, COV, =NNHV, =$NNR_5$, $NZR_5$, NZV, NCONV (ureas), $NCONR_5$, $NR_3$, carbazole, indole or phthalimide;

wherein each R is independently —H; —F; straight chained or branched $C_1$–$C_7$ alkyl, monofluoroalkyl or polyfluoroalkyl; straight chained or branched $C_2$–$C_7$ alkenyl or alkynyl; —$N(R_3)_2$; —$NO_2$; —CN; —$CO_2R_3$; —$OCOR_3$; —$OR_3$; or —$N(R_3)COR_3$; —$CON(R_3)_2$;

wherein each $R_3$ is independently —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl;

wherein each $R_5$ is —H; —$NO_2$; —$N_3$; —CN; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —$N(R_3)_2$; —$OR_3$; —$(CH_2)_pOR_3$; —$COR_3$; —$CO_2R_3$; —$OCOR_3$; —$CON(R_3)_2$; —$N(R_3)COR_3$; aryl or heteroaryl, wherein the aryl or heteroaryl is optionally substituted with one or more F; Cl; Br; I; $COR_6$; $CO_2R_3$; —$OCOR_3$; —$CON(R_3)_2$; —$N(R_3)COR_3$; CN; —$NO_2$; —$N(R_3)_2$; —$OR_6$; —$SR_6$; $(CH_2)_qOR_6$; $(CH_2)_qSR_6$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein $R_6$ is —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —$N(R_3)_2$; —$OR_3$; —$(CH_2)_pOR_3$; —$COR_3$; —$CO_2R_3$; —$OCOR_3$; —$CON(R_3)_2$; —$N(R_3)COR_3$; aryl, benzyl or heteroaryl, optionally substituted with one or more F; Cl; Br; I; $COR_3$; $CO_2R_3$; —$OCOR_3$; —$CON(R_3)_2$; —$N(R_3)COR_3$, CN; —$NO_2$; —$N(R_3)_2$; —$OR_3$; —$SR_3$; $(CH_2)_qOR_3$; $(CH_2)_qSR_3$; straight chained or branched $C_1$–$C_7$ alkyl, monofluoroalkyl, polyfluoroalkyl, aminoalkyl, or carboxamidoalkyl; aryl; benzyl; straight chained or branched $C_2$–$C_7$ alkenyl, $C_2$–$C_7$ alkynyl; $C_3$–$C_7$ cycloalkyl, monofluorocycloalkyl, polyfluorocycloalkyl or cycloalkenyl;

wherein Z is CO, SO$_2$ or SO$_2$NR$_6$;

wherein each m is independently an integer from 0 to 3 inclusive;

wherein each n is independently an integer from 0 to 5 inclusive;

wherein each p is independently an integer from 1 to 7 inclusive; and wherein q is an integer from 1 to 3 inclusive;

or a pharmaceutically acceptable salt thereof.

As used in the present invention, the term "cycloalkyl" includes C$_3$–C$_7$ cycloalky moieties which may be substituted with one or more of the following: F; CN; —NO$_2$; straight chained or branched C$_1$–C$_7$ alkyl, straight chained or branched C$_1$–C$_7$ monofluoroalkyl, straight chained or branched C$_1$–C$_7$ polyfluoroalkyl, straight chained or branched C$_2$–C$_7$ alkenyl, straight chained or branched C$_2$–C$_7$ alkynyl; C$_3$–C$_7$ cycloalkyl, C$_3$–C$_7$ monofluorocycloalkyl, C$_3$–C$_7$ polyfluorocycloalkyl, C$_5$–C$_7$ cycloalkenyl, —N(R$_3$)$_2$; —OR$_3$; —NCOR$_3$; —COR$_3$; —CO$_2$R$_3$; —CON(R$_3$)$_2$ or (CH$_2$)$_p$—O—(CH$_3$)$_m$—CH$_3$—

In the present invention, the term "cycloalkenyl" includes C$_5$–C$_7$ cycloalkenyl moieties which may be substituted with one or more of the following: —F; —Cl; —Br; —I; CN; —NO$_2$; straight chained or branched C$_1$–C$_7$ alkyl, straight chained or branched C$_1$–C$_7$ monofluoroalkyl, straight chained or branched C$_1$–C$_7$ polyfluoroalkyl, straight chained or branched C$_2$–C$_7$ alkenyl, straight chained or branched C$_2$–C$_7$ alkynyl; C$_3$–C$_7$ cycloalkyl, C$_3$–C$_7$ monofluorocycloalkyl, C$_3$–C$_7$ polyfluorocycloalkyl, C$_5$–C$_7$ cycloalkenyl, —N(R$_3$)$_2$; —OR$_3$; —NCOR$_3$; —COR$_3$; —CO$_2$R$_3$; —CON(R$_3$)$_2$ or (CH$_2$)$_p$—O—(CH$_3$)$_m$—CH$_3$.

As used in the present invention, the term "heteroaryl" is used to include five and six membered unsaturated rings that may contain one or more oxygen, sulfur, or nitrogen atoms. Examples of heteroaryl groups include, but are not limited to, furanyl, thienyl, pyrrolyl, oxazolyl, thiazolyl, imidazolyl, pyrazolyl, isoxazolyl, isothiazolyl, oxadiazolyl, triazzolyl, thiadiazolyl, pyridyl, pyridazinyl, pyrimidinyl, pyrazinyl, and triazinyl.

In addition, the term "heteroaryl" is used to include fused bicyclic ring systems that may contain one or more heteroatoms such as oxygen, sulfur and nitrogen. Examples of such heteroaryl groups include, but are not limited to, indolizinyl, indolyl, isoindolyl, benzo[b]furanyl, benzo[b]thiophenyl, indazolyl, benzimidazolyl, purinyl, benzoxazolyl, benzisoxazolyl, benzo[b]thiazolyl, imidazo[2,1-b]thiazolyl, cinnolinyl, quinazolinyl, quinoxalinyl, 1,8-naphthyridinyl, pteridinyl, quinolinyl, isoquinolinyl, phthalimidyl and 2,1,3-benzothiazolyl.

The term "heteroaryl" also includes those chemical moieties recited above which may be substituted with one or more of the following: —F; —Cl; —Br, —I; CN; —NO$_2$; straight chained or branched C$_1$–C$_7$ alkyl, straight chained or branched C$_1$–C$_7$ monofluoroalkyl, straight chained or branched C$_1$–C$_7$ polyfluoroalkyl, straight chained or branched C$_2$–C$_7$ alkenyl, straight chained or branched C$_2$–C$_7$ alkynyl; C$_3$–C$_7$ cycloalkyl, C$_3$–C$_7$ monofluorocycloalkyl, C$_3$–C$_7$ polyfluorocycloalkyl, C$_5$–C$_7$ cycloalkenyl, —N(R$_3$)$_2$; —OR$_3$; —NCOR$_3$; —COR$_3$; —CO$_2$R$_3$; —CON(R$_3$)$_2$ or (CH$_2$)$_p$—O—(CH$_3$)$_m$—CH$_3$.

In still another embodiment of the above described invention, the compound has the structure:

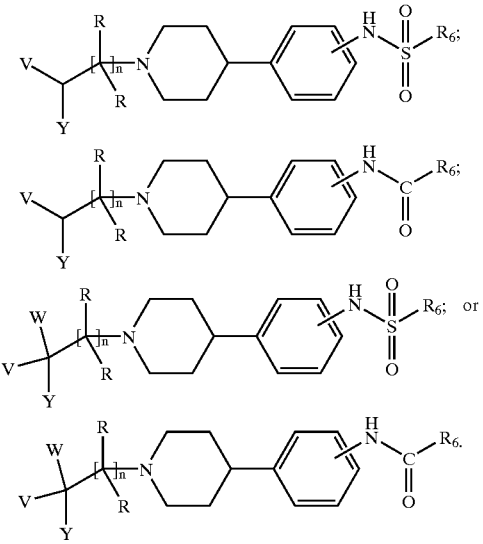

In a further embodiment of the instant invention, R$_6$ is straight chained or branched C$_1$–C$_7$ alkyl; C$_3$–C$_7$ cycloalkyl; —N(R$_3$)$_2$; —OR$_3$; —(CH$_2$)$_p$OR$_3$; aryl, benzyl or heteroaryl, optionally substituted with one or more F; Cl; Br; I; —OR$_3$; —(CH$_2$)$_q$OR$_3$; or straight chained or branched C$_1$–C$_7$ alkyl.

In an embodiment of the present invention, the compound has the structure:

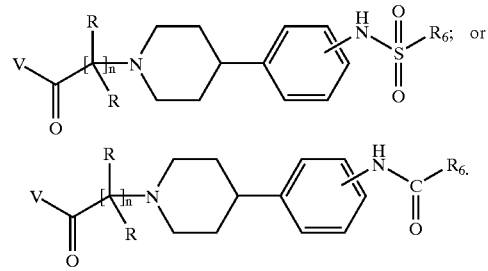

In a further embodiment of the present invention, at least one V is phenyl optionally substituted with one or more F; Cl; Br; —OR$_3$; (CH$_2$)$_q$OR$_3$; straight chained or branched C$_1$–C$_7$ alkyl; C$_1$–C$_7$ polyfluoroalkyl; or phenoxy.

In one embodiment of the present invention, the compound is:

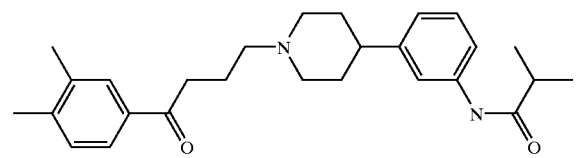

In one embodiment, the compound is:

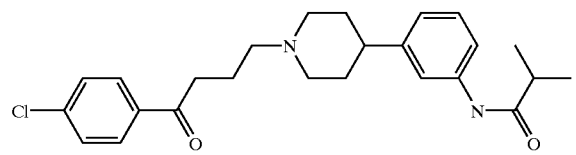

In one embodiment, the compound is:

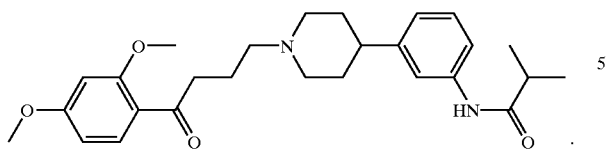

In another embodiment of the present invention, the compound has the structure:

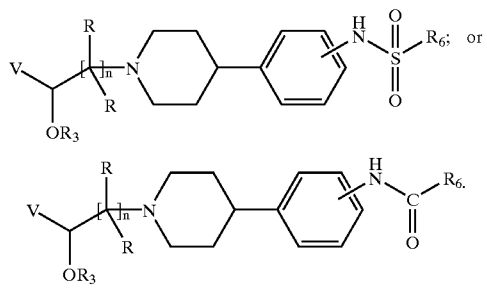

In a further embodiment of the present invention, at least one V is phenyl optionally substituted with one or more F; Cl; Br; —OR$_3$; (CH$_2$)$_q$OR$_3$; straight chained or branched C$_1$–C$_7$ alkyl; C$_1$–C$_7$ polyfluoroalkyl; or phenoxy.

In another embodiment of the present invention, the compound is

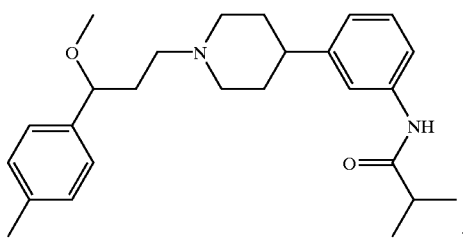

In one embodiment, the compound is

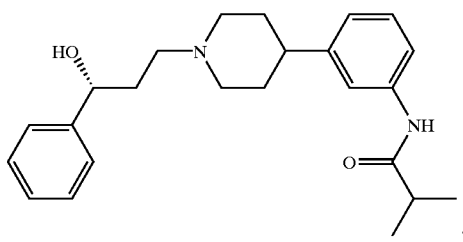

In a further embodiment of the present invention, the compound has the structure:

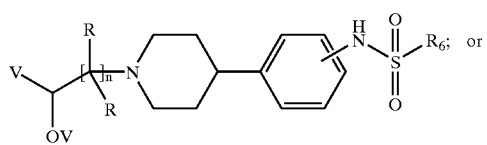

In another embodiment of the present invention, at least one V is phenyl optionally substituted with one or more F; Cl; Br; —OR$_3$; —COR$_3$; (CH$_2$)$_q$OR$_3$; straight chained or branched C$_1$–C$_7$ alkyl; C$_1$–C$_7$ polyfluoroalkyl; aryl or phenoxy.

In yet another embodiment of the present invention, the compound is

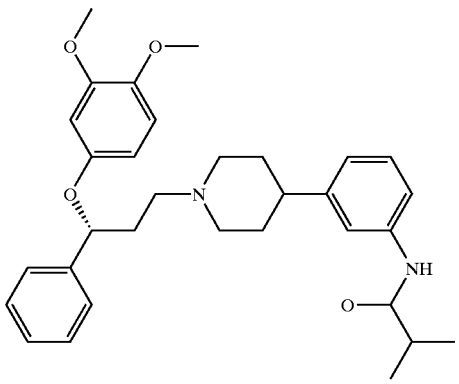

In one embodiment, the compound is

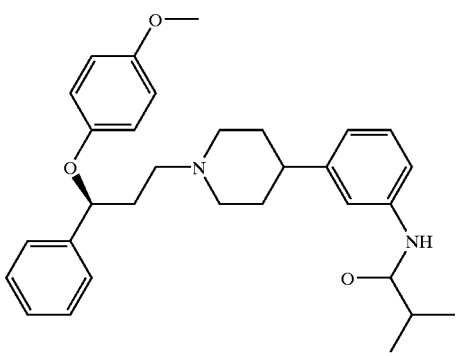

In one embodiment, the compound is

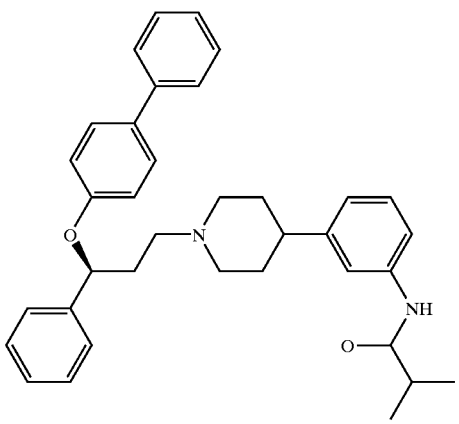

In one embodiment, the compound is

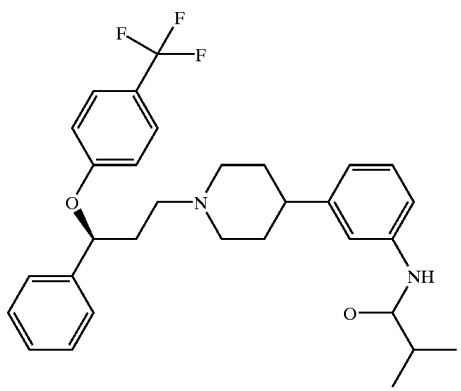

In one embodiment, the compound is

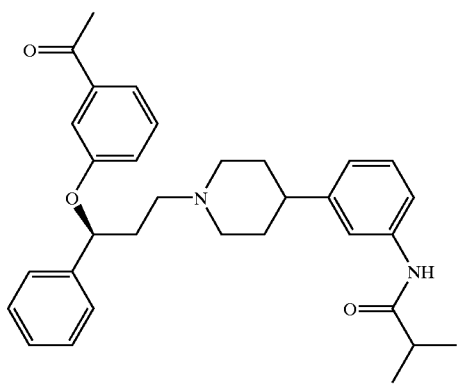

In one embodiment, the compound is

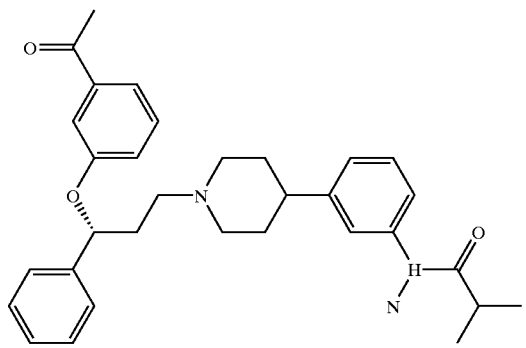

In an embodiment of the present invention, the compound has the structure:

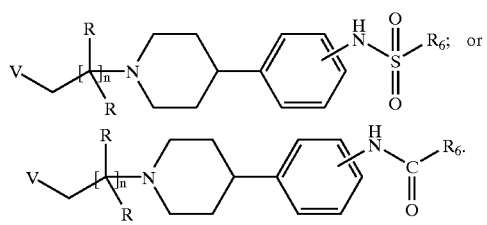

In a further embodiment of the present invention, at least one V is phenyl optionally substituted with one or more F; Cl; Br; —OR$_3$; (CH$_2$)$_q$OR$_3$; straight chained or branched C$_1$–C$_7$ alkyl; C$_1$–C$_7$ polyfluoroalkyl; or phenoxy.

In yet another embodiment of the present invention, the compound is

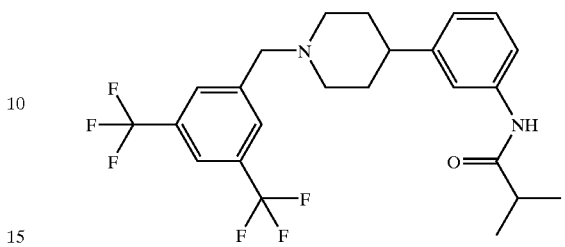

In one embodiment, the compound has the structure:

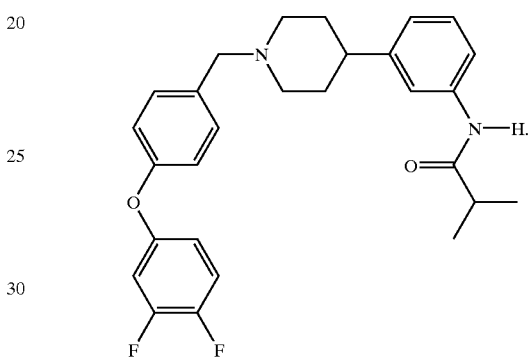

In one embodiment, the compound has the structure:

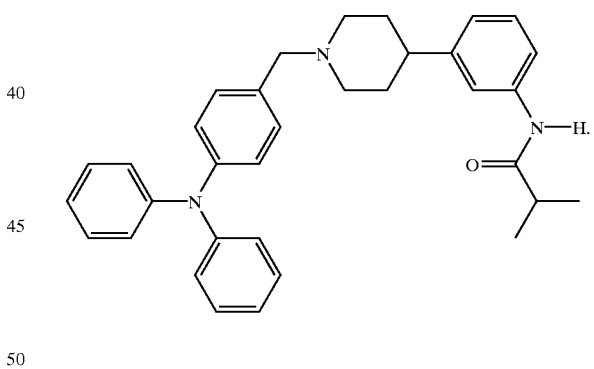

In one embodiment, the compound has the structure:

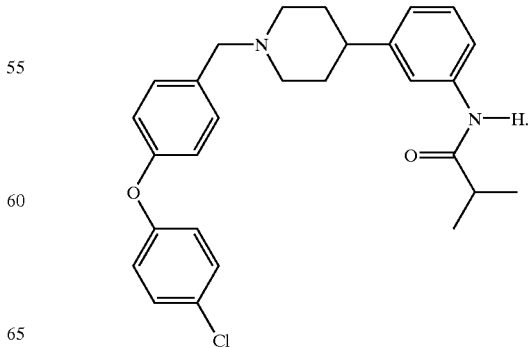

In one embodiment, the compound has the structure:

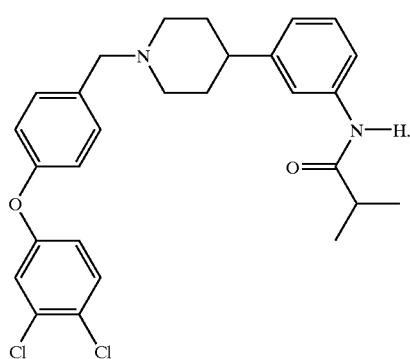

In one embodiment, the compound has the structure:

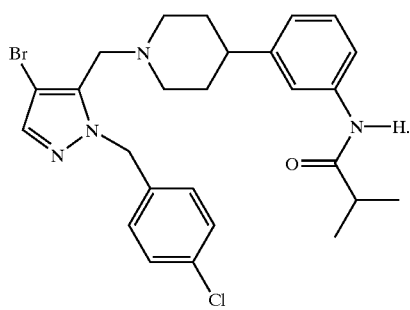

In one embodiment, the compound has the structure:

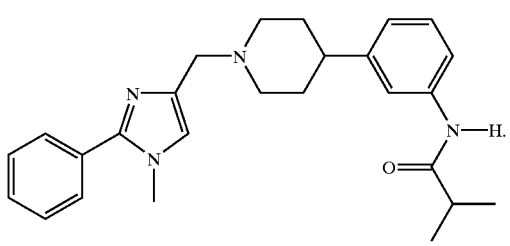

In one embodiment, the compound has the structure:

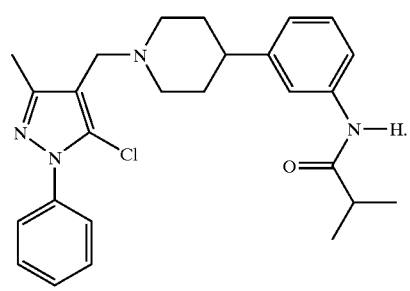

In one embodiment, the compound has the structure:

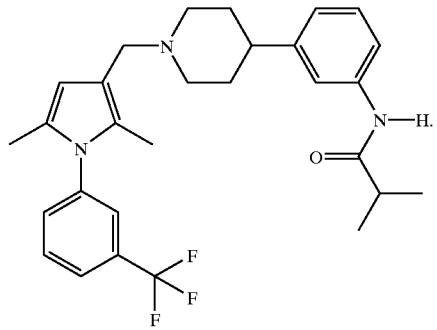

In an additional embodiment of the present invention, Y is hydrogen and V is phthalimide.

In an additional embodiment of the present invention, $R_6$ is straight chained or branched $C_1$–$C_7$ alkyl; $C_3$–$C_7$ cycloalkyl; —$N(R_3)_2$; —$OR_3$; —$(CH_2)_pOR_3$; aryl, benzyl or heteroaryl, optionally substituted with one or more F; Cl; Br; I; —$OR_3$; —$(CH_2)_qOR_3$; or straight chained or branched $C_1$–$C_7$ alkyl.

In a further embodiment of the present invention, the compound is

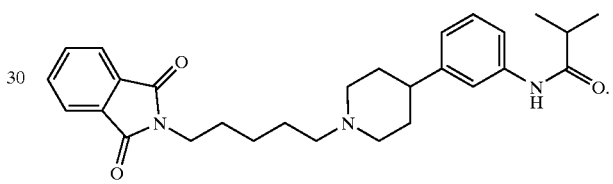

In one embodiment, the compound has the structure:

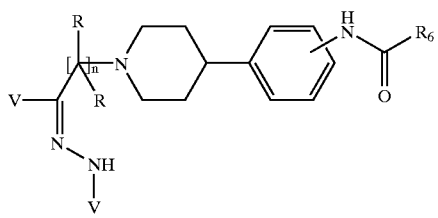

In one embodiment of the compound, at least one V is phenyl or heteroaryl optionally substituted with one or more F; Cl; Br; I; $R_5$; —$OR_5$; —$(CH_2)_qOR_5$; —$(CH_2)_qR_5$; straight chained or branched $C_1$–$C_7$ alkyl; $C_1$–$C_7$ monoflouroalkyl or polyflouroalkyl; or phenoxy.

In one embodiment, the compound has the structure:

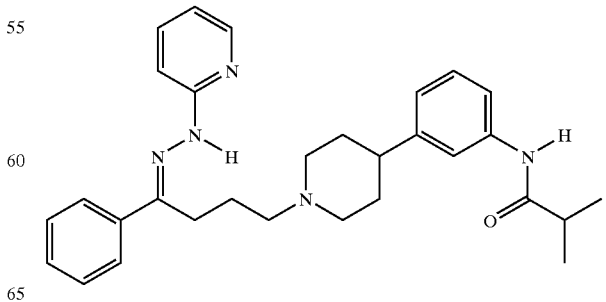

In one embodiment, the compound has the structure:

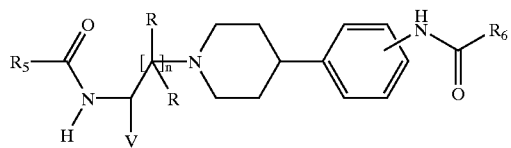

In one embodiment of the compound, V is phenyl which is optionally substituted with one or more F; Cl; Br; —OR$_5$; —(CH$_2$)$_q$OR$_5$; —(CH$_2$)$_q$R$_5$; straight chained or branched C$_1$–C$_7$ alkyl; C$_1$–C$_7$ monoflouroalkyl or polyflouroalkyl; or phenoxy.

In one embodiment, the compound has the structure:

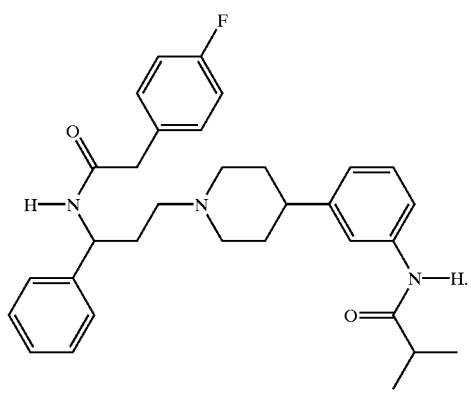

In one embodiment, the compound has the structure:

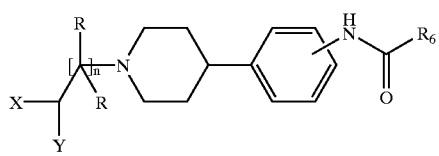

In one embodiment, the compound has the structure:

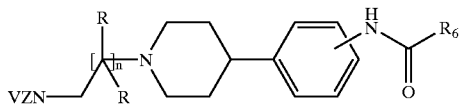

In one embodiment, the compound has the structure:

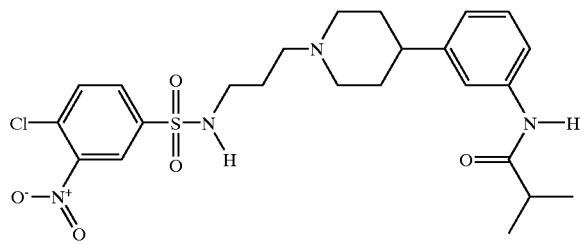

In one embodiment, the compound has the structure:

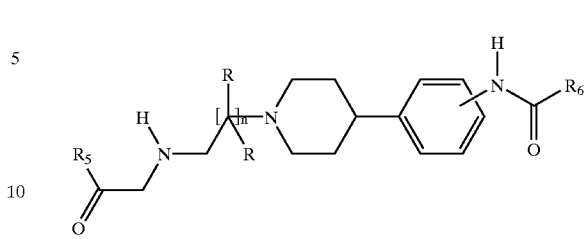

In one embodiment of the compound, R$_5$ is straight chained or branched C$_1$–C$_7$ alkyl; C$_3$–C$_7$ cycloalkyl; —N(R$_6$)$_2$; —OR$_6$; —(OH$_2$)$_q$OR$_6$; —CH(R$_6$)$_2$; —(CH$_2$)$_q$R$_6$; or aryl benzyl or heteroaryl, wherein the aryl, benzyl or heteroaryl is optionally substituted with one or more F; Cl; I; R$_6$; —N(R$_6$)$_2$; —OR$_6$; —(CH$_2$)$_q$OR$_6$; —(CH$_2$)$_q$R$_6$; or straight chained or branched C$_1$–C$_7$ alkyl.

In one embodiment, the compound has the structure:

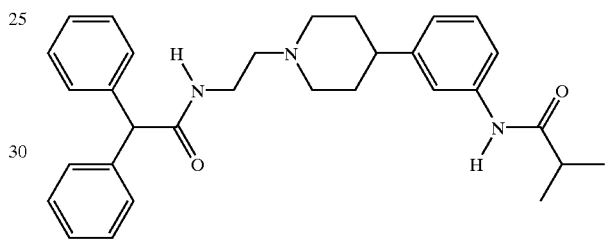

In one embodiment, the compound has the structure:

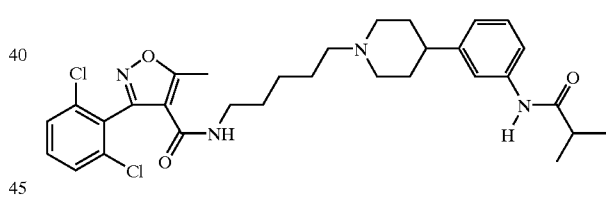

In one embodiment of the compound, X is hydrogen and Y is carbazole optionally substituted with one or more F; Cl; Br; R$_5$; —OR$_5$; —(CH$_2$)$_q$OR$_5$; —(CH$_2$)$_q$R$_5$; straight chained or branched C$_1$–C$_7$ alkyl; or C$_1$–C$_7$ monoflouroalkyl or polyflouroalkyl; or phenoxy.

In one embodiment, the compound has the structure:

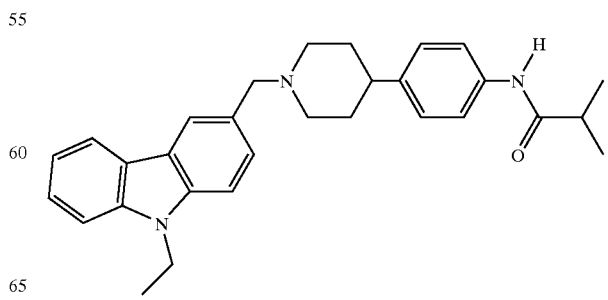

In one embodiment, the compound has the structure:

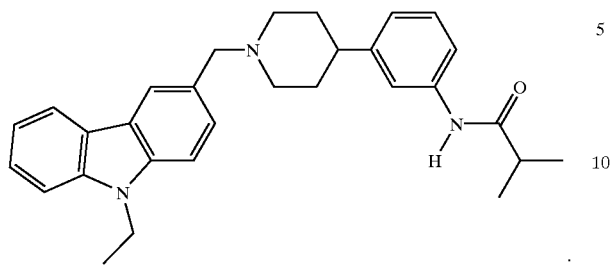

In one embodiment of the compound, Y is hydrogen and V is an indole, which can be optionally substituted with one or more F; Cl; Br; $R_5$; —$CO_2R_5$; —$OR_5$; —$(CH_2)_qOR_5$; —$(CH_2)_qR_5$; straight chained or branched $C_1$–$C_7$ alkyl; $C_1$–$C_7$ monoflouroalkyl or polyflouroalkyl; or phenoxy on the 1, 2, 3, 4, 5, 6 or 7 positions.

In one embodiment, the compound has the structure:

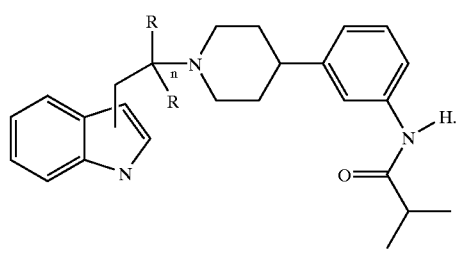

In one embodiment, the compound has the structure:

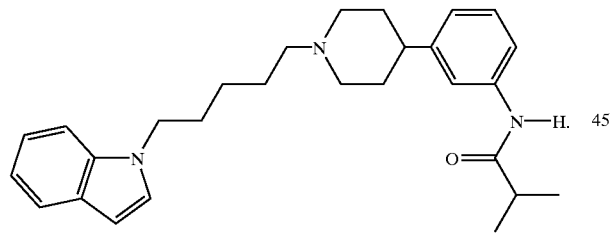

In one embodiment, the compound has the structure:

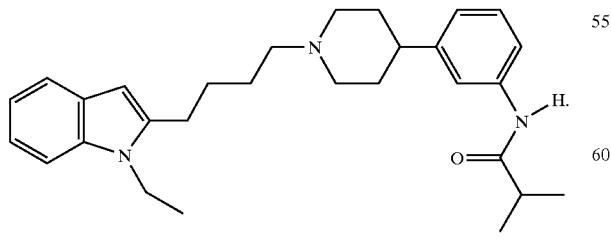

In one embodiment, the compound has the structure:

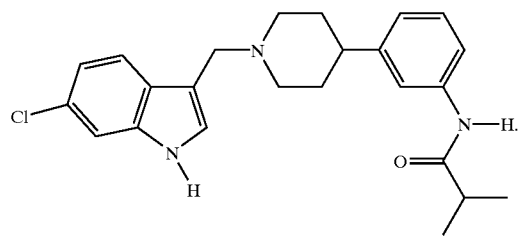

In one embodiment, the compound has the structure:

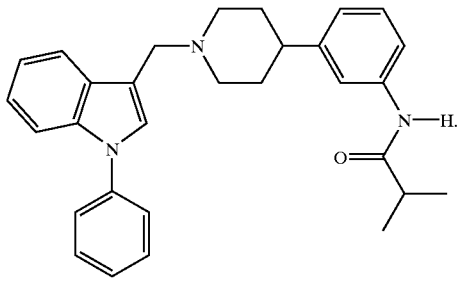

In one embodiment, the compound has the structure:

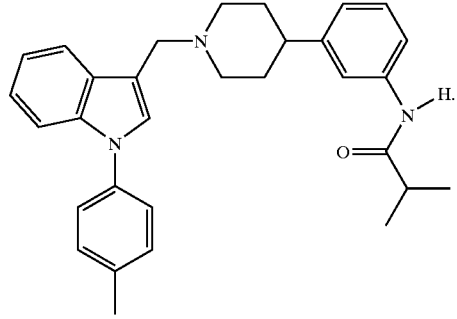

In one embodiment, the compound has the structure:

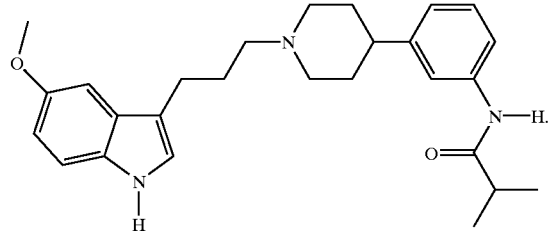

In one embodiment, the compound has the structure:

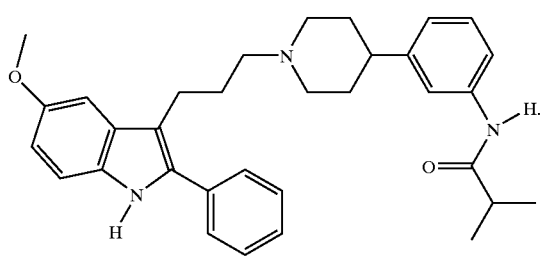

In one embodiment, the compound has the structure:

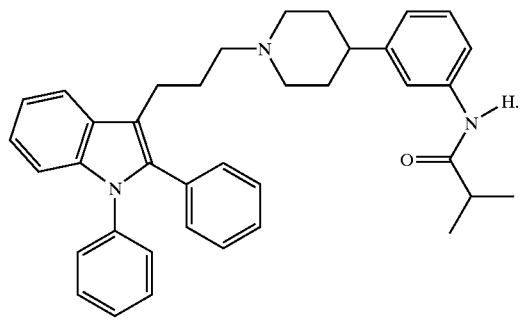

In one embodiment, the compound has the structure:

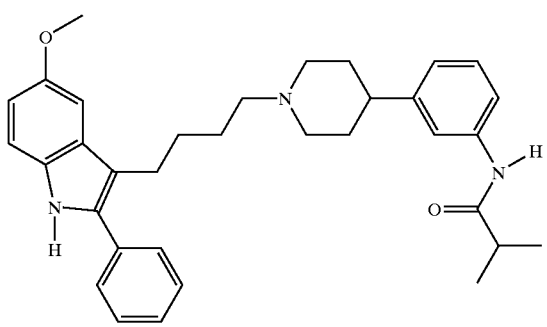

In one embodiment, the compound has the structure:

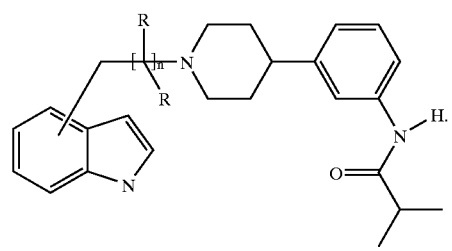

In one embodiment, the compound has the structure:

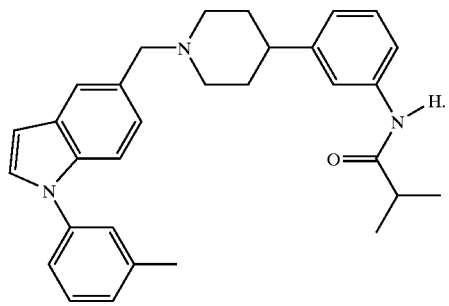

In one embodiment, the compound has the structure:

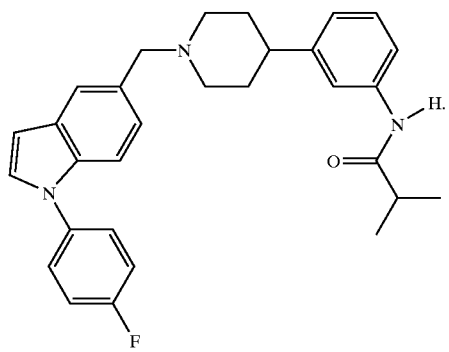

In one embodiment, the compound has the structure:

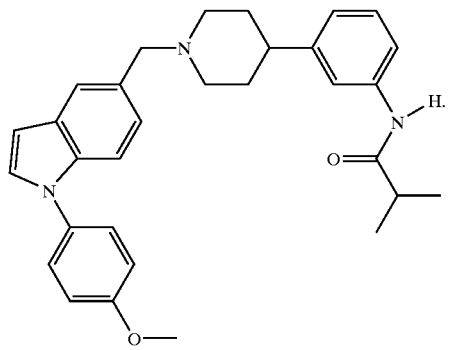

In one embodiment, the compound has the structure:

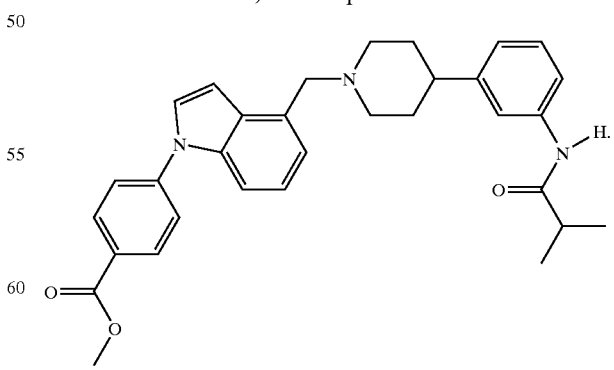

The present invention provides a compound having the structure:

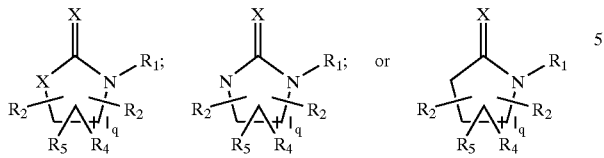

wherein each X is independently O or S;

wherein q is 1 or 2;

wherein each $R_2$ is independently H; —$(CH_2)_tXR_3$; —$(CH_2)_tC(X)N(R_3)_2$; —$(CH_2)_tCO_2R_3$; —$CO_2R_3$; straight chained or branched $C_1$–$C_7$ alkyl optionally substituted with —$N(R_3)_2$; —$CON(R_3)_2$ or —$N(R_3)C(O)R_3$; straight chained or branched $C_2$–$C_7$ alkenyl, or alkynyl; or $C_3$–$C_7$ cycloalkyl or $C_5$–$C_7$ cycloalkenyl;

wherein each t is independently an integer from 1 to 4 inclusive;

wherein each $R_3$ is independently H; straight chained or branched $C_1$–$C_7$ alkyl, straight chained or branched $C_2$–$C_7$ alkenyl, or alkynyl; or $C_3$–$C_7$ cycloalkyl or $C_5$–$C_7$ cycloalkenyl;

wherein $R_4$ is aryl, heteroaryl, $C_1$–$C_7$ alkyl substituted with one or two aryl, or $C_1$–$C_7$ alkyl substituted with one or two heteroaryl; wherein the aryl or heteroaryl may be substituted with one or more of F, Cl, Br, I, —CN, —$NO_2$, —$N(R_3)_2$, —$COR_3$, —$(CH_2)_nXR_3$, —$(CH_2)_nC(X)NR_3$, —$(CH_2)_nN(R_3)C(X)R_3$, —$(CH_2)_nCO_2R_3$, —$(CH_2)_nOCOR_3$, straight chained or branched $C_1$–$C_7$ alkyl, monofluoroalkyl OR polyfluoroalkyl or straight chained or branched $C_2$–$C_7$ aminoalkyl, alkenyl or alkynyl, or $C_3$–$C_7$ cycloalkyl or $C_5$–$C_7$ cycloalkenyl;

wherein each n independently is an integer from 0 to 7 inclusive;

wherein $R_5$ is H; aryl, $C_1$–$C_7$ alkyl substituted with aryl, heteroaryl, or $C_1$–$C_7$ alkyl substituted with heteroaryl;

wherein the aryl or heteroaryl may be substituted with one or more of F, Cl, Br, I, —CN, —$NO_2$, —$N(R_3)_2$, —$COR_3$, —$(CH_2)_nXR_3$, —$(CH_2)_nC(X)NR_3$, —$(CH_2)_nCO_2R_3$, straight chained or branched $C_1$–$C_7$ alkyl, monofluoroalkyl, polyfluoroalkyl or carboxamidoalkyl, or straight chained or branched $C_2$–$C_7$ aminoalkyl, alkenyl or alkynyl, or $C_3$–$C_7$ cycloalkyl or $C_5$–$C_7$ cycloalkenyl;

where $R_5$ and one $R_2$ on adjacent carbon atoms together may form aryl, heteroaryl, indane or tetrahydronaphthyl, $C_3$–$C_7$ cycloalkyl, or heterocycloalkyl wherein one or two heteroatoms may be O, N or S;

wherein $R_1$ is

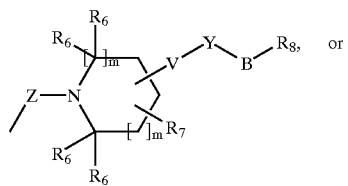

-continued

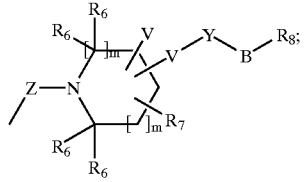

wherein each V is independently aryl, phenoxy or heteroaryl, wherein the aryl, phenoxy or heteroaryl is optionally substituted with one or more F; Cl; Br; I; $COR_5$; $CO_2R_5$; —$OCOR_5$; —$CON(R_5)_2$; —$N(R_5)COR_5$; CN; —$NO_2$; —$N(R_5)_2$; —$OR_5$; —$SR_5$; $(CH_2)_qOR_5$; $(CH_2)_qSR_5$; straight chained or branched $C_1$–$C_7$ alkyl optionally substituted with —$CON(R_5)_2$, —$N(R_5)C(O)R_3$ or $N(R_3)_2$, straight chained or branched monofluoroalkyl or polyfluoroalkyl, straight chained or branched $C_2$–$C_7$ alkenyl, $C_2$–$C_7$ alkynyl; phenoxy; or $C_3$–$C_7$ cycloalkyl, monofluorocycloalkyl, polyfluorocycloalkyl or cycloalkenyl;

wherein each $R_6$ is independently H; $(CH_2)_tXR_3$; $(CH_2)_tC(X)NR_3$; $(CH_2)_tN(R_3)C(X)R_3$; $(CH_2)_tCO_2R_3$; $(CH_2)_tOCOR_3$; straight chained or branched $C_1$–$C_7$ alkyl optionally substituted with —$CON(R_3)_2$ or —$NC(O)R_3$; straight chained or branched $C_2$–$C_7$ alkyl substituted with —$N(R_3)_2$; straight chained or branched $C_2$–$C_7$ alkenyl or alkynyl; or $C_3$–$C_7$ cycloalkyl or $C_5$–$C_7$ cycloalkenyl;

where each $R_7$ is independently H; F; Cl; Br; I; —$COR_3$; —$CO_2R_3$; —$(CH_2)_nXR_3$; —$(CH_2)_nN(R_3)C(O)R_3$; $(CH_2)_nC(X)N(R_3)_2$; $(CH_2)_nCO_2R_3$; —CN; —$NO_2$; —$N(R_3)_2$; straight chained or branched $C_1$–$C_7$ alkyl, hydroxyalkyl, aminoalkyl, carboxamidoalkyl, alkoxyalkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or $C_5$–$C_7$ cycloalkenyl, wherein the alkyl, aminoalkyl, carboxamidoalkyl, hydroxyalkyl, alkoxyalkyl, alkenyl, alkynyl, cycloalkyl or cycloalkenyl may be substituted with one or more aryl or heteroaryl, wherein the aryl or heteroaryl may be substituted with one or more of F, Cl, Br, I, —$(CH_2)_nXR_3$, —$COR_3$, —$(CH_2)_nC(X)N(R_3)_2$, —$(CH_2)_nCO_2R_3$, —CN, —$NO_2$, —$(CH_2)_nN(R_3)C(O)R_3$; —$N(R_3)2$, —$SO_2R_3$, straight chained or branched $C_1$–$C_7$ alkyl, monofluoroalkyl or polyfluoroalkyl, straight chained or branched $C_2$–$C_7$ alkenyl or alkynyl, or $C_3$–$C_7$ cycloalkyl, monofluorocycloalkyl, polyfluorocycloalkyl or $C_5$–$C_7$ cycloalkenyl; aryl or heteroaryl, wherein the aryl or heteroaryl may be substituted with one or more of F, Cl, Br, I, —$(CH_2)_nXR_3$, —$COR_3$, —$(CH_2)_nC(X)N(R_3)_2$, —$(CH_2)_nCO_2R_3$, —$(CH_2)_nN(R_3)C(O)R_3$; —CN, —$NO_2$, —$N(R_3)_2$, —$SO_2R_3$, straight chained or branched $C_1$–$C_7$ alkyl, straight chained or branched $C_1$–$C_7$ monofluoroalkyl or polyfluoroalkyl, straight chained or branched $C_2$–$C_7$ alkenyl or alkynyl, or $C_3$–$C_7$ cycloalkyl, monofluorocycloalkyl, polyfluorocycloalkyl or $C_5$–$C_7$ cycloalkenyl;

wherein B is CO, $SO_2$ or $SO_2NR_6$;

wherein $R_8$ is —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —$N(R_3)_2$; —$NR_3C(O)R_3$;

—OR$_3$; —(CH$_2$)$_p$OR$_3$; —COR$_3$; —CO$_2$R$_3$; —OCOR$_3$; —CON(R$_3$)$_2$; aryl or heteroaryl, optionally substituted with one or more F; Cl; Br; I; COR$_3$; CO$_2$R$_3$; —OCOR$_3$; —NR$_3$C(O)R$_3$; —CON(R$_3$)$_2$; CN; —NO$_2$; —N(R$_3$)$_2$; —OR$_3$; —SR$_3$; (CH$_2$)$_q$OR$_3$; (CH$_2$)$_q$SR$_3$; straight chained or branched C$_1$–C$_7$ alkyl optionally substituted with —CON(R$_3$)$_2$, —NR$_3$C(O)R$_3$ or —N(R$_3$)$_2$; straight chained or branched monofluoroalkyl, polyfluoroalkyl; straight chained or branched C$_2$–C$_7$ alkenyl, C$_2$–C$_7$ alkynyl; C$_3$–C$_7$ cycloalkyl, monofluorocycloalkyl, polyfluorocycloalkyl or cycloalkenyl;

wherein each m independently is an integer from 0 to 3 inclusive;

wherein Z is

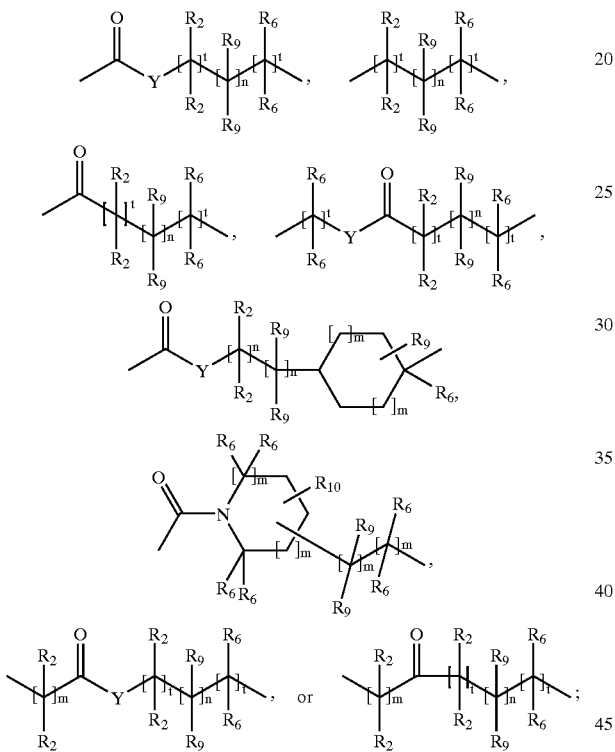

or C$_2$–C$_7$ alkenyl, wherein the C$_2$–C$_7$ alkenyl may be unsubstituted or substituted with one or more R$_9$ groups;

wherein each R$_9$ is independently H; F; Cl; Br; I; —(CH$_2$)$_m$XR$_3$; (CH$_2$)$_m$C(X)NR$_3$; (CH$_2$)$_m$CO$_2$R$_3$; straight chained or branched C$_1$–C$_7$ alkyl, monofluoroalkyl, polyfluoroalkyl, aminoalkyl, or carboxamidoalkyl; straight chained or branched C$_2$–C$_7$ alkenyl, or alkynyl; or C$_3$–C$_7$ cycloalkyl or C$_5$–C$_7$ cycloalkenyl;

wherein R$_{10}$ is H; (CH$_2$)$_t$XR$_3$; (CH$_2$)$_t$C(X)NR$_3$; (CH$_2$)$_t$CO$_2$R$_3$; straight chained or branched C$_1$–C$_7$ alkyl, carboxamidoalkyl; straight chained or branched C$_2$–C$_7$ aminoalkyl, alkenyl, or alkynyl; or C$_3$–C$_7$ cycloalkyl or C$_5$–C$_7$ cycloalkenyl;

wherein Y is S, O, or NR$_{10}$;

wherein each p is independently an integer from 1 to 7 inclusive;

or a pharmaceutically acceptable salt thereof.

In a further embodiment of the present invention, the compound has the following structure:

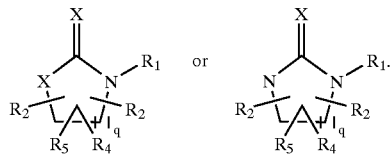

In an additional embodiment of the present invention, the compound has the structure:

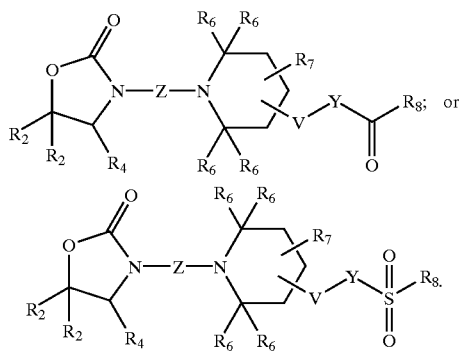

In an additional embodiment of the present invention, the compound has the structure:

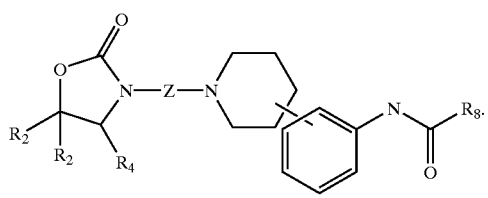

In one embodiment of the present invention, Z is:

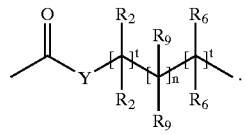

In one embodiment of the present invention, Z is:

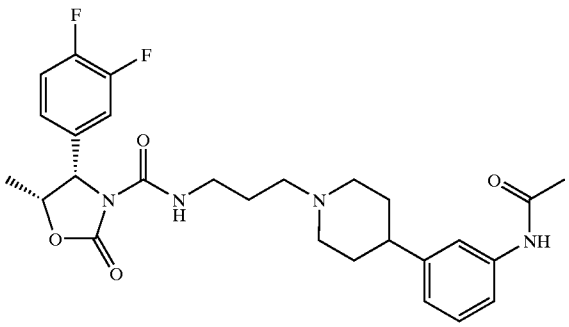

In an additional embodiment of the present invention, the compound has the structure:

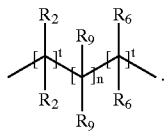

In one embodiment of the present invention, the compound has the structure:

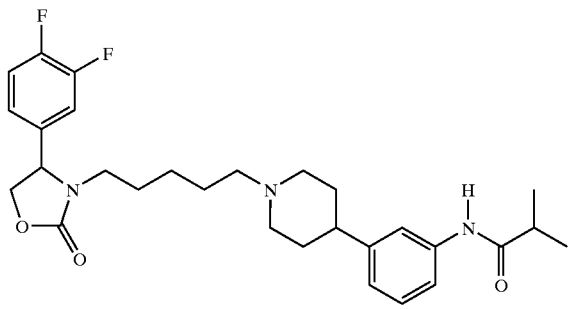

This invention provides a compound having the structure:

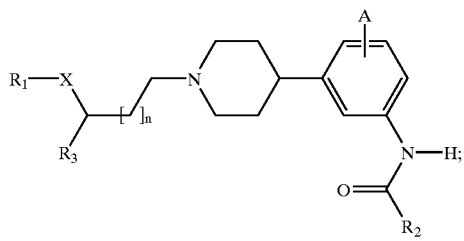

wherein R₁ is hydrogen, straight chained or branched C$_1$–C$_7$ alkyl, monofluoroalkyl or polyfluoroalkyl, aryl or heteroaryl, wherein the aryl or heteroaryl is optionally substituted with one or more —F, —Cl, —Br, —I, —CN, —NO$_2$, —CH$_3$, —CF$_3$, —COCH$_3$, —CO$_2$R$_2$, phenyl, phenoxy or straight chained or branched C$_1$–C$_7$ alkyl;

wherein R$_2$ is straight-chained or branched C$_3$–C$_4$ alkyl or cyclopropyl;

wherein R$_3$ is aryl or heteroaryl, wherein the aryl or heteroaryl is optionally substituted with one or more —F, —Cl, —Br, —I, —CN, —NO$_2$, straight chained or branched C$_1$–C$_7$ alkyl;

wherein A is —H, —F, —Cl, —Br, —CN, —NO$_2$, —COR$_3$, —CO$_2$R$_3$, straight chained or branched C$_1$–C$_7$ alkyl, monofluoroalkyl or polyfluoroalkyl;

wherein X is O or NH;

wherein n is an integer from 0 to 5 inclusive;

In one embodiment, R$_1$ is aryl optionally substituted with one or more —F, —Cl, —Br, —I, —CN, —NO$_2$, —COCH$_3$, —CO$_2$R$_2$, straight chained or branched C$_1$–C$_7$ alkyl;

wherein R$_3$ is phenyl;

wherein A is H; and wherein X is O.

In one embodiment, R$_2$ is isopropyl.

In a preferred embodiment, X is NH, R$_1$ is alkyl and n is 1 or 2.

In the most preferred embodiment, X is O, R$_1$ is 3-acetyl phenyl, R$_2$ is isopropyl, R$_3$ is phenyl and n is 1.

In one embodiment, the compound has the structure:

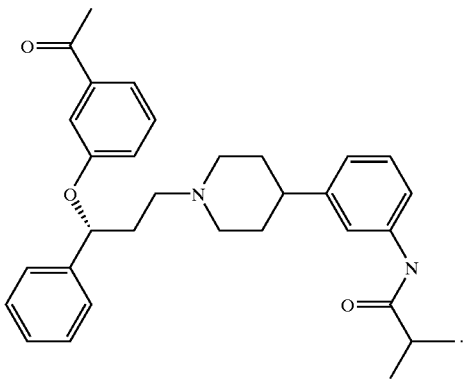

In one embodiment, compound has the structure:

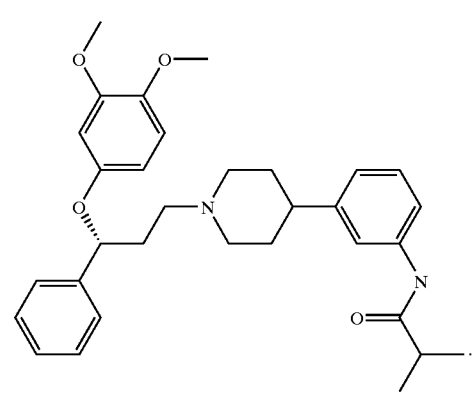

In one embodiment, R$_1$ is hydrogen, straight chained or branched C$_1$–C$_7$ alkyl; and wherein R$_3$ is aryl.

In one embodiment, R$_2$ is isopropyl; and A is hydrogen.

In one embodiment, the compound has the structure:

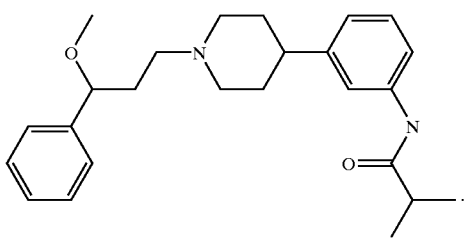

In one embodiment, the compound has the structure:

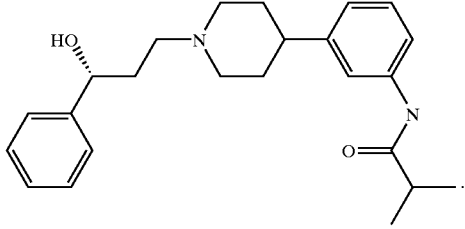

The present invention also provides a compound having the structure:

wherein R₁ is aryl or heteroaryl optionally substituted with one or more —F, —Cl, —Br, —I, —CN, —NO₂, —OCH₃, phenoxy, fused cyclopentanyl, straight chained or branched $C_1$–$C_7$ alkyl, monofluoroalkyl or polyfluoroalkyl;

wherein R₂ is straight-chained or branched $C_1$–$C_4$ alkyl or cyclopropyl;

wherein A is —H, —F, —Cl, —Br, —CN, —NO₂, straight chained or branched $C_1$–$C_7$ alkyl, monofluoroalkyl or polyfluoroalkyl; and wherein n is an integer from 1 to 5 inclusive.

In one embodiment, R₁ is aryl optionally substituted with one or more —F, —Cl, —Br, —I or straight chained or branched $C_1$–$C_4$ alkyl; and wherein A is H.

In one embodiment, R₂ is isopropyl; and wherein n is 2.

In a preferred embodiment, n is 2 and R₂ is isopropyl.

In one embodiment, the compound has the structure:

In one embodiment, the compound has the structure:

In one embodiment, the compound has the structure:

In one embodiment, R₁ is thienyl; and wherein A is H.
In one embodiment, R₂ is isopropyl.

In one embodiment, the compound has the structure:

The invention provides a compound having the structure:

wherein W is wherein each R₁ is independently hydrogen, methyl or ethyl;

wherein R₂ is straight-chained or branched $C_3$–$C_4$ alkyl or wherein R₂ is straight- chained or branched $C_3$–$C_4$ alkyl or cyclopropyl;

wherein R₃ is hydrogen, aryl or heteroaryl, wherein the aryl or heteroaryl is optionally substituted with one or more —H, —F, —Cl, —Br, —I, —CN, —NO₂, straight chained or branched $C_1$–$C_7$ alkyl.

wherein each A is independently —H, —F, —Cl, —Br, —CN, —NO₂, —COR₃, —CO₂R₃, straight chained or branched $C_1$–$C_7$ alkyl, monofluoroalkyl or polyfluoroalkyl;

wherein X is O, NR₃, CO or may be absent; and wherein Y is hydrogen, aryl or heteroaryl, wherein the aryl or heteroaryl is optionally substituted with one or more —F, —Cl, —Br, —I, —CN, —NO₂, straight chained or branched $C_1$–$C_7$ alkyl.

In one embodiment, W is and wherein X is O or may be absent.
In one embodiment, R₂ is isopropyl.

In one embodiment, the compound has the structure:

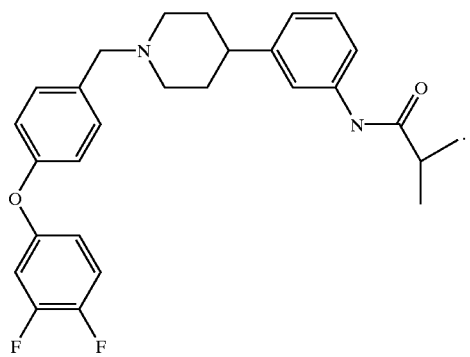

In one embodiment, the compound has the structure:

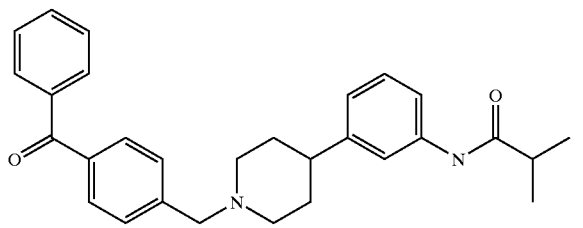

In one embodiment, W is

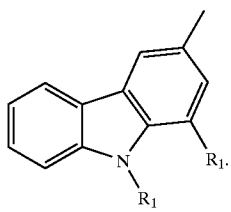

In one embodiment, A is —H, —F, —Cl, —Br.
In one embodiment, $R_2$ is isopropyl; and A is hydrogen.
In one embodiment, the compound has the structure:

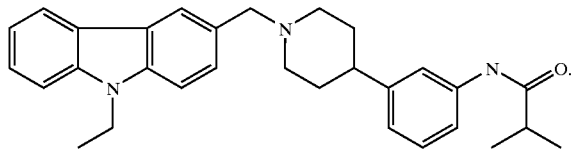

This invention provides a compound having the structure:

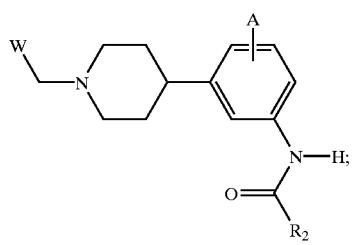

wherein W is

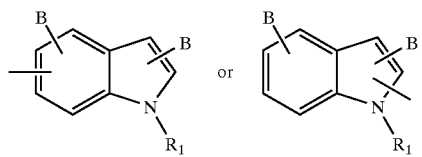

wherein $R_1$ is hydrogen, straight chained or branched $C_1$–$C_7$ alkyl, aryl or heteroaryl, wherein the aryl or heteroaryl is optionally substituted with one or more —F, —Cl, —Br, —CN, —NO$_2$, —OCH$_3$, —CO$_2$CH$_3$, —CF$_3$, phenyl, straight chained or branched $C_1$–$C_7$ alkyl;

wherein $R_2$ is straight-chained or branched $C_3$–$C_4$ alkyl or cyclopropyl;

wherein A is —H, —F, —Cl, —Br, —CN, —NO$_2$, —COR$_1$, —CO$_2$R$_1$, straight chained or branched $C_1$–$C_7$ alkyl, monofluoroalkyl or polyfluoroalkyl or phenyl.

wherein each B is independently —H, —F, —Cl, —Br, —I, —CN, —NO$_2$, —COR$_1$, —CO$_2$R$_1$, —OCH$_3$, —OCF$_3$, —CF$_3$, straight chained or branched $C_1$–$C_7$ alkyl, monofluoroalkyl or polyfluoroalkyl or aryl, phenoxy or benzyloxy, wherein the aryl, phenoxy or benzyloxy is optionally substituted with one or more —F, —Cl, —Br, —CN, —NO$_2$, —COR$_1$, —CO$_2$R$_1$, —OCH$_3$, —OCF$_3$, —CF$_3$ or straight chained or branched $C_1$–$C_3$ alkyl.

In one embodiment, W is

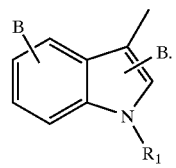

In one embodiment, $R_1$ is hydrogen or phenyl optionally substituted with one or more —F, —Cl, —Br, —CN, —NO$_2$, straight chained or branched $C_1$–$C_7$ alkyl.

In one embodiment, $R_2$ is isopropyl.

In one embodiment, the compound has the structure:

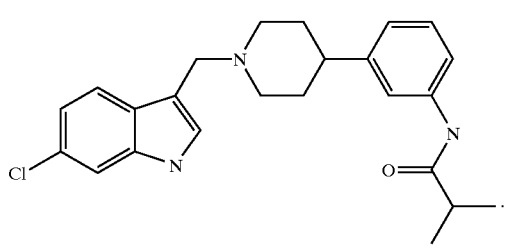

In one embodiment, the compound has the structure:

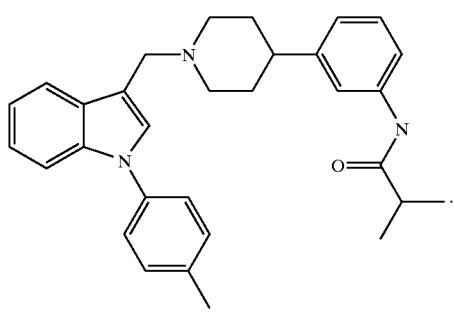

This invention provides a compound having the structure:

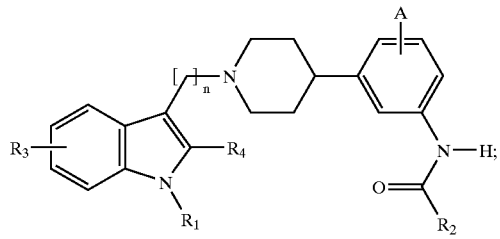

wherein R₁ is hydrogen, straight chained or branched C₁–C₇ alkyl, aryl or heteroaryl, wherein the aryl or heteroaryl is optionally substituted with one or more —F, —Cl, —Br, —CN, —NO₂, —CF₃, —OCH₃, straight chained or branched C₁–C₃ alkyl;

wherein R₂ is straight-chained or branched C₃–C₄ alkyl or cyclopropyl;

wherein R₃ is —H, —F, —Cl, —Br, —I, —CN, —NO₂, —CF₃, —OCH₃, or straight chained or branched C₁–C₃ alkyl, monofluoroalkyl or polyfluoroalkyl, or a phenyl ring fused to C₆ and C₇ of the indole moiety;

wherein R₄ is hydrogen or aryl optionally substituted with one or more —F, —Cl, —Br, —I, —CN, —NO₂, —CF₃, straight chained or branched C₁–C₃ alkyl;

wherein A is —H, —F, —Cl, —Br, —CN, —NO₂, straight chained or branched C₁–C₇ alkyl, monofluoroalkyl or polyfluoroalkyl; and wherein n is an integer from 2 to 4 inclusive.

In one embodiment, R₃ is —H, —F, —Cl, —Br, —I, —CN, —NO₂, —OCF₃ or —OCH₃; and wherein R₄ is hydrogen or phenyl optionally substituted with one or more —F, —Cl or —CF₃.

In one embodiment, R₁ is hydrogen or phenyl optionally substituted with one or more —F, —Cl, —Br, —CN, —NO₂, —CF₃, —OCH₃ or straight chained or branched C₁–C₃ alkyl;

In one embodiment, R₂ is isopropyl.

In one embodiment, the compound has the structure:

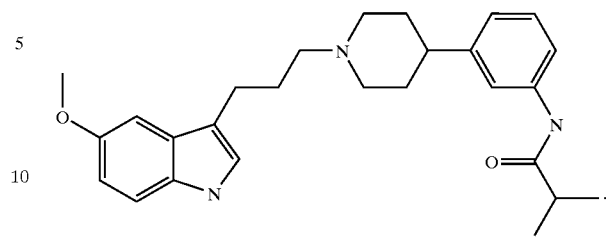

In one embodiment, the compound has the structure:

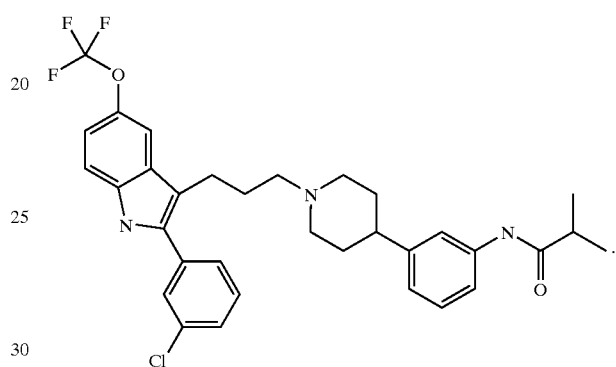

In one embodiment, the compound has the structure:

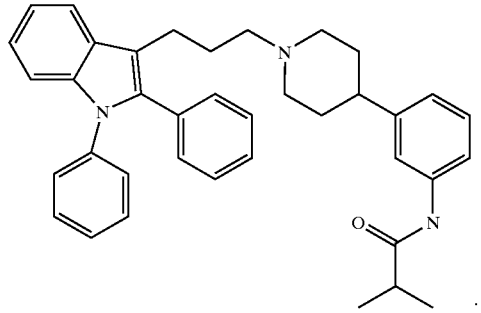

This invention provides a compound having the structure:

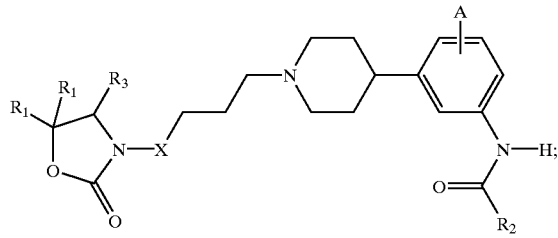

wherein each R₁ is independently hydrogen or CH₃;

wherein R₂ is straight-chained or branched C₁–C₄ alkyl or cyclopropyl;

wherein R₃ is benzyl or phenyl, wherein the benzyl or phenyl is optionally substituted with a methylenedioxy group or one or more —F or —Cl;

wherein A is —H, —F, —Cl, —Br, —CN, —NO₂, straight chained or branched C₁–C₇ alkyl, monofluoroalkyl or polyfluoroalkyl;

wherein X is (CH₂)₂, COCH₂ or CONH;

In one embodiment, R₃ is phenyl optionally substituted with one or more —F; and wherein A is hydrogen.

In one embodiment, X is CONH.

In one embodiment, R₂ is methyl.

In one embodiment, the compound has the structure:

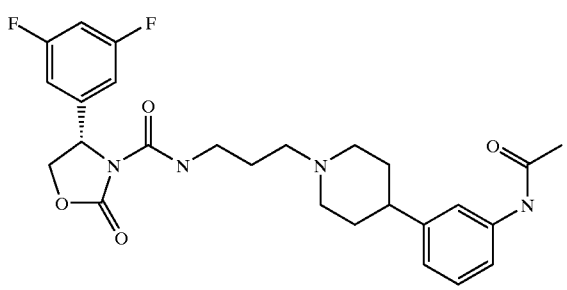

In one embodiment, the compound has the structure:

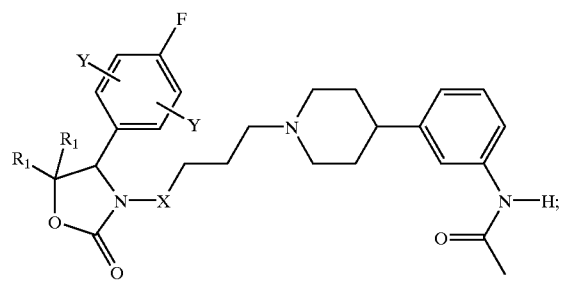

wherein each Y is independently hydrogen or —F.

In one embodiment, the compound has the structure:

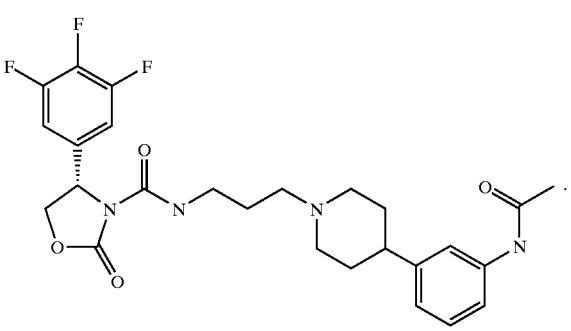

In one embodiment, the compound has the structure:

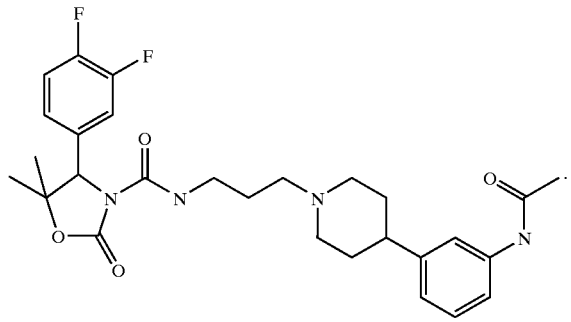

In one embodiment, R₃ is benzyl optionally substituted with a methylenedioxy group or one or more —F or —Cl.

In one embodiment, the compound has the structure:

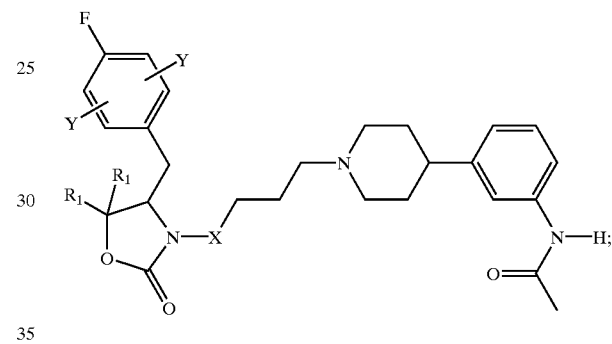

wherein each Y is independently hydrogen or —F.

In one embodiment, the compound has the structure:

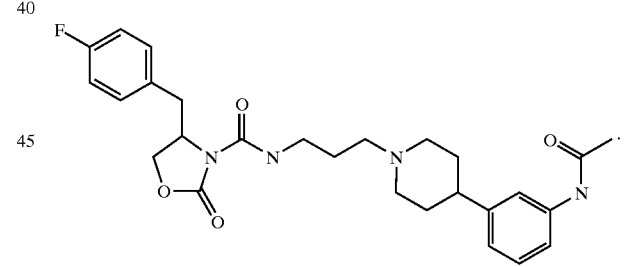

In one embodiment, the compound is enantiomerically pure.

In one embodiment, the compound is diastereomerically pure.

In one embodiment, the compound is enantiomerically and diastereomerically pure.

This invention also provides a pharmaceutical composition comprising a therapeutically amount of a compound of the invention and a pharmaceutically acceptable carrier.

In one embodiment, the amount of the compound is from about 0.01 mg to about 500 mg.

In one embodiment, the amount of the compound is from about 0.1 mg to about 60 mg.

In one embodiment, the amount of the compound is from about 1 mg to about 20 mg.

In one embodiment, the pharmaceutical composition consists of a carrier which is a liquid and the composition is a solution.

In one embodiment, the pharmaceutical composition consists of a carrier which is a solid and the composition is a tablet.

In one embodiment, the pharmaceutical composition consists of a carrier which is a gel and the composition is a suppository.

The invention also provides a process for making a pharmaceutical composition comprising admixing a therapeutically effective amount of the compound of any of the invention and a pharmaceutically acceptable carrier.

This invention also provides the method of treating a subject suffering from a disorder selected from the group consisting of depression, anxiety, urge incontinence, or obesity comprising administering to the subject a therapeutically effective amount of the compound of the invention.

In one embodiment, the therapeutically effective amount is between about 0.03 and about 1000 mg per day.

In one embodiment, the therapeutically effective amount is between about 0.30 and about 300 mg per day.

In one embodiment, the therapeutically effective amount is between about 1.0 and about 100 mg per day.

In one embodiment, the disorder is depression.

In one embodiment, the disorder is anxiety.

In one embodiment, the disorder is obesity.

In one embodiment, the disorder is urge incontinence.

The invention provides the method of reducing the body mass of a subject, which comprises administering to the subject an amount of a compound of the invention effective to reduce the body mass of the subject.

The invention provides the method of treating a subject suffering from depression, which comprises administering to the subject an amount of a compound of any of claims of the invention effective to treat the subject's depression.

The invention provides the method of treating a subject suffering from anxiety, which comprises administering to the subject an amount of a compound of the invention effective to treat the subject's anxiety.

The invention provides the method of alleviating urge urinary incontinence in a subject suffering from an overactive bladder, which comprises administering to the subject an amount of the compound of the invention effective to alleviate the subject's urge urinary incontinence.

The invention provides the method of managing obesity in a subject in need of weight loss, which comprises administering to the subject an amount of a compound of the invention effective to induce weight loss in the subject.

The invention provides the method of managing obesity in a subject who has experienced weight loss, which comprises administering to the subject an amount of a compound of the invention effective to maintain such weight loss in the subject.

The invention provides the method of treating overactive bladder in a subject, which comprises administering to the subject an amount of a compound of any of the invention effective to treat the subject's overactive bladder.

The invention provides the method of treating a disorder in a subject, wherein the symptoms of the subject can be alleviated by treatment with an MCH1 antagonist, wherein the MCH1 antagonist is the compound of the invention.

The invention provides the method of alleviating the symptoms of a disorder in a subject, which comprises administering to the subject an amount of an MCH1 antagonist effective to alleviate the symptoms, wherein the MCH1 antagonist is the compound of the invention As used in the present invention, the term "heteroaryl" is used to include five and six membered unsaturated rings that may contain one or more oxygen, sulfur, or nitrogen atoms. Examples of heteroaryl groups include, but are not limited to, carbazole, furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, and triazinyl.

In addition, the term "heteroaryl" is used to include fused bicyclic ring systems that may contain one or more heteroatoms such as oxygen, sulfur and nitrogen. Examples of such heteroaryl groups include, but are not limited to, indolizinyl, indolyl, isoindolyl, benzo[b]furanyl, benzo[b]thiophenyl, indazolyl, benzimidazolyl, purinyl, benzoxazolyl, benzisoxazolyl, benzo[b]thiazolyl, imidazo[2,1-b]thiazolyl, cinnolinyl, quinazolinyl, quinoxalinyl, 1,8-naphthyridinyl, pteridinyl, quinolinyl, isoquinolinyl, phthalimidyl and 2,1, 3-benzothiazolyl.

The term "heteroaryl" also includes those chemical moieties recited above which may be substituted with one or more of the following: —F, —Cl, —Br, —I, CN, —NO$_2$, straight chained or branched $C_1$–$C_7$ alkyl, straight chained or branched $C_1$–$C_7$ monofluoroalkyl, straight chained or branched $C_1$–$C_7$ polyfluoroalkyl, straight chained or branched $C_2$–$C_7$ alkenyl, straight chained or branched $C_2$–$C_7$ alkynyl; $C_3$–$C_7$ cycloalkyl, $C_3$–$C_7$ monofluorocycloalkyl, $C_3$–$C_7$ polyfluorocycloalkyl, $C_5$–$C_7$ cycloalkenyl, The term "heteroaryl" further includes the N-oxides of those chemical moieties recited above which include at least one nitrogen atom.

In the present invention, the term "aryl" is phenyl or naphthyl.

The invention provides for each pure stereoisomer of any of the compounds described herein. Such stereoisomers may include enantiomers, diastereomers, or E or Z alkene or imine isomers. The invention also provides for stereoisomeric mixtures, including racemic mixtures, diastereomeric mixtures, or E/Z isomeric mixtures. Stereoisomers can be synthesized in pure form (Nógrádi, M.; *Stereoselective Synthesis*, (1987) VCH Editor Ebel, H. and *Asymmetric Synthesis*, Volumes 3 B 5, (1983) Academic Press, Editor Morrison, J.) or they can be resolved by a variety of methods such as crystallization and chromatographic techniques (Jaques, J.; Collet, A.; Wilen, S.; *Enantiomer, Racemates, and Resolutions*, 1981, John Wiley and Sons and *Asymmetric Synthesis*, Vol. 2, 1983, Academic Press, Editor Morrison, J).

In addition the compounds of the present invention may be present as enantiomers, diasteriomers, isomers or two or more of the compounds may be present to form a racemic or diastereomeric mixture.

The compounds of the present invention are preferably 80% pure, more preferably 90% pure, and most preferably 95% pure. Included in this invention are pharmaceutically acceptable salts and complexes of all of the compounds described herein. The acids and bases from which these salts are prepared include but are not limited to the acids and bases listed herein. The acids include, but are not limited to, the following inorganic acids: hydrochloric acid, hydrobromic acid, hydroiodic acid, sulfuric acid and boric acid. The acids include, but are not limited to, the following organic acids: acetic acid, malonic acid, succinic acid, fumaric acid, tartaric acid, maleic acid, citric acid, methanesulfonic acid, benzoic acid, glycolic acid, lactic acid and mandelic acid. The bases include, but are not limited to ammonia, methylamine, ethylamine, propylamine, dimethylamine, diethylamine, trimethylamine, triethylamine, ethylenediamine, hydroxyethylamine, morpholine, piperazine and guanidine. This invention further provides for the hydrates and polymorphs of all of the compounds described herein.

The present invention includes within its scope prodrugs of the compounds of the invention. In general, such prodrugs will be functional derivatives of the compounds of the invention which are readily convertible in vivo into the required compound. Thus, in the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in Design of Prodrugs, ed. H. Bundgaard, Elsevier, 1985.

The present invention further includes metabolites of the compounds of the present invention. Metabolites include active species produced upon introduction of compounds of this invention into the biological milieu.

This invention further provides a pharmaceutical composition comprising a therapeutically effective amount of the compound of the invention and a pharmaceutically acceptable carrier. In one embodiment, the amount of the compound is from about 0.01 mg to about 800 mg. In another embodiment, the amount of the compound is from about 0.01 mg to about 500 mg. In yet another embodiment, the amount of the compound is from about 0.1 mg to about 250 mg. In another embodiment, the amount of the compound is from about 0.1 mg to about 60 mg. In yet another embodiment, the amount of the compound is from about 1 mg to about 20 mg. In a further embodiment, the carrier is a liquid and the composition is a solution. In another embodiment, the carrier is a solid and the composition is a tablet. In another embodiment, the carrier is a gel and the composition is a capsule, suppository or a cream. In a further embodiment the compound may be formulated as a part of a pharmaceutically acceptable transdermal patch. In yet a further embodiment, the compound may be delivered to the subject by means of a spray or inhalant.

This invention also provides a pharmaceutical composition made by combining a therapeutically effective amount of the compound of this invention and a pharmaceutically acceptable carrier.

This invention provides a process for making a pharmaceutical composition comprising combining a therapeutically effective amount of the compound of this invention and a pharmaceutically acceptable carrier.

A solid carrier can include one or more substances which may also act as endogenous carriers (e.g. nutrient or micronutrient carriers), flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, coloring agents, viscosity regulators, stabilizers or osmoregulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate or isopropyl myristate. Sterile liquid carriers are useful in sterile liquid form compositions for parenteral administration. The liquid carrier for pressurized compositions can be a halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings. The compound can be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like.

The compound can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspenions.

Optimal dosages to be administered may be determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration.

In the subject application a "therapeutically effective amount" is any amount of a compound which, when administered to a subject suffering from a disease against which the compounds are effective, causes reduction, remission, or regression of the disease. In a subject application, a "subject" is a vertebrate, a mammal or a human.

This invention provides a method of treating a subject suffering from an abnormality wherein the abnormality is alleviated by decreasing the activity of an MCH1 receptor which comprises administering to the subject an amount of a compound of the invention which is an MCH1 receptor antagonist effective to treat the subject's abnormality.

In separate embodiments, the abnormality is a regulation of a steroid or pituitary hormone disorder, an epinephrine release disorder, a gastrointestinal disorder, a cardiovascular disorder, an electrolyte balance disorder, hypertension, diabetes, a respiratory disorder, asthma, a reproductive function disorder, an immune disorder, an endocrine disorder, a musculoskeletal disorder, a neuroendocrine disorder, a cognitive disorder, a memory disorder such as Alzheimer's disease, a sensory modulation and transmission disorder, a motor coordination disorder, a sensory integration disorder, a motor integration disorder, a dopaminergic function disorder such as Parkinson's disease, a sensory transmission disorder, an olfaction disorder, a sympathetic innervation disorder, an affective disorder such as depression and anxiety, a stress-related disorder, a fluid-balance disorder, a seizure disorder, pain, psychotic behavior such as schizophrenia, morphine tolerance, opiate addiction, migraine or a urinary disorder such as urinary incontinence.

The following description of depressive and anxiety disorders is for the purpose of illustrating the utility of the compounds of this invention. The definitions of depressive and anxiety disorders given below are those listed in Diagnostic and Statistical Manual of Mental Disorders. 4th ed. (DSM-IV; American Psychiatric Association, 1994a) or Diagnostic and Statistical Manual of Mental Disorders. 3rd ed. Revised (DSM-III-R; American Psychiatric Association, 1987). Additional information regarding these disorders can be found in this reference, as well as the others cited below, all of which are incorporated herein by reference.

Depressive disorders include major depressive disorder and dysthymic disorder (American Psychiatric Association, 1994a; American Psychiatric Association, 1994b). Major depressive disorder is characterized by the occurrence of one or more major depressive episodes without manic or hypomanic episodes. A major depressive episode is defined as a prominent and relatively persistent depressed or dysphoric mood that usually interferes with daily functioning (nearly every day for at least 2 weeks); it should include at least 4 of the following 8 symptoms: change in appetite, change in sleep, psychomotor agitation or retardation, loss of interest in usual activities or decrease in sexual drive, increased fatigue, feelings of guilt or worthlessness, slowed thinking or impaired concentration, and a suicide attempt or suicidal ideation (Medical Economics Company, 2002). Dysthymic disorder involves a type of depression that is not severe enough to be called a major depressive episode, but that lasts much longer than major depressive disorder, without high phases.

It is contemplated that the compounds of this invention will be effective in treating depression in patients who have been diagnosed with depression by administration of any of the following tests: Hamilton Depression Rating Scale (HDRS), Hamilton depressed mood item, Clinical Global Impressions (CGI)-Severity of Illness. It is further contemplated that the compounds of the invention will be effective in inducing improvements in certain of the factors measured in these tests, such as the HDRS subfactor scores, including the depressed mood item, sleep disturbance factor and anxiety factor, and the CGI-Severity of Illness rating. It is also contemplated that the compounds of this invention will be effective in preventing relapse of major depressive episodes.

Anxiety disorders include panic disorder, agoraphobia with or without history of panic disorder, specific phobia, social phobia, obsessive-compulsive disorder, post-traumatic stress disorder, acute stress disorder and generalized anxiety disorder. It is contemplated that the compounds of this invention will be effective in treating any of all of these disorders in patients who have been diagnosed with these disorders.

Obsessive compulsive disorder is characterized by recurrent and persistent ideas, thoughts, impulses or images (obsessions) that are ego-dystonic and/or repetitive, purposeful and intentional behaviors (compulsions) that are recognized by the person as excessive or unreasonable (American Psychiatric Association, 1994a). The obsessions or compulsions cause marked distress, are time-consuming, or significantly interfere with social or occupational functioning.

It is contemplated that the compounds of this invention will be effective in treating obsessions and compulsions in patients who have been diagnosed with obsessive compulsive disorder by administration of appropriate tests, which may include, but are not limited to any of the following: Yale Brown Obsessive Compulsive Scale (YBOCS) (Goodman, 1989) (for adults), National Institute of Mental Health Global OCD Scale (NIMH GOCS), CGI-Severity of Illness scale. It is further contemplated that the compounds of the invention will be effective in inducing improvements in certain of the factors measured in these tests, such as a reduction of several points in the YBOCS total score. It is also contemplated that the compounds of this invention will be effective in preventing relapse of obsessive compulsive disorder.

Panic disorder is characterized by recurrent unexpected panic attacks and associated concern about having additional attacks, worry about the implications or consequences of the attacks, and/or a significant change in behavior related to the attacks (American Psychiatric Association, 1994a). A panic attack is defined as a discrete period of intense fear or discomfort in which four (or more) of the following symptoms develop abruptly and reach a peak within 10 minutes: (1) palpitations, pounding heart, or accelerated heart rate; (2) sweating; (3) trembling or shaking; (4) sensations of shortness of breath or smothering; (5) feeling of choking; (6) chest pain or discomfort; (7) nausea or abdominal distress; (8) feeling dizzy, unsteady, lightheaded, or faint; (9) derealization (feelings of unreality) or depersonalization (being detached from oneself); fear of losing control; (11) fear of dying; (12) paresthesias (numbness or tingling sensations); (13) chills or hot flushes. Panic disorder may or may not be associated with agoraphobia, or an irrational and often disabling fear of being out in public.

It is contemplated that the compounds of this invention will be effective in treating panic disorder in patients who have been diagnosed with panic disorder on the basis of frequency of occurrence of panic attacks, or by means of the CGI-Severity of Illness scale. It is further contemplated that the compounds of the invention will be effective in inducing improvements in certain of the factors measured in these evaluations, such as a reduction in frequency or elimination of panic attacks, an improvement in the CGI-Severity of Illness scale or a CGI-Global Improvement score of 1 (very much improved), 2 (much improved) or 3 (minimally improved). It is also contemplated that the compounds of this invention will be effective in preventing relapse of panic disorder. Social anxiety disorder, also known as social phobia, is characterized by a marked and persistent fear of one or more social or performance situations in which the person is exposed to unfamiliar people or to possible scrutiny by others (American Psychiatric Association, 1994a). Exposure to the feared situation almost invariably provokes anxiety, which may approach the intensity of a panic attack. The feared situations are avoided or endured with intense anxiety or distress. The avoidance, anxious anticipation, or distress in the feared situation(s) interferes significantly with the person's normal routine, occupational or academic functioning, or social activities or relationships, or there is marked distress about having the phobias. Lesser degrees of performance anxiety or shyness generally do not require psychopharmacological treatment.

It is contemplated that the compounds of this invention will be effective in treating social anxiety disorder in patients who have been diagnosed with social anxiety disorder by administration of any of the following tests: the Liebowitz Social Anxiety Scale (LSAS), the CGI-Severity of Illness scale, the Hamilton Rating Scale for Anxiety (HAM-A), the Hamilton Rating Scale for Depression (HAM-D), the axis V Social and Occupational Functioning Assessment Scale of DSM-IV, the axis II (ICD-10) World Health Organization Disability Assessment, Schedule 2 (DAS-2), the Sheehan Disability Scales, the Schneier Disability Profile, the World Health Organization Quality of Life-100 (WHOQOL-100), or other tests as described in Bobes, 1998, which is incorporated herein by reference. It is further contemplated that the compounds of the invention will be effective in inducing improvements as measured by these tests, such as the a change from baseline in the Liebowitz Social Anxiety Scale (LSAS), or a CGI-Global Improvement score of 1 (very much improved), 2 (much improved) or 3 (minimally improved). It is also contemplated that the compounds of this invention will be effective in preventing relapse of social anxiety disorder.

Generalized anxiety disorder is characterized by excessive anxiety and worry (apprehensive expectation) that is persistent for at least 6 months and which the person finds difficult to control (American Psychiatric Association, 1994a). It must be associated with at least 3 of the following 6 symptoms: restlessness or feeling keyed up or on edge, being easily fatigued, difficulty concentrating or mind going blank, irritability, muscle tension, sleep disturbance. The diagnostic criteria for this disorder are described in further detail in DSM-IV, which is incorporated herein by reference (American Psychiatric Association, 1994a).

It is contemplated that the compounds of this invention will be effective in treating generalized anxiety disorder in patients who have been diagnosed with this disorder according to the diagnostic criteria described in DSM-IV. It is further contemplated that the compounds of the invention will be effective in reducing symptoms of this disorder, such as the following: excessive worry and anxiety, difficulty controlling worry, restlessness or feeling keyed up or on edge, being easily fatigued, difficulty concentrating or mind going blank, irritability, muscle tension, or sleep disturbance. It is also contemplated that the compounds of this invention will be effective in preventing relapse of general anxiety disorder.

Post-traumatic stress disorder (PTSD), as defined by DSM-III-R/IV (American Psychiatric Association, 1987, American Psychiatric Association, 1994a), requires exposure to a traumatic event that involved actual or threatened death or serious injury, or threat to the physical integrity of self or others, and a response which involves intense fear, helplessness, or horror. Symptoms that occur as a result of exposure to the traumatic event include re-experiencing of the event in the form of intrusive thoughts, flashbacks or dreams, and intense psychological distress and physiological reactivity on exposure to cues to the event; avoidance of situations reminiscent of the traumatic event, inability to recall details of the event, and/or numbing of general responsiveness manifested as diminished interest in significant activities, estrangement from others, restricted range of affect, or sense of foreshortened future; and symptoms of autonomic arousal including hypervigilance, exaggerated startle response, sleep disturbance, impaired concentration, and irritability or outbursts of anger. A PTSD diagnosis requires that the symptoms are present for at least a month and that they cause clinically significant distress or impairment in social, occupational, or other important areas of functioning.

It is contemplated that the compounds of this invention will be effective in treating PTSD in patients who have been diagnosed with PTSD by administration of any of the following tests: Clinician-Administered PTSD Scale Part 2 (CAPS), the patient-rated Impact of Event Scale (IES) (Medical Economics Company, 2002, p. 2752). It is further contemplated that the compounds of the invention will be effective in inducing improvements in the scores of the CAPS, IES, CGI-Severity of Illness or CGI-Global Improvement tests. It is also contemplated that the compounds of this invention will be effective in preventing relapse of PTSD.

In a preferred embodiment, the subject invention provides a method of treatment or management of the following indications: depressive disorders, anxiety disorders, eating/body weight disorders, and urinary disorders. Examples of depressive disorders are major depressive disorder or dysthymic disorder. Examples of anxiety disorders are panic disorder, agoraphobia without history of panic disorder, specific phobia, social phobia, obsessive-compulsive disorder, post-traumatic stress disorder, acute stress disorder or generalized anxiety disorder. Examples of eating/body weight disorders are obesity, weight gain, bulimia, bulimia nervosa or anorexia nervosa. Examples of urinary disorders include, but are not limited to urinary incontinence overactive bladder, urge incontinence, urinary frequency, urinary urgency, nocturia or enuresis. Overactive bladder and urinary urgency may or may not be associated with benign prostatic hyperplasia.

This invention provides a method of modifying the feeding behavior of a subject, which comprises administering to the subject an amount of a compound of the invention effective to decrease the consumption of food by the subject. This invention also provides a method of treating an eating disorder in a subject, which comprises administering to the subject an amount of a compound of the invention effective to treat the eating disorder. In an embodiment of the present invention, the eating disorder is obesity, bulimia, bulimia nervosa or anorexia nervosa.

The present invention further provides a method of reducing the body mass of a subject, which comprises administering to the subject an amount of a compound of the invention effective to reduce the body mass of the subject. This invention also provides a method of managing obesity in a subject in need of weight loss, which comprises administering to the subject an amount of a compound of the invention effective to induce weight loss in the subject. This invention also provides a method of managing obesity in a subject who has experienced weight loss, which comprises administering to the subject an amount of a compound of the invention effective to maintain such weight loss in the subject.

The present invention also provides a method of treating depression in a subject, which comprises administering to the subject an amount of a compound of the invention effective to treat the subject's depression. This invention also provides a method of treating anxiety in a subject, which comprises administering to the subject an amount of a compound of the invention effective to treat the subject's anxiety. This invention also provides a method of treating depression and anxiety in a subject, which comprises administering to the subject an amount of a compound of the invention effective to treat the subject's depression and anxiety. This invention also provides a method of treating major depressive disorder in a subject, which comprises administering to the subject an amount of a compound of the invention effective to treat the subject's major depressive disorder. This invention also provides a method of treating dysthymic disorder in a subject, which comprises administering to the subject an amount of a compound of the invention effective to treat the subject's dysthymic disorder. This invention also provides a method of treating obsessions and compulsions in a subject with obsessive compulsive disorder, which comprises administering to the subject an amount of a compound of the invention effective to treat the subject's obsessions and compulsions. This invention also provides a method of treating panic disorder, with or without agoraphobia, in a subject, which comprises administering to the subject an amount of a compound of the invention effective to treat the subject's panic disorder. This invention also provides a method of treating social anxiety disorder in a subject, which comprises administering to the subject an amount of a compound of the invention effective to treat the subject's social anxiety disorder. This invention also provides a method of treating generalized anxiety disorder in a subject, which comprises administering to the subject an amount of a compound of the invention effective to treat the subject's generalized anxiety disorder. This invention also provides a method of treating post-traumatic stress disorder in a subject, which comprises administering to the subject an amount of a compound of the invention effective to treat the subject's post-traumatic stress disorder.

It is contemplated that the compounds of this invention will be effective in treating obesity, including weight loss and maintenance of weight loss in patients, who have been diagnosed with obesity by the one or more of the following measurements: an increased body mass index, increased waist circumference (an indicator of intra-adominal fat), Dual Energy X-Ray Absorptiometry (DEXA) and trucal (android) fat mass. It is further contemplated that the compounds of the invention will be effective in inducing improvements in certain factors measured in these tests.

It is contemplated that the compounds of this invention will be effective in treating urinary disorders in patients who have urge or mixed (with a predominance of urge) incontinence as evidenced by the number of unnecessary episodes per week, the number of unnecessary micturitions per day and a low volume voided per micturition. It is further contemplated that the compounds of the invention will be effective in inducing improvements in certain factors measured in these tests.

The present invention also provides a method of treating a subject suffering from bipolar I or II disorder, schizoaffective disorder, a cognitive disorder with depressed mood, a personality disorder, insomnia, hypersomnia, narcolepsy, circadian rhythm sleep disorder, nightmare disorder, sleep terror disorder or sleepwalking disorder.

The present invention provides a method of treating overactive bladder with symptoms of urge urinary incontinence, urgency and/or frequency in a subject, which comprises administering to the subject an amount of a compound of the invention effective to treat the subject's overactive bladder. This invention also provides a method of alleviating urge urinary incontinence in a subject suffering from overactive bladder, which comprises administering to the subject an amount of a compound of the invention effective to alleviate the subject's urge urinary incontinence. This invention further provides a method of alleviating urinary urgency in a subject suffering from overactive bladder, which comprises administering to the subject an amount of a compound of the invention effective to alleviate the subject's urinary urgency. Additionally, this invention provides a method of alleviating urinary frequency in a subject suffering from overactive bladder, which comprises administering to the subject an amount of a compound of the invention effective to alleviate the subject's urinary frequency.

The present invention also provides a method of treating a subject suffering from a urinary disorder, which comprises administering to the subject an amount of a compound of the invention effective to treat the subject's urinary disorder. In some embodiments the urinary disorder is urinary incontinence, overactive bladder, urge incontinence, urinary frequency, urinary urgency, nocturia or enuresis.

The present invention provides a method of alleviating the symptoms of a disorder in a subject, which comprises administering to the subject an amount of an MCH1 antagonist effective to alleviate the symptoms, wherein the MCH1 antagonist is any of the compounds of the invention.

In an embodiment of the invention, the subject is a vertebrate, a mammal, a human or a canine. In another embodiment, the compound is administered orally. In yet another embodiment, the compound is administered in combination with food.

This invention will be better understood from the Experimental Details In a preferred embodiment, the subject invention provides a method of treatment for the following indications: depression, anxiety, eating/body weight disorders, and urinary disorders. Examples of eating/body weight disorders are obesity, bulimia, or bulimia nervosa. Examples of urinary disorders include, but are not limited to, urinary incontinence, overactive bladder, urge incontinence, urinary frequency, urinary urgency, nocturia, or enuresis. Overactive bladder and urinary urgency may or may not be associated with benign prostatic hyperplasia.

This invention provides a method of modifying the feeding behavior of a subject which comprises administering to the subject an amount of a compound of the invention effective to decrease the consumption of food by the subject.

This invention also provides a method of treating an eating disorder in a subject which comprises administering to the subject an amount of a compound of this invention effective to decrease the consumption of food by the subject. In an embodiment of the present invention, the eating disorder is bulimia, obesity or bulimia nervosa. In an embodiment of the present invention, the subject is a vertebrate, a mammal, a human or a canine. In a further embodiment, the compound is administered in combination with food.

The present invention further provides a method of reducing the body mass of a subject which comprises administering to the subject an amount of a compound of the invention effective to reduce the body mass of the subject.

The present invention also provides a method of treating a subject suffering from depression which comprises administering to the subject an amount of a compound of this invention effective to treat the subject's depression. The present invention further provides a method of treating a subject suffering from anxiety which comprises administering to the subject an amount of a compound of this invention effective to treat the subject's anxiety. The present invention also provides a method of treating a subject suffering from depression and anxiety which comprises administering to the subject an amount of a compound of this invention effective to treat the subject's depression and anxiety.

The present invention also provides a method of treating a subject suffering from major depressive disorder, dysthymic disorder, bipolar I and II disorders, schizoaffective disorder, cognitive disorders with depressed mood, personality disorders, insomnia, hypersomnia, narcolepsy, circadian rhythm sleep disorder, nightmare disorder, sleep terror disorder, sleepwalking disorder, obsessive-compulsive disorder, panic disorder, with or without agoraphobia, post-traumatic stress disorder, social anxiety disorder, social phobia and generalized anxiety disorder.

The present invention also provides a method of treating a subject suffering from a urinary disorder which comprises administering to the subject an amount of a compound of this invention effective to treat the subject's a urinary disorder. In some embodiments, the urinary disorder is urinary incontinence, overactive bladder, urge incontinence, urinary frequency, urinary urgency, nocturia, or enuresis.

This invention will be better understood from the Experimental Details which follow. However, one skilled in the art will readily appreciate that the specific methods and results discussed are merely illustrative of the invention as described more fully in the claims which follow thereafter.

EXPERIMENTAL SECTION

I. Synthetic Methods for Examples

General Methods: All reactions (except for those done by parallel synthesis reaction arrays) were performed under an Argon atmosphere and the reagents, neat or in appropriate solvents, were transferred to the reaction vessel via syringe and cannula techniques. The parallel synthesis reaction arrays were performed in vials (without an inert atmosphere) using J-KEM heating shakers (Saint Louis, Mo.). Anhydrous solvents were purchased from Aldrich Chemical Company and used as received. The examples described in the patent were named using ACD/Name program (version 2.51, Advanced Chemistry Development Inc., Toronto, Ontario, M5H2L3, Canada). Unless otherwise noted, the $^1$H spectra were recorded at 300 and 400 MHz (QE Plus and Brüker respectively) with tetramethylsilane as internal standard. s=singlet; d=doublet; t=triplet; q=quartet; p=pentet; sext; sept; br=broad; m=multiplet. Elemental analyses were performed by Robertson Microlit Laboratories, Inc. Unless otherwise noted, mass spectra were obtained using low-resolution electrospray (ESMS) and MH$^+$ is reported. Thin-layer chromatography (TLC) was carried out on glass plates precoated with silica gel 60 F$_{254}$ (0.25 mm, EM Separations Tech.). Preparative thin-layer chromatography was carried out on glass sheets precoated with silica gel GF (2 mm, Analtech). Flash column chromatography was performed on Merck silica gel 60 (230–400 mesh). Melting points (mp) were determined in open capillary tubes on a Mel-Temp apparatus and are uncorrected.

Piperidine Side Chain Intermediates

TERT-BUTYL 4-{[(TRIFLUOROMETHYL)SULFONYL]OXY}-1,2,3,6-TETRAHYDRO-1-PYRIDINECARBOXYLATE: n-Butyl lithium (17.6 mL, 44.2 mmol, 2.5 M in hexanes) was added to a solution of diisopropyl amine (96.2 mL, 44.2 mmol) in 40 mL of dry THF at 0° C. and stirred for 20 minutes. The reaction mixture was cooled to −78° C. and tert-butyl 4-oxo-1-piperidinecarboxylate (Aldrich Chemical Company, 40.0 mmol) in THF (40 mL) was added dropwise to the reaction mixture and stirred for 30 minutes. Tf$_2$NPh (42.0 mmol, 15.0 g) in THF (40 mL) was added dropwise to the reaction mixture and stirred at ° C. overnight. The reaction mixture was concentrated in vacuo, re-dissolved in hexanes:EtOAc (9:1), passed through a plug of alumina and the alumina plug was washed with hexanes:EtOAc (9:1). The combined extracts were concentrated to yield 16.5 g of the desired product that was contaminated with some starting Tf$_2$NPh.

$^1$H NMR (400 MHz, 400 MHz, CDCl$_3$) δ 5.77 (s, 1H), 4.05 (dm, 2H, J=3.0 Hz), 3.63 (t, 2H, J=5.7 Hz), 2.45 (m, 2H), 1.47 (s, 9H).

TERT-BUTYL 4-[3-(AMINO)PHENYL]-1,2,3,6-TETRAHYDRO-1-PYRIDINECARBOXYLATE: A mixture of 2 M aqueous Na$_2$CO$_3$ solution (4.2 mL), tert-butyl 4-{[(trifluoromethyl)sulfonyl]oxy}-1,2,3,6-tetrahydro-1-pyridine-carboxylate (0.500 g, 1.51 mmol), 3-aminophenylboronic acid hemisulfate (0.393 g, 2.11 mmol), lithium chloride (0.191 g, 4.50 mmol) and tetrakis-triphenylphosphine palladium(0) (0.080 g, 0.075 mmol) in dimethoxyethane (5 mL) was heated at reflux temperature for 3 hours, under an inert atmosphere (an initial degassing of the mixture is recommended to prevent the formation of triphenylphosphine oxide). The organic layer of the cooled reaction mixture was separated and the aqueous layer was washed with ethyl acetate (3×). The combined organic extracts were dried and concentrated in vacuo. The crude product was chromatographed (silica, hexanes:EtOAc:dichloromethane (6:1:1) with 1% added isopropylamine to protect the BOC group from hydrolysis) to give 0.330 g of the desired product in 81% yield. $^1$H NMR (400 MHz, CDCl$_3$) δ 7.12 (t, 1H, J=7.60 Hz), 6.78 (d, 1H, J=8.4 Hz), 6.69 (t, 1H, J=2.0 Hz), 6.59 (dd, 1H, J=2.2, 8.0 Hz), 6.01 (m, 1H), 4.10–4.01 (d, 2H, J=2.4 Hz), 3.61 (t, 2H, J=5.6 Hz), 2.52–2.46 (m, 2H), 1.49 (s, 9H); ESMS m/e: 275.2 (M+H)$^+$. Anal. Calc. for C$_{16}$H$_{24}$N$_2$O$_2$: C, 70.04; H, 8.08; N, 10.21. Found: C, 69.78; H, 7.80; N, 9.92.

TERT-BUTYL 4-[3-(AMINO)PHENYL]-1-PIPERIDINECARBOXYLATE: A mixture of 3.10 g of tert-butyl 4-(3-aminophenyl)-1,2,3,6-tetrahydropyridine-1-carboxylate (11.3 mmol) and 1.0 g of 10% Pd/C in 200 mL of ethanol was hydrogenated at room temperature using the balloon method for 2 days. The reaction mixture was filtered and washed with ethanol. The combined ethanol extracts were concentrated in vacuo and the residue was chromatographed on silica (dichloromethane:methanol 95:5 with 1% isopropylamine added to protect the BOC group from hydrolysis) to give 2.63 g of the desired product (84%). $^1$H NMR (400 MHz, CDCl$_3$) δ 7.10 (t, 1H, J=7.60 Hz), 6.62 (d, 1H, J=8.4 Hz), 6.60–6.59 (m, 2H), 4.27–4.18 (m, 2H), 3.62–3.58 (m, 2H), 2.80–2.72 (m, 2H), 2.62–2.59 (m, 1H), 1.89–1.52 (m, 4H), 1.49 (s, 9H); ESMS m/e: 277.2 (M+H)$^+$.

TERT-BUTYL 4-[3-(ACETYLAMINO)PHENYL]-1,2,3,6-TETRAHYDRO-1-PYRIDINECARBOXYLATE: A mixture of saturated aqueous Na$_2$CO$_3$ solution (25 mL), tert-butyl 4-{[(trifluoromethyl)sulfonyl]oxy}-1,2,3,6-tetrahydro-1-pyridine-carboxylate (20 mmol), 3-acetamidophenylboronic acid (30 mmol) and tetrakis-triphenylphosphine palladium(0) (1.15 g) and dimethoxyethane (40 mL) was heated at reflux temperature overnight. The organic layer of the cooled reaction mixture was separated and the aqueous layer was washed with ethyl acetate (3×). The combined organic extracts were dried and concentrated in vacuo. The crude product was chromatographed, giving the desired product: $^1$H NMR (CDCl$_3$) δ 8.11 (br s, 1H), 7.57 (br s, 1H), 7.41 (br d, 1H, J=7.8 Hz), 7.25 (apparent t, 1H, J=7.8 Hz), 7.08 (br d, 1H, J=7.8 Hz), 5.99 (br s, 1H), 4.03 (br m, 2H, J=2.7 Hz), 3.59 (t, 2H, J=5.7 Hz), 2.46 (m, 2H), 2.16 (s, 3H), 1.49 (s, 9H).

N1-[3-(1,2,3,6-TETRAHYDRO-4-PYRIDINYL)PHENYL]ACETAMIDE: A solution of 4 M HCl in dioxane (10 mL) was added to tert-butyl 4-[3-(acetylamino)phenyl]-

1,2,3,6-tetrahydro-1-pyridinecarboxylate (8.25 mmol) in dichloromethane (30 mL). The reaction mixture was stirred at room temperature overnight, concentrated in vacuo, giving the desired product as the hydrochloride salt (2.1 g): $^1$H NMR (CDCl$_3$) δ 7.41–7.00 (m, 4H), 6.10 (br, 1H), 3.55 (m, 2H), 3.16 (t, 2H, J=5.7 Hz), 2.44 (m, 2H), 2.19 (s, 3H).

TERT-BUTYL N-(3-BROMOPROPYL)CARBAMATE: Prepared from 3-bromopropylamine hydrobromide and BOC$_2$O in the presence of base in dichloromethane, 9.89 mmol: $^1$H NMR (CDCl$_3$) δ 5.07 (br, 1H), 3.31 (t, 2H, J=6.6 Hz), 3.12 (apparent br q, 2H, J=6.0 Hz), 1.92 (p, 2H, J=6.6 Hz), 1.30 (s, 9H).

TERT-BUTYL N-(3-{4-[3-(ACETYLAMINO)PHENYL]-1,2,3,6-TETRAHYDRO-1-PYRIDINYL}PROPYL)CARBAMATE: A solution of N1-[3-(1,2,3,6-tetrahydro-4-pyridinyl)phenyl]acetamide.HCl (8.24 mmol), tert-butyl N-(3-bromopropyl)carbamate and potassium carbonate (33 mmol) in dry dioxane (30 mL) was heated at reflux temperature overnight. The solids were removed by filtration, the solution was concentrated in vacuo and the product was chromatograghed, giving the desired product (110 mg). $^1$H NMR (CDCl$_3$) δ 7.65 (s, 1H), 6.98 (s, 1H), 7.45 (d, 1H, J=7.8 Hz), 7.16 (apparent t, 1H, J=7.8 Hz), 7.10 (d, 1H, J=7.8 Hz), 6.02 (s, 1H), 5.23 (b, 1H), 3.40 (b, 2H), 3.30–1.80 (m, 10H), 2.18 (s, 3H), 1.45 (s, 9H).

N1-{3-[1-(3-AMINOPROPYL)-1,2,3,6-TETRAHYDRO-4-PYRIDINYL]PHENYL}ACETAMIDE: A 1:1 solution of TFA:CH$_2$Cl$_2$ (5 mL) was added to tert-butyl N-(3-{4-[3-(acetylamino)phenyl]-1,2,3,6-tetrahydro-1-pyridinyl}propyl)carbamate in dichloromethane (5 mL). The resulting solution was stirred at room temperature for 1–3 days, saturated NaHCO$_3$ was added until pH>6, the organic layer was separated, and dried in vacuo, giving the desired product (45 mg): $^1$H NMR (CDCl$_3$) δ 7.68 (br, 1H), 7.35 (dm, 1H, J=7.8 Hz), 7.25 (apparent t, 1H, J=7.8 Hz), 7.15 (dm, 1H, J=7.8 Hz), 6.12 (m, 1H), 3.22 (m, 2H), 3.03 (t, 2H, J=7.3 Hz), 2.78 (t, 2H, J=5.5 Hz), 2.70–2.50 (m, 4H), 2.10 (s, 3H), 1.87 (p, 2H, J=7.3 Hz).

TERT-BUTYL 4-[3-(ACETYLAMINO)PHENYL]-1-PIPERIDINECARBOXYLATE: A mixture tert-butyl 4-[3-(acetylamino)phenyl]-1,2,3,6-tetrahydro-1-pyridinecarboxylate (710 mg) and 5% Pd/C (100 mg) in EtOH (10 mL) was hydrogenated (balloon technique) at room temperature overnight. The reaction mixture was passed through a pad of Celite 545 and the pad of Celite was washed with ethanol. The combined ethanol extracts were concentrated and chromatograghed, giving the desired product (660 mg): $^1$H NMR (CDCl$_3$) δ 7.80 (s, 1H), 7.41–7.20 (m, 3H), 6.94 (d, 1H, J=7.5 Hz), 4.21 (m, 2H), 2.75 (m, 2H), 2.62 (m, 1H), 2.16 (s, 3H), 1.78 (m, 2H), 1.56 (m, 2H), 1.48 (s, 9H).

N1-[3-(4-PIPERIDYL)PHENYL]ACETAMIDE: A solution of HCl in dioxane (4N, 5 mL) was added to tert-butyl 4-[3-(acetylamino)phenyl]-1-piperidinecarboxylate (660 mg) in dry dichloromethane (15 mL). The reaction mixture was stirred at room temperature overnight and concentrated in vacuo, giving the desired product (550 mg): mp 102–104° C.; $^1$H NMR (CDCl$_3$) δ 2.02 (d, J=13.2 Hz, 2H), 2.11–2.45 (m, 5H), 2.67–2.77 (m, 1H), 3.00–3.10 (m, 2H), 3.51 (d, J=10.5 Hz, 2H), 6.94 (d, J=7.5 Hz, 1H), 7.20–7.46 (m, 3H), 7.60 (s, 1H); Anal. Calcd. For C$_{13}$H$_{19}$N$_2$OCl+0.86 CH$_2$Cl$_2$: C, 50.78; H, 6.37; N, 8.55. Found: C, 50.80; H, 7.55; N, 7.01.

TERT-BUTYL N-(3-{4-[3-(ACETYLAMINO)PHENYL]PIPERIDINO}PROPYL)CARBAMATE: A solution of N1-[3-(4-piperidyl)phenyl]acetamide (550 mg, 0.210 mmol), tert-butyl N-(3-bromopropyl)carbamate (550 mg, 0.230 mmol), K$_2$CO$_3$ (1.10 g, 0.890 mmol), diisopropylethyl amine (1.50 mL) and a few crystals of KI in dioxane (20 mL) was heated at reflux temperature for 2 days. The precipitated salts were removed by filtration, concentrated in vacuo and the crude product was chromatographed, giving the desired product (340 mg): $^1$H NMR (CDCl$_3$) δ 8.15 (s, 1H), 7.47–7.44 (m, 2H), 7.22 (t, 1H, J=7.8 Hz), 6.94 (d, 1H, J=7.8 Hz), 5.53 (b, 1H), 3.23 (b, 6H), 2.80–1.60 (m, 9H), 2.20 (s, 3H), 1.45 (s, 9H).

N1-{3-[1-(3-AMINOPROPYL)-4-PIPERIDYL]PHENYL}ACETAMIDE: TFA (1.0 mL) was added to a solution of tert-butyl N-(3-{4-[3-(acetylamino)phenyl]piperidino}propyl)carbamate (340 mg) in dry dichloromethane (10 mL) and stirred at room temperature for 5 h. A 10% aqueous solution of KOH was added to the reaction mixture until pH>6 and then the dichloromethane was removed in vacuo. The aqueous layer was frozen and lyophilized to give a solid, which was extracted with methanol. Removal of the solvent gave the desired product (120 mg) as an oil: $^1$H NMR (CDCl$_3$) δ 7.23–7.16 (apparent t, 1H, J=7.5 Hz), 6.95–6.92 (m, 1H), 3.03–2.99 (m, 2H), 2.77–2.73 (t, 2H, J=6.6 Hz), 2.50–1.60 (m, 10H), 2.13 (s, 3H).

TERT-BUTYL 4-(3-NITROPHENYL)-3,6-DIHYDRO-1(2H)-PYRIDINECARBOXYLATE: According to the procedure used for the synthesis of tert-butyl 4-[3-(amino)phenyl]-1,2,3,6-tetrahydro-1-pyridinecarboxylate,a mixture of 2 M aqueous Na$_2$CO$_3$ solution (2.2 mL), tert-butyl 4-{[(trifluoromethyl)sulfonyl]oxy}-1,2,3,6-tetrahydro-1-pyridine-carboxylate (0.500 g, 1.51 mmol), 3-nitrophenylboronic acid (0.353 g, 2.11 mmol), lithium chloride (0.191 9, 4.50 mmol) and tetrakis-triphenylphosphine palladium(0) (0.080 g, 0.075 mmol) in dimethoxyethane (5 mL) afforded 0.380g of the desired product.

$^1$H NMR (400 MHz, CDCl$_3$) δ 8.23 (s, 1H), 8.11 (d, 1H, J=8.0 Hz), 7.69 (d, 1H, J=8.0 Hz), 7.51 (t, 1H, J=8.0 Hz), 6.20 (m, 1H), 4.17–4.08 (m, 2H), 3.67 (t, 2H, J=5.6 Hz), 2.61–2.52 (m, 2H), 1.50 (s, 9H); ESMS m/e: 249.1 (M+H–C$_4$H$_8$)$^+$.

1,2,3,6-TETRAHYDRO-4-(3-NITROPHENYL)PYRIDINE: Into a stirred solution of 5.00 g (16.0 mmol) of tert-butyl 1,2,3,6-tetrahydro-4-(3-nitrophenyl)pyridine-1-carboxylate in 100 ml of 1,4-dioxane at 0° C. was bubbled HCl gas for 10 minutes. The reaction mixture was allowed to warm to room temperature and the bubbling of the HCl gas was continued for an additional 1 hour. The solvent was removed in vacuo, the residue was dissolved in 50 mL of water and was neutralized by the addition of KOH pellets. The aqueous solution was extracted with 3×80 mL of dichloromethane and the combined organic extracts were dried (MgSO$_4$), filtered and concentrated in vacuo. The residue was purified by column chromatography (silica, 9:1, dichloromethane:methanol+1% isopropyl amine) to afford 2.85 g (87.5% yield) of the desired product: $^1$H NMR (400 MHz, CDCl$_3$) δ 8.24 (s, 1H), 8.09 (d, 1H, J=8.4 Hz), 7.71 (d, 1H, J=8.0 Hz), 7.49 (t, 1H, J=8.0 Hz), 6.35–6.25 (m, 1H), 3.58 (apparent q, 2H, J=3.0 Hz), 3.14 (t, 2H, J=5.6 Hz), 2.54–2.46 (m, 2H).

TERT-BUTYL 3-(4-(3-NITROPHENYL)-3,6-DIHYDRO-1(2H)-PYRIDINYL)PROPYLCARBAMATE: A mixture of 2.80 g (14.0 mmol) of 1,2,3,6-tetrahydro-4-(3-nitrophenyl)pyridine, 3.60 g (15.0 mmol) of tert-butyl N-(3-bromopropyl)carbamate, 11.6 g (84.0 mmol) of K$_2$CO$_3$, 14.6 mL (84.0 mmol) of diisopropylethylamine and 0.78 g (2.00 mmol) of tetrabutylammonium iodide in 250 mL of 1,4-dioxane was heated at reflux temperature for 14 hours. The reaction mixture was filtered and the filtrate was dried (MgSO$_4$), concentrated in vacuo and the residue was purified by column chromatography (silica, 9:1, dichloromethane:methanol+1% isopropyl amine) to afford 4.35 g (85.7% yield) of the desired product: $^1$H NMR (400 MHz, CDCl$_3$) δ 8.24 (t, 1H, J=1.9 Hz), 8.09 (dd, 1H, J=1.9, 8.0 Hz), 7.70 (apparent d, 1H, J=8.0 Hz), 7.49 (t, 1H, J=8.0 Hz), 6.23 (m, 1H), 3.29–3.18 (m, 4H), 2.75 (t, 2H, J=5.6 Hz), 2.64–2.54 (m, 4H), 1.82–1.70 (m, 2H), 1.44 (s, 9H); ESMS m/e: 362.2 (M+H)$^+$.

3-(4-(3-NITROPHENYL)-3,6-DIHYDRO-1(2H)-PYRIDINYL)-1-PROPANAMINE: Into a stirred solution of 4.35 (12.0 mmol) of tert-butyl 3-(4-(3-nitrophenyl)-3,6-dihydro-1(2H)-pyridinyl)propylcarbamate in 100 ml of 1,4-dioxane at 0° C. was bubbled HCl gas for 10 minutes. The reaction mixture was allowed to warm to room temperature and the bubbling was continued for an additional 1 hour. The solvent was removed in vacuo, the residue was dissolved in 50 mL of water and was neutralized by the addition of KOH pellets. The aqueous solution was extracted with 3×80 mL of dichloromethane, the combined organic extracts were dried (MgSO$_4$), filtered and concentrated in vacuo. The residue was purified by column chromatography (silica, 9:1, dichloromethane:methanol+1% isopropyl amine) to afford 3.05 g (97.0% yield) of the desired product: $^1$H NMR (400 MHz, CDCl$_3$) δ 8.24 (t, 1H, J=1.8 Hz), 8.09 (dd, 1H, J=1.8, 8.2 Hz), 7.69 (dd, 1H, J=1.8, 8.2 Hz), 7.48 (t, 1H, J=8.2 Hz), 6.24 (m, 1H), 3.21 (d, 2H, J=3.6 Hz), 2.84 (t, 2H, J=6.6 Hz), 2.75 (t, 2H, J=5.8 Hz), 2.64–2.54 (m, 4H), 1.76 (m, 2H); ESMS m/e: 262.2 (M+H)+; Anal. Calc. for C$_{14}$H$_{19}$N$_3$O$_2$ (0.06 CHCl$_3$): C, 62.90; H, 7.16; N, 15.65. Found: C, 63.20; H, 7.16; N, 15.65.

METHYL(4S)-3-[({3-[4-(3-AMINOPHENYL)-1-PIPERIDINYL]PROPYL}AMINO)CARBONYL]-4-(3,4-DIFLUOROPHENYL)-6-(METHOXYMETHYL)-2-OXO-1,2,3,4-TETRAHYDRO-5-PYRIMIDINECARBOXYLATE: A mixture of 3.02 g (6.33 mmol) 5-methyl 1-(4-nitrophenyl) (6S)-6-(3,4-difluorophenyl)-4-(methoxymethyl)-2-oxo-3,6-dihydro-1,5(2H)-pyrimidinedicarboxylate, 1.50 g (5.80 mmol) of 3-(4-(3-nitrophenyl)-3,6-dihydro-1(2H)-pyridinyl)-1-propanamine, 7.94 g (75.5 mmol) of K$_2$CO$_3$ and 1.00 mL of methanol in 200 mL dichloromethane (under argon) was stirred at room temperature for 1 hour. The reaction mixture was filtered and concentrated in vacuo. The residue was dissolved in 100 mL of ethyl acetate and washed 3×50 mL of 5% aqueous NaOH solution, the organic layer was dried (MgSO$_4$) and concentrated in vacuo. The residue was dissolved in 100 mL of anhydrous ethanol containing 0.50 g 10% Pd/C and the reaction mixture was stirred under a hydrogen balloon for 24 hours. The reaction mixture was passed through a column of Celite 545 filtering agent, washed with ethanol, the filtrate was dried (MgSO$_4$) and concentrated in vacuo. The residue was purified by column chromatography (silica, 9.5:0.5, dichloromethane:methanol+1% isopropyl amine) to afford 1.65 g (52.0% yield) of the desired product: $^1$H NMR (400 MHz, CDCl$_3$) δ 7.80 (s, 1H), 7.22–7.02 (m, 2H), 6.95 (t, J=8.70 Hz, 1H), 6.63–6.44 (m, 4H), 4.56 (Abq, 2H), 3.62 (s, 3H), 3.33 (s, 3H), 3.32–3.20 (m, 4H), 2.96 (br s, 2H), 2.33 (t, J=7.50 Hz, 2H), 2.11–1.94 (m, 3H), 1.81–1.64 (m, 4H); ESMS m/e: 572.3 (M+H)$^+$;

TERT-BUTYL 4-[3-(ISOBUTYRYLAMINO) PHENYL]-3,6-DIHYDRO-1(2H)-PYRIDINECARBOXYLATE: Into a solution of 4.00 g (16.0 mmol) of tert-butyl 4-(3-aminophenyl)-3,6-dihydro-1 (2H)-pyridinecarboxylate and 5.60 mL (32.0 mmol) of diisopropylethylamine in 100 mL dichloromethane was slowly added 1.90 mL (19.0 mmol) of isobutyryl chloride. The reaction mixture was stirred at room temperature for 2 hours, washed with water, dried (MgSO$_4$), and concentrated in vacuo. The residue was purified by column chromatography (silica, 50:46:3:1, hexanes:dichloromethane:methanol:isopropyl amine) to afford 2.90 g (52.0% yield) of the desired product: $^1$H NMR (400 MHz, CDCl$_3$) δ 7.69 (s, 1H), 7.34 (d, 1H, J=7.8 Hz), 7.27 (t, 1H, J=7.8 Hz), 7.11 (d, 1H, J=7.8 Hz), 6.04 (s, 1H), 4.05 (s, 2H), 3.62 (apparent t, 2H, J=4.9 Hz), 2.51 (m, 3H), 1.49 (s, 9H), 1.25 (d, 6H, J=7.4 Hz); ESMS m/e: 345.5 (M+H)$^+$. Anal. Calc. for C$_{20}$H$_{28}$N$_2$O$_3$+0.175 CHCl$_3$: C, 66.33; H, 7.77; N, 7.67. Found: C, 66.20; H, 7.41; N, 7.88.

TERT-BUTYL 4-[3-(ISOBUTYRYLAMINO) PHENYL]-1-PIPERIDINECARBOXYLATE: A mixture of 2.90 g (8.40 mmol) of tert-butyl 4-[3-(isobutyrylamino) phenyl]-3,6-dihydro-1(2H)-pyridinecarboxylate and 0.80 g of 10% yield Pd/C in 100 mL of ethanol was stirred under a hydrogen balloon for 24 hours. The reaction mixture was passed through a column of Celite 545 filtering agent, the filtrate was dried (MgSO$_4$) and concentrated in vacuo. The residue was purified by column chromatography (silica, 9.5:0.5, dichloromethane:methanol+1% isopropyl amine) to afford 2.40 g (84.0% yield) of the desired product: $^1$H NMR (400 MHz, CDCl$_3$) δ 7.49–7.44 (m, 2H), 7.24 (t, 1H, J=7.6 Hz), 6.93 (d, 1H, J=7.6 Hz), 4.20–4.10 (m, 2H), 2.86–2.45 (m, 4H), 1.86–1.75 (m, 4H), 1.48 (s, 9H), 1.24 (d, 6H, J=6.8 Hz); ESMS m/e: 345.2 (M+H)$^+$; Anal. Calc. for C$_{20}$H$_{30}$N$_2$O$_3$+0.3H$_2$O: C, 68.27; H, 8.77; N, 7.96. Found: C, 68.25; H, 8.54; N, 7.84.

2-METHYL-N-[3-(4-PIPERIDINYL)PHENYL] PROPANAMIDE: Into a stirred solution of 2.20 (6.50 mmol) of tert-butyl 4-[3-(isobutyrylamino)phenyl]-1-piperidinecarboxylate in 100 ml of 1,4-dioxane at 0° C. was bubbled HCl gas for 10 minutes. The reaction mixture was allowed to warm to room temperature and the bubbling of the HCl gas was continued for 1 hour. The solvent was removed in vacuo, the residue was dissolved in 50 mL of water and was neutralized by the addition of KOH pellets. The aqueous solution was extracted with 3×80 mL of dichloromethane, the combined organic extracts were dried (MgSO$_4$), filtered and concentrated in vacuo. The residue was purified by column chromatography (silica, 9:1, dichloromethane:methanol+1% isopropyl amine) to afford 0.700 g (46.0% yield) of the desired product: $^1$H NMR (400 MHz, CDCl$_3$) δ 7.47 (s, 1H), 7.40 (d, 1H, J=7.8 Hz), 7.24 (t, 1H, J=7.8 Hz), 7.00 (d, 1H, J=7.8 Hz), 3.23–3.14 (m, 5H), 2.82–2.57 (m, 4H), 1.20 (d, 6H, J=6.8 Hz); ESMS m/e: 247.2 (M+H)$^+$; The hydrochloride salt was used for the combustion analysis: Anal. Calc. for C$_{15}$H$_{22}$N$_2$O+HCl+0.15 CHCl$_3$: C, 60.51; H, 7.76; N, 9.32. Found: C, 60.57; H, 7.83; N, 8.88.

3-(4-PIPERIDINYL)ANILINE: A solution of 4 M HCl in dioxane (25 mL) was added to tert-butyl 4-[3-(amino) phenyl]-1-piperidinecarboxylate (2.60 g, 9.00 mmol) in dichloromethane (250 mL). The reaction mixture was stirred at room temperature overnight, concentrated in vacuo, and the residue was dissolved in water (50 mL). The mixture was nuetralized using KOH pellets and extracted with methylene chloride (3×50 mL). The combined organic extracts were dried (MgSO$_4$), concentrated and chromatographed to give the desired product (1.03 g). $^1$H NMR (400 MHz, CDCl$_3$) δ 7.01 (t, 1H, J=7.6 Hz), 6.62–6.54 (m, 3H), 3.16 (br d, 2H, J=10.3 Hz), 2.75 (dt, 2H, J=2.7, 12.3 Hz), 2.56 (tt, 1H, J=3.6, 12.3 Hz), 1.81 (br d, 2H, J=12.3 Hz), 1.65 (dq, 2H, J=4.0, 12.3 Hz); ESMS m/e: 177.2 (M+H)$^+$.

TERT-BUTYL 4-(4-NITROPHENYL)-3,6-DIHYDRO-1 (2H)-PYRIDINECARBOXYLATE: To a 25-mL RB flask, equipped with a condensor, was added tert-butyl 4-{[(trifluoromethyl)sulfonyl]oxy}-3,6-dihydro-1(2H)-pyridinecarboxylate (1.0 g), 4-nitrophenylboronic acid (0.71 g), sodium carbonate (0.430 mL of 2M solution), lithium chloride (0.382 g), tetrakis(triphenylphosphine)-palladium (0) (0.173 g) and ethylene glycol dimethyl ether (10 mL). The reaction mixture was flushed with Argon three times, then the reaction mixture was heated to 100° C. for 3 hrs. After cooling to room temperature, the reaction mixture was diluted with methylene chloride (30 mL) and water (30 mL) and the organic layer was separated. The aqueous layer was extracted with methylene chloride (3×20 mL) and the combined organic extracts were washed with sat $NH_4Cl$ (20 mL) and brine (20 mL), dried over $MgSO_4$ and concentrated under reduced pressure. The residue was purified by chromatography (6:1=hexane:ethyl acetate with 1% $NH_3$) to afford the product (0.55 g, 59.9%) as a yellow oil. The compound is not stable at room temperature and should be used as promptly as practical: $^1$H NMR (400 MHz, $CDCl_3$) δ 8.20 (d, 2H, J=8.6 Hz), 7.51 (d, 2H, J=8.6 Hz), 6.24 (m, 1H), 4.13 (m, 2H), 3.67 (apparent t, 2H, J=5.5 Hz), 2.55 (m, 2H), 1.49 (s, 9H).

4-(4-NITROPHENYL)-1,2,3,6-TETRAHYDROPYRIDINE: 4-(4-Nitrophenyl)-1,2,3,6-tetrahydropyridine was prepared by a similar procedure to that used for the preparation of 2-methyl-N-[3-(4-piperidinyl)phenyl]propanamide using HCl gas and tert-Butyl 4-(4-Nitrophenyl)-3,6-dihydro-1(2H)-pyridinecarboxylate (130 mg) in dioxane (5.0 mL) at room temperature. The reaction mixture was concentrated in vacuo to give the crude product (69.8 mg) which used in the next reaction without further purification.

Oxazolidinone Intermediates:

AMINO-(3,4-DIFLUOROPHENYL)-ACETONITRILE: Through a solution of 3,4-difluorobenzaldehyde (25.0 g, 0.176 mol) in MeOH (500 mL) in a round bottom flask, was bubbled ammonia gas for two hours at room temperature. The flask was then cooled to 0° C. and trimethylsilyl cyanide was then added slowly. The reaction mixture was stirred for 2 h, at which time TLC analysis indicated that the reaction was complete ($R_f$=0.35, 3:2 hexane/EtOAc). The solvent was removed in vacuo and the residue was subjected to flash column chromatography on silica gel to obtain the desired product, which was used in the next step without purification.

AMINO-(3,4-DIFLUOROPHENYL)-ACETIC ACID METHYL ESTER: Into a well-stirred solution of amino-(3, 4-difluorophenyl)-acetonitrile (22.0 g, 0.130 mol), a solution of HCl in MeOH (200 mL) was added at room temperature. The resulting yellow solution was stirred at room temperature for 10 h and was heated at reflux temperature for 1.5 h. After cooling, the solvent was removed in vacuo and the resulting yellow solid was dissolved in water (200 mL). The aqueous solution was then carefully basified with 20% NaOH solution to pH 9. The aqueous layer was extracted with $CH_2Cl_2$ (3×100 mL). The organic layer was separated and dried over $Na_2SO_4$, filtered and the solvent was removed in vacuo to obtain the desired product which was used in the next step without purification.

2-AMINO-2-(3,4-DIFLUOROPHENYL)-ETHANOL: Into a well-stirred suspension of $LiAlH_4$ (4.7 g, 0.125 mol) in THF (120 mL) in a 3-necked round bottom flask fitted with a condenser and a dropping funnel, was added a solution of amino-(3,4-difluorophenyl)-acetic acid methyl ester (10.0 g, 0.05 mol) in THF (100 mL) dropwise at 0° C. The resulting greenish brown suspension was heated at reflux temperature for 2 h. The reaction mixture was cooled to 0° C. and then carefully quenched sequentially with 5 mL of water, 5 mL of 3N NaOH followed by 15 mL of water. The resulting suspension was filtered through a fritted glass funnel. To the filter cake was added 100 mL $Et_2O$ and the suspension was heated at reflux temperature for 20 min. The suspension was filtered and the combined filtrates were dried over $MgSO_4$, filtered and the solvent was removed in vacuo. 2-Amino-2-(3,4-difluorophenyl)-ethanol was obtained as a yellow glassy syrup which was used in the next step without further purification.

[1-(3,4-DIFLUOROPHENYL)-2-HYDROXY-ETHYL]-CARBAMIC ACID-TERT-BUTYL ESTER: Into a solution of 2-amino-2-(3,4-difluorophenyl)-ethanol (8.6 g, 49.7 mmol) in $CHCl_3$ (150 mL) at 0° C. was added a solution of di-tert-butyl dicarbonate (11.4 g, 52.0 mmol) in $CHCl_3$ (50 mL) in one portion and the resulting solution was stirred overnight at room temperature. The solvent was removed in vacuo and the residue was subjected to column chromatography on silica gel (2:1 hexane-EtOAc followed by EtOAc) to obtain [1-(3,4-difluorophenyl)-2-hydroxy-ethyl]-carbamic acid-tert-butyl ester as a white solid (10.0 g, 74% yield).

(+)-4-(3,4-DIFLUOROPHENYL)-OXAZOLIDIN-2-ONE: Into a well-stirred suspension of NaH (1.1 g, 45.8 mmol) in THF (40 mL) at R.T. was added a solution of [1-(3,5-difluorophenyl)-2-hydroxy- ethyl]-carbamic acid-tert-butyl ester (5.0 g, 18.3 mmol) in THF (20 mL) via a dropping funnel at room temperature. The resulting suspension was stirred for 3 h and then quenched carefully with 10 mL of water. The biphasic mixture was extracted with 100 mL of $Et_2O$, washed with brine, filtered and the solvent was removed in vacuo. The gummy residue thus obtained was purified by column chromatography over silica gel ($R_f$=0.15, 3:2 hexane-EtOAc) to obtain 4-(3,5-difluorophenyl)-oxazolidin-2-one as a white flaky solid (2.8 g, 77% yield). M.P. 81–83° C.; $^1$H NMR (300 MHz, $CDCl_3$) δ 7.23–7.03 (m, 3H), 6.08 (br s, 1H), 4.94 (dd, J=6.6 Hz, J=8.7 Hz, 1H), 4.73 (t, J=8.7 Hz, 1H), 4.13 (dd, J=6.6 Hz, J=8.7 Hz, 1H). The enantiomers were separated by HPLC on a Chiralcel OD (20×250 mm) column using 80% hexane/20% isopropyl alcohol as the eluting system at 12.0 mL/min (U.V. 254 nm). The retention times for the two isomers were 16.19 min and 20.08 min respectively.

4-NITROPHENYL(4S)-4-(3,4-DIFLUOROPHENYL)-2-OXO-1,3-OXAZOLIDINE-3-CARBOXYLATE: Into a suspension of NaH (0.14 g, 5.30 mmol) in 20 mL of anhydrous THF under argon, a solution of (+)-4-(3,4-difluorophenyl)-oxazolidin-2-one (0.88 g, 4.42 mmol) in THF was added dropwise (dropping funnel). The resulting suspension was stirred at room temperature for 30 min. This suspension was then added dropwise via cannula into another round bottom flask containing a solution of 4-nitrophenylchloroformate (1.11 g, 5.30 mmol) in 25 mL of THF and cooled at −78° C. over a period of 15 min. The stirring was continued for 2 h after which the solvent was removed and the residue was purified by column chromatography on silica gel with 1:1 hexane/$CH_2Cl_2$ followed by $CH_2Cl_2$ ($R_f$=0.4, $CH_2Cl_2$) to obtain the desired product as a white solid (1.55 g, 86% yield). Similarly, following the above procedure, 4-(3,5-difluorophenyl)-2-oxo-oxazolidine-3-carboxylic acid-4-nitro-phenyl ester and 4-(3, 4,5-trifluorophenyl)-2-oxo-oxazolidine-3-carboxylic acid-4-nitro-phenyl ester were obtained by substituting 3,4-diflourobenzaldehyde in the first step with 3,5-diflourobenzaldehyde or 3,4,5-triflourobenzaldehyde, respectively. The oxazolidinone enantiomers were resolved by HPLC on a Chiralcel OD column (as in the previous example) and the 4-nitro-phenyl carbamates were prepared using 4-nitrophenyl chloroformate.

4-NITROPHENYL(4S)-4-(3,5-DIFLUOROPHENYL)-2-OXO-1,3-OXAZOLIDINE-3-CARBOXYLATE: Following the procedure for the synthesis of 4-(3,4-difluorophenyl)-2-oxo-oxazolidine-3-carboxylic acid-4-nitro-phenyl ester, 3,5-diflourobenzaldehyde yielded the desired product. $^1$H NMR (400 MHz, CDCl$_3$) δ 8.26 (d, 2H, J=9.3 Hz), 7.33–6.81 (m, 5H), 5.41 (dd, 1H, J=4.1, 8.7 Hz), 4.81 (t, 1H, J=9.3 Hz), 4.33 (dd, 1H, J=4.1, 9.3 Hz); Anal. Calc. for $C_{16}H_{10}F_2N_2O_6$+0.2EtOAc: C, 52.84; H, 3.06; N, 7.34. Found: C, 53.26; H, 2.83; N, 7.73.

4-NITROPHENYL(4S)-2-OXO-4-(3,4,5-TRIFLUOROPHENYL)-1,3-OXAZOLIDINE-3-CARBOXYLATE: Following the procedure for the synthesis of 4-(3,4-difluorophenyl)-2-oxo-oxazolidine-3-carboxylic acid-4-nitro-phenyl ester, 3,4,5-triflourobenzaldehyde yielded the desired product. $^1$H NMR (400 MHz, CDCl$_3$) δ 8.27 (d, 2H, J=9.0 Hz), 7.31 (d, 2H, J=9.0 Hz), 7.11–7.02 (m, 2H), 5.37 (dd, 1H, J=4.1, 9.0 Hz), 4.81 (apparent t, 1H, J=9.0 Hz), 4.33 (dd, 1H, J=4.1, 9.0 Hz); Anal. Calc. for $C_{16}H_9F_3N_2O_6$: C, 50.27; H, 2.37; N, 7.33. Found: C, 50.56; H, 2.50; N, 7.49.

1-(3,4-DIFLUOROPHENYL)-2-METHYL-2-HYDROXYPROPYLAMINE: Into a well-stirred solution of methyl 2-amino-2-(3,4-difluorophenyl)acetate (10.5 g, 52.19 mmol) in anhydrous ether (200 mL) at 0° C. a solution of methylmagnesium bromide (3 M, 87 mL, 261 mmol) in ether was added over 10 minutes. The reaction mixture was stirred at 0° C. for 2.5 h and allowed to warm to room temperature. After 12 h, the reaction mixture was carefully poured onto a mixture of ice (300 g) and saturated aqueous ammonium chloride (50 9). The ether layer was separated and the aqueous layer was extracted with more ether (4×200 mL). The combined extracts were dried with magnesium sulfate and the solvent evaporated. The crude product was purified by column chromatography on silica gel using chloroform/methanol/2M ammonia in methanol (1000:20:10, 1000:40:20, 1000:80:40) as the eluent to give the product as an oil (6.5 g, 62% yield) which was used in the next step without further purification.

4-(3,4-DIFLUOROPHENYL)-5,5-DIMETHYL-2-OXO-OXAZOLIDINE: A mixture of 1-(3,4-difluorophenyl)-2-methyl-2-hydroxypropylamine (3.00 g, 14.9 mmol) and carbonyldiimidazole (2.418 g, 14.9 mmol) in dichloromethane (150 mL) was heated at reflux temperature for 36 h and the solvent evaporated. The residue was purified by column chromatography on silica gel using chloroform/ethyl acetate (9:1) to give the product as a viscous oil which solidified on standing (1.80 g, 50% yield). The product was used in the next step without further characterization.

4-NITROPHENYL 4-(3,4-DIFLUOROPHENYL)-5,5-DIMETHYL-2-OXO-1,3-OXAZOLIDINE-3-CARBOXYLATE: Into a stirred suspension of sodium hydride (60% suspension in paraffin 203 mg, 1.4 eq.) in THF (20 mL) at 0° C., a solution of 4-(3,4-difluorophenyl)-5,5-dimethyl-2-oxo-oxazolidine (870 mg, 3.622 mmol) in THF (5 mL) was added followed by stirring for 30 minutes. This suspension was added to a solution of 4-nitrophenyl chloroformate (950 mg, 4.71 mmol) in THF (20 mL) at −78° C. under argon and the stirring was continued for 2 h. It was slowly warmed to room temperature and after 4 h the solvent was evaporated. The residue was mixed with dichloromethane (150 mL), washed with 0.05 N sodium hydroxide (3×10 mL), and dried (sodium sulfate). The solvent was evaporated and the residue was purified by column chromatography on silica gel using chloroform/ethyl acetate (9:1) as the eluent to give the product as a white powder (860 mg, 59% yield).

$^1$H NMR (400 MHz, CDCl$_3$) δ 8.24 (d, 2H, J=9 Hz), 7.29–6.97 (m, 5H), 5.04 (s, 1H), 1.09 (s, 6H); Anal. Calc. for $C_{18}H_{14}F_2N_2O_6$+0.2% H$_2$O: C, 54.61; H, 3.67; N, 7.08. Found: C, 54.89; H, 3.59; N, 7.41.

(3,4-DIFLOUROPHENYL)-N (DIPHENYLMETHYLENE)METHANAMINE: Into a solution of 3,4-difluorobenzylamine (9.8 g, 69 mmol) and benzophenone (13.0 g, 71.0 mmol) in toluene (200 mL) was added a catalytic amount of BF$_3$.OEt$_2$ and the resulting solution was heated at reflux temperature for 12 h. The reaction mixture was concentrated in vacuo, yielding an oil (21 g, >95%), which was characterized by NMR analysis and subjected to the following reaction without any further purification. $^1$H NMR (CDCl$_3$) δ 4.57 (s, 2H), 7.80–6.80 (m, 13H).

1-(3,4-DIFLOUROPHENYL)-1-[(DIPHENYLMETHYLENE)AMINO]PROPAN-2-OL: Into a solution of the benzhydrylindene-(3,4-difluorobenzyl)-amine (21 g, 69 mmol) in 250 ml of dry THF was added tert-butyllithium (1.7 M, 60 ml) dropwise and the resulting solution was stirred at −78° C. for 0.5 h. To the solution was added acetaldehyde (10 ml, 180 mmol) in 100 ml of THF and the solution was stirred at −78° C. for 2 h and 25° C. for 1 h. The reaction mixture was quenched by addition of brine. The reaction mixture was diluted with 500 ml of Et$_2$O and washed with brine. The organic layer was dried over Na$_2$SO$_4$ and concentrated in vacuo to give an oil, which was taken to the next step without any further purification. $^1$H NMR (CDCl$_3$) δ 1.04 (d, 3H), 2.77 (broad s. 1H), 4.08 (m, 1H), 4.15 (d, 1H), 7.80–6.80 (m, 13H).

1-AMINO-1-(3,4-DIFLUORO-PHENYL)-PROPAN-2-OL: A solution of crude product from the previous procedure and MeONH$_2$.HCl (10 g, 120 mmol) was diluted in 200 ml of MeOH and stirred for 12 h. The reaction mixture was concentrated in vacuo, yielding an oily residue, which was re-dissolved in 200 ml of EtOAc and washed with brine. The organic layer was concentrated in vacuo to produce an oily mixture, which was subjected to column chromatography [5% NH$_3$ (2.0 M in MeOH) in CHCl$_3$] to yield the desired product (8.8 g, 68% yield from 3,4-difluorobenzylamine) as a mixture of diastereomers. $^1$H NMR (CDCl$_3$) (~4:1 mixture of the diastereomers) δ 1.02 (d, J=6.0 Hz, 3H), 1.04 (d, J=6.3 Hz, 3H), 2.10 (br, 6H), 3.56–3.69 (m, 2H), 3.88–3.92 (m, 2H), 7.02–7.17 (m, 6H).

[1-(3,4-DIFLUOROPHENYL)-2-HYDROXY-PROPYL]-CARBAMIC ACID-TERT-BUTYL ESTER: Into a solution of 1-amino-1-(3,4-difluorophenyl)-propan-2-ol (13.1 g, 70.1 mmol) in CHCl$_3$ (150 mL) at 0° C. was added a solution of di-tert-butyl dicarbonate (19.3 g, 87.6 mmol) in CHCl$_3$ (50 mL) in one portion and the resulting solution was stirred overnight at room temperature. The solvent was removed in vacuo and the residue was subjected to column chromatography on silica gel (2:1 hexane-EtOAc followed by EtOAc) to obtain [1-(3,4-difluorophenyl)-2-hydroxy-propyl]-carbamic acid-tert-butyl ester as a viscous oil (18.4 g, 91% yield). $^1$H NMR (CDCl$_3$) (~4:1 mixture of the diastereomers) δ 1.05 (d, J=6.6 Hz, 3H), 1.25 (d, J=6.0 Hz, 3H), 1.41 (br, 20H), 3.92–4.19 (br, 2H), 4.45–4.60 (m, 2H), 5.41–5.49 (br, 2H), 7.02–7.17 (m, 6H).

4-(3,4-DIFLUOROPHENYL)-5-METHYL-OXAZOLIDIN-2-ONE: Into a well-stirred solution of [1-(3,4-difluorophenyl)-2-hydroxy-propyl]-carbamic acid-tert-butyl ester (0.43 g, 1.5 mmol) in THF (20 mL) was added 95% NaH (0.09 g, 3.8 mmol) at room temperature. When the reaction was carried out on a larger (>5 g) scale, 1.0 equivalent of KH and 1.5 eq. of NaH was used as the base. The resulting suspension was stirred for 3 h at about 35° C. (warm water bath) and then quenched carefully with ice. The biphasic mixture was extracted with 100 mL of EtOAc, washed with brine, dried over $Na_2SO_4$, filtered and the solvent was removed in vacuo. The two diastereomers were separated by column chromatography over silica gel (First isomer: 0.16 g, $R_f$=0.6, 3:1 hexane-EtOAc; second isomer: 0.18 g, $R_f$=0.5, 3:1 hexane-EtOAc). NOE experiments suggested that the first diastereomer had the methyl and the aryl group in trans configuration while the second diastereomer had cis relationship between the two groups. The $^1$H NMR spectrum for the trans diastereomer is as follows. $^1$H NMR ($CDCl_3$) δ 1.49 (d, J=6.0 Hz, 3H), 4.37 (dq, J=6.0 Hz, J=7.2 Hz, 1H), 4.45 (d, J=7.2 Hz, 1H), 6.63 (br s, 1H), 7.08–7.28 (m, 3H).

The $^1$H NMR spectrum for the cis diastereomer is as follows. $^1$H NMR ($CDCl_3$) δ 0.96 (d, J=6.6 Hz, 3H), 4.91 (d, J=8.1 Hz, 1H), 4.99 (dq, J=6.6 Hz, J=8.1 Hz, 1H), 6.63 (br s, 1H), 7.08–7.28 (m, 3H).

4-(3,4-DIFLUOROPHENYL)-5-METHYL-2-OXO-OXAZOLIDINE-3-CARBOXYLIC ACID-4-NITRO-PHENYL ESTER: Into a solution of one of the two diastereomers of 4-(3,4-difluorophenyl)-5-methyl-oxazolidin-2-one (0.97 g, 4.55 mmol) in 60 mL THF was added a solution of n-butyllithium in hexane (3.06 mmol, 4.9 mmol) dropwise via a syringe under argon atmosphere at –78° C. The resulting yellow solution was stirred at –78° C. for 40 min. This solution was then added dropwise via a cannula into another round bottom flask containing a solution of 4-nitrophenylchloroformate (1.03 g, 5.1 mmol) in 60 mL of THF, cooled at –78°0 C., over a period of 15 min. After five minutes, the flask was removed from the cooling bath and stirring was continued for 1 h. The reaction mixture was quenched by adding ice and it was extracted with EtOAc. The organic extracts were washed with brine and the organic layer was dried over $Na_2SO_4$. The solvent was removed after filtration and the residue was purified by column chromatography on silica gel with 1:1 hexane/$CH_2Cl_2$ followed by $CH_2Cl_2$ to give the desired product.

The relative configurations of the cis and trans isomers were assigned on the basis of $^1$H NMR analysis of the respective p-nitrophenyloxycarbonyl derivatives. For the trans isomer, an NOE was observed between the protons of the C-5 methyl group and the proton at C-4. No NOE was observed between the protons at the C-4 and C-5 positions of this isomer, which was thus assigned trans stereochemistry. For the cis isomer, no NOE was observed between the protons of the C-5 methyl group and the proton at C-4. However, a NOE was observed between the protons at the C-4 and C-5 positions, leading us to assign this isomer cis stereochemistry. The vicinal coupling constants of the C-4 protons of cis (J=7.8 Hz) and trans (J=5.1 Hz) are also consistent with the values reported for similar oxazolidinones, and were thus helpful in making the stereochemical assignments (Dondoni, A.; Perrone, D.; Semola, T. *Synthesis* 1995, 181).

Enantiomers of the diastereomers were separated by HPLC by using a Chiralcel OD column (20×250 mm) with 80% hexane/20% isopropyl alcohol/0.1% diethylamine as the eluting system (12 mL/min) under isocratic conditions (U.V. 254 nm).

In order to assign the absolute configurations at the stereogenic centers of the oxazolidinone rings, a new synthetic route was designed which employed an enantiomerically pure substrate derived from the chiral pool. Commercially available (S)-(+)-methyl lactate was converted into its pyrrolidine amide according to the method of Martin et al (Martin, R.; Pascual, O.; Romea, P.; Rovira, R.; Urpi, F.; Vilarrasa, J. *Tetrahedron Lett.* 1997, 38, 1633). Following the protection of the hydroxy group of (2S)-1-oxo-1-(1-pyrrolidinyl)-2-propanol to a TBDMS group, treatment of tert-butyl(dimethyl)silyl(1S)-1-methyl-2-oxo-2-(1-pyrrolidinyl)ethyl ether with 3,4-difluorophenyllithium yielded (2S)-2-{[tert-butyl(dimethyl)silyl]oxy}-1-(3,4-difluorophenyl)-1-propanone as the sole product, which was then converted to (2S)-2-{[tert-butyl(dimethyl)silyl]oxy}-1-(3,4-difluorophenyl)-1-propanone oxime. Reduction of the (2S)-2-{[tert-butyl(dimethyl)silyl]oxy}-1-(3,4-difluorophenyl)-1-propanone oxime with $LiAlH_4$, N-acylation, and base induced cyclization provided oxazolidinone diastereomers, which were separated by flash column chromatography. The enantiomeric purity of these isomers was confirmed by chiral HPLC analysis and their relative configurations were assigned by comparison of their $^1$H NMR spectra with those of the racemic isomers. As the absolute configuration at C-5 of the lactic acid derived oxazolidinone described above is (S), the C-4 center in trans compounds also has the (S) configuration. Accordingly, the absolute configurations for the stereogenic centers in the cis compounds are assigned accordingly (4R,5S).

4-NITROPHENYL(4S,5R)-4-(3,4-DIFLUOROPHENYL)-5-METHYL-2-OXO-1,3-OXAZOLIDINE-3–CARBOXYLATE: $^1$H NMR (400 MHz, $CDCl_3$) δ 8.25 (d, 2H, J=8.8 Hz), 7.30–6.99 (m, 5H), 5.35 (d, 1H, J=7.7 Hz), 5.07 (apparent quintet, 1H), 1.17 (d, 3H, J=6.5 Hz); Anal. Calc. for $C_{17}H_{12}F_2N_2O_6$+0.5$H_2O$: C, 52.72; H, 3.38; N, 7.23. Found: C, 53.09; H, 3.19; N, 7.50.

(+)-2-AMINO-3-(3,4-DIFLUORO)-PHENYL-PROPAN-1-OL: (+)-3,4-difluorophenyl alanine (1.0 g, 5.0 mmol) was added in small portions to a stirring suspension of $LiAlH_4$ (0.480 g, 12.5 mmol) in THF (30 mL) at 0° C. The resulting gray suspension was then heated at reflux for 2 h. The reaction mixture was cooled to 0° C. and then carefully quenched sequentially with water (0.5 mL), 3 N NaOH (0.5 mL), and water (1.50 mL). The resulting suspension was filtered through a fritted glass funnel. Ether (50 mL) was added to the filter cake and the suspension was heated at reflux temperature for 20 min. The suspension was filtered and was combined with the previous filtrate. The combined organics were dried over $MgSO_4$, filtered and the solvent was removed in vacuo. 2-Amino-3-(3,4-difluoro)-phenyl-propan-1-ol was obtained as a white solid (0.500 g, 100%) which was used in the next step without further purification.

(+)-[1-(3,4-DIFLUOROBENZYL)-2-HYDROXY-ETHYL]-CARBAMIC ACID-TERT-BUTYL ESTER: A solution of di-tert-butyl dicarbonate (0.640 g, 2.90 mmol) in $CHCl_3$ (10 mL) was added in one portion to a solution of (+)-2-amino-3-(3,4-difluoro)-phenyl-propan-1-ol (0.500 g, 2.62 mmol) in $CHCl_3$ (20 mL) at 0° C. and the resulting solution was stirred overnight at room temperature. The solvent was removed in vacuo and the residue was chromatographed (2:1 hexane-EtOAc, followed by EtOAc), giving (+)-[1-(3,4-difluorobenzyl)-2-hydroxy-ethyl]-carbamic acid-tert-butyl ester as a white solid (0.640 g, 99%).

(+)-4-(3,4-DIFLUORO-BENZYL)-OXAZOLIDIN-2-ONE: A solution of (+)-[1-(3,4-difluorobenzyl)-2-hydroxy-ethyl]-carbamic acid-tert-butyl ester (1.00 g, 4.00 mmol) in THF (10 mL) was added via a dropping funnel to a stirring suspension of 95% NaH (0.12 g, 5.0 mmol) in THF (20 mL) at room temperature. The resulting suspension was stirred for 3 h and then quenched carefully with water (10 mL). The biphasic mixture was extracted with Et$_2$O (50 mL), washed with brine, filtered and the solvent was removed in vacuo. The resulting gummy residue was purified by column chromatography (R$_f$=0.25, 3:2 hexane-EtOAc), to give the desired product as a white solid (0.320 g, 76%).

(+)-4-(3,4-DIFLUORO-BENZYL)-OXAZOLIDIN-2-ONE-3-CARBOXYLIC ACID-4-NITRO-PHENYL ESTER: A solution of (+)-4-(3,4-difluoro-benzyl)-oxazolidin-2-one (0.210 g, 1.0 mmol) in THF (10 mL) was added dropwise via a dropping funnel to a stirring suspension of NaH (30.0 mg, 1.30 mmol) in anhydrous THF (10 mL) under argon. The resulting suspension was stirred at room temperature for 30 min. This suspension was then added dropwise via cannula to a solution of 4-nitrophenylchloroformate (0.300 g, 1.50 mmol) in THF (20 mL) at −78° C. over 15 min. Stirring was continued for 2 h after which the solvent was removed and the residue was purified by column chromatography (1:1 hexane/CH$_2$Cl$_2$, followed by CH$_2$Cl$_2$; R$_f$=0.4, CH$_2$Cl$_2$), to give the desired product as a yellow solid (0.350 g, 82%).

Similarly, following the above procedure, 4-nitrophenyl 4-(4-fluorobenzyl)-2-oxo-1,3-oxazolidine-3-carboxylate was obtained by substituting (+)-3,4-diflourophenyl alanine with p-fluorophenyl alanine:

4-NITROPHENYL 4-(4-FLUOROBENZYL)-2-OXO-1,3-OXAZOLIDINE-3-CARBOXYLATE: $^1$H NMR (400 MHz, CDCl$_3$) δ 8.32 (d, 2H, J=9.3 Hz), 7.42 (d, 2H, J=8.9 Hz), 7.24–6.99 (m, 4H), 4.69–4.59 (m, 1H), 4.35 (t, 1H, J=8.6 Hz), 4.23 (dd, 1H, J=2.7, 9.3 Hz), 3.37 (dd, 1H, J=3.8, 13.6 Hz), 2.94 (dd, 1H, J=9.3, 13.6 Hz); Anal. Calc. for C$_{17}$H$_{13}$FN$_2$O$_6$: C, 56.67; H, 3.64; N, 7.77. Found: C, 56.94; H, 3.76; N, 7.71.

2-[6-(4-PHENYL-1-PIPERIDINYL)HEXYL]-1H-ISOINDOLE-1,3(2H)-DIONE: To the 500 ml RB-flask was added 4-phenylpiperidine hydrochloride (5 g, 25 mmol), N-(6-bromohexyl)phthalimide (15.5 g, 50 mmol), N,N-diisopropylethylamine (21.8 ml, 125 mmol), tetrabutylammonium iodide (0.2 g), and dioxane (250 ml) at room temperature. The reaction mixture was stirred at 100° C. for 72 h. The solvent was removed in vacuo and the crude product was purified by flash chromatography (98:2= Chloroform:2N ammonia in methanol) to afford 7.67 g of the desired product (77% yield): $^1$H NMR (400 MHz, CDCl$_3$) δ 7.78–7.79 (m, 2H), 7.74–7.65 (m, 2H), 7.32–7.14 (m, 5H), 3.69 (t, 2H, J=7.35 Hz), 3.06 (d, 2H, J=11.0 Hz), 2.49 (quintet, 1H, J=7.6 Hz), 2.36 (t, 2H, J=7.6 Hz), 2.02 (t, 2H, J=12.5 Hz), 1.82 (br s, 4H), 1.69 (t, 2H, J=6.3 Hz), 1.54 (br s, 2H), 1.37 (br s, 4H); ESMS m/e: 391.3 (M+H)$^+$; Anal. Calc. for C$_{25}$H$_{30}$N$_2$O$_2$+0.2H$_2$O: C, 76.19; H, 7.77; N, 7.11. Found: C, 76.14; H, 7.38; N, 7.13.

METHOD I. General procedure for the Preparation of the substituted 4-[4-(3-aminophenyl)-1-piperidinyl]-1-(phenyl)-1-butanones: A mixture of 4-(3-aminophenyl) piperidine (2.0 mmol), 2.4 mmol of the appropriate substituted phenyl butyryl chloride (e.g. 4-chloro-4'-phenoxybutyrophenone, 4-chloro-3',4'-dimethylbutyrophenone, 4-chloro-4'-chlorobutyrophenone, γ-chlorobutyrophenone, 4-chloro-3',4'-dimethoxybutyrophenone), 3.0 mmol of K$_2$CO$_3$, and 10 mg of 18-crown-6 in 5 mL of toluene were heated at 110° C. for 2.5 days. The reaction mixture was concentrated and chromatographed on silica (5% methanol in dichloromethane) to give the desired compound:

4-[4-(3-AMINOPHENYL)-1-PIPERIDINYL]-1-(4-PHENOXYPHENYL)-1-BUTANONE: Using Method I, the desired product was obtained. 305 mg; ESMS m/e: 415.4 (M+H)$^+$.

4-[4-(3-AMINOPHENYL)-1-PIPERIDINYL]-1-(3,4-DIMETHYLPHENYL)-1-BUTANONE: Using Method I, the desired product was obtained. 320 mg; ESMS m/e: 351.3 (M+H)$^+$.

4-[4-(3-AMINOPHENYL)-1-PIPERIDINYL]-1-(4-CHLOROPHENYL)-1-BUTANONE: Using Method I, the desired product was obtained. 500 mg; Anal. Calc for C$_{21}$H$_{25}$ClN$_2$O+0.3H$_2$O: C, 69.62; H, 7.12; N, 7.73. Found: C, 69.63; H, 7.34; N, 7.60; ESMS m/e: 357.3 (M+H)$^+$.

4-[4-(3-AMINOPHENYL)-1-PIPERIDINYL]-1-PHENYL-1-BUTANONE: Using Method I, the desired product was obtained. 250 mg; Anal. Calc for C$_{21}$H$_{26}$N$_2$O+ 0.2H$_2$O: C, 77.36; H, 8.16; N, 8.59. Found: C, 77.55; H, 8.12; N, 8.75; ESMS m/e: 323.3 (M+H)$^+$.

4-[4-(3-ANINOPHENYL)-1-PIPERIDINYL]-1-(2,4-DIMETHOXYPHENYL)-1-BUTANONE: Using Method I, the desired product was obtained. 330 mg; Anal. Calc for C$_{23}$H$_{30}$N$_2$O$_3$+0.5H$_2$O: C, 70.56; H, 7.98; N, 7.16. Found: C, 70.69; H, 7.87; N, 6.99; ESMS m/e: 383.3 (M+H)$^+$.

METHOD II. General Procedure for the Acylation or Sulfonylation of the Substituted 4-[4-(3-Aminophenyl)-1-piperidinyl]-1-(4-phenyl)-1-butanones: A mixture of 1 equivalent of a substituted 4-[4-(3-aminophenyl)-1-piperidinyl]-1-(4-phenyl)-1-butanone, 1.5 equivalent of an acid chloride or a sulfonyl chloride, and 5 equivalents of diisopropylethylamine, in dichloromethane was stirred at room temperature for two days. The reaction mixture was applied to a preparative TLC plate and eluted with dichloromethane:methanol (15:1, containing 1% isopropyl amine) to give the desired product.

METHOD III. General procedure for the Preparation of the substituted 4-N-(3-{1-[4-(phenyl)-4-oxobutyl]-4-piperidinyl}phenyl)acetamides: A mixture of N-[3-(4-piperidinyl)phenyl]acetamide (1.0 eq) and an aryl substituted chlorobutyrophenone (2.0 eq), K$_2$CO$_3$ (5.0 eq), diisopropylethylamine (3.0 eq) and tetrabutylammonium iodide (cat. 5–10%) in dioxane (0.5 to 1.0 M) were heated at reflux temperature for 16 h. The reaction mixture was filtered and concentrated in vacuo. The crude product was chromatographed using silica preparative TLC (chloroform:methanol containing 0.5% isopropyl amine) to give the desired product.

EXAMPLE 1

N-(3-{1-[4-(3,4-DIMETHYLPHENYL)-4-OXOBUTYL]-4-PIPERIDINYL}PHENYL) ACETAMIDE: Using Method III, the desired product was obtained. $^1$H NMR (CDCl$_3$) δ 7.75 (s, 1H), 7.71 (d, 1H, J=7.6 Hz), 7.45 (d, 2H, J=7.2 Hz), 7.35 (s, 1H), 7.26–7.22 (m, 2H), 6.93 (d, 1H, J=7.6 Hz), 3.24–3.21 (m, 2H), 3.04 (t, 2H, J=7.0 Hz), 2.67–2.63 (m, 2H), 2.59–2.48 (m, 1H), 2.32 (s, 6H), 2.30–2.27 (m, 2H), 2.18 (s, 3H), 2.14–2.06 (m, 2H), 2.00–1.80 (m, 4H); ESMS m/e: 393.3 (M+H)$^+$.

EXAMPLE 2

N-(3-{1-[4-(3,4-DIMETHYLPHENYL)-4-OXOBUTYL]-4-PIPERIDINYL}PHENYL)-2-METHYLPROPANAMIDE: A mixture of 0.0500 g (0.200 mmol) of 2-methyl-N-[3-(4-piperidinyl)phenyl] propanamide, 0.100 g (0.480 mmol) of 4-chloro-3',4'-dimethylbutyrophenone, 0.080 g (0.600 mmol) of K$_2$CO$_3$ and 0.090 g (0.600 mmol) of NaI in 5 mL of DMF was heated at reflux temperature for 18 hours. The reaction mixture was filtered, the filtrate was poured into 5 mL of water and washed with 3×5 mL of ethyl acetate. The combined organic extracts were dried (MgSO$_4$), concentrated in vacuo and purified by preparative TLC (silica; 9.5:0.5, dichloromethane:methanol+1% isopropyl amine) to afford 0.067 g (80.0% yield) of the desired product: $^1$H NMR (400 MHz, CDCl$_3$) δ 7.72 (d, 1H, J=8.0 Hz), 7.44 (s, 1H), 7.38 (d, 1H, J=8.0 Hz), 7.23–7.20 (m, 2H), 7.16 (s, 1H), 6.95 (d, 1H, J=6.8 Hz), 3.13–3.11 (m, 2H), 3.02 (t, 2H, J=7.0 Hz), 2.56–2.40 (m, 4H), 2.32 (s, 6H), 2.17–2.15 (m, 2H), 2.04–1.78 (m, 6H), 1.25 (d, 6H, J=6.8 Hz); ESMS m/e 421.3 (M+H)$^+$.

EXAMPLE 3

N-(3-{1-[4-(3,4-DIMETHYLPHENYL)-4-OXOBUTYL]-4-PIPERIDINYL}PHENYL)CYCLOHEXANECARBOXAMIDE: Using Method II, the desired compound was obtained. $^1$H NMR (400 MHz, CDCl$_3$) δ 7.80–6.81 (m, 7H), 3.41–3.00 (m, 4H), 2.95–2.41 (m, 4H), 2.32 (s, 6H), 2.22–1.05 (m, 18H); ESMS m/e 461.4 (M+H)$^+$.

EXAMPLE 4

N-(3-{1-[4-(3,4-DIMETHYLPHENYL)-4-OXOBUTYL]-4-PIPERIDINYL}PHENYL)-2-PHENYLACETAMIDE: Using Method II, the desired product was obtained. $^1$H NMR (400 MHz, CDCl$_3$) δ 7.85–7.65 (m, 2H), 7.45–6.92 (m, 10H), 3.76 (s, 2H), 3.10–2.90 (m, 4H), 2.50–2.35 (m, 3H), 2.32 (s, 6H), 2.10–1.85 (m, 4H), 1.80–1.60 (m, 4H); ESMS m/e: 469.4 (M+H)$^+$.

EXAMPLE 5

N-(3-{1-[4-(3,4-DIMETHYLPHENYL)-4-OXOBUTYL]-4-PIPERIDINYL}PHENYL)-2-(3-METHOXYPHENYL)ACETAMIDE: Using Method II, the desired product was obtained. $^1$H NMR (400 MHz, CDCl$_3$) δ 7.76–7.65 (m, 2H), 7.38–7.12 (m, 6H), 6.95–6.80 (m, 3H), 3.82 (s, 3H), 3.70 (s, 2H), 3.10–2.90 (m, 4H), 2.50–2.38 (m, 3H), 2.32 (s, 6H), 2.10–1.85 (m, 4H), 1.80–1.60 (m, 4H); ESMS m/e: 499.4 (M+H)$^+$.

EXAMPLE 6

N-(3-{1-[4-(3,4-DIMETHYLPHENYL)-4-OXOBUTYL]-4-PIPERIDINYL}PHENYL)-2-METHOXYACETAMIDE: Using Method II, the desired product was obtained. $^1$H NMR (400 MHz, CDCl$_3$) δ 7.80–7.75 (m, 2H), 7.50–7.38 (m, 2H), 7.34–6.90 (m, 3H), 4.00 (s, 2H), 3.51 (s, 3H), 3.30–2.95 (m, 4H), 2.70–2.50 (m, 3H), 2.32 (s, 6H), 2.15–1.80 (m, 8H); ESMS m/e: 423.3 (M+H)$^+$.

EXAMPLE 7

N-(3-{1-[4-(3,4-DIMETHYLPHENYL)-4-OXOBUTYL]-4-PIPERIDINYL}PHENYL)METHANESULFONAMIDE: Using Method II, the desired product was obtained. $^1$H NMR (400 MHz, CDCl$_3$) δ 7.82–7.10 (m, 7H), 3.41 (s, 3H), 3.40–2.85 (m, 4H), 2.82–2.35 (m, 5H), 2.32 (s, 6H), 2.22–1.80 (m, 6H); ESMS m/e: 429.3 (M+H)$^+$.

EXAMPLE 8

N-(3-{1-[4-(3,4-DIMETHYLPHENYL)-4-OXOBUTYL]-4-PIPERIDINYL}PHENYL)ETHANESULFONAMIDE: Using Method II, the desired product was obtained. $^1$H NMR (400 MHz, CDCl$_3$) δ 7.75 (s, 1H), 7.71 (d, 1H, J=7.6 Hz), 7.30–7.09 (m, 4H), 7.02 (d, 1H, J=7.2 Hz), 3.36–3.05 (m, 6H), 2.77–2.52 (m, 3H), 2.32 (s, 6H), 2.15–1.82 (m, 8H), 1.37 (t, 3H, J=7.4 Hz); ESMS m/e: 443.3 (M+H)$^+$.

EXAMPLE 9

N-(3-{1-[4-(4-CHLOROPHENYL)-4-OXOBUTYL]-4-PIPERIDINYL}PHENYL)ACETAMIDE: Using Method III, the desired product was obtained. $^1$H NMR (400 MHz, CDCl$_3$) δ 7.92 (d, 2H, J=8.8 Hz), 7.55–7.40 (m, 3H), 7.35 (s, 1H), 7.22 (t, 1H, J=8.0 Hz), 6.92 (d, 1H, J=8.0 Hz), 3.30–3.27 (m, 2H), 3.09 (t, 2H, J=7.0 Hz), 2.76–2.39 (m, 5H), 2.20 (s, 3H), 2.17–1.85 (m, 6H); ESMS m/e: 399.3 (M+H)$^+$.

EXAMPLE 10

N-(3-{1-[4-(4-CHLOROPHENYL)-4-OXOBUTYL]-4-PIPERIDINYL}PHENYL)-2-METHYLPROPANAMIDE: Using Method II, the desired product was obtained. $^1$H NMR (400 MHz, CDCl$_3$) δ 7.93 (d, 2H, J=8.6 Hz), 7.45 (d, 2H, J=8.6 Hz), 7.39 (d, 1H, J=7.2 Hz), 7.32 (s, 1H), 7.24 (t, 1H, J=7.8 Hz), 6.94 (d, 1H, J=8.4 Hz), 3.21–3.18 (m, 2H), 3.05 (t, 2H, J=7.0 Hz), 2.64–2.51 (m, 4H), 2.28–1.86 (m, 8H), 1.26 (d, 6H, J=6.8 Hz); ESMS m/e: 427.3 (M+H)$^+$.

EXAMPLE 11

N-(3-{1-[4-(4-CHLOROPHENYL)-4-OXOBUTYL]-4-PIPERIDINYL}PHENYL)CYCLOHEXANECARBOXAMIDE: Using Method II, the desired product was obtained. $^1$H NMR (400 MHz, CDCl$_3$) δ 7.93 (d, 2H, J=8.4 Hz), 7.55–7.19 (m, 5H), 6.93 (d, 1H, J=7.6 Hz), 3.25–3.00 (m, 4H), 2.65–2.45 (m, 4H), 2.30–1.50 (m, 18H); ESMS m/e: 467.3 (M+H)$^+$.

EXAMPLE 12

N-(3-{1-[4-(4-CHLOROPHENYL)-4-OXOBUTYL]-4-PIPERIDINYL}PHENYL)-2-PHENYLACETAMIDE: Using Method II, the desired product was obtained. $^1$H NMR (400 MHz, CDCl$_3$) δ 7.92 (d, 2H, J=8.4 Hz), 7.46–7.26 (m, 9H), 7.20 (t, 1H, J=7.6 Hz), 6.92 (d, 1H, J=7.6 Hz), 3.75 (s, 2H), 3.15–3.13 (m, 2H), 3.03 (t, 2H, J=7.0 Hz), 2.64–2.46 (m, 3H), 2.22–1.60 (m, 8H); ESMS m/e: 475.3 (M+H)$^+$.

EXAMPLE 13

N-(3-{1-[4-(4-CHLOROPHENYL)-4-OXOBUTYL]-4-PIPERIDINYL}PHENYL)-2-(3-METHOXYPHENYL)ACETAMIDE: Using Method II, the desired product was obtained. $^1$H NMR (400 MHz, CDCl$_3$) δ 7.92 (d, 2H, J=8.4 Hz), 7.44 (d, 2H, J=8.4 Hz) 7.38 (s, 1H), 7.35–7.25 (m, 3H), 7.19 (t, 1H, J=7.8 Hz), 6.94–6.86 (m, 3H), 3.81 (s, 3H), 3.72 (s, 2H), 3.12–3.09 (m, 2H), 3.02 (t, 2H, J=6.8 Hz), 2.57–2.44 (m, 3H), 2.20–1.60 (m, 8H); ESMS m/e: 505.3 (M+H)$^+$.

EXAMPLE 14

N-(3-{1-[4-(4-CHLOROPHENYL)-4-OXOBUTYL]-4-PIPERIDINYL}PHENYL)-2-METHOXYACETAMIDE: Using Method II, the desired product was obtained. $^1$H NMR (400 MHz, CDCl$_3$) δ 7.93 (d, 2H, J=8.4 Hz), 7.50–7.25 (m, 5H), 6.98 (d, 1H, J=7.8 Hz), 4.01 (s, 2H), 3.57 (s, 3H), 3.30–3.15 (m, 2H), 3.06 (t, 2H, J=6.8 Hz), 2.70–2.50 (m, 3H), 2.35–1.80 (m, 8H); ESMS m/e: 429.3 (M+H)$^+$.

EXAMPLE 15

N-(3-{1-[4-(4-CHLOROPHENYL)-4-OXOBUTYL]-4-PIPERIDINYL}PHENYL)METHANESULFONAMIDE:

Using Method II, the desired product was obtained. ¹H NMR (400 MHz, CDCl$_3$) δ 7.95–6.96 (m, 8H), 3.48 (s, 3H), 3.28–2.90 (m, 6H), 2.80–2.57 (m, 3H), 2.38–1.86 (m, 6H); ESMS m/e: 435.2 (M+H)$^+$.

EXAMPLE 16

N-(3-{1-[4-(4-CHLOROPHENYL)-4-OXOBUTYL]-4-PIPERIDINYL}PHENYL)ETHANESULFONAMIDE: Using Method II, the desired product was obtained. ¹H NMR (400 MHz, CDCl$_3$) δ 7.93 (d, 2H, J=8.2 Hz), 7.45 (d, 2H, J=8.2 Hz), 7.30–7.08 (m, 3H), 6.99 (d, 1H, J=7.6 Hz), 3.26–3.02 (m, 6H), 2.69–2.45 (m, 3H), 2.32–1.75 (m, 8H), 1.36 (t, 3H, J=7.4 Hz); ESMS m/e: 449.3 (M+H)$^+$.

EXAMPLE 17

N-{3-[1-(4-OXO-4-PHENYLBUTYL)-4-PIPERIDINYL]PHENYL}ACETAMIDE: Using Method III, the desired product was obtained. ¹H NMR (400 MHz, CDCl$_3$) δ 8.10–6.80 (m, 9H), 3.40–2.95 (m, 4H), 2.85–2.20 (m, 3H), 2.19 (s, 3H), 2.15–1.70 (m, 8H); ESMS m/e: 365.3 (M+H)$^+$.

EXAMPLE 18

2-METHYL-N-{3-[1-(4-OXO-4-PHENYLBUTYL)-4-PIPERIDINYL]PHENYL}PROPANAMIDE: Using Method II, the desired product was obtained. ¹H NMR (400 MHz, CDCl$_3$) δ 7.99 (d, 2H, J=7.4 Hz), 7.57 (t, 1H, J=7.4 Hz), 7.48 (t, 2H, J=7.4 Hz), 7.45–7.20 (m, 2H), 7.24 (t, 1H, J=8.0 Hz), 6.94 (d, 1H, 8.0 Hz), 3.24–3.21 (m, 2H), 3.09 (t, 2H, J=7.0 Hz), 2.57–2.25 (m, 4H), 2.31–1.84 (m, 8H), 1.26 (d, 6H, J=7.2 Hz); ESMS m/e: 393.3 (M+H)$^+$.

EXAMPLE 19

N-{3-[1-(4-OXO-4-PHENYLBUTYL)-4-PIPERIDINYL]PHENYL}-2-PHENYLACETAMIDE: Using Method II, the desired product was obtained. ¹H NMR (400 MHz, CDCl$_3$) δ 7.98 (d, 2H, J=7.6 Hz), 7.65–7.15 (m, 11H), 6.92 (d, 2H, J=7.2 Hz), 3.74 (s, 2H), 3.20–2.95 (m, 4H), 2.65–2.40 (m, 3H), 2.25–1.70 (m, 8H); ESMS m/e: 441.3 (M+H)$^+$.

EXAMPLE 20

2-(3-METHOXYPHENYL)-N-{3-[1-(4-OXO-4-PHENYLBUTYL)-4-PIPERIDINYL]PHENYL}ACETAMIDE: Using Method II, the desired product was obtained. ¹H NMR (400 MHz, CDCl$_3$) δ 7.98 (d, 2H, J=7.6 Hz), 7.56 (t, 1H, J=7.62 Hz), 7.46 (t, 2H, J=7.6 Hz), 7.40 (s, 1H), 7.37–7.26 (m, 2H), 7.19 (t, 1H, J=7.8 Hz), 6.94–6.86 (m, 3H), 3.81 (s, 3H), 3.71 (s, 3H), 3.12–3.03 (m, 4H), 2.57–2.44 (m, 3H), 2.16–1.77 (m, 8H); ESMS m/e: 471.3 (M+H)$^+$.

EXAMPLE 21

N-(3-{1-[4-(2,4-DIMETHOXYPHENYL)-4-OXOBUTYL]-4-PIPERIDINYL}PHENYL)ACETAMIDE: Using Method III, the desired product was obtained. ¹H NMR (400 MHz, CDCl$_3$) δ 7.82 (d, 1H, J=8.8 Hz), 7.54 (d, 1H, J=7.6 Hz), 7.33 (s, 1H), 7.22 (t, 1H, J=7.6 Hz), 6.93 (d, 1H, J=7.6 Hz), 6.53 (d, 1H, J=8.8 Hz), 6.46 (s, 1H), 3.90 (s, 3H), 3.86 (s, 3H), 3.48–3.27 (m, 2H), 3.05 (t, 2H, J=6.8 Hz), 2.90–2.68 (m, 2H), 2.65–2.38 (m, 3H), 2.25 (s, 3H), 2.18–1.80 (m, 8H); ESMS m/e: 425.3 (M+H)$^+$.

EXAMPLE 22

N-(3-{1-[4-(2,4-DIMETHOXYPHENYL)-4-OXOBUTYL]-4-PIPERIDINYL}PHENYL)-2-METHYLPROPANAMIDE: Using Method II, the desired product was obtained. ¹H NMR (400 MHz, CDCl$_3$) δ 7.98 (d, 1H, J=8.6 Hz), 7.41–7.37 (m, 2H), 7.24 (t, 1H, J=7.8 Hz), 6.96 (d, 1H, J=7.8 Hz), 6.54 (d, 1H, J=8.6 Hz), 6.46 (s, 1H), 3.89 (s, 3H), 3.86 (s, 3H), 3.11–3.08 (m, 2H), 2.98 (t, 2H, J=7.2 Hz), 2.53–2.46 (m, 4H), 2.13–1.79 (m, 8H), 1.25 (d, 6H, J=6.8 Hz); ESMS m/e: 453.3 (M+H)$^+$.

EXAMPLE 23

N-(3-{1-[4-(2,4-DIMETHOXYPHENYL)-4-OXOBUTYL]-4-PIPERIDINYL)PHENYL)-2-PHENYLACETAMIDE: Using Method II, the desired product was obtained. ¹H NMR (400 MHz, CDCl$_3$) δ 7.85 (m, 12H), 3.89 (s, 3H), 3.86 (s, 3H), 3.74 (s, 2H), 3.22–2.90 (m, 4H), 2.64–2.40 (m, 3H), 2.25–1.70 (m, 8H); ESMS m/e: 501.3 (M+H)$^+$.

EXAMPLE 24

N-(3-{1-[4-(2,4-DIMETHOXYPHENYL)-4-OXOBUTYL]-4-PIPERIDINYL}PHENYL)-2-(3-METHOXYPHENYL)ACETAMIDE: Using Method II, the desired product was obtained. ¹H NMR (400 MHz, CDCl$_3$) δ 7.82 (d, 1H, J=8.8 Hz), 7.48–7.15 (m, 5H), 6.95–6.80 (m, 3H), 6.58–6.45 (m, 2H), 3.89 (s, 3H), 3.86 (s, 3H), 3.81 (s, 3H), 3.72 (s, 2H), 3.25–2.95 (m, 4H), 2.65–2.40 (m, 3H), 2.30–1.95 (m, 4H), 1.93–1.72 (m, 4H); ESMS m/e: 531.3 (M+H)$^+$.

EXAMPLE 25

N-(3-{1-[4-OXO-4-(4-PHENOXYPHENYL)BUTYL]-4-PIPERIDINYL}PHENYL)ACETAMIDE: Using Method III, the desired product was obtained. ¹H NMR (400 MHz, CDCl$_3$) δ 8.15–6.75 (m, 13H), 3.30–2.80 (m, 4H), 2.75–2.10 (m, 5H), 2.03 (s, 3H), 2.00–1.60 (m, 6H); ESMS m/e: 457.3 (M+H)$^+$.

EXAMPLE 26

2-METHYL-N-(3-{1-[4-OXO-4-(4-PHENOXYPHENYL)BUTYL]-4-PIPERIDINYL}PHENYL)PROPANAMIDE: Using Method II, the desired product was obtained. ¹H NMR (400 MHz, CDCl$_3$) δ 7.96 (d, 2H, J=8.8 Hz), 7.43–7.15 (m, 6H), 7.10–6.93 (m, 5H), 3.42–2.95 (m, 4H), 2.80–2.45 (m, 4H), 2.20–1.80 (m, 8H), 1.14 (d, 6H, J=6.8 Hz); ESMS m/e: 485.4 (M+H)$^+$.

EXAMPLE 27

2-(3-METHOXYPHENYL)-N-(3-{1-[4-OXO-4-(4-PHENOXYPHENYL)BUTYL]-4-PIPERIDINYL}PHENYL)ACETAMIDE: Using Method II, the desired product was obtained. ¹H NMR (400 MHz, CDCl$_3$) δ 7.97 (d, 2H, J=8.8 Hz), 7.41–7.18 (m, 7H), 7.08–6.99 (m, 5H), 6.94–6.87 (m, 3H), 3.82 (s, 3H), 3.70 (s, 2H), 3.10–2.95 (m, 4H), 2.55–2.40 (m, 3H), 2.15–1.95 (m, 4H), 1.81–1.70 (m, 4H); ESMS m/e 563.4 (M+H)$^+$.

EXAMPLE 28

N'-(3-{1-[4-(4-CHLOROPHENYL)-4-OXOBUTYL]-4-PIPERIDINYL}PHENYL)-N,N-DIMETRYLSULFAMIDE: Using Method II, the desired product was obtained. ¹H NMR (400 MHz, CDCl$_3$) δ 7.93 (d, 2H, J=8.8 Hz), 7.44 (d, 2H, J=8.8 Hz), 7.27 (s, 1H), 7.25–7.10 (m, 2H), 6.94 (d, 1H, J=7.6 Hz), 3.30–3.10 (m, 2H), 3.04 (t, 2H, J=6.8 Hz), 2.83 (s, 6H), 2.68–2.45 (m, 3H), 2.30–1.75 (m, 8H); ESMS m/e: 464.3 (M+H)$^+$.

EXAMPLE 29

N-(3-{1-[4-OXO-4-(2-THIENYL)BUTYL]-4-PIPERIDINYL}PHENYL)ACETAMIDE: Using Method III, the desired product was obtained. $^1$H NMR (400 MHz, CDCl$_3$) δ 7.90–6.78 (m, 7H), 3.22–2.88 (m, 4H), 2.69–2.25 (m, 5H), 2.02 (s, 3H), 2.00–1.64 (m, 6H); ESMS m/e: 371.2 (M+H)$^+$.

EXAMPLE 30

N-(3-{1-[4-(4-ISOPROPYLPHENYL)-4-OXOBUTYL]-4-PIPERIDINYL}PHENYL)ACETAMIDE: Using Method III, the desired product was obtained. $^1$H NMR (400 MHz, CDCl$_3$) δ 8.00–6.78 (m, 8H), 3.15–2.98 (m, 4H), 2.77–2.15 (m, 4H), 2.03 (s, 3H), 2.00–1.62 (m, 8H), 0.927 (d, 6H, J=6.0 Hz); ESMS m/e: 407.3 (M+H)$^+$.

EXAMPLE 31

N-(3-{1-[4-(4-METHYLPHENYL)-4-OXOBUTYL]-4-PIPERIDINYL}PHENYL)ACETAMIDE: Using Method III, the desired product was obtained. $^1$H NMR (400 MHz, CDCl$_3$) δ 7.90–6.80 (m, 8H), 3.10–2.45 (m, 7H), 2.32 (s, 3H), 2.02 (s, 3H), 2.01–1.68 (m, 8H); ESMS m/e: 379.3 (M+H)$^+$.

EXAMPLE 32

N-(3-{1-[4-(4-BROMOPHENYL)-4-OXOBUTYL]-4-PIPERIDINYL}PHENYL)ACETAMIDE: Using Method III, the desired product was obtained. $^1$H NMR (400 MHz, CDCl$_3$) δ 7.90–6.80 (m, 8H), 3.30–3.05 (m, 4H), 2.70–2.45 (m, 3H), 2.05 (s, 3H), 1.98–1.65 (m, 8H); ESMS m/e: 444.0 (M+H)$^+$.

EXAMPLE 33

N-(3-{1-[4-(3,4-DIMETHYLPHENYL)-4-OXOBUTYL]-4-PIPERIDINYL}PHENYL)-2-PROPANESULFONAMIDE: Using Method II, the desired product was obtained. $^1$H NMR (400 MHz, CDCl$_3$) δ 7.75 (s, 1H), 7.71 (d, 1H, J=7.6 Hz), 7.27–7.00 (m, 5H), 3.32–3.24 (m, 3H), 3.10–3.02 (m, 2H), 2.78–2.50 (m, 3H), 2.32 (s, 6H), 2.19–1.84 (m, 8H), 1.39 (d, 6H, J=6.8 Hz); ESMS m/e: 457.4 (M+H)$^+$.

EXAMPLE 34

N-(3-{1-[4-OXO-4-(4-PHENOXYPHENYL)BUTYL]-4-PIPERIDINYL}PHENYL)-2-PROPANESULFONAMIDE: Using Method II, the desired product was obtained. $^1$H NMR (400 MHz, CDCl$_3$) δ 7.97 (d, 2H, J=7.6 Hz), 7.44 (t, 2H, J=7.6 Hz), 7.27–7.00 (m, 9H), 3.35–2.96 (m, 5H), 2.69–2.45 (m, 3H), 2.14–1.79 (m, 8H), 1.39 (d, 6H, J=6.8 Hz); ESMS m/e: 521.4 (M+H)$^+$.

EXAMPLE 35

N-(3-{1-[3-(4-CHLOROPHENYL)-3-METHOXYPROPYL]-4-PIPERIDINYL}PHENYL)-2-METHYLPROPANAMIDE: A mixture of 3-methoxy-3-(p-chlorophenyl)-1-chloropropane (27.4 mg, 0.125 mmol), 2-methyl-N-[3-(4-piperidinyl)phenyl]propanamide (28.3 mg, 0.125 mmol), diisopropylethylamine (0.50 mL) and catalytic amount of tetrabutylammonium iodide in dioxane (2.0 mL) was stirred at 90° C. for 72 hrs. The reaction mixture was concentrated to a small volume and chromatographed using preparative TLC plates [2.5% of NH$_3$ (2.0 M in methanol) in CHCl$_3$] gave N-(3-{1-[3-(4-chlorophenyl)-3-methoxypropyl]-4-piperidinyl}phenyl)-2-methylpropanamide (39.5 mg, 73.8% yield) as a thick oil: $^1$H NMR δ 7.48 (s, 1H), 7.34–7.3 (m, 2H), 7.25 (m, 4H), 6.96 (d, 1H, J=7.4 Hz), 4.20 (apparent dd, 1H, J=5.9, 7.6 Hz), 3.2 (s, 3H), 3.04 (d, 1H, J=10.1 Hz), 2.99 (d, 1H, J=10.1 Hz), 2.49 (h, 4H, J=6.6 Hz), 2.20–2.10 (m, 4H), 1.82 (m, 4H), 1.25 (d, 6H, J=7.1 Hz); ESMS m/e: 429.4 (M+H)$^+$.

EXAMPLE 36

N-(3-{1-[6-(1,3-DIOXO-1,3-DIHYDRO-2H-ISOINDOL-2-YL)HEXYL]-4-PIPERIDINYL}PHENYL)-2-METHYLPROPANAMIDE: The synthetic method is the same as described for 2-[6-(4-phenyl-1-piperidinyl)hexyl]-1H-isoindole-1,3(2H)-dione. N-(3-{1-[6-(1,3-dioxo-1,3-dihydro-2H-isoindol-2-yl)hexyl]-4-piperidinyl}phenyl)-2-methylpropanamide: 506 mg (56% yield); $^1$H NMR (400 MHz, CDCl$_3$) δ 7.86–7.80 (m, 2H), 7.73–7.68 (m, 2H), 7.44 (s, 1H), 7.37 (d, 1H, J=8.3 Hz), 7.22 (t, 1H, J=7.7 Hz), 6.96 (d, 1H, J=7.7 Hz), 3.69 (t, 2H, J=7.2 Hz), 3.01 (apparent d, 2H, J=11.3 Hz), 2.58–2.40 (m, 2H), 2.33 (m, 2H) 1.98 (dt, 2H, J=3.2, 11.3 Hz), 1.84–1.64 (m, 4H), 1.51 (q, 2H, J=7.1 Hz), 1.43–1.30 (m, 6H), 1.24 (d, 6H, J=6.8 Hz); ESMS m/e: 476.4 (M+H)$^+$.

EXAMPLE 37

N-{3-[1-(3-METHOXY-3-PHENYLPROPYL)-4-PIPERIDINYL]PHENYL}-2-METHYLPROPANAMIDE: A mixture of 3-methoxy-3-phenyl-1-chloropropane (23.1 mg, 0.126 mmol), 2-methyl-N-[3-(4-piperidinyl)phenyl]propanamide (28.3 mg, 0.126 mmol), diisopropylethylamine (0.50 mL) and catalytic amount of tetrabutylammonium iodide in dioxane (2.0 mL) was stirred at 90° C. for 72 hrs. Chromatography using silica preparative TLC plates [2.5% of NH$_3$ (2.0 M in methanol) in CHCl$_3$] gave N-{3-[1-(3-methoxy-3-phenylpropyl)-4-piperidinyl]phenyl}-2-methylpropanamide (45.4 mg, 91.2% yield) as a thick oil: $^1$H NMR (400 MHz, CDCl$_3$) δ 7.45 (s, 1H), 7.34–7.25 (m, 5H), 7.25 (m, 2H), 6.96 (d, 1H, J=7.4 Hz), 4.20 (apparent dd, 1H, J=5.9, 7.6 Hz), 3.2 (s, 3H), 3.04 (d, 1H, J=10.1 Hz), 2.99 (d, 1H, J=10.1 Hz), 2.49 (apparent sept, partially hidden, 4H, J=6.6 Hz), 2.3–2.1 (m, 4H), 1.82 (m, 4H), 1.25 (d, 6H, J=7.1 Hz); ESMS m/e: 395.4 (M+H)$^+$.

EXAMPLE 38

N-(3-{1-[4-(1,3-DIOXO-1,3-DIHYDRO-2H-ISOINDOL-2-YL)BUTYL]-4-PIPERIDINYL}PHENYL)-2-METHYLPROPANAMIDE: The synthetic method is the same as described for 2-[6-(4-phenyl-1-piperidinyl)hexyl]-1H-isoindole-1,3(2H)-dione. N-(3-{1-[4-(1,3-dioxo-1,3-dihydro-2H-isoindol-2-yl)butyl]-4-piperidinyl}phenyl)-2-methylpropanamide: 664 mg (74% yield); $^1$H NMR (400 MHz, CDCl$_3$) δ 7.87–7.78 (m, 2H), 7.76–7.64 (m, 2H), 7.47 (s, 1H), 7.39 (d, 1H, J=7.6 Hz), 7.21 (t, 1H, J=8.1 Hz), 6.94 (d, 1H, J=7.6 Hz), 3.72 (t, 2H, J=6.8 Hz), 3.37–3.22 (m, 2H), 3.0 (apparent d, 2H, J=10.7 Hz), 2.75 (q, 2H, J=7.0 Hz), 2.64–2.33 (m, 4H), 1.99 (dt, 2H, J=2.6, 11.7 Hz), 1.86–1.65 (m, 2H), 1.63–1.50 (m, 2H), 1.23 and 1,21 (two d, 6H, J=5.5 Hz); ESMS m/e: 448.4 (M+H)+; Anal. Calc. for C$_{27}$H$_{34}$N$_3$ClO$_3$+0.4H$_2$O: C, 66.02; H, 7.14; N, 8.55. Found: C, 66.07; H, 6.78; N, 8.65.

EXAMPLE 39

N-(3-{1-[4-(1,3-DIOXO-1,3-DIHYDRO-2H-ISOINDOL-2-YL)BUTYL]-4-PIPERIDINYL}PHENYL)-2-METHYLPROPANAMIDE: The synthetic method is the same as described for 2-[6-(4-phenyl-1-piperidinyl)hexyl]-

1H-isoindole-1,3(2H)-dione. N-(3-(1-[5-(1,3-dioxo-1,3-dihydro-2H-isoindol-2-yl)pentyl]-4-piperidinyl}phenyl)-2-methylpropanamide: 614 mg (64% yield); $^1$H NMR (400 MHz, CDCl$_3$) δ 7.87–7.8 (m, 2H), 7.76–7.68 (m, 2H), 7.48 (s, 1H), 7.41 (d, 1H, J=7.6 Hz), 7.21 (t, 1H, J=7.6 Hz), 6.95 (d, 1H, J=7.6 Hz), 3.69 (t, 2H, J=7.2 Hz), 3.39–3.28 (m, 2H), 3.02 (apparent d, 2H, J=11.6 Hz), 2.78 (q, 2H, J=7.2 Hz), 2.64–2.52 (m, 1H), 2.52–2.40 (m, 1H), 2.40–2.31 (m, 2H), 2.01 (dt, 2H, J=3.7, 11.1 Hz), 1.85–1.64 (m, 2H), 1.58 (q, 2H, J=7.6 Hz), 1.45–1.32 (m, 2H), 1.23 (d, 6H, J=6.9 Hz); ESMS m/e: 462.4 (M+H)+; Anal. Calc. for C$_{28}$H$_{36}$N$_3$ClO$_3$: C, 67.52; H, 7.29; N, 8.44. Found: C, 67.04; H, 7.06; N, 8.38.

EXAMPLE 40

2-METHYL-N-{3-[1-(4-PHENYLBUTYL)-4-PIPERIDINYL]PHENYL)PROPANAMIDE: A mixture of 2-methyl-N-[3-(4-piperidinyl)phenyl]propanamide (28.3 mg, 0.100 mmol), 4-phenyl-1-chlorobutane (21.1 mg, 0.125 mmol), diisopropylethylamine (0.50 mL), catalytic amount of tetrabutylammonium iodide and dioxane (2.0 mL) was heated at reflux temperature for 3 days. The reaction mixture was concentrated and chromatographed using preparative TLC plates [2.5% of NH$_3$ (2.0 M in methanol) in CHCl$_3$] afforded the product, 2-methyl-N-{3-[1-(4-phenylbutyl)-4-piperidinyl]phenyl}propanamide (9.50 mg, 25.1% yield) as a thick oil: $^1$H NMR δ 7.37 (s, 1H), 7.29 (apparent d, 1H, J=7.9 Hz), 7.18 (m, 3H), 7.11 (m, 3H), 6.90 (apparent d, 1H, J=7.9 Hz), 3.02 (d, 2H, J=6.8 Hz), 2.41 (m, 4H, partially hidden), 2.01 (m, 2H), 1.78 (m, 4H), 1.57 (m, 4H), 1.18 (d, 6H, J=7.7 Hz); ESMS m/e: 379.4 (M+H)$^+$.

EXAMPLE 41

N-(3-{1-[3-(1,3-DIOXO-1,3-DIHYDRO-2H-ISOINDOL-2-YL)PROPYL]-4-PIPERIDINYL}PHENYL)-2-METHYLPROPANAMIDE: The synthetic method is the same as described for 2-[6-(4-phenyl-1-piperidinyl)hexyl]-1H-isoindole-1,3(2H)-dione. N-(3-{1-[3-(1,3-dioxo-1,3-dihydro-2H-isoindol-2-yl)propyl]-4-piperidinyl}phenyl)-2-methylpropanamide: 810 mg (93% yield); $^1$H NMR (400 MHz, CDCl$_3$) δ 7.87–7.82 (m, 2H), 7.73–7.68 (m, 2H), 7.57 (s, 1H), 7.36 (d, 1H, J=8.5 Hz), 7.18 (t, 1H, J=7.7 Hz), 6.79 (d, 1H, J=7.1 Hz), 3.78 (t, 2H, J=6.8 Hz), 3.06 (quintet, 2H, J=6 Hz), 2.95 (apparent d, 2H, J=12.2 Hz), 2.58–2.31 (m, 4H), 1.96–1.83 (m, 2H), 1.70 (apparent d, 2H, J=12.1 Hz), 1.52 (dt, 2H, J=3.5, 12.5 Hz), 1.03 (d, 6H, J=6.5 Hz); ESMS m/e: 434.4 (M+H)$^+$.

EXAMPLE 42

N-(3-{1-[(3S)-3-HYDROXY-3-PHENYLPROPYL]-4-PIPERIDINYL}PHENYL)-2-METHYLPROPANAMIDE: A mixture of (S)-(–)-3-chloro-1-phenyl-1-propanol (0.426 g, 2.50 mmol, 99%ee), 2-methyl-N-[3-(4-piperidinyl)phenyl]propanamide (0.565 g, 2.00 mmol), diisopropylethylamine (1.29 g, 10.0 mmol), dioxane (5.0 mL) and catalytic amount of tetrabutylammonium iodide was stirred at 90° C. for 72 hrs. Chromatography using silica preparative TLC plates [2.5% of NH$_3$ (2.0 M in methanol) in CHCl$_3$] gave the desired product (306 mg, 39.3% yield) as a thick oil: $^1$H NMR (400 MHz, CDCl$_3$) δ 7.46 (s, 1H), 7.42 (d, 4H, J=8.1 Hz), 7.35 (m, 1H), 7.30 (d, 1H, J=8.0 Hz), 7.23 (t, 1H, J=8.1 Hz), 7.12 (s, 1H), 6.96 (apparent dd, 1H, J=8.0 Hz), 5.0 (apparent dd, 1H, J=4.4, 8.3 Hz), 3.18 (apparent dd, 2H, J=2.5, 12.5 Hz), 2.74 (m, 2H), 2.50 (m, 2H), 2.3–2.1 (m, 6H), 1.8 (m, 2H), 1.25 (d, 6H, J=7.1 Hz); ESMS m/e: 389.2 (M+H)$^+$.

EXAMPLE 43

N-(3-{1-[3-METHOXY-3-(4-METHYLPHENYL)PROPYL]-4-PIPERIDINYL}PHENYL)-2-METHYLPROPANAMIDE: A mixture of 3-methoxy-3-(p-tolyl)-1-chloropropane (24.9 mg, 0.126 mmol), 2-methyl-N-[3-(4-piperidinyl)phenyl]propanamide (28.3 mg, 0.126 mmol), diisopropylethylamine (0.50 mL) and catalytic amount of tetrabutylammonium iodide in dioxane (2.0 mL) was stirred at 90° C. for 72 hrs. Chromatography using silica preparative TLC plates [2.5% of NH$_3$ (2.0 M in methanol) in CHCl$_3$] gave the desired product (10.9 mg, 21.2% yield) as a thick oil: $^1$H NMR (400 MHz, CDCl$_3$) δ 7.44 (s, 1H), 7.38 (m, 1H), 7.3–7.1 (m, 5H), 6.96 (d, 1H, J=7.4 Hz), 4.18 (apparent dd, 1H, J=5.6, 7.9 Hz), 3.24 (d, 1H, J=8.2 Hz), 3.2 (s, 3H), 3.11 (m, 2H, J=10.1 Hz), 2.49 (m, 4H), 2.35 (s, 3H), 2.3–2.1 (m, 3H), 1.92 (d, 4H), 1.25 (d, 6H, J=7.1 Hz); ESMS m/e: 409.4 (M+H)$^+$.

EXAMPLE 44

N-{3-[1-(3-ISOPROPOXY-3-PHENYLPROPYL)-4-PIPERIDINYL]PHENYL)-2-METHYLPROPANAMIDE: A mixture of 3-isopropyl-3'-phenyl-1- chloropropane (26.6 mg, 0.126 mmol), 2-methyl-N-(3-(4-piperidinyl)phenyl]propanamide (28.3 mg, 0.126 mmol), diisopropylethylamine (0.50 mL) and catalytic amount of tetrabutylammonium iodide in dioxane (2.0 mL) was stirred at 90° C. for 72 hrs. Chromatography using silica preparative TLC plates [2.5% of NH$_3$ (2.0 M in methanol) in CHCl$_3$] gave the desired product (14.1 mg, 26.5% yield) as a thick oil: $^1$H NMR (400 MHz, CDCl$_3$) δ 7.46 (s, 1H), 7.43–7.37 (m, 2H), 7.33 (m, 3H), 7.23 (m, 2H), 6.95 (d, 1H, J=8.4 Hz), 4.46 (apparent dd, 1H, J=5.0, 8.3 Hz), 3.49 (apparent sept, 1H, J=7.1 Hz), 3.10 (s, 2H), 2.70 (m, 2H), 2.52 (apparent sept, partially hidden, 4H, J=6.6 Hz), 2.30–2.10 (m, 2H), 1.90–1.80 (d, 4H), 1.25 (d, 6H, J=7.1 Hz), 1.15 (d, 3H, J=6.4 Hz), 1.08 (d, 3H, J=6.4 Hz); ESMS m/e: 423.4 (M+H)$^+$.

EXAMPLE 45

N-(3-{1-[4,4-BIS(4-FLUOROPHENYL)BUTYL]-4-PIPERIDINYL}PHENYL)-2-METHYLPROPANAMIDE: A mixture of 4,4-bis(4-fluoro-phenyl)-1-chloro-butane (39.0 mg, 0.126 mmol), 2-methyl-N-[3-(4-piperidinyl)phenyl]propanamide (28.3 mg, 0.126 mmol), diisopropylethylamine (0.50 mL) and catalytic amount of tetrabutylammonium iodide in dioxane (2.0 mL) was stirred at 90° C. for 72 hrs. Chromatography using silica preparative TLC plates [2.5% of NH$_3$ (2.0 M in methanol) in CHCl$_3$] gave the desired product (15.9 mg, 25.2% yield) as a thick oil: $^1$H NMR (400 MHz, CDCl$_3$) δ 8.02 (s, 1H), 7.41 (s, 1H), 7.3–7.15 (m, 4H), 7.10 (m, 3H), 6.89 (apparent t, 5H), 3.81 (t, 1H, J=7.8 Hz), 3.30 (s, 1H), 2.91 (d, 1H, J=12,5 Hz), 2.80 (m, 1H), 2.40 (m, 2H), 2.31 (t, 1H, J=8.0 Hz), 1.93 (apparent q, 3H, J=8.0 Hz), 1.72 (m, 3H), 1.40 (m, 2H), 1.20 (m, 2H), 1.15 (d, 6H, J=8.1 Hz); ESMS m/e: 491.4 (M+H)$^+$.

EXAMPLE 46

N-{3-[1-(3-METHOXYBENZYL)-4-PIPERIDINYL]PHENYL}-2-METHYLPROPANAMIDE: A mixture of 2-methyl-N-[3-(4-piperidinyl)phenyl]propanamide (28.3 mg, 0.100 mmol), 3-methoxybenzyl chloride (19.6 mg, 0.125 mmol), diisopropylethylamine (0.50 mL), catalytic amount of tetrabutylammonium iodide and dioxane (2.0 mL). Chromatography using silica preparative TLC plates [2.5% of NH$_3$ (2.0 M in methanol) in CHCl$_3$] afforded the desired product (10.2 mg, 27.9% yield) as a yellow solid: $^1$H NMR (400 MHz, CDCl$_3$) δ 7.46 (s, 1H), 7.35 (apparent d, 1H, J=8.3 Hz), 7.27–7.21 (m, 2H), 6.95 (apparent t, 3H, J=6.9 Hz), 6.82 (apparent dd, 1H, J=2.4, 8.3 Hz), 3.84 (m, 3H), 3.56 (s, 2H), 3.05 (d, 2H, J=10.5 Hz), 2.51 (apparent sept, partially hidden, 4H, J=7.2 Hz), 2.13 (apparent t, 2H, J=9.7 Hz), 1.88 (m, 2H), 1.25 (d, 6H, J=6.7 Hz); ESMS m/e: 367.3 (M+H)$^+$.

EXAMPLE 47

N-(3-{1-[3,5-BIS(TRIFLUOROMETHYL)BENZYL]-4-PIPERIDINYL}PHENYL)-2-METHYLPROPANAMIDE: A mixture of 2-methyl-N-[3-(4-piperidinyl)phenyl]propanamide (28.3 mg, 0.100 mmol), 3,5-bis(trifluoromethyl)benzyl bromide (38.4 mg, 0.125 mmol), diisopropylethylamine (0.50 mL), catalytic amount of tetrabutylammonium iodide and dioxane (2.0 mL). Chromatography using silica preparative TLC plates [2.5% of NH$_3$ (2.0 M in methanol) in CHCl$_3$] gave the desired product (12.2 mg, 25.8% yield) as a thick oil: $^1$H NMR (400 MHz, CDCl$_3$) δ 7.83 (s, 2H), 7.77 (s, 1H), 7.53 (s, 1H), 7.30–7.21 (m, 2H), 7.16 (s, 1H), 6.98 (apparent d, 1H, J=7.6 Hz), 3.62 (s, 2H), 2.94 (d, 2H, J=9.4 Hz), 2.51 (apparent sept, partially hidden, 2H, J=6.6 Hz), 2.14 (m, 2H), 1.82 (m, 4H), 1.25 (d, 6H, J=6.6 Hz); ESMS m/e: 473.2 (M+H)$^+$.

EXAMPLE 48

N-(3-{1-[(3R)-3-(3,4-DIMETHOXYPHENOXY)-3-PHENYLPROPYL]-4-PIPERIDINYL}PHENYL)-2-METHYLPROPANAMIDE

Method A

4-{[(1R)-3-chloro-1-phenylpropyl]oxy}-1,2-dimethoxybenzene: A mixture of 3,4-dimethoxyphenol (4.07 g, 26.4 mmol), (S)-(−)-3-chloro-phenyl-1-propanol (4.50 g, 26.4 mmol, 99%ee, Aldrich Chemical Co.), triphenylphosphine (6.92 g, 26.4 mmol) and diethyl azodicarboxylate (4.59 g, 26.4 mmol) in THF (110 mL) was stirred at room temperature for 24 h. The reaction mixture was concentrated in vacuo. At this point, the residue can either be washed with pentane (×3) and the combined pentane extracts were concentrated and chromatographed (silica with hexanes-EtOAc 8:1 as the eluent) to give the desired product (as described as a general procedure by: Srebnik, M.; Ramachandran, P. V.; Brown, H. C. *J. Org. Chem.* 1988, 53, 2916–2920). This procedure was performed on a smaller scale reaction and only a 40% yield of the product was realized.

Alternatively, on a larger scale (26.4 mmol), the crude product was triturated with a small amount of dichloromethane and the precipitated triphenylphosphine oxide was filtered. The filtrate was concentrated and the crude product was chromatographed to give the desired product as a thick yellow oil (7.30 g, 88.9% yield): $^1$H NMR (400 MHz, CDCl$_3$) δ 7.39–7.32 (m, 4H), 7.20 (m, 1H), 6.64 (d, 1H, J=8.7 Hz), 6.51 (d, 1H, J=2.7 Hz), 6.30 (dd, 1H, J=2.7, 8.7 Hz), 5.27 (apparent dd, 1H, J=4.5, 8.7 Hz), 3.79 (s, 3H), 3.77 (s, 3H), 3.61 (m, 1H), 2.45 (m, 1H), 2.20 (m, 1H), 1.80 (s, 1H); ESMS m/e: 307.11 (M+H)$^+$.

N-(3-{1-[(3R)-3-(3,4-DIMETHOXYPHENOXY)-3-PHENYLPROPYL]-4-PIPERIDINYL}PHENYL)-2-METHYLPROPANAMIDE: A mixture of potassium carbonate (321 mg, 2.32 mmol), sodium iodide (522 mg, 3.48 mmol), 2-methyl-N-[3-(4-piperidinyl)phenyl]propanamide (570 mg, 2.32 mmol) and 4-{[(1R)-3-chloro-1-phenylpropyl]oxy}-1,2-dimethoxybenzene (712 mg, 2.32 mmol) in DMF (5.0 mL) was stirred at 100° C. for 3 hrs, at which time TLC indicated that the reaction was complete. The reaction mixture was poured into water (50 mL) and the aqueous layer was extracted with methylene chloride (3×30 mL). The combined organic extracts were washed with brine (30 mL), dried over MgSO$_4$ and concentrated under reduced pressure. The crude product was purified by Prep-TLC plates [2.5% of NH$_3$ (2.0 M in methanol) in CHCl$_3$] to afford the product (970 mg, 90.1%) as a thick oil.

Method B

Into a 25-mL RB-flask was added triphenylphosphine (9.80 mg, 0.0375 mmol), diethyl azodicarboxylate (5.22 mg, 0.0300 mmol), N-(3-{1-[(3S)-3-hydroxy-3-phenylpropyl]-4-piperidinyl}phenyl)-2-methylpropanamide (9.53 mg, 0.0250 mmol), 3,4-dimethoxyphenol (7.70 mg, 0.050 mmol) and THF (1.0 mL) at room temperature. The reaction mixture was stirred at room temperature overnight (16 hrs). The solvent was removed under reduced pressure and the residue was purified by preparative TLC plates [2.5% of NH$_3$ (2.0 M in methanol) in CHCl$_3$] to afford the desired product (4.4 mg, 34.1% yield) as a thick oil: $^1$H NMR (400 MHz, CDCl$_3$) δ 7.46 (s, 1H), 7.40–7.30 (m, 4H), 7.25 (m, 3H), 6.97 (d, 1H, J=7.8 Hz), 6.64 (d, 1H, J=9.1 Hz), 6.51 (d, 1H, J=2.6 Hz), 6.29 (d, 1H, J=2.6, 9.1 Hz), 5.20 (apparent dd, 1H, J=4.4, 8.5 Hz), 3.80 (s, 3H), 3.77 (s, 3H), 3.23 (m, 2H), 2.77 (m, 2H), 2.5 (m, 2H), 2.3–2.1 (m, 6H), 1.80 (m, 2H), 1.25 (d, 6H, J=7.9 Hz); ESMS m/e: 517.4 (M+H)$^+$.

EXAMPLE 49

2-METHYL-N-(3-{1-[(3S)-3-PHENOXY-3-PHENYLPROPYL]-4-PIPERIDINYL}PHENYL)PROPANAMIDE: A mixture of N-(3-{1-[(3R)-3-hydroxy-3-phenylpropyl]-4-piperidinyl}phenyl)-2-methylpropanamide (9.53 mg, 0.0250 mmol), phenol (4.70 mg, 0.050 mmol), triphenylphosphine (9.80 mg, 0.0375 mmol) and diethyl azodicarboxylate (5.22 mg, 0.0300 mmol) in THF (1.0 mL) was stirred at room temperature for 3 days. Chromatography using silica preparative TLC plates [2.5% of NH$_3$ (2.0 M in methanol) in CHCl$_3$] gave the desired product (2.7 mg, 23.6% yield) as a thick oil: $^1$H NMR δ 7.46 (s, 2H), 7.40–7.30 (m, 4H), 7.25 (m, 3H), 7.20 (m, 2H), 6.97 (apparent d, 1H, J=7.4 Hz), 6.89 (apparent tt, 1H, J=0.8, 7.6 Hz), 6.84 (apparent dt, 1H, J=0.8, 8.0 Hz), 5.20 (apparent dd, 1H, J=4.4, 8.5 Hz), 3.35 (m, 2H), 2.91 (m, 2H), 2.60 (m, 2H), 2.30–2.10 (m, 6H), 1.90 (m, 2H), 1.25 (d, 6H, J=7.9 Hz); ESMS m/e: 457.4 (M+H)$^+$;

EXAMPLE 50

N-(3-{1-[(3S)-3-(4-METHOXYPHENOXY)-3-PHENYLPROPYL]-4-PIPERIDINYL}PHENYL)-2-METHYLPROPANAMIDE: A mixture of N-(3-{1-[(3R)-3-hydroxy-3-phenylpropyl]-4-piperidinyl}phenyl)-2-methylpropanamide (9.53 mg, 0.0250 mmol), 4-methoxyphenol (6.20 mg, 0.050 mmol), triphenylphosphine (9.80 mg, 0.0375 mmol) and diethyl azodicarboxylate (5.2 mg, 0.0300 mmol) in THF (1.0 mL) was stirred at room temperature for 3 days. Chromatography using silica preparative TLC plates [2.5% of NH$_3$ (2.0 M in methanol) in CHCl$_3$] gave the desired product (4.6 mg, 37.9% yield) as a thick oil. $^1$H NMR (400 MHz, CDCl$_3$) δ 7.38–7.14 (m, 8H), 6.90 (apparent d, 1H, J=7.7 Hz), 6.72–6.46 (m, 4H), 5.09 (apparent dd, 1H, J=4.8, 8.1 Hz), 3.64 (s, 3H), 3.18 (m, 2H), 2.73 (m, 2H), 2.50 (m, 2H), 2.37–1.72 (m, 8H), 1.25 (d, 6H, J=7.4 Hz); ESMS m/e: 487.4 (M+H)$^+$.

EXAMPLE 51

N-(3-{1-[(3S)-3-(3-CHLOROPHENOXY)-3-PHENYLPROPYL]-4-PIPERIDINYL}PHENYL)-2-

METHYLPROPANAMIDE: A mixture of N-(3-{1-[(3R)-3-hydroxy-3-phenylpropyl]-4-piperidinyl}phenyl)-2-methylpropanamide (9.53 mg, 0.0250 mmol), 3-chlorophenol (6.40 mg, 0.050 mmol), triphenylphosphine (9.80 mg, 0.0375 mmol) and diethyl azodicarboxylate (5.22 mg, 0.0300 mmol) in THF (1.0 mL) was stirred at room temperature for 3 days. Chromatography using silica preparative TLC plates [2.5% of $NH_3$ (2.0 M in methanol) in $CHCl_3$] gave the desired product (4.9 mg, 40.0% yield) as a thick oil: $^1$H NMR (400 MHz, $CDCl_3$) δ 7.39 (s, 1H), 7.35–7.10 (m, 7H), 7.02 (t, 1H, J=8.0 Hz), 6.90 (d, 1H, J=7.6 Hz), 6.84–6.75 (m, 2H), 6.65 (m, 1H), 5.09 (apparent dd, 1H, J=4.99, 8.1 Hz), 3.10 (m, 2H), 2.60 (m, 2H), 2.50 (m, 2H), 2.30–1.70 (m, 8H), 1.18 (d, 6H, J=6.8 Hz); ESMS m/e: 491.4 (M+H)$^+$.

EXAMPLE 52

N-(3-{1-[(3S)-3-(4-CHLOROPHENOXY)-3-PHENYLPROPYL]-4-PIPERIDINYL}PHENYL)-2-METHYLPROPANAMIDE: A mixture of N-(3-{1-[(3R)-3-hydroxy-3-phenylpropyl]-4-piperidinyl}phenyl)-2-methylpropanamide (9.53 mg, 0.0250 mmol), 4-chlorophenol (6.40 mg, 0.050 mmol), triphenylphosphine (9.80 mg, 0.0375 mmol) and diethyl azodicarboxylate (5.22 mg, 0.0300 mmol) in THF (1.0 mL) was stirred at room temperature for 3 days. Chromatography using silica preparative TLC plates [2.5% of $NH_3$ (2.0 M in methanol) in $CHCl_3$] gave the desired product (3.3 mg, 26.9% yield) as a thick oil: $^1$H NMR δ 7.36 (s, 1H), 7.35–7.22 (m, 7H), 7.12 (m, 2H), 6.97 (apparent d, 1H, J=7.2 Hz), 6.77 (m, 2H), 5.23 (m, 1H), 3.18 (m, 2H), 2.70 (m, 2H), 2.50 (m, 2H), 2.40–1.80 (m, 8H), 1.25 (d, 6H, J=6.8 Hz); ESMS m/e: 491.4 (M+H)$^+$.

EXAMPLE 53

2-METHYL-N-[3-(1-{(3S)-3-PHENYL-3-[4-(TRIFLUOROMETHYL)PHENOXY]PROPYL}-4-PIPERIDINYL)PHENYL]PROPANAMIDE: A mixture of N-(3-{1-[(3R)-3-hydroxy-3-phenylpropyl]-4-piperidinyl}phenyl)-2-methylpropanamide (9.53 mg, 0.0250 mmol), 4-trifluoromethylphenol (8.100 mg, 0.050 mmol), triphenylphosphine (9.8 mg, 0.0375 mmol) and diethyl azodicarboxylate (5.22 mg, 0.0300 mmol) in THF (1.0 mL) was stirred at room temperature for 3 days. Chromatography using silica preparative TLC plates [2.5% of $NH_3$ (2.0 M in methanol) in $CHCl_3$] gave the desired product (5.10 mg, 38.9% yield) as a thick oil: $^1$H NMR δ 8.06 (s, 1H), 7.49 (s, 1H), 7.44 (apparent d, 2H, J=0.6 Hz), 7.38–7.30 (m, 4H), 7.30–7.20 (m, 3H), 6.96 (apparent d, 1H, J=7.6 Hz), 6.91 (apparent d, 2H, J=8.6 Hz), 5.34 (m, 1H), 3.19 (m, 2H), 2.72 (m, 2H), 2.53 (m, 2H), 2.40–1.80 (m, 8H), 1.25 (d, 6H, J=6.8 Hz); ESMS m/e: 525.4 (M+H)$^+$.

EXAMPLE 54

N-(3-{1-[(3R)-3-(2,5-DIFLUOROPHENOXY)-3-PHENYLPROPYL]-4-PIPERIDINYL}PHENYL)-2-METHYLPROPANAMIDE: A mixture of N-(3-{1-[(3R)-3-hydroxy-3-phenylpropyl]-4-piperidinyl}phenyl)-2-methylpropanamide (9.53 mg, 0.0250 mmol), 2,5-difluorophenol (6.50 mg, 0.050 mmol), triphenylphosphine (9.80 mg, 0.0375 mmol) and diethyl azodicarboxylate (5.22 mg, 0.0300 mmol) in THF (1.0 mL) was stirred at room temperature for 3 days. Chromatography using silica preparative TLC plates [2.5% of $NH_3$ (2.0 M in methanol) in $CHCl_3$] gave the desired product (3.60 mg, 29.3% yield) as a thick oil: $^1$H NMR δ 7.46 (s, 1H), 7.40–7.32 (m, 4H), 7.31–7.20 (m, 2H), 7.17 (s, 1H), 7.01–6.92 (m, 2H), 6.65–6.42 (m, 2H), 5.27 (m, 1H), 3.13 (m, 2H), 2.64 (m, 2H), 2.51 (m, 2H), 2.28–1.80 (m, 8H), 1.25 (d, 6H, J=7.1 Hz); ESMS m/e: 493.4 (M+H)$^+$.

EXAMPLE 55

N-(3-{1-[(3R)-3-(3,4-DICHLOROPHENOXY)-3-PHENYLPROPYL]-4-PIPERIDINYL}PHENYL)-2-METHYLPROPANAMIDE: A mixture of N-(3-{1-[(3S)-3-hydroxy-3-phenylpropyl]-4-piperidinyl}phenyl)-2-methylpropanamide (9.53 mg, 0.0250 mmol), 3,4-dichlorophenol (8.20 mg, 0.050 mmol), triphenylphosphine (9.80 mg, 0.0375 mmol) and diethyl azodicarboxylate (5.22 mg, 0.0300 mmol) in THF (1.0 mL) was stirred at room temperature for 3 days. Chromatography using silica preparative TLC plates [2.5% of $NH_3$ (2.0 M in methanol) in $CHCl_3$] gave the desired product (5.20 mg, 39.7% yield) as a thick oil: $^1$H NMR ($CDCl_3$) δ 7.70–7.63 (m, 2H), 7.55 (m, 1H), 7.47–7.43 (m, 3H), 7.40–7.19 (m, 3H), 7.00–6.50 (m, 2H), 6.69 (dd, 1H, J=2.2, 8.8 Hz), 5.25 (m, 1H), 3.20 (m, 2H), 2.70 (m, 2H), 2.53 (m, 2H), 2.40–2.20 (m, 4H), 2.10–1.80 (m, 4H), 1.25 (d, 6H, J=7.1 Hz); ESMS m/e: 525.4 (M+H)$^+$.

EXAMPLE 56

2-METHYL-N-(3-{1-[(3R)-3-PHENOXY-3-PHENYLPROPYL]-4-PIPERIDINYL}PHENYL)PROPANAMIDE: A mixture of N-(3-{1-[(3S)-3-hydroxy-3-phenylpropyl]-4-piperidinyl}phenyl)-2-methylpropanamide (9.53 mg, 0.0250 mmol), phenol (4.70 mg, 0.050 mmol), triphenylphosphine (9.80 mg, 0.0375 mmol) and diethyl azodicarboxylate (5.22 mg, 0.0300 mmol) in THF (1.0 mL) was stirred at room temperature for 3 days. Chromatography using silica preparative TLC plates [2.5% of $NH_3$ (2.0 M in methanol) in $CHCl_3$] gave the desired product (4.1 mg, 36.0% yield) as a thick oil: $^1$H NMR (400 MHz, $CDCl_3$) δ 7.45 (s, 1H), 7.40–7.15 (m, 10H), 6.97 (d, 1H, J=7.6 Hz), 6.88–6.82 (m, 2H), 5.26 (m, 1H), 3.18 (m, 2H), 2.75 (m, 2H), 2.53 (m, 2H), 2.40–2.10 (m, 4H), 2.10–1.80 (m, 4H), 1.25 (d, 6H, J=6.9 Hz); ESMS m/e: 457.4 (M+H)$^+$.

EXAMPLE 57

N-(3-{1-[(3R)-3-HYDROXY-3-PHENYLPROPYL]-4-PIPERIDINYL}PHENYL)-2-METHYLPROPANAMIDE

Method A

Into a 25-mL RB-flask was added (R)-(+)-3-chloro-1-phenyl-1-propanol (0.545 g, 3.19 mmol, 99%ee, Aldrich Chemical Co.), 2-methyl-N-[3-(4-piperidinyl)phenyl] propanamide (0.748 g, 3.04 mmol), potassium carbonate (0.420 g, 3.04 mmol) and sodium iodide (0.684 g, 4.56 mmol) and DMF (6.0 mL) at room temperature. After stirring at 100° C. for 3 hrs, the TLC showed the reaction was complete. The reaction mixture was poured into water (50 mL) and the aqueous layer was extracted with methylene chloride (3×20 mL). The combined organic extracts were washed with brine (20 mL), dried over $Na_2SO_4$ and concentrated under reduced pressure. The residue was purified by flash chromatography (1:1=hexane:ethyl acetate with 1% isopropylamine) to afford the desired product (1.09 g, 94.3% yield) as light-yellow solid: $^1$H NMR (400 MHz, $CDCl_3$) δ 8.10 (s, 1H), 7.46–7.35 (m, 6H), 7.27 (m, 2H), 6.98 (apparent d, 1H, J=7.6 Hz), 5.02 (apparent dd, 1H, J=4.4, 8.1 Hz), 3.18 (apparent dd, 2H, J=2.5, 12.5 Hz), 2.74 (m, 2H), 2.50 (m, 2H), 2.30–2.10 (m, 6H), 1.80 (m, 2H), 1.25 (d, 6H, J=7.1 Hz); ESMS m/e: 381.2 (M+H)$^+$.

The hydrochloric salt was prepared by addition of a slight excess of 1 N HCl in ether (1.2 eq.) to a solution of the free base in dichloromethane. The solvent was removed under reduced pressure, the residue was washed with ether and dried under reduced pressure: Anal. Calc. for $C_{24}H_{32}N_2O_2$+ HCl+0.8H$_2$O: C, 66.82; H, 8.08; N, 6.49; Cl, 8.22. Found: C, 66.90; H, 7.78; N, 6.63; Cl, 8.52.

Method B

Into a 25-mL RB-flask was added (R)-(+)-3-chloro-1-phenyl-1-propanol (0.426 g, 2.50 mmol), 2-methyl-N-[3-(4-piperidinyl)phenyl]propanamide (0.565 g, 2.00 mmol), diisopropylethylamine (1.29 g, 10.0 mmol), dioxane (5.0 mL) and catalytic amount of tetrabutylammonium iodide at room temperature. After stirring at 90° C. for 72 hrs, the reaction mixture was poured into water (50 mL) and the aqueous layer was extracted with methylene chloride (3×20 mL). The combined organic extracts were washed with brine (20 mL), dried over Na$_2$SO$_4$ and concentrated under reduced pressure. The residue was purified by preparative TLC plates (1:5:100=isopropylamine:methanol:ethyl acetate) to afford the desired product (0.260 g, 34.2% yield) as light-yellow solid.

EXAMPLE 58

N-(3-{1-[(3S)-3-(4-CYANO-PHEONXY)-3-PHENYLPROPYL]-4-PIPERIDINYL}PHENYL)-2-METHYLPROPANAMIDE: N-(3-{1-[(3S)-3-(4-cyanophenoxy)-3-phenylpropyl]-4-piperidinyl}phenyl)-2-methylpropanamide A mixture of N-(3-{1-[(3R)-3-hydroxy-3-phenylpropyl]-4-piperidinyl}phenyl)-2-methylpropanamide (5.20 mg, 0.0137 mmol), 4-cyanophenol (100 mg), triphenylphosphine (30.0 mg, 0.115 mmol) and diethyl azodicarboxylate (7.42 mg, 0.0426 mmol) in THF (0.50 mL) was stirred at room temperature for 3 days. Chromatography using silica preparative TLC plates [2.5% of NH$_3$ (2.0 M in methanol) in CHCl$_3$] gave the desired product (4.70 mg, 71.3% yield) as a thick oil: $^1$H NMR (400 MHz, CDCl$_3$) δ 7.54 (m, 2H), 7.48 (d, 2H, J=8.4 Hz), 7.30–7.20 (m, 3H), 7.20 (m, 3H), 6.97 (apparent d, 1H, J=8.4 Hz), 6.92 (apparent d, 2H, J=8.4 Hz), 5.36 (apparent dd, 1H, J=3.9, 7.6 Hz), 3.12 (m, 2H), 2.61 (m, 2H), 2.53 (apparent sept, partially hidden, 2H, J=7.6 Hz), 2.30–2.10 (m, 6H), 1.82 (m, 2H), 1.25 (d, 6H, J=6.8 Hz); ESMS m/e: 482.2 (M+H)$^+$.

EXAMPLE 59

N-(3-{1-[(3S)-3-(4-FLUOROPHENOXY)-3-PHENYLPROPYL]-4-PIPERIDINYL}PHENYL)-2-METHYLPROPANAMIDE: A mixture of N-(3-{1-[(3R)-3-hydroxy-3-phenylpropyl]-4-piperidinyl}phenyl)-2-methylpropanamide (5.20 mg, 0.0137 mmol), 4-fluorophenol (100 mg), triphenylphosphine (30.0 mg, 0.115 mmol) and diethyl azodicarboxylate (7.42 mg, 0.0426 mmol) in THF (0.50 mL) was stirred at room temperature for 3 days. Chromatography using silica preparative TLC plates [2.5% of NH$_3$ (2.0 M in methanol) in CHCl$_3$] gave the desired product (4.20 mg, 64.7% yield) as a thick oil: $^1$H NMR (400 MHz, CDCl$_3$) δ 7.40 (m, 2H), 7.30–7.20 (m, 5H), 7.20 (m, 3H), 6.97 (apparent d, 1H, J=7.7 Hz), 6.87 (m, 1H), 6.76 (m, 1H), 5.26 (apparent dd, 1H, J=4.0, 8.1 Hz), 3.09 (m, 2H), 2.66 (m, 2H), 2.51 (m, 2H), 2.3–2.1 (m, 6H), 1.82 (m, 2H), 1.25 (d, 6H, overlapped); ESMS m/e: 475.2 (M+H)$^+$.

EXAMPLE 60

N-(3-{1-[(3S)-3-(4-BROMOPHENOXY)-3-PHENYLPROPYL]-4-PIPERIDINYL}PHENYL)-2-METHYLPROPANAMIDE: A mixture of N-(3-{1-[(3R)-3-hydroxy-3-phenylpropyl]-4-piperidinyl}phenyl)-2-methylpropanamide (5.20 mg, 0.0137 mmol), 4-bromophenol (100 mg), triphenylphosphine (30.0 mg, 0.115 mmol) and diethyl azodicarboxylate (7.42 mg, 0.0426 mmol) in THF (0.50 mL) was stirred at room temperature for 3 days. Chromatography using silica preparative TLC plates [2.5% of NH$_3$ (2.0 M in methanol) in CHCl$_3$] the desired product (0.70 mg, 9.6% yield) as a thick oil: $^1$H NMR (400 MHz, CDCl$_3$) δ 8.06 (s, 1H), 7.48 (m, 2H), 7.30–7.20 (m, 5H), 7.20 (m, 3H), 6.97 (apparent d, 1H, J=8.5 Hz), 6.73 (apparent d, 2H, J=8.5 Hz), 5.22 (apparent dd, 1H, J=4.9, 7.8 Hz), 3.15 (m, 2H), 2.65 (m, 2H), 2.51 (apparent sept, partially hidden, 2H, J=7.6 Hz), 2.30–2.10 (m, 6H), 1.82 (m, 2H), 1.25 (d, 6H, J=6.8 Hz); ESMS m/e: 535.1 (M+H)$^+$.

EXAMPLE 61

N-(3-{1-[(3S)-3-(3-METHOXYPHENOXY)-3-PHENYLPROPYL]-4-PIPERIDINYL}PHENYL)-2-METHYLPROPANAMIDE: A mixture of N-(3-{1-[(3R)-3-hydroxy-3-phenylpropyl]-4-piperidinyl}phenyl)-2-methylpropanamide (5.20 mg, 0.0137 mmol), 3-methoxyphenol (100 mg), triphenylphosphine (30.0 mg, 0.115 mmol) and diethyl azodicarboxylate (7.42 mg, 0.0426 mmol) in THF (0.50 mL) was stirred at room temperature for 3 days. Chromatography using silica preparative TLC plates [2.5% of NH$_3$ (2.0 M in methanol) in CHCl$_3$] gave the desired product (3.1 mg, 46.6% yield) as a thick oil: $^1$H NMR (400 MHz, CDCl$_3$) δ 7.47 (d, 1H, J=6.7 Hz), 7.42 (s, 1H), 7.3–7.20 (m, 3H), 7.20 (m, 3H), 7.07 (t, 1H, J=8.4 Hz), 6.97 (apparent d, 1H, J=6.7 Hz), 6.40 (m, 3H), 5.27 (apparent dd, 1H, J=5.3, 8.0 Hz), 3.74 (s, 3H), 3.38 (m, 2H), 2.93 (m, 2H), 2.61 (s, 1H), 2.53 (apparent sept, partially hidden, 1H, J=6.5 Hz), 2.30–2.10 (m, 6H), 1.82 (m, 2H), 1.25 (d, 6H, J=6.9 Hz); ESMS m/e: 487.3 (M+H)$^+$.

EXAMPLE 62

N-(3-{1-[(3S)-3-(4-CYANO-2-METHOXYPHENOXY)-3-PHENYLPROPYL]-4-PIPERIDINYL}PHENYL)-2-METHYLPROPANAMIDE: A mixture of N-(3-{1-[(3R)-3-hydroxy-3-phenylpropyl]-4-piperidinyl}phenyl)-2-methylpropanamide (5.20 mg, 0.0137 mmol), 2-methoxy-4-cyanophenol (100 mg), triphenylphosphine (30.0 mg, 0.115 mmol) and diethyl azodicarboxylate (7.42 mg, 0.0426 mmol) in THF (0.50 mL) was stirred at room temperature for 3 days. Chromatography using silica preparative TLC plates [2.5% of NH$_3$ (2.0 M in methanol) in CHCl$_3$] gave the desired product (5.50 mg, 76.5% yield) as a thick oil: $^1$H NMR (400 MHz, CDCl$_3$) δ 7.51 (s, 1H), 7.38 (s, 1H), 7.37 (d, 2H, J=2.4 Hz), 7.20 (m, 4H), 7.10 (d, 1H, J=2.4 Hz), 7.08 (s, 1H), 6.99 (apparent d, 1H, J=8.3 Hz), 6.76 (apparent d, 1H, J=8.3 Hz), 5.43 (apparent dd, 1H, J=5.1, 8.0 Hz), 3.91 (s, 3H), 3.34 (m, 2H), 2.63 (m, 2H), 2.63 (s, 1H), 2.53 (apparent sept, partially hidden, 1H, J=7.7 Hz), 2.30–2.10 (m, 6H), 1.82 (m, 2H), 1.28 (d, 6H, J=6.8 Hz); ESMS m/e: 512.2 (M+H)$^+$.

EXAMPLE 63

N-(3-{1-[(3S)-3-(5-ACETYL-2-METHOXYPHENOXY)-3-PHENYLPROPYL]-4-PIPERIDINYL}PHENYL)-2-METHYLPROPANAMIDE: A mixture of N-(3-{1-[(3R)-3-hydroxy-3-phenylpropyl]-4-piperidinyl}phenyl)-2-methylpropanamide (5.20 mg, 0.0137 mmol), 2-methoxy-5-acetylphenol (100 mg), triphenylphosphine (30.0 mg, 0.115 mmol) and diethyl azodicarboxylate (7.42 mg, 0.0426 mmol) in THF (0.50 mL) was stirred at room temperature for 3 days. Chromatography using silica preparative TLC plates [2.5% of NH$_3$ (2.0 M in methanol) in CHCl$_3$] gave the desired product (1.60 mg, 22.2% yield) as a thick oil: $^1$H NMR (400 MHz, CDCl$_3$) δ 7.52 (d, 2H, J=2.4 Hz), 7.3–7.2 (m, 5H), 7.20 (m, 3H), 6.97 (apparent d, 1H, J=6.7 Hz), 6.69 (apparent d, 1H, J=8.0 Hz), 5.47 (apparent dd, 1H, J=4.3, 7.8 Hz), 3.95 (s, 3H), 3.38 (m, 2H), 2.93 (m, 2H), 2.61 (s, 1H), 2.53 (apparent sept, partially hidden, 1H, J=7.6 Hz), 2.50 (s, 3H), 2.30–2.10 (m, 6H), 1.82 (m, 2H), 1.25 (d, 6H, J=6.8 Hz); ESMS m/e: 529.6 (M+H)$^+$.

EXAMPLE 64

N-(3-{1-[(3R)-3-(2-ACETYLPHENOXY)-3-PHENYLPROPYL]-4-PIPERIDINYL}PHENYL)-2-METHYLPROPANAMIDE: A mixture of N-(3-{1-[(3S)-3-hydroxy-3-phenylpropyl]-4-piperidinyl}phenyl)-2-methylpropanamide (5.2 mg, 0.0137 mmol), 2-acetylphenol (100 mg), triphenylphosphine (30.0 mg, 0.115 mmol) and diethyl azodicarboxylate (7.42 mg, 0.0426 mmol) in THF (0.50 mL) was stirred at room temperature for 3 days. Chromatography using silica preparative TLC plates [2.5% of NH$_3$ (2.0 M in methanol) in CHCl$_3$] gave the desired product (1.70 mg, 24.9% yield) as a thick oil: $^1$H NMR (400 MHz, CDCl$_3$) δ 7.65 (m, 1H), 7.55 (s, 1H), 7.30–7.20 (m, 5H), 7.20 (m, 3H), 6.97 (m, 2H), 6.76 (apparent d, 1H), 5.49 (apparent dd, 1H, J=4.3, 8.0 Hz), 3.38 (m, 2H), 2.93 (m, 2H), 2.71 (s, 3H), 2.60 (s, 1H), 2.53 (apparent sept, partially hidden, 1H, J=7.6 Hz), 2.30–2.10 (m, 6H), 1.82 (m, 2H) 1.25 (d, 6H, J=6.9 Hz); ESMS m/e: 498.8 (M$^+$).

EXAMPLE 65

N-[3-(1-{(3R)-3-[2-FLUORO-5-(TRIFLUOROMETHYL)PHENOXY]-3-PHENYLPROPYL}-4-PIPERIDINYL)PHENYL]-2-METHYLPROPANAMIDE: A mixture of N-(3-{1-[(3S)-3-hydroxy-3-phenylpropyl]-4-piperidinyl}phenyl)-2-methylpropanamide (5.20 mg, 0.0137 mmol), 2-fluoro-5-trifluoromethylphenol (100 mg), triphenylphosphine (30.0 mg, 0.115 mmol) and diethyl azodicarboxylate (7.42 mg, 0.0426 mmol) in THF (0.50 mL) was stirred at room temperature for 3 days. Chromatography using silica preparative TLC plates [2.5% of NH$_3$ (2.0 M in methanol) in CHCl$_3$] gave the desired product (2.50 mg, 33.7% yield) as a thick oil: $^1$H NMR (400 MHz, CDCl$_3$) δ 8.07 (s, 1H), 7.67 (m, 1H), 7.54 (m, 1H), 7.45 (m, 2H), 7.30–7.10 (m, 6H), 7.14 (d, 1H, J=7.4 Hz), 6.97 (apparent d, 1H, J=7.7 Hz), 5.37 (apparent dd, 1H, J=5.0, 8.5 Hz), 3.4 (m, 2H), 2.8 (m, 2H), 2.6 (s, 1H), 2.53 (apparent sept, partially hidden, 1H, J=7.4 Hz), 2.30–2.10 (m, 6H), 1.80 (m, 2H), 1.25 (d, 6H, J=7.1 Hz, overlapped); ESMS m/e: 542.6 (M+), 543.54 (M+H)$^+$.

EXAMPLE 66

N-[3-(1-{(3S)-3-[2-FLUORO-5-(TRIFLUOROMETHYL)PHENOXY]-3-PHENYLPROPYL}-4-PIPERIDINYL)PHENYL]-2-METHYLPROPANAMIDE: A mixture of N-(3-{1-[(3R)-3-hydroxy-3-phenylpropyl]-4-piperidinyl}phenyl)-2-methylpropanamide (5.20 mg, 0.0137 mmol), 2-fluoro-5-trifluoromethylphenol (100 mg), triphenylphosphine (30.0 mg, 0.115 mmol) and diethyl azodicarboxylate (7.42 mg, 0.0426 mmol) in THF (0.50 mL) was stirred at room temperature for 3 days. Chromatography using silica preparative TLC plates [2.5% of NH$_3$ (2.0 M in methanol) in CHCl$_3$] gave the desired product (3.00 mg, 40.4% yield) as a thick oil: $^1$H NMR (400 MHz, CDCl$_3$) δ 8.06 (s, 1H), 7.67 (m, 2H), 7.55 (m, 2H), 7.50–7.40 (m, 3H), 7.30–7.10 (m, 3H), 7.17 (d, 1H, J=8.9 Hz), 7.07 (apparent d, 1H, J=6.7 Hz), 6.97 (apparent d, 1H, J=7.8 Hz), 5.37 (apparent dd, 1H, J=4.2, 8.1 Hz), 3.37 (m, 2H), 2.93 (m, 2H), 2.63 (s, 1H), 2.50 (apparent sept, partially hidden, 1H, J=7.9 Hz), 2.30–2.10 (m, 6H), 1.85 (m, 2H), 1.25 (d, 6H, J=6.9 Hz); ESMS m/e: 542.7 (M+H)$^+$.

EXAMPLE 67

N-(3-{1-[(3S)-3-(2,5-DIFLUOROPHENOXY)-3-PHENYLPROPYL]-4-PIPERIDINYL}PHENYL)-2-METHYLPROPANAMIDE: A mixture of N-(3-{1-[(3R)-3-hydroxy-3-phenylpropyl]-4-piperidinyl}phenyl)-2-methylpropanamide (5.20 mg, 0.0137 mmol), 2,5-difluorophenol (100 mg), triphenylphosphine (30.0 mg, 0.115 mmol) and diethyl azodicarboxylate (7.42 mg, 0.0426 mmol) in THF (0.50 mL) was stirred at room temperature for 3 days. Chromatography using silica preparative TLC plates [2.5% of NH$_3$ (2.0 M in methanol) in CHCl$_3$] gave the desired product (2.70 mg, 40.1% yield) as a thick oil: $^1$H NMR (400 MHz, CDCl$_3$) δ 7.46 (s, 1H), 7.40–7.30 (m, 4H), 7.20 (m, 2H), 7.17 (s, 1H), 6.97 (m, 2H), 6.58 (m, 1H), 6.51 (m, 1H), 5.27 (apparent dd, 1H, J=5.1, 8.2 Hz), 3.13 (apparent d, J=9.7 Hz, 2H), 2.64 (m, 2H), 2.51 (m, 2H), 2.34 (apparent sept, partially hidden, J=7.1 Hz, 1H), 2.17 (m, 3H), 1.90–1.80 (m, 4H), 1.25 (d, 6H, J=7.1 Hz); ESMS m/e: 493.1 (M+H)$^+$.

EXAMPLE 68

N-(3-{1-[(3R)-3-(3-CHLOROPHENOXY)-3-PHENYLPROPYL]-4-PIPERIDINYL}PHENYL)-2-METHYLPROPANAMIDE: A mixture of N-(3-{1-[(3S)-3-hydroxy-3-phenylpropyl]-4-piperidinyl}phenyl)-2-methylpropanamide (5.20 mg, 0.0137 mmol), 3-chlorophenol (100 mg), triphenylphosphine (30.0 mg, 0.115 mmol) and diethyl azodicarboxylate (7.42 mg, 0.0426 mmol) in THF (0.50 mL) was stirred at room temperature for 3 days. Chromatography using silica preparative TLC plates [2.5% of NH$_3$ (2.0 M in methanol) in CHCl$_3$] gave the desired product (2.4 mg, 35.8% yield) as a thick oil: $^1$H NMR (400 MHz, CDCl$_3$) δ 7.30 (m, 2H), 7.30–7.20 (m, 3H), 7.20 (m, 3H), 6.90 (apparent d, 1H, J=7.7 Hz), 6.71 (apparent d, 1H, J=2.9 Hz), 6.69 (apparent t, 1H, J=2.9 Hz), 6.67 (apparent t, 1H, J=2.9 Hz), 6.65 (apparent d, 1H, J=2.9 Hz), 5.09 (apparent dd, 1H, J=4.8, 8.1 Hz), 3.18 (m, 2H), 2.73 (m, 2H), 2.50 (apparent sept, partially hidden, 2H, J=7.1 Hz), 2.30–2.10 (m, 6H), 1.89 (m, 2H), 1.25 (d, 6H, overlapped); ESMS m/e: 491.1 (M+H)$^+$.

EXAMPLE 69

(1S)-3-{4-[3-(ISOBUTYRYLAMINO)PHENYL]-1-PIPERIDINYL}-1-PHENYLPROPYL 1-NAPHTHOATE: Into a 25-mL RB-flask was added N-(3-{1-[(3S)-3-hydroxy-3-phenylpropyl]-4-piperidinyl}phenyl)-2-methylpropanamide (5.20 mg, 0.0137 mmol), 1-naphthalenecarbonyl chloride (100 mg), diisopropylethylamine (0.30 mL) in THF (0.50 mL) at room temperature. After stirring for 16 hrs at room temperature, the reaction mixture was concentrated under reduced pressure. The residue was purified using preparative TLC plates [2.5% of NH$_3$ (2.0 M in methanol) in CHCl$_3$] gave the desired product (4.70 mg, 71.3% yield) as a thick oil: $^1$H NMR (400 MHz, CDCl$_3$) δ 8.90 (d, 1H, J=8.9 Hz), 8.28 (apparent dd, 1H, J=1.5, 7.2 Hz), 8.03 (d, 1H, J=8.7 Hz), 7.88 (dm, 2H, J=8.7 Hz), 7.60–7.48 (m, 7H), 7.40–7.32 (m, 3H), 7.25 (m, 1H), 6.90 (apparent d, 1H, J=7.4 Hz), 6.18 (apparent dd, 1H, J=5.7, 7.8 Hz), 3.42 (m, 2H), 2.84 (m, 2H), 2.53 (m, 2H), 2.44 (apparent sept, partially hidden, 4H, J=7.5 Hz), 2.30–2.10 (m, 2H), 1.82 (m, 2H), 1.25 (d, 6H, J=6.8 Hz); ESMS m/e: 535.6 (M+H)⁺.

EXAMPLE 70

N-(3-{1-[(3S)-3-(3-ACETYLPHENOXY)-3-PHENYLPROPYL]-4-PIPERIDINYL}PHENYL)-2-METHYLPROPANAMIDE: A mixture of N-(3-{1-[(3R)-3-hydroxy-3-phenylpropyl]-4-piperidinyl}phenyl)-2-methylpropanamide (5.20 mg, 0.0137 mmol), 2-acetylphenol (100 mg), triphenylphosphine (30.0 mg, 0.115 mmol) and diethyl azodicarboxylate (7.42 mg, 0.0426 mmol) in THF (0.50 mL) was stirred at room temperature for 3 days. Chromatography using silica preparative TLC plates [2.5% of $NH_3$ (2.0 M in methanol) in $CHCl_3$] gave the desired product (1.50 mg, 22.0% yield) as a thick oil: ¹H NMR (400 MHz, $CDCl_3$) δ 7.65 (m, 1H), 7.55 (s, 1H), 7.30–7.20 (m, 5H), 7.20 (m, 3H), 6.97 (m, 2H), 6.76 (apparent d, 1H), 5.49 (apparent dd, 1H, J=4.3, 8.0 Hz), 3.38 (m, 2H), 2.93 (m, 2H), 2.75 (s, 3H), 2.53 (apparent sept, partially hidden, 2H, J=7.6 Hz), 2.30–2.10 (m, 6H), 1.92 (m, 2H), 1.25 (d, 6H, J=6.9 Hz); ESMS m/e: 498.81 (M⁺), 499.6 (M+H)⁺.

EXAMPLE 71

N-(3-{1-[(3S)-3-(2-FLUOROPHENOXY)-3-PHENYLPROPYL]-4-PIPERIDINYL}PHENYL)-2-METHYLPROPANAMIDE: A mixture of N-(3-{1-[(3R)-3-hydroxy-3-phenylpropyl]-4-piperidinyl}phenyl)-2-methylpropanamide (5.20 mg, 0.0137 mmol), 2-fluorophenol (100 mg), triphenylphosphine (30.0 mg, 0.115 mmol) and diethyl azodicarboxylate (7.42 mg, 0.0426 mmol) in THF (0.50 mL) was stirred at room temperature for 3 days. Chromatography using silica preparative TLC plates [2.5% of $NH_3$ (2.0 M in methanol) in $CHCl_3$] gave the desired product (3.5 mg, 53.9% yield) as a thick oil: ¹H NMR (400 MHz, $CDCl_3$) δ 8.07 (s, 1H), 7.65 (m, 1H), 7.41 (s, 1H), 7.40–7.10 (m, 5H), 7.05 (m, 2H), 6.97 (apparent d, 1H, J=8.7 Hz), 6.86 (m, 2H), 6.79 (apparent dt, 1H, J=2.4, 7.9 Hz), 5.31 (apparent dd, 1H, J=4.5, 8.0 Hz), 3.39 (m, 2H), 2.97 (m, 2H), 2.53 (apparent sept, partially hidden, 2H, J=7.5 Hz), 2.3–2.1 (m, 6H), 1.92 (m, 2H), 1.25 (d, 6H, J=6.7 Hz); ESMS m/e: 475.7 (M+H)⁺.

EXAMPLE 72

(4S)-N-(3-{4-[3-(ACETYLAMINO)PHENYL]-1-PIPERIDINYL}PROPYL)-4-(3,5-DIFLUOROPHENYL)-2-OXO-1,3-OXAZOLIDINE-3-CARBOXAMIDE

Method: Into a 20 ml vial was added N1-{3-[1-(3-aminopropyl)-4-piperidyl]phenyl}acetamide (15 mg, 0.054 mmol), (4S)-4-(3,5-difluorophenyl)-2-oxo-oxazolidine-3-carboxylic acid-4-nitro-phenyl ester (39.3 mg, 1.08 mmol, 2 eq) and dichloromethane with 0.6% of methanol (3 ml) at room temperature. After stirring at room temperature for 3 hrs, the reaction mixture was filtered, and purified by preparative silica TLC (19:1=chloroform:methanol) to afford the desired product (18.3 mg, 68% yield); ¹H NMR (400 MHz, $CDCl_3$) δ 8.09 (br s, 1H), 7.40 (d, 1H, J=8.0 Hz), 7.36–7.28 (m, 2H), 7.24 (t, 1H, J=8.0 Hz), 6.99 (d, 1H, J=8.0 Hz), 6.86–6.82 (m, 2H), 5.41 (dd, 1H, J=4.1, 9.0 Hz), 4.72 (t, 1H, J=9.0 Hz), 4.22 (dd, 1H, J=3.9, 9.1 Hz), 3.42–3.29 (m, 2H), 3.02 (d, 2H J=11.1 Hz), 2.52–2.38 (m, 3H), 2.16 (s, 3H), 2.08–1.98 (m, 2H), 1.86–1.70 (m, 6H); ESMS m/e: 501.2 (M+H)⁺; Anal. Calc. for $C_{26}H_{30}F_2N_4O_4+0.5H_2O$: C, 60.64; H, 6.18; N, 10.88. Found: C, 60.67; H, 5.79; N, 10.86.

EXAMPLE 73

The synthetic method is the same as described for the synthesis of (4S)-N-(3-{4-[3-(acetylamino)phenyl]-1-piperidinyl}propyl)-4-(3,5-difluorophenyl)-2-oxo-1,3-oxazolidine-3-carboxamide.

(4S)-N-(3-{4-[3-(ACETYLAMINO)PHENYL]-1-PIPERIDINYL}PROPYL)-2-OXO-4-(3,4,5-TRIFLUOROPHENYL)-1,3-OXAZOLIDINE-3-CARBOXAMIDE: 18.8 mg (67% yield); ¹H NMR (400 MHz, $CDCl_3$) δ 8.09 (br s, 1H), 7.41–7.20 (m, 3H), 7.02–6.91 (m, 3H), 5.37 (dd, 1H, J=3.8, 8.9 Hz), 4.71 (t, 1H, J=9 Hz), 4.21 (dd, 1H, J=4, 9.3 Hz), 3.43–3.27 (m, 2H), 3.02 (d, 2H, J=11.0 Hz), 2.53–2.37 (m, 3H), 2.16 (s, 3H), 2.08–1.97 (m, 2H), 1.85–1.69 (m, 6H); ESMS m/e: 519.2 (M+H)⁺; Anal. Calc. for $C_{26}H_{29}F_3N_4O_4+0.5H_2O$: C, 59.20; H, 5.73; N, 10.62. Found: C, 59.40; H, 5.35; N, 10.65.

EXAMPLE 74

The synthetic method is the same as described for the synthesis of (4S)-N-(3-{4-[3-(acetylamino)phenyl]-1-piperidinyl}propyl)-4-(3,5-difluorophenyl)-2-oxo-1,3-oxazolidine-3-carboxamide.

N-(3-{4-[3-(ACETYLAMINO)PHENYL]-1-PIPERIDINYL}PROPYL)-4-(3,4-DIFLUOROPHENYL)-5,5-DIMETHYL-2-OXO-1,3-OXAZOLIDINE-3-CARBOXAMIDE: 19.6 mg (68% yield); ¹H NMR (400 MHz, $CDCl_3$) δ 8.18 (t, 1H, J=5.9 Hz), 7.41 (d, 1H, J=8.8 Hz), 7.33 (s, 1H), 7.27–7.14 (m, 2H), 7.02–6.88 (m, 3H), 5.04 (s, 1H), 3.34 (qm, 2H, J=6.3 Hz), 3.02 (dm, 2H, J=10.9 Hz), 2.53–2.38 (m, 3H), 2.16 (s, 3H), 2.07–1.96 (m, 2H), 1.87–1.69 (m, 6H), 1.62 (s, 3H), 1.02 (s, 3H); ESMS m/e: 529.3 (M+H)⁺; Anal. Calc. for $C_{28}H_{34}F_2N_4O_4$: C, 63.62; H, 6.48; N, 10.60. Found: C, 63.15; H, 6.27; N, 10.48.

EXAMPLE 75

The synthetic method is the same as described for the synthesis of (4S)-N-(3-{4-[3-(acetylamino)phenyl]-1-piperidinyl}propyl)-4-(3,5-difluorophenyl)-2-oxo-1,3-oxazolidine-3-carboxamide.

(4S,5R)-N-(3-{4-[3-(ACETYLAMINO)PHENYL]-1-PIPERIDINYL}PROPYL)-4-(3,4-DIFLUOROPHENYL)-5-METHYL-2-OXO-1,3-OXAZOLIDINE-3-CARBOXAMIDE: 20.5 mg (74% yield); ¹H NMR (400 MHz, $CDCl_3$) δ 8.14 (t, 1H, J=5.5 Hz), 7.40 (d, 1H, J=7.8 Hz), 7.37–6.89 (m, 6H), 5.35 (d, 1H, J=7.5 Hz), 5.02–4.93 (m, 1H), 3.41–3.25 (m, 2H), 3.02 (d, 2H, J=10.8 Hz), 2.53–2.37 (m, 3H), 2.16 (s, 3H), 2.07 (m, 2H), 1.89–1.68 (m, 6H), 1.04 (d, 3H, J=6.4 Hz); ESMS m/e: 515.3 (M+H)⁺; Anal. Calc. for $C_{27}H_{32}F_2N_4O_4+0.5H_2O$: C, 61.94; H, 6.35; N, 10.70. Found: C, 61.90; H, 6.13; N, 10.64.

EXAMPLE 76

The synthetic method is the same as described for the synthesis of (4S)-N-(3-{4-[3-(acetylamino)phenyl]-1-piperidinyl}propyl)-4-(3,5-difluorophenyl)-2-oxo-1,3-oxazolidine-3-carboxamide.

N-(3-{4-[3-(ACETYLAMINO)PHENYL]-1-PIPERIDINYL}PROPYL)-4-(4-FLUOROBENZYL)-2-OXO-1,3-OXAZOLIDINE-3-CARBOXAMIDE: 17.4 mg (65% yield); ¹H NMR (400 MHz, $CDCl_3$) δ 8.08 (t, 1H, J=5.6 Hz), 7.4 (d, 1H, J=7.2 Hz), 7.34 (s, 1H), 7.28–7.14 (m, 3H), 7.05–6.95 (m, 3H), 4.69–4.60 (m, 1H), 4.26 (t, 1H, J=8.8 Hz), 4.15 (dd, 1H, J=3.2, 9 Hz), 3.43 (q, 2H, J=6.2 Hz), 3.3 (dm 1H, J=13.6 Hz), 3.04 (dm, 2H, J=11 Hz), 2.87 (dd, 1H, J=9.3, 14.4 Hz), 2.53–2.42 (m, 3H), 2.16 (s, 3H), 2.09–1.99 (m, 2H), 1.87–1.65 (m, 6H); ESMS m/e: 497.3 (M+H)⁺; Anal. Calc. for $C_{27}H_{33}FN_4O_4+0.5H_2O$: C, 64.14; H, 6.78; N, 11.08. Found: C, 64.26; H, 6.39; N, 11.12.

EXAMPLE 77

2-METHYL-N-(3-{1-[(3R)-3-(2-NITROPHENOXY)-3-PHENYLPROPYL]-4-PIPERIDINYL}PHENYL) PROPANAMIDE: A mixture of N-(3-{1-[(3S)-3-hydroxy-3-phenylpropyl]-4-piperidinyl}phenyl)-2-methylpropanamide (5.20 mg, 0.0137 mmol), 2-nitrophenol (100 mg), triphenylphosphine (30.0 mg, 0.115 mmol) and diethyl azodicarboxylate (7.42 mg, 0.0426 mmol) in THF (0.50 mL) was stirred at room temperature for 3 days. Chromatography using silica preparative TLC plates [2.5% of $NH_3$ (2.0 M in methanol) in $CHCl_3$] gave the desired product (2.37 mg, 34.5% yield) as a thick oil: $^1$H NMR (400 MHz, $CDCl_3$) δ 7.84 (d, 1H), 7.90 (m, 1H), 7.45 (m 1H), 7.30–7.20 (m, 5H), 7.20 (m, 2H), 6.98 (m, 2H), 6.89 (apparent d, 1H, J=7.7 Hz), 5.62 (apparent dd, 1H, J=4.1, 8.9 Hz), 3.10 (m, 2H), 2.60 (m, 2H), 2.53 (m, 2H), 2.30–2.10 (m, 6H), 1.90 (m, 2H), 1.25 (d, 6H, overlapped); ESMS m/e: 502.3 $(M+H)^+$.

EXAMPLE 78

N-(3-{1-[(3S)-3-([1,1'-BIPHENYL]-4-YLOXY)-3-PHENYLPROPYL]-4-PIPERIDINYL}PHENYL)-2-METHYLPROPANAMIDE: A mixture of N-(3-{1-[(3R)-3-hydroxy-3-phenylpropyl]-4-piperidinyl}phenyl)-2-methylpropanamide (5.20 mg, 0.0137 mmol), 4-phenylphenol (100 mg), triphenylphosphine (30.0 mg, 0.115 mmol) and diethyl azodicarboxylate (7.42 mg, 0.0426 mmol) in THF (0.50 mL) was stirred at room temperature for 3 days. Chromatography using silica preparative TLC plates [2.5% of $NH_3$ (2.0 M in methanol) in $CHCl_3$] gave the desired product (3.00 mg, 41.2% yield) as a thick oil: $^1$H NMR (400 MHz, $CDCl_3$) δ 8.06 (s, 1H), 7.48 (m, 2H), 7.40–7.30 (m, 8H), 7.30–7.25 (m, 4H), 6.97 (apparent d, 1H, J=7.6 Hz), 6.91 (apparent d, 2H, J=8.7 Hz), 5.34 (apparent dd, 1H, J=4.4, 8.0 Hz), 3.40 (m, 2H), 2.98 (m, 2H), 2.53 (apparent sept, partially hidden, 1H, J=8.1 Hz), 2.44 (m, 1H), 2.30–2.10 (m, 6H), 1.93 (d, 2H), 1.26 (d, 6H, J=6.9 Hz); ESMS m/e: 533.4 $(M+H)^+$.

EXAMPLE 79

2-METHYL-N-(3-{1-[(3R)-3-(3-NITROPHENOXY)-3-PHENYLPROPYL]-4-PIPERIDINYL}PHENYL) PROPANAMIDE: A mixture of N-(3-{1-[(3S)-3-hydroxy-3-phenylpropyl]-4-piperidinyl}phenyl)-2-methylpropanamide (5.20 mg, 0.0137 mmol), 3-nitrophenol (100 mg), triphenylphosphine (30.0 mg, 0.115 mmol) and diethyl azodicarboxylate (7.42 mg, 0.0426 mmol) in THF (0.50 mL) was stirred at room temperature for 3 days. Chromatography using silica preparative TLC plates [2.5% of $NH_3$ (2.0 M in methanol) in $CHCl_3$] gave the desired product (2.80 mg, 40.8% yield) as a thick oil: $^1$H NMR (400 MHz, $CDCl_3$) δ 7.76 (dm, 1H), 7.71 (t, 1H, J=1.8 Hz), 7.50–7.40 (m, 2H), 7.40–7.25 (m, 7H), 7.17 (apparent dd, 1H, J=2.4, 8.2), 6.97 (apparent d, 1H, J=7.7 Hz), 5.45 (apparent dd, 1H, J=5.0, 8.1 Hz), 3.45 (m, 2H), 2.89 (m, 2H), 2.53 (apparent sept, partially hidden, 2H, J=8.3 Hz), 2.30–2.10 (m, 6H), 1.92 (m, 2H), 1.25 (d, 6H, J=6.8 Hz); ESMS m/e: 502.3 $(M+H)^+$.

EXAMPLE 80

N-(3-{1-[(3S)-3-(2-ETHOXYPHENOXY)-3-PHENYLPROPYL]-4-PIPERIDINYL}PHENYL)-2-METHYLPROPANAMIDE: A mixture of N-(3-{1-[(3R)-3-hydroxy-3-phenylpropyl]-4-piperidinyl}phenyl)-2-methylpropanamide (5.20 mg, 0.0137 mmol), 2-ethoxyphenol (100 mg), triphenylphosphine (30.0 mg, 0.115 mmol) and diethyl azodicarboxylate (7.42 mg, 0.0426 mmol) in THF (0.50 mL) was stirred at room temperature for 3 days. Chromatography using silica preparative TLC plates [2.5% of $NH_3$ (2.0 M in methanol) in $CHCl_3$] gave the desired product (1.16 mg, 15.5% yield) as a thick oil: $^1$H NMR (400 MHz, $CDCl_3$) δ 8.06 (s, 1H), 7.52 (s, 1H), 7.40–7.33 (m, 4H), 7.30–7.20 (m, 3H), 6.97 (apparent d, 1H, J=7.7 Hz), 6.88 (m, 2H), 6.68 (m, 2H), 5.21 (m, 1H), 4.11 (q, 2H, J=7.3 Hz), 3.37 (m, 2H), 2.71 (m, 2H), 2.53 (apparent sept, partially hidden, 2H, J=7.6 Hz), 2.30–2.10 (m, 6H), 1.89 (m, 2H), 1.49 (t, 3H, J=7.3 Hz), 1.25 (d, 6H, J=6.8 Hz); ESMS m/e: 501.4 $(M+H)^+$.

EXAMPLE 81

2-METHYL-N-(3-{1-[(3S)-3-(1-NAPHTHYLOXY)-3-PHENYLPROPYL]-4-PIPERIDINYL}PHENYL) PROPANAMIDE: A mixture of N-(3-{1-[(3R)-3-hydroxy-3-phenylpropyl]-4-piperidinyl}phenyl)-2-methylpropanamide (5.20 mg, 0.0137 mmol), 1-naphthol (100 mg), triphenylphosphine (30.0 mg, 0.115 mmol) and diethyl azodicarboxylate (7.42 mg, 0.0426 mmol) in THF (0.50 mL) was stirred at room temperature for 3 days. Chromatography using silica preparative TLC plates [2.5% of $NH_3$ (2.0 M in methanol) in $CHCl_3$] gave the desired product (4.30 mg, 66.2% yield) as a thick oil: $^1$H NMR (400 MHz, $CDCl_3$) δ 8.06 (s, 1H), 7.72 (d, 1H, J=8.5 Hz), 7.59 (d, 1H, J=8.5 Hz), 7.5 (m, 2H), 7.45–7.30 (m, 6H), 7.25 (m, 3H), 7.17 (apparent dd, 1H, J=2.6, 9.0 Hz), 7.01 (apparent d, 1H, J=2.6 Hz), 6.97 (apparent d, 1H, J=7.9 Hz), 5.46 (apparent dd, 1H, J=4.5, 8.1 Hz), 3.12 (m, 2H), 2.61 (m, 2H), 2.53 (apparent sept, partially hidden, 2H, J=7.9 Hz), 2.30–2.10 (m, 6H), 1.90 (m, 2H), 1.25 (d, 6H, J=7.3 Hz, overlapped); ESMS m/e: 507.2 $(M+H)^+$.

EXAMPLE 82

N-(3-{1-[(3S)-3-(1,3-DIOXO-1,3-DIHYDRO-2H-ISOINDOL-2-YL)-3-PHENYLPROPYL]-4-PIPERIDINYL}PHENYL)-2-METHYLPROPANAMIDE

Step 1:

2-[(1S)-3-CHLORO-1-PHENYLPROPYL]-1H-ISOINDOLE-1,3(2H)-DIONE: According to the general procedure descibed in Srebnik, M.; Ramachandran, P. V.; Brown, H. C. *J. Org. Chem.* 1988, 53, 2916–2920, a mixture of phthalimide (0.147 g, 1.0 mmol), (R)-(+)-3-chlorophenyl-1-propanol (0.171 g, 1.0 mmol), triphenylphosphine (0.262 g, 1.0 mmol) and diethyl azodicarboxylate (0.174 g, 1.0 mmol) in 5.0 mL of THF was stirred at room temperature for 24 h. The reaction mixture was concentrated in vacuo. The residue was washed with pentane (×3) and the combined pentane extracts were concentrated and chromatographed (silica with hexanes-EtOAc 8:1 as the eluent) to give the desired product (0.121 g, 50.2%) as a yellow solid: $^1$H NMR (400 MHz, $CDCl_3$) δ 7.82 (apparent dd, 2H, J=2.9 Hz), 7.70 (apparent dd, 2H, J=2.9 Hz), 7.56 (m, 2H), 7.39–7.27 (m, 3H), 5.64 (apparent dd, 1H, J=7.0, 9.2 Hz), 3.57 (m, 2H), 3.05 (m, 1H), 2.82 (apparent sept, 1H, J=7.0 Hz); ESMS m/e: 300.13 $(M+H)^+$.

Step 2:

N-(3-{1-[(3S)-3-(1,3-DIOXO-1,3-DIHYDRO-2H-ISOINDOL-2-YL)-3-PHENYLPROPYL]-4-PIPERIDINYL}PHENYL)-2-METHYLPROPANAMIDE: A mixture of potassium carbonate (29.2 mg, 0.211 mmol), sodium iodide (47.5 mg, 0.317 mmol), 2-methyl-N-[3-(4-piperidinyl)phenyl]propanamide (51.8 mg, 0.211 mmol) 2-[(1S)-3-chloro-1-phenylpropyl]-1H-isoindole-1,3(2H)- dione (63.1 mg, 0.211 mmol) in DMF (5.0 mL) was stirred at 100° C. for 3 hrs, at which time TLC indicated that the reaction was complete. The reaction mixture was poured into water (50 mL) and the aqueous layer was extracted with methylene chloride (3×30 mL). The combined organic extracts were washed with brine (30 mL), dried over $MgSO_4$ and concentrated under reduced pressure. The crude product was purified by Prep-TLC plates [2.5% of $NH_3$ (2.0 M in methanol) in $CHCl_3$] to give the desired product (74.1 mg, 77.1%) as a thick oil: $^1H$ NMR (400 MHz, $CDCl_3$) δ 7.83 (apparent dd, 2H, J=2.9 Hz), 7.69 (apparent dd, 2H, J=2.9 Hz), 7.56 (apparent dt, 3H, J=2.9, 7.3 Hz), 7.33 (m, 4H), 7.21 (t, 1H, J=7.8 Hz), 7.09 (s, 1H), 6.81 (apparent d, 1H, J=7.8 Hz), 5.49 (apparent dd, 1H, J=5.5, 9.5 Hz), 2.98 (d, 1H, J=9.5 Hz), 2.87 (m, 2H) 2.50 (apparent sept, 1H, J=6.7 Hz), 2.40–2.35 (m, 4H), 1.94 (m, 2H), 1.70–1.50 (m, 4H), 1.25 (d, 6H, J=7.9 Hz); ESMS m/e: 510.37 (M+H)$^+$.

EXAMPLE 83

2-METHYL-N-(3-{1-[(3S)-3-(4-PHENOXYPHENOXY)-3-PHENYLPROPYL]-4-PIPERIDINYL}PHENYL)PROPANAMIDE

STEP 1:

4-{[(1S)-3-CHLORO-1-PHENYLPROPYL]OXY}-(4-PHENOXY)BENZENE: A mixture of 4-phenoxyphenol (1.86 g, 10.0 mmol), (R)-(−)-3-chloro-phenyl-1-propanol (1.70 g, 10.0 mmol), triphenylphosphine (2.62 g, 10.0 mmol), diethyl azodicarboxylate (1.57 mL, 10.0 mmol) in 5.0 mL of THF was stirred at room temperature for 24 h. The reaction mixture was concentrated in vacuo. The residue was washed with pentane (×3) and the combined pentane extracts were concentrated and chromatographed (silica with hexanes-EtOAc 97:3 as the eluent) to give the desired product as a thick oil which solidified on standing (2.51 g, 75.7%): $^1H$ NMR (400 MHz, $CDCl_3$) δ 7.4–7.23 (m, 7H), 7.03 (apparent t, 1H, J=7.3 Hz), 6.91 (apparent dm, 2H, J=7.8 Hz), 6.93 (apparent q, 4H, J=7.8 Hz), 5.31 (apparent dd, 1H, J=4.5, 8.6 Hz), 3.82 (m, 1H), 3.62 (apparent quintet, 1H, J=5.6 Hz), 2.47 (m, 1H), 2.20 (m, 1H).

Step 2:

2-METHYL-N-(3-{1-[(3S)-3-(4-PHENOXYPHENOXY)-3-PHENYLPROPYL]-4-PIPERIDINYL}PHENYL)PROPANAMIDE: A mixture of 2-methyl-N-[3-(4-piperidinyl)phenyl]propanamide (65.5 mg, 0.266 mmol), 4-{[(1S)-3-chloro-1-phenylpropyl]oxy}-(4-phenoxy)benzene (0.100 mg, 0.296 mmol), potassium carbonate (40.9 mg, 0.296 mmol) and sodium iodide (67.0 mg, 0.444 mmol) in DMF (1.0 mL) at 100° C. for 3 hours. The reaction mixture was poured into water (50 mL) and the aqueous layer was extracted with methylene chloride (3×30 mL). The combined organic extracts were washed with brine (30 mL), dried over $MgSO_4$ and concentrated under reduced pressure. The crude product was purified by Prep-TLC plates [2.5% of $NH_3$ (2.0 M in methanol) in $CHCl_3$] to give the desired product (0.109 g, 74.6%) as a thick oil: $^1H$ NMR (400 MHz, $CDCl_3$) δ 7.48 (s, 1H), 7.40–7.30 (m, 4H), 7.20–7.10 (m, 6H), 7.09 (s, 1H), 6.99 (apparent d, 1H, J=7.8 Hz), 6.98 (apparent t, 1H, J=7.8 Hz), 6.93 (apparent d, 2H, J=8.4 Hz), 6.84 (m, 2H), 5.20 (apparent dd, 1H, J=4.4, 8.5 Hz), 3.03 (m, 2H), 2.51 (m, 4H), 2.24 (apparent sept, 1H, J=7.8 Hz), 2.20–2.10 (m, 3H), 1.90 (m, 4H), 1.25 (d, 6H, J=7.9 Hz); ESMS m/e: 549.41 (M+H)$^+$; Anal. Calc. for $C_{36}H_{40}N_2O_3$: C, 78.80; H, 7.35; N, 5.11. Found: C, 78.58; H, 7.48; N, 5.09.

EXAMPLE 84

N-(4-{1-[(3R)-3-(3,4-DIMETHOXYPHENOXY)-3-PHENYLPROPYL]-4-PIPERIDINYL}PHENYL)-2-METHYLPROPANAMIDE

Step 1:

1-[(3R)-3-(3,4-DIMETHOXYPHENOXY)-3-PHENYLPROPYL]-4-(4-NITROPHENYL)-1,2,3,6-TETRAHYDROPYRIDINE: A mixture of potassium carbonate (24.0 mg, 0.174 mmol), sodium iodide (39.0 mg, 0.260 mmol), 4-(4-nitrophenyl)-1,2,3,6-tetrahydropyridine (35.4 mg, 0.174 mmol) and 4-{[(1R)-3-chloro-1-phenylpropyl]oxy}-1,2-dimethoxybenzene (53.4 mg, 0.174 mmol) in DMF (0.5 mL) was stirred at 100° C. for 3 hrs, at which time TLC indicated that the reaction was complete. The reaction mixture was poured into water (5.0 mL) and the aqueous layer was extracted with methylene chloride (3×30 mL). The combined organic extracts were washed with brine (30 mL), dried over $MgSO_4$ and concentrated under reduced pressure. The crude product was purified by Prep-TLC plates [1:1=hexane:ethyl acetate with 1% $NH_3$] afforded the product (63.1 mg, 76.6%) as a yellow oil. The product was used in next reaction without further purification.

Step 2:

4-{1-[(3R)-3-(3,4-DIMETHOXYPHENOXY)-3-PHENYLPROPYL]-4-PIPERIDINYL}ANILINE: A 25-mL RB flask, equipped with a hydrogen-filled balloon, was charged with 1-[(3R)-3-(3,4-dimethoxyphenoxy)-3-phenylpropyl]-4-(4-nitrophenyl)-1,2,3,6-tetrahydropyridine (63.0 mg, 0.133 mmol), palladium on carbon (5.0 mol-eq%, 0.00665 mmol, 7.04 mg) and ethanol (2.0 mL) at room temperature. After 1 hr the reaction mixture was filtered through a plug of Celite 545 and concentrated under reduced pressure. The crude product (54.1 mg, 89.4%) was used in next reaction without further purification.

STEP 3:

N-(4-{1-[(3R)-3-(3,4-DIMETHOXYPHENOXY)-3-PHENYLPROPYL]-4-PIPERIDINYL}PHENYL)-2-METHYLPROPANAMIDE: A mixture of 4-{1-[(3R)-3-(3,4-dimethoxyphenoxy)-3-phenylpropyl]-4-piperidinyl}aniline (5.31 mg, 0.0119 mmol), isobutyryl chloride (2.08 mg, 0.019 mmol), N,N-diisopropylethylamine (8.40 mg, 0.0650 mmol) in methylene chloride (1.0 mL) was stirred at room temperature for 24 hours. The reaction mixture was concentrated and chromatographed using a preparative TLC plate [2.5% of $NH_3$ (2.0 M in methanol) in $CHCl_3$] to give the product (3.5 mg, 56.5%) as a thick oil: $^1H$ NMR (400 MHz, $CDCl_3$) δ 7.38 (d, 1H, J=8.6 Hz), 7.30–7.20 (m, 4H), 7.20 (m, 1H), 7.11 (d, 2H, J=8.6 Hz), 7.04 (s, 1H), 6.57 (d, 1H, J=8.3 Hz), 6.44 (d, 1H, J=2.6 Hz), 6.22 (dd, 1H, J=2.6, 8.3 Hz), 5.09 (apparent dd, 1H, J=4.4, 8.1 Hz), 3.72 (s, 3H), 3.70 (s, 3H), 3.08 (m, 2H), 2.57 (m, 2H), 2.43 (apparent sept, partially hidden, 2H, J=6.8 Hz), 2.30–2.10 (m, 6H), 1.80 (m, 2H), 1.25 (d, 6H, J=7.9 Hz); ESMS m/e: 517.3 (M+H)$^+$.

EXAMPLE 85

N-(3-{1-[(3S)-3-(3-ACETYLPHENOXY)-3-PHENYLPROPYL]-4-PIPERIDINYL}PHENYL)-2-METHYLPROPANAMIDE: Into a 25-mL RB-flask was added triphenylphosphine (9.80 mg, 0.0375 mmol), diethyl azodicarboxylate (5.22 mg, 0.0300 mmol), N-(3-{1-[(3R)-3-hydroxy-3-phenylpropyl]-4-piperidinyl}phenyl)-2-methylpropanamide (9.53 mg, 0.0250 mmol), 3-hydroxyacetophenone (100 mg) and THF (1.0 mL) at room temperature. The reaction mixture was stirred at room temperature overnight (16 hrs). The solvent was removed under reduced pressure and the residue was purified by preparative TLC plates [2.5% of $NH_3$ (2.0 M in methanol) in $CHCl_3$] to afford the desired product (2.73 mg, 39.9%) as a thick oil: $^1H$ NMR ($CDCl_3$) δ 7.70–7.64 (m, 2H), 7.54 (m, 2H), 7.49–7.44 (m, 6H), 7.25 (m, 1H), 7.05 (d, 1H, J=8.3 Hz), 6.96 (apparent d, 1H, J=7.7 Hz), 5.34 (apparent dd, 1H, J=4.8, 8.2 Hz), 3.15 (m, 2H), 2.67 (m, 2H), 2.52 (s, 3H), 2.53 (apparent sept, partially hidden, 2H, J=7.6 Hz), 2.30–2.10 (m, 6H), 1.89 (m, 2H), 1.25 (d, 6H, J=6.9 Hz); ESMS m/e: 499.4 $(M+H)^+$.

Scheme A. Synthesis of tert-Butyl 4-(3-aminophenyl)-1-piperidinecarboxylate

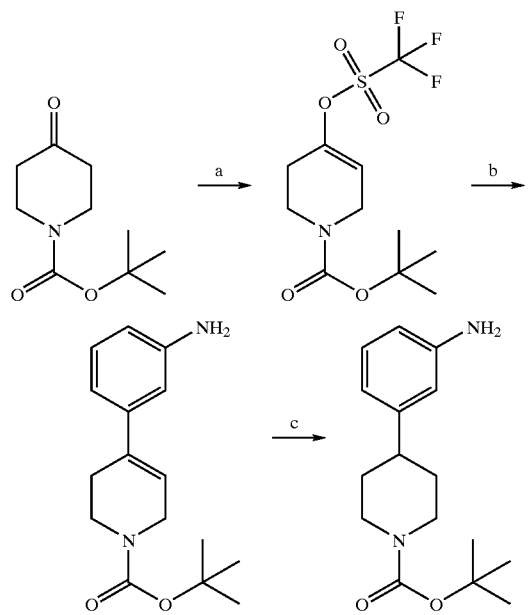

a. n-BuLi, diisopropylamine, THF, PhN(Tf)$_2$, -78° C. to room temperature, 81%
b. 3-aminophenylboronic acid hemisulfate, LiCl, tetrakis-triphenylphosphine-palladium (0), Na$_2$CO$_3$, DME-H$_2$O, reflux, 81%
c. 10% Pd/C, ethanol, H$_2$, room temperature, balloon method, 84%

Scheme B1. A General Synthesis of the MCH Anatagonists

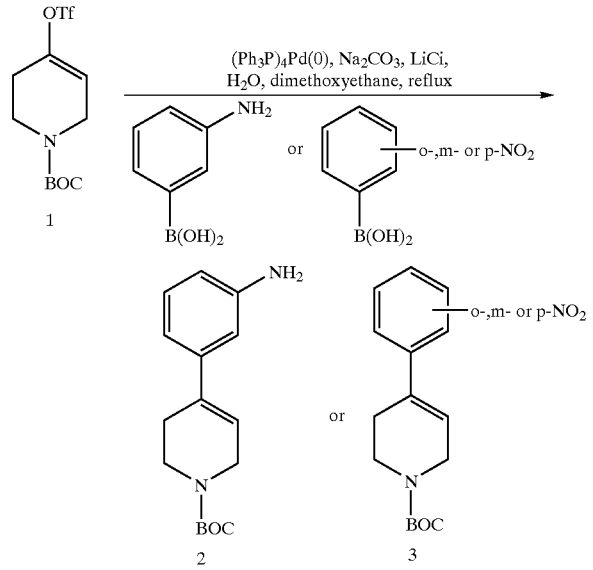

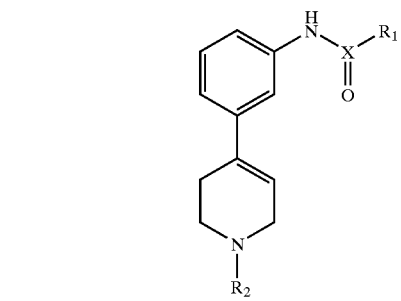

1. R$_1$X(=O)Cl
2. H$_2$, Pd/C, EtOH
3. HCl in dioxane
4. R$_2$-halide, cat. Bu$_4$Nl, dioxane, reflux
   or R2-halide, cat. 18-crown-6, toluene, reflux
   or R$_2$-halide, cat. NaI, Na$_2$CO$_3$, DMF, 100° C.

1. H$_2$, Pd/C, EtOH
2. HCl in dioxane
3. R$_2$-halide, cat. Bu$_4$Nl, dioxane, reflux
   or R2-halide, cat. 18-crown-6, toluene, reflux
   or R$_2$-halide, cat. NaI, Na$_2$CO$_3$, DMF, 100° C.
4. R$_1$X(=O)Cl Scheme B2. A General Synthesis of the MCH Antagonists

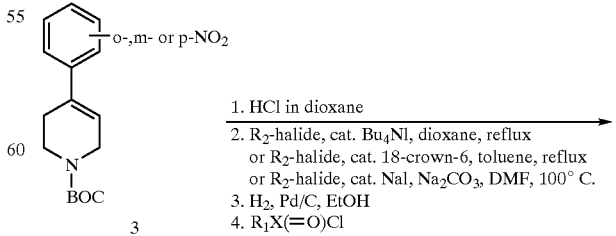

1. HCl in dioxane
2. R$_2$-halide, cat. Bu$_4$Nl, dioxane, reflux
   or R2-halide, cat. 18-crown-6, toluene, reflux
   or R$_2$-halide, cat. NaI, Na$_2$CO$_3$, DMF, 100° C.
3. H$_2$, Pd/C, EtOH
4. R$_1$X(=O)Cl

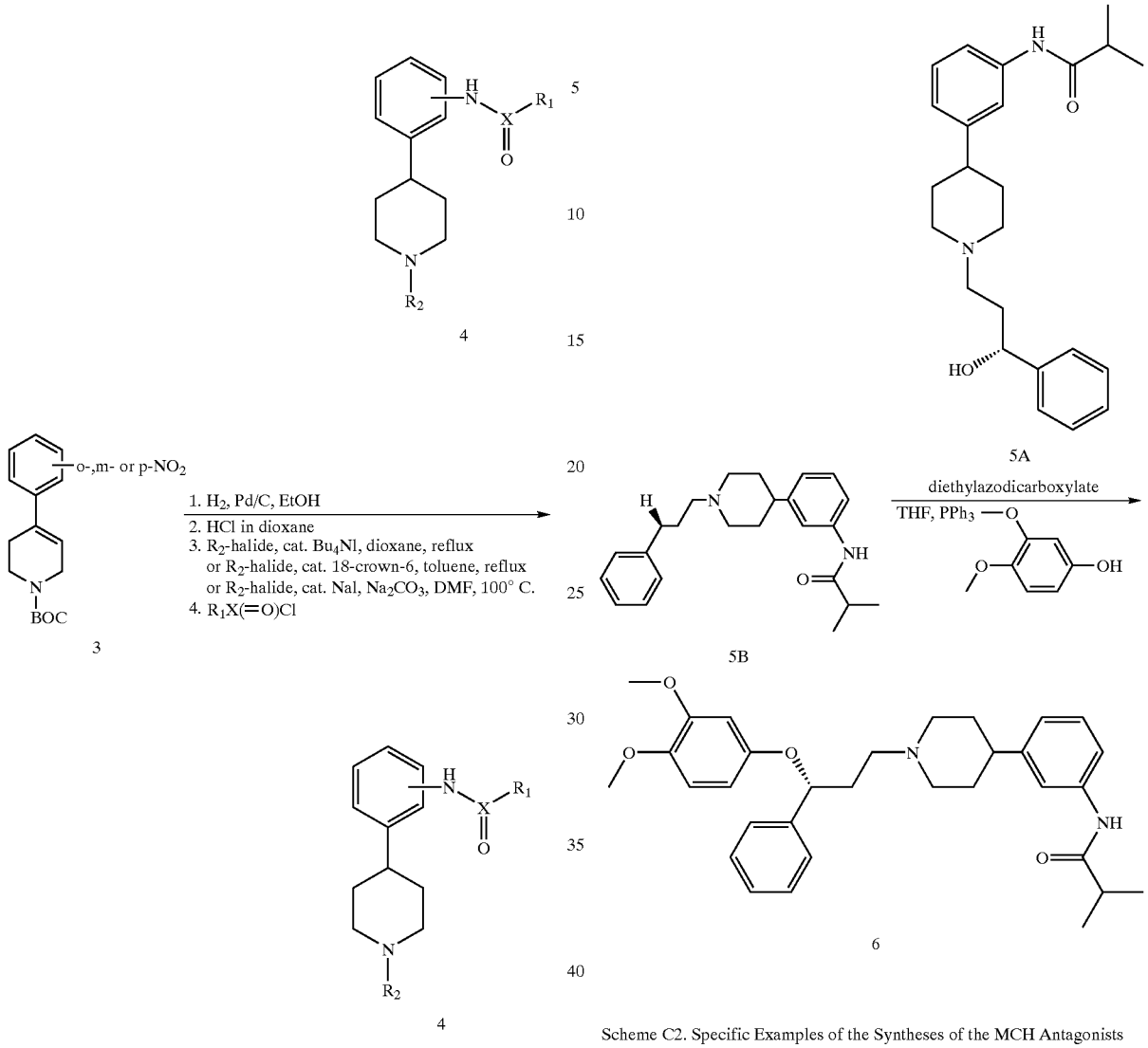
Scheme C1. Specific Examples of the Syntheses of the MCH Anatagonists
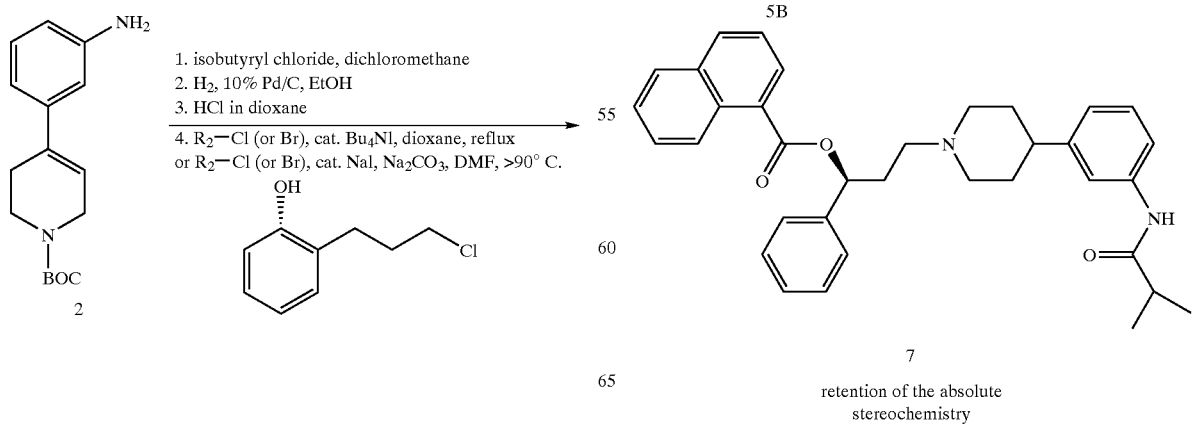
Scheme C2. Specific Examples of the Syntheses of the MCH Antagonists -continued
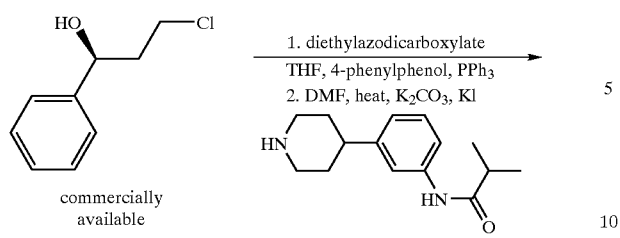
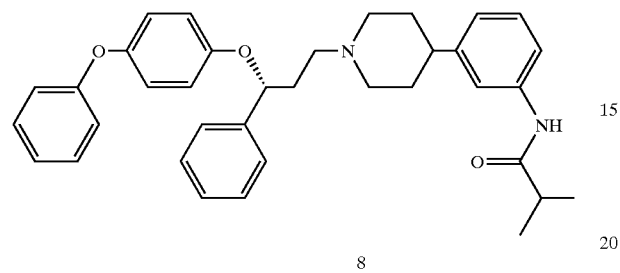
8
inversion of sterochemistry
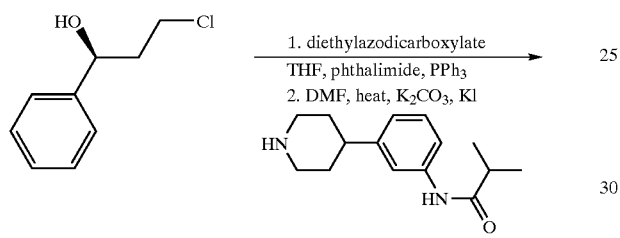
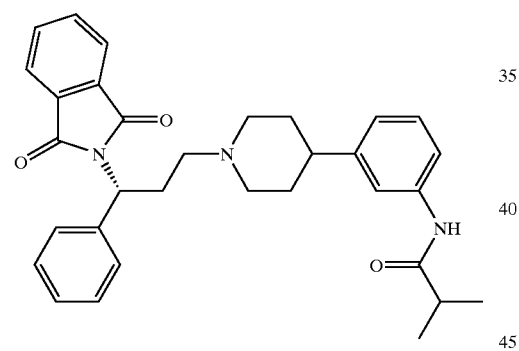
9
inversion of sterochemistry
Scheme D1. Specific Examples of the Syntheses of the MCH Antagonists
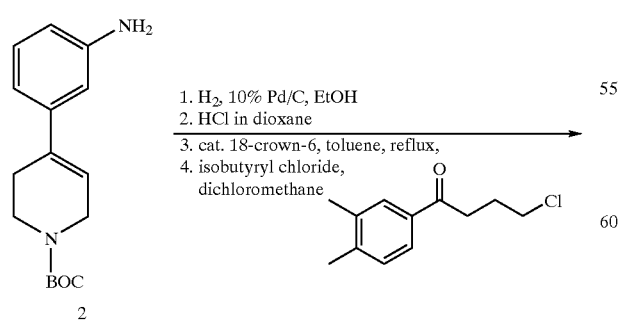
-continued
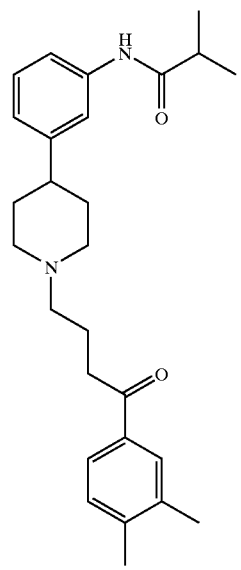
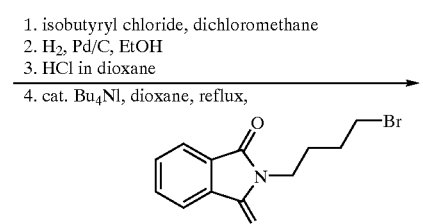
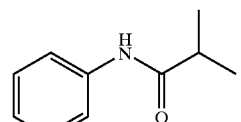
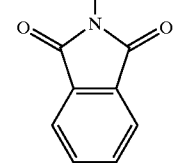

Scheme D2. Specific Examples of the Syntheses of the MCH Antagonists

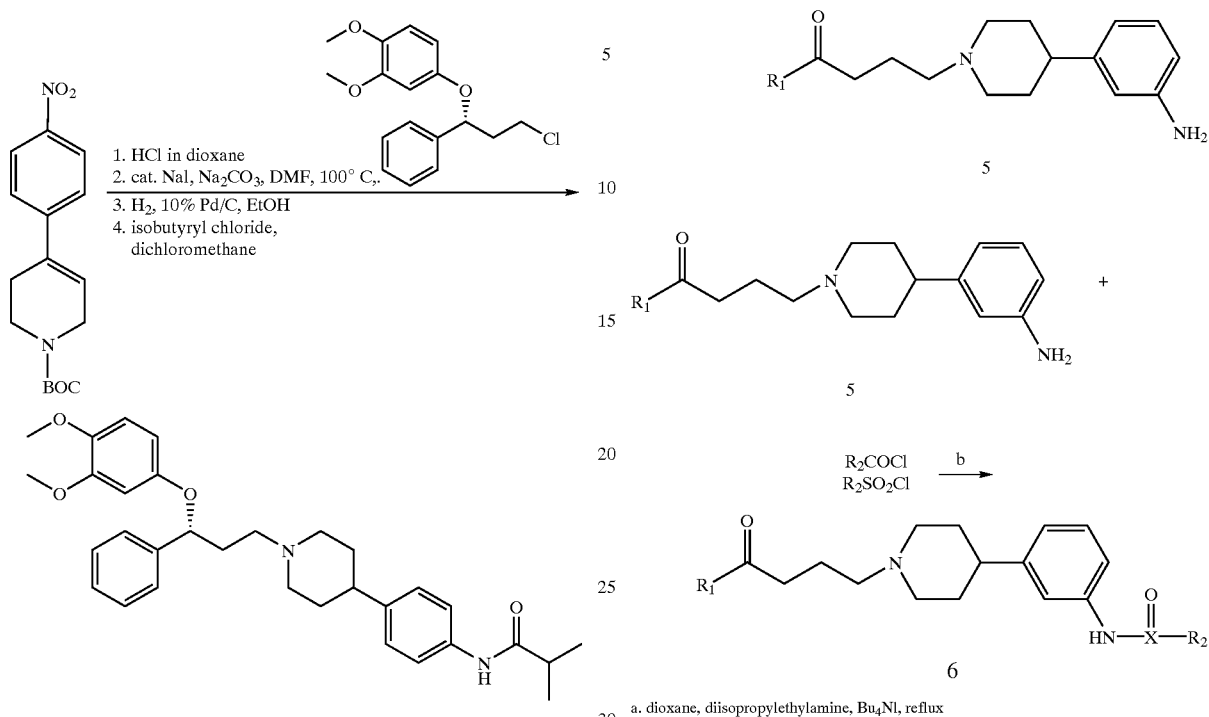

Scheme E: General Synthesis of the MCH Antagonists

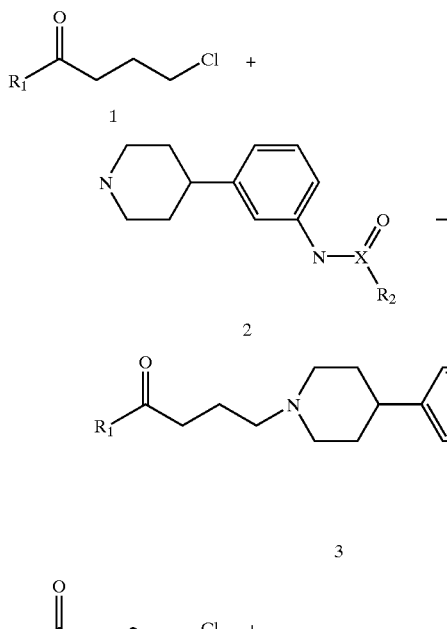

a. dioxane, diisopropylethylamine, Bu₄NI, reflux
   or DMF, KI, Na₂CO₃, 90–100° C.
   or toluene, 100° C,. 18-crown-6
b. diisopyropylethylamine, dichloromethane X = S(=O), C
R₁ = Aromatic, substituted aromatic or heterocyclic
R₂ = aliphatic or aromatic Scheme F. General Synthesis of the MCH Antagonists

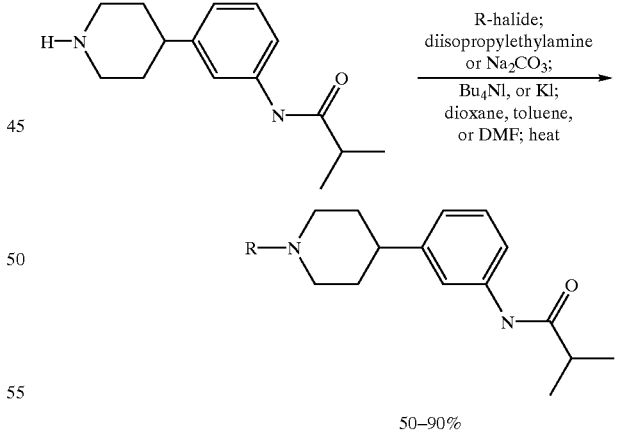

If R = (CH₂)ₙCHOH—Ar, then,

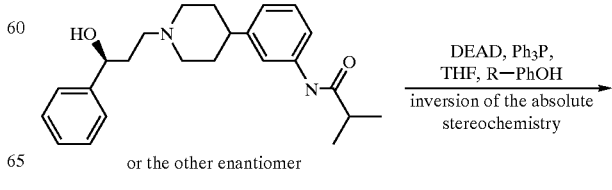

99
-continued
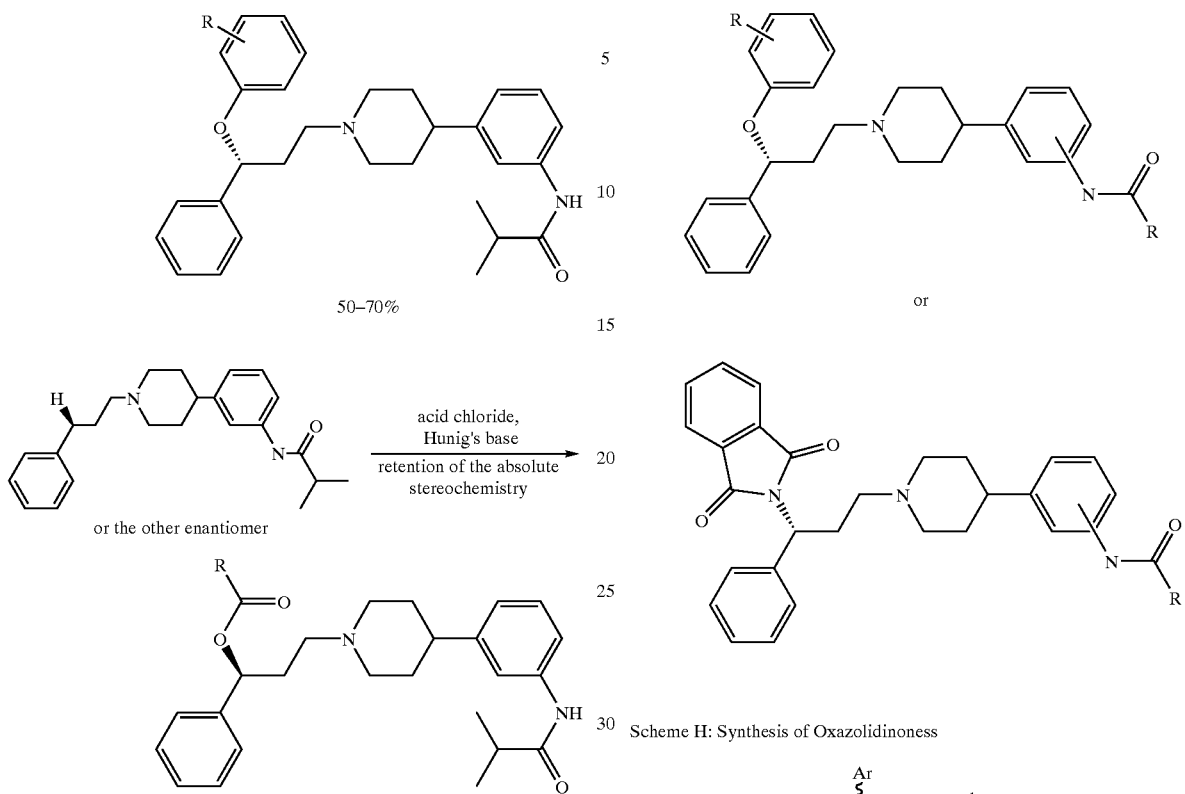
Scheme G. General Synthesis of the MCH Antagonists
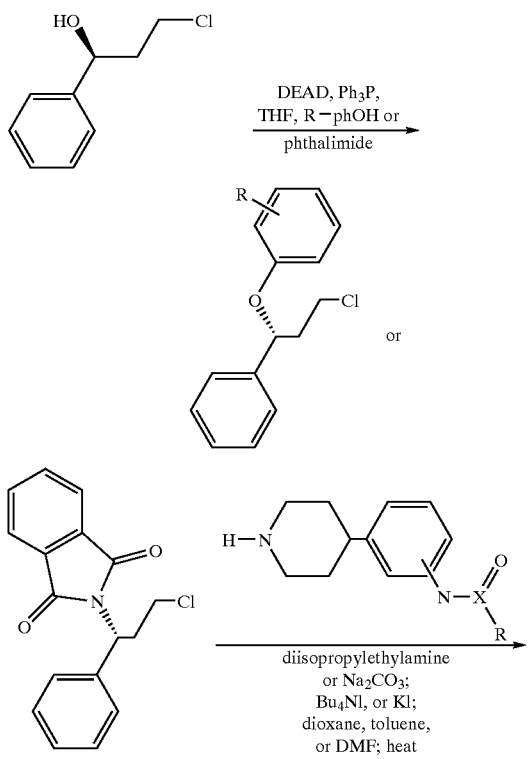
100
-continued
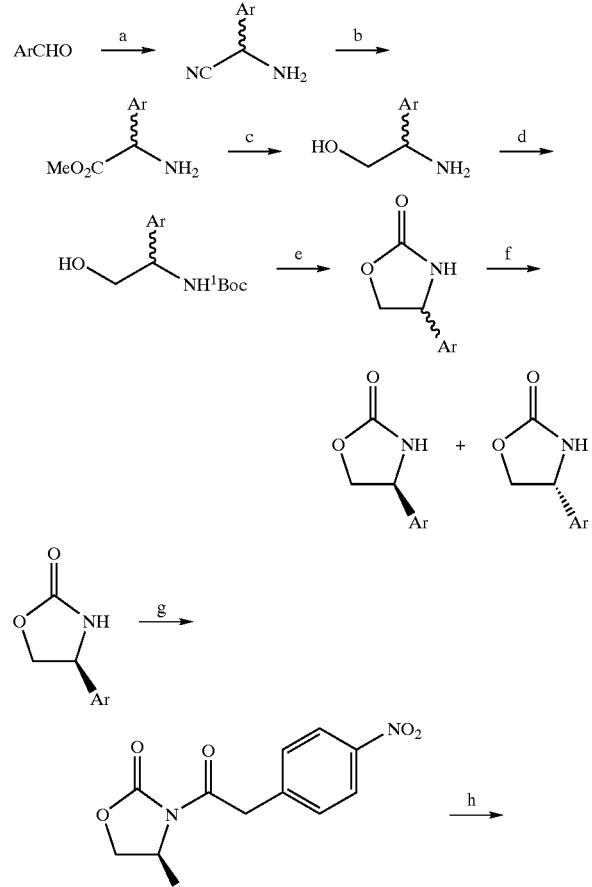
Scheme H: Synthesis of Oxazolidinoness

101
-continued

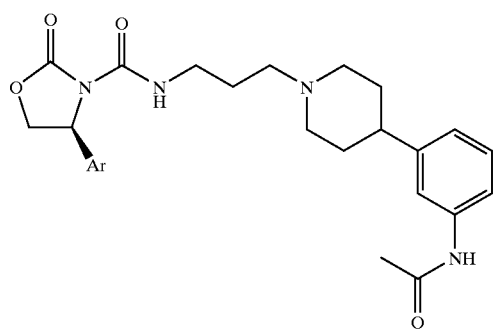

a. NH₃, then TMS—CN; b. HCl in MeOH (room temperature to reflux);
c. LAH, THF, reflux; d. (BOC)₂O, chloroform; e. NaH, THF; f. Chiralcel OD column
g. NaH, p-nitrophenyl chloroformate, THF;
h. an amine such as N-{3-[1-(3-aminopropyl)-4-piperidinyl]phenyl}acetamide Ar = 3,4-difluorophenyl, 3,5-difluorophenyl or 3,4,5-trifluorophenyl Scheme I: Synthesis of gem-Dialkyl Substituted Oxazolidinones

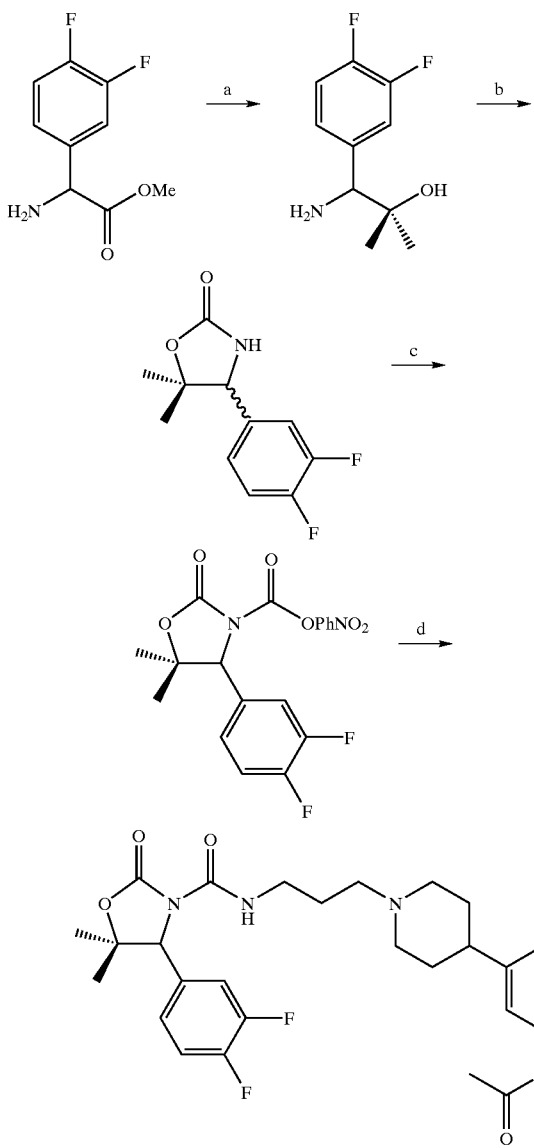

102
-continued a. methyl magnesium bromide, THF; b. N,N-carbonyldiimidazole, DCM;
c. NaH, THF, p-nitrophenylchloroformate; d. an amine such as
N-{3-[1-(3-aminopropyl)-4-piperidinyl]phenyl}acetamide Scheme J: Synthesis and Chiral Resolution of Oxazolidinones

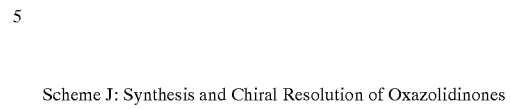

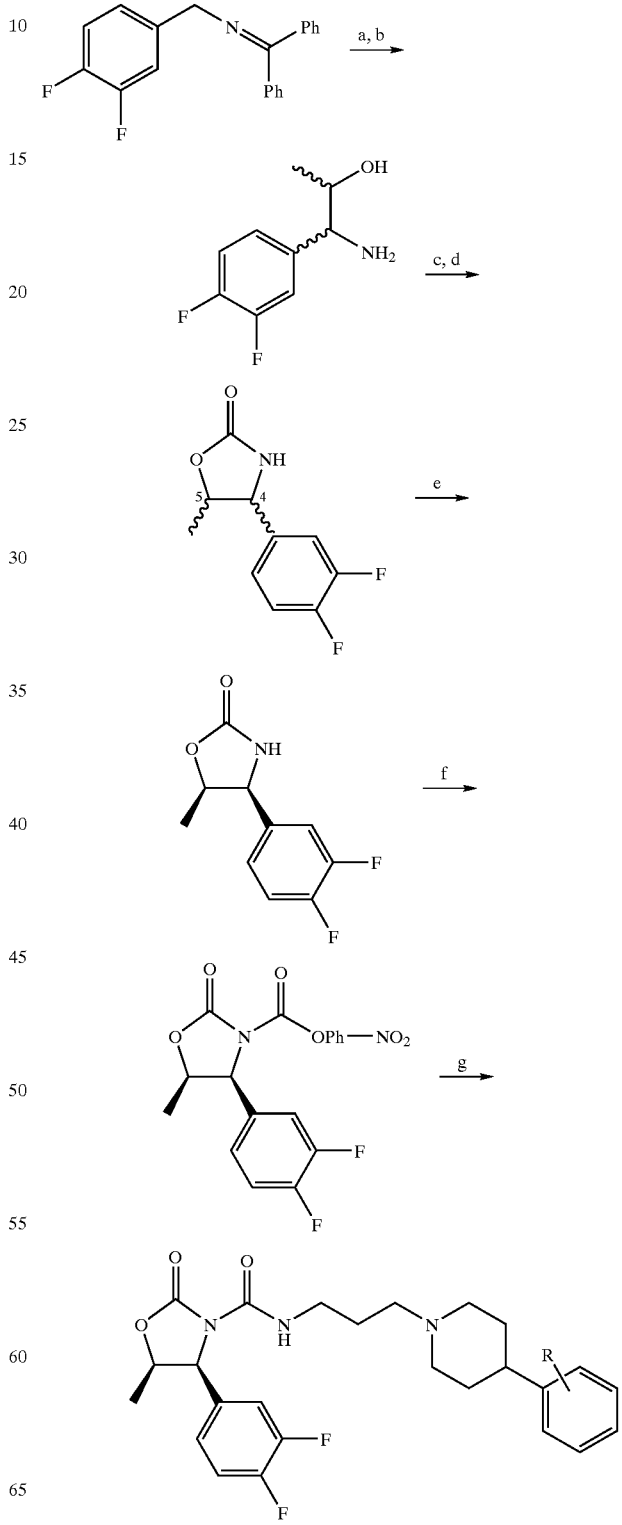

<sup>a</sup>(a) t-BuLi, THF, RCHO (b) CH₃ONH₂•HCl, MeOH, 50–68% over 2 steps
(c) Boc₂O, CHCl₃ >90% (d) NaH, THF, 76–92% (e) separate diastereomers by
column chromatography and separate enantiomers by chiral phase HPLC, 10–16%
(f) N-BuLi, THF, 4-nitrophenylchloroformate, -75%
(g) THF, >80%, an amine such as N-{3-[1-(3-aminopropyl)
-4-piperidinyl]phenyl}acetamide Scheme K: Synthesis Oxazolidinones from Amino Acids

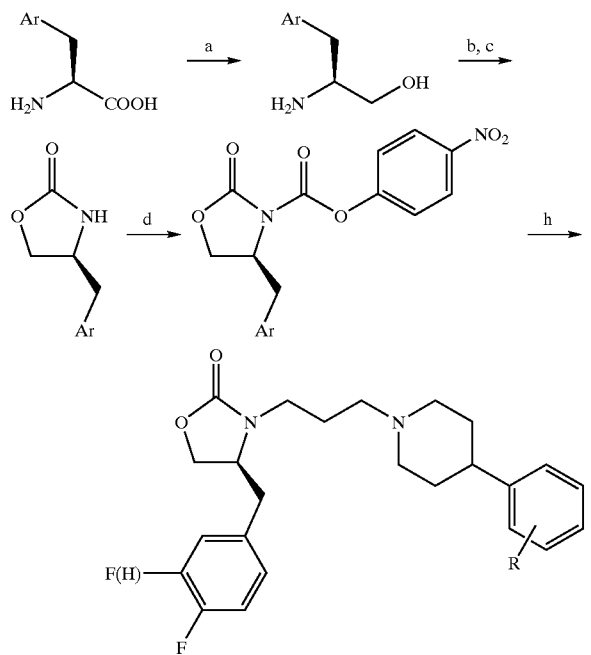

a. LAH, THF; b. (BOC₂)O, CHCl₃; c. NAH, THF;
d. p-nitrophenylchloroformate, NaH, THF;
h. an amine such as N-{3-[1-(3-aminopropyl)-4-piperidinyl]phenyl}
acetamide Ar = aromatic such as 4-fluorophenyl or 3,4-difluorophenyl Scheme L: Determination of the Absolute Stereohemistry of the
Di-Substituted Oxazolidinones Using Lactic Acid Derivatives

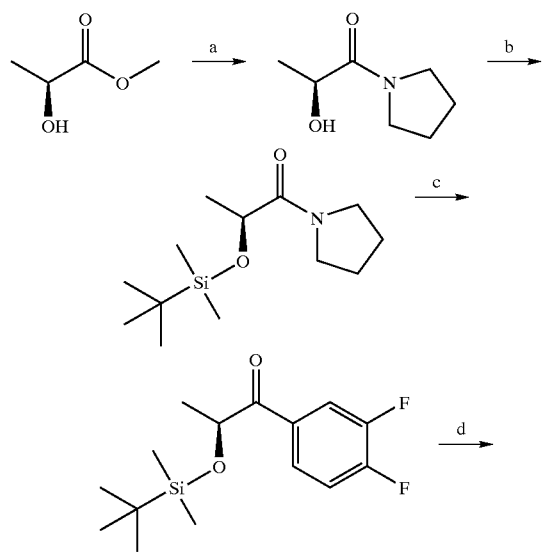

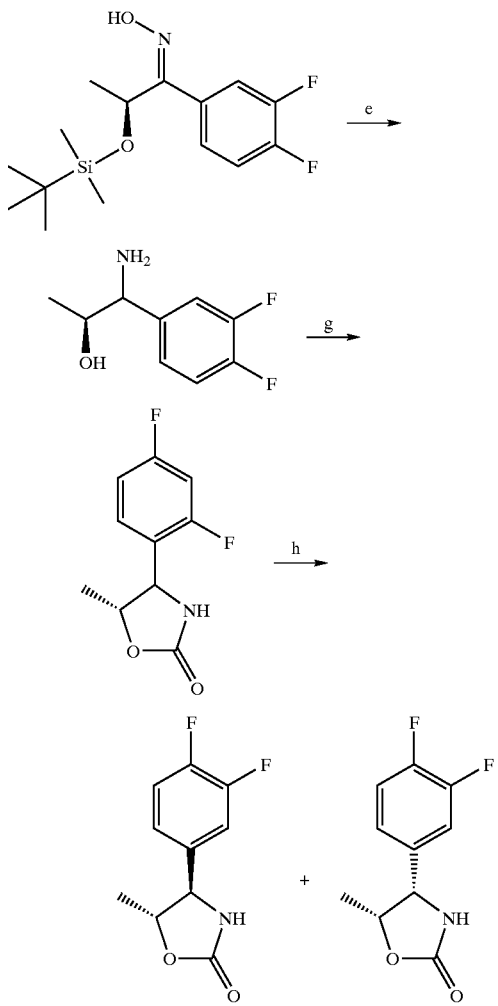

a. pyrrolidine, methanol, heat; b. t-butyldimethylsilyl chloride;
c. LAH, ether, reflux d. (BOC)₂O, chloroform; e. NaH, THF;
h. silica gel chromatography For more details, See: Lagu, B.; Wetzel, J. M.; Forray, C.; Patane, M. A .; Bock, M. G.
"Determination of the Relative and Absolute Stereochemistry of a Potent α 1A Selective
Adrenoceptor Antagonist" Bioorg. Med. Chem. Lett. 2000, 10, 2705.

Scheme M

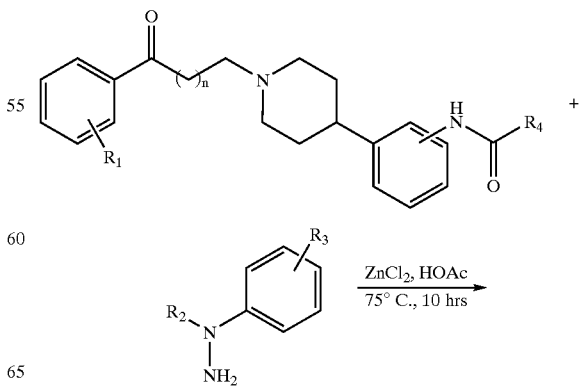

105
-continued
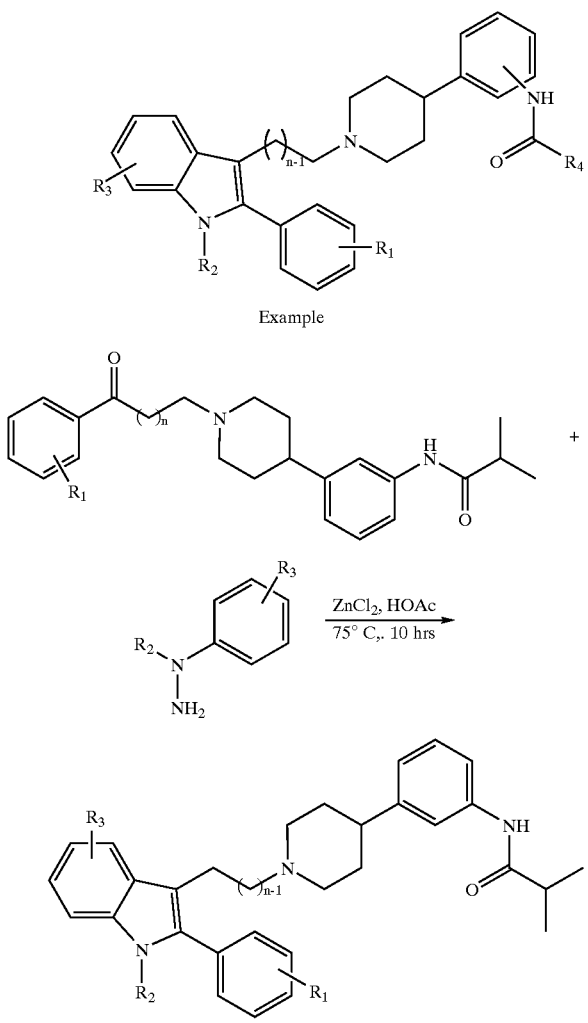
Example
n = 2, R1 = H, R2 = Ph, R3 = H
n = 5, R1 = H, R2 = H, R3 = 5-OMe
n = 1, R1 = H, R2 = Ph, R3 = H
n = 4, R1 = H, R2 = H, R3 = 5-OMe
Scheme N
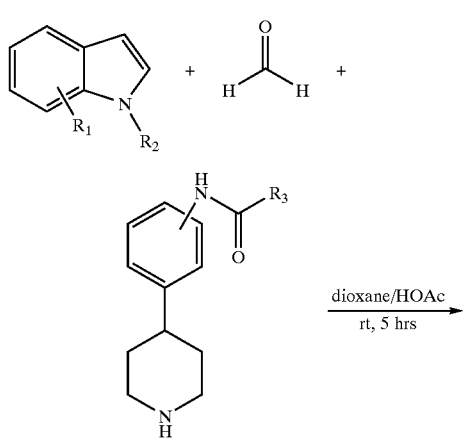
106
-continued
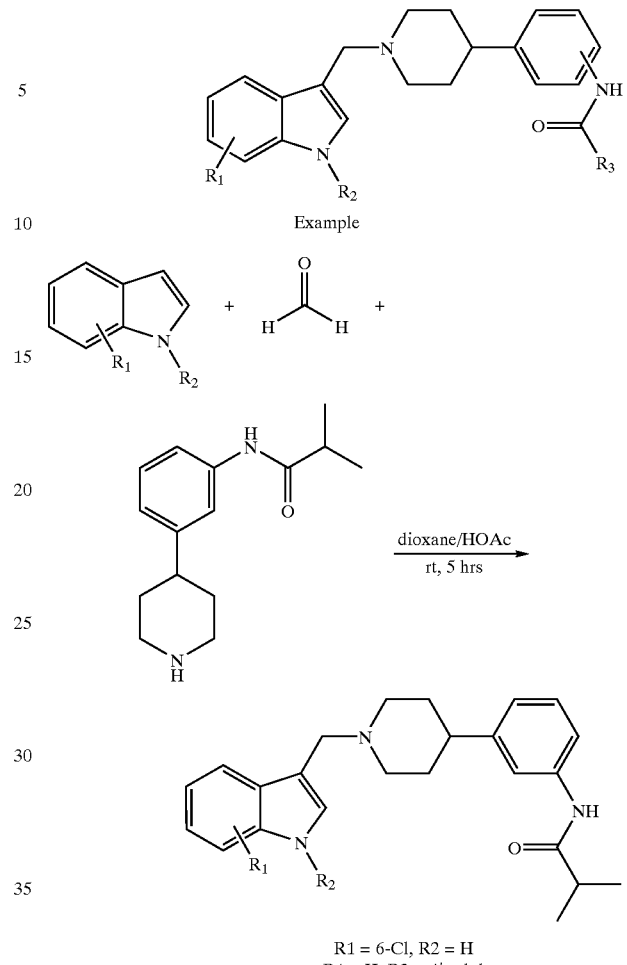
R1 = 6-Cl, R2 = H
R1 = H, R2 = 4'-tolyl
Scheme P
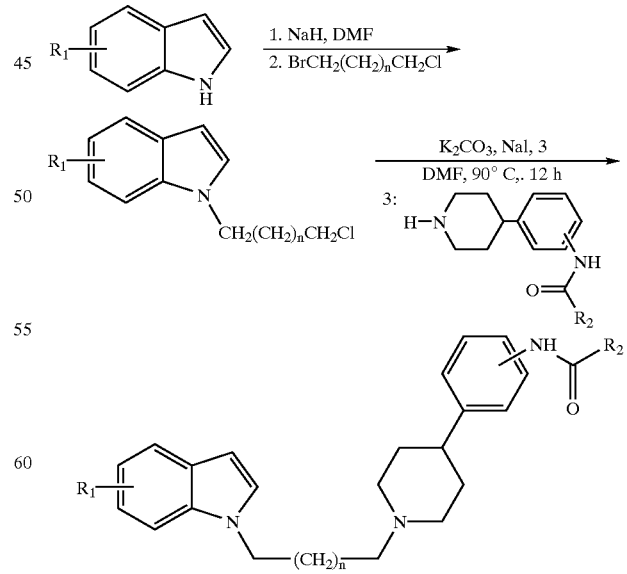

Example
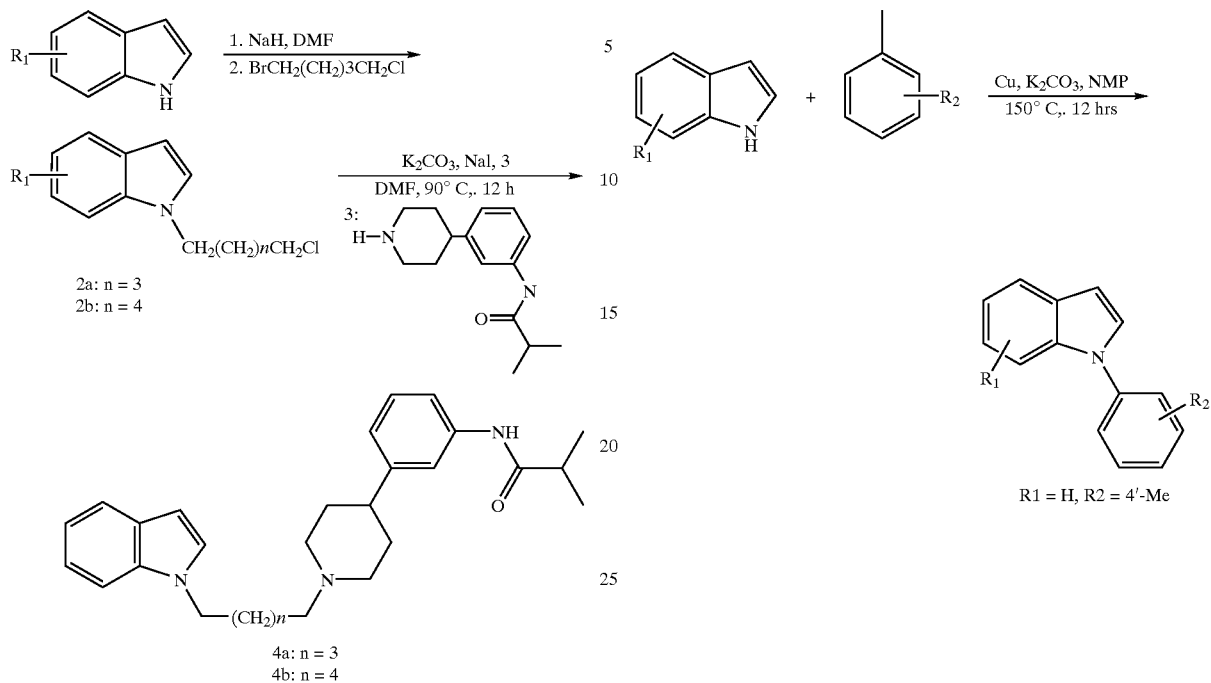
Scheme O
Scheme Q
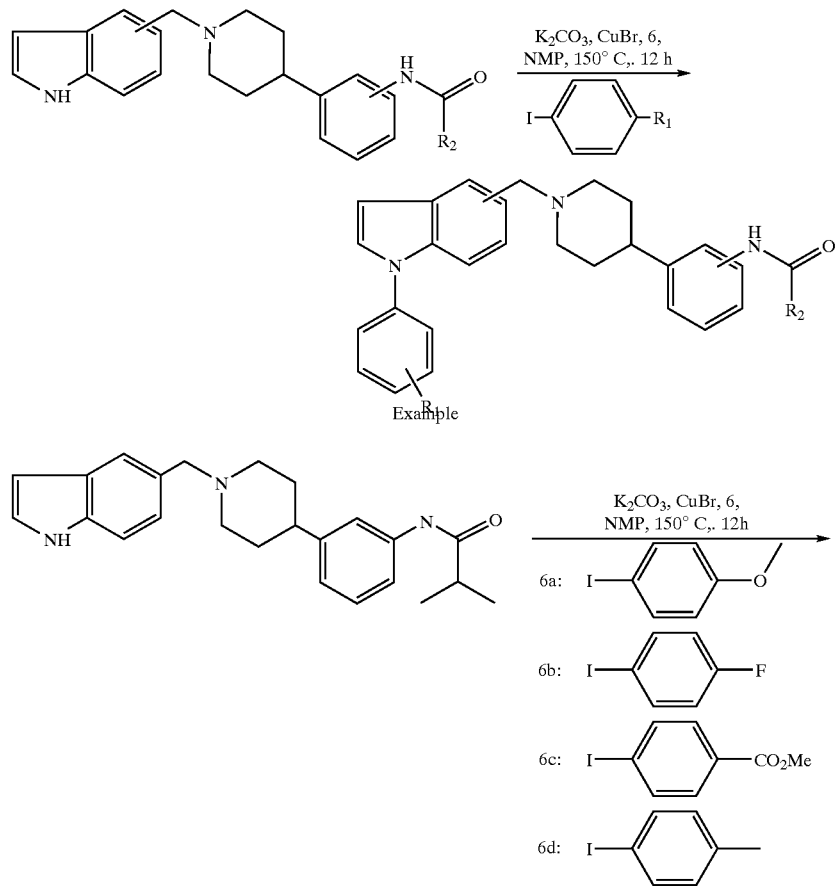
Example

-continued

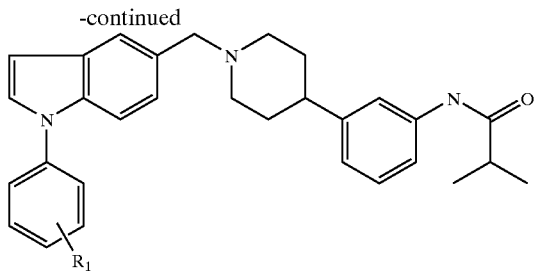

7a: R1 = p-OMe
7b: R1 = p-F
7c: R1 = p-CO₂Me
7d: R1 = p-Me

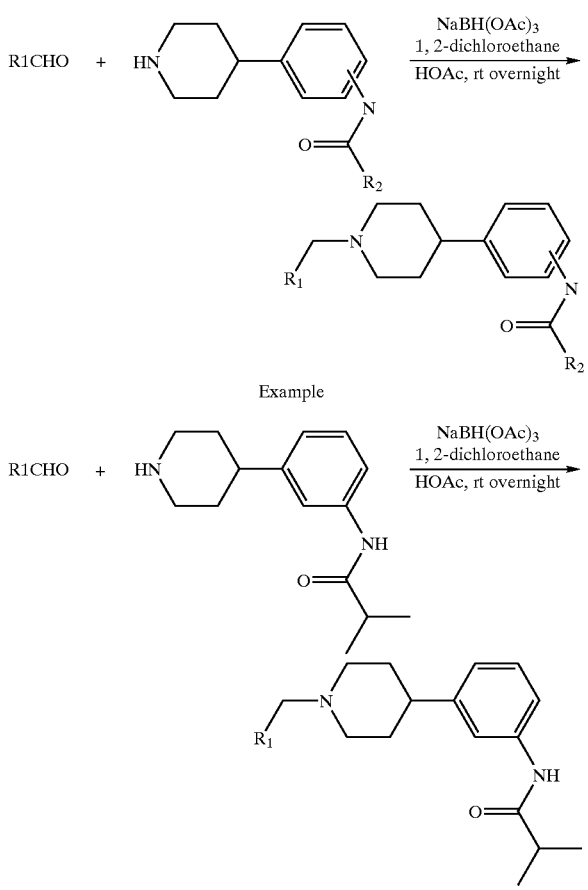

EXPERIMENTAL SECTION

The following additional abbreviations are used: HOAc, acetic acid; DMF, N,N-dimethylformamide; EtOAc, ethyl acetate; MeOH, methanol; NMP, 1-methyl-2-pyrrolidinone; TEA, triethylamine; THF, tetrahydrofuran; All solvent ratios are volume/volume unless stated otherwise.

1-(4-METHYLPHENYL)1H-INDOLE: A mixture of 1-H-indole (58.5 mg, 0.500 mmol), 1-(iodo)-4-methylbenzene (0.218 g, 1.00 mmol), copper powder (32.0 mg, 0.500 mmol), and K₂CO₃ (0.138 g, 1.00 mmol) in 1-methyl-2-pyrrolidinone (1 mL) was heated at 150° C. for 12 h under argon. The resulting mixture was diluted with H₂O (6 mL). The aqueous layer was extracted with CH₂Cl₂ (3×10 mL). The combined organic extracts were washed with brine 10 mL), dried over MgSO₄, and concentrated in vacuo. The residue was purified by preparative TLC using EtOAc/hexane (1:4) to give the desired product (82 mg, 79%). ¹H NMR (400 MHz, CDCl₃) δ 7.67 (d, 1H, J=7.7 Hz), 7.52 (d, 1H, J=7.4 Hz), 7.38 (d, 2H, J=8.4 Hz), 7.34–7.29 (m, 3H), 7.21 (t, 1H, J=7.0 Hz), 7.15 (t, 1H, J=7.0 Hz), 6.66 (d, 1H, 3.3 Hz), 2.43 (s, 3H); ESMS m/e: 208.0 (M+H)⁺.

EXAMPLE 86

N-(3-{1-[(6-CHLORO-1H-INDOL-3-YL)METHYL]-4-PIPERIDINYL}PHENYL)-2-METHYLPROPANAMIDE: A solution of 2-methyl-N-[3-(4-piperidinyl)phenyl]propanamide (0.369 g, 1.50 mmol) and 37 wt % aqueous formaldehyde (30.0 mg, 1.50 mmol) in 1 mL of HOAc:dioxane (1:4) was added to 6-chloro-1-H-indole (0.152 g, 1.00 mmol) and the reaction mixture was stirred for 12 h at room temperature. The resulting mixture was diluted with H₂O (10 mL). The aqueous layer was extracted with CH₂Cl₂ (3×100 mL). The combined organic extracts were washed with brine (10 mL), dried over MgSO₄, and concentrated in vacuo. The residue was purified by preparative TLC on silica using 5% of NH₃ (2.0 M in methanol) in CH₂Cl₂ to give the desired product (79 mg, 42%). ¹H NMR (400 MHz, CDCl₃) δ 9.14 (s, 1H), 8.04 (s, 1H), 7.52 (t, 2H, J=8.1 Hz), 7.35 (d, 2H, J=13.3 Hz), 7.18 (t, 1H, J=7.9 Hz), 7.09 (dd, 1H, J=1.9, 8.5 Hz), 6.85 (d, 1H, J=7.4 Hz), 5.18 (s, 1H), 4.01 (s, 2H), 2.55 (septet, 1H, J=6.8 Hz), 2.48–2.34 (m, 3H), 2.08–1.95 (m, 4H), 1.78 (d, 2H, J=12.8 Hz), 1.22 (d, 6H, J=6.8 Hz); ESMS m/e: 410.1 (M+H)⁺.

EXAMPLE 87

2-METHYL-N-[3-(1-{[1-(4-METHYLPHENYL)-1H-INDOL-3-YL]METHYL}-4-PIPERIDINYL)PHENYL]PROPANAMIDE: According to the procedure used for the synthesis of N-(3-{1-[(6-chloro-1H-indol-3-yl)methyl]-4-piperidinyl}phenyl)-2-methylpropanamide, 1-(4-methylphenyl)-1H-indole (0.207 g, 1.00 mmol) provided 2-methyl-N-[3-(1-{[1-(4-methylphenyl)-1H-indol-3-yl]methyl}-4-piperidinyl)phenyl]propanamide (0.441 g, 78%). ¹H NMR (400 MHz, CDCl₃) δ 7.90 (s, 1H), 7.73 (d, 1H, J=7.2 Hz), 7.58–7.51 (m, 2H), 7.43–7.36 (m, 3H), 7.35–7.29 (m, 3H), 7.26–7.15 (m, 3H), 6.89 (d, 1H, J=7.7 Hz), 4.07 (s, 2H), 3.36 (d, 2H, J=11.6 Hz), 2.59–2.39 (m, 6H), 2.55 (sept, 1H, J=6.7 Hz), 2.10–1.98 (m, 2H), 1.83 (d, 2H, J=12.9 Hz), 1.23 (d, 6H, J=6.9 Hz); ESMS m/e: 466.2 (M+H)⁺.

2-[(1S)-3-CHLORO-1-PHENYLPROPYL]-1H-ISOINDOLE-1,3(2H)-DIONE: Triphenylphosphine (5.25 g, 20.0 mmol) and diethyl azodicarboxylate (3.58 g, 20.0 mmol) were added to a solution of (1R)-3-chloro-1-phenyl-1-propanol (3.42 g, 20.0 mmol) and phthalimide (2.94 g, 20.0 mmol) in THF (100 mL). The reaction mixture was stirred for 4 h at room temperature. The solvent was removed under reduced pressure and the residue was triturated with pentane (3×50 mL). The combined pentane fractions were concentrated in vacuo and the crude product was purified by chromatography on silica using EtOAc/hexane (3:97) to give the desired product (4.40 g, 74%). $^1$H NMR (400 MHz, CDCl$_3$) δ 7.82 (d, 1H, J=5.7 Hz), 7.81 (d, 1H, J=5.5 Hz), 7.70 (d, 1H, J=5.4 Hz), 7.69 (d, 1H, J=5.8 Hz), 7.55 (d, 2H, J=7.2 Hz), 7.38–7.28 (m, 3H), 5.64 (dd, 1H, J=6.8, 9.2 Hz), 3.56 (t, 2H, J=6.4 Hz), 3.11–3.02 (m, 1H) 2.85–2.75 (m, 1H); ESMS m/e: 300.1 (M+H)$^+$.

N-(3-{1-[(3S)-3-(1,3-DIOXO-1,3-DIHYDRO-2H-ISOINDOL-2-YL)-3-PHENYLPROPYL]-4-PIPERIDINYL}PHENYL)-2-METHYLPROPANAMIDE: A mixture of 2-[(1S)-3-chloro-1-phenylpropyl]-1H-isoindole-1,3(2H)-dione (4.50 g, 15.0 mmol), 2-methyl-N-[3-(4-piperidinyl)phenyl]propanamide (4.26 g, 15.0 mmol), K$_2$CO$_3$ (4.16 g, 30.0 mmol), and NaI (3.40 g, 20.0 mmol) in DMF (40 mL) was stirred at 90° C. for 12 hrs. The reaction mixture was diluted with water (50 mL), extracted with CH$_2$Cl$_2$ (3×50 mL), and the combined organic extracts were washed with brine (50 mL), dried over MgSO$_4$, and concentrated under reduced pressure. The residue was purified by chromatography on silica using 5% of NH$_3$ (2.0 M in methanol) in CH$_2$Cl$_2$ to give the desired product (5.10 g, 74%). $^1$H NMR (400 MHz, CDCl$_3$) δ 7.83 (d, 1H, J=5.5 Hz), 7.82 (d, 1H, J=5.5 Hz), 7.71 (d, 1H, J=5.5 Hz), 7.70 (d, 1H, J=5.4 Hz), 7.56 (d, 2H, J=7.1 Hz), 7.35–7.27 (m, 5H), 7.22 (t, 1H, J=7.5 Hz), 7.09 (s, 1H), 6.81 (d, 1H, J=7.8 Hz), 5.49 (dd, 1H, J=5.5, 9.6 Hz), 2.97 (d, 1H, J=10.1 Hz), 2.92–2.82 (m, 2H), 2.44 (sept, 1H, J=6.7 Hz), 2.40–2.29 (m, 3H), 2.00–1.83 (m, 2H), 1.79–1.39 (m, 5H), 1.26 (d, 6H, J=6.9 Hz); ESMS m/e: 510.4 (M+H)$^+$.

N-(3-{1-[(3S)-3-AMINO-3-PHENYLPROPYL]-4-PIPERIDINYL}PHENYL)-2-METHYLPROPANAMIDE: A mixture of N-(3-{1-[(3S)-3-(1,3-dioxo-1,3-dihydro-2H-isoindol-2-yl)-3-phenylpropyl]-4-piperidinyl}phenyl)-2-methylpropanamide (4.60 g, 9.06 mmol) and hydrazine (3.62 g, 72.4 mmol) in ethanol (150 mL) was refluxed for 12 h. The resulting white precipitate was filtered out and the filtrate was concentrated under vacuum. The residue was washed with CH$_2$Cl$_2$/EtOAc (1:1, 3×50 mL) and the combined organic fractions were concentrated in vacuo to give the desired product (2.90 g, 95%). $^1$H NMR (400 MHz, CDCl$_3$) δ 7.45 (s, 1H), 7.39–7.30 (m, 6H), 7.29–7.19 (m, 2H), 6.95 (d, 1H, J=7.2), 4.01 (t, 1H, J=6.8 Hz), 3.04 (t, 2H, J=10.6 Hz), 2.62–2.30 (m, 6H), 2.05–1.70 (m, 8H), 1.24 (d, 6H, J=6.8 Hz); ESMS m/e: 380.4 (M+H)$^+$.

EXAMPLE 88

2-METHYL-N-(3-{1-[(3S)-3-PHENYL-3-(PROPIONYLAMINO)PROPYL]-4-PIPERIDINYL}PHENYL)PROPANAMIDE: According to the procedure used for the synthesis of N-(3-{1-[(3S)-3-(acetylamino)-3-phenylpropyl]-4-piperidinyl}phenyl)-2-methylpropanamide, N-(3-{1-[(3S)-3-amino-3-phenylpropyl]-4-piperidinyl}phenyl)-2-methylpropanamide (11.0 mg, 0.0280 mmol) and propionyl chloride (3.80 mg, 0.0420 mmol) provided 2-methyl-N-(3-{1-[(3S)-3-phenyl-3-(propionylamino)propyl]-4-piperidinyl}phenyl) propanamide (12 mg, 97% yield). $^1$H NMR (400 MHz, CDCl$_3$) δ 8.05 (s, 1H), 7.59 (s, 1H), 7.40–7.20 (m, 7H), 6.96 (s, 1H), 5.19–5.12 (m, 1H), 3.18 (d, 1H, J=12.0 Hz), 2.99 (d, 1H, J=10.4 Hz), 2.93–2.86 (m, 1H), 2.61–2.40 (m, 3H), 2.38–2.23 (m, 3H), 2.19–1.75 (m, 8H), 1.25 (d, 6H, J=6.9 Hz), 1.22–1.08 (m, 3H); ESMS m/e: 436.4 (M+H)$^+$.

EXAMPLE 89

N-{3-[1-((3S)-3-{[(4-FLUOROPHENYL)ACETYL]AMINO}-3-PHENYLPROPYL)-4-PIPERIDINYL]PHENYL}-2-METHYLPROPANAMIDE: A mixture of N-(3-{1-[(3S)-3-amino-3-phenylpropyl]-4-piperidinyl}phenyl)-2-methylpropanamide (11.0 mg, 0.0280 mmol) and (4-fluorophenyl)acetyl chloride (7.20 mg, 0.0420 mmol) in THF (5 mL) was stirred at room temperature for 4 h. The solvent was removed under reduced pressure and the residue was purified by preparative TLC using Hexane:EtOAc (2:1) to give the desired product (13 mg, 90% yield). $^1$H NMR (400 MHz, CDCl$_3$) δ 7.89 (d, 1H, J=8.4 Hz), 7.59 (s, 1H), 7.31–6.93 (m, 13H), 5.13 (q, 1H, J=6.0 Hz), 3.56 (s, 2H), 3.07 (d, 1H, J=11.7 Hz), 2.91 (d, 1H, J=11.0 Hz), 2.62–2.42 (m, 2H), 2.40–2.30 (m, 1H), 2.12–1.54 (m, 9H), 1.24 (d, 6H, J=6.7 Hz); ESMS m/e: 515.3 (M+H)$^+$.

EXAMPLE 90

N-(3-{1-[3-(1,2-DIPHENYL-1H-INDOL-3-YL)PROPYL]-4-PIPERIDINYL}PHENYL)-2-METHYLPROPANAMIDE: A mixture of 1,1-diphenylhydrazine hydrochloride (10.3 mg, 0.0470 mmol), 2-methyl-N-(3-[1-(5-oxo-5-phenylpentyl)-4-piperidinyl]phenyl}propanamide (14.7 mg, 0.0362 mmol), ZnCl$_2$ (14.85 mg, 0.109 mmol), and HOAC (0.5 mL) was heated for 4 h at 80° C. The resulting crude mixture was diluted with water (10 mL), the aqueous layer was neutralized with saturated K$_2$CO$_3$ and extracted with CH$_2$Cl$_2$ (3×20 mL). The combined organic layers were concentrated in vacuo and the residue was purified by preparative TLC using 5% of NH$_3$ (2.0 M in methanol) in CH$_2$Cl$_2$ to give the desired product N-(3-{1-[3-(1,2-diphenyl-1H-indol-3-yl)propyl]-4-piperidinyl}phenyl)-2-methylpropanamide (4.1 mg, 37%). $^1$H NMR (400 MHz, CDCl$_3$) δ 7.71–7.65 (m, 1H), 7.42 (d, 1H, J=7.4 Hz), 7.39 (s, 1H), 7.36–7.15 (m, 15H), 6.94 (d, 1H, J=7.8 Hz), 3.12 (d, 2H, J=11.2 Hz), 2.90 (t, 2H, J=7.8 Hz), 2.59–2.45 (m, 3H), 2.19–1.91 (m, 7H), 1.82 (d, 2H, J=13.5 Hz), 1.24 (d, 6H, J=6.9 Hz); ESMS m/e: 555.3 (M+H)$^+$.

EXAMPLE 91

N-(3-{1-[3-(5-METHOXY-2-PHENYL-1H-INDOL-3-YL)PROPYL]-4-PIPERIDINYL}PHENYL)-2-METHYLPROPANAMIDE: According to the procedure used for the synthesis of N-(3-{1-[3-(1,2-diphenyl-1H-indol-3-yl)propyl]-4-piperidinyl}phenyl)-2-methylpropanamide, 2-methyl-N-{3-[1-(5-oxo-5-phenylpentyl)-4-piperidinyl]phenyl}propanamide (15.6 mg, 38.2 mmol), and 1-(4-methoxyphenyl)hydrazine hydrochloride (8.00 mg, 0.0458 mmol) provided N-(3-{1-[3-(5-methoxy-2-phenyl-1H-indol-3-yl)propyl]-4-piperidinyl}phenyl)-2-methylpropanamide (3.9 mg, 20%). $^1$H NMR (400 MHz, CDCl$_3$) δ 8.06 (s, 1H), 7.55 (d, 2H, J=7.4 Hz), 7.43–7.39 (m, 3H), 7.38–7.35 (m, 2H), 7.27–7.19 (m, 3H), 7.08 (d, 1H, J=7.4 Hz), 6.94 (d, 1H, J=7.6 Hz), 6.87 (dd, 1H, J=4.0, 6.6 Hz), 3.88 (s, 3H), 3.80–3.69 (m, 1H), 2.99 (d, 2H, J=11.7 Hz), 2.89 (t, 2H, J=7.3), 2.55–2.39 (m, 4H), 2.02–1.88 (m, 3H), 1.82–1.68 (m, 4H), 1.24 (d, 6H, J=6.9 Hz); ESMS m/e: 510.3 (M+H)$^+$.

EXAMPLE 92

N-(3-{1-[4-(5-METHOXY-2-PHENYL-1H-INDOL-3-YL)BUTYL]-4-PIPERIDINYL}PHENYL)-2-

METHYLPROPANAMIDE: According to the procedure used for the synthesis of N-(3-(1-[3-(1,2-diphenyl-1H-indol-3-yl)propyl]-4-piperidinyl}phenyl)-2-methylpropanamide, 2-methyl-N-{3-[1-(6-oxo-6-phenylhexyl)-4-piperidinyl]phenyl}propanamide (14.3 mg, 0.0339 mmol) and 1-(4-methoxyphenyl)hydrazine hydrochloride (7.10 mg, 0.0407 mmol) provided N-(3-{1-[4-(5-methoxy-2-phenyl-1H-indol-3-yl)butyl]-4-piperidinyl}phenyl)-2-methylpropanamide (5.8 mg, 33%). $^1$H NMR (400 MHz, CDCl$_3$) δ 7.95 (d, 2H, J=7.8 Hz), 7.61–7.15 (m, 11H), 6.97 (d, 1H, J=7.0 Hz), 3.88 (s, 3H), 3.09 (d, 2H, J=11.3 Hz), 2.99 (t, 2H, J=7.0 Hz), 2.55–2.35 (m, 4H), 2.12–1.70 (m, 6H), 1.68–1.52 (m, 2H), 1.48–1.34 (m, 2H), 1.25 (d, 6H, J=6.7 Hz); ESMS m/e: 524.3 (M+H)$^+$.

EXAMPLE 93

2-METHYL-N-(3-{1-[(1-PHENYL-1H-INDOL-3-YL)METHYL]-4-PIPERIDINYL}PHENYL)PROPANAMIDE: According to the procedure used for the synthesis of N-(3-{1-[3-(1,2-diphenyl-1H-indol-3- yl)propyl]-4-piperidinyl}phenyl)-2-methylpropanamide, N-{3-[1-(3,3-dimethoxypropyl)-4-piperidinyl]phenyl}-2-methylpropanamide (15.2 mg, 0.0436 mmol) and 1,1-diphenylhydrazine hydrochloride (11.6 mg, 0.0524 mmol) provided 2-methyl-N-(3-{1-[(1-phenyl-1H-indol-3-yl)methyl]-4-piperidinyl}phenyl)propanamide (11 mg, 56%). $^1$H NMR (400 MHz, CDCl$_3$) δ 7.79 (d, 1H, J=7.8 Hz), 7.57 (d, 1H, J=7.7 Hz), 7.54–7.47 (m, 4H), 7.43–7.32 (m, 4H), 7.25–7.16 (m, 4H), 6.95 (d, 1H, J=7.8 Hz), 3.87 (s, 2H), 2.53–2.47 (m, 2H), 2.21 (dt, 2H, J=3.0, 10.5 Hz), 2.12–1.77 (m, 6H), 1.24 (d, 6H, J=6.9 Hz); ESMS m/e: 451.3 (M+H)$^+$.

EXAMPLE 94

2-METHYL-N-(3-{1-[(4E)-4-PHENYL-4-(2-PYRIDINYLHYDRAZONO)BUTYL]-4-PIPERIDINYL}PHENYL)PROPANAMIDE: According to the procedure used for the synthesis of N-(3-{1-[3-(1,2-diphenyl-1H-indol-3-yl)propyl]-4-piperidinyl}phenyl)-2-methylpropanamide, 2-methyl-N-{3-[1-(4-oxo-4-phenylbutyl)-4-piperidinyl]phenyl}propanamide (8.70 mg, 0.0223 mmol) and 2-hydrazinopyridine (2.92 mg, 0.0268 mmol) provided 2-methyl-N-(3-{1-[(4E)-4-phenyl-4-(2-pyridinylhydrazono)butyl]-4-piperidinyl}phenyl)propanamide (2.5 mg, 24%). $^1$H NMR (400 MHz, CDCl$_3$) δ 7.97 (d, 1H, J=8.6 Hz), 7.85 (d, 1H, J=7.3 Hz), 7.64–7.27 (m, 9H), 7.09 (d, 1H, J=8.0 Hz), 6.97 (d, 1H, J=8.4 Hz), 6.73 (q, 1H, J=6.6 Hz), 3.52–3.48 (m, 2H), 3.20–3.10 (m, 2H), 2.85–1.75 (m, 13H), 1.26 (d, 6H, J=6.8 Hz); ESMS m/e: 484.4 (M+H)$^+$.

EXAMPLE 95

N-(3-{1-[3-(5-METHOXY-1H-INDOL-3-YL)PROPYL]-4-PIPERIDINYL}PHENYL)-2-METHYLPROPANAMIDE: According to the procedure used for the synthesis of N-(3-{1-[3-(1,2-diphenyl-1H-indol-3-yl)propyl]-4-piperidinyl}phenyl)-2-methylpropanamide, N-(3-{1-[4-(1,3-dioxolan-2-yl)butyl]-4-piperidinyl}phenyl)-2-methylpropanamide (23.5 mg, 0.0628 mmol) and 1-(4-methoxyphenyl)hydrazine hydrochloride (13.2 mg, 0.0774 mmol) provided N-(3-{1-[3-(5-methoxy-1H-indol-3-yl)propyl]-4-piperidinyl}phenyl)-2-methylpropanamide (11 mg, 42%). $^1$H NMR (400 MHz, CDCl$_3$) δ 7.86 (s, 1H), 7.45 (s, 1H), 7.32 (d, 1H, J=8.4 Hz), 7.28–7.21 (m, 2H), 7.10 (s, 1H), 7.05 (d, 1H, J=2.3 Hz), 7.00–6.91 (m, 2H), 6.85 (dd, 1H, J=2.7, 9.0 Hz), 3.87 (s, 3H), 3.06 (d, 2H, J=11.6 Hz), 2.75 (t, 2H, J=7.2 Hz), 2.55–2.42 (m, 4H), 2.08–1.90 (m, 4H), 1.88–1.74 (m, 4H), 1.25 (d, 6H, J=6.9 Hz); ESMS m/e: 434.2 (M+H)$^+$.

TERT-BUTYL 4-[3-(PROPIONYLAMINO)PHENYL]-1-PIPERIDINECARBOXYLATE: Propionyl chloride (5.53 g, 0.0597 mol) was added dropwise to a solution of tert-butyl 4-(3-aminophenyl)-1-piperidinecarboxylate (15.0 g, 0.0543 mol) and TEA (16.5 g, 0.163 mol) in THF (200 mL) and the mixture was stirred at room temperature for 3 h. Water (50 mL) was added to the reaction mixture, the aqueous layer was extracted with CH$_2$Cl$_2$ (3×100 mL), and the combined organic extracts were washed with brine (50 mL), dried over Na$_2$SO$_4$ and concentrated under reduced pressure. The residue was purified by chromatography on silica using hexane/EtOAc (10:1) to afford the product (18.8 g, 99%). $^1$H NMR (400 MHz, CDCl$_3$) δ 7.48 (s, 1H), 7.34–7.21 (m, 3H), 6.93 (d, 1H, J=7.4 Hz), 2.77 (t, 2H, J=11.5 Hz), 2.68–2.58 (m, 1H), 2.38 (q, 2H, J=7.6 Hz), 1.87–1.67 (m, 4H), 1.67–1.54 (m, 2H), 1.48 (s, 9H), 1.25 (t, 3H, J=7.5 Hz); ESMS m/e: 333.4 (M+H)$^+$.

N-[3-(4-PIPERIDINYL)PHENYL]PROPANAMIDE: Into a stirred solution of tert-butyl 4-[3-(propionylamino)phenyl]-1-piperidinecarboxylate (18.8 g, 0.0543 mmol) in dioxane (100 mL) at 5° C. was bubbled HCl gas for 2 h. The solvent was removed in vacuo, the residue was dissolved in water (100 mL) and neutralized by adding 10% KOH aqueous solution. The aqueous layer was extracted (3×200 mL) with a mixture of CHCl$_3$/isopropyl alcohol (3:1), and the combined organic layers were washed with brine (100 mL), dried over Na$_2$SO$_4$, filtered and concentrated in vacuo. The residue was purified by column chromatography on silica using 5% of NH$_3$ (2.0 M in methanol) in CH$_2$Cl$_2$ to afford the desired product (12.6 g, 99%). $^1$H NMR (400 MHz, CDCl$_3$) δ 7.44 (s, 1H), 7.32 (d, 1H, J=7.2 Hz), 7.28–7.21 (m, 1H), 7.09 (s, 1H), 6.97 (d, 1H, J=7.6 Hz), 3.18 (d, 2H, J=12.6 Hz), 2.73 (dt, 2H, J=2.2, 11.2 Hz), 2.65–2.57 (m, 1H), 2.38 (q, 2H, J=7.4 Hz), 1.83 (d, 2H, J=12.1 Hz), 1.70–1.61 (m, 3H), 1.25 (t, 3H, J=7.5 Hz); ESMS m/e: 233.1 (M+H)$^+$.

TERT-BUTYL 4-{3-[(CYCLOPROPYLCARBONYL)AMINO]PHENYL}-1-PIPERIDINECARBOXYLATE: According to the procedure used for the synthesis of tert-butyl 4-[3-(propionylamino)phenyl]-1-piperidinecarboxylate, tert-butyl 4-(3-aminophenyl)-1-piperidinecarboxylate (16.47 g 0.0596 mol) and cyclopropanecarbonyl chloride (6.27 g, 0.0597 mol) provided the tert-butyl 4-{3-[(cyclopropylcarbonyl)amino]phenyl}-1-piperidinecarboxylate (18.1 g, 100%). $^1$H NMR (400 MHz, CDCl$_3$) δ 7.55–7.46 (m, 2H), 7.29–7.21 (m, 2H), 6.96–6.89 (m, 1H), 2.79 (t, 2H, J 12.1 Hz), 2.68–2.58 (m, 1H), 1.84 (d, 2H, J=12.6 Hz), 1.83–1.76 (m, 4H), 1.48 (s, 9H), 1.19–1.12 (m, 1H), 1.09–1.05 (m, 2H), 0.89–0.75 (m, 2H); ESMS m/e: 345.5 (M+H)$^+$.

N-[3-(4-PIPERIDINYL)PHENYL]CYCLOPROPANECARBOXAMIDE: According to the procedure used for the synthesis of N-[3-(4-piperidinyl)phenyl]propanamide, tert-butyl 4-{3-[(cyclopropylcarbonyl)amino]phenyl}-1-piperidinecarboxylate (18.9 g, 0.0543 mol) provided N-[3-(4-piperidinyl)phenyl]cyclopropanecarboxamide (13.2 g, 100%). $^1$H NMR (400 MHz, CDCl$_3$) δ 7.46 (s, 1H), 7.36–7.22 (m, 3H), 7.23 (d, 1H, J=6.9 Hz), 3.17 (d, 2H, J=11.9 Hz), 2.72 (dt, 2H, J=2.6, 12.2 Hz), 2.65–2.55 (m, 1H), 1.82 (d, 2H, J=13.9 Hz), 1.63 (dt, 3H, J=4.1, 12.5 Hz), 1.53–1.45 (m, 1H), 1.11–1.06 (m, 2H), 0.87–5.81 (m, 2H); ESMS m/e: 245.03 (M+H)$^+$.

1-(6-CHLOROHEXYL)-1H-INDOLE: To a mixture of NaH (0.249 g, 10.0 mmol) in DMF (5 mL) at 0° C. was added a solution of 1-H-indole (0.585 g, 5.00 mmol) in DMF (2 mL). The reaction mixture was stirred for 30 minutes and warmed up to room temperature. Then 1-bromo-6-chlorohexane (0.998 g, 5.00 mmol) was added dropwise by syringe and the reaction mixture was stirred overnight. The reaction mixture was diluted with EtOAc (30 mL), washed with water (3×10 mL), dried over $MgSO_4$, concentrated in vacuo and purified by chromatography using hexane/EtOAc (97.5:2.5) to give the desired product (0.900 g, 76%) $^1H$ NMR ($CDCl_3$) δ 7.76–7.54 (m, 1H), 7.47–6.96 (m, 4H), 6.60–6.34 (m, 1H), 4.13 (t, 2H, J=6.8 Hz), 3.50 (t, 2H, J=5.6 Hz), 1.98–1.79 (m, 2H), 1.79–1.64 (m, 2H), 1.54–1.17 (m, 4H).

1-(5-CHLOROPENTYL)-1H-INDOLE: According to the procedure used for the synthesis of 1-(6-chlorohexyl)-1H-indole, 1-H-indole (0.585 g, 5.00 mmol) and 1-bromo-5-chloropentane (0.928 g, 5.00 mmol) gave the desired product (0.890 g, 80%). $^1H$ NMR ($CDCl_3$) δ 7.76–7.51 (m, 1H), 7.44–6.96 (m, 4H), 6.60–6.38 (m, 1H), 4.11 (t, 2H, J=6.8 Hz), 3.47 (t, 2H, J=6.4 Hz), 1.97–1.79 (m, 2H), 1.79–1.61 (m, 2H), 1.58–1.32 (m, 2H).

EXAMPLE 96

N-(3-{1-[6-(1H-INDOL-1-YL)HEXYL]-4-PIPERIDINYL}PHENYL)-2-METHYLPROPANAMIDE: 1-(6-Chlorohexyl)-1H-indole (23.6 mg, 0.100 mmol), 2-methyl-N-[3-(4-piperidinyl)phenyl]propanamide (24.6 mg, 0.100 mmol), $K_2CO_3$ (27.6 mg, 0.200 mmol), NaI (22.5 mg, 0.150 mmol) and DMF (1.00 mL) were combined and stirred overnight at 100° C. The reaction mixture was cooled to room temperature and the crude material was purified by preparative TLC using 5% of $NH_3$ (2.0 M in methanol) in $CH_2Cl_2$ to give the desired product as a yellow solid (40 mg, 90%). $^1H$ NMR (400 MHz, $CDCl_3$) δ 8.08–6.52 (m, 11H) 4.17 (t, 2H, J=7.2 Hz), 3.26 (d, 2H, J=11.6 Hz), 2.74–2.52 (m, 4H), 2.44–2.28 (m, 2H), 2.20–2.02 (m, 2H), 1.98–1.82 (m, 4H), 1.78–1.62 (m, 2H), 1.43–1.28 (m, 4H), 1.28 (d, 6H, J=6.8 Hz); ESMS m/e: 446.5 $(M+H)^+$.

EXAMPLE 97

N-(3-{1-[5-(1H-INDOL-1-YL)PENTYL]-4-PIPERIDINYL}PHENYL)-2-METHYLPROPANAMIDE: Prepared as above, using 1-(5-chloropentyl)-1H-indole (22.2 mg, 0.100 mmol), 2-methyl-N-[3-(4-piperidinyl) phenyl]propanamide (24.6 mg, 0.100 mmol), $K_2CO_3$ (27.6 mg, 0.200 mmol), NaI (23.0 mg, 0.150 mmol) and DMF (1.00 mL), giving the desired product as a yellow oil (36 mg, 81%). $^1H$ NMR (400 MHz, $CDCl_3$) δ 8.08–6.52 (m, 11H), 4.19 (t, 2H, J=7.2 Hz), 3.26–3.10 (m, 2H), 2.71–2.55 (m, 2H), 2.55–2.42 (m, 2H), 2.35–2.12 (m, 2H), 2.12–1.80 (m, 6H), 1.80–1.57 (m, 2H), 1.51–1.34 (m, 2H), 1.31 (d, 6H, J=6.8 Hz); ESMS m/e: 432.2 $(M+H)^+$.

EXAMPLE 98

N-(4-{1-[(9-ETHYL-9H-CARBAZOL-3-YL) METHYL]-4-PIPERIDINYL}PHENYL)-2-METHYLPROPANAMIDE: According to the procedure used for the synthesis of N-(3-{1-[4-(4-CHLOROPHENOXY)BENZYL]-4-PIPERIDINYL}PHENYL)-2-METHYLPROPANAMIDE (Example 108) N-(3-{1-[3-(1,2-diphenyl-1H-indol-3-yl) propyl]-4-piperidinyl}phenyl)-2-methylpropanamide, 9-ethyl-9H-carbazole-3-carbaldehyde (22.3 mg, 0.100 mmol) and 2-methyl-N-[4-(4-piperidinyl)phenyl] propanamide (24.6 mg, 0.100 mmol) provided N-(4-{1-[(9-ethyl-9H-carbazol-3-yl)methyl]-4-piperidinyl}phenyl)-2-methylpropanamide. The product was obtained as a white crystalline solid (20 mg, 44%). $^1H$ NMR (400 MHz, $CDCl_3$) δ 8.21–7.09 (m, 12H), 4.38 (q, 2H, J=7.2 Hz), 3.81 (s, 2H), 3.25–3.03 (m, 2H), 2.60–2.38 (m, 2H), 2.31–2.09 (m, 2H), 1.98–1.69 (m, 4H), 1.44 (t, 3H, J=7.2 Hz), 1.23 (d, 6H, J=6.8 Hz); ESMS m/e: 454.3 $(M+H)^+$.

EXAMPLE 99

N-(3-{1-[(9-ETHYL-9H-CARBAZOL-3-YL) METHYL]-4-PIPERIDINYL}PHENYL)-2-METHYLPROPANAMIDE: According to the procedure used for the synthesis of N-(3-{1-[4-(4-CHLOROPHENOXY)BENZYL]-4-PIPERIDINYL}PHENYL)-2-METHYLPROPANAMIDE (Example 108) N-(4-{1-[(9-ethyl-9H-carbazol-3-yl) methyl]-4-piperidinyl}phenyl)-2-methylpropanamide, 9-ethyl-9H-carbazole-3-carbaldehyde and 2-methyl-N-[3-(4-piperidinyl)phenyl]propanamide afforded N-(3-{1-[(9-ethyl-9H-carbazol-3-yl)methyl]-4-piperidinyl}phenyl)-2-methylpropanamide (37 mg, 95%). $^1H$ NMR (400 MHz, $CDCl_3$) δ 8.24–6.29 (m, 12H), 4.37 (q, 2H, J=7.2 Hz), 3.82 (s, 2H), 3.23–3.06 (m, 2H), 2.65–2.38 (m, 2H), 2.31–2.11 (m, 2H), 2.01–1.73 (m, 4H), 1.43 (t, 3H, J=7.2 Hz), 1.25 (d, 6H, J=4.0 Hz); ESMS m/e: 454.3 $(M+H)^+$.

EXAMPLE 100

N-[3-(1-{[1-(4-METHOXYPHENYL)-1H-INDOL-5-YL]METHYL}-4-PIPERIDINYL)PHENYL]-2-METHYLPROPANAMIDE: According to the procedure used for the synthesis of 1-(4-methylphenyl)1H-indole, N-{3-[1-(1H-indol-5-ylmethyl)-4-piperidinyl]phenyl}-2-methylpropanamide (37.5 mg, 0.100 mmol) and 1-iodo-4-methoxybenzene (46.8 mg, 0.200 mmol) gave the desired product (27 mg, 56%). $^1H$ NMR (400 MHz, $CDCl_3$) δ 7.70–6.58 (m, 14H), 3.88 (s, 3H), 3.67 (s, 2H), 3.14–3.01 (m, 2H), 2.57–2.41 (m, 2H), 2.25–2.01 (m, 2H), 1.93–1.69 (m, 4H), 1.24 (d, 6H, J=7.2 Hz); ESMS m/e: 482.2 $(M+H)^+$.

EXAMPLE 101

N-[3-(1-{[1-(4-FLUOROPHENYL)-1H-INDOL-5-YL] METHYL}-4-PIPERIDINYL)PHENYL]-2-METHYLPROPANAMIDE: According to the procedure used for the synthesis of 1-(4-methylphenyl)1H-indole, N-{3-[1-(1H-indol-5-ylmethyl)-4-piperidinyl]phenyl}-2-methylpropanamide (37.5 mg, 0.100 mmol) and 1-fluoro-4-iodobenzene (44.4 mg, 0.200 mmol) gave the desired product (21 mg, 45%). $^1H$ NMR (400 MHz, $CDCl_3$) δ 7.71–6.60 (m, 14H), 3.69 (s, 2H), 3.19–2.99 (m, 2H), 2.62–2.41 (m, 2H), 2.22–2.07 (m, 2H), 1.94–1.70 (m, 4H), 1.24 (d, 6H, J=6.8 Hz); ESMS m/e: 470.2 $(M+H)^+$.

EXAMPLE 102

METHYL-4-[5-({4-[3-(ISOBUTYRYLAMINO) PHENYL]-1-IPERIDINYL}METHYL)-1H-INDOL-1-YL] BENZOATE: According to the procedure used for the synthesis of 1-(4-methylphenyl)1H-indole, N-{3-[1-(1H-indol-5-ylmethyl)-4-piperidinyl]phenyl}-2-methylpropanamide (37.5 mg, 0.100 mmol) and methyl 4-iodobenzoate (52.4 mg, 0.200 mmol) gave the desired product (11 mg, 22%). $^1H$ NMR (400 MHz, $CDCl_3$) δ 8.31–6.64 (m, 14H), 3.96 (s, 3H), 3.67 (s, 2H), 3.16–2.96 (m, 2H), 2.57–2.41 (m, 2H), 2.18–2.02 (m, 2H), 1.91–1.73 (m, 4H), 1.24 (d, 6H, J=6.8 Hz); ESMS m/e: 510.2 $(M+H)^+$.

EXAMPLE 103

2-METHYL-N-[3-(1-{[1-(3-METHYLPHENYL)-1H-INDOL-5-YL]METHYL}-4-PIPERIDINYL)PHENYL]

PROPANAMIDE: According to the procedure used for the synthesis of 1-(4-methylphenyl)1H-indole, N-{3-[1-(1H-indol-5-ylmethyl)-4-piperidinyl]phenyl}-2-methylpropanamide (37.5 mg, 0.100 mmol) and 1-iodo-3-methylbenzene (43.6 mg, 0.200 mmol) gave the desired product (28 mg, 60%). $^1$H NMR (400 MHz, CDCl$_3$) δ 7.68–6.60 (m, 14H), 3.66 (s, 2H), 3.16–2.96 (m, 2H), 2.59–2.44 (m, 2H), 2.44 (s, 3H), 2.18–2.01 (m, 2H), 1.91–1.68 (m, 4H), 1.24 (d, 6H, J=6.8 Hz); ESMS m/e: 466.2 (M+H)$^+$.

EXAMPLE 104

N-{3-[1-(3-{[(4-CHLORO-3-NITROPHENYL)SULFONYL]AMINO}PROPYL)-4-PIPERIDINYL]PHENYL}-2-METHYLPROPANAMIDE: A mixture of N-{3[1-(2-aminopropyl)-4-piperidinyl]phenyl}-2-methylpropanamide (10.0 mg, 0.0350 mmol), 4-chloro-3-nitrobenzenesulfonyl chloride (9.90. mg, 0.0380 mmol), and TEA (7.00 mg, 0.0700 mmol) in THF (2 mL) was stirred for 12 h at room temperature. The crude product was purified by preparative TLC (CH$_2$Cl$_2$/MeOH/isopropyl amine= 19:1:0.2) to give the desired product (16 mg, 86%). $^1$H NMR (400 MHz, CDCl$_3$) δ 8.45–8.38 (m, 1H), 8.02 (d, 1H, J=8.4 Hz), 7.72 (d, 1H, J=8.8 Hz), 7.48–7.40 (m, 3H), 7.29–7.24 (m, 2H), 6.96 (d, 1H, J=7.5 Hz), 3.17–3.09 (m, 4H), 2.63–2.48 (m, 4H), 2.15 (t, 2H, J=11.8 Hz), 1.96–1.72 (m, 6H), 1.25 (d, 6H, J=6.9 Hz); ESMS m/e: 523.2 (M+H)$^+$.

EXAMPLE 105

N-[3-(1-{5-[4-(3,4-DIFLUOROPHENYL)-2-OXO-1,3-OXAZOLIDIN-3-YL]PENTYL}-4-PIPERIDINYL)PHENYL]-2-METHYLPROPANAMIDE: A mixture of 3-(5-bromopentyl)-4-(3,4-difluorophenyl)-1,3-oxazolidin-2-one (38.0 mg, 0.110 mmol), 2-methyl-N-[3-(4-piperidinyl)phenyl]propanamide (26.0 mg, 0.100 mmol), NaI (23.0 mg, 0.150 mmol), and K$_2$CO$_3$ (14.0 mg, 0.100 mmol) in DMF (2 mL) was heated for 1 h at 50° C. The crude product was purified by preparative TLC using CH$_2$Cl$_2$/MeOH/isopropyl amine (19:1:0.2) to give the desired product (21 mg, 41%). $^1$H NMR (400 MHz, CDCl$_3$) δ 7.49 (s, 1H), 7.39–7.32 (m, 2H), 7.26–7.20 (m, 2H), 7.18–7.11 (m, 1H), 7.10–7.03 (m, 1H), 6.96 (d, 1H, J=7.6 Hz), 4.80–4.73 (m, 1H), 4.62 (t, 1H, J=7.9 Hz), 4.09–4.04 (m, 1H), 3.51–3.42 (m, 1H), 3.03 (d, 2H, J=11.7 Hz), 2.82–2.72 (m, 1H), 2.51–2.42 (m, 2H), 2.32 (t, 2H, J=7.9 Hz), 2.11 (s, 1H), 2.03–1.97 (m, 2H), 1.85–1.70 (m, 4H), 1.49 (m, 4H), 1.31–1.27 (m, 1H), 1.24 (d, 6H, J=6.9 Hz); ESMS m/e: 514.4 (M+H)$^+$.

EXAMPLE 106

3-(2,6-DICHLOROPHENYL)-N-(5-{4-[3-(ISOBUTYRYLAMINO)PHENYL]-1-PIPERIDINYL}PENTYL)-5-METHYL-4-ISOXAZOLECARBOXAMIDE: A mixture of 3-(2,6-dichlorophenyl)-4-formyl-5-isoxazolecarbonyl chloride (69.0 mg, 0.250 mmol), N-{3-[1-(5-aminopentyl)-4-piperidinyl]phenyl}-2-ethylpropanamide (44.0 mg, 0.150 mmol), TEA (30.0 mg, 0.300 mmol) in THF (2 mL) was stirred for 12 h at room temperature. The crude product was purified by preparative TLC using CH$_2$Cl$_2$/MeOH/isopropyl amine (19:1:0.2) to give the desired product (52 mg, 67%). $^1$H NMR (400 MHz, CDCl$_3$) δ 7.52–7.49 (m, 2H), 7.49–7.41 (m, 2H), 7.39–7.31 (m, 2H), 7.29–7.21 (m, 2H), 6.92 (d, 1H, J=7.6 Hz), 3.25–3.11 (m, 5H), 2.81–2.74 (m, 4H), 2.58–2.44 (m, 4H), 2.30–2.19 (m, 2H), 1.93–1.78 (m, 4H), 1.56–1.44 (m, 2H), 1.31–1.28 (m, 2H), 1.24 (d, 6H, J=6.6 Hz); ESMS m/e: 585.2 (M+H)$^+$.

EXAMPLE 107

N-[3-(1-{2-[(DIPHENYLACETYL)AMINO]ETHYL}-4-PIPERIDINYL)PHENYL]-2-METHYLPROPANAMIDE: A mixture of N-{3[1-(2-aminoethyl)-4-piperidinyl]phenyl}-2-methylpropanamide (20.0 mg, 0.0700 mmol), diphenylacetyl chloride (23.0 mg, 0.110 mmol), and TEA (20.0 mg, 0.140 mmol) in THF (2 mL) was stirred overnight at 23° C. The crude product was purified by preparative TLC using CH$_2$Cl$_2$/MeOH/isopropyl amine (19:1:0.2) to give the desired product (8.0 mg, 47%). $^1$H NMR (400 MHz, CDCl$_3$) δ 7.53 (s, 1H), 7.37–7.20 (m, 13H), 6.97–6.92 (m, 1H), 6.67 (s, 1H), 4.98 (s, 1H), 3.43 (q, 2H, J=5.9 Hz), 2.90 (d, 2H, J=11.6 Hz), 2.57–2.42 (m, 4H), 2.11 (t, 2H, J=10.4 Hz), 1.75 (d, 2H, J=12.4 Hz), 1.70–1.58 (m, 2H), 1.25 (d, 6H, J=6.7 Hz); ESMS m/e: 484.2 (M+H)$^+$.

EXAMPLE 108

N-(3-{1-[4-(4-CHLOROPHENOXY)BENZYL]-4-PIPERIDINYL}PHENYL)-2-METHYLPROPANAMIDE: 4-(4-chlorophenoxy)benzaldehyde (0.119 g, 0.510 mmol) and 2-methyl-N-[3-(4-piperidinyl)phenyl]propanamide (0.126 g, 0.510 mmol) were mixed in 1,2-dichloroethane (5 mL) and then treated with sodium triacetoxyborohydride (0.424 g, 2.00 mmol) and HOAc (0.03 mL, 0.5 mmol). The mixture was stirred overnight at room temperature. The reaction mixture was neutralized with saturated NaHCO$_3$ aqueous solution and the aqueous layer was extracted with CH$_2$Cl$_2$ (3×10 mL). The combined organic layers were washed with brine, dried over MgSO$_4$, concentrated in vacuo, and purified by preparative TLC using 5% of NH$_3$ (2.0 M in methanol) in CH$_2$Cl$_2$ to give the desired product (53 mg, 23%). $^1$H NMR (400 MHz, CDCl$_3$) δ 7.50 (s, 1H), 7.34–7.19 (m, 7H), 6.98–6.87 (m, 5H), 3.50 (s, 2H), 2.98 (d, 2H, J=11.8 Hz), 2.58–2.44 (m, 2H), 2.10–1.98 (m, 2H), 1.83–1.76 (m, 4H), 1.24 (d, 6H, J=6.8 Hz); ESMS m/e: 463.2 (M+H)$^+$.

EXAMPLE 109

N-{3-[3-({2,5-DIMETHYL-1-[3-(TRIFLUOROMETHYL)PHENYL]-1H-PYRROL-3-YL}METHYL)-4-PIPERIDINYL]PHENYL}-2-METHYLPROPANAMIDE: Prepared by the procedure described in example 108, substituting 2,5-dimethyl-1-[3-(trifluoromethyl)phenyl]-1H-pyrrole-3-carbaldehyde (0.136 g, 0.510 mmol) for 4-(4-chlorophenoxy)benzaldehyde. $^1$H NMR (400 MHz, CDCl$_3$) δ 7.69–7.56 (m, 2H), 7.53–7.32 (m, 4H), 7.28–7.18 (m, 2H), 6.99 (s, 1H) 5.98 (s, 1H) 3.43 (s, 2H), 3.16–3.06 (m, 2H) 2.57–2.42 (m, 2H), 2.07–1.95 (m, 8H) 1.89–1.76 (m, 4H), 1.24 (d, 6H, J=6.8 Hz); ESMS m/e: 498.2 (M+H)$^+$.

EXAMPLE 110

N-(3-{1-[4-(3,4-DIFLUOROPHENOXY)BENZYL]-4-PIPERIDINYL}PHENYL)-2-METHYLPROPANAMIDE: Prepared by the procedure described in example 108, substituting 4-(3,4-difluorophenoxy)benzaldehyde (0.119 g, 0.510 mmol) for 4-(4-chlorophenoxy)benzaldehyde. $^1$H NMR (400 MHz, CDCl$_3$) δ 7.52 (s, 1H), 7.32 (d, 2H, J=8.4 Hz), 7.28–7.21 (m, 2H), 7.14–7.06 (m, 2H), 6.98–6.94 (m, 3H), 6.86–6.79 (m, 1H), 6.76–6.69 (m, 1H), 3.51 (s, 2H), 2.99 (d, 2H, J=11.7 Hz), 2.55–2.44 (m, 2H), 2.12–2.02 (m, 2H), 1.86–1.74 (m, 4H), 1.25 (d, 6H, J=7.0 Hz); ESMS m/e: 465.2 (M+H)$^+$.

EXAMPLE 111

N-(3-{1-[(5-CHLORO-3-METHYL-1-PHENYL-1H-PYRAZOL-4-YL)METHYL]-4-

PIPERIDINYL}PHENYL)-2-METHYLPROPANAMIDE: Prepared by the procedure described in example 108, substituting 5-chloro-3-methyl-1-phenyl-1H-pyrazole-4-carbaldehyde (0.113 g, 0.510 mmol) for 4-(4-chlorophenoxy)benzaldehyde. $^1$H NMR (400 MHz, CDCl$_3$) δ 7.62–7.19 (m, 9H), 6.97 (s, 1H), 3.43 (s, 2H), 3.08–2.98 (m, 2H), 2.58–2.43 (m, 2H), 2.39–2.32 (m, 3H), 2.18–1.71 (m, 6H), 1.24 (d, 6H, J=6.9 Hz); ESMS m/e: 451.2 (M+H)$^+$.

EXAMPLE 112

N-(3-{1-[4-(3,4-DICHLOROPHENOXY)BENZYL]-4-PIPERIDINYL}PHENYL)-2-METHYLPROPANAMIDE: Prepared by the procedure described in example 108, substituting 4-(3,4-dichlorophenoxy)benzaldehyde (0.136 g, 0.510 mmol) for 4-(4-chlorophenoxy)benzaldehyde. $^1$H NMR (400 MHz, CDCl$_3$) δ 7.53 (s, 1H), 7.36–7.18 (m, 6H), 7.08 (d, 1H, J=1.8 Hz), 6.96 (d, 3H, J=6.8 Hz), 6.84 (dd, 1H, J=2.8, 8.9 Hz), 3.51 (s, 2H), 2.99 (d, 2H, J=11.5 Hz), 2.55–2.42 (m, 2H), 2.12–2.02 (m, 2H), 1.84–1.73 (m, 4H), 1.24 (d, 6H, J=7.0 Hz); ESMS m/e: 497.1 (M+H)$^+$.

EXAMPLE 113

2-METHYL-N-(3-{1-[(2-PHENYL-1H-IMIDAZOL-4-YL)METHYL]-4-PIPERIDINYL}PHENYL) PROPANAMIDE: Prepared by the procedure described in example 108, substituting 2-phenyl-1H-imidazole-4-carbaldehyde (88.0 mg, 0.510 mmol) for 4-(4-chlorophenoxy)benzaldehyde. $^1$H NMR (400 MHz, CDCl$_3$) δ 7.92 (d, 2H, J=7.4 Hz), 7.65–7.31 (m, 6H), 7.28–7.18 (m, 2H), 7.12–7.05 (m, 1H), 6.95–6.88 (m, 1H), 3.69 (s, 2H), 3.17–3.05 (m, 2H), 2.62–2.45 (m, 2H), 2.28–2.18 (m, 2H), 1.88–1.70 (m, 4H), 1.25 (d, 6H, J=6.8 Hz); ESMS m/e: 403.2 (M+H)$^+$.

EXAMPLE 114

N-(3-{1-[4-(DIPHENYLAMINO)BENZYL]-4-PIPERIDINYL}PHENYL)-2-METHYLPROPANAMIDE: Prepared by the procedure described in example 108, substituting 4-(diphenylamino)benzaldehyde (0.139 g, 0.510 mmol) for 4-(4-chlorophenoxy)benzaldehyde. $^1$H NMR (400 MHz, CDCl$_3$) δ 7.49 (s, 1H), 7.39–6.92 (m, 18H), 3.49 (s, 2H), 3.02–2.99 (m, 2H), 2.59–2.43 (m, 2H), 2.15–2.03 (m, 2H), 1.92–1.76 (m, 4H), 1.23 (d, 6H, J=6.8 Hz); ESMS m/e: 504.2 (M+H)$^+$.

EXAMPLE 115

N-[3-(1-{[4-BROMO-1-(4-CHLOROBENZYL)-1H-PYRAZOL-5-YL]METHYL}-4-PIPERIDINYL) PHENYL]-2-METHYLPROPANAMIDE: Prepared by the procedure described in example 108, substituting 4-bromo-1-(4-chlorobenzyl)-1H-pyrazole-5-carbaldehyde (0.153 9, 0.510 mmol) for 4-(4-chlorophenoxy)benzaldehyde. $^1$H NMR (400 MHz, CDCl$_3$) δ 7.41 (s, 1H), 7.36 (d, 1H, J=8.8 Hz), 7.34–7.30 (m, 3H), 7.29–7.26 (m, 1H), 7.22 (t, 1H, J=7.8 Hz), 7.16 (d, 2H, J=8.6 Hz), 6.95 (d, 1H, J=7.5 Hz), 5.24 (s, 2H), 3.61 (s, 2H), 3.09 (d, 2H, J=11.9 Hz), 2.55–2.42 (m, 2H), 2.19 (dt, 2H, J=4.4, 11.4 Hz), 1.89–1.76 (m, 4H), 1.24 (d, 6H, J=6.7 Hz); ESMS m/e: 529.1 (M+H)$^+$.

1-(3-[{(1R)-3-CHLORO-PHENYLPROPYL] OXY}PHENYL)ETHANONE: Azodicarboxylate (5.37 g, 0.0310 mol) was added to a solution of triphenylphosphine (8.09 g, 0.0308 mol), 1S-3-chloro-1-phenyl-1-propanol (4.20 g, 0.031 mol) and, 1-(3-hydroxyphenyl)ethanone in THF (150 mL). The reaction mixture was stirred for 4 days at 23° C. The solvent was removed under reduced pressure and the residue was triturated with ether/hexane (1:2, (3×100 mL). The combined organic fractions were concentrated in vacuo and the crude product was purified by chromatography using EtOAc/hexane (1:14) to give the desired product (6.55 g, 74%). $^1$H NMR (400 MHz, CDCl$_3$) δ 7.48–7.31 (m, 6H), 7.26 (t, 2H, J=8.2 Hz), 7.04 (d, 1H, J=8.1 Hz), 5.44 (dd, 1H, J=4.4, 8.1 Hz), 3.83–3.74 (m, 1H), 3.63–3.56 (m, 1H), 2.51 (s, 3H), 2.51–2.45 (m, 1H), 2.29–2.17 (m, 1H); ESMS m/e: 289.0 (M+H)$^+$.

EXAMPLE 116

N-(3-{1-[(3R)-3-(3-ACETYLPHENOXY)-3-PHENYLPROPYL]-4-PIPERIDINYL}PHENYL)-2-METHYLPROPANAMIDE: A mixture of 1-(3-{[(1R)-3-chloro-1-phenylpropyl]oxy}phenyl)ethanone (58.5 mg, 0.200 mmol), 2-methyl-N-[3-(4-piperidinyl)phenyl] propanamide (56.8 mg, 0.200 mmol), NaI (34.0 mg, 0.200 mmol) and K$_2$CO$_3$ (55.5 mg, 0.400 mmol) in DMF (1 mL) was stirred at 100° C. for 3 h. The solvent was removed under reduced pressure and the residue was purified by chromatography on silica using 5% of NH$_3$ (2.0 M in methanol) in CH$_2$Cl$_2$ to give the desired product (98 mg, 98%). $^1$H NMR (400 MHz, CDCl$_3$) δ 8.01 (s, 1H), 7.49–7.21 (m, 11H), 7.09–7.03 (m, 1H), 6.96 (d, 1H, J=7.9 Hz), 5.32 (dd, 1H, J=5.0, 7.9 Hz), 3.08–2.98 (m, 2H), 2.57–2.43 (m, 6H), 2.11–1.72 (m, 9H), 1.25 (d, 6H, J=6.8 Hz); ESMS m/e: 499.4 (M+H)$^+$.

Procedures:

Procedure A (See Also Example 48)

N-(3-{1-[(3R)-3-(3,4-DIMETHOXYPHENOXY)-3-PHENYLPROPYL]-4-PIPERIDINYL}PHENYL)-2-METHYLPROPANAMIDE:

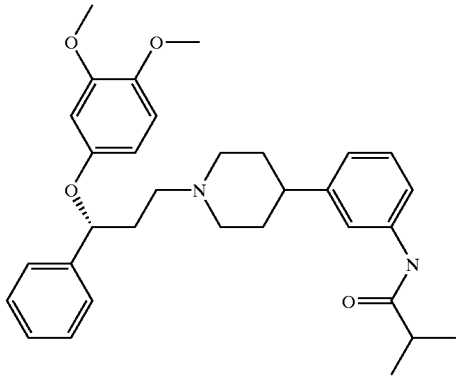

Method A

4-{[(1R)-3-CHLORO-1-PHENYLPROPYL]OXY}-1,2-DIMETHOXYBENZENE: A mixture of 3,4-dimethoxyphenol (4.07 g, 26.4 mmol), (S)-(−)-3-chloro-phenyl-1-propanol (4.50 g, 26.4 mmol, 99% ee, Aldrich Chemical Co.), triphenylphosphine (6.92 g, 26.4 mmol) and diethyl azodicarboxylate (4.59 g, 26.4 mmol) in THF (110 mL) was stirred at room temperature for 24 h. The reaction mixture was concentrated in vacuo. At this point, the residue can either be washed with pentane and the combined pentane extracts were concentrated and chromatographed with hexane:EtOAc (8:1) as the eluent to give the desired product (as described as a general procedure by: Srebnik, M.; Ramachandran, P. V.; Brown, H. C. *J. Org. Chem.* 1988, 53, 2916–2920). This procedure was performed on a smaller scale reaction and only a 40% yield of the product was realized.

Alternatively, on a larger scale (26.4 mmol), the crude product was triturated with a small amount of dichloromethane and the precipitated triphenylphosphine oxide was filtered. The filtrate was concentrated and the crude product was chromatographed to give the desired product as a thick yellow oil (7.30 g, 88.9% yield): $^1$H NMR (400 MHz, CDCl$_3$) δ 7.39–7.32 (m, 4H), 7.20 (m, 1H), 6.64 (d, 1H, J=8.7 Hz), 6.51 (d, 1H, J=2.7 Hz), 6.30 (dd, 1H, J=2.7, 8.7 Hz), 5.27 (apparent dd, 1H, J=4.5, 8.7 Hz), 3.79 (s, 3H), 3.77 (s, 3H), 3.61 (m, 1H), 2.45 (m, 1H), 2.20 (m, 1H), 1.80 (s, 1H); ESMS m/e: 307.1 (M+H)$^+$.

N-(3-{1-[(3R)-3-(3,4- DIMETHOXYPHENOXY)-3-PHENYLPROPYL]-4-PIPERIDINYL}PHENYL)-2-METHYLPROPANAMIDE: A mixture of potassium carbonate (321 mg, 2.32 mmol), sodium iodide (522 mg, 3.48 mmol), 2-methyl-N-[3-(4-piperidinyl)phenyl]propanamide (570 mg, 2.32 mmol) and 4-{[(1R)-3-chloro-1-phenylpropyl]oxy)-1,2-dimethoxybenzene (712 mg, 2.32 mmol) in DMF (5.00 mL) was stirred at 100° C. for 3 h, at which time TLC indicated that the reaction was complete. The reaction mixture was poured into water (50 mL) and the aqueous layer was extracted with methylene chloride (3×30 mL). The combined organic extracts were washed with brine (30 mL), dried over MgSO$_4$ and concentrated under reduced pressure. The crude product was purified by Preparatory TLC [2.5% of NH$_3$ (2.0 M in methanol) in CHCl$_3$] to afford the product (970 mg, 90.1%) as a thick oil.

Method B

Into a 25-mL RB-flask was added triphenylphosphine (9.80 mg, 0.0375 mmol), diethyl azodicarboxylate (5.22 mg, 0.0300 mmol), N-(3-{1-[(3S)-3-hydroxy-3-phenylpropyl]-4-piperidinyl}phenyl)-2-methylpropanamide (9.53 mg, 0.0250 mmol), 3,4-dimethoxyphenol (7.70 mg, 0.0500 mmol) and THF (1.00 mL) at room temperature. The reaction mixture was stirred at room temperature overnight (16 h). The solvent was removed under reduced pressure and the residue was purified by preparative TLC plates [2.5% of NH$_3$ (2.0 M in methanol) in CHCl$_3$] to afford the desired product (4.40 mg, 34.1% yield) as a thick oil: $^1$H NMR (400 MHz, CDCl$_3$) δ 7.46 (s, 1H), 7.40–7.30 (m, 4H), 7.25 (m, 3H), 6.97 (d, 1H, J=7.8 Hz), 6.64 (d, 1H, J=9.1 Hz), 6.51 (d, 1H, J=2.6 Hz), 6.29 (d, 1H, J=2.6, 9.1 Hz), 5.20 (apparent dd, 1H, J=4.4, 8.5 Hz), 3.80 (s, 3H), 3.77 (s, 3H), 3.23 (m, 2H), 2.77 (m, 2H), 2.5 (m, 2H), 2.3–2.1 (m, 6H), 1.80 (m, 2H), 1.25 (d, 6H, J=7.9 Hz); ESMS m/e: 517.4 (M+H)$^+$.

Procedure B (See Also Example 49)

2-METHYL-N-(3-{1-[(3S)-3-PHENOXY-3-PHENYLPROPYL]-4-PIPERIDINYL}PHENYL) PROPANAMIDE: A mixture of N-(3-{1-[(3R)-3-hydroxy-3-phenylpropyl]-4-piperidinyl}phenyl)-2-methylpropanamide (9.53 mg, 0.0250 mmol), phenol (4.70 mg, 0.050 mmol), triphenylphosphine (9.80 mg, 0.0375 mmol) and diethyl azodicarboxylate (5.22 mg, 0.0300 mmol) in THF (1.00 mL) was stirred at room temperature for 3 days. Chromatography using silica preparative TLC plates [2.5% of NH$_3$ (2.0 M in methanol) in CHCl$_3$] gave the desired product (2.70 mg, 23.6% yield) as a thick oil: $^1$H NMR 5 7.46 (s, 2H), 7.40–7.30 (m, 4H), 7.25 (m, 3H), 7.20 (m, 2H), 6.97 (apparent d, 1H, J=7.4 Hz), 6.89 (apparent tt, 1H, J=0.8, 7.6 Hz), 6.84 (apparent dt, 1H, J=0.8, 8.0 Hz), 5.20 (apparent dd, 1H, J=4.4, 8.5 Hz), 3.35 (m, 2H), 2.91 (m, 2H), 2.60 (m, 2H), 2.30–2.10 (m, 6H), 1.90 (m, 2H), 1.25 (d, 6H, J=7.9 Hz); ESMS m/e: 457.4 (M+H)$^+$;

Procedure C

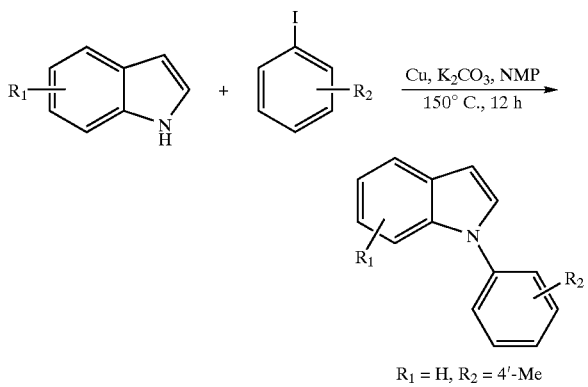

1-(4-METHYLPHENYL)1H-INDOLE: A mixture of 1-H-indole (58.5 mg, 0.500 mmol), 1-iodo-4-methylbenzene (0.218 g, 1.00 mmol), copper powder (32.0 mg, 0.500 mmol), and K$_2$CO$_3$ (0.138 g, 1.00 mmol) in 1-methyl-2-pyrrolidinone (1.00 mL) was heated at 150° C. for 12 h under argon. The resulting mixture was diluted with H$_2$O (6 mL). The aqueous layer was extracted with CH$_2$Cl$_2$ (3×10 mL). The combined organic extracts were washed with brine (10 mL), dried over MgSO$_4$, and concentrated in vacuo. The residue was purified by preparative TLC using EtOAc:hexane (1:4) to give the desired product (82.0 mg, 79.0%): $^1$H NMR (400 MHz, CDCl$_3$) δ 7.67 (d, 1H, J=7.7 Hz), 7.52 (d, 1H, J=7.4 Hz), 7.38 (d, 2H, J=8.4 Hz), 7.34–7.29 (m, 3H), 7.21 (t, 1H, J=7.0 Hz), 7.15 (t, 1H, J=7.0 Hz), 6.66 (d, 1H, J=3.3 Hz), 2.43 (s, 3H); ESMS m/e: 208.0 (M+H)$^+$.

Procedure D (See Also Example 86)

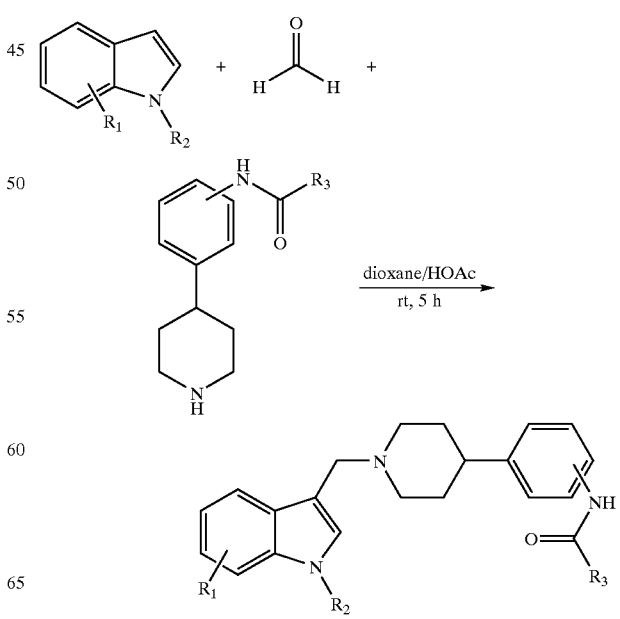

-continued
Example

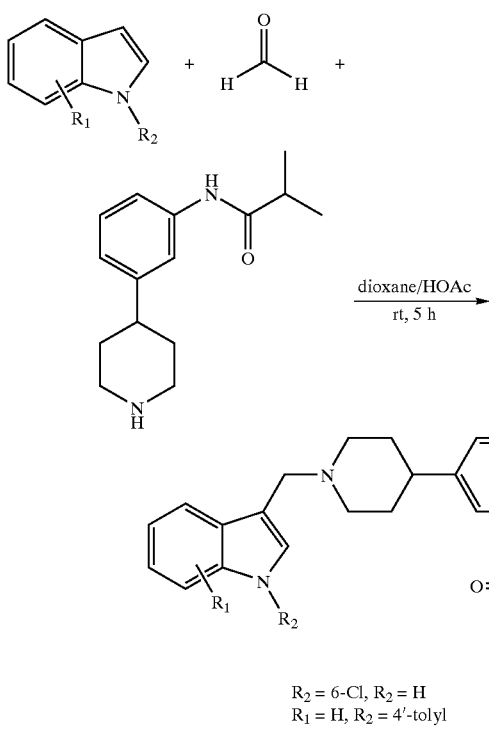

R₁ = 6-Cl, R₂ = H
R₁ = H, R₂ = 4'-tolyl

N-(3-{1-[(6-CHLORO-1H-INDOL-3-YL)METHYL]-4-PIPERIDINYL}PHENYL)-2-METHYLPROPANAMIDE: A solution of 2-methyl-N-[3-(4-piperidinyl)phenyl] propanamide (0.369 g, 1.50 mmol) and 37 wt % aqueous formaldehyde (30.0 mg, 1.50 mmol) in 1.00 mL of HOAc-:dioxane (1:4) was added to 6-chloro-1-H-indole (0.152 g, 1.00 mmol) and the reaction mixture was stirred for 12 h at room temperature. The resulting mixture was diluted with H₂O (10 mL). The aqueous layer was extracted with CH₂Cl₂ (3×100 mL). The combined organic extracts were washed with brine (10 mL), dried over MgSO₄, and concentrated in vacuo. The residue was purified by preparative TLC plates using 5% of NH₃ (2.0 M in methanol) in CH₂Cl₂ to give the desired product (79.0 mg, 42.0%): ¹H NMR (400 MHz, CDCl₃) δ 9.14 (s, 1H), 8.04 (s, 1H), 7.52 (t, 2H, J=8.1 Hz), 7.35 (d, 2H, J=13.3 Hz), 7.18 (t, 1H, J=7.9 Hz), 7.09 (dd, 1H, J=1.9, 8.5 Hz), 6.85 (d, 1H, J=7.4 Hz), 5.18 (s, 1H), 4.01 (s, 2H), 2.55 (septet, 1H, J=6.8 Hz), 2.48–2.34 (m, 3H), 2.08–1.95 (m, 4H), 1.78 (d, 2H, J=12.8 Hz), 1.22 (d, 6H, J=6.8 Hz); ESMS m/e: 410.1 (M+H)⁺.

Procedure E (See Also Example 90)

Scheme M

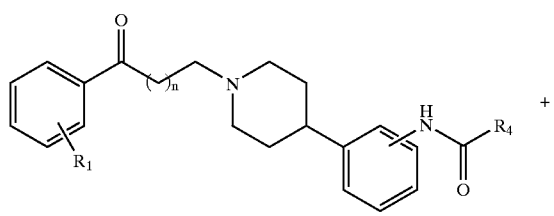

+

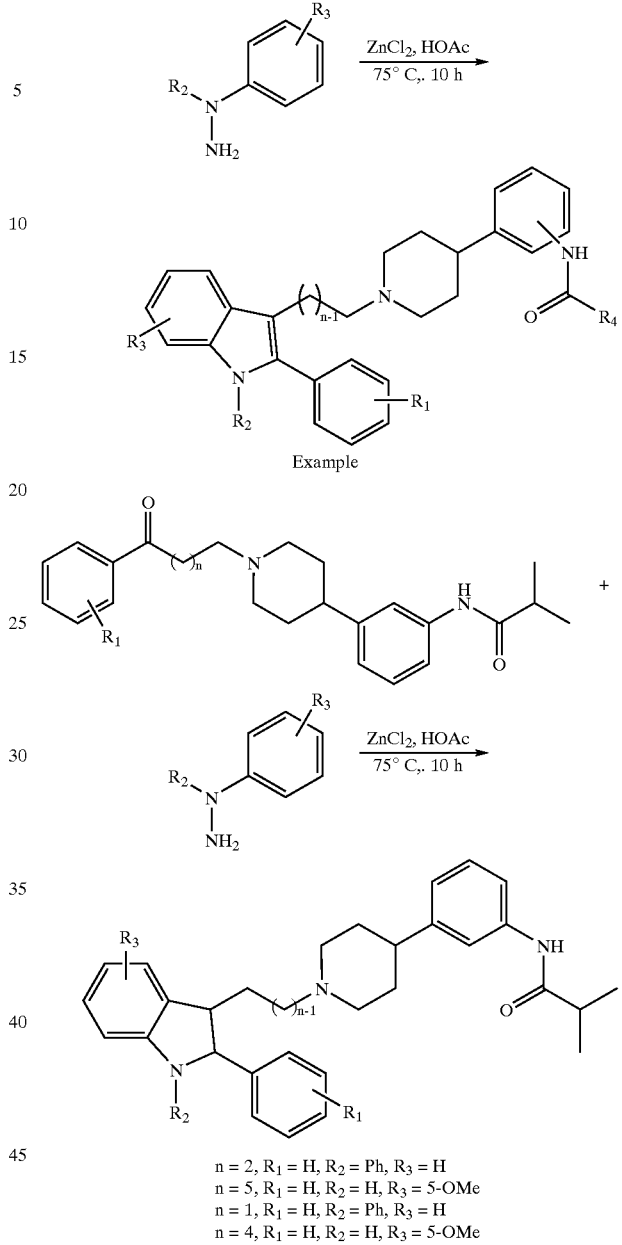

Example n = 2, R₁ = H, R₂ = Ph, R₃ = H
n = 5, R₁ = H, R₂ = H, R₃ = 5-OMe
n = 1, R₁ = H, R₂ = Ph, R₃ = H
n = 4, R₁ = H, R₂ = H, R₃ = 5-OMe N-(3-{1-[3-(1,2-DIPHENYL-1H-INDOL-3-YL)PROPYL]-4-PIPERIDINYL}PHENYL)-2-METHYLPROPANAMIDE: A mixture of 1,1-diphenylhydrazine hydrochloride (10.3 mg, 0.0470 mmol), 2-methyl-N-{3-[1-(5-oxo-5-phenylpentyl)-4-piperidinyl] phenyl}propanamide (14.7 mg, 0.0362 mmol), ZnCl₂ (14.8 mg, 0.109 mmol), and HOAc (0.500 mL) was heated for 4 h at 80° C. The resulting crude mixture was diluted with water (10 mL), the aqueous layer was neutralized with saturated K₂CO₃ (10 mL) and extracted with CH₂Cl₂ (3×20 mL). The combined organic layers were concentrated in vacuo and the residue was purified by preparative TLC plates using 5% of NH₃ (2.0 M in methanol) in CH₂Cl₂ to give the desired product N-(3-{1-[3-(1,2-diphenyl-1H-indol-3-yl)propyl]-4-piperidinyl}phenyl)-2-methylpropanamide (4.10 mg, 37.0%): ¹H NMR (400 MHz, CDCl₃) δ 7.71–7.65 (m, 1H), 7.42 (d, 1H, J=7.4 Hz), 7.39 (s, 1H), 7.36–7.15 (m, 15H), 6.94 (d, 1H, J=7.8 Hz), 3.12 (d, 2H, J=11.2 Hz), 2.90 (t, 2H, J=7.8 Hz), 2.59–2.45 (m, 3H), 2.19–1.91 (m, 7H), 1.82 (d, 2H, J=13.5 Hz), 1.24 (d, 6H, J=6.9 Hz); ESMS m/e: 555.3 (M+H)+.

Procedure F (See Also Example 108)

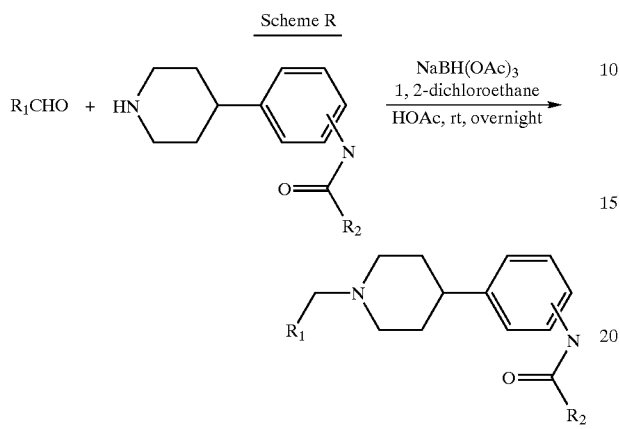

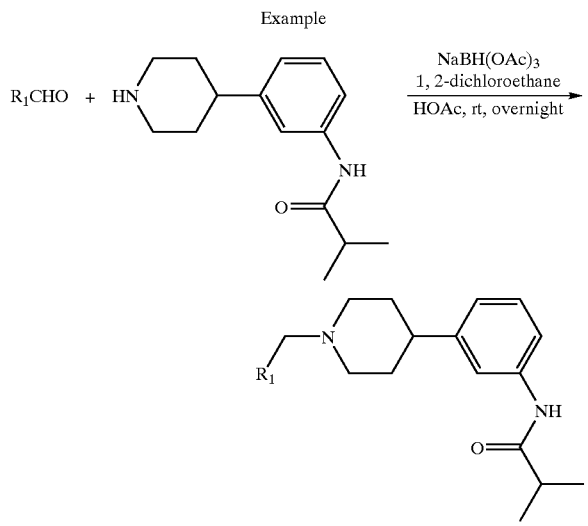

N-(3-{1-[4-(4-CHLOROPHENOXY)BENZYL]-4-PIPERIDINYL}PHENYL)-2-METHYLPROPANAMIDE: A solution of 4-(4-chlorophenoxy)benzaldehyde (0.119 g, 0.510 mmol) and 2-methyl-N-[3-(4-piperidinyl)phenyl] propanamide (0.126 g, 0.510 mmol) in 1,2-dichloroethane (5.00 mL) was treated with sodium triacetoxyborohydride (0.424 g, 2.00 mmol) and HOAC (0.0300 mL, 0.500 mmol) at room temperature. The mixture was stirred overnight at room temperature. The reaction mixture was neutralized with saturated NaHCO₃ aqueous solution (10 mL) and the aqueous layer was extracted with CH₂Cl₂ (3×10 mL). The combined organic layers were washed with brine, dried over MgSO₄, concentrated in vacuo and purified by preparative TLC plates using 5% of NH₃ (2.0 M in methanol) in CH₂Cl₂ to give the desired product (53.0 mg, 23.0%): ¹H NMR (400 MHz, CDCl₃) δ 7.50 (s, 1H), 7.34–7.19 (m, 7H), 6.98–6.87 (m, 5H), 3.50 (s, 2H), 2.98 (d, 2H, J=11.8 Hz), 2.58–2.44 (m, 2H), 2.10–1.98 (m, 2H), 1.83–1.76 (m, 4H), 1.24 (d, 6H, J=6.8 Hz); ESMS m/e: 463.2 (M+H)+.

Procedure G (See Also Example 116)

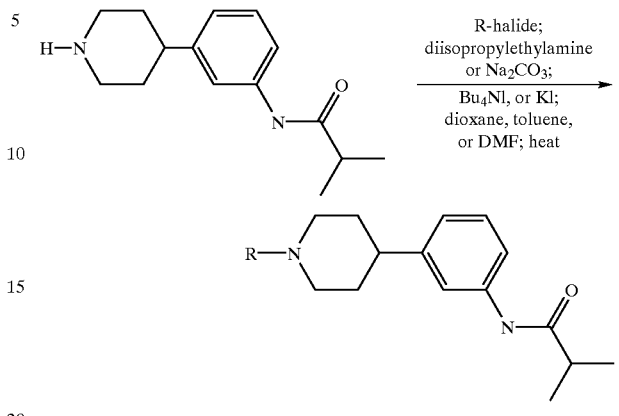

N-(3-{1-[(3R)-3-(3-ACETYLPHENOXY)-3-PHENYLPROPYL]-4-PIPERIDINYL}PHENYL)-2-METHYLPROPANAMIDE: A mixture of 1-(3-{[(1R)-3-chloro-1-phenylpropyl]oxy}phenyl)ethanone (58.5 mg, 0.200 mmol), 2-methyl-N-[3-(4-piperidinyl)phenyl] propanamide (56.8 mg, 0.200 mmol), NaI (34.0 mg, 0.200 mmol) and K₂CO₃ (55.5 mg, 0.400 mmol) in DMF (1.00 mL) was stirred at 100° C. for 3 h. The solvent was removed under reduced pressure and the residue was purified by chromatography on silica using 5% of NH₃ (2.0 M in methanol) in CH₂Cl₂ to give the desired product (98.0 mg, 98.0%): ¹H NMR (400 MHz, CDCl₃) δ 8.01 (s, 1H), 7.49–7.21 (m, 11H), 7.09–7.03 (m, 1H), 6.96 (d, 1H, J=7.9 Hz), 5.32 (dd, 1H, J=5.0, 7.9 Hz), 3.08–2.98 (m, 2H), 2.57–2.43 (m, 6H), 2.11–1.72 (m, 9H), 1.25 (d, 6H, J=6.8 Hz); ESMS m/e: 499.4 (M+H)+.

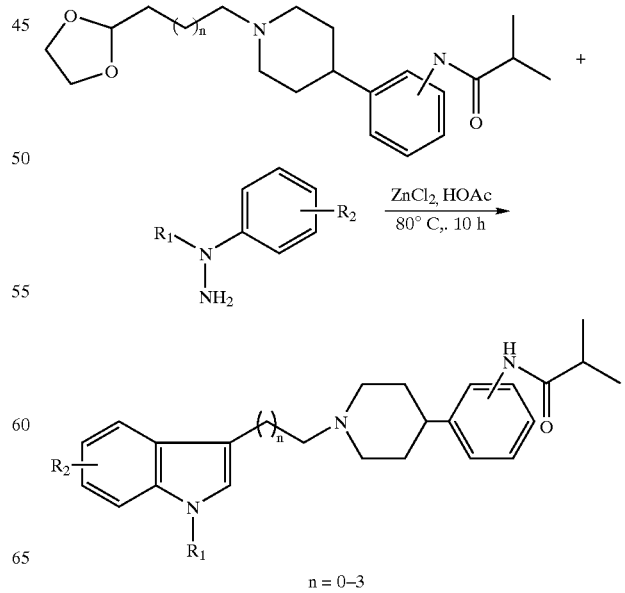

Procedure H

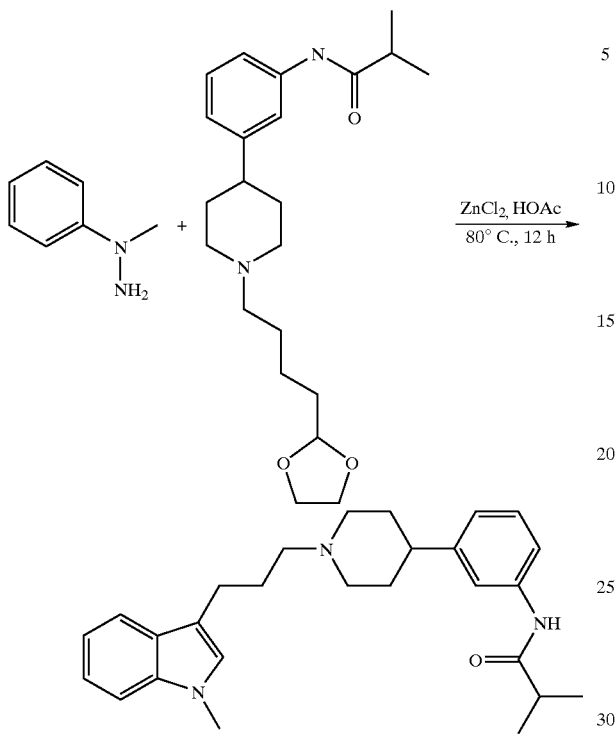

ZnCl₂, HOAc
80° C., 12 h

2-METHYL-N-(3-{1-[3-(1-METHYL-1H-INDOL-3-YL)PROPYL]-4-PIPERIDINYL}PHENYL)PROPANAMIDE: A mixture of N-(3-{-[4-(1,3-dioxolan-2-yl)butyl]-4-piperidinyl}phenyl)-2-methylpropanamide (100 mg, 0.270 mmol), 1-methyl-1-phenylhydrazine (106 mg, 0.870 mmol), ZnCl₂ (119 mg, 0.870 mmol), and HOAC (1.00 mL) was heated for 12 h at 80° C. The resulting crude mixture was diluted with water (20 mL), the aqueous layer was neutralized with saturated K₂CO₃ solution (10 mL) and extracted with CH₂Cl₂ (3×20 mL). The combined organic layers were concentrated in vacuo and the residue was purified by preparative TLC using 3% of NH₃ (2.0 M in methanol) in CH₂Cl₂ to give the desired product 2-methyl-N-(3-{1-[3-(1-methyl-1H-indol-3-yl)propyl]-4-piperidinyl}phenyl)propanamide (20.7 mg, 18.7 g): $^1$H NMR (400 MHz, CDCl₃) δ 7.60 (d, 1H, J=8.1 Hz), 7.45 (s, 1H), 7.35 (d, 1H, J=7.4 Hz), 7.26–7.24 (m, 4H), 7.09 (t, 1H, J=7.3 Hz), 6.97 (d, 1H, J=7.3 Hz), 6.86 (s, 1H), 3.75 (s, 3H), 3.11 (d, 2H, J=11.6 Hz), 2.79 (t, 2H, J=7.3 Hz), 2.51–2.50 (m, 4H), 2.12–1.81 (m, 8H), 1.25 (d, 6H, J=7.1 Hz); Anal. Calcd for C₂₇H₃₅N₃O+0.225CHCl₃: C, 73.57; H, 7.99; N, 9.45. Found: C, 73.93; H, 7.90; N, 9.23; ESMS m/e: 418.2 (M+H)⁺.

Procedure I

Scheme T

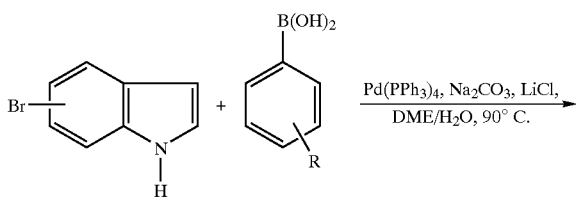

Pd(PPh₃)₄, Na₂CO₃, LiCl,
DME/H₂O, 90° C.

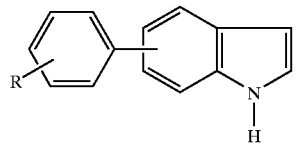

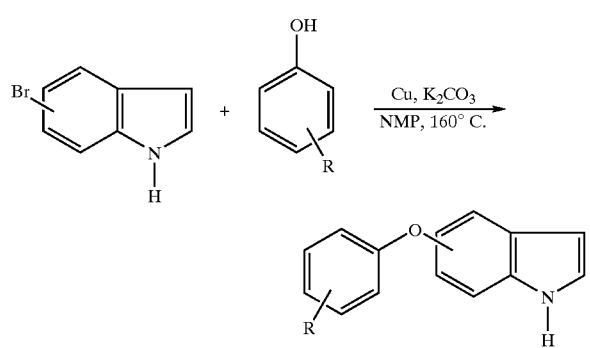

7-(2-FLUOROPHENYL)-1H-INDOLE: A mixture of 2-fluorophenylboronic acid (83.4 mg, 0.600 mmol), 7-bromo-1H-indole (98.0 mg, 0.500 mmol), LiCl (42.0 mg, 1.00 mmol), Na₂CO₃ (2.0 M, 0.100 mL), Pd(PPh₃)₄ (115 mg, 0.100 mmol) and DME (2.00 mL) was heated at 75° C. for 12 h under Argon. The resulting crude mixture was diluted with water (40 mL), the aqueous layer was extracted with CH₂Cl₂ (3×20 mL). The combined organic layers were washed with brine (30 mL), dried over Na₂SO₄, filtered, and concentrated in vacuo. The residue was purified by preparative TLC using hexane:EtOAc (8:1) to give the desired product 7-(2-fluorophenyl)-1H-indole (108 mg, 100%): $^1$H NMR (400 MHz, CDCl₃) 8.21 (br s, 1H), 7.71 (dm, 1H, J=7.3), 7.55 (dt, 1H, J=7.3, 1.6 Hz), 7.39 (m, 1H), 7.30–7.19 (m, 5H), 6.62 (dd, 1H, J=2.1–3.3 Hz); ESMS m/e: 211.9 (M+H)⁺.

Procedure J

Scheme U

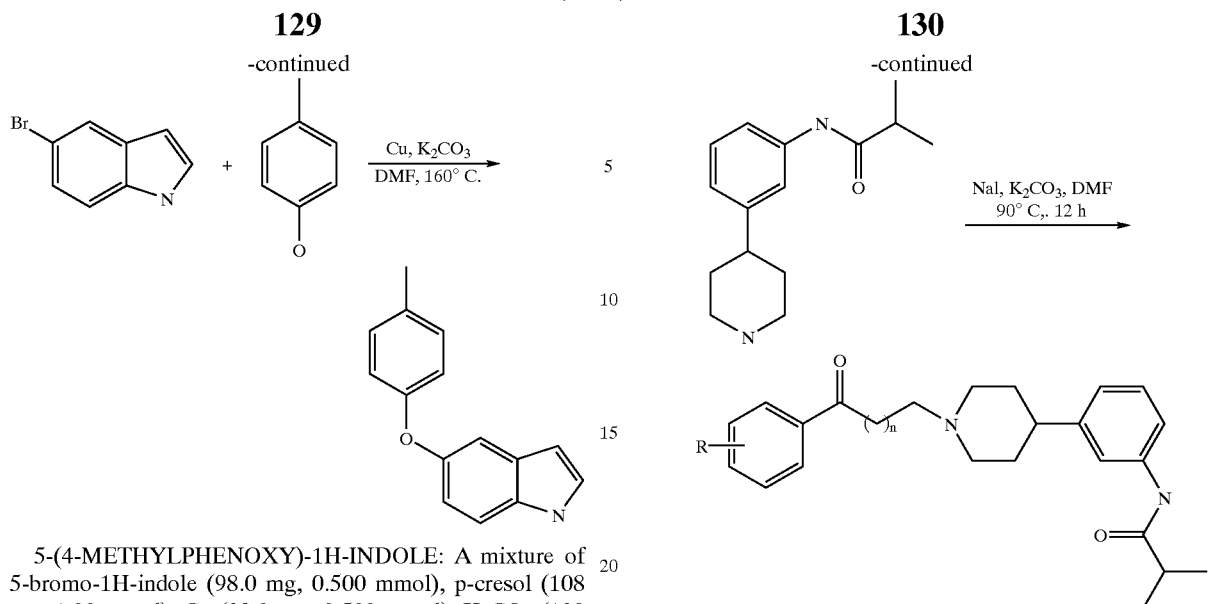

5-(4-METHYLPHENOXY)-1H-INDOLE: A mixture of 5-bromo-1H-indole (98.0 mg, 0.500 mmol), p-cresol (108 mg, 1.00 mmol), Cu (32.0 mg, 0.500 mmol), $K_2CO_3$ (138 mg, 1.00 mL) and DMF (1.00 mL) was heated at 160° C. for 12 h. The resulting crude mixture was diluted with water (40 mL), the aqueous layer was extracted with $CH_2Cl_2$ (3×20 mL). The combined organic layers were washed with brine (30 mL), dried over $Na_2SO_4$, filtered, and concentrated in vacuo. The residue was purified by preparative TLC using hexane:EtOAc (4:1) to give the desired product 5-(4-methylphenoxy)-1H-indole (57.5 mg, 51.5%): ESMS m/e: 224.0 $(M+H)^+$.

Procedure K

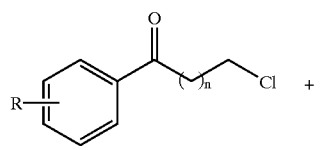

N-(3-{1-[7-(2-FLUOROPHENYL)-7-OXOHEPTYL]-4-PIPERIDINYL}PHENYL)-2-METHYLPROPANAMIDE: A 50-mL round-bottom flask was charged with a solution of 7-chloro-1-oxo-1-(2-fluorophenyl)heptane (2.42 g, 10.0 mmol), 2-methyl-N-[3-(4-piperidyl)phenyl]propanamide (2.46 g, 10.0 mmol), $K_2CO_3$ (2.76 g, 20.0 mmol) and NaI (2.25 g, 15.0 mmol) in DMF (25.0 mL). The mixture was stirred for 10 min at 25° C. and then heated at 100° C. for 12 h, cooled to 25° C. and diluted with EtOAc (100 mL) The reaction mixture was washed with water (4×50 mL) and the aqueous layer was extracted with EtOAc (100 mL). The organic layers were washed with brine (50 mL), dried over $MgSO_4$, concentrated in vacuo and the crude product was purified by chromatography (EtOAc:MeOH 97:3) to give the desired product (3.70 g, 82.0%).

Procedure L

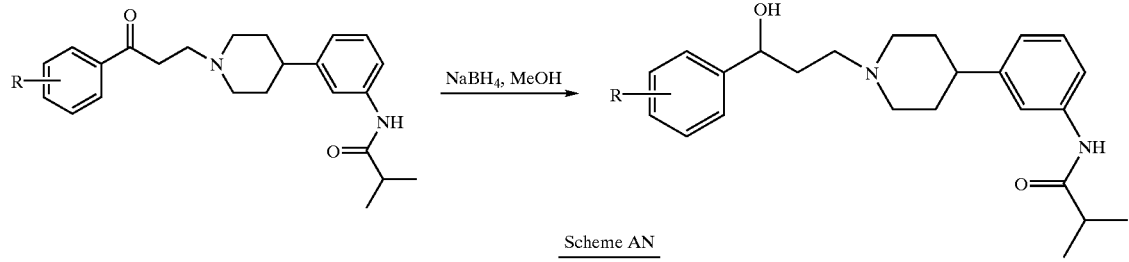

Scheme AN

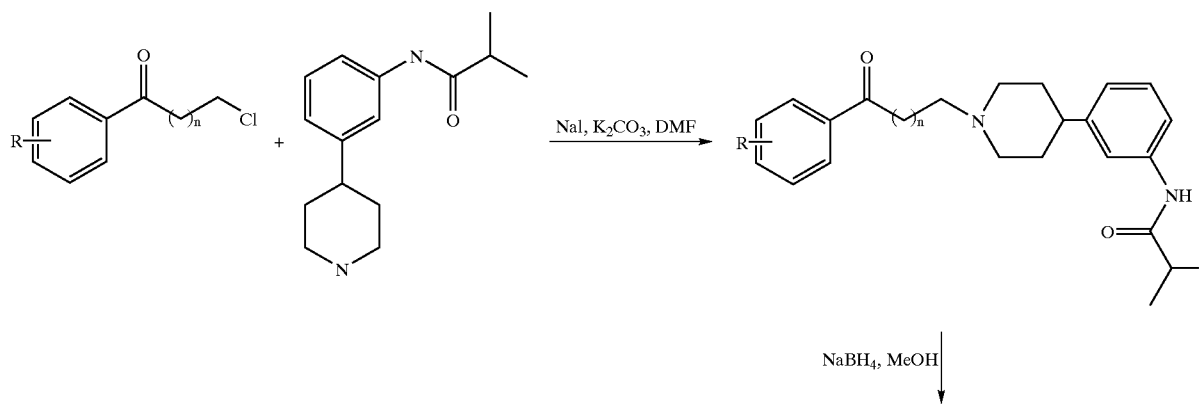

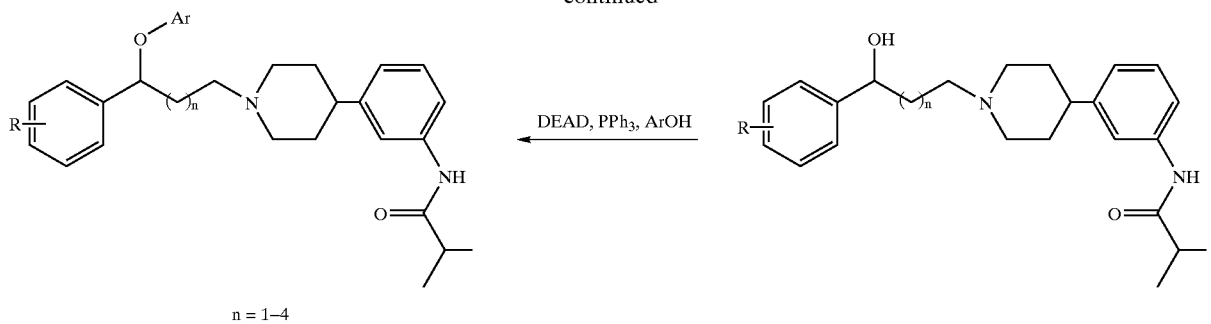

n = 1–4

N-(3-{1-[7-(2-FLUOROPHENYL)-7-HYDROXYHEPTYL]-4-PIPERIDINYL}PHENYL)-2-METHYLPROPANAMIDE: To a 50-mL round-bottomed flask charged with N-(3-{1-[7-(2-fluorophenyl)-7-oxoheptyl]-4-piperidinyl}phenyl)-2-methylpropanamide (5.0 mmol) and methanol (20 mL) was added NaBH₄ (7.5 mmol) at 0° C. in an ice-bath. The reaction mixture was warmed to 25° C. and stirred for 2 h. The reaction was monitored by TLC (EtOAc:MeOH 95:5). If necessary, another 5.0 mmol of NaBH₄ was added to the reaction mixture and the reaction mixture was refluxed for 1 h. The reaction was quenched with water (5.0 mL) and diluted with EtOAc (10 mL). The organic layer was separated, washed with saturated NaHCO₃ solution (10 mL), dried over MgSO₄ and concentrated in vacuo. The crude product was purified by chromatography (EtOAc:MeOH 97:3) to give the desired product (90%).

Procedure M

Step 1: If reacted individually, a solution of the amine or aniline (1.00 eq), diisopropylethylamine or TEA (2.00 eq) and an electrophile (1.50 eq) in CH₂Cl₂ was stirred for 24 h at 23° C. The solvent was removed in vacuo and the crude product was chromatographed (silica) to give the final product.

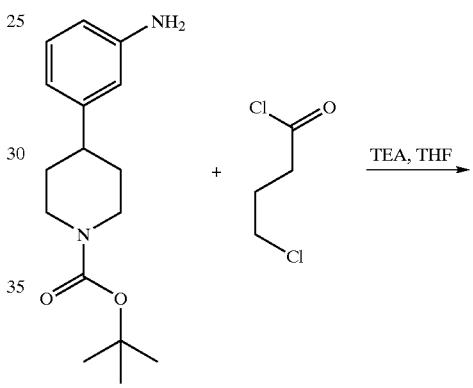

Scheme A

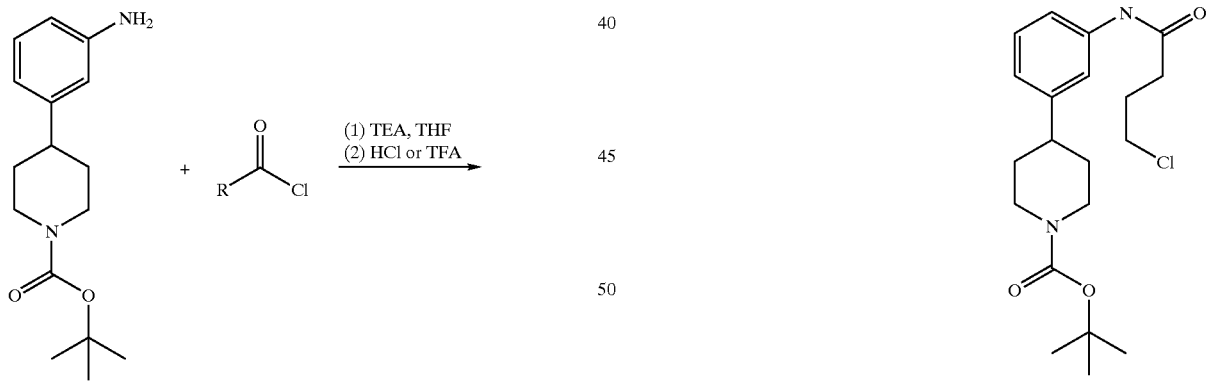

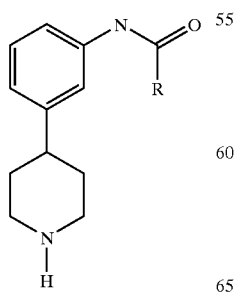

TERT-BUTYL 4-{3-[(4-CHLOROBUTANOYL)AMINO]PHENYL}-1-PIPERIDINECARBOXYLATE (3.32 g, 87.4%) was synthesized according to Scheme A and Procedure M: ¹H NMR (400 MHz, CDCl₃) δ 7.55 (s, 1H), 7.47 (s, 1H), 7.37 (m, 1H), 7.28 (m, 1H), 6.97 (d, 1H, J=7.6 Hz), 3.89 (t, 1H, J=6.4 Hz), 3.74 (m, 2H), 2.79–2.75 (m, 4H), 2.64 (m, 2H), 1.88–1.77 (m, 4H), 1.60–1.59 (m, 4H), 1.48 (s, 9H).

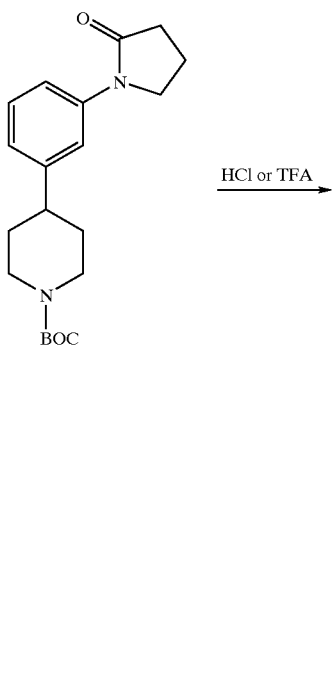

HCl or TFA

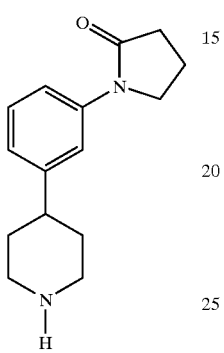

Step B:

TERT-BUTYL 4-[3-(2-OXO-1-PYRROLIDINYL)PHENYL]-1-PIPERIDINECARBOXYLATE: To a solution of tert-butyl 4-[3-(2-oxo-1-pyrrolidinyl)phenyl]-1-piperidinecarboxylate (0.429 g, 16.9 mmol) in dioxane (100 mL) was bubbled HCl gas for 1 h at 25° C. The resulting crude mixture was basified with 10% KOH solution (100 mL), the aqueous layer was extracted with 3:1 CHCl₃:isopropyl alcohol (3×150 mL). The combined organic layers were washed with brine (100 mL), dried over Na₂SO₄, filtered, and concentrated in vacuo. The residue was purified by preparative TLC using 20% NH₃ (2.0 M in MeOH) in CH₂Cl₂ solution to give the desired product tert-butyl 4-[3-(2-oxo-1-pyrrolidinyl)phenyl]-1-piperidinecarboxylate (245 mg, 78.7%): $^1$H NMR (400 MHz, CDCl₃) δ 7.52 (t, 1H, J=1.8 Hz), 7.41 (ddd, 1H, J=8.1, 2.3, 0.9 Hz), 7.30 (t, 1H, J=7.9 Hz), 7.02 (d, 1H, J=7.9 Hz), 3.86 (t, 2H, J=7.3 Hz), 3.21 (dt, 2H, J=11.9, 2.9 Hz), 2.76 (dt, 2H, J=12.1, 2.4 Hz), 2.65 (tt, 1H, J=11.9, 3.5 Hz), 2.61 (t, 2H, J=8.3 Hz), 2.22 (br s, 1H), 2.16 (qt, 2H, J=7.5 Hz), 1.85 (d, 2H, J=12.4 Hz), 1.67 (dq, 2H, J=12.5, 4.0 Hz).

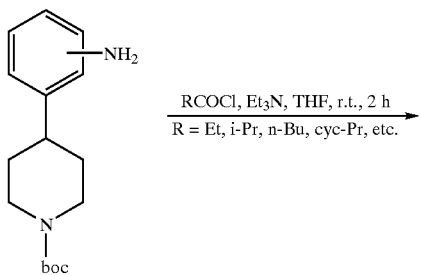

RCOCl, Et₃N, THF, r.t., 2 h
R = Et, i-Pr, n-Bu, cyc-Pr, etc.

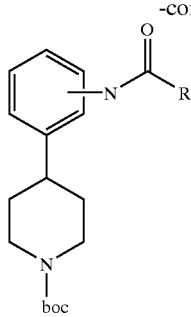

TFA, CH₂Cl₂, r.t., 6 h

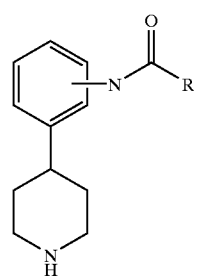

TERT-BUTYL 4-(4-AMINOPHENYL)-1-PIPERIDINECARBOXYLATE: Available from Arch Chemical Company, NJ.

2-METHYL-N-[4-(4-PIPERIDINYL)PHENYL]PROPANAMIDE: To a solution of tert-butyl 4-(4-aminophenyl)-1-piperidinecarboxylate (8.20 g, 29.7 mmol) and triethylamine (8.4 mL, 60 mmol) in dry THF (100 mL) at 0° C. was slowly added a solution of 2-methylpropanoyl chloride (3.84 g, 36.0 mmol) in THF (50 mL). The reaction mixture was then warmed up to room temperature and stirred for 2 h. After removing the solvent in vacuo, the crude product was purified by recrystallization (hexane/THF), affording the desired amide, tert-butyl 4-[4-(isobutyrylamino)phenyl]-1-piperidinecarboxylate, as a white solid (8.60 g, 84%). The tert-butyl 4-[4-(isobutyrylamino)phenyl]-1-piperidinecarboxylate was dissolved in CH₂Cl₂ (50 mL) at room temperature, TFA (13.68 g, 120 mmol, 5 equiv.) was added by syringe. The reaction mixture was stirred for 3 or 4 h and another 5 equivalents of TFA was added and the mixture was stirred for 2 or 3 more hours. The reaction solution was then basified to pH >14 by KOH (aq, 2 M). The solution was extracted with CH₂Cl₂ K₂CO₃. Removal of solvent under reduced pressure gave the free amine, 2-methyl-N-[4-(4-piperidinyl)phenyl]propanamide, as a brownish solid (5.99 g, 98%). $^1$H NMR (400 MHz, CDCl₃) δ 7.55–7.35 (m, 2H), 7.35–6.9 (m, 3H), 3.26–2.98 (m, 2H), 2.84–2.64 (m, 2H), 2.64–2.53 (m, 1H), 2.53–2.32 (m, 1H), 1.90–1.68 (m, 2H), 1.68–1.36 (m, 3H), 1.22 (d, 6H, J=6.0 Hz); ESMS m/e: 247.1 (M+H)⁺.

N-[4-(4-PIPERIDINYL)PHENYL]PROPANAMIDE: Prepared by the procedure for 2-methyl-N-[4-(4-piperidinyl)phenyl]propanamide using tert-butyl 4-(4-aminophenyl)-1-piperidinecarboxylate and propanoyl chloride: ESMS m/e: 233.1 (M+H)⁺.

N-[4-(4-PIPERIDINYL)PHENYL]BUTANAMIDE: Prepared by the procedure for 2-methyl-N-[4-(4-piperidinyl)phenyl]propanamide using tert-butyl 4-(4-aminophenyl)-1-piperidinecarboxylate and butanoyl chloride: ESMS m/e: 247.2 (M+H)⁺.

N-[3-(4-PIPERIDINYL)PHENYL]CYCLOPROPANECARBOXAMIDE: Prepared by the procedure for 2-methyl-N-[4-(4-piperidinyl)phenyl]propanamide using tert-butyl 4-(3-aminophenyl)-1- piperidinecarboxylate and cyclopropanecarbonyl chloride: Anal. Calcd for $C_{15}H_{20}N_2O+0.15CH_2Cl_2$: C, 70.8; H, 7.87; N, 10.9. found: C, 70.9; H, 7.68; N, 11.1; ESMS m/e: 245.0 $(M+H)^+$.

N-[3-(4-PIPERIDINYL)PHENYL]PROPANAMIDE: Prepared by the procedure for 2-methyl-N-[4-(4-piperidinyl) phenyl]propanamide using tert-butyl 4-(3-aminophenyl)-1-piperidinecarboxylate and propanoyl chloride: Anal. Calcd for $C_{14}H_{20}N_2O$: C, 72.2; H, 8.63; N, 12.1. found: C, 72.4; H, 8.68; N, 12.1; ESMS m/e: 233.1.

Procedure N

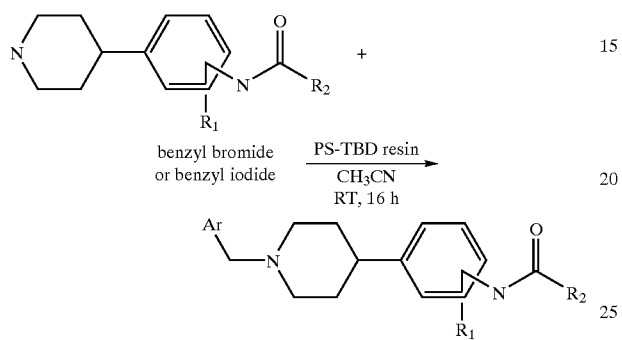

Scheme AV

The library was constructed in polypropylene Robbins 46 well plates Reactor Blocks. In the initial incubation period, each well was charged with PS-TBD resin (from Argonaut Technologies, 0.280 mmol, 2.50 eq, 200 mg) and piperidine (0.120 mmol, 1.10 eq) in acetonitrile (0.500 mL) and agitated for 1 h. A solution of benzyl iodide or bromide (0.110 mmol, 1.00 eq) in acetonitrile (0.500 mL) was added to each well followed by additional acetonitrile (1.00 mL) to make a total volume of 2.00 mL and the mixture was rotated in a Robbins rotating oven at room temperature for 16 h. Then AP-Isocyanate resin (Argonaut Technologies, 250 mg, 0.430 mmol, 4.00 eq) was added to each well and reacted further at room temperature for another 12 h. The mixture was filtered and the filtrate was concentrated in vacuo to obtain the desired product that was characterized via LC-MS.

Procedure O

Alkylation of Piperidines Using Alcohols and PS-TSCl Resin in Robbins 48 well "Reactor Blocks"

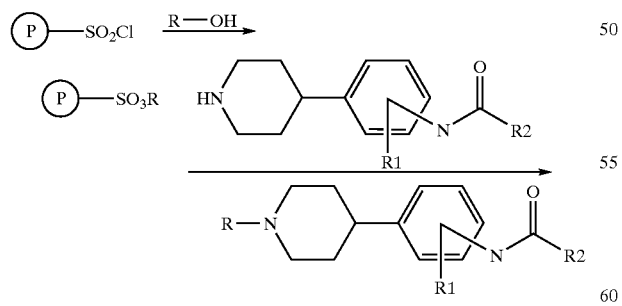

Scheme W

The library was constructed in polypropylene Robbins "Reactor Blocks", 46 well plates. PS-TSCl resin (100 mg, 1.00 eq, purchased from Argonaut Technologies) was placed in each well of the "Reactor Blocks" 46 well plates. To each well was added an alcohol (1.50 mmol) in 3.00 mL of $CH_2Cl_2$ and pyridine (1:1). The mixture was stirred for 5 h and the resin was washed with $CH_2Cl_2$ (3×4mL), DMF (5×4.0 mL), DMF/$H_2O$ (3:1, 5×4.0 mL), THF (3×4.0 mL), $CH_2Cl_2$ (3×4.0 mL), acetonitrile (2×4.0 mL) and dried under reduced pressure. A solution of an amine (0.0750 mmol, 0.500 eq) and N,N-diisopropylethyl amine (19.0 mg, 0.150 mmol, 1.00 eq) in acetonitrile (3.00 mL) was added to the well containing the derivatized resin and the mixture was reacted at 70° C. for 16 h. Finally, AP-Isocyanate resin (120 mg, 0.150 mmol, 1.00 eq) and THF (2.00 mL) was added to the reaction vessel and reacted at room temperature for another 3 h. The solution was filtered into the Robbins receiving plates and concentrated in vacuo to give the desired tertiary amine, which was analyzed via LC-MS.

Procedure P

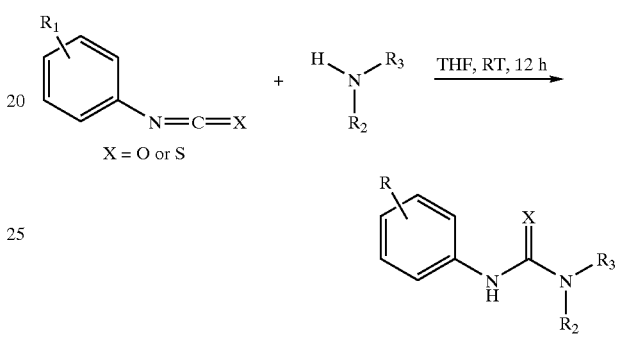

Scheme AB

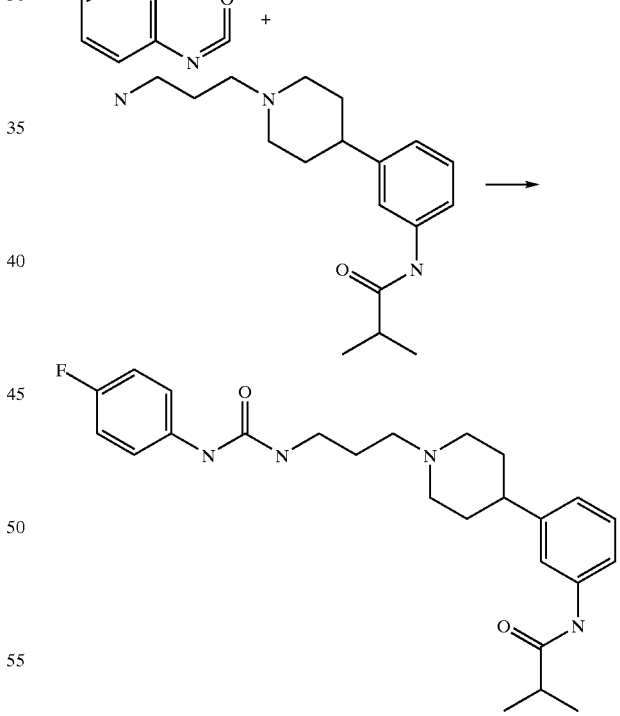

N-{3-[1-(3-{[(4-FLUOROANILINO)CARBONYL] AMINO}PROPYL)-4-PIPERIDINYL]PHENYL}-2-METHYLPROPANAMIDE: A solution of N-{3-[1-(3-aminopropyl)-4-piperidinyl]phenyl}-2-methylpropanamide (26.4 mg, 0.0870 mol), 1-fluoro-4-isocyanatobenzene (11.9 mg, 0.0870 mmol), in THF (1.00 mL) was stirred for 12 h at 25° C. The resulting crude mixture was diluted with water (10 mL), the aqueous layer was extracted with $CH_2Cl_2$ (3×20 mL). The combined organic layers were concentrated in vacuo and the residue was purified by preparative TLC using 2.5% of NH$_3$ (2.0 M in methanol) in CH$_2$Cl$_2$ to give the desired product N-{3-[1-(3-{[(4-fluoroanilino)carbonyl]amino}propyl)-4-piperidinyl]phenyl}-2-methylpropanamide (4.18 mg, 10.9%): $^1$H NMR (400 MHz, CDCl$_3$) 7.45 (q, 2H, J=4.7 Hz), 7.23–7.21 (m, 4H), 7.05 (t, 4H, J=7.8 Hz), 6.75 (m, 1H), 4.05 (m, 1H), 3.19 (s, 1H), 2.71 (m, 1H), 2.53 (m, 1H), 2.26–2.21 (m, 3H), 1.80–1.60 (m, 9H), 1.25 (d, 6H, J=6.4 Hz); ESMS m/e: 439.4 (M+H)$^+$.

Procedure Q

Scheme AT

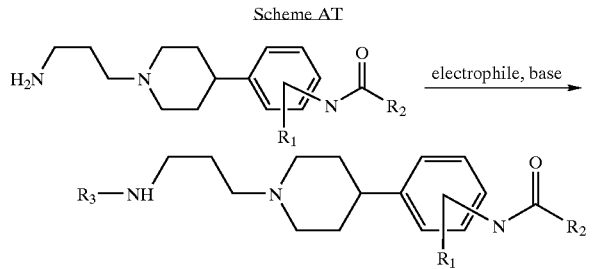

If reacted individually, a solution of the amine (1.0 eq), an electrophile (1.5 eq), diisopropylethylamine (2.0 eq) in CH$_2$Cl$_2$ was stirred for 1 day. The solvent was removed in vacuo and the crude product was chromatographed to give the final product.

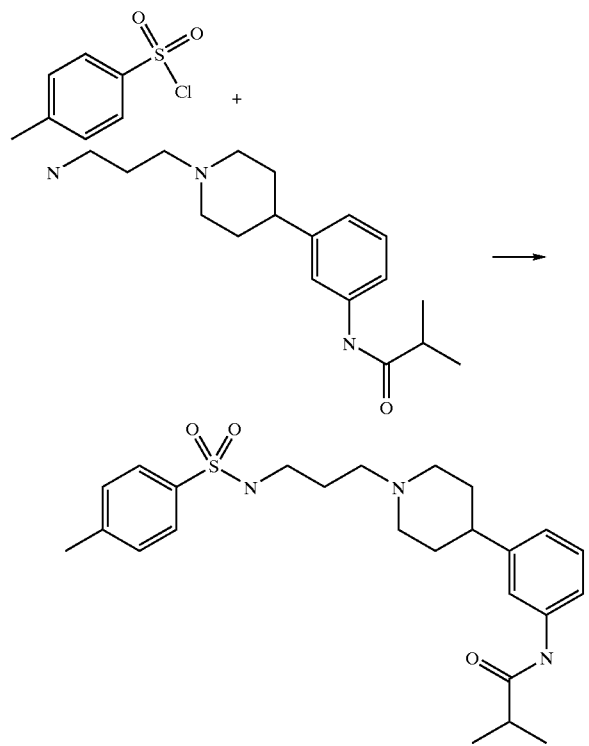

2-METHYL-N-{3-[1-(3-{[(4-METHYLPHENYL)SULFONYL]AMINO}PROPYL)-4-PIPERIDINYL]PHENYL}PROPANAMIDE: A solution of 4-methylbenzenesulfonyl chloride (16.6 mg, 0.0870 mmol), N-{3-[1-(3-aminopropyl)-4-piperidinyl]phenyl}-2-methylpropanamide (26.4 mg, 0.0870 mmol), TEA (10.0 mg, 0.174 mmol) in THF (1.00 mL) was stirred for 12 h at 25° C. The resulting crude mixture was diluted with water (20 mL), the aqueous layer was extracted with CH$_2$Cl$_2$ (2×20 mL). The combined organic layers were concentrated in vacuo and the residue was purified by preparative TLC using 2.5% of NH$_3$ (2.0 M in methanol) in CH$_2$Cl$_2$ to give the desired product 2-methyl-N-{3-[1-(3-{[(4-methylphenyl)sulfonyl]amino}propyl)-4-piperidinyl]phenyl}propanamide (17.3 mg, 43.6%): $^1$H NMR (400 MHz, CDCl$_3$) δ 8.19 (s, 1H), 7.53 (s, 1H), 7.41 (s, 1H), 7.32–7.21 (m, 4H), 7.16 (s, 1H), 6.97 (d, 1H, J=7.9 Hz), 3.44 (t, 2H, J=6.3 Hz), 3.15 (d, 2H, J=9.8 Hz), 2.62–2.45 (m, 4H), 2.15 (m, 3H), 2.05 (s, 3H), 1.95–1.71 (m, 5H), 1.26 (d, 6H, J=6.6 Hz); ESMS m/e: 458.2 (M+H)$^+$.

Procedure Q$_2$

The Capture and Release Method for the Synthesis and Purification of the Piperidine Library The commercially obtained Amberlyst 15 exchange resin (Aldrich) was activated using the following procedure:
1. The resin was shaken in methanol for 24 hr.
2. The resin was filtered and washed with methanol on a fritted funnel.
3. The resin was neutralized with 2N NH$_3$ in MeOH (pH checked)—shaken for 1 hr.
4. The neutralized resin was acidified with 3M HCl in MeOH (pH checked)—shaken for 1 hr.
5. The resin was captured on a fritted funnel and washed with MeOH.
6. The resin was dried in vacuo and stored.

Synthesis (Acylation of the Amines): The library was constructed in polypropylene Robbins "Reactor Blocks", 46 well plates. In each plate an array of 5 amines (0.10 mmol) and 8 electrophiles (acid chlorides, sulfonyl chlorides, 1.5 eq.) in the presence of triethylamine (2.0 eq) in THF/DCM 3:1 (2.0 mL) were reacted overnight to give 40 compounds/plate. The reactions were rigorously monitored via TLC to the depletion of the starting amine due to the ensuing purification methodology via the acidic Amberlyst 15 resin. Following the disappearance of the starting amine, the desired products were captured and then released using the process outlined below.

Purification of the Piperidine Products: Activated Amberlyst 15 ion-exchange resin (0.90 g, Aldrich) was added to each well, and the plates were rotated for 2 hours in a Robbins rotating oven to capture the desired final product from the reaction mixture. The solvent was filtered and the resin was washed with CH$_3$OH and CH$_2$Cl$_2$ (×3) alternately with each of the solvents (for 10 minutes each time). After the last filtration, 2 N ammonia in methanol was added to the resin (2 mL to each well) and the reaction blocks were rotated for 2 hours to release the desired compounds from the resin. The final compounds were filtered into Robbins' "Receiving Blocks", the solvent was removed and the compounds were analyzed via LC-MS.

Procedure R

Scheme Z

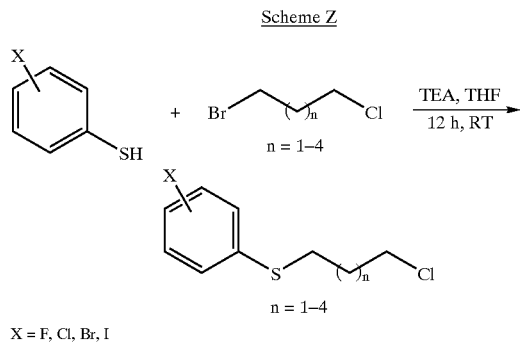

X = F, Cl, Br, I

[(3-CHLOROPROPYL)SULFANYL]BENZENE: A mixture of benzenethiol (0.550 9, 5.00 mmol), 1-bromo-3-chloropropane (106 mg, 5.50 mmol), TEA (1.01 g, 10.0 mmol) and THF (10.0 mL) was stirred for 12 h at 25° C. The resulting crude mixture was diluted with water (40 mL), the aqueous layer was extracted with CH₂Cl₂ (3×30 mL). The combined organic layers were concentrated in vacuo and the residue was purified by preparative TLC using hexane:EtOAc (10:1) to give the desired product [(3-chloropropyl)sulfanyl]benzene (1.05 g, 100%).

Scheme AA

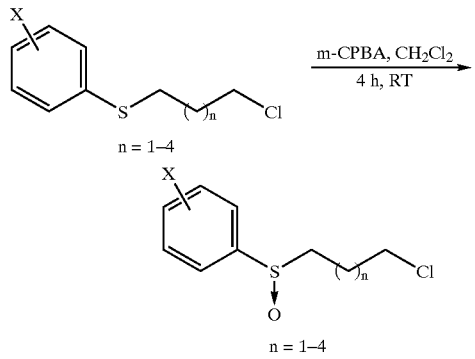

X = F, Cl, Br, I

Procedure S

3-CHLOROPROPYL 4-FLUOROPHENYL SULFOXIDE: A solution of 3-chloropropyl 4-fluorophenyl sulfide (77.5 mg, 0.380 mmol) in CH₂Cl₂ (2.00 mL) was cooled to 0° C. To this solution m-CPBA (78.7 mg, 0.460 mmol) was added. The reaction mixture was stirred at 0° C. for 30 min, then at 23° C. for 4 h. The resulting crude mixture was diluted with 10% aqueous Na₂SO₃ (10 mL), the aqueous layer was extracted with CH₂Cl₂ (2×15 mL). The combined organic layers were washed with brine (10 mL), dried over Na₂SO₄, filtered, and concentrated in vacuo. The residue was purified by preparative TLC using 2.5% of NH₃ (2.0 M in methanol) in CH₂Cl₂ to give the desired product 3-chloropropyl 4-fluorophenyl sulfoxide (47.8 mg, 57.0%).

Procedure T

N-(3-{1-[4-(3,4-DIMETHYLPHENYL)-4-OXOBUTYL]-4-PIPERIDINYL}PHENYL)-N,2-DIMETHYLPROPANAMIDE: A mixture of N-(3-{1-[4-(3,4-dimethylphenyl)-4-oxobutyl]-4-piperidinyl}phenyl)-2-methylpropanamide (15.0 mg, 0.0357 mmol), MeI (5.07 mg, 0.0357 mmol), NaOtBu (6.86 mg, 0.0714 mmol) and THF (1.00 mL) was stirred for 5 h at 25° C. The resulting crude mixture was diluted with water (10 mL), the aqueous layer was extracted with CH₂Cl₂ (3×20 mL). The combined organic layers were concentrated in vacuo and the residue was purified by preparative TLC using 4.0% of NH₃ (2.0 M in methanol) in CH₂Cl₂ to afford the desired product N-(3-{1-[4-(3,4-dimethylphenyl)-4-oxobutyl]-4-piperidinyl}phenyl)-N,2-dimethypropanamide (13.8 mg, 89.1%) $^1$H NMR (400 MHz, CDCl₃) 7.76 (s, 1H), 7.72 (dd, 1H, J=1.8, 7.7 Hz), 7.33 (t, 1H, J=8.8 Hz), 7.22 (d, 1H, J=7.8 Hz), 7.18 (d, 1H, J=8.8 Hz), 7.01 (m, 2H), 3.24 (s, 3H), 3.10 (d, 1H, J=10.6 Hz), 3.00 (t, 1H, J=7. 6 Hz), 2.49–2.44 (m, 4H), 2.33 (s, 6H), 2.11–2.10 (m, 2H), 1.99 (m, 1H), 1.79–1.77 (m, 4H), 1.26 (t, 2H, J=7.6 Hz), 1.02 (d, 6H, J=7.6 Hz); ESMS m/e: 435.2 (M+H)⁺.

Procedure U

Scheme AK

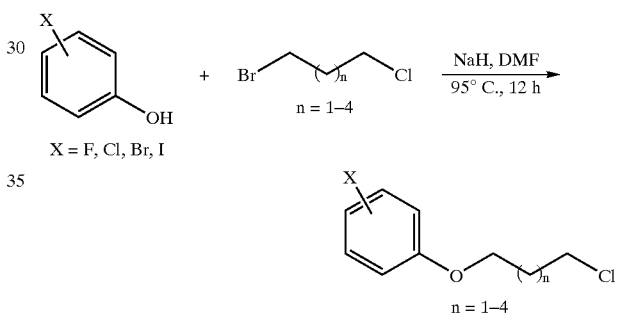

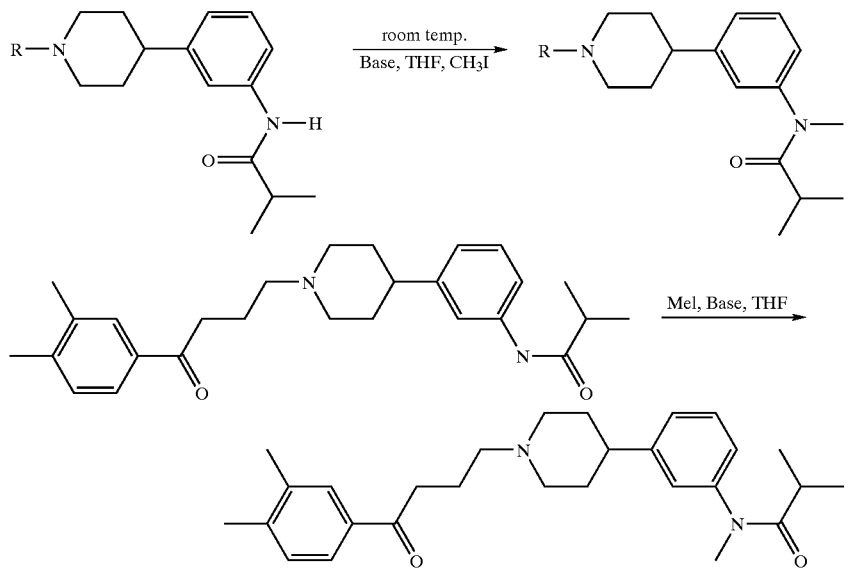

-continued

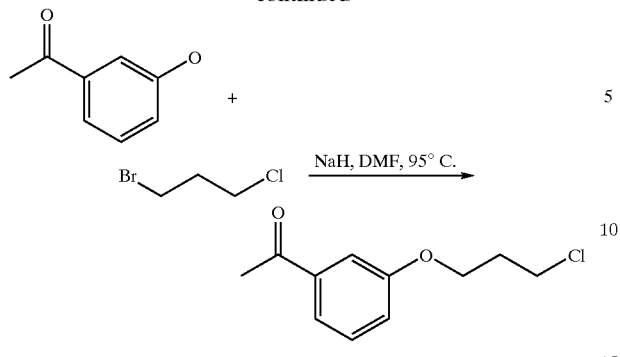

1-[3-(3-CHLOROPROPOXY)PHENYL]ETHANONE: To a suspension of NaH (50.5 mg, 2.00 mmol) in DMF (1.00 mL) was added 1-(3-hydroxyphenyl)ethanone (136 mg, 1.00 mmol) at 0° C. The reaction mixture was stirred at room temperature for 1 h. To this mixture was added a solution of 1-bromo-3-chloropropane (188 mg, 1.20 mmol) in DMF (0.500 mL). The reaction mixture was stirred at room temperature for 5 h. The resulting crude mixture was diluted with water (20 mL), the aqueous layer was extracted with CH$_2$Cl$_2$ (3×20 mL). The combined organic layers were washed with brine (20 mL), dried over Na$_2$SO$_4$, filtered, and concentrated in vacuo. The residue was purified by preparative TLC using hexane:EtOAc (4:1) to afford the desired product 1-[3-(3-chloropropoxy)phenyl]ethanone (235 mg, 55.2%): $^1$H NMR (400 MHz, CDCl$_3$) δ 7.7 (d, 1H, J=6.6 Hz), 7.52 (s, 1H), 7.25 (t, 1H, J=6.6 Hz), 7.01 (m, 1H), 4.11 (t, 2H, J=7.9 Hz), 3.69 (t, 2H, J=7.9 Hz), 2.61 (s, 3H), 1.95–1.92 (m, 2H).

Procedure V

Scheme AE

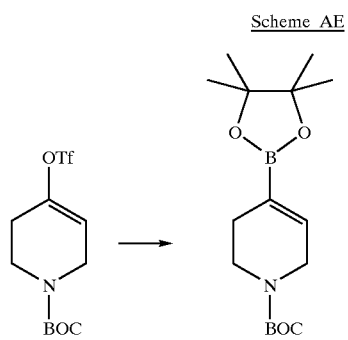

1-[(2,2-DIMETHYLPROPANOYL)OXY]-4-(4,4,5,5-TETRAMETHYL-1,3,2-DIOXABOROLAN-2-YL)-1,2,3,6-TETRAHYDROPYRIDINE: To a 50-mL RB-flask, charged with bis(pinacolato)diboron (422 mg, 1.66 mmol), KOAc (444 mg, 4.53 mmol) and PdCl$_2$dppf (37.0 mg, 3.00 mol %), dppf (25.0 mg, 3.00 mol %), was added a solution of 1-[(2,2-dimethylpropanoyl)oxy]-1,2,3,6-tetrahydro-4-pyridinyl trifluoromethanesulfonate (500 mg, 1.51 mmol) in 1,4-dioxane (10.0 mL) at room temperature under argon. The mixture was heated at 80° C. overnight. After cooled to room temperature, the mixture was filtered through celite and the celite was washed with EtOAc (3×20 mL). The filtrates were concentrated in vacuo. The resulting residue was dissolved in EtOAc and washed with H$_2$O and brine, dried over MgSO$_4$, filtered and concentrated in vacuo. The crude material was purified by flash chromatography (1:9 EtOAc:hexane) to give 1-[(2,2-dimethylpropanoyl)oxy]-4-(4,4,5,5-tetramethyl-1,3,2-dioxaborolan-2-yl)-1,2,3,6-tetrahydropyridine (355 mg, 76.0%).

Procedure W

Scheme AF

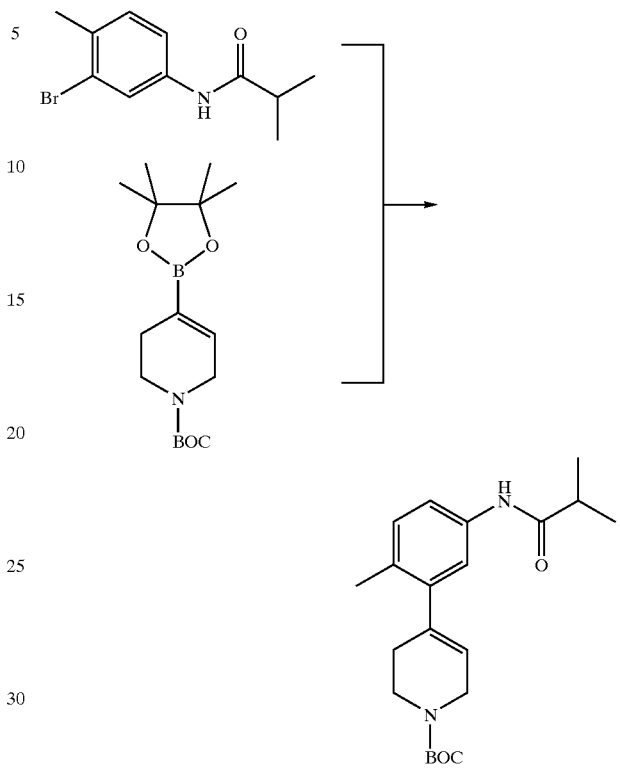

TERT-BUTYL 4-[5-(ISOBUTYRYLAMINO)-2-METHYLPHENYL]-3,6-DIHYDRO-1(2H)-PYRIDINECARBOXYLATE: To a 50-mL RB flask containing 1-[(2,2-dimethylpropanoyl)oxy]-4-(4,4,5,5-tetramethyl-1,3,2-dioxaborolan-2-yl)-1,2,3,6-tetrahydropyridine (500 mg, 1.62 mmol), K$_2$CO$_3$ (670 mg, 4.86 mmol) and PdCl$_2$dppf (155 mg) was added a solution of N-(3-bromo-4-methylphenyl)-2-methylpropanamide (415 mg, 1.62 mmol) in DMF (10.0 mL) at room temperature under argon. The mixture was heated to 80° C. under argon overnight. After cooled to room temperature, the mixture was filtered through celite and the celite was washed with EtOAc (3×20 mL). The filtrates were washed with H$_2$O (20 mL), brine (20 mL), dried over MgSO$_4$, filtered and concentrated in vacuo. The crude material was purified flash chromatography (20% EtOAc/hexane) to give tert-butyl 4-[5-(isobutyrylamino)-2-methylphenyl]-3,6-dihydro-1(2H)-pyridinecarboxylate (360 mg, 62.0%)

Scheme AG

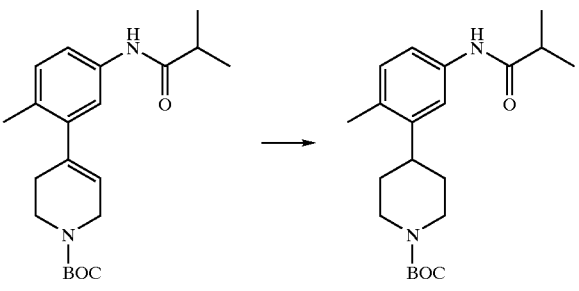

Procedure X

TERT-BUTYL 4-[5-(ISOBUTYRYLAMINO)-2-METHYLPHENYL]-1-PIPERIDINECARBOXYLATE: A solution of tert-butyl 4-[5-(isobutyrylamino)-2-methylphenyl]-3,6-dihydro-1(2H)-pyridinecarboxylate (335 mg, 0.93 mmol) and 10% Pd/C (35.0 mg) in EtOH (20.0 mL) was hydrogenated at room temperature overnight using the hydrogen balloon method. The reaction mixture was filtered through celite and washed with ethanol (3×10 mL). The combined extracts were concentrated in vacuo to afford tert-butyl 4-[5-(isobutyrylamino)-2-methylphenyl]-1-piperidinecarboxylate (335 mg, 100%).

Procedure Y

Scheme AH

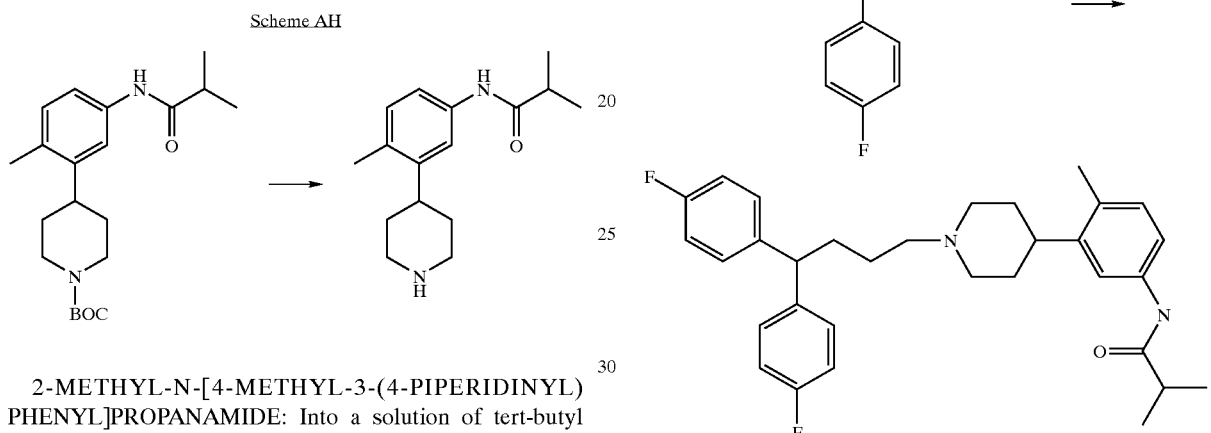

2-METHYL-N-[4-METHYL-3-(4-PIPERIDINYL)PHENYL]PROPANAMIDE: Into a solution of tert-butyl 4-[5-(isobutyrylamino)-2-methylphenyl]-1-piperidinecarboxylate (335 mg, 0.930 mmol) in $CH_2Cl_2$ (10.0 mL) was added TFA (10.0 mL) at room temperature. The reaction mixture was stirred for 2 h and concentrated in vacuo. The residue was dissolved in 20 mL of $CHCl_3$/i-PrOH (3:1) and was basified with 5% KOH solution (10 mL). The aqueous layer was extracted with $CHCl_3$/i-PrOH (3:1, 3×10 mL). The combined organic extracts were washed with brine, dried over $MgSO_4$, filtered and concentrated in vacuo to give 2-methyl-N-[4-methyl-3-(4-piperidinyl)phenyl]propanamide (190 mg, 78.0%).

Procedure Z

N-(3-{1-[4,4-BIS(4-FLUOROPHENYL)BUTYL]-4-PIPERIDINYL}-4-METHYLPHENYL)-2-METHYLPROPANAMIDE: A solution of 2-methyl-N-[4-methyl-3-(4-piperidinyl)phenyl]propanamide (49.0 mg, 0.190 mmol), 1-[4-chloro-1-(4-fluorophenyl)butyl]-4-fluorobenzene (58.0 mg, 0.210 mmol), NaI (42.0 mg, 0.280 mmol) and $K_2CO_3$ (52.0 mg, 0.380 mmol) in DMF (10.0 mL) was heated at 95° C. overnight. The mixture was diluted with water (20 mL) and the aqueous layer was extracted with EtOAc (3×20 mL). The combined organic layers were washed with brine, dried over $MgSO_4$ and concentrated in vacuo. The crude product was purified by flash chromatography [5% $NH_3$ (2.0 M in MeOH) in $CH_2Cl_2$] to afford N-(3-{1-[4,4-bis(4-fluorophenyl)butyl]-4-piperidinyl}-4-methylphenyl)-2-methylpropanamide (37.0 mg, 38.0%).

Procedure AA

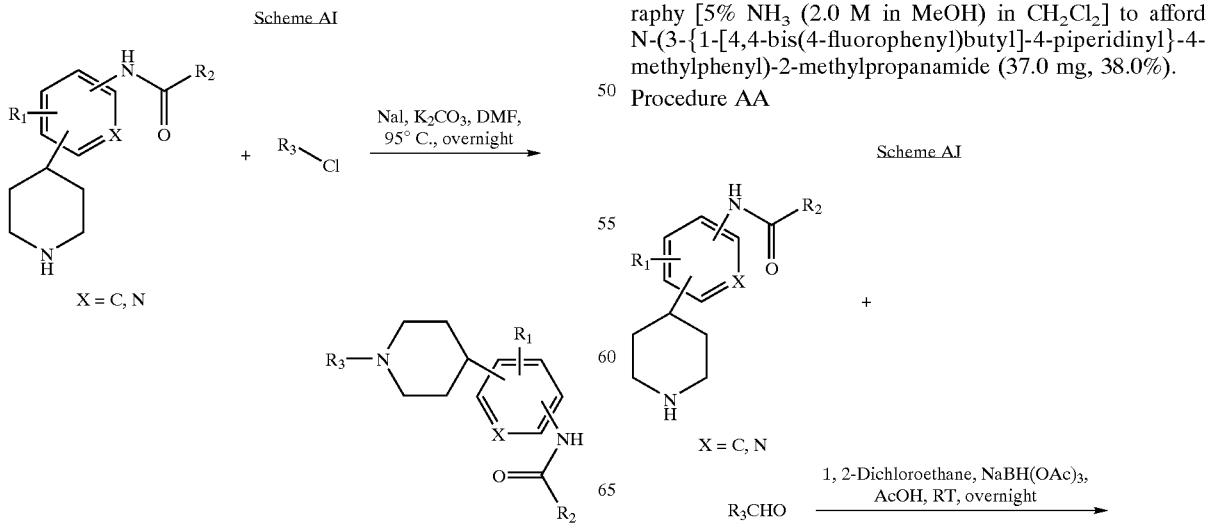

145

-continued

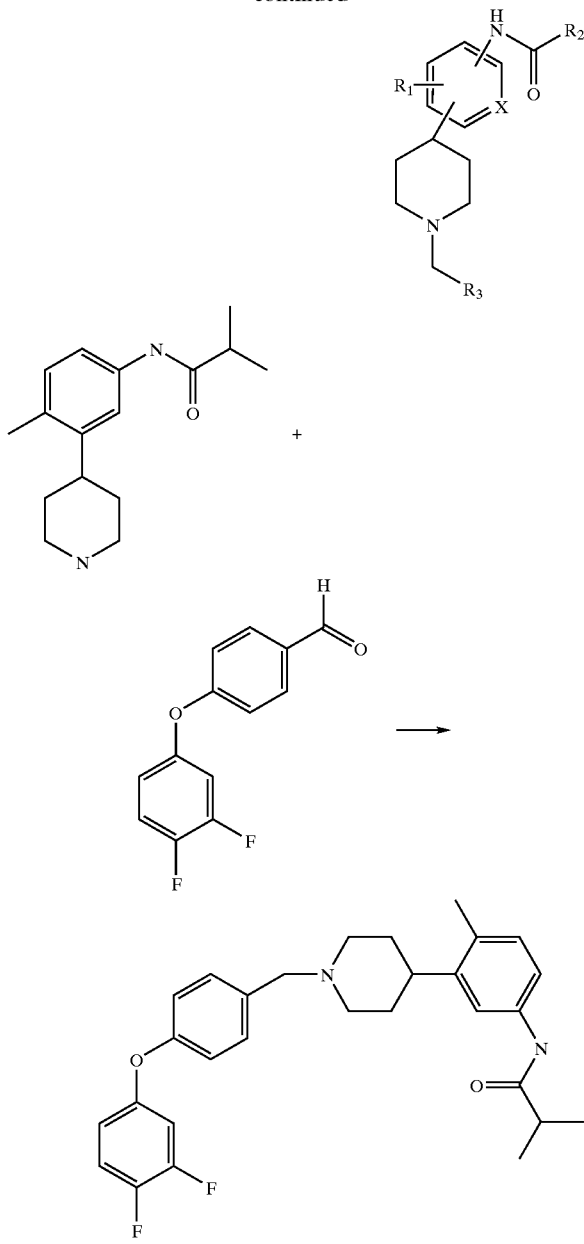

N-(3-{1-[4-(3,4-DIFLUOROPHENOXY)BENZYL]-4-PIPERIDINYL}-4-METHYLPHENYL)-2-METHYLPROPANAMIDE: To a solution of 4-(3,4-Difluorophenoxy)benzaldehyde (41.0 mg, 0.170 mmol) and 2-methyl-N-[4-methyl-3-(4-piperidinyl)phenyl]propanamide (45.0 mg, 0.170 mmol) in 1,2-dichloroethane (5.00 mL) was added sodium triacetoxyborohydride (110 mg, 0.520 mmol) and ACOH (10.0 µL, 0.170 mmol) at room temperature. The mixture was stirred overnight. The reaction mixture was quenched by saturated $NaHCO_3$ solution (10 mL) and extracted with $CH_2Cl_2$ (3×10 mL). The combined organic layers were washed with brine, dried over $MgSO_4$, concentrated in vacuo. The crude product was purified by preparative TLC using 5% $NH_3$ (2.0 M in MeOH) in $CH_2Cl_2$ to give the desired product N-(3-{1-[4-(3,4-difluorophenoxy)benzyl]-4-piperidinyl}-4-methylphenyl)-2-methylpropanamide (44.0 mg, 54.0%)

146

Procedure AC

Scheme AT: Synthesis of Amides using PS-Carbodiimide Resin

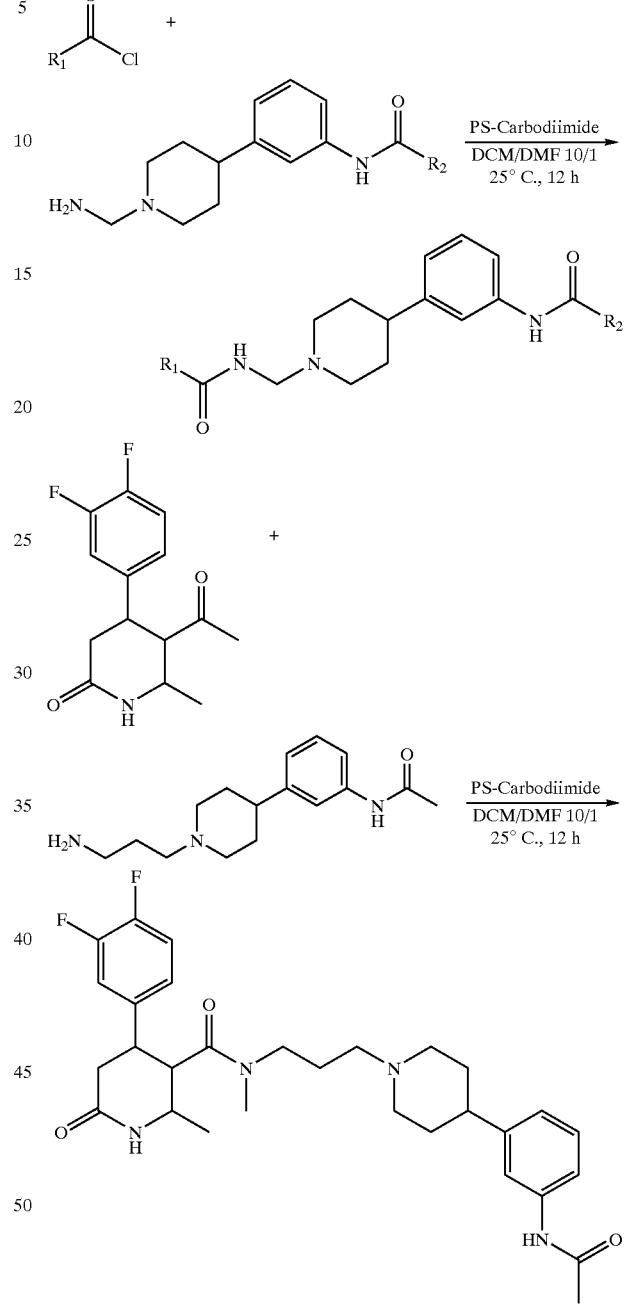

A mixture of a carboxylic acid (0.0800 mmol) and PS-Carbodiimide Resin (2.00 eq, 80.0 mg, 1.34 mmol/g) in DCM:DMF (10:1, 3.00 mL) was shaken for 30 min. To the reaction mixture was added amine (0.0540 mmol) and the resulting mixture was shaken for 12 h at room temperature. The reaction mixture was filtered and the resin was washed with $CH_2Cl_2$. The combined organic extracts were concentrated to a small volume, applied to a preparative TLC plate and eluted with 6% $NH_3$ (2.0 M in MeOH) in $CH_2Cl_2$ to give the desired product.

Procedure AD

Scheme X

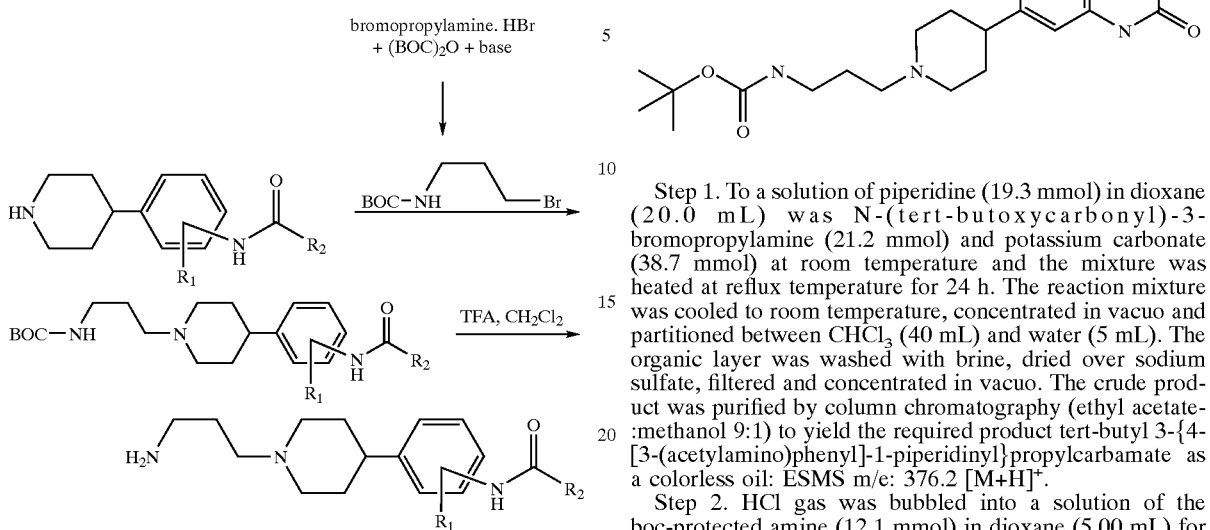

TERT-BUTYL N-(3-BROMOPROPYL)CARBAMATE: Prepared from 3-bromopropylamine hydrobromide and $BOC_2O$ in the presence of base in $CH_2Cl_2$: $^1H$ NMR (300 MHz) δ 5.07 (br, 1H), 3.31 (t, 2H, J=6.6 Hz), 3.12 (apparent br q, 2H, J=6.0 Hz), 1.92 (p, 2H, J=6.6 Hz), 1.30 (s, 9H).

Step 1. To a solution of piperidine (19.3 mmol) in dioxane (20.0 mL) was N-(tert-butoxycarbonyl)-3-bromopropylamine (21.2 mmol) and potassium carbonate (38.7 mmol) at room temperature and the mixture was heated at reflux temperature for 24 h. The reaction mixture was cooled to room temperature, concentrated in vacuo and partitioned between $CHCl_3$ (40 mL) and water (5 mL). The organic layer was washed with brine, dried over sodium sulfate, filtered and concentrated in vacuo. The crude product was purified by column chromatography (ethyl acetate-:methanol 9:1) to yield the required product tert-butyl 3-{4-[3-(acetylamino)phenyl]-1-piperidinyl}propylcarbamate as a colorless oil: ESMS m/e: 376.2 $[M+H]^+$.

Step 2. HCl gas was bubbled into a solution of the boc-protected amine (12.1 mmol) in dioxane (5.00 mL) for 10–20 minutes at 0–5° C. The resulting solution was stirred at 0–5° C. for 1 h, concentrated, neutralized with 10% KOH solution (10 mL) and extracted into $CH_2Cl_2$ (25 mL). The organic extract was washed with brine, dried over sodium sulfate and concentrated in vacuo. The crude product was chromatographed to give the desired product N-{3-[1-(3-aminopropyl)-4-piperidinyl]phenyl}acetamide: ESMS m/e: 276.1 $[M+H]^+$.

Procedure AE

Scheme Y

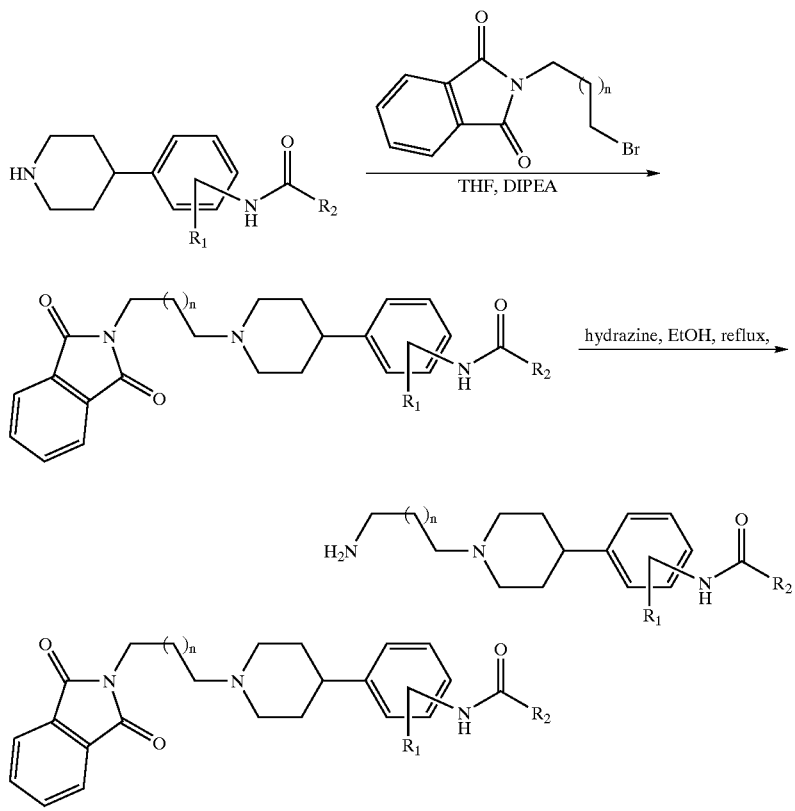

Step 1: A mixture of piperidine (1.00 eq, 0.0226 mmol), N-(bromoalkyl)phthalimide (1.50 eq, 0.0338 mmol), Bu₄NI (200 mg) and diisopropylethylamine (5.00 eq, 0.113 mmol) in dioxane (200 mL) was heated at 99° C. for 24 h. The reaction was followed by TLC analysis (95:5 CH₂Cl₂:methanol). If necessary additional 0.0113 mmol of the appropriate bromoalkylphthalimides was added to each reaction mixture and the heating was continued for additional 48 h. The reaction mixture was cooled to room temperature, the ammonium salts were filtered out and the solvent was removed under reduced pressure. The crude product was chromatographed to give the desired product.

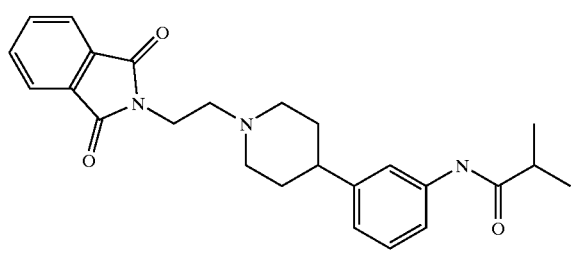

ESMS m/e: 420.2
[M + H]⁺

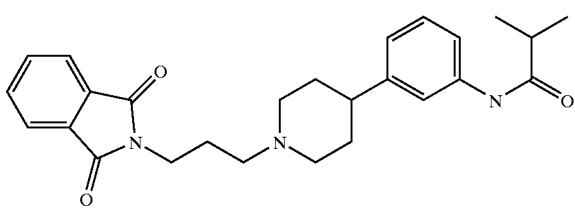

ESMS m/e: 434.4
[M + H]⁺

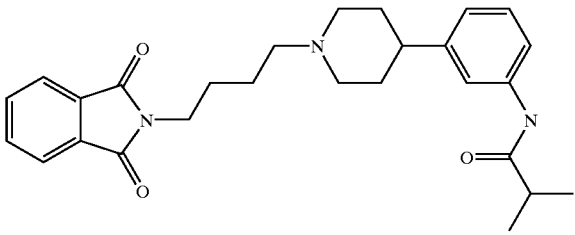

ESMS m/e: 448.4
[M + H]⁺

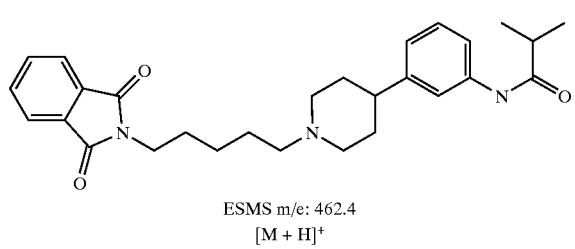

ESMS m/e: 462.4
[M + H]⁺

-continued

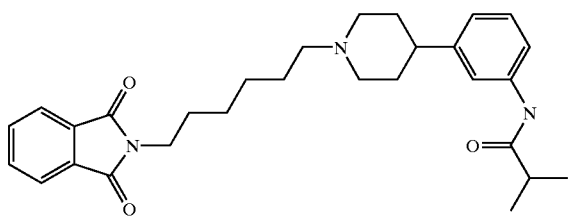

ESMS m/e: 476.4
[M + H]⁺

Step 2: Deprotection of the resulting phthalimides was conducted by heating a solution of phthaliamide-protected amines with excess hydrazine hydrate (10 eq) in ethanol (0.5–1.0 M) at 90° C. for 4 h. The reaction mixture was monitored by TLC to completion. Upon the reaction was completed, the mixture was cooled to room temperature, the insoluble by-products were filtered out through celite and the solvent was removed in vacuo. The crude product was chromatographed (dichloromethane-methanol-isoprpylamine) to give the desired products.

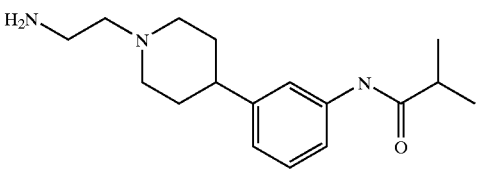

ESMS m/e: 290.2 [M + H]⁺

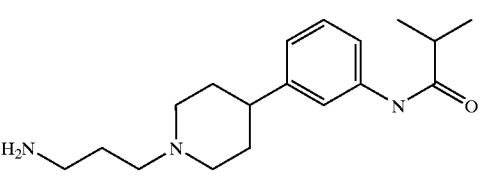

ESMS m/e: 304.1 [M + H]⁺

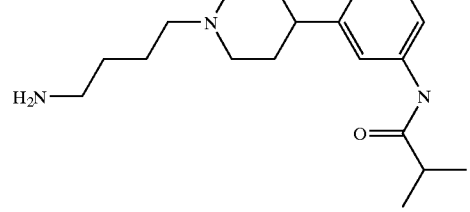

ESMS m/e: 318.2 [M + H]⁺

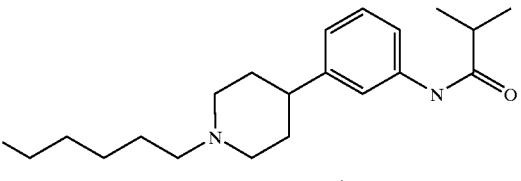

ESMS m/e: 332.2 [M + H]⁺

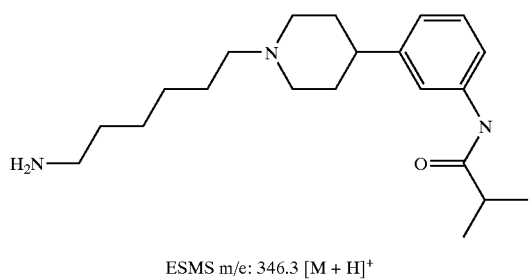

ESMS m/e: 346.3 [M + H]+

Procedure AF

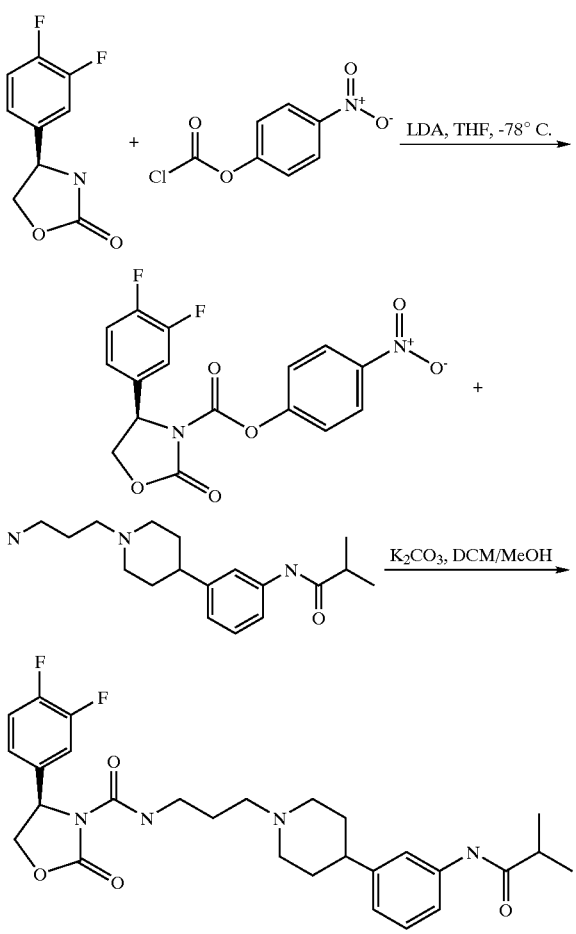

Scheme H

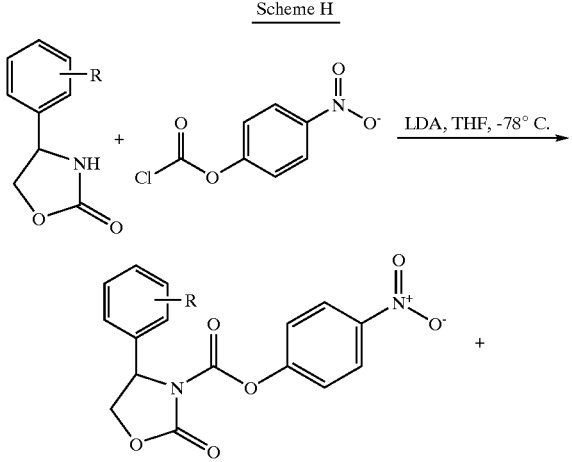

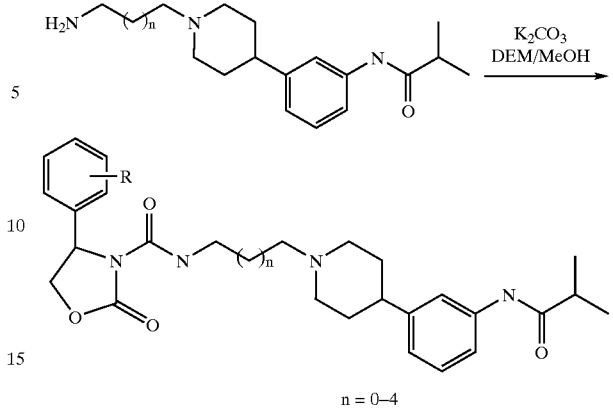

n = 0–4

(4R)-4-(3,4-DIFLUOROPHENYL)-N-(3-{4-[3-(ISOBUTYRYLAMINO)PHENYL]-1-PIPERIDINYL}PROPYL)-2-OXO-1,3-OXAZOLIDINE-3-CARBOXAMIDE was synthesized according to Scheme H and Procedure AF: To a solution of (4R)-4-(3,4-difluorophenyl)-1,3-oxazolidin-2-one (this compound and analogs were prepared according to *J. Med. Chem* 2000, 43, 2775) (0.300 mol, 60.0 mg) in THF (5.00 mL) was added LDA (2.0 M in THF, 0.390 mmol, 0.200 mL) at −78° C. under argon. After 30 min at −78° C., to the mixture was added a solution of 4-nitrophenyl chloroformate (0.330 mmol, 51.2 mg) in THF (0.500 mL) at −78° C. After stirring for 30 min at −78° C. the reaction mixture was diluted with a saturated Na$_2$CO$_3$ solution (5.0 mL) and the aqueous layer was extracted with CH$_2$Cl$_2$ (3×10 mL). The combined organic layers were washed with brine (10 mL), dried over Na$_2$SO$_4$ and concentrated in vacuo. The residue was purified by preparative TLC plates (10:1 hexane:ethyl acetate) to afford 4-nitrophenyl (4R)-4-(3,4-difluorophenyl)-2-oxo-1,3-oxazolidine-3-carboxylate (51.5 mg, 54.0%). 4-Nitrophenyl (4R)-4-(3,4-difluorophenyl)-2-oxo-1,3-oxazolidine-3-carboxylate (169 mg, 0.465 mmol), N-{3-[1-(3-aminopropyl)-4-piperidinyl]phenyl}-2-methylpropanamide (141 mg, 0.465 mmol), K$_2$CO$_3$ (0.193 g, 1.39 mmol), CH$_2$Cl$_2$ (10 mL), and methanol (0.1 mL) were combined in a flask. The mixture was stirred overnight at room temperature, the solvent was removed in vacuo, and the residue was purified by chromatography [2.5% of NH$_3$ (2.0 M in methanol) in CH$_2$Cl$_2$] to afford the desired product (26.1 mg, 10.6%): $^1$H NMR (400 MHz, CDCl$_3$) δ 8.08 (t, 1H, J=5.5 Hz), 7.45 (s, 2H), 7.38 (d, 1H, J=8.6 Hz), 7.24–7.12 (m, 3H), 7.06 (m, 1H), 6.97 (d, 1H, J=8.6 Hz), 5.40 (dd, 1H, J=3.9–8.8 Hz), 4.71 (t, 1H, J=8.8 Hz), 4.23 (dd, 1H, J=4.4, 9.1 Hz), 3.32 (qt, 2H, J=6.1 Hz), 2.99 (d, 2H, J=11.0 Hz), 2.49 (qt, 2H, J=7.0 Hz), 2.41 (t, 2H, J=7.0 Hz), 1.99–1.97 (m, 2H), 1.82–1.68 (m, 6H), 1.23 (d, 6H, J=7.3 Hz); Anal. Calcd. for C$_{28}$H$_{34}$F$_2$N$_4$O$_4$+HCl+0.185CHCl$_3$: C, 57.6; H, 6.04; N, 9.54. Found: C, 58.5; H, 6.08; N, 9.47; ESMS m/e: 529.1 (M+H)+.

Procedure AG

Scheme AR:

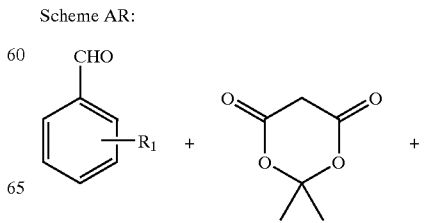

-continued

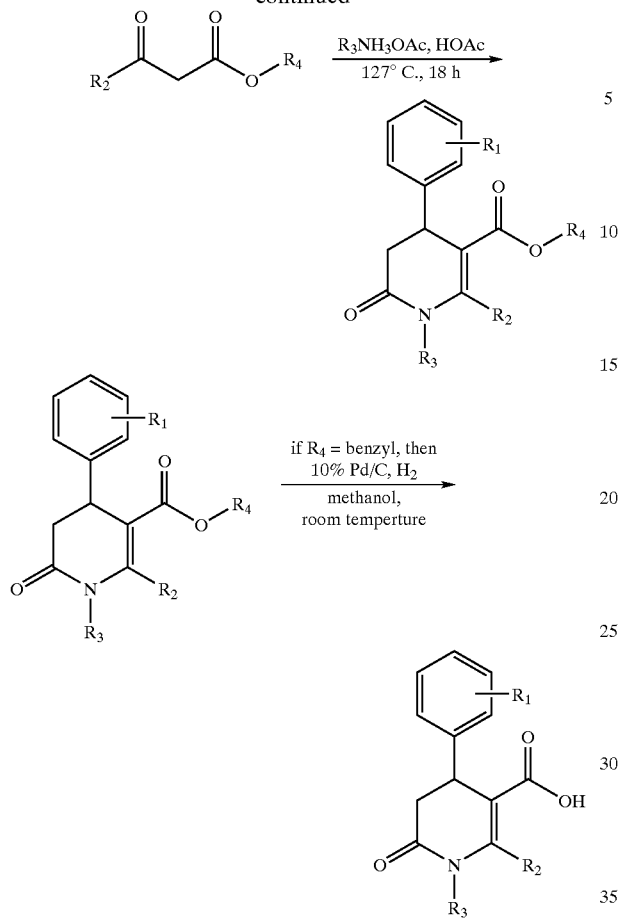

Step 1: A solution of ketoester (10 mmol), Meldrum's acid (10 mmol), aldehyde (10 mmol) and an ammonium acetate (11 mmol) in HOAc (10 mL) was heated at reflux temperature for 18 h.[1] The cooled reaction mixture was poured over ice (100 g). The precipitated oils were collected and dried under reduced pressure. The benzyl ester protected analogs solidified upon trituration with a mixture of ether/hexane.

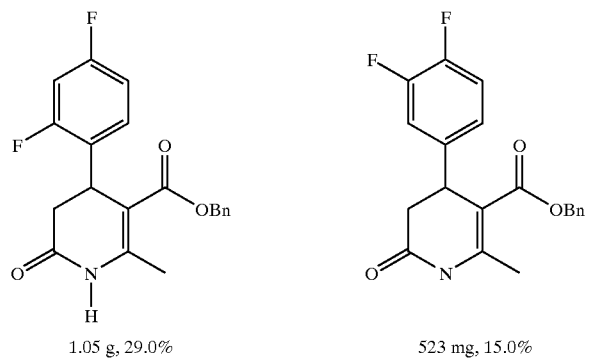

1.05 g, 29.0%          523 mg, 15.0%

[1] MORALES, A.; OCHOA, E.; SUAREZ, M.; VERDECIA, Y.; GONZALEZ, L.; MARTIN, N.; QUINTEIRO, M.; SEOANE, C.; SOTO, J. L.; *J. Heterocycl. Chem.* [JHTCAD] 1996, 33 (1), 103–107.

Step 2: A mixture of a benzyl ester and 10% Pd/C in methanol was hydrogenated using the balloon method at room temperature. The reaction mixture was monitored (TLC) to completion, filtered through Celite 545 and the Celite filter cake was washed with methanol (3×10 mL). The combined methanol extracts were concentrated in vacuo to give the desired carboxylic acid that was used in the next step without any further purification.

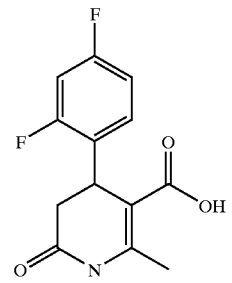

4-(2,4-DIFLUOROPHENYL)-2-METHYL-6-OXO-1,4,5,6-TETRAHYDRO-3-PYRIDINECARBOXYLIC ACID was synthesized according to Procedure AG and Scheme AR: $^1$H NMR (CDCl$_3$, 400 MHz) δ 7.82 (s, 1H), 7.00–6.72 (m, 3H), 4.51 (d, 1H, J=8.4 Hz), 2.90 (dd, 1H, J=8.4, 16.3 Hz), 2.68 (d, 1H, J=16.3 Hz), 2.46 (s, 3H).

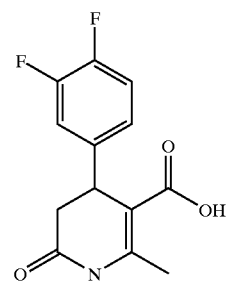

4-(3,4-DIFLUOROPHENYL)-2-METHYL-6-OXO-1,4,5,6-TETRAHYDRO-3-PYRIDINECARBOXYLIC ACID was synthesized according to Procedure AG and Scheme AR: $^1$H NMR (CDCl$_3$, avg. Hz), 2.93 (dd, 1H, J=16.8, 7.5 avg. Hz), 2.68 (d, 1H, J=16.5 avg. Hz), 2.45 (s, 3H).

Procedure AH

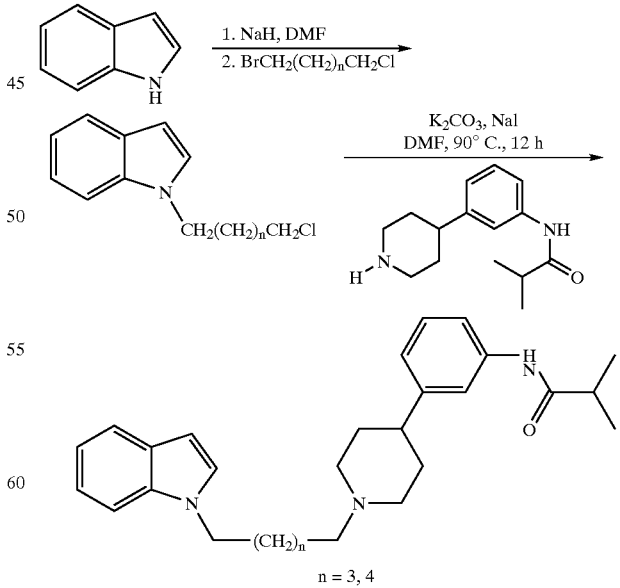

n = 3, 4

1-(6-CHLOROHEXYL)-1H-INDOLE: To a mixture of NaH (0.249 g, 10.0 mmol) in DMF (5.00 mL) was added a solution of 1-H-indole (0.585 g, 5.00 mmol) in DMF (2.00 mL) at 0° C. The reaction mixture was stirred for 30 minutes at 0° C. and warmed up to room temperature. To the reaction mixture 1-bromo-6-chlorohexane (0.998 g, 5.00 mmol) was added dropwise via syringe and the reaction mixture was stirred overnight. The reaction mixture was diluted with EtOAc (30 mL), washed with water (3×10 mL), brine (10 mL), dried over MgSO$_4$, concentrated in vacuo and purified by chromatography using hexane:EtOAc (97.5:2.5) to give the desired product (0.900 g, 76.0%): $^1$H NMR (400 MHz, CDCl$_3$) δ 7.76–7.54 (m, 1H), 7.47–6.96 (m, 4H), 6.60–6.34 (m, 1H), 4.13 (t, 2H, J=6.8 Hz), 3.50 (t, 2H, J=5.6 Hz), 1.98–1.79 (m, 2H), 1.79–1.64 (m, 2H) 1.54–1.17 (m, 4H).

N-(3-{1-[6-(1H-INDOL-1-YL)HEXYL]-4-PIPERIDINYL}PHENYL)-2-METHYLPROPANAMIDE: A mixture of 1-(6-Chlorohexyl)-1H-indole (23.6 mg, 0.100 mmol), 2-methyl-N-[3-(4-piperidinyl)phenyl]propanamide (24.6 mg, 0.100 mmol), K$_2$CO$_3$ (27.6 mg, 0.200 mmol), NaI (22.5 mg, 0.150 mmol) and DMF (1.00 mL) was heated at 100° C. for 12 h. The reaction mixture was cooled to room temperature and the crude material was purified by preparative TLC using 5% of NH$_3$ (2.0 M in methanol) in CH$_2$Cl$_2$ to give the desired product as a yellow solid (40 mg, 90%) $^1$H NMR (400 MHz, CDCl$_3$) δ 8.08–6.52 (m, 11H), 4.17 (t, 2H, J=7.2 Hz), 3.26 (d, 2H, J=11.6 Hz), 2.74–2.52 (m, 4H), 2.44–2.28 (m, 2H), 2.20–2.02 (m, 2H), 1.98–1.82 (m, 4H), 1.78–1.62 (m, 2H), 1.43–1.28 (m, 4H), 1.28 (d, 6H, J=6.8 Hz); ESMS m/e: 446.5 (M+H)$^+$.

Procedure AI:

Scheme AU: Preparation of tert-Piperdines Usingd PS-SO2Cl Resin

The library was constructed in polypropylene Robbins "Reactor Blocks", 48 well plates. PS-TSCl resin (100 mg, 1.00 eq, purchased from Argonaut Technologies) was placed in each well of the "Reactor Blocks" 48 well plates. To each well was added 2–10 eq of an alcohol in dichloromethane:pyridine (1:1, 3.00 mL). The mixture was stirred at room temperature for 5 h and the resin was washed with dichloromethane (3×4.00 mL), DMF (5×4.00 mL), DMF/H$_2$O (3:1, 5×4.00 mL), THF (3×4.00 mL), dichloromethane (3×4.00 mL), acetonitrile (2×4.00 mL) and dried under reduced pressure. A solution of an amine (0.0750 mmol, 0.500 eq) and N,N-diisopropylethyl amine (19.0 mg, 0.150 mmol, 1.00 eq) in acetonitrile (3.00 mL) was added to the well containing the derivatized resin and the mixture was reacted at 70° C. for 16 h in the Robbins rotating oven. After cooling, AP-isocyanate resin (120 mg, 0.150 mmol, 1.00 eq) and THF (2.00 mL) was added to the each reaction vessel and reacted at room temperature for additional 3 h. The solution was filtered into the Robbins receiving plates and concentrated in vacuo to give the desired tertiary amines which were analyzed via LC-MS.

Procedure AJ:

Scheme AV: Preparation of tert-Piperidines using Piperdines,

The library was constructed in polypropylene Robbins 48 well plates Reactor Blocks. In the initial incubation period, each well was charged with PS-TBD resin (from Argonaut Technologies, 200 mg, 0.280 mmol, 2.50 eq) and piperidine (0.120 mmol, 1.10 eq) in acetonitrile (0.500 mL) and agitated for 1 h. A solution of benzyl iodide or bromide (0.110 mmol, 1.00 eq) in acetonitrile (0.500 mL) was added to each well followed by additional acetonitrile (1.00 mL) to make a total volume of 2 mL and the mixture was rotated in a Robbins rotating oven at room temperature for 16 h. Then AP-Isocyanate resin (Argonaut Technologies, 250 mg (0.430 mmol, 4.00 eq) was added to each well and reacted further at room temperature for another 12 h. The mixture was filtered and the filtrate was concentrated in vacuo to obtain the desired product that was characterized via LC-MS.

Scheme AX

Example 117

N-(3-{1-[3-(4-BROMOPHENYL)-3-OXOPROPYL]-4-PIPERIDINYL}PHENYL)-2-METHYLPROPANAMIDE: Procedure K (KI) and Scheme E (K$_2$CO$_3$) using 1-(4-bromophenyl)-3-chloro-1-propanone and 2-methyl-N-[3-(4-piperidinyl)phenyl]propanamide: ESMS m/e: 457.1 (M+H)$^+$.

EXAMPLE 118

N-(3-{1-[3-(4-CHLOROPHENYL)-3-OXOPROPYL]-4-PIPERIDINYL}PHENYL)-2-METHYLPROPANAMIDE: Procedure K (KI) and Scheme E ($K_2CO_3$) using 3-chloro-1-(4-chlorophenyl)-1-propanone and 2-methyl-N-[3-(4-piperidinyl)phenyl]propanamide: ESMS m/e: 413.1 (M+H)$^+$.

EXAMPLE 119

N-(3-{1-[3-(4-METHOXYPHENYL)-3-OXOPROPYL]-4-PIPERIDINYL}PHENYL)-2-METHYLPROPANAMIDE: Procedure K (KI) and Scheme E ($K_2cO_3$) using 3-chloro-1-(4-methoxyphenyl)-1-propanone and 2-methyl-N-[3-(4-piperidinyl)phenyl]propanamide: ESMS m/e: 409.2 (M+H)$^+$.

EXAMPLE 120

N-(3-{1-[3-(2,3-DIHYDRO-1H-INDEN-5-YL)-3-OXOPROPYL]-4-PIPERIDINYL}PHENYL)-2-METHYLPROPANAMIDE: Procedure K (KI) and Scheme E ($K_2CO_3$) using 3-chloro-1-(2,3-dihydro-1H-inden-5-yl)-1-propanone and 2-methyl-N-[3-(4-piperidinyl)phenyl]propanamide: ESMS m/e: 419.2 (M+H)$^+$.

EXAMPLE 121

2-METHYL-N-{3-[1-(3-OXO-3-PHENYLPROPYL)-4-PIPERIDINYL]PHENYL}PROPANAMIDE: Procedure K (KI) and Scheme E ($K_2CO_3$) using 3-chloro-1-phenyl-1-propanone and 2-methyl-N-[3-(4-piperidinyl)phenyl]propanamide: ESMS m/e: 379.2 (M+H)$^+$.

EXAMPLE 122

2-METHYL-N-(3-{1-[3-(4-METHYLPHENYL)-3-OXOPROPYL]-4-PIPERIDINYL}PHENYL)PROPANAMIDE: Procedure K (KI) and Scheme E ($K_2CO_3$) using 3-chloro-1-(4-methylphenyl)-1-propanone and 2-methyl-N-[3-(4-piperidinyl)phenyl]propanamide: ESMS m/e: 393.2 (M+H)$^+$.

EXAMPLE 123

N-(3-{1-[3-(4-FLUOROPHENYL)-3-OXOPROPYL]-4-PIPERIDINYL}PHENYL)-2-METHYLPROPANAMIDE: Procedure K (KI) and Scheme E ($K_2CO_3$) using 3-chloro-1-(4-fluorophenyl)-1-propanone and 2-methyl-N-[3-(4-piperidinyl)phenyl]propanamide: ESMS m/e: 397.2 (M+H)$^+$.

EXAMPLE 124

N-(3-{1-[3-(4-CHLOROPHENYL)-3-HYDROXYPROPYL]-4-PIPERIDINYL}PHENYL)-2-METHYLPROPANAMIDE: Prepared by Procedure L and Scheme AN using N-(3-{1-[3-(4-chlorophenyl)-3-oxopropyl]-4-piperidinyl}phenyl)-2-methylpropanamide: ESMS m/e: 415.1 (M+H)$^+$.

EXAMPLE 125

N-(3-{1-[3-(4-CHLOROPHENYL)-3-(3,4-DIFLUOROPHENOXY)PROPYL]-4-PIPERIDINYL}PHENYL)-2-METHYLPROPANAMIDE: Prepared by Procedure A and Scheme AN using N-(3-{1-[3-(4-chlorophenyl)-3-hydroxypropyl]-4-piperidinyl}phenyl)-2-methylpropanamide and 3,4-difluorophenol: ESMS m/e: 526.8 (M+H)$^+$.

EXAMPLE 126

N-(3-{1-[3-(4-CHLOROPHENYL)-3-(2-METHYLPHENOXY)PROPYL]-4-PIPERIDINYL}PHENYL)-2-METHYLPROPANAMIDE: Prepared by Procedure A and Scheme AN using N-(3-{1-[3-(4-chlorophenyl)-3-hydroxypropyl]-4-piperidinyl}phenyl)-2-methylpropanamide and o-cresol: ESMS m/e: 505.4 (M+H)$^+$.

EXAMPLE 127

N-(3-{1-[3-(4-FLUOROPHENYL)-3-HYDROXYPROPYL]-4-PIPERIDINYL}PHENYL)-2-METHYLPROPANAMIDE: Prepared by Procedure L and Scheme AN using N-(3-{1-[3-(4-fluorophenyl)-3-oxopropyl]-4-piperidinyl}phenyl)-2-methylpropanamide: ESMS m/e: 399.2 (M+H)$^+$.

EXAMPLE 128

N-(3-{1-[3-HYDROXY-3-(4-METHOXYPHENYL)PROPYL]-4-PIPERIDINYL}PHENYL)-2-METHYLPROPANAMIDE: Prepared by Procedure L and Scheme AN using N-(3-{1-[3-(4-methoxyphenyl)-3-oxopropyl]-4-piperidinyl}phenyl)-2-methylpropanamide: ESMS m/e: 411.2 (M+H)$^+$.

EXAMPLE 129

N-(3-{1-[3-(4-BROMOPHENYL)-3-HYDROXYPROPYL]-4-PIPERIDINYL}PHENYL)-2-METHYLPROPANAMIDE: Prepared by Procedure L and Scheme AN using N-(3-{1-[3-(4-bromophenyl)-3-oxopropyl]-4-piperidinyl}phenyl)-2-methylpropanamide: ESMS m/e: 459.1 (M+H)$^+$.

EXAMPLE 130

N-(3-{1-[3-(4-CHLOROPHENYL)-3-(4-METHOXYPHENOXY)PROPYL]-4-PIPERIDINYL}PHENYL)-2-METHYLPROPANAMIDE: Prepared by Procedure A and Scheme AN using N-(3-{1-[3-(4-chlorophenyl)-3-hydroxypropyl]-4-piperidinyl}phenyl)-2-methylpropanamide and 4-methoxyphenol: ESMS m/e: 520.8 (M+H)$^+$.

EXAMPLE 131

N-(3-{1-[3-(4-CHLOROPHENOXY)-3-(4-FLUOROPHENYL)PROPYL]-4-PIPERIDINYL}PHENYL)-2-METHYLPROPANAMIDE: Prepared by Procedure A and Scheme AN using N-(3-{1-[3-(4-fluorophenyl)-3-hydroxypropyl]-4-piperidinyl}phenyl)-2-methylpropanamide and 4-chlorophenol: ESMS m/e: 509.1 (M+H)$^+$.

EXAMPLE 132

N-(3-{1-[3-(4-FLUOROPHENYL)-3-(2,3,4,5,6-PENTAFLUOROPHENOXY)PROPYL]-4-PIPERIDINYL}PHENYL)-2-METHYLPROPANAMIDE: Prepared by Procedure A and Scheme AN using N-(3-{1-[3-(4-fluorophenyl)-3-hydroxypropyl]-4-piperidinyl}phenyl)-2-methylpropanamide and 2,3,4,5,6-pentafluorophenol: ESMS m/e: 564.7 (M+H)$^+$.

EXAMPLE 133

N-(3-{1-[3-(4-BROMOPHENYL)-3-(2-METHYLPHENOXY)PROPYL]-4-

PIPERIDINYL}PHENYL)-2-METHYLPROPANAMIDE: Prepared by Procedure A and Scheme AN using N-(3–1-[3-(4-bromophenyl)-3-hydroxypropyl]-4-piperidinyl}phenyl)-2-methylpropanamide and 2-methylphenol: ESMS m/e: 548.8 (M+H)$^+$.

EXAMPLE 134

N-(3-{1-[3-(3,4-DIFLUOROPHENOXY)-3-(4-FLUOROPHENYL)PROPYL]-4-PIPERIDINYL}PHENYL)-2-METHYLPROPANAMIDE: Prepared by Procedure A and Scheme AN using N-(3-{1-[3-(4-fluorophenyl)-3-hydroxypropyl]-4-piperidinyl}phenyl)-2-methylpropanamide and 3,4-difluorophenol: ESMS m/e: 511.1 (M+H)$^+$.

EXAMPLE 135

N-(3-{1-[3-(4-BROMOPHENOXY)-3-(4-FLUOROPHENYL)PROPYL]-4-PIPERIDINYL}PHENYL)-2-METHYLPROPANAMIDE: Prepared by Procedure A and Scheme AN using N-(3-{1-[3-(4-fluorophenyl)-3-hydroxypropyl]-4-piperidinyl}phenyl)-2-methylpropanamide and 4-bromophenol: ESMS m/e: 553.0 (M+H)$^+$.

EXAMPLE 136

N-(3-{1-[3-(3,4-DICHLOROPHENOXY)-3-(4-FLUOROPHENYL)PROPYL]-4-PIPERIDINYL}PHENYL)-2-METHYLPROPANAMIDE: Prepared by Procedure A and Scheme AN using N-(3-{1-[3-(4- fluorophenyl)-3-hydroxypropyl]-4-piperidinyl}phenyl)-2-methylpropanamide and 3,4-dichlorophenol: ESMS m/e: 542.7 (M+H)$^+$.

EXAMPLE 137

N-[3-(1-{3-(4-FLUOROPHENYL)-3-[4-(TRIFLUOROMETHYL)PHENOXY]PROPYL}-4-PIPERIDINYL)PHENYL]-2-METHYLPROPANAMIDE: Prepared by Procedure A and Scheme AN using N-(3-{1-[3-(4-fluorophenyl)-3-hydroxypropyl]-4-piperidinyl}phenyl)-2-methylpropanamide and 4-(trifluoromethyl)phenol: ESMS m/e: 543.1 (M+H)$^+$.

EXAMPLE 138

N-(3-{1-[3-(3-BROMOPHENOXY)-3-(4-FLUOROPHENYL)PROPYL]-4-PIPERIDINYL}PHENYL)-2-METHYLPROPANAMIDE: Prepared by Procedure A and Scheme AN using N-(3-{1-[3-(4-fluorophenyl)-3-hydroxypropyl]-4-piperidinyl}phenyl)-2-methylpropanamide and 3-bromophenol: ESMS m/e: 552.7 (M+H)$^+$.

EXAMPLE 139

N-(3-{1-[3-(4-FLUOROPHENOXY)-3-(4-FLUOROPHENYL)PROPYL]-4-PIPERIDINYL}PHENYL)-2-METHYLPROPANAMIDE: Prepared by Procedure A and Scheme AN using N-(3-{1-[3-(4-fluorophenyl)-3-hydroxypropyl]-4-piperidinyl}phenyl)-2-methylpropanamide and 4-fluorophenol: ESMS m/e: 493.2 (M+H)$^+$.

EXAMPLE 140

N-(3-{1-[3-(3-FLUOROPHENOXY)-3-(4-FLUOROPHENYL)PROPYL]-4-PIPERIDINYL}PHENYL)-2-METHYLPROPANAMIDE: Prepared by Procedure A and Scheme AN using N-(3-{1-[3-(4-fluorophenyl)-3-hydroxypropyl]-4-piperidinyl}phenyl)-2-methylpropanamide and 3-fluorophenol: ESMS m/e: 492.9 (M+H)$^+$.

EXAMPLE 141

N-(3-{1-[3-(2,6-DICHLOROPHENOXY)-3-(4-FLUOROPHENYL)PROPYL]-4-PIPERIDINYL}PHENYL)-2-METHYLPROPANAMIDE: Prepared by Procedure A and Scheme AN using N-(3-{1-[3-(4-fluorophenyl)-3-hydroxypropyl]-4-piperidinyl}phenyl)-2-methylpropanamide and 2,6-dichlorophenol: ESMS m/e: 543.0 (M+H)$^+$.

EXAMPLE 142

N-(3-{1-[3-(2,5-DIFLUOROPHENOXY)-3-(4-FLUOROPHENYL)PROPYL]-4-PIPERIDINYL}PHENYL)-2-METHYLPROPANAMIDE: Prepared by Procedure A and Scheme AN using N-(3-{1-[3-(4-fluorophenyl)-3-hydroxypropyl]-4-piperidinyl}phenyl)-2-methylpropanamide and 2,5-difluorophenol: ESMS m/e: 511.5 (M+H)$^+$.

EXAMPLE 143

N-(3-{1-[3-(3-CHLOROPHENOXY)-3-(4-FLUOROPHENYL)PROPYL]-4-PIPERIDINYL}PHENYL)-2-METHYLPROPANAMIDE: Prepared by Procedure A and Scheme AN using N-(3-{1-[3-(4-fluorophenyl)-3-hydroxypropyl]-4-piperidinyl}phenyl)-2-methylpropanamide and 3-chlorophenol: ESMS m/e: 509.1 (M+H)$^+$.

EXAMPLE 144

N-(3-{1-[3-(4-BROMOPHENYL)-3-(3-METHYLPHENOXY)PROPYL]-4-PIPERIDINYL}PHENYL)-2-METHYLPROPANAMIDE: Prepared by Procedure A and Scheme AN using N-(3-{1-[3-(4-bromophenyl)-3-hydroxypropyl]-4-piperidinyl}phenyl)-2-methylpropanamide and 3-methylphenol: ESMS m/e: 549.1 (M+H)$^+$.

EXAMPLE 145

N-(3-{1-[3-([1,1'-BIPHENYL]-4-YLOXY)-3-(4-BROMOPHENYL)PROPYL]-4-PIPERIDINYL}PHENYL)-2-METHYLPROPANAMIDE: Prepared by Procedure A and Scheme AN using N-(3-{1-[3-(4-bromophenyl)-3-hydroxypropyl]-4-piperidinyl}phenyl)-2-methylpropanamide and 4-phenylphenol: ESMS m/e: 611.2 (M+H)$^+$.

EXAMPLE 146

N-(3-{1-[3-(2,4-DIFLUOROPHENOXY)-3-(4-FLUOROPHENYL)PROPYL]-4-PIPERIDINYL}PHENYL)-2-METHYLPROPANAMIDE: Prepared by Procedure A and Scheme AN using N-(3-{1-[3-(4-fluorophenyl)-3-hydroxypropyl]-4-piperidinyl}phenyl)-2-methylpropanamide and 2,4-difluorophenol: ESMS m/e: 511.1 (M+H)$^+$.

EXAMPLE 147

N-(3-{1-[3-(4-BROMOPHENYL)-3-(3-METHOXYPHENOXY)PROPYL]-4-PIPERIDINYL}PHENYL)-2-METHYLPROPANAMIDE: Prepared by Procedure A and Scheme AN using N-(3-{1-

[3-(4-bromophenyl)-3-hydroxypropyl]-4-piperidinyl}phenyl)-2-methylpropanamide and 3-methoxyphenol: ESMS m/e: 564.6 (M+H)$^+$.

EXAMPLE 148

METHYL 4-(1-(4-BROMOPHENYL)-3-{4-[3-(ISOBUTYRYLAMINO)PHENYL]-1-PIPERIDINYL}PROPOXY)BENZOATE: Prepared by Procedure A and Scheme AN using N-(3-{1-[3-(4-bromophenyl)-3-hydroxypropyl]-4-piperidinyl}phenyl)-2-methylpropanamide and methyl 4-hydroxybenzoate: ESMS m/e: 593.0 (M+H)$^+$.

EXAMPLE 149

N-(3-{1-[3-(4-BROMOPHENYL)-3-(4-PHENOXYPHENOXY)PROPYL]-4-PIPERIDINYL}PHENYL)-2-METHYLPROPANAMIDE: Prepared by Procedure A and Scheme AN using N-(3-{1-[3-(4-bromophenyl)-3-hydroxypropyl]-4-piperidinyl}phenyl)-2-methylpropanamide and 4-phenoxyphenol: ESMS m/e: 626.6 (M+H)$^+$.

EXAMPLE 150

N-(3-{1-[3-(4-BROMOPHENYL)-3-(2-CHLORO-4-METHYLPHENOXY)PROPYL]-4-PIPERIDINYL}PHENYL)-2-METHYLPROPANAMIDE: Prepared by Procedure A and Scheme AN using N-(3-{1-[3-(4-bromophenyl)-3-hydroxypropyl]-4-piperidinyl}phenyl)-2-methylpropanamide and 2-chloro-4-methylphenol: ESMS m/e: 583.0 (M+H)$^+$.

EXAMPLE 151

N-(3-{1-[3-(4-BROMOPHENYL)-3-PHENOXYPROPYL]-4-PIPERIDINYL}PHENYL)-2-METHYLPROPANAMIDE: Prepared by Procedure A and Scheme AN using N-(3-{1-[3-(4-bromophenyl)-3-hydroxypropyl]-4-piperidinyl}phenyl)-2-methylpropanamide and phenol: ESMS m/e: 535.0 (M+H)$^+$.

EXAMPLE 152

N-[3-(1-{3-(4-BROMOPHENYL)-3-[4-(TRIFLUOROMETHYL)PHENOXY]PROPYL}-4-PIPERIDINYL)PHENYL]-2-METHYLPROPANAMIDE: Prepared by Procedure A and Scheme AN using N-(3-{1-[3-(4-bromophenyl)-3-hydroxypropyl]-4-piperidinyl}phenyl)-2-methylpropanamide and 4-(trifluoromethyl)phenol: ESMS m/e: 603.1 (M+H)$^+$.

EXAMPLE 153

N-(3-{1-[3-(2-ACETYLPHENOXY)-3-(4-BROMOPHENYL)PROPYL]-4-PIPERIDINYL}PHENYL)-2-METHYLPROPANAMIDE: Prepared by Procedure A and Scheme AN using N-(3-{1-[3-(4-bromophenyl)-3-hydroxypropyl]-4-piperidinyl}phenyl)-2-methylpropanamide and 2-acetylphenol: ESMS m/e: 576.6 (M+H)$^+$.

EXAMPLE 154

N-(3-{1-[3-(3-ACETYLPHENOXY)-3-(4-BROMOPHENYL)PROPYL]-4-PIPERIDINYL}PHENYL)-2-METHYLPROPANAMIDE: Prepared by Procedure A and Scheme AN using N-(3-{1-[3-(4-bromophenyl)-3-hydroxypropyl]-4-piperidinyl}phenyl)-2-methylpropanamide and 3-acetylphenol: ESMS m/e: 576.9 (M+H)$^+$.

EXAMPLE 155

N-(3-{1-[3-(3-ACETYLPHENOXY)-3-(2,3-DIHYDRO-1H-INDEN-5-YL)PROPYL]-4-PIPERIDINYL}PHENYL)-2-METHYLPROPANAMIDE: Prepared by Procedure A and Scheme AN using N-(3-{1-[3-(2,3-dihydro-1H-inden-5-yl)-3-hydroxypropyl]-4-piperidinyl}phenyl)-2-methylpropanamide and 3-acetylphenol: ESMS m/e: 539.2 (M+H)$^+$.

EXAMPLE 156

N-(3-{1-[3-(2,3-DIHYDRO-1H-INDEN-5-YL)-3-PHENOXYPROPYL]-4-PIPERIDINYL}PHENYL)-2-METHYLPROPANAMIDE: Prepared by Procedure A and Scheme AN using N-(3-{1-[3-(2,3-dihydro-1H-inden-5-yl)-3-hydroxypropyl]-4-piperidinyl}phenyl)-2-methylpropanamide and phenol: ESMS m/e: 497.2 (M+H)$^+$.

EXAMPLE 157

N-(3-{1-[3-(2-ACETYLPHENOXY)-3-(2,3-DIHYDRO-1H-INDEN-5-YL)PROPYL]-4-PIPERIDINYL}PHENYL)-2-METHYLPROPANAMIDE: Prepared by Procedure A and Scheme AN using N-(3-{1-[3-(2,3-dihydro-1H-inden-5-yl)-3-hydroxypropyl]-4-piperidinyl}phenyl)-2-methylpropanamide 2-acetylphenol: ESMS m/e: 539.1 (M+H)$^+$.

EXAMPLE 158

N-(3-{1-[3-(4-BROMOPHENOXY)-3-(4-BROMOPHENYL)PROPYL]-4-PIPERIDINYL}PHENYL)-2-METHYLPROPANAMIDE: Prepared by Procedure A and Scheme AN using N-(3-{1-[3-(4-bromophenyl)-3-hydroxypropyl]-4-piperidinyl}phenyl)-2-methylpropanamide and 4-bromophenol: ESMS m/e: 612.7 (M+H)$^+$.

EXAMPLE 159

N-(3-{1-[3-(4-BROMOPHENYL)-3-(4-CHLOROPHENOXY)PROPYL]-4-PIPERIDINYL}PHENYL)-2-METHYLPROPANAMIDE: Prepared by Procedure A and Scheme AN using N-(3-{1-[3-(4-bromophenyl)-3-hydroxypropyl]-4-piperidinyl}phenyl)-2-methylpropanamide and 4-chlorophenol: ESMS m/e: 568.7 (M+H)$^+$.

EXAMPLE 160

N-(3-{1-[3-(4-BROMOPHENYL)-3-(4-FLUOROPHENOXY)PROPYL]-4-PIPERIDINYL}PHENYL)-2-METHYLPROPANAMIDE: Prepared by Procedure A and Scheme AN using N-(3-{1-[3-(4-bromophenyl)-3-hydroxypropyl]-4-piperidinyl}phenyl)-2-methylpropanamide and 4-fluorophenol: ESMS m/e: 552.8 (M+H)$^+$.

EXAMPLE 161

N-(3-{1-[3-(2,3-DIHYDRO-1H-INDEN-5-YL)-3-(4-METHOXYPHENOXY)PROPYL]-4-PIPERIDINYL}PHENYL)-2-METHYLPROPANAMIDE: Prepared by Procedure A and Scheme AN using N-(3-{1-[3-(2,3-dihydro-1H-inden-5-yl)-3-hydroxypropyl]-4-piperidinyl}phenyl)-2-methylpropanamide and 4-methoxyphenol: ESMS m/e: 527.3 (M+H)$^+$.

EXAMPLE 162

N-(3-{1-[3-(2,3-DIHYDRO-1H-INDEN-5-YL)-3-(4-FLUOROPHENOXY)PROPYL]-4-

PIPERIDINYL}PHENYL)-2-METHYLPROPANAMIDE: Prepared by Procedure A and Scheme AN using N-(3-{1-[3-(2,3-dihydro-1H-inden-5-yl)-3-hydroxypropyl]-4-piperidinyl}phenyl)-2-methylpropanamide and 4-fluorophenol: ESMS m/e: 515.2 (M+H)$^+$.

EXAMPLE 163

N-(3-{1-[3-(2,3-DIHYDRO-1H-INDEN-5-YL)-3-HYDROXYPROPYL]-4-PIPERIDINYL}PHENYL)-2-METHYLPROPANAMIDE Prepared by Procedure L and Scheme AN using N-(3-{1-[3-(2,3-dihydro-1H-inden-5-yl)-3-oxopropyl]-4-piperidinyl}phenyl)-2-methylpropanamide: ESMS m/e: 421.2 (M+H)$^+$.

EXAMPLE 164

N-[3-(1-{3-(2,3-DIHYDRO-1H-INDEN-5-YL)-3-[4-(TRIFLUOROMETHYL)PHENOXY]PROPYL}-4-PIPERIDINYL)PHENYL]-2-METHYLPROPANAMIDE: Prepared by Procedure A and Scheme AN using N-(3-{1-[3-(2,3-dihydro-1H-inden-5-yl)-3-hydroxypropyl]-4-piperidinyl}phenyl)-2-methylpropanamide and 4-trifluoromethylphenol: ESMS m/e: 565.0 (M+H)$^+$.

EXAMPLE 165

N-(3-{1-[3-(4-BROMOPHENOXY)-3-(2,3-DIHYDRO-1H-INDEN-5-YL)PROPYL]-4-PIPERIDINYL}PHENYL)-2-METHYLPROPANAMIDE: Prepared by Procedure A and Scheme AN using N-(3-{1-[3-(2,3-dihydro-1H-inden-5-yl)-3-hydroxypropyl]-4-piperidinyl}phenyl)-2-methylpropanamide and 4-bromophenol: ESMS m/e: 577.4 (M+H)$^+$.

EXAMPLE 166

N-(3-{1-[3-(3-ACETYLPHENOXY)-3-(4-CHLOROPHENYL)PROPYL]-4-PIPERIDINYL}PHENYL)-2-METHYLPROPANAMIDE: Prepared by Procedure A and Scheme AN using N-(3-{1-[3-(4-chlorophenyl)-3-hydroxypropyl]-4-piperidinyl}phenyl)-2-methylpropanamide and 3-acetylphenol: SMS m/e: 533.1 (M+H)$^+$.

EXAMPLE 167

N-(3-{1-[3-(4-METHOXYPHENOXY)-3-(4-METHOXYPHENYL)PROPYL]-4-PIPERIDINYL}PHENYL)-2-METHYLPROPANAMIDE: Prepared by Procedure A and Scheme AN using N-(3-{1-[3-hydroxy-3-(4-methoxyphenyl)propyl]-4-piperidinyl}phenyl)-2-methylpropanamide and 4-methoxyphenol: ESMS m/e: 517.4 (M+H)$^+$.

EXAMPLE 168

N-(3-{1-[3-(4-CHLOROPHENOXY)-3-(2,3-DIHYDRO-1-INDEN-5-YL)PROPYL]-4-PIPERIDINYL}PHENYL)-2-METHYLPROPANAMIDE: Prepared by Procedure A and Scheme AN using N-(3-{1-[3-(2,3-dihydro-1H-inden-5-yl)-3-hydroxypropyl]-4-piperidinyl}phenyl)-2-methylpropanamide and 4-chlorophenol: ESMS m/e: 531.1 (M+H)$^+$.

EXAMPLE 169

N-(3-{1-[3-(2-ACETYLPHENOXY)-3-(4-CHLOROPHENYL)PROPYL]-4-PIPERIDINYL}PHENYL)-2-METHYLPROPANAMIDE: Prepared by Procedure A and Scheme AN using N-(3-{1-[3-(4-chlorophenyl)-3-hydroxypropyl]-4-piperidinyl}phenyl)-2-methylpropanamide and 2-acetylphenol: ESMS m/e: 533.4 (M+H)$^+$.

EXAMPLE 170

N-(3-{1-[3-(4-BROMOPHENYL)-3-(4-METHOXYPHENOXY)PROPYL]-4-PIPERIDINYL}PHENYL)-2-METHYLPROPANAMIDE: Prepared by Procedure A and Scheme AN using N-(3-{1-[3-(4-bromophenyl)-3-hydroxypropyl]-4-piperidinyl}phenyl)-2-methylpropanamide and 4-methoxyphenol: ESMS m/e: 565.0 (M+H)$^+$.

EXAMPLE 171

N-(3-{1-[3-(4-BROMOPHENOXY)-3-(4-CHLOROPHENYL)PROPYL]-4-PIPERIDINYL}PHENYL)-2-METHYLPROPANAMIDE: Prepared by Procedure A and Scheme AN using N-(3-{1-[3-(4-chlorophenyl)-3-hydroxypropyl]-4-piperidinyl}phenyl)-2-methylpropanamide and 4-bromophenol: ESMS m/e: 568.8 (M+H)$^+$.

EXAMPLE 172

N-(3-{1-[3-(4-CHLOROPHENOXY)-3-(4-CHLOROPHENYL)PROPYL]-4-PIPERIDINYL}PHENYL)-2-METHYLPROPANAMIDE: Prepared by Procedure A and Scheme AN using N-(3-{1-[3-(4-chlorophenyl)-3-hydroxypropyl]-4-piperidinyl}phenyl)-2-methylpropanamide and 4-chlorophenol: ESMS m/e: 525.0 (M+H)$^+$.

EXAMPLE 173

N-(3-{1-[3-(4-METHOXYPHENYL)-3-PHENOXYPROPYL]-4-PIPERIDINYL}PHENYL)-2-METHYLPROPANAMIDE: Prepared by Procedure A and Scheme AN using N-(3-{1-[3-hydroxy-3-(4-methoxyphenyl)propyl]-4-piperidinyl}phenyl)-2-methylpropanamide and phenol: ESMS m/e: 487.4 (M+H)$^+$.

EXAMPLE 174

N-(3-{1-[3-(4-FLUOROPHENYL)-3-PHENOXYPROPYL]-4-PIPERIDINYL}PHENYL)-2-METHYLPROPANAMIDE: Prepared by Procedure A and Scheme AN using N-(3-{1-[3-(4-fluorophenyl)-3-hydroxypropyl]-4-piperidinyl}phenyl)-2-methylpropanamide and phenol: ESMS m/e: 475.6 (M+H)$^+$.

EXAMPLE 175

N-(3-{1-[3-(2-ACETYLPHENOXY)-3-(4-FLUOROPHENYL)PROPYL]-4-PIPERIDINYL}PHENYL)-2-METHYLPROPANAMIDE: Prepared by Procedure A and Scheme AN using N-(3-{1-[3-(4-fluorophenyl)-3-hydroxypropyl]-4-piperidinyl}phenyl)-2-methylpropanamide and 2-acetylphenol: ESMS m/e: 517.1 (M+H)$^+$.

EXAMPLE 176

N-(3-{1-[3-(3-ACETYLPHENOXY)-3-(4-FLUOROPHENYL)PROPYL]-4-PIPERIDINYL}PHENYL)-2-METHYLPROPANAMIDE: Prepared by Procedure A and Scheme AN using N-(3-{1-[3-(4-fluorophenyl)-3-hydroxypropyl]-4-piperidinyl}phenyl)-2-methylpropanamide and 3-acetylphenol: ESMS m/e: 516.9 (M+H)$^+$.

EXAMPLE 177

N-(3-{1-[3-(4-FLUOROPHENYL)-3-(4-METHOXYPHENOXY)PROPYL]-4-PIPERIDINYL}PHENYL)-2-METHYLPROPANAMIDE: Prepared by Procedure A and Scheme AN using N-(3-{1-[3-(4-fluorophenyl)-3-hydroxypropyl]-4-piperidinyl}phenyl)-2-methylpropanamide and 4-methoxyphenol: ESMS m/e: 505.2 (M+H)$^+$.

EXAMPLE 178

N-(3-{1-[3-(4-CHLOROPHENOXY)-3-(4-METHOXYPHENYL)PROPYL]-4-PIPERIDINYL}PHENYL)-2-METHYLPROPANAMIDE: Prepared by Procedure A and Scheme AN using N-(3-{1-[3-hydroxy-3-(4-methoxyphenyl)propyl]-4-piperidinyl}phenyl)-2-methylpropanamide and 4-cholorophenol: ESMS m/e: 521.5 (M+H)$^+$.

EXAMPLE 179

N-(3-{1-[3-(3-ACETYLPHENOXY)-3-(4-METHOXYPHENYL)PROPYL]-4-PIPERIDINYL}PHENYL)-2-METHYLPROPANAMIDE: Prepared by Procedure A and Scheme AN using N-(3-{1-[3-hydroxy-3-(4-methoxyphenyl)propyl]-4-piperidinyl}phenyl)-2-methylpropanamide and 3-acetylphenol: ESMS m/e: 529.0 (M+H)$^+$.

EXAMPLE 180

N-(3-{1-[3-(4-CHLOROPHENYL)-3-PHENOXYPROPYL]-4-PIPERIDINYL}PHENYL)-2-METHYLPROPANAMIDE: Prepared by Procedure A and Scheme AN using N-(3-{1-[3-(4-chlorophenyl)-3-hydroxypropyl]-4-piperidinyl}phenyl)-2-methylpropanamide and phenol. ESMS m/e: 490.9 (M+H)$^+$.

EXAMPLE 181

N-(3-{1-[3-(4-BROMOPHENOXY)-3-(4-METHOXYPHENYL)PROPYL]-4-PIPERIDINYL}PHENYL)-2-METHYLPROPANAMIDE: Prepared by Procedure A and Scheme AN using N-(3-{1-[3-hydroxy-3-(4-methoxyphenyl)propyl]-4-piperidinyl}phenyl)-2-methylpropanamide and 4-bromophenol: ESMS m/e: 564.9 (M+H)$^+$.

EXAMPLE 182

N-[3-(1-{3-(4-METHOXYPHENYL)-3-[4-(TRIFLUOROMETHYL)PHENOXY]PROPYL}-4-PIPERIDINYL)PHENYL]-2-METHYLPROPANAMIDE: Prepared by Procedure A and Scheme AN using N-(3-{1-[3-hydroxy-3-(4-methoxyphenyl)propyl]-4-piperidinyl}phenyl)-2-methylpropanamide and 4-trifluoromethyphenol: ESMS m/e: 555.1 (M+H)$^+$.

EXAMPLE 183

N-(3-{1-[3-(4-CHLOROPHENYL)-3-(4-FLUOROPHENOXY)PROPYL]-4-PIPERIDINYL}PHENYL)-2-METHYLPROPANAMIDE: Prepared by Procedure A and Scheme AN using N-(3-{1-[3-(4-chlorophenyl)-3-hydroxypropyl]-4-piperidinyl}phenyl)-2-methylpropanamide and 4-fluorophenol: ESMS m/e: 509.1 (M+H)$^+$.

EXAMPLE 184

N-(3-{1-[3-(4-FLUOROPHENOXY)-3-(4-METHOXYPHENYL)PROPYL]-4-PIPERIDINYL}PHENYL)-2-METHYLPROPANAMIDE: Prepared by Procedure A and Scheme AN using N-(3-{1-[3-hydroxy-3-(4-methoxyphenyl)propyl]-4-piperidinyl}phenyl)-2-methylpropanamide and 4-fluorophenol: ESMS m/e: 505.5 (M+H)$^+$.

EXAMPLE 185

N-(3-{1-[3-(2-ACETYLPHENOXY)-3-(4-METHOXYPHENYL)PROPYL]-4-PIPERIDINYL}PHENYL)-2-METHYLPROPANAMIDE: Prepared by Procedure A and Scheme AN using N-(3-{1-[3-hydroxy-3-(4-methoxyphenyl)propyl]-4-piperidinyl}phenyl)-2-methylpropanamide and 2-acetylphenol: ESMS m/e: 529.2 (M+H)$^+$.

EXAMPLE 186

N-[3-(1-{3-(4-CHLOROPHENYL)-3-[4-(TRIFLUOROMETHYL)PHENOXY]PROPYL}-4-PIPERIDINYL)PHENYL]-2-METHYLPROPANAMIDE: Prepared by Procedure A and Scheme AN using N-(3-{1-[3-(4-chlorophenyl)-3-hydroxypropyl]-4-piperidinyl}phenyl)-2-methylpropanamide and 4-trifluoromethylphenol: SMS m/e: 559.1 (M+H)$^+$.

EXAMPLE 187

N-(3-{1-[(3S)-3-(3-ACETYLPHENOXY)-3-PHENYLPROPYL]-4-PIPERIDINYL}-4-METHYLPHENYL)-2-METHYLPROPANAMIDE: Prepared by Procedure G and Scheme AI using 1-(3-{[(1S)-3-chloro-1-phenylpropyl]oxy}phenyl)ethanone and 2-methyl-N-[4-methyl-3-(4-piperidinyl)phenyl]propanamide: ESMS m/e: 513.0 (M+H)$^+$.

2-(ISOPENTYLOXY)-1-NAPHTHALDEHYDE: 2-Hydroxy-1-naphthaldehyde (1.72 g, 10.0 mmol) and THF (50 ml) were combined in a flask. NaH (312 mg, 13 mmol) was added, followed by 1-bromo-3-methylbutane (1.20 mL, 10.0 mmol). The solution was stirred at room temperature overnight, the solvent was removed in vacuo, and the residue was purified by chromatography (5–10% ethyl acetate/hexane): $^1$H NMR (400 MHz, CDCl$_3$) δ 10.9 (s, 1H), 9.28 (dd, 1H, J=0.7 Hz, 8.6 Hz), 8.02 (d, 1H, J=9.1 Hz), 7.75 (d, 1H, J=8.1 Hz), 7.63–7.59 (m, 1H), 7.43–7.39 (m, 1H), 7.27 (d, 1H, J=9.2 Hz), 4.25 (t, 2H, J=6.5 Hz), 1.98–1.84 (m, 1H), 1.80–1.75 (m, 2H), 0.99 (d, 6H, J=6.6 Hz); ESMS m/e: 242.8 (M+H)$^+$.

EXAMPLE 188

N-[3-(1-{[2-(ISOPENTYLOXY)-1-NAPHTHYL]METHYL}-4-PIPERIDINYL)PHENYL]-2-METHYLPROPANAMIDE: Prepared by Procedure F and Scheme R using 2-(isopentyloxy)-1-naphthaldehyde and 2-methyl-N-[3-(4-piperidinyl)phenyl]propanamide: ESMS m/e: 473.3 (M+H)$^+$.

2-PROPOXY-1-NAPHTHALDEHYDE: Prepared according to the Procedure for 2-(isopentyloxy)-1-naphthaldehyde using 2-hydroxy-1-naphthaldehyde and 1-bromopropane.

EXAMPLE 189

2-METHYL-N-(3-{1-[(2-PROPOXY-1-NAPHTHYL)METHYL]-4-PIPERIDINYL}PHENYL)PROPANAMIDE: Prepared by Procedure F and Scheme R using 2-propoxy-1-naphthaldehyde and 2-methyl-N-[3-(4-piperidinyl)phenyl]propanamide: ESMS m/e: 445.2 (M+H)$^+$.

4-{[(1-FORMYL-2-NAPHTHYL)OXY]METHYL}BENZONITRILE: Prepared according to the

Procedure for 2-(isopentyloxy)-1-naphthaldehyde using 2-hydroxy-1-naphthaldehyde and 4-(bromomethyl) benzonitrile.

EXAMPLE 190

N-{3-[1-({2-[(4-CYANOBENZYL)OXY]-1-NAPHTHYL}METHYL)-4-PIPERIDINYL]PHENYL}-2-METHYLPROPANAMIDE: Prepared by Procedure F and Scheme R using 4-{[(1-formyl-2-naphthyl)oxy]methyl}benzonitrile and 2-methyl-N-[3-(4-piperidinyl)phenyl]propanamide: ESMS m/e: 518.2 (M+H)$^+$.

[(1-FORMYL-2-NAPHTHYL)OXY]ACETONITRILE: Prepared according to the Procedure for 2-(isopentyloxy)-1-naphthaldehyde using 2-hydroxy-1-naphthaldehyde and bromoacetonitrile.

EXAMPLE 191

N-[3-(1-({2-(CYANOMETHOXY)-1-NAPHTHYL]METHYL}-4-PIPERIDINYL)PHENYL]-2-METHYLPROPANAMIDE: Prepared by Procedure F and Scheme R using [(1-formyl-2-naphthyl)oxy]acetonitrile and 2-methyl-N-[3-(4-piperidinyl)phenyl]propanamide: ESMS m/e: 442.2 (M+H)$^+$.

2-[(3-CHLOROBENZYL)OXY]-1-NAPHTHALDEHYDE: Prepared according to the Procedure for 2-(isopentyloxy)-1-naphthaldehyde using 2-hydroxy-1-naphthaldehyde and 1-(bromomethyl)-3-chlorobenzene.

EXAMPLE 192

N-{3-[1-({2-[(3-CHLOROBENZYL)OXY]-1-NAPHTHYL}METHYL)-4-PIPERIDINYL]PHENYL}-2-METHYLPROPANAMIDE: Prepared by Procedure F and Scheme R using 2-[(3-chlorobenzyl)oxy]-1-naphthaldehyde and 2-methyl-N-[3-(4-piperidinyl)phenyl]propanamide: ESMS m/e: 527.2 (M+H)$^+$.

EXAMPLE 193

N-(3-{1-[4-(4-CHLOROPHENOXY)BENZYL]-4-PIPERIDINYL}PHENYL)-2-METHYLPROPANAMIDE: Prepared by Procedure F and Scheme R using 4-(4-chlorophenoxy)benzaldehyde and 2-methyl-N-[3-(4-piperidinyl)phenyl]propanamide: $^1$H NMR (400 MHz, CDCl$_3$) δ 7.50 (s, 1H), 7.34–7.19 (m, 7H), 6.98–6.87 (m, 5H), 3.50 (s, 2H), 2.98 (d, 2H, J=11.8 Hz), 2.58–2.44 (m, 2H), 2.10–1.98 (m, 2H), 1.83–1.76 (m, 4H), 1.24 (d, 6H, J=6.8 Hz); ESMS m/e: 463.2 (M+H)$^+$.

EXAMPLE 194

N-(3-{1-[4-(3,4- DIFLUOROPHENOXY)BENZYL]-4-PIPERIDINYL}PHENYL)-2-METHYLPROPANAMIDE: Prepared by Procedure F and Scheme R using 4-(3,4-difluorophenoxy)benzaldehyde and 2-methyl-N-[3-(4-piperidinyl)phenyl]propanamide: ESMS m/e: 465.2 (M+H)$^+$.

4-(ISOPENTYLOXY)-1-NAPHTHALDEHYDE: Prepared according to the Procedure for 2-(isopentyloxy)-1-naphthaldehyde using 4-hydroxy-1-naphthaldehyde and 1-bromo-3-methylbutane.

EXAMPLE 195

N-[3-(1-{[4-(ISOPENTYLOXY)-1-NAPHTHYL]METHYL}-4-PIPERIDINYL)PHENYL]-2-METHYLPROPANAMIDE: Prepared by Procedure F and Scheme R using 4-(isopentyloxy)-1-naphthaldehyde and 2-methyl-N-[3-(4-piperidinyl)phenyl]propanamide: ESMS m/e: 473.3 (M+H)$^+$.

EXAMPLE 196

N-(3-{1-[4-(4-METHOXYPHENOXY)BENZYL]-4-PIPERIDINYL}PHENYL)-2-METHYLPROPANAMIDE: Prepared by Procedure F and Scheme R using 4-(4-methoxyphenoxy)benzaldehyde and 2-methyl-N-[3-(4-piperidinyl)phenyl]propanamide: ESMS m/e: 459.2 (M+H)$^+$.

4-PROPOXY-1-NAPHTHALDEHYDE: Prepared according to the Procedure for 2-(isopentyloxy)-1-naphthaldehyde using 4-hydroxy-1-naphthaldehyde and 1-bromopropane.

EXAMPLE 197

2-METHYL-N-(3-{1-[(4-PROPOXY-1-NAPHTHYL)METHYL]-4-PIPERIDINYL}PHENYL)PROPANAMIDE: Prepared by Procedure F and Scheme R using 4- propoxy-1-naphthaldehyde and 2-methyl-N-[3-(4-piperidinyl)phenyl]propanamide: ESMS m/e: 445.2 (M+H)$^+$.

EXAMPLE 198

N-(3-{1-[4-(3,4-DICHLOROPHENOXY)BENZYL]-4-PIPERIDINYL}PHENYL)-2-METHYLPROPANAMIDE: Prepared by Procedure F and Scheme R using 4-(3,4-dichlorophenoxy)benzaldehyde and 2-methyl-N-[3-(4-piperidinyl)phenyl]propanamide: ESMS m/e: 497.1 (M+H)$^+$.

EXAMPLE 199

N-(3-{1-[4-(DIPHENYLAMINO)BENZYL]-4-PIPERIDINYL}PHENYL)-2-METHYLPROPANAMIDE: Prepared by Procedure F and Scheme R using 4-(diphenylamino)benzaldehyde and 2-methyl-N-[3-(4-piperidinyl)phenyl]propanamide: ESMS m/e: 504.2 (M+H)$^+$.

EXAMPLE 200

N-{3-[1-({2,5-DIMETHYL-1-[3-(TRIFLUOROMETHYL)PHENYL]-1H-PYRROL-3-YL}METHYL)-4-PIPERIDINYL]PHENYL}-2-METHYLPROPANAMIDE: Prepared by Procedure F and Scheme R using 2,5-dimethyl-1-[3-(trifluoromethyl)phenyl]-1H-pyrrole-3-carbaldehyde and 2-methyl-N-[3-(4-piperidinyl)phenyl]propanamide: ESMS m/e: 498.2 (M+H)$^+$.

EXAMPLE 201

2-METHYL-N-(3-{1-[1-(2-PHENYL-1,3-THIAZOL-4-YL)ETHYL]-4-PIPERIDINYL}PHENYL) PROPANAMIDE: Prepared by Procedure F and Scheme R using 1-(2-phenyl-1,3-thiazol-4-yl)ethanone and 2-methyl-N-[3-(4-piperidinyl)phenyl]propanamide: ESMS m/e: 434.2 (M+H)$^+$.

EXAMPLE 202

N-(3-{1-[(S-CHLORO-3-METHYL-1-PHENYL-1H-PYRAZOL-4-YL)METHYL]-4-PIPERIDINYL}PHENYL)-2-METHYLPROPANAMIDE: Prepared by Procedure F and Scheme R using 5-chloro-3-methyl-1-phenyl-1H-pyrazole-4-carbaldehyde and 2-methyl-N-[3-(4-piperidinyl)phenyl]propanamide: ESMS m/e: 451.2 (M+H)$^+$.

EXAMPLE 203

2-METHYL-N-(3-{1-[(2-PHENYL-1H-IMIDAZOL-4-YL)METHYL]-4-PIPERIDINYL}PHENYL)PROPANAMIDE: Prepared by Procedure F and Scheme R using 2-phenyl-1H-imidazole-4-carbaldehyde and 2-methyl-N-[3-(4-piperidinyl)phenyl]propanamide: ESMS m/e: 403.2 (M+H)+.

EXAMPLE 204

N-[3-(1-{[4-BROMO-1-(4-CHLOROBENZYL)-1H-PYRAZOL-5-YL]METHYL}-4-PIPERIDINYL)PHENYL]-2-METHYLPROPANAMIDE: Prepared by Procedure F and Scheme R using 4-bromo-1-(4-chlorobenzyl)-1H-pyrazole-5-carbaldehyde and 2-methyl-N-[3-(4-piperidinyl)phenyl]propanamide: ESMS m/e: 529.1 (M+H)+.

EXAMPLE 205

2-METHYL-N-{3-[1-(3-PHENOXYBENZYL)-4-PIPERIDINYL]PHENYL}PROPANAMIDE: Prepared by Procedure F and Scheme R using 3-phenoxybenzaldehyde and 2-methyl-N-[3-(4-piperidinyl)phenyl]propanamide: ESMS m/e: 429.2 (M+H)+.

EXAMPLE 206

N-(3-{1-[3-(3,4-DICHLOROPHENOXY)BENZYL]-4-PIPERIDINYL}PHENYL)-2-METHYLPROPANAMIDE: Prepared by Procedure F and Scheme R using 3-(3,4-dichlorophenoxy)benzaldehyde and 2-methyl-N-[3-(4-piperidinyl)phenyl]propanamide: ESMS m/e: 497.15 (M+H)+.

EXAMPLE 207

N-(3-{1-[3-(3,5-dichlorophenoxy)benzyl]-4-piperidinyl}phenyl)-2-methylpropanamide: Prepared by Procedure F and Scheme R using 3-(3,5-dichlorophenoxy)benzaldehyde and 2-methyl-N-[3-(4-piperidinyl)phenyl]propanamide: ESMS m/e: 497.2 (M+H)+.

EXAMPLE 208

2-METHYL-N-(3-{1-[3-(4-METHYLPHENOXY)BENZYL]-4-PIPERIDINYL}PHENYL)PROPANAMIDE: Prepared by Procedure F and Scheme R using 3-(4-methylphenoxy)benzaldehyde and 2-methyl-N-[3-(4-piperidinyl)phenyl]propanamide: ESMS m/e: 443.2 (M+H)+.

EXAMPLE 209

2-METHYL-N-[3-(1-{3-[3-(TRIFLUOROMETHYL)PHENOXY]BENZYL}-4-PIPERIDINYL)PHENYL]PROPANAMIDE: Prepared by Procedure F and Scheme R using 3-[3-(trifluoromethyl)phenoxy]benzaldehyde and 2-methyl-N-[3-(4-piperidinyl)phenyl]propanamide: ESMS m/e: 497.2 (M+H)+.

EXAMPLE 210

N-(3-{1-[3-(4-CHLOROPHENOXY)BENZYL]-4-PIPERIDINYL}PHENYL)-2-METHYLPROPANAMIDE: Prepared by Procedure F and Scheme R using 3-(4-chlorophenoxy)benzaldehyde and 2-methyl-N-[3-(4-piperidinyl)phenyl]propanamide: ESMS m/e: 463.2 (M+H)+.

EXAMPLE 211

N-(3-{1-[3-(DIMETHYLAMINO)BENZYL]-4-PIPERIDINYL}PHENYL)-2-METHYLPROPANAMIDE: Prepared by Procedure F and Scheme R using 3-(dimethylamino)benzaldehyde and 2-methyl-N-[3-(4-piperidinyl)phenyl]propanamide: ESMS m/e: 380.2 (M+H)+.

EXAMPLE 212

N-(3-{1-[3-(4-METHOXYPHENOXY)BENZYL]-4-PIPERIDINYL}PHENYL)-2-METHYLPROPANAMIDE: Prepared by Procedure F and Scheme R using 3-(4-methoxyphenoxy)benzaldehyde and 2-methyl-N-[3-(4-piperidinyl)phenyl]propanamide: ESMS m/e: 459.2 (M+H)+.

EXAMPLE 213

N-(3-{1-[3-(4-TERT-BUTYLPHENOXY)BENZYL]-4-PIPERIDINYL}PHENYL)-2-METHYLPROPANAMIDE: Prepared by Procedure F and Scheme R using 3-(4-tert-butylphenoxy)benzaldehyde and 2-methyl-N-[3-(4-piperidinyl)phenyl]propanamide: ESMS m/e: 485.3 (M+H)+.

EXAMPLE 214

2-METHYL-N-(3-{1-[3-NITRO-4-(1-PIPERIDINYL)BENZYL]-4-PIPERIDINYL}PHENYL)PROPANAMIDE: Prepared by Procedure F and Scheme R using 3-nitro-4-(1-piperidinyl)benzaldehyde and 2-methyl-N-[3-(4-piperidinyl)phenyl]propanamide: ESMS m/e: 465.2 (M+H)+.

EXAMPLE 215

N-(3-{1-[(3,4-DIMETHYLTHIENO[2,3-B]THIEN-2-YL)METHYL]-4-PIPERIDINYL}PHENYL)-2-METHYLPROPANAMIDE: Prepared by Procedure F and Scheme R using 3,4-dimethylthieno[2,3-b]thiophene-2-carbaldehyde and 2-methyl-N-[3-(4-piperidinyl)phenyl]propanamide: ESMS m/e: 427.1 (M+H)+.

EXAMPLE 216

2-METHYL-N-{3-[1-({3-[4-(TRIFLUOROMETHYL)PHENYL]-1H-PYRAZOL-4-YL}METHYL)-4-PIPERIDINYL]PHENYL}PROPANAMIDE: Prepared by Procedure F and Scheme R using 3-[4-(trifluoromethyl)phenyl]-1H-pyrazole-4-carbaldehyde and 2-methyl-N-[3-(4-piperidinyl)phenyl]propanamide: ESMS m/e: 471.1 (M+H)+.

EXAMPLE 217

2-METHYL-N-(3-{1-[4-(1H-1,2,4-TRIAZOL-1-YL)BENZYL]-4-PIPERIDINYL}PHENYL)PROPANAMIDE: Prepared by Procedure F and Scheme R using 4-(1H-1,2,4-triazol-1-yl)benzaldehyde and 2-methyl-N-[3-(4-piperidinyl)phenyl]propanamide: ESMS m/e: 404.1 (M+H)+.

EXAMPLE 218

2-METHYL-N-(3-{1-[(5-METHYL-1-PHENYL-1H-PYRAZOL-4-YL)METHYL]-4-PIPERIDINYL}PHENYL)PROPANAMIDE: Prepared by Procedure F and Scheme R using 5-methyl-1-phenyl-1H-pyrazole-4-carbaldehyde and 2-methyl-N-[3-(4-piperidinyl)phenyl]propanamide: ESMS m/e: 417.1 (M+H)+.

EXAMPLE 219

2-METHYL-N-(3-{1-[4-(4-MORPHOLINYL)-3-NITROBENZYL]-4-PIPERIDINYL}PHENYL)

PROPANAMIDE: Prepared by Procedure F and Scheme R using 4-(4-morpholinyl)-3-nitrobenzaldehyde and 2-methyl-N-[3-(4-piperidinyl)phenyl]propanamide: ESMS m/e: 467.1 (M+H)$^+$.

EXAMPLE 220

N-{3-[1-({5-[2-CHLORO-4-(TRIFLUOROMETHYL) PHENYL]-2-FURYL}METHYL)-4-PIPERIDINYL] PHENYL}-2-METHYLPROPANAMIDE: Prepared by Procedure F and Scheme R using 5-[2-chloro-4-(trifluoromethyl)phenyl]-2-furaldehyde and 2-methyl-N-[3-(4-piperidinyl)phenyl]propanamide: ESMS m/e: 505.0 (M+H)$^+$.

EXAMPLE 221

ETHYL 4-({4-[3-(ISOBUTYRYLAMINO)PHENYL]-1-PIPERIDINYL}METHYL)-2,5-DIMETHYL-1-PHENYL-1H-PYRROLE-3-CARBOXYLATE: Prepared by Procedure F and Scheme R using ethyl 4-formyl-2,5-dimethyl-1-phenyl-1H-pyrrole-3-carboxylate and 2-methyl-N-[3-(4-piperidinyl)phenyl]propanamide: ESMS m/e: 502.2 (M+H)$^+$.

EXAMPLE 222

ETHYL 5-(4-CHLOROPHENYL)-2-({4-[3-(ISOBUTYRYLAMINO)PHENYL]-1-PIPERIDINYL}METHYL)-3-FUROATE: Prepared by Procedure F and Scheme R using ethyl 5-(4-chlorophenyl)-2-formyl-3-furoate and 2-methyl-N-[3-(4-piperidinyl)phenyl] propanamide: ESMS m/e: 509.0 (M+H)$^+$.

EXAMPLE 223

N-{3-[1-(2,3-DIHYDRO-1,4-BENZODIOXIN-6-YLMETHYL)-4-PIPERIDINYL]PHENYL}-2-METHYLPROPANAMIDE: Prepared by Procedure F and Scheme R using 2,3-dihydro-1,4-benzodioxine-6-carbaldehyde and 2-methyl-N-[3-(4-piperidinyl)phenyl] propanamide: ESMS m/e: 395.1 (M+H)$^+$.

EXAMPLE 224

2-METHYL-N-(3-{1-[(6-PHENOXY-3-PYRIDINYL) METHYL]-4-PIPERIDINYL}PHENYL)PROPANAMIDE: Prepared by Procedure F and Scheme R using 6-phenoxynicotinaldehyde and 2-methyl-N-[3-(4-piperidinyl)phenyl]propanamide: ESMS m/e: 430.1 (M+H)$^+$.

EXAMPLE 225

2-METHYL-N-[3-(1-{[5-(2-PYRIDINYL)-2-THIENYL]METHYL}-4-PIPERIDINYL)PHENYL] PROPANAMIDE: Prepared by Procedure F and Scheme R using 5-(2-pyridinyl)-2-thiophenecarbaldehyde and 2-methyl-N-[3-(4-piperidinyl)phenyl]propanamide: ESMS m/e: 420.1 (M+H)$^+$.

EXAMPLE 226

2-METHYL-N-{3-[1-({5-[1-METHYL-3-(TRIFLUOROMETHYL)-1H-PYRAZOL-5-YL]-2-THIENYL}METHYL)-4-PIPERIDINYL] PHENYL}PROPANAMIDE: Prepared by Procedure F and Scheme R using 5-[1-methyl-3-(trifluoromethyl)-1H-pyrazol-5-yl]-2-thiophenecarbaldehyde and 2-methyl-N-[3-(4-piperidinyl)phenyl]propanamide: ESMS m/e: 491.0 (M+H)$^+$.

EXAMPLE 227

2-METHYL-N-[3-(1-{[1-(PHENYLSULFONYL)-1H-INDOL-3-YL]METHYL}-4-PIPERIDINYL)PHENYL] PROPANAMIDE: Prepared by Procedure F and Scheme R using 1-(phenylsulfonyl)-1H-indole-3-carbaldehyde and 2-methyl-N-[3-(4-piperidinyl)phenyl]propanamide: ESMS m/e: 516.1 (M+H)$^+$.

EXAMPLE 228

N-(3-{1-[(1,5-DIMETHYL-3-OXO-2-PHENYL-2,3-DIHYDRO-1H-PYRAZOL-4-YL)METHYL]-4-PIPERIDINYL}PHENYL)-2-METHYLPROPANAMIDE: Prepared by Procedure F and Scheme R using 1,5-dimethyl-3-oxo-2-phenyl-2,3-dihydro-1H-pyrazole-4-carbaldehyde and 2-methyl-N-[3-(4-piperidinyl)phenyl]propanamide: ESMS m/e: 447.2 (M+H)$^+$.

EXAMPLE 229

N-(3-{1-[4-(4-TERT-BUTYL-1,3-THIAZOL-2-YL) BENZYL]-4-PIPERIDINYL}PHENYL)-2-METHYLPROPANAMIDE: Prepared by Procedure F and Scheme R using 4-(4-tert-butyl-1,3-thiazol-2-yl) benzaldehyde and 2-methyl-N-[3-(4-piperidinyl)phenyl] propanamide.

EXAMPLE 230

N-{3-[1-(2,3-DIHYDRO-1-BENZOFURAN-5-YLMETHYL)-4-PIPERIDINYL]PHENYL}-2-METHYLPROPANAMIDE: Prepared by Procedure F and Scheme R using 2,3-dihydro-1-benzofuran-5-carbaldehyde and 2-methyl-N-[3-(4-piperidinyl)phenyl]propanamide: ESMS m/e: 379.1 (M+H)$^+$.

EXAMPLE 231

2-METHYL-N-(3-{1-[(4-METHYL-2-PHENYL-5-PYRIMIDINYL)METHYL]-4-PIPERIDINYL}PHENYL) PROPANAMIDE: Prepared by Procedure F and Scheme R using 4-methyl-2-phenyl-5-pyrimidinecarbaldehyde and 2-methyl-N-[3-(4-piperidinyl)phenyl]propanamide: ESMS m/e: 429.2 (M+H)$^+$.

EXAMPLE 232

N-{3-[1-(2,1,3-BENZOTHIADIAZOL-5-YLMETHYL)-4-PIPERIDINYL]PHENYL}-2-METHYLPROPANAMIDE: Prepared by Procedure F and Scheme R using 2,1,3-benzothiadiazole-5-carbaldehyde and 2-methyl- N-[3-(4-piperidinyl)phenyl]propanamide: ESMS m/e: 395.1 (M+H)$^+$.

EXAMPLE 233

2-METHYL-N-(3-{1-[(S-PHENYL-2-THIENYL) METHYL]-4-PIPERIDINYL}PHENYL)PROPANAMIDE: Prepared by Procedure F and Scheme R using 5-phenyl-2-thiophenecarbaldehyde and 2-methyl-N-[3-(4-piperidinyl) phenyl]propanamide: ESMS m/e: 419.1 (M+H)$^+$.

EXAMPLE 234

N-{3-[1-(3,4-DIHYDRO-2H-1,5-BENZODIOXEPIN-7-YLMETHYL)-4-PIPERIDINYL]PHENYL)-2-METHYLPROPANAMIDE: Prepared by Procedure F and Scheme R using 3,4-dihydro-2H-1,5-benzodioxepine-7-carbaldehyde and 2-methyl-N-[3-(4-piperidinyl)phenyl] propanamide: ESMS m/e: 409.2 (M+H)$^+$.

EXAMPLE 235

2-METHYL-N-[3-(1-{[3-(2-THIENYL)-1H-PYRAZOL-4-YL]METHYL}-4-PIPERIDINYL)PHENYL]PROPANAMIDE: Prepared by Procedure F and Scheme R using 3-(2-thienyl)-1H-pyrazole-4-carbaldehyde and 2-methyl-N-[3-(4-piperidinyl)phenyl]propanamide: ESMS m/e: 409.1 (M+H)+.

EXAMPLE 236

N-{3-[1-([1,1'-BITHIENYL]-4-YLMETHYL)-4-PIPERIDINYL]PHENYL}-2-METHYLPROPANAMIDE: Prepared by Procedure F and Scheme R using 2,2'-Bithiophene-5-carboxaldehyde and 2-methyl-N-[3-(4-piperidinyl)phenyl]propanamide: ESMS m/e: 425.0 (M+H)+.

EXAMPLE 237

N-(3-{1-[(2,2-DIMETHYL-3,4-DIHYDRO-2H-CHROMEN-6-YL)METHYL]-4-PIPERIDINYL}PHENYL)-2-METHYLPROPANAMIDE: Prepared by Procedure F and Scheme R using 2,2-dimethyl-6-chromanecarbaldehyde and 2-methyl-N-[3-(4-piperidinyl)phenyl]propanamide: ESMS m/e: 421.2 (M+H)+.

EXAMPLE 238

2-METHYL-N-{3-[1-({5-[1-METHYL-5-(TRIFLUOROMETHYL)-1H-PYRAZOL-3-YL]-2-THIENYL}METHYL)-4-PIPERIDINYL]PHENYL}PROPANAMIDE: Prepared by Procedure F and Scheme R using 5-[1-methyl-5-(trifluoromethyl)-1H-pyrazol-3-yl]-2-thiophenecarbaldehyde and 2-methyl-N-[3-(4-piperidinyl)phenyl]propanamide: ESMS m/e: 491.1 (M+H)+.

EXAMPLE 239

2-METHYL-N-(3-{1-[(2-PHENYL-1,3-THIAZOL-4-YL)METHYL]-4-PIPERIDINYL}PHENYL)PROPANAMIDE: Prepared by Procedure F and Scheme R using 2-phenyl-1,3-thiazole-4-carbaldehyde and 2-methyl-N-[3-(4-piperidinyl)phenyl]propanamide: ESMS m/e: 420.0 (M+H)+.

EXAMPLE 240

2-METHYL-N-(3-{1-[(3-PHENOXY-2-THIENYL)METHYL]-4-PIPERIDINYL}PHENYL)PROPANAMIDE: Prepared by Procedure F and Scheme R using 3-phenoxy-2-thiophenecarbaldehyde and 2-methyl-N-[3-(4-piperidinyl)phenyl]propanamide: ESMS m/e: 435.0 (M+H)+.

EXAMPLE 241

N-{3-[1-({2-[(4-CHLOROPHENYL)SULFANYL]-3-THIENYL}METHYL)-4-PIPERIDINYL]PHENYL}-2-METHYLPROPANAMIDE: Prepared by Procedure F and Scheme R using 2-[(4-chlorophenyl)sulfanyl]-3-thiophenecarbaldehyde and 2-methyl-N-[3-(4-piperidinyl)phenyl]propanamide: ESMS m/e: 485.0 (M+H)+.

EXAMPLE 242

N-[3-(1-{[1-(4-CHLOROPHENYL)-1H-PYRROL-2-YL]METHYL}-4-PIPERIDINYL)PHENYL]-2-METHYLPROPANAMIDE: Prepared by Procedure F and Scheme R using 1-(4-chlorophenyl)-1H-pyrrole-2-carbaldehyde and 2-methyl-N-[3-(4-piperidinyl)phenyl]propanamide: ESMS m/e: 436.0 (M+H)+.

EXAMPLE 243

2-METHYL-N-{3-[1-((5-[2-(TRIFLUOROMETHOXY)PHENYL]-2-FURYL}METHYL)-4-PIPERIDINYL]PHENYL}PROPANAMIDE: Prepared by Procedure F and Scheme R using 5-[2-(trifluoromethoxy)phenyl]-2-furaldehyde and 2-methyl-N-[3-(4-piperidinyl)phenyl]propanamide: ESMS m/e: 487.1 (M+H)+.

EXAMPLE 244

2-METHYL-N-(3-{1-[2-(4-MORPHOLINYL)BENZYL]-4-PIPERIDINYL}PHENYL)PROPANAMIDE: Prepared by Procedure F and Scheme R using 2-(4-morpholinyl)benzaldehyde and 2-methyl-N-[3-(4-piperidinyl)phenyl]propanamide: ESMS m/e: 422.2 (M+H)+.

EXAMPLE 245

N-[3-(1-{[3-(4-METHOXYPHENYL)-1H-PYRAZOL-4-YL]METHYL}-4-PIPERIDINYL)PHENYL]-2-METHYLPROPANAMIDE: Prepared by Procedure F and Scheme R using 3-(4-methoxyphenyl)-1H-pyrazole-4-carbaldehyde and 2-methyl-N-[3-(4-piperidinyl)phenyl]propanamide: ESMS m/e: 433.1 (M+H)+.

EXAMPLE 246

2-METHYL-N-(3-{1-[4-(1H-PYRAZOL-1-YL)BENZYL]-4-PIPERIDINYL}PHENYL)PROPANAMIDE: Prepared by Procedure F and Scheme R using 4-(1H-pyrazol-1-yl)benzaldehyde and 2-methyl-N-[3-(4-piperidinyl)phenyl]propanamide: ESMS m/e: 402.8 (M+H)+.

EXAMPLE 247

2-METHYL-N-{3-[1-(4-QUINOLINYLMETHYL)-4-PIPERIDINYL]PHENYL}PROPANAMIDE: Prepared by Procedure F and Scheme R using 4-quinolinecarbaldehyde and 2-methyl-N-[3-(4-piperidinyl)phenyl]propanamide: ESMS m/e: 388.1 (M+H)+.

EXAMPLE 248

2-METHYL-N-(3-{1-[4-(4-MORPHOLINYL)BENZYL]-4-PIPERIDINYL}PHENYL)PROPANAMIDE: Prepared by Procedure F and Scheme R using 4-(4-morpholinyl)benzaldehyde and 2-methyl-N-[3-(4-piperidinyl)phenyl]propanamide: ESMS m/e: 422.5 (M+H)+.

EXAMPLE 249

2-METHYL-N-(3-{1-[4-(2-THIENYL)BENZYL]-4-PIPERIDINYL}PHENYL)PROPANAMIDE: Prepared by Procedure F and Scheme R using 4-(2-thienyl)benzaldehyde and 2-methyl-N-[3-(4-piperidinyl)phenyl]propanamide: ESMS m/e: 419.1 (M+H)+.

EXAMPLE 250

2-METHYL-N-(3-{1-[(2-METHYL-5-PHENYL-3-FURYL)METHYL]-4-PIPERIDINYL}PHENYL)PROPANAMIDE: Prepared by Procedure F and Scheme R using 2-methyl-5-phenyl-3-furaldehyde and 2-methyl-N-[3-(4-piperidinyl)phenyl]propanamide: ESMS m/e: 417.2 (M+H)+.

EXAMPLE 251

N-(3-{1-[3-(CYCLOPENTYLOXY)-4-METHOXYBENZYL]-4-PIPERIDINYL}PHENYL)-2-

METHYLPROPANAMIDE: Prepared by Procedure F and Scheme R using 3-(cyclopentyloxy)-4-methoxybenzaldehyde and 2-methyl-N-[3-(4-piperidinyl)phenyl]propanamide: ESMS m/e: 451.1 (M+H)+.

EXAMPLE 252

2-METHYL-N-{3-[1-({5-[4-(TRIFLUOROMETHOXY)PHENYL]-2-FURYL}METHYL)-4-PIPERIDINYL]PHENYL}PROPANAMIDE: Prepared by Procedure F and Scheme R using 5-[4-(trifluoromethoxy)phenyl]-2-furaldehyde and 2-methyl-N-[3-(4-piperidinyl)phenyl]propanamide: ESMS m/e: 487.1 (M+H)+.

EXAMPLE 253

N-{3-[1-(1-BENZOTHIEN-2-YLMETHYL)-4-PIPERIDINYL]PHENYL}-2-METHYLPROPANAMIDE: Prepared by Procedure F and Scheme R using 1-benzothiophene-2-carbaldehyde and 2-methyl-N-[3-(4-piperidinyl)phenyl]propanamide: ESMS m/e: 393.2 (M+H)+.

EXAMPLE 254

2-METHYL-N-{3-[1-({5-[3-(TRIFLUOROMETHOXY)PHENYL]-2-FURYL}METHYL)-4-PIPERIDINYL]PHENYL}PROPANAMIDE: Prepared by Procedure F and Scheme R using 5-[3-(trifluoromethoxy)phenyl]-2-furaldehyde and 2-methyl-N-[3-(4-piperidinyl)phenyl]propanamide: ESMS m/e: 487.2 (M+H)+.

EXAMPLE 255

2-METHYL-N-{3-[1-(2-QUINOLINYLMETHYL)-4-PIPERIDINYL]PHENYL}PROPANAMIDE: Prepared by Procedure F and Scheme R using 2-quinolinecarbaldehyde and 2-methyl-N-[3-(4-piperidinyl)phenyl]propanamide: ESMS m/e: 388.1 (M+H)+.

EXAMPLE 256

N-(3-{1-[4-(1H-IMIDAZOL-1-YL)BENZYL]-4-PIPERIDINYL}PHENYL)-2-METHYLPROPANAMIDE: Prepared by Procedure F and Scheme R using 4-(1H-imidazol-1-yl)benzaldehyde and 2-methyl-N-[3-(4-piperidinyl)phenyl]propanamide: ESMS m/e: 403.2 (M+H)+.

EXAMPLE 257

N-{3-[1-(9H-FLUOREN-2-YLMETHYL)-4-PIPERIDINYL]PHENYL}-2-METHYLPROPANAMIDE: Prepared by Procedure F and Scheme R using 9H-fluorene-2-carbaldehyde and 2-methyl-N-[3-(4-piperidinyl)phenyl]propanamide: ESMS m/e: 425.1 (M+H)+.

EXAMPLE 258

METHYL 3-[5-({4-[3-(ISOBUTYRYLAMINO)PHENYL]-1-PIPERIDINYL}METHYL)-2-FURYL]-2-THIOPHENECARBOXYLATE: Prepared by Procedure F and Scheme R using methyl 3-(5-formyl-2-furyl)-2-thiophenecarboxylate and 2-methyl-N-[3-(4-piperidinyl)phenyl]propanamide: ESMS m/e: 467.1 (M+H)+.

EXAMPLE 259

2-METHYL-N-{3-[1-(4-PHENOXYBENZYL)-4-PIPERIDINYL]PHENYL}PROPANAMIDE: Prepared by Procedure F and Scheme R using 4-phenoxybenzaldehyde and 2-methyl-N-[3-(4-piperidinyl)phenyl]propanamide: ESMS m/e: 429.2 (M+H)+.

EXAMPLE 260

N-{3-[1-([1,1'-BIPHENYL]-4-YLMETHYL)-4-PIPERIDINYL]PHENYL}-2-METHYLPROPANAMIDE: Prepared by Procedure F and Scheme R using [1,1'-biphenyl]-4-carbaldehyde and 2-methyl-N-[3-(4-piperidinyl)phenyl]propanamide: ESMS m/e: 413.2 (M+H)+.

EXAMPLE 261

N-(3-{1-[4-(DIBUTYLAMINO)BENZYL]-4-PIPERIDINYL}PHENYL)-2-METHYLPROPANAMIDE: Prepared by Procedure F and Scheme R using 4-(dibutylamino)benzaldehyde and 2-methyl-N-[3-(4-piperidinyl)phenyl]propanamide: ESMS m/e: 464.6 (M+H)+.

EXAMPLE 262

2-METHYL-N-[3-(1-{4-[(4-METHYLPHENYL)SULFANYL]-3-NITROBENZYL}-4-PIPERIDINYL)PHENYL]PROPANAMIDE: Prepared by Procedure F and Scheme R using 4-[(4-methylphenyl)sulfanyl]-3-nitrobenzaldehyde and 2-methyl-N-[3-(4-piperidinyl)phenyl]propanamide: ESMS m/:e 504.2 (M+H)+.

EXAMPLE 263

2-METHYL-N-(3-{1-[4-(1,2,3-THIADIAZOL-4-YL)BENZYL]-4-PIPERIDINYL}PHENYL)PROPANAMIDE: Prepared by Procedure F and Scheme R using 4-(1,2,3-thiadiazol-4-yl)benzaldehyde and 2-methyl-N-[3-(4-piperidinyl)phenyl]propanamide: ESMS m/e: 421.1 (M+H)+.

1-(3-{[(1S)-3-CHLORO-1-PHENYLPROPYL]OXY}PHENYL)ETHANONE: (1R)-3-Chloro-1-phenyl-1-propanol (1.000 g, 5.86 mmol), 1-(3-hydroxyphenyl)ethanone (0.797 9, 5.86 mmol), triphenylphosphine (1.54 g, 5.86 mmol) and diethylazodicarboxylate (1.53 g, 8.79 mmol) were combined in a flask, which was immediately flushed with argon. THF (20 mL) was added and the mixture was stirred overnight under argon. THF was removed in vacuo, the crude product was dissolved in 50 mL of $CH_2Cl_2$/$H_2O$ (1:1) and the organic layer was separated and dried over $MgSO_4$. After removing the solvent in vacuo, the residue was purified by flash chromatography using 10% ethyl acetate/hexane to yield the desired product (900 mg, 76.0%): $^1$H NMR (400 MHz, $CDCl_3$) δ 7.49–7.46 (m, 2H), 7.40–7.26 (m, 6H), 7.07–7.04 (m, 1H), 5.46–5.43 (dd, 1H, J=4.4 Hz, 8.8 Hz), 3.84–3.78 (m, 1H), 3.64–3.59 (m, 1H), 2.52 (s, 3H), 2.51–2.46 (m, 1H), 2.29–2.22 (m, 1H).

4-(3,4-DIFLUOROPHENOXY)BENZALDEHYDE: 4-Fluorobenzaldehyde (5.32 mL, 49.6 mmol), 3,4-difluorophenol (7.10 g, 54.6 mmol) and $K_2CO_3$ (8.31 g, 60.1 mmol) were combined in a flask, which was immediately flushed with argon. DMF (50.0 mL) was added and the mixture was heated at ref lux under argon for 6 h. Upon cooling to room temperature, EtOAc (100 mL) and $H_2O$ (100 mL) were added; the ethyl acetate layer was separated and washed with $H_2O$ (2×100 mL). The combined organic layers were washed with brine, dried over $MgSO_4$, and the solvent was removed in vacuo. The desired product was obtained (11.4 g, 98.0%): $^1$H NMR (400 MHz, $CDCl_3$) δ 9.95 (s, 1H), 7.88 (dd, 2H, J=0.8 Hz, 8.8 Hz), 7.24–7.17 (m, 1H), 7.07 (d, 2H, J=8.8 Hz), 6.97–6.92 (m, 1H), 6.86–6.82 (m, 1H); ESMS m/e: 235.0 (M+H)+.

TERT-BUTYL 4-(4,4,5,5-TETRAMETHYL-1,3,2-DIOXABOROLAN-2-YL)-3,6-DIHYDRO-1(2H)-PYRIDINECARBOXYLATE: To a flask were added bis(pinacolato)diboron (422 mg, 1.66 mmol), KOAc (444 mg, 4.53 mmol), PdCl$_2$dppf (37.0 mg, 3.00 mol %), dppf (25.0 mg, 3.00 mol %) and the flask was flushed with argon. A solution of tert-butyl 4-{[(trifluoromethyl)sulfonyl]oxy}-1,2,3,6-tetrahydro-1-pyridinecarboxylate (500 mg, 1.51 mmol) in 1,4-dioxane (10.0 ml) was added and the mixture was stirred at 80° C. overnight. The mixture was filtered through Celite and the filtrate was evaporated in vacuo. The resulting residue was dissolved in EtOAc and washed with H$_2$O, followed by brine. The organic layer was dried over MgSO$_4$, filtered and concentrated in vacuo. The crude material was purified by flash chromatography (10% EtOAC/hexane) to give tert-butyl 4-(4,4,5,5-tetramethyl-1,3,2-dioxaborolan-2-yl)-3,6-dihydro-1(2H)-pyridinecarboxylate (355 mg, 76.0%): $^1$H NMR (400 MHz, CDCl$_3$) δ 6.44 (br s, 1H), 3.93 (br s, 2H), 3.42 (br s, 2H), 2.21 (br s, 2H), 1.45 (s, 9H), 1.25 (s, 12H); ESMS m/e: 310.4 (M+H)$^+$.

N-(6-BROMO-2-PYRIDINYL)-2-METHYLPROPANAMIDE: Prepared by Procedure Q1 using 2-methylpropanoyl chloride and 6-bromo-2-pyridinamine: ESMS m/e: 242.8 (M+H)$^+$.

TERT-BUTYL 4-[6-(ISOBUTYRYLAMINO)-2-PYRIDINYL]-3,6-DIHYDRO-1(2H)-PYRIDINECARBOXYLATE: Prepared by Procedure W and Scheme AF using N-(6-bromo-2-pyridinyl)-2-methylpropanamide and tert-butyl 4-(4,4,5,5-tetramethyl-1,3,2-dioxaborolan-2-yl)-3,6-dihydro-1(2H)-pyridinecarboxylate: ESMS m/e: 245.8 (M - 100)$^+$.

2-METHYL-N-[6-(4-PIPERIDINYL)-2-PYRIDINYL]PROPANAMIDE: Prepared by Procedures X and Y, Schemes AG and AH, respectively using tert-butyl 4-[6-(isobutyrylamino)-2-pyridinyl]-3,6-dihydro-1(2H)-pyridinecarboxylate: ESMS m/e: 248.1 (M+H)$^+$.

EXAMPLE 264

N-(6-{1-[4-(3,4-DIMETHYLPHENYL)-4-OXOBUTYL]-4-PIPERIDINYL}-2-PYRIDINYL)-2-METHYLPROPANAMIDE: Prepared by Procedure G and Scheme AI using 4-chloro-1-(3,4-dimethylphenyl)-1-butanone and 2-methyl-N-[6-(4-piperidinyl)-2-pyridinyl]propanamide: ESMS m/e: 422.1 (M+H)$^+$.

EXAMPLE 265

N-(6-{1-[4,4-BIS(4-FLUOROPHENYL)BUTYL]-4-PIPERIDINYL}-2-PYRIDINYL)-2-METHYLPROPANAMIDE: Prepared by Procedure G and Scheme AI using 1-[4-chloro-1-(4-fluorophenyl)butyl]-4-fluorobenzene and 2-methyl-N-[6-(4-piperidinyl)-2-pyridinyl]propanamide: ESMS m/e: 492.2 (M+H)$^+$.

EXAMPLE 266

N-(6-{1-[4-(3,4-DIFLUOROPHENOXY)BENZYL]-4-PIPERIDINYL}-2-PYRIDINYL)-2-METHYLPROPANAMIDE: Prepared by Procedure AA and Scheme AJ using 4-(3,4-difluorophenoxy)benzaldehyde and 2-methyl-N-[6-(4-piperidinyl)-2-pyridinyl]propanamide: ESMS m/e: 466.0 (M+H)$^+$.

N-(3-BROMO-4-METHYLPHENYL)-2-METHYLPROPANAMIDE: Prepared by Procedure Q1 using 2-methylpropanoyl chloride and 3-bromo-4-methylaniline: ESMS m/e: 255.9 (M+H)$^+$.

TERT-BUTYL 4-[5-(ISOBUTYRYLAMINO)-2-METHYLPHENYL]-3,6-DIHYDRO-1(2H)-PYRIDINECARBOXYLATE: Prepared by Procedure W and Scheme AF using N-(3-bromo-4-methylphenyl)-2-methylpropanamide and tert-butyl 4-(4,4,5,5-tetramethyl-1,3,2-dioxaborolan-2-yl)-3,6-dihydro-1(2H)-pyridinecarboxylate: ESMS m/e: 259.1 (M–100)$^+$.

2-METHYL-N-[4-METHYL-3-(4-PIPERIDINYL)PHENYL]PROPANAMIDE: Prepared by Procedures X and Y, Schemes AG and AH, respectively using tert-butyl 4-[5-(isobutyrylamino)-2-methylphenyl]-3,6-dihydro-1(2H)-pyridinecarboxylate: ESMS m/e: 261.0 (M+H)$^+$.

EXAMPLE 267

N-(3-{1-[4-(3,4-DIFLUOROPHENOXY)BENZYL]-4-PIPERIDINYL}-4-METHYLPHENYL)-2-METHYLPROPANAMIDE: Prepared by Procedure AA and Scheme AJ using 4-(3,4-difluorophenoxy)benzaldehyde and using 2-methyl-N-[4-methyl-3-(4-piperidinyl)phenyl]propanamide: ESMS m/e: 479.1 (M+H)$^+$.

N-(5-BROMO-2-METHYLPHENYL)-2-METHYLPROPANAMIDE: Prepared by Procedure Q1 using 2-methylpropanoyl chloride and 5-bromo-2-methylaniline: ESMS m/e: 255.9 (M+H)$^+$.

TERT-BUTYL 4-[3-(ISOBUTYRYLAMINO)-4-METHYLPHENYL]-3,6-DIHYDRO-1(2H)-PYRIDINECARBOXYLATE: Prepared by Procedure W and Scheme AF using N-(5-bromo-2-methylphenyl)-2-methylpropanamide and tert-butyl 4-(4,4,5,5-tetramethyl-1,3,2-dioxaborolan-2-yl)-3,6-dihydro-1(2H)-pyridinecarboxylate: ESMS m/e: 259.1 (M - 100)$^+$.

2-METHYL-N-[2-METHYL-5-(4-PIPERIDINYL)PHENYL]PROPANAMIDE: Prepared by Procedures X and Y, Schemes AG and AH, respectively using tert-butyl 4-[3-(isobutyrylamino)-4-methylphenyl]-3,6-dihydro-1(2H)-pyridinecarboxylate: ESMS m/e: 261.0 (M+H)$^+$.

EXAMPLE 268

N-(5-{1-[(9-ETHYL-9H-CARBAZOL-3-YL)METHYL]-4-PIPERIDINYL}-2-METHYLPHENYL)-2-METHYLPROPANAMIDE: Prepared by Procedure AA and Scheme AJ using 9-ethyl-9H-carbazole-3-carbaldehyde and 2-methyl-N-[2-methyl-5-(4-piperidinyl)phenyl]propanamide: ESMS m/e: 468.1 (M+H)$^+$.

EXAMPLE 269

N-(5-{1-[4-(3,4-DIFLUOROPHENOXY)BENZYL]-4-PIPERIDINYL}-2-METHYLPHENYL)-2-METHYLPROPANAMIDE: Prepared by Procedure AA and Scheme AJ using 4-(3,4-difluorophenoxy)benzaldehyde and 2-methyl-N-[2-methyl-5-(4-piperidinyl)phenyl]propanamide: ESMS m/e: 479.2 (M+H)$^+$.

EXAMPLE 270

N-(3-{1-[(9-ETHYL-9H-CARBAZOL-3-YL)METHYL]-4-PIPERIDINYL}-4-METHYLPHENYL)-2-METHYLPROPANAMIDE: Prepared by Procedure AA and Scheme AJ using 9-ethyl-9H-carbazole-3-carbaldehyde and 2-methyl-N-[4-methyl-3-(4-piperidinyl)phenyl]propanamide: ESMS m/e: 468.1 (M+H)$^+$.

EXAMPLE 271

2-METHYL-N-[2-METHYL-5-(4-PIPERIDINYL)PHENYL]PROPANAMIDE: Prepared by Procedure G and Scheme AI using 1-[4-chloro-1-(4-fluorophenyl)butyl]-4-fluorobenzene and 2-methyl-N-[2-methyl-5-(4-piperidinyl)phenyl]propanamide: ESMS m/e: 505.1 (M+H)$^+$.

EXAMPLE 272

N-(3-{1-[(3S)-3-(3-ACETYLPHENOXY)-3-PHENYLPROPYL]-4-PIPERIDINYL}-4-METHYLPHENYL)-2-METHYLPROPANAMIDE: Prepared by Procedure G and Scheme AI using 1-(3-{[(1S)-3-chloro-1-phenylpropyl]oxy}phenyl)ethanone and 2-methyl-N-[4-methyl-3-(4-piperidinyl)phenyl]propanamide: ESMS m/e: 513.0 (M+H)$^+$.

EXAMPLE 273

N-(5-{1-[(3S)-3-(3-ACETYLPHENOXY)-3-PHENYLPROPYL]-4-PIPERIDINYL}-2-METHYLPHENYL)-2-METHYLPROPANAMIDE: Prepared by Procedure G and Scheme AI using 1-(3-{[(1S)-3-chloro-1-phenylpropyl]oxy}phenyl)ethanone and 2-methyl-N-[2-methyl-5-(4-piperidinyl)phenyl]propanamide: ESMS m/e: 512.9 (M+H)$^+$.

N-(2-IODOPHENYL)-2-METHYLPROPANAMIDE: Prepared by Procedure Q1 using 2-methylpropanoyl chloride and 2-iodoaniline: ESMS m/e: 289.9 (M+H)$^+$.

TERT-BUTYL 4-[2-(ISOBUTYRYLAMINO)PHENYL]-3,6-DIHYDRO-1(2H)-PYRIDINECARBOXYLATE: Prepared by Procedure W and Scheme AF using N-(2-iodophenyl)-2-methylpropanamide and tert-butyl 4-(4,4,5,5-tetramethyl-1,3,2-dioxaborolan-2-yl)-3,6-dihydro-1(2H)-pyridinecarboxylate: ESMS m/e: 245.1 (M−100)$^+$.

2-METHYL-N-[2-(4-PIPERIDINYL)PHENYL]PROPANAMIDE: Prepared by Procedures X and Y, Schemes AG and AH, respectively using tert-butyl 4-[2-(isobutyrylamino)phenyl]-3,6-dihydro-1(2H)-pyridinecarboxylate: ESMS m/e: 247.1 (M+H)$^+$.

EXAMPLE 274

N-(2-{1-[(9-ETHYL-9H-CARBAZOL-3-YL)METHYL]-4-PIPERIDINYL}PHENYL)-2-METHYLPROPANAMIDE: Prepared by Procedure AA and Scheme AJ using 9-ethyl-9H-carbazole-3-carbaldehyde and 2-methyl-N-[2-(4-piperidinyl)phenyl]propanamide: ESMS m/e: 454.1 (M+H)$^+$.

EXAMPLE 275

N-(3-{1-[4,4-BIS(4-FLUOROPHENYL)BUTYL]-4-PIPERIDINYL}-4-METHYLPHENYL)-2-METHYLPROPANAMIDE: Prepared by Procedure G and Scheme AI using 1-[4-chloro-1-(4-fluorophenyl)butyl]-4-fluorobenzene and 2-methyl-N-[4-methyl-3-(4-piperidinyl)phenyl]propanamide: ESMS m/e: 505.0 (M+H)$^+$.

EXAMPLE 276

N-(2-{1-[4,4-BIS(4-FLUOROPHENYL)BUTYL]-4-PIPERIDINYL}PHENYL)-2-METHYLPROPANAMIDE: Prepared by Procedure G and Scheme AI using 1-[4-chloro-1-(4-fluorophenyl)butyl]-4-fluorobenzene and 2-methyl-N-[2-(4-piperidinyl)phenyl]propanamide: ESMS m/e: 490.9 (M+H)$^+$.

N-[2-BROMO-4-(TRIFLUOROMETHOXY)PHENYL]-2-METHYLPROPANAMIDE: Prepared by Procedure Q1 using 2-methylpropanoyl chloride and 2-bromo-4-(trifluoromethoxy)aniline: ESMS m/e: 325.9 (M+H)$^+$.

TERT-BUTYL 4-[2-(ISOBUTYRYLAMINO)-5-(TRIFLUOROMETHOXY)PHENYL]-3,6-DIHYDRO-1(2H)-PYRIDINECARBOXYLATE: Prepared by Procedure W and Scheme AF using N-[2-bromo-4-(trifluoromethoxy)phenyl]-2-methylpropanamide and tert-butyl 4-(4,4,5,5-tetramethyl-1,3,2-dioxaborolan-2-yl)-3,6-dihydro-1(2H)-pyridinecarboxylate: ESMS m/e: 329.0 (M−100)$^+$.

2-METHYL-N-[2-(4-PIPERIDINYL)-4-(TRIFLUOROMETHOXY)PHENYL]PROPANAMIDE: Prepared by Procedures X and Y, Schemes AG and AH, respectively using tert-butyl 4-[2-(isobutyrylamino)-5-(trifluoromethoxy)phenyl]-3,6-dihydro-1(2H)-pyridinecarboxylate: ESMS m/e: 330.9 (M+H)$^+$.

EXAMPLE 277

N-[2-{1-[4,4-BIS(4-FLUOROPHENYL)BUTYL]-4-PIPERIDINYL}-4-(TRIFLUOROMETHOXY)PHENYL]-2-METHYLPROPANAMIDE: Prepared by Procedure G and Scheme AI using 1-[4-chloro-1-(4-fluorophenyl)butyl]-4-fluorobenzene and 2-methyl-N-[2-(4-piperidinyl)-4-(trifluoromethoxy)phenyl]propanamide: ESMS m/e: 574.8 (M+H)$^+$.

N-{3-[1-(4-HYDROXYBUTYL)-4-PIPERIDINYL]PHENYL}-2-METHYLPROPANAMIDE: Prepared by Procedure G and Scheme B1 using 4-chloro-1-butanol and 2-methyl-N-[3-(4-piperidinyl)phenyl]propanamide: ESMS m/e: 319.3 (M+H)$^+$.

N-{3-[1-(5-HYDROXYPENTYL)-4-PIPERIDINYL]PHENYL}-2-METHYLPROPANAMIDE: Prepared by Procedure G and Scheme B1 using 5-chloro-1-pentanol and 2-methyl-N-[3-(4-piperidinyl)phenyl]propanamide: ESMS m/e: 333.3 (M+H)$^+$.

N-{3-[1-(6-HYDROXYHEXYL)-4-PIPERIDINYL]PHENYL}-2-METHYLPROPANAMIDE: Prepared by Procedure G and Scheme B1 using 6-chloro-1-hexanol and 2-methyl-N-[3-(4-piperidinyl)phenyl]propanamide: ESMS m/e: 347.3 (M+H)$^+$.

N-{3-[1-(3-HYDROXYPROPYL)-4-PIPERIDINYL]PHENYL}-2-METHYLPROPANAMIDE: Prepared by Procedure G and Scheme B1 using 3-chloro-1-propanol and 2-methyl-N-[3-(4-piperidinyl)phenyl]propanamide: ESMS m/e: 305.3 (M+H)$^+$.

N-(3-{1-[(2S)-2-HYDROXY-2-PHENYLETHYL]-4-PIPERIDINYL}PHENYL)-2-METHYLPROPANAMIDE: Prepared by Procedure G and Scheme B1 using (1S)-2-chloro-1-phenylethanol and 2-methyl-N-[3-(4-piperidinyl)phenyl]propanamide: ESMS m/e: 367.2 (M+H)$^+$.

N-(3-{1-[(2R)-2-HYDROXY-2-PHENYLETHYL]-4-PIPERIDINYL}PHENYL)-2-METHYLPROPANAMIDE: Prepared by Procedure G and Scheme B1 using (1R)-2-chloro-1-phenylethanol and 2-methyl-N-[3-(4-piperidinyl)phenyl]propanamide: ESMS m/e: 367.2 (M+H)$^+$.

N-(3-{1-[(2S)-3-HYDROXY-2-METHYLPROPYL]-4-PIPERIDINYL}PHENYL)-2-METHYLPROPANAMIDE: Prepared by Procedure G and Scheme B1 using (2R)-3-chloro-2-methyl-1-propanol and 2-methyl-N-[3-(4-piperidinyl)phenyl]propanamide: ESMS m/e: 319.2 (M+H)$^+$.

N-(3-{1-[(2R)-3-HYDROXY-2-METHYLPROPYL]-4-PIPERIDINYL}PHENYL)-2-METHYLPROPANAMIDE: Prepared by Procedure G and Scheme B1 using (2S)-3-chloro-2-methyl-1-propanol and 2-methyl-N-[3-(4-piperidinyl)phenyl]propanamide: ESMS m/e: 319.2 (M+H)$^+$.

EXAMPLE 278

N-(3-{1-[(3R)-3-HYDROXY-3-PHENYLPROPYL]-4-PIPERIDINYL}PHENYL)

CYCLOPROPANECARBOXAMIDE: Prepared by Procedure G and Scheme B1 using (1R)-3-chloro-1-phenyl-1-propanol and N-[3-(4-piperidinyl)phenyl]cyclopropanecarboxamide: ESMS m/e: 379.2 (M+H)+.

EXAMPLE 279

N-{3-[1-(4-HYDROXY-4-PHENYLBUTYL)-4-PIPERIDINYL]PHENYL}-2-METHYLPROPANAMIDE: Prepared by Procedure L and Scheme AN, Step 1 using 2-methyl-N-{3-[1-(4-oxo-4-phenylbutyl)-4-piperidinyl]phenyl}propanamide: Anal. Calcd for C25H34N2O2+ 0.08CHCl$_3$: C, 74.5; H, 8.50; N, 6.93. Found: C, 74.5; H, 8.63; N, 6.81; ESMS m/e: 395.2 (M+H)+.

EXAMPLE 280

N-{3-[1-(5-HYDROXY-5-PHENYLPENTYL)-4-PIPERIDINYL]PHENYL}-2-METHYLPROPANAMIDE: Prepared by Procedure L and Scheme AN, Step 1 using 2-methyl-N-{3-[1-(5-oxo-5-phenylpentyl)-4-piperidinyl]phenyl}propanamide: Anal. Calcd for C26H36N2O2+ 0.25CHCl$_3$: C, 71.9; H, 8.33; N, 6.39. Found: C, 71.3; H, 8.96; N, 6.86; ESMS m/e: 409.2 (M+H)+.

EXAMPLE 281

N-{3-[1-(6-HYDROXY-6-PHENYLHEXYL)-4-PIPERIDINYL]PHENYL}-2-METHYLPROPANAMIDE: Prepared by Procedure L and Scheme AN, Step 1 using 2-methyl-N-{3-[1-(6-oxo-6-phenylhexyl)-4-piperidinyl]phenyl}propanamide: Anal. Calcd for C27H38N2O2+ 0.1CHCl$_3$: C, 75.5; H, 8.93; N, 6.50. Found: C, 75.3; H, 8.52; N, 6.00; ESMS m/e: 423.2 (M+H)+.

EXAMPLE 282

N-{3-[1-(7-HYDROXY-7-PHENYLHEPTYL)-4-PIPERIDINYL]PHENYL}-2-METHYLPROPANAMIDE: Prepared by Procedure L and Scheme AN, Step 1 using 2-methyl-N-(3-[1-(7-oxo-7-phenylheptyl)-4-piperidinyl]phenylpropanamide: Anal. Calcd for C28H40N2O2+ 0.1CHCl$_3$: C, 75.8; H, 9.10; N, 6.29. Found: C, 75.1; H, 9.24; N, 6.51; ESMS m/e: 437.1 (M+H)+.

EXAMPLE 283

N-(3-{1-[4-(4-FLUOROPHENYL)-4-HYDROXYBUTYL]-4-PIPERIDINYL}PHENYL)-2-METHYLPROPANAMIDE: Prepared by Procedure L and Scheme AN, Step 1 using N-(3-{1-[4-(4-fluorophenyl)-4-oxobutyl]-4-piperidinyl}phenyl)-2-methylpropanamide: ESMS m/e: 413.1 (M+H)+.

EXAMPLE 284

4-{4-[3-(ISOBUTYRYLAMINO)PHENYL]-1-PIPERIDINYL}-1-PHENYLBUTYL 3-(2,6-DICHLOROPHENYL)-5-METHYL-4-ISOXAZOLECARBOXYLATE: Prepared by Procedure Q1 and Scheme C2 (TEA) using N-{3-[1-(4-hydroxy-4-phenylbutyl)-4-piperidinyl]phenyl}-2-methylpropanamide and 3-(2,6-dichlorophenyl)-5-methyl-4-isoxazolecarbonyl chloride: $^1$H NMR (400 MHz, CDCl$_3$) δ 7.56 (m, 1H), 7.47 (m, 2H), 7.44–7.39 (m, 3H), 7.25 (m, 2H), 7.09 (s, 1H), 7.03 (m, 2H), 6.95 (m, 1H), 6.83 (m, 1H), 5.75 (t, 1H, J=7.1 Hz), 3.03 (t, 2H, J=7.2 Hz), 2.93 (m, 2H), 2.78 (s, 3H), 2.48 (m, 3H), 2.25 (m, 2H), 1.48 (m, 3H), 1.77 (m, 2H), 1.54 (m, 2H), 1.25 (d, 6H, J=7.3 Hz); ESMS m/e: 647.7 (M+H)+.

EXAMPLE 285

4-{4-[3-(ISOBUTYRYLAMINO)PHENYL]-1-PIPERIDINYL}-1-PHENYLBUTYL(4-FLUOROPHENYL)ACETATE: Prepared by Procedure Q1 and Scheme C2 (TEA) using N-{3-[1-(4-hydroxy-4-phenylbutyl)-4-piperidinyl]phenyl}-2-methylpropanamide and (4-fluorophenyl)acetyl chloride: $^1$H NMR (400 MHz, CDCl$_3$) δ 7.45 (s, 1H), 7.34–7.19 (m, 8H), 7.11 (m, 1H), 6.98 (m, 3H), 5.75 (t, 1H, J=6.8 Hz), 3.61 (s, 2H), 2.92 (d, 2H, J=8.1 Hz), 2.48 (m, 2H), 2.31 (m, 2H), 1.99–1.84 (m, 4H), 1.84–1.67 (m, 5H), 1.55–1.35 (m, 2H), 1.25 (d, 6H, J=6.9 Hz); ESMS m/e: 531.1 (M+H)+.

EXAMPLE 286

3-{4-[3-(ISOBUTYRYLAMINO)PHENYL]-1-PIPERIDINYL}PROPYL(4-FLUOROPHENYL)ACETATE: Prepared by Procedure Q1 and Scheme C2 (TEA) using N-{3-[1-(3-hydroxypropyl)-4-piperidinyl]phenyl}-2-methylpropanamide and (4-fluorophenyl)acetyl chloride: ESMS m/e: 441.3 (M+H)+.

EXAMPLE 287

3-{4-[3-(ISOBUTYRYLAMINO)PHENYL]-1-PIPERIDINYL}PROPYL 3-(2-CHLORO-6-FLUOROPHENYL)-5-METHYL-4-ISOXAZOLECARBOXYLATE: Prepared by Procedure Q1 and Scheme C2 (TEA) using N-{3-[1-(3-hydroxypropyl)-4-piperidinyl]phenyl}-2-methylpropanamide and 3-(2-chloro-6-fluorophenyl)-5-methyl-4-isoxazolecarbonyl chloride: ESMS m/e: 542.2 (M+H)+.

EXAMPLE 288

3-{4-[3-(ISOBUTYRYLAMINO)PHENYL]-1-PIPERIDINYL}PROPYL 3-(2,6-DICHLOROPHENYL)-5-METHYL-4-ISOXAZOLECARBOXYLATE: Prepared by Procedure Q1 and Scheme C2 (TEA) using N-{3-[1-(3-hydroxypropyl)-4-piperidinyl]phenyl}-2-methylpropanamide and 3-(2,6-dichlorophenyl)-5-methyl-4-isoxazolecarbonyl chloride: ESMS m/e: 558.2 (M+H)+.

EXAMPLE 289

3-{4-[3-(ISOBUTYRYLAMINO)PHENYL]-1-PIPERIDINYL}PROPYL 3-(2-CHLOROPHENYL)-5-METHYL-4-ISOXAZOLECARBOXYLATE: Prepared by Procedure Q1 and Scheme C2 (TEA) using N-{3-[1-(3-hydroxypropyl)-4-piperidinyl]phenyl}-2-methylpropanamide and 3-(2-chlorophenyl)-5-methyl-4-isoxazolecarbonyl chloride: ESMS m/e: 524.2 (M+H)+.

EXAMPLE 290

(1S)-3-{4-[3-(ISOBUTYRYLAMINO)PHENYL]-1-PIPERIDINYL}-1-PHENYLPROPYL 3-(2,6-DICHLOROPHENYL)-5-METHYL-4-ISOXAZOLECARBOXYLATE: Prepared by Procedure Q1 and Scheme C2 (TEA) using N-(3-{1-[(3S)-3-hydroxy-3-phenylpropyl]-4-piperidinyl}phenyl)-2-methylpropanamide and 3-(2,6-dichlorophenyl)-5-methyl-4-isoxazolecarbonyl chloride: ESMS m/e: 633.6 (M+H)+.

EXAMPLE 291

4-{4-[3-(ISOBUTYRYLAMINO)PHENYL]-1-PIPERIDINYL}BUTYL 3-(2-CHLORO-6-FLUOROPHENYL)-5-METHYL-4-ISOXAZOLECARBOXYLATE: Prepared by Procedure Q1 and Scheme C2 (TEA) using N-{3-[1-(4-hydroxybutyl)-4-piperidinyl]phenyl}-2-methylpropanamide and 3-(2-chloro-6-fluorophenyl)-5-methyl-4-isoxazolecarbonyl chloride:

Anal. Calcd for C30H35ClFN3O4+CH2Cl2: C, 63.3; H, 6.23; N, 7.33. Found: C, 63.0; H, 6.39; N, 7.03; ESMS m/e: 556.2 (M+H)+.

EXAMPLE 292

4-{4-[3-(ISOBUTYRYLAMINO)PHENYL]-1-PIPERIDINYL}BUTYL 3-(2-CHLOROPHENYL)-5-METHYL-4-ISOXAZOLECARBOXYLATE: Prepared by Procedure Q1 and Scheme C2 (TEA) using N-{3-[1-(4-hydroxybutyl)-4-piperidinyl]phenyl}-2-methylpropanamide and 3-(2-chlorophenyl)-5-methyl-4-isoxazolecarbonyl chloride: ESMS m/e: 538.2 (M+H)+.

EXAMPLE 293

3-{4-[3-(ISOBUTYRYLAMINO)PHENYL]-1-PIPERIDINYL}PROPYL 5-METHYL-3-PHENYL-4-ISOXAZOLECARBOXYLATE: Prepared by Procedure Q1 and Scheme C2 (TEA) using N-{3-[1-(3-hydroxypropyl)-4-piperidinyl]phenyl}-2-methylpropanamide and 5-methyl-3-phenyl-4-isoxazolecarbonyl chloride: ESMS m/e: 490.3 (M+H)+.

EXAMPLE 294

4-{4-[3-(ISOBUTYRYLAMINO)PHENYL]-1-PIPERIDINYL}BUTYL 3-(2,6-DICHLOROPHENYL)-5-METHYL-4-ISOXAZOLECARBOXYLATE: Prepared by Procedure Q1 and Scheme C2 (TEA) using N-{3-[1-(4-hydroxybutyl)-4-piperidinyl]phenyl}-2-methylpropanamide and 3-(2,6-dichlorophenyl)-5-methyl-4-isoxazolecarbonyl chloride: ESMS m/e: 572.2 (M+H)+.

EXAMPLE 295

4-{4-[3-(ISOBUTYRYLAMINO)PHENYL]-1-PIPERIDINYL}-1-PHENYLBUTYL 3-(2-CHLORO-6-FLUOROPHENYL)-5-METHYL-4-ISOXAZOLECARBOXYLATE: Prepared by Procedure Q1 and Scheme C2 (TEA) using N-{3-[1-(4-hydroxy-4-phenylbutyl)-4-piperidinyl]phenyl}-2-methylpropanamide and 3-(2-chloro-6-fluorophenyl)-5-methyl-4-isoxazolecarbonyl chloride: Anal. Calcd for C36H39ClFN3O4+0.54CHCl3: C, 63.0; H, 5.72; N, 6.03. Found: C, 63.0; H, 5.54; N, 6.05; ESMS m/e: 632.2 (M+H)+.

EXAMPLE 296

4-{4-[3-(ISOBUTYRYLAMINO)PHENYL]-1-PIPERIDINYL}BUTYL 5-METHYL-3-PHENYL-4-ISOXAZOLECARBOXYLATE: Prepared by Procedure Q1 and Scheme C2 (TEA) using N-{3-[1-(4-hydroxybutyl)-4-piperidinyl]phenyl}-2-methylpropanamide and 5-methyl-3-phenyl-4-isoxazolecarbonyl chloride: ESMS m/e: 504.3 (M+H)+.

EXAMPLE 297

6-{4-[3-(ISOBUTYRYLAMINO)PHENYL]-1-PIPERIDINYL}HEXYL 3-(2,6-DICHLOROPHENYL)-5-METHYL-4-ISOXAZOLECARBOXYLATE: Prepared by Procedure Q1 and Scheme C2 (TEA) using N-{3-[1-(6-hydroxyhexyl)-4-piperidinyl]phenyl}-2-methylpropanamide and 3-(2,6-dichlorophenyl)-5-methyl-4-isoxazolecarbonyl chloride: ESMS m/e: 600.0 (M+H)+.

EXAMPLE 298

6-{4-[3-(ISOBUTYRYLAMINO)PHENYL]-1-PIPERIDINYL}HEXYL 5-METHYL-3-PHENYL-4-ISOXAZOLECARBOXYLATE: Prepared by Procedure Q1 and Scheme C2 (TEA) using N-{3-[1-(6-hydroxyhexyl)-4-piperidinyl]phenyl}-2-methylpropanamide and 5-methyl-3-phenyl-4-isoxazolecarbonyl chloride: ESMS m/e: 532.1 (M+H)+.

EXAMPLE 299

4-{4-[3-(ISOBUTYRYLAMINO)PHENYL]-1-PIPERIDINYL}BUTYL(4-FLUOROPHENYL)ACETATE: Prepared by Procedure Q1 and Scheme C2 (TEA) using N-{3-[1-(4-hydroxybutyl)-4-piperidinyl]phenyl}-2-methylpropanamide and (4-fluorophenyl)acetyl chloride: ESMS m/e: 455.3 (M+H)+.

EXAMPLE 300

4-{4-[3-(ISOBUTYRYLAMINO)PHENYL]-1-PIPERIDINYL}-1-PHENYLBUTYL 3-(2-CHLOROPHENYL)-5-METHYL-4-ISOXAZOLECARBOXYLATE: Prepared by Procedure Q1 and Scheme C2 (TEA) using N-{3-[1-(4-hydroxy-4-phenylbutyl)-4-piperidinyl]phenyl}-2-methylpropanamide and 3-(2-chlorophenyl)-5-methyl-4-isoxazolecarbonyl chloride: ESMS m/e: 614.2 (M+H)+.

EXAMPLE 301

4-{4-[3-(ISOBUTYRYLAMINO)PHENYL]-1-PIPERIDINYL}-1-PHENYLBUTYL 5-METHYL-3-PHENYL-4-ISOXAZOLECARBOXYLATE: Prepared by Procedure Q1 and Scheme C2 (TEA) using N-{3-[1-(4-hydroxy-4-phenylbutyl)-4-piperidinyl]phenyl}-2-methylpropanamide and 5-methyl-3-phenyl-4-isoxazolecarbonyl chloride: ESMS m/e: 580.0 (M+H)+.

EXAMPLE 302

(1S)-3-{4-[3-(ISOBUTYRYLAMINO)PHENYL]-1-PIPERIDINYL}-1-PHENYLPROPYL(4-FLUOROPHENYL)ACETATE: Prepared by Procedure Q1 and Scheme C2 (TEA) using N-(3-{1-[(3S)-3-hydroxy-3-phenylpropyl]-4-piperidinyl}phenyl)-2-methylpropanamide and (4-fluorophenyl)acetyl chloride: Anal. Calcd for C32H37FN2O3+0.07CHCl3: C, 73.4; H, 7.12; N, 5.34. Found: C, 73.4; H, 6.96; N, 5.14; ESMS m/e: 517.1 (M+H)+.

EXAMPLE 303

N-((1S)-3-{4-[3-(ISOBUTYRYLAMINO)PHENYL]-1-PIPERIDINYL}-1-PHENYLPROPYL)BENZAMIDE: Prepared by Procedure Q1 and Scheme AC using N-(3-{1-[(3S)-3-amino-3-phenylpropyl]-4-piperidinyl}phenyl)-2-methylpropanamide and benzoyl chloride: Anal. Calcd for C31H37N3O2+0.55CHCl3: C, 69.0; H, 6.89; N, 7.65. Found: C, 69.7; H, 6.73; N, 6.03; ESMS m/e: 484.4 (M+H)+.

EXAMPLE 304

N-[3-(1-{(3S)-3-[(DIPHENYLACETYL)AMINO]-3-PHENYLPROPYL}-4-PIPERIDINYL)PHENYL]-2-METHYLPROPANAMIDE: Prepared by Procedure Q1 and Scheme AC using N-(3-{1-[(3S)-3-amino-3-phenylpropyl]-4-piperidinyl}phenyl)-2-methylpropanamide and diphenylacetyl chloride: ESMS m/e: 574.3 (M+H)+.

EXAMPLE 305

3-CHLORO-N-((1S)-3-{4-[3-(ISOBUTYRYLAMINO)PHENYL]-1-PIPERIDINYL}-1-PHENYLPROPYL)BENZAMIDE: Prepared by Procedure Q1 and Scheme AC using N-(3-{1-[(3S)-3-amino-3-phenylpropyl]-4-piperidinyl}phenyl)-2-methylpropanamide and 3-chlorobenzoyl chloride: ESMS m/e: 518.3 (M+H)+.

EXAMPLE 306

3,5-DICHLORO-N-((1S)-3-{4-[3-(ISOBUTYRYLAMINO)PHENYL]-1-PIPERIDINYL}-1-PHENYLPROPYL)BENZAMIDE: Prepared by Procedure Q1 and Scheme AC using N-(3-{1-[(3S)-3-amino-3-phenylpropyl]-4-piperidinyl}phenyl)-2-methylpropanamide and 3,5-dichlorobenzoyl chloride: ESMS m/e: 552.3 (M+H)+.

EXAMPLE 307

2-(ETHYLSULFANYL)-N-((1S)-3-{4-[3-(ISOBUTYRYLAMINO)PHENYL]-1-PIPERIDINYL}-1-PHENYLPROPYL)NICOTINAMIDE: Prepared by Procedure Q1 and Scheme AC using N-(3-{1-[(3S)-3-amino-3-phenylpropyl]-4-piperidinyl}phenyl)-2-methylpropanamide and 2-(ethylsulfanyl)nicotinoyl chloride: ESMS m/e: 545.3 (M+H)+.

EXAMPLE 308

N-((1S)-3-{4-[3-(ISOBUTYRYLAMINO)PHENYL]-1-PIPERIDINYL}-1-PHENYLPROPYL)[1,1'-BIPHENYL]-4-CARBOXAMIDE: Prepared by Procedure Q1 and Scheme AC using N-(3-{1-[(3S)-3-amino-3-phenylpropyl]-4-piperidinyl}phenyl)-2-methylpropanamide and [1,1'-biphenyl]-4-carbonyl chloride: ESMS m/e: 560.3 (M+H)+.

EXAMPLE 309

N-((1S)-3-{4-[3-(ISOBUTYRYLAMINO)PHENYL]-1-PIPERIDINYL}-1-PHENYLPROPYL)-2-PYRIDINECARBOXAMIDE: Prepared by Procedure Q1 and Scheme AC using N-(3-{1-[(3S)-3-amino-3-phenylpropyl]-4-piperidinyl}phenyl)-2-methylpropanamide and 2-pyridinecarbonyl chloride: ESMS m/e: 484.6 (M+H)+.

EXAMPLE 310

N-((1S)-3-{4-[3-(ISOBUTYRYLAMINO)PHENYL]-1-PIPERIDINYL}-1-PHENYLPROPYL)-2-METHOXYBENZAMIDE: Prepared by Procedure Q1 and Scheme AC using N-(3-{1-[(3S)-3-amino-3-phenylpropyl]-4-piperidinyl}phenyl)-2-methylpropanamide and 2-methoxybenzoyl chloride: ESMS m/e: 514.1 (M+H)+.

EXAMPLE 311

N-((1S)-3-{4-[3-(ISOBUTYRYLAMINO)PHENYL]-1-PIPERIDINYL}-1-PHENYLPROPYL)-1-NAPHTHAMIDE: Prepared by Procedure Q1 and Scheme AC using N-(3-{1-[(3S)-3-amino-3-phenylpropyl]-4-piperidinyl}phenyl)-2-methylpropanamide and 1-naphthoyl chloride: ESMS m/e: 533.7 (M+H)+.

EXAMPLE 312

2,4-DIFLUORO-N-((1S)-3-{4-[3-(ISOBUTYRYLAMINO)PHENYL]-1-PIPERIDINYL}-1-PHENYLPROPYL)BENZAMIDE: Prepared by Procedure Q1 and Scheme AC using N-(3-{1-[(3S)-3-amino-3-phenylpropyl]-4-piperidinyl}phenyl)-2-methylpropanamide and 2,4-difluorobenzoyl chloride: ESMS m/e: 520.2 (M+H)+.

EXAMPLE 313

3-(2-CHLORO-6-FLUOROPHENYL)-N-((1S)-3-{4-[3-(ISOBUTYRYLAMINO)PHENYL]-1-PIPERIDINYL}-1-PHENYLPROPYL)-5-METHYL-4-ISOXAZOLECARBOXAMIDE: Prepared by Procedure Q1 and Scheme AC using N-(3-{1-[(3S)-3-amino-3-phenylpropyl]-4-piperidinyl}phenyl)-2-methylpropanamide and 3-(2-chloro-6-fluorophenyl)-5-methyl-4-isoxazolecarbonyl chloride: ESMS m/e: 617.2 (M+H)+.

EXAMPLE 314

3-CHLORO-N-((1S)-3-{4-[3-(ISOBUTYRYLAMINO)PHENYL]-1-PIPERIDINYL}-1-PHENYLPROPYL)-2-THIOPHENECARBOXAMIDE: Prepared by Procedure Q1 and Scheme AC using N-(3-{1-[(3S)-3-amino-3-phenylpropyl]-4-piperidinyl}phenyl)-2-methylpropanamide and 3-chloro-2-thiophenecarbonyl chloride: ESMS m/e: 524.2 (M+H)+.

EXAMPLE 315

N-((1S)-3-{4-[3-(ISOBUTYRYLAMINO)PHENYL]-1-PIPERIDINYL}-1-PHENYLPROPYL)-2-PHENOXYNICOTINAMIDE: Prepared by Procedure Q1 and Scheme AC using N-(3-{1-[(3S)-3-amino-3-phenylpropyl]-4-piperidinyl}phenyl)-2-methylpropanamide and 2-phenoxynicotinoyl chloride: ESMS m/e: 577.3 (M+H)+.

EXAMPLE 316

1-(4-CHLOROPHENYL)-N-((1S)-3-{4-[3-(ISOBUTYRYLAMINO)PHENYL]-1-PIPERIDINYL}-1-PHENYLPROPYL)-3-PROPYL-1H-PYRAZOLE-4-CARBOXAMIDE: Prepared by Procedure Q1 and Scheme AC using N-(3-{1-[(3S)-3-amino-3-phenylpropyl]-4-piperidinyl}phenyl)-2-methylpropanamide and 1-(4-chlorophenyl)-3-propyl-1H-pyrazole-4-carbonyl chloride: ESMS m/e: 626.3 (M+H)+.

EXAMPLE 317

4-CHLORO-N-((1S)-3-{4-[3-(ISOBUTYRYLAMINO)PHENYL]-1-PIPERIDINYL}-1-PHENYLPROPYL)-1,3-DIMETHYL-1H-PYRAZOLO[3,4-B]PYRIDINE-5-CARBOXAMIDE: Prepared by Procedure Q1 and Scheme AC using N-(3-{1-[(3S)-3-amino-3-phenylpropyl]-4-piperidinyl}phenyl)-2-methylpropanamide and 4-chloro-1,3-dimethyl-1H-pyrazolo[3,4-b]pyridine-5-carbonyl chloride: ESMS m/e: 587.3 (M+H)+.

EXAMPLE 318

5-(3,5-DICHLOROPHENOXY)-N-((1S)-3-{4-[3-(ISOBUTYRYLAMINO)PHENYL]-1-PIPERIDINYL}-1-PHENYLPROPYL)-1H-PYRROLE-2-CARBOXAMIDE: Prepared by Procedure Q1 and Scheme AC using N-(3-{1-[(3S)-3-amino-3-phenylpropyl]-4-piperidinyl}phenyl)-2-methylpropanamide and 5-(3,5-dichlorophenoxy)-1H-pyrrole-2-carbonyl chloride: ESMS m/e: 634.2 (M+H)+.

EXAMPLE 319

N-((1S)-3-{4-[3-(ISOBUTYRYLAMINO)PHENYL]-1-PIPERIDINYL}-1-PHENYLPROPYL)NICOTINAMIDE: Prepared by Procedure Q1 and Scheme AC using N-(3-{1-[(3S)-3-amino-3-phenylpropyl]-4-piperidinyl}phenyl)-2-methylpropanamide and nicotinoyl chloride: ESMS m/e: 485.3 (M+H)+.

EXAMPLE 320

3,4-DIFLUORO-N-((1S)-3-{4-[3-(ISOBUTYRYLAMINO)PHENYL]-1-PIPERIDINYL}-1-

PHENYLPROPYL)BENZAMIDE: Prepared by Procedure Q1 and Scheme AC using N-(3-{1-[(3S)-3-amino-3-phenylpropyl]-4-piperidinyl}phenyl)-2-methylpropanamide and 3,4-difluorobenzoyl chloride: ESMS m/e: 520.3 (M+H)$^+$.

EXAMPLE 321

N-((1S)-3-{4-[3-(ISOBUTYRYLAMINO)PHENYL]-1-PIPERIDINYL}-1-PHENYLPROPYL)-1-PHENYL-3-PROPYL-1H-PYRAZOLE-4-CARBOXAMIDE: Prepared by Procedure Q1 and Scheme AC using N-(3-{1-[(3S)-3-amino-3-phenylpropyl]-4-piperidinyl}phenyl)-2-methylpropanamide and 1-phenyl-3-propyl-1H-pyrazole-4-carbonyl chloride: ESMS m/e: 592.2 (M+H)$^+$.

EXAMPLE 322

4-(DIMETHYLAMINO)-N-((1S)-3-{4-[3-(ISOBUTYRYLAMINO)PHENYL]-1-PIPERIDINYL}-1-PHENYLPROPYL)BENZAMIDE: Prepared by Procedure Q1 and Scheme AC using N-(3-{1-[(3S)-3-amino-3-phenylpropyl]-4-piperidinyl}phenyl)-2-methylpropanamide and 4-(dimethylamino)benzoyl chloride: ESMS m/e: 527.3 (M+H)$^+$.

EXAMPLE 323

N-((1S)-3-{4-[3-(ISOBUTYRYLAMINO)PHENYL]-1-PIPERIDINYL}-1-PHENYLPROPYL)-2-THIOPHENECARBOXAMIDE: Prepared by Procedure Q1 and Scheme AC using N-(3-{1-[(3S)-3-amino-3-phenylpropyl]-4-piperidinyl}phenyl)-2-methylpropanamide and 2-thiophenecarbonyl chloride: ESMS m/e: 490.2 (M+H)$^+$.

EXAMPLE 324

N-((1S)-3-{4-[3-(ISOBUTYRYLAMINO)PHENYL]-1-PIPERIDINYL}-1-PHENYLPROPYL)-5-NITRO-2-FURAMIDE: Prepared by Procedure Q1 and Scheme AC using N-(3-{1-[(3S)-3-amino-3-phenylpropyl]-4-piperidinyl}phenyl)-2-methylpropanamide and 5-nitro-2-furoyl chloride: ESMS m/e: 519.2 (M+H)$^+$.

EXAMPLE 325

N-(3-{4-[3-(ISOBUTYRYLAMINO)PHENYL]-1-PIPERIDINYL}PROPYL)-5-METHYL-3-PHENYL-4-ISOXAZOLECARBOXAMIDE: Prepared by Procedure Q1 and Scheme AC using N-{3-[1-(3-aminopropyl)-4-piperidinyl]phenyl}-2-methylpropanamide and 5-methyl-3-phenyl-4-isoxazolecarbonyl chloride: ESMS m/e: 489.1 (M+H)$^+$.

EXAMPLE 326

N-((1S)-3-{4-[3-(ISOBUTYRYLAMINO)PHENYL]-1-PIPERIDINYL}-1-PHENYLPROPYL)-2-FURAMIDE: Prepared by Procedure Q1 and Scheme AC using N-{3-[1-(3-aminopropyl)-4-piperidinyl]phenyl}-2-methylpropanamide and 2-furoyl chloride: ESMS m/e: 474.2 (M+H)$^+$.

EXAMPLE 327

N-((1S)-3-{4-[3-(ISOBUTYRYLAMINO)PHENYL]-1-PIPERIDINYL}-1-PHENYLPROPYL)-1-(4-NITROPHENYL)-5-(TRIFLUOROMETHYL)-1H-PYRAZOLE-4-CARBOXAMIDE: Prepared by Procedure Q1 and Scheme AC using N-(3-{1-[(3S)-3-amino-3-phenylpropyl]-4-piperidinyl}phenyl)-2-methylpropanamide and 1-(4-nitrophenyl)-5-(trifluoromethyl)-1H-pyrazole-4-carbonyl chloride: ESMS m/e: 663.2 (M+H)$^+$.

EXAMPLE 328

3-(2-CHLORO-6-FLUOROPHENYL)-N-(3-{4-[3-(ISOBUTYRYLAMINO)PHENYL]-1-PIPERIDINYL}PROPYL)-5-METHYL-4-ISOXAZOLECARBOXAMIDE: Prepared by Procedure Q1 and Scheme AC using N-{3-[1-(3-aminopropyl)-4-piperidinyl]phenyl}-2-methylpropanamide and 3-(2-chloro-6-fluorophenyl)-5-methyl-4-isoxazolecarbonyl chloride: ESMS m/e: 541.2 (M+H)$^+$.

EXAMPLE 329

N-[3-(1-{3-[(DIPHENYLACETYL)AMINO]PROPYL}-4-PIPERIDINYL)PHENYL]-2-METHYLPROPANAMIDE: Prepared by Procedure Q1 and Scheme AC using N-{3-[1-(3-aminopropyl)-4-piperidinyl]phenyl}-2-methylpropanamide and diphenylacetyl chloride: $^1$H NMR (400 MHz, CDCl$_3$) δ 7.51 (s, 1H), 7.33–7.21 (m, 13H), 6.94 (m, 2H), 4.88 (s, 1H), 3.39 (t, 2H, J=5.6 Hz), 2.93 (d, 2H, J=11.3 Hz), 2.52–2.36 (m, 4H), 1.97 (t, 2H, J=11.3 Hz), 1.83–1.58 (m, 6H), 1.24 (d, 6H, J=7.6 Hz); Anal. Calcd for C$_{32}$H$_{39}$N$_3$O$_2$+HCl+0.19CHCl$_3$: C, 69.44; H, 7.27; N, 7.55. Found: C, 69.44; H, 7.43; N, 7.43; ESMS m/e: 498.4 (M+H)$^+$.

EXAMPLE 330

N-(3-{4-[3-(ISOBUTYRYLAMINO)PHENYL]-1-PIPERIDINYL}PROPYL)-1-BENZOTHIOPHENE-3-CARBOXAMIDE: Prepared by Procedure Q1 and Scheme AC using N-{3-[1-(3-aminopropyl)-4-piperidinyl]phenyl}-2-methylpropanamide and 1-benzothiophene-3-carbonyl chloride: ESMS m/e: 464.2 (M+H)$^+$.

EXAMPLE 331

3-(2-CHLOROPHENYL)-N-(3-{4-[3-(ISOBUTYRYLAMINO)PHENYL]-1-PIPERIDINYL}PROPYL)-5-METHYL-4-ISOXAZOLECARBOXAMIDE: Prepared by Procedure Q1 and Scheme AC using N-{3-[1-(3-aminopropyl)-4-piperidinyl]phenyl}-2-methylpropanamide and 3-(2-chlorophenyl)-5-methyl-4-isoxazolecarbonyl chloride: ESMS m/e: 523.1 (M+H)$^+$.

EXAMPLE 332

3-(2,6-DICHLOROPHENYL)-N-(3-{4-[3-(ISOBUTYRYLAMINO)PHENYL]-1-PIPERIDINYL}PROPYL)-5-METHYL-4-ISOXAZOLECARBOXAMIDE: Prepared by Procedure Q1 and Scheme AC using N-{3-[1-(3-aminopropyl)-4-piperidinyl]phenyl}-2-methylpropanamide and 3-(2,6-dichlorophenyl)-5-methyl-4-isoxazolecarbonyl chloride: $^1$H NMR (400 MHz, CDCl$_3$) δ 7.50 (d, 1H, J=2.3 Hz), 7.48 (s, 1H), 7.4 (m, 1H), 7.39 (s, 1H), 7.37 (m, 2H), 7.24 (t, 1H, J=7.2 Hz), 6.92 (d, 1H, J=7.9 Hz), 6.06 (s, 1H), 3.31 (q, 2H, J=6.4 Hz), 2.94 (d, 2H, J=10.8 Hz), 2.79 (s, 3H), 2.53 (q, 1H, J=6.1), 2.47 (tt, 1H, J=4.2, 11.4 Hz), 2.29 (t, 2H, J=7.2 Hz), 1.99 (t, 2H, J=11.4 Hz), 1.81 (m, 2H), 1.69 (dt, 2H, J=2.4, 11.6), 1.59 (q, 2H, J=6.6 Hz), 1.24 (d, 6H, J=6.5 Hz); ESMS m/e: 557.0 (M+H)$^+$.

1-[3-(3-CHLOROPROPOXY)PHENYL]ETHANONE: Prepared by Procedure U and Scheme AK using 1-(3-hydroxyphenyl)ethanone and 1-bromo-3-chloropropane.

1-(3-CHLOROPROPOXY)-2-FLUOROBENZENE: Prepared by Procedure U and Scheme AK using 2-fluorophenol and 1-bromo-3-chloropropane.

1-CHLORO-3-(3-CHLOROPROPOXY)BENZENE: Prepared by Procedure U and Scheme AK using 3-chlorophenol and 1-bromo-3-chloropropane.

1-CHLORO-4-(3-CHLOROPROPOXY)BENZENE: Prepared by Procedure U and Scheme AK using 4-chlorophenol and 1-bromo-3-chloropropane.

1-(3-CHLOROPROPOXY)-3-FLUOROBENZENE: Prepared by Procedure U and Scheme AK using 3-fluorophenol and 1-bromo-3-chloropropane.

1-(3-CHLOROPROPOXY)-4-FLUOROBENZENE: Prepared by Procedure U and Scheme AK using 4-fluorophenol and 1-bromo-3-chloropropane.

1-CHLORO-2-(3-CHLOROPROPOXY)BENZENE: Prepared by Procedure U and Scheme AK using 2-chlorophenol and 1-bromo-3-chloropropane.

4-(3-CHLOROPROPOXY)-1,2-DIMETHYLBENZENE: Prepared by Procedure U and Scheme AK using 3,4-dimethylphenol and 1-bromo-3-chloropropane.

1-BROMO-2-(3-CHLOROPROPOXY)BENZENE: Prepared by Procedure U and Scheme AK using 2-bromophenol and 1-bromo-3-chloropropane.

1-BROMO-3-(3-CHLOROPROPOXY)BENZENE: Prepared by Procedure U and Scheme AK using 3-bromophenol and 1-bromo-3-chloropropane.

1-BROMO-4-(3-CHLOROPROPOXY)BENZENE: Prepared by Procedure U and Scheme AK using 4-bromophenol and 1-bromo-3-chloropropane.

1-(3-CHLOROPROPOXY)-4-METHYLBENZENE: Prepared by Procedure U and Scheme AK using p-cresol and 1-bromo-3-chloropropane.

4-BROMOPHENYL(2R)-3-CHLORO-2-METHYLPROPYL ETHER: Prepared by Procedure U and Scheme AK using 4-bromophenol and (2S)-1-bromo-3-chloro-2-methylpropane.

1-{[(2R)-3-CHLORO-2-METHYLPROPYL]OXY}-2,4,5-TRIFLUOROBENZENE: Prepared by Procedure U and Scheme AK using 2,4,5-trifluorophenol and (2S)-1-bromo-3-chloro-2-methylpropane.

1-CHLORO-3-{[(2R)-3-CHLORO-2-METHYLPROPYL]OXY}BENZENE: Prepared by Procedure U and Scheme AK using 3-chlorophenol and (2S)-1-bromo-3-chloro-2-methylpropane.

1-{[(2R)-3-CHLORO-2-METHYLPROPYL]OXY}-4-FLUOROBENZENE: Prepared by Procedure U and Scheme AK using 4-fluorophenol and (2S)-1-bromo-3-chloro-2-methylpropane.

1-{[(2R)-3-CHLORO-2-METHYLPROPYL]OXY}-3-FLUOROBENZENE: Prepared by Procedure U and Scheme AK using 3-fluorophenol and (2S)-1-bromo-3-chloro-2-methylpropane.

1-CHLORO-2-{[(2R)-3-CHLORO-2-METHYLPROPYL]OXY}BENZENE: Prepared by Procedure U and Scheme AK using 2-chlorophenol and (2S)-1-bromo-3-chloro-2-methylpropane.

1-{[(2R)-3-CHLORO-2-METHYLPROPYL]OXY}-2-FLUOROBENZENE: Prepared by Procedure U and Scheme AK using 2-fluorophenol and (2S)-1-bromo-3-chloro-2-methylpropane.

1-CHLORO-4-{[(2R)-3-CHLORO-2-METHYLPROPYL]OXY}BENZENE: Prepared by Procedure U and Scheme AK using 4-chlorophenol and (2S)-1-bromo-3-chloro-2-methylpropane.

3-BROMOPHENYL(2R)-3-CHLORO-2-METHYLPROPYL ETHER: Prepared by Procedure U and Scheme AK using 3-bromophenol and (2S)-1-bromo-3-chloro-2-methylpropane.

2-BROMOPHENYL(2R)-3-CHLORO-2-METHYLPROPYL ETHER: Prepared by Procedure U and Scheme AK using 2-bromophenol and (2S)-1-bromo-3-chloro-2-methylpropane.

1-{[(2S)-3-CHLORO-2-METHYLPROPYL]OXY}-3-FLUOROBENZENE: Prepared by Procedure U and Scheme AK using 3-fluorophenol and (2R)-1-bromo-3-chloro-2-methylpropane.

1-{[(2S)-3-CHLORO-2-METHYLPROPYL]OXY}-4-FLUOROBENZENE: Prepared by Procedure U and Scheme AK using 4-fluorophenol and (2R)-1-bromo-3-chloro-2-methylpropane.

1-{[(2S)-3-CHLORO-2-METHYLPROPYL]OXY}-2-FLUOROBENZENE: Prepared by Procedure U and Scheme AK using 2-fluorophenol and (2R)-1-bromo-3-chloro-2-methylpropane.

1-CHLORO-2-{[(2S)-3-CHLORO-2-METHYLPROPYL]OXY}BENZENE: Prepared by Procedure U and Scheme AK using 2-chlorophenol and (2R)-1-bromo-3-chloro-2-methylpropane.

1-CHLORO-4-{[(2S)-3-CHLORO-2-METHYLPROPYL]OXY}BENZENE: Prepared by Procedure U and Scheme AK using 4-chlorophenol and (2R)-1-bromo-3-chloro-2-methylpropane.

4-BROMOPHENYL(2S)-3-CHLORO-2-METHYLPROPYL ETHER: Prepared by Procedure U and Scheme AK using 4-bromophenol and (2R)-1-bromo-3-chloro-2-methylpropane.

3-BROMOPHENYL(2S)-3-CHLORO-2-METHYLPROPYL ETHER: Prepared by Procedure U and Scheme AK using 3-bromophenol and (2R)-1-bromo-3-chloro-2-methylpropane.

2-BROMOPHENYL(2S)-3-CHLORO-2-METHYLPROPYL ETHER: Prepared by Procedure U and Scheme AK using 2-bromophenol and (2R)-1-bromo-3-chloro-2-methylpropane.

1-CHLORO-3-{[(2S)-3-CHLORO-2-METHYLPROPYL]OXY}BENZENE: Prepared by Procedure U and Scheme AK using 3-chlorophenol and (2R)-1-bromo-3-chloro-2-methylpropane.

1-[3-(4-CHLOROBUTOXY)PHENYL]ETHANONE: Prepared by Procedure U and Scheme AK using 1-(3-hydroxyphenyl)ethanone and 1-bromo-4-chlorobutane.

1-[3-(4-CHLOROBUTOXY)PHENYL]ETHANONE: Prepared by Procedure U and Scheme AK using 1-(3-hydroxyphenyl)ethanone and 1-bromo-4-chlorobutane.

1-(4-CHLOROBUTOXY)-3-METHOXYBENZENE: Prepared by Procedure U and Scheme AK using 3-methoxyphenol and 1-bromo-4-chlorobutane.

1-(4-CHLOROBUTOXY)-4-METHOXYBENZENE: Prepared by Procedure U and Scheme AK using 4-methoxyphenol and 1-bromo-4-chlorobutane.

1-(4-CHLOROBUTOXY)-2-METHOXYBENZENE: Prepared by Procedure U and Scheme AK using 2-methoxyphenol and 1-bromo-4-chlorobutane.

4-(4-CHLOROBUTOXY)-1,2-DIMETHYLBENZENE: Prepared by Procedure U and Scheme AK using 3,4-dimethylphenol and 1-bromo-4-chlorobutane.

1-{3-[(5-CHLOROPENTYL)OXY]
PHENYL}ETHANONE: Prepared by Procedure U and
Scheme AK using 1-(3-hydroxyphenyl)ethanone and
1-bromo-5-chloropentane.

1-{3-[(5-CHLOROPENTYL)OXY]
PHENYL}ETHANONE: Prepared by Procedure U and
Scheme AK using 1-(3-hydroxyphenyl)ethanone and
1-bromo-5-chloropentane.

1-{3-[(6-CHLOROHEXYL)OXY]
PHENYL}ETHANONE: Prepared by Procedure U and
Scheme AK using 1-(3-hydroxyphenyl)ethanone and
1-bromo-6-chlorohexane.

1-{3-[(6-CHLOROHEXYL)OXY]
PHENYL}ETHANONE: Prepared by Procedure U and
Scheme AK using 1-(3-hydroxyphenyl)ethanone and
1-bromo-6-chlorohexane.

EXAMPLE 333

N-(3-{1-[(2S)-2-(3-ACETYLPHENOXY)-2-PHENYLETHYL]-4-PIPERIDINYL}PHENYL)-2-METHYLPROPANAMIDE: Prepared by Procedure B and Scheme B1 using 1-(3-hydroxyphenyl)ethanone and N-(3-{1-[(2R)-2-hydroxy-2-phenylethyl]-4-piperidinyl}phenyl)-2-methylpropanamide: ESMS m/e: 485.0 (M+H)$^+$.

EXAMPLE 334

N-(3-{1-[(2S)-2-(2-ACETYLPHENOXY)-2-PHENYLETHYL]-4-PIPERIDINYL}PHENYL)-2-METHYLPROPANAMIDE: Prepared by Procedure B and Scheme B1 using 1-(2-hydroxyphenyl)ethanone and N-(3-{1-[(2R)-2-hydroxy-2-phenylethyl]-4-piperidinyl}phenyl)-2-methylpropanamide: ESMS m/e: 485.2 (M+H)$^+$.

EXAMPLE 335

N-(3-{1-[(2S)-2-(3-CHLOROPHENOXY)-2-PHENYLETHYL]-4-PIPERIDINYL}PHENYL)-2-METHYLPROPANAMIDE: Prepared by Procedure B and Scheme B1 using 3-chlorophenol and N-(3-{1-[(2R)-2-hydroxy-2-phenylethyl]-4-piperidinyl}phenyl)-2-methylpropanamide: ESMS m/e: 477.1 (M+H)$^+$.

EXAMPLE 336

N-(3-{1-[(2S)-2-(3,4-DIMETHOXYPHENOXY)-2-PHENYLETHYL]-4-PIPERIDINYL}PHENYL)-2-METHYLPROPANAMIDE: Prepared by Procedure B and Scheme B1 using 3,4-dimethoxyphenol and N-(3-{1-[(2R)-2-hydroxy-2-phenylethyl]-4-piperidinyl}phenyl)-2-methylpropanamide: ESMS m/e: 503.2 (M+H)$^+$.

EXAMPLE 337

N-(3-{1-[(2R)-2-(4-FLUOROPHENOXY)-2-PHENYLETHYL]-4-PIPERIDINYL}PHENYL)-2-METHYLPROPANAMIDE: Prepared by Procedure B and Scheme B1 using 4-fluorophenol and N-(3-{1-[(2S)-2-hydroxy-2-phenylethyl]-4-piperidinyl}phenyl)-2-methylpropanamide: ESMS m/e: 461.2 (M+H)$^+$.

EXAMPLE 338

N-(3-{1-[(2R)-2-(3-METHOXYPHENOXY)-2-PHENYLETHYL]-4-PIPERIDINYL}PHENYL)-2-METHYLPROPANAMIDE: Prepared by Procedure B and Scheme B1 using 3-methoxyphenol and N-(3-{1-[(2S)-2-hydroxy-2-phenylethyl]-4-piperidinyl}phenyl)-2-methylpropanamide: ESMS m/e: 472.9 (M+H)$^+$.

EXAMPLE 339

N-(3-{1-[(2R)-2-(3-CHLOROPHENOXY)-2-PHENYLETHYL]-4-PIPERIDINYL}PHENYL)-2-METHYLPROPANAMIDE: Prepared by Procedure B and Scheme B1 using 3-chlorophenol and N-(3-{1-[(2S)-2-hydroxy-2-phenylethyl]-4-piperidinyl}phenyl)-2-methylpropanamide: ESMS m/e: 478.5 (M+H)$^+$.

N-{3-[1-(3,3-DIMETHOXYPROPYL)-4-PIPERIDINYL]PHENYL}-2-METHYLPROPANAMIDE: Prepared by Procedure G and Scheme B1 using 3-bromo-1,1-dimethoxypropane and 2-methyl-N-[3-(4-piperidinyl)phenyl]propanamide: ESMS m/e: 349.2 (M+H)$^+$.

EXAMPLE 340

N-(3-{1-[(3S)-3-(3-ACETYLPHENOXY)-3-PHENYLPROPYL]-4-PIPERIDINYL}PHENYL)CYCLOPROPANECARBOXAMIDE: Prepared by Procedure B and Scheme B1 using 1-(3-hydroxyphenyl)ethanone and N-(3-{1-[(3R)-3-hydroxy-3-phenylpropyl]-4-piperidinyl}phenyl)cyclopropanecarboxamide: ESMS m/e: 497.1 (M+H)$^+$.

EXAMPLE 341

N-(3-{1-[3-(3-ACETYLPHENOXY)PROPYL]-4-PIPERIDINYL}PHENYL)-2-METHYLPROPANAMIDE: Prepared by Procedure G and Scheme B1 using 1-[3-(3-chloropropoxy)phenyl]ethanone and 2-methyl-N-[3-(4-piperidinyl)phenyl]propanamide: ESMS m/e: 423.2 (M+H)$^+$.

EXAMPLE 342

N-(3-{1-[3-(3-ACETYLPHENOXY)PROPYL]-4-PIPERIDINYL}PHENYL)PROPANAMIDE: Prepared by Procedure G and Scheme B1 using 1-[3-(3-chloropropoxy)phenyl]ethanone and N-[3-(4-piperidinyl)phenyl]cyclopropanecarboxamide: ESMS m/e: 421.2 (M+H)$^+$.

EXAMPLE 343

N-(3-{1-[3-(2-FLUOROPHENOXY)PROPYL]-4-PIPERIDINYL}PHENYL)-2-METHYLPROPANAMIDE: Prepared by Procedure G and Scheme B1 using 1-(3-chloropropoxy)-2-fluorobenzene and 2-methyl-N-[3-(4-piperidinyl)phenyl]propanamide: ESMS m/e: 399.2 (M+H)$^+$.

EXAMPLE 344

N-(3-{1-[3-(3-CHLOROPHENOXY)PROPYL]-4-PIPERIDINYL}PHENYL)-2-METHYLPROPANAMIDE: Prepared by Procedure G and Scheme B1 using 1-chloro-3-(3-chloropropoxy)benzene and 2-methyl-N-[3-(4-piperidinyl)phenyl]propanamide: ESMS m/e: 415.2 (M+H)$^+$.

EXAMPLE 345

N-(3-{1-[3-(4-CHLOROPHENOXY)PROPYL]-4-PIPERIDINYL}PHENYL)-2-METHYLPROPANAMIDE: Prepared by Procedure G and Scheme B1 using 1-chloro-4-(3-chloropropoxy)benzene and 2-methyl-N-[3-(4-piperidinyl)phenyl]propanamide: $^1$H NMR (400 MHz, CDCl$_3$) δ 7.71 (dd, 1H, J=3.2, 5.7 Hz), 7.53 (dd, 1H, J=3.2, 5.7 Hz), 7.50 (m, 1H), 7.31 (m, 1H), 7.24–7.20 (m, 2H), 6.94 (d, 1H, J=7.9 Hz), 6.85–6.82 (m, 2H), 4.00 (t, 2H, J=6.1 Hz), 3.07 (d, 2H, J=10.9 Hz), 2.55 (m, 3H), 2.50 (sept, 1H, J=6.2 Hz), 2.08 (dt, 2H, J=3.1, 10.9 Hz), 2.00 (m, 2H), 1.83 (m, 3H), 1.69 (qt, 1H, J=6.2 Hz), 1.24 (d, 6H, J=6.8 Hz); Anal. Calcd for $C_{24}H_{31}ClN_2O_2$+HCl: C, 63.8; H, 7.09; N, 6.21. Found: C, 63.3; H, 7.04; N, 6.27; ESMS m/e: 415.2 (M+H)$^+$.

EXAMPLE 346

N-(3-{1-[3-(3-FLUOROPHENOXY)PROPYL]-4-PIPERIDINYL}PHENYL)-2-METHYLPROPANAMIDE: Prepared by Procedure G and Scheme B1 using 1-(3-chloropropoxy)-3-fluorobenzene and 2-methyl-N-[3-(4-piperidinyl)phenyl]propanamide: ESMS m/e: 399.2 (M+H)$^+$.

EXAMPLE 347

N-(3-{1-[3-(4-FLUOROPHENOXY)PROPYL]-4-PIPERIDINYL}PHENYL)-2-METHYLPROPANAMIDE: Prepared by Procedure G and Scheme B1 using 1-(3-chloropropoxy)-4-fluorobenzene and 2-methyl-N-[3-(4-piperidinyl)phenyl]propanamide: ESMS m/e: 399.2 (M+H)$^+$.

EXAMPLE 348

N-(3-{1-[3-(2-CHLOROPHENOXY)PROPYL]-4-PIPERIDINYL}PHENYL)-2-METHYLPROPANAMIDE: Prepared by Procedure G and Scheme B1 using 1-chloro-2-(3-chloropropoxy)benzene and 2-methyl-N-[3-(4-piperidinyl)phenyl]propanamide: ESMS m/e: 415.2 (M+H)$^+$.

EXAMPLE 349

N-(3-{1-[3-(3,4-DIMETHYLPHENOXY)PROPYL]-4-PIPERIDINYL}PHENYL)-2-METHYLPROPANAMIDE: Prepared by Procedure G and Scheme B1 using 4-(3-chloropropoxy)-1,2-dimethylbenzene and 2-methyl-N-[3-(4-piperidinyl)phenyl]propanamide: ESMS m/e: 409.2 (M+H)$^+$.

EXAMPLE 350

N-(3-{1-[3-(2-BROMOPHENOXY)PROPYL]-4-PIPERIDINYL}PHENYL)-2-METHYLPROPANAMIDE: Prepared by Procedure G and Scheme B1 using 1-bromo-2-(3-chloropropoxy)benzene and 2-methyl-N-[3-(4-piperidinyl)phenyl]propanamide: $^1$H NMR (400 MHz, CDCl$_3$) δ 7.53 (dd, 1H, J=1.6, 7.9 Hz), 7.48 (s, 1H), 7.32 (m, 1H), 7.28–7.22 (m, 3H), 7.17 (s, 1H), 6.98 (d, 1H, J=7.7 Hz), 6.93 (dd, 1H, J=1.4, 8.4 Hz), 6.82 (dt, 1H, J=7.6, 1.4 Hz), 4.11 (t, 2H, J=6.3 Hz), 3.07 (d, 2H, J=11.3 Hz), 2.61 (t, 2H, J=6.9 Hz), 2.50 (m, 3H), 2.07 (m, 1H), 1.8–1.75 (m, 5H), 1.25 (d, 6H, J=6.7 Hz); Anal. Calcd for $C_{24}H_{31}BrN_2O_2$·HCl+0.2CHCl$_3$: C, 55.9; H, 6.24; N, 5.39. Found: C, 55.8; H, 6.23; N, 5.47; ESMS m/e: 459.1 (M+H)$^+$.

EXAMPLE 351

N-(3-{1-[3-(3-BROMOPHENOXY)PROPYL]-4-PIPERIDINYL}PHENYL)-2-METHYLPROPANAMIDE: Prepared by Procedure G and Scheme B1 using 1-bromo-3-(3-chloropropoxy)benzene and 2-methyl-N-[3-(4-piperidinyl)phenyl]propanamide: ESMS m/e: 459.1 (M+H)$^+$.

EXAMPLE 352

N-(3-{1-[3-(4-BROMOPHENOXY)PROPYL]-4-PIPERIDINYL}PHENYL)-2-METHYLPROPANAMIDE: Prepared by Procedure G and Scheme B1 using 1-bromo-4-(3-chloropropoxy)benzene and 2-methyl-N-[3-(4-piperidinyl)phenyl]propanamide: $^1$H NMR (400 MHz, CDCl$_3$) δ 7.51 (s, 1H), 7.37 (d, 2H, J=7.6 Hz), 7.26 (m, 3H), 6.97 (d, 1H, J=7.7 Hz), 6.79 (d, 2H, J=7.7 Hz), 4.01 (t, 2H, J=5.6 Hz), 3.08 (d, 2H, J=9.4 Hz), 2.53 (m, 4H), 2.05 (m, 4H), 1.84 (m, 4H), 1.24 (d, 6H, J=5.9 Hz); Anal. Calcd for $C_{24}H_{31}BrN_2O_2$·HCl+0.34CHCl$_3$: C, 54.5; H, 6.08; N, 5.22. Found: C, 54.5; H, 6.22; N, 5.22; ESMS m/e: 459.1 (M+H)$^+$.

EXAMPLE 353

N-(3-{1-[(3R)-3-(3,4-DIMETHOXYPHENOXY)-3-PHENYLPROPYL]-4-PIPERIDINYL}PHENYL)-N,2-DIMETHYLPROPANAMIDE: Prepared by Procedure T and Scheme AD using N-(3-{1-[(3R)-3-(3,4-dimethoxyphenoxy)-3-phenylpropyl]-4-piperidinyl}phenyl)-2-methylpropanamide and methyl iodide: ESMS m/e: 531.2 (M+H)$^+$.

EXAMPLE 354

N-(3-{1-[(3R)-3-(3-ACETYLPHENOXY)-3-PHENYLPROPYL]-4-PIPERIDINYL}PHENYL)-N,2-DIMETHYLPROPANAMIDE: Prepared by Procedure T and Scheme AD using N-(3-{1-[(3R)-3-(3-acetylphenoxy)-3-phenylpropyl]-4-piperidinyl}phenyl)-2-methylpropanamide and methyl iodide: ESMS m/e: 513.2 (M+H)$^+$.

EXAMPLE 355

N-(3-{1-[(3S)-3-(3-ACETYLPHENOXY)-3-PHENYLPROPYL]-4-PIPERIDINYL}PHENYL)-N,2-DIMETHYLPROPANAMIDE: Prepared by Procedure T and Scheme AD using N-(3-{1-[(3S)-3-(3-acetylphenoxy)-3-phenylpropyl]-4-piperidinyl}phenyl)-2-methylpropanamide and methyl iodide: ESMS m/e: 513.2 (M+H)$^+$.

EXAMPLE 356

N-(3-{1-[(2S)-3-(4-BROMOPHENOXY)-2-METHYLPROPYL]-4-PIPERIDINYL}PHENYL)-2-METHYLPROPANAMIDE: Prepared by Procedure G and Scheme B1 using 4-bromophenyl(2R)-3-chloro-2-methylpropyl ether and 2-methyl-N-[3-(4-piperidinyl)phenyl]propanamide: ESMS m/e: 473.0 (M+H)$^+$.

EXAMPLE 357

2-METHYL-N-(3-{1-[(2S)-2-METHYL-3-(2,4,5-TRIFLUOROPHENOXY)PROPYL]-4-PIPERIDINYL}PHENYL)PROPANAMIDE: Prepared by Procedure G and Scheme B1 using 1-{[(2R)-3-chloro-2-methylpropyl]oxy}-2,4,5-trifluorobenzene and 2-methyl-N-[3-(4-piperidinyl)phenyl]propanamide: ESMS m/e: 449.2 (M+H)$^+$.

EXAMPLE 358

N-(3-{1-[(2S)-3-(3-CHLOROPHENOXY)-2-METHYLPROPYL]-4-PIPERIDINYL}PHENYL)-2-METHYLPROPANAMIDE: Prepared by Procedure G and Scheme B1 using 1-chloro-3-{[(2R)-3-chloro-2-methylpropyl]oxy}benzene and 2-methyl-N-[3-(4-piperidinyl)phenyl]propanamide: ESMS m/e: 429.2 (M+H)$^+$.

EXAMPLE 359

N-(3-{1-[(2S)-3-(4-FLUOROPHENOXY)-2-METHYLPROPYL]-4-PIPERIDINYL}PHENYL)-2-

METHYLPROPANAMIDE: Prepared by Procedure G and Scheme B1 using 1-{[(2R)-3-chloro-2-methylpropyl]oxy}-4-fluorobenzene and 2-methyl-N-[3-(4-piperidinyl)phenyl]propanamide: ESMS m/e: 413.2 (M+H)$^+$.

EXAMPLE 360

N-(3-{1-[(2S)-3-(3-FLUOROPHENOXY)-2-METHYLPROPYL]-4-PIPERIDINYL}PHENYL)-2-METHYLPROPANAMIDE: Prepared by Procedure G and Scheme B1 using 1-{[(2R)-3-chloro-2-methylpropyl]oxy}-3-fluorobenzene and 2-methyl-N-[3-(4-piperidinyl)phenyl]propanamide: ESMS m/e: 413.2 (M+H)$^+$.

EXAMPLE 361

N-(3-{1-[(2S)-3-(2-CHLOROPHENOXY)-2-METHYLPROPYL]-4-PIPERIDINYL}PHENYL)-2-METHYLPROPANAMIDE: Prepared by Procedure G and Scheme B1 using 1-chloro-2-{[(2R)-3-chloro-2-methylpropyl]oxy}benzene and 2-methyl-N-[3-(4-piperidinyl)phenyl]propanamide: ESMS m/e: 429.1 (M+H)$^+$.

EXAMPLE 362

N-(3-{1-[(2S)-3-(2-FLUOROPHENOXY)-2-METHYLPROPYL]-4-PIPERIDINYL}PHENYL)-2-METHYLPROPANAMIDE: Prepared by Procedure G and Scheme B1 using 1-{[(2R)-3-chloro-2-methylpropyl]oxy}-2-fluorobenzene and 2-methyl-N-[3-(4-piperidinyl)phenyl]propanamide: ESMS m/e: 413.2 (M+H)$^+$.

EXAMPLE 363

N-(3-{1-[(2S)-3-(4-CHLOROPHENOXY)-2-METHYLPROPYL]-4-PIPERIDINYL}PHENYL)-2-METHYLPROPANAMIDE: Prepared by Procedure G and Scheme B1 using 1-chloro-4-{[(2R)-3-chloro-2-methylpropyl]oxy}benzene and 2-methyl-N-[3-(4-piperidinyl)phenyl]propanamide: ESMS m/e: 429.2 (M+H)$^+$.

EXAMPLE 364

N-(3-{1-[(2S)-3-(3-BROMOPHENOXY)-2-METHYLPROPYL]-4-PIPERIDINYL}PHENYL)-2-METHYLPROPANAMIDE: Prepared by Procedure G and Scheme B using 3-bromophenyl(2R)-3-chloro-2-methylpropyl ether and 2-methyl-N-[3-(4-piperidinyl)phenyl]propanamide: ESMS m/e: 474.0 (M+H)$^+$.

EXAMPLE 365

N-(3-{1-[(2S)-3-(2-BROMOPHENOXY)-2-METHYLPROPYL]-4-PIPERIDINYL}PHENYL)-2-METHYLPROPANAMIDE: Prepared by Procedure G and Scheme B1 using 2-bromophenyl(2R)-3-chloro-2-methylpropyl ether and 2-methyl-N-[3-(4-piperidinyl)phenyl]propanamide: ESMS m/e: 473.0 (M+H)$^+$.

EXAMPLE 366

N-(3-{1-[(2R)-3-(3-FLUOROPHENOXY)-2-METHYLPROPYL]-4-PIPERIDINYL}PHENYL)-2-METHYLPROPANAMIDE: Prepared by Procedure G and Scheme B using 1-{[(2S)-3-chloro-2-methylpropyl]oxy}-3-fluorobenzene and 2-methyl-N-[3-(4-piperidinyl)phenyl]propanamide: ESMS m/e: 413.2 (M+H)$^+$.

EXAMPLE 367

N-(3-{1-[(2R)-3-(4-FLUOROPHENOXY)-2-METHYLPROPYL]-4-PIPERIDINYL}PHENYL)-2-METHYLPROPANAMIDE: Prepared by Procedure G and Scheme B1 using 1-{[(2S)-3-chloro-2-methylpropyl]oxy}-4-fluorobenzene and 2-methyl-N-[3-(4-piperidinyl)phenyl]propanamide: ESMS m/e: 413.8 (M+H)$^+$.

EXAMPLE 368

N-(3-{1-[(2R)-3-(2-CHLOROPHENOXY)-2-METHYLPROPYL]-4-PIPERIDINYL}PHENYL)-2-METHYLPROPANAMIDE: Prepared by Procedure G and Scheme B1 using 1-chloro-2-{[(2S)-3-chloro-2-methylpropyl]oxy}benzene and 2-methyl-N-[3-(4-piperidinyl)phenyl]propanamide: ESMS m/e: 429.1 (M+H)$^+$.

EXAMPLE 369

N-(3-{1-[(2R)-3-(4-CHLOROPHENOXY)-2-METHYLPROPYL]-4-PIPERIDINYL}PHENYL)-2-METHYLPROPANAMIDE: Prepared by Procedure G and Scheme B1 using 1-chloro-4-{[(2S)-3-chloro-2-methylpropyl]oxy}benzene and 2-methyl-N-[3-(4-piperidinyl)phenyl]propanamide: ESMS m/e: 429.1 (M+H)$^+$.

EXAMPLE 370

N-(3-{1-[(2R)-3-(4-BROMOPHENOXY)-2-METHYLPROPYL]-4-PIPERIDINYL}PHENYL)-2-METHYLPROPANAMIDE: Prepared by Procedure G and Scheme B1 using 4-bromophenyl(2S)-3-chloro-2-methylpropyl ether and 2-methyl-N-[3-(4-piperidinyl)phenyl]propanamide: ESMS m/e: 473.0 (M+H)$^+$.

EXAMPLE 371

N-(3-{1-[(2R)-3-(3-BROMOPHENOXY)-2-METHYLPROPYL]-4-PIPERIDINYL}PHENYL)-2-METHYLPROPANAMIDE: Prepared by Procedure G and Scheme B1 using 3-bromophenyl(2S)-3-chloro-2-methylpropyl ether and 2-methyl-N-[3-(4-piperidinyl)phenyl]propanamide: ESMS m/e: 473.0 (M+H)$^+$.

EXAMPLE 372

N-(3-{1-[(2R)-3-(2-BROMOPHENOXY)-2-METHYLPROPYL]-4-PIPERIDINYL}PHENYL)-2-METHYLPROPANAMIDE: Prepared by Procedure G and Scheme B1 using 2-bromophenyl(2S)-3-chloro-2-methylpropyl ether and 2-methyl-N-[3-(4-piperidinyl)phenyl]propanamide: ESMS m/e: 473.0 (M+H)$^+$.

EXAMPLE 373

N-(3-{1-[(2R)-3-(3-CHLOROPHENOXY)-2-METHYLPROPYL]-4-PIPERIDINYL}PHENYL)-2-METHYLPROPANAMIDE: Prepared by Procedure G and Scheme B1 using 1-chloro-3-{[(2S)-3-chloro-2-methylpropyl]oxy}benzene and 2-methyl-N-[3-(4-piperidinyl)phenyl]propanamide: ESMS m/e: 429.1 (M+H)$^+$.

EXAMPLE 374

N-(3-{1-[3-(5,5-DIMETHYL-1,3-DIOXAN-2-YL)PROPYL]-4-PIPERIDINYL}PHENYL)-2-METHYLPROPANAMIDE: Prepared by Procedure G and Scheme B1 using 2-(3-bromopropyl)-5,5-dimethyl-1,3-dioxane and 2-methyl-N-[3-(4-piperidinyl)phenyl]propanamide: ESMS m/e: 403.2 (M+H)$^+$.

EXAMPLE 375

N-(3-{1-[4-(3-ACETYLPHENOXY)BUTYL]-4-PIPERIDINYL}PHENYL)-2-METHYLPROPANAMIDE:

Prepared by Procedure G and Scheme B1 using 1-[3-(4-chlorobutoxy)phenyl]ethanone and 2-methyl-N-[3-(4-piperidinyl)phenyl]propanamide: ESMS m/e: 437.2 (M+H)$^+$.

EXAMPLE 376

N-(3-{1-[4-(3-METHOXYPHENOXY)BUTYL]-4-PIPERIDINYL}PHENYL)-2-METHYLPROPANAMIDE: Prepared by Procedure G and Scheme B1 using 1-(4-chlorobutoxy)-3-methoxybenzene and 2-methyl-N-[3-(4-piperidinyl)phenyl]propanamide: ESMS m/e: 425.2 (M+H)$^+$.

EXAMPLE 377

N-(3-{1-[4-(4-METHOXYPHENOXY)BUTYL]-4-PIPERIDINYL}PHENYL)-2-METHYLPROPANAMIDE: Prepared by Procedure G and Scheme B1 using 1-(4-chlorobutoxy)-4-methoxybenzene and 2-methyl-N-[3-(4-piperidinyl)phenyl]propanamide: ESMS m/e: 425.2 (M+H)$^+$.

EXAMPLE 378

N-(3-{1-[4-(2-METHOXYPHENOXY)BUTYL]-4-PIPERIDINYL}PHENYL)-2-METHYLPROPANAMIDE: Prepared by Procedure G and Scheme B1 using 1-(4-chlorobutoxy)-2-methoxybenzene and 2-methyl-N-[3-(4-piperidinyl)phenyl]propanamide: ESMS m/e: 425.2 (M+H)$^+$.

EXAMPLE 379

N-(3-{1-[4-(3,4-DIMETHYLPHENOXY)BUTYL]-4-PIPERIDINYL}PHENYL)-2-METHYLPROPANAMIDE: Prepared by Procedure G and Scheme B1 using 4-(4-chlorobutoxy)-1,2-dimethylbenzene and 2-methyl-N-[3-(4-piperidinyl)phenyl]propanamide: ESMS m/e: 423.2 (M+H)$^+$.

EXAMPLE 380

N-(3-{1-[4-(1,3-DIOXOLAN-2-YL)BUTYL]-4-PIPERIDINYL}PHENYL)-2-METHYLPROPANAMIDE: Prepared by Procedure G and Scheme B1 using 2-(4-chlorobutyl)-1,3-dioxolane and 2-methyl-N-[3-(4-piperidinyl)phenyl]propanamide: ESMS m/e: 375.2 (M+H)$^+$.

EXAMPLE 381

N-(3-{1-[5-(3-ACETYLPHENOXY)PENTYL]-4-PIPERIDINYL}PHENYL)-2-METHYLPROPANAMIDE: Prepared by Procedure G and Scheme B1 using 1-{3-[(5-chloropentyl)oxy]phenyl}ethanone and 2-methyl-N-[3-(4-piperidinyl)phenyl]propanamide: ESMS m/e: 451.3 (M+H)$^+$.

EXAMPLE 382

N-(3-{1-[5-(3-ACETYLPHENOXY)PENTYL]-4-PIPERIDINYL}PHENYL) CYCLOPROPANECARBOXAMIDE: Prepared by Procedure G and Scheme B1 using 1-{3-[(5-chloropentyl)oxy]phenyl}ethanone and N-[3-(4-piperidinyl)phenyl]cyclopropanecarboxamide: ESMS m/e: 449.2 (M+H)$^+$.

EXAMPLE 383

N-(3-{1-[6-(3-ACETYLPHENOXY)HEXYL]-4-PIPERIDINYL}PHENYL)-2-METHYLPROPANAMIDE: Prepared by Procedure G and Scheme B1 using 1-{3-[(6-chlorohexyl)oxy]phenyl}ethanone and 2-methyl-N-[3-(4-piperidinyl)phenyl]propanamide: ESMS m/e: 465.3 (M+H)$^+$.

EXAMPLE 384

N-(3-{1-[6-(3-ACETYLPHENOXY)HEXYL]-4-PIPERIDINYL}PHENYL) CYCLOPROPANECARBOXAMIDE: Prepared by Procedure G and Scheme B1 using 1-{3-[(6-chlorohexyl)oxy]phenyl}ethanone and N-[3-(4-piperidinyl)phenyl]cyclopropanecarboxamide: ESMS m/e: 463.3 (M+H)$^+$.

EXAMPLE 385

N-(3-{1-[4-(4-CHLOROPHENOXY)-4-(4-CHLOROPHENYL)BUTYL]-4-PIPERIDINYL}PHENYL)-2-METHYLPROPANAMIDE: Prepared by Procedure B and Scheme AN using 4-chlorophenol and N-(3-{1-[4-(4-chlorophenyl)-4-hydroxybutyl]-4-piperidinyl}phenyl)-2-methylpropanamide: ESMS m/e: 562.9 (M+23)$^+$.

EXAMPLE 386

2-METHYL-N-(3-{1-[2-(1-METHYL-2-PHENYL-1H-INDOL-3-YL)ETHYL]-4-PIPERIDINYL}PHENYL)PROPANAMIDE: Prepared by Procedure E and Scheme M using 2-methyl-N-{3-[1-(4-oxo-4-phenylbutyl)-4-piperidinyl]phenyl}propanamide and 1-methyl-1-phenylhydrazine: ESMS m/e: 480.3 (M+H)$^+$.

EXAMPLE 387

2-METHYL-N-(3-{1-[2-(2-PHENYL-1H-BENZO[G]INDOL-3-YL)ETHYL]-4-PIPERIDINYL}PHENYL)PROPANAMIDE: Prepared by Procedure E and Scheme M using 2-methyl-N-{3-[1-(4-oxo-4-phenylbutyl)-4-piperidinyl]phenyl}propanamide and 1-(1-naphthyl)hydrazine hydrochloride: ESMS m/e: 516.4 (M+H)$^+$.

EXAMPLE 388

2-METHYL-N-(3-{1-[3-(2-PHENYL-1H-BENZO[G]INDOL-3-YL)PROPYL]-4-PIPERIDINYL}PHENYL)PROPANAMIDE: Prepared by Procedure E and Scheme M using 2-methyl-N-{3-[1-(5-oxo-5-phenylpentyl)-4-piperidinyl]phenyl}propanamide and 1-(1-naphthyl)hydrazine hydrochloride: ESMS m/e: 530.2 (M+H)$^+$.

EXAMPLE 389

2-METHYL-N-[3-(1-{3-[2-PHENYL-5-(TRIFLUOROMETHOXY)-1H-INDOL-3-YL]PROPYL}-4-PIPERIDINYL)PHENYL]PROPANAMIDE: Prepared by Procedure E and Scheme M using 2-methyl-N-{3-[1-(5-oxo-5-phenylpentyl)-4-piperidinyl]phenyl}propanamide and 1-[4-(trifluoromethoxy)phenyl]hydrazine hydrochloride: ESMS m/e: 564.2 (M+H)$^+$.

EXAMPLE 390

2-METHYL-N-[3-(1-{4-[2-PHENYL-5-(TRIFLUOROMETHOXY)-1H-INDOL-3-YL]BUTYL}-4-PIPERIDINYL)PHENYL]PROPANAMIDE: Prepared by Procedure E and Scheme M using 2-methyl-N-{3-[1-(6-oxo-6-phenylhexyl)-4-piperidinyl]phenyl}propanamide and 1-[4-(trifluoromethoxy)phenyl]hydrazine hydrochloride: ESMS m/e: 578.2 (M+H)$^+$.

EXAMPLE 391

2-METHYL-N-(3-{1-[3-(1-METHYL-2-PHENYL-1H-INDOL-3-YL)PROPYL]-4-PIPERIDINYL}PHENYL)

PROPANAMIDE: Prepared by Procedure E and Scheme M using 2-methyl-N-{3-[1-(5-oxo-5-phenylpentyl)-4-piperidinyl]phenyl}propanamide and 1-methyl-1-phenylhydrazine: ESMS m/e: 495.3 (M+H)+.

EXAMPLE 392

N-(3-{1-[4-(1,2-DIPHENYL-1H-INDOL-3-YL)BUTYL]-4-PIPERIDINYL}PHENYL)-2-METHYLPROPANAMIDE: Prepared by Procedure E and Scheme M using 2-methyl-N-{3-[1-(6-oxo-6-phenylhexyl)-4-piperidinyl]phenyl}propanamide and 1,1-diphenylhydrazine hydrochloride: ESMS m/e: (M+H)+. 570.3.

EXAMPLE 393

2-METHYL-N-[3-(1-{5-[2-PHENYL-5-(TRIFLUOROMETHOXY)-1H-INDOL-3-YL]PENTYL}-4-PIPERIDINYL)PHENYL]PROPANAMIDE: Prepared by Procedure E and Scheme M using 2-methyl-N-{3-[1-(7-oxo-7-phenylheptyl)-4-piperidinyl]phenyl}propanamide and 1-[4-(trifluoromethoxy)phenyl]hydrazine hydrochloride: ESMS m/e: 592.3 (M+H)+.

EXAMPLE 394

N-(3-{1-[5-(1,2-DIPHENYL-1H-INDOL-3-YL)PENTYL]-4-PIPERIDINYL}PHENYL)-2-METHYLPROPANAMIDE: Prepared by Procedure E and Scheme M using 2-methyl-N-{3-[1-(7-oxo-7-phenylheptyl)-4-piperidinyl]phenyl}propanamide and 1,1-diphenylhydrazine hydrochloride: ESMS m/e: 584.3 (M+H)+.

EXAMPLE 395

2-METHYL-N-(3-{1-[5-(1-METHYL-2-PHENYL-1H-INDOL-3-YL)PENTYL]-4-PIPERIDINYL}PHENYL)PROPANAMIDE: Prepared by Procedure E and Scheme M using 2-methyl-N-{3-[1-(7-oxo-7-phenylheptyl)-4-piperidinyl]phenyl}propanamide and 1-methyl-1-phenylhydrazine: ESMS m/e: 522.3 (M+H)+.

EXAMPLE 396

2-METHYL-N-(3-{1-[4-(2-PHENYL-1H-BENZO[G]INDOL-3-YL)BUTYL]-4-PIPERIDINYL}PHENYL)PROPANAMIDE: Prepared by Procedure E and Scheme M using 2-methyl-N-{3-[1-(6-oxo-6-phenylhexyl)-4-piperidinyl]phenyl}propanamide and 1-(1-naphthyl)hydrazine hydrochloride: ESMS m/e: 544.3 (M+H)+.

EXAMPLE 397

2-METHYL-N-(3-{1-[4-(1-METHYL-2-PHENYL-1H-INDOL-3-YL)BUTYL]-4-PIPERIDINYL}PHENYL)PROPANAMIDE: Prepared by Procedure E and Scheme M using 2-methyl-N-{3-[1-(6-oxo-6-phenylhexyl)-4-piperidinyl]phenyl}propanamide and 1-methyl-1-phenylhydrazine: ESMS m/e: 508.3 (M+H)+.

EXAMPLE 398

2-METHYL-N-(3-{1-[5-(2-PHENYL-1H-BENZO[G]INDOL-3-YL)PENTYL]-4-PIPERIDINYL}PHENYL)PROPANAMIDE: Prepared by Procedure E and Scheme M using 2-methyl-N-{3-[1-(7-oxo-7-phenylheptyl)-4-piperidinyl]phenyl}propanamide and 1-(1-naphthyl)hydrazine hydrochloride: ESMS m/e: 558.2 (M+H)+.

EXAMPLE 399

2-METHYL-N-(3-{1-[2-(5-METHYL-2-PHENYL-1H-INDOL-3-YL)ETHYL]-4-PIPERIDINYL}PHENYL)PROPANAMIDE: Prepared by Procedure E and Scheme M using 2-methyl-N-{3-[1-(4-oxo-4-phenylbutyl)-4-piperidinyl]phenyl}propanamide and 1-(4-methylphenyl)hydrazine hydrochloride: ESMS m/e: 480.2 (M+H)+.

EXAMPLE 400

N-(3-{1-[2-(7-METHOXY-2-PHENYL-1H-INDOL-3-YL)ETHYL]-4-PIPERIDINYL}PHENYL)-2-METHYLPROPANAMIDE: Prepared by Procedure E and Scheme M using 2-methyl-N-{3-[1-(4-oxo-4-phenylbutyl)-4-piperidinyl]phenyl}propanamide and 1-(2-methoxyphenyl)hydrazine hydrochloride: ESMS m/e: 496.2 (M+H)+.

EXAMPLE 401

2-METHYL-N-(3-{1-[2-(7-METHYL-2-PHENYL-1H-INDOL-3-YL)ETHYL]-4-PIPERIDINYL}PHENYL)PROPANAMIDE: Prepared by Procedure E and Scheme M using 2-methyl-N-{3-[1-(4-oxo-4-phenylbutyl)-4-piperidinyl]phenyl}propanamide and 1-(2-methylphenyl)hydrazine hydrochloride: ESMS m/e: 480.2 (M+H)+.

EXAMPLE 402

N-(3-{1-[3-(7-METHOXY-2-PHENYL-1H-INDOL-3-YL)PROPYL]-4-PIPERIDINYL}PHENYL)-2-METHYLPROPANAMIDE: Prepared by Procedure E and Scheme M using 2-methyl-N-{3-[1-(5-oxo-5-phenylpentyl)-4-piperidinyl]phenyl)propanamide and 1-5-phenylpentyl)-4-piperidinyl]phenyl}propanamide and 1-(2-methoxyphenyl)hydrazine hydrochloride: ESMS m/e: 510.2 (M+H)+.

EXAMPLE 403

2-METHYL-N-(3-{1-[4-(7-METHYL-2-PHENYL-1H-INDOL-3-YL)BUTYL]-4-PIPERIDINYL}PHENYL)PROPANAMIDE: Prepared by Procedure E and Scheme M using 2-methyl-N-(3-{1-[(6-oxo-6-phenylhexyl)-4-piperidinyl]phenylpropanamide and 1-(2-methylphenyl)hydrazine hydrochloride: ESMS m/e: 508.3 (M+H)+.

EXAMPLE 404

N-(3-{1-[2-(5-METHOXY-2-PHENYL-1H-INDOL-3-YL)ETHYL]-4-PIPERIDINYL}PHENYL)-2-METHYLPROPANAMIDE: Prepared by Procedure E and Scheme M using 2-methyl-N-{3-[1-(4-oxo-4-phenylbutyl)-4-piperidinyl]phenyl}propanamide and 1-(4-methoxyphenyl)hydrazine hydrochloride: ESMS m/e: 496.2 (M+H)+.

EXAMPLE 405

2-METHYL-N-(3-{1-[3-(5-METHYL-2-PHENYL-1H-INDOL-3-YL)PROPYL]-4-PIPERIDINYL}PHENYL)PROPANAMIDE: Prepared by Procedure E and Scheme M using 2-methyl-N-{3-[1-(5-oxo-5-phenylpentyl)-4-piperidinyl]phenyl}propanamide and 1-(4-methylphenyl)hydrazine hydrochloride: ESMS m/e: 494.3 (M+H)+.

EXAMPLE 406

N-(3-{1-[4-(7-METHOXY-2-PHENYL-1H-INDOL-3-YL)BUTYL]-4-PIPERIDINYL}PHENYL)-2-METHYLPROPANAMIDE Prepared by Procedure E and Scheme M using 2-methyl-N-{3-[1-(6-oxo-6-phenylhexyl)-4-piperidinyl]phenyl}propanamide and 1-(2-methoxyphenyl)hydrazine hydrochloride: ESMS m/e: 524.3 (M+H)+.

EXAMPLE 407

2-METHYL-N-(3-{1-[3-(1-PHENYL-1H-INDOL-3-YL)PROPYL]-4-PIPERIDINYL}PHENYL)PROPANAMIDE: Prepared by Procedure H and Scheme S using N-(3-{1-[4-(1,3-dioxolan-2-yl)butyl]-4-piperidinyl}phenyl)-2-methylpropanamide and 1,1-diphenylhydrazine hydrochloride: ESMS m/e: 480.2 (M+H)$^+$.

EXAMPLE 408

2-METHYL-N-(3-{1-[2-(1-PHENYL-1H-INDOL-3-YL)ETHYL]-4-PIPERIDINYL}PHENYL)PROPANAMIDE: Prepared by Procedure H and Scheme S using N-(3-{1-[3-(1,3-dioxolan-2-yl)propyl]-4-piperidinyl}phenyl)-2-methylpropanamide and 1,1-diphenylhydrazine hydrochloride: ESMS m/e: 466.2 (M+H)$^+$.

EXAMPLE 409

2-METHYL-N-(3-{1-[2-(7-METHYL-1H-INDOL-3-YL)ETHYL]-4-PIPERIDINYL}PHENYL)PROPANAMIDE: Prepared by Procedure H and Scheme S using N-(3-{1-[3-(1,3-dioxolan-2-yl)propyl]-4-piperidinyl}phenyl)-2-methylpropanamide and 1-(2-methylphenyl)hydrazine hydrochloride: ESMS m/e: 404.2 (M+H)$^+$.

EXAMPLE 410

2-METHYL-N-(3-{1-[2-(1-METHYL-1H-INDOL-3-YL)ETHYL]-4-PIPERIDINYL}PHENYL)PROPANAMIDE: Prepared by Procedure H and Scheme S using N-(3-{1-[3-(1,3-dioxolan-2-yl)propyl]-4-piperidinyl}phenyl)-2-methylpropanamide and 1-methyl-1-phenylhydrazine: ESMS m/e: 404.2 (M+H)$^+$.

EXAMPLE 411

2-METHYL-N-(3-{1-[2-(5-METHYL-1H-INDOL-3-YL)ETHYL]-4-PIPERIDINYL}PHENYL)PROPANAMIDE: Prepared by Procedure H and Scheme S using N-(3-{1-[3-(1,3-dioxolan-2-yl)propyl]-4-piperidinyl}phenyl)-2-methylpropanamide and 1-(4-methylphenyl)hydrazine hydrochloride: ESMS m/e: 404.2 (M+H)$^+$.

EXAMPLE 412

2-METHYL-N-[3-(1-{2-[5-(TRIFLUOROMETHOXY)-1H-INDOL-3-YL]ETHYL}-4-PIPERIDINYL)PHENYL]PROPANAMIDE: Prepared by Procedure H and Scheme S using N-(3-{1-[3-(1,3-dioxolan-2-yl)propyl]-4-piperidinyl}phenyl)-2-methylpropanamide and 1-[4-(trifluoromethoxy)phenyl]hydrazine hydrochloride: ESMS m/e: 474.2 (M+H)$^+$.

EXAMPLE 413

N-(3-{1-[3-(1H-BENZO[G]INDOL-3-YL)PROPYL]-4-PIPERIDINYL}PHENYL)-2-METHYLPROPANAMIDE: Prepared by Procedure H and Scheme S using N-(3-{1-[4-(1,3-dioxolan-2-yl)butyl]-4-piperidinyl}phenyl)-2-methylpropanamide and 1-(1-naphthyl)hydrazine hydrochloride: ESMS 454.2 m/e: (M+H)$^+$.

EXAMPLE 414

2-METHYL-N-(3-{1-[3-(1-METHYL-1H-INDOL-3-YL)PROPYL]-4-PIPERIDINYL}PHENYL)PROPANAMIDE: Prepared by Procedure H and Scheme S.

A mixture of N-(3-{1-[4-(1,3-dioxolan-2-yl)butyl]-4-piperidinyl}phenyl)-2-methylpropanamide (100 mg, 0.270 mmol), 1-methyl-1-phenylhydrazine (106 mg, 0.870 mmol), ZnCl$_2$ (119 mg, 0.870 mmol) and HOAc (1.00 mL) was heated for 12 h at 80° C. The resulting crude mixture was diluted with water (20 mL), the aqueous layer was neutralized with a saturated K$_2$CO$_3$ solution (10 mL) and extracted with CH$_2$Cl$_2$ (3×20 mL). The combined organic layers were concentrated in vacuo and the residue was purified by preparative TLC using 3% of NH$_3$ (2.0 M in methanol) in CH$_2$Cl$_2$ to give the desired product 2-methyl-N-(3-{1-[3-(1-methyl-1H-indol-3-yl)propyl]-4-piperidinyl}phenyl)propanamide (20.7 mg, 18.7%): $^1$H NMR (400 MHz, CDCl$_3$) δ 7.60 (d, 1H, J=8.1 Hz), 7.45 (s, 1H), 7.35 (d, 1H, J=7.4 Hz), 7.25 (m, 4H), 7.09 (t, 1H, J=7.3 Hz), 6.97 (d, 1H, J=7.3 Hz), 6.86 (s, 1H), 3.75 (s, 3H), 3.11 (d, 2H, J=11.6 Hz), 2.79 (t, 2H, J=7.3 Hz), 2.51 (m, 4H), 2.12–1.81 (m, 8H), 1.25 (d, 6H, J=7.1 Hz); Anal. Calcd for C$_{27}$H$_{35}$N$_3$O+ 0.225 CHCl$_3$: C, 73.57; H, 7.99; N, 9.45. Found: C, 73.93; H, 7.90; N, 9.23; ESMS m/e: 418.2 (M+H)$^+$.

EXAMPLE 415

2-METHYL-N-(3-{1-[3-(5-METHYL-1H-INDOL-3-YL)PROPYL]-4-PIPERIDINYL}PHENYL)PROPANAMIDE: Prepared by Procedure H and Scheme S using N-(3-{1-[4-(1,3-dioxolan-2-yl)butyl]-4-piperidinyl}phenyl)-2-methylpropanamide and 1-(4-methylphenyl)hydrazine hydrochloride: ESMS m/e: 418.2 (M+H)$^+$.

EXAMPLE 416

2-METHYL-N-[3-(1-{3-[5-(TRIFLUOROMETHOXY)-1H-INDOL-3-YL]PROPYL}-4-PIPERIDINYL)PHENYL]PROPANAMIDE: Prepared by Procedure H and Scheme S using N-(3-{1-[4-(1,3-dioxolan-2-yl)butyl]-4-piperidinyl}phenyl)-2-methylpropanamide and 1-[4-(trifluoromethoxy)phenyl]hydrazine hydrochloride: ESMS m/e: 488.2 (M+H)$^+$.

EXAMPLE 417

2-METHYL-N-(3-{1-[3-(7-METHYL-1H-INDOL-3-YL)PROPYL]-4-PIPERIDINYL}PHENYL)PROPANAMIDE: Prepared by Procedure H and Scheme S using N-(3-{1-[4-(1,3-dioxolan-2-yl)butyl]-4-piperidinyl}phenyl)-2-methylpropanamide and 1-(2-methylphenyl)hydrazine hydrochloride: ESMS m/e: 418.2 (M+H)$^+$.

EXAMPLE 418

N-(3-{1-[3-(7-METHOXY-1H-INDOL-3-YL)PROPYL]-4-PIPERIDINYL}PHENYL)-2-METHYLPROPANAMIDE: Prepared by Procedure H and Scheme S using N-(3-{1-[4-(1,3-dioxolan-2-yl)butyl]-4-piperidinyl}phenyl)-2-methylpropanamide and 1-(2-methoxyphenyl)hydrazine hydrochloride: ESMS m/e: 434.0 (M+H)$^+$.

EXAMPLE 419

N-(3-{1-[2-(7-METHOXY-1H-INDOL-3-YL)ETHYL]-4-PIPERIDINYL}PHENYL)-2-METHYLPROPANAMIDE: Prepared by Procedure H and Scheme S using N-(3-{1-[3-(1,3-dioxolan-2-yl)propyl]-4-piperidinyl}phenyl)-2-methylpropanamide and 1-(2-methoxyphenyl)hydrazine hydrochloride: ESMS m/e: 420.2 (M+H)$^+$.

EXAMPLE 420

N-(3-{1-[2-(5-METHOXY-1H-INDOL-3-YL)ETHYL]-4-PIPERIDINYL}PHENYL)-2-METHYLPROPANAMIDE: Prepared by Procedure H and Scheme S using N-(3-{1-[3-(1,3-dioxolan-2-yl)propyl]-4-piperidinyl}phenyl)-2-methylpropanamide and 1-(4-methoxyphenyl)hydrazine hydrochloride: ESMS m/e: 420.2 (M+H)$^+$.

EXAMPLE 421

2-METHYL-N-(3-{1-[4-(5-METHYL-2-PHENYL-1H-INDOL-3-YL)BUTYL]-4-PIPERIDINYL}PHENYL)PROPANAMIDE: Prepared by Procedure E and Scheme M using 2-methyl-N-{3-[1-(6-oxo-6-phenylhexyl)-4-piperidinyl]phenyl}propanamide and 1-(4-methylphenyl)hydrazine hydrochloride: ESMS m/e: 508.3 (M+H)$^+$.

EXAMPLE 422

2-METHYL-N-[4-(1-{[1-(4-METHYLPHENYL)-1H-INDOL-3-YL]METHYL}-4-PIPERIDINYL)PHENYL]PROPANAMIDE: Prepared by Procedure D and Scheme N using 2-methyl-N-[4-(4-piperidinyl)phenyl]propanamide and 1-(4-methylphenyl)-1H-indole: ESMS m/e: 466.2 (M+H)$^+$.

EXAMPLE 423

N-[4-(1-{[1-(4-METHYLPHENYL)-1H-INDOL-3-YL]METHYL}-4-PIPERIDINYL)PHENYL]BUTANAMIDE: Prepared by Procedure D and Scheme N using N-[4-(4-piperidinyl)phenyl]butanamide and 1-(4-methylphenyl)-1H-indole: ESMS m/e: 466.2 (M+H)$^+$.

EXAMPLE 424

N-[3-(1-{[2-(2-AMINOPHENYL)-1H-INDOL-3-YL]METHYL}-4-PIPERIDINYL)PHENYL]-2-METHYLPROPANAMIDE: Prepared by Procedure D and Scheme N using 2-methyl-N-[3-(4-piperidinyl)phenyl]propanamide and 2-(1H-indol-2-yl)aniline: ESMS m/e: 467.2 (M+H)$^+$.

EXAMPLE 425

ETHYL 3-({4-[3-(ISOBUTYRYLAMINO)PHENYL]-1-PIPERIDINYL}METHYL)-1H-INDOLE-2-CARBOXYLATE: Prepared by Procedure D and Scheme N using 2-methyl-N-[3-(4-piperidinyl)phenyl]propanamide and ethyl 1H-indole-2-carboxylate: ESMS m/e: 448.2 (M+H)$^+$.

EXAMPLE 426

2-METHYL-N-(3-{1-[(1-METHYL-1H-INDOL-3-YL)METHYL]-4-PIPERIDINYL}PHENYL)PROPANAMIDE: Prepared by Procedure D and Scheme N using 2-methyl-N-[3-(4-piperidinyl)phenyl]propanamide and 1-methyl-1H-indole: ESMS m/e: 390.2 (M+H)$^+$.

EXAMPLE 427

N-(3-{1-[(5-METHOXY-2-METHYL-1H-INDOL-3-YL)METHYL]-4-PIPERIDINYL}PHENYL)-2-METHYLPROPANAMIDE: Prepared by Procedure D and Scheme N using 2-methyl-N-[3-(4-piperidinyl)phenyl]propanamide and 5-methoxy-2-methyl-1H-indole: ESMS m/e: 420.2 (M+H)$^+$.

EXAMPLE 428

2-METHYL-N-(3-{1-[(1-METHYL-2-PHENYL-1H-INDOL-3-YL)METHYL]-4-PIPERIDINYL}PHENYL)PROPANAMIDE: Prepared by Procedure D and Scheme N using 2-methyl-N-[3-(4-piperidinyl)phenyl]propanamide and 1-methyl-2-phenyl-1H-indole: ESMS m/e: 466.2 (M+H)$^+$.

EXAMPLE 429

2-METHYL-N-(3-{1-[(5-NITRO-1H-INDOL-3-YL)METHYL]-4-PIPERIDINYL}PHENYL)PROPANAMIDE: Prepared by Procedure D and Scheme N using 2-methyl-N-[3-(4-piperidinyl)phenyl]propanamide and 5-nitro-1H-indole: ESMS m/e: 421.1 (M+H)$^+$.

EXAMPLE 430

2-METHYL-N-(3-{1-[(2-METHYL-1H-INDOL-3-YL)METHYL]-4-PIPERIDINYL}PHENYL)PROPANAMIDE: Prepared by Procedure D and Scheme N using 2-methyl-N-[3-(4-piperidinyl)phenyl]propanamide and 2-methyl-1H-indole: ESMS m/e: 390.2 (M+H)$^+$.

EXAMPLE 431

N-(3-{1-[(4-BROMO-1H-INDOL-3-YL)1METHYL]-4-PIPERIDINYL}PHENYL)-2-METHYLPROPANAMIDE: Prepared by Procedure D and Scheme N using 2-methyl-N-[3-(4-piperidinyl)phenyl]propanamide and 4-bromo-1H-indole: ESMS m/e: 455.0 (M+H)$^+$.

EXAMPLE 432

N-[3-(1-{[2-(4-FLUOROPHENYL)-1H-INDOL-3-YL]METHYL}-4-PIPERIDINYL)PHENYL]-2-METHYLPROPANAMIDE: Prepared by Procedure D and Scheme N using 2-methyl-N-[3-(4-piperidinyl)phenyl]propanamide and 2-(4-fluorophenyl)-1H-indole: ESMS m/e: 470.0 (M+H)$^+$.

EXAMPLE 433

N-(3-{1-[(1,2-DIPHENYL-1H-INDOL-3-YL)METHYL]-4-PIPERIDINYL}PHENYL)-2-METHYLPROPANAMIDE: Prepared by Procedure D and Scheme N using 2-methyl-N-[3-(4-piperidinyl)phenyl]propanamide and 1,2-diphenyl-1H-indole: ESMS m/e: 528.2 (M+H)$^+$.

EXAMPLE 434

N-[3-(1-{[2-(4-CHLOROPHENYL)-1-ETHYL-1H-INDOL-3-YL]METHYL}-4-PIPERIDINYL)PHENYL]-2-METHYLPROPANAMIDE: Prepared by Procedure D and Scheme N using 2-methyl-N-[3-(4-piperidinyl)phenyl]propanamide and 2-(4-chlorophenyl)-1-ethyl-1H-indole: ESMS m/e: 514.1 (M+H)$^+$.

EXAMPLE 435

N-(3-{1-[(5-CHLORO-2-METHYL-1H-INDOL-3-YL)METHYL]-4-PIPERIDINYL}PHENYL)-2-METHYLPROPANAMIDE: Prepared by Procedure D and Scheme N using 2-methyl-N-[3-(4-piperidinyl)phenyl]propanamide and 5-chloro-2-methyl-1H-indole: ESMS m/e: 424.1 (M+H)$^+$.

EXAMPLE 436

N-(3-{1-[(5-CYANO-1H-INDOL-3-YL)METHYL]-4-PIPERIDINYL}PHENYL)-2-METHYLPROPANAMIDE: Prepared by Procedure D and Scheme N using 2-methyl-N-[3-(4-piperidinyl)phenyl]propanamide and 1H-indole-5-carbonitrile: ESMS m/e: 401.1 (M+H)$^+$.

EXAMPLE 437

2-METHYL-N-(3-{1-[(5-METHYL-2-PHENYL-1H-INDOL-3-YL)METHYL]-4-PIPERIDINYL}PHENYL)PROPANAMIDE: Prepared by Procedure D and Scheme N using 2-methyl-N-[3-(4-piperidinyl)phenyl]propanamide and 5-methyl-2-phenyl-1H-indole: ESMS m/e: 466.2 (M+H)$^+$.

EXAMPLE 438

2-METHYL-N-[3-(1-{[1-(4-NITROPHENYL)-1H-INDOL-3-YL]METHYL}-4-PIPERIDINYL)PHENYL]PROPANAMIDE: Prepared by Procedure D and Scheme N using 2-methyl-N-[3-(4-piperidinyl)phenyl]propanamide and 1-(4-nitrophenyl)-1H-indole: ESMS m/e: 497.2 (M+H)$^+$.

EXAMPLE 439

N-[3-(1-{[1-(2-FLUOROPHENYL)-1H-INDOL-3-YL]METHYL}-4-PIPERIDINYL)PHENYL]-2-METHYLPROPANAMIDE: Prepared by Procedure D and Scheme N using 2-methyl-N-[3-(4-piperidinyl)phenyl]propanamide and 1-(2-fluorophenyl)-1H-indole: ESMS m/e: 470.1 (M+H)$^+$.

EXAMPLE 440

N-(3-{1-[(5,6-DIMETHOXY-1H-INDOL-3-YL)METHYL]-4-PIPERIDINYL}PHENYL)-2-METHYLPROPANAMIDE: Prepared by Procedure D and Scheme N using 2-methyl-N-[3-(4-piperidinyl)phenyl]propanamide and 5,6-dimethoxy-1H-indole: ESMS m/e: 436.2 (M+H)$^+$.

EXAMPLE 441

2-METHYL-N-[3-(1-{[1-(3-METHYLPHENYL)-1H-INDOL-3-YL]METHYL}-4-PIPERIDINYL)PHENYL]PROPANAMIDE: Prepared by Procedure D and Scheme N using 2-methyl-N-[3-(4-piperidinyl)phenyl]propanamide and 1-(3-methylphenyl)-1H-indole: ESMS m/e: 466.2 (M+H)$^+$.

EXAMPLE 442

2-METHYL-N-{3-[1-({1-[3-(TRIFLUOROMETHYL)PHENYL]-1H-INDOL-3-YL}METHYL)-4-PIPERIDINYL]PHENYL}PROPANAMIDE: Prepared by Procedure D and Scheme N using 2-methyl-N-[3-(4-piperidinyl)phenyl]propanamide and 1-[3-(trifluoromethyl)phenyl]-1H-indole: ESMS m/e: 520.2 (M+H)$^+$.

EXAMPLE 443

N-[3-(1-{[1-(4-METHOXYPHENYL)-1H-INDOL-3-YL]METHYL}-4-PIPERIDINYL)PHENYL]-2-METHYLPROPANAMIDE: Prepared by Procedure D and Scheme N using 2-methyl-N-[3-(4-piperidinyl)phenyl]propanamide and 1-(4-methoxyphenyl)-1H-indole: ESMS m/e: 482.2 (M+H)$^+$.

EXAMPLE 444

N-(3-{1-[(5-METHOXY-2-PHENYL-1H-INDOL-3-YL)METHYL]-4-PIPERIDINYL}PHENYL)-2-METHYLPROPANAMIDE: Prepared by Procedure D and Scheme N using 2-methyl-N-[3-(4-piperidinyl)phenyl]propanamide and 5-methoxy-2-phenyl-1H-indole: ESMS m/e: 482.2 (M+H)$^+$.

EXAMPLE 445

2-METHYL-N-(3-{1-[(5-METHYL-1H-INDOL-3-YL)METHYL]-4-PIPERIDINYL}PHENYL)PROPANAMIDE: Prepared by Procedure D and Scheme N using 2-methyl-N-[3-(4-piperidinyl)phenyl]propanamide and 5-methyl-1H-indole: ESMS m/e: 390.2 (M+H)$^+$.

EXAMPLE 446

N-[3-(1-{[1-(2-NITROPHENYL)-1H-INDOL-3-YL]METHYL}-4-PIPERIDINYL)PHENYL]-2-METHYLPROPANAMIDE: Prepared by Procedure D and Scheme N using 1-(2-nitrophenyl)-1H-indole and 2-methyl-N-[3-(4-piperidinyl)phenyl]propanamide: ESMS m/e: 497.2 (M+H)$^+$.

EXAMPLE 447

N-[3-(1-{[1-(2-METHOXYPHENYL)-1H-INDOL-3-YL]METHYL}-4-PIPERIDINYL)PHENYL]-2-METHYLPROPANAMIDE: Prepared by Procedure D and Scheme N using 1-(2-methoxyphenyl)-1H-indole and 2-methyl-N-[3-(4-piperidinyl)phenyl]propanamide: ESMS m/e: 482.2 (M+H)$^+$.

EXAMPLE 448

N-(3-{1-[(5-METHOXY-1H-INDOL-3-YL)METHYL]-4-PIPERIDINYL}PHENYL)-2-METHYLPROPANAMIDE: Prepared by Procedure D and Scheme N using 1H-indol-5-yl methyl ether and 2-methyl-N-[3-(4-piperidinyl)phenyl]propanamide: ESMS m/e: 406.2 (M+H)$^+$.

EXAMPLE 450

N-[3-(1-{[1-(4-FLUOROPHENYL)-1H-INDOL-3-YL]METHYL}-4-PIPERIDINYL)PHENYL]-2-METHYLPROPANAMIDE: Prepared by Procedure D and Scheme N using 1-(4-fluorophenyl)-1H-indole and 2-methyl-N-[3-(4-piperidinyl)phenyl]propanamide: ESMS m/e: 470.2 (M+H)$^+$.

EXAMPLE 451

N-[3-(1-{[1-(3-METHOXYPHENYL)-1H-INDOL-3-YL]METHYL}-4-PIPERIDINYL)PHENYL]-2-METHYLPROPANAMIDE: Prepared by Procedure D and Scheme N using 1-(3-methoxyphenyl)-1H-indole and 2-methyl-N-[3-(4-piperidinyl)phenyl]propanamide: ESMS m/e: 482.2 (M+H)$^+$.

EXAMPLE 452

2-METHYL-N-[3-(1-{[1-(2-METHYLPHENYL)-1H-INDOL-3-YL]METHYL}-4-PIPERIDINYL)PHENYL]PROPANAMIDE: Prepared by Procedure D and Scheme N using 1-(2-methylphenyl)-1H-indole and 2-methyl-N-[3-(4-piperidinyl)phenyl]propanamide: ESMS m/e: 466.2 (M+H)$^+$.

EXAMPLE 453

ETHYL 3-({4-[3-(ISOBUTYRYLAMINO)PHENYL]-1-PIPERIDINYL}METHYL)-5-METHOXY-1H-INDOLE-2-CARBOXYLATE: Prepared by Procedure D and Scheme N using ethyl 5-methoxy-1H-indole-2-carboxylate and 2-methyl-N-[3-(4-piperidinyl)phenyl]propanamide: ESMS m/e: 478.2 (M+H)$^+$.

EXAMPLE 454

N-(3-{1-[(5-FLUORO-1H-INDOL-3-YL)METHYL]-4-PIPERIDINYL}PHENYL)-2-METHYLPROPANAMIDE:

Prepared by Procedure D and Scheme N using 5-fluoro-1H-indole and 2-methyl-N-[3-(4-piperidinyl)phenyl]propanamide: ESMS m/e: 394.2 (M+H)+.

1-PHENYL-1H-INDOLE: Prepared by Procedure C and Scheme O using 1H-indole and iodobenzene: ESMS m/e: 193.9 (M+H)+.

1-(4-CHLOROPHENYL)-1H-INDOLE: Prepared by Procedure C and Scheme O using 1H-indole and 1-chloro-4-iodobenzene: ESMS m/e: 227.9 (M+H)+.

1-(3-CHLOROPHENYL)-1H-INDOLE: Prepared by Procedure C and Scheme O using 1H-indole and 1-chloro-3-iodobenzene: ESMS m/e: 227.9 (M+H)+.

1-(2-CHLOROPHENYL)-1H-INDOLE: Prepared by Procedure C and Scheme O using 1H-indole and 1-chloro-2-iodobenzene: ESMS m/e: 227.9 (M+H)+.

1-[2-(TRIFLUOROMETHYL)PHENYL]-1H-INDOLE: Prepared by Procedure C and Scheme O using 1H-indole and 1-iodo-2-(trifluoromethyl)benzene: ESMS m/e: 262.0 (M+H)+.

4-(1H-INDOL-1-YL)BENZONITRILE: Prepared by Procedure C and Scheme O using 1H-indole and 4-iodobenzonitrile: ESMS m/e: 219.0 (M+H)+.

1-(4-NITROPHENYL)-1H-INDOLE: Prepared by Procedure C and Scheme O using 1H-indole and 1-iodo-4-nitrobenzene: ESMS m/e: 238.2 (M+H)+.

1-(2-NITROPHENYL)-1H-INDOLE: Prepared by Procedure C and Scheme O using 1H-indole and 1-iodo-2-nitrobenzene: ESMS m/e: 238.2 (M+H)+.

EXAMPLE 455

N-[3-(1-{[1-(4-CHLOROPHENYL)-1H-INDOL-3-YL]METHYL}-4-PIPERIDINYL)PHENYL]PROPANAMIDE: Prepared by Procedure D and Scheme N using 1-(4-chlorophenyl)-1H-indole and N-[3-(4-piperidinyl)phenyl]propanamide: ESMS m/e: 472.1 (M+H)+.

EXAMPLE 456

N-[3-(1-{[1-(3-CHLOROPHENYL)-1H-INDOL-3-YL]METHYL}-4-PIPERIDINYL)PHENYL]PROPANAMIDE: Prepared by Procedure D and Scheme N using 1-(3-chlorophenyl)-1H-indole and N-[3-(4-piperidinyl)phenyl]propanamide: ESMS m/e: 472.1 (M+H)+.

EXAMPLE 457

N-[3-(1-{[1-(2-CHLOROPHENYL)-1H-INDOL-3-YL]METHYL}-4-PIPERIDINYL)PHENYL]CYCLOPROPANECARBOXAMIDE: Prepared by Procedure D and Scheme N using 1-(2-chlorophenyl)-1H-indole and N-[3-(4-piperidinyl)phenyl]cyclopropanecarboxamide: ESMS m/e: 484.1 (M+H)+.

EXAMPLE 458

N-[3-(1-{[1-(3-CHLOROPHENYL)-1H-INDOL-3-YL]METHYL}-4-PIPERIDINYL)PHENYL]-2-METHYLPROPANAMIDE: Prepared by Procedure D and Scheme N using 1-(3-chlorophenyl)-1H-indole and 2-methyl-N-[3-(4-piperidinyl)phenyl]propanamide: ESMS m/e: 486.1 (M+H)+.

EXAMPLE 459

N-[3-(1-{[1-(4-CHLOROPHENYL)-1H-INDOL-3-YL]METHYL}-4-PIPERIDINYL)PHENYL]-2-METHYLPROPANAMIDE: Prepared by Procedure D and Scheme N using 1-(4-chlorophenyl)-1H-indole and 2-methyl-N-[3-(4-piperidinyl)phenyl]propanamide: ESMS m/e: 486.2 (M+H)+.

EXAMPLE 460

N-[3-(1-{[1-(2-CHLOROPHENYL)-1H-INDOL-3-YL]METHYL}-4-PIPERIDINYL)PHENYL]-2-METHYLPROPANAMIDE: Prepared by Procedure D and Scheme N using 1-(2-chlorophenyl)-1H-indole and 2-methyl-N-[3-(4-piperidinyl)phenyl]propanamide: ESMS m/e: 486.2 (M+H)+.

EXAMPLE 461

N-[3-(1-{[1-(2-CHLOROPHENYL)-1H-INDOL-3-YL]METHYL}-4-PIPERIDINYL)PHENYL]PROPANAMIDE: Prepared by Procedure D and Scheme N using 1-(2-chlorophenyl)-1H-indole and N-[3-(4-piperidinyl)phenyl]propanamide: ESMS m/e: 472.1 (M+H)+.

EXAMPLE 462

N-[3-(1-{[1-(4-CHLOROPHENYL)-1H-INDOL-3-YL]METHYL}-4-PIPERIDINYL)PHENYL]CYCLOPROPANECARBOXAMIDE: Prepared by Procedure D and Scheme N using 1-(4-chlorophenyl)-1H-indole and N-[3-(4-piperidinyl)phenyl]cyclopropanecarboxamide: ESMS m/e: 484.1 (M+H)+.

EXAMPLE 463

N-[3-(1-{[1-(3-CHLOROPHENYL)-1H-INDOL-3-YL]METHYL}-4-PIPERIDINYL)PHENYL]CYCLOPROPANECARBOXAMIDE: Prepared by Procedure D and Scheme N using 1-(3-chlorophenyl)-1H-indole and N-[3-(4-piperidinyl)phenyl]cyclopropanecarboxamide: ESMS m/e: 484.1 (M+H)+.

EXAMPLE 464

N-(3-{1-[(1-PHENYL-1H-INDOL-3-YL)METHYL]-4-PIPERIDINYL}PHENYL)PROPANAMIDE: Prepared by Procedure D and Scheme N using 1-phenyl-1H-indole and N-[3-(4-piperidinyl)phenyl]propanamide: ESMS m/e: 438.2 (M+H)+.

EXAMPLE 465

N-(3-{1-[(1-PHENYL-1H-INDOL-3-YL)METHYL]-4-PIPERIDINYL}PHENYL)CYCLOPROPANECARBOXAMIDE: Prepared by Procedure D and Scheme N using 1-phenyl-1H-indole and N-[3-(4-piperidinyl)phenyl]cyclopropanecarboxamide: ESMS m/e: 450.2 (M+H)+.

6-CHLORO-1-(4-NITROPHENYL)-1H-INDOLE: Prepared by Procedure C and Scheme O using 6-chloro-1H-indole and 1-iodo-4-nitrobenzene: ESMS m/e: 272.6 (M+H)+.

6-CHLORO-1-(2,3-DICHLOROPHENYL)-1H-INDOLE: Prepared by Procedure C and Scheme O using 6-chloro-1H-indole and 1,2-dichloro-3-iodobenzene: ESMS m/e: 296.5 (M+H)+.

6-CHLORO-1-(3-METHYLPHENYL)-1H-INDOLE: Prepared by Procedure C and Scheme O using 6-chloro-1H-indole and 1-iodo-3-methylbenzene: ESMS m/e: 241.9 (M+H)+.

6-CHLORO-1-(2-METHYLPHENYL)-1H-INDOLE: Prepared by Procedure C and Scheme O using 6-chloro-1H-indole and 1-iodo-2-methylbenzene: ESMS m/e: 241.9 (M+H)+.

2-(6-CHLORO-1H-INDOL-1-YL)PHENYL METHYL ETHER: Prepared by Procedure C and Scheme O using 6-chloro-1H-indole and 1-iodo-2-methoxybenzene: ESMS m/e: 257.9 (M+H)$^+$.

6-CHLORO-1-[3-(TRIFLUOROMETHYL)PHENYL]-1H-INDOLE: Prepared by Procedure C and Scheme O using 6-chloro-1H-indole and 1-iodo-3-(trifluoromethyl)benzene: ESMS m/e: 295.6 (M+H)$^+$.

6-CHLORO-1-(2-FLUOROPHENYL)-1H-INDOLE: Prepared by Procedure C and Scheme O using 6-chloro-1H-indole and 1-fluoro-2-iodobenzene: ESMS m/e: 245.9 (M+H)$^+$.

6-CHLORO-1-(3-CHLOROPHENYL)-1H-INDOLE: Prepared by Procedure C and Scheme O using 6-chloro-1H-indole and 1-chloro-3-iodobenzene: ESMS m/e: 261.9 (M+H)$^+$.

6-CHLORO-1-(4-CHLOROPHENYL)-1H-INDOLE: Prepared by Procedure C and Scheme O using 6-chloro-1H-indole and 1-chloro-4-iodobenzene: ESMS m/e: 262.9 (M+H)$^+$.

6-CHLORO-1-(2-CHLOROPHENYL)-1H-INDOLE: Prepared by Procedure C and Scheme O using 6-chloro-1H-indole and 1-chloro-2-iodobenzene: ESMS m/e: 262.9 (M+H)$^+$.

3-(6-CHLORO-1H-INDOL-1-YL)PHENYL METHYL ETHER: Prepared by Procedure C and Scheme O using 6-chloro-1H-indole and 1-iodo-3-methoxybenzene: ESMS m/e: 257.9 (M+H)$^+$.

6-CHLORO-1-[4-(TRIFLUOROMETHYL)PHENYL]-1H-INDOLE: Prepared by Procedure C and Scheme O using 6-chloro-1H-indole and 1-iodo-4-(trifluoromethyl)benzene ESMS m/e: 295.6 (M+H)$^+$.

6-CHLORO-1-(4-METHYLPHENYL)-1H-INDOLE: Prepared by Procedure C and Scheme O using 6-chloro-1H-indole and 1-iodo-4-methylbenzene: ESMS m/e: 241.9 (M+H)$^+$.

6-CHLORO-1-(4-FLUOROPHENYL)-1H-INDOLE: Prepared by Procedure C and Scheme O using 6-chloro-1H-indole and 1-fluoro-4-iodobenzene: ESMS m/e: 245.9 (M+H)$^+$.

EXAMPLE 466

N-[3-(1-{[6-CHLORO-1-(4-FLUOROPHENYL)-1H-INDOL-3-YL]METHYL}-4-PIPERIDINYL)PHENYL] CYCLOPROPANECARBOXAMIDE: Prepared by Procedure D and Scheme N using 6-chloro-1-(4-fluorophenyl)-1H-indole and N-[3-(4-piperidinyl)phenyl] cyclopropanecarboxamide: ESMS m/e: 502.1 (M+H)$^+$.

EXAMPLE 467

N-[3-(1-{[6-CHLORO-1-(4-FLUOROPHENYL)-1H-INDOL-3-YL]METHYL}-4-PIPERIDINYL)PHENYL] PROPANAMIDE: Prepared by Procedure D and Scheme N using 6-chloro-1-(4-fluorophenyl)-1H-indole and N-[3-(4-piperidinyl)phenyl]propanamide: ESMS m/e: 490.1 (M+H)$^+$.

EXAMPLE 468

N-(3-{1-[(6-FLUORO-1H-INDOL-3-YL)METHYL]-4-PIPERIDINYL}PHENYL)PROPANAMIDE: Prepared by Procedure D and Scheme N using 6-fluoro-1H-indole and N-[3-(4-piperidinyl)phenyl]propanamide: ESMS m/e: 380.1 (M+H)$^+$.

EXAMPLE 469

N-(3-{1-[(6-FLUORO-1H-INDOL-3-YL)METHYL]-4-PIPERIDINYL}PHENYL) CYCLOPROPANECARBOXAMIDE: Prepared by Procedure D and Scheme N using 6-fluoro-1H-indole and N-[3-(4-piperidinyl)phenyl]cyclopropanecarboxamide: ESMS m/e: 392.1 (M+H)$^+$.

EXAMPLE 470

N-(3-{1-[(6-FLUORO-1H-INDOL-3-YL)METHYL]-4-PIPERIDINYL}PHENYL)-2-METHYLPROPANAMIDE: Prepared by Procedure D and Scheme N using 6-fluoro-1H-indole and 2-methyl-N-[3-(4-piperidinyl)phenyl] propanamide: ESMS m/e: 394.1 (M+H)$^+$.

EXAMPLE 471

N-[3-(1-{[6-CHLORO-1-(4-FLUOROPHENYL)-1H-INDOL-3-YL]METHYL}-4-PIPERIDINYL)PHENYL]-2-METHYLPROPANAMIDE: Prepared by Procedure D and Scheme N using 6-chloro-1-(4-fluorophenyl)-1H-indole and 2-methyl-N-[3-(4-piperidinyl)phenyl]propanamide: ESMS m/e: 504.1 (M+H)$^+$.

EXAMPLE 472

N-[3-(1-{[6-CHLORO-1-(2-FLUOROPHENYL)-1H-INDOL-3-YL]METHYL}-4-PIPERIDINYL)PHENYL] PROPANAMIDE: Prepared by Procedure D and Scheme N using 6-chloro-1-(2-fluorophenyl)-1H-indole and N-[3-(4-piperidinyl)phenyl]propanamide: ESMS m/e: 490.1 (M+H)$^+$.

EXAMPLE 473

N-[3-(1-{[6-CHLORO-1-(2-FLUOROPHENYL)-1H-INDOL-3-YL]METHYL}-4-PIPERIDINYL)PHENYL] CYCLOPROPANECARBOXAMIDE: Prepared by Procedure D and Scheme N using 6-chloro-1-(2-fluorophenyl)-1H-indole and N-[3-(4-piperidinyl)phenyl] cyclopropanecarboxamide: ESMS m/e: 502.1 (M+H)$^+$.

EXAMPLE 474

N-[3-(1-{[6-CHLORO-1-(2-FLUOROPHENYL)-1H-INDOL-3-YL]METHYL}-4-PIPERIDINYL)PHENYL]-2-METHYLPROPANAMIDE: Prepared by Procedure D and Scheme N using 6-chloro-1-(2-fluorophenyl)-1H-indole and 2-methyl-N-[3-(4-piperidinyl)phenyl]propanamide ESMS m/e: 504.1 (M+H)$^+$.

EXAMPLE 475

N-[3-(1-{[6-CHLORO-1-(4-CHLOROPHENYL)-1H-INDOL-3-YL]METHYL}-4-PIPERIDINYL)PHENYL] PROPANAMIDE: Prepared by Procedure D and Scheme N using 6-chloro-1-(4-chlorophenyl)-1H-indole and N-[3-(4-piperidinyl)phenyl]propanamide ESMS m/e: 506.1 (M+H)$^+$.

EXAMPLE 476

N-[3-(1-{[6-CHLORO-1-(4-CHLOROPHENYL)-1H-INDOL-3-YL]METHYL}-4-PIPERIDINYL)PHENYL] CYCLOPROPANECARBOXAMIDE: Prepared by Procedure D and Scheme N using 6-chloro-1-(4-chlorophenyl)-1H-indole and N-[3-(4-piperidinyl)phenyl] cyclopropanecarboxamide ESMS m/e: 518.1 (M+H)$^+$.

EXAMPLE 477

N-[3-(1-{[6-CHLORO-1-(4-CHLOROPHENYL)-1H-INDOL-3-YL]METHYL}-4-PIPERIDINYL)PHENYL]-2-METHYLPROPANAMIDE: Prepared by Procedure D and Scheme N using 6-chloro-1-(4-chlorophenyl)-1H-indole and 2-methyl-N-[3-(4-piperidinyl)phenyl]propanamide ESMS m/e: 520.1 (M+H)$^+$.

EXAMPLE 478

N-[3-(1-{[6-CHLORO-1-(3-CHLOROPHENYL)-1H-INDOL-3-YL]METHYL}-4-PIPERIDINYL)PHENYL] PROPANAMIDE: Prepared by Procedure D and Scheme N using 6-chloro-1-(3-chlorophenyl)-1H-indole and N-[3-(4-piperidinyl)phenyl]propanamide: ESMS m/e: 506.1 (M+H)$^+$.

EXAMPLE 479

N-[3-(1-{[6-CHLORO-1-(3-CHLOROPHENYL)-1H-INDOL-3-YL]METHYL}-4-PIPERIDINYL)PHENYL] CYCLOPROPANECARBOXAMIDE: Prepared by Procedure D and Scheme N using 6-chloro-1-(3-chlorophenyl)-1H-indole and N-[3-(4-piperidinyl)phenyl] cyclopropanecarboxamide: $^1$H NMR (400 MHz, CDCl$_3$) δ 7.72 (d, 1H, J=8.4 Hz), 7.68 (s, 1H), 7.49 (m, 2H), 7.44 (d, 2H, J=7.9 Hz), 7.49–7.25 (m, 4H), 7.21 (d, 1H, J=7.9 Hz), 7.17 (d, 1H, J=7.9 Hz), 6.93 (d, 1H, J=7.9 Hz), 3.79 (s, 2H), 3.13 (d, 2H, J=9.4 Hz), 2.48 (sept, 1H, J=7.5 Hz), 2.16 (m, 2H), 1.80 (m, 4H), 1.51 (s, 1H), 1.06 (m, 2H), 0.806 (m, 2H); Anal. Calcd for C$_{30}$H$_{29}$Cl$_2$N$_3$O+HCl+1.4H$_2$O: C, 62.11; H, 5.70; N, 7.24. Found: C, 62.19; H, 6.21; N, 7.06; ESMS m/e: 519.2 (M+H)$^+$.

EXAMPLE 480

N-[3-(1-{[6-CHLORO-1-(3-CHLOROPHENYL)-1H-INDOL-3-YL]METHYL}-4-PIPERIDINYL)PHENYL]-2-METHYLPROPANAMIDE: Prepared by Procedure D and Scheme N using 6-chloro-1-(3-chlorophenyl)-1H-indole and 2-methyl-N-[3-(4-piperidinyl)phenyl]propanamide: ESMS m/e: 520.1 (M+H)$^+$.

EXAMPLE 481

N-(3-{1-[(5-FLUORO-1H-INDOL-3-YL)METHYL]-4-PIPERIDINYL}PHENYL) CYCLOPROPANECARBOXAMIDE: Prepared by Procedure D and Scheme N using 5-fluoro-1H-indole and N-[3-(4-piperidinyl)phenyl]cyclopropanecarboxamide: ESMS m/e: 392.1 (M+H)$^+$.

EXAMPLE 482

N-[3-(1-{[6-CHLORO-1-(2-CHLOROPHENYL)-1H-INDOL-3-YL]METHYL}-4-PIPERIDINYL)PHENYL]-2-METHYLPROPANAMIDE: Prepared by Procedure D and Scheme N using 6-chloro-1-(2-chlorophenyl)-1H-indole and 2-methyl-N-[3-(4-piperidinyl)phenyl]propanamide: ESMS m/e: 520.2 (M+H)$^+$.

EXAMPLE 483

N-[3-(1-{[6-CHLORO-1-(3-METHOXYPHENYL)-1H-INDOL-3-YL]METHYL}-4-PIPERIDINYL)PHENYL]-2-METHYLPROPANAMIDE: Prepared by Procedure D and Scheme N using 3-(6-chloro-1H-indol-1-yl)phenyl methyl ether and 2-methyl-N-[3-(4-piperidinyl)phenyl] propanamide: ESMS m/e: 516.2 (M+H)$^+$.

EXAMPLE 484

N-[3-(1-{[6-CHLORO-1-(2-METHOXYPHENYL)-1H-INDOL-3-YL]METHYL}-4-PIPERIDINYL)PHENYL]-2-METHYLPROPANAMIDE: Prepared by Procedure D and Scheme N using 2-(6-chloro-1H-indol-1-yl)phenyl methyl ether and 2-methyl-N-[3-(4-piperidinyl)phenyl] propanamide: ESMS m/e: 516.2 (M+H)$^+$.

EXAMPLE 485

N-[3-(1-{[6-CHLORO-1-(2,3-DICHLOROPHENYL)-1H-INDOL-3-YL]METHYL}-4-PIPERIDINYL) PHENYL]-2-METHYLPROPANAMIDE: Prepared by Procedure D and Scheme N using 6-chloro-1-(2,3-dichlorophenyl)-1H-indole and 2-methyl-N-[3-(4-piperidinyl)phenyl]propanamide: ESMS m/e: 555.1 (M+H)$^+$.

EXAMPLE 486

N-[3-(1-{[6-CHLORO-1-(4-METHYLPHENYL)-1H-INDOL-3-YL]METHYL}-4-PIPERIDINYL)PHENYL]-2-METHYLPROPANAMIDE: Prepared by Procedure D and Scheme N using 6-chloro-1-(4-methylphenyl)-1H-indole and 2-methyl-N-[3-(4-piperidinyl)phenyl]propanamide: ESMS m/e: 500.2 (M+H)$^+$.

EXAMPLE 487

N-{3-[1-({6-CHLORO-1-[3-(TRIFLUOROMETHYL) PHENYL]-1H-INDOL-3-YL}METHYL)-4-PIPERIDINYL]PHENYL}-2-METHYLPROPANAMIDE: Prepared by Procedure D and Scheme N using 6-chloro-1-[3-(trifluoromethyl)phenyl]-1H-indole and 2-methyl-N-[3-(4-piperidinyl)phenyl]propanamide: ESMS m/e: 554.2 (M+H)$^+$.

EXAMPLE 488

N-{3-[1-({6-CHLORO-1-[4-(TRIFLUOROMETHYL) PHENYL]-1H-INDOL-3-YL}METHYL)-4-PIPERIDINYL]PHENYL}-2-METHYLPROPANAMIDE: Prepared by Procedure D and Scheme N using 6-chloro-1-[4-(trifluoromethyl)phenyl]-1H-indole and 2-methyl-N-[3-(4-piperidinyl)phenyl]propanamide: ESMS m/e: 554.2 (M+H)$^+$.

EXAMPLE 489

N-[3-(1-{[6-CHLORO-1-(2-METHYLPHENYL)-1H-INDOL-3-YL]METHYL}-4-PIPERIDINYL)PHENYL]-2-METHYLPROPANAMIDE: Prepared by Procedure D and Scheme N using 6-chloro-1-(2-methylphenyl)-1H-indole and 2-methyl-N-[3-(4-piperidinyl)phenyl]propanamide: ESMS m/e: 500.2 (M+H)$^+$.

EXAMPLE 490

N-[3-(1-{[6-CHLORO-1-(3-METHYLPHENYL)-1H-INDOL-3-YL]METHYL}-4-PIPERIDINYL)PHENYL]-2-METHYLPROPANAMIDE: Prepared by Procedure D and Scheme N using 6-chloro-1-(3-methylphenyl)-1H-indole and 2-methyl-N-[3-(4-piperidinyl)phenyl]propanamide: ESMS m/e: 500.2 (M+H)$^+$.

EXAMPLE 491

N-(3-{1-[(7-CHLORO-1H-INDOL-3-YL)METHYL]-4-PIPERIDINYL}PHENYL) CYCLOPROPANECARBOXAMIDE: Prepared by Procedure D and Scheme N using 7-chloro-1H-indole and N-[3-(4-piperidinyl)phenyl]cyclopropanecarboxamide: ESMS m/e: 408.1 (M+H)$^+$.

EXAMPLE 492

N-(3-{1-[(7-CHLORO-1H-INDOL-3-YL)METHYL]-4-PIPERIDINYL}PHENYL)-2-METHYLPROPANAMIDE:

Prepared by Procedure D and Scheme N using 7-chloro-1H-indole and 2-methyl-N-[3-(4-piperidinyl)phenyl]propanamide: ESMS m/e: 410.1 (M+H)+.

EXAMPLE 493

N-(3-{1-[(4-FLUORO-1H-INDOL-3-YL)METHYL]-4-PIPERIDINYL}PHENYL)PROPANAMIDE: Prepared by Procedure D and Scheme N using 4-fluoro-1H-indole and N-[3-(4-piperidinyl)phenyl]propanamide: ESMS m/e: 380.2 (M+H)+.

EXAMPLE 494

N-(3-{1-[(7-CHLORO-1H-INDOL-3-YL)METHYL]-4-PIPERIDINYL}PHENYL)PROPANAMIDE: Prepared by Procedure D and Scheme N using 7-chloro-1H-indole and N-[3-(4-piperidinyl)phenyl]propanamide: ESMS m/e: 396.1 (M+H)+.

EXAMPLE 495

2-METHYL-N-(3-{1-[(6-METHYL-1H-INDOL-3-YL)METHYL]-4-PIPERIDINYL}PHENYL)PROPANAMIDE: Prepared by Procedure D and Scheme N using 6-methyl-1H-indole and 2-methyl-N-[3-(4-piperidinyl)phenyl]propanamide: ESMS m/e: 390.2 (M+H)+.

EXAMPLE 496

N-[3-(1-{[6-(BENZYLOXY)-1H-INDOL-3-YL]METHYL}-4-PIPERIDINYL)PHENYL]-2-METHYLPROPANAMIDE: Prepared by Procedure D and Scheme N using 6-(benzyloxy)-1H-indole and 2-methyl-N-[3-(4-piperidinyl)phenyl]propanamide: ESMS m/e: 482.2 (M+H)+.

EXAMPLE 497

N-(3-{1-[(6-METHOXY-1H-INDOL-3-YL)METHYL]-4-PIPERIDINYL}PHENYL)-2-METHYLPROPANAMIDE: Prepared by Procedure D and Scheme N using 1H-indol-6-yl methyl ether and 2-methyl-N-[3-(4-piperidinyl)phenyl]propanamide: ESMS m/e: 406.2 (M+H)+.

EXAMPLE 498

METHYL 3-({4-[3-(ISOBUTYRYLAMINO)PHENYL]-1-PIPERIDINYL}METHYL)-1H-INDOLE-6-CARBOXYLATE: Prepared by Procedure D and Scheme N using methyl 1H-indole-6-carboxylate and 2-methyl-N-[3-(4-piperidinyl)phenyl]propanamide: ESMS m/e: 434.2 (M+H)+.

EXAMPLE 499

2-METHYL-N-[3-(1-{[6-(TRIFLUOROMETHYL)-1H-INDOL-3-YL]METHYL}-4-PIPERIDINYL)PHENYL]PROPANAMIDE: Prepared by Procedure D and Scheme N using 6-(trifluoromethyl)-1H-indole and 2-methyl-N-[3-(4-piperidinyl)phenyl]propanamide: $^1$H NMR (400 MHz, CDCl$_3$) δ 8.11 (s, 1H), 7.66 (s, 1H), 7.63 (s, 2H), 7.44 (d, 1H, J=8.4 Hz), 7.39 (s, 2H), 7.32 (d, 1H, J=8.4 Hz), 7.16 (t, 1H, J=8.4 Hz), 6.84 (d, 1H, J=8.4 Hz), 4.06 (s, 2H), 3.27 (d, 2H, J=11.6 Hz), 2.56 (sept, 1H, J=6.8 Hz), 2.37 (m, 3H), 1.93 (m, 2H), 1.75 (m, 2H), 1.22 (d, 6H, J=6.8 Hz); Anal. Calcd for C$_{25}$H$_{28}$F$_3$N$_3$O+2HCl+0.5EtOAc: C, 57.8; H, 6.11; N, 7.50. Found: C, 56.5; H, 6.46; N, 7.77; ESMS m/e: 444.2 (M+H)+.

1-(2-PYRIDINYL)-1H-INDOLE: Prepared by Procedure C and Scheme O using 2-iodopyridine and 1H-indole: ESMS m/e: 195.0 (M+H)+.

1-(3-PYRIDINYL)-1H-INDOLE: Prepared by Procedure C and Scheme O using 3-iodopyridine and 1H-indole: ESMS m/e: 195.0 (M+H)+.

EXAMPLE 500

2-METHYL-N-[3-(1-{[1-(3-PYRIDINYL)-1H-INDOL-3-YL]METHYL}-4-PIPERIDINYL)PHENYL]PROPANAMIDE: Prepared by Procedure D and Scheme N using 1-(3-pyridinyl)-1H-indole and 2-methyl-N-[3-(4-piperidinyl)phenyl]propanamide: ESMS m/e: 453.2 (M+H)+.

EXAMPLE 501

2-METHYL-N-[3-(1-{[1-(2-PYRIDINYL)-1H-INDOL-3-YL]METHYL}-4-PIPERIDINYL)PHENYL]PROPANAMIDE: Prepared by Procedure D and Scheme N using 1-(2-pyridinyl)-1H-indole and 2-methyl-N-[3-(4-piperidinyl)phenyl]propanamide: ESMS m/e: 453.2 (M+H)+.

EXAMPLE 502

N-(3-{1-[(6-FLUORO-1-PHENYL-1H-INDOL-3-YL)METHYL]-4-PIPERIDINYL}PHENYL)-2-METHYLPROPANAMIDE: Prepared by Procedure D and Scheme N using 6-fluoro-1-phenyl-1H-indole and 2-methyl-N-[3-(4-piperidinyl)phenyl]propanamide: ESMS m/e: 470.2 (M+H)+.

EXAMPLE 503

N-(3-{1-[(6-CHLORO-1-PHENYL-1H-INDOL-3-YL)METHYL]-4-PIPERIDINYL}PHENYL)-2-METHYLPROPANAMIDE: Prepared by Procedure D and Scheme N using 6-chloro-1-phenyl-1H-indole and 2-methyl-N-[3-(4-piperidinyl)phenyl]propanamide: ESMS m/e: 486.2 (M+H)+.

7-METHYL-1-PHENYL-1H-INDOLE: Prepared by Procedure C and Scheme O using 7-methyl-1H-indole and iodobenzene: ESMS m/e: 208.1 (M+H)+.

METHYL 1-PHENYL-1H-INDOLE-6-CARBOXYLATE: Prepared by Procedure C and Scheme O using methyl 1H-indole-6-carboxylate and iodobenzene: ESMS m/e: 252.0 (M+H)+.

6-METHYL-1-PHENYL-1H-INDOLE: Prepared by Procedure C and Scheme O using 6-methyl-1H-indole and iodobenzene: ESMS m/e: 208.0 (M+H)+.

7-CHLORO-1-PHENYL-1H-INDOLE: Prepared by Procedure C and Scheme O using 7-chloro-1H-indole and iodobenzene: ESMS m/e: 228.0 (M+H)+.

6-NITRO-1-PHENYL-1H-INDOLE: Prepared by Procedure C and Scheme O using 6-nitro-1H-indole and iodobenzene: ESMS m/e: 238.2 (M+H)+.

6-METHOXY-1-PHENYL-1H-INDOLE: Prepared by Procedure C and Scheme O using 1H-indol-6-yl methyl ether and iodobenzene: ESMS m/e: 224.0 (M+H)+.

BENZYL 1-PHENYL-1H-INDOL-6-YL ETHER: Prepared by Procedure C and Scheme O using 6-(benzyloxy)-1H-indole and iodobenzene: ESMS m/e: 300.0 (M+H)+.

1-PHENYL-1H-INDOL-6-YL TRIFLUOROMETHYL ETHER: Prepared by Procedure C and Scheme O using 6-(trifluoromethoxy)-1H-indole and iodobenzene: ESMS m/e: 278.0 (M+H)+.

7-METHOXY-1-PHENYL-1H-INDOLE: Prepared by Procedure C and Scheme O using 1H-indol-7-yl methyl ether and iodobenzene: ESMS m/e: 224.0 (M+H)+.

1-PHENYL-6-(TRIFLUOROMETHYL)-1H-INDOLE: Prepared by Procedure C and Scheme O using 6-(trifluoromethyl)-1H-indole and iodobenzene: ESMS m/e: 262.0 (M+H)$^+$.

1-(4-PYRIDINYL)-1H-INDOLE: Prepared by Procedure C and Scheme O using 1H-indole and 4-iodopyridine: ESMS m/e: 195 (M+H)$^+$.

EXAMPLE 504

N-[3-(1-{[6-(BENZYLOXY)-1-PHENYL-1H-INDOL-3-YL]METHYL}-4-PIPERIDINYL)PHENYL]-2-METHYLPROPANAMIDE: Prepared by Procedure D and Scheme N using benzyl 1-phenyl-1H-indol-6-yl ether and 2-methyl-N-[3-(4-piperidinyl)phenyl]propanamide: ESMS m/e: 558.0 (M+H)$^+$.

EXAMPLE 505

2-METHYL-N-(3-{1-[(6-METHYL-1-PHENYL-1H-INDOL-3-YL)METHYL]-4-PIPERIDINYL}PHENYL)PROPANAMIDE: Prepared by Procedure D and Scheme N using 6-methyl-1-phenyl-1H-indole and 2-methyl-N-[3-(4-piperidinyl)phenyl]propanamide: $^1$H NMR (400 MHz, CDCl$_3$) δ 7.66 (s, 1H), 7.64 (d, 1H, J=7.8 Hz), 7.51 (d, 1H, J=3.9 Hz), 7.50 (m, 3H), 7.4 (m, 2H), 7.36–7.32 (m, 2H), 7.31 (s, 1H), 7.19 (t, 1H, J=7.8 Hz), 7.04 (d, 1H, J=7.8 Hz), 6.91 (d, 1H, J=7.8 Hz), 3.94 (s, 2H), 3.25 (d, 2H, J=9.2 Hz), 2.52 (sept, 1H, J=6.4 Hz), 2.46 (s, 3H), 2.28 (dt, 2H, J=11.8, 2.6 Hz), 1.89 (dq, 2H, J=2.9 Hz), 1.80 (m, 3H), 1.22 (d, 6H, J=6.9 Hz); Anal. Calcd for C$_{31}$H$_{35}$N$_3$O+HCl+0.6EtOAc: C, 72.2; H, 7.41; N, 7.57. Found: C, 71.0; H, 7.40; N, 7.66; ESMS m/e: 466 (M+H)$^+$.

EXAMPLE 506

METHYL 3-({4-[3-(ISOBUTYRYLAMINO)PHENYL]-1-PIPERIDINYL}METHYL)-1-PHENYL-1H-INDOLE-6-CARBOXYLATE: Prepared by Procedure D and Scheme N using methyl 1-phenyl-1H-indole-6-carboxylate and 2-methyl-N-[3-(4-piperidinyl)phenyl]propanamide: ESMS m/e: 510.0 (M+H)$^+$.

EXAMPLE 507

2-METHYL-N-(3-{1-[(6-NITRO-1H-INDOL-3-YL)METHYL]-4-PIPERIDINYL}PHENYL)PROPANAMIDE: Prepared by Procedure D and Scheme N using 6-nitro-1H-indole and 2-methyl-N-[3-(4-piperidinyl)phenyl]propanamide: ESMS m/e: 421.0 (M+H)$^+$.

EXAMPLE 508

2-METHYL-N-[3-(1-{[1-PHENYL-6-(TRIFLUOROMETHYL)-1H-INDOL-3-YL]METHYL}-4-PIPERIDINYL)PHENYL]PROPANAMIDE: Prepared by Procedure D and Scheme N using 1-phenyl-6-(trifluoromethyl)-1H-indole and 2-methyl-N-[3-(4-piperidinyl)phenyl]propanamide: ESMS m/e: 520.0 (M+H)$^+$.

EXAMPLE 509

2-METHYL-N-(3-{1-[(7-METHYL-1-PHENYL-1H-INDOL-3-YL)METHYL]-4-PIPERIDINYL}PHENYL)PROPANAMIDE: Prepared by Procedure D and Scheme N using 7-methyl-1-phenyl-1H-indole and 2-methyl-N-[3-(4-piperidinyl)phenyl]propanamide: ESMS m/e: 466.0 (M+H)$^+$.

EXAMPLE 510

N-(3-{1-[(7-METHOXY-1H-INDOL-3-YL)METHYL]-4-PIPERIDINYL}PHENYL)-2-METHYLPROPANAMIDE: Prepared by Procedure D and Scheme N using 1H-indol-7-yl methyl ether and 2-methyl-N-[3-(4-piperidinyl)phenyl]propanamide: ESMS m/e: 406.0 (M+H)$^+$.

EXAMPLE 511

N-(3-{1-[(7-METHOXY-1-PHENYL-1H-INDOL-3-YL)METHYL]-4-PIPERIDINYL}PHENYL)-2-METHYLPROPANAMIDE: Prepared by Procedure D and Scheme N using 7-methoxy-1-phenyl-1H-indole and 2-methyl-N-[3-(4-piperidinyl)phenyl]propanamide: ESMS m/e: 482.0 (M+H)$^+$.

EXAMPLE 512

N-(3-{1-[(7-CHLORO-1-PHENYL-1H-INDOL-3-YL)METHYL]-4-PIPERIDINYL}PHENYL)-2-METHYLPROPANAMIDE: Prepared by Procedure D and Scheme N using 7-chloro-1-phenyl-1H-indole and 2-methyl-N-[3-(4-piperidinyl)phenyl]propanamide: ESMS m/e: 488.6 (M+H)$^+$.

EXAMPLE 513

2-METHYL-N-(3-{1-[(7-NITRO-1H-INDOL-3-YL)METHYL]-4-PIPERIDINYL}PHENYL)PROPANAMIDE: Prepared by Procedure D and Scheme N using 7-nitro-1H-indole and 2-methyl-N-[3-(4-piperidinyl)phenyl]propanamide: ESMS m/e: 421.1 (M+H)$^+$.

EXAMPLE 514

N-(3-{1-[(7-NITRO-1H-INDOL-3-YL)METHYL]-4-PIPERIDINYL}PHENYL)CYCLOPROPANECARBOXAMIDE: Prepared by Procedure D and Scheme N using 7-nitro-1H-indole and N-[3-(4-piperidinyl)phenyl]cyclopropanecarboxamide: ESMS m/e: 419.5 (M+H)$^+$.

EXAMPLE 515

N-(3-{1-[(7-NITRO-1H-INDOL-3-YL)METHYL]-4-PIPERIDINYL}PHENYL)PROPANAMIDE: Prepared by Procedure D and Scheme N using 7-nitro-1H-indole and N-[3-(4-piperidinyl)phenyl]propanamide: ESMS m/e: 407.3. (M+H)$^+$.

7-(2-FLUOROPHENYL)-1H-INDOLE: Prepared by Procedure I and Scheme T using 7-bromo-1H-indole and 2-fluorophenylboronic acid: ESMS m/e: 211.9 (M+H)$^+$.

EXAMPLE 516

N-[3-(1-{[7-(2-FLUOROPHENYL)-1H-INDOL-3-YL]METHYL}-4-PIPERIDINYL)PHENYL]-2-METHYLPROPANAMIDE: Prepared by Procedure D and Scheme N. A solution of 2-methyl-N-[3-(4-piperidinyl)phenyl]propanamide (23.3 mg, 0.0948 mmol) and 37 wt % aqueous formaldehyde (11.4 mg, 0.142 mmol) in 1.00 mL of HOAc:dioxane (1:4) was added to 7-(2-fluorophenyl)-1H-indole (20.0 mg, 0.0948 mmol) and the reaction mixture was stirred for 12 h at room temperature. The resulting mixture was diluted with H$_2$O (10 mL). The aqueous layer was extracted with CH$_2$Cl$_2$ (3×10 mL). The combined organic extracts were washed with brine (10 mL), dried over MgSO$_4$, and concentrated in vacuo. The residue was purified by preparative TLC on silica using 4% of NH$_3$ (2.0 M in methanol) in CH$_2$Cl$_2$ to give the desired product (56.1 mg, 100%): $^1$H NMR (400 MHz, CDCl$_3$) δ 8.58 (s, 1H), 7.73 (dd, 1H, J=2.8, 6.3 Hz), 7.69 (s, 1H), 7.53 (dt, 1H, J=1.8, 7.6

Hz), 7.44 (d, 1H, J=8.1 Hz), 7.38 (m, 2H), 7.32 (s, 1H), 7.27–7.21 (m, 4H), 7.17 (t, 1H, J=7.6 Hz), 6.88 (d, 1H, J=7.6 Hz), 3.92 (s, 2H); 3.20 (d, 1H, J=11.6 Hz), 2.51 (qt, 1H, J=6.7 Hz), 2.42 (m, 1H), 2.25 (dt, 2H, J=2.2, 11.6 Hz), 1.89–1.72 (m, 5H), 1.22 (d, 6H, J=7.3 Hz); ESMS m/e: 470.1 (M+H)+.

7-(4-ETHYLPHENYL)-1H-INDOLE: Prepared by Procedure I and Scheme T using 7-bromo-1H-indole and 4-ethylphenylboronic acid: ESMS m/e: 222.0 (M+H)+.

7-(2-NAPHTHYL)-1H-INDOLE: Prepared by Procedure I and Scheme T using 7-bromo-1H-indole and 2-naphthylboronic acid: ESMS m/e: 244.0 (M+H)+.

7-(3-CHLOROPHENYL)-1H-INDOLE: Prepared by Procedure I and Scheme T using 7-bromo-1H-indole and 3-chlorophenylboronic acid: ESMS m/e: 227.9 (M+H)+.

6-(2-FLUOROPHENYL)-1H-INDOLE: Prepared by Procedure I and Scheme T using 6-bromo-1H-indole and 2-fluorophenylboronic acid: ESMS m/e: 211.9 (M+H)+.

7-(3-NITROPHENYL)-1H-INDOLE: Prepared by Procedure I and Scheme T using 7-bromo-1H-indole and 3-nitrophenylboronic acid: ESMS m/e: 238.9 (M+H)+.

1-[4-(1H-INDOL-7- YL)PHENYL]ETHANONE: Prepared by Procedure I and Scheme T using 7-bromo-1H-indole and 4-acetylphenylboronic acid: ESMS m/e: 235.2 (M+H)+.

6-(2-METHYLPHENYL)-1H-INDOLE: Prepared by Procedure I and Scheme T using 6-bromo-1H-indole and 2-methylphenylboronic acid: ESMS m/e: 207.9 (M+H)+.

6-(3-CHLOROPHENYL)-1H-INDOLE: Prepared by Procedure I and Scheme T using 6-bromo-1H-indole and 3-chlorophenylboronic acid: ESMS m/e: 227.9 (M+H)+.

1-[4-(1H-INDOL-6-YL)PHENYL]ETHANONE: Prepared by Procedure I and Scheme T using 6-bromo-1H-indole and 4-acetylphenylboronic acid: ESMS m/e: 235.8 (M+H)+.

7-(2-METHYLPHENYL)-1H-INDOLE: Prepared by Procedure I and Scheme T using 7-bromo-1H-indole and 2-methylphenylboronic acid: ESMS m/e: 208 (M+H)+.

6-(4-ETHYLPHENYL)-1H-INDOLE: Prepared by Procedure I and Scheme T using 6-bromo-1H-indole and 4-ethylphenylboronic acid: ESMS m/e: 221.9 (M+H)+.

EXAMPLE 517

2-METHYL-N-[3-(1-{[7-(2-NAPHTHYL)-1H-INDOL-3-YL]METHYL}-4-PIPERIDINYL)PHENYL]PROPANAMIDE: Prepared by Procedure D and Scheme N using 7-(2-naphthyl)-1H-indole and 2-methyl-N-[3-(4-piperidinyl)phenyl]propanamide: ESMS m/e: 502.2 (M+H)+.

EXAMPLE 518

N-[3-(1-{[7-(4-ETHYLPHENYL)-1H-INDOL-3-YL]METHYL}-4-PIPERIDINYL)PHENYL]-2-METHYLPROPANAMIDE: Prepared by Procedure D and Scheme N using 7-(4-ethylphenyl)-1H-indole and 2-methyl-N-[3-(4-piperidinyl)phenyl]propanamide: ESMS m/e: 480.2 (M+H)+.

EXAMPLE 519

2-METHYL-N-[3-(1-{[6-(2-METHYLPHENYL)-1H-INDOL-3-YL]METHYL}-4-PIPERIDINYL)PHENYL]PROPANAMIDE: Prepared by Procedure D and Scheme N using 6-(2-methylphenyl)-1H-indole and 2-methyl-N-[3-(4-piperidinyl)phenyl]propanamide: $^1$H NMR (400 MHz, CDCl$_3$) δ 8.2 (s, 1H), 7.53 (m, 4H), 7.41 (d, 1H, J=8.4 Hz), 7.34 (m, 2H), 7.27–7.12 (m, 5H), 6.81 (d, 1H, J=8.4 Hz), 4.09 (s, 2H), 3.32 (d, 2H, J=11.4 Hz), 2.57 (q, 2H, J=7.6 Hz), 2.43 (m, 3H), 2.08 (s, 3H), 1.98 (m, 1H), 1.75 (m, 2H), 1.22 (d, 6H, J=6.3 Hz); Anal. Calcd for C$_{31}$H$_{35}$N$_3$O+CHCl$_3$+DMF: C, 57.0; H, 6.09; N, 8.06. Found: C, 56.5; H, 5.94; N, 7.76; ESMS m/e: 466.2 (M+H)+.

EXAMPLE 520

N-[3-(1-{[7-(3-CHLOROPHENYL)-1H-INDOL-3-YL]METHYL}-4-PIPERIDINYL)PHENYL]-2-METHYLPROPANAMIDE: Prepared by Procedure D and Scheme N using 7-(3-chlorophenyl)-1H-indole and 2-methyl-N-[3-(4-piperidinyl)phenyl]propanamide: ESMS m/e: 486.1 (M+H)+.

EXAMPLE 521

2-METHYL-N-[3-(1-{[7-(3-NITROPHENYL)-1H-INDOL-3-YL]METHYL}-4-PIPERIDINYL)PHENYL]PROPANAMIDE: Prepared by Procedure D and Scheme N using 7-(3-nitrophenyl)-1H-indole and 2-methyl-N-[3-(4-piperidinyl)phenyl]propanamide: ESMS m/e: 497.0 (M+H)+.

EXAMPLE 522

N-[3-(1-{[7-(4-ACETYLPHENYL)-1H-INDOL-3-YL]METHYL}-4-PIPERIDINYL)PHENYL]-2-METHYLPROPANAMIDE: Prepared by Procedure D and Scheme N using 1-[4-(1H-indol-7-yl)phenyl]ethanone and 2-methyl-N-[3-(4-piperidinyl)phenyl]propanamide: ESMS m/e: 493.6 (M+H)+.

EXAMPLE 523

N-[3-(1-{[6-(4-ETHYLPHENYL)-1H-INDOL-3-YL]METHYL}-4-PIPERIDINYL)PHENYL]-2-METHYLPROPANAMIDE: Prepared by Procedure D and Scheme N using 6-(4-ethylphenyl)-1H-indole and 2-methyl-N-[3-(4-piperidinyl)phenyl]propanamide: ESMS m/e: 480.1 (M+H)+.

EXAMPLE 524

2-METHYL-N-[3-(1-{[7-(2-METHYLPHENYL)-1H-INDOL-3-YL]METHYL}-4-PIPERIDINYL)PHENYL]PROPANAMIDE: Prepared by Procedure D and Scheme N using 7-(2-methylphenyl)-1H-indole and 2-methyl-N-[3-(4-piperidinyl)phenyl]propanamide: ESMS m/e: 466.1 (M+H)+.

EXAMPLE 525

N-[3-(1-{[6-(2-FLUOROPHENYL)-1H-INDOL-3-YL]METHYL}-4-PIPERIDINYL)PHENYL]-2-METHYLPROPANAMIDE: Prepared by Procedure D and Scheme N using 6-(2-fluorophenyl)-1H-indole and 2-methyl-N-[3-(4-piperidinyl)phenyl]propanamide: ESMS m/e: 470.2 (M+H)+.

5-(4-METHYLPHENOXY)-1H-INDOLE: Prepared by Procedure J and Scheme U using 5-bromo-1H-indole and p-cresol: ESMS m/e: 224.0 (M+H)+.

EXAMPLE 526

N-(3-{1-[(5-BROMO-1H-INDOL-3-YL)METHYL]-4-PIPERIDINYL}PHENYL)-2-METHYLPROPANAMIDE: Prepared by Procedure D and Scheme N using 5-bromo-1H-indole and 2-methyl-N-[3-(4-piperidinyl)phenyl]propanamide: ESMS m/e: 454.0 (M+H)+.

1-(4-PYRIDINYL)-6-(TRIFLUOROMETHYL)-1H-INDOLE: Prepared by Procedure C and Scheme O using 6-(trifluoromethyl)-1H-indole and 4-iodopyridine: ESMS m/e: 262.9 (M+H)+.

EXAMPLE 527

2-METHYL-N-[3-(1-{[5-(4-METHYLPHENOXY)-1H-INDOL-3-YL]METHYL}-4-PIPERIDINYL)PHENYL]PROPANAMIDE: Prepared by Procedure D and Scheme N using 5-(4-methylphenoxy)-1H-indole and 2-methyl-N-[3-(4-piperidinyl)phenyl]propanamide: ESMS m/e: 481.9 (M+H)+.

1-(4-METHYLPHENYL)-1H-INDOLE: Prepared by Procedure C and Scheme O using 1H-indole and 1-iodo-4-methylbenzene: ESMS m/e: 208.0 (M+H)+.

1-(3-METHYLPHENYL)-1H-INDOLE: Prepared by Procedure C and Scheme O using 1H-indole and 1-iodo-3-methylbenzene: ESMS m/e: 208.0 (M+H)+.

1-[3-(TRIFLUOROMETHYL)PHENYL]-1H-INDOLE: Prepared by Procedure C and Scheme O using 1H-indole and 1-iodo-3-(trifluoromethyl)benzene: ESMS m/e: 262.0 (M+H)+.

1-(4-METHOXYPHENYL)-1H-INDOLE: Prepared by Procedure C and Scheme O using 1H-indole and 1-iodo-4-methoxybenzene: ESMS m/e: 224.0 (M+H)+.

1-(2-METHOXYPHENYL)-1H-INDOLE: Prepared by Procedure C and Scheme O using 1H-indole and 1-iodo-2-methoxybenzene: ESMS m/e: 224.0 (M+H)+.

1-(3-METHOXYPHENYL)-1H-INDOLE: Prepared by Procedure C and Scheme O using 1H-indole and 1-iodo-3-methoxybenzene: ESMS m/e: 224.0 (M+H)+.

1-(2-METHYLPHENYL)-1H-INDOLE: Prepared by Procedure C and Scheme O using 1H-indole and 1-iodo-2-methylbenzene: ESMS m/e: 208.0 (M+H)+.

6-FLUORO-1-PHENYL-1H-INDOLE: Prepared by Procedure C and Scheme O using 6-fluoro-1H-indole and iodobenzene: ESMS m/e: 212.0 (M+H)+.

6-CHLORO-1-PHENYL-1H-INDOLE: Prepared by Procedure C and Scheme O using 6-chloro-1H-indole and iodobenzene: ESMS m/e: 228.0 (M+H)+.

7-CHLORO-1-PHENYL-1H-INDOLE: Prepared by Procedure C and Scheme O using 7-chloro-1H-indole and iodobenzene: ESMS m/e: 228.0 (M+H)+.

6-(2-FLUOROPHENYL)-1H-INDOLE: Prepared by Procedure I and Scheme T using 6-bromo-1H-indole and 2-fluorophenylboronic acid: ESMS m/e: 211.9 (M+H)+.

EXAMPLE 528

2-METHYL-N-{3-[1-(7-OXO-7-PHENYLHEPTYL)-4-PIPERIDINYL]PHENYL}PROPANAMIDE: Prepared by Procedure K and Scheme B1 using 7-chloro-1-phenyl-1-heptanone and 2-methyl-N-[3-(4-piperidinyl)phenyl]propanamide: ESMS m/e: 435.1 (M+H)+.

EXAMPLE 529

2-METHYL-N-{3-[1-(6-OXO-6-PHENYLHEXYL)-4-PIPERIDINYL]PHENYL}PROPANAMIDE: Prepared by Procedure K and Scheme B1 using 6-chloro-1-phenyl-1-hexanone and 2-methyl-N-[3-(4-piperidinyl)phenyl]propanamide: Anal. Calcd for C27H36N2O2+0.1CHCl3: C, 75.3; H, 8.39; N, 6.46. Found: C, 75.4; H, 7.89; N, 6.18; ESMS m/e: 421.1 (M+H)+.

EXAMPLE 530

2-METHYL-N-{3-[1-(5-OXO-5-PHENYLPENTYL)-4-PIPERIDINYL]PHENYL}PROPANAMIDE: Prepared by Procedure K and Scheme B1 using 5-chloro-1-phenyl-1-pentanone and 2-methyl-N-[3-(4-piperidinyl)phenyl]propanamide: ESMS m/e: 407.1 (M+H)+.

EXAMPLE 531

N-(3-{1-[4-(4-METHOXYPHENYL)-4-OXOBUTYL]-4-PIPERIDINYL}PHENYL)PROPANAMIDE: Prepared by Procedure K and Scheme B1 using 4-chloro-1-(4-methoxyphenyl)-1-butanone and N-[3-(4-piperidinyl)phenyl]propanamide: ESMS m/e: 409.2 (M+H)+.

EXAMPLE 532

N-(3-{1-[4-(4-CHLOROPHENYL)-4-OXOBUTYL]-4-PIPERIDINYL}PHENYL)PROPANAMIDE: Prepared by Procedure K and Scheme B1 using 4-chloro-1-(4-chlorophenyl)-1-butanone and N-[3-(4-piperidinyl)phenyl]propanamide: ESMS m/e: 413.1 (M+H)+.

EXAMPLE 533

N-(3-{1-[4-(4-BROMOPHENYL)-4-OXOBUTYL]-4-PIPERIDINYL}PHENYL)PROPANAMIDE: Prepared by Procedure K and Scheme B1 using 1-(4-bromophenyl)-4-chloro-1-butanone and N-[3-(4-piperidinyl)phenyl]propanamide: ESMS m/e: 457.1 (M+H)+.

EXAMPLE 534

N-(3-{1-[4-(4-TERT-BUTYLPHENYL)-4-OXOBUTYL]-4-PIPERIDINYL}PHENYL)PROPANAMIDE: Prepared by Procedure K and Scheme B using 1-(4-tert-butylphenyl)-4-chloro-1-butanone and N-[3-(4-piperidinyl)phenyl]propanamide: ESMS m/e: 435.2 (M+H)+.

EXAMPLE 535

N-(3-{1-[4-(4-FLUOROPHENYL)-4-OXOBUTYL]-4-PIPERIDINYL}PHENYL)PROPANAMIDE: Prepared by Procedure K and Scheme B1 using 4-chloro-1-(4-fluorophenyl)-1-butanone and N-[3-(4-piperidinyl)phenyl]propanamide: ESMS m/e: 397.2 (M+H)+.

EXAMPLE 536

N-(3-{1-[4-OXO-4-(4-PHENOXYPHENYL)BUTYL]-4-PIPERIDINYL}PHENYL)PROPANAMIDE: Prepared by Procedure K and Scheme B1 using 4-chloro-1-(4-phenoxyphenyl)-1-butanone and N-[3-(4-piperidinyl)phenyl]propanamide: ESMS m/e: 471.2 (M+H)+.

EXAMPLE 537

N-(3-{1-[4-(4-ISOPROPYLPHENYL)-4-OXOBUTYL]-4-PIPERIDINYL}PHENYL)CYCLOPROPANECARBOXAMIDE: Prepared by Procedure K and Scheme B1 using 4-chloro-1-(4-isopropylphenyl)-1-butanone and N-[3-(4-piperidinyl)phenyl]cyclopropanecarboxamide: ESMS m/e: 433.2 (M+H)+.

EXAMPLE 538

N-(3-{1-[4-(4-METHOXYPHENYL)-4-OXOBUTYL]-4-PIPERIDINYL}PHENYL)CYCLOPROPANECARBOXAMIDE: Prepared by Procedure K and Scheme B1 using 4-chloro-1-(4-methoxyphenyl)-1-butanone and N-[3-(4-piperidinyl)phenyl]cyclopropanecarboxamide: ESMS m/e: 421.2 (M+H)+.

EXAMPLE 539

N-(3-{1-[4-OXO-4-(4-PHENOXYPHENYL)BUTYL]-4-PIPERIDINYL}PHENYL)CYCLOPROPANECARBOXAMIDE: Prepared by Procedure K and Scheme B1 using 4-chloro-1-(4-phenoxyphenyl)-1-butanone and N-[3-(4-piperidinyl)phenyl]cyclopropanecarboxamide: ESMS m/e: 483.2 (M+H)$^+$.

EXAMPLE 540

N-(3-{1-[4-(4-ISOPROPYLPHENYL)-4-OXOBUTYL]-4-PIPERIDINYL}PHENYL)PROPANAMIDE: Prepared by Procedure K and Scheme B1 using 4-chloro-1-(4-isopropylphenyl)-1-butanone and N-[3-(4-piperidinyl)phenyl]propanamide: ESMS m/e: 421.3 (M+H)$^+$.

EXAMPLE 541

N-(3-{1-[4-(4-TERT-BUTYLPHENYL)-4-OXOBUTYL]-4-PIPERIDINYL}PHENYL)CYCLOPROPANECARBOXAMIDE: Prepared by Procedure K and Scheme B using 1-(4-tert-butylphenyl)-4-chloro-1-butanone and N-[3-(4-piperidinyl)phenyl]cyclopropanecarboxamide: ESMS m/e: 447.2 (M+H)$^+$.

EXAMPLE 542

N-(3-{1-[4-(4-METHYLPHENYL)-4-OXOBUTYL]-4-PIPERIDINYL}PHENYL)PROPANAMIDE: Prepared by Procedure K and Scheme B1 using 4-chloro-1-(4-methylphenyl)-1-butanone and N-[3-(4-piperidinyl)phenyl]propanamide: ESMS m/e: 393.2 (M+H)$^+$.

EXAMPLE 543

N-(3-{1-[4-(3,4-DIMETHYLPHENYL)-4-OXOBUTYL]-4-PIPERIDINYL}PHENYL)PROPANAMIDE: Prepared by Procedure K and Scheme 81 using 4-chloro-1-(3,4-dimethylphenyl)-1-butanone and N-[3-(4-piperidinyl)phenyl]propanamide: ESMS m/e: 407.2 (M+H)$^+$.

EXAMPLE 544

N-(3-{1-[4-(4-BROMOPHENYL)-4-OXOBUTYL]-4-PIPERIDINYL}PHENYL)CYCLOPROPANECARBOXAMIDE: Prepared by Procedure K and Scheme B using 1-(4-bromophenyl)-4-chloro-1-butanone and N-[3-(4-piperidinyl)phenyl]cyclopropanecarboxamide: ESMS m/e: 469.1 (M+H)$^+$.

EXAMPLE 545

N-(3-{1-[5-(4-FLUOROPHENYL)-5-OXOPENTYL]-4-PIPERIDINYL}PHENYL)PROPANAMIDE: Prepared by Procedure K and Scheme B using 5-chloro-1-(4-fluorophenyl)-1-pentanone and N-[3-(4-piperidinyl)phenyl]propanamide: ESMS m/e: 411.2 (M+H)$^+$.

EXAMPLE 546

N-(3-{1-[4-(3,4-DIMETHYLPHENYL)-4-OXOBUTYL]-4-PIPERIDINYL}PHENYL)CYCLOPROPANECARBOXAMIDE: Prepared by Procedure K and Scheme B1 using 4-chloro-1-(3,4-dimethylphenyl)-1-butanone and N-[3-(4-piperidinyl)phenyl]cyclopropanecarboxamide: ESMS m/e: 419.2 (M+H)$^+$.

EXAMPLE 547

N-(3-{1-[4-(4-METHYLPHENYL)-4-OXOBUTYL]-4-PIPERIDINYL}PHENYL)CYCLOPROPANECARBOXAMIDE: Prepared by Procedure K and Scheme B1 using 4-chloro-1-(4-methylphenyl)-1-butanone and N-[3-(4-piperidinyl)phenyl]cyclopropanecarboxamide: ESMS m/e: 405.2 (M+H)$^+$.

EXAMPLE 548

N-(3-{1-[4-(4-FLUOROPHENYL)-4-OXOBUTYL]-4-PIPERIDINYL}PHENYL)CYCLOPROPANECARBOXAMIDE: Prepared by Procedure K and Scheme B1 using 4-chloro-1-(4-fluorophenyl)-1-butanone and N-[3-(4-piperidinyl)phenyl]cyclopropanecarboxamide: ESMS m/e: 409.2 (M+H)$^+$.

EXAMPLE 549

N-(3-{1-[5-(3-FLUOROPHENYL)-5-OXOPENTYL]-4-PIPERIDINYL}PHENYL)CYCLOPROPANECARBOXAMIDE: Prepared by Procedure K and Scheme B1 using 5-chloro-1-(3-fluorophenyl)-1-pentanone and N-[3-(4-piperidinyl)phenyl]cyclopropanecarboxamide: ESMS m/e: 423.2 (M+H)$^+$.

EXAMPLE 550

N-[3-(1-{5-OXO-5-[4-(TRIFLUOROMETHYL)PHENYL]PENTYL}-4-PIPERIDINYL)PHENYL]PROPANAMIDE: Prepared by Procedure K and Scheme B1 using 5-chloro-1-[4-(trifluoromethyl)phenyl]-1-pentanone and N-[3-(4-piperidinyl)phenyl]propanamide: ESMS m/e: 461.2 (M+H)$^+$.

EXAMPLE 551

N-(3-{1-[5-(4-FLUOROPHENYL)-5-OXOPENTYL]-4-PIPERIDINYL}PHENYL)CYCLOPROPANECARBOXAMIDE: Prepared by Procedure K and Scheme B1 using 5-chloro-1-(4-fluorophenyl)-1-pentanone and N-[3-(4-piperidinyl)phenyl]cyclopropanecarboxamide: ESMS m/e: 423.2 (M+H)$^+$.

EXAMPLE 552

N-(3-{1-[5-(3-NITROPHENYL)-5-OXOPENTYL]-4-PIPERIDINYL}PHENYL)PROPANAMIDE: Prepared by Procedure K and Scheme B using 5-chloro-1-(3-nitrophenyl)-1-pentanone and N-[3-(4-piperidinyl)phenyl]propanamide: ESMS m/e: 438.2 (M+H)$^+$.

EXAMPLE 553

N-(3-{1-[5-(3-NITROPHENYL)-5-OXOPENTYL]-4-PIPERIDINYL}PHENYL)CYCLOPROPANECARBOXAMIDE: Prepared by Procedure K and Scheme B1 using 5-chloro-1-(3-nitrophenyl)-1-pentanone and N-[3-(4-piperidinyl)phenyl]cyclopropanecarboxamide: ESMS m/e: 450.2 (M+H)$^+$.

EXAMPLE 554

N-(3-{1-[5-(2-FLUOROPHENYL)-5-OXOPENTYL]-4-PIPERIDINYL}PHENYL)PROPANAMIDE: Prepared by Procedure K and Scheme B1 using 5-chloro-1-(2-fluorophenyl)-1-pentanone and N-[3-(4-piperidinyl)phenyl]propanamide: ESMS m/e: 411.2 (M+H)$^+$.

EXAMPLE 555

N-(3-{1-[5-(3-FLUOROPHENYL)-5-OXOPENTYL]-4-PIPERIDINYL}PHENYL)PROPANAMIDE: Prepared by Procedure K and Scheme B using 5-chloro-1-(3- fluorophenyl)-1-pentanone and N-[3-(4-piperidinyl)phenyl]propanamide: ESMS m/e: 411.2 (M+H)$^+$.

EXAMPLE 556

N-(3-{1-[5-(4-NITROPHENYL)-5-OXOPENTYL]-4-PIPERIDINYL}PHENYL)PROPANAMIDE: Prepared by Procedure K and Scheme B1 using 5-chloro-1-(4-nitrophenyl)-1-pentanone and N-[3-(4-piperidinyl)phenyl]propanamide: ESMS m/e: 438.1 (M+H)$^+$.

EXAMPLE 557

N-(3-{1-[5-(4-NITROPHENYL)-5-OXOPENTYL]-4-PIPERIDINYL}PHENYL)CYCLOPROPANECARBOXAMIDE: Prepared by Procedure K and Scheme B1 using 5-chloro-1-(4-nitrophenyl)-1-pentanone and N-[3-(4-piperidinyl)phenyl]cyclopropanecarboxamide: ESMS m/e: 450.1 (M+H)$^+$.

EXAMPLE 558

N-(3-{1-[5-(4-CHLOROPHENYL)-5-OXOPENTYL]-4-PIPERIDINYL}PHENYL)CYCLOPROPANECARBOXAMIDE: Prepared by Procedure K and Scheme B1 using 5-chloro-1-(4-chlorophenyl)-1-pentanone and N-[3-(4-piperidinyl)phenyl]cyclopropanecarboxamide: ESMS m/e: 439.1 (M+H)$^+$.

EXAMPLE 559

N-[3-(1-{5-OXO-5-[2-(TRIFLUOROMETHYL)PHENYL]PENTYL}-4-PIPERIDINYL)PHENYL]PROPANAMIDE: Prepared by Procedure K and Scheme B1 using 5-chloro-1-[2-(trifluoromethyl)phenyl]-1-pentanone and N-[3-(4-piperidinyl)phenyl]propanamide: ESMS m/e: 461.2 (M+H)$^+$.

EXAMPLE 560

N-[3-(1-{5-OXO-5-[2-(TRIFLUOROMETHYL)PHENYL]PENTYL}-4-PIPERIDINYL)PHENYL]CYCLOPROPANECARBOXAMIDE: Prepared by Procedure K and Scheme B1 using 5-chloro-1-[2-(trifluoromethyl)phenyl]-1-pentanone and N-[3-(4-piperidinyl)phenyl]cyclopropanecarboxamide: ESMS m/e: 473.2 (M+H)$^+$.

EXAMPLE 561

N-(3-{1-[5-(4-CHLOROPHENYL)-5-OXOPENTYL]-4-PIPERIDINYL}PHENYL)PROPANAMIDE: Prepared by Procedure K and Scheme B1 using 5-chloro-1-(4-chlorophenyl)-1-pentanone and N-[3-(4-piperidinyl)phenyl]propanamide: ESMS m/e: 427.1 (M+H)$^+$.

EXAMPLE 562

N-(3-{1-[5-(3-CHLOROPHENYL)-5-OXOPENTYL]-4-PIPERIDINYL}PHENYL)PROPANAMIDE: Prepared by Procedure K and Scheme B1 using 5-chloro-1-(3-chlorophenyl)-1-pentanone and N-[3-(4-piperidinyl)phenyl]propanamide: ESMS m/e: 427.1 (M+H)$^+$.

EXAMPLE 563

N-(3-{1-[5-(2-FLUOROPHENYL)-5-OXOPENTYL]-4-PIPERIDINYL}PHENYL)CYCLOPROPANECARBOXAMIDE: Prepared by Procedure K and Scheme B1 using 5-chloro-1-(2-fluorophenyl)-1-pentanone and N-[3-(4-piperidinyl)phenyl]cyclopropanecarboxamide: ESMS m/e: 423.1 (M+H)$^+$.

EXAMPLE 564

N-(3-{1-[5-(3-CHLOROPHENYL)-5-OXOPENTYL]-4-PIPERIDINYL}PHENYL)CYCLOPROPANECARBOXAMIDE: Prepared by Procedure K and Scheme B1 using 5-chloro-1-(3-chlorophenyl)-1-pentanone and N-[3-(4-piperidinyl)phenyl]cyclopropanecarboxamide: ESMS m/e: 439.1 (M+H)$^+$.

EXAMPLE 565

N-[3-(1-{5-OXO-5-[4-(TRIFLUOROMETHYL)PHENYL]PENTYL}-4-PIPERIDINYL)PHENYL]CYCLOPROPANECARBOXAMIDE: Prepared by Procedure K and Scheme B1 using 5-chloro-1-[4-(trifluoromethyl)phenyl]-1-pentanone and N-[3-(4-piperidinyl)phenyl]cyclopropanecarboxamide: ESMS m/e: 473.2 (M+H)$^+$.

EXAMPLE 566

N-(3-{1-[5-(2-CHLOROPHENYL)-5-OXOPENTYL]-4-PIPERIDINYL}PHENYL)PROPANAMIDE: Prepared by Procedure K and Scheme B1 using 5-chloro-1-(2-chlorophenyl)-1-pentanone and N-[3-(4-piperidinyl)phenyl]propanamide: ESMS m/e: 427.1 (M+H)$^+$.

EXAMPLE 567

N-(3-{1-[5-(2-CHLOROPHENYL)-5-OXOPENTYL]-4-PIPERIDINYL}PHENYL)CYCLOPROPANECARBOXAMIDE: Prepared by Procedure K and Scheme B1 using 5-chloro-1-(2-chlorophenyl)-1-pentanone and N-[3-(4-piperidinyl)phenyl]cyclopropanecarboxamide: ESMS m/e: 439.1 (M+H)$^+$.

EXAMPLE 568

N-[3-(1-{5-OXO-5-[3-(TRIFLUOROMETHYL)PHENYL]PENTYL}-4-PIPERIDINYL)PHENYL]CYCLOPROPANECARBOXAMIDE: Prepared by Procedure K and Scheme B1 using 5-chloro-1-[3-(trifluoromethyl)phenyl]-1-pentanone and N-[3-(4-piperidinyl)phenyl]cyclopropanecarboxamide: ESMS m/e: 473.2 (M+H)$^+$.

EXAMPLE 569

N-(3-{1-[4-(3,4-DIMETHYLPHENYL)-4-OXOBUTYL]-4-PIPERIDINYL}PHENYL)-N,2-DIMETHYLPROPANAMIDE: Prepared by Procedure T and Scheme AD using N-(3-{1-[4-(3,4-dimethylphenyl)-4-oxobutyl]-4-piperidinyl}phenyl)-2-methylpropanamide and methyl iodide: $^1$H NMR (400 MHz, CDCl$_3$) δ 7.76 (s, 1H), 7.72 (dd, 1H, J=1.8, 7.7 Hz), 7.33 (t, 1H, J=8.8 Hz), 7.22 (d, 1H, J=7.8 Hz), 7.18 (d, 1H, J=8.8 Hz), 7.01 (m, 2H), 3.24 (s, 3H), 3.10 (d, 1H, J=10.6 Hz), 3.00 (t, 1H, J=7.6 Hz), 2.49 (m, 4H), 2.33 (s, 6H), 2.11 (m, 3H), 1.99 (m, 1H), 1.79 (m, 4H), 1.26 (t, 2H, J=7.6 Hz), 1.02 (d, 6H, J=7.6 Hz); ESMS m/e: 435.2 (M+H)$^+$.

EXAMPLE 570

2-METHYL-N-{3-[1-(1-METHYL-4-OXO-4-PHENYLBUTYL)-4-PIPERIDINYL]PHENYL}PROPANAMIDE: Prepared by Procedure K and Scheme B1 using 4-chloro-1-phenyl-1-pentanone and 2-methyl-N-[3-(4-piperidinyl)phenyl]propanamide: ESMS m/e: 407.2 (M+H)$^+$.

EXAMPLE 571

N-[3-(1-{5-OXO-5-[3-(TRIFLUOROMETHYL)PHENYL]PENTYL}-4-PIPERIDINYL)PHENYL]

PROPANAMIDE: Prepared by Procedure K and Scheme B1 using 5-chloro-1-[3-(trifluoromethyl)phenyl]-1-pentanone and N-[3-(4-piperidinyl)phenyl]propanamide: ESMS m/e: 461.2 (M+H)+.

3-(5-CHLOROPENTANOYL)-4-(3,4-DIFLUOROPHENYL)-1,3-OXAZOLIDIN-2-ONE: Prepared by Procedure AF and Scheme H using 4-(3,4-difluorophenyl)-1,3-oxazolidin-2-one and 5-chloropentanoyl chloride.

3-(5-CHLOROPENTYL)-4-(3,4-DIFLUOROPHENYL)-1,3-OXAZOLIDIN-2-ONE: Prepared by Procedure G and Scheme C1 using 4-(3,4-difluorophenyl)-1,3-oxazolidin-2-one and 1-bromo-5-chloropentane.

EXAMPLE 572

N-[3-(1-{5-[(4R)-4-(3,4-DIFLUOROPHENYL)-2-OXO-1,3-OXAZOLIDIN-3-YL]-5-OXOPENTYL}-4-PIPERIDINYL)PHENYL]-2-METHYLPROPANAMIDE: Prepared by Procedure G and Scheme B1 using (4R)-3-(5-chloropentanoyl)-4-(3,4-difluorophenyl)-1,3-oxazolidin-2-one and 2-methyl-N-[3-(4-piperidinyl)phenyl]propanamide: ESMS m/e: 528.2 (M+H)+.

EXAMPLE 573

(4R)-4-(3,4-DIFLUOROPHENYL)-N-(3-{4-[3-(ISOBUTYRYLAMINO)PHENYL]-1-PIPERIDINYL}PROPYL)-2-OXO-1,3-OXAZOLIDINE-3-CARBOXAMIDE: Prepared by Procedure AF and Scheme H using 4-nitrophenyl(4R)-4-(3,4-difluorophenyl)-2-oxo-1,3-oxazolidine-3-carboxylate and N-{3-[1-(3-aminopropyl)-4-piperidinyl]phenyl)-2-methylpropanamide: 1H NMR (400 MHz, CDCl3) δ 8.08 (t, 1H, J=5.5 Hz), 7.45 (s, 2H), 7.38 (d, 1H, J=8.6 Hz), 7.24–7.12 (m, 3H), 7.06 (m, 1H), 6.97 (d, 1H, J=8.6 Hz), 5.40 (dd, 1H, J=3.9,8.8 Hz), 4.71 (t, 1H, J=8.8 Hz), 4.23 (dd, 1H, J=4.4, 9.1 Hz), 3.32 (qt, 2H, J=6.1 Hz), 2.99 (d, 2H, J=11.0 Hz), 2.49 (qt, 2H, J=7.0 Hz), 2.41 (t, 2H, J=7.0 Hz), 1.99 (m, 2H), 1.82–1.68 (m, 6H), 1.23 (d, 6H, J=7.3 Hz); ESMS m/e: 529.1 (M+H)+.

(4S)-3-(5-CHLOROPENTYL)-4-(3,4-DIFLUOROPHENYL)-1,3-OXAZOLIDIN-2-ONE: Prepared by Procedure G and Scheme C1 using (4S)-4-(3,4-difluorophenyl)-1,3-oxazolidin-2-one and 1-bromo-5-chloropentane.

EXAMPLE 574

N-[3-(1-{5-[(4S)-4-(3,4-DIFLUOROPHENYL)-2-OXO-1,3-OXAZOLIDIN-3-YL]PENTYL}-4-PIPERIDINYL)PHENYL]-2-METHYLPROPANAMIDE: Prepared by Procedure G and Scheme B1 using (4S)-3-(5-chloropentyl)-4-(3,4-difluorophenyl)-1,3-oxazolidin-2-one and 2-methyl-N-[3-(4-piperidinyl)phenyl]propanamide: 1H NMR (400 MHz, CDCl3) δ 7.48 (s, 1H), 7.32 (d, 1H, J=8.6 Hz), 7.26–7.21 (m, 2H), 7.20–7.12 (m, 2H), 7.06 (m, 1H), 6.97 (d, 1H, J=6.96 Hz), 4.76 (dd, 1H, J=6.3, 8.3 Hz), 4.62 (t, 1H, J=9.0 Hz), 4.06 (dd, 1H, J=6.4, 8.7 Hz), 3.46 (m, 3H), 3.0 (d, 2H, J=9.0 Hz), 2.77 (q, 1H, J=6.8 Hz), 2.50 (q, 2H, J=6.8 Hz), 2.31 (t, 2H, J=6.8 Hz), 2.01 (m, 4H), 1.81 (m, 4H), 1.48 (m, 4H), 1.26 (d, 6H, J=7.3 Hz); Anal. Calcd for C28H37F2N3O3+HCl+0.25CHCl3: C, 60.6; H, 6.65; N, 7.25. Found: C, 60.7; H, 6.91; N, 7.05; ESMS m/e: 514.2 (M+H)+.

EXAMPLE 575

N-[3-(1-{5-[(4S)-4-(3,4-DIFLUOROPHENYL)-2-OXO-1,3-OXAZOLIDIN-3-YL]-5-OXOPENTYL}-4-PIPERIDINYL)PHENYL]-2-METHYLPROPANAMIDE: Prepared by Procedure G and Scheme B1 using (4S)-3-(5-chloropentanoyl)-4-(3,4-difluorophenyl)-1,3-oxazolidin-2-one and 2-methyl-N-[3-(4-piperidinyl)phenyl]propanamide: ESMS m/e: 528.1 (M+H)+.

EXAMPLE 576

(4S)-4-(3,4-DIFLUOROPHENYL)-N-(3-{4-[3-(ISOBUTYRYLAMINO)PHENYL]-1-PIPERIDINYL}PROPYL)-2-OXO-1,3-OXAZOLIDINE-3-CARBOXAMIDE: Prepared by Procedure AF and Scheme H using 4-nitrophenyl(4S)-4-(3,4-difluorophenyl)-2-oxo-1,3-oxazolidine-3-carboxylate and N-{3-[1-(3-aminopropyl)-4-piperidinyl]phenyl}-2-methylpropanamide: ESMS m/e: 529.1 (M+H)+.

EXAMPLE 577

(4S)-N-(3-{4-[3-(ISOBUTYRYLAMINO)PHENYL]-1-PIPERIDINYL}PROPYL)-2-OXO-4-(3,4,5-TRIFLUOROPHENYL)-1,3-OXAZOLIDINE-3-CARBOXAMIDE: Prepared by Procedure AF and Scheme H using 4-nitrophenyl(4S)-4-(3,4-difluorophenyl)-2-oxo-1,3-oxazolidine-3-carboxylate and N-{3-[1-(3-aminopropyl)-4-piperidinyl]phenyl}-2-methylpropanamide: ESMS m/e: 547.1 (M+H)+.

EXAMPLE 578

(4S)-4-(3,5-DIFLUOROPHENYL)-N-(3-{4-[3-(ISOBUTYRYLAMINO)PHENYL]-1-PIPERIDINYL}PROPYL)-2-OXO-1,3-OXAZOLIDINE-3-CARBOXAMIDE: Prepared by Procedure AF and Scheme H using 4-nitrophenyl(4S)-4-(3,4-difluorophenyl)-2-oxo-1,3-oxazolidine-3-carboxylate and N-{3-[1-(3-aminopropyl)-4-piperidinyl]phenyl}-2-methylpropanamide: ESMS m/e: 529.2 (M+H)+.

EXAMPLE 579

N-(3-{1-[3-(PHENYLSULFANYL)PROPYL]-4-PIPERIDINYL}PHENYL)PROPANAMIDE: Prepared by Procedure G and Scheme B1 using [(3-chloropropyl)sulfanyl]benzene and N-[3-(4-piperidinyl)phenyl]propanamide: ESMS m/e: 382.9 (M+H)+.

EXAMPLE 580

N-(3-{1-[3-(PRHENYLSULFANYL)PROPYL]-4-PIPERIDINYL}PHENYL)CYCLOPROPANECARBOXAMIDE: Prepared by Procedure G and Scheme B1 using [(3-chloropropyl)sulfanyl3benzene and N-[3-(4-piperidinyl)phenyl]cyclopropanecarboxamide: ESMS m/e: 395.1 (M+H)+.

EXAMPLE 581

2-METHYL-N-(3-{1-[3-(PHENYLSULFANYL)PROPYL]-4-PIPERIDINYL}PHENYL)PROPANAMIDE: Prepared by Procedure G and Scheme B1 using [(3-chloropropyl)sulfanyl]benzene and 2-methyl-N-[3-(4-piperidinyl)phenyl]propanamide: 1H NMR (400 MHz, CDCl3) δ 7.63 (s, 1H), 7.48 (s, 1H), 7.33 (m, 3H), 7.27 (t, 2H, J=7.5 Hz), 7.20 (t, 1H, J=7.9 Hz), 7.15 (tt, 1H, J=7.2, 1.4 Hz), 6.95 (d, 1H, J=7.6 Hz), 2.97 (t, 4H, J=7.3 Hz), 2.46 (m, 4H), 1.99 (dt, 2H, J=11.4, 3.0 Hz), 1.84 (qt, 2H, J=7.3 Hz), 1.77 (m, 4H), 1.21 (d, 6H, J=6.8 Hz); ESMS m/e: 396.8 (M+H)+.

EXAMPLE 582

N-(3-({-[6-(PHENYLSULFANYL)HEXYL]-4-PIPERIDINYL}PHENYL)

CYCLOPROPANECARBOXAMIDE: Prepared by Procedure G and Scheme B1 using [(6-chlorohexyl)sulfanyl]benzene and N-(3-(4-piperidinyl)phenyl] cyclopropanecarboxamide: ESMS m/e: 437.4 (M+H)+.

EXAMPLE 583

N-(3-{1-[4-(PHENYLSULFANYL)BUTYL]-4-PIPERIDINYL}PHENYL)PROPANAMIDE: Prepared by Procedure G and Scheme B using [(4-chlorobutyl)sulfanyl]benzene and N-[3-(4-piperidinyl)phenyl]propanamide: ESMS m/e: 396.8 (M+H)+.

EXAMPLE 584

N-(3-{1-[4-(PHENYLSULFANYL)BUTYL]-4-PIPERIDINYL}PHENYL) CYCLOPROPANECARBOXAMIDE: Prepared by Procedure G and Scheme B1 using [(4-chlorobutyl)sulfanyl]benzene and N-[3-(4-piperidinyl)phenyl] cyclopropanecarboxamide: ESMS m/e: 409.5 (M+H)+.

EXAMPLE 585

2-METHYL-N-(3-{1-[4-(PHENYLSULFANYL)BUTYL]-4-PIPERIDINYL}PHENYL)PROPANAMIDE: Prepared by Procedure G and Scheme B1 using [(4-chlorobutyl)sulfanyl]benzene and 2-methyl-N-[3-(4-piperidinyl)phenyl]propanamide: ESMS m/e: 410.6 (M+H)+.

EXAMPLE 586

2-METHYL-N-(3-{1-[5-(PHENYLSULFANYL)PENTYL]-4-PIPERIDINYL}PHENYL)PROPANAMIDE: Prepared by Procedure G and Scheme B1 using [(5-chloropentyl)sulfanyl]benzene and 2-methyl-N-[3-(4-piperidinyl)phenyl]propanamide: ESMS m/e: 425.1 (M+H)+.

EXAMPLE 587

N-(3-{1-[5-(PHENYLSULFANYL)PENTYL]-4-PIPERIDINYL}PHENYL) CYCLOPROPANECARBOXAMIDE: Prepared by Procedure G and Scheme B1 using [(5-chloropentyl)sulfanyl]benzene and N-[3-(4-piperidinyl)phenyl] cyclopropanecarboxamide: ESMS m/e: 423.1 (M+H)+.

[(6-CHLOROHEXYL)SULFANYL]BENZENE: Prepared by Procedure R and Scheme Z using benzenethiol and 1-bromo-6-chlorohexane.

[(4-CHLOROBUTYL)SULFANYL]BENZENE: Prepared by Procedure R and Scheme Z using benzenethiol and 1-bromo-4-chlorobutane.

EXAMPLE 588

N-(3-{1-[6-(PHENYLSULFANYL)HEXYL]-4-PIPERIDINYL}PHENYL)PROPANAMIDE: Prepared by Procedure G and Scheme B1 using [(6-chlorohexyl)sulfanyl]benzene and N-[3-(4-piperidinyl)phenyl] propanamide: ESMS m/e: 425.4 (M+H)+.

[(5-CHLOROPENTYL)SULFANYL]BENZENE: Prepared by Procedure R and Scheme Z using benzenethiol and 1-bromo-5-chloropentane.

[(3-CHLOROPROPYL)SULFANYL]BENZENE: Prepared by Procedure R and Scheme Z using benzenethiol and 1-bromo-3-chloropropane: $^1$H NMR (400 MHz, CDCl$_3$) δ 7.37–7.34 (m, 2H), 7.32–7.26 (m, 2H), 7.19 (tt, 1H, J=1.4, 7.3 Hz), 3.67 (t, 2H, J=6.6 Hz), 3.08 (t, 2H, J=6.6 Hz), 2.06 (qt, 2H, J=6.6 Hz).

EXAMPLE 589

N-(3-{1-[5-(PHENYLSULFANYL)PENTYL]-4-PIPERIDINYL}PHENYL)PROPANAMIDE: Prepared by Procedure G and Scheme B1 using [(5-chloropentyl)sulfanyl]benzene and N-[3-(4-piperidinyl)phenyl] propanamide: ESMS m/e: 411.1 (M+H)+.

3-CHLOROPROPYL 4-FLUOROPHENYL SULFIDE: Prepared by Procedure R and Scheme Z using 4-fluorobenzenethiol and 1-bromo-3-chloropropane.

1-BROMO-2-[(3-CHLOROPROPYL)SULFANYL] BENZENE: Prepared by Procedure R and Scheme Z using 2-bromobenzenethiol and 1-bromo-3-chloropropane.

3-CHLOROPROPYL 4-FLUOROPHENYL SULFOXIDE: Prepared by Procedure S and Scheme AA using 3-chloropropyl 4-fluorophenyl sulfide and 1 eq m-CPBA: $^1$H NMR (400 MHz, CDCl$_3$) δ 7.65–7.62 (m, 2H), 7.28–7.21 (m, 2H), 3.65 (m, 2H), 2.94 (m, 2H), 2.28 (m, 1H), 2.06 (m, 1H); ESMS m/e: 220.9 (M+H)+.

3-CHLOROPROPYL 3-FLUOROPHENYL SULFIDE: Prepared by Procedure R and Scheme Z using 3-fluorobenzenethiol and 1-bromo-3-chloropropane.

3-CHLOROPROPYL 2-FLUOROPHENYL SULFIDE: Prepared by Procedure R and Scheme Z using 2-fluorobenzenethiol and 1-bromo-3-chloropropane.

1-BROMO-2-[(3-CHLOROPROPYL)SULFINYL] BENZENE: Prepared by Procedure S and Scheme AA using 1-bromo-2-[(3-chloropropyl)sulfanyl]benzene and 1 eq M-CPBA: ESMS m/e: 282.8 (M+H)+.

1-CHLORO-2-[(3-CHLOROPROPYL)SULFANYL] BENZENE: Prepared by Procedure R and Scheme Z using 2-chlorobenzenethiol and 1-bromo-3-chloropropane.

1-CHLORO-3-[(3-CHLOROPROPYL)SULFANYL] BENZENE: Prepared by Procedure R and Scheme Z using 3-chlorobenzenethiol and 1-bromo-3-chloropropane.

1-CHLORO-4-[(3-CHLOROPROPYL)SULFANYL] BENZENE: Prepared by Procedure R and Scheme Z using 4-chlorobenzenethiol and 1-bromo-3-chloropropane.

1-BROMO-3-[(3-CHLOROPROPYL)SULFANYL] BENZENE: Prepared by Procedure R and Scheme Z using 3-bromobenzenethiol and 1-bromo-3-chloropropane.

1-BROMO-4-[(3-CHLOROPROPYL)SULFANYL] BENZENE: Prepared by Procedure R and Scheme Z using 4-bromobenzenethiol and 1-bromo-3-chloropropane.

3-CHLOROPROPYL 3,4-DIMETHYLPHENYL SULFIDE: Prepared by Procedure R and Scheme Z using 3,4-dimethylbenzenethiol and 1-bromo-3-chloropropane.

EXAMPLE 590

N-[3-(1-{3-[(4-FLUOROPHENYL)SULFINYL] PROPYL}-4-PIPERIDINYL)PHENYL]-2-METHYLPROPANAMIDE: Prepared by Procedure G and Scheme B1 using 3-chloropropyl 4-fluorophenyl sulfoxide and 2-methyl-N-[3-(4-piperidinyl)phenyl]propanamide: $^1$H NMR (400 MHz, CDCl$_3$) δ 7.64 (m, 2H), 7.53 (s, 1H), 7.24 (m, 5H), 6.94 (d, 1H, J=7.7 Hz), 2.89 (m, 4H), 2.45 (m, 4H ), 1.99 (m, 3H), 1.77 (m, 5H), 1.24 (d, 6H, J=6.8 Hz); Anal. Calcd for $C_{24}H_{31}FN_2O_2S$+0.6EtOAc: C, 65.5; H, 7.45; N, 5.79. Found: C, 65.4; H, 7.30; N, 5.73; ESMS m/e: 431.1 (M+H)+.

EXAMPLE 591

N-[3-(1-{3-[(2-BROMOPHENYL)SULFINYL] PROPYL}-4-PIPERIDINYL)PHENYL]-2-

METHYLPROPANAMIDE: Prepared by Procedure G and Scheme B1 using 1-bromo-2-[(3-chloropropyl)sulfinyl] benzene and 2-methyl-N-[3-(4-piperidinyl)phenyl] propanamide: Anal. Calcd for $C_{24}H_{31}BrN_2O_2S+0.3CHCl_3$: ESMS m/e: 491.0 (M+H)$^+$.

EXAMPLE 592

N-{3-[1-((3S)-3-{[(3,4-DIFLUOROPHENYL) SULFONYL]AMINO}-3-PHENYLPROPYL)-4-PIPERIDINYL]PHENYL}-2-METHYLPROPANAMIDE: Prepared by Procedure Q1 and Scheme AC using 3,4-difluorobenzenesulfonyl chloride and N-(3-{1-[(3S)-3-amino-3-phenylpropyl]-4-piperidinyl}phenyl)-2-methylpropanamide: ESMS m/e: 556.2 (M+H)$^+$.

EXAMPLE 593

3-CHLORO-N-((1S)-3-{4-[3-(ISOBUTYRYLAMINO) PHENYL]-1-PIPERIDINYL}-1-PHENYLPROPYL)-2-THIOPHENECARBOXAMIDE: Prepared by Procedure Q1 and Scheme AC using 3-chloro-2-thiophenecarbonyl chloride and N-(3-{1-[(3S)-3-amino-3-phenylpropyl]-4-piperidinyl}phenyl)-2-methylpropanamide: ESMS m/e: 524.2 (M+H)$^+$.

EXAMPLE 594

N-(3-{1-[(3S)-3-({[5-(DIMETHYLAMINO)-1-NAPHTHYL]SULFONYL}AMINO)-3-PHENYLPROPYL]-4-PIPERIDINYL}PHENYL)-2-METHYLPROPANAMIDE: Prepared by Procedure Q1 and Scheme AC using 5-(dimethylamino)-1-naphthalenesulfonyl chloride and N-(3-{1-[(3S)-3-amino-3-phenylpropyl]-4-piperidinyl}phenyl)-2-methylpropanamide: ESMS m/e: 613.3 (M+H)$^+$.

EXAMPLE 595

2-METHYL-N-{3-[1-((3S)-3-{[(4-METHYLPHENYL) SULFONYL]AMINO}-3-PHENYLPROPYL)-4-PIPERIDINYL]PHENYL}PROPANAMIDE: Prepared by Procedure Q1 and Scheme AC using 4-methylbenzenesulfonyl chloride and N-(3-{1-[(3S)-3-amino-3-phenylpropyl]-4-piperidinyl}phenyl)-2-methylpropanamide: ESMS m/e: 534.2 (M+H)$^+$.

EXAMPLE 596

N-{3-[1-((3S)-3-{[(3,5-DICHLORO-2-HYDROXYPHENYL)SULFONYL]AMINO}-3-PHENYLPROPYL)-4-PIPERIDINYL]PHENYL}-2-METHYLPROPANAMIDE: Prepared Procedure Q1 and Scheme AC using 3,5-dichloro-2-hydroxybenzenesulfonyl chloride and N-(3-{1-[(3S)-3-amino-3-phenylpropyl]-4-piperidinyl}phenyl)-2-methylpropanamide: ESMS m/e: 605.4 (M+H)$^+$.

EXAMPLE 597

2-METHYL-N-[3-(1-{(3S)-3-[(METHYLSULFONYL) AMINO]-3-PHENYLPROPYL}-4-PIPERIDINYL) PHENYL]PROPANAMIDE: Prepared by Procedure Q1 and Scheme AC using methanesulfonyl chloride and N-(3-{1-[(3S)-3-amino-3-phenylpropyl]-4-piperidinyl}phenyl)-2-methylpropanamide: ESMS m/e: 458.6 (M+H)$^+$.

EXAMPLE 598

N-{3-[1-((3S)-3-{[(4-FLUOROPHENYL)SULFONYL] AMINO}-3-PHENYLPROPYL)-4-PIPERIDINYL] PHENYL}-2-METHYLPROPANAMIDE: Prepared by Procedure Q1 and Scheme AC using 4-fluorobenzenesulfonyl chloride and N-(3-{1-[(3S)-3-amino-3-phenylpropyl]-4-piperidinyl}phenyl)-2-methylpropanamide: ESMS m/e: 538.1 (M+H)$^+$.

EXAMPLE 599

N-{3-[1-((3S)-3-{[(4-TERT-BUTYLPHENYL) SULFONYL]AMINO}-3-PHENYLPROPYL)-4-PIPERIDINYL]PHENYL}-2-METHYLPROPANAMIDE: Prepared by Procedure Q1 and Scheme AC using 4-tert-butylbenzenesulfonyl chloride and N-(3-{1-[(3S)-3-amino-3-phenylpropyl]-4-piperidinyl}phenyl)-2-methylpropanamide: ESMS m/e: 576.2 (M+H)$^+$.

EXAMPLE 600

N-{3-[1-((3S)-3-{[(2,5-DICHLOROPHENYL) SULFONYL]AMINO}-3-PHENYLPROPYL)-4-PIPERIDINYL]PHENYL}-2-METHYLPROPANAMIDE: Prepared by Procedure Q1 and Scheme AC using 2,5-dichlorobenzenesulfonyl chloride and N-(3-{1-[(3S)-3-amino-3-phenylpropyl]-4-piperidinyl}phenyl)-2-methylpropanamide: ESMS m/e: 588.0 (M+H)$^+$.

EXAMPLE 601

2-METHYL-N-[3-(1-{(3S)-3-PHENYL-3-[(PROPYLSULFONYL)AMINO]PROPYL}-4-PIPERIDINYL)PHENYL]PROPANAMIDE: Prepared by Procedure Q1 and Scheme AC using 1-propanesulfonyl chloride and N-(3-{1-[(3S)-3-amino-3-phenylpropyl]-4-piperidinyl}phenyl)-2-methylpropanamide: ESMS m/e: 486.2 (M+H)$^+$.

EXAMPLE 602

N-{3-[1-((3S)-3-{[(3,5-DIMETHYL-4-ISOXAZOLYL) SULFONYL]AMINO}-3-PHENYLPROPYL)-4-PIPERIDINYL]PHENYL}-2-METHYLPROPANAMIDE: Prepared by Procedure Q1 and Scheme AC using 3,5-dimethyl-4-isoxazolesulfonyl chloride and N-(3-{1-[(3S)-3-amino-3-phenylpropyl]-4-piperidinyl}phenyl)-2-methylpropanamide: $^1$H NMR (400 MHz, CDCl$_3$) δ 7.53 (s, 2H), 7.3–7.1 (m, 5H), 7.05 (t, 2H, J=6.5 Hz), 6.81 (d, 1H, J=7.1 Hz), 4.65 (dd, 1H, J=6.3, 2.2 Hz), 3.11 (t, 2H, J=7.2 Hz), 2.4 (m, 4H), 2.2 (s, 3H), 2.05 (m, 2H), 2.01 (s, 3H), 2.0–1.8 (m, 7H), 1.21 (d, 6H, J=7.1 Hz); ESMS m/e: 539.5 (M+H)$^+$.

EXAMPLE 603

METHYL 3-{[(3-{4-[3-(ISOBUTYRYLAMINO) PHENYL]-1-PIPERIDINYL}PROPYL)AMINO] SULFONYL}-2-THIOPHENECARBOXYLATE: Prepared Procedure Q1 and Scheme AC using methyl 3-(chlorosulfonyl)-2-thiophenecarboxylate and N-{3-[1-(3-aminopropyl)-4-piperidinyl]phenyl}-2-methylpropanamide: Anal. Calcd for $C_{24}H_{33}N_3O_5S$·HCl: C, 6.00; H, 5.30; N, 7.72. Found: C, 52.9; H, 6.04; N, 7.59; ESMS m/e: 508.2 (M+H)$^+$.

EXAMPLE 604

2-METHYL-N-{3-[1-((3S)-3-{[(4-PHENOXYANILINO)CARBONYL]AMINO}-3-PHENYLPROPYL)-4-PIPERIDINYL] PHENYL}PROPANAMIDE: Prepared by Procedure P and Scheme AB using 1-isocyanato-4-phenoxybenzene and N-(3-{1-[(3S)-3-amino-3-phenylpropyl]-4-piperidinyl}phenyl)-2-methylpropanamide: ESMS m/e: 591.3 (M+H)+.

PIPERIDINYL]PHENYL}-2-METHYLPROPANAMIDE: Prepared by Procedure Q1 and Scheme AC using 3,5-dimethyl-4-isoxazolesulfonyl chloride and N-(3-{1-[(3S)-3-amino-3-phenylpropyl]-4-piperidinyl}phenyl)-2-methylpropanamide: $^1$H NMR (400 MHz, CDCl$_3$) δ 7.53 (s, 2H), 7.3–7.1 (m, 5H), 7.05 (t, 2H, J=6.5 Hz), 6.81 (d, 1H, J=7.1 Hz), 4.65 (dd, 1H, J=6.3, 2.2 Hz), 3.11 (t, 2H, J=7.2 Hz), 2.4 (m, 4H), 2.2 (s, 3H), 2.05 (m, 2H), 2.01 (s, 3H), 2.0–1.8 (m, 7H), 1.21 (d, 6H, J=7.1 Hz); ESMS m/e: 539.5 (M+H)+.

EXAMPLE 603

METHYL 3-{[(3-{4-[3-(ISOBUTYRYLAMINO)PHENYL]-1-PIPERIDINYL}PROPYL)AMINO]SULFONYL}-2-THIOPHENECARBOXYLATE: Prepared Procedure Q1 and Scheme AC using methyl 3-(chlorosulfonyl)-2-thiophenecarboxylate and N-{3-[1-(3-aminopropyl)-4-piperidinyl]phenyl}-2-methylpropanamide: Anal. Calcd for C$_{24}$H$_{33}$N$_3$O$_5$S.HCl: C, 6.00; H, 5.30; N, 7.72. Found: C, 52.9; H, 6.04; N, 7.59; ESMS m/e: 508.2 (M+H)+.

EXAMPLE 604

2-METHYL-N-{3-[1-((3S)-3-{[(4-PHENOXYANILINO)CARBONYL]AMINO}-3-PHENYLPROPYL)-4-PIPERIDINYL]PHENYL}PROPANAMIDE: Prepared by Procedure P and Scheme AB using 1-isocyanato-4-phenoxybenzene and N-(3-{1-[(3S)-3-amino-3-phenylpropyl]-4-piperidinyl}phenyl)-2-methylpropanamide: ESMS m/e: 591.3 (M+H)+.

EXAMPLE 605

N-[3-(1-{(3S)-3-[(ANILINOCARBONYL)AMINO]-3-PHENYLPROPYL}-4-PIPERIDINYL)PHENYL]-2-METHYLPROPANAMIDE: Prepared by Procedure P and Scheme AB using isocyanatobenzene and N-(3-{1-[(3S)-3-amino-3-phenylpropyl]-4-piperidinyl}phenyl)-2-methylpropanamide: ESMS m/e: 499.2 (M+H)+.

EXAMPLE 606

N-{3-[1-((3S)-3-{[(TERT-BUTYLAMINO)CARBOTHIOYL]AMINO}-3-PHENYLPROPYL)-4-PIPERIDINYL]PHENYL}-2-METHYLPROPANAMIDE: Prepared by Procedure P and Scheme AB using 2-isothiocyanato-2-methylpropane and N-(3-{1-[(3S)-3-amino-3-phenylpropyl]-4-piperidinyl}phenyl)-2-methylpropanamide: ESMS m/e: 495.1 (M+H)+.

EXAMPLE 607

N-{3-[1-((3S)-3-{[(2-FLUOROANILINO)CARBONYL]AMINO}-3-PHENYLPROPYL)-4-PIPERIDINYL]PHENYL}-2-METHYLPROPANAMIDE: Prepared by Procedure P and Scheme AB using 1-fluoro-2-isocyanatobenzene and N-(3-{1-[(3S)-3-amino-3-phenylpropyl]-4-piperidinyl}phenyl)-2-methylpropanamide: ESMS m/e: 517.0 (M+H)+.

EXAMPLE 608

2-METHYL-N-[3-(1-{(3S)-3-PHENYL-3-[(2-TOLUIDINOCARBOTHIOYL)AMINO]PROPYL}-4-PIPERIDINYL)PHENYL]PROPANAMIDE: Prepared by Procedure P and Scheme AB using 1-isothiocyanato-2-methylbenzene and N-(3-{1-[(3S)-3-amino-3-phenylpropyl]-4-piperidinyl}phenyl)-2-methylpropanamide: ESMS m/e: 529.1 (M+H)+.

EXAMPLE 609

N-{3-[1-((3S)-3-{[(BENZYLAMINO)CARBONYL]AMINO}-3-PHENYLPROPYL)-4-PIPERIDINYL]PHENYL}-2-METHYLPROPANAMIDE: phenylpropyl]-4-piperidinyl}phenyl)-2-methylpropanamide: $^1$H NMR (400 MHz, CDCl$_3$) δ 8.44 (s, 1H), 7.67 (d, 1H, J=7.9 Hz), 7.31–7.13 (m, 13H), 6.38 (s, 1H), 6.80 (d, 1H, J=7.9 Hz), 5.54 (m, 1H), 4.81 (m, 1H), 4.41 (dd, 1H, J=14.8, 6.2 Hz), 4.29 (dd, 1H, J=14.9, 5.4 Hz), 2.99 (d, 1H, J=11.2 Hz), 2.87 (d, 1H, J=11.2 Hz), 2.67 (q, 1H, J=6.2 Hz), 2.3 (m, 3H), 2.0–1.5 (m, 7H), 1.23 (d, 6H, J=6.7 Hz); ESMS m/e: 513.2 (M+H)+.

EXAMPLE 610

2-METHYL-N-{3-[1-((3S)-3-{[(2-NITROANILINO)CARBONYL]AMINO}-3-PHENYLPROPYL)-4-PIPERIDINYL]PHENYL}PROPANAMIDE: Prepared by Procedure P and Scheme AB using 1-isocyanato-2-nitrobenzene and N-(3-{1-[(3S)-3-amino-3-phenylpropyl]-4-piperidinyl}phenyl)-2-methylpropanamide: ESMS m/e: 543.6 (M+H)+.

EXAMPLE 611

N-{3-[1-((3S)-3-{[(3,4-DICHLOROANILINO)CARBONYL]AMINO}-3-PHENYLPROPYL)-4-PIPERIDINYL]PHENYL}-2-METHYLPROPANAMIDE: Prepared by Procedure P and Scheme AB using 1,2-dichloro-4-isocyanatobenzene and N-(3-{1-[(3S)-3-amino-3-phenylpropyl]-4-piperidinyl}phenyl)-2-methylpropanamide: ESMS m/e: 567.1 (M+H)+.

EXAMPLE 612

2-METHYL-N-(3-{1-[(3S)-3-({[2-(METHYLSULFANYL)ANILINO]CARBONYL}AMINO)-3-PHENYLPROPYL]-4-PIPERIDINYL}PHENYL)PROPANAMIDE: Prepared by Procedure P and Scheme AB using 1-isocyanato-2-(methylsulfanyl)benzene and N-(3-{1-[(3S)-3-amino-3-phenylpropyl]-4-piperidinyl}phenyl)-2-methylpropanamide: ESMS m/e: 545.0 (M+H)+.

EXAMPLE 613

N-{3-[1-(3-{[(4-FLUOROANILINO)CARBONYL]AMINO}PROPYL)-4-PIPERIDINYL]PHENYL}-2-METHYLPROPANAMIDE: Prepared by Procedure P and Scheme AB using 1-fluoro-4-isocyanatobenzene and N-{3-[1-(3-aminopropyl)-4-piperidinyl]phenyl}-2-methylpropanamide: $^1$H NMR (400 MHz, CDCl$_3$) δ 7.45 (q, 2H, J=4.7 Hz), 7.23 (m, 4H), 7.05 (t, 4H, J=7.8 Hz), 6.75 (m, 1H), 4.05 (m, 1H), 3.19 (s, 1H), 2.71 (m, 1H), 2.53 (m, 1H) 2.25 (m, 3H), 1.8 (m, 9H), 1.25 (d, 6H, J=6.4 Hz); ESMS m/e: 441.1 (M+H)+.

EXAMPLE 614

N-{3-[1-(3-{[(3,4-DICHLOROANILINO)CARBONYL]AMINO}PROPYL)-4-PIPERIDINYL]PHENYL}-2-METRYLPROPANAMIDE: Prepared by Procedure P and Scheme AB using 1,2-dichloro-4-isocyanatobenzene and N-{3-[1-(3-aminopropyl)-4-piperidinyl]phenyl}-2-methylpropanamide: ESMS m/e: 493.2 (M+H)⁺.

EXAMPLE 615

2-METHYL-N-[3-(1-{3-[(2-TOLUIDINOCARBOTHIOYL)AMINO]PROPYL}-4-PIPERIDINYL)PHENYL]PROPANAMIDE: Prepared by Procedure P and Scheme AB using 1-isothiocyanato-2-methylbenzene and N-{3-[1-(3-aminopropyl)-4-piperidinyl]phenyl}-2-methylpropanamide: ESMS m/e: 453.2 (M+H)⁺.

EXAMPLE 616

N-{3-[1-(3-{[(BENZYLAMINO)CARBONYL]AMINO}PROPYL)-4-PIPERIDINYL]PHENYL}-2-METHYLPROPANAMIDE: Prepared by Procedure P and Scheme AB using (isocyanatomethyl)benzene and N-{3-[1-(3-aminopropyl)-4-piperidinyl]phenyl}-2-methylpropanamide: ESMS m/e: 437.2 (M+H)⁺.

EXAMPLE 617

N-{3-[1-(3-{[(4-ETHOXYANILINO)CARBONYL]AMINO}PROPYL)-4-PIPERIDINYL]PHENYL}-2-METHYLPROPANAMIDE: Prepared by Procedure P and Scheme AB using 1-ethoxy-4-isocyanatobenzene and N-{3-[1-(3-aminopropyl)-4-piperidinyl]phenyl}-2-methylpropanamide: ESMS m/e: 467.2 (M+H)⁺.

EXAMPLE 618

N-[3-(1-{3-[(ANILINOCARBONYL)AMINO]PROPYL}-4-PIPERIDINYL)PHENYL]-2-METHYLPROPANAMIDE: Prepared by Procedure P and Scheme AB using isocyanatobenzene and N-{3-[1-(3-aminopropyl)-4-piperidinyl]phenyl}-2-methylpropanamide: ESMS m/e: 422.9 (M+H)⁺.

EXAMPLE 619

2-METHYL-N-(3-{1-[3-({[2-(METHYLSULFANYL)ANILINO]CARBONYL}AMINO)PROPYL]-4-PIPERIDINYL}PHENYL)PROPANAMIDE: Prepared by Procedure P and Scheme AB using 1-isocyanato-2-(methylsulfanyl)benzene and N-{3-[1-(3-aminopropyl)-4-piperidinyl]phenyl}-2-methylpropanamide: ESMS m/e: 469.1 (M+H)⁺.

EXAMPLE 620

N-{3-[1-(3-{[(TERT-BUTYLAMINO)CARBOTHIOYL]AMINO}PROPYL)-4-PIPERIDINYL]PHENYL}-2-METHYLPROPANAMIDE: Prepared by Procedure P and Scheme AB using 2-isothiocyanato-2-methylpropane and N-{3-[1-(3-aminopropyl)-4-piperidinyl]phenyl}-2-methylpropanamide: ESMS m/e: 419.0 (M+H)⁺.

EXAMPLE 621

2-METHYL-N-{3-[1-(3-{[(4-PHENOXYANILINO)CARBONYL]AMINO}PROPYL)-4-PIPERIDINYL]PHENYL}PROPANAMIDE: Prepared by Procedure P and Scheme AM using 1-isocyanato-4-phenoxybenzene and N-{3-[1-(3-aminopropyl)-4-piperidinyl]phenyl}-2-methylpropanamide: ESMS m/e: 515.5 (M+H)⁺.

EXAMPLE 622

N-(3-{4-[3-(ACETYLAMINO)PHENYL]-1-PIPERIDINYL}PROPYL)-4-(2,4-DIFLUOROPHENYL)-2-METHYL-6-OXO-1,4,5,6-TETRAHYDRO-3-PYRIDINECARBOXAMIDE: Prepared by Procedure AC and Scheme AM using N-{3-[1-(3-aminopropyl)-4-piperidinyl]phenyl}acetamide and 4-(2,4-difluorophenyl)-2-methyl-6-oxo-1,4,5,6-tetrahydro-3-pyridinecarboxylic acid: ESMS m/e: 525.2 (M+H)⁺.

EXAMPLE 623

N-(3-{4-[3-(ACETYLAMINO)PHENYL]-1-PIPERIDINYL}PROPYL)-4-(3,4-DIFLUOROPHENYL)-2-METHYL-6-OXO-1,4,5,6-TETRAHYDRO-3-PYRIDINECARBOXAMIDE: Prepared by Procedure AC and Scheme AM using N-{3-[1-(3-aminopropyl)-4-piperidinyl]phenyl}acetamide and 4-(3,4-difluorophenyl)-2-methyl-6-oxo-1,4,5,6-tetrahydro-3-pyridinecarboxylic acid: ESMS m/e: 525.2 (M+H)⁺.

EXAMPLE 624

N-(6-{4-[3-(ISOBUTYRYLAMINO)PHENYL]-1-PIPERIDINYL}HEXYL)-1-(4-NITROPHENYL)-5-(TRIFLUOROMETHYL)-1H-PYRAZOLE-4-CARBOXAMIDE: Prepared by Procedure Q1 (THF) and Scheme AT using N-{3-[1-(6-aminohexyl)-4-piperidinyl]phenyl}-2-methylpropanamide and 1-(4-nitrophenyl)-5-(trifluoromethyl)-1H-pyrazole-4-carbonyl chloride: ESMS m/e: 629.2 (M+H)⁺.

EXAMPLE 625

N-[3-(1-{6-[(DIPHENYLACETYL)AMINO]HEXYL}-4-PIPERIDINYL)PHENYL]-2-METHYLPROPANAMIDE: Prepared by Procedure Q1 (THF) and Scheme AT using N-{3-[1-(6-aminohexyl)-4-piperidinyl]phenyl}-2-methylpropanamide and diphenylacetyl chloride: ESMS m/e: 540.3 (M+H)⁺.

EXAMPLE 626

5-(3,5-DICHLOROPHENOXY)-N-(6-{4-[3-(ISOBUTYRYLAMINO)PHENYL]-1-PIPERIDINYL}HEXYL)-2-FURAMIDE: Prepared by Procedure Q1 (THF) and Scheme AT using N-{3-[1-(6-aminohexyl)-4-piperidinyl]phenyl}-2-methylpropanamide and 5-(3,5-dichlorophenoxy)-2-furoyl chloride: ESMS m/e: 600.2 (M+H)⁺.

EXAMPLE 627

N-(6-{4-[3-(ISOBUTYRYLAMINO)PHENYL]-1-PIPERIDINYL}HEXYL)-2-PHENOXYNICOTINAMIDE: Prepared by Procedure Q1 (THF) and Scheme AT using N-{3-[1-(6-aminohexyl)-4-piperidinyl]phenyl}-2-methylpropanamide and 2-phenoxynicotinoyl chloride: ESMS m/e: 543.3 (M+H)⁺.

EXAMPLE 628

N-(6-{4-[3-(ISOBUTYRYLAMINO)PHENYL]-1-PIPERIDINYL}HEXYL)-2-NAPHTHAMIDE: Prepared by Procedure Q1 (THF) and Scheme AT using N-{3-[1-(6-aminohexyl)-4-piperidinyl]phenyl}-2-methylpropanamide and 2-naphthoyl chloride: ESMS m/e: 500.3 (M+H)⁺.

EXAMPLE 629

1-BENZYL-3-TERT-BUTYL-N-(6-{4-[3-(ISOBUTYRYLAMINO)PHENYL]-1-PIPERIDINYL}HEXYL)-1H-PYRAZOLE-5-CARBOXAMIDE: Prepared by Procedure Q1 (THF) and Scheme AT using N-{3-[1-(6-aminohexyl)-4-piperidinyl]phenyl}-2-methylpropanamide and 1-benzyl-3-tert-butyl-1H-pyrazole-5-carbonyl chloride: ESMS m/e: 586.3 (M+H)$^+$.

EXAMPLE 630

3-CHLORO-N-(6-{4-[3-(ISOBUTYRYLAMINO)PHENYL]-1-PIPERIDINYL}HEXYL)-4-(ISOPROPYLSULFONYL)-2-THIOPHENECARBOXAMIDE: Prepared by Procedure Q1 (THF) and Scheme AT using N-{3-[1-(6-aminohexyl)-4-piperidinyl]phenyl}-2-methylpropanamide and 3-chloro-4-(isopropylsulfonyl)-2-thiophenecarbonyl chloride: ESMS m/e: 596.2 (M+H)$^+$.

EXAMPLE 631

N-[3-(1-{6-[(ANILINOCARBONYL)AMINO]HEXYL}-4-PIPERIDINYL)PHENYL]-2-METHYLPROPANAMIDE: Prepared by Procedure Q1 (THF) and Scheme AT using N-{3-[1-(6-aminohexyl)-4-piperidinyl]phenyl}-2-methylpropanamide and phenyl isocyanate: ESMS m/e: 465.2 (M+H)$^+$.

EXAMPLE 632

N-{3-[1-(6-{[(2,4-DICHLOROANILINO)CARBONYL]AMINO}HEXYL)-4-PIPERIDINYL]PHENYL}-2-METHYLPROPANAMIDE: Prepared by Procedure Q1 (THF) and Scheme AT using N-{3-[1-(6-aminohexyl)-4-piperidinyl]phenyl}-2-methylpropanamide and 2,4-dichlorophenyl isocyanate: ESMS m/e: 533.2 (M+H)$^+$.

EXAMPLE 633

N-(6-{4-[3-(ISOBUTYRYLAMINO)PHENYL]-1-PIPERIDINYL}HEXYL)-1-PHENYL-5-PROPYL-1H-PYRAZOLE-4-CARBOXAMIDE: Prepared by Procedure Q1 (THF) and Scheme AT using N-{3-[1-(6-aminohexyl)-4-piperidinyl]phenyl}-2-methylpropanamide and 1-phenyl-5-propyl-1H-pyrazole-4-carbonyl chloride: ESMS m/e: 558.3 (M+H)$^+$.

EXAMPLE 634

2-METHYL-N-{3-[1-(6-{[(1-NAPHTHYLAMINO)CARBONYL]AMINO}HEXYL)-4-PIPERIDINYL]PHENYL}PROPANAMIDE: Prepared by Procedure Q1 (THF) and Scheme AT using N-{3-[1-(6-aminohexyl)-4-piperidinyl]phenyl}-2-methylpropanamide and 1-naphthyl isocyanate: ESMS m/e: 515.3 (M+H)$^+$.

EXAMPLE 635

N-{3-[1-(6-{[([1,1'-BIPHENYL]-4-YLAMINO)CARBONYL]AMINO}HEXYL)-4-PIPERIDINYL]PHENYL}-2-METHYLPROPANAMIDE: Prepared by Procedure Q1 (THF) and Scheme AT using N-{3-[1-(6-aminohexyl)-4-piperidinyl]phenyl}-2-methylpropanamide and 4-biphenyl isocyanate: ESMS m/e: 541.3 (M+H)$^+$.

EXAMPLE 636

2-METHYL-N-{3-[1-(6-{[(2-NAPHTHYLAMINO)CARBONYL]AMINO}HEXYL)-4-PIPERIDINYL]PHENYL}PROPANAMIDE: Prepared by Procedure Q1 (THF) and Scheme AT using N-{3-[1-(6-aminohexyl)-4-piperidinyl]phenyl}-2-methylpropanamide and 2-naphthyl isocyanate: ESMS m/e: 515.3 (M+H)$^+$.

EXAMPLE 637

N-{3-[1-(3-{[(3,4-DIMETHOXYPHENYL)SULFONYL]AMINO}PROPYL)-4-PIPERIDINYL]PHENYL}-2-METHYLPROPANAMIDE: Prepared by Procedure Q1 (THF) and Scheme AT using N-{3-[1-(3-aminopropyl)-4-piperidinyl]phenyl}-2-methylpropanamide and 3,4-dimethoxybenzenesulfonyl chloride: ESMS m/e: 504.2 (M+H)$^+$.

EXAMPLE 638

N-(3-{4-[3-(ISOBUTYRYLAMINO)PHENYL]-1-PIPERIDINYL}PROPYL)-5-METHYL-3-PHENYL-4-ISOXAZOLECARBOXAMIDE: Prepared by Procedure Q1 (THF) and Scheme AT using N-{3-[1-(3-aminopropyl)-4-piperidinyl]phenyl}-2-methylpropanamide and 5-methyl-3-phenyl-4-isoxazolecarbonyl chloride: ESMS m/e: 489.3 (M+H)$^+$.

EXAMPLE 639

N-{3-[1-(3-{[(4-FLUOROPHENYL)ACETYL]AMINO}PROPYL)-4-PIPERIDINYL]PHENYL}-2-METHYLPROPANAMIDE: Prepared by Procedure Q1 (THF) and Scheme AT using N-{3-[1-(3-aminopropyl)-4-piperidinyl]phenyl}-2-methylpropanamide and (4-fluorophenyl)acetyl chloride: ESMS m/e: 440.3 (M+H)$^+$.

EXAMPLE 640

N-{3-[1-(3-{[(4-CHLORO-3-NITROPHENYL)SULFONYL]AMINO}PROPYL)-4-PIPERIDINYL]PHENYL}-2-METHYLPROPANAMIDE: Prepared by Procedure Q1 (THF) and Scheme AT using N-{3-[1-(3-aminopropyl)-4-piperidinyl]phenyl}-2-methylpropanamide and 4-chloro-3-nitrobenzenesulfonyl chloride: ESMS m/e: 523.1 (M+H)$^+$.

EXAMPLE 641

2-(4-CHLOROPHENOXY)-N-(3-{4-[3-(ISOBUTYRYLAMINO)PHENYL]-1-PIPERIDINYL}PROPYL)NICOTINAMIDE: Prepared by Procedure Q1 (THF) and Scheme AT using N-{3-[1-(3-aminopropyl)-4-piperidinyl]phenyl}-2-methylpropanamide and 2-(4-chlorophenoxy)nicotinoyl chloride: ESMS m/e: 535.2 (M+H)$^+$.

EXAMPLE 642

5-(3,5-DICHLOROPHENOXY)-N-(3-{4-[3-(ISOBUTYRYLAMINO)PHENYL]-1-PIPERIDINYL}PROPYL)-2-FURAMIDE: Prepared by Procedure Q1 (THF) and Scheme AT using N-{3-[1-(3-aminopropyl)-4-piperidinyl]phenyl}-2-methylpropanamide and 5-(3,5-dichlorophenoxy)-2-furoyl chloride: ESMS m/e: 558.2 (M+H)$^+$.

EXAMPLE 643

N-{3-[1-(3-{[(2-FLUOROPHENYL)SULFONYL]AMINO}PROPYL)-4-PIPERIDINYL]PHENYL}-2-METHYLPROPANAMIDE: Prepared by Procedure Q1 (THF) and Scheme AT using N-{3-[1-(3-aminopropyl)-4-piperidinyl]phenyl}-2-methylpropanamide and 2-fluorobenzenesulfonyl chloride: ESMS m/e: 462.2 (M+H)$^+$.

EXAMPLE 644

N-{3-[1-(3-{[(3,5-DIMETHYL-4-ISOXAZOLYL)SULFONYL]AMINO}PROPYL)-4-PIPERIDINYL]PHENYL}-2-METHYLPROPANAMIDE: Prepared by Procedure Q1 (THF) and Scheme AT using N-{3-[1-(3- aminopropyl)-4-piperidinyl]phenyl}-2-methylpropanamide and 3,5-dimethyl-4-isoxazolesulfonyl chloride: ESMS m/e: 463.2 (M+H)⁺.

EXAMPLE 644

N-{3-[1-(3-{[(4-TERT-BUTYLPHENYL)SULFONYL]AMINO}PROPYL)-4-PIPERIDINYL]PHENYL}-2-METHYLPROPANAMIDE: Prepared by Procedure Q1 (THF) and Scheme AT using N-{3-[1-(3-aminopropyl)-4-piperidinyl]phenyl}-2-methylpropanamide and 4-tert-butylbenzenesulfonyl chloride: ESMS m/e: 500.3 (M+H)⁺.

EXAMPLE 646

N-{3-[1-(6-AMINOHEXYL)-4-PIPERIDINYL]PHENYL}-2-METHYLPROPANAMIDE: Prepared by Procedure AE and Scheme Y using N-(3-{1-[6-(1,3-dioxo-1,3-dihydro-2H-isoindol-2-yl)hexyl]-4-piperidinyl}phenyl)-2-methylpropanamide and hydrazine hydrate: ESMS m/e: 346.2 (M+H)⁺.

EXAMPLE 647

N-{3-[1-(2-{[([1,1'-BIPHENYL]-4-YLAMINO)CARBONYL]AMINO}ETHYL)-4-PIPERIDINYL]PHENYL}-2-METHYLPROPANAMIDE: Prepared by Procedure Q1 (THF) and Scheme AT using N-{3-[1-(2-aminoethyl)-4-piperidinyl]phenyl}-2-methylpropanamide and 4-biphenyl isocyanate: ESMS m/e: 485.2 (M+H)⁺.

EXAMPLE 648

5-(3,5-DICHLOROPHENOXY)-N-(2-{4-[3-(ISOBUTYRYLAMINO)PHENYL]-1-PIPERIDINYL}ETHYL)-3-FURAMIDE: Prepared by Procedure Q1 (THF) and Scheme AT using N-{3-[1-(2-aminoethyl)-4-piperidinyl]phenyl}-2-methylpropanamide and 5-(3,5-dichlorophenoxy)-3-furoyl chloride: ESMS m/e: 544.1 (M+H)⁺.

EXAMPLE 649

N-[3-(1-{2-[(DIPHENYLACETYL)AMINO]ETHYL}-4-PIPERIDINYL)PHENYL]-2-METHYLPROPANAMIDE: Prepared by Procedure Q1 (THF) and Scheme AT using N-{3-[1-(2-aminoethyl)-4-piperidinyl]phenyl}-2-methylpropanamide and diphenylacetyl chloride: ESMS m/e: 484.2 (M+H)⁺.

EXAMPLE 650

N-(2-{4-[3-(ISOBUTYRYLAMINO)PHENYL]-1-PIPERIDINYL}ETHYL)-2-NAPHTHAMIDE: Prepared by Procedure Q1 (THF) and Scheme AT using N-(3-[1-(2-aminoethyl)-4-piperidinyl]phenyl)-2-methylpropanamide and 2-naphthoyl chloride: ESMS m/e: 444. 2 (M+H)⁺.

EXAMPLE 651

3-(2,6-DICHLOROPHENYL)-N-(4-{4-[3-(ISOBUTYRYLAMINO)PHENYL]-1-PIPERIDINYL}BUTYL)-5-METHYL-4-ISOXAZOLECARBOXAMIDE: Prepared by Procedure Q1 (THF) and Scheme AT using N-{3-[1-(4-aminobutyl)-4-piperidinyl]phenyl}-2-methylpropanamide and 3-(2,6-dichlorophenyl)-5-methyl-4-isoxazolecarbonyl chloride: ESMS m/e: 571.2 (M+H)⁺.

EXAMPLE 652

3-(2,6-DICHLOROPHENYL)-N-(5-{4-[3-(ISOBUTYRYLAMINO)PHENYL]-1-PIPERIDINYL}PENTYL)-5-METHYL-4-ISOXAZOLECARBOXAMIDE: Prepared by Procedure Q1 (THF) and Scheme AT using N-{3-[1-(5-aminopentyl)-4-piperidinyl]phenyl}-2-methylpropanamide and 3-(2,6-dichlorophenyl)-5-methyl-4-isoxazolecarbonyl chloride. ESMS m/e: 585.2 (M+H)⁺.

EXAMPLE 653

N-[3-(1-{4-[(DIPHENYLACETYL)AMINO]BUTYL}-4-PIPERIDINYL)PHENYL]-2-METHYLPROPANAMIDE: Prepared by Procedure Q2 (THF/DCM, 1:3)) and Scheme AT using N-{3-[1-(4-aminobutyl)-4-piperidinyl]phenyl)-2-methylpropanamide and diphenylacetyl chloride: ESMS m/e: 512.0 (M+H)⁺.

EXAMPLE 654

N-[3-(1-{5-[(DIPHENYLACETYL)AMINO]PENTYL}-4-PIPERIDINYL)PHENYL]-2-METHYLPROPANAMIDE: Prepared by Procedure Q2 (THF/DCM, 1:3)) and Scheme AT using N-{3-[1-(5-aminopentyl)-4-piperidinyl]phenyl}-2-methylpropanamide and diphenylacetyl chloride: ESMS m/e: 526.0 (M+H)⁺.

EXAMPLE 655

3,5-DICHLORO-N-(4-{4-[3-(ISOBUTYRYLAMINO)PHENYL]-1-PIPERIDINYL}BUTYL)BENZAMIDE: Prepared by Procedure Q2 (THF/DCM, 1:3) and Scheme AT using N-{3-[1-(4-aminobutyl)-4-piperidinyl]phenyl}-2-methylpropanamide and 3,5-dichlorobenzoyl chloride: ESMS m/e: 490.0 (M+H)⁺.

EXAMPLE 656

5-(3,5-DICHLOROPHENOXY)-N-(4-{4-[3-(ISOBUTYRYLAMINO)PHENYL]-1-PIPERIDINYL}BUTYL)-2-FURAMIDE: Prepared by Procedure Q2 (THF/DCM, 1:3) and Scheme AT using N-{3-[1-(4-aminobutyl)-4-piperidinyl]phenyl}-2-methylpropanamide and 5-(3,5-dichlorophenoxy)-2-furoyl chloride: ESMS m/e: 572.0 (M+H)⁺.

EXAMPLE 657

3-CHLORO-N-(4-{4-[3-(ISOBUTYRYLAMINO)PHENYL]-1-PIPERIDINYL}BUTYL)BENZAMIDE: Prepared by Procedure Q2 (THF/DCM, 1:3) and Scheme AT using N-{3-[1-(4-aminobutyl)-4-piperidinyl]phenyl}-2-methylpropanamide and 3-chlorobenzoyl chloride: ESMS m/e: 456.0 (M+H)⁺.

EXAMPLE 658

3,4-DIFLUORO-N-(4-{4-[3-(ISOBUTYRYLAMINO)PHENYL]-1-PIPERIDINYL}BUTYL)BENZAMIDE: Prepared by Procedure Q2 (THF/DCM, 1:3) and Scheme AT using N-{3-[1-(4-aminobutyl)-4-piperidinyl]phenyl}-2-methylpropanamide and 3,4-difluorobenzoyl chloride: ESMS m/e: 458.0 (M+H)⁺.

EXAMPLE 659

N-{3-[1-(4-{[(3,5-DICHLOROANILINO)CARBONYL]AMINO}BUTYL)-4-PIPERIDINYL]PHENYL}-2-METHYLPROPANAMIDE: Prepared by Procedure Q2 (THF/DCM, 1:3) and Scheme AT using N-(3-{1-[4-(formylamino)butyl]-4-piperidinyl}phenyl)-2-methylpropanamide and 3,5-dichlorophenyl isocyanate: ESMS m/e: 505.0 (M+H)⁺.

EXAMPLE 660

N-{3-[1-(4-{[([1,1'-BIPHENYL]-4-YLAMINO)CARBONYL]AMINO}BUTYL)-4-PIPERIDINYL]PHENYL}-2-METHYLPROPANAMIDE: Prepared by Procedure Q2 (THF/DCM, 1:3) and Scheme AT using N-{3-[1-(4-aminobutyl)-4-piperidinyl]phenyl}-2-methylpropanamide and 4-biphenyl isocyanate: ESMS m/e: 513.0 (M+H)$^+$.

EXAMPLE 661

2-METHYL-N-(3-{1-[5-(4-NITROPHENYL)-5-OXOPENTYL]-4-PIPERIDINYL}PHENYL)PROPANAMIDE: Prepared by Procedure K and Scheme B1 ($K_2CO_3$) using 5-chloro-1-(4-nitrophenyl)-1-pentanone and 2-methyl-N-[3-(4-piperidinyl)phenyl]propanamide: ESMS m/e: 452.2 (M+H)$^+$.

EXAMPLE 662

N-(3-{1-[5-(4-FLUOROPHENYL)-5-OXOPENTYL]-4-PIPERIDINYL}PHENYL)-2-METHYLPROPANAMIDE: Prepared by Procedure K and Scheme B1 ($K_2CO_3$) using 5-chloro-1-(4-fluorophenyl)-1-pentanone and 2-methyl-N-[3-(4-piperidinyl)phenyl]propanamide: ESMS m/e: 425.2 (M+H)$^+$.

EXAMPLE 663

2-METHYL-N-[3-(1-{5-OXO-5-[2-(TRIFLUOROMETHYL)PHENYL]PENTYL}-4-PIPERIDINYL)PHENYL]PROPANAMIDE: Prepared by Procedure K and Scheme B1 ($K_2CO_3$) using 5-chloro-1-[2-(trifluoromethyl)phenyl]-1-pentanone and 2-methyl-N-[3-(4-piperidinyl)phenyl]propanamide: ESMS m/e: 475.2 (M+H)$^+$.

EXAMPLE 664

N-(3-{1-[5-(3-BROMOPHENYL)-5-OXOPENTYL]-4-PIPERIDINYL}PHENYL)-2-METHYLPROPANAMIDE: Prepared by Procedure K and Scheme B1 ($K_2CO_3$) using 1-(3-bromophenyl)-5-chloro-1-pentanone and 2-methyl-N-[3-(4-piperidinyl)phenyl]propanamide: ESMS m/e: 485.1 (M+H)$^+$.

EXAMPLE 665

2-METHYL-N-(3-{1-[5-(3-NITROPHENYL)-5-OXOPENTYL]-4-PIPERIDINYL}PHENYL)PROPANAMIDE: Prepared by Procedure K and Scheme B1 ($K_2CO_3$) using 5-chloro-1-(3-nitrophenyl)-1-pentanone and 2-methyl-N-[3-(4-piperidinyl)phenyl]propanamide: ESMS m/e: 452.2 (M+H)$^+$.

EXAMPLE 666

N-(3-{1-[5-(3-CHLOROPHENYL)-5-OXOPENTYL]-4-PIPERIDINYL}PHENYL)-2-METHYLPROPANAMIDE: Prepared by Procedure K and Scheme B1 ($K_2CO_3$) using 1-(3-chlorophenyl)-5-chloro-1-pentanone and 2-methyl-N-[3-(4-piperidinyl)phenyl]propanamide: ESMS m/e: 441.1 (M+H)$^+$.

EXAMPLE 667

N-(3-{1-[5-(4-BROMOPHENYL)-5-OXOPENTYL]-4-PIPERIDINYL}PHENYL)-2-METHYLPROPANAMIDE: Prepared by Procedure K and Scheme B1 ($K_2CO_3$) using 1-(4-bromophenyl)-5-chloro-1-pentanone and 2-methyl-N-[3-(4-piperidinyl)phenyl]propanamide: ESMS m/e: 485.1 (M+H)$^+$.

EXAMPLE 668

N-(3-{1-[5-(2-IODOPHENYL)-5-OXOPENTYL]-4-PIPERIDINYL}PHENYL)-2-METHYLPROPANAMIDE: Prepared by Procedure K and Scheme B1 ($K_2CO3$) using 1-(2-iodophenyl)-5-chloro-1-pentanone and 2-methyl-N-[3-(4-piperidinyl)phenyl]propanamide: ESMS m/e: 533.0 (M+H)$^+$.

EXAMPLE 669

N-(3-{1-[5-(3-FLUOROPHENYL)-5-OXOPENTYL]-4-PIPERIDINYL}PHENYL)-2-METHYLPROPANAMIDE: Prepared by Procedure K and Scheme B ($K_2CO_3$) using 1-(3-fluorophenyl)-5-chloro-1-pentanone and 2-methyl-N-[3-(4-piperidinyl)phenyl]propanamide: ESMS m/e: 425.2 (M+H)$^+$.

EXAMPLE 670

2-METHYL-N-[3-(1-{5-OXO-5-[3-(TRIFLUOROMETHYL)PHENYL]PENTYL}-4-PIPERIDINYL)PHENYL]PROPANAMIDE: Prepared by Procedure K and Scheme B1 ($K_2CO_3$) using 1-[3-(trifluoromethyl)phenyl]-5-chloro-1-pentanone and 2-methyl-N-[3-(4-piperidinyl)phenyl]propanamide: ESMS m/e: 475.2 (M+H)$^+$.

EXAMPLE 671

N-(3-{1-[5-(2-FLUOROPHENYL)-5-OXOPENTYL]-4-PIPERIDINYL}PHENYL)-2-METHYLPROPANAMIDE: Prepared by Procedure K and Scheme B1 ($K_2CO_3$) using 1-(2-fluorophenyl)-5-chloro-1-pentanone and 2-methyl-N-[3-(4-piperidinyl)phenyl]propanamide: ESMS m/e: 425.2 (M+H)$^+$.

EXAMPLE 672

N-(3-{1-[5-(3-IODOPHENYL)-5-OXOPENTYL]-4-PIPERIDINYL}PHENYL)-2-METHYLPROPANAMIDE: Prepared by Procedure K and Scheme B1 ($K_2CO_3$) using 1-(3-iodophenyl)-5-chloro-1-pentanone and 2-methyl-N-[3-(4-piperidinyl)phenyl]propanamide: ESMS m/e: 533.0 (M+H)$^+$.

EXAMPLE 673

N-(3-{1-[5-(2-CHLOROPHENYL)-5-OXOPENTYL]-4-PIPERIDINYL}PHENYL)-2-METHYLPROPANAMIDE: Prepared by Procedure K and Scheme B1 ($K_2CO_3$) using 1-(2-chlorophenyl)-5-chloro-1-pentanone and 2-methyl-N-[3-(4-piperidinyl)phenyl]propanamide: ESMS m/e: 441.1 (M+H)$^+$.

EXAMPLE 674

2-METHYL-N-[3-(1-{5-OXO-5-[4-(TRIFLUOROMETHYL)PHENYL]PENTYL}-4-PIPERIDINYL)PHENYL]PROPANAMIDE: Prepared by Procedure K and Scheme B1 ($K_2CO_3$) using 1-[4-(trifluoromethyl)phenyl]-5-chloro-1-pentanone and 2-methyl-N-[3-(4-piperidinyl)phenyl]propanamide: ESMS m/e: 475.2 (M+H)$^+$.

EXAMPLE 675

N-(3-{1-[5-(4-CHLOROPHENYL)-5-OXOPENTYL]-4-PIPERIDINYL}PHENYL)-2-METHYLPROPANAMIDE: Prepared by Procedure K and Scheme B1 ($K_2CO_3$) using 1-(4-chlorophenyl)-5-chloro-1-pentanone and 2-methyl-N-[3-(4-piperidinyl)phenyl]propanamide: ESMS m/e: 441.1 (M+H)$^+$.

EXAMPLE 676

N-(3-{1-[5-(4-IODOPHENYL)-5-OXOPENTYL]-4-PIPERIDINYL}PHENYL)-2-METHYLPROPANAMIDE: Prepared by Procedure K and Scheme B1 ($K_2CO_3$) using 1-(4-iodophenyl)-5-chloro-1-pentanone and 2-methyl-N-[3-(4-piperidinyl)phenyl]propanamide: ESMS m/e: 533 (M+H)$^+$.

EXAMPLE 677

N-(3-{1-[5-(2-BROMOPHENYL)-5-OXOPENTYL]-4-PIPERIDINYL}PHENYL)-2-METHYLPROPANAMIDE: Prepared by Procedure K and Scheme B1 ($K_2CO_3$) using 1-(2-bromophenyl)-5-chloro-1-pentanone and 2-methyl-N-[3-(4-piperidinyl)phenyl]propanamide: ESMS m/e: 485.1 (M+H)$^+$.

EXAMPLE 678

2-(4-CHLOROPHENOXY)-N-(4-{4-[3-(ISOBUTYRYLAMINO)PHENYL]-1-PIPERIDINYL}BUTYL)NICOTINAMIDE: Prepared by Procedure Q2 (THF/DCM, 1:3) and Scheme AT using N-{3-[1-(4-aminobutyl)-4-piperidinyl]phenyl}-2-methylpropanamide and 2-(4-chlorophenoxy)nicotinoyl chloride: ESMS m/e: 549.0 (M+H)$^+$.

EXAMPLE 679

N-(4-{4-[3-(ISOBUTYRYLAMINO)PHENYL]-1-PIPERIDINYL}BUTYL)-3,4-DIMETHOXYBENZAMIDE: Prepared by Procedure Q2 (THF/DCM, 1:3) and Scheme AT using N-{3-[1-(4-aminobutyl)-4-piperidinyl]phenyl}-2-methylpropanamide and 3,4-dimethoxybenzoyl chloride: ESMS m/e: 482.0 (M+H)$^+$.

EXAMPLE 680

3-(2-CHLOROPHENYL)-N-(4-{4-[3-(ISOBUTYRYLAMINO)PHENYL]-1-PIPERIDINYL}BUTYL)-5-METHYL-4-ISOXAZOLECARBOXAMIDE: Prepared by Procedure Q2 (THF/DCM, 1:3) and Scheme AT using N-{3-[1-(4-aminobutyl)-4-piperidinyl]phenyl}-2-methylpropanamide and 3-(2-chlorophenyl)-5-methyl-4-isoxazolecarbonyl chloride: ESMS m/e: 537.0 (M+H)$^+$.

EXAMPLE 681

3-(2-CHLOROPHENYL)-N-(5-{4-[3-(ISOBUTYRYLAMINO)PHENYL]-1-PIPERIDINYL}PENTYL)-5-METHYL-4-ISOXAZOLECARBOXAMIDE: Prepared by Procedure Q2 (THF/DCM, 1:3) and Scheme AT using N-{3-[1-(5-aminopentyl)-4-piperidinyl]phenyl}-2-methylpropanamide and 3-(2-chlorophenyl)-5-methyl-4-isoxazolecarbonyl chloride: ESMS m/e: 551.0 (M+H)$^+$.

EXAMPLE 682

2-METHYL-N-{3-[1-(3-{1-METHYL-2-[4-(TRIFLUOROMETHYL)PHENYL]-1H-INDOL-3-YL}PROPYL)-4-PIPERIDINYL]PHENYL}PROPANAMIDE: Prepared by Procedure E and Scheme M using 2-methyl-N-[3-(1-{5-oxo-5-[4-(trifluoromethyl)phenyl]pentyl}-4-piperidinyl)phenyl]propanamide and 1-methyl-1-phenylhydrazine: ESMS m/e: 562.2 (M+H)$^+$.

EXAMPLE 683

2-METHYL-N-{3-[1-(3-{1-METHYL-2-[4-(TRIFLUOROMETHYL)PHENYL]-1H-INDOL-3-YL}PROPYL)-4-PIPERIDINYL]PHENYL}PROPANAMIDE: Prepared by Procedure E and Scheme M using 2-methyl-N-[3-(1-{5-oxo-5-[4-(trifluoromethyl)phenyl]pentyl}-4-piperidinyl)phenyl]propanamide and 4-(trifluoromethoxy)phenylhydrazine hydrochloride: ESMS m/e: 632.2 (M+H)$^+$.

EXAMPLE 684

2-METHYL-N-{3-[1-(3-{2-[4-(TRIFLUOROMETHYL)PHENYL]-1H-INDOL-3-YL}PROPYL)-4-PIPERIDINYL]PHENYL}PROPANAMIDE: Prepared by Procedure E and Scheme M using 2-methyl-N-[3-(1-{5-oxo-5-[4-(trifluoromethyl)phenyl]pentyl}-4-piperidinyl)phenyl]propanamide and phenylhydrazine: ESMS m/e: 548.2 (M+H)$^+$.

EXAMPLE 685

2-METHYL-N-{3-[1-(3-{1-PHENYL-2-[4-(TRIFLUOROMETHYL)PHENYL]-1H-INDOL-3-YL}PROPYL)-4-PIPERIDINYL]PHENYL}PROPANAMIDE: Prepared by Procedure E and Scheme M using 2-methyl-N-[3-(1-{5-oxo-5-[4-(trifluoromethyl)phenyl]pentyl}-4-piperidinyl)phenyl]propanamide and 1,1-diphenylhydrazine hydrochloride: ESMS m/e: 624.2 (M+H)$^+$.

EXAMPLE 686

2-METHYL-N-{3-[1-(3-(2-[4-(TRIFLUOROMETHYL)PHENYL]-1H-BENZO [G]INDOL-3-YL}PROPYL)-4-PIPERIDINYL]PHENYL}PROPANAMIDE: Prepared by Procedure E and Scheme M using 2-methyl-N-[3-(1-{5-oxo-5-[4-(trifluoromethyl)phenyl]pentyl}-4-piperidinyl)phenyl]propanamide and 1-naphthylhydrazine hydrochloride: ESMS m/e: 598.2 (M+H)$^+$.

EXAMPLE 687

2-METHYL-N-{3-[1-(3-{7-METHYL-2-[4-(TRIFLUOROMETHYL)PHENYL]-1H-INDOL-3-YL}PROPYL)-4-PIPERIDINYL]PHENYL}PROPANAMIDE: Prepared by Procedure E and Scheme M using 2-methyl-N-[3-(1-{5-oxo-5-[4-(trifluoromethyl)phenyl]pentyl}-4-piperidinyl)phenyl]propanamide and 1-(2-methylphenyl)hydrazine hydrochloride: ESMS m/e: 562.2(M+H)$^+$.

EXAMPLE 688

2-METHYL-N-{3-[1-(3-{5-METHYL-2-[4-(TRIFLUOROMETHYL)PHENYL]-1H-INDOL-3-YL}PROPYL)-4-PIPERIDINYL]PHENYL}PROPANAMIDE: Prepared by Procedure E and Scheme M using 2-methyl-N-[3-(1-{5-oxo-5-[4-(trifluoromethyl)phenyl]pentyl}-4-piperidinyl)phenyl]propanamide and 4-methylphenylhydrazine hydrochloride: ESMS m/e: 562.2(M+H)$^+$.

EXAMPLE 689

N-{3-[1-(3-{5-METHOXY-2-[4-(TRIFLUOROMETHYL)PHENYL]-1H-INDOL-3-YL}PROPYL)-4-PIPERIDINYL]PHENYL}-2-METHYLPROPANAMIDE: Prepared by Procedure E and Scheme M using 2-methyl-N-[3-(1-{5-oxo-5-[4-(trifluoromethyl)phenyl]pentyl}-4-piperidinyl)phenyl]propanamide and 4-methoxyphenylhydrazine hydrochloride: ESMS m/e: 578.2 (M+H)$^+$.

EXAMPLE 690

N-[3-(1-{3-[2-(3-FLUOROPHENYL)-7-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(3-fluorophenyl)-5-oxopentyl]-4-piperidinyl}phenyl)-2-methylpropanamide and 1-(2-methylphenyl)hydrazine hydrochloride: ESMS m/e: 512.2 (M+H)$^+$.

EXAMPLE 691

N-[3-(1-{3-[2-(4-CHLOROPHENYL)-1-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(4-chlorophenyl)-5-oxopentyl]-4-piperidinyl}phenyl)-2-methylpropanamide and 1-methyl-1-phenylhydrazine: ESMS m/e: 528.2 (M+H)$^+$.

EXAMPLE 692

N-[3-(1-{3-[2-(4-FLUOROPHENYL)-5-METHOXY-1H-INDOL-3-YL]PROPYL}-4-PIPERIDINYL)PHENYL]-2-METHYLPROPANAMIDE: Prepared by Procedure E and Scheme M using N-(3-{1-[5-(4-fluorophenyl)-5-oxopentyl]-4-piperidinyl}phenyl)-2-methylpropanamide and 4-methoxyphenylhydrazine hydrochloride: ESMS m/e: 528.2 (M+H)$^+$.

EXAMPLE 693

N-[3-(1-{3-[2-(2-FLUOROPHENYL)-1H-INDOL-3-YL]PROPYL}-4-PIPERIDINYL)PHENYL]-2-METHYLPROPANAMIDE: Prepared by Procedure E and Scheme M using N-(3-{1-[5-(2-fluorophenyl)-5-oxopentyl]-4-piperidinyl}phenyl)-2-methylpropanamide and phenylhydrazine: ESMS m/e: 498.2 (M+H)$^+$.

EXAMPLE 694

N-[3-(1-{3-[2-(3-FLUOROPHENYL)-5-(TRIFLUOROMETHOXY)-1H-INDOL-3-YL]PROPYL}-4-PIPERIDINYL)PHENYL]-2-METHYLPROPANAMIDE: Prepared by Procedure E and Scheme M using N-(3-{1-[5-(3-fluorophenyl)-5-oxopentyl]-4-piperidinyl}phenyl)-2-methylpropanamide and 4-(trifluoromethoxy)phenylhydrazine hydrochloride: ESMS m/e: 582.2 (M+H)$^+$.

EXAMPLE 695

N-[3-(1-{3-[2-(2-FLUOROPHENYL)-5-(TRIFLUOROMETHOXY)-1H-INDOL-3-YL]PROPYL}-4-PIPERIDINYL)PHENYL]-2-METHYLPROPANAMIDE: Prepared by Procedure E and Scheme M using N-(3-{1-[5-(2-fluorophenyl)-5-oxopentyl]-4-piperidinyl}phenyl)-2-methylpropanamide and 4-(trifluoromethoxy)phenylhydrazine hydrochloride: ESMS m/e: 582.2 (M+H)$^+$.

EXAMPLE 696

N-[3-(1-{3-[2-(4-FLUOROPHENYL)-1-PHENYL-1H-INDOL-3-YL]PROPYL}-4-PIPERIDINYL)PHENYL]-2-METHYLPROPANAMIDE: Prepared by Procedure E and Scheme M using N-(3-{1-[5-(4-fluorophenyl)-5-oxopentyl]-4-piperidinyl}phenyl)-2-methylpropanamide and 1,1-diphenylhydrazine hydrochloride: ESMS m/e: 548.2 (M+H)$^+$.

EXAMPLE 697

N-[3-(1-{3-[2-(2-FLUOROPHENYL)-1H-BENZO[G]INDOL-3-YL]PROPYL}-4-PIPERIDINYL)PHENYL]-2-METHYLPROPANAMIDE: Prepared by Procedure E and Scheme M using N-(3-{1-[5-(2-fluorophenyl)-5-oxopentyl]-4-piperidinyl}phenyl)-2-methylpropanamide and 1-naphthylhydrazine hydrochloride: ESMS m/e: 547.7 (M+H)$^+$.

EXAMPLE 698

N-[3-(1-{3-[2-(2-FLUOROPHENYL)-5-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(2-fluorophenyl)-5-oxopentyl]-4-piperidinyl}phenyl)-2-methylpropanamide and 4-methylphenylhydrazine hydrochloride: ESMS m/e: 512.2 (M+H)$^+$.

EXAMPLE 699

N-[3-(1-{3-[2-(3-FLUOROPHENYL)-1H-BENZO[G]INDOL-3-YL]PROPYL}-4-PIPERIDINYL)PHENYL]-2-METHYLPROPANAMIDE: Prepared by Procedure E and Scheme M using N-(3-{1-[5-(3-fluorophenyl)-5-oxopentyl]-4-piperidinyl}phenyl)-2-methylpropanamide and 1-naphthylhydrazine hydrochloride: ESMS m/e: 548.2 (M+H)$^+$.

EXAMPLE 700

N-[3-(1-{3-[2-(4-FLUOROPHENYL)-1-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(4-fluorophenyl)-5-oxopentyl]-4-piperidinyl}phenyl)-2-methylpropanamide and 1-methyl-1-phenylhydrazine: ESMS m/e: 512.2 (M+H)$^+$.

EXAMPLE 701

N-[3-(1-{3-[2-(3-FLUOROPHENYL)-5-METHOXY-1H-INDOL-3-YL]PROPYL}-4-PIPERIDINYL)PHENYL]-2-METHYLPROPANAMIDE: Prepared by Procedure E and Scheme M using N-(3-{1-[5-(3-fluorophenyl)-5-oxopentyl]-4-piperidinyl}phenyl)-2-methylpropanamide and 4-methoxyphenylhydrazine hydrochloride: ESMS m/e: 528.2 (M+H)$^+$.

EXAMPLE 702

N-[3-(1-{3-[2-(3-FLUOROPHENYL)-1-PHENYL-1H-INDOL-3-YL]PROPYL}-4-PIPERIDINYL)PHENYL]-2-METHYLPROPANAMIDE: Prepared by Procedure E and Scheme M using N-(3-{1-[5-(3-fluorophenyl)-5-oxopentyl]-4-piperidinyl}phenyl)-2-methylpropanamide and 1,1-diphenylhydrazine hydrochloride: ESMS m/e: 574.2 (M+H)$^+$.

EXAMPLE 703

N-[3-(1-{3-[2-(4-CHLOROPHENYL)-5-(TRIFLUOROMETHOXY)-1H-INDOL-3-YL]PROPYL}-4-PIPERIDINYL)PHENYL]-2-METHYLPROPANAMIDE: Prepared by Procedure E and Scheme M using N-(3-{1-[5-(4-chlorophenyl)-5-oxopentyl]-4-piperidinyl}phenyl)-2-methylpropanamide and 4-(trifluoromethoxy)phenylhydrazine hydrochloride: ESMS m/e: 598.2 (M+H)$^+$.

EXAMPLE 704

N-[3-(1-{3-[2-(3-FLUOROPHENYL)-1H-INDOL-3-YL]PROPYL}-4-PIPERIDINYL)PHENYL]-2-

METHYLPROPANAMIDE: Prepared by Procedure E and Scheme M using N-(3-{1-[5-(3-fluorophenyl)-5-oxopentyl]-4-piperidinyl}phenyl)-2-methylpropanamide and phenylhydrazine: ESMS m/e: 498.2 (M+H)$^+$.

EXAMPLE 705

N-[3-(1-{3-[2-(3-FLUOROPHENYL)-1-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(3-fluorophenyl)-5-oxopentyl]-4-piperidinyl}phenyl)-2-methylpropanamide and 1-methyl-1-phenylhydrazine: ESMS m/e: 512.2 (M+H)$^+$.

EXAMPLE 706

N-[3-(1-{3-[2-(3-FLUOROPHENYL)-5-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(3-fluorophenyl)-5-oxopentyl]-4-piperidinyl}phenyl)-2-methylpropanamide and 4-methylphenylhydrazine hydrochloride: ESMS m/e: 512.2 (M+H)$^+$.

EXAMPLE 707

N-[3-(1-{3-[2-(4-CHLOROPHENYL)-1H-BENZO[G]INDOL-3-YL]PROPYL}-4-PIPERIDINYL)PHENYL]-2-METHYLPROPANAMIDE: Prepared by Procedure E and Scheme M using N-(3-{1-[5-(4-chlorophenyl)-5-oxopentyl]-4-piperidinyl}phenyl)-2-methylpropanamide and 1-naphthylhydrazine hydrochloride: ESMS m/e: 564.2 (M+H)$^+$.

EXAMPLE 708

N-[3-(1-{3-[2-(4-CHLOROPHENYL)-1H-INDOL-3-YL]PROPYL}-4-PIPERIDINYL)PHENYL]-2-METHYLPROPANAMIDE: Prepared by Procedure E and Scheme M using N-(3-{1-[5-(4-chlorophenyl)-5-oxopentyl]-4-piperidinyl}phenyl)-2-methylpropanamide and 1-phenylhydrazine hydrochloride: ESMS m/e: 514.2 (M+H)$^+$.

EXAMPLE 709

N-[3-(1-{3-[2-(2-FLUOROPHENYL)-1-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(2-fluorophenyl)-5-oxopentyl]-4-piperidinyl}phenyl)-2-methylpropanamide and 1-methyl-1-phenylhydrazine: ESMS m/e: 512.2 (M+H)$^+$.

EXAMPLE 710

N-[3-(1-{3-[2-(2-FLUOROPHENYL)-7-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(2-fluorophenyl)-5-oxopentyl]-4-piperidinyl}phenyl)-2-methylpropanamide and 1-(2-methylphenyl)hydrazine hydrochloride: ESMS m/e: 512.2 (M+H)$^+$.

EXAMPLE 711

N-[3-(1-{3-[2-(2-FLUOROPHENYL)-1-PHENYL-1H-INDOL-3-YL]PROPYL}-4-PIPERIDINYL)PHENYL]-2-METHYLPROPANAMIDE: Prepared by Procedure E and Scheme M using N-(3-{1-[5-(2-fluorophenyl)-5-oxopentyl]-4-piperidinyl}phenyl)-2-methylpropanamide and 1,1-diphenylhydrazine hydrochloride: ESMS m/e: 574.2 (M+H)$^+$.

EXAMPLE 712

N-[3-(1-{3-[2-(2-FLUOROPHENYL)-5-METHOXY-1H-INDOL-3-YL]PROPYL}-4-PIPERIDINYL)PHENYL]-2-METHYLPROPANAMIDE: Prepared by Procedure E and Scheme M using N-(3-{1-[5-(2-fluorophenyl)-5-oxopentyl]-4-piperidinyl}phenyl)-2-methylpropanamide and 4-methoxyphenylhydrazine hydrochloride: ESMS m/e: 528.2 (M+H)$^+$.

EXAMPLE 713

N-[3-(1-{3-[2-(4-CHLOROPHENYL)-5-METHOXY-1H-INDOL-3-YL]PROPYL}-4-PIPERIDINYL)PHENYL]-2-METHYLPROPANAMIDE: Prepared by Procedure E and Scheme M using N-(3-{1-[5-(4-chlorophenyl)-5-oxopentyl]-4-piperidinyl}phenyl)-2-methylpropanamide and 4-methoxyphenylhydrazine hydrochloride: ESMS m/e: 544.2 (M+H)$^+$.

EXAMPLE 714

N-[3-(1-{3-[2-(4-FLUOROPHENYL)-1H-BENZO[G]INDOL-3-YL]PROPYL}-4-PIPERIDINYL)PHENYL]-2-METHYLPROPANAMIDE: Prepared by Procedure E and Scheme M using N-(3-{1-[5-(4-fluorophenyl)-5-oxopentyl]-4-piperidinyl}phenyl)-2-methylpropanamide and 1-naphthylhydrazine hydrochloride: ESMS m/e: 548.2 (M+H)$^+$.

EXAMPLE 715

N-[3-(1-{3-[2-(4-FLUOROPHENYL)-5-(TRIFLUOROMETHOXY)-1H-INDOL-3-YL]PROPYL}-4-PIPERIDINYL)PHENYL]-2-METHYLPROPANAMIDE: Prepared by Procedure E and Scheme M using N-(3-{1-[5-(4-fluorophenyl)-5-oxopentyl]-4-piperidinyl}phenyl)-2-methylpropanamide and 4-(trifluoromethoxy)phenylhydrazine hydrochloride: ESMS m/e: 582.9 (M+H)$^+$.

EXAMPLE 716

N-[3-(1-{3-[2-(4-FLUOROPHENYL)-7-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(4-fluorophenyl)-5-oxopentyl]-4-piperidinyl}phenyl)-2-methylpropanamide and 1-(2-methylphenyl)hydrazine hydrochloride: ESMS m/e: 512.2 (M+H)$^+$.

EXAMPLE 717

N-[3-(1-{3-[2-(4-FLUOROPHENYL)-1H-INDOL-3-YL]PROPYL}-4-PIPERIDINYL)PHENYL]-2-METHYLPROPANAMIDE: Prepared by Procedure E and Scheme M using N-(3-{1-[5-(4-fluorophenyl)-5-oxopentyl]-4-piperidinyl}phenyl)-2-methylpropanamide and phenylhydrazine: ESMS m/e: 498.2 (M+H)$^+$.

EXAMPLE 718

N-[3-(1-{3-[2-(4-FLUOROPHENYL)-5-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(4-fluorophenyl)-5-oxopentyl]-4-piperidinyl}phenyl)-2-methylpropanamide and 4-methylphenylhydrazine hydrochloride: ESMS m/e: 512.2 (M+H)+.

EXAMPLE 719

N-[3-(1-{3-[2-(4-CHLOROPHENYL)-7-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(4-chlorophenyl)-5-oxopentyl]-4-piperidinyl}phenyl)-2-methylpropanamide and 1-(2-methylphenyl)hydrazine hydrochloride: ESMS m/e: 528.2 (M+H)+.

EXAMPLE 720

N-[3-(1-{3-[2-(4-CHLOROPHENYL)-5-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(4-chlorophenyl)-5-oxopentyl]-4-piperidinyl}phenyl)-2-methylpropanamide and 4-methylphenylhydrazine hydrochloride: ESMS m/e: 528.2 (M+H)+.

EXAMPLE 721

N-[3-(1-{3-[2-(4-CHLOROPHENYL)-1-PHENYL-1H-INDOL-3-YL]PROPYL}-4-PIPERIDINYL)PHENYL]-2-METHYLPROPANAMIDE: Prepared by Procedure E and Scheme M using N-(3-{1-[5-(4-chlorophenyl)-5-oxopentyl]-4-piperidinyl}phenyl)-2-methylpropanamide and 1,1-diphenylhydrazine hydrochloride: ESMS m/e: 590.2 (M+H)+.

EXAMPLE 722

N-[3-(1-{3-[2-(3-CHLOROPHENYL)-7-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(3-chlorophenyl)-5-oxopentyl]-4-piperidinyl}phenyl)-2-methylpropanamide and 1-(2-methylphenyl)hydrazine hydrochloride: ESMS m/e: 528.1 (M+H)+.

EXAMPLE 723

N-[3-(1-{3-[2-(3-CHLOROPHENYL)-5-(TRIFLUOROMETHOXY)-1H-INDOL-3-YL]PROPYL}-4-PIPERIDINYL)PHENYL]-2-METHYLPROPANAMIDE: Prepared by Procedure E and Scheme M using N-(3-{1-[5-(3-chlorophenyl)-5-oxopentyl]-4-piperidinyl}phenyl)-2-methylpropanamide and 4-(trifluoromethoxy)phenylhydrazine hydrochloride: ESMS m/e: 598.2 (M+H)+.

EXAMPLE 724

N-[3-(1-{3-[2-(3-CHLOROPHENYL)-1-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(3-chlorophenyl)-5-oxopentyl]-4-piperidinyl}phenyl)-2-methylpropanamide and 1-methyl-1-phenylhydrazine: ESMS m/e: 528.2 (M+H)+.

EXAMPLE 725

N-[3-(1-{3-[2-(3-CHLOROPHENYL)-1-PHENYL-1H-INDOL-3-YL]PROPYL}-4-PIPERIDINYL)PHENYL]-2-METHYLPROPANAMIDE: Prepared by Procedure E and Scheme M using N-(3-{1-[5-(3-chlorophenyl)-5-oxopentyl]-4-piperidinyl}phenyl)-2-methylpropanamide and 1,1-diphenylhydrazine hydrochloride: ESMS m/e: 590.3 (M+H)+.

EXAMPLE 726

N-[3-(1-{3-[2-(3-CHLOROPHENYL)-5-METHOXY-1H-INDOL-3-YL]PROPYL}-4-PIPERIDINYL)PHENYL]-2-METHYLPROPANAMIDE: Prepared by Procedure E and Scheme M using N-(3-{1-[5-(3-chlorophenyl)-5-oxopentyl]-4-piperidinyl}phenyl)-2-methylpropanamide and 4-methoxyphenylhydrazine hydrochloride: ESMS m/e: 544.3 (M+H)+.

EXAMPLE 727

N-[3-(1-{3-[2-(3-CHLOROPHENYL)-5-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(3-chlorophenyl)-5-oxopentyl]-4-piperidinyl}phenyl)-2-methylpropanamide and 4-methylphenylhydrazine hydrochloride: ESMS m/e: 528.2 (M+H)+.

EXAMPLE 728

N-[3-(1-{3-[2-(3-CHLOROPHENYL)-1H-BENZO[G]INDOL-3-YL]PROPYL}-4-PIPERIDINYL)PHENYL]-2-METHYLPROPANAMIDE: Prepared by Procedure E and Scheme M using N-(3-{1-[5-(3-chlorophenyl)-5-oxopentyl]-4-piperidinyl}phenyl)-2-methylpropanamide and 1-naphthylhydrazine hydrochloride: ESMS m/e: 564.2 (M+H)+.

EXAMPLE 729

N-[3-(1-{3-[2-(3-CHLOROPHENYL)-1H-INDOL-3-YL]PROPYL}-4-PIPERIDINYL)PHENYL]-2-METHYLPROPANAMIDE: Prepared by Procedure E and Scheme M using N-(3-{1-[5-(3-chlorophenyl)-5-oxopentyl]-4-piperidinyl}phenyl)-2-methylpropanamide and phenylhydrazine: ESMS m/e: 514.2 (M+H)+.

EXAMPLE 730

N-[3-(1-{3-[2-(2-CHLOROPHENYL)-1H-INDOL-3-YL]PROPYL}-4-PIPERIDINYL)PHENYL]-2-METHYLPROPANAMIDE: Prepared by Procedure E and Scheme M using N-(3-{1-[5-(2-chlorophenyl)-5-oxopentyl]-4-piperidinyl}phenyl)-2-methylpropanamide and phenylhydrazine: ESMS m/e: 514.2 (M+H)+.

EXAMPLE 731

N-[3-(1-{3-[2-(2-CHLOROPHENYL)-5-(TRIFLUOROMETHOXY)-1H-INDOL-3-YL]PROPYL}-4-PIPERIDINYL)PHENYL]-2-METHYLPROPANAMIDE: Prepared by Procedure E and Scheme M using N-(3-{1-[5-(2-chlorophenyl)-5-oxopentyl]-4-piperidinyl}phenyl)-2-methylpropanamide and 4-(trifluoromethoxy)phenylhydrazine hydrochloride: ESMS m/e: 598.2 (M+H)+.

EXAMPLE 732

N-[3-(1-{3-[2-(2-CHLOROPHENYL)-1H-BENZO[G]INDOL-3-YL]PROPYL}-4-PIPERIDINYL)PHENYL]-2-METHYLPROPANAMIDE: Prepared by Procedure E and Scheme M using N-(3-{1-[5-(2-chlorophenyl)-5-oxopentyl]-4-piperidinyl}phenyl)-2-methylpropanamide and 1-naphthylhydrazine hydrochloride: ESMS m/e: 564.2 (M+H)+.

EXAMPLE 733

N-[3-(1-{3-[2-(2-CHLOROPHENYL)-7-METHYL-1H-INDOL-3-YL]PROPYL}-4-PIPERIDINYL)PHENYL]-2-

METHYLPROPANAMIDE: Prepared by Procedure E and Scheme M using N-(3-{1-[5-(2-chlorophenyl)-5-oxopentyl]-4-piperidinyl}phenyl)-2-methylpropanamide and 1-(2-methylphenyl)hydrazine hydrochloride: ESMS m/e: 528.2 (M+H)+.

EXAMPLE 734

N-[3-(1-{3-[2-(2-CHLOROPHENYL)-1-PHENYL-1H-INDOL-3-YL]PROPYL}-4-PIPERIDINYL)PHENYL]-2-METHYLPROPANAMIDE: Prepared by Procedure E and Scheme M using N-(3-{1-[5-(2-chlorophenyl)-5-oxopentyl]-4-piperidinyl}phenyl)-2-methylpropanamide and 1,1-diphenylhydrazine hydrochloride: ESMS m/e: 590.2 (M+H)+.

EXAMPLE 735

N-[3-(1-{3-[2-(2-CHLOROPHENYL)-1-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(2-chlorophenyl)-5-oxopentyl]-4-piperidinyl}phenyl)-2-methylpropanamide and 1-methyl-1-phenylhydrazine: ESMS m/e: 528.2 (M+H)+.

EXAMPLE 736

N-[3-(1-{3-[2-(2-CHLOROPHENYL)-5-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(2-chlorophenyl)-5-oxopentyl]-4-piperidinyl}phenyl)-2-methylpropanamide and 4-methylphenylhydrazine hydrochloride: ESMS m/e: 528.2 (M+H)+.

EXAMPLE 737

N-[3-(1-{3-[2-(3-IODOPHENYL)-1H-INDOL-3-YL]PROPYL}-4-PIPERIDINYL)PHENYL]-2-METHYLPROPANAMIDE: Prepared by Procedure E and Scheme M using N-(3-{1-[5-(3-iodophenyl)-5-oxopentyl]-4-piperidinyl}phenyl)-2-methylpropanamide and phenylhydrazine: ESMS m/e: 606.2 (M+H)+.

EXAMPLE 738

N-[3-(1-{3-[2-(3-IODOPHENYL)-1-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(3-iodophenyl)-5-oxopentyl]-4-piperidinyl}phenyl)-2-methylpropanamide and 1-methyl-1-phenylhydrazine: ESMS m/e: 620.2 (M+H)+.

EXAMPLE 739

N-[3-(1-{3-[2-(3-IODOPHENYL)-1-PHENYL-1H-INDOL-3-YL]PROPYL}-4-PIPERIDINYL)PHENYL]-2-METHYLPROPANAMIDE: Prepared by Procedure E and Scheme M using N-(3-{1-[5-(3-iodophenyl)-5-oxopentyl]-4-piperidinyl}phenyl)-2-methylpropanamide and 1,1-diphenylhydrazine hydrochloride: ESMS m/e: 682.2 (M+H)+.

EXAMPLE 740

N-[3-(1-{3-[2-(3-IODOPHENYL)-1H-BENZO[G]INDOL-3-YL]PROPYL}-4-PIPERIDINYL)PHENYL]-2-METHYLPROPANAMIDE: Prepared by Procedure E and Scheme M using N-(3-{1-[5-(3-iodophenyl)-5-oxopentyl]-4-piperidinyl}phenyl)-2-methylpropanamide and 1-naphthylhydrazine hydrochloride: ESMS m/e: 656.2 (M+H)+.

EXAMPLE 741

N-[3-(1-{3-[2-(3-IODOPHENYL)-5-(TRIFLUOROMETHOXY)-1H-INDOL-3-YL]PROPYL}-4-PIPERIDINYL)PHENYL]-2-METHYLPROPANAMIDE: Prepared by Procedure E and Scheme M using N-(3-{1-[5-(3-iodophenyl)-5-oxopentyl]-4-piperidinyl}phenyl)-2-methylpropanamide and 4-(trifluoromethoxy)phenylhydrazine hydrochloride: ESMS m/e: 690.2 (M+H)+.

EXAMPLE 742

N-[3-(1-{3-[2-(3-IODOPHENYL)-5-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(3-iodophenyl)-5-oxopentyl]-4-piperidinyl}phenyl)-2-methylpropanamide and 4-methylphenylhydrazine hydrochloride: ESMS m/e: 620.2 (M+H)+.

EXAMPLE 743

N-[3-(1-{3-[2-(3-IODOPHENYL)-7-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(3-iodophenyl)-5-oxopentyl]-4-piperidinyl}phenyl)-2-methylpropanamide and 1-(2-methylphenyl)hydrazine hydrochloride: ESMS m/e: 620.2 (M+H)+.

EXAMPLE 744

N-[3-(1-{3-[2-(4-IODOPHENYL)-5-(TRIFLUOROMETHOXY)-1H-INDOL-3-YL]PROPYL}-4-PIPERIDINYL)PHENYL]-2-METHYLPROPANAMIDE: Prepared by Procedure E and Scheme M using N-(3-{1-[5-(4-iodophenyl)-5-oxopentyl]-4-piperidinyl}phenyl)-2-methylpropanamide and 4-(trifluoromethoxy)phenylhydrazine hydrochloride: ESMS m/e: 690.1 (M+H)+.

EXAMPLE 745

N-[3-(1-{3-[2-(4-IODOPHENYL)-5-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(4-iodophenyl)-5-oxopentyl]-4-piperidinyl}phenyl)-2-methylpropanamide and 4-methylphenylhydrazine hydrochloride: ESMS m/e: 620.1 (M+H)+.

EXAMPLE 746

N-[3-(1-{3-[2-(4-IODOPHENYL)-7-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(4-iodophenyl)-5-oxopentyl]-4-piperidinyl}phenyl)-2-methylpropanamide and 1-(2-methylphenyl)hydrazine hydrochloride: ESMS m/e: 620.1 (M+H)+.

EXAMPLE 747

N-[3-(1-{3-[2-(4-IODOPHENYL)-1-PHENYL-1H-INDOL-3-YL]PROPYL}-4-PIPERIDINYL)PHENYL]-2-METHYLPROPANAMIDE: Prepared by Procedure E and Scheme M using N-(3-{1-[5-(4-iodophenyl)-5-oxopentyl]-4-piperidinyl}phenyl)-2-methylpropanamide and 1,1-diphenylhydrazine hydrochloride: ESMS m/e: 682.1 (M+H)+.

EXAMPLE 748

N-[3-(1-{3-[2-(4-IODOPHENYL)-1-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(4-iodophenyl)-5-oxopentyl]-4-piperidinyl}phenyl)-2-methylpropanamide and 1-methyl-1-phenylhydrazine: ESMS m/e: 620.1 (M+H)$^+$.

EXAMPLE 749

N-[3-(1-{3-[2-(4-IODOPHENYL)-1H-BENZO[G]INDOL-3-YL]PROPYL}-4-PIPERIDINYL)PHENYL]-2-METHYLPROPANAMIDE: Prepared by Procedure E and Scheme M using N-(3-{1-[5-(4-iodophenyl)-5-oxopentyl]-4-piperidinyl}phenyl)-2-methylpropanamide and 1-naphthylhydrazine hydrochloride: ESMS m/e: 656.1 (M+H)$^+$.

EXAMPLE 750

N-[3-(1-{3-[2-(4-IODOPHENYL)-1H-INDOL-3-YL]PROPYL}-4-PIPERIDINYL)PHENYL]-2-METHYLPROPANAMIDE: Prepared by Procedure E and Scheme M using N-(3-{1-[5-(4-iodophenyl)-5-oxopentyl]-4-piperidinyl}phenyl)-2-methylpropanamide and phenylhydrazine: ESMS m/e: 606.1 (M+H)$^+$.

EXAMPLE 751

N-[3-(1-{3-[2-(3-BROMOPHENYL)-5-(TRIFLUOROMETHOXY)-1H-INDOL-3-YL]PROPYL}-4-PIPERIDINYL)PHENYL]-2-METHYLPROPANAMIDE: Prepared by Procedure E and Scheme M using N-(3-{1-[5-(3-bromophenyl)-5-oxopentyl]-4-piperidinyl}phenyl)-2-methylpropanamide and 4-(trifluoromethoxy)phenylhydrazine hydrochloride: ESMS m/e: 642.0 (M+H)$^+$.

EXAMPLE 752

N-[3-(1-{3-[2-(4-BROMOPHENYL)-1H-BENZO[G]INDOL-3-YL]PROPYL}-4-PIPERIDINYL)PHENYL]-2-METHYLPROPANAMIDE: Prepared by Procedure E and Scheme M using N-(3-{1-[5-(4-bromophenyl)-5-oxopentyl]-4-piperidinyl}phenyl)-2-methylpropanamide and 1-naphthylhydrazine hydrochloride: ESMS m/e: 608.0 (M+H)$^+$.

EXAMPLE 753

N-[3-(1-{3-[2-(4-BROMOPHENYL)-7-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(4-bromophenyl)-5-oxopentyl]-4-piperidinyl}phenyl)-2-methylpropanamide and 1-(2-methylphenyl)hydrazine hydrochloride: ESMS m/e: 572 (M+H)$^+$.

EXAMPLE 754

N-[3-(1-{3-[2-(4-BROMOPHENYL)-5-(TRIFLUOROMETHOXY)-1H-INDOL-3-YL]PROPYL}-4-PIPERIDINYL)PHENYL]-2-METHYLPROPANAMIDE: Prepared by Procedure E and Scheme M using N-(3-{1-[5-(4-bromophenyl)-5-oxopentyl]-4-piperidinyl}phenyl)-2-methylpropanamide and 4-(trifluoromethoxy)phenylhydrazine hydrochloride: ESMS m/e: 642 (M+H)$^+$.

EXAMPLE 755

N-[3-(1-{3-[2-(3-BROMOPHENYL)-1H-BENZO[G]INDOL-3-YL]PROPYL}-4-PIPERIDINYL)PHENYL]-2-METHYLPROPANAMIDE: Prepared by Procedure E and Scheme M using N-(3-{1-[5-(3-bromophenyl)-5-oxopentyl]-4-piperidinyl}phenyl)-2-methylpropanamide and 1-naphthylhydrazine hydrochloride: ESMS m/e: 608.0 (M+H)$^+$.

EXAMPLE 756

N-[3-(1-{3-[2-(4-BROMOPHENYL)-1H-INDOL-3-YL]PROPYL}-4-PIPERIDINYL)PHENYL]-2-METHYLPROPANAMIDE: Prepared by Procedure E and Scheme M using N-(3-{1-[5-(4-bromophenyl)-5-oxopentyl]-4-piperidinyl}phenyl)-2-methylpropanamide and phenylhydrazine: ESMS m/e: 558.1 (M+H)$^+$.

EXAMPLE 757

N-[3-(1-{3-[2-(3-BROMOPHENYL)-1-PHENYL-1H-INDOL-3-YL]PROPYL}-4-PIPERIDINYL)PHENYL]-2-METHYLPROPANAMIDE: Prepared by Procedure E and Scheme M using N-(3-{1-[5-(3-bromophenyl)-5-oxopentyl]-4-piperidinyl}phenyl)-2-methylpropanamide and 1,1-diphenylhydrazine hydrochloride: ESMS m/e: 634.0 (M+H)$^+$.

EXAMPLE 758

N-[3-(1-{3-[2-(3-BROMOPHENYL)-1-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(3-bromophenyl)-5-oxopentyl]-4-piperidinyl}phenyl)-2-methylpropanamide and 1-methyl-1-phenylhydrazine: ESMS m/e: 572.0 (M+H)$^+$.

EXAMPLE 759

N-[3-(1-{3-[2-(4-BROMOPHENYL)-1-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(4-bromophenyl)-5-oxopentyl]-4-piperidinyl}phenyl)-2-methylpropanamide and 1-methyl-1-phenylhydrazine: ESMS m/e: 572.0 (M+H)$^+$.

EXAMPLE 760

N-[3-(1-{3-[2-(4-BROMOPHENYL)-1-PHENYL-1H-INDOL-3-YL]PROPYL}-4-PIPERIDINYL)PHENYL]-2-METHYLPROPANAMIDE: Prepared by Procedure E and Scheme M using N-(3-{1-[5-(4-bromophenyl)-5-oxopentyl]-4-piperidinyl}phenyl)-2-methylpropanamide and 1,1-diphenylhydrazine hydrochloride: ESMS m/e: 634.0 (M+H)$^+$.

EXAMPLE 761

N-[3-(1-{3-[2-(4-BROMOPHENYL)-5-METHOXY-1H-INDOL-3-YL]PROPYL}-4-PIPERIDINYL)PHENYL]-2-METHYLPROPANAMIDE: Prepared by Procedure E and Scheme M using N-(3-{1-[5-(4-bromophenyl)-5-oxopentyl]-4-piperidinyl}phenyl)-2-methylpropanamide and 4-methoxyphenylhydrazine hydrochloride: ESMS m/e: 588.1 (M+H)$^+$.

EXAMPLE 762

N-[3-(1-{3-[2-(3-BROMOPHENYL)-7-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(3-bromophenyl)-5- oxopentyl]-4-piperidinyl}phenyl)-2-methylpropanamide and 1-(2-methylphenyl)hydrazine hydrochloride: ESMS m/e: 572 (M+H)+.

EXAMPLE 763

N-[3-(1-{3-[2-(3-BROMOPHENYL)-5-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(3-bromophenyl)-5-oxopentyl]-4-piperidinyl}phenyl)-2-methylpropanamide and 4-methylphenylhydrazine hydrochloride: ESMS m/e: 572 (M+H)+.

EXAMPLE 764

N-[3-(1-{3-[2-(4-BROMOPHENYL)-5-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(4-bromophenyl)-5-oxopentyl]-4-piperidinyl}phenyl)-2-methylpropanamide and 4-methylphenylhydrazine hydrochloride: ESMS m/e: 572.0 (M+H)+.

EXAMPLE 765

N-[3-(1-{3-[2-(3-BROMOPHENYL)-5-METHOXY-1H-INDOL-3-YL]PROPYL}-4-PIPERIDINYL)PHENYL]-2-METHYLPROPANAMIDE: Prepared by Procedure E and Scheme M using N-(3-{1-[5-(3-bromophenyl)-5-oxopentyl]-4-piperidinyl}phenyl)-2-methylpropanamide and 4-methoxyphenylhydrazine hydrochloride: ESMS m/e: 588.0 (M+H)+.

EXAMPLE 766

2-METHYL-N-[3-(1-{3-[2-(3-NITROPHENYL)-1H-INDOL-3-YL]PROPYL}-4-PIPERIDINYL)PHENYL] PROPANAMIDE: Prepared by Procedure E and Scheme M using 2-methyl-N-(3-{1-[5-(3-nitrophenyl)-5-oxopentyl]-4-piperidinyl}phenyl)propanamide and phenylhydrazine: ESMS m/e: 525.2 (M+H)+.

EXAMPLE 767

2-METHYL-N-[3-(1-{3-[2-(3-NITROPHENYL)-1H-BENZO[G]INDOL-3-YL]PROPYL}-4-PIPERIDINYL) PHENYL]PROPANAMIDE: Prepared by Procedure E and Scheme M using 2-methyl-N-(3-{1-[5-(3-nitrophenyl)-5-oxopentyl]-4-piperidinyl}phenyl)propanamide and 1-naphthylhydrazine hydrochloride: ESMS m/e: 575.1 (M+H)+.

EXAMPLE 768

2-METHYL-N-[3-(1-{3-[2-(3-NITROPHENYL)-5-(TRIFLUOROMETHOXY)-1H-INDOL-3-YL]PROPYL}-4-PIPERIDINYL)PHENYL]PROPANAMIDE: Prepared by Procedure E and Scheme M using 2-methyl-N-(3-{1-[5-(3-nitrophenyl)-5-oxopentyl]-4-piperidinyl}phenyl) propanamide and 4-(trifluoromethoxy)phenylhydrazine hydrochloride: ESMS m/e: 609.1 (M+H)+.

EXAMPLE 769

2-METHYL-N-[3-(1-{3-[5-METHYL-2-(3-NITROPHENYL)-1H-INDOL-3-YL]PROPYL}-4-PIPERIDINYL)PHENYL]PROPANAMIDE: Prepared by Procedure E and Scheme M using 2-methyl-N-(3-({[5-(3-nitrophenyl)-5-oxopentyl]-4-piperidinyl}phenyl) propanamide and 4-methylphenylhydrazine hydrochloride: ESMS m/e: 539.2 (M+H)+.

EXAMPLE 770

N-[3-(1-{3-[5-METHOXY-2-(3-NITROPHENYL)-1H-INDOL-3-YL]PROPYL}-4-PIPERIDINYL)PHENYL]-2-METHYLPROPANAMIDE: Prepared by Procedure E and Scheme M using 2-methyl-N-(3-{1-[5-(3-nitrophenyl)-5-oxopentyl]-4-piperidinyl}phenyl)propanamide and 4-methoxyphenylhydrazine hydrochloride: ESMS m/e: 555.2 (M+H)+.

EXAMPLE 771

2-METHYL-N-[3-(1-{3-[2-(3-NITROPHENYL)-1-PHENYL-1H-INDOL-3-YL]PROPYL}-4-PIPERIDINYL) PHENYL]PROPANAMIDE: Prepared by Procedure E and Scheme M using 2-methyl-N-(3-{1-[5-(3-nitrophenyl)-5-oxopentyl]-4-piperidinyl}phenyl)propanamide and 1,1-diphenylhydrazine hydrochloride: ESMS m/e: 601.1 (M+H)+.

EXAMPLE 772

2-METHYL-N-[3-(1-{3-[1-METHYL-2-(3-NITROPHENYL)-1H-INDOL-3-YL]PROPYL}-4-PIPERIDINYL)PHENYL]PROPANAMIDE:
Prepared by Procedure E and Scheme M using 2-methyl-N-(3-{1-[5-(3-nitrophenyl)-5-oxopentyl]-4-piperidinyl}phenyl)propanamide and 1-methyl-1-phenylhydrazine: ESMS m/e: 539.2 (M+H)+.

EXAMPLE 773

2-METHYL-N-[3-(1-{3-[7-METHYL-2-(3-NITROPHENYL)-1H-INDOL-3-YL]PROPYL}-4-PIPERIDINYL)PHENYL]PROPANAMIDE: Prepared by Procedure E and Scheme M using 2-methyl-N-(3-{1-[5-(3-nitrophenyl)-5-oxopentyl]-4-piperidinyl}phenyl) propanamide and 1-(2-methylphenyl)hydrazine hydrochloride: ESMS m/e: 539.2 (M+H)+.

EXAMPLE 774

N-[3-(1-{3-[5-METHOXY-2-(4-NITROPHENYL)-1H-INDOL-3-YL]PROPYL}-4-PIPERIDINYL)PHENYL]-2-METHYLPROPANAMIDE: Prepared by Procedure E and Scheme M using 2-methyl-N-(3-{1-[5-(4-nitrophenyl)-5-oxopentyl]-4-piperidinyl}phenyl)propanamide and 4-methoxyphenylhydrazine hydrochloride: ESMS m/e: 555.6 (M+H)+.

EXAMPLE 775

N-[3-(1-{3-[2-(2-BROMOPHENYL)-1H-INDOL-3-YL] PROPYL}-4-PIPERIDINYL)PHENYL]-2-METHYLPROPANAMIDE: Prepared by Procedure E and Scheme M using N-(3-{1-[5-(2-bromophenyl)-5-oxopentyl]-4-piperidinyl}phenyl)-2-methylpropanamide and phenylhydrazine: ESMS m/e: 557.9 (M+H)+.

EXAMPLE 776

2-METHYL-N-[3-(1-{3-[5-METHYL-2-(4-NITROPHENYL)-1H-INDOL-3-YL]PROPYL}-4-PIPERIDINYL)PHENYL]PROPANAMIDE: Prepared by Procedure E and Scheme M using 2-methyl-N-(3-{1-[5-(4-nitrophenyl)-5-oxopentyl]-4-piperidinyl}phenyl) propanamide and 4-methylphenylhydrazine hydrochloride: ESMS m/e: 539.1 (M+H)+.

EXAMPLE 777

2-METHYL-N-[3-(1-{3-[2-(4-NITROPHENYL)-1H-BENZO[G]INDOL-3-YL]PROPYL}-4-PIPERIDINYL)

PHENYL]PROPANAMIDE: Prepared by Procedure E and Scheme M using 2-methyl-N-(3-{1-[5-(4-nitrophenyl)-5-oxopentyl]-4-piperidinyl}phenyl)propanamide and 1-naphthylhydrazine hydrochloride: ESMS m/e: 574.7 (M+H)$^+$.

EXAMPLE 778

2-METHYL-N-(3-{1-[(5E)-5-(4-NITROPHENYL)-5-(PHENYLHYDRAZONO)PENTYL]-4-PIPERIDINYL}PHENYL)PROPANAMIDE: Prepared by Procedure E and Scheme AX using 2-methyl-N-(3-{1-[5-(4-nitrophenyl)-5-oxopentyl]-4-piperidinyl}phenyl)propanamide and phenylhydrazine: ESMS m/e: 542.4 (M+H)$^+$.

EXAMPLE 779

2-METHYL-N-[3-(1-{3-[7-METHYL-2-(4-NITROPHENYL)-1H-INDOL-3-YL]PROPYL}-4-PIPERIDINYL)PHENYL]PROPANAMIDE: Prepared by Procedure E and Scheme M using 2-methyl-N-(3-{1-[5-(4-nitrophenyl)-5-oxopentyl]-4-piperidinyl}phenyl)propanamide and 1-(2-methylphenyl)hydrazine hydrochloride: ESMS m/e: 538.8 (M+H)$^+$.

EXAMPLE 780

2-METHYL-N-{3-[1-((5E)-5-(4-NITROPHENYL)-5-{[4-(TRIFLUOROMETHOXY)PHENYL]HYDRAZONO}PENTYL)-4-PIPERIDINYL]PHENYL}PROPANAMIDE: Prepared by Procedure E and Scheme M using 2-methyl-N-(3-{1-[5-(4-nitrophenyl)-5-oxopentyl]-4-piperidinyl}phenyl)propanamide and 4-(trifluoromethoxy)phenylhydrazine hydrochloride: ESMS m/e: 626.2 (M+H)$^+$.

EXAMPLE 781

N-[3-(1-{3-[2-(2-BROMOPHENYL)-1H-BENZO[G]INDOL-3-YL]PROPYL}-4-PIPERIDINYL)PHENYL]-2-METHYLPROPANAMIDE: Prepared by Procedure E and Scheme M using N-(3-{1-[5-(2-bromophenyl)-5-oxopentyl]-4-piperidinyl}phenyl)-2-methylpropanamide and 1-naphthylhydrazine hydrochloride: ESMS m/e: 608.0 (M+H)$^+$.

EXAMPLE 782

N-[3-(1-{3-[2-(2-BROMOPHENYL)-5-(TRIFLUOROMETHOXY)-1H-INDOL-3-YL]PROPYL}-4-PIPERIDINYL)PHENYL]-2-METRYLPROPANAMIDE:Prepared by Procedure E and Scheme M using N-(3-{1-[5-(2-bromophenyl)-5-oxopentyl]-4-piperidinyl}phenyl)-2-methylpropanamide and 4-(trifluoromethoxy)phenylhydrazine hydrochloride: ESMS m/e: 641.9 (M+H)$^+$.

EXAMPLE 783

N-[3-(1-{3-[2-(2-BROMOPHENYL)-7-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(2-bromophenyl)-5-oxopentyl]-4-piperidinyl}phenyl)-2-methylpropanamide and 1-(2-methylphenyl)hydrazine hydrochloride: ESMS m/e: 572.0 (M+H)$^+$.

EXAMPLE 784

N-[3-(1-{3-[2-(2-BROMOPHENYL)-1-PHENYL-1H-INDOL-3-YL]PROPYL}-4-PIPERIDINYL)PHENYL]-2-METHYLPROPANAMIDE: Prepared by Procedure E and Scheme M using N-(3-{1-[5-(2-bromophenyl)-5-oxopentyl]-4-piperidinyl}phenyl)-2-methylpropanamide and 1,1-diphenylhydrazine hydrochloride: ESMS m/e: 634 (M+H)$^+$.

EXAMPLE 785

N-[3-(1-{3-[2-(2-BROMOPHENYL)-5-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(2-bromophenyl)-5-oxopentyl]-4-piperidinyl}phenyl)-2-methylpropanamide and 4-methylphenylhydrazine hydrochloride: ESMS m/e: 572.0 (M+H)$^+$.

EXAMPLE 786

N-[3-(1-{3-[2-(2-IODOPHENYL)-5-(TRIFLUOROMETHOXY)-1H-INDOL-3-YL]PROPYL}-4-PIPERIDINYL)PHENYL]-2-METHYLPROPANAMIDE: Prepared by Procedure E and Scheme M using N-(3-{1-[5-(2-iodophenyl)-5-oxopentyl]-4-piperidinyl}phenyl)-2-methylpropanamide and 4-(trifluoromethoxy)phenylhydrazine hydrochloride: ESMS m/e: 690.0 (M+H)$^+$.

EXAMPLE 787

N-[3-(1-{3-[2-(2-IODOPHENYL)-5-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(2-iodophenyl)-5-oxopentyl]-4-piperidinyl}phenyl)-2-methylpropanamide and 4-methylphenylhydrazine hydrochloride: ESMS m/e: 620.2 (M+H)$^+$.

EXAMPLE 788

2-METHYL-N-[3-(1-{3-[1-METHYL-2-(4-NITROPHENYL)-1H-INDOL-3-YL]PROPYL}-4-PIPERIDINYL)PHENYL]PROPANAMIDE: Prepared by Procedure E and Scheme M using 2-methyl-N-(3-{1-[5-(4-nitrophenyl)-5-oxopentyl]-4-piperidinyl}phenyl)propanamide and 1-methyl-1-phenylhydrazine: ESMS m/e: 539.6 (M+H)$^+$.

EXAMPLE 789

2-METHYL-N-[3-(1-{3-[2-(4-NITROPHENYL)-1-PHENYL-1H-INDOL-3-YL]PROPYL}-4-PIPERIDINYL)PHENYL]PROPANAMIDE: Prepared by Procedure E and Scheme M using 2-methyl-N-(3-{1-[5-(4-nitrophenyl)-5-oxopentyl]-4-piperidinyl}phenyl)propanamide and 1,1-diphenylhydrazine hydrochloride: ESMS m/e: 601.6 (M+H)$^+$.

EXAMPLE 790

N-[3-(1-{3-[2-(2-IODOPHENYL)-1H-INDOL-3-YL]PROPYL}-4-PIPERIDINYL)PHENYL]-2-METHYLPROPANAMIDE: Prepared by Procedure E and Scheme M using N-(3-{1-[5-(2-iodophenyl)-5-oxopentyl]-4-piperidinyl}phenyl)-2-methylpropanamide and phenylhydrazine: ESMS m/e: 606.1 (M+H)$^+$.

EXAMPLE 791

N-[3-(1-{3-[2-(2-IODOPHENYL)-1H-BENZO[G]INDOL-3-YL]PROPYL}-4-PIPERIDINYL)PHENYL]-2-METHYLPROPANAMIDE: Prepared by Procedure E and Scheme M using N-(3-{1-[5-(2-iodophenyl)-5-oxopentyl]-4-piperidinyl}phenyl)-2-methylpropanamide and 1-naphthylhydrazine hydrochloride: ESMS m/e: 656.1 (M+H)+.

EXAMPLE 792

N-[3-(1-{3-[2-(2-IODOPHENYL)-1-PHENYL-1H-INDOL-3-YL]PROPYL}-4-PIPERIDINYL)PHENYL]-2-METHYLPROPANAMIDE: Prepared by Procedure E and Scheme M using N-(3-{1-[5-(2-iodophenyl)-5-oxopentyl]-4-piperidinyl}phenyl)-2-methylpropanamide and 1,1-diphenylhydrazine hydrochloride: ESMS m/e: 682.1 (M+H)+.

EXAMPLE 793

N-[3-(1-{3-[2-(2-IODOPHENYL)-7-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(2-iodophenyl)-5-oxopentyl]-4-piperidinyl}phenyl)-2-methylpropanamide and 1-(2-methylphenyl)hydrazine hydrochloride: ESMS m/e: 619.6 (M+H)+.

EXAMPLE 794

N-[3-(1-{3-[2-(2-BROMOPHENYL)-1-METHYL-1H-INDOL-3-YL]PROPYL}-4-PIPERIDINYL)PHENYL]-2-METHYLPROPANAMIDE: Prepared by Procedure E and Scheme M using N-(3-{1-[5-(2-bromophenyl)-5-oxopentyl]-4-piperidinyl}phenyl)-2-methylpropanamide and 1-methyl-1-phenylhydrazine: ESMS m/e: 572 (M+H)+.

EXAMPLE 795

4-(3,4-DIFLUOROPHENYL)-N-(3-{4-[3-(ISOBUTYRYLAMINO)PHENYL]-1-PIPERIDINYL}PROPYL)-2-METHYL-6-OXO-1,4,5,6-TETRAHYDRO-3-PYRIDINECARBOXAMIDE: Prepared by Procedure AC and Scheme AM using 4-(3,4-difluorophenyl)-2-methyl-6-oxo-1,4,5,6-tetrahydro-3-pyridinecarboxylic acid and N-{3-[1-(3-aminopropyl)-4-piperidinyl]phenyl}-2-methylpropanamide: ESMS m/e: 553.0 (M+H)+.

EXAMPLE 796

4-(2,4-DIFLUOROPHENYL)-N-(3-{4-[3-(ISOBUTYRYLAMINO)PHENYL]-1-PIPERIDINYL}PROPYL)-2-METHYL-6-OXO-1,4,5,6-TETRAHYDRO-3-PYRIDINECARBOXAMIDE: Prepared by Procedure AC and Scheme AM using 4-(2,4-difluorophenyl)-2-methyl-6-oxo-1,4,5,6-tetrahydro-3-pyridinecarboxylic acid and N-{3-[1-(3-aminopropyl)-4-piperidinyl]phenyl}-2-methylpropanamide: ESMS m/e: 553.0 (M+H)+.

EXAMPLE 797

N-(3-{1-[4-(4-METHOXYPHENYL)BUTYL]-4-PIPERIDINYL}PHENYL)-2-METHYLPROPANAMIDE: Prepared by Procedure O and Scheme W using 4-(4-methoxyphenyl)-1-butanol and 2-methyl-N-[3-(4-piperidinyl)phenyl]propanamide: ESMS m/e: 409 (M+H)+.

EXAMPLE 798

N-(4-{1-[3-(1,2-DIPHENYL-1H-INDOL-3-YL)PROPYL]-4-PIPERIDINYL}PHENYL)PROPANAMIDE: Prepared by Procedure O and Scheme W using 3-(1,2-diphenyl-1H-indol-3-yl)-1-propanol and N-[4-(4-piperidinyl)phenyl]propanamide: ESMS m/e: 542.0 (M+H)+.

EXAMPLE 799

N-{4-[1-(3,3-DIPHENYLPROPYL)-4-PIPERIDINYL]PHENYL}PROPANAMIDE: Prepared by Procedure O and Scheme W using 3,3-diphenyl-1-propanol and N-[4-(4-piperidinyl)phenyl]propanamide: ESMS m/e: 427.0 (M+H)+.

EXAMPLE 800

2-METHYL-N-(3-{1-[4-(4-NITROPHENYL)BUTYL]-4-PIPERIDINYL}PHENYL): Prepared by Procedure O and Scheme W using 4-(4-nitrophenyl)-1-butanol and 2-methyl-N-[3-(4-piperidinyl)phenyl]propanamide: ESMS m/e: 424.2 (M+H)+.

EXAMPLE 801

2-METHYL-N-(3-{1-[2-(1-NAPHTHYL)ETHYL]-4-PIPERIDINYL}PHENYL)PROPANAMIDE Prepared by Procedure O and Scheme W using 2-(1-naphthyl)ethanol and 2-methyl-N-[3-(4-piperidinyl)phenyl]propanamide: ESMS m/e: 401.2 (M+H)+.

EXAMPLE 802

N-{3-[1-(3,3-DIPHENYLPROPYL)-4-PIPERIDINYL]PHENYL}-2-METHYLPROPANAMIDE: Prepared by Procedure O and Scheme W using 3,3-diphenyl-1-propanol and 2-methyl-N-[3-(4-piperidinyl)phenyl]propanamide: ESMS m/e: 441.2 (M+H)+.

EXAMPLE 803

N-(3-{1-[3-(3,4-DIMETHOXYPHENYL)PROPYL]-4-PIPERIDINYL}PHENYL)-2-METHYLPROPANAMIDE: Prepared by Procedure O and Scheme W using 3-(3,4-dimethoxyphenyl)-1-propanol and 2-methyl-N-[3-(4-piperidinyl)phenyl]propanamide: ESMS m/e: 425.2 (M+H)+.

EXAMPLE 804

2-METHYL-N-{3-[1-(3-PHENYLPROPYL)-4-PIPERIDINYL]PHENYL}PROPANAMIDE: Prepared by Procedure O and Scheme W using 3-phenyl-1-propanol and 2-methyl-N-[3-(4-piperidinyl)phenyl]propanamide: ESMS m/e: 365.2 (M+H)+.

EXAMPLE 805

2-METHYL-N-(3-{1-[3-(4-PYRIDINYL)PROPYL]-4-PIPERIDINYL}PHENYL)PROPANAMIDE: Prepared by Procedure O and Scheme W using 3-(4-pyridinyl)-1-propanol and 2-methyl-N-[3-(4-piperidinyl)phenyl]propanamide: ESMS m/e: 366.2 (M+H)+.

EXAMPLE 806

N-{3-[1-(4-TERT-BUTYLBENZYL)-4-PIPERIDINYL]PHENYL}-2-METHYLPROPANAMIDE: Prepared by Procedure AJ and Scheme AV using 1-bromomethyl)-4-tert-butylbenzene and 2-methyl-N-[3-(4-piperidinyl)phenyl]propanamide: ESMS m/e: 393.0 (M+H)+.

EXAMPLE 807

N-{3-[1-(4-BENZOYLBENZYL)-4-PIPERIDINYL]PHENYL}-2-METHYLPROPANAMIDE: Prepared by Procedure AJ and Scheme AV using [4-(bromomethyl)phenyl](phenyl)methanone and 2-methyl-N-[3-(4-piperidinyl)phenyl]propanamide: ESMS m/e: 441.0 (M+H)$^+$.

1,2-DICHLORO-4-{[(1S)-3-CHLORO-1-PHENYLPROPYL]OXY}BENZENE: Prepared by Procedure A using 3,4-dichlorophenol and (1R)-3-chloro-1-phenyl-1-propanol.

EXAMPLE 808

N-(3-{1-[(3S)-3-(3,4-DICHLOROPHENOXY)-3-PHENYLPROPYL]-4-PIPERIDINYL}PHENYL)-2-METHYLPROPANAMIDE: Prepared by Procedure A using 1,2-dichloro-4-{[(1S)-3-chloro-1-phenylpropyl]oxy}benzene and 2-methyl-N-[3-(4-piperidinyl)phenyl]propanamide: ESMS m/e: 525.3 (M+H)$^+$.

EXAMPLE 809

N-(3-{1-[6-(2-FLUOROPHENYL)-6-HYDROXYHEXYL]-4-PIPERIDINYL}PHENYL)-2-METHYLPROPANAMIDE: Prepared by Procedure L and Scheme AN using N-(3-{1-[6-(2-fluorophenyl)-6-oxohexyl]-4-piperidinyl}phenyl)-2-methylpropanamide: ESMS m/e: 441.3 (M+H)$^+$.

EXAMPLE 810

N-[3-(1-{5-HYDROXY-5-[4-(TRIFLUOROMETHYL)PHENYL]PENTYL}-4-PIPERIDINYL)PHENYL]-2-METHYLPROPANAMIDE: Prepared by Procedure L and Scheme AN using 2-methyl-N-[3-(1-{5-oxo-5-[4-(trifluoromethyl)phenyl]pentyl}-4-piperidinyl)phenyl]propanamide: ESMS m/e: 477.2 (M+H)$^+$.

EXAMPLE 811

N-(3-{1-[5-(4-FLUOROPHENYL)-5-HYDROXYPENTYL]-4-PIPERIDINYL}PHENYL)-2-METHYLPROPANAMIDE: Prepared by Procedure L and Scheme AN using N-(3-{1-[5-(4-fluorophenyl)-5-oxopentyl]-4-piperidinyl}phenyl)-2-methylpropanamide: ESMS m/e: 427.2 (M+H)$^+$.

EXAMPLE 812

N-(3-{1-[7-(2-FLUOROPHENYL)-7-HYDROXYHEPTYL]-4-PIPERIDINYL}PHENYL)-2-METHYLPROPANAMIDE: Prepared by Procedure L and Scheme AN using N-(3-{1-[7-(2-fluorophenyl)-7-oxoheptyl]-4-piperidinyl}phenyl)-2-methylpropanamide: ESMS m/e: 455.2 (M+H)$^+$.

EXAMPLE 813

N-(3-{1-[6-(3-FLUOROPHENYL)-6-HYDROXYHEXYL]-4-PIPERIDINYL}PHENYL)-2-METHYLPROPANAMIDE: Prepared by Procedure L and Scheme AN using N-(3-{1-[6-(3-fluorophenyl)-6-oxohexyl]-4-piperidinyl}phenyl)-2-methylpropanamide: ESMS m/e: 441.2 (M+H)$^+$.

EXAMPLE 814

N-(3-{1-[5-(2-FLUOROPHENYL)-5-HYDROXYPENTYL]-4-PIPERIDINYL}PHENYL)-2-METHYLPROPANAMIDE: Prepared by Procedure L and Scheme AN using N-(3-{1-[5-(2-fluorophenyl)-5-oxopentyl]-4-piperidinyl}phenyl)-2-methylpropanamide: ESMS m/e: 427.2 (M+H)$^+$.

EXAMPLE 815

N-(3-{1-[5-(3-FLUOROPHENYL)-5-HYDROXYPENTYL]-4-PIPERIDINYL}PRENYL)-2-METHYLPROPANAMIDE: Prepared by Procedure L and Scheme AN using N-(3-{1-[5-(3-fluorophenyl)-5-oxopentyl]-4-piperidinyl}phenyl)-2-methylpropanamide: ESMS m/e: 427.2 (M+H)$^+$.

EXAMPLE 816

N-(3-{1-[5-(3-CHLOROPHENYL)-5-HYDROXYPENTYL]-4-PIPERIDINYL)PHENYL)-2-METRYLPROPANAMIDE: Prepared by Procedure L and Scheme AN using N-(3-{1-[5-(3-chlorophenyl)-5-oxopentyl]-4-piperidinyl}phenyl)-2-methylpropanamide: ESMS m/e: 443.1 (M+H)$^+$.

EXAMPLE 817

N-(3-{1-[6-(4-FLUOROPHENYL)-6-HYDROXYHEXYL]-4-PIPERIDINYL}PHENYL)-2-METHYLPROPANAMIDE: Prepared by Procedure L and Scheme AN using N-(3-{1-[6-(4-fluorophenyl)-6-oxohexyl]-4-piperidinyl}phenyl)-2-methylpropanamide: ESMS m/e: 441.2 (M+H)$^+$.

EXAMPLE 818

N-(3-{1-[6-(4-CHLOROPHENYL)-6-HYDROXYHEXYL]-4-PIPERIDINYL}PHENYL)-2-METHYLPROPANAMIDE: Prepared by Procedure L and Scheme AN using N-(3-{1-[6-(4-chlorophenyl)-6-oxohexyl]-4-piperidinyl}phenyl)-2-methylpropanamide: ESMS m/e: 456.9 (M+H)$^+$.

EXAMPLE 819

N-(3-{1-[5-(4-CHLOROPHENYL)-5-HYDROXYPENTYL]-4-PIPERIDINYL}PHENYL)-2-METHYLPROPANAMIDE: Prepared by Procedure L and Scheme AN using N-(3-{1-[5-(4-chlorophenyl)-5-oxopentyl]-4-piperidinyl}phenyl)-2-methylpropanamide: ESMS m/e: 443.0 (M+H)$^+$.

EXAMPLE 820

N-(4-{1-[(9-ETHYL-9H-CARBAZOL-3-YL)METHYL]-4-PIPERIDINYL}PHENYL)BUTANAMIDE: Prepared by Procedure F and Scheme R, without HOAc, using 9-ethyl-9H-carbazole-3-carbaldehyde and N-[4-(4-piperidinyl)phenyl]butanamide: ESMS m/e: 454.2 (M+H)$^+$.

EXAMPLE 821

N-(3-{1-[(9-ETHYL-9H-CARBAZOL-3-YL)METHYL]-4-PIPERIDINYL}PHENYL)PROPANAMIDE: Prepared by Procedure F and Scheme R, without HOAc, using 9-ethyl-9H-carbazole-3-carbaldehyde and N-[3-(4-piperidinyl)phenyl]propanamide: ESMS m/e: 440.5 (M+H)$^+$.

EXAMPLE 822

N-(3-{1-[(1,9-DIMETHYL-9H-CARBAZOL-3-YL)METRYL]-4-PIPERIDINYL}PHENYL)-2-METHYLPROPANAMIDE: Prepared by Procedure F and Scheme R, without HOAc, using 1,9-dimethyl-9H-carbazole-3-carbaldehyde and 2-methyl-N-[3-(4-piperidinyl)phenyl]propanamide: $^1$H NMR (400 MHz, CDCl$_3$) δ 8.05–6.77 (m, 10H), 5.20–5.12 (m, 1H), 4.04 (s, 3H), 3.93 (s, 2H), 3.34–3.24 (m, 2H), 2.79 (s, 3H), 2.56–2.38 (m, 2H), 2.38–2.26 (m, 2H), 2.08–1.88 (m, 2H), 1.82–1.70 (m, 2H), 1.16 (d, 6H, J=6.8 Hz); ESMS m/e: 454.2 (M+H)+.

EXAMPLE 823

N-(3-{1-[(9-ETHYL-9H-CARBAZOL-3-YL)METHYL]-4-PIPERIDINYL}PHENYL)CYCLOPROPANECARBOXAMIDE: Prepared by Procedure F and Scheme R, without HOAc, using 9-ethyl-9H-carbazole-3-carbaldehyde and N-[3-(4-piperidinyl)phenyl]cyclopropanecarboxamide: ESMS m/e: 452.6 (M+H)+.

EXAMPLE 824

1-(3-{1-[(9-ETHYL-9H-CARBAZOL-3-YL)METHYL]-4-PIPERIDINYL}PHENYL)-2-PYRROLIDINONE: Prepared by Scheme R and Procedure F. A solution of 1-(9-ethyl-9H-carbazol-3-yl)ethanone (22.3 mg, 0.100 mmol) and 1-[3-(4-piperidinyl)phenyl]-2-pyrrolidinone (27.2 mg, 0.100 mmol) in 1,2-dichloroethane (1.00 mL) was treated with sodium triacetoxyborohydride (63.6 mg, 0.300 mmol) and HOAc (5.70 uL, 0.100 mmol). The mixture was stirred overnight at room temperature. The reaction mixture was treated with a saturated aqueous NaHCO$_3$ solution (10 mL). The aqueous layer was extracted with CH$_2$Cl$_2$ (3×10 mL) and the combined organic layers were washed with brine (10 mL), dried over MgSO$_4$ and concentrated in vacuo. The residue was purified by preparative TLC using 5% of NH$_3$ (2.0 M in methanol) in CH$_2$Cl$_2$ to give the desired product 1-(3-{1-[(9-ethyl-9H-carbazol-3-yl)methyl]-4-piperidinyl}phenyl)-2-pyrrolidinone (4.60 mg, 9.43%) $^1$H NMR (400 MHz, CDCl$_3$) δ 8.04 (d, 1H, J=7.4 Hz), 7.99 (s, 1H), 7.43–7.28 (m, 5H), 6.96 (d, 1H, J=7.4 Hz), 4.31 (q, 2H, J=6.8 Hz), 3.77 (t, 2H, J=7.3 Hz), 3.70 (s, 2H), 3.06 (d, 2H, J=10.6 Hz), 2.56–2.42 (m, 3H), 2.07 (m, 4H), 1.77 (m, 4H), 1.36 (m, 3H); ESMS m/e: 452.5 (M+H)+.

N-{3-[1-(H-INDOL-5-YLMETHYL)-4-PIPERIDINYL]PHENYL}-2-METHYLPROPANAMIDE: Prepared by Procedure F and Scheme R, without HOAc, using 1H-indole-5-carbaldehyde and 2-methyl-N-[3-(4-piperidinyl)phenyl]propanamide: ESMS m/e: 376.2 (M+H)+.

1-(4-CHLOROBUTYL)-1H-INDOLE: Prepared by Procedure AH, and Scheme P using 1H-indole and 1-bromo-4-chlorobutane: $^1$NMR (400 MHz, CDCl$_3$) δ 7.72–7.02 (m, 5H), 6.49 (d, 1H, J=2.8 Hz), 4.13 (t, 2H, J=6.8 Hz), 3.48 (t, 2H, J=6.8 Hz), 2.06–1.92 (m, 2H), 1.80–1.70 (m, 2H).

1-(3-CHLOROPROPYL)-1H-INDOLE: Prepared by Procedure AH, and Scheme P using 1H-indole and 1-bromo-3-chloropropane: $^1$H NMR (400 MHz, CDCl$_3$) δ 7.70–7.04 (m, 5H), 6.50 (d, 1H, J=2.8 Hz), 4.31 (t, 2H, J=6.8 Hz), 3.42 (t, 2H, J=6.4 Hz), 2.28–2.20 (m, 2H).

EXAMPLE 825

N-(4-{1-[5-(1H-INDOL-1-YL)PENTYL]-4-PIPERIDINYL}PHENYL)-2-METHYLPROPANAMIDE: Prepared by Procedure AH and Scheme P using 1-(5-chloropentyl)-1H-indole and 2-methyl-N-[4-(4-piperidinyl)phenyl]propanamide: ESMS m/e: 432.3 (M+H)+.

EXAMPLE 826

N-(4-{1-[5-(1H-INDOL-1-YL)PENTYL]-4-PIPERIDINYL}PHENYL)BUTANAMIDE: Prepared by Procedure AH and Scheme P using 1-(5-chloropentyl)-1H-indole and N-[4-(4-piperidinyl)phenyl]butanamide: ESMS m/e: 432.3 (M+H)+.

EXAMPLE 827

N-(4-{1-[(5-1H-INDOL-1-YL)PENTYL]-4-PIPERIDINYL}PHENYL)PROPANAMIDE: Prepared by Procedure AH and Scheme P using 1-(5-chloropentyl)-1H-indole and N-[4-(4-piperidinyl)phenyl]propanamide: ESMS m/e: 418.2 (M+H)+.

EXAMPLE 828

N-(4-{1-[6-(1H-INDOL-1-YL)HEXYL]-4-PIPERIDINYL}PHENYL)PROPANAMIDE: Prepared by Procedure AH and Scheme P using 1-(6-chlorohexyl)-1H-indole and N-[4-(4-piperidinyl)phenyl]propanamide: ESMS m/e: 432.3 (M+H)+.

EXAMPLE 829

2-METHYL-N-(3-{1-[(1-METHYL-1H-INDOL-2-YL)METHYL]-4-PIPERIDINYL}PHENYL)PROPANAMIDE: Prepared by Procedure F and Scheme R, without HOAc, using 1-methyl-1H-indole-2-carbaldehyde and 2-methyl-N-[3-(4-piperidinyl)phenyl]propanamide: ESMS m/e: 390.3 (M+H)+.

EXAMPLE 830

N-{3-[1-(1H-INDOL-4-YLMETHYL)-4-PIPERIDINYL]PHENYL}-2-METHYLPROPANAMIDE: Prepared by Procedure F and Scheme R, without HOAc, using 1H-indole-4-carbaldehyde and 2-methyl-N-[3-(4-piperidinyl)phenyl]propanamide: ESMS m/e: 376.2 (M+H)+.

EXAMPLE 831

N-(4-{1-[6-(1H-INDOL-1-YL)HEXYL]-4-PIPERIDINYL}PHENYL)-2-METHYLPROPANAMIDE: Prepared by Procedure AH and Scheme P using 1-(6-chlorohexyl)-1H-indole and 2-methyl-N-[4-(4-piperidinyl)phenyl]propanamide: ESMS m/e: 446.3 (M+H)+.

EXAMPLE 832

N-{3-[1-(L-INDOL-7-YLMETHYL)-4-PIPERIDINYL]PHENYL}-2-METHYLPROPANAMIDE: Prepared by Procedure F and Scheme R, without HOAc, using 1H-indole-7-carbaldehyde and 2-methyl-N-[3-(4-piperidinyl)phenyl]propanamide: ESMS m/e: 376.2 (M+H)+.

EXAMPLE 833

N-[3-(1-{[1-(4-METHOXYPHENYL)-1H-INDOL-5-YL]METHYL}-4-PIPERIDINYL)PHENYL]-2-METHYLPROPANAMIDE: Prepared by Procedure C and Scheme Q1, with CuBr in place of Cu, using 1-iodo-4-methoxybenzene and N-{3-[1-(1H-indol-5-ylmethyl)-4-piperidinyl]phenyl}-2-methylpropanamide: ESMS m/e: 482.0 (M+H)+.

EXAMPLE 834

METHYL 4-[4-({4-[3-(ISOBUTYRYLAMINO)PHENYL]-1-PIPERIDINYL}METHYL)-1H-INDOL-1-YL]BENZOATE: Prepared by Procedure C and Scheme Q1, with CuBr in place of Cu, using methyl 4-iodobenzoate and N-{3-[1-(1H-indol-4-ylmethyl)-4-piperidinyl]phenyl}-2-methylpropanamide: ESMS m/e: 510.3 (M+H)+.

EXAMPLE 835

2-METHYL-N-[3-(1-{[1-(3-METHYLPHENYL)-1H-INDOL-5-YL]METHYL}-4-PIPERIDINYL)PHENYL]PROPANAMIDE: Prepared by Procedure C and Scheme Q1, with CuBr in place of Cu, using 1-iodo-3-methylbenzene and N-{3-[1-(1H-indol-5-ylmethyl)-4-piperidinyl]phenyl}-2-methylpropanamide: ESMS m/e: 466.3 (M+H)$^+$.

EXAMPLE 836

N-[3-(1-{[1-(4-FLUOROPHENYL)-1H1-INDOL-4-YL]METHYL}-4-PIPERIDINYL)PHENYL]-2-METHYLPROPANAMIDE: Prepared by Procedure C and Scheme Q1, with CuBr in place of Cu, using 1-fluoro-4-iodobenzene and N-{3-[1-(1H-indol-4-ylmethyl)-4-piperidinyl]phenyl}-2-methylpropanamide: $^1$H NMR (400 MHz, CDCl$_3$) δ 7.66–6.92 (m, 12H), 6.65 (d, 1H, J=3.2 Hz), 3.69 (s, 2H), 3.15–3.02 (m, 2H), 2.58–2.40 (m, 2H), 2.20–2.04 (m, 2H), 1.94–1.76 (m, 4H), 1.25 (d, 6H, J=6.8 Hz); ESMS m/e: 470.6 (M+H)$^+$.

EXAMPLE 837

N-(3-{1-[4-(1H-INDOL-1-YL)BUTYL]-4-PIPERIDINYL}PHENYL)-2-METHYLPROPANAMIDE: Prepared by Procedure AH and Scheme P using 1-(4-chlorobutyl)-1H-indole and 2-methyl-N-[3-(4-piperidinyl)phenyl]propanamide: ESMS m/e: 418.3 (M+H)$^+$.

EXAMPLE 838

N-[3-(1-{[1-(4-CHLOROPHENYL)-1H-INDOL-5-YL]METHYL}-4-PIPERIDINYL)PHENYL]-2-METHYLPROPANAMIDE: Prepared by Procedure C and Scheme Q1, with CuBr in place of Cu, using 1-chloro-4-iodobenzene and N-{3-[1-(1H-indol-5-ylmethyl)-4-piperidinyl]phenyl}-2-methylpropanamide: ESMS m/e: 486.2 (M+H)$^+$.

EXAMPLE 839

N-[3-(1-{[1-(3-METHOXYPHENYL)-1H-INDOL-5-YL]METHYL}-4-PIPERIDINYL)PHENYL]-2-METHYLPROPANAMIDE: Prepared by Procedure C and Scheme Q1, with CuBr in place of Cu, using 1-iodo-3-methoxybenzene and N-{3-[1-(1H-indol-5-ylmethyl)-4-piperidinyl]phenyl}-2-methylpropanamide: ESMS m/e: 482.2 (M+H)$^+$.

EXAMPLE 840

N-(4-{1-[4-(1H-INDOL-1-YL)BUTYL]-4-PIPERIDINYL}PHENYL)BUTANAMIDE: Prepared by Procedure AH and Scheme P using 1-(4-chlorobutyl)-1H-indole and N-[4-(4-piperidinyl)phenyl]butanamide: ESMS m/e: 418.2 (M+H)$^+$.

EXAMPLE 841

N-[3-(1-{[1-(2-METHOXYPHENYL)-1H-INDOL-5-YL]METHYL}-4-PIPERIDINYL)PHENYL]-2-METHYLPROPANAMIDE: Prepared by Procedure C and Scheme Q1, with CuBr in place of Cu, using 1-iodo-2-methoxybenzene and N-{3-[1-(1H-indol-5-ylmethyl)-4-piperidinyl]phenyl}-2-methylpropanamide: ESMS m/e: 482.2 (M+H)$^+$.

EXAMPLE 842

N-[3-(1-{[1-(3-CHLOROPHENYL)-1H-INDOL-5-YL]METHYL}-4-PIPERIDINYL)PHENYL]-2-METHYLPROPANAMIDE: Prepared by Procedure C and Scheme Q1, with CuBr in place of Cu, using 1-chloro-3-iodobenzene and N-{3-[1-(1H-indol-5-ylmethyl)-4-piperidinyl]phenyl}-2-methylpropanamide: ESMS m/e: 486.2 (M+H)$^+$.

EXAMPLE 843

METHYL 2-[5-({4-[3-(ISOBUTYRYLAMINO)PHENYL]-1-PIPERIDINYL}METHYL)-1H-INDOL-1-YL]BENZOATE: Prepared by Procedure C and Scheme Q1, with CuBr in place of Cu, using methyl 2-iodobenzoate and N-{3-[1-(1H-indol-5-ylmethyl)-4-piperidinyl]phenyl}-2-methylpropanamide: ESMS m/e: 510.2 (M+H)$^+$.

EXAMPLE 844

N-(3-{1-[3-(1H-INDOL-1-YL)PROPYL]-4-PIPERIDINYL}PHENYL)-2-METHYLPROPANAMIDE: Prepared by Procedure AH and Scheme P using 1-(3-chloropropyl)-1H-indole and 2-methyl-N-[3-(4-piperidinyl)phenyl]propanamide: ESMS m/e: 404.2 (M+H)$^+$.

EXAMPLE 845

2-METHYL-N-{3-[1-({1-[4-(TRIFLUOROMETHYL)PHENYL]-1H-INDOL-5-YL}METHYL)-4-PIPERIDINYL]PHENYL}PROPANAMIDE: Prepared by Procedure C and Scheme Q1, with CuBr in place of Cu, using 1-iodo-4-(trifluoromethyl)benzene and N-{3-[1-(1H-indol-5-ylmethyl)-4-piperidinyl]phenyl}-2-methylpropanamide: ESMS m/e: 520.2 (M+H)$^+$.

EXAMPLE 846

N-(3-{1-[(1-[1,1'-BIPHENYL]-2-YL-1H-INDOL-5-YL)METHYL]-4-PIPERIDINYL}PHENYL)-2-METHYLPROPANAMIDE: Prepared by Procedure C and Scheme Q1, with CuBr in place of Cu, using 2-iodo-1,1'-biphenyl and N-{3-[1-(1H-indol-5-ylmethyl)-4-piperidinyl]phenyl}-2-methylpropanamide: ESMS m/e: 528.3 (M+H)$^+$.

EXAMPLE 847

2-METHYL-N-[3-(1-{[1-(2-METHYLPHENYL)-1H-INDOL-5-YL]METHYL}-4-PIPERIDINYL)PHENYL]PROPANAMIDE: Prepared by Procedure C and Scheme Q1, with CuBr in place of Cu, using 1-iodo-2-methylbenzene and N-{3-[1-(1H-indol-5-ylmethyl)-4-piperidinyl]phenyl}-2-methylpropanamide: ESMS m/e: 466.2 (M+H)$^+$.

EXAMPLE 848

2-METHYL-N-[3-(1-{[1-(4-METHYLPHENYL)-1H-INDOL-5-YL]METHYL}-4-PIPERIDINYL)PHENYL]PROPANAMIDE: Prepared by Procedure C and Scheme Q1, with CuBr in place of Cu, using 1-iodo-4-methylbenzene and N-{3-[1-(1H-indol-5-ylmethyl)-4-piperidinyl]phenyl}-2-methylpropanamide: ESMS m/e: 466.3 (M+H)$^+$.

EXAMPLE 849

N-[3-(1-{[1-(2-CHLOROPHENYL)-1H-INDOL-5-YL]METHYL}-4-PIPERIDINYL)PHENYL]-2-METHYLPROPANAMIDE: Prepared by Procedure C and Scheme Q1, with CuBr in place of Cu, using 1-chloro-2-iodobenzene and N-{3-[1-(1H-indol-5-ylmethyl)-4-piperidinyl]phenyl}-2-methylpropanamide: ESMS m/e: 486.2 (M+H)$^+$.

EXAMPLE 850

2-METHYL-N-{3-[1-({1-[3-(TRIFLUOROMETHYL)PHENYL]-1H-INDOL-5-YL}METHYL)-4-PIPERIDINYL]PHENYL}PROPANAMIDE: Prepared by Procedure C and Scheme Q1, with CuBr in place of Cu, using 1-iodo-3-(trifluoromethyl)benzene and N-{3-[1-(1H-indol-5-ylmethyl)-4-piperidinyl]phenyl}-2-methylpropanamide: $^1$H NMR (400 MHz, CDCl$_3$) δ 7.80–6.94 (m, 12H), 6.69 (d, 1H, J=3.6 Hz), 3.36 (s, 2H), 3.10–3.00 (m, 2H), 2.58–2.42 (m, 2H), 2.16–2.02 (m, 2H), 1.85–1.75 (m, 4H), 1.25 (d, 6H, J=7.2 Hz); ESMS m/e: 520.2 (M+H)$^+$.

EXAMPLE 851

2-METHYL-N-[3-(1-{[1-(2-NITROPHENYL)-1H-INDOL-5-YL]METHYL}-4-PIPERIDINYL)PHENYL]PROPANAMIDE: Prepared by Procedure C and Scheme Q1, with CuBr in place of Cu, using 1-iodo-2-nitrobenzene and N-{3-[1-(1H-indol-5-ylmethyl)-4-piperidinyl]phenyl}-2-methylpropanamide: ESMS m/e: 497.2 (M+H)$^+$.

EXAMPLE 852

N-[3-(1-{[1-(2-FLUOROPHENYL)-1H-INDOL-5-YL]METHYL}-4-PIPERIDINYL)PHENYL]-2-METHYLPROPANAMIDE: Prepared by Procedure C and Scheme Q1, with CuBr in place of Cu, using 1-fluoro-2-iodobenzene and N-{3-[1-(1H-indol-5-ylmethyl)-4-piperidinyl]phenyl}-2-methylpropanamide: ESMS m/e: 470.2 (M+H)$^+$.

EXAMPLE 853

2-METHYL-N-[3-(1-{[1-(1-NAPHTHYL)-1H-INDOL-5-YL]METHYL}-4-PIPERIDINYL)PHENYL]PROPANAMIDE: Prepared by Procedure C and Scheme Q1, with CuBr in place of Cu, using 1-iodonaphthalene and N-{3-[1-(1H-indol-5-ylmethyl)-4-piperidinyl]phenyl}-2-methylpropanamide: ESMS m/e: 502.2 (M+H)$^+$.

EXAMPLE 854

N-[3-(1-{[1-(2,3-DICHLOROPHENYL)-1H-INDOL-5-YL]METHYL}-4-PIPERIDINYL)PHENYL]-2-METHYLPROPANAMIDE: Prepared by Procedure C and Scheme Q1, with CuBr in place of Cu, using 1,2-dichloro-3-iodobenzene and N-{3-[1-(1H-indol-5-ylmethyl)-4-piperidinyl]phenyl}-2-methylpropanamide: $^1$H NMR (400 MHz, CDCl$_3$) δ 7.68–6.94 (m, 12H), 6.68 (d, 1H, J=2.8 Hz), 3.69 (s, 2H), 3.15–3.02 (m, 2H), 2.54–2.42 (m, 2H), 2.18–2.02 (m, 2H), 1.88–1.76 (m, 4H), 1.25 (d, 6H, J=6.8 Hz); ESMS m/e: 520.1 (M+H)$^+$.

EXAMPLE 855

N-[3-(1-{[1-(2,3-DICHLOROPHENYL)-1H-INDOL-7-YL]METHYL}-4-PIPERIDINYL)PHENYL]-2-METHYLPROPANAMIDE: Prepared by Procedure C and Scheme Q1, with CuBr in place of Cu, using 1,2-dichloro-3-iodobenzene and N-{3-[1-(1H-indol-7-ylmethyl)-4-piperidinyl]phenyl}-2-methylpropanamide: ESMS m/e: 520.2 (M+H)$^+$.

EXAMPLE 856

N-[3-(1-{[1-(3-METHOXYPHENYL)-1H-INDOL-4-YL]METHYL}-4-PIPERIDINYL)PHENYL]-2-METHYLPROPANAMIDE: Prepared by Procedure C and Scheme Q1, with CuBr in place of Cu, using 1-iodo-3-methoxybenzene and N-{3-[1-(1H-indol-4-ylmethyl)-4-piperidinyl]phenyl}-2-methylpropanamide: ESMS m/e: 482.3 (M+H)$^+$.

EXAMPLE 857

N-[3-(1-{[1-(2,3-DICHLOROPHENYL)-1H-INDOL-4-YL]METHYL}-4-PIPERIDINYL)PHENYL]-2-METHYLPROPANAMIDE: Prepared by Procedure C and Scheme Q1, with CuBr in place of Cu, using 1,2-dichloro-3-iodobenzene and N-{3-[1-(1H-indol-4-ylmethyl)-4-piperidinyl]phenyl}-2-methylpropanamide: ESMS m/e: 520.2 (M+H)$^+$.

EXAMPLE 858

N-[3-(1-{[1-(3-CHLOROPHENYL)-1H-INDOL-4-YL]METHYL}-4-PIPERIDINYL)PHENYL]-2-METHYLPROPANAMIDE: Prepared by Procedure C and Scheme Q1, with CuBr in place of Cu, using 1-chloro-3-iodobenzene and N-{3-[1-(1H-indol-4-ylmethyl)-4-piperidinyl]phenyl}-2-methylpropanamide: ESMS m/e: 486.2 (M+H)$^+$.

EXAMPLE 859

2-METHYL-N-[3-(1-{[1-(3-METHYLPHENYL)-1H-INDOL-4-YL]METHYL}-4-PIPERIDINYL)PHENYL]PROPANAMIDE: Prepared by Procedure C and Scheme Q1, with CuBr in place of Cu, using 1-iodo-3-methylbenzene and N-{3-[1-(1H-indol-4-ylmethyl)-4-piperidinyl]phenyl}-2-methylpropanamide: ESMS m/e: 466.3 (M+H)$^+$.

EXAMPLE 860

N-[3-(1-{[1-(3-METHOXYPHENYL)-1H-INDOL-7-YL]METHYL}-4-PIPERIDINYL)PHENYL]-2-METHYLPROPANAMIDE: Prepared by Procedure C and Scheme Q1, with CuBr in place of Cu, using 1-iodo-3-methoxybenzene and N-{3-[1-(1H-indol-7-ylmethyl)-4-piperidinyl]phenyl}-2-methylpropanamide: ESMS m/e: 482.3 (M+H)$^+$.

EXAMPLE 861

2-METHYL-N-{3-[1-({1-[3-(TRIFLUOROMETHYL)PHENYL]-1H-INDOL-4-YL}METHYL)-4-PIPERIDINYL]PHENYL}PROPANAMIDE: Prepared by Procedure C and Scheme Q1, with CuBr in place of Cu, using 1-iodo-3-(trifluoromethyl)benzene and N-{3-[1-(1H-indol-4-ylmethyl)-4-piperidinyl]phenyl}-2-methylpropanamide: ESMS m/e: 520.2 (M+H)$^+$.

EXAMPLE 862

N-[3-(1-{[1-(3,4-DIMETHYLPHENYL)-1H-INDOL-4-YL]METHYL}-4-PIPERIDINYL)PHENYL]-2-METHYLPROPANAMIDE: Prepared by Procedure C and Scheme Q1, with CuBr in place of Cu, using N-{3-[1-(1H-indol-4-ylmethyl)-4-piperidinyl]phenyl}-2-methylpropanamide and 4-iodo-1,2-dimethylbenzene: ESMS m/e: 480.0 (M+H)$^+$.

EXAMPLE 863

N-[3-(1-{[1-(3,4-DIFLUOROPHENYL)-1H-INDOL-4-YL]METHYL}-4-PIPERIDINYL)PHENYL]-2-METHYLPROPANAMIDE: Prepared by Procedure C and Scheme Q1, with CuBr in place of Cu, using 1,3-dichloro-5-iodobenzene and N-{3-[1-(1H-indol-4-ylmethyl)-4- piperidinyl]phenyl}-2-methylpropanamide: ESMS m/e: 520.0 (M+H)⁺.

EXAMPLE 864

N-[3-(1-{[1-(3,4-DICHLOROPHENYL)-1H-INDOL-4-YL]METHYL}-4-PIPERIDINYL)PHENYL]-2-METHYLPROPANAMIDE: Prepared by Procedure C and Scheme Q1, with CuBr in place of Cu, using 1,2-dichloro-4-iodobenzene and N-{3-[1-(1H-indol-4-ylmethyl)-4-piperidinyl]phenyl}-2-methylpropanamide: ESMS m/e: 520.0 (M+H)⁺.

EXAMPLE 865

N-[3-(1-{[1-(2-CHLORO-4-FLUOROPHENYL)-1H-INDOL-4-YL]METHYL}-4-PIPERIDINYL)PHENYL]-2-METHYLPROPANAMIDE: Prepared by Procedure C and Scheme Q1, with CuBr in place of Cu, using 2-chloro-4-fluoro-1-iodobenzene and N-{3-[1-(1H-indol-4-ylmethyl)-4-piperidinyl]phenyl}-2-methylpropanamide: ESMS m/e: 504.0 (M+H)⁺.

EXAMPLE 866

N-[3-(1-{[1-(2,4-DIFLUOROPHENYL)-1H-INDOL-4-YL]METHYL}-4-PIPERIDINYL)PHENYL]-2-METHYLPROPANAMIDE: Prepared by Procedure C and Scheme Q1, with CuBr in place of Cu, using 2,4-difluoro-1-iodobenzene and N-{3-[1-(1H-indol-4-ylmethyl)-4-piperidinyl]phenyl}-2-methylpropanamide: ESMS m/e: 488.0 (M+H)⁺.

EXAMPLE 867

2-METHYL-N-[3-(1-{[1-(3-PYRIDINYL)-1H-INDOL-7-YL]METHYL}-4-PIPERIDINYL)PHENYL]PROPANAMIDE: Prepared by Procedure C and Scheme Q1, with CuBr in place of Cu, using 3-iodopyridine and N-{3-[1-(1H-indol-7-ylmethyl)-4-piperidinyl]phenyl}-2-methylpropanamide: ESMS m/e: 453.1 (M+H)⁺.

EXAMPLE 868

N-{3-[1-(1H-INDOL-6-YLMETHYL)-4-PIPERIDINYL]PHENYL}-2-METHYLPROPANAMIDE: Prepared by Procedure F and Scheme R using 1H-indole-6-carbaldehyde and 2-methyl-N-[3-(4-piperidinyl)phenyl] propanamide: ESMS m/e: 376.2 (M+H)⁺.

EXAMPLE 869

2-METHYL-N-[3-(1-{[1-(4-PYRIDINYL)-1H-INDOL-4-YL]METHYL}-4-PIPERIDINYL)PHENYL]PROPANAMIDE: Prepared by Procedure C and Scheme Q1, with CuBr in place of Cu, using 4-iodopyridine and N-{3-[1-(1H-indol-4-ylmethyl)-4-piperidinyl]phenyl}-2-methylpropanamide: ESMS m/e: 453.2 (M+H)⁺.

EXAMPLE 870

2-METHYL-N-[3-(1-{[1-(2-PYRIDINYL)-1H-INDOL-4-YL]METHYL}-4-PIPERIDINYL)PHENYL]PROPANAMIDE: Prepared by Procedure C and Scheme Q1, with CuBr in place of Cu, using 2-iodopyridine and N-{3-[1-(1H-indol-4-ylmethyl)-4-piperidinyl]phenyl}-2-methylpropanamide: ESMS m/e: 453.2 (M+H)⁺.

EXAMPLE 871

N-[3-(1-{[1-(2-FLUOROPHENYL)-1H-INDOL-4-YL]METHYL}-4-PIPERIDINYL)PHENYL]-2-METHYLPROPANAMIDE: Prepared by Procedure C and Scheme Q1, with CuBr in place of Cu, using 1-fluoro-2-iodobenzene and N-{3-[1-(1H-indol-4-ylmethyl)-4-piperidinyl]phenyl}-2-methylpropanamide: ESMS m/e: 470.1 (M+H)⁺.

EXAMPLE 872

N-[3-(1-{[1-(4-CHLOROPHENYL)-1H-INDOL-4-YL]METHYL}-4-PIPERIDINYL)PHENYL]-2-METHYLPROPANAMIDE: Prepared by Procedure C and Scheme Q1, with CuBr in place of Cu, using 1-chloro-4-iodobenzene and N-{3-[1-(1H-indol-4-ylmethyl)-4-piperidinyl]phenyl}-2-methylpropanamide: ESMS m/e: 486.1 (M+H)⁺.

EXAMPLE 873

2-METHYL-N-[3-(1-{[1-(3-PYRIDINYL)-1H-INDOL-4-YL]METHYL}-4-PIPERIDINYL)PHENYL]PROPANAMIDE: Prepared by Procedure C and Scheme Q1, with CuBr in place of Cu, using 3-iodopyridine and N-{3-[1-(1H-indol-4-ylmethyl)-4-piperidinyl]phenyl}-2-methylpropanamide: ESMS m/e: 453.2 (M+H)⁺.

EXAMPLE 874

N-[3-(1-{[1-(2,3-DIMETHYLPHENYL)-1H-INDOL-4-YL]METHYL}-4-PIPERIDINYL)PHENYL]-2-METHYLPROPANAMIDE: Prepared by Procedure C and Scheme Q1, with CuBr in place of Cu, using 1-iodo-2,3-dimethylbenzene and N-{3-[1-(1H-indol-4-ylmethyl)-4-piperidinyl]phenyl}-2-methylpropanamide: ESMS m/e: 480.1 (M+H)⁺.

EXAMPLE 875

N-[3-(1-{[1-(3-FLUOROPHENYL)-1H-INDOL-4-YL]METHYL}-4-PIPERIDINYL)PHENYL]-2-METHYLPROPANAMIDE: Prepared by Procedure C and Scheme Q1, with CuBr in place of Cu, using 1-fluoro-3-iodobenzene and N-{3-[1-(1H-indol-4-ylmethyl)-4-piperidinyl]phenyl}-2-methylpropanamide: ESMS m/e: 470.1 (M+H)⁺.

EXAMPLE 876

2-METHYL-N-{3-[1-({1-[2-(TRIFLUOROMETHYL)PHENYL]-1H-INDOL-4-YL}METHYL)-4-PIPERIDINYL]PHENYL}PROPANAMIDE: Prepared by Procedure C and Scheme Q1, with CuBr in place of Cu, using 1-iodo-2-(trifluoromethyl)benzene and N-{3-[1-(1H-indol-4-ylmethyl)-4-piperidinyl]phenyl}-2-methylpropanamide: ESMS m/e: 520.1 (M+H)⁺.

EXAMPLE 877

N-[3-(1-{[1-(2-CHLOROPHENYL)-1H-INDOL-4-YL]METHYL}-4-PIPERIDINYL)PHENYL]-2-METHYLPROPANAMIDE: Prepared by Procedure C and Scheme Q1, with CuBr in place of Cu, using 1-chloro-2-iodobenzene and N-{3-[1-(1H-indol-4-ylmethyl)-4-piperidinyl]phenyl}-2-methylpropanamide: ESMS m/e: 486.1 (M+H)⁺.

EXAMPLE 878

N-[3-(1-{[1-(2,3-DIMETHYLPHENYL)-1H-INDOL-7-YL]METHYL}-4-PIPERIDINYL)PHENYL]-2-METHYLPROPANAMIDE: Prepared by Procedure C and Scheme Q1, with CuBr in place of Cu, using 1-iodo-2,3- dimethylbenzene and N-{3-[1-(1H-indol-7-ylmethyl)-4-piperidinyl]phenyl}-2-methylpropanamide: ESMS m/e: 480.0 (M+H)⁺.

2-METHYL-N-[3-(1-{5-OXO-5-[4-(TRIFLUOROMETHYL)PHENYL]PENTYL}-4-PIPERIDINYL)PHENYL]PROPANAMIDE: Prepared by Procedure K and Scheme E using 5-chloro-1-[4-(trifluoromethyl)phenyl]-1-pentanone and 2-methyl-N-[3-(4-piperidinyl)phenyl]propanamide: ESMS m/e: 475.1 (M+H)⁺.

N-(3-{1-[5-(4-FLUOROPHENYL)-5-OXOPENTYL]-4-PIPERIDINYL}PHENYL)-2-METHYLPROPANAMIDE: Prepared by Procedure K and Scheme E using 5-chloro-1-(4-fluorophenyl)-1-pentanone and 2-methyl-N-[3-(4-piperidinyl)phenyl]propanamide: ESMS m/e: 425.2 (M+H)⁺.

N-(3-{1-[5-(3-FLUOROPHENYL)-5-OXOPENTYL]-4-PIPERIDINYL}PHENYL)-2-METHYLPROPANAMIDE: Prepared by Procedure K and Scheme E using 5-chloro-1-(3-fluorophenyl)-1-pentanone and 2-methyl-N-[3-(4-piperidinyl)phenyl]propanamide: ESMS m/e: 425.2 (M+H)⁺.

N-(3-{1-[5-(3-CHLOROPHENYL)-5-OXOPENTYL]-4-PIPERIDINYL}PHENYL)-2-METHYLPROPANAMIDE: Prepared by Procedure K and Scheme E using 5-chloro-1-(3-chlorophenyl)-1-pentanone and 2-methyl-N-[3-(4-piperidinyl)phenyl]propanamide: ESMS m/e: 441.1 (M+H)⁺.

N-(3-{1-[5-(4-CHLOROPHENYL)-5-OXOPENTYL]-4-PIPERIDINYL}PHENYL)-2-METHYLPROPANAMIDE: Prepared by Procedure K and Scheme E using 5-chloro-1-(4-chlorophenyl)-1-pentanone and 2-methyl-N-[3-(4-piperidinyl)phenyl]propanamide: ESMS m/e: 441.1 (M+H)⁺.

EXAMPLE 879

2-METHYL-N-{3-[1-(3-OXO-3-PHENYLPROPYL)-4-PIPERIDINYL]PHENYL}PROPANAMIDE: Prepared by Procedure K and Scheme E using K₂CO₃ instead of Na₂CO₃ and NaI instead S of KI and 3-chloro-1-phenyl-1-propanone and 2-methyl-N-[3-(4-piperidinyl)phenyl]propanamide: ESMS m/e: 379.3 (M+H)⁺.

EXAMPLE 880

N-(3-{1-[7-(2-FLUOROPHENYL)-7-OXOHEPTYL]-4-PIPERIDINYL}PHENYL)-2-METHYLPROPANAMIDE: Prepared by Procedure K and Scheme E using K₂CO₃ instead of Na₂CO₃ and NaI instead of KI and 7-chloro-1-(2-fluorophenyl)-1-heptanone and 2-methyl-N-[3-(4-piperidinyl)phenyl]propanamide: ¹H NMR (400 MHz, CDCl₃), δ 8.17 (s, br, 1H), 8.06–6.88 (m, 8H), 3.08–2.94 (m, 4H), 2.62–2.48 (m, 1H), 2.48–2.38 (m, 1H) 2.38–2.15 (m, 2H), 2.02–1.92 (m, 2H), 1.84–1.77 (m, 4H), 1.77–1.66 (m, 2H), 1.62–1.46 (m, 2H), 1.46–1.29 (M, 4H), 1.21 (d, 6H, J=6.8 Hz); ESMS m/e: 453.2 (M+H)⁺.

EXAMPLE 881

N-(3-{1-[5-(2-FLUOROPHENYL)-5-OXOPENTYL]-4-PIPERIDINYL}PHENYL)-2-METHYLPROPANAMIDE: Prepared by Procedure K and Scheme E using K₂CO₃ instead of Na₂CO₃ and NaI instead of KI and 5-chloro-1-(2-fluorophenyl)-1-pentanone and 2-methyl-N-[3-(4-piperidinyl)phenyl]propanamide: ESMS m/e: 425.2 (M+H)⁺.

EXAMPLE 882

N-(3-{1-[6-(3-FLUOROPHENYL)-6-OXOHEXYL]-4-PIPERIDINYL}PHENYL)-2-METHYLPROPANAMIDE: Prepared by Procedure K and Scheme E using K₂CO₃ instead of Na₂CO₃ and NaI instead of KI and 6-chloro-1-(3-fluorophenyl)-1-hexanone and 2-methyl-N-[3-(4-piperidinyl)phenyl]propanamide: ESMS m/e: 439.2 (M+H)⁺.

EXAMPLE 883

N-(3-{1-[6-(2-FLUOROPHENYL)-6-OXOHEXYL]-4-PIPERIDINYL}PHENYL)-2-METHYLPROPANAMIDE: Prepared by Procedure K and Scheme E using K₂CO₃ instead of Na₂CO₃ and NaI instead of KI and 6-chloro-1-(2-fluorophenyl)-1-hexanone and 2-methyl-N-[3-(4-piperidinyl)phenyl]propanamide: ESMS m/e: 439.2 (M+H)⁺.

EXAMPLE 884

N-(3-{1-[7-(4-FLUOROPHENYL)-7-OXOHEPTYL]-4-PIPERIDINYL}PHENYL)-2-METHYLPROPANAMIDE: Prepared by Procedure K and Scheme E using K₂CO₃ instead of Na₂CO₃ and NaI instead of KI and 7-chloro-1-(4-fluorophenyl)-1-heptanone and 2-methyl-N-[3-(4-piperidinyl)phenyl]propanamide: ESMS m/e: 453.2 (M+H)⁺.

EXAMPLE 885

N-(3-{1-[6-(4-CHLOROPHENYL)-6-OXOHEXYL]-4-PIPERIDINYL}PHENYL)-2-METHYLPROPANAMIDE: Prepared by Procedure K and Scheme E using K₂CO₃ instead of Na₂CO₃ and NaI instead of KI and 6-chloro-1-(4-chlorophenyl)-1-hexanone and 2-methyl-N-[3-(4-piperidinyl)phenyl]propanamide: ESMS m/e: 455.1 (M+H)⁺.

EXAMPLE 886

N-(3-{1-[7-(4-CHLOROPHENYL)-7-OXOHEPTYL]-4-PIPERIDINYL}PHENYL)-2-METHYLPROPANAMIDE: Prepared by Procedure K and Scheme E using K₂CO₃ instead of Na₂CO₃ and NaI instead of KI and 7-chloro-1-(4-chlorophenyl)-1-heptanone and 2-methyl-N-[3-(4-piperidinyl)phenyl]propanamide: ESMS m/e: 469.1 (M+H)⁺.

EXAMPLE 887

N-(3-{1-[6-(4-FLUOROPHENYL)-6-OXOHEXYL]-4-PIPERIDINYL}PHENYL)-2-METHYLPROPANAMIDE: Prepared by Procedure K and Scheme E using K₂CO₃ instead of Na₂CO₃ and NaI instead of KI and 6-chloro-1-(4-fluorophenyl)-1-hexanone and 2-methyl-N-[3-(4-piperidinyl)phenyl]propanamide: ESMS m/e: 439.1 (M+H)⁺.

EXAMPLE 888

N-(3-{1-[6-(3-ACETYLPHENOXY)-6-(2-FLUOROPHENYL)HEXYL]-4-PIPERIDINYL}PHENYL)-2-METHYLPROPANAMIDE: Prepared by Procedure A and Scheme AN using 1-(3-hydroxyphenyl)ethanone and N-(3-(-1-[6-(2-fluorophenyl)-6-hydroxyhexyl]-4-piperidinyl}phenyl)-2-methylpropanamide: ESMS m/e: 559.5 (M+H)⁺.

EXAMPLE 889

N-(3-{1-[6-(2-FLUOROPHENOXY)-6-(2-FLUOROPHENYL)HEXYL]-4-PIPERIDINYL}PHENYL)-2-METHYLPROPANAMIDE:

Prepared by Procedure A and Scheme AN using 2-fluorophenol and N-(3-{1-[6-(2-fluorophenyl)-6-hydroxyhexyl]-4-piperidinyl}phenyl)-2-methylpropanamide: ESMS m/e: 535.1 (M+H)$^+$.

EXAMPLE 890

N-(3-{1-[6-(4-FLUOROPHENOXY)-6-(2-FLUOROPHENYL)HEXYL]-4-PIPERIDINYL}PHENYL)-2-METHYLPROPANAMIDE: Prepared by Procedure A and Scheme AN using 4-fluorophenol and N-(3-(1-[6-(2-fluorophenyl)-6-hydroxyhexyl]-4-piperidinyl}phenyl)-2-methylpropanamide: $^1$H NMR (400 MHz, CDCl$_3$), HCl salt δ 7.72–6.72 (m, 12H), 5.42–5.34 (m, 1H), 3.68–3.58 (m, br, 2H), 3.02–2.92 (m, 2H), 2.80–2.46 (m, 6H), 2.05–1.78 (m, 6H), 1.68–1.56 (m, 1H), 1.56–1.38 (m, 3H), 1.25 (d, 6H, J=6.8 Hz); ESMS m/e: 535.1 (M+H)$^+$.

EXAMPLE 891

N-(3-{1-[6-(2-FLUOROPHENYL)-6-(2-METHOXYPHENOXY)HEXYL]-4-PIPERIDINYL}PHENYL)-2-METHYLPROPANAMIDE: Prepared by Procedure A and Scheme AN using 2-methoxyphenol and N-(3-[1-[6-(2-fluorophenyl)-6-hydroxyhexyl]-4-piperidinyl}phenyl)-2-methylpropanamide: ESMS m/e: 547.0 (M+H)$^+$.

EXAMPLE 892

N-(3-{1-[6-(2-FLUOROPHENYL)-6-(4-METHOXYPHENOXY)HEXYL]-4-PIPERIDINYL}PHENYL)-2-METHYLPROPANAMIDE: Prepared by Procedure A and Scheme AN using 4-methoxyphenol and N-(3-{1-[6-(2-fluorophenyl)-6-hydroxyhexyl]-4-piperidinyl}phenyl)-2-methylpropanamide: ESMS m/e: 547.1 (M+H)$^+$.

EXAMPLE 893

N-(3-{1-[6-(4-ACETYLPHENOXY)-6-(2-FLUOROPHENYL)HEXYL]-4-PIPERIDINYL)PHENYL)-2-METRYLPROPANAMIDE: Prepared by Procedure A and Scheme AN using 1-(4-hydroxyphenyl)ethanone and N-(3-{1-[6-(2-fluorophenyl)-6-hydroxyhexyl]-4-piperidinyl}phenyl)-2-methylpropanamide: ESMS m/e: 559.2 (M+H)$^+$.

EXAMPLE 894

N-(3-{1-(6-(3,4-DIMETHOXYPHENOXY)-6-(2-FLUOROPHENYL)HEXYL]-4-PIPERIDINYL)PRENYL)-2-METHYLPROPANAMIDE: Prepared by Procedure A and Scheme AN using 3,4-dimethoxyphenol and N-(3-{1-[6-(2-fluorophenyl)-6-hydroxyhexyl]-4-piperidinyl}phenyl)-2-methylpropanamide: ESMS m/e: 577.6 (M+H)$^+$.

EXAMPLE 895

N-(3-{1-[6-(2-ETHOXYPHENOXY)-6-(2-FLUOROPHENYL)HEXYL]-4-PIPERIDINYL}PHENYL)-2-METHYLPROPANAMIDE: Prepared by Procedure A and Scheme AN using 2-ethoxyphenol and N-(3-{1-[6-(2-fluorophenyl)-6-hydroxyhexyl]-4-piperidinyl}phenyl)-2-methylpropanamide: ESMS m/e: 561.1 (M+H)$^+$.

EXAMPLE 896

N-(3-{1-[6-(4-BROMOPHENOXY)-6-PHENYLHEXYL]-4-PIPERIDINYL}PHENYL)-2-METHYLPROPANAMIDE: Prepared by Procedure A and Scheme AN using 4-bromophenol and N-{3-[1-(6-hydroxy-6-phenylhexyl)-4-piperidinyl]phenyl}-2-methylpropanamide: ESMS m/e: 577.0 (M+H)$^+$.

EXAMPLE 897

N-(3-{1-[6-(4-FLUOROPHENOXY)-6-(4-FLUOROPHENYL)HEXYL]-4-PIPERIDINYL}PHENYL)-2-METHYLPROPANAMIDE: Prepared by Procedure A and Scheme AN using 4-fluorophenol and N-(3-{1-[6-(4-fluorophenyl)-6-hydroxyhexyl]-4-piperidinyl}phenyl)-2-methylpropanamide: $^1$H NMR (400 MHz, CDCl$_3$), HCl salt δ 8.22 (s, br, 1H), 7.74–6.70 (m, 12H), 5.05–4.94 (m, 1H), 3.66–3.52 (m, br, 2H), 3.02–2.83 (m, br, 2H), 2.81–2.58 (m, br, 4H), 2.58–2.36 (m, br, 2H), 2.02–1.66 (m, br, 6H), 1.66–1.46 (m, br, 1H), 1.46–1.35 (m, br, 3H), 1.26 (d, 6H, J=6.0 Hz); ESMS m/e: 535.1 (M+H)$^+$.

EXAMPLE 898

N-(3-{1-[6-(4-METHOXYPHENOXY)-6-PHENYLHEXYL]-4-PIPERIDINYL}PHENYL)-2-METHYLPROPANAMIDE: Prepared by Procedure A and Scheme AN using 4-methoxyphenol and N-{3-[1-(6-hydroxy-6-phenylhexyl)-4-piperidinyl]phenyl}-2-methylpropanamide: ESMS m/e: 529.6 (M+H)$^+$.

EXAMPLE 899

N-(3-{1-[6-(4-CHLOROPHENOXY)-6-(4-CHLOROPHENYL)HEXYL]-4-PIPERIDINYL}PHENYL)-2-METHYLPROPANAMIDE: Prepared by Procedure A and Scheme AN using 4-chlorophenol and N-(3-{1-[6-(4-chlorophenyl)-6-hydroxyhexyl]-4-piperidinyl}phenyl)-2-methylpropanamide: ESMS m/e: 566.9 (M+H)$^+$.

EXAMPLE 900

N-(3-{1-[6-(4-BROMOPHENOXY)-6-(4-FLUOROPHENYL)HEXYL]-4-PIPERIDINYL}PHENYL)-2-METHYLPROPANAMIDE: Prepared by Procedure A and Scheme AN using 4-bromophenol and N-(3-{1-[6-(4-fluorophenyl)-6-hydroxyhexyl]-4-piperidinyl}phenyl)-2-methylpropanamide: ESMS m/e: 595.0 (M+H)$^+$.

EXAMPLE 901

N-(3-{1-[6-(4-CHLOROPHENOXY)-6-(4-FLUOROPHENYL)HEXYL]-4-PIPERIDINYL}PHENYL)-2-METHYLPROPANAMIDE: Prepared by Procedure A and Scheme AN using 4-chlorophenol and N-(3-(1-[6-(4-fluorophenyl)-6-hydroxyhexyl]-4-piperidinyl}phenyl)-2-methylpropanamide: $^1$H NMR (400 MHz, CDCl$_3$), HCl salt δ 7.93 (s, 1H), 7.72–6.68 (m, 12H), 5.06–4.98 (m, 1H), 3.66–3.50 (m, br, 2H), 3.02–2.82 (m, br, 2H), 2.80–2.57 (m, br, 4H), 2.57–2.38 (m, br, 2H), 2.02–1.76 (m, br, 6H), 1.64–1.48 (m, br, 1H), 1.48–1.36 (m, br, 3H), 1.25 (d, 6H, J=6.8 Hz); Anal. Calc. for C$_{33}$H$_{41}$Cl$_2$FN$_2$O$_2$.0.5EtOAc: C, 66.55; H, 7.18; N, 4.43; Found: C, 66.35; H, 6.86; N, 4.46. ESMS m/e: 550.8 (M+H)$^+$.

EXAMPLE 902

N-(3-{1-[6-(4-CHLOROPHENYL)-6-(4-FLUOROPHENOXY)HEXYL]-4-

PIPERIDINYL}PHENYL)-2-METHYLPROPANAMIDE: Prepared by Procedure A and Scheme AN using 4-fluorophenol and N-(3-{1-[6-(4-chlorophenyl)-6-hydroxyhexyl]-4-piperidinyl}phenyl)-2-methylpropanamide: $^{1}$H NMR (400 MHz, CDCl$_{3}$), HCl salt δ 8.22 (s, br, 1H), 7.74–6.68 (m, 12H), 5.04–4.92 (m, 1H), 3.66–3.50 (m, br, 2H), 3.00–2.82 (br, 2H), 2.80–2.58 (m, br, 4H), 2.58–2.40 (m, br, 2H), 2.00–1.68 (m, br, 6H), 1.66–1.46 (m, br, 1H), 1.46–1.36 (br, 3H), 1.25 (d, 6H, J=7.2 Hz); ESMS m/e: 551.1 (M+H)$^{+}$.

EXAMPLE 903

N-(3-{1-[6-(3-ACETYLPHENOXY)-6-PHENYLHEXYL]-4-PIPERIDINYL}PHENYL)-2-METHYLPROPANAMIDE: Prepared by Procedure A and Scheme AN using 1-(3-hydroxyphenyl)ethanone and N-{3-[1-(6-hydroxy-6-phenylhexyl)-4-piperidinyl]phenyl}-2-methylpropanamide: ESMS m/e: 541.2 (M+H)$^{+}$.

EXAMPLE 904

N-(3-{1-[6-(4-CHLOROPHENOXY)-6-PHENYLHEXYL]-4-PIPERIDINYL}PHENYL)-2-METHYLPROPANAMIDE: Prepared by Procedure A and Scheme AN using 4-chlorophenol and N-{3-[1-(6-hydroxy-6-phenylhexyl)-4-piperidinyl]phenyl}-2-methylpropanamide: $^{1}$H NMR (400 MHz, CDCl$_{3}$), HCl salt δ 8.28 (s, 1H), 7.78–6.70 (m, 13H), 5.08–4.98 (m, 1H), 3.64–3.46 (m, br, 2H), 3.02–2.82 (br, 2H), 2.82–2.56 (m, br, 4H), 2.56–2.34 (m, br, 2H), 2.05–1.75 (m, br, 6H), 1.64–1.48 (m, br, 1H), 1.48–1.34 (br, 3H), 1.25 (d, 6H, J=6.8 Hz); ESMS m/e: 533.1 (M+H)$^{+}$.

EXAMPLE 905

N-(3-{1-[6-(4-BROMOPHENOXY)-6-(4-CHLOROPHENYL)HEXYL]-4-PIPERIDINYL}PHENYL)-2-METHYLPROPANAMIDE: Prepared by Procedure A and Scheme AN using 4-bromophenol and N-(3-{1-[6-(4-chlorophenyl)-6-hydroxyhexyl]-4-piperidinyl}phenyl)-2-methylpropanamide: ESMS m/e: 611.0 (M+H)$^{+}$.

EXAMPLE 906

N-(3-{1-[6-(4-CHLOROPHENYL)-6-(4-METHOXYPHENOXY)HEXYL]-4-PIPERIDINYL}PHENYL)-2-METHYLPROPANAMIDE: Prepared by Procedure A and Scheme AN using 4-methoxyphenol and N-(3-{1-[6-(4-chlorophenyl)-6-hydroxyhexyl]-4-piperidinyl}phenyl)-2-methylpropanamide: ESMS m/e: 563.1 (M+H)$^{+}$.

EXAMPLE 907

N-(3-{1-[6-(4-FLUOROPHENYL)-6-(4-METHOXYPHENOXY)HEXYL]-4-PIPERIDINYL}PHENYL)-2-METHYLPROPANAMIDE: Prepared by Procedure A and Scheme AN using 4-methoxyphenol and N-(3-{1-[6-(4-fluorophenyl)-6-hydroxyhexyl]-4-piperidinyl}phenyl)-2-methylpropanamide: $^{1}$H NMR (400 MHz, CDCl$_{3}$), HCl salt δ 8.11 (s, 1H), 7.65–6.84 (m, 12H), 5.21–5.10 (m, 1H), 3.66–3.56 (m, br, 2H), 3.02–2.82 (br, 2H), 2.82–2.56 (m, br, 4H), 2.54 (s, 3H), 2.53–2.32 (m, br, 2H), 2.02–1.70 (m, br, 6H), 1.64–1.48 (m, br, 1H), 1.48–1.34 (br, 3H), 1.25 (d, 6H, J=6.8 Hz); ESMS m/e: 547.1 (M+H)$^{+}$.

EXAMPLE 908

N-(3-{1-[6-(3-ACETYLPHENOXY)-6-(4-FLUOROPHENYL)HEXYL]-4-PIPERIDINYL}PHENYL)-2-METHYLPROPANAMIDE: Prepared by Procedure A and Scheme AN using 1-(3-hydroxyphenyl)ethanone and N-(3-{1-[6-(4-fluorophenyl)-6-hydroxyhexyl]-4-piperidinyl}phenyl)-2-methylpropanamide: ESMS m/e: 559.1 (M+H)$^{+}$.

EXAMPLE 909

N-(3-{1-[6-(4-FLUOROPHENOXY)-6-PHENYLHEXYL]-4-PIPERIDINYL}PHENYL)-2-METHYLPROPANAMIDE: Prepared by Procedure A and Scheme AN using 4-fluorophenol and N-{3-[1-(6-hydroxy-6-phenylhexyl)-4-piperidinyl]phenyl}-2-methylpropanamide: $^{1}$H NMR (400 MHz, CDCl$_{3}$), HCl salt δ 8.05 (s, br, 1H), 7.72–6.70 (m, 13H), 5.06–4.96 (m, 1H), 3.66–3.51 (m, 2H), 3.01–2.82 (m, br, 2H), 2.82–2.57 (m, br, 4H), 2.57–2.34 (m, br, 2H), 2.05–1.78 (m, br, 6H), 1.64–1.52 (m, br, 1H), 1.52–1.16 (m, br, 3H), 1.25 (d, 6H, J=7.2 Hz); ESMS m/e: 517.0 (M+H)$^{+}$.

EXAMPLE 910

N-(3-{1-[6-(2-ACETYLPHENOXY)-6-(2-FLUOROPHENYL)HEXYL]-4-PIPERIDINYL}PHENYL)-2-METHYLPROPANAMIDE: Prepared by Procedure A and Scheme AN using 1-(2-hydroxyphenyl)ethanone and N-(3-{1-[6-(2-fluorophenyl)-6-hydroxyhexyl]-4-piperidinyl}phenyl)-2-methylpropanamide: ESMS m/e: 559.0 (M+H)$^{+}$.

EXAMPLE 911

N-[3-(1-{6-(4-FLUOROPHENYL)-6-[2-FLUORO-5-(TRIFLUOROMETHYL)PHENOXY]HEXYL}-4-PIPERIDINYL)PHENYL]-2-METHYLPROPANAMIDE: Prepared by Procedure A and Scheme AN using 2-fluoro-5-(trifluoromethyl)phenol and N-(3-{1-[6-(4-fluorophenyl)-6-hydroxyhexyl]-4-piperidinyl}phenyl)-2-methylpropanamide: $^{1}$H NMR (400 MHz, CDCl$_{3}$), HCl salt δ 8.23 (s, br, 1H), 7.74–6.88 (m, 11H), 5.20–5.12 (m, 1H), 3.68–3.52 (m, br, 2H), 3.02–2.82 (m, br, 2H), 2.82–2.60 (m, 4H), 2.58–2.38 (m, br, 2H), 2.12–2.02 (m, br, 1H), 2.02–1.80 (m, br, 5H), 1.68–1.52 (m, br, 1H), 1.52–1.36 (br, 3H), 1.25 (d, 6H, J=7.2 Hz); ESMS m/e: 603.3 (M+H)$^{+}$.

EXAMPLE 912

N-(3-{1-[6-(3-ACETYLPHENOXY)-6-(4-CHLOROPHENYL)HEXYL]-4-PIPERIDINYL}PHENYL)-2-METHYLPROPANAMIDE: Prepared by Procedure A and Scheme AN using 1-(3-hydroxyphenyl)ethanone and N-(3-{1-[6-(4-chlorophenyl)-6-hydroxyhexyl]-4-piperidinyl}phenyl)-2-methylpropanamide: $^{1}$H NMR (400 MHz, CDCl$_{3}$), HCl salt δ 8.41 (s, 1H), 7.72–6.84 (m, 12H), 5.18–5.10 (m, 1H), 3.62–3.50 (m, br, 2H), 3.00–2.92 (m, 2H), 2.90–2.58 (m, 4H), 2.54 (s, 3H), 2.50–2.12 (m, 2H), 2.02–1.70 (m, br, 6H), 1.64–1.50 (m, br, 1H), 1.50–1.14 (m, br, 3H), 1.25 (d, 6H, J=6.8 Hz); ESMS m/e: 575.3 (M+H)$^{+}$.

EXAMPLE 913

N-[3-(1-{6-(2-FLUOROPHENYL)-6-[2-FLUORO-5-(TRIFLUOROMETHYL)PHENOXY]HEXYL}-4-PIPERIDINYL)PHENYL]-2-METHYLPROPANAMIDE: Prepared by Procedure A and Scheme AN using 2-fluoro-5-(trifluoromethyl)phenol and N-(3-(1-[6-(2-fluorophenyl)-6-hydroxyhexyl]-4-piperidinyl}phenyl)-2-methylpropanamide: $^{1}$H NMR (400 MHz, CDCl$_{3}$), HCl salt δ 8.35 (s, 1H), 7.68–6.82 (m, 11H), 5.58–5.48 (m, 1H), 3.64–3.50 (m, 2H), 3.01–2.94 (m, br, 2H), 2.92–2.54 (m, 4H), 2.48–2.32 (m, br, 2H), 2.20–2.04 (m, 1H), 2.01–1.80 (m, 5H), 1.70–1.54 (m, 1H), 1.54–1.36 (m, 3H), 1.25 (d, 6H, J=7.2 Hz). Anal. Calc. for $C_{34}H_{40}ClF_5N_2O_2 \cdot 0.6MeOH$: C, 63.12; H, 6.49; N, 4.25; Found: C, 63.38; H, 6.61; N, 3.95. ESMS m/e: 603.3 $(M+H)^+$.

EXAMPLE 914

N-[3-(1-{6-(4-CHLOROPHENYL)-6-[2-FLUORO-5-(TRIFLUOROMETHYL)PHENOXY]HEXYL}-4-PIPERIDINYL)PHENYL]-2-METHYLPROPANAMIDE: Prepared by Procedure A and Scheme AN using 2-fluoro-5-(trifluoromethyl)phenol and N-(3-{1-[6-(4-chlorophenyl)-6-hydroxyhexyl]-4-piperidinyl}phenyl)-2-methylpropanamide: ESMS m/e: 619.2 $(M+H)^+$.

EXAMPLE 915

N-[3-(1-{6-(3-FLUOROPHENYL)-6-[2-FLUORO-5-(TRIFLUOROMETHYL)PHENOXY]HEXYL}-4-PIPERIDINYL)PHENYL]-2-METHYLPROPANAMIDE: Prepared by Procedure A and Scheme AN using 2-fluoro-5-(trifluoromethyl)phenol and N-(3-{1-[6-(3-fluorophenyl)-6-hydroxyhexyl]-4-piperidinyl}phenyl)-2-methylpropanamide: ESMS m/e: 603.3 $(M+H)^+$.

EXAMPLE 916

N-[3-(1-{6-[2-FLUORO-5-(TRIFLUOROMETHYL)PHENOXY]-6-PHENYLHEXYL}-4-PIPERIDINYL)PHENYL]-2-METHYLPROPANAMIDE: Prepared by Procedure A and Scheme AN using 2-fluoro-5-(trifluoromethyl)phenol and N-{3-[1-(6-hydroxy-6-phenylhexyl)-4-piperidinyl]phenyl}-2-methylpropanamide: ESMS m/e: 585.3 $(M+H)^+$.

EXAMPLE 917

N-[3-(1-{7-(2-FLUOROPHENYL)-7-[2-FLUORO-5-(TRIFLUOROMETHYL)PHENOXY]HEPTYL}-4-PIPERIDINYL)PHENYL]-2-METHYLPROPANAMIDE: Prepared by Procedure A and Scheme AN using 2-fluoro-5-(trifluoromethyl)phenol and N-(3-{1-[7-(2-fluorophenyl)-7-hydroxyheptyl]-4-piperidinyl}phenyl)-2-methylpropanamide: ESMS m/e: 617.3 $(M+H)^+$.

EXAMPLE 918

N-(3-{1-[5-(4-FLUOROPHENYL)-5-(4-METHOXYPHENOXY)PENTYL]-4-PIPERIDINYL}PHENYL)-2-METHYLPROPANAMIDE: Prepared by Procedure A and Scheme AN using 4-methoxyphenol and N-(3-{1-[5-(4-fluorophenyl)-5-hydroxypentyl]-4-piperidinyl}phenyl)-2-methylpropanamide: ESMS m/e: 533.1 $(M+H)^+$.

EXAMPLE 919

N-(3-{1-[5-(4-BROMOPHENOXY)-5-(4-FLUOROPHENYL)PENTYL]-4-PIPERIDINYL}PHENYL)-2-METHYLPROPANAMIDE: Prepared by Procedure A and Scheme AN using 4-bromophenol and N-(3-{1-[5-(4-fluorophenyl)-5-hydroxypentyl]-4-piperidinyl}phenyl)-2-methylpropanamide: $^1$H NMR (400 MHz, $CDCl_3$), HCl salt δ 7.94 (s, br, 1H), 7.68–6.64 (m, 12H), 5.12–5.04 (m, 1H), 3.68–3.52 (m, br, 2H), 3.01–2.82 (br, 2H), 2.78–2.58 (m, br, 4H), 2.57–2.38 (m, br, 2H), 2.05–1.80 (m, br, 6H), 1.64–1.38 (m, br, 2H), 1.25 (d, 6H, J=7.2 Hz); ESMS m/e: 581.0 $(M+H)^+$.

EXAMPLE 920

N-(3-{1-[5-(4-CHLOROPHENOXY)-5-(4-CHLOROPHENYL)PENTYL]-4-PIPERIDINYL}PHENYL)-2-METHYLPROPANAMIDE: Prepared by Procedure A and Scheme AN using 4-chlorophenol and N-(3-{1-[5-(4-chlorophenyl)-5-hydroxypentyl]-4-piperidinyl}phenyl)-2-methylpropanamide: $^1$H NMR (400 MHz, $CDCl_3$), HCl salt δ 7.86 (s, br, 1H), 7.62–6.72 (m, 12H), 5.12–5.02 (m, 1H), 3.68–3.52 (m, br, 2H), 3.02–2.82 (br, 2H), 2.82–2.56 (m, br, 4H), 2.56–2.40 (m, br, 2H), 2.06–1.80 (m, br, 6H), 1.64–1.40 (m, br, 2H), 1.25 (d, 6H, J=6.8 Hz). Anal. Calc. for $C_{32}H_{39}Cl_3N_2O_2 \cdot 1.3MeOH$: C, 63.25; H, 7.07; N, 4.42; Found: C, 63.41; H, 6.99; N, 4.17. ESMS m/e: 553.0 $(M+H)^+$.

EXAMPLE 921

N-(3-{1-[5-(4-CHLOROPHENOXY)-5-PHENYLPENTYL]-4-PIPERIDINYL}PHENYL)-2-METHYLPROPANAMIDE: Prepared by Procedure A and Scheme AN using 4-chlorophenol and N-{3-[1-(5-hydroxy-5-phenylpentyl)-4-piperidinyl]phenyl}-2-methylpropanamide: $^1$H NMR (400 MHz, $CDCl_3$), HCl salt δ 7.72–6.72 (m, 13H), 5.12–5.04 (m, 1H), 3.66–3.52 (m, br, 2H), 3.01–2.83 (br, 2H), 2.68–2.62 (m, br, 2H), 2.62–2.48 (m, br, 4H), 2.04–1.82 (m, br, 6H), 1.62–1.40 (m, br, 2H), 1.25 (d, 6H, J=7.2 Hz); ESMS m/e: 519.1 $(M+H)^+$.

EXAMPLE 922

N-(3-{1-[5-(3-ACETYLPHENOXY)-5-(4-FLUOROPHENYL)PENTYL]-4-PIPERIDINYL}PHENYL)-2-METHYLPROPANAMIDE: Prepared by Procedure A and Scheme AN using 1-(3-hydroxyphenyl)ethanone and N-(3-{1-[5-(4-fluorophenyl)-5-hydroxypentyl]-4-piperidinyl}phenyl)-2-methylpropanamide: ESMS m/e: 545.1 $(M+H)^+$.

EXAMPLE 923

N-(3-{1-[5-(4-CHLOROPHENYL)-5-(4-FLUOROPHENOXY)PENTYL]-4-PIPERIDINYL}PHENYL)-2-METHYLPROPANAMIDE: Prepared by Procedure A and Scheme AN using 4-fluorophenol and N-(3-{1-[5-(4-chlorophenyl)-5-hydroxypentyl]-4-piperidinyl}phenyl)-2-methylpropanamide: $^1$H NMR (400 MHz, $CDCl_3$), HCl salt δ 8.05 (s, br, 1H), 7.74–6.68 (m, 12H), 5.08–4.99 (m, 1H), 3.67–3.56 (m, br, 2H), 3.02–2.82 (br, 2H), 2.80–2.57 (m, br, 4H), 2.57–2.38 (m, br, 2H), 2.05–1.80 (m, br, 6H), 1.64–1.40 (m, br, 2H), 1.25 (d, 6H, J=7.2 Hz). Anal. Calc. for $C_{32}H_{39}Cl_2FN_2O_2 \cdot 1.3EtOAc$: C, 64.93; H, 7.24; N, 4.07. Found: C, 65.01; H, 6.97; N, 3.85. ESMS m/e: 537.1 $(M+H)^+$.

EXAMPLE 924

N-(3-{1-[5-(4-BROMOPHENOXY)-5-PHENYLPENTYL]-4-PIPERIDINYL}PHENYL)-2-METHYLPROPANAMIDE: Prepared by Procedure A and Scheme AN using 4-bromophenol and N-{3-[1-(5-hydroxy-5-phenylpentyl)-4-piperidinyl]phenyl}-2-methylpropanamide: $^1$H NMR (400 MHz, $CDCl_3$), HCl salt δ 7.74–6.66 (m, 13H), 5.13–5.02 (m, 1H), 3.73–3.51 (m, br, 2H), 3.05–2.83 (br, 2H), 2.83–2.62 (br, 4H), 2.62–2.42 (m, br, 2H), 2.10–1.80 (m, br, 6H), 1.65–1.37 (m, br, 2H), 1.25 (d, 6H, J=6.8 Hz); ESMS m/e: 562.9 $(M+H)^+$.

EXAMPLE 925

N-(3-{1-[5-(4-CHLOROPHENYL)-5-(4-METHOXYPHENOXY)PENTYL]-4-

PIPERIDINYL}PHENYL)-2-METHYLPROPANAMIDE: Prepared by Procedure A and Scheme AN using 4-methoxyphenol and N-(3-{1-[5-(4-chlorophenyl)-5-hydroxypentyl]-4-piperidinyl}phenyl)-2-methylpropanamide: $^1$H NMR (400 MHz, CDCl$_3$), HCl salt δ 8.13 (s, br, 1H), 7.72–6.70 (m, 12H), 5.08–4.97 (m, 1H), 3.72 (s, 3H), 3.66–3.50 (m, br, 2H), 3.03–2.82 (br, 2H), 2.80–2.54 (m, br, 4H), 2.53–2.17 (m, br, 2H), 2.08–1.78 (m, br, 6H), 1.65–1.38 (m, br, 2H), 1.25 (d, 6H, J=6.8 Hz). Anal. Calc. for C$_{33}$H$_{42}$Cl$_2$N$_2$O$_3$.0.54CH$_2$Cl$_2$: C, 63.80; H, 6.88; N, 4.44. Found: C, 63.84; H, 7.18; N, 4.00. ESMS m/e: 549.1 (M+H)$^+$.

EXAMPLE 926

N-(3-{1-[5-(4-FLUOROPHENOXY)-5-(4-FLUOROPHENYL)PENTYL]-4-PIPERIDINYL}PHENYL)-2-METHYLPROPANAMIDE: Prepared by Procedure A and Scheme AN using 4-fluorophenol and N-(3-{1-[5-(4-fluorophenyl)-5-hydroxypentyl]-4-piperidinyl}phenyl)-2-methylpropanamide: $^1$H NMR (400 MHz, CDCl$_3$), HCl salt δ 7.62–6.70 (m, 12H), 5.10–5.00 (m, 1H), 3.71–3.56 (m, br, 2H), 3.04–2.82 (br, 2H), 2.78–2.64 (m, br, 3H), 2.64–2.48 (m, br, 3H), 2.05–1.82 (m, br, 6H), 1.62–1.42 (m, br, 2H), 1.25 (d, 6H, J=6.0 Hz); ESMS m/e: 521.2 (M+H)$^+$.

EXAMPLE 927

N-(3-{1-[5-(3-ACETYLPHENOXY)-5-PHENYLPENTYL]-4-PIPERIDINYL}PHENYL)-2-METHYLPROPANAMIDE: Prepared by Procedure A and Scheme AN using 1-(3-hydroxyphenyl)ethanone and N-{3-[1-(5-hydroxy-5-phenylpentyl)-4-piperidinyl]phenyl}-2-methylpropanamide: ESMS m/e: 526.9 (M+H)$^+$.

EXAMPLE 928

N-(3-{1-[5-(4-METHOXYPHENOXY)-5-PHENYLPENTYL]-4-PIPERIDINYL}PHENYL)-2-METHYLPROPANAMIDE: Prepared by Procedure A and Scheme AN using 4-methoxyphenol and N-{3-[1-(5-hydroxy-5-phenylpentyl)-4-piperidinyl]phenyl}-2-methylpropanamide: ESMS m/e: 515.6 (M+H)$^+$.

EXAMPLE 929

N-[3-(1-{5-[2-FLUORO-5-(TRIFLUOROMETHYL)PHENOXY]-5-[4-(TRIFLUOROMETHYL)PHENYL]PENTYL}-4-PIPERIDINYL)PHENYL]-2-METHYLPROPANAMIDE: Prepared by Procedure A and Scheme AN using 2-fluoro-5-(trifluoromethyl)phenol and N-[3-(1-{5-hydroxy-5-[4-(trifluoromethyl)phenyl]pentyl}-4-piperidinyl)phenyl]-2-methylpropanamide: ESMS m/e: 639.2 (M+H)$^+$.

EXAMPLE 930

N-[3-(1-{5-(3-CHLOROPHENYL)-5-[2-FLUORO-5-(TRIFLUOROMETHYL)PHENOXY]PENTYL}-4-PIPERIDINYL)PHENYL]-2-METHYLPROPANAMIDE: Prepared by Procedure A and Scheme AN using 2-fluoro-5-(trifluoromethyl)phenol and N-(3-{1-[5-(3-chlorophenyl)-5-hydroxypentyl]-4-piperidinyl}phenyl)-2-methylpropanamide: $^1$H NMR (400 MHz, CDCl$_3$), HCl salt δ 8.17 (s, br, 1H), 7.75–6.88 (m, 11H), 5.26–5.14 (m, 1H), 3.68–3.56 (m, br, 2H), 3.05–2.90 (br, 2H), 2.90–2.60 (m, br, 4H), 2.56–2.36 (m, br, 2H), 2.18–1.84 (m, br, 6H), 1.70–1.44 (m, br, 2H), 1.25 (d, 6H, J=7.2 Hz). Anal. Calc. for C$_{33}$H$_{38}$Cl$_2$F$_4$N$_2$O$_2$.0.9EtOAc: C, 60.98; H, 6.32; N, 3.89; Found: C, 60.99; H, 6.17; N, 3.81. ESMS m/e: 605.2 (M+H)$^+$.

EXAMPLE 931

N-[3-(1-{5-(2-FLUOROPHENYL)-5-[2-FLUORO-5-(TRIFLUOROMETHYL)PHENOXY]PENTYL}-4-PIPERIDINYL)PHENYL]-2-METHYLPROPANAMIDE: Prepared by Procedure A and Scheme AN using 2-fluoro-5-(trifluoromethyl)phenol and N-(3-{1-[5-(2-fluorophenyl)-5-hydroxypentyl]-4-piperidinyl}phenyl)-2-methylpropanamide: $^1$H NMR (400 MHz, CDCl$_3$), HCl salt δ 7.89 (s, br, 1H), 7.72–6.88 (m, 11H), 5.59–5.48 (m, 1H), 3.70–3.48 (br, 2H), 3.05–2.84 (br, 2H), 2.82–2.58 (m, br, 4H), 2.58–2.40 (m, br, 2H), 2.22–1.82 (m, br, 6H), 1.71–1.42 (m, br, 2H), 1.25 (d, 6H, J=6.4 Hz); ESMS m/e: 589.3 (M+H)$^+$.

EXAMPLE 932

N-[3-(1-{5-(3-FLUOROPHENYL)-5-[2-FLUORO-5-(TRIFLUOROMETHYL)PHENOXY]PENTYL}-4-PIPERIDINYL)PHENYL]-2-METHYLPROPANAMIDE: Prepared by Procedure A and Scheme AN using 2-fluoro-5-(trifluoromethyl)phenol and N-(3-{1-[5-(3-fluorophenyl)-5-hydroxypentyl]-4-piperidinyl}phenyl)-2-methylpropanamide: $^1$H NMR (400 MHz, CDCl$_3$), HCl salt δ 7.79 (s, br, 1H), 7.63–6.82 (m, 11H), 5.24–5.15 (m, 1H), 3.70–3.56 (br, 2H), 3.04–2.84 (br, 2H), 2.82–2.60 (m, br, 4H), 2.60–2.42 (m, br, 2H), 2.20–1.83 (m, br, 6H), 1.70–1.44 (m, br, 2H), 1.25 (d, 6H, J=6.4 Hz); ESMS m/e: 589.3 (M+H)$^+$.

EXAMPLE 933

N-(3-{1-[5-(3-ACETYLPHENOXY)-5-(4-CHLOROPHENYL)PENTYL]-4-PIPERIDINYL}PHENYL)-2-METHYLPROPANAMIDE: Prepared by Procedure A and Scheme AN using 1-(3-hydroxyphenyl)ethanone and N-(3-{1-[5-(4-chlorophenyl)-5-hydroxypentyl]-4-piperidinyl}phenyl)-2-methylpropanamide: $^1$H NMR (400 MHz, CDCl$_3$), HCl salt δ 8.05 (s, br, 1H), 7.74–6.88 (m, 12H), 5.27–5.16 (m, 1H), 3.69–3.52 (m, br, 2H), 3.10–2.81 (br, 2H), 2.81–2.57 (m, br, 4H), 2.54 (s, 3H), 2.52–2.40 (m, br, 2H), 2.05–1.80 (m, br, 6H), 1.66–1.42 (m, br, 2H), 1.25 (d, 6H, J=6.8 Hz); Anal. Calc. for C$_{34}$H$_{42}$Cl$_2$N$_2$O$_3$.0.5CH$_2$Cl$_2$.1.0H$_2$O: C, 63.46; H, 6.91; N, 4.30. Found: C, 63.46; H, 7.09; N, 4.00. ESMS m/e: 561.1 (M+H)$^+$.

EXAMPLE 934

N-[3-(1-{5-(4-CHLOROPHENYL)-5-[2-FLUORO-5-(TRIFLUOROMETHYL)PHENOXY]PENTYL}-4-PIPERIDINYL)PHENYL]-2-METHYLPROPANAMIDE: Prepared by Procedure A and Scheme AN using 2-fluoro-5-(trifluoromethyl)phenol and N-(3-{1-[5-(4-chlorophenyl)-5-hydroxypentyl]-4-piperidinyl}phenyl)-2-methylpropanamide: $^1$H NMR (400 MHz, CDCl$_3$), HCl salt δ 7.61–6.92 (m, 11H), 5.24–5.16 (m, 1H), 3.70–3.58 (m, 2H), 3.02–2.91 (br, 2H), 2.80–2.64 (m, br, 3H), 2.64–2.50 (m, 3H), 2.18–1.94 (m, br, 6H), 1.62–1.44 (m, br, 2H), 1.25 (d, 6H, J=7.2 Hz); ESMS m/e: 605.3 (M+H)$^+$.

EXAMPLE 935

N-[3-(1-{5-(4-FLUOROPHENYL)-5-[2-FLUORO-5-(TRIFLUOROMETHYL)PHENOXY]PENTYL}-4-PIPERIDINYL)PHENYL]-2-METHYLPROPANAMIDE: Prepared by Procedure A and Scheme AN using 2-fluoro-5-(trifluoromethyl)phenol N-(3-{1-[5-(4-fluorophenyl)-5-hydroxypentyl]-4-piperidinyl}phenyl)-2-methylpropanamide: ESMS m/e: 589.3 (M+H)$^+$.

EXAMPLE 936

N-(3-{1-[5-(4-BROMOPHENOXY)-5-(4-CHLOROPHENYL)PENTYL]-4-PIPERIDINYL}PHENYL)-2-METHYLPROPANAMIDE: Prepared by Procedure A and Scheme AN using 4-bromophenol and N-(3-{1-[5-(4-chlorophenyl)-5-hydroxypentyl]-4-piperidinyl}phenyl)-2-methylpropanamide: ESMS m/e: 597.2 (M+H)$^+$.

EXAMPLE 937

N-(3-{1-[5-(4-CHLOROPHENOXY)-5-(4-FLUOROPHENYL)PENTYL]-4-PIPERIDINYL}PHENYL)-2-METHYLPROPANAMIDE: Prepared by Procedure A and Scheme AN using 4-chlorophenol and N-(3-{1-[5-(4-fluorophenyl)-5-hydroxypentyl]-4-piperidinyl}phenyl)-2-methylpropanamide: ESMS m/e: 537.3 (M+H)$^+$.

EXAMPLE 938

N-(3-{1-[5-(2-ACETYLPHENOXY)-5-PHENYLPENTYL]-4-PIPERIDINYL}PHENYL)-2-METHYLPROPANAMIDE: Prepared by Procedure A and Scheme AN using 1-(2-hydroxyphenyl)ethanone and N-{3-[1-(5-hydroxy-5-phenylpentyl)-4-piperidinyl]phenyl}-2-methylpropanamide: ESMS m/e: 527.0 (M+H)$^+$.

EXAMPLE 939

N-(3-{1-[5-(2-ETHOXYPHENOXY)-5-PHENYLPENTYL]-4-PIPERIDINYL}PHENYL)-2-METHYLPROPANAMIDE: Prepared by Procedure A and Scheme AN using 2-ethoxyphenol and N-{3-[1-(5-hydroxy-5-phenylpentyl)-4-piperidinyl]phenyl}-2-methylpropanamide: ESMS m/e: 529.2 (M+H)$^+$.

EXAMPLE 940

N-(3-{1-[5-(4-FLUOROPHENOXY)-5-PHENYLPENTYL]-4-PIPERIDINYL}PHENYL)-2-METHYLPROPANAMIDE: Prepared by Procedure A and Scheme AN using 4-fluorophenol and N-{3-[1-(5-hydroxy-5-phenylpentyl)-4-piperidinyl]phenyl}-2-methylpropanamide: ESMS m/e: 503.2 (M+H)$^+$.

EXAMPLE 941

N-(3-{1-[4-(4-FLUOROPHENYL)-4-OXOBUTYL]-4-PIPERIDINYL}PHENYL)-2-METHYLPROPANAMIDE: Prepared by Procedure K (KI) and Scheme E (K$_2$CO$_3$) using 2-methyl-N-[3-(4-piperidinyl)phenyl]propanamide and 4-chloro-1-(4-fluorophenyl)-1-butanone: ESMS m/e: 411.2 (M+H)$^+$.

EXAMPLE 942

2-METHYL-N-(3-{1-[3-(1H-PYRROL-3-YL)PROPYL]-4-PIPERIDINYL}PHENYL)PROPANAMIDE: Prepared by Procedure K (KI) and Scheme E (K$_2$CO$_3$) using 2-methyl-N-[3-(4-piperidinyl)phenyl]propanamide and 3-(3-bromopropyl)-1H-pyrrole: ESMS m/e: 354.2 (M+H)$^+$.

EXAMPLE 943

N-(3-{1-[4-(4-ISOPROPYLPHENYL)-4-OXOBUTYL]-4-PIPERIDINYL}PHENYL)-2-METHYLPROPANAMIDE: Prepared by Procedure K (KI) and Scheme E (K$_2$CO$_3$) using 2-methyl-N-[3-(4-piperidinyl)phenyl]propanamide and 4-chloro-1-(4-isopropylphenyl)-1-butanone: ESMS m/e: 435.2 (M+H)$^+$.

EXAMPLE 944

N-(3-{1-[4-(4-METHOXYPHENYL)-4-OXOBUTYL]-4-PIPERIDINYL}PHENYL)-2-METHYLPROPANAMIDE: Prepared by Procedure K (KI) and Scheme E (K$_2$CO$_3$) using 2-methyl-N-[3-(4-piperidinyl)phenyl]propanamide and 4-chloro-1-(4-methoxyphenyl)-1-butanone: ESMS m/e:423.2 (M+H)$^+$.

EXAMPLE 945

2-METHYL-N-(3-{1-[4-(4-METHYLPHENYL)-4-OXOBUTYL]-4-PIPERIDINYL}PHENYL)PROPANAMIDE: Prepared by Procedure K (KI) and Scheme E (K$_2$CO$_3$) using 2-methyl-N-[3-(4-piperidinyl)phenyl]propanamide and 4-chloro-1-(4-methylphenyl)-1-butanone: ESMS m/e: 407.2 (M+H)$^+$.

EXAMPLE 946

N-(3-{1-[4-(4-TERT-BUTYLPHENYL)-4-OXOBUTYL]-4-PIPERIDINYL}PHENYL)-2-METHYLPROPANAMIDE: Prepared by Procedure K (KI) and Scheme E (K$_2$CO$_3$) using 2-methyl-N-[3-(4-piperidinyl)phenyl]propanamide and 1-(4-tert-butylphenyl)-4-chloro-1-butanone: ESMS m/e: 449.2 (M+H)$^+$.

EXAMPLE 947

N-(3-{1-[4-(4-BROMOPHENYL)-4-OXOBUTYL]-4-PIPERIDINYL}PHENYL)-2-METHYLPROPANAMIDE: Prepared by Procedure K (KI) and Scheme E (K$_2$CO$_3$) using 2-methyl-N-[3-(4-piperidinyl)phenyl]propanamide and 1-(4-bromophenyl)-4-chloro-1-butanone: ESMS m/e: 471.3 (M+H)$^+$.

EXAMPLE 948

2-METHYL-N-(3-{1-[4-OXO-4-(2-THIENYL)BUTYL]-4-PIPERIDINYL}PHENYL)PROPANAMIDE: Prepared by Procedure K (KI) and Scheme E (K$_2$CO$_3$) using 2-methyl-N-[3-(4-piperidinyl)phenyl]propanamide and 4-chloro-1-(2-thienyl)-1-butanone: ESMS m/e: 399.1 (M+H)$^+$.

II. Synthetic Methods for General Structures

The examples described in Section I are merely illustrative of the methods used to synthesize MCH1 antagonists. Further derivatives may be obtained utilizing generalized methods based on the synthetic methods used to synthesize the examples.

It may be necessary to incorporate protection and deprotection strategies for substituents such as amino, amido, carboxylic acid, and hydroxyl groups in the generalized synthetic methods to form further derivatives. Methods for protection and deprotection of such groups are well-known in the art, and may be found, for example in Green, T. W. and Wuts, P. G. M. (1991) *Protection Groups in Organic Synthesis*, 2$^{nd}$ Edition John Wiley & Sons, New York.

III. Oral Compositions

As a specific embodiment of an oral composition of a compound of this invention, 100 mg of one of the compounds described herein is formulated with sufficient finely divided lactose to provide a total amount of 580 to 590 mg to fill a size O hard gel capsule.

IV. Pharmacological Evaluation of Compounds at Cloned Rat MCH1 Receptor

The pharmacological properties of the compounds of the present invention were evaluated at the cloned rat MCH1 receptor using protocols described below.

Host Cells

A broad variety of host cells can be used to study heterologously expressed proteins. These cells include but are not restricted to assorted mammalian lines such as: Cos-7, CHO, LM(tk-), HEK293, Peak rapid 293, etc.; insect cell lines such as: Sf9, Sf21, etc.; amphibian cells such as xenopus oocytes; and others.

COS 7 cells are grown on 150 mm plates in DMEM with supplements (Dulbecco's Modified Eagle Medium with 10% bovine calf serum, 4 mM glutamine, 100 units/ml penicillin/100 Fg/ml streptomycin) at 37° C., 5% $CO_2$. Stock plates of COS-7 cells are trypsinized and split 1:6 every 3–4 days.

Human embryonic kidney 293 cells are grown on 150 mm plates in DMEM with supplements (10% bovine calf serum, 4 mM glutamine, 100 units/ml penicillin/100 Fg/ml streptomycin) at 37° C., 5% $CO_2$. Stock plates of 293 cells are trypsinized and split 1:6 every 3–4 days.

Human embryonic kidney Peak rapid 293 (Peakr293) cells are grown on 150 mm plates in DMEM with supplements (10% fetal bovine serum, 10% L-glutamine, 50 Fg/ml gentamycin) at 37° C., 5% $CO_2$. Stock plates of Peak rapid 293 cells are trypsinized and split 1:12 every 3–4 days. Mouse fibroblast LM(tk-) cells are grown on 150 mm plates in DMEM with supplements (Dulbecco's Modified Eagle Medium with 10% bovine calf serum, 4 mM glutamine, 100 units/ml penicillin/100 Fg/ml streptomycin) at 37° C., 5% $CO_2$. Stock plates of LM(tk-) cells are trypsinized and split 1:10 every 3–4 days.

Chinese hamster ovary (CHO) cells were grown on 150 mm plates in HAM's F-12 medium with supplements (10% bovine calf serum, 4 mM L-glutamine and 100 units/ml penicillin/100 Fg/ml streptomycin) at 37° C., 5% $CO_2$. Stock plates of CHO cells are trypsinized and split 1:8 every 3–4 days.

Mouse embryonic fibroblast NIH-3T3 cells are grown on 150 mm plates in Dulbecco's Modified Eagle Medium (DMEM) with supplements (10% bovine calf serum, 4 mM glutamine, 100 units/ml penicillin/100 Fg/ml streptomycin) at 37° C., 5% $CO_2$. Stock plates of NIH-3T3 cells are trypsinized and split 1:15 every 3–4 days.

Sf9 and Sf21 cells are grown in monolayers on 150 mm tissue culture dishes in TMN-FH media supplemented with 10% fetal calf serum, at 27° C., no $CO_2$. High Five insect cells are grown on 150 mm tissue culture dishes in Ex-Cell 400™ medium supplemented with L-Glutamine, also at 27° C., no $CO_2$.

In some cases, cell lines that grow as adherent monolayers can be converted to suspension culture to increase cell yield and provide large batches of uniform assay material for routine receptor screening projects.

Transient Expression

DNA encoding proteins to be studied can be transiently expressed in a variety of mammalian, insect, amphibian and other cell lines by several methods including but not restricted to; calcium phosphate-mediated, DEAE-dextran mediated, Liposomal-mediated, viral-mediated, electroporation-mediated and microinjection delivery.

Each of these methods may require optimization of assorted experimental parameters depending on the DNA, cell line, and the type of assay to be subsequently employed.

A typical protocol for the calcium phosphate method as applied to Peak rapid 293 cells is described as follows:

Adherent cells are harvested approximately twenty-four hours before transfection and replated at a density of 3.5× $10^6$ cells/dish in a 150 mm tissue culture dish and allowed to incubate over night at 37° C. at 5% $CO_2$. 250 Fl of a mixture of $CaCl_2$ and DNA (15 Fg DNA in 250 mM $CaCl_2$) is added to a 5 ml plastic tube and 500 Fl of 2×HBS (280 mM NaCl, 10 mM KCl, 1.5 mM $Na_2HPO_4$, 12 mM dextrose, 50 mM HEPES) is slowly added with gentle mixing. The mixture is allowed to incubate for 20 minutes at room temperature to allow a DNA precipitate to form. The DNA precipitate mixture is then added to the culture medium in each plate and incubated for 5 hours at 37° C., 5% $CO_2$. After the incubation, 5 ml of culture medium (DMEM, 10% FBS, 10% L-glut and 50 $\mu$g/ml gentamycin) is added to each plate. The cells are then incubated for 24 to 48 hours at 37° C., 5% $CO_2$.

A typical protocol for the DEAE-dextran method as applied to Cos-7 cells is described as follows; Cells to be used for transfection are split 24 hours prior to the transfection to provide flasks which are 70–80% confluent at the time of transfection. Briefly, 8 Fg of receptor DNA plus 8 Fg of any additional DNA needed (e.g. $G_\alpha$ protein expression vector, reporter construct, antibiotic resistance marker, mock vector, etc.) are added to 9 ml of complete DMEM plus DEAE-dextran mixture (10 mg/ml in PBS). Cos-7 cells plated into a T225 flask (sub-confluent) are washed once with PBS and the DNA mixture is added to each flask. The cells are allowed to incubate for 30 minutes at 37° C., 5% $CO_2$. Following the incubation, 36 ml of complete DMEM with 80 FM chloroquine is added to each flask and allowed to incubate an additional 3 hours. The medium is then aspirated and 24 ml of complete medium containing 10% DMSO for exactly 2 minutes and then aspirated. The cells are then washed 2 times with PBS and 30 ml of complete DMEM added to each flask. The cells are then allowed to incubate over night. The next day the cells are harvested by trypsinization and reseeded as needed depending upon the type of assay to be performed.

A typical protocol for liposomal-mediated transfection as applied to CHO cells is described as follows; Cells to be used for transfection are split 24 hours prior to the transfection to provide flasks which are 70–80% confluent at the time of transfection. A total of 10 Fg of DNA which may include varying ratios of receptor DNA plus any additional DNA needed (e.g. $G_\alpha$ protein expression vector, reporter construct, antibiotic resistance marker, mock vector, etc.) is used to transfect each 75 $cm^2$ flask of cells. Liposomal mediated transfection is carried out according to the manufacturer's recommendations (LipofectAMINE, GibcoBRL, Bethesda, Md.). Transfected cells are harvested 24 hours post transfection and used or reseeded according the requirements of the assay to be employed.

A typical protocol for the electroporation method as applied to Cos-7 cells is described as follows; Cells to be used for transfection are split 24 hours prior to the transfection to provide flasks which are subconfluent at the time of transfection. The cells are harvested by trypsinization resuspended in their growth media and counted. 4×$10^6$ cells are suspended in 300 Fl of DMEM and placed into an electroporation cuvette. 8 Fg of receptor DNA plus 8 Fg of any additional DNA needed (e.g. $G_\alpha$ protein expression vector, reporter construct, antibiotic resistance marker, mock vector, etc.) is added to the cell suspension, the cuvette is placed into a BioRad Gene Pulser and subjected to an electrical pulse (Gene Pulser settings: 0.25 kV voltage, 950 FF capacitance). Following the pulse, 800 Fl of complete DMEM is added to each cuvette and the suspension transferred to a sterile tube. Complete medium is added to each tube to bring the final cell concentration to $1\times10^5$ cells/100 Fl. The cells are then plated as needed depending upon the type of assay to be performed.

A typical protocol for viral mediated expression of heterologous proteins is described as follows for baculovirus infection of insect Sf9 cells. The coding region of DNA encoding the receptor disclosed herein may be subcloned into pBlueBacIII into existing restriction sites or sites engineered into sequences 5' and 3' to the coding region of the polypeptides. To generate baculovirus, 0.5 Fg of viral DNA (BaculoGold) and 3 Fg of DNA construct encoding a polypeptide may be co-transfected into $2\times10^6$ Spodoptera frugiperda insect Sf9 cells by the calcium phosphate co-precipitation method, as outlined in by Pharmingen (in "Baculovirus Expression Vector System: Procedures and Methods Manual"). The cells then are incubated for 5 days at 27° C. The supernatant of the co-transfection plate may be collected by centrifugation and the recombinant virus plaque purified. The procedure to infect cells with virus, to prepare stocks of virus and to titer the virus stocks are as described in Pharmingen's manual. Similar principals would in general apply to mammalian cell expression via retro-viruses, Simliki forest virus and double stranded DNA viruses such as adeno-, herpes-, and vacinia-viruses, and the like.

Stable Expression

Heterologous DNA can be stably incorporated into host cells, causing the cell to perpetually express a foreign protein. Methods for the delivery of the DNA into the cell are similar to those described above for transient expression but require the co-transfection of an ancillary gene to confer drug resistance on the targeted host cell. The ensuing drug resistance can be exploited to select and maintain cells that have taken up the heterologous DNA. An assortment of resistance genes are available including but not restricted to Neomycin, Kanamycin, and Hygromycin. For the purposes of receptor studies, stable expression of a heterologous receptor protein is carried out in, but not necessarily restricted to, mammalian cells including, CHO, HEK293, LM(tk-), etc.

Cell Membrane Preparation

For binding assays, pellets of transfected cells are suspended in ice-cold buffer (20 mM Tris.HCl, 5 mM EDTA, pH 7.4) and homogenized by sonication for 7 sec. The cell lysates are centrifuged at 200×g for 5 min at 4° C. The supernatants are then centrifuged at 40,000×g for 20 min at 4° C. The resulting pellets are washed once in the homogenization buffer and suspended in binding buffer (see methods for radioligand binding). Protein concentrations are determined by the method of Bradford (1976) using bovine serum albumin as the standard. Binding assays are usually performed immediately, however it is possible to prepare membranes in batch and store frozen in liquid nitrogen for future use.

Radioligand Binding Assays

Radioligand binding assays for the rat MCH1 receptor were carried out using plasmid pcDNA3.1-rMCH1-f (ATCC Patent Deposit Designation No. PTA-3505). Plasmid pcDNA3.1-rMCH1-f comprises the regulatory elements necessary for expression of DNA in a mammalian cell operatively linked to DNA encoding the rat MCH1 receptor so as to permit expression thereof. Plasmid pcDNA3.1-rMCH1-f was deposited on Jul. 5, 2001, with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure and was accorded ATCC Patent Deposit Designation No. PTA-3505.

Binding assays can also be performed as described hereinafter using plasmid pEXJ.HR-TL231 (ATCC Accession No. 203197) Plasmid pEXJ.HR-TL231 encodes the human MCH1 receptor and was deposited on Sep. 17, 1998, with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure and was accorded ATCC Accession No. 203197.

Human embryonic kidney Peak rapid 293 cells (Peakr293 cells) were transiently transfected with DNA encoding the MCH1 receptor utilizing the calcium phosphate method and cell membranes were prepared as described above. Binding experiments with membranes from Peakr293 cells transfected with the rat MCH1 receptor were performed with 0.08 nM [$^3$H] Compound A (the synthesis of Compound A is described in detail below) using an incubation buffer consisting of 50 mM Tris pH 7.4, 10 mM $MgCl_2$, 0.16 mM PMSF, 1 mM 1,10 phenantroline and 0.2% BSA. Binding was performed at 25° C. for 90 minutes. Incubations were terminated by rapid vacuum filtration over GF/C glass fiber filters, presoaked in 5% PEI using 50 nM Tris pH 7.4 as wash buffer. In all experiments, nonspecific binding is defined using 10 pM Compound A.

Functional Assays

Cells may be screened for the presence of endogenous mammalian receptor using functional assays. Cells with no or a low level of endogenous receptor present may be transfected with the exogenous receptor for use in functional assays.

A wide spectrum of assays can be employed to screen for receptor activation. These range from traditional measurements of phosphatidyl inositol, cAMP, $Ca^{++}$, and $K^+$, for example; to systems measuring these same second messengers but which have been modified or adapted to be higher throughput, more generic, and more sensitive; to cell based platforms reporting more general cellular events resulting from receptor activation such as metabolic changes, differentiation, and cell division/proliferation, for example; to high level organism assays which monitor complex physiological or behavioral changes thought to be involved with receptor activation including cardiovascular, analgesic, orexigenic, anxiolytic, and sedation effects, for example.

Radioligand Binding Assay Results

The compounds described above were assayed using cloned rat MCH1. The binding affinities of the compounds are shown in Table I.

| EXAMPLE No. | STRUCTURE | Ki (nM) rMCH1 |
|---|---|---|
| 1 | 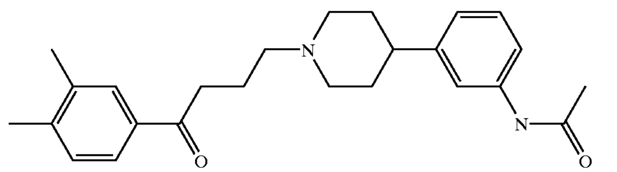 | 90 |
| 2 | 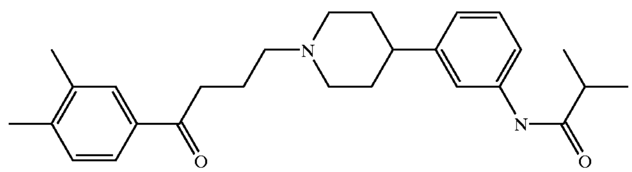 | 3.9 |
| 3 | 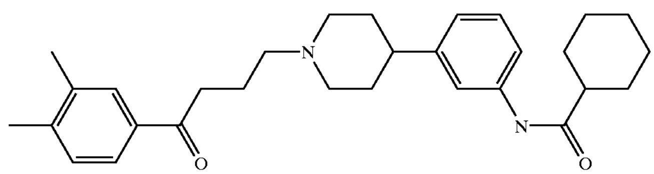 | 768 |
| 4 | 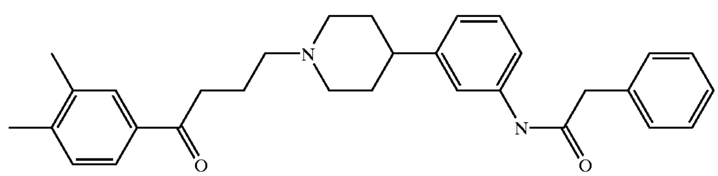 | 357 |
| 5 | 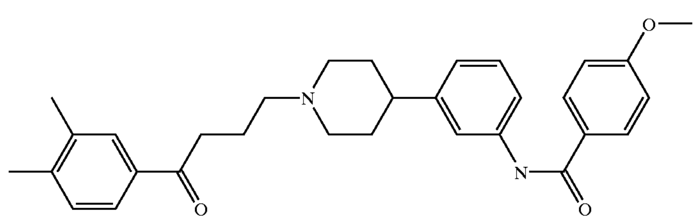 | 14.2 |
| 6 | 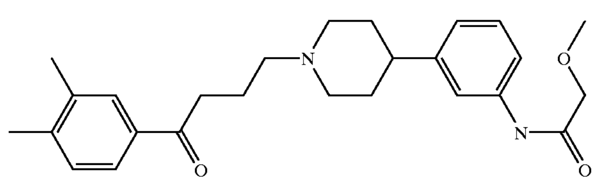 | 274 |
| 7 | 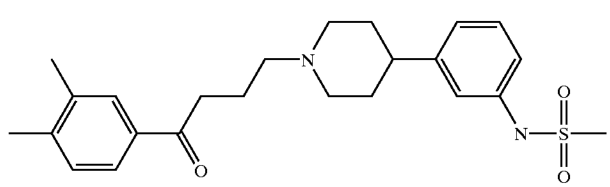 | 1000 |
| 8 | 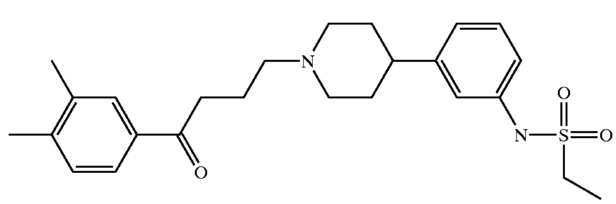 | 627 |

| | | |
|---|---|---|
| | -continued | |
| 9 | | 69 |
| 10 | | 2.8 |
| 11 | | 197 |
| 12 | | 84 |
| 13 | | 11.9 |
| 14 | | 167 |
| 15 | | 720 |
| 16 | | 272 |
| 17 | | 342 |

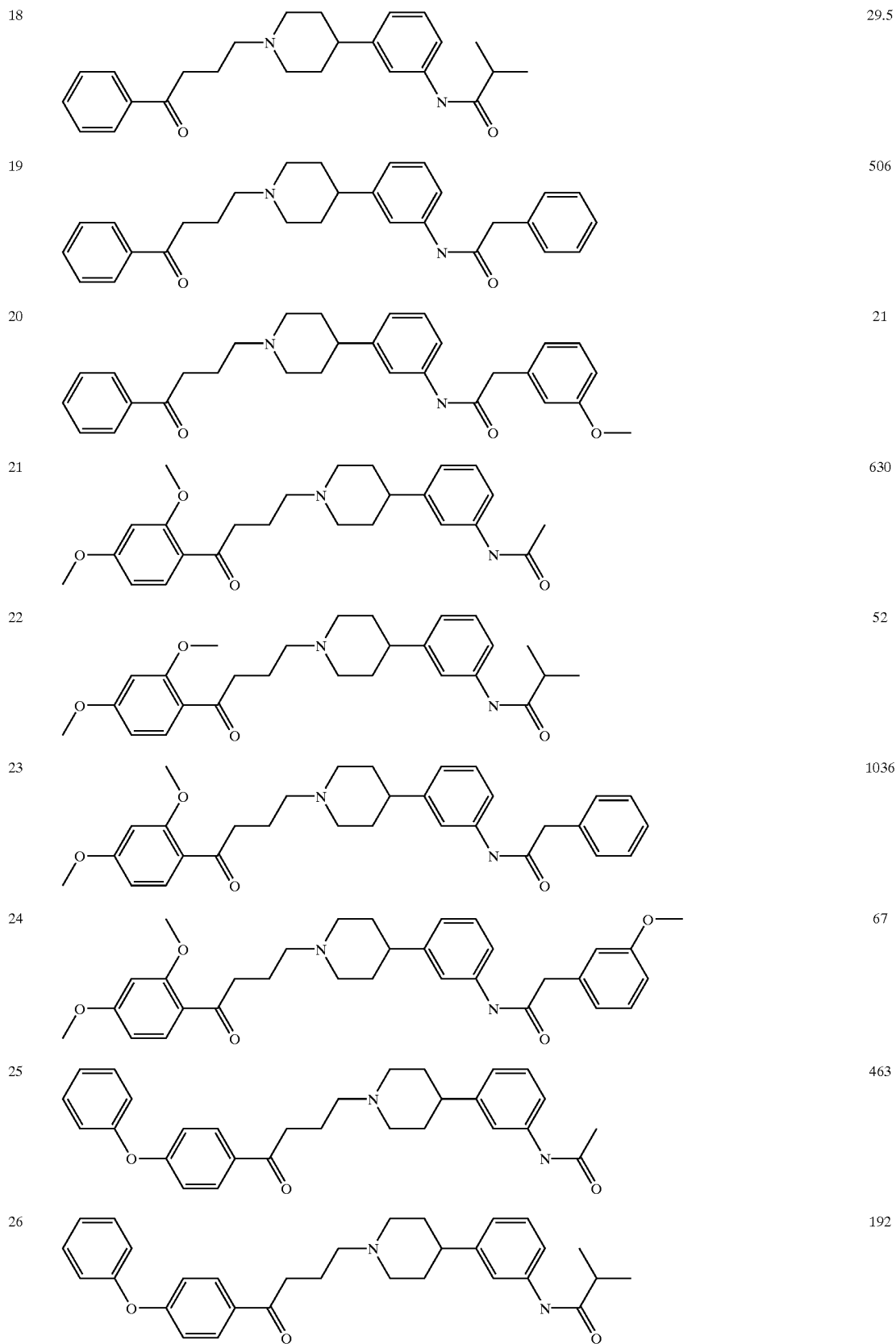

-continued
| | | |
|---|---|---|
| 27 | 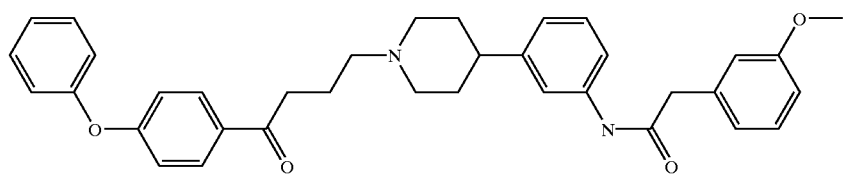 | 91 |
| 28 | 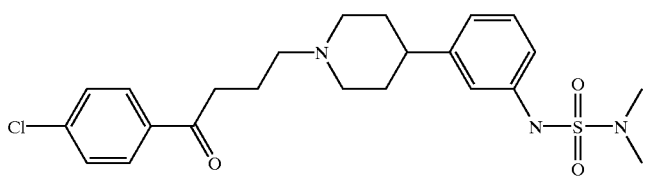 | 511 |
| 29 | 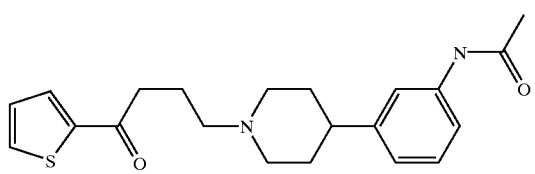 | 654 |
| 30 | 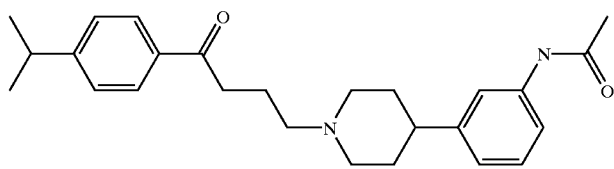 | 382 |
| 31 | 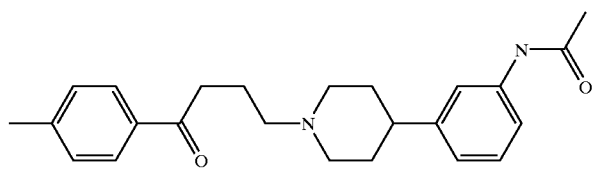 | 362 |
| 32 | 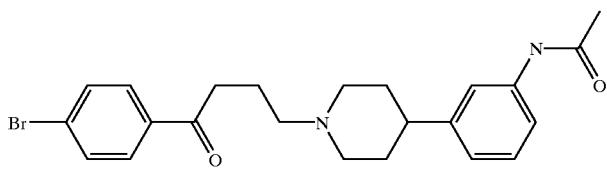 | 160 |
| 33 | 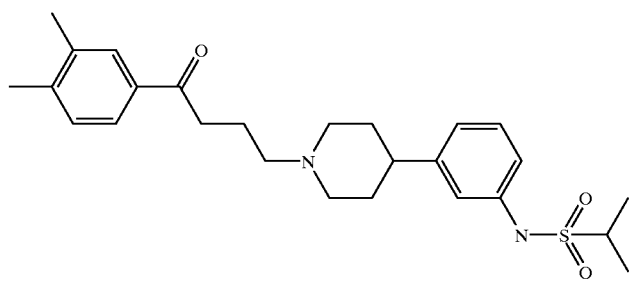 | 615 |

-continued
| | | |
|---|---|---|
| 34 | 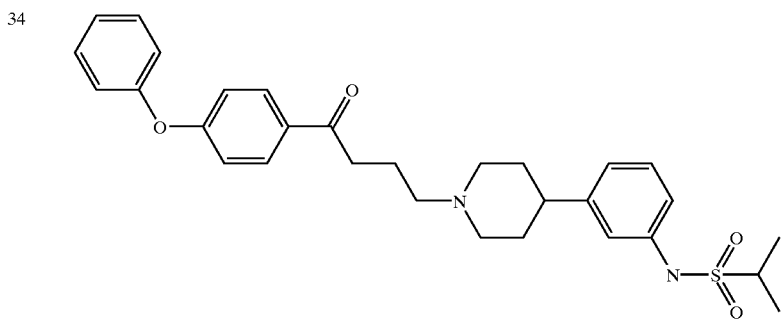 | 651 |
| 35 | 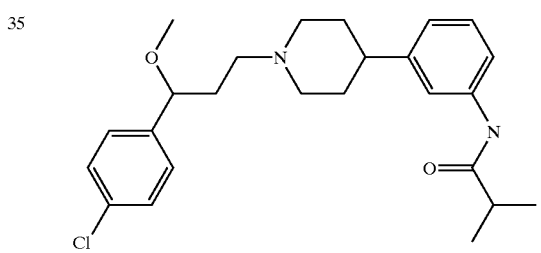 | 11.5 |
| 36 | 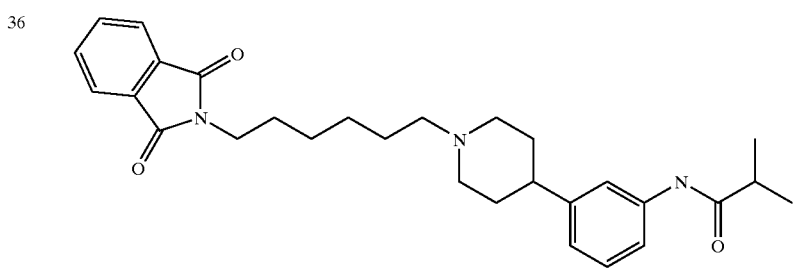 | 62 |
| 37 | 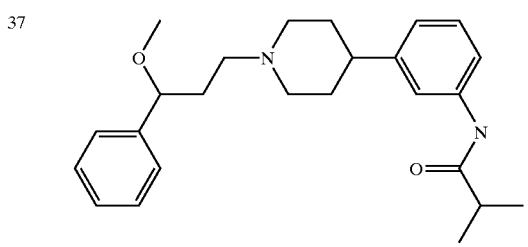 | 29.1 |
| 38 | 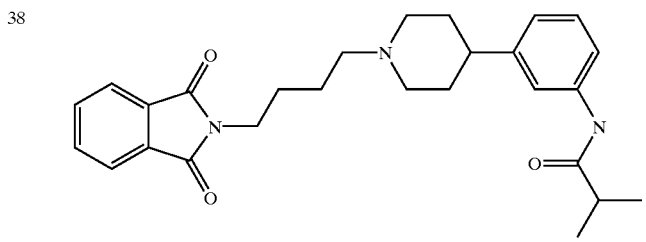 | 18.2 |
| 39 | 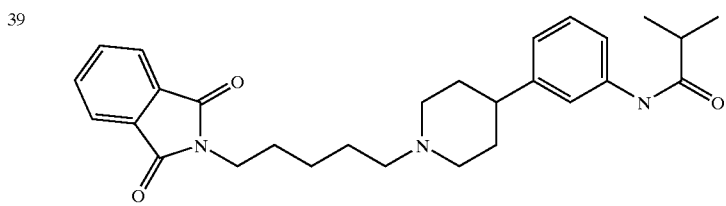 | 11.8 |

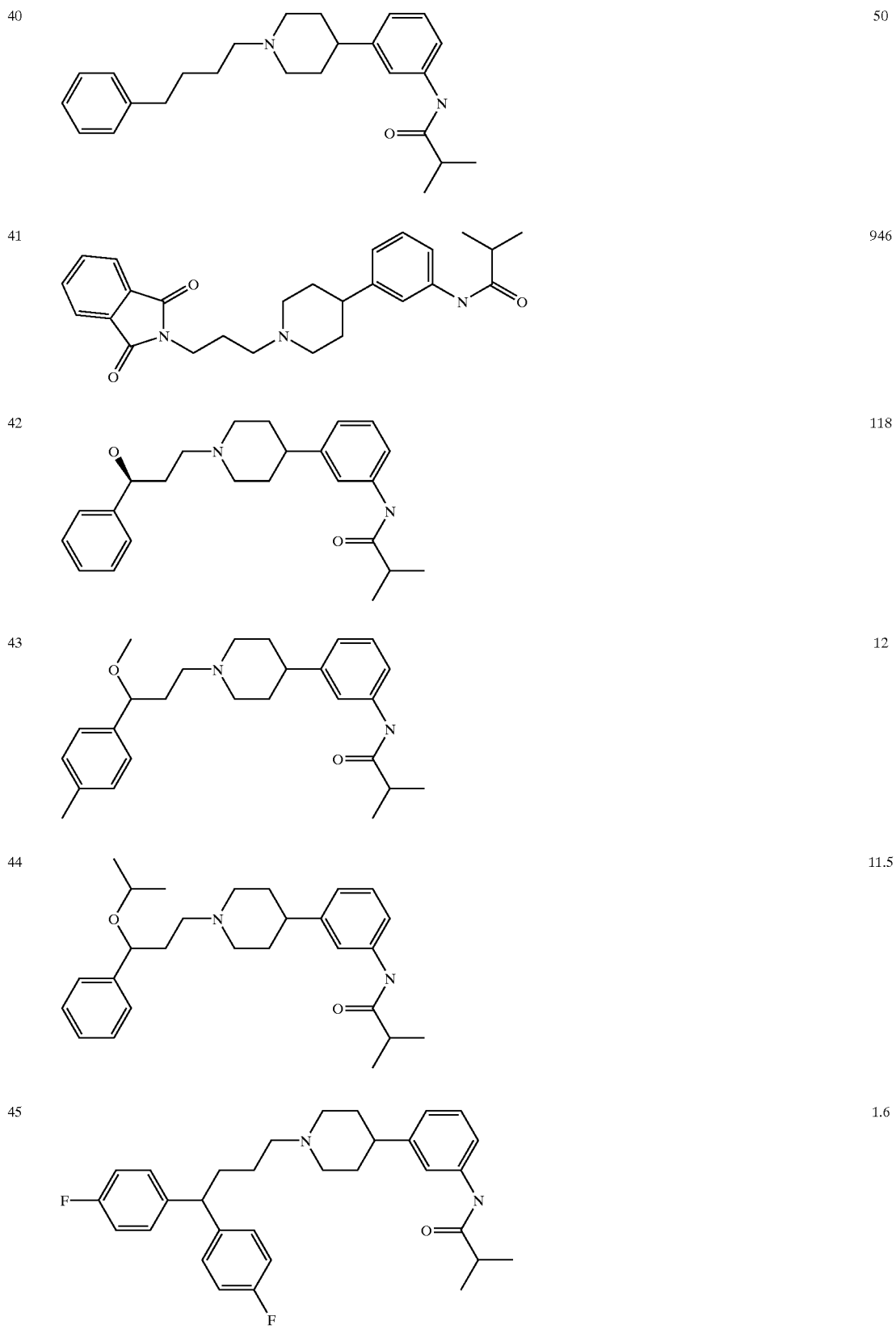

-continued
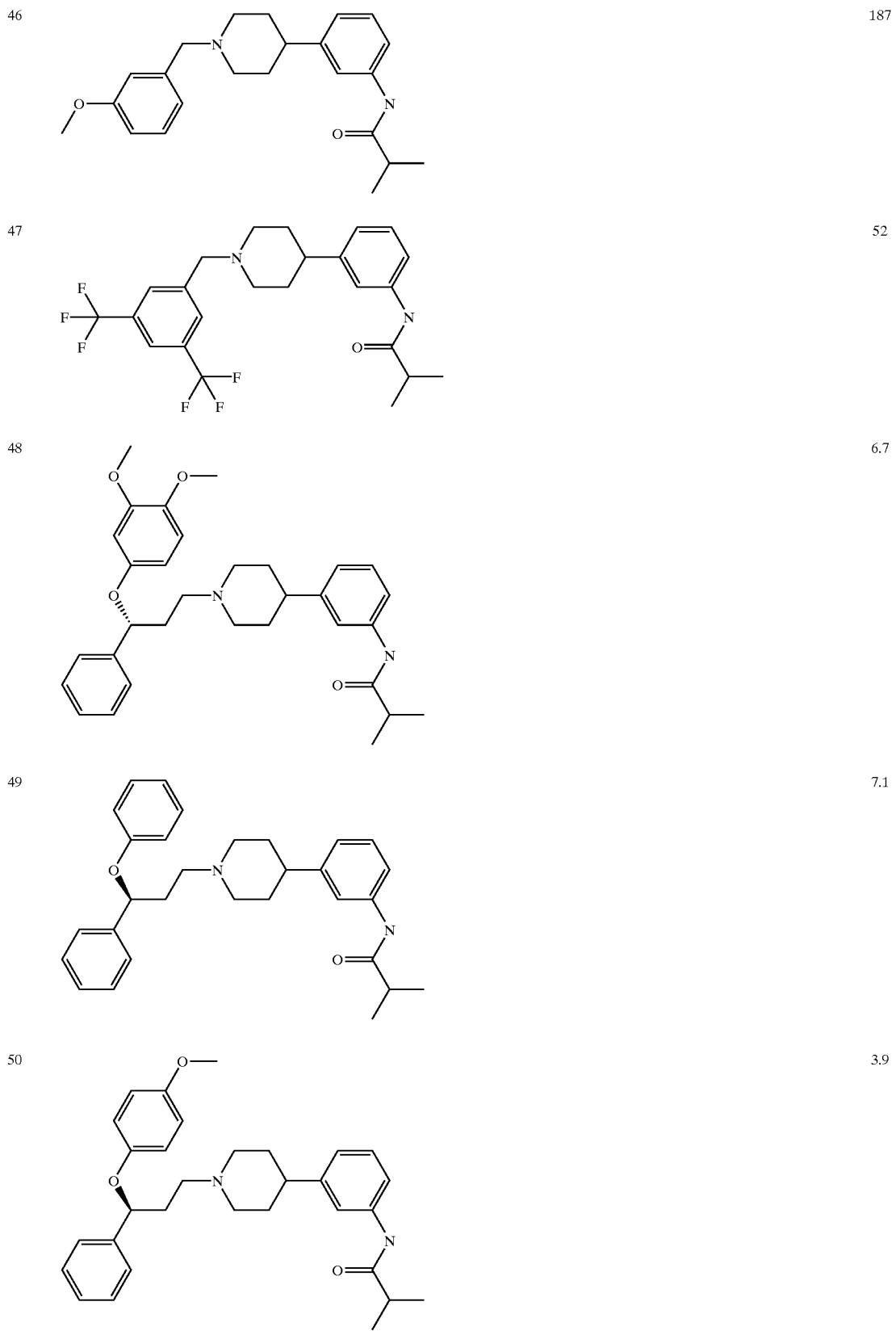
| 46 | 187 |
| 47 | 52 |
| 48 | 6.7 |
| 49 | 7.1 |
| 50 | 3.9 |

-continued
| | | |
|---|---|---|
| 51 | 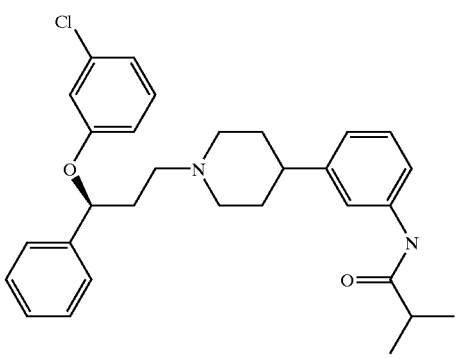 | 3.1 |
| 52 | 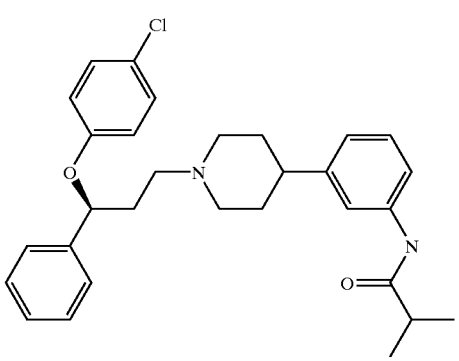 | 3.8 |
| 53 | 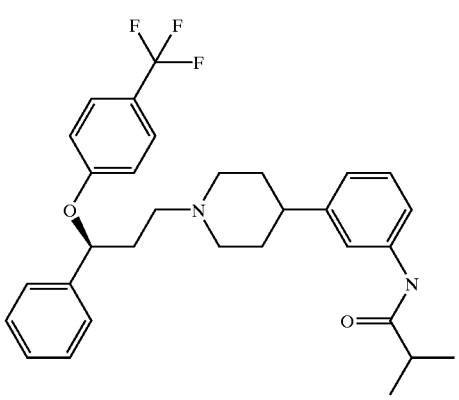 | 7.1 |
| 54 | 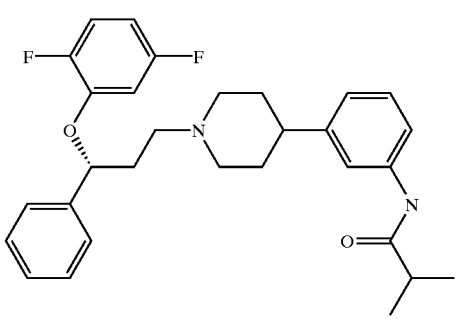 | 4.9 |

| | | |
|---|---|---|
| 55 | 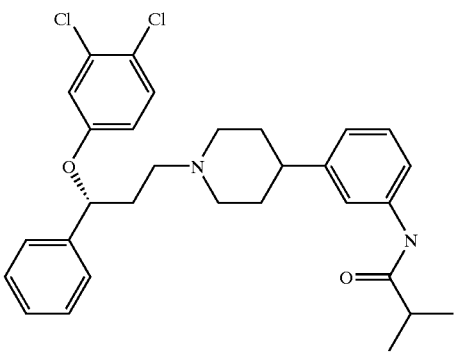 | 5 |
| 56 | 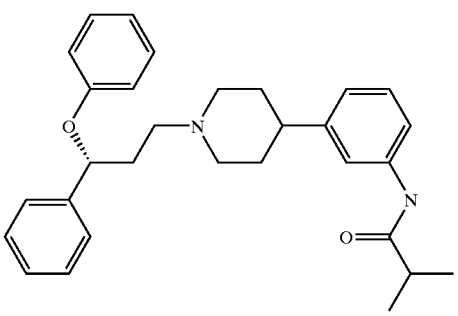 | 22.3 |
| 57 | 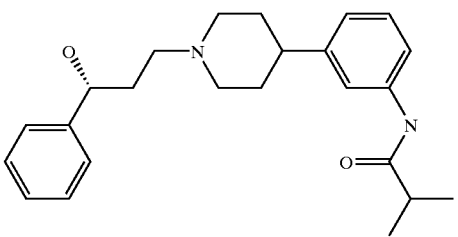 | 16.6 |
| 58 | 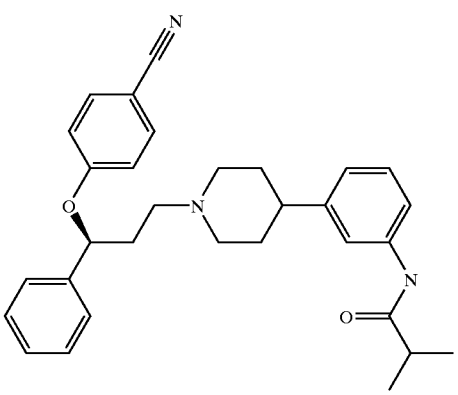 | 2.01 |

-continued
| | | |
|---|---|---|
| 59 | 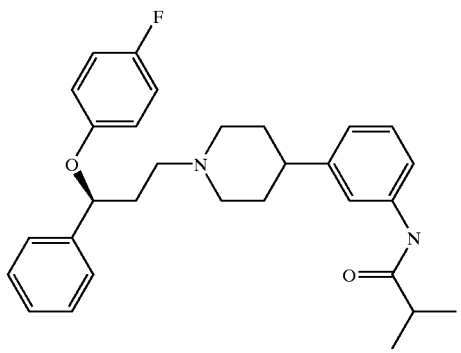 | 12.9 |
| 60 | 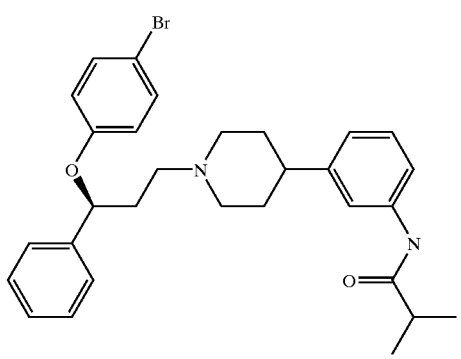 | 0.923 |
| 61 | 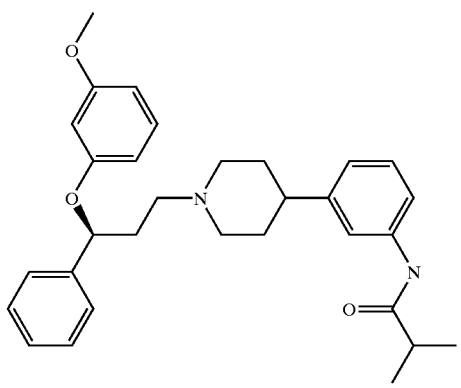 | 13.6 |
| 62 | 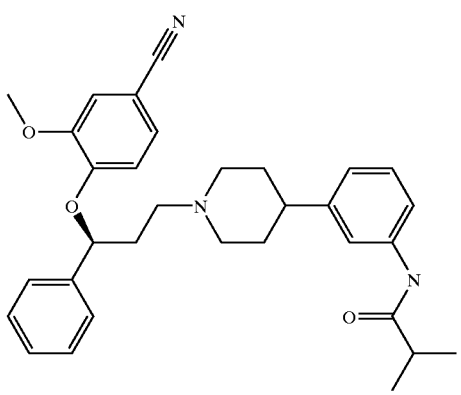 | 12.8 |

-continued
| | | |
|---|---|---|
| 63 | 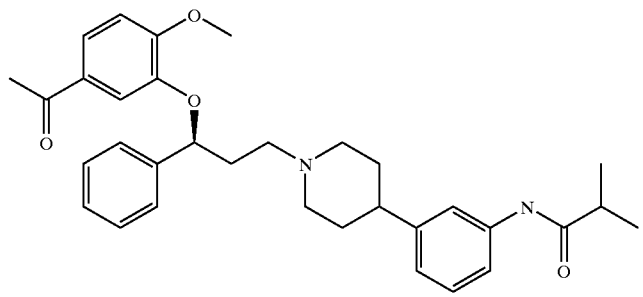 | 22.4 |
| 64 | 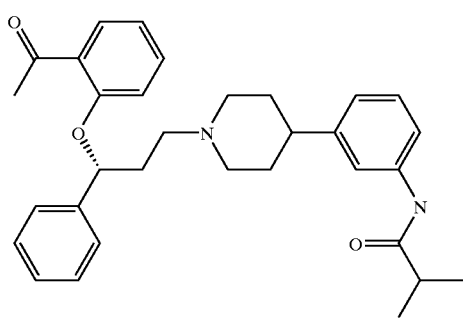 | 14.8 |
| 65 | 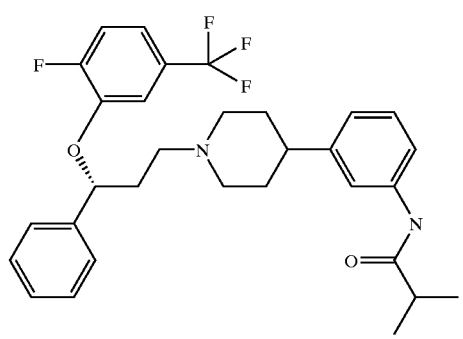 | 17 |
| 66 | 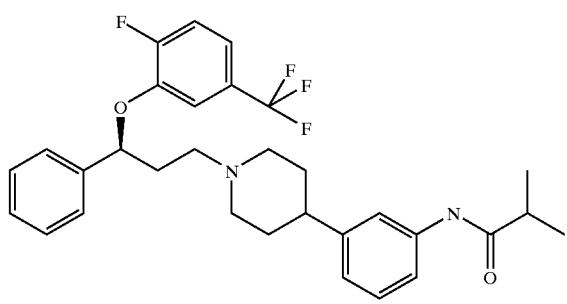 | 3.3 |
| 67 | 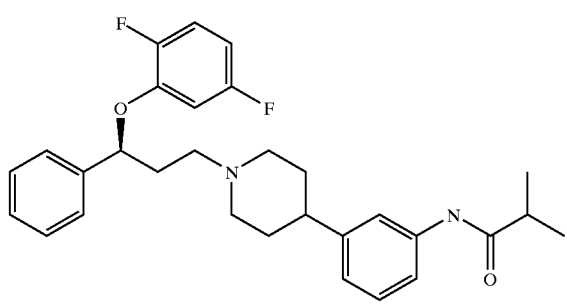 | 5.9 |

-continued
| | | |
|---|---|---|
| 68 | 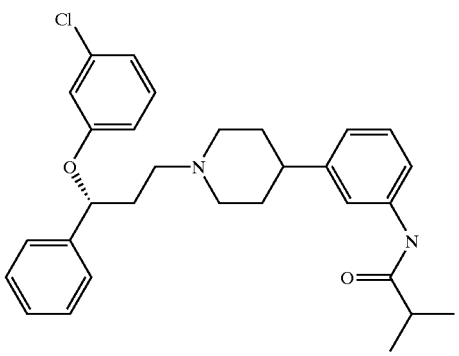 | 9.3 |
| 69 | 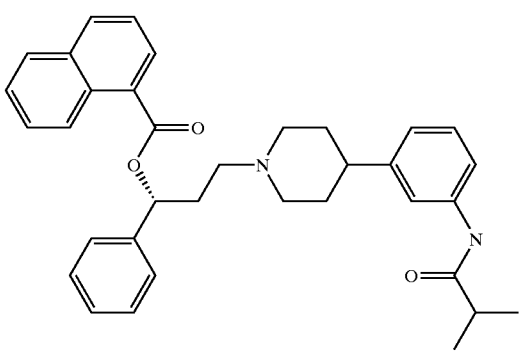 | 32.5 |
| 70 | 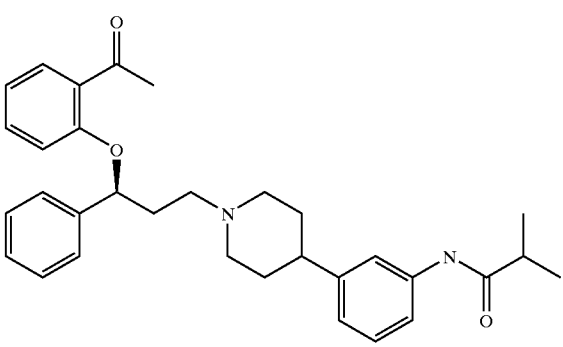 | 50 |
| 71 | 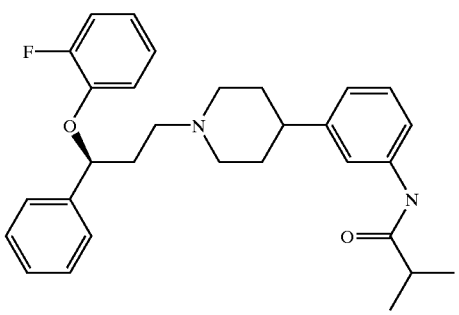 | 6.6 |

-continued
| | | |
|---|---|---|
| 72 | 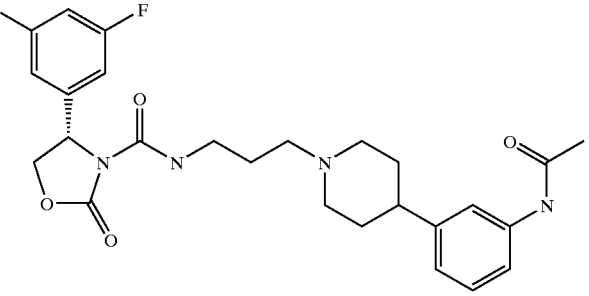 | 31.4 |
| 73 | 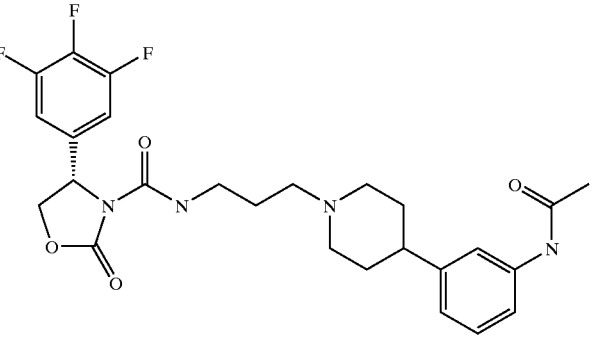 | 22.3 |
| 74 | 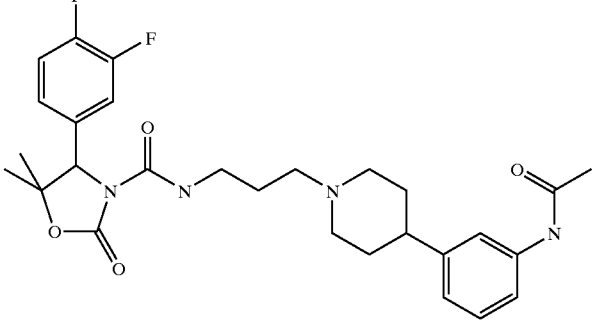 | 48.6 |
| 75 | 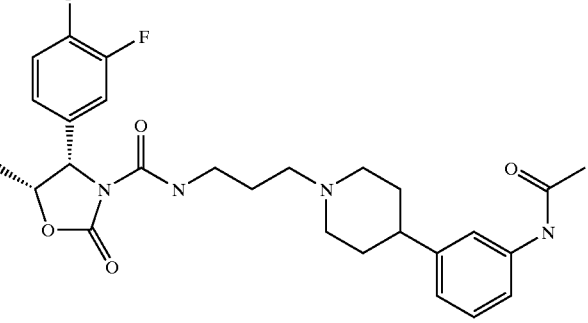 | 11.8 |

-continued
| | | |
|---|---|---|
| 76 | 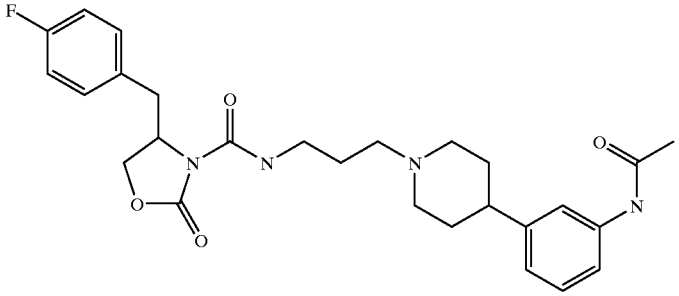 | 44.6 |
| 77 | 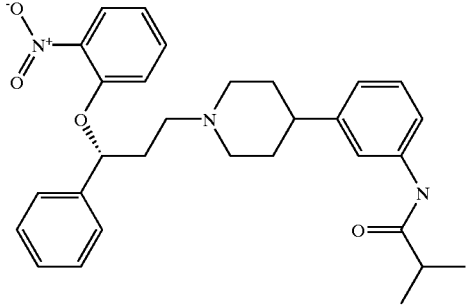 | 25.7 |
| 78 | 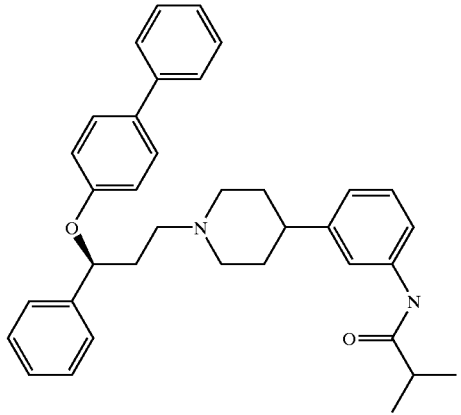 | 22.2 |
| 79 | 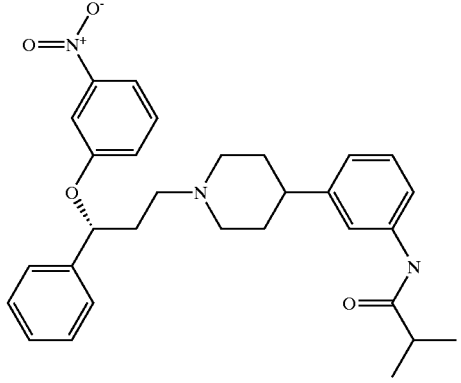 | 19.4 |

-continued
| | | |
|---|---|---|
| 80 | 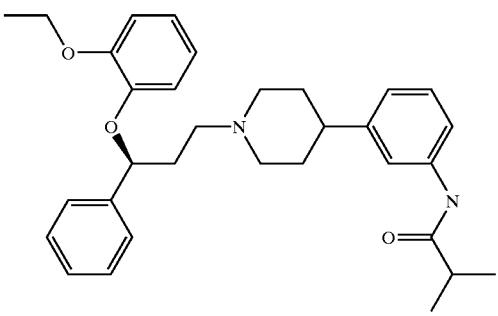 | 14.3 |
| 81 | 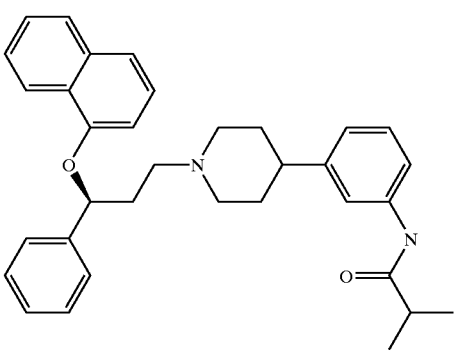 | 377 |
| 82 | 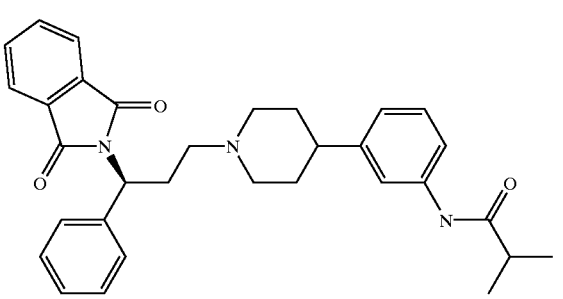 | 11.2 |
| 83 | 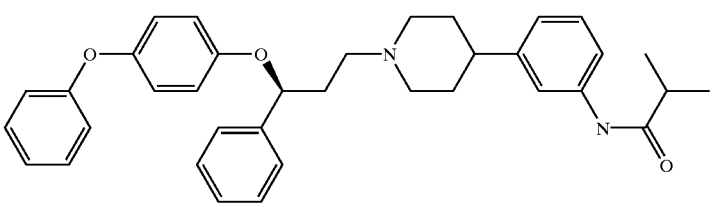 | 48.1 |
| 84 | 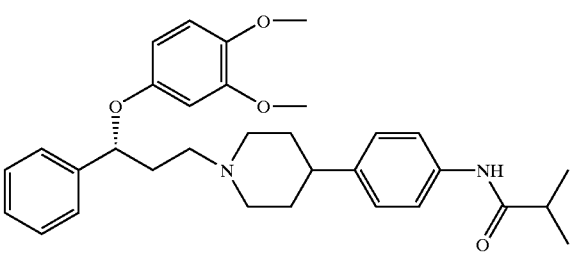 | 121 |

-continued
| | | |
|---|---|---|
| 85 | 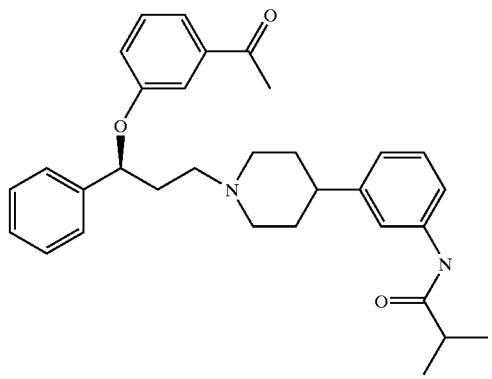 | 3.2 |
| 86 | 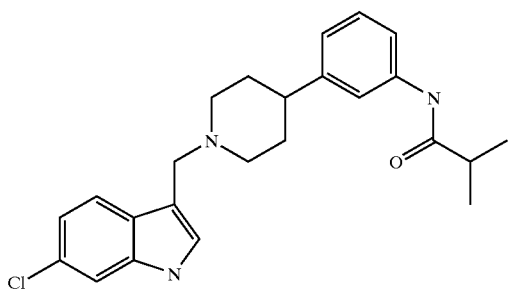 | 20.6 |
| 87 | 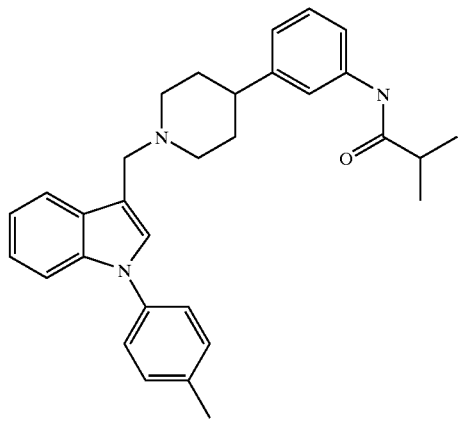 | 14.9 |
| 88 | 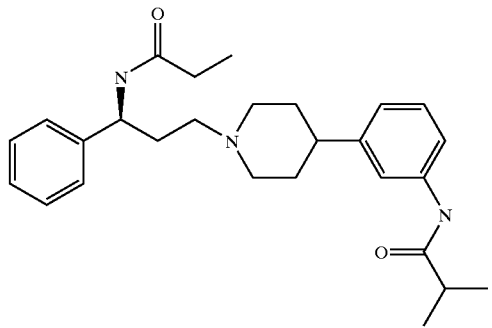 | 16.0 |

-continued
| | | |
|---|---|---|
| 89 | 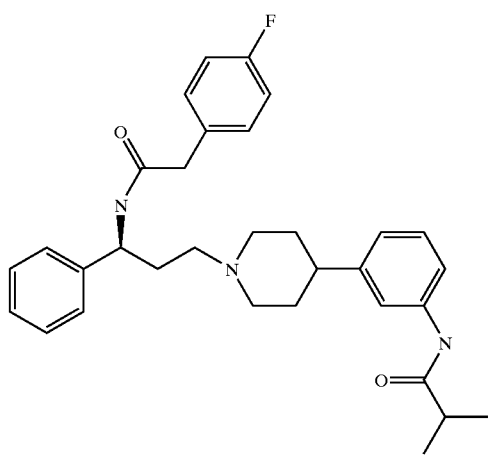 | 3.0 |
| 90 | 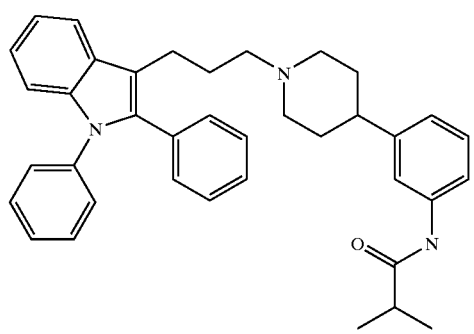 | 3.0 |
| 91 | 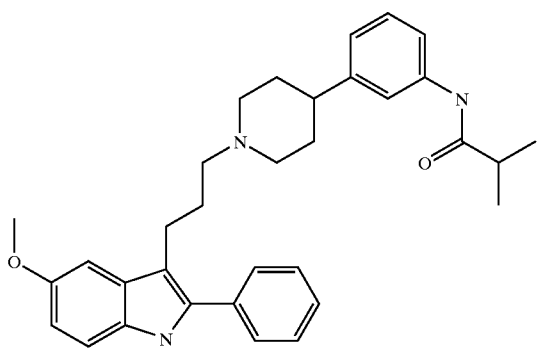 | 2.3 |
| 92 | 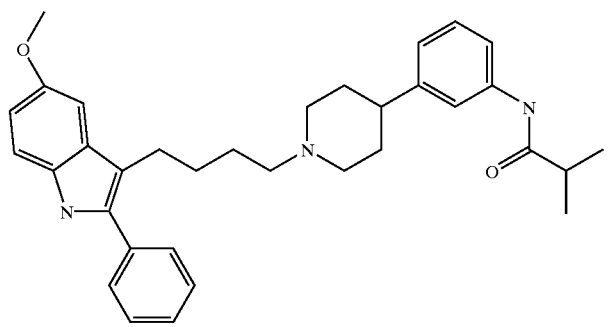 | 8.0 |

-continued
| | | |
|---|---|---|
| 93 | 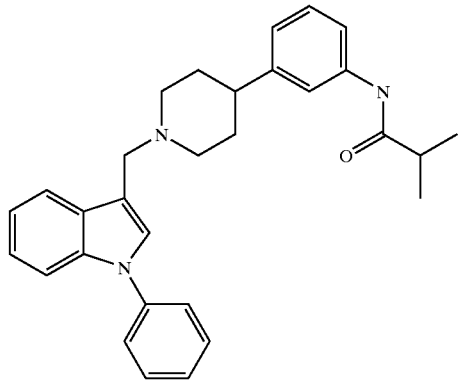 | 4.2 |
| 94 | 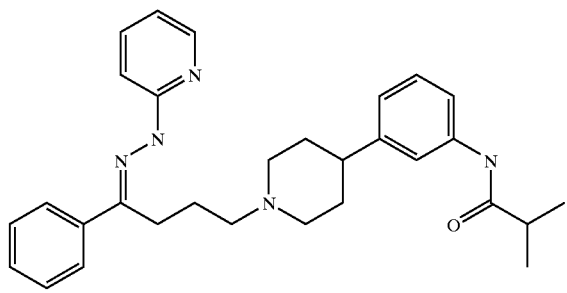 | 2.3 |
| 95 | 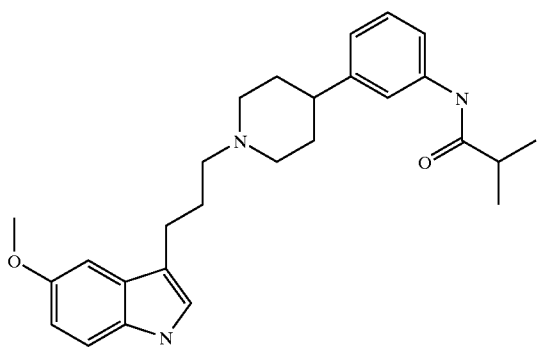 | 5.4 |
| 96 | 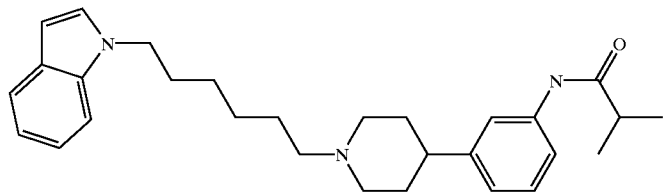 | 15.9 |
| 97 | 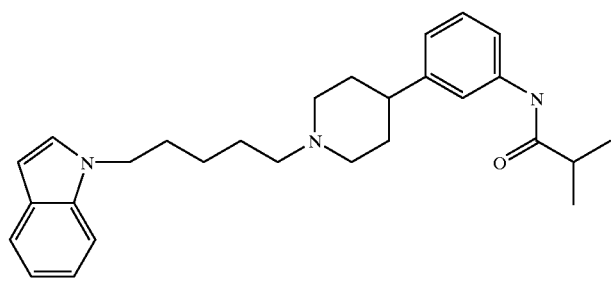 | 27.3 |

| | | |
|---|---|---|
| 98 | 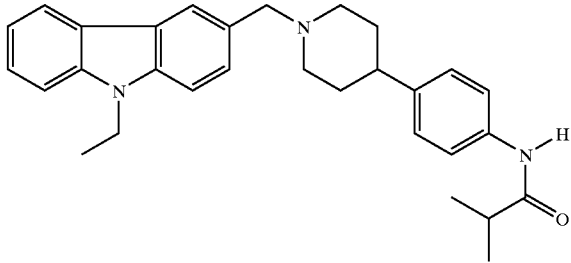 | 37.9 |
| 99 | 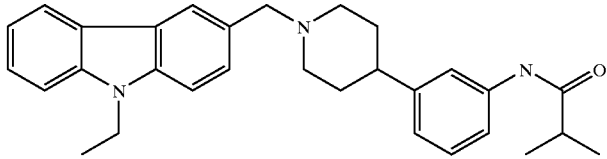 | 1.7 |
| 100 | 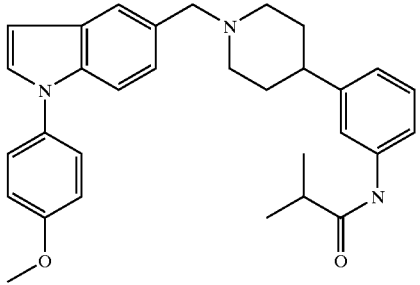 | 27.5 |
| 101 | 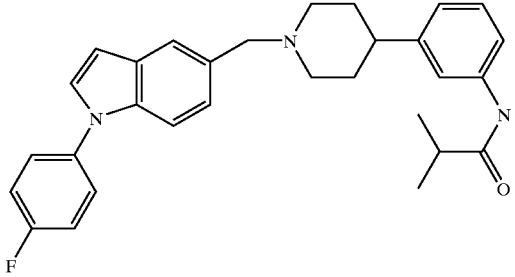 | 7.8 |
| 102 | 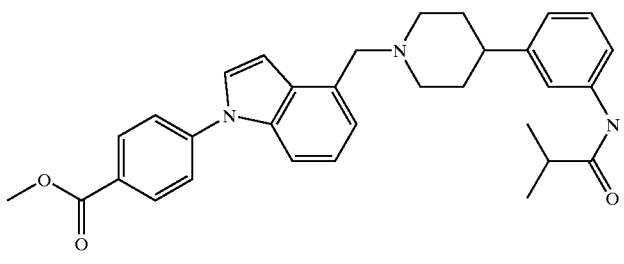 | 38.4 |
| 103 | 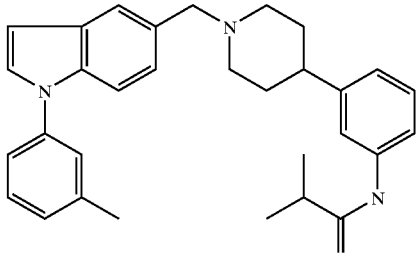 | 21.3 |

-continued
| 104 | 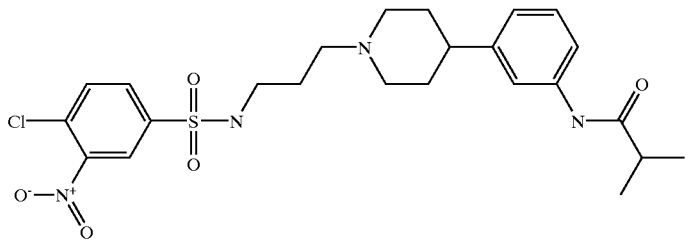 | 11.2 |
| 105 | 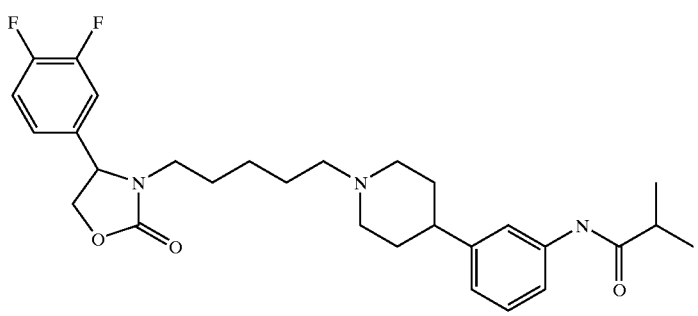 | 4.6 |
| 106 | 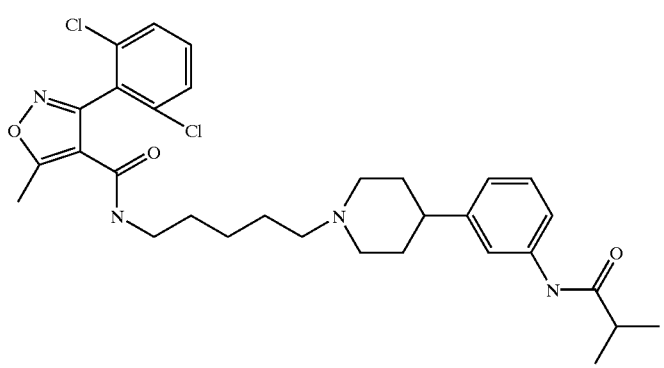 | 7.1 |
| 107 | 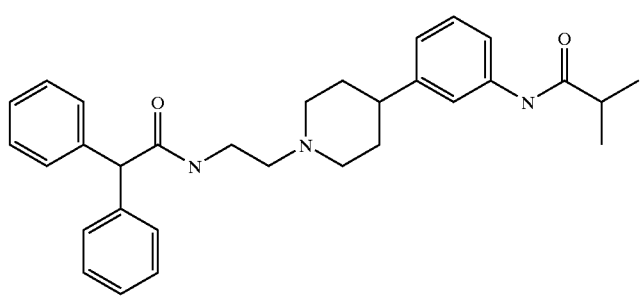 | 1.7 |
| 108 | 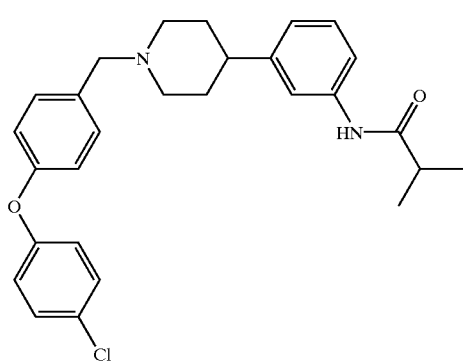 | 5.2 |

-continued
| | | |
|---|---|---|
| 109 | 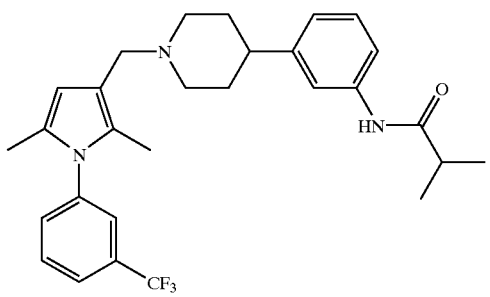 | 20.9 |
| 110 | 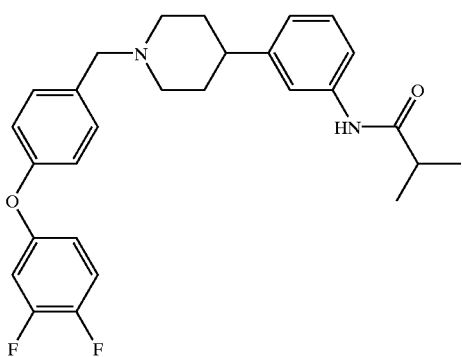 | 1.8 |
| 111 | 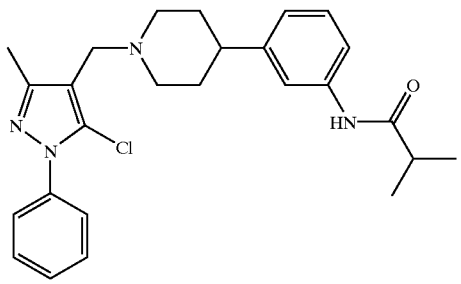 | ND |
| 112 | 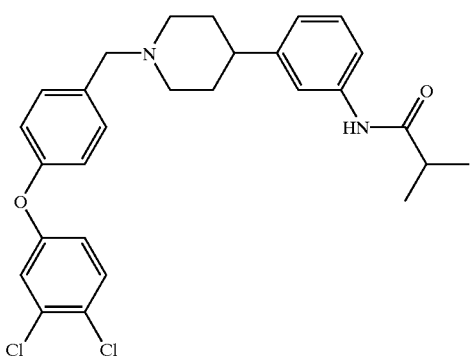 | 6.1 |
| 113 | 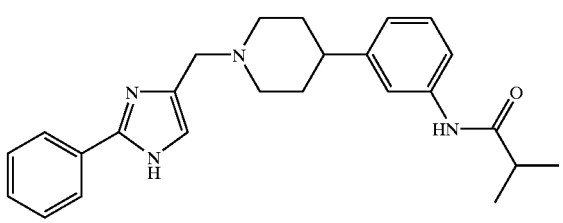 | ND |

-continued
| | | |
|---|---|---|
| 114 | 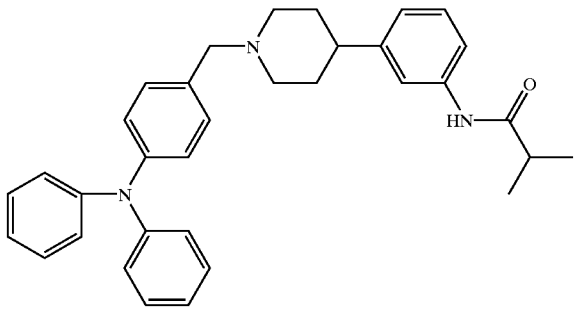 | 3.6 |
| 115 | 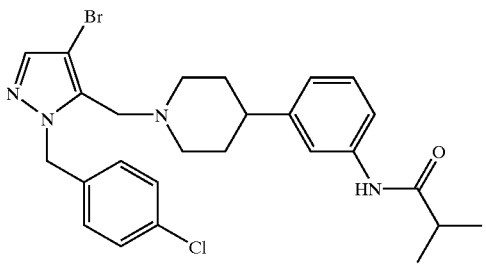 | ND |
| 116 | 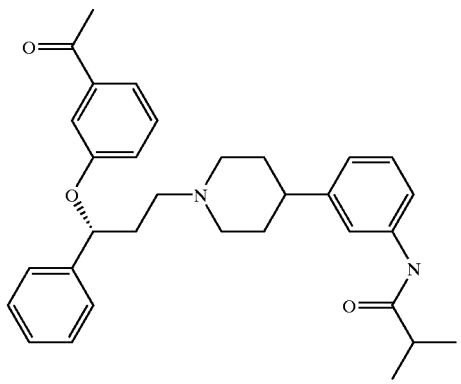 | 3.8 |
| 117 | 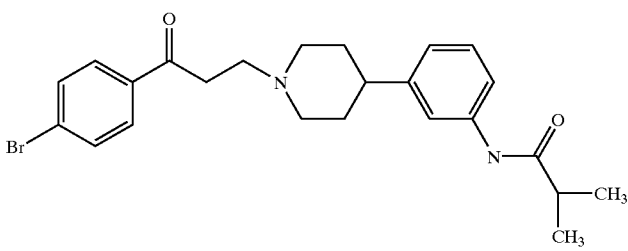 | 19.0 |
| 118 | 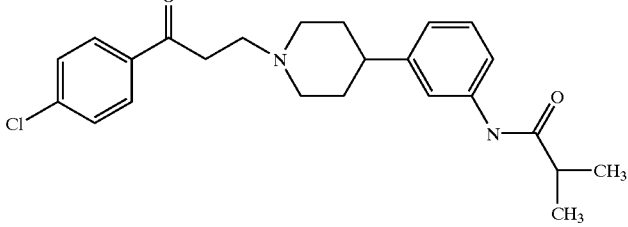 | 43.6 |

-continued
| | | |
|---|---|---|
| 119 | 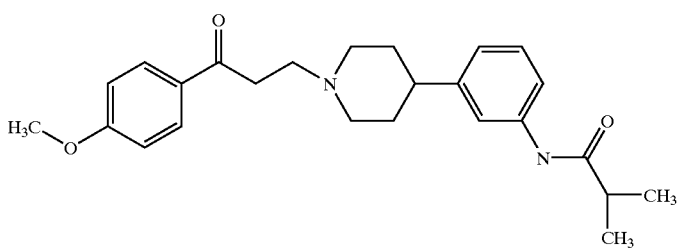 | 75.7 |
| 120 | 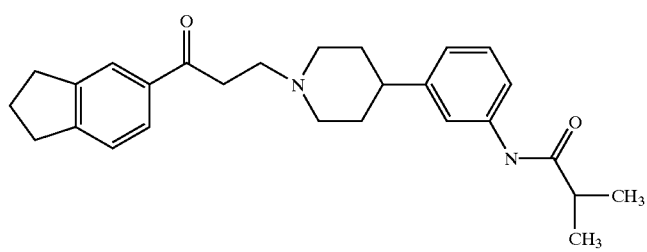 | 31.1 |
| 121 | 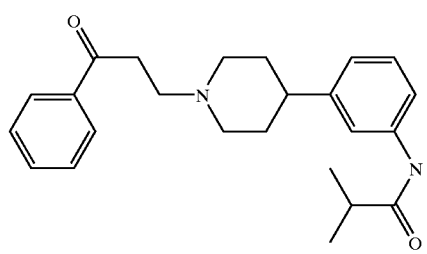 | 183.7 |
| 122 | 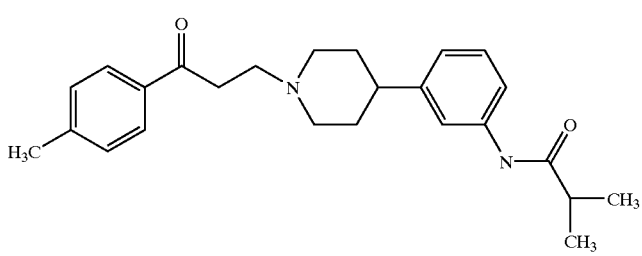 | 85.1 |
| 123 | 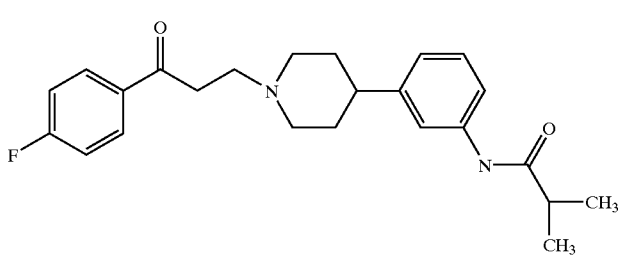 | 449.8 |
| Example | Structure | rMCH1 Ki (nM) |
|---|---|---|
| 124 | 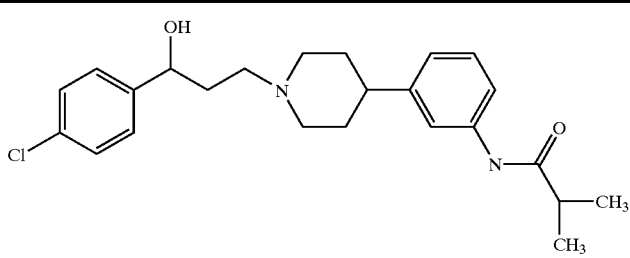 | 33.0 |

| | | -continued | |
|---|---|---|---|
| 125 | 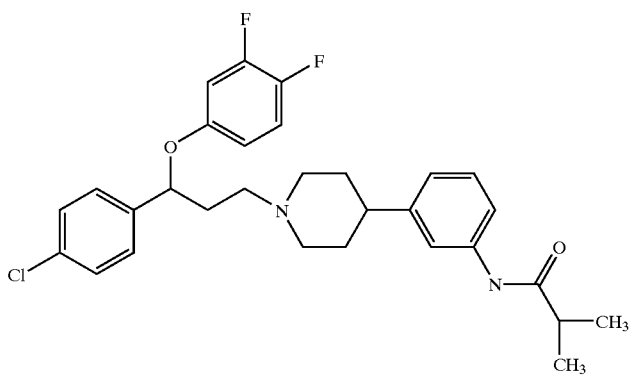 | | 5.4 |
| 126 | 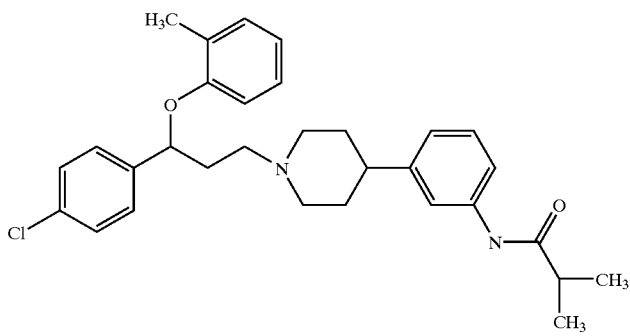 | | 13.8 |
| 127 | 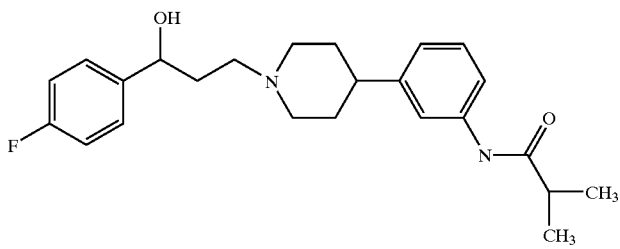 | | 168.5 |
| 128 | 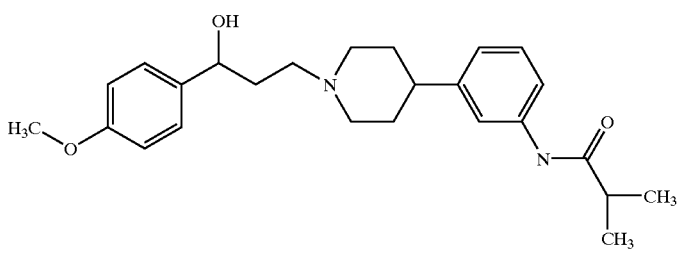 | | 328.8 |
| 129 | 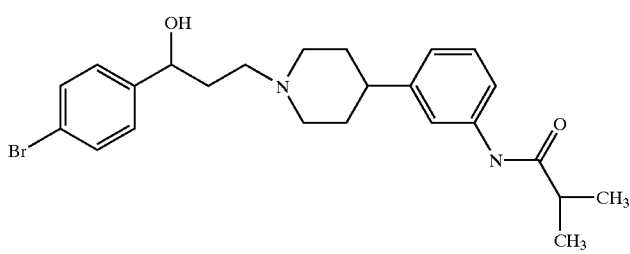 | | 38.8 |

-continued
| | | |
|---|---|---|
| 130 | 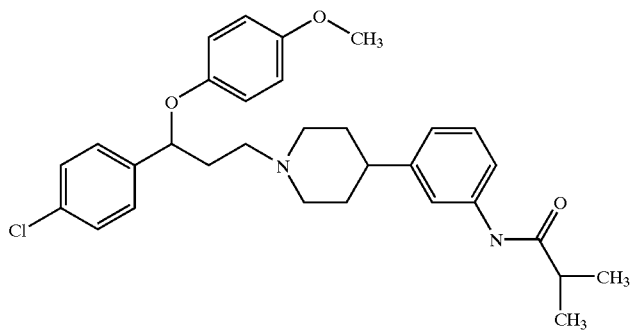 | 6.0 |
| 131 | 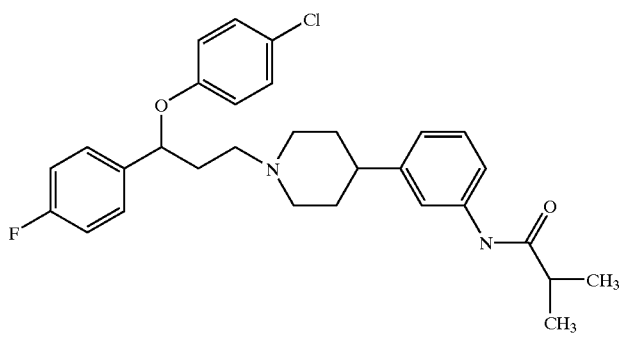 | 11.9 |
| 132 | 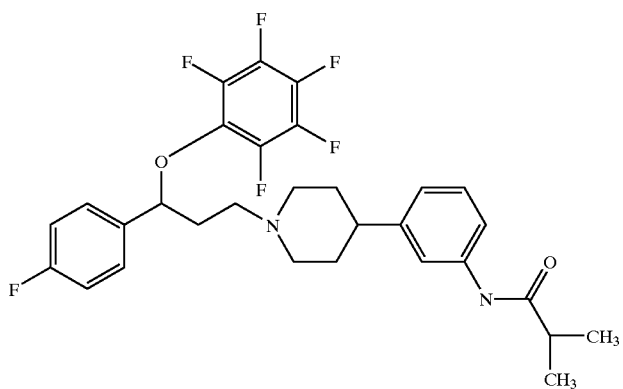 | 41.7 |
| 133 | 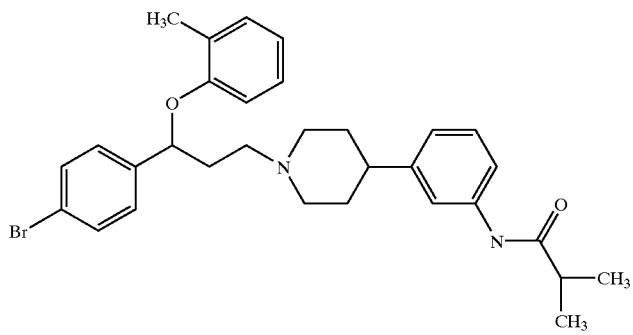 | 14.1 |

-continued
| 134 | 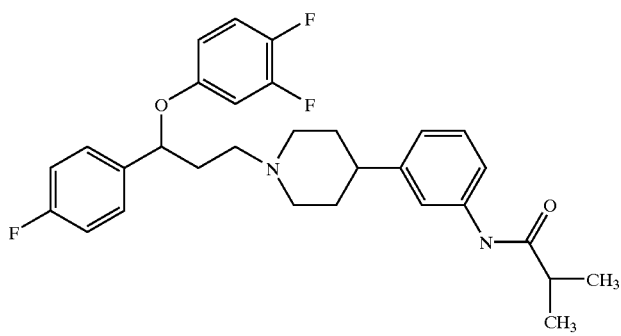 | 36.6 |
| 135 | 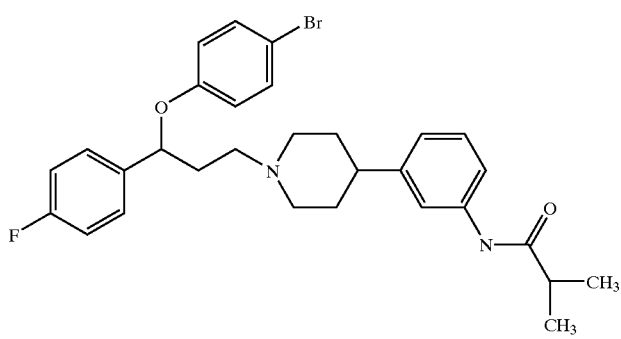 | 10.9 |
| 136 | 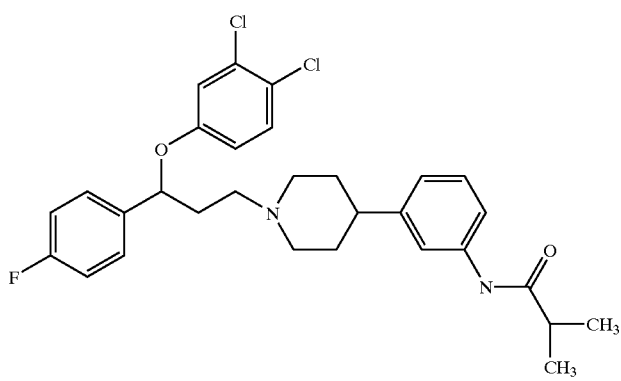 | 15.9 |
| 137 | 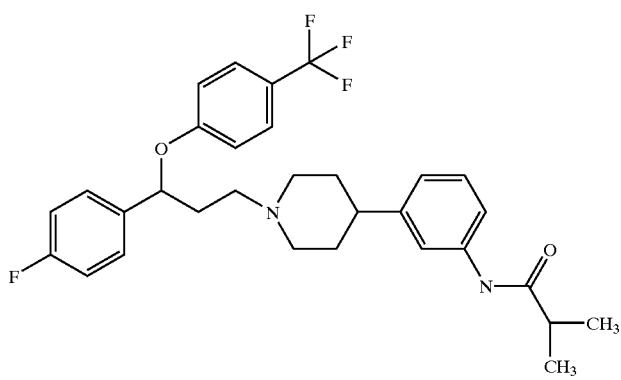 | 25.2 |

-continued
| | | |
|---|---|---|
| 138 | 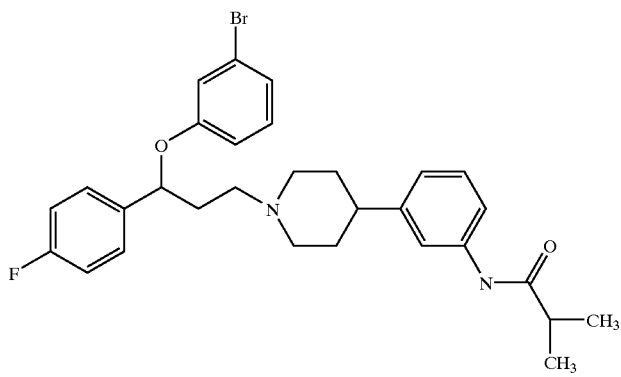 | 9.3 |
| 139 | 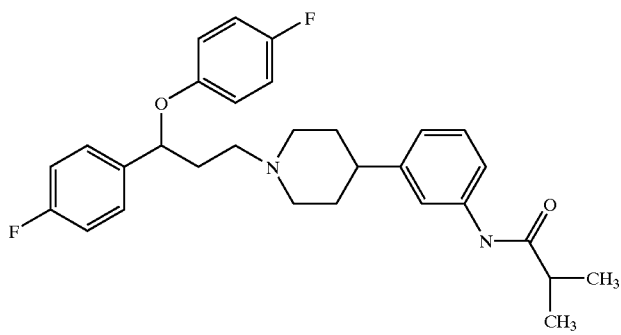 | 38.7 |
| 140 | 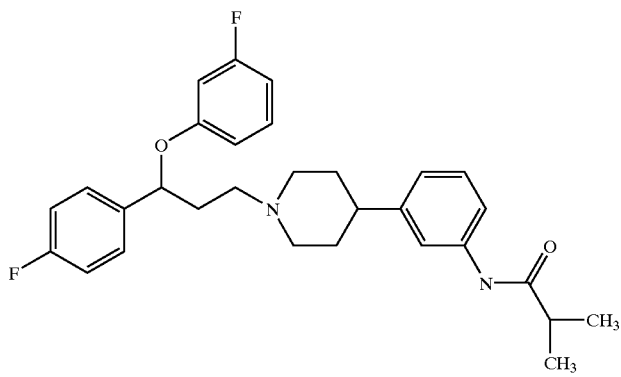 | 27.4 |
| 141 | 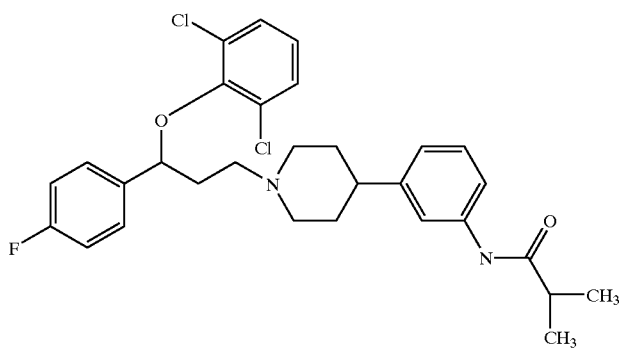 | 61.0 |

| | | |
|---|---|---|
| 142 | 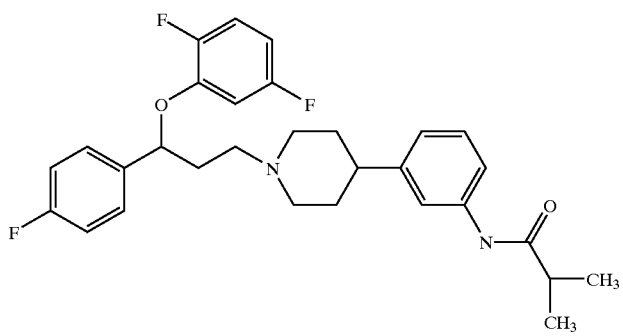 | 18.3 |
| 143 | 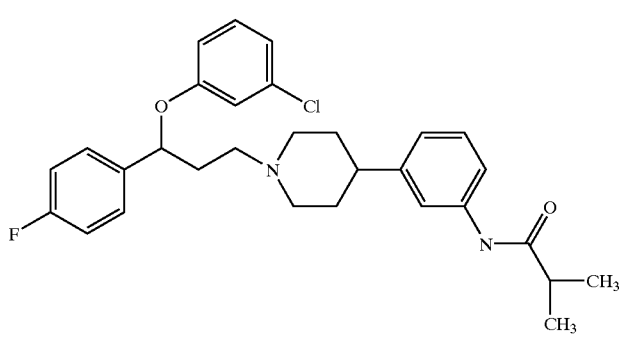 | 8.7 |
| 144 | 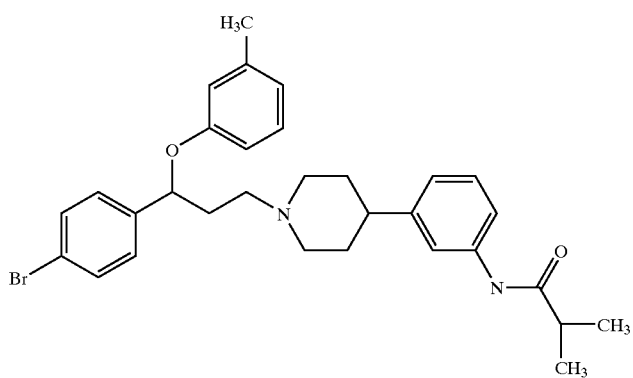 | 13.4 |
| 145 | 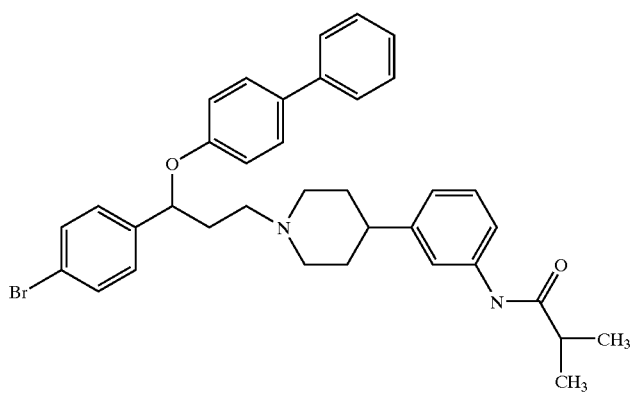 | 196.8 |

-continued
| | | |
|---|---|---|
| 146 | 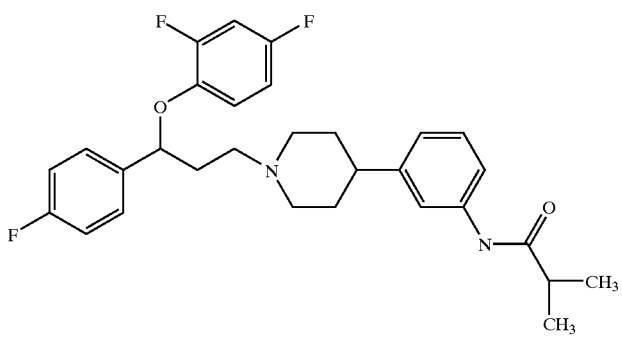 | 19.2 |
| 147 | 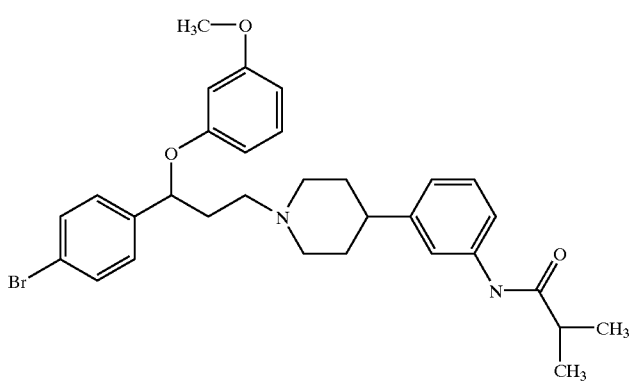 | 8.7 |
| 148 | 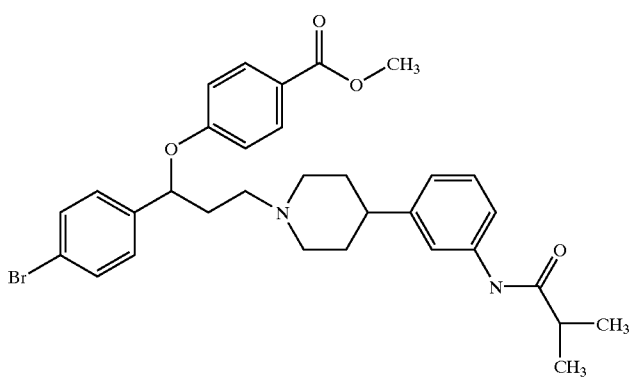 | 24.7 |
| 149 | 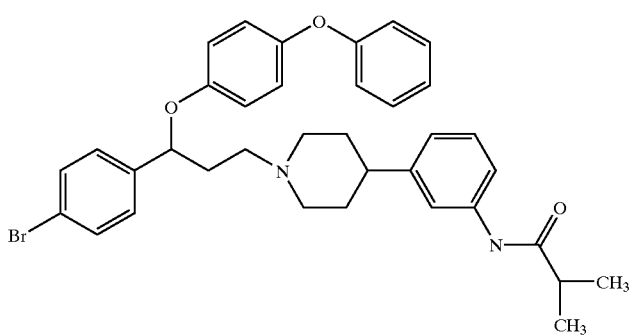 | 148.9 |

-continued
| 150 | 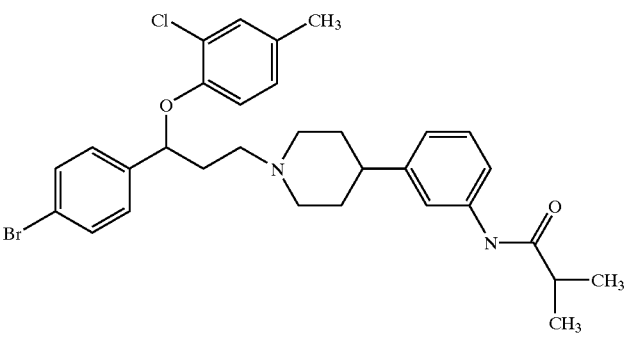 | 8.0 |
| 151 | 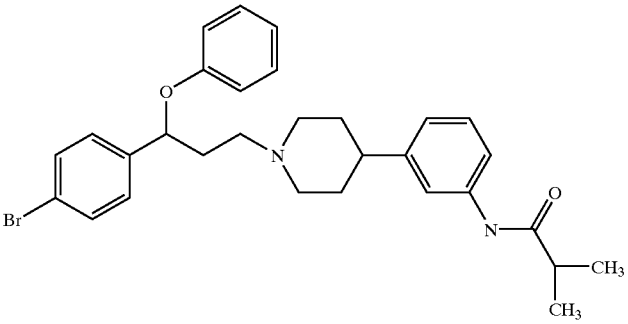 | 14.2 |
| 152 | 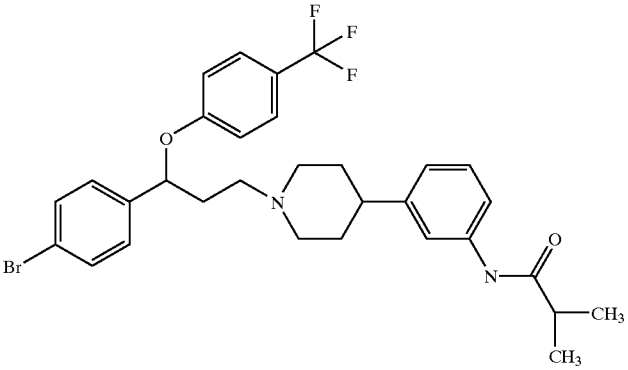 | 13.3 |
| 153 | 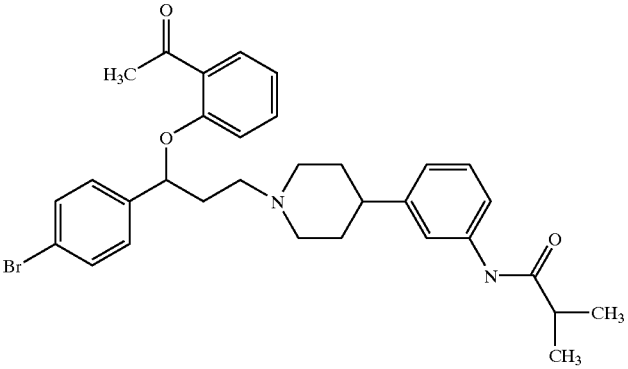 | 8.1 |

| | | |
|---|---|---|
| 154 | 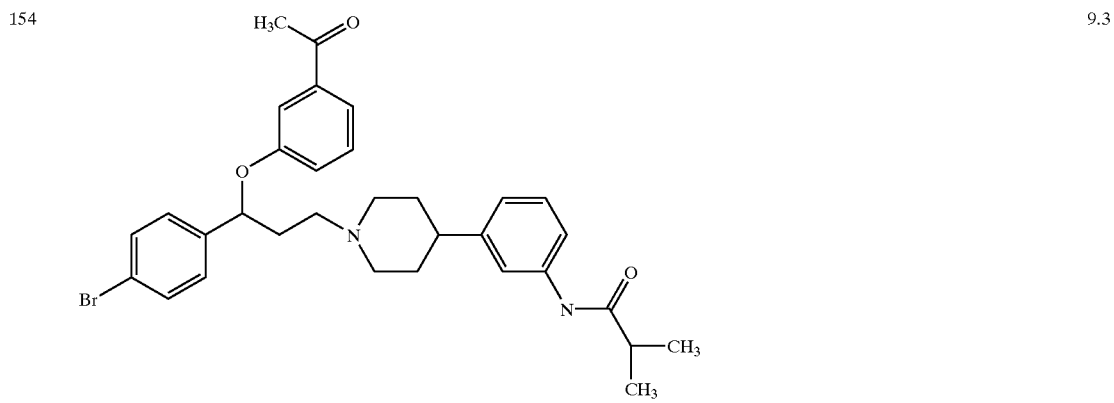 | 9.3 |
| 155 |  | 7.4 |
| 156 | 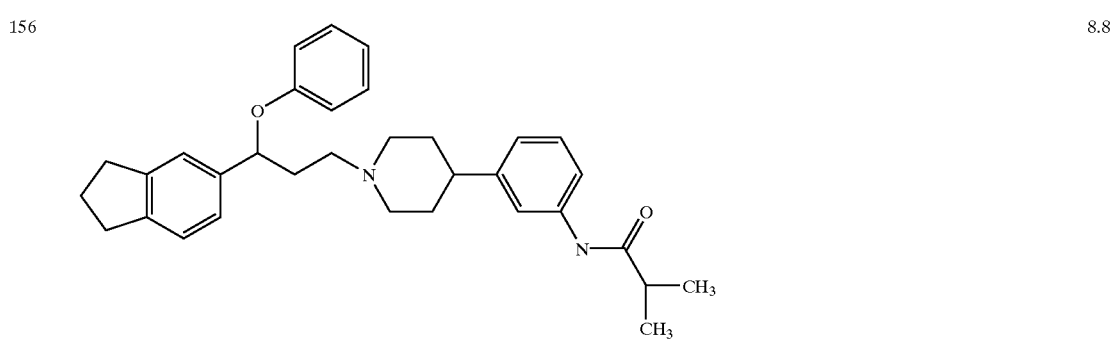 | 8.8 |
| 157 | 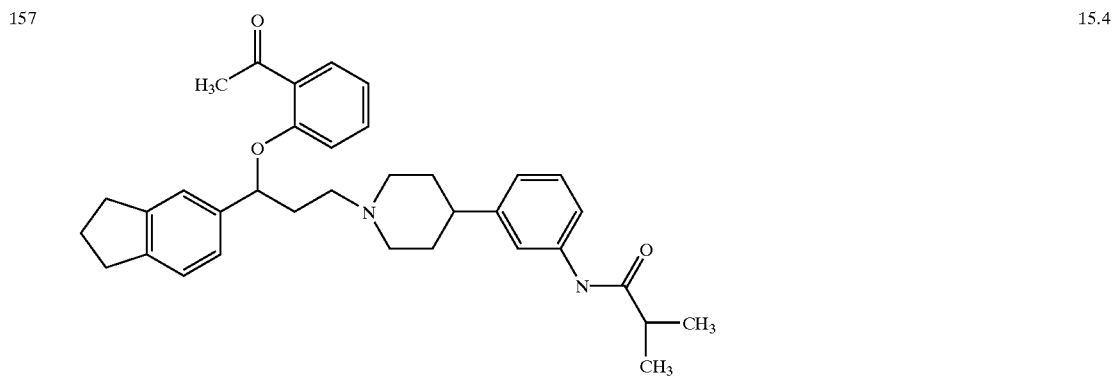 | 15.4 |

-continued
| 158 | 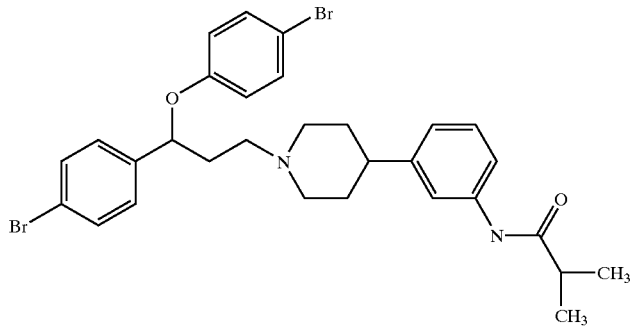 | 7.8 |
| 159 | 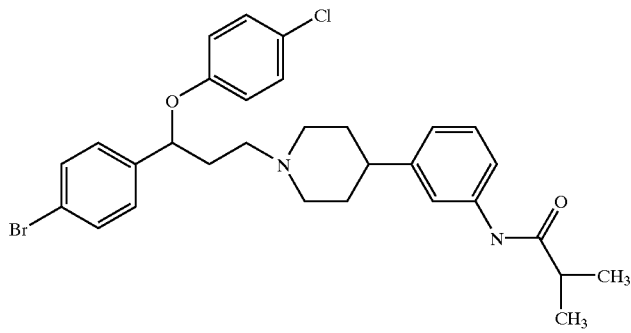 | 4.5 |
| 160 | 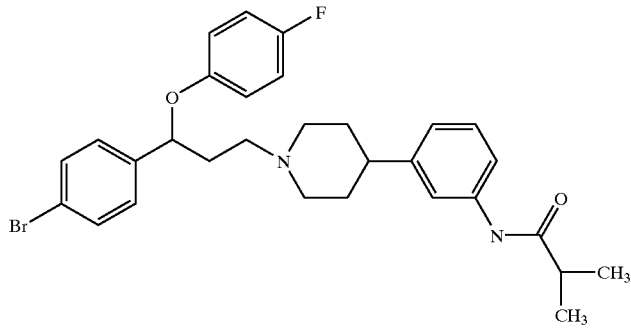 | 6.2 |
| 161 | 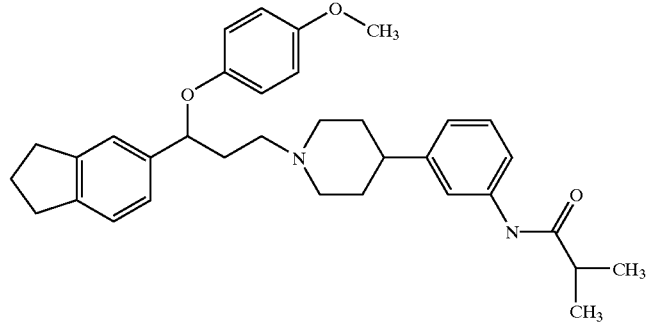 | 7.9 |

-continued
| 162 | 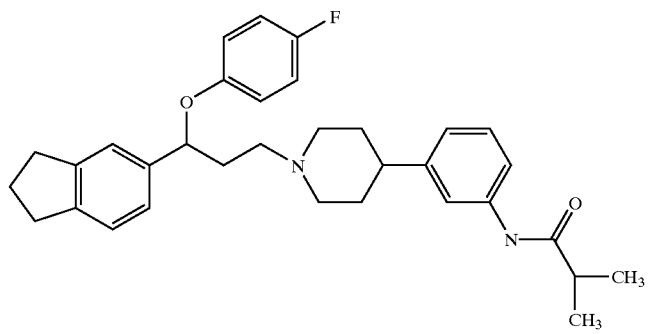 | 7.2 |
| 163 | 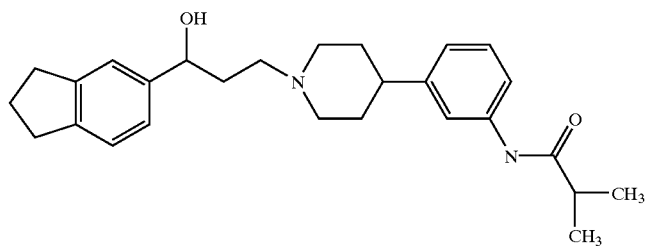 | 58.3 |
| 164 | 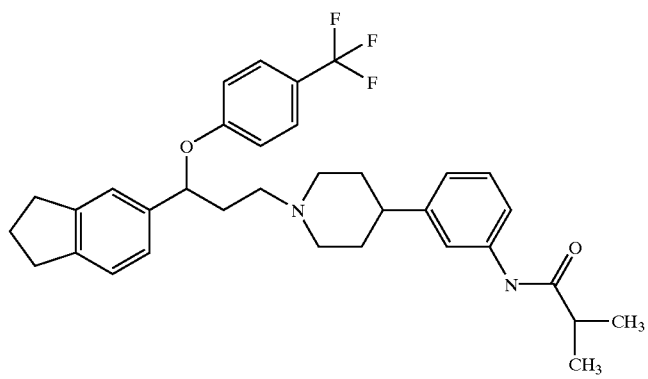 | 16.3 |
| 165 | 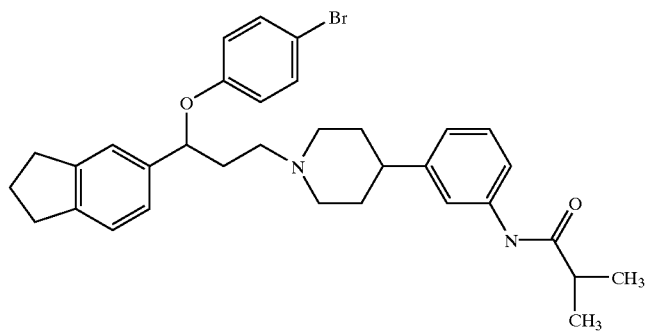 | 6.2 |

| | | |
|---|---|---|
| 166 | 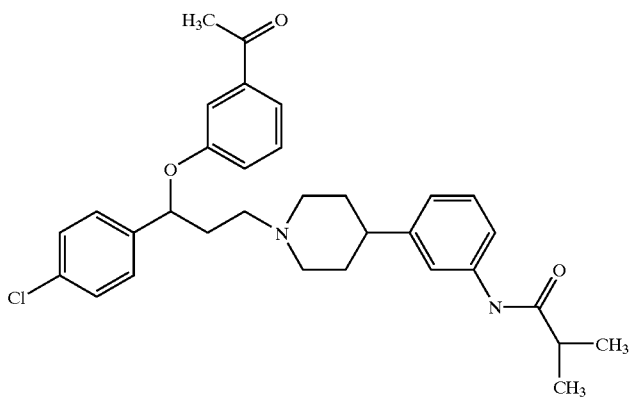 | 7.7 |
| 167 | 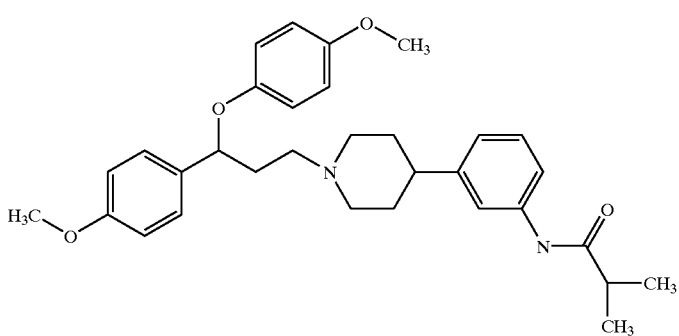 | 80.4 |
| 168 | 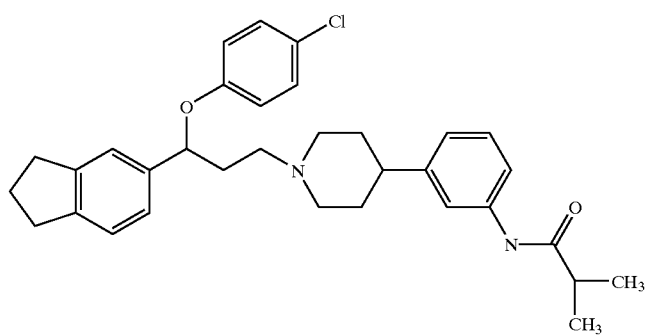 | 7.0 |
| 169 | 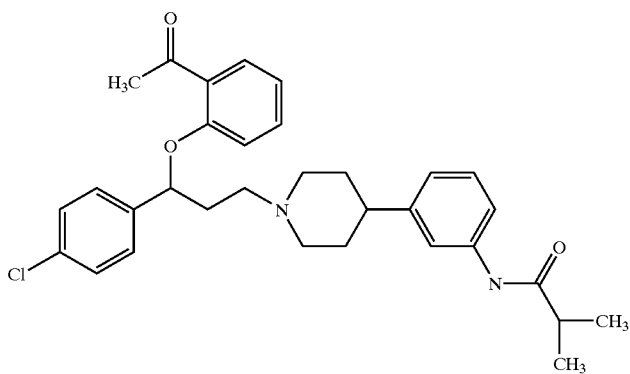 | 7.7 |

-continued
| | | |
|---|---|---|
| 170 | 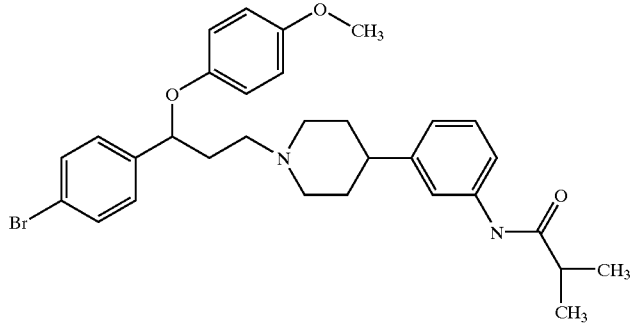 | 3.0 |
| 171 | 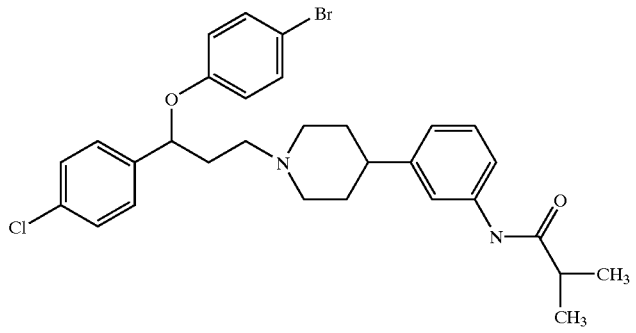 | 3.7 |
| 172 | 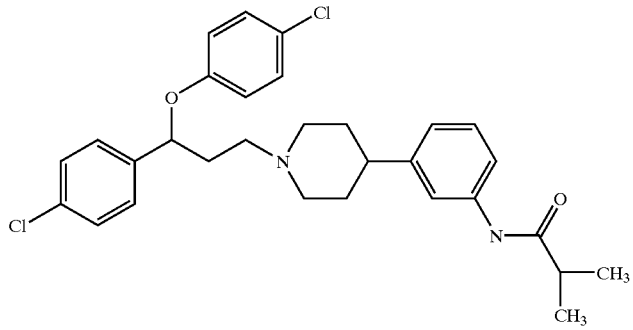 | 3.0 |
| 173 | 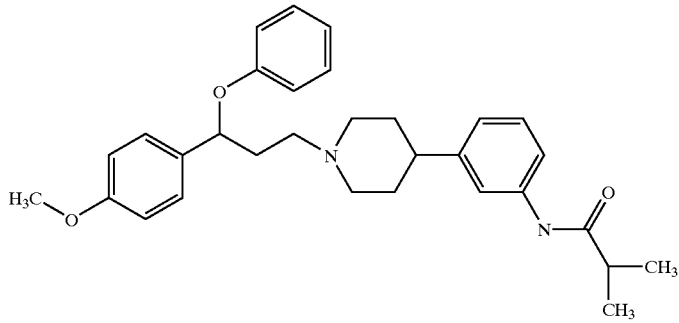 | 112.3 |

-continued
| 174 | 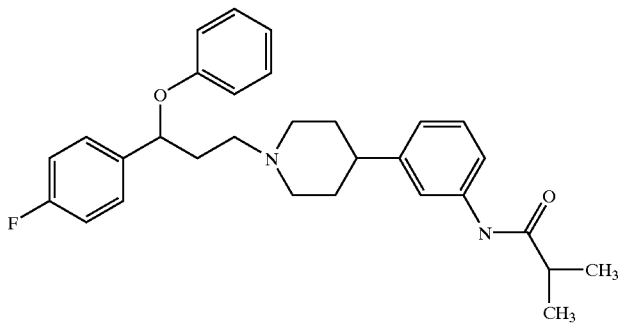 | 17.0 |
| 175 | 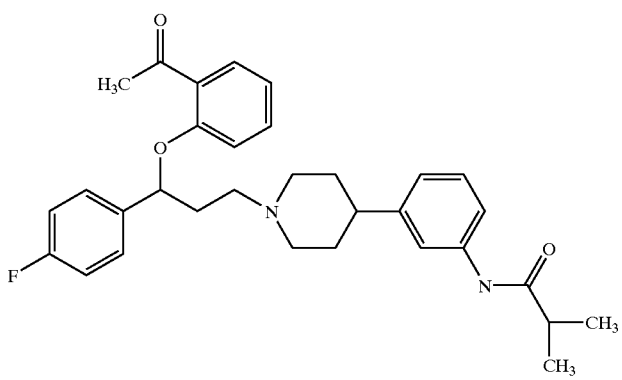 | 16.2 |
| 176 | 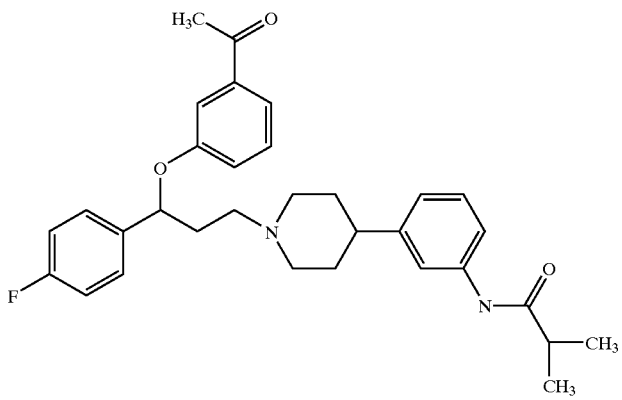 | 11.8 |
| 177 | 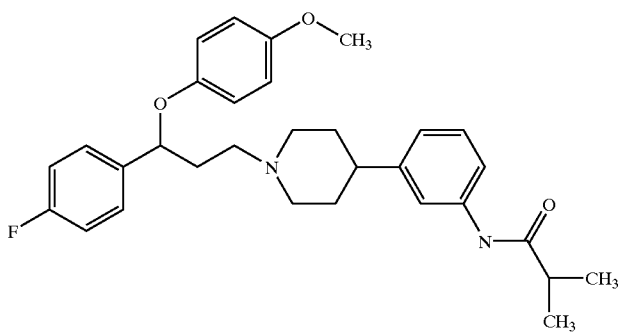 | 6.8 |

-continued
| 178 | 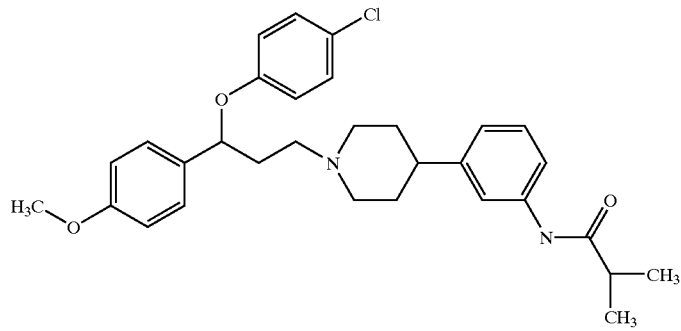 | 119.2 |
| 179 | 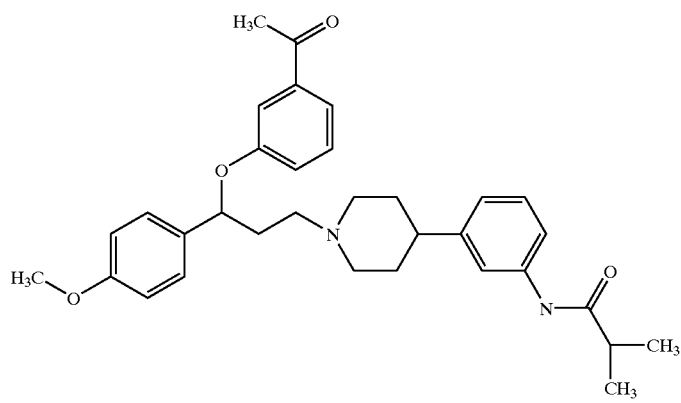 | 82.3 |
| 180 | 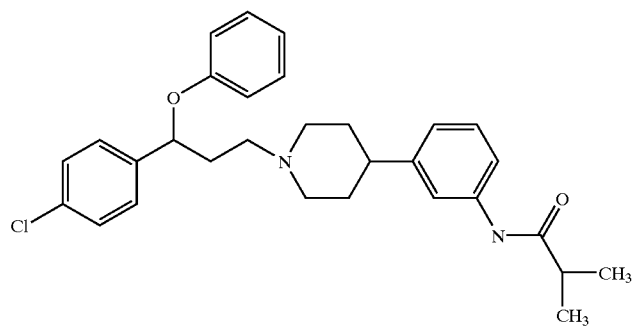 | 9.7 |
| 181 | 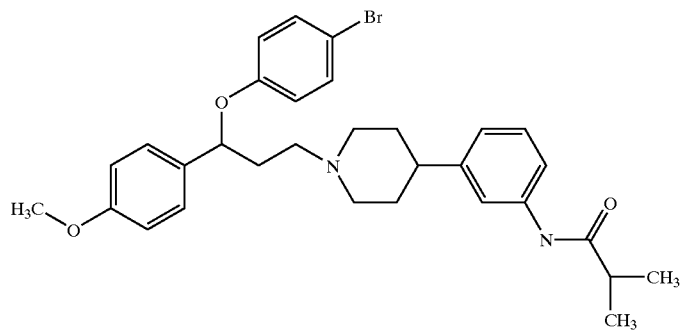 | 91.9 |

-continued
| | | |
|---|---|---|
| 182 | 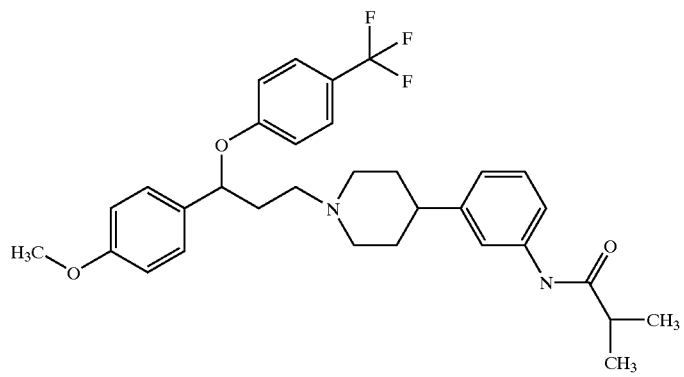 | 101.3 |
| 183 | 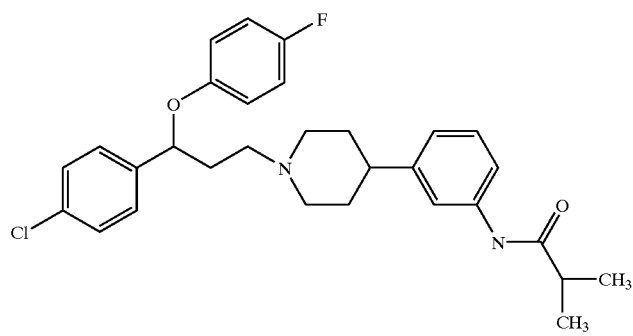 | 4.0 |
| 184 | 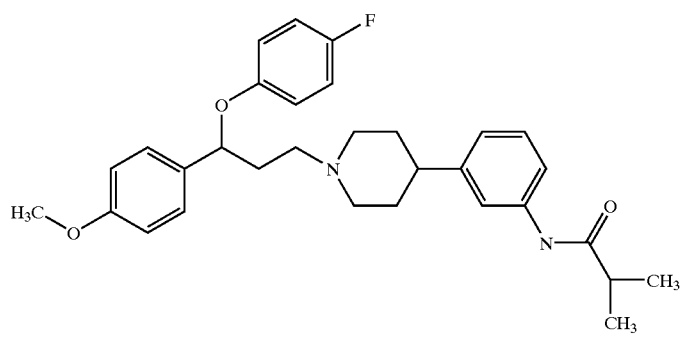 | 105.2 |
| 185 | 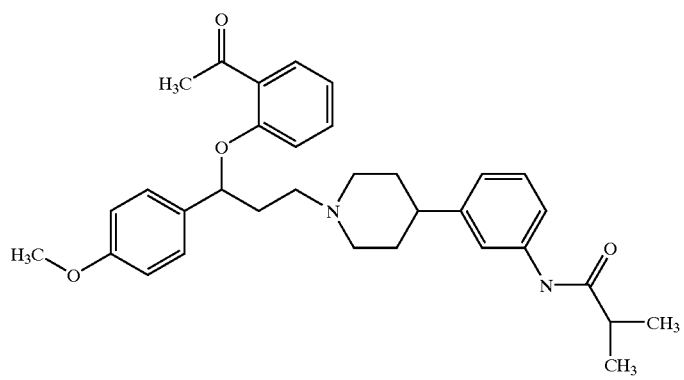 | 20.6 |

| | | |
|---|---|---|
| 186 | 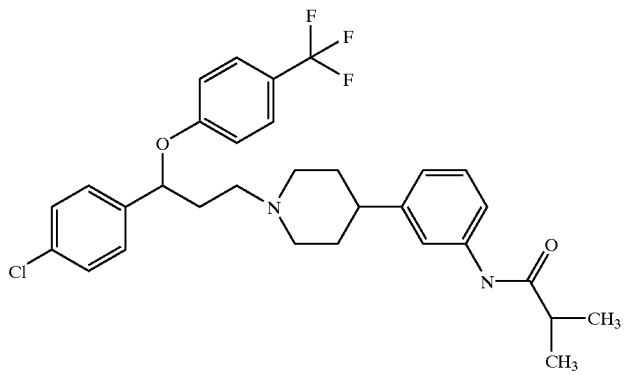 | 4.9 |
| 187 | 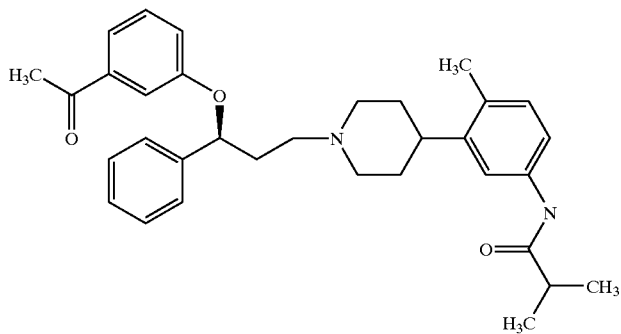  Chiral | 15.6 |
| 188 | 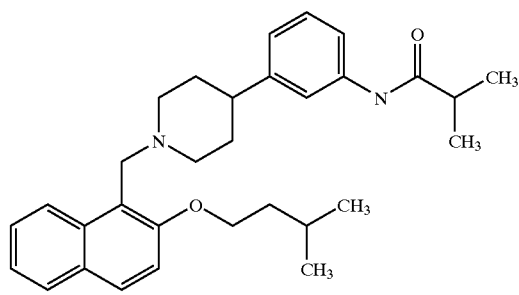 | 531.5 |
| 189 | 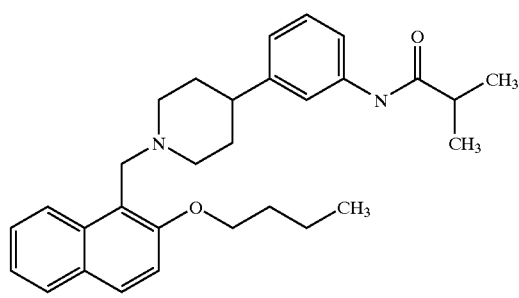 | 438.3 |

-continued
| | | |
|---|---|---|
| 190 | 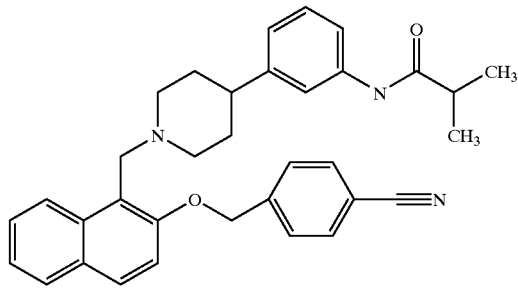 | 435.6 |
| 191 | 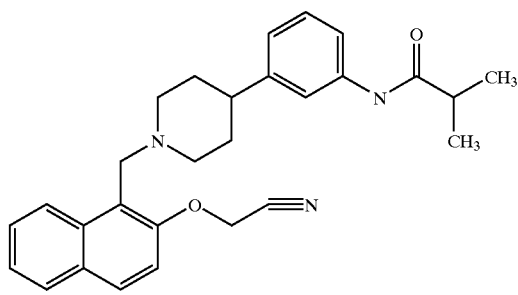 | 648.7 |
| 192 | 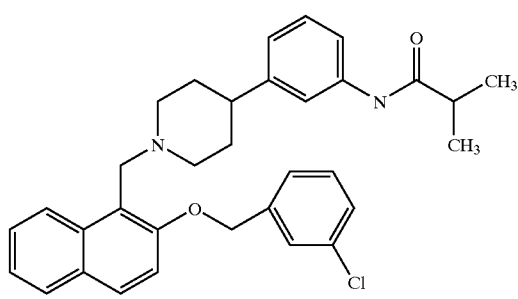 | 80.5 |
| 193 | 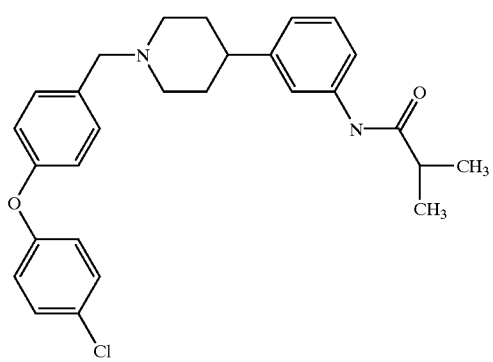 | 5.2 |
| 194 | 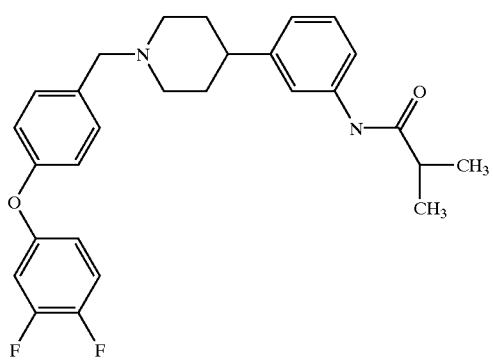 | 1.8 |

| | | |
|---|---|---|
| 195 | 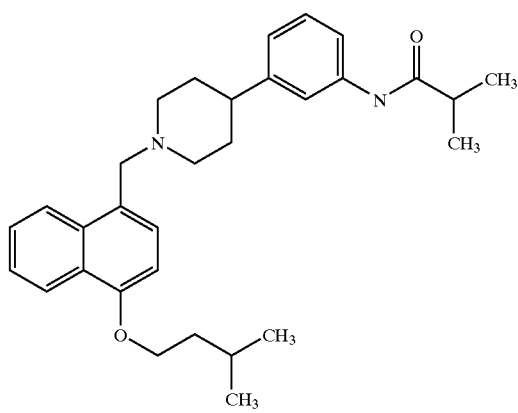 | 106.0 |
| 196 | 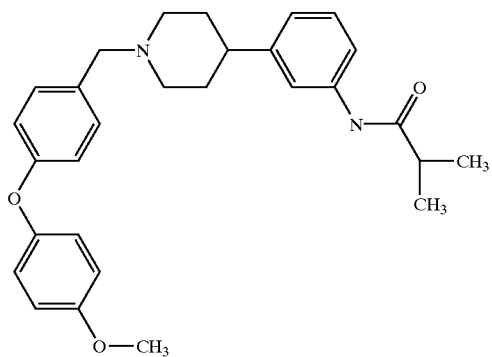 | 35.2 |
| 197 | 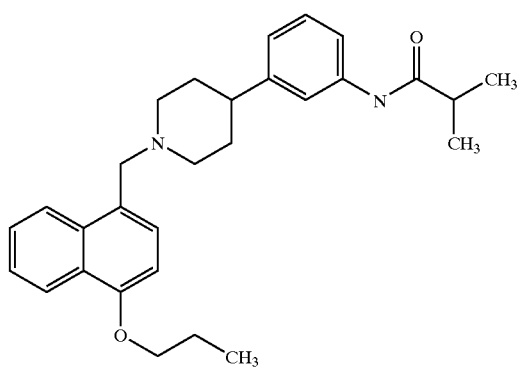 | 63.1 |
| 198 | 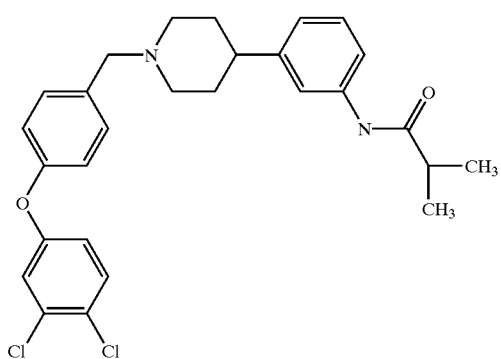 | 6.1 |

-continued
| | | |
|---|---|---|
| 199 | 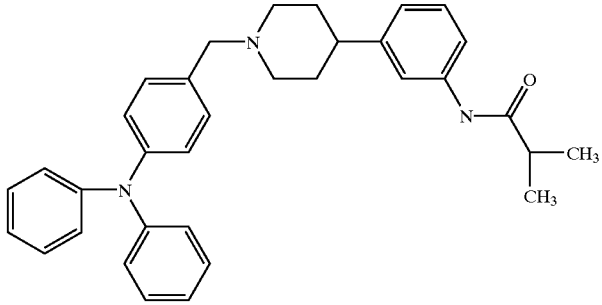 | 3.6 |
| 200 | 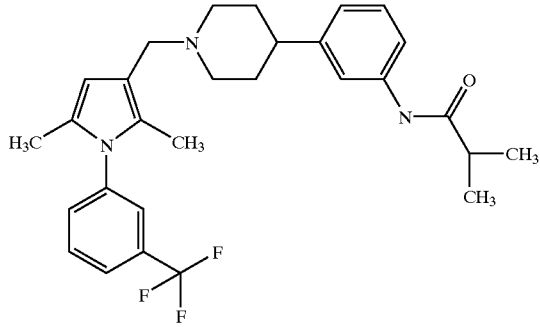 | 20.9 |
| 201 | 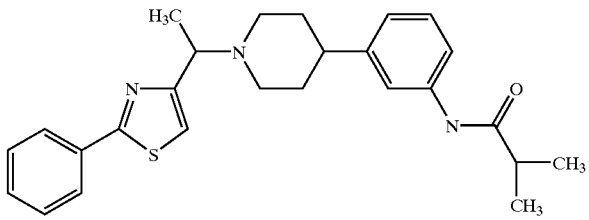 | 996.1 |
| 202 | 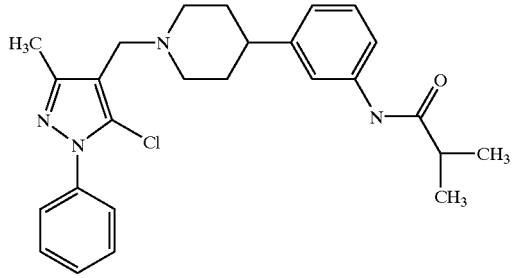 | 154.7 |
| 203 | 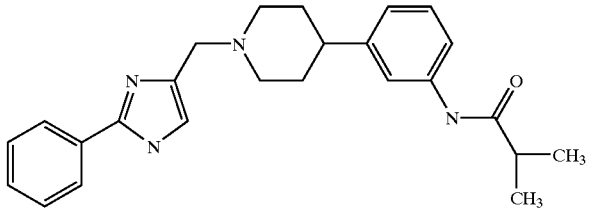 | 79.6 |

| | | |
|---|---|---|
| 204 | 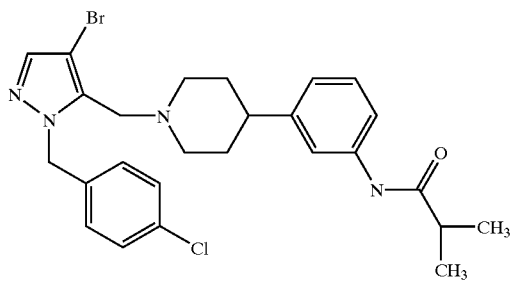 | 39.8 |
| 205 | 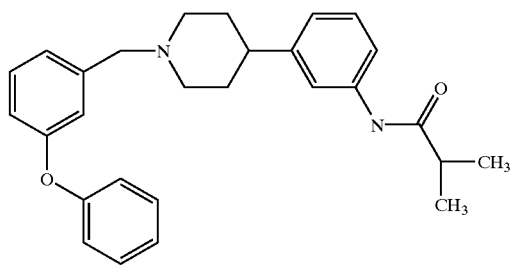 | 28.0 |
| 206 | 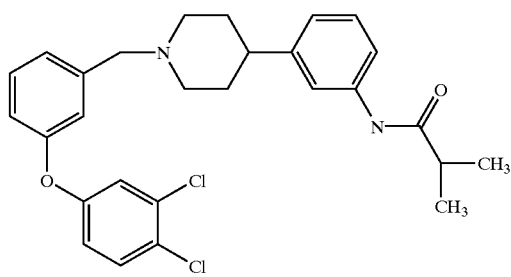 | 17.7 |
| 207 | 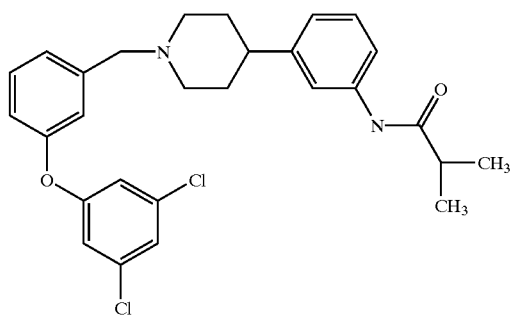 | 136.8 |
| 208 | 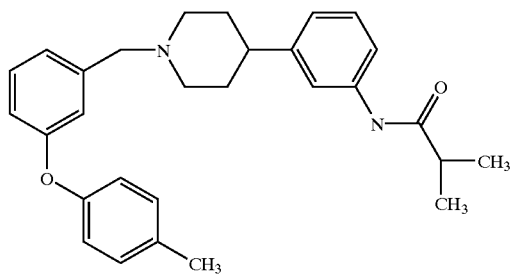 | 30.8 |

-continued
| | | |
|---|---|---|
| 209 | 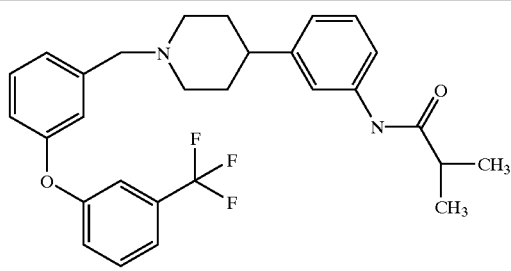 | 64.8 |
| 210 | 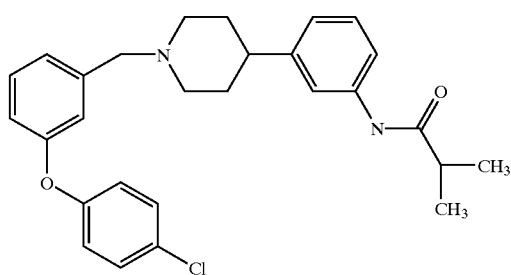 | 23.3 |
| 211 | 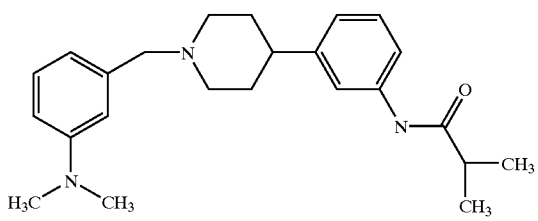 | 111.3 |
| 212 | 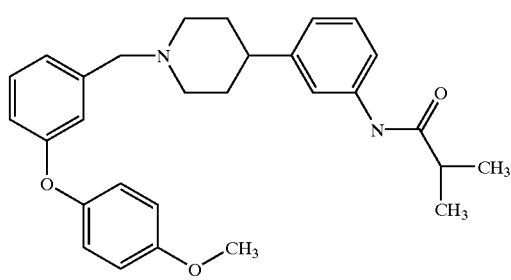 | 43.0 |
| 213 | 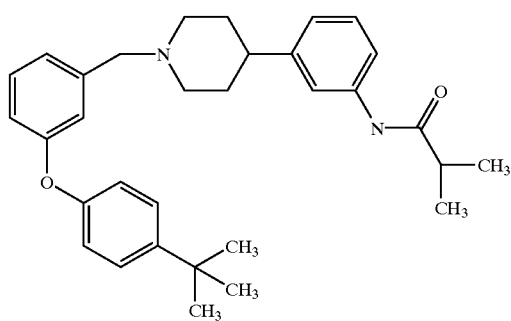 | 519.1 |

-continued
| | | |
|---|---|---|
| 214 | 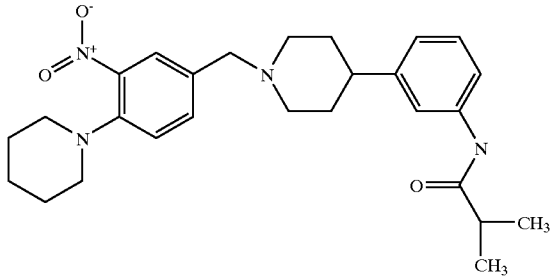 | 56.3 |
| 215 | 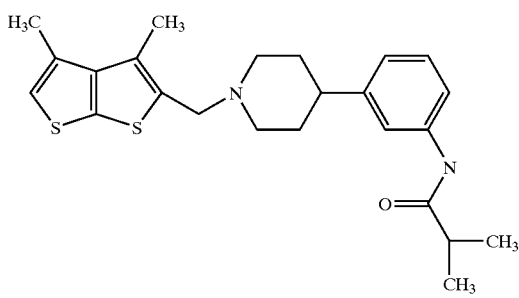 | 283.1 |
| 216 | 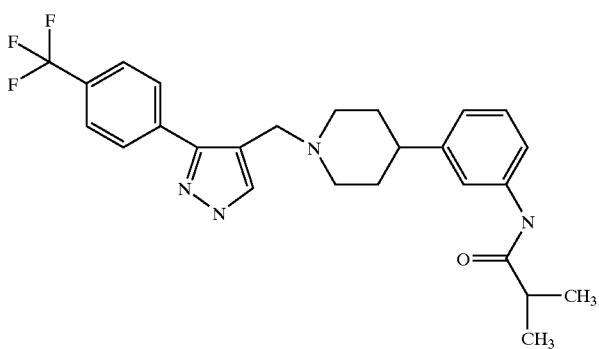 | 817.9 |
| 217 | 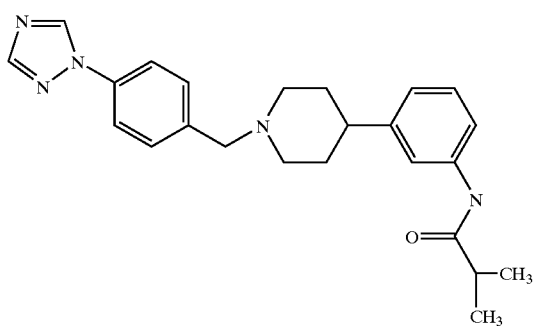 | 300.1 |
| 218 | 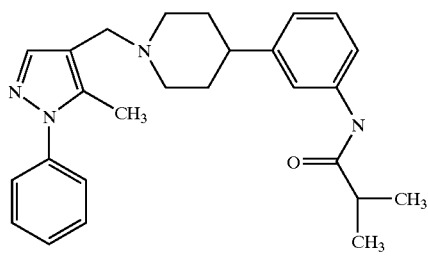 | 125.6 |

-continued
| | | |
|---|---|---|
| 219 | 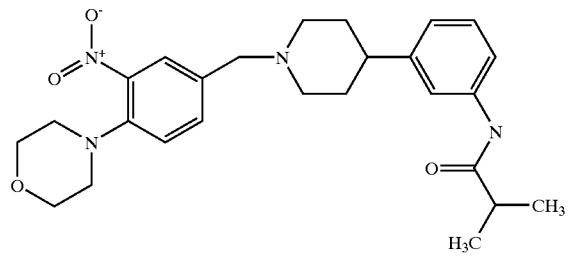 | 68.8 |
| 220 | 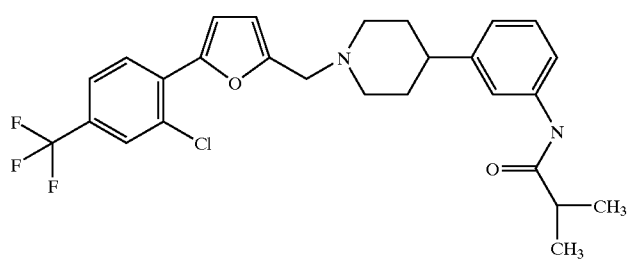 | 158.6 |
| 221 | 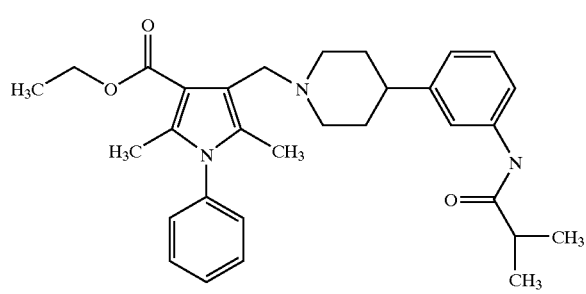 | 545.7 |
| 222 | 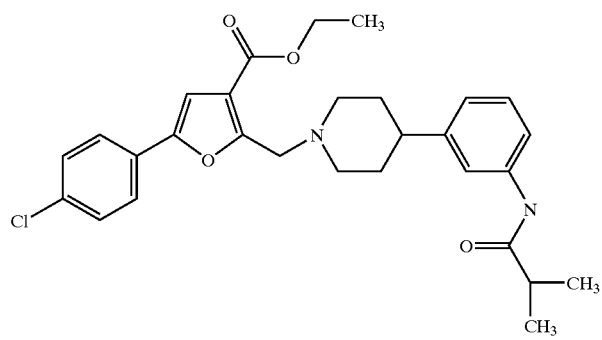 | 152.4 |
| 223 | 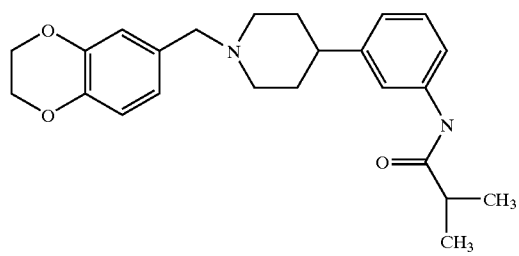 | 318.2 |

-continued
| 224 | 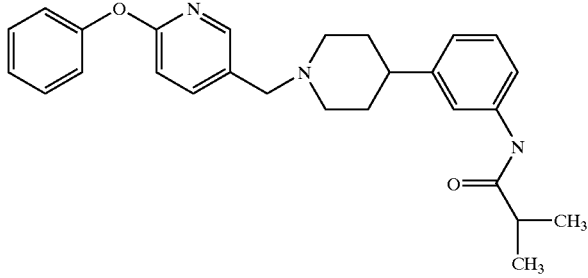 | 48.0 |
| --- | --- | --- |
| 225 | 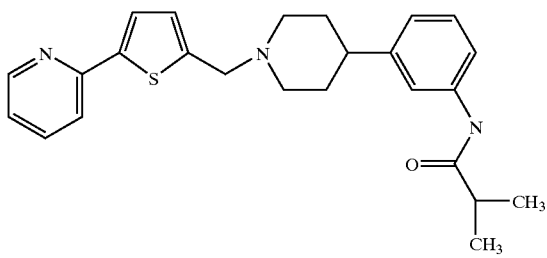 | 213.6 |
| 226 | 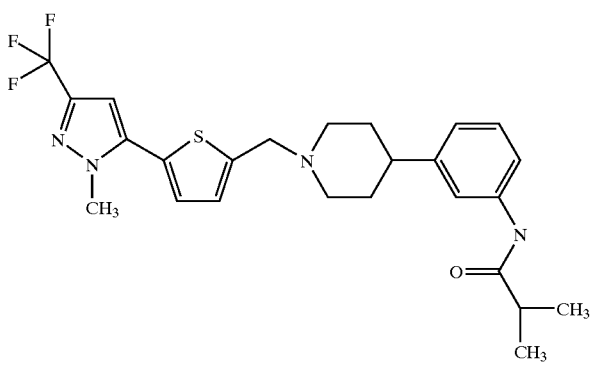 | 238.8 |
| 227 | 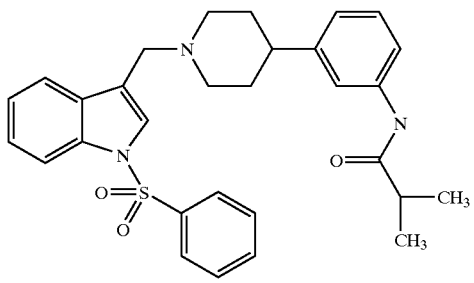 | 261.6 |
| 228 | 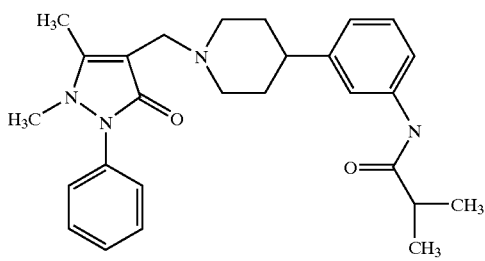 | 841.1 |

-continued
| | | |
|---|---|---|
| 229 | 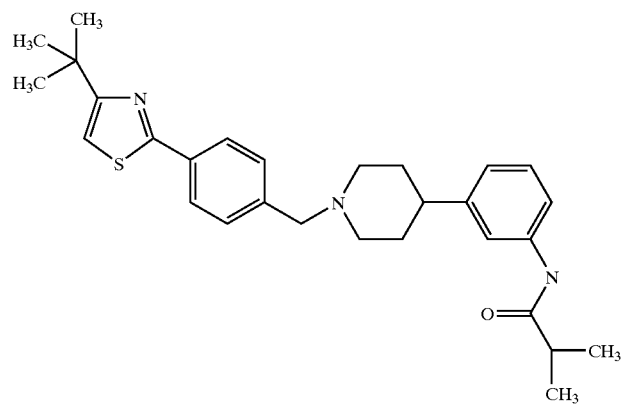 | 884.5 |
| 230 | 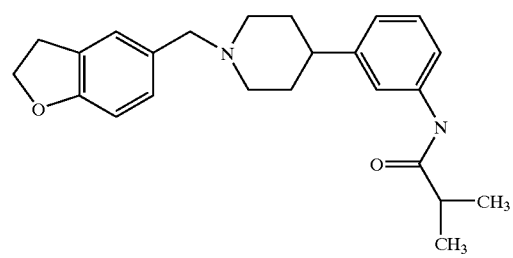 | |
| 231 | 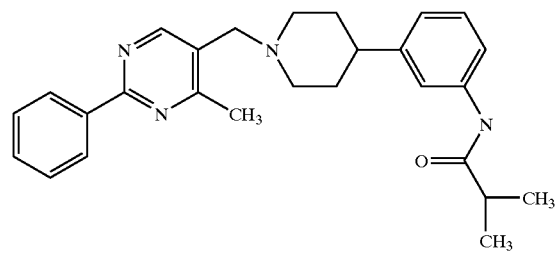 | 596.4 |
| 232 | 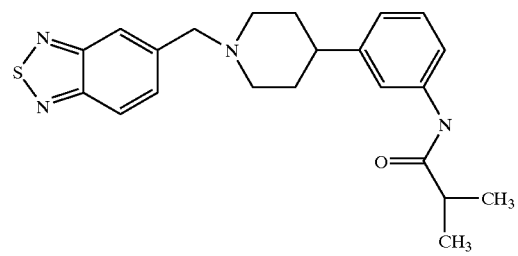 | 431.2 |
| 233 | 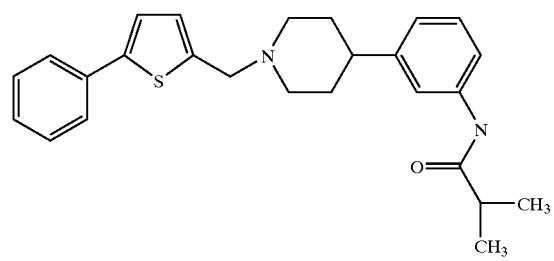 | 124.7 |

-continued
| | | |
|---|---|---|
| 234 | 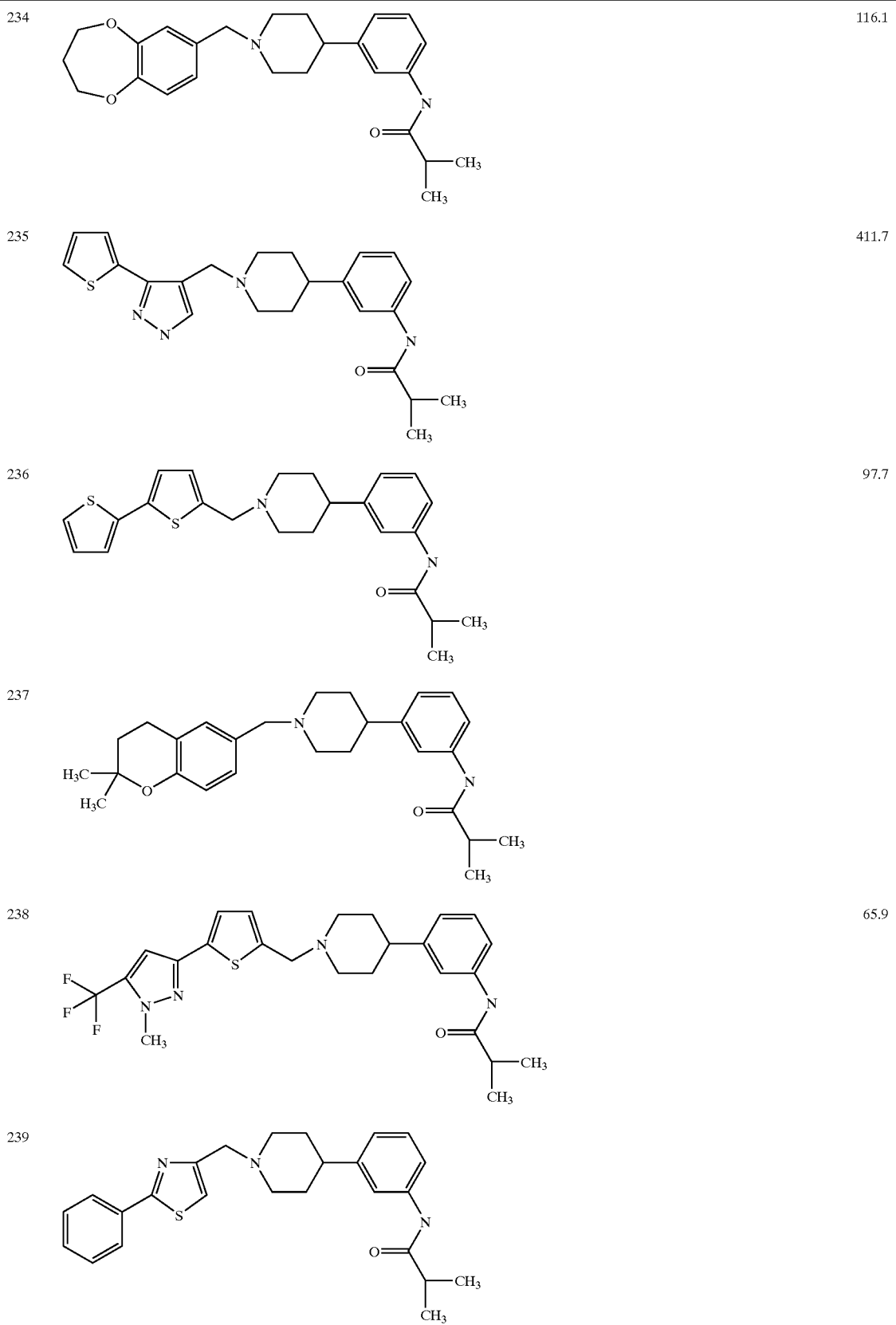 | 116.1 |
| 235 | | 411.7 |
| 236 | | 97.7 |
| 237 | | |
| 238 | | 65.9 |
| 239 | | |

240 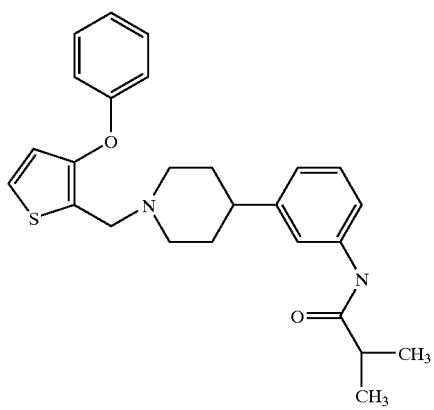
241 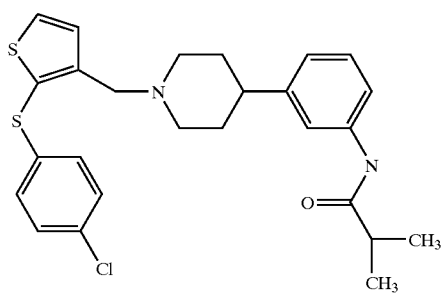
242 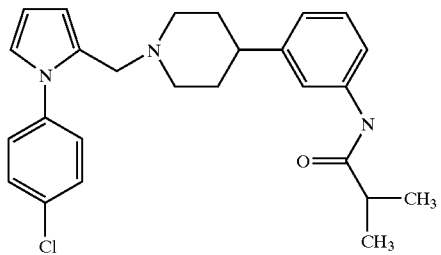
243 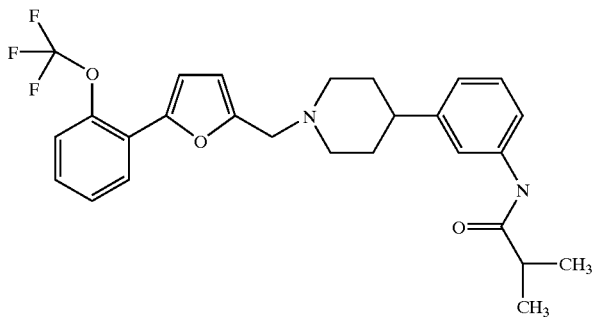

-continued
244
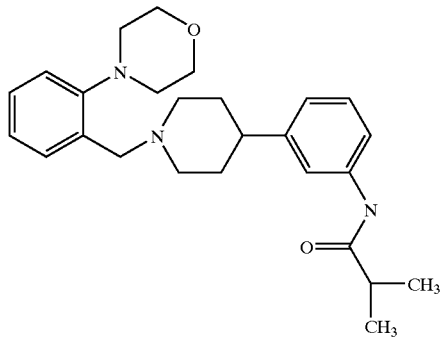
245
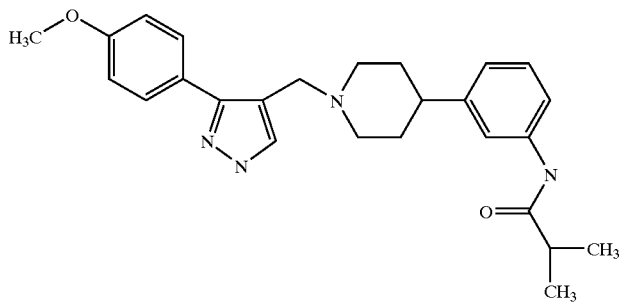
246
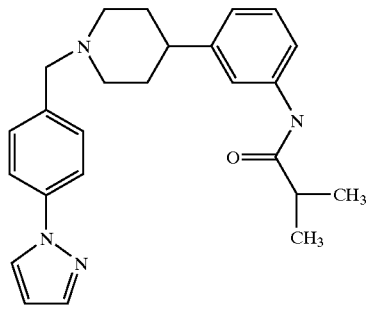
247
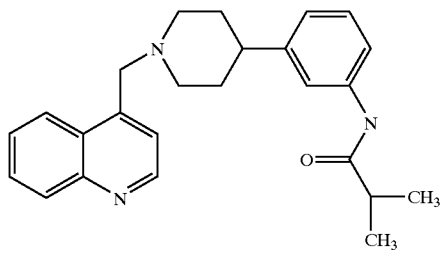
248
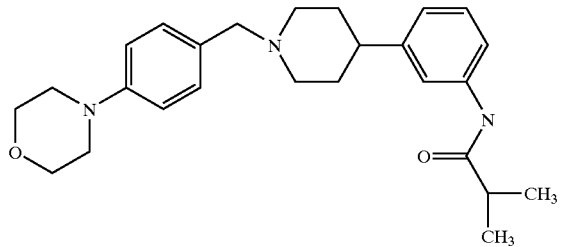

-continued
| 249 | 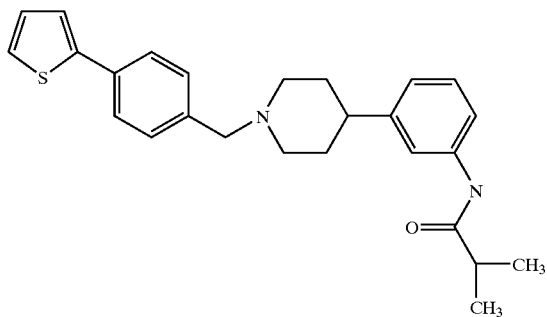 | |
| --- | --- | --- |
| 250 | 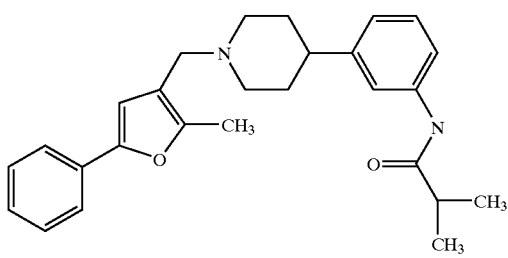 | |
| 251 | 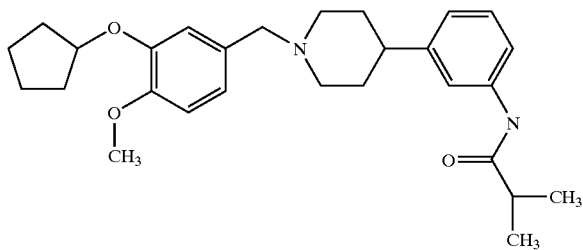 | |
| 252 | 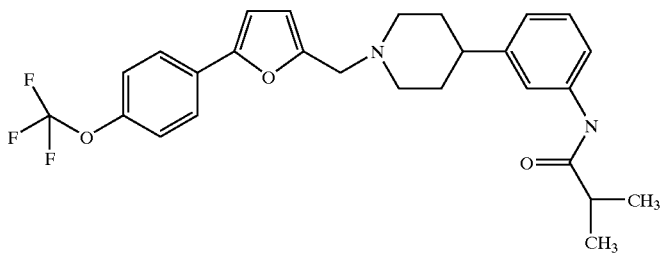 | |
| 253 | 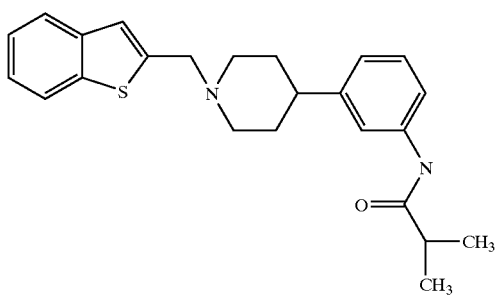 | 361.6 |

-continued
| | | |
|---|---|---|
| 254 | 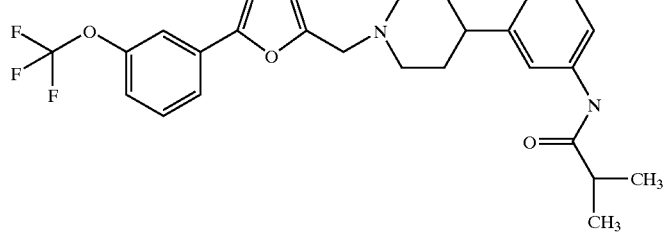 | 400.7 |
| 255 | 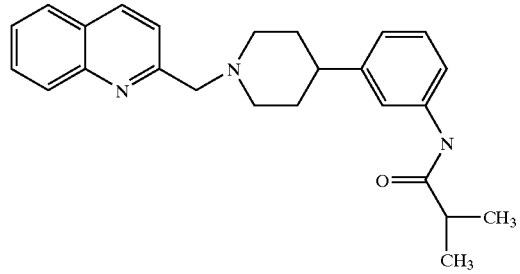 | 589.8 |
| 256 | 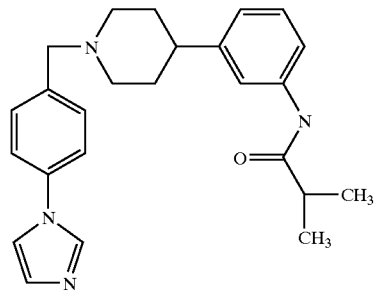 | 320.5 |
| 257 | 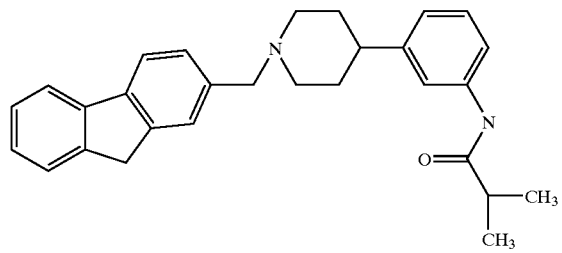 | 37.2 |
| 258 | 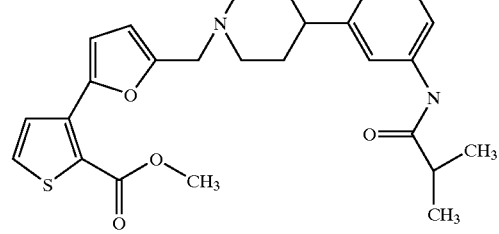 | 110.3 |
| 259 | 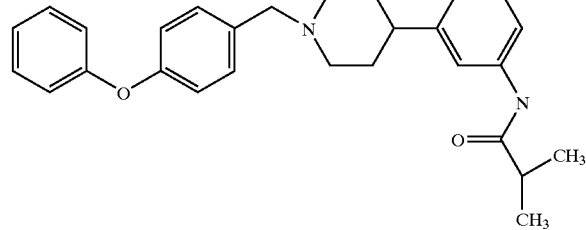 | 15.4 |

-continued
| | | rMCH-1 Ki (nM) |
|---|---|---|
| 260 | 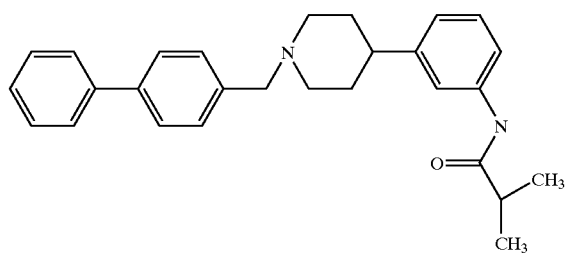 | 77.7 |
| 261 | 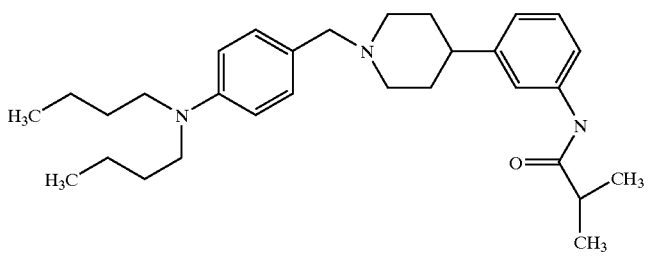 | 6.5 |
| 262 | 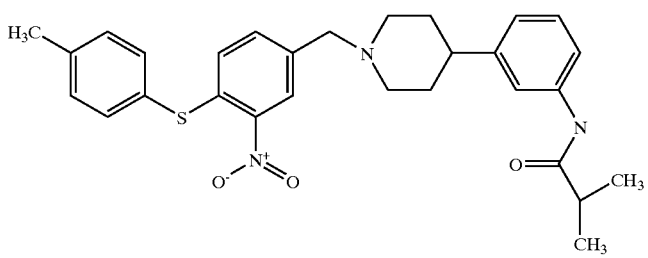 | 64.1 |
| 263 | 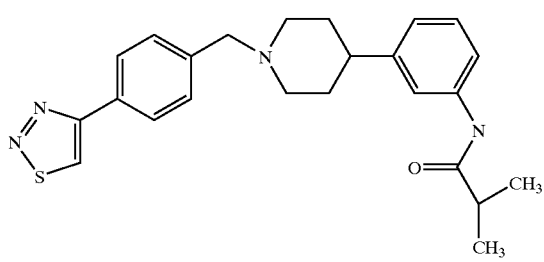 | 156.0 |
| Example | Structure | rMCH-1 Ki (nM) |
|---|---|---|
| 264 | 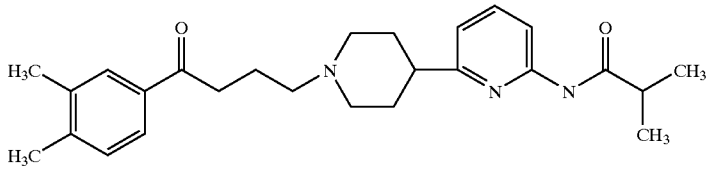 | 54.7 |
| 265 | 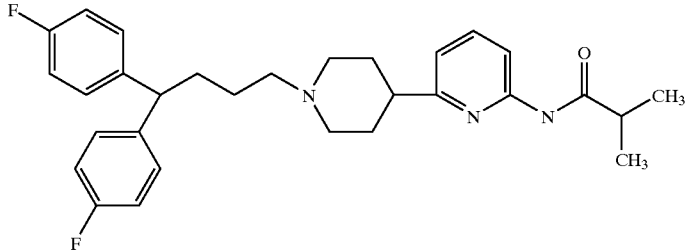 | 13.5 |

-continued
| | | |
|---|---|---|
| 266 | 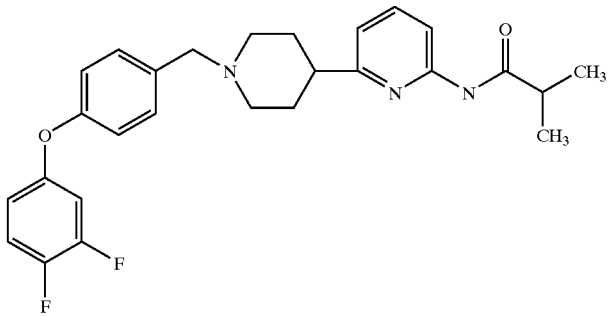 | 6.4 |
| 267 | 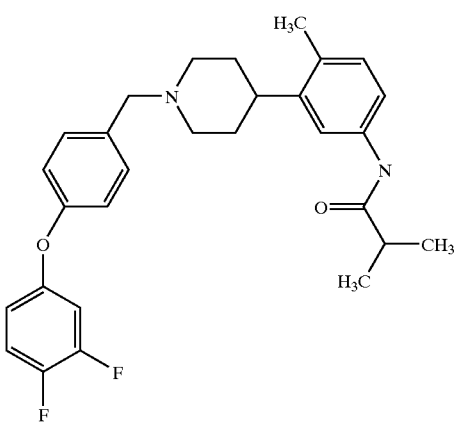 | 2.2 |
| 268 | 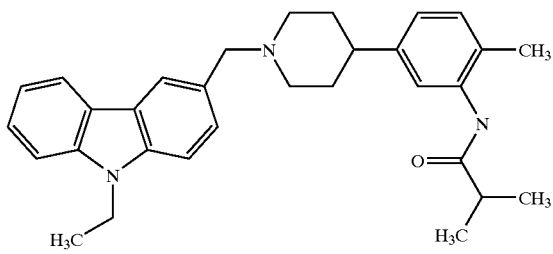 | 20.3 |
| 269 | 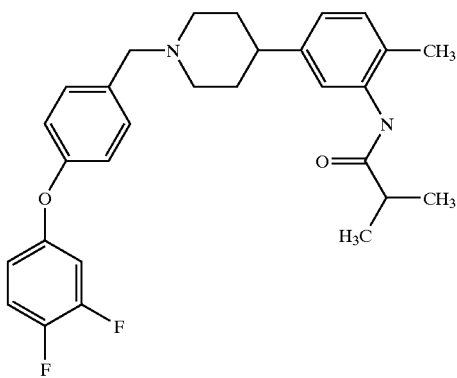 | 27.4 |

-continued
| | | |
|---|---|---|
| 270 | 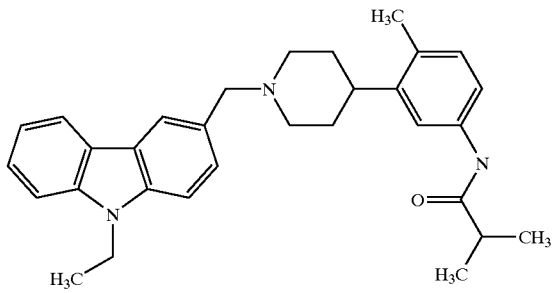 | 3.4 |
| 271 | 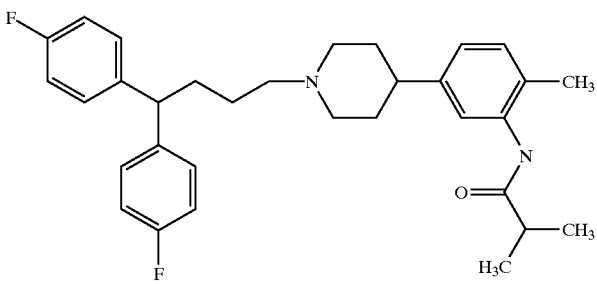 | 40.1 |
| 272 | 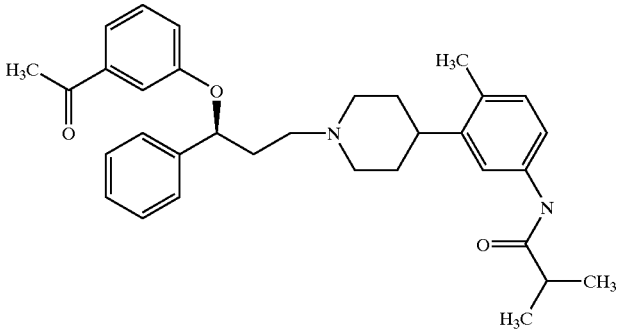<br>Chiral | 15.6 |
| 273 | 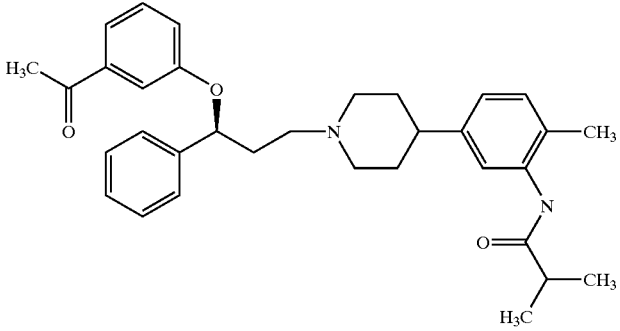<br>Chiral | 196.4 |

-continued
| | | |
|---|---|---|
| 274 | 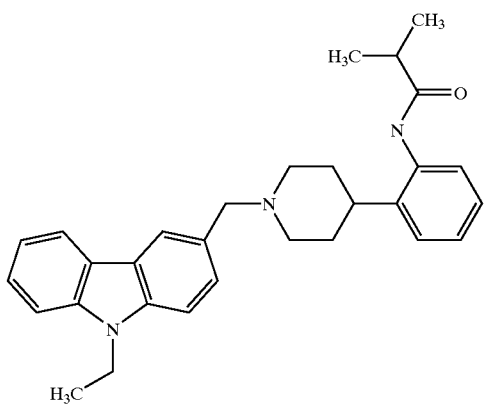 | 843.5 |
| 275 | 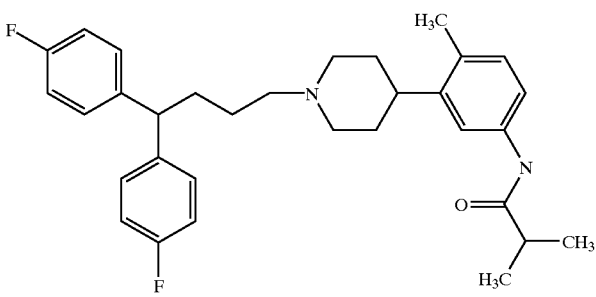 | 3.1 |
| 276 | 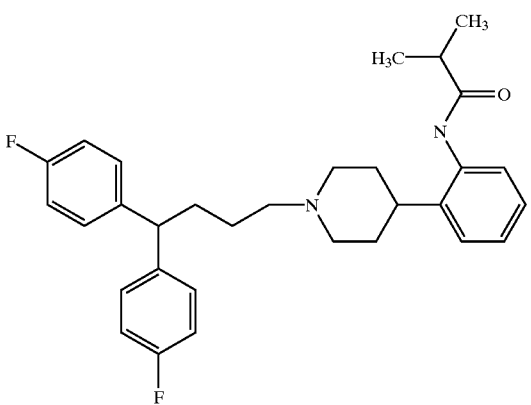 | 734.4 |
| 277 | 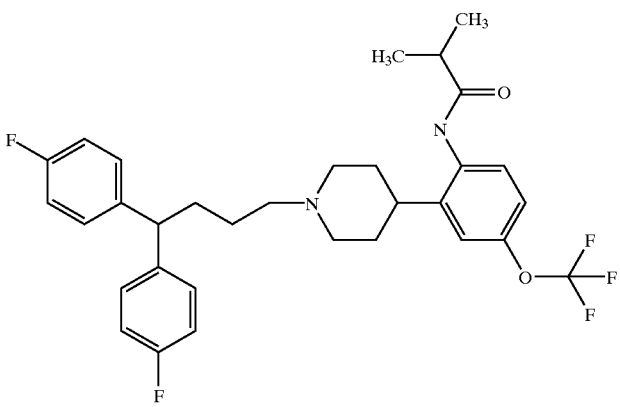 | 117.8 |

-continued
| | | |
|---|---|---|
| 278 | 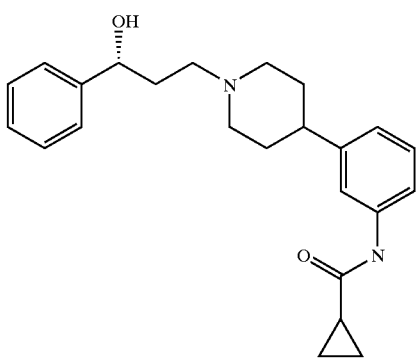 Chiral | 85.8 |
| 279 | 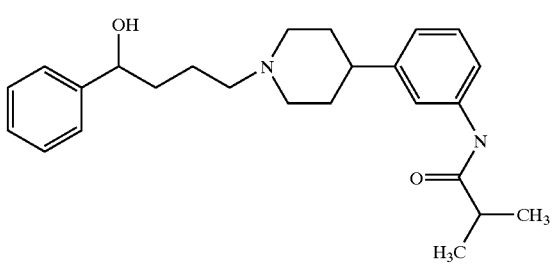 | 74.5 |
| 280 | 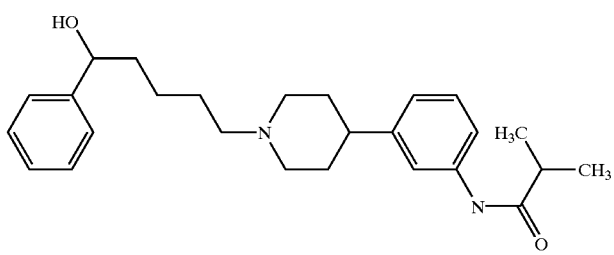 | 27.6 |
| 281 | 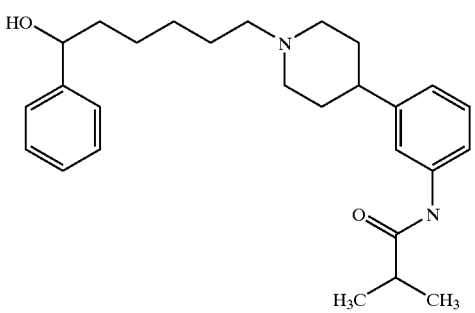 | 7.9 |
| 282 | 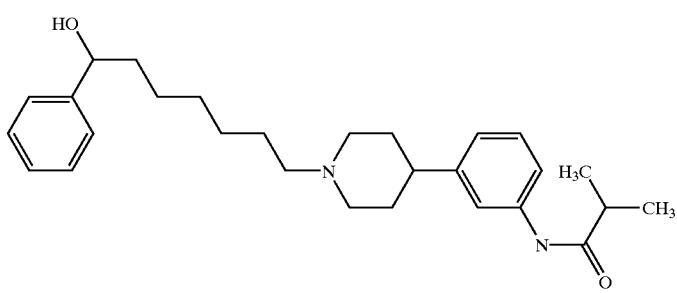 | 23.5 |

-continued
283 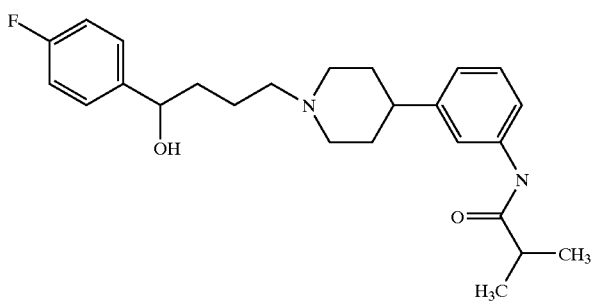
284 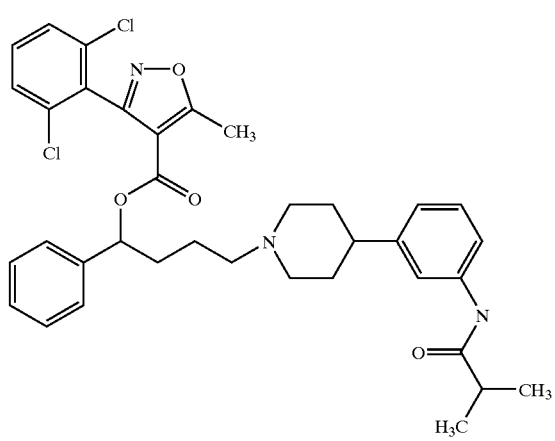 16.3
285 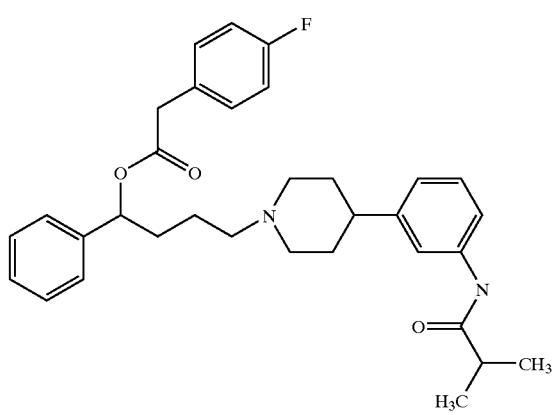 10.3
286 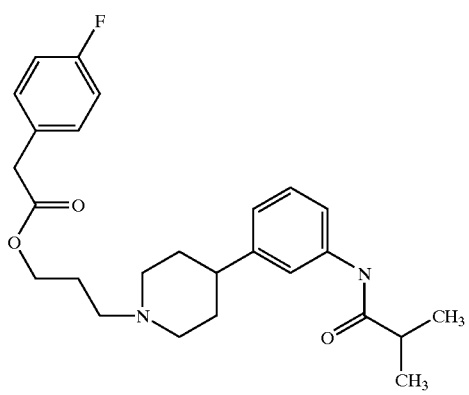 67.8

-continued
| | | |
|---|---|---|
| 287 | 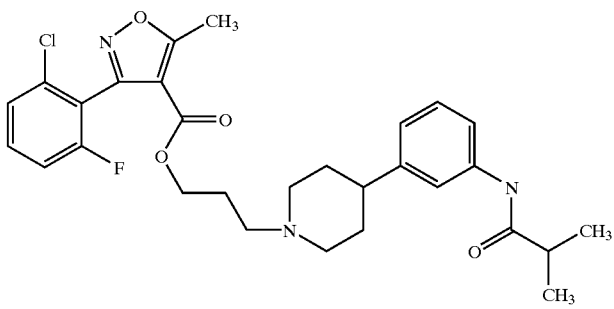 | 34.3 |
| 288 | 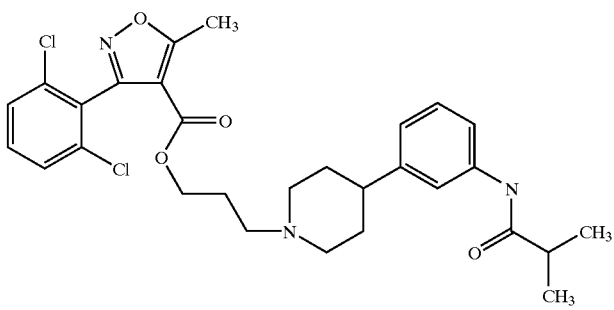 | 30.2 |
| 289 | 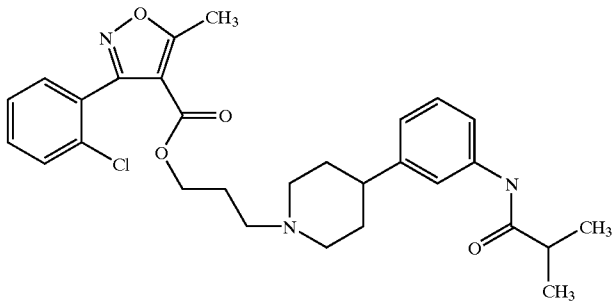 | 31.8 |
| 290 | 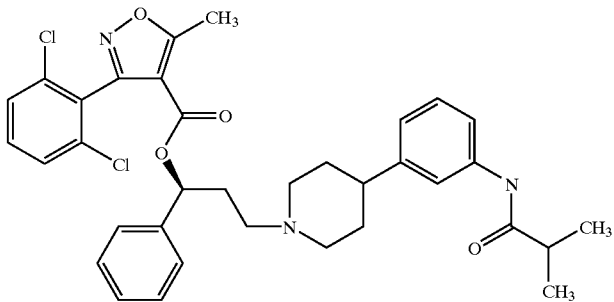 | 51.9 |

| | | |
|---|---|---|
| 291 | 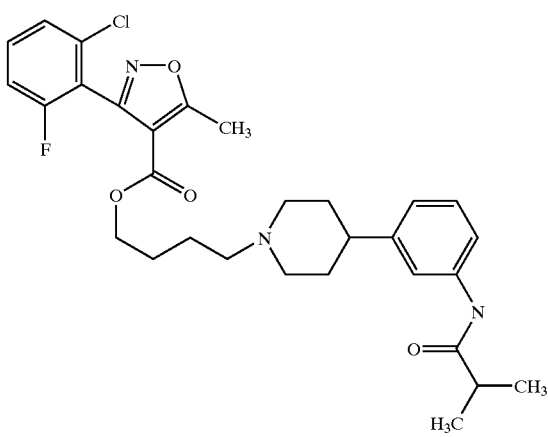 | 24.3 |
| 292 | 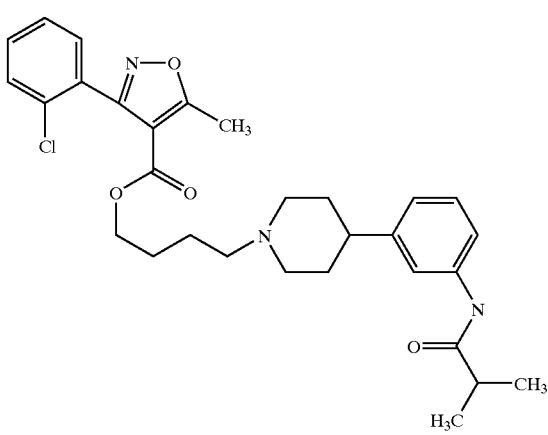 | 18.4 |
| 293 | 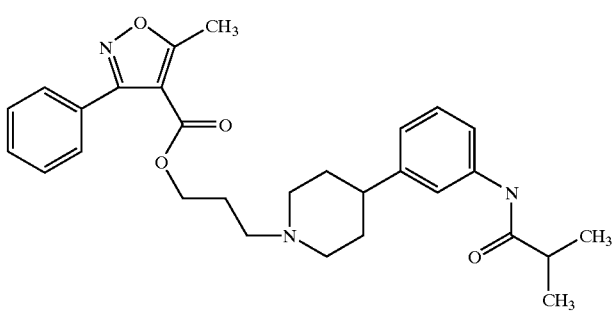 | 39.9 |
| 294 | 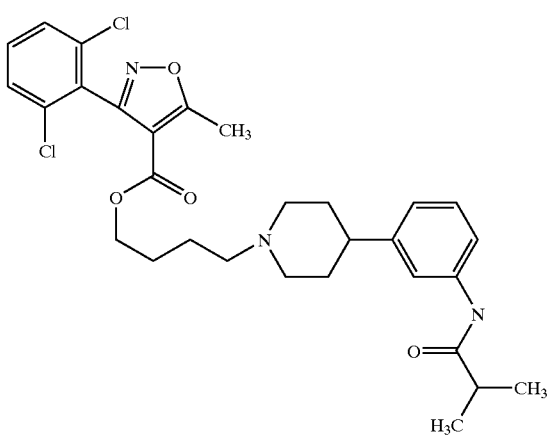 | 15.8 |

| | | -continued | |
|---|---|---|---|
| 295 | 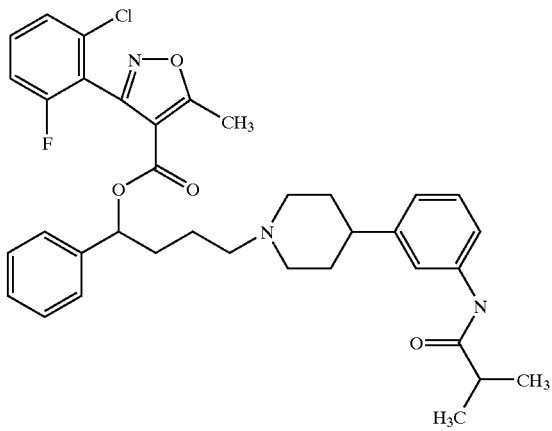 | | 8.7 |
| 296 | 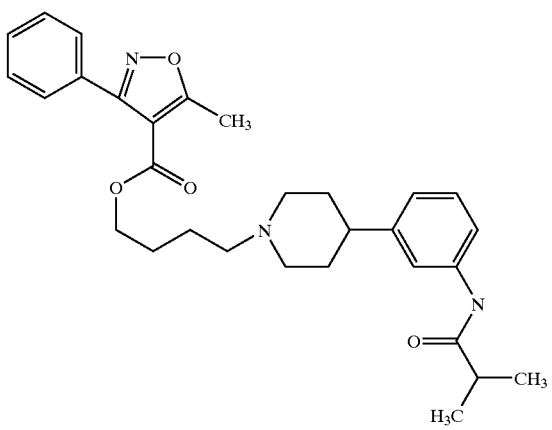 | | 20.0 |
| 297 | 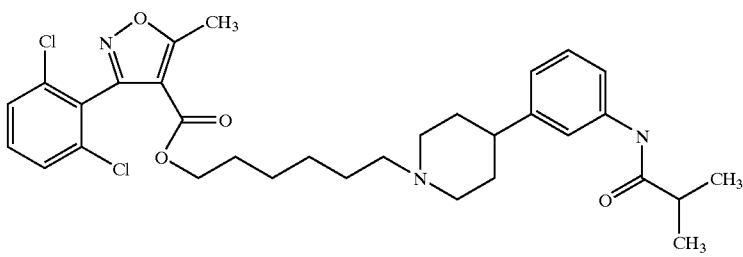 | | 11.9 |
| 298 | 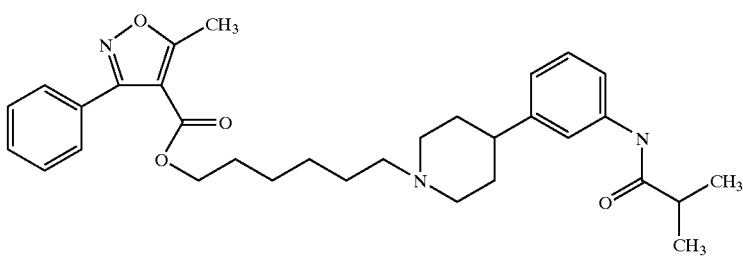 | | 40.1 |

| | | |
|---|---|---|
| 299 | 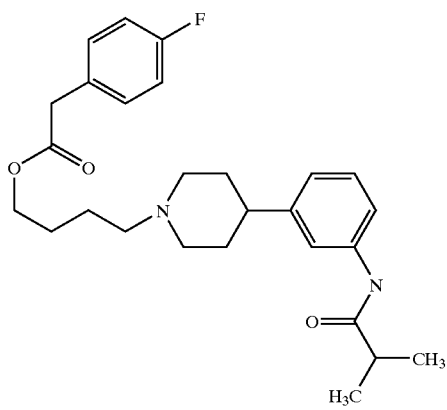 | 37.5 |
| 300 | 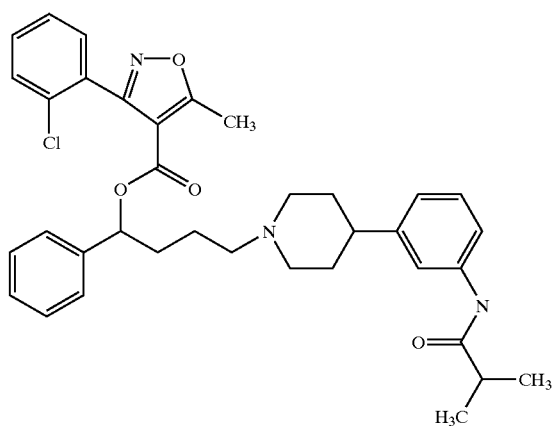 | 7.6 |
| 301 | 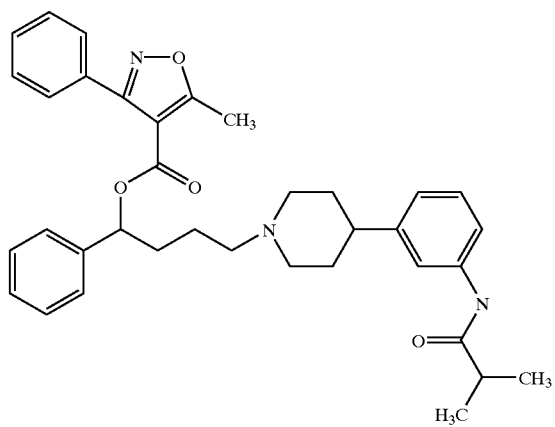 | |

-continued
| | | |
|---|---|---|
| 302 | 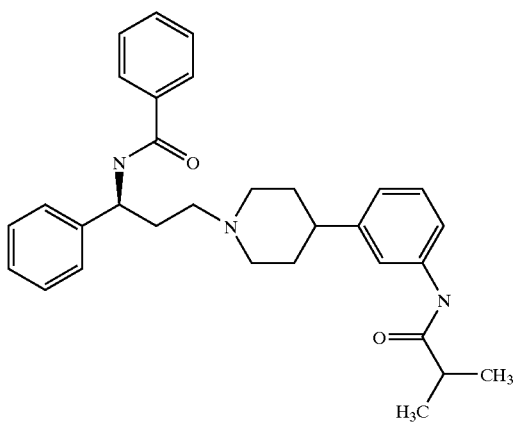<br>Chiral | 20.5 |
| 303 | 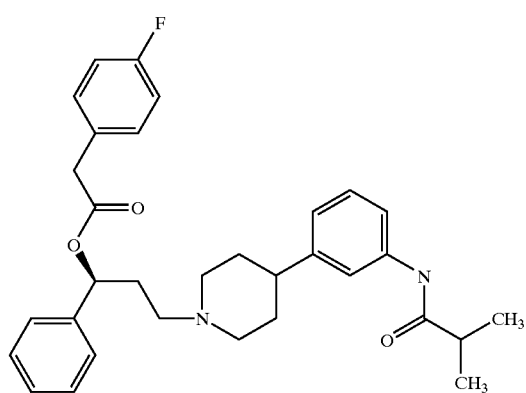 | 9.5 |
| 304 | 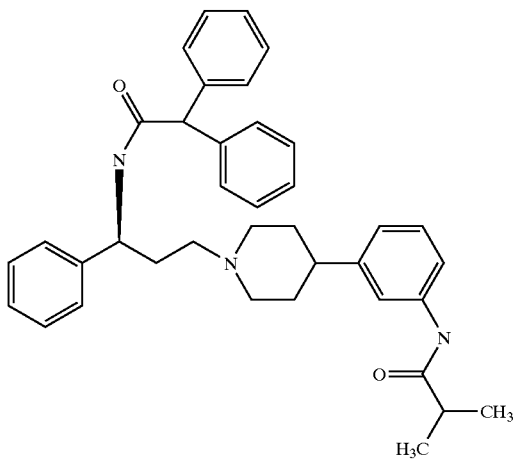<br>Chiral | 4.0 |

| | |
|---|---|
| 305 | 177.2 |
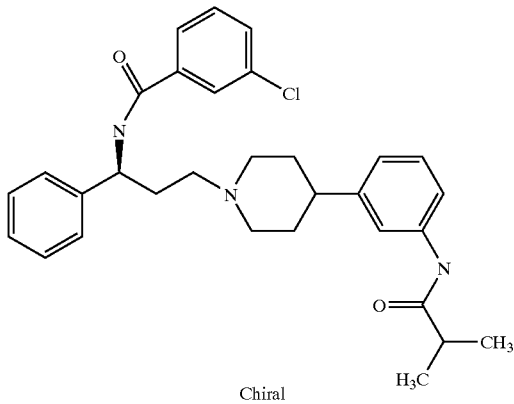
Chiral
| | |
|---|---|
| 306 | 167.9 |
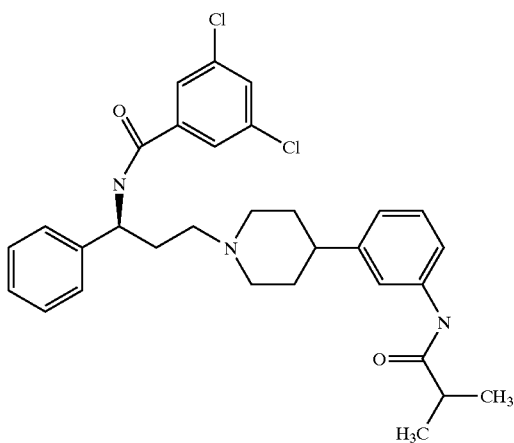
Chiral
| | |
|---|---|
| 307 | 97.4 |
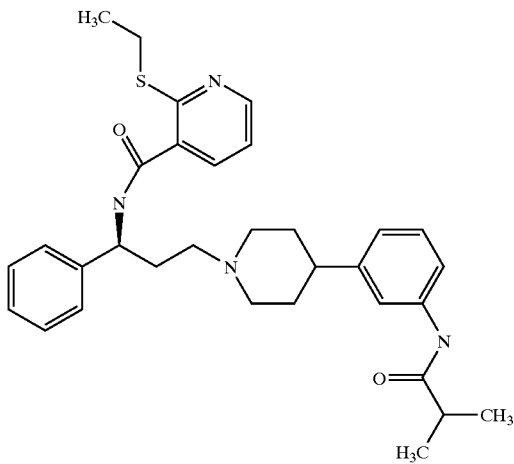
Chiral -continued
| 308 | 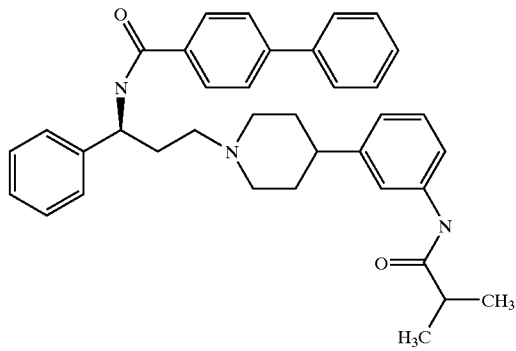 Chiral | 401.6 |
| 309 | 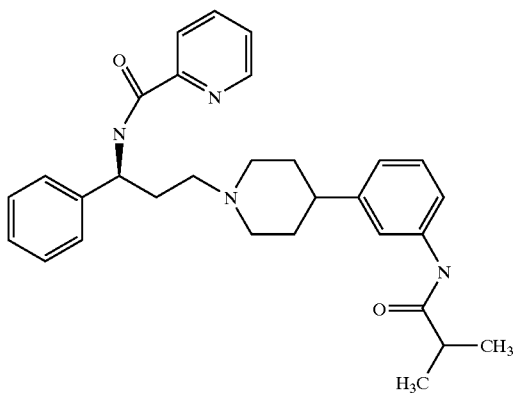 Chiral | 310.1 |
| 310 | 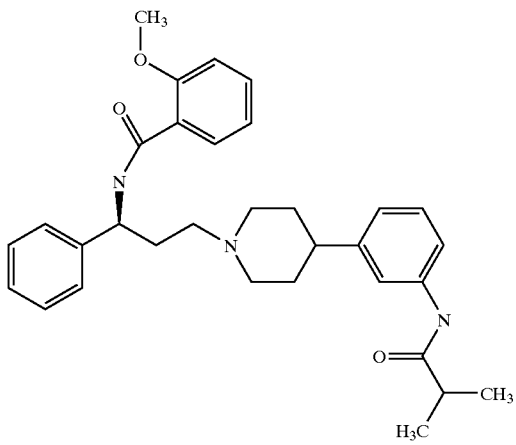 Chiral | 152.2 |

-continued
| | | |
|---|---|---|
| 311 | 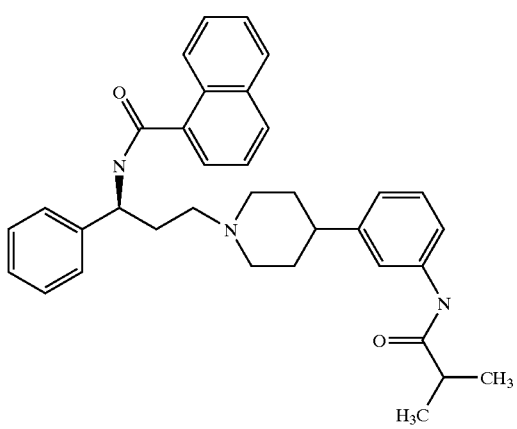
Chiral | 43.0 |
| 312 | 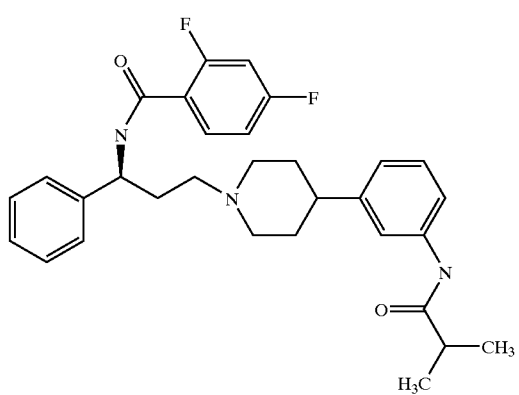
Chiral | 61.5 |
| 313 | 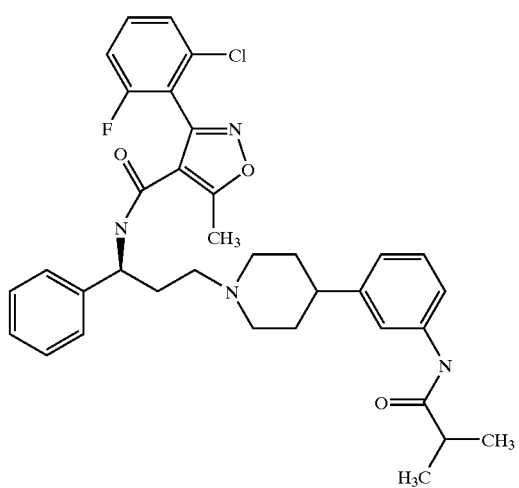
Chiral | 249.3 |

-continued
| | | |
|---|---|---|
| 314 | 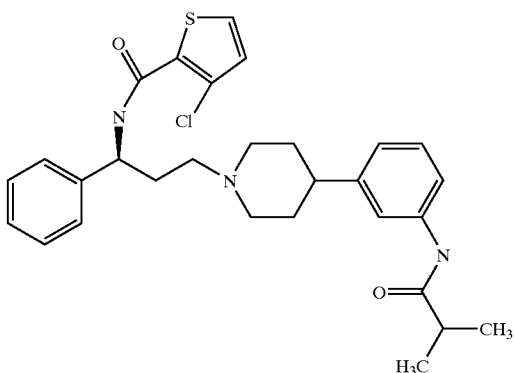 Chiral | 7.6 |
| 315 | 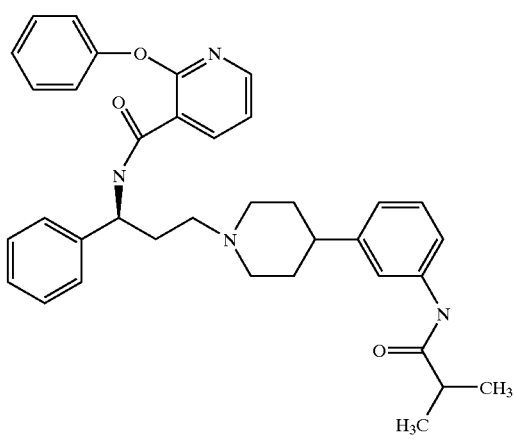 Chiral | 11.4 |
| 316 | 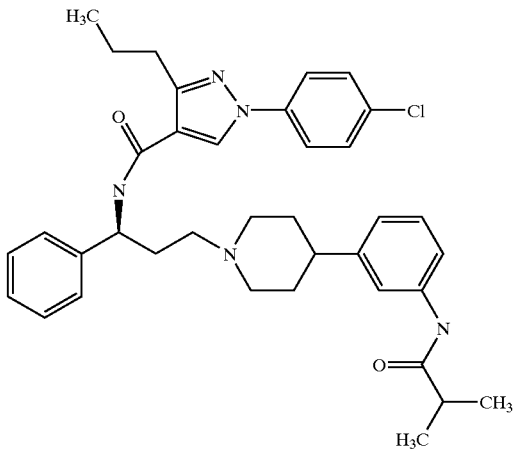 Chiral | 8.3 |

-continued
| | | |
|---|---|---|
| 317 | 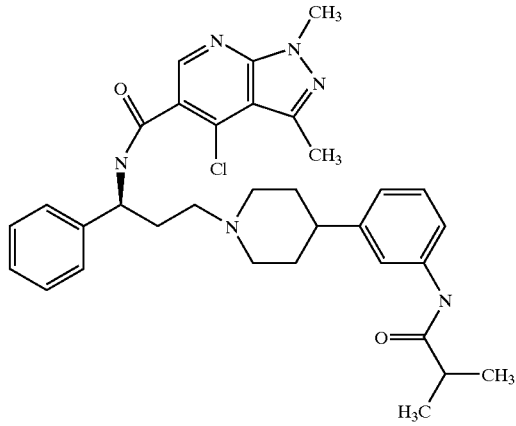<br>Chiral | 110.2 |
| 318 | 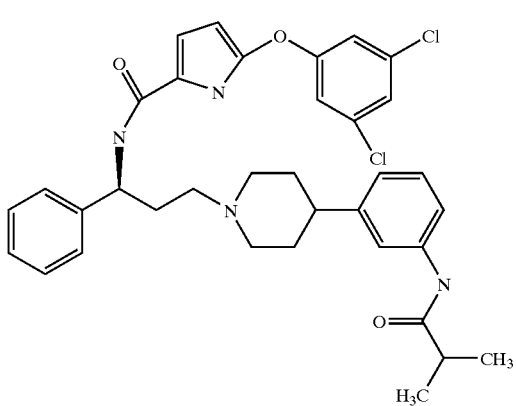<br>Chiral | 251.2 |
| 319 | 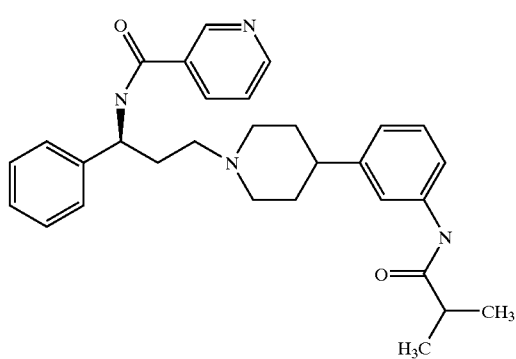<br>Chiral | 89.8 |

-continued
| | | |
|---|---|---|
| 320 | 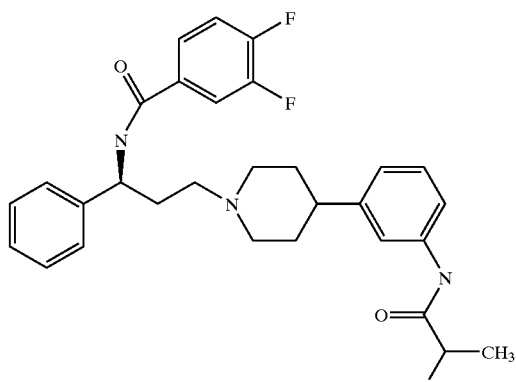 Chiral | 10.6 |
| 321 | 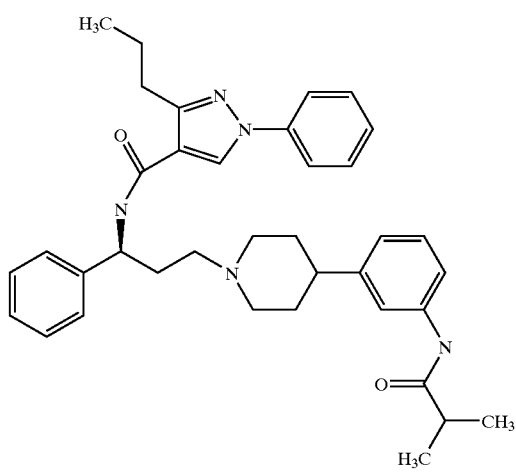 Chiral | 50.9 |
| 322 | 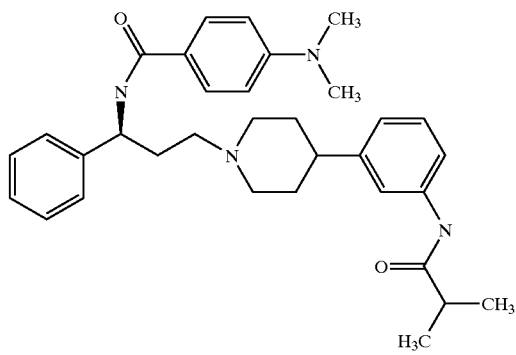 Chiral | 99.9 |

-continued
| 323 | 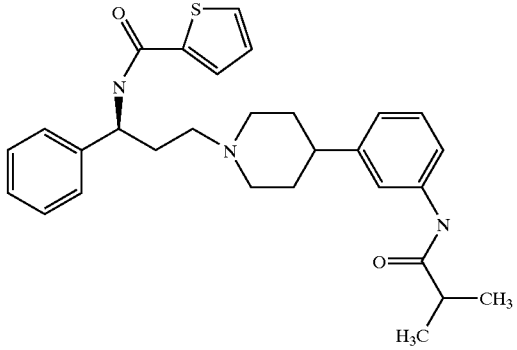 Chiral | 37.0 |
| 324 | 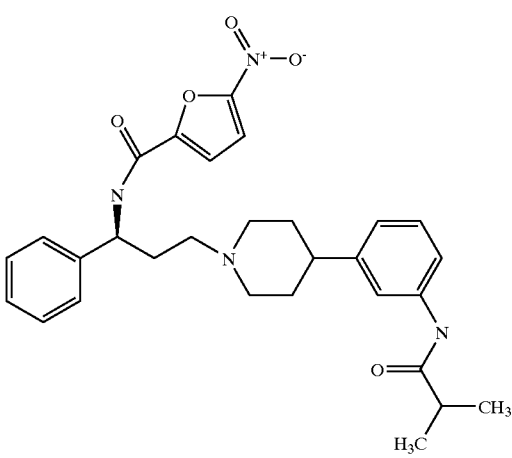 Chiral | 76.8 |
| 325 | 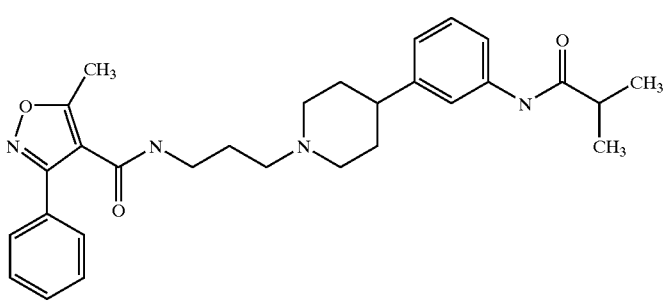 | 29.8 |
| 326 | 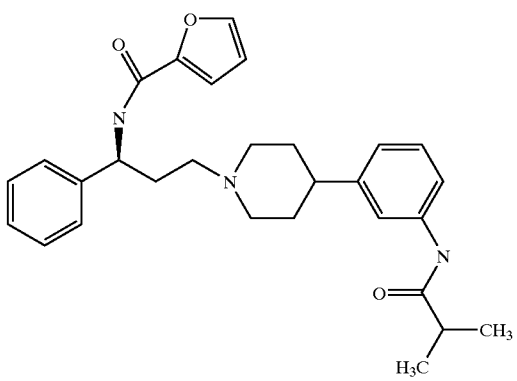 Chiral | 19.2 |

-continued
| 327 | 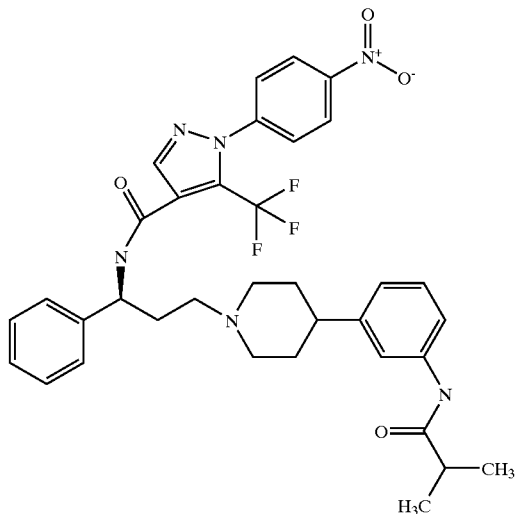 Chiral | 7.7 |
| 328 | 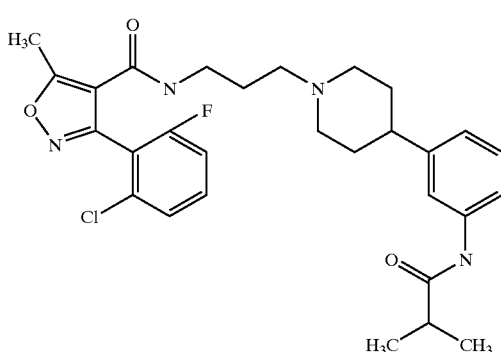 | 47.6 |
| 329 | 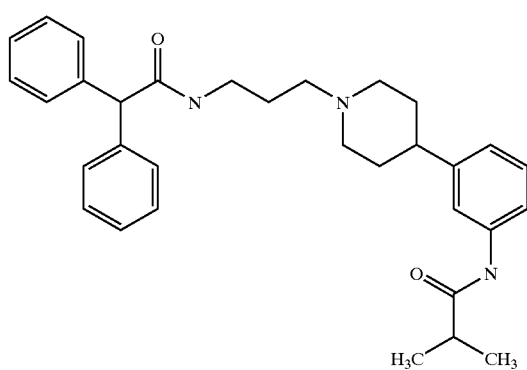 | 2.9 |
| 330 | 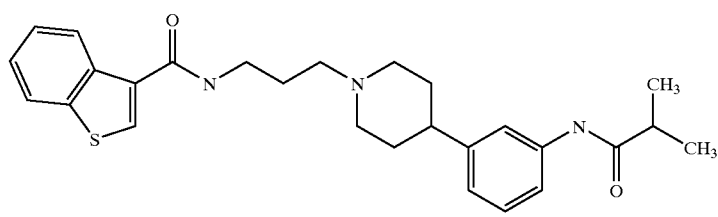 | 215.0 |

| | | |
|---|---|---|
| 331 | 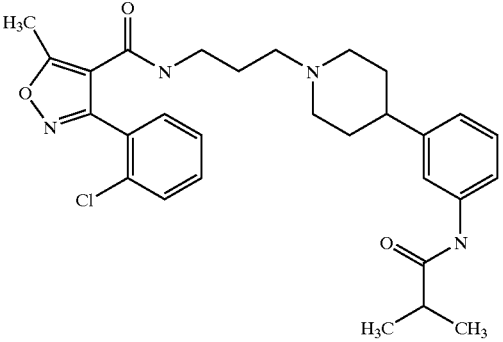 | 51.3 |
| 332 | 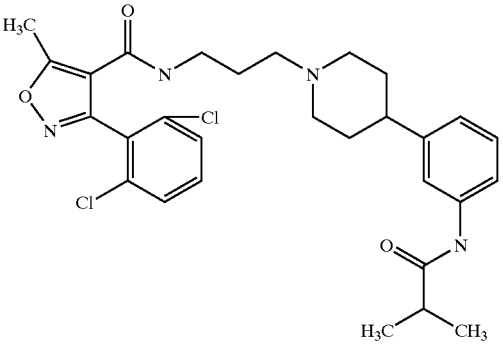 | 29.0 |
| 333 | 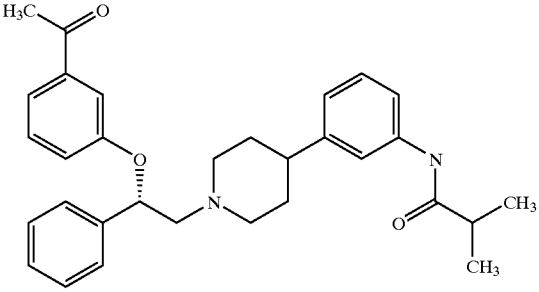<br>Chiral | 567.8 |
| 334 | 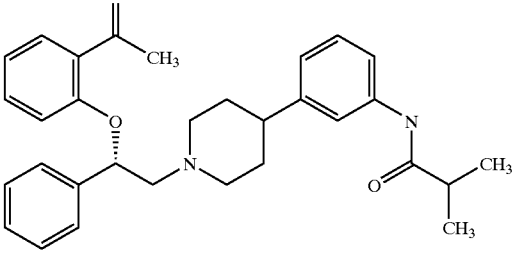<br>Chiral | 602.8 |

-continued
| | | |
|---|---|---|
| 335 | 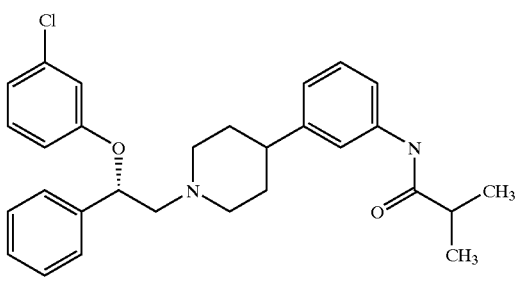 Chiral | 887.7 |
| 336 | 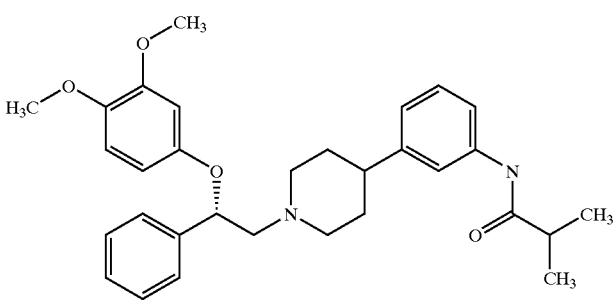 Chiral | 693.0 |
| 337 | 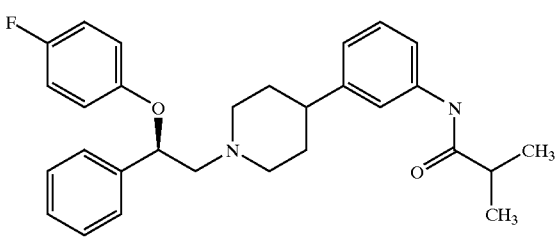 Chiral | 907.4 |
| 338 | 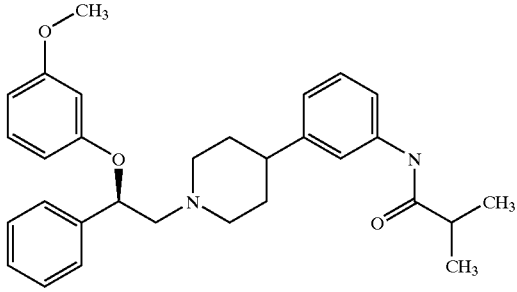 Chiral | 843.9 |
| 339 | 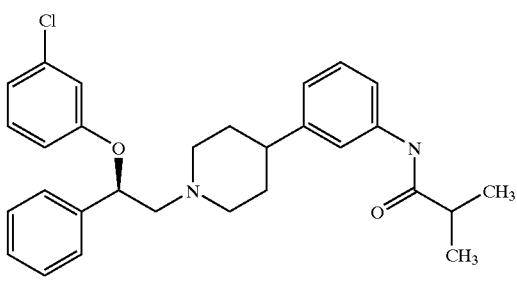 Chiral | 889.9 |

-continued
| | | |
|---|---|---|
| 340 | 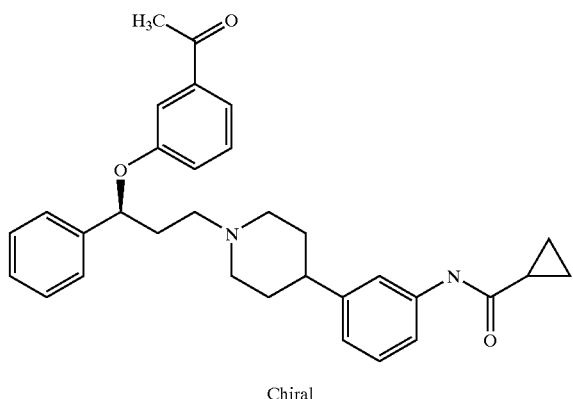<br>Chiral | 15.6 |
| 341 | 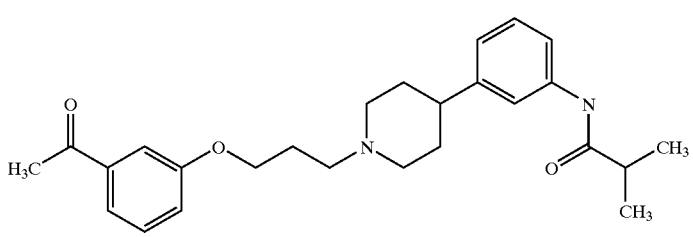 | 255.6 |
| 342 | 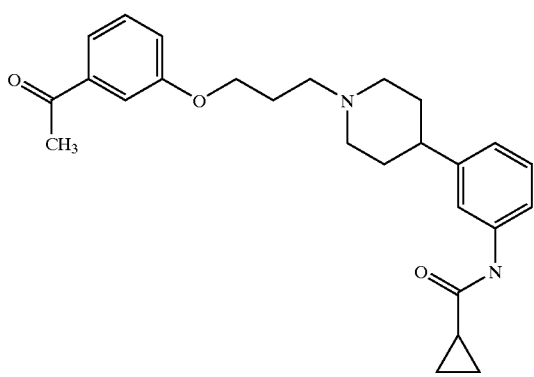 | 183.0 |
| 343 | 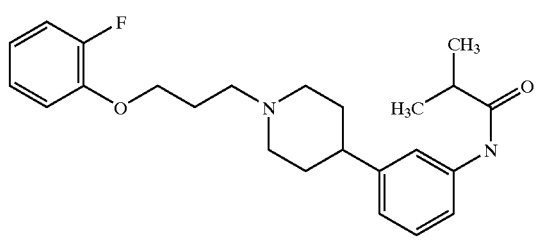 | 194.7 |
| 344 | 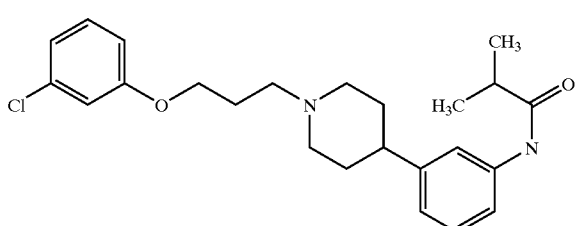 | 44.6 |

-continued
| | | |
|---|---|---|
| 345 | 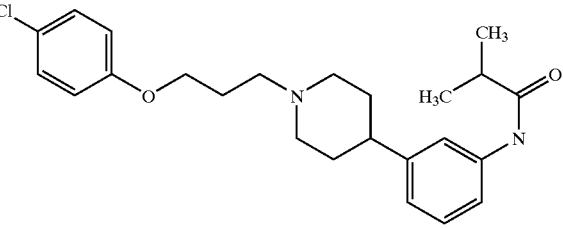 | 15.4 |
| 346 | 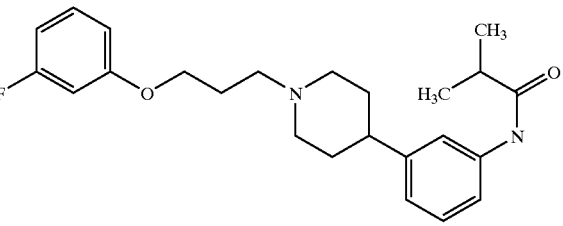 | 106.9 |
| 347 | 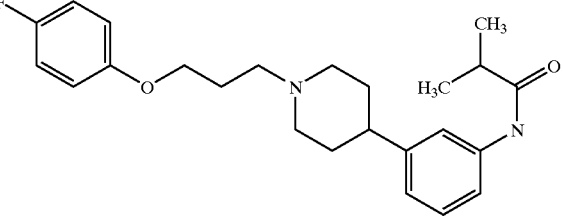 | 54.8 |
| 348 | 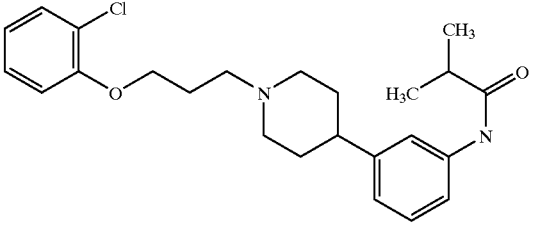 | 84.0 |
| 349 | 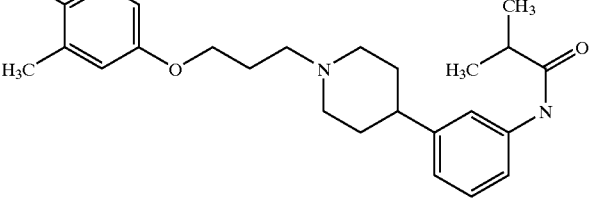 | 20.4 |
| 350 | 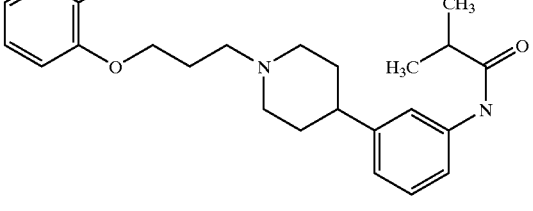 | 12.1 |

| | | |
|---|---|---|
| 351 | 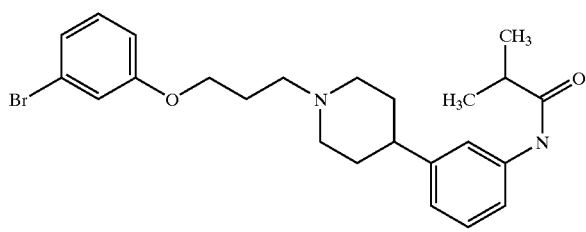 | 61.8 |
| 352 | 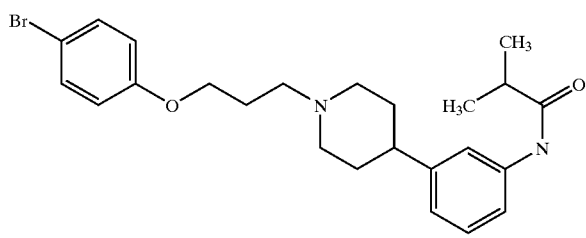 | 13.3 |
| 353 | 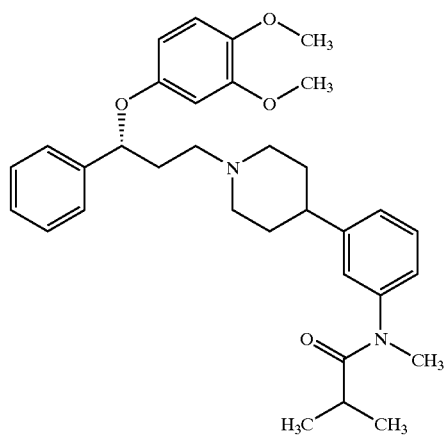
Chiral | 41.8 |
| 354 | 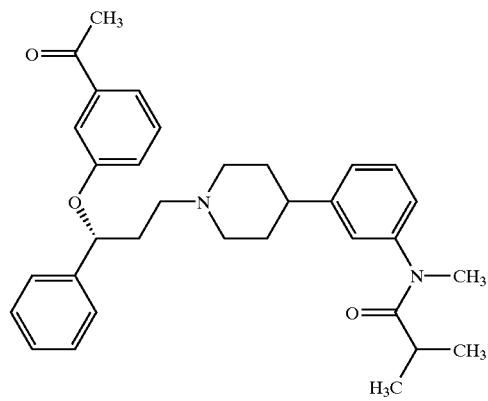
Chiral | 81.6 |

| | | |
|---|---|---|
| 355 | 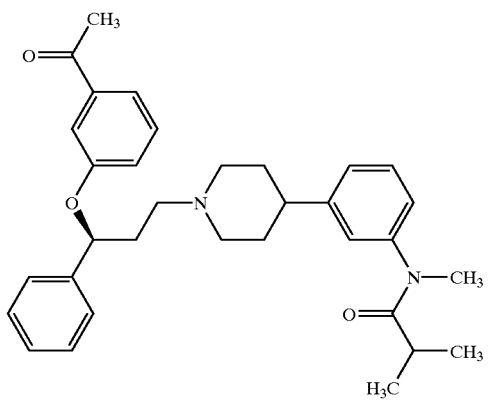<br>Chiral | 116.6 |
| 356 | 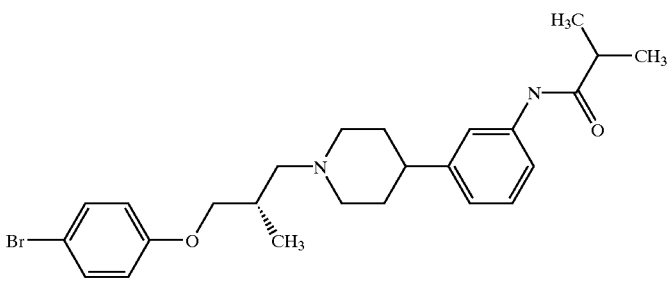<br>Chiral | 54.5 |
| 357 | 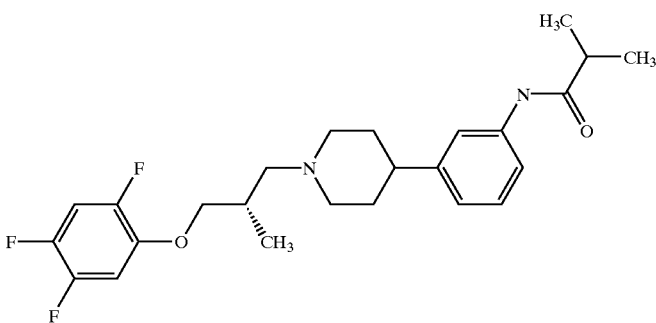 | 115.4 |
| 358 | 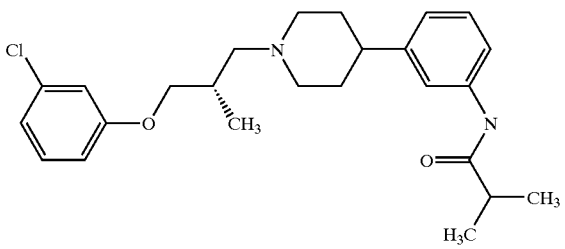<br>Chiral | 135.7 |

-continued
| | | |
|---|---|---|
| 359 | 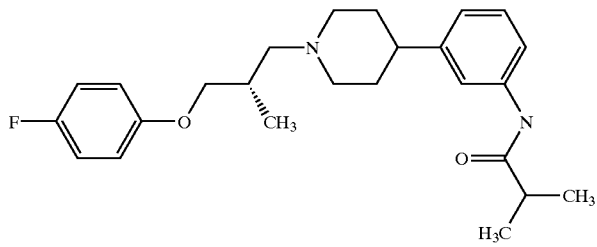<br>Chiral | 83.2 |
| 360 | 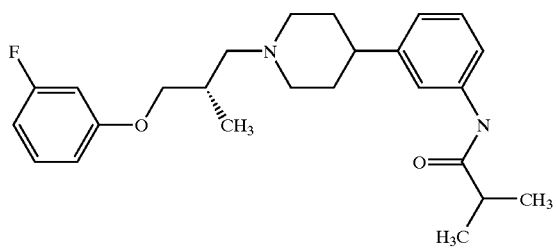<br>Chiral | 163.0 |
| 361 | 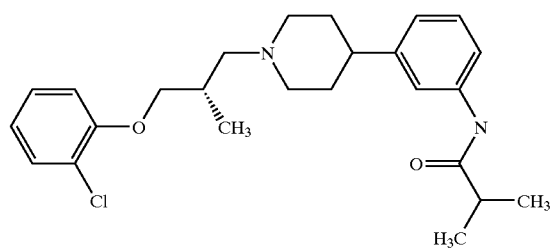<br>Chiral | 311.2 |
| 362 | 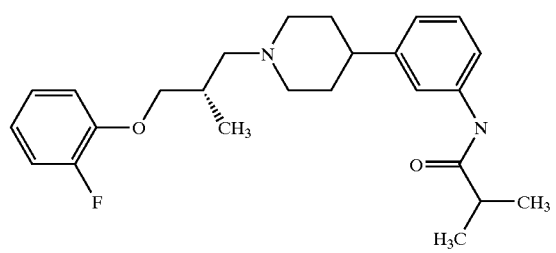<br>Chiral | 281.2 |
| 363 | 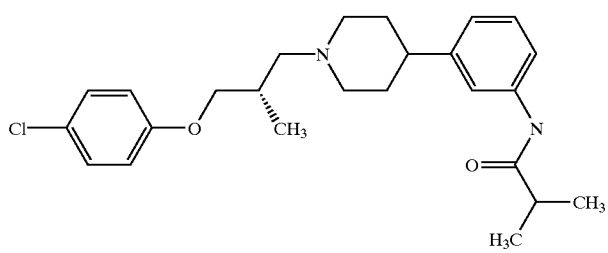<br>Chiral | 31.6 |

| | | -continued | |
|---|---|---|---|
| 364 | 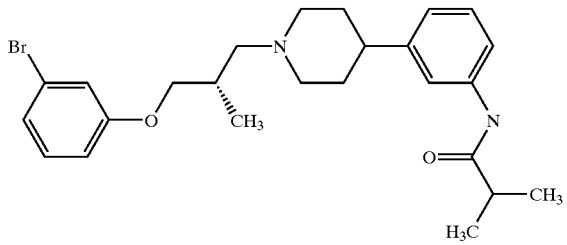 Chiral | | 144.4 |
| 365 | 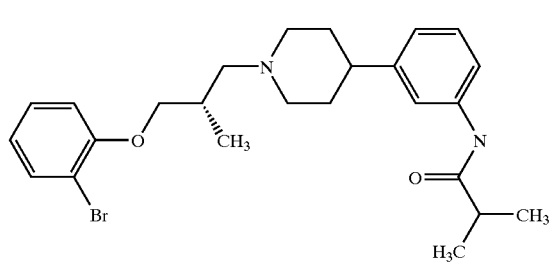 Chiral | | 42.9 |
| 366 | 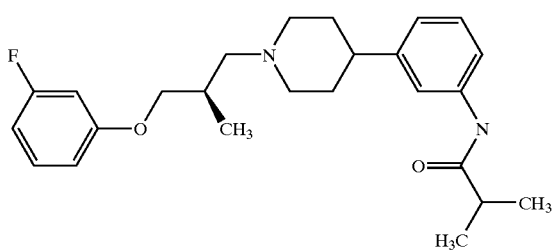 Chiral | | 645.5 |
| 367 | 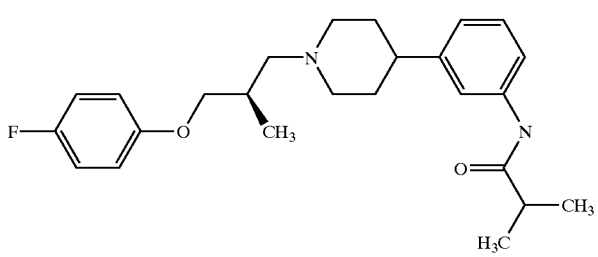 Chiral | | 235.7 |
| 368 | 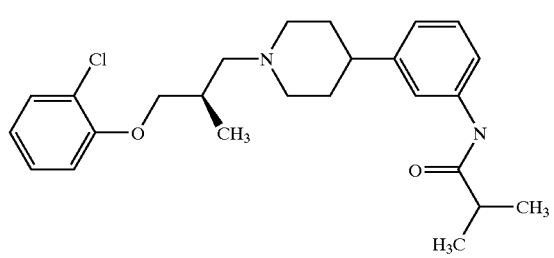 Chiral | | 313.0 |

-continued
| | | |
|---|---|---|
| 369 | 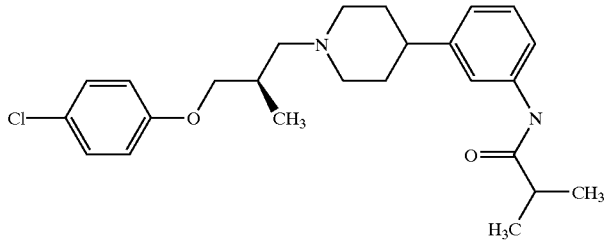<br>Chiral | 145.0 |
| 370 | 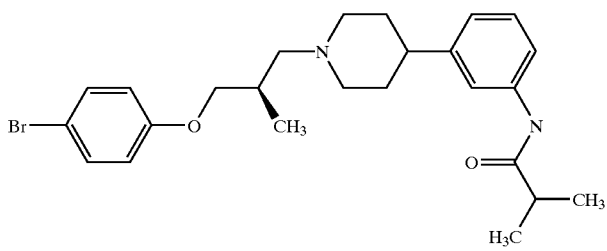<br>Chiral | |
| 371 | 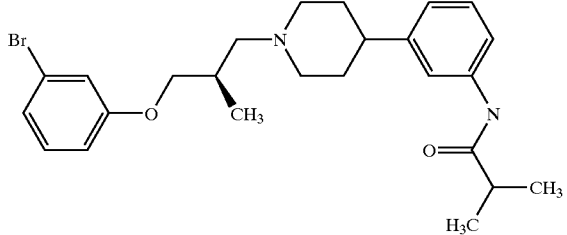<br>Chiral | 162.7 |
| 372 | 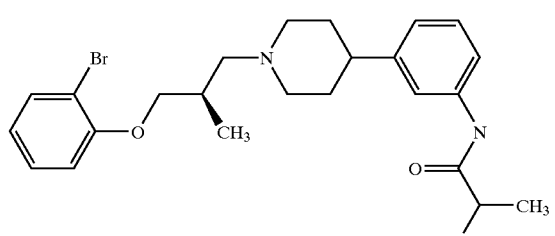<br>Chiral | 357.7 |
| 373 | 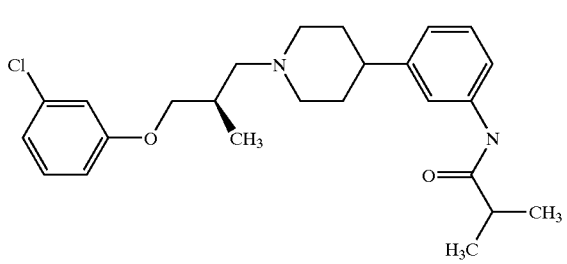<br>Chiral | 428.5 |

-continued
| | | |
|---|---|---|
| 374 | 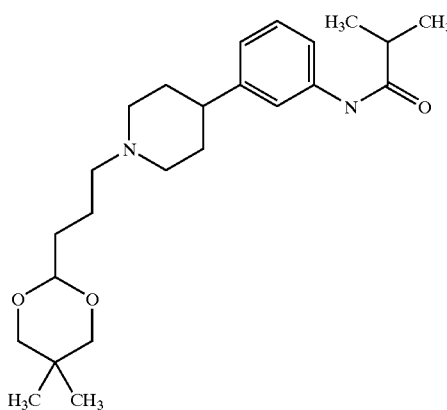 | 96.8 |
| 375 | 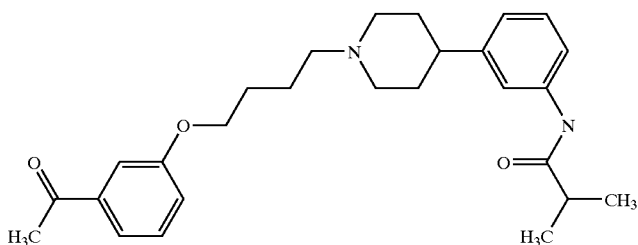 | 185.6 |
| 376 | 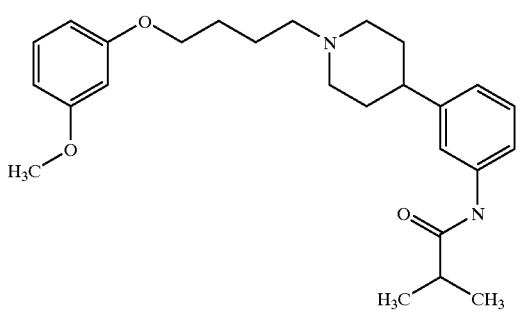 | 887.6 |
| 377 | 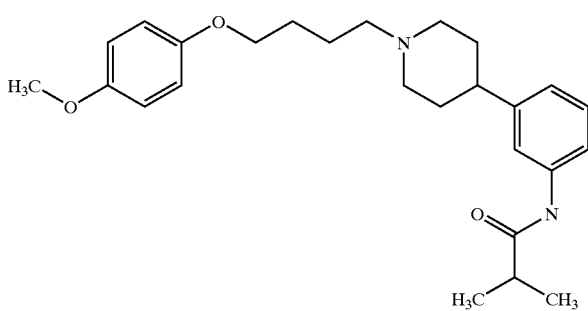 | 711.9 |
| 378 | 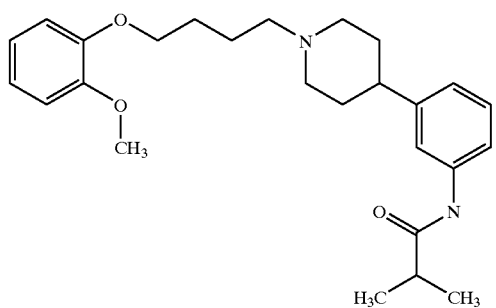 | 307.8 |

-continued
| | | |
|---|---|---|
| 379 | 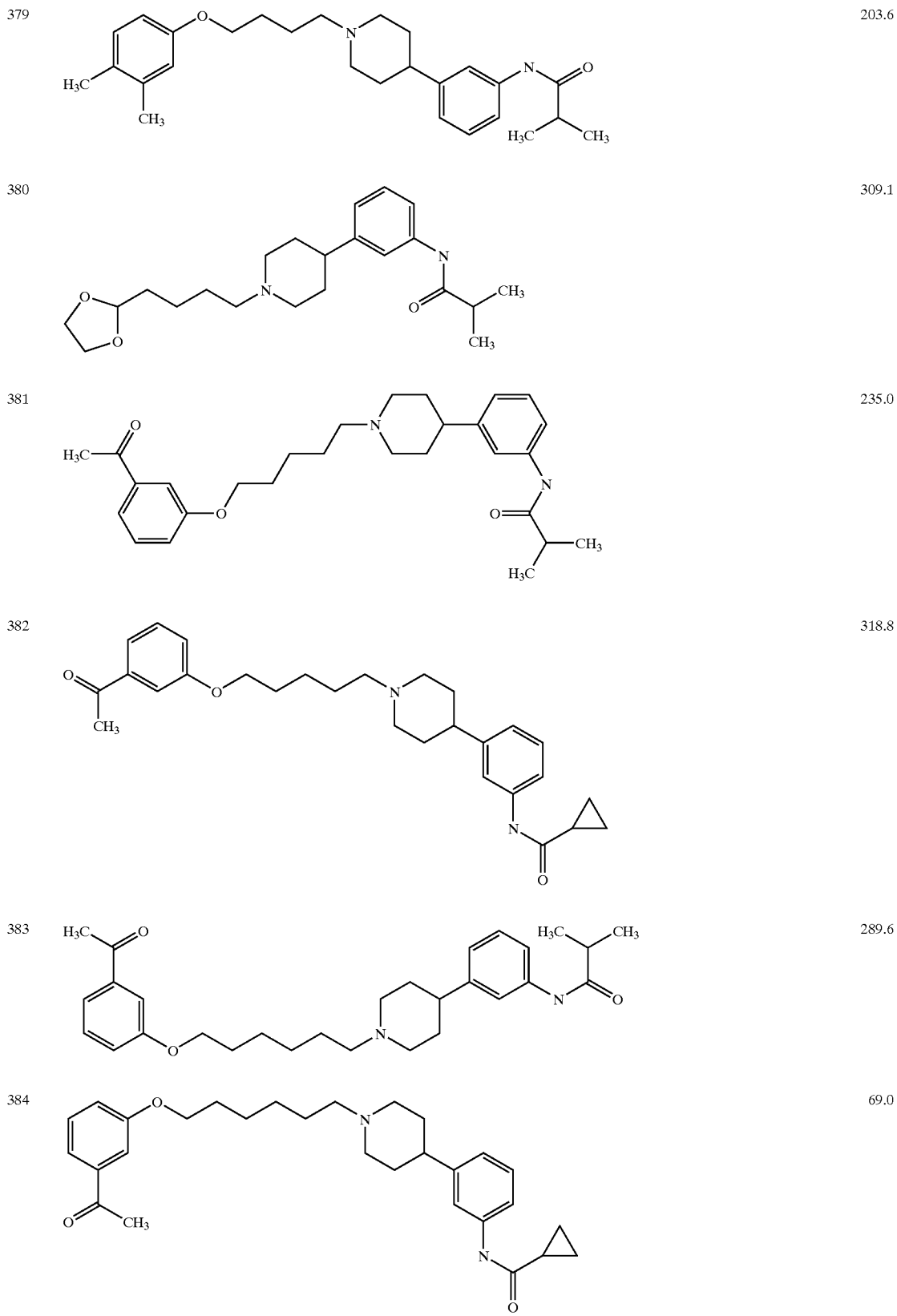 | 203.6 |
| 380 | | 309.1 |
| 381 | | 235.0 |
| 382 | | 318.8 |
| 383 | | 289.6 |
| 384 | | 69.0 |

-continued
| | | rMCH1 Ki (nM) |
|---|---|---|
| 385 | 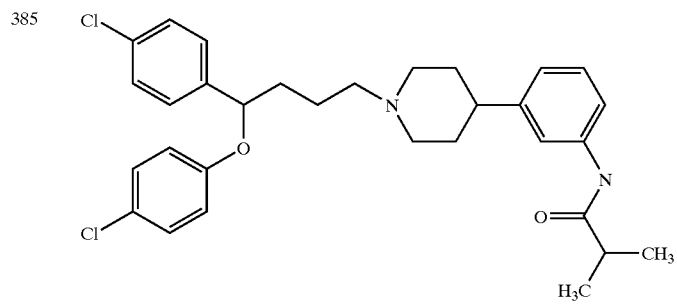 | 324.6 |
| Example | Structure | rMCH1 Ki (nM) |
|---|---|---|
| 386 | 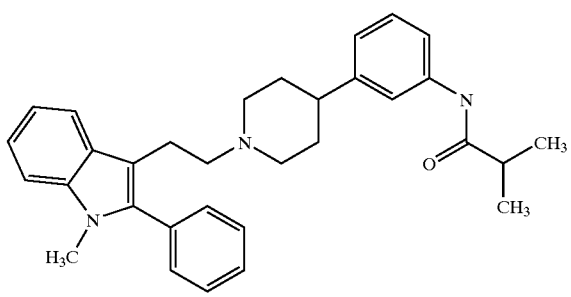 | 26.3 |
| 387 | 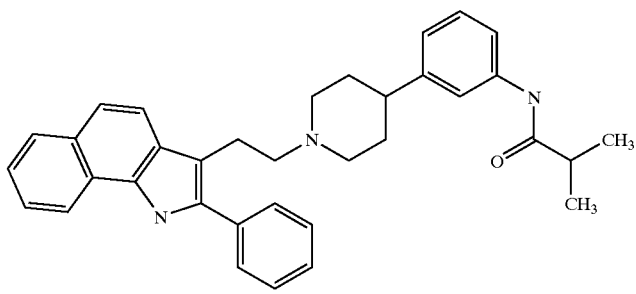 | 19.7 |
| 388 | 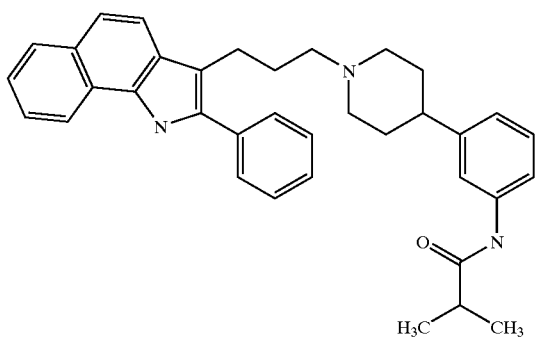 | 20.7 |

-continued
| | | |
|---|---|---|
| 389 | 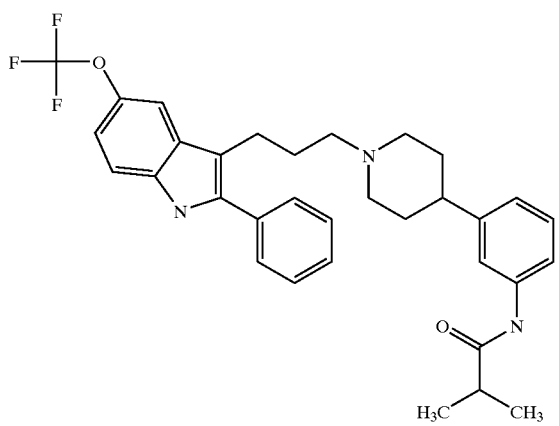 | 2.2 |
| 390 | 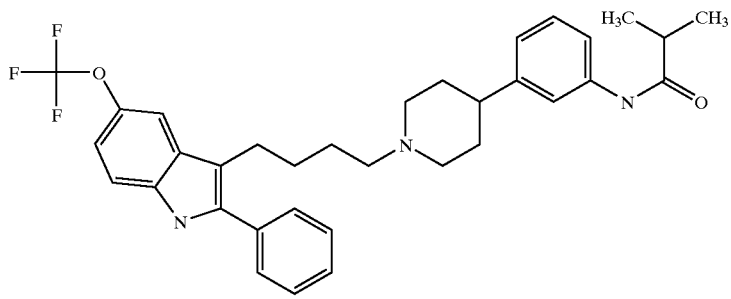 | 1.0 |
| 391 | 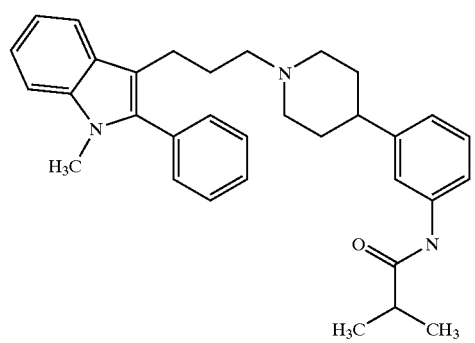 | 21.9 |
| 392 | 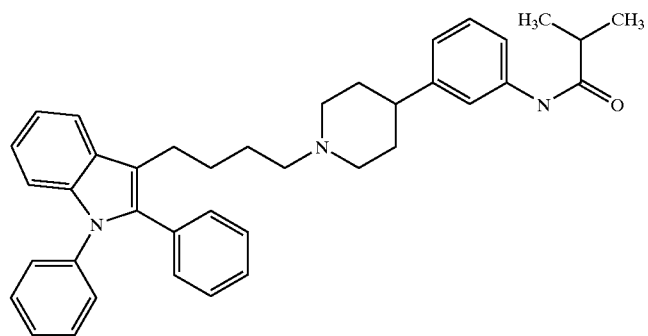 | 18.1 |

-continued
| | | |
|---|---|---|
| 393 | 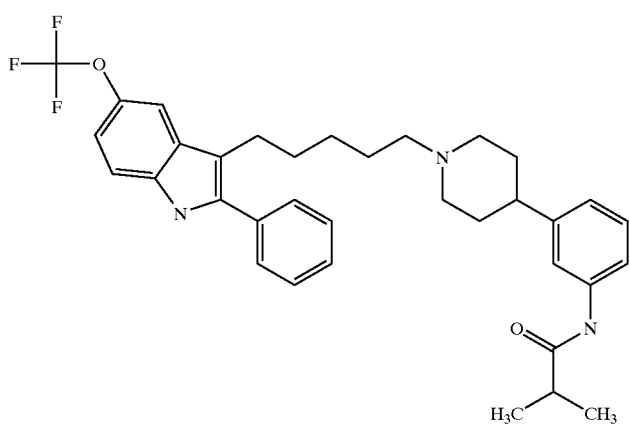 | 9.5 |
| 394 | 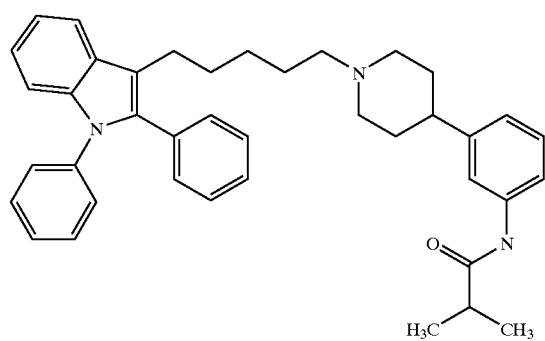 | |
| 395 | 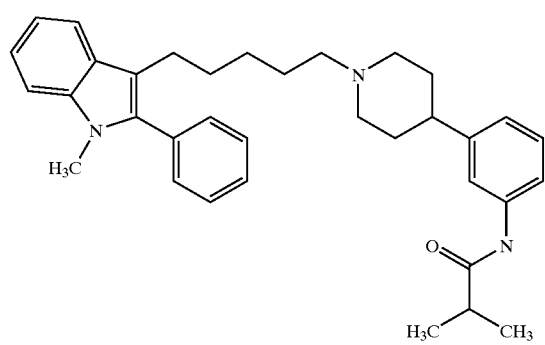 | 2.4 |
| 396 | 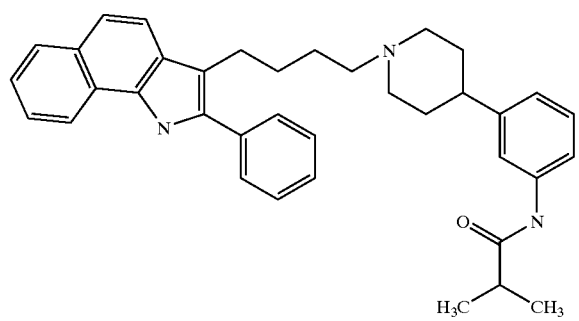 | |

| | | |
|---|---|---|
| 397 | 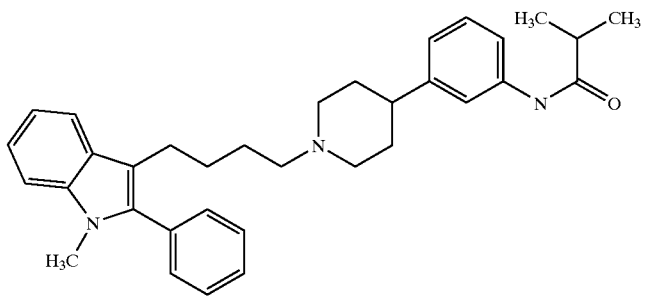 | |
| 398 | 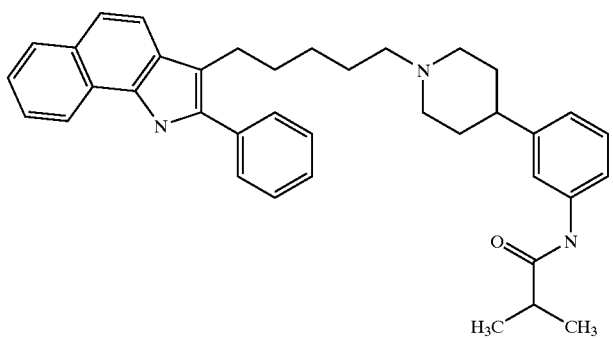 | 13.6 |
| 399 | 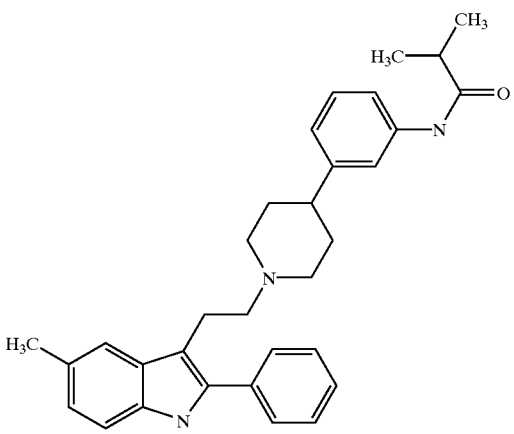 | 31.9 |
| 400 | 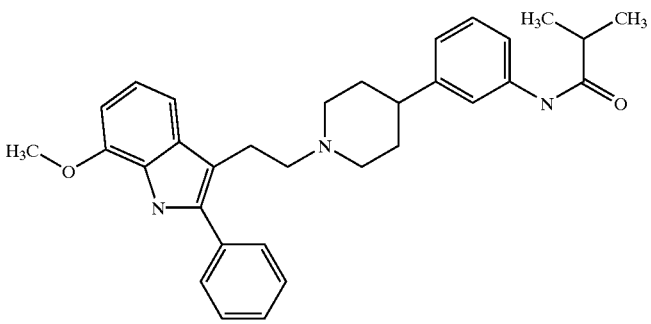 | 43.9 |

| | | |
|---|---|---|
| 401 | 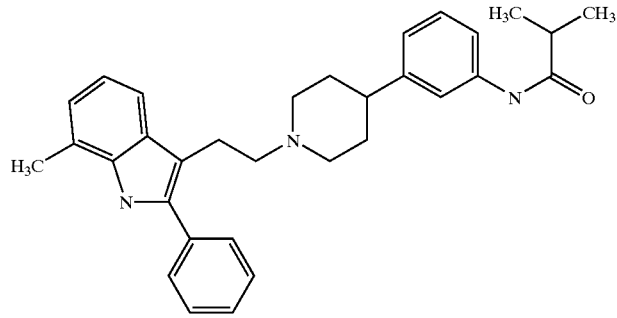 | 44.6 |
| 402 | 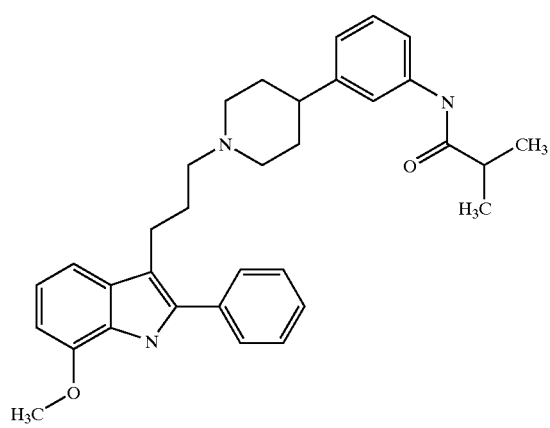 | |
| 403 | 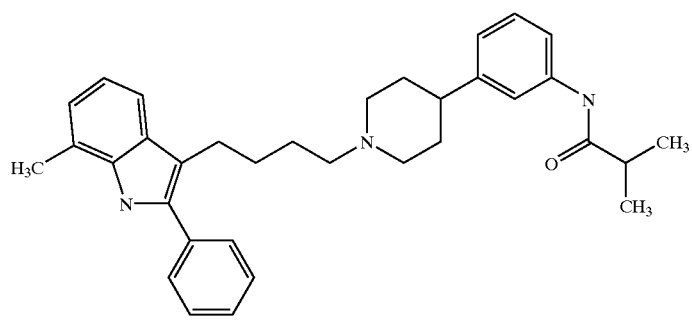 | 11.7 |
| 404 | 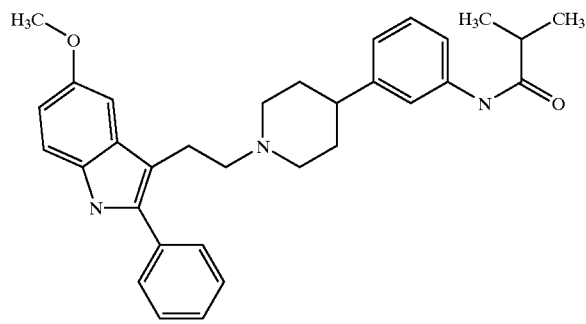 | |

| | | |
|---|---|---|
| 405 | 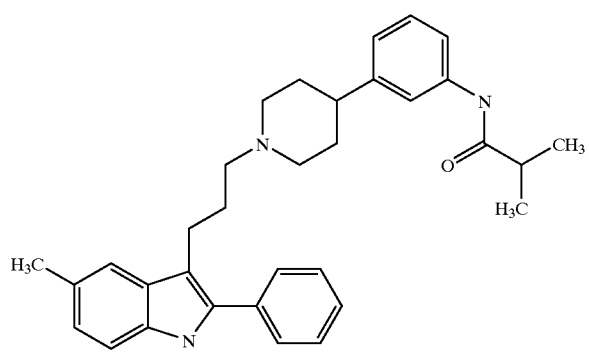 | |
| 406 | 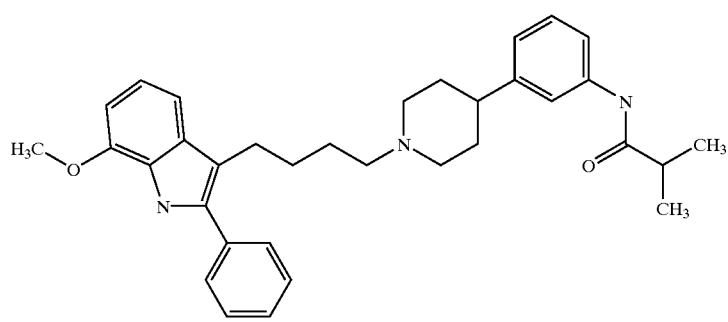 | 12.3 |
| 407 | 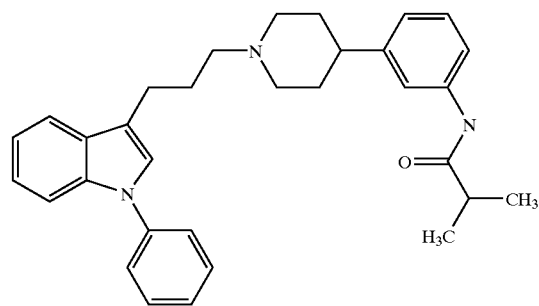 | 16.6 |
| 408 | 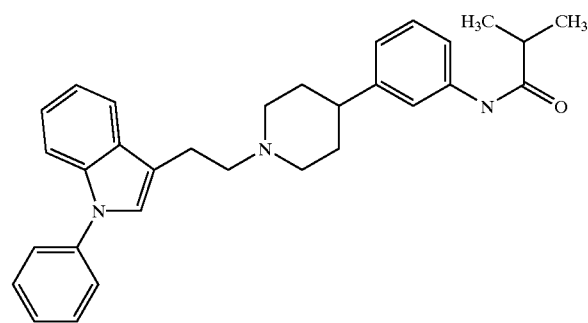 | 21.6 |

-continued
| | | |
|---|---|---|
| 409 | 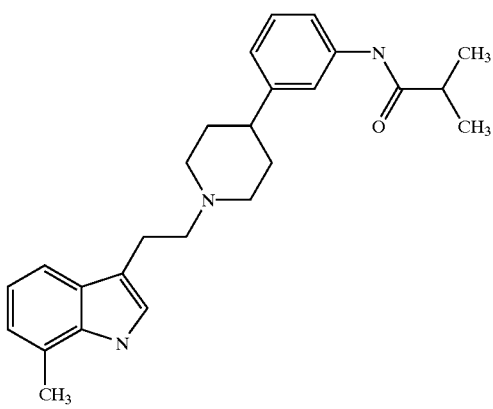 | 96.7 |
| 410 | 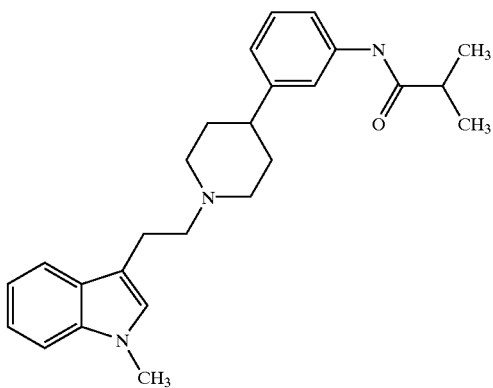 | 262.7 |
| 411 | 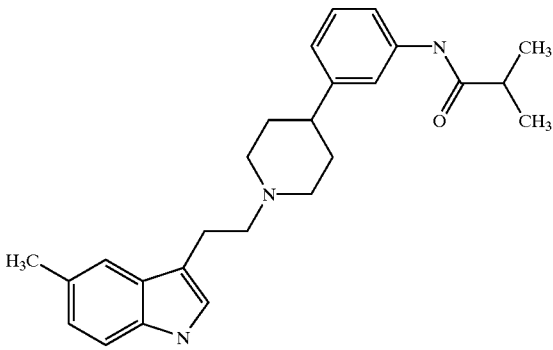 | 82.3 |
| 412 | 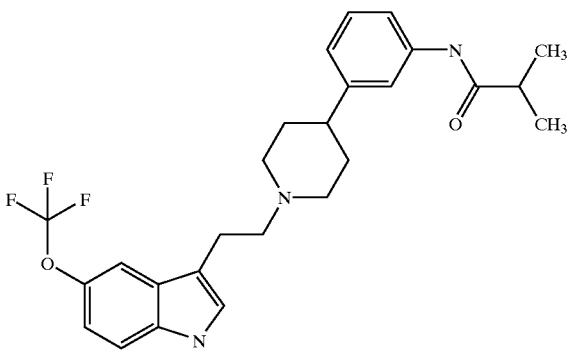 | 27.0 |

-continued
| | | |
|---|---|---|
| 413 | 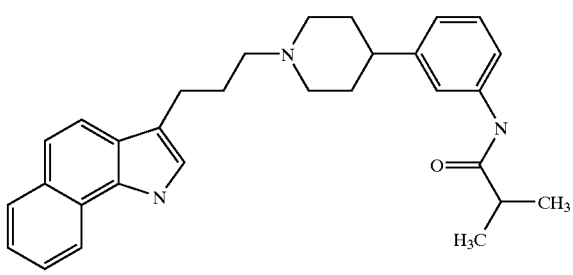 | 76.8 |
| 414 | 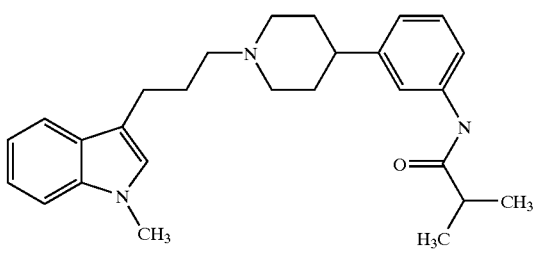 | 2.9 |
| 415 | 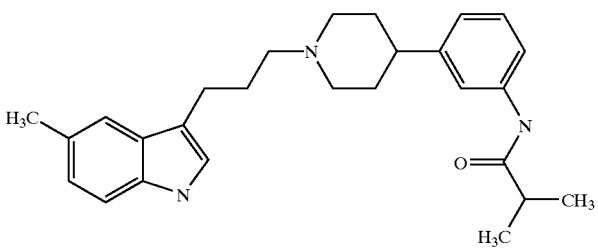 | 8.1 |
| 416 | 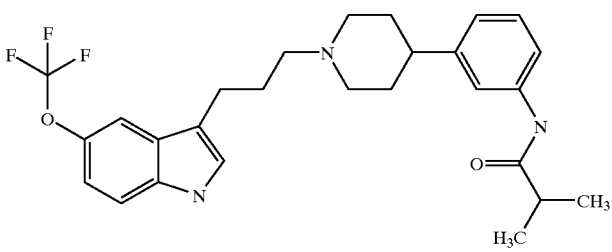 | 12.6 |
| 417 | 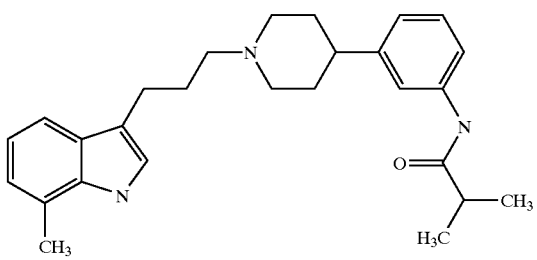 | 20.5 |
| 418 | 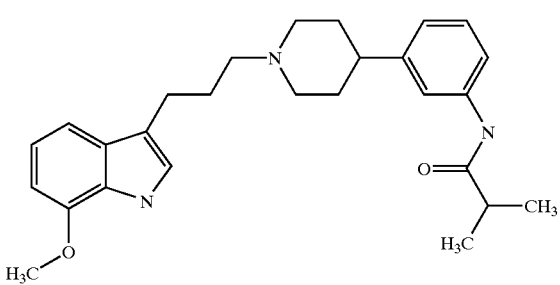 | 51.6 |

-continued
| | | |
|---|---|---|
| 419 | 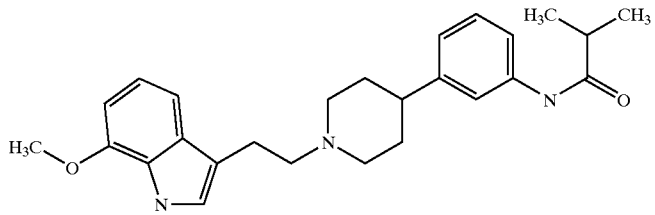 | 83.9 |
| 420 | 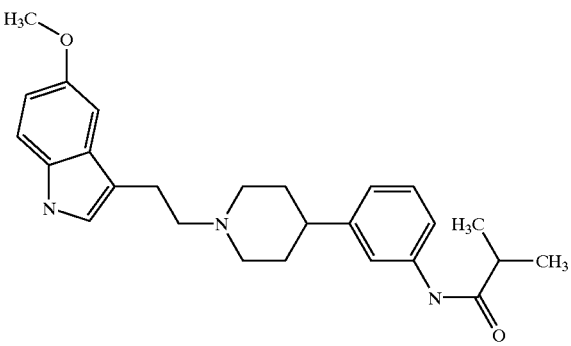 | |
| 421 | 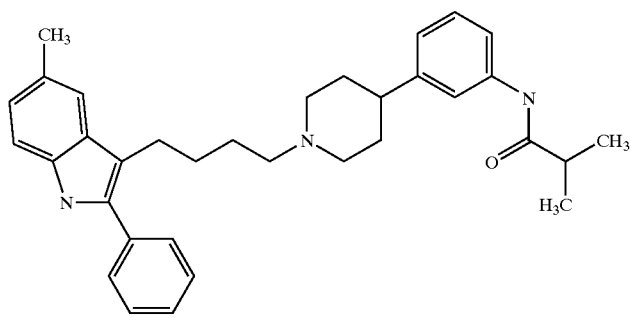 | 1.8 |
| 422 | 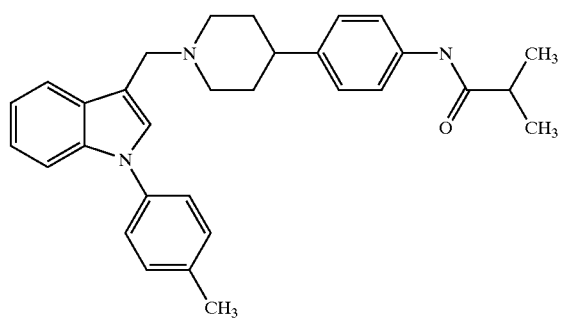 | 173.0 |
| 423 | 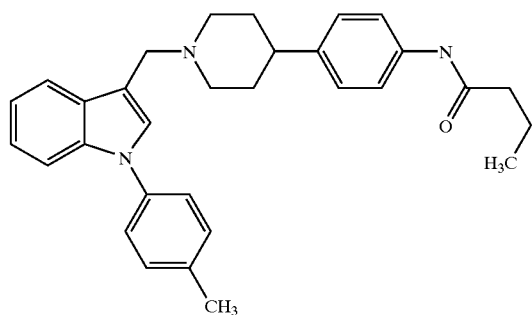 | 405.2 |

| | | |
|---|---|---|
| 424 | 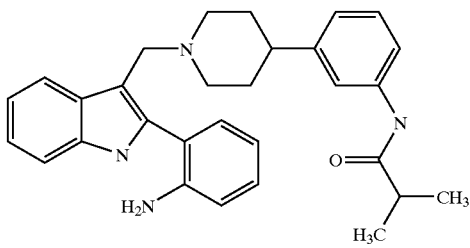 | 114.2 |
| 425 | 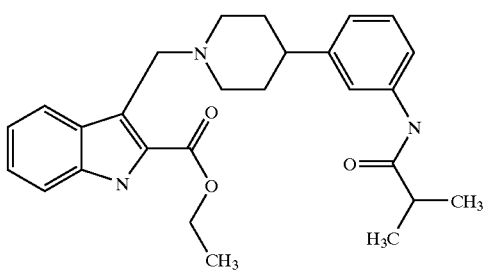 | 599.3 |
| 426 | 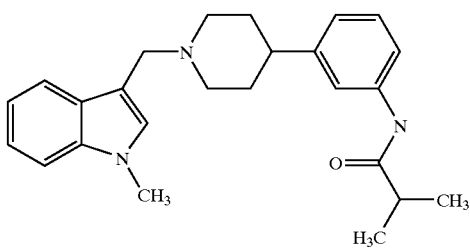 | 556.1 |
| 427 | 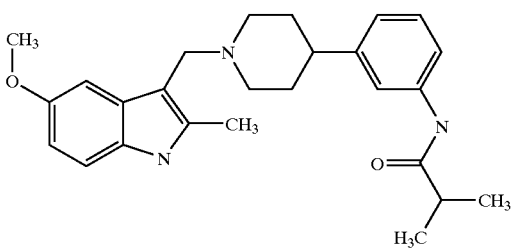 | 248.3 |
| 428 | 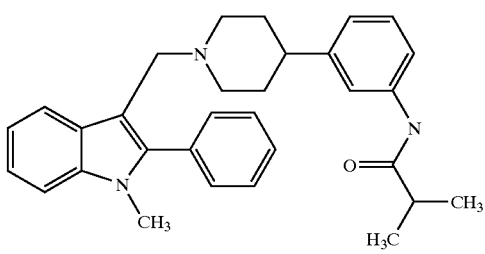 | 132.4 |
| 429 | 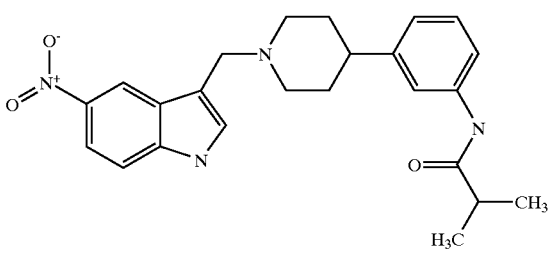 | 121.4 |

-continued
| | | |
|---|---|---|
| 430 | 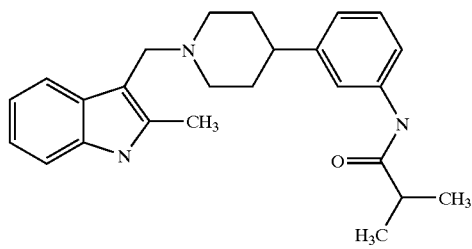 | 647.4 |
| 431 | 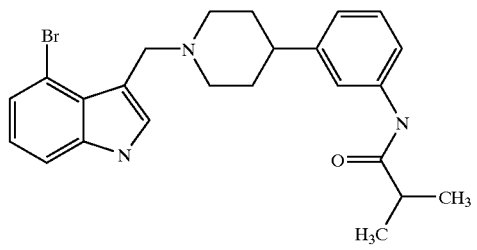 | 967.7 |
| 432 | 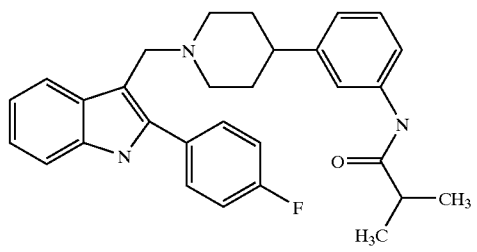 | 198.2 |
| 433 | 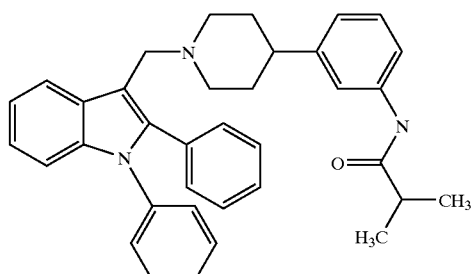 | 30.4 |
| 434 | 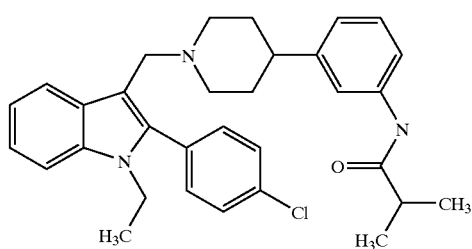 | 214.2 |
| 435 | 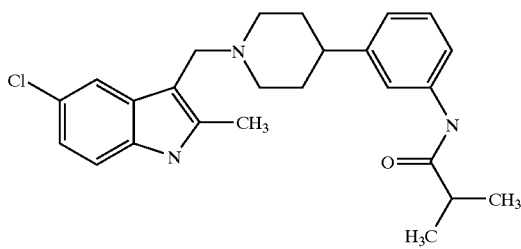 | 215.4 |

-continued
| | | |
|---|---|---|
| 436 | 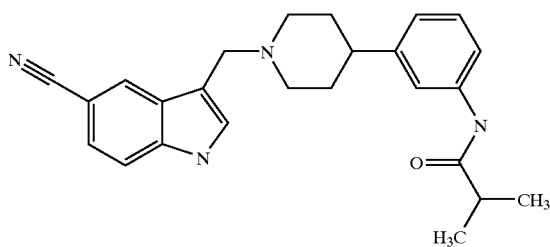 | 434.3 |
| 437 | 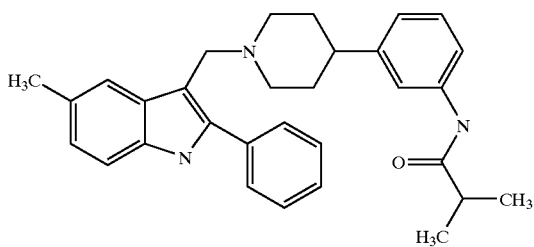 | 552.1 |
| 438 | 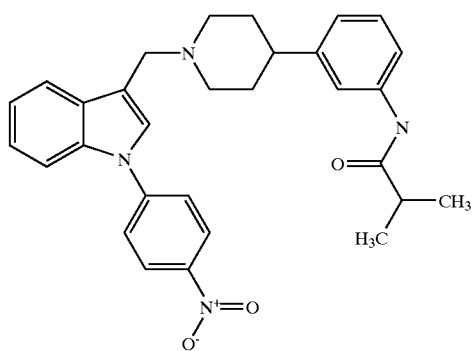 | 1.3 |
| 439 | 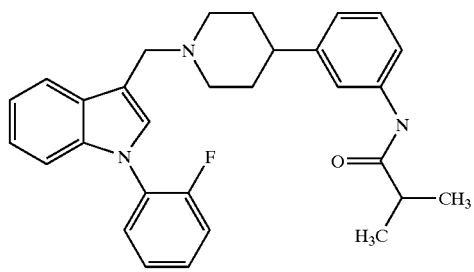 | 8.5 |
| 440 | 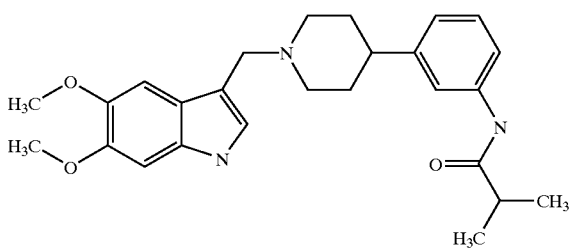 | 106.9 |

-continued
| | | |
|---|---|---|
| 441 | 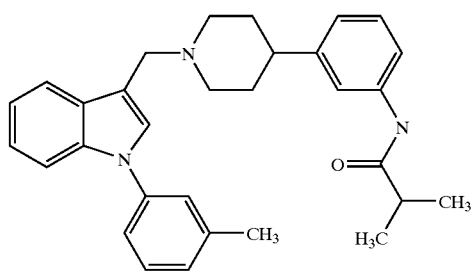 | 10.1 |
| 442 | 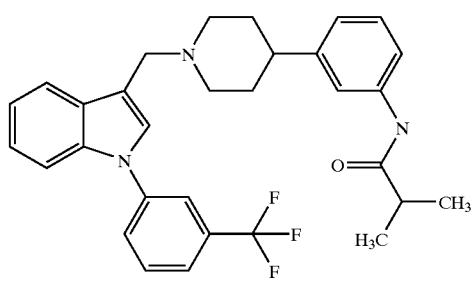 | 7.8 |
| 443 | 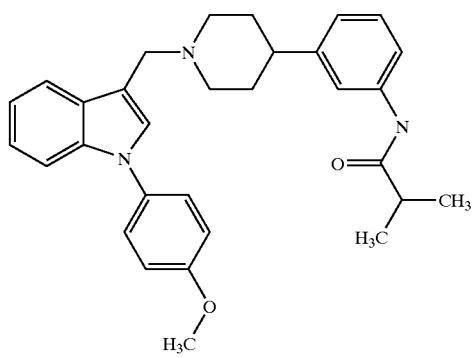 | 23.4 |
| 444 | 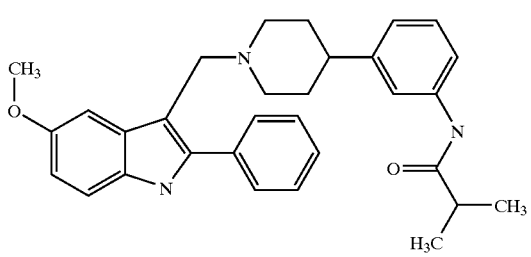 | 544.7 |
| 445 | 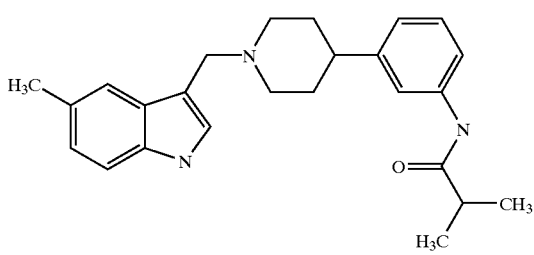 | 486.3 |

-continued
| | | |
|---|---|---|
| 446 | 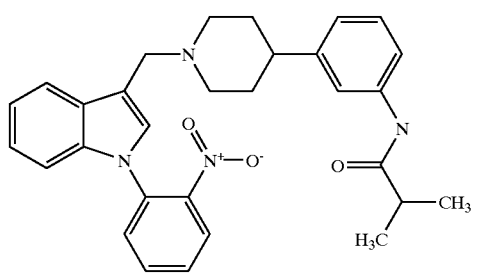 | 17.9 |
| 447 | 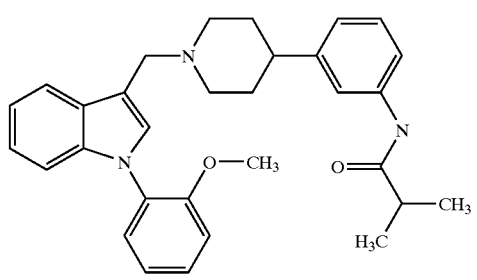 | 9.8 |
| 448 | 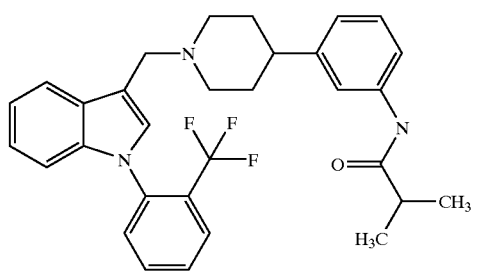 | 61.0 |
| 449 | 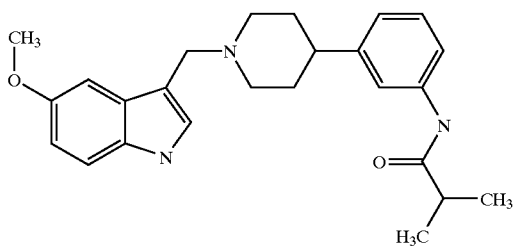 | 623.4 |
| 450 | 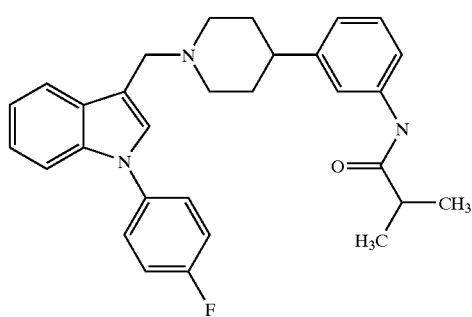 | 7.1 |

-continued
| | | |
|---|---|---|
| 451 | 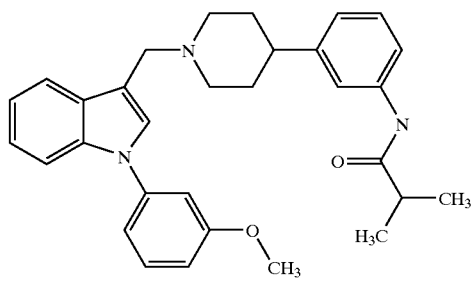 | 18.7 |
| 452 | 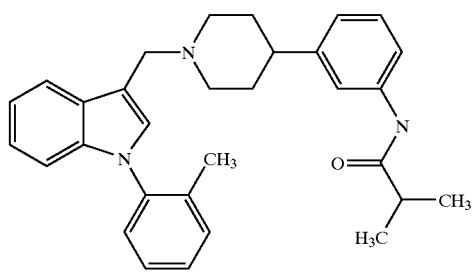 | 12.7 |
| 453 | 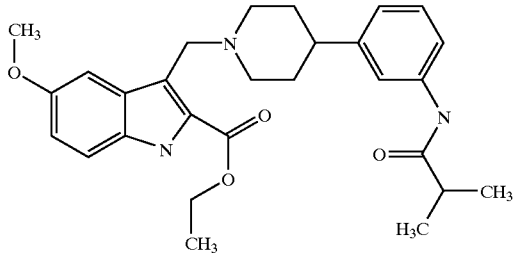 | 194.8 |
| 258 | 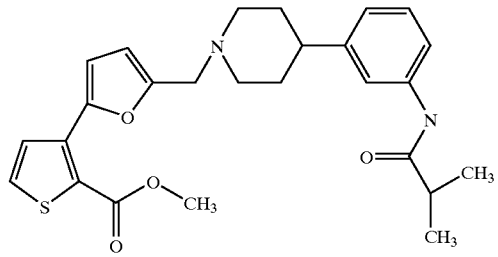 | 110.3 |
| 259 | 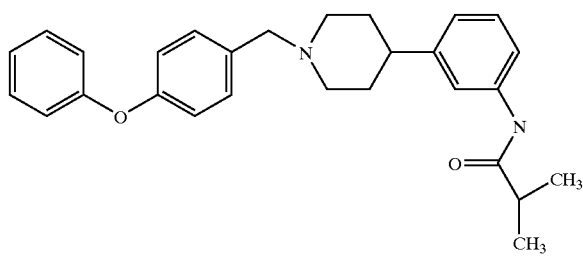 | 15.4 |
| 260 | 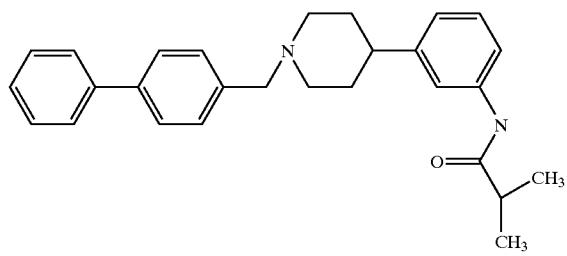 | 77.7 |

-continued
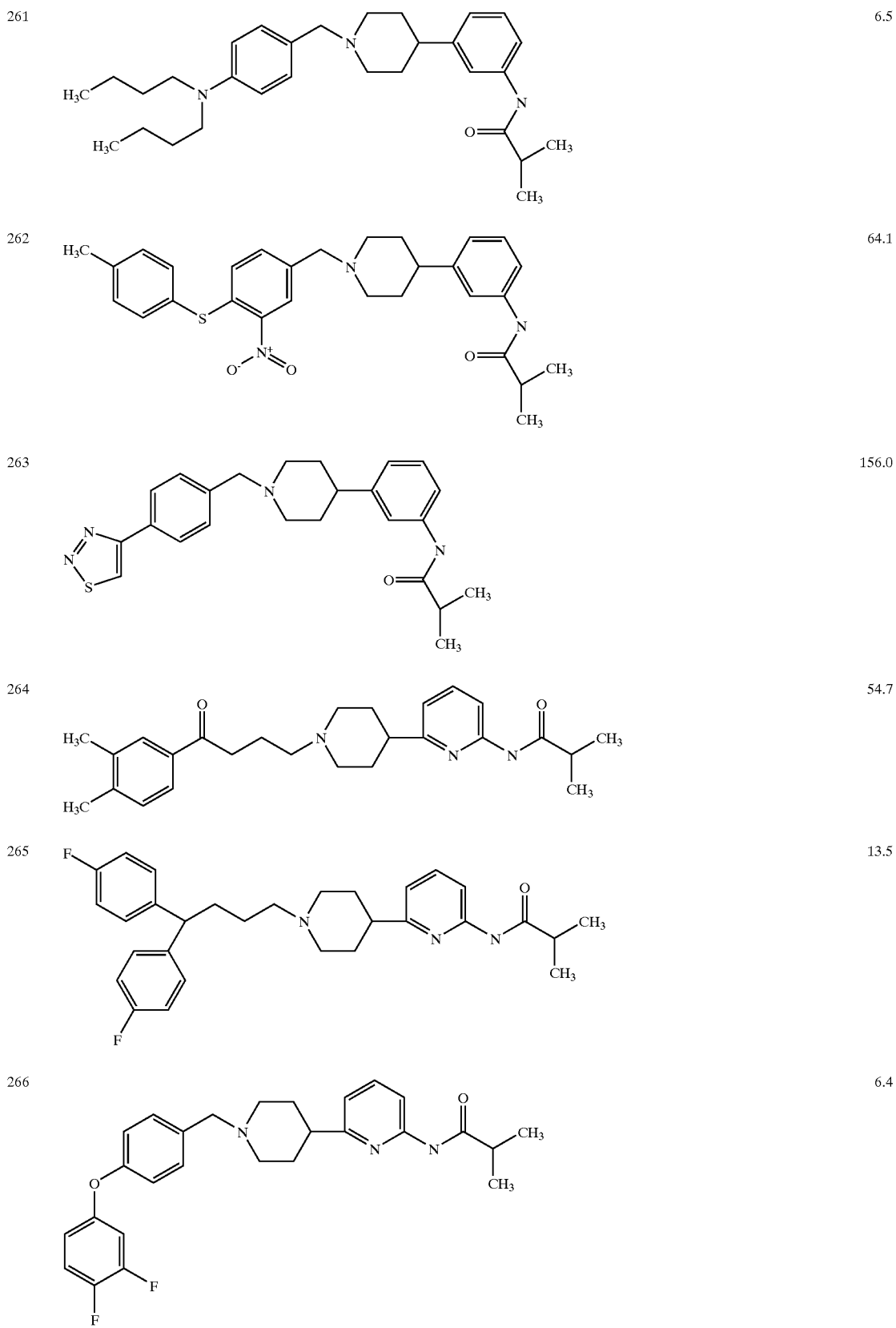
| | |
|---|---|
| 261 | 6.5 |
| 262 | 64.1 |
| 263 | 156.0 |
| 264 | 54.7 |
| 265 | 13.5 |
| 266 | 6.4 |

-continued
| 267 | 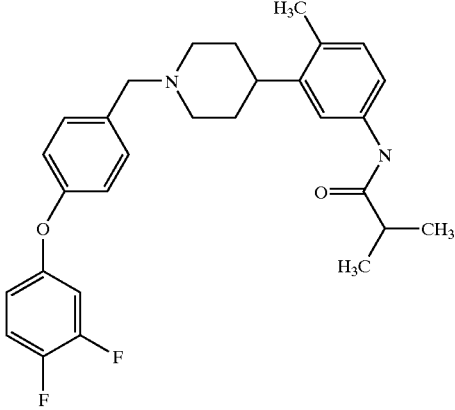 | 2.2 |
| 268 | 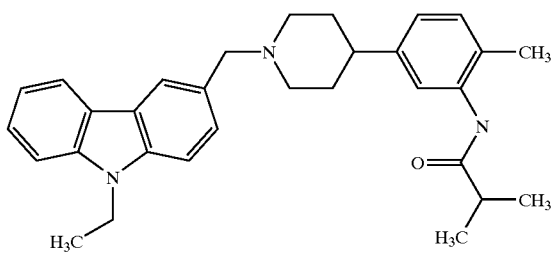 | 20.3 |
| 269 | 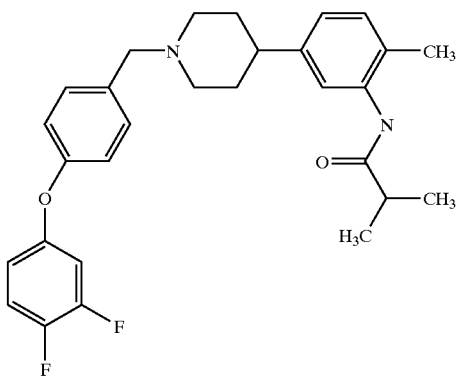 | 27.4 |
| 270 | 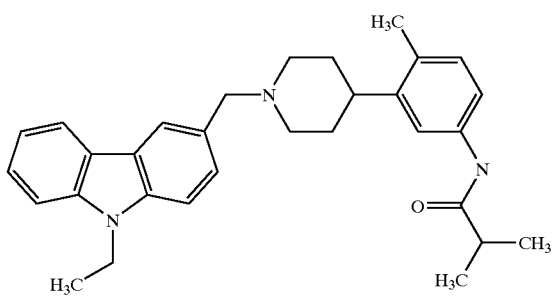 | 3.4 |

| | | |
|---|---|---|
| 271 | 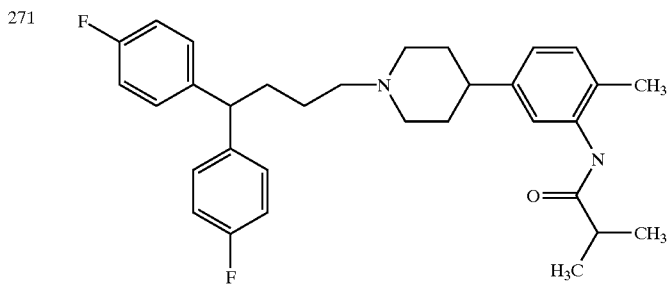 | 40.1 |
| 272 | 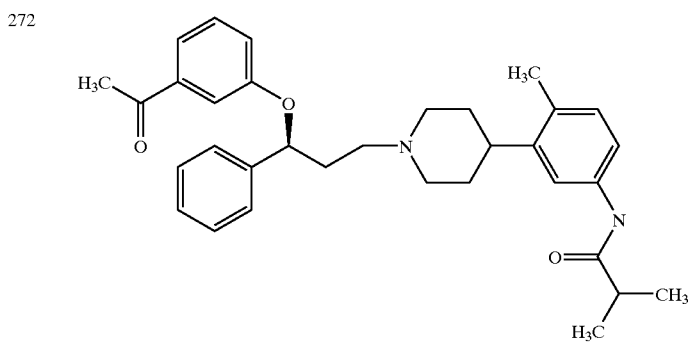
Chiral | 15.6 |
| 273 | 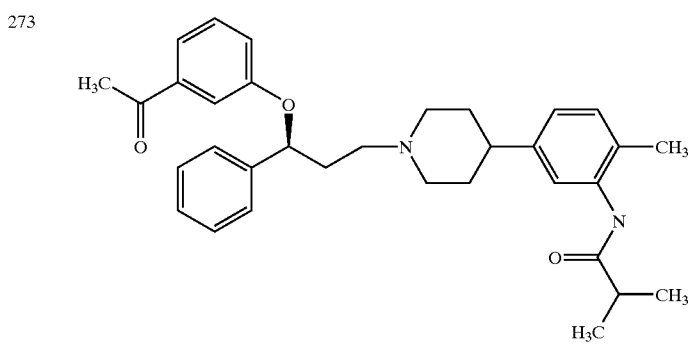
Chiral | 196.4 |
| 274 | 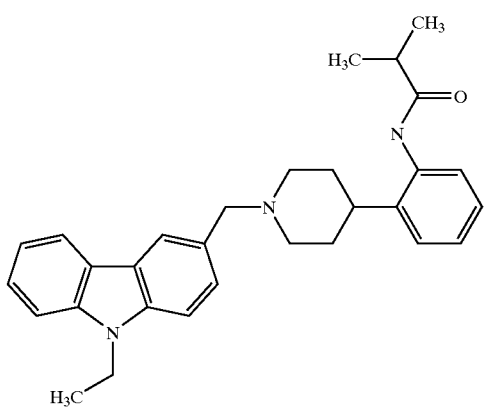 | 843.5 |

-continued
| | | |
|---|---|---|
| 275 | 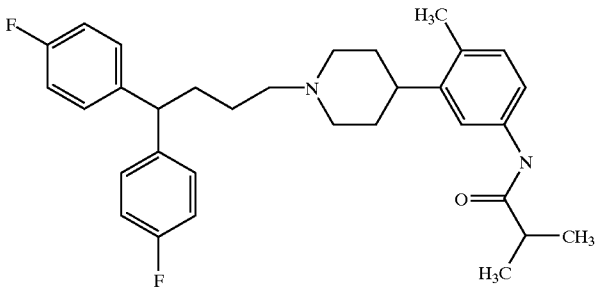 | 3.1 |
| 276 | 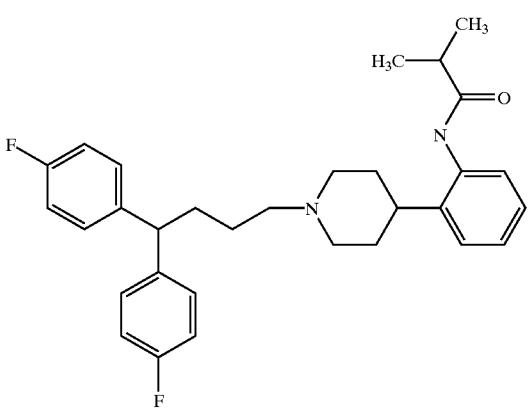 | 734.4 |
| 277 | 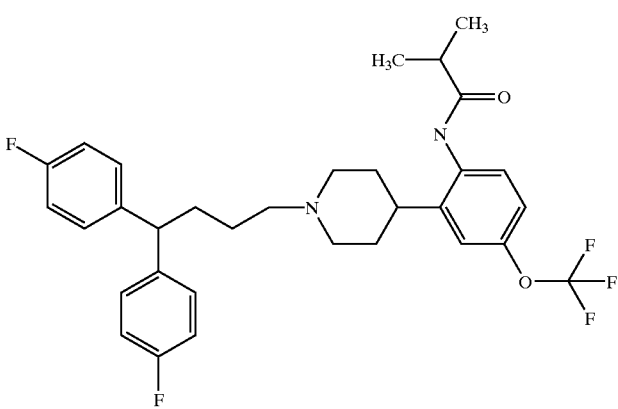 | 117.8 |
| 278 | 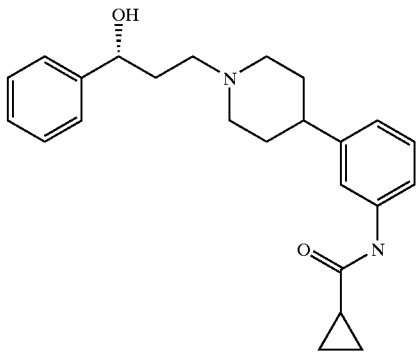
Chiral | 85.8 |

-continued
| | | |
|---|---|---|
| 279 | 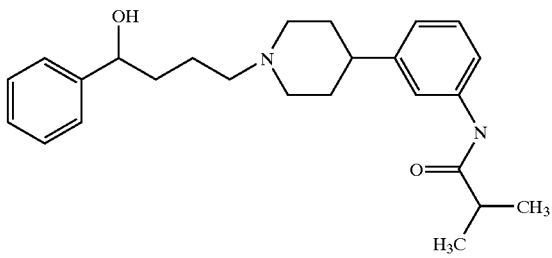 | 74.5 |
| 280 | 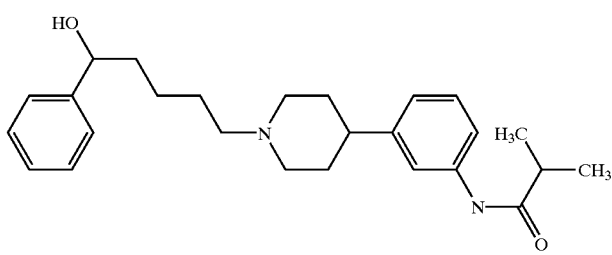 | 27.6 |
| 281 | 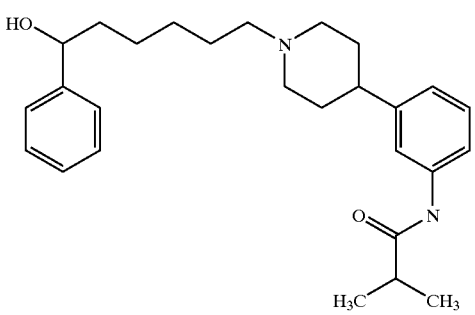 | 7.9 |
| 282 | 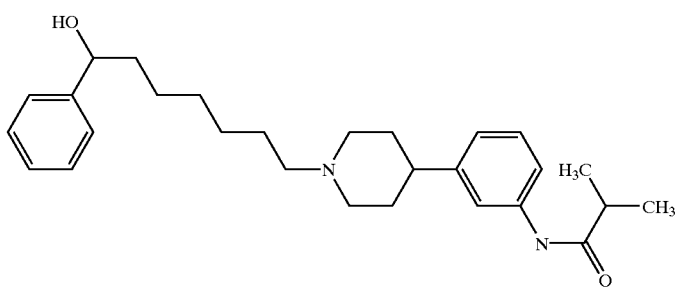 | 23.5 |
| 283 | 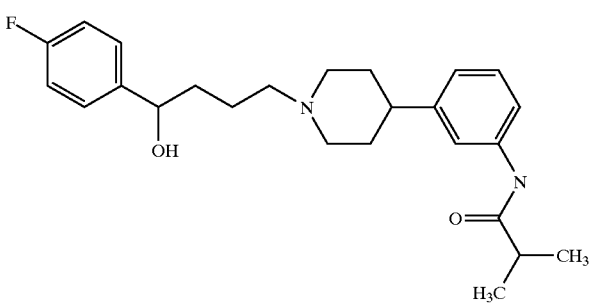 | |

| | | |
|---|---|---|
| 284 | 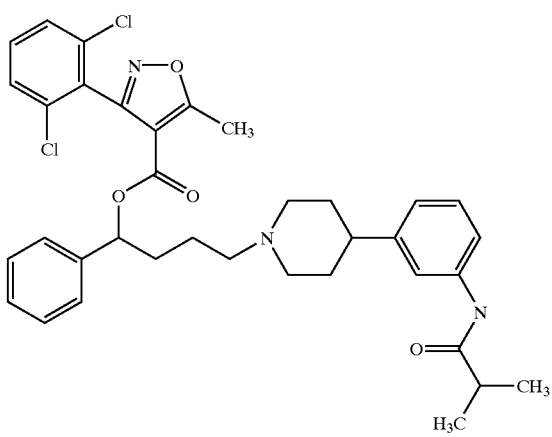 | 16.3 |
| 285 | 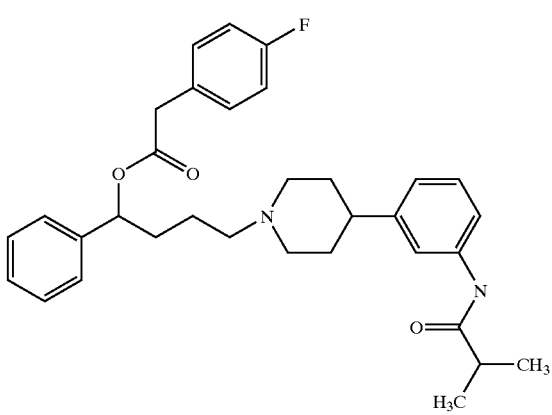 | 10.3 |
| 286 | 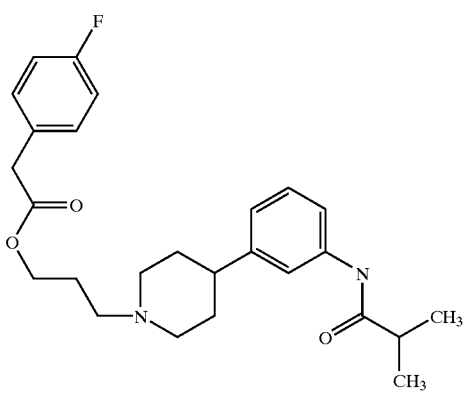 | 67.8 |
| 287 | 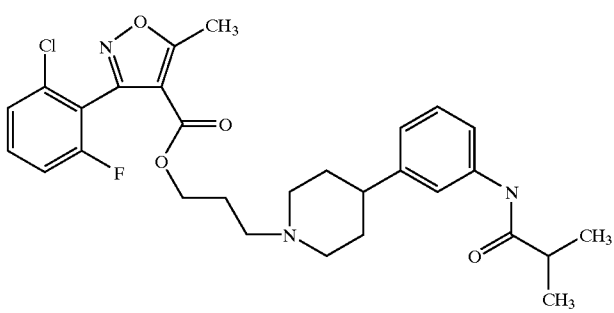 | 34.3 |

| | | |
|---|---|---|
| 288 | 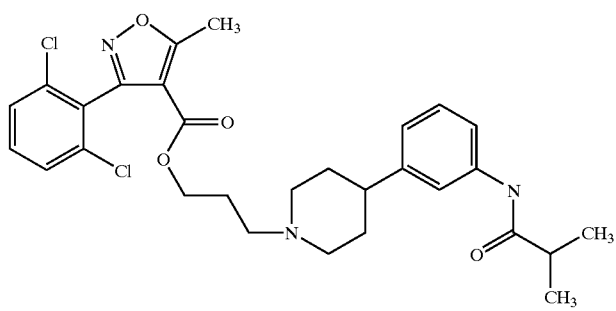 | 30.2 |
| 289 | 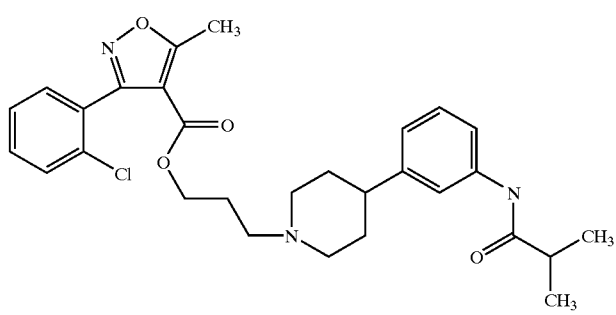 | 31.8 |
| 290 | 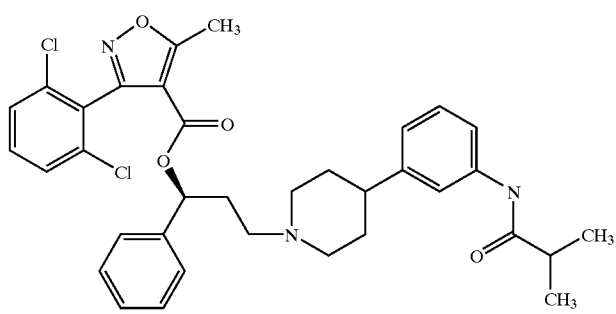 | 51.9 |
| 291 | 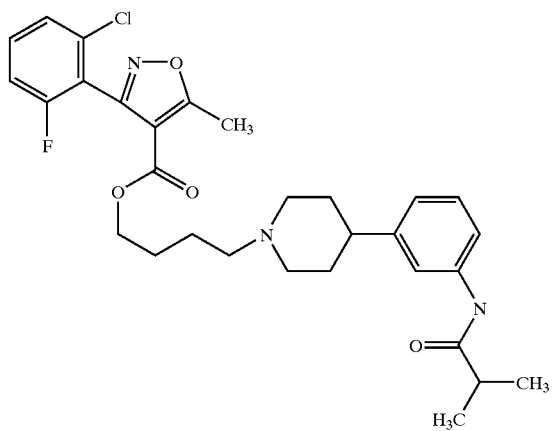 | 24.3 |

| | | |
|---|---|---|
| 292 | 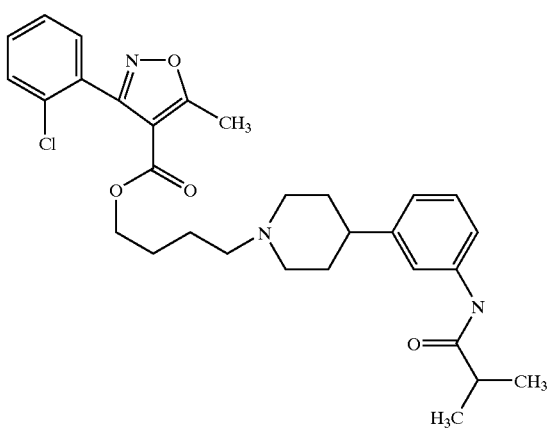 | 18.4 |
| 293 | 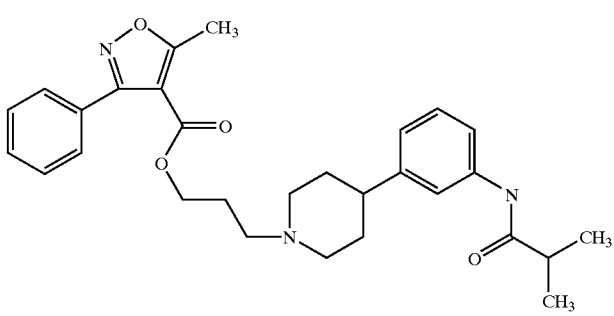 | 39.9 |
| 294 | 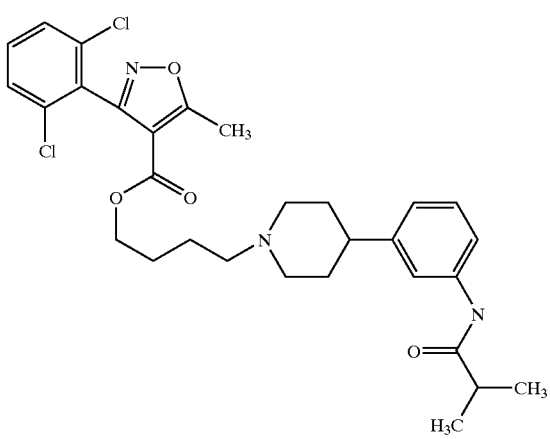 | 15.8 |
| 295 | 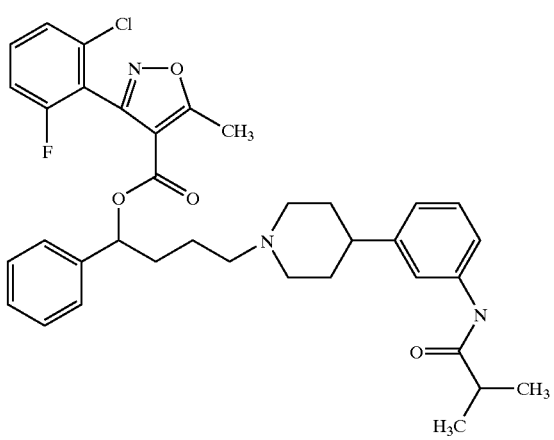 | 8.7 |

| 296 | 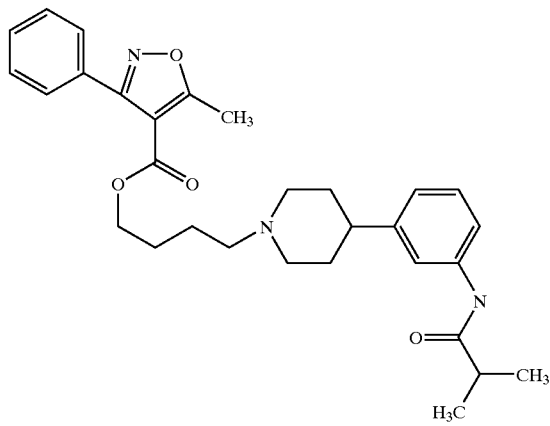 | 20.0 |
| --- | --- | --- |
| 297 | 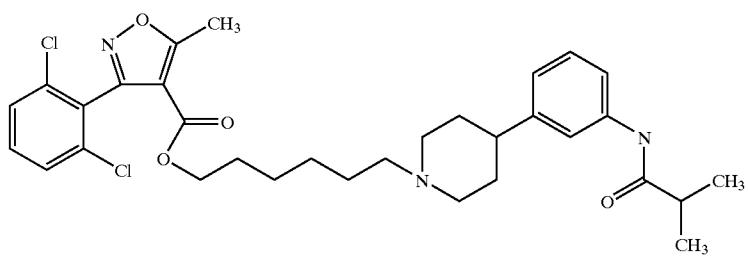 | 11.9 |
| 298 | 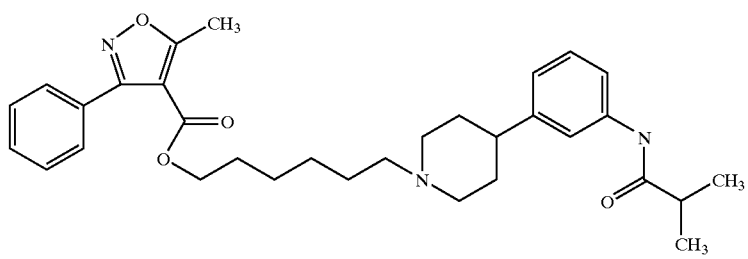 | 40.1 |
| 299 | 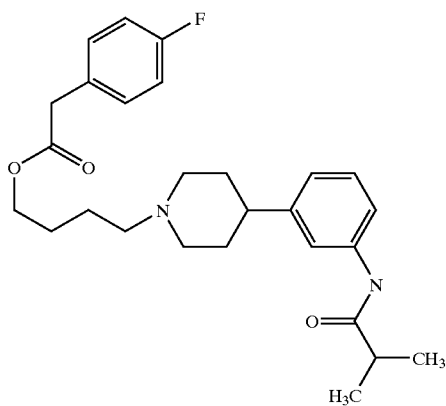 | 37.5 |

| | | |
|---|---|---|
| 300 | 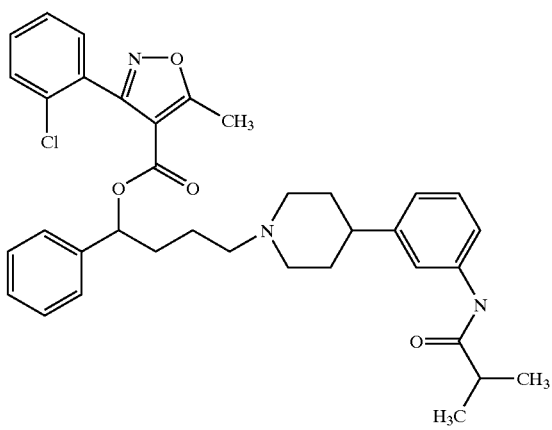 | 7.6 |
| 301 | 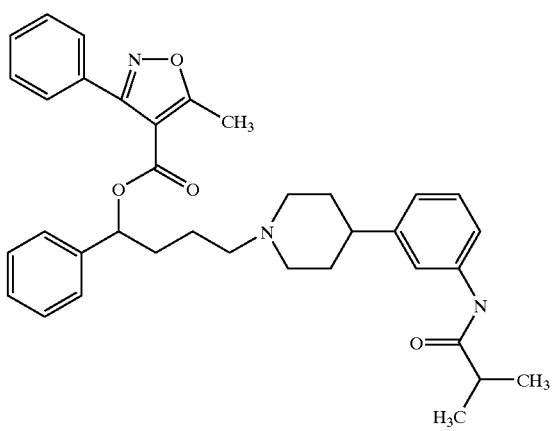 | |
| 302 | 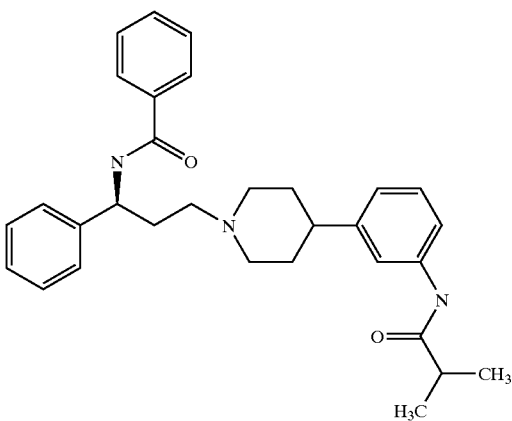<br>Chiral | 20.5 |

| | | -continued | |
|---|---|---|---|
| 303 | 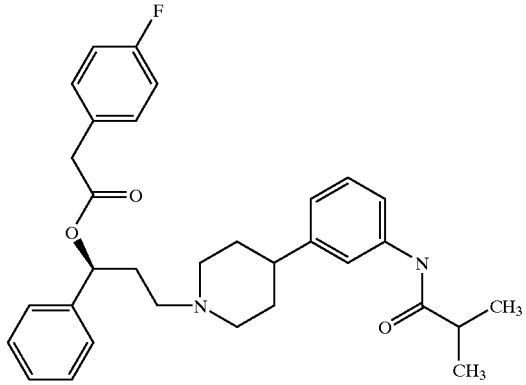 | | 9.5 |
| 304 | 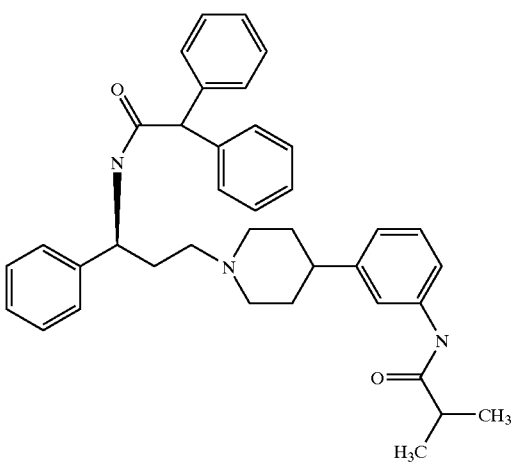<br>Chiral | | 4.0 |
| 305 | 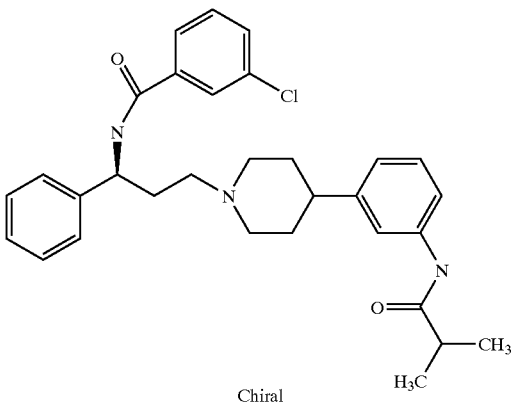<br>Chiral | | 177.2 |

-continued
| | | |
|---|---|---|
| 306 | 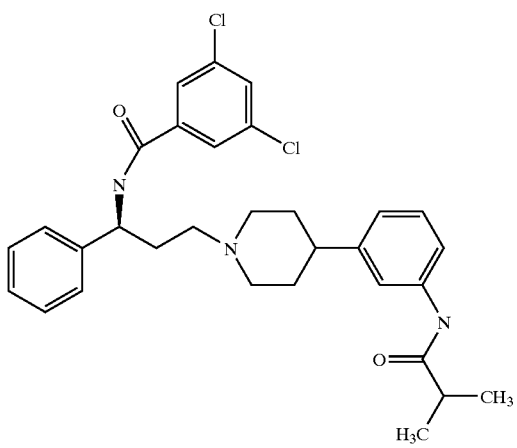 Chiral | 167.9 |
| 307 | 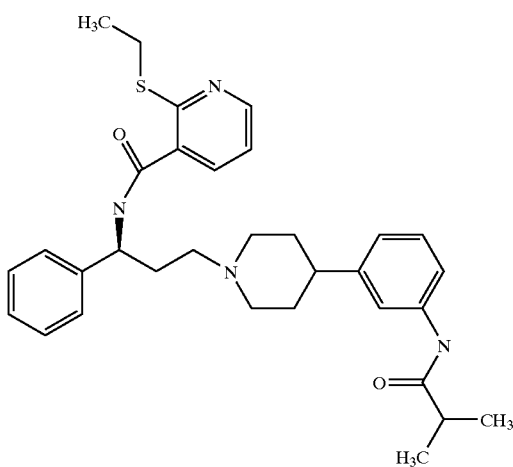 Chiral | 97.4 |
| 308 | 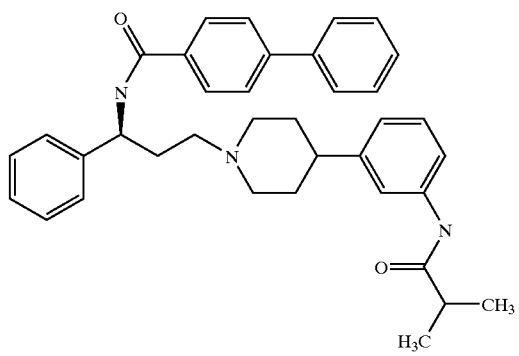 Chiral | 401.6 |

-continued
| | |
|---|---|
| 309 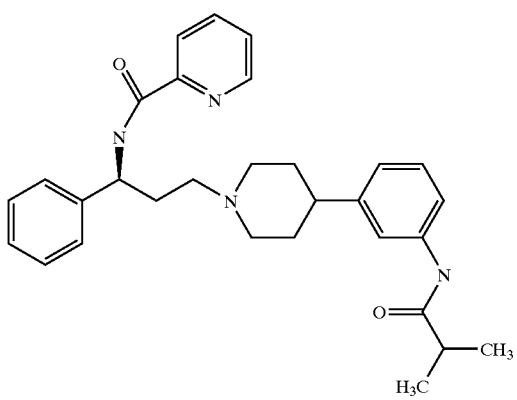 Chiral | 310.1 |
| 310 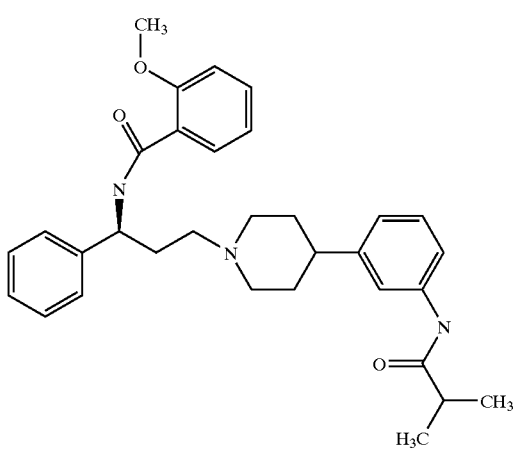 Chiral | 152.2 |
| 311 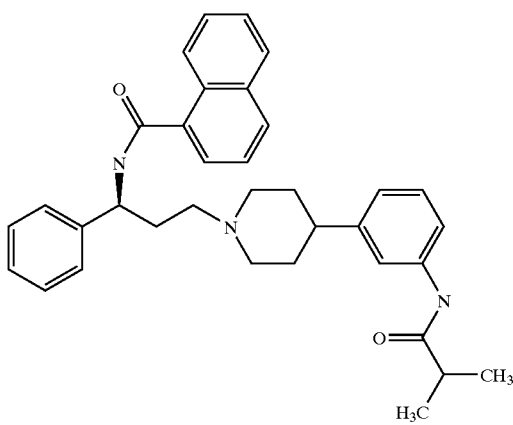 Chiral | 43.0 |

-continued
| 312 | 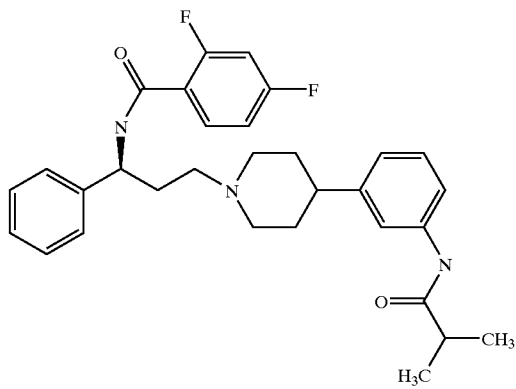  Chiral | 61.5 |
| 313 | 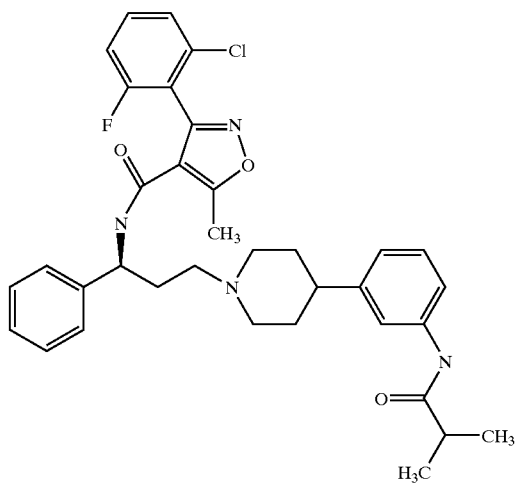  Chiral | 249.3 |
| 314 | 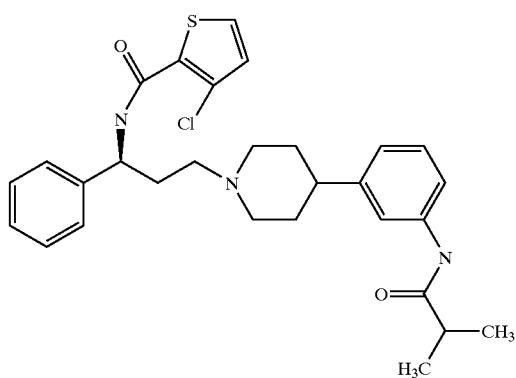  Chiral | 7.6 |

-continued
| | | |
|---|---|---|
| 315 | 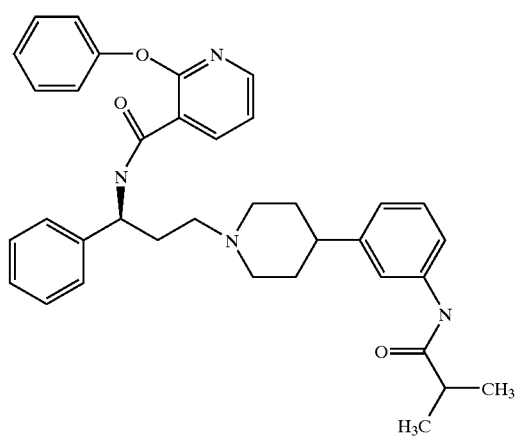<br>Chiral | 11.4 |
| 316 | 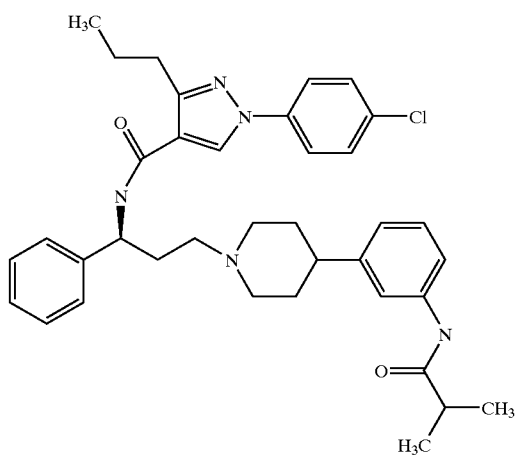<br>Chiral | 8.3 |
| 317 | 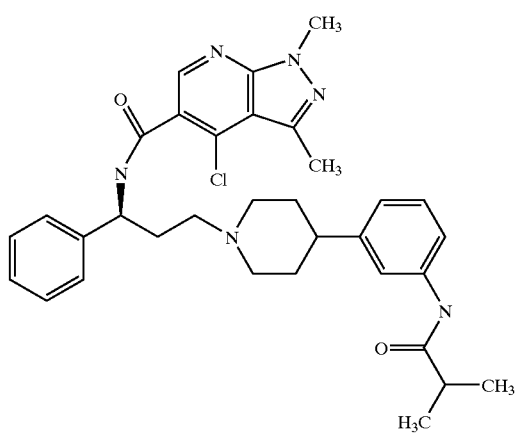<br>Chiral | 110.2 |

-continued
| | | |
|---|---|---|
| 318 | 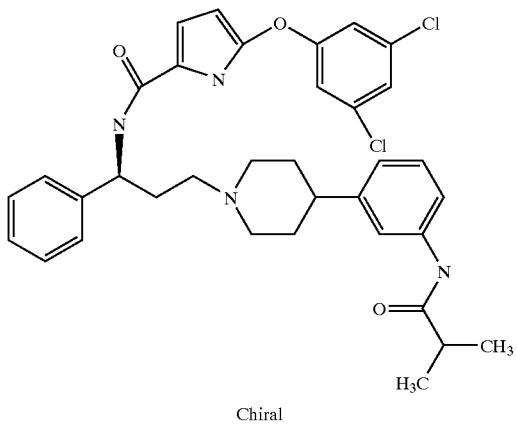<br>Chiral | 251.2 |
| 319 | 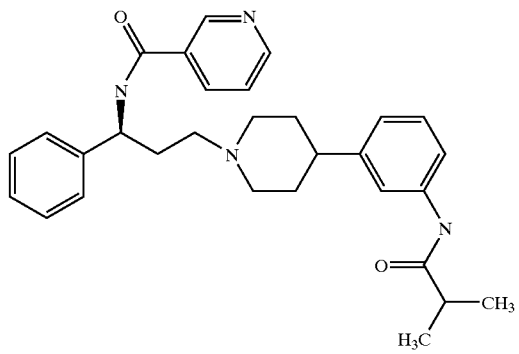<br>Chiral | 89.8 |
| 320 | 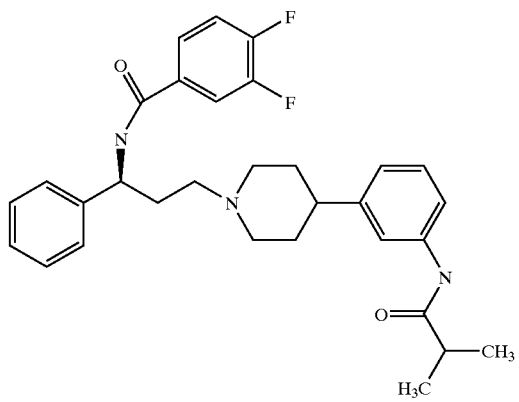<br>Chiral | 10.6 |

-continued
| | | |
|---|---|---|
| 321 | 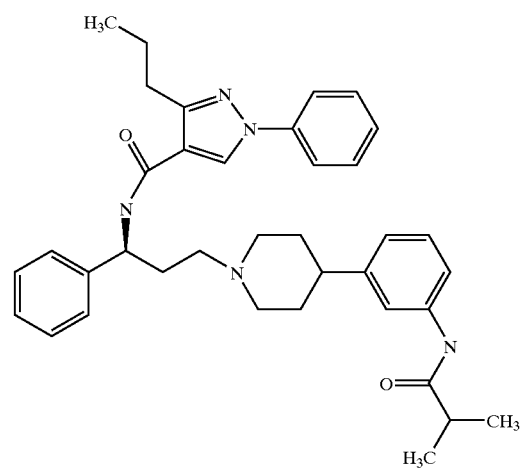 Chiral | 50.9 |
| 322 | 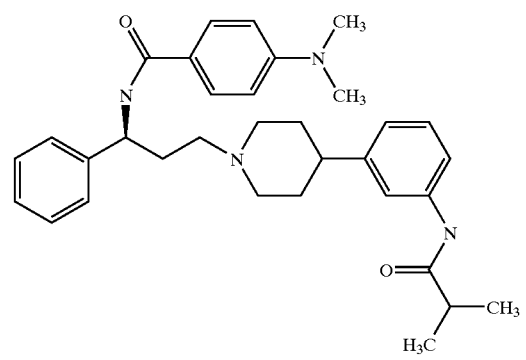 Chiral | 99.9 |
| 323 | 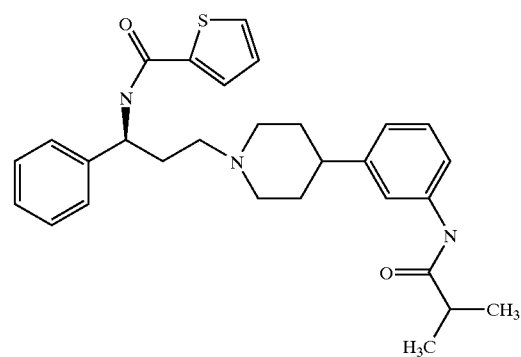 Chiral | 37.0 |

| | | |
|---|---|---|
| 324 | 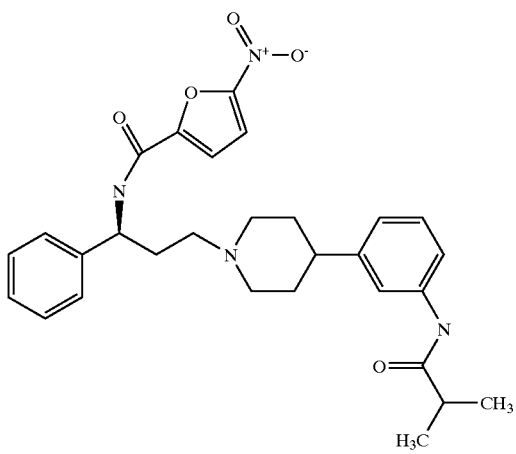 Chiral | 76.8 |
| 325 | 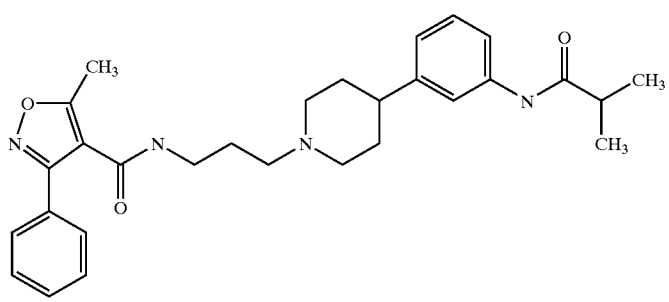 | 29.8 |
| 326 | 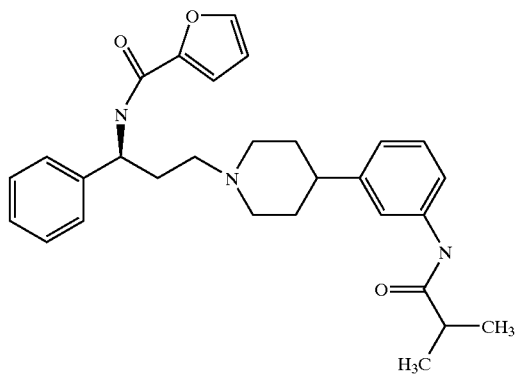 Chiral | 19.2 |

-continued
| | | |
|---|---|---|
| 327 | 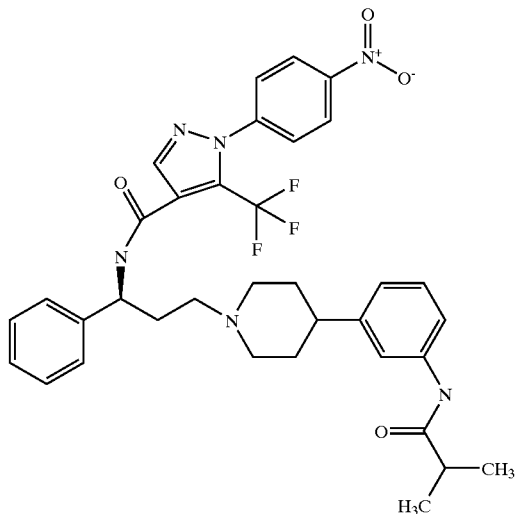  Chiral | 7.7 |
| 328 | 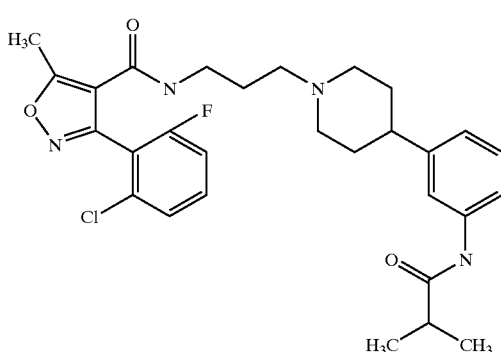 | 47.6 |
| 329 | 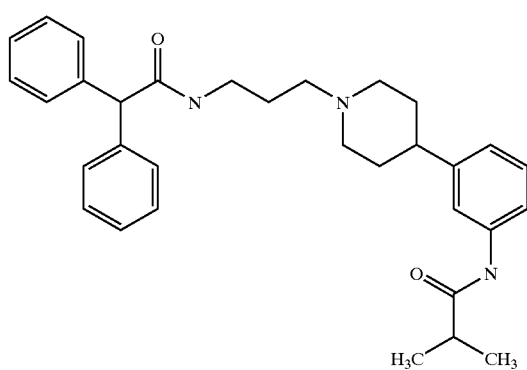 | 2.9 |
| 330 | 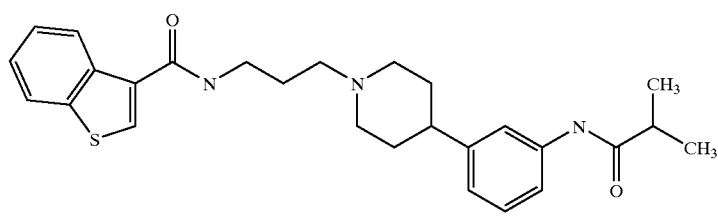 | 215.0 |

| | | |
|---|---|---|
| 331 | 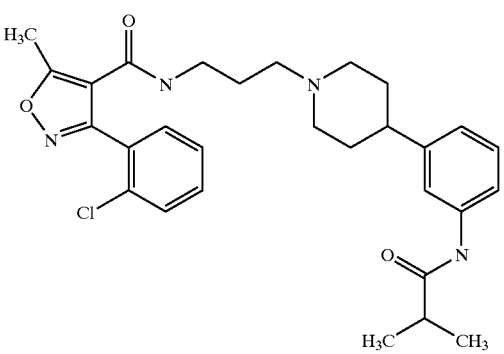 | 51.3 |
| 332 | 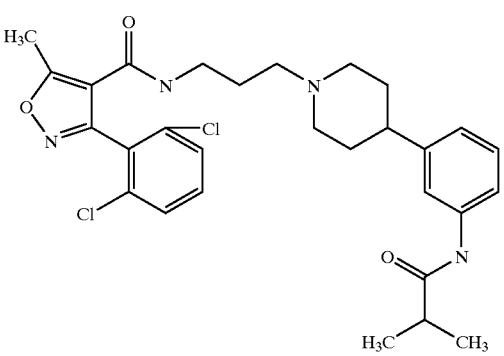 | 29.0 |
| 333 | 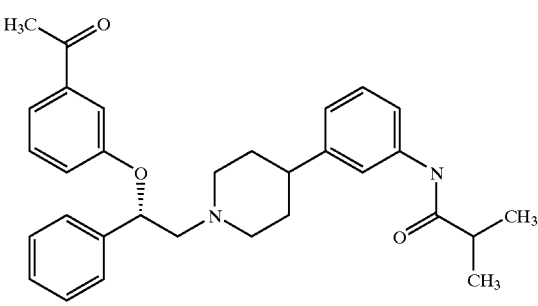
Chiral | 567.8 |
| 334 | 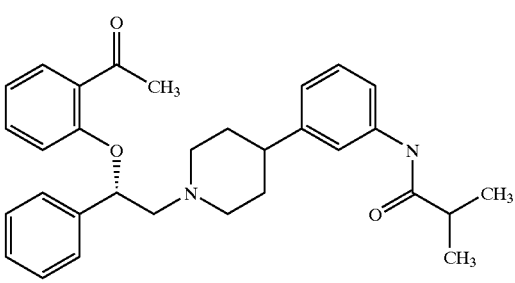
Chiral | 602.8 |

-continued
| | | |
|---|---|---|
| 335 | 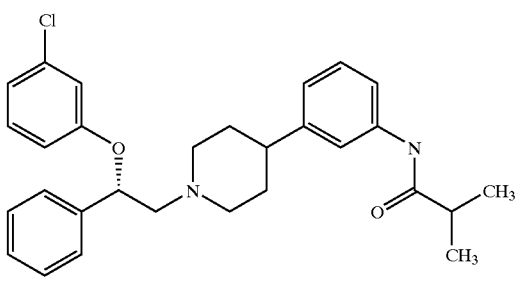 Chiral | 887.7 |
| 336 | 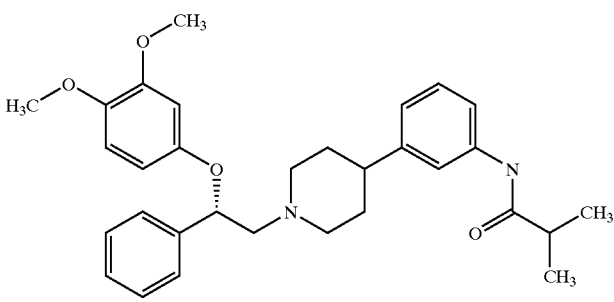 Chiral | 693.0 |
| 337 | 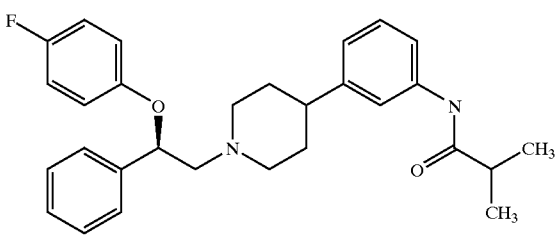 Chiral | 907.4 |
| 338 | 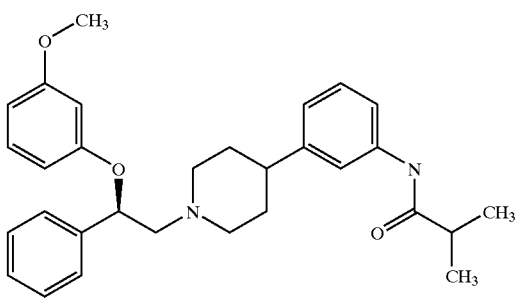 Chiral | 843.9 |
| 339 | 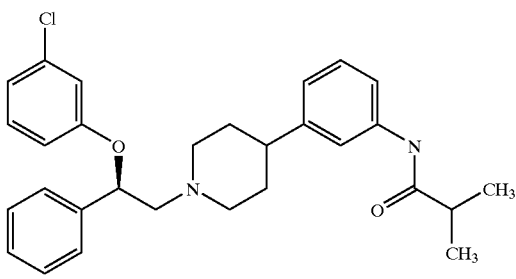 Chiral | 889.9 |

-continued
| | | |
|---|---|---|
| 340 | 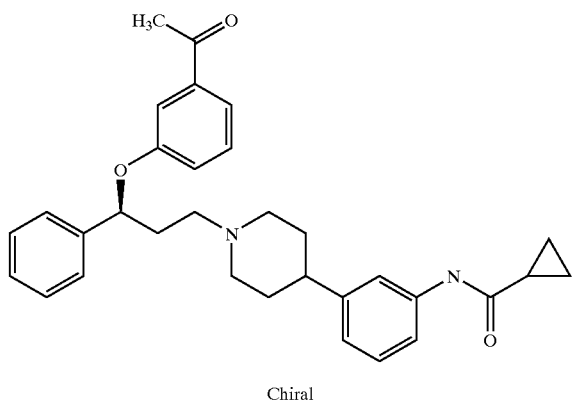  Chiral | 15.6 |
| 341 | 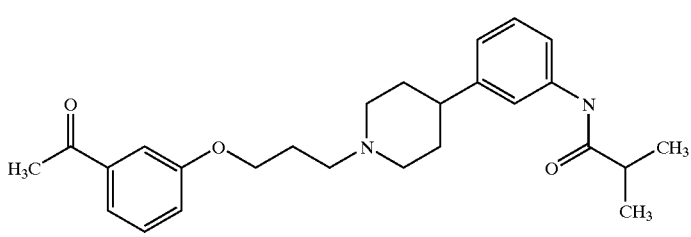 | 255.6 |
| 342 | 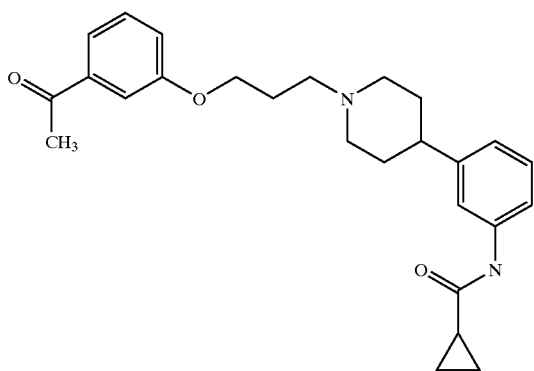 | 183.0 |
| 343 | 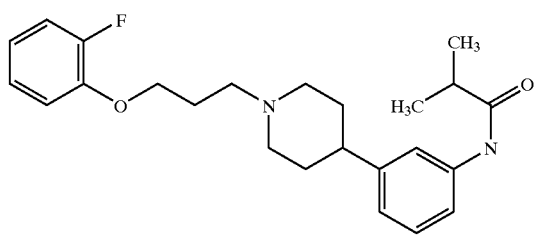 | 194.7 |
| 344 | 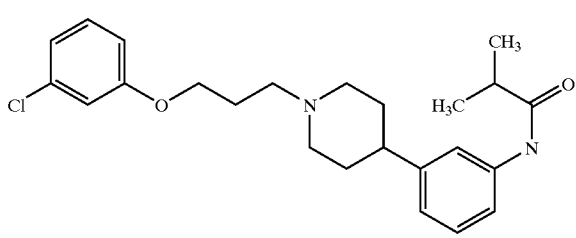 | 44.6 |

-continued
| | | |
|---|---|---|
| 345 | 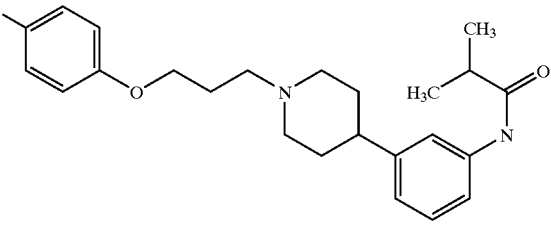 | 15.4 |
| 346 | 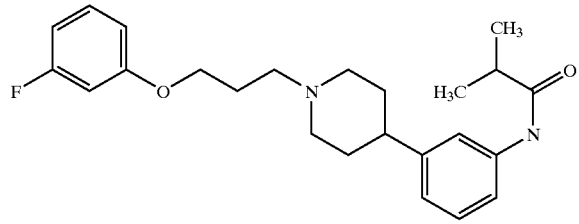 | 106.9 |
| 347 | 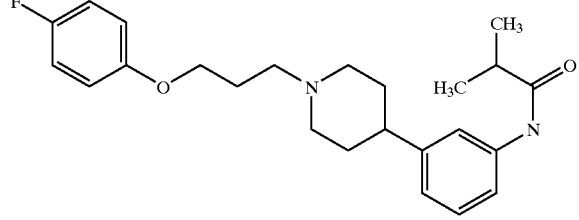 | 54.8 |
| 348 | 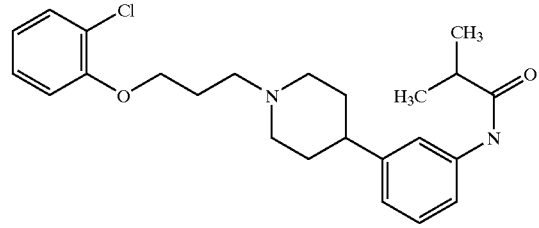 | 84.0 |
| 349 | 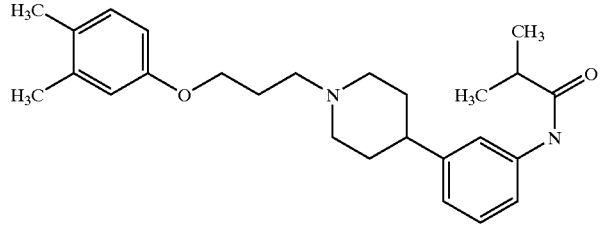 | 20.4 |
| 350 | 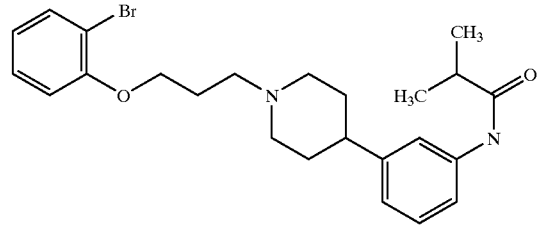 | 12.1 |

-continued
| | | |
|---|---|---|
| 351 | 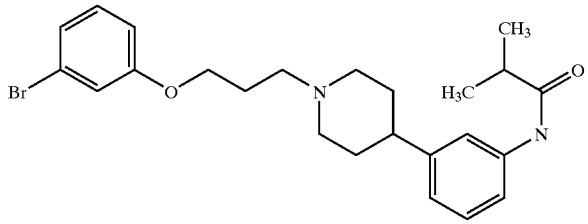 | 61.8 |
| 352 | 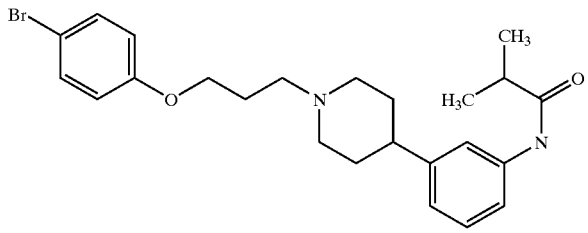 | 13.3 |
| 353 | 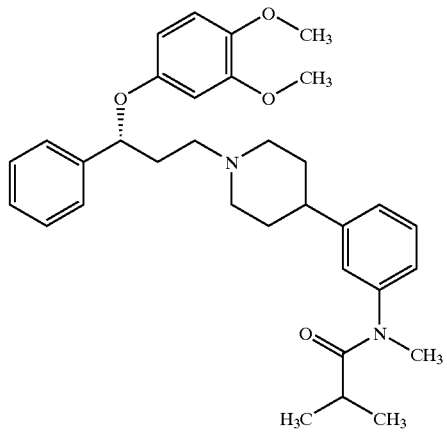<br>Chiral | 41.8 |
| 354 | 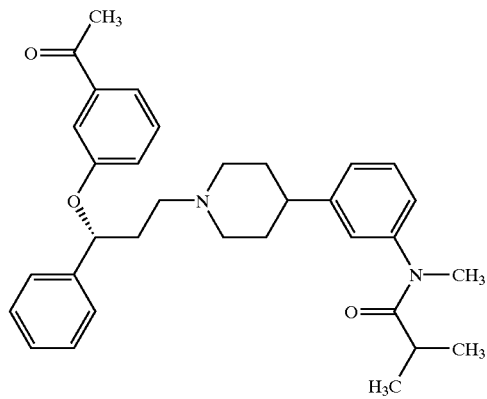<br>Chiral | 81.6 |

| | | |
|---|---|---|
| 355 | 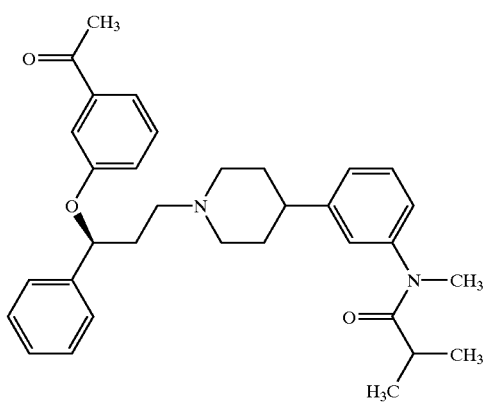 Chiral | 116.6 |
| 356 | 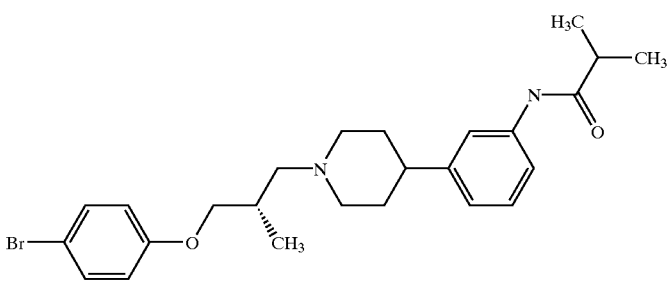 Chiral | 54.5 |
| 357 | 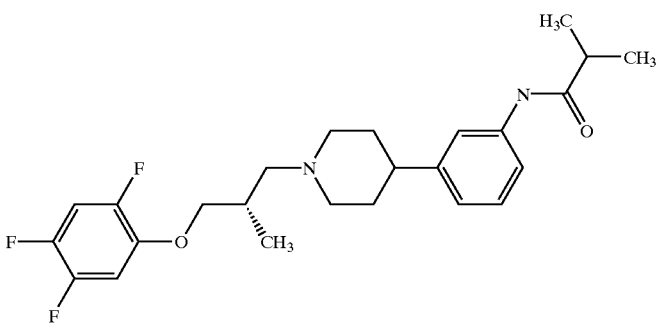 | 115.4 |
| 358 | 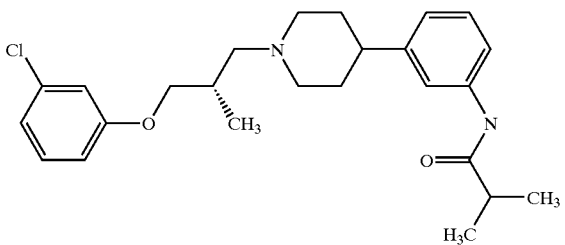 Chiral | 135.7 |

-continued
| | | |
|---|---|---|
| 359 | 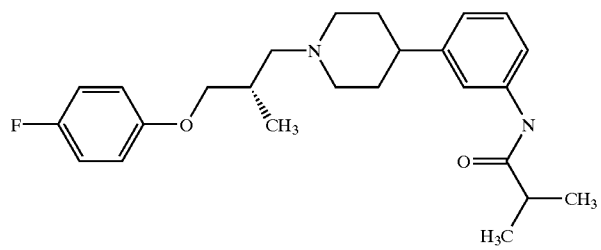 Chiral | 83.2 |
| 360 | 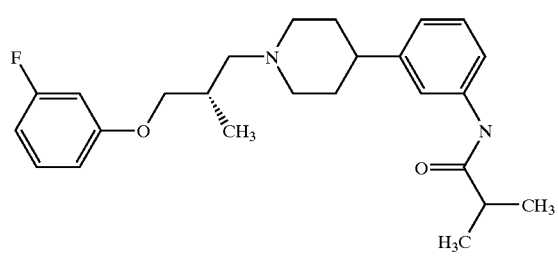 Chiral | 163.0 |
| 361 | 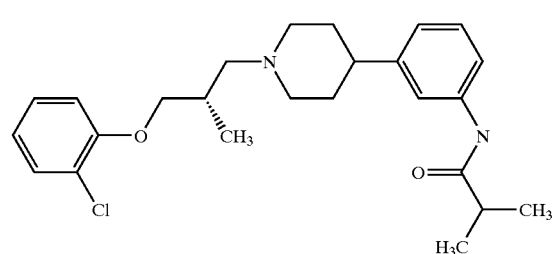 Chiral | 311.2 |
| 362 | 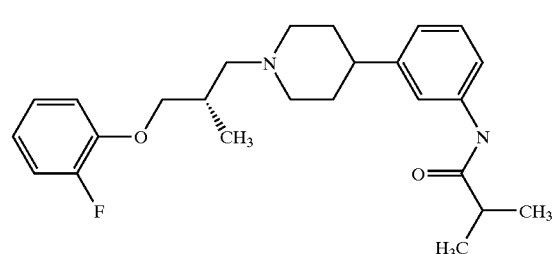 Chiral | 281.2 |
| 363 | 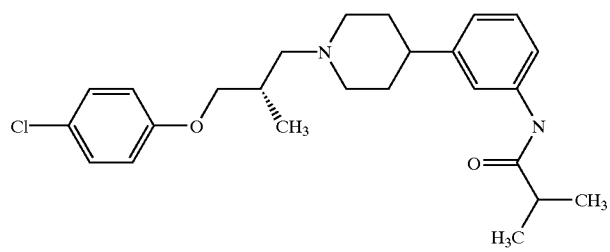 Chiral | 31.6 |

-continued
| | | |
|---|---|---|
| 364 | 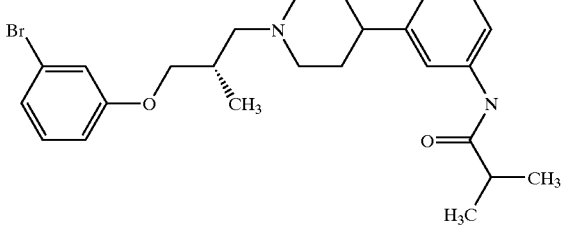<br>Chiral | 144.4 |
| 365 | 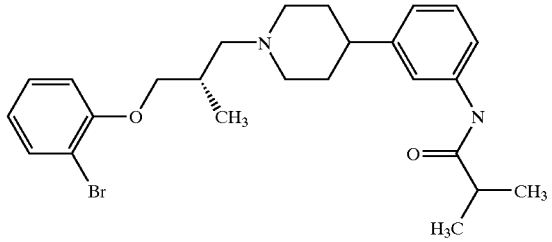<br>Chiral | 42.9 |
| 366 | 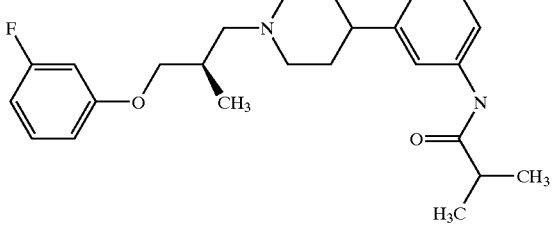<br>Chiral | 645.5 |
| 367 | 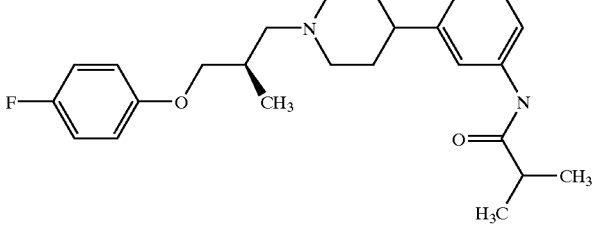<br>Chiral | 235.7 |
| 368 | 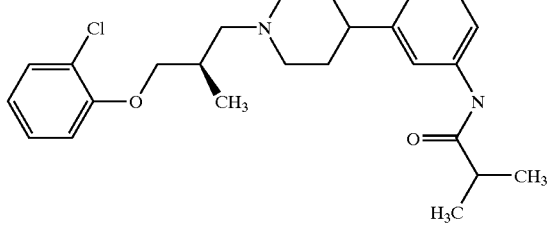<br>Chiral | 313.0 |

| | | |
|---|---|---|
| 369 | 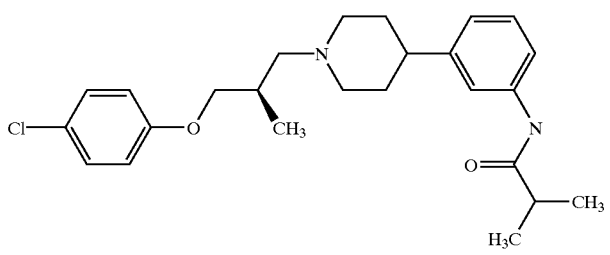 Chiral | 145.0 |
| 370 | 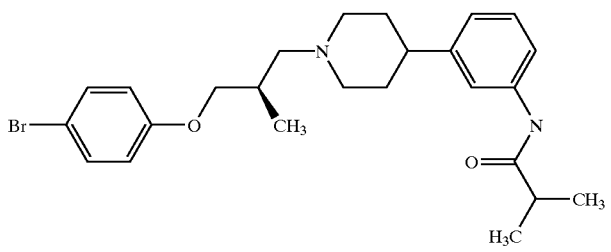 Chiral | |
| 371 | 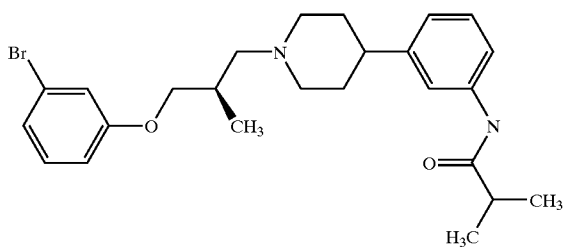 Chiral | 162.7 |
| 372 | 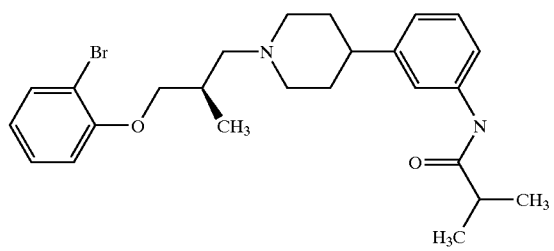 Chiral | 357.7 |
| 373 | 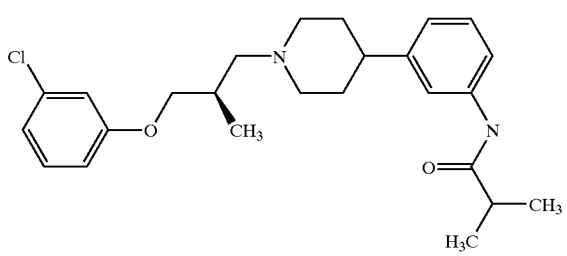 Chiral | 428.5 |

-continued
| | | |
|---|---|---|
| 374 | 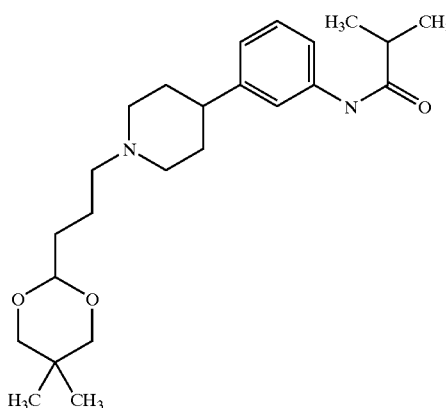 | 96.8 |
| 375 | 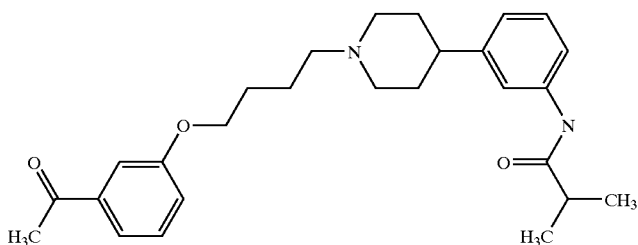 | 185.6 |
| 376 | 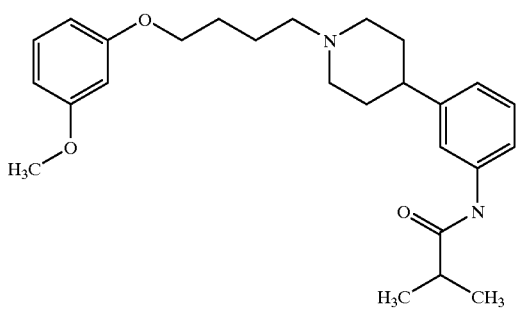 | 887.6 |
| 377 | 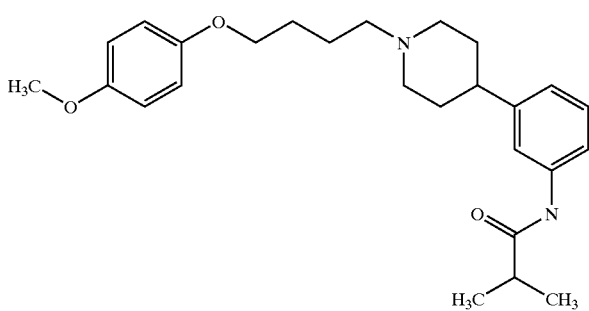 | 711.9 |
| 378 | 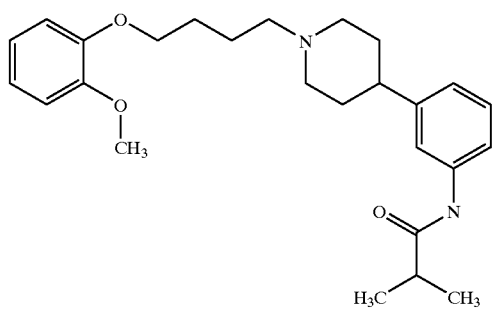 | 307.8 |

-continued
| | | |
|---|---|---|
| 379 | 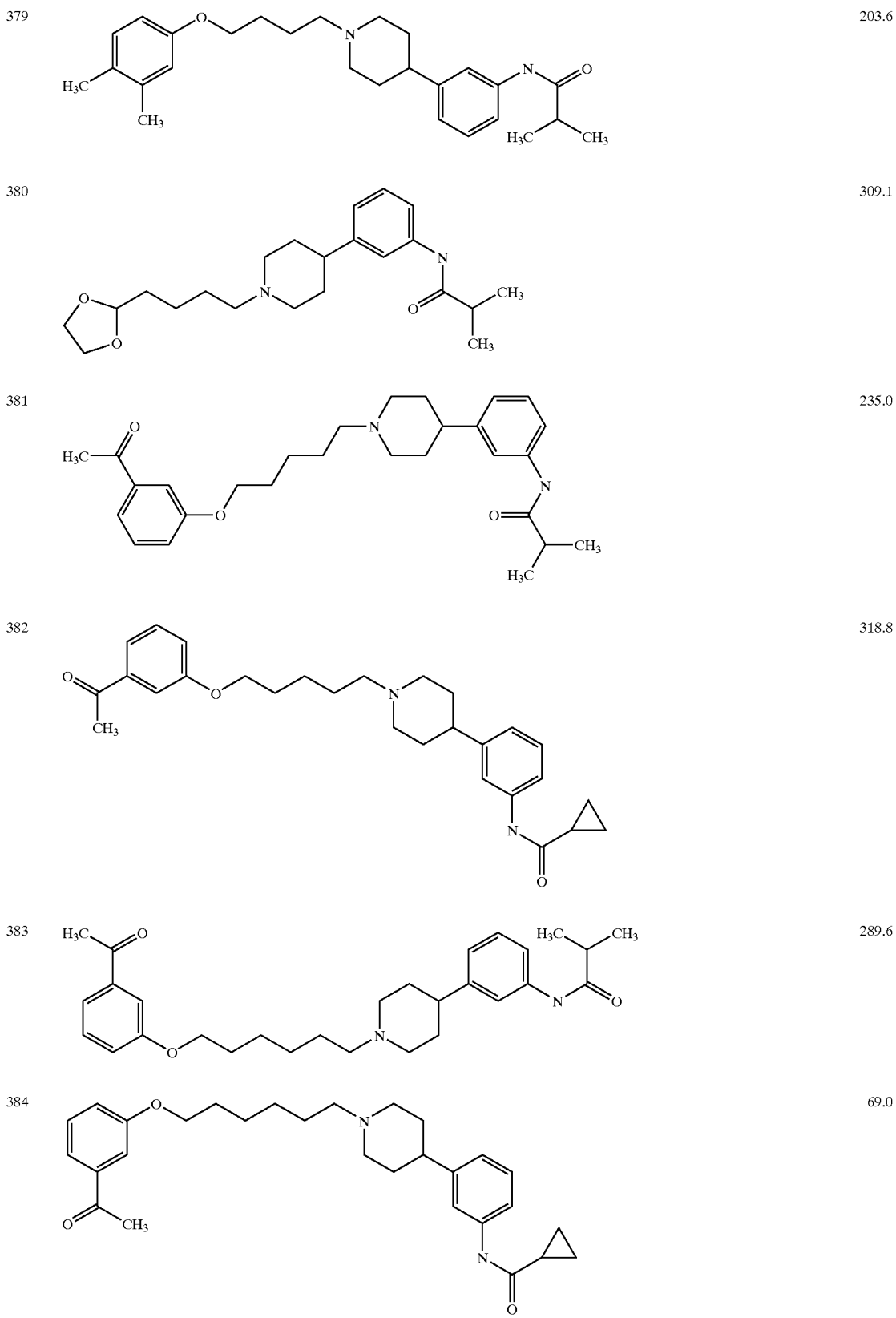 | 203.6 |
| 380 | | 309.1 |
| 381 | | 235.0 |
| 382 | | 318.8 |
| 383 | | 289.6 |
| 384 | | 69.0 |

| | | |
|---|---|---|
| 385 | 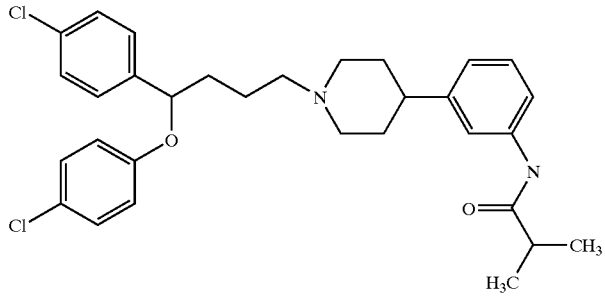 | 324.6 |
| 386 | 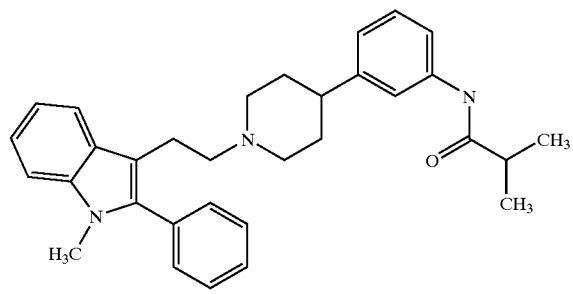 | 26.3 |
| 387 | 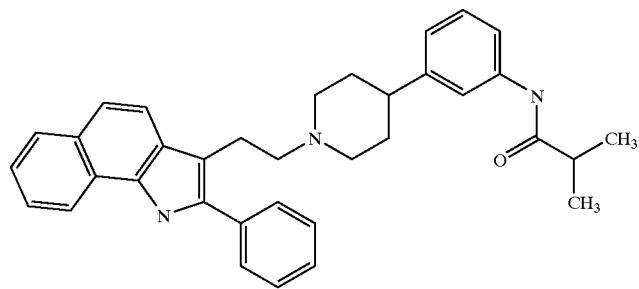 | 19.7 |
| 388 | 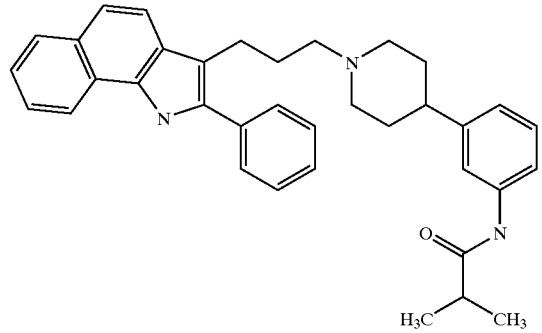 | 20.7 |

-continued
| 389 | 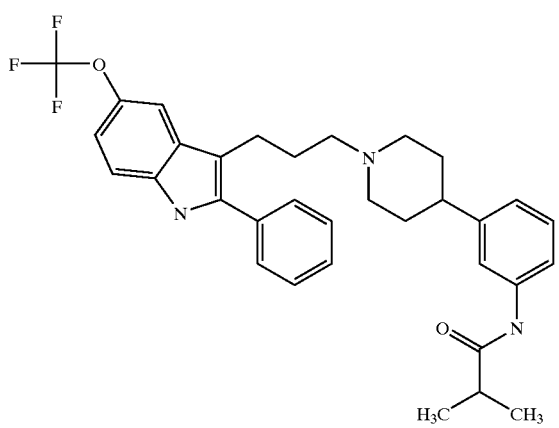 | 2.2 |
| 390 | 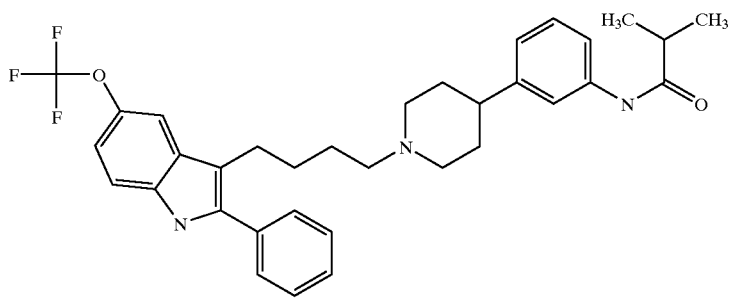 | 1.0 |
| 391 | 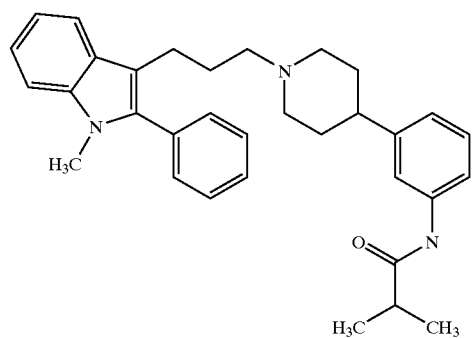 | 21.9 |
| 392 | 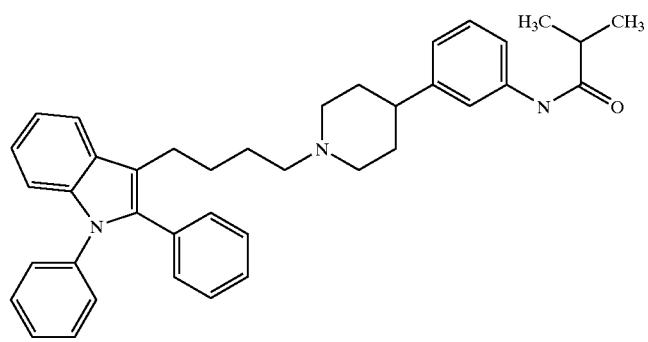 | 18.1 |

| | | |
|---|---|---|
| 393 | 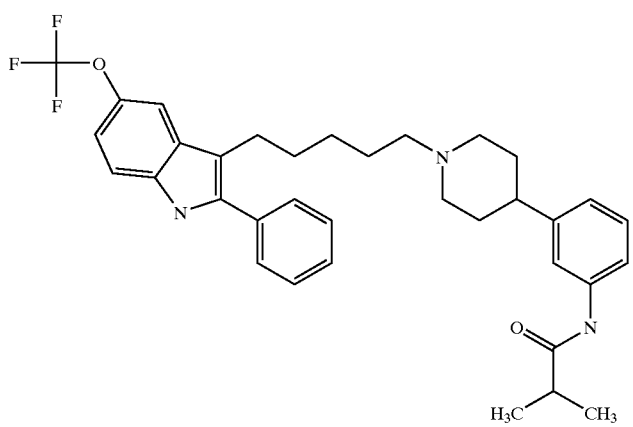 | 9.5 |
| 394 | 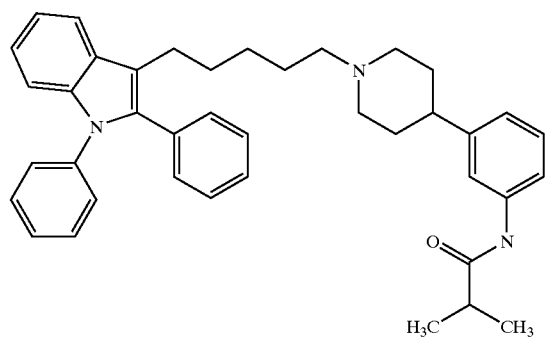 | |
| 395 | 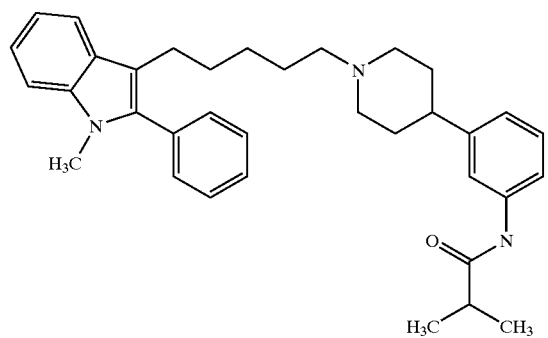 | 2.4 |
| 396 | 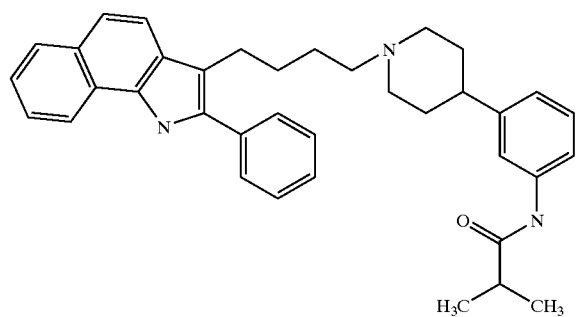 | |

| | | |
|---|---|---|
| 397 | 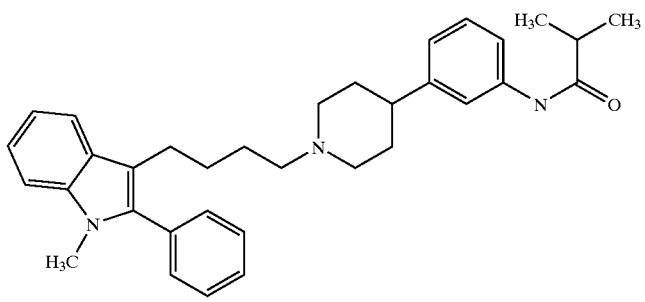 | |
| 398 | 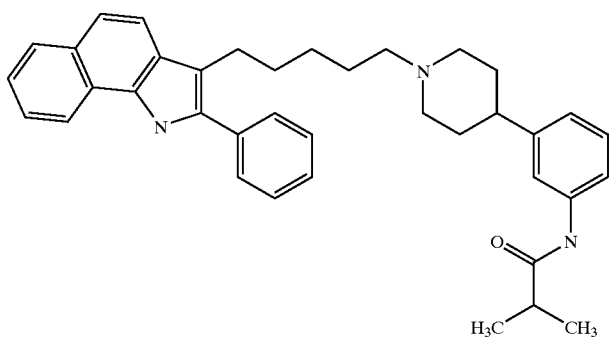 | 13.6 |
| 399 | 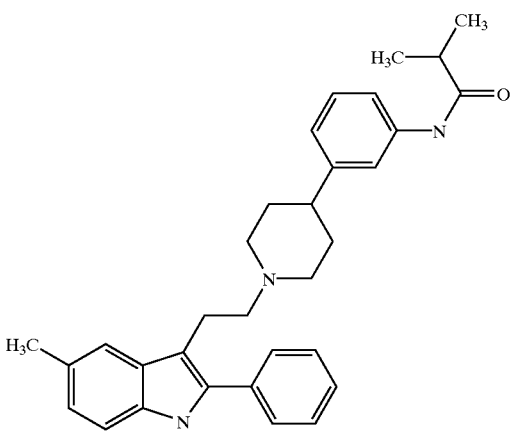 | 31.9 |
| 400 | 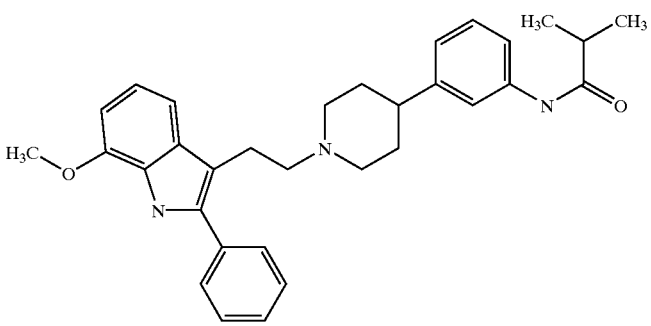 | 43.9 |

| | | |
|---|---|---|
| 401 | 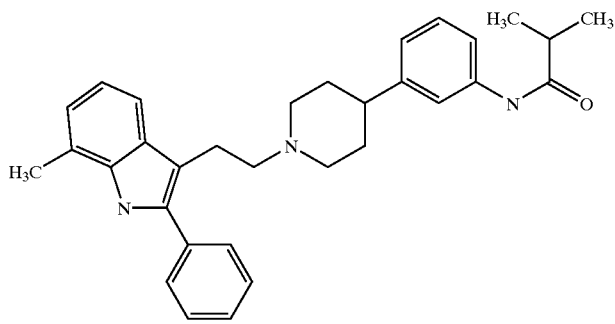 | 44.6 |
| 402 | 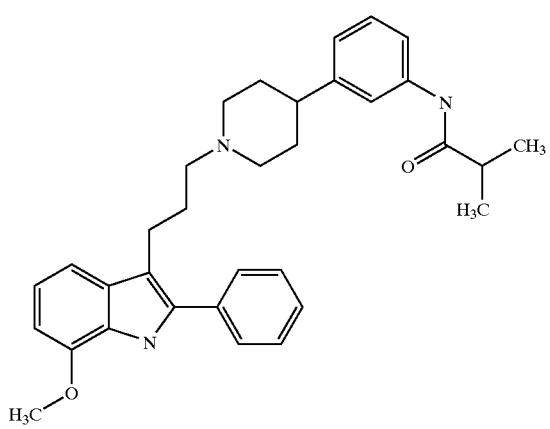 | |
| 403 | 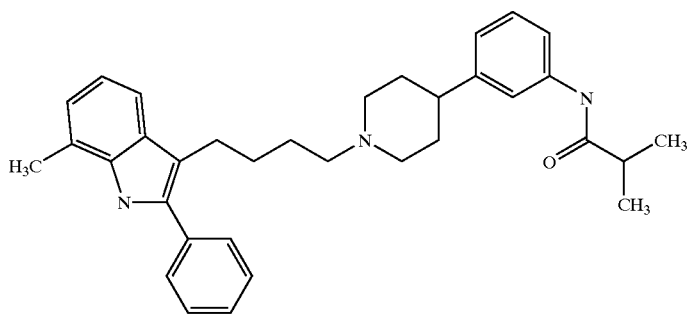 | 11.7 |
| 404 | 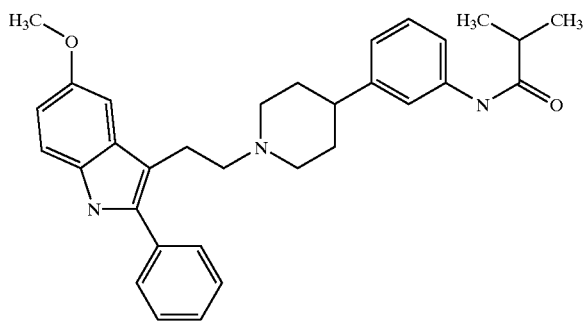 | |

| | | |
|---|---|---|
| 405 | 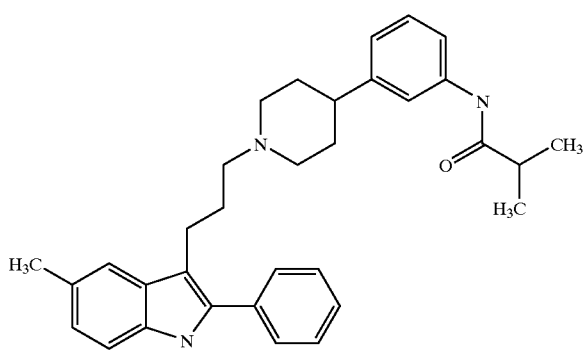 | |
| 406 | 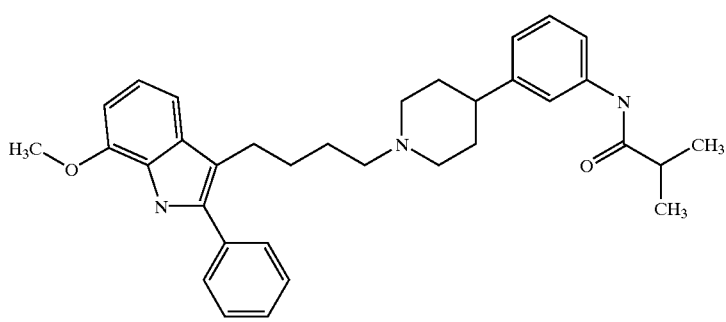 | 12.3 |
| 407 | 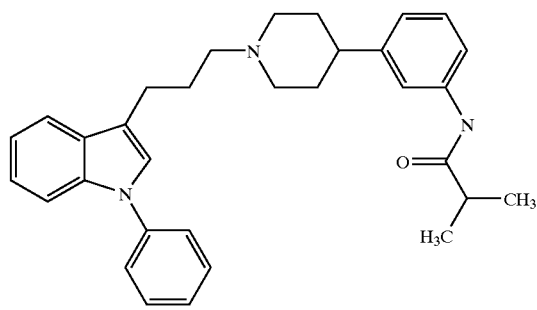 | 16.6 |
| 408 | 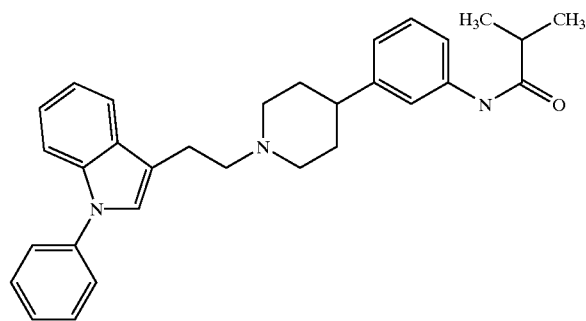 | 21.6 |

409 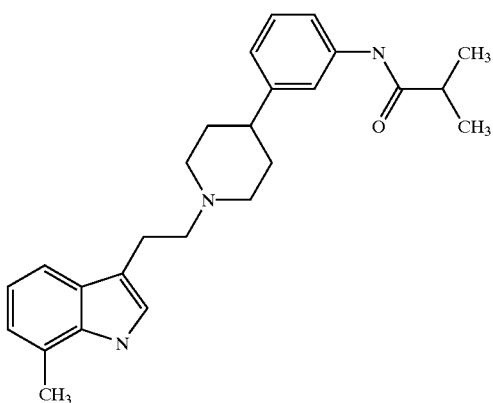 96.7
410 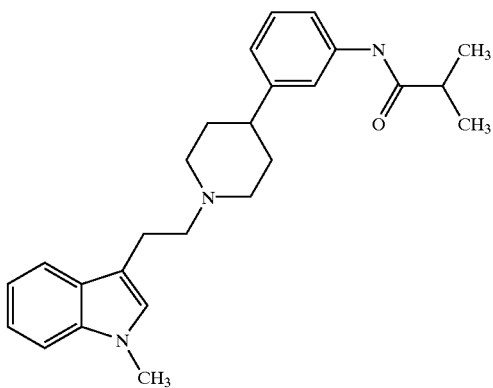 262.7
411 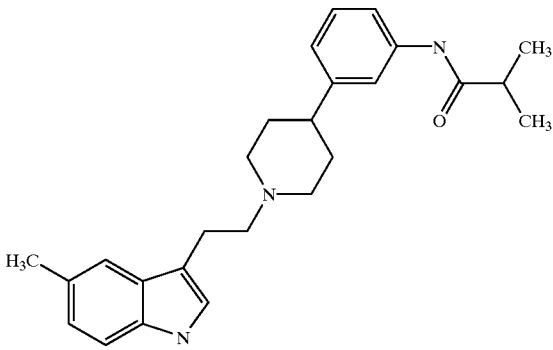 82.3
412 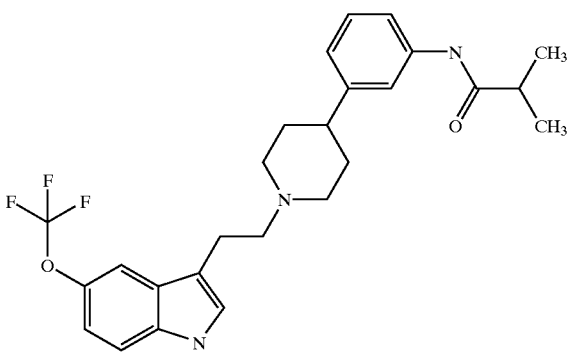 27.0

-continued
| | | |
|---|---|---|
| 413 | 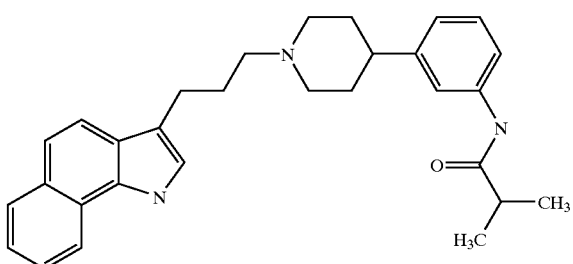 | 76.8 |
| 414 | 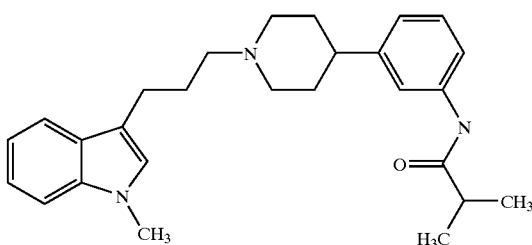 | 2.9 |
| 415 | 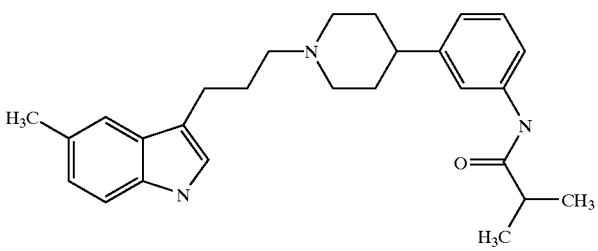 | 8.1 |
| 416 | 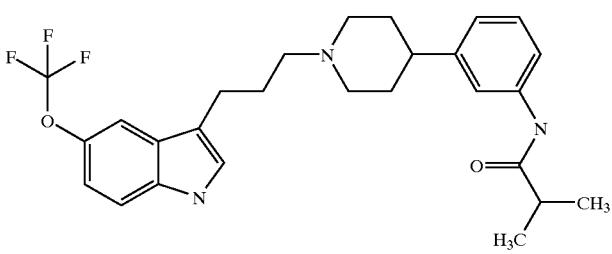 | 12.6 |
| 417 | 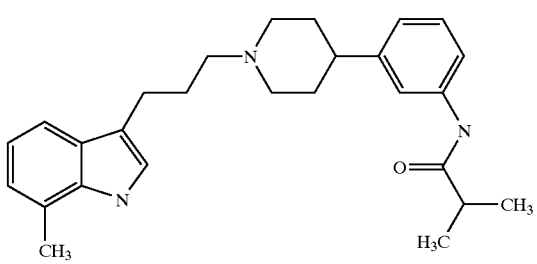 | 20.5 |
| 418 | 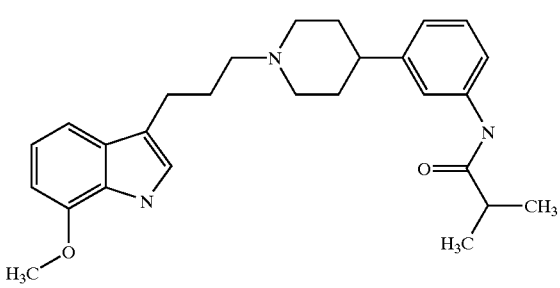 | 51.6 |

-continued
| | | |
|---|---|---|
| 419 | 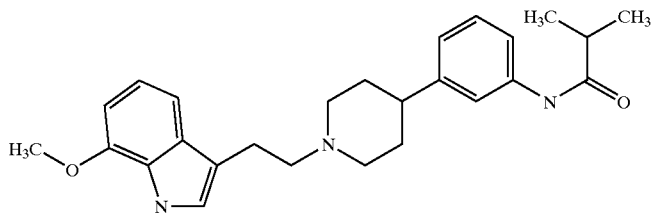 | 83.9 |
| 420 | 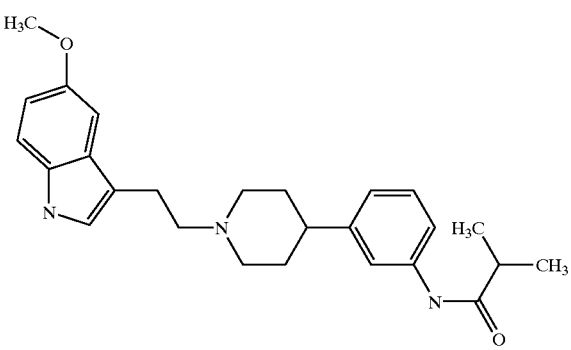 | |
| 421 | 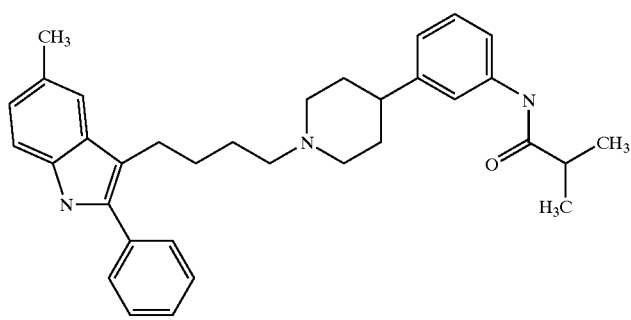 | 1.8 |
| 422 | 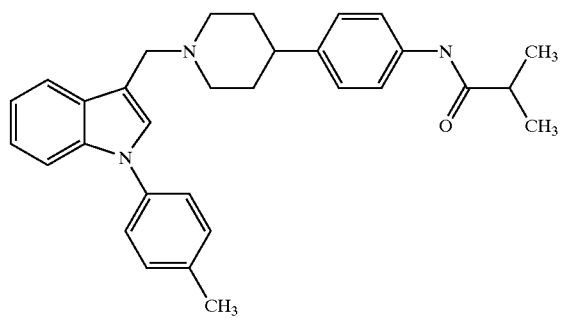 | 173.0 |
| 423 | 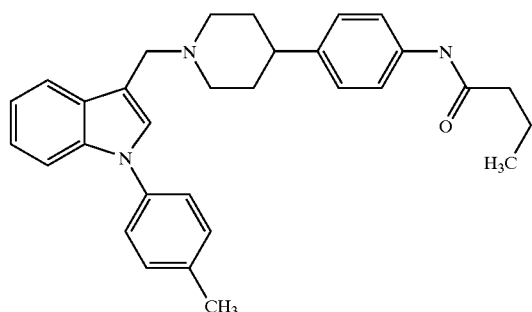 | 405.2 |

-continued
| | | |
|---|---|---|
| 424 | 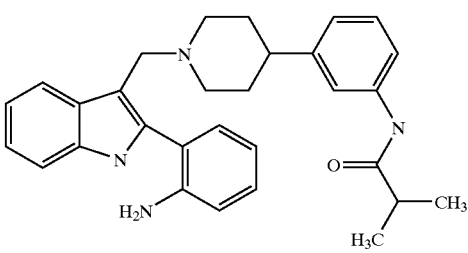 | 114.2 |
| 425 | 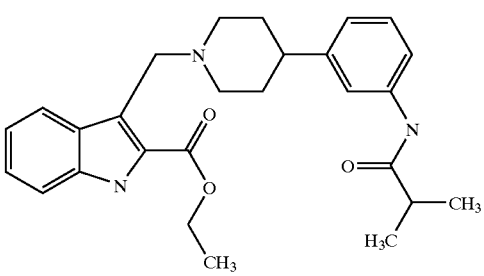 | 599.3 |
| 426 | 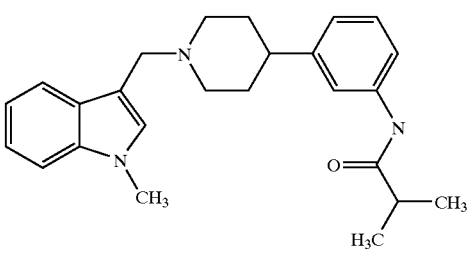 | 556.1 |
| 427 | 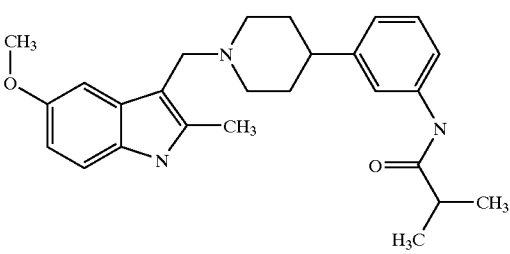 | 248.3 |
| 428 | 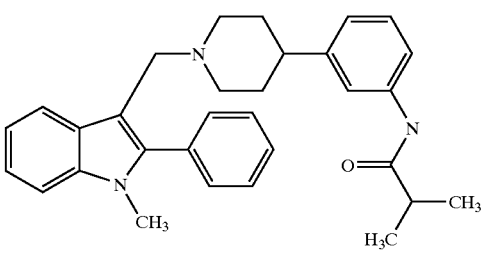 | 132.4 |
| 429 | 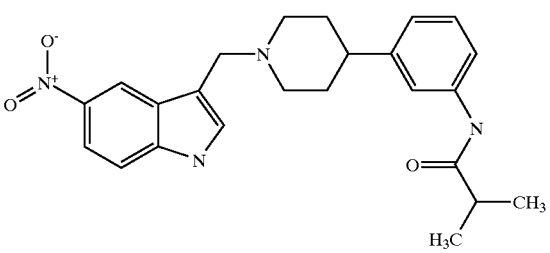 | 121.4 |

-continued
| | | |
|---|---|---|
| 430 | 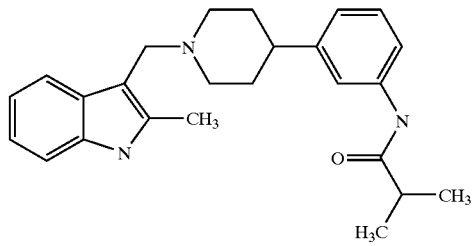 | 647.4 |
| 431 | 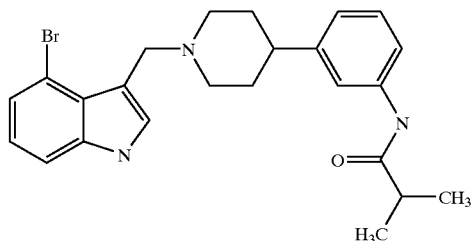 | 967.7 |
| 432 | 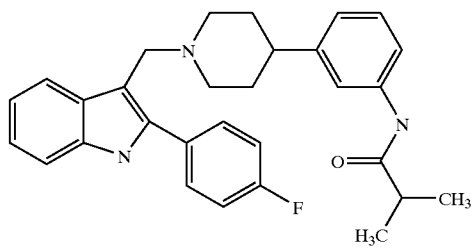 | 198.2 |
| 433 | 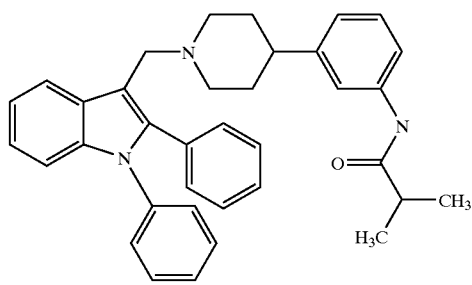 | 30.4 |
| 434 | 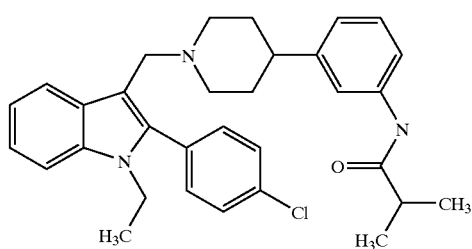 | 214.2 |
| 435 | 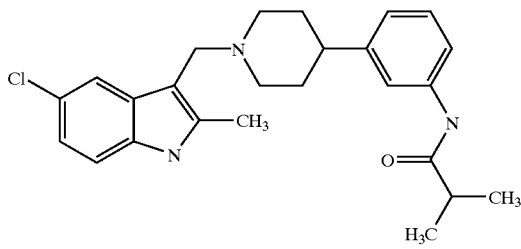 | 215.4 |

-continued
| | | |
|---|---|---|
| 436 | 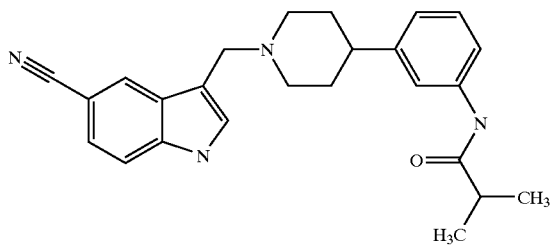 | 434.3 |
| 437 | 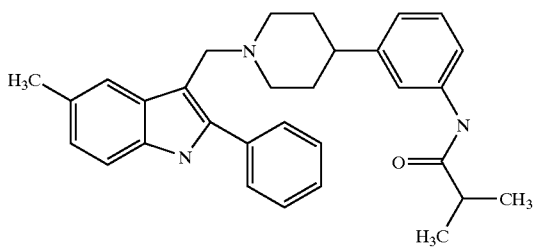 | 552.1 |
| 438 | 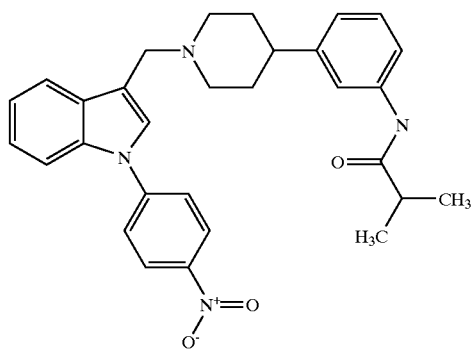 | 1.3 |
| 439 | 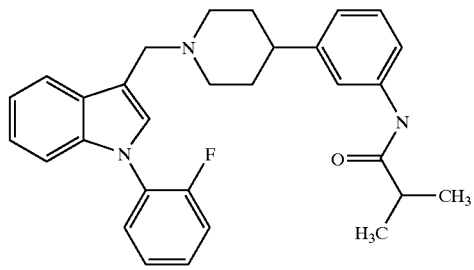 | 8.5 |
| 440 | 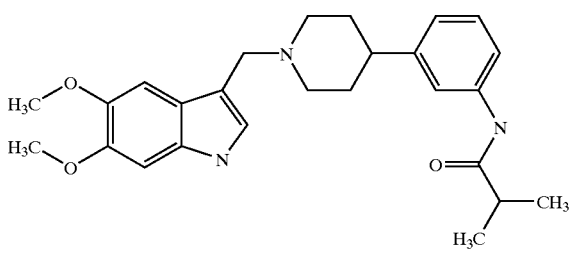 | 106.9 |

-continued
| | | |
|---|---|---|
| 441 | 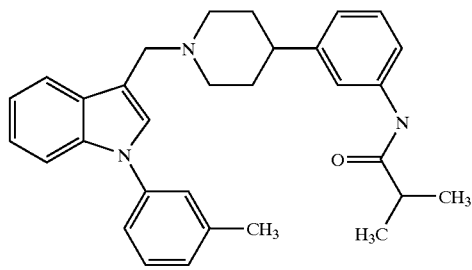 | 10.1 |
| 442 | 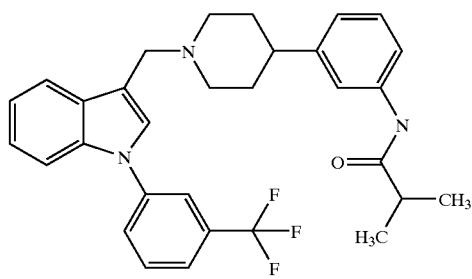 | 7.8 |
| 443 | 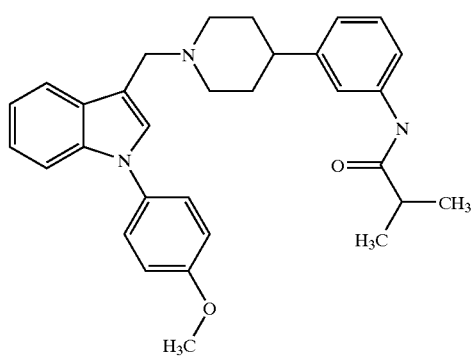 | 23.4 |
| 444 | 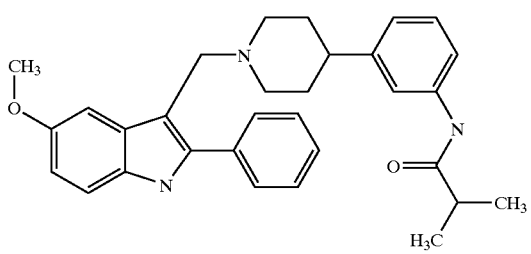 | 544.7 |
| 445 | 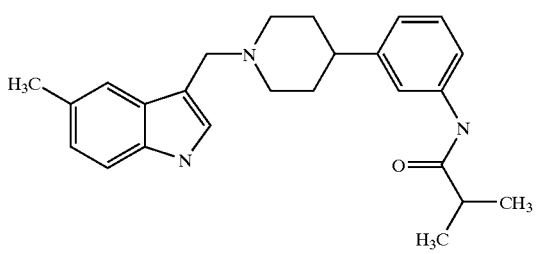 | 486.3 |

-continued
| | | |
|---|---|---|
| 446 | 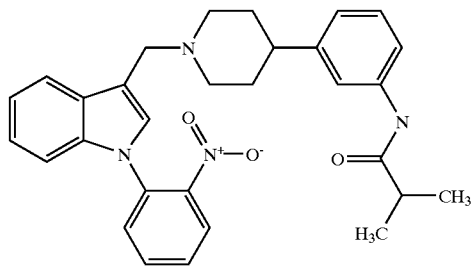 | 17.9 |
| 447 | 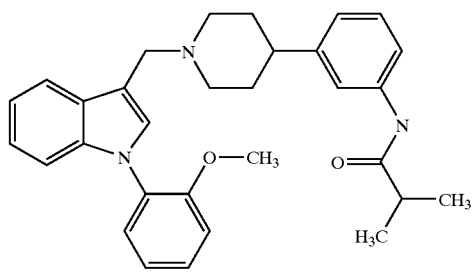 | 9.8 |
| 448 | 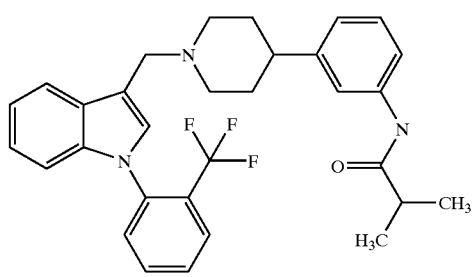 | 61.0 |
| 449 | 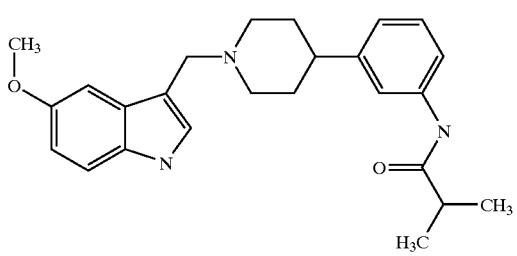 | 623.4 |
| 450 | 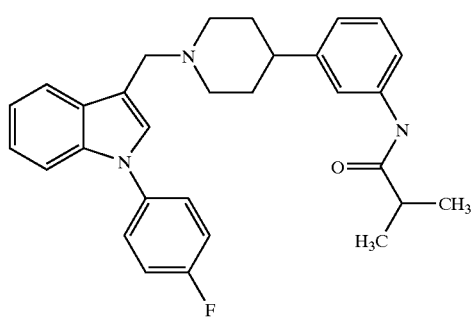 | 7.1 |

| | | -continued | |
|---|---|---|---|
| 451 | 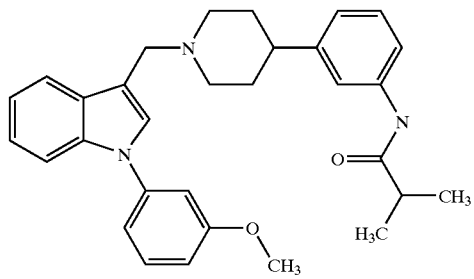 | | 18.7 |
| 452 | 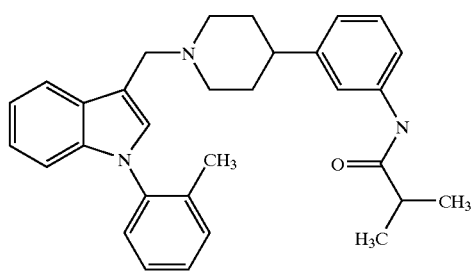 | | 12.7 |
| 453 | 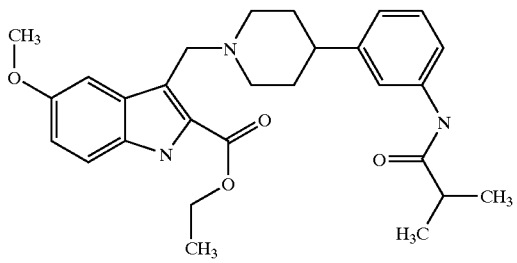 | | 194.8 |
| 454 | 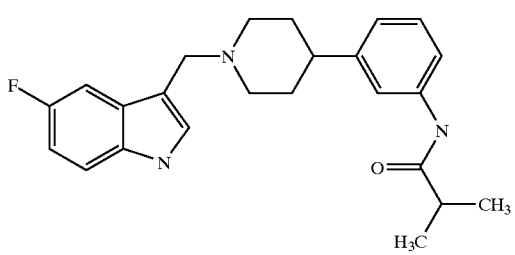 | | 772.0 |
| 455 | 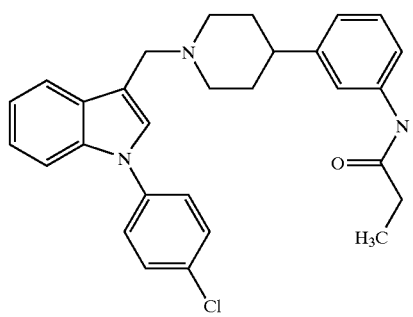 | | 10.6 |

-continued
| | | |
|---|---|---|
| 456 | 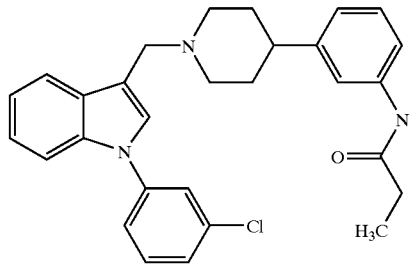 | 28.0 |
| 457 | 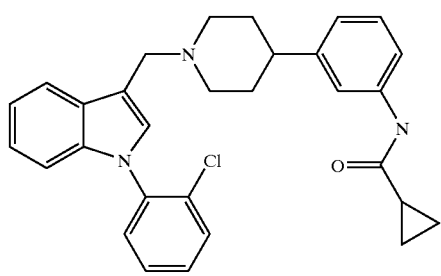 | 27.4 |
| 458 | 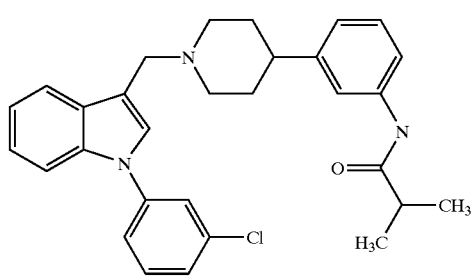 | 15.3 |
| 459 | 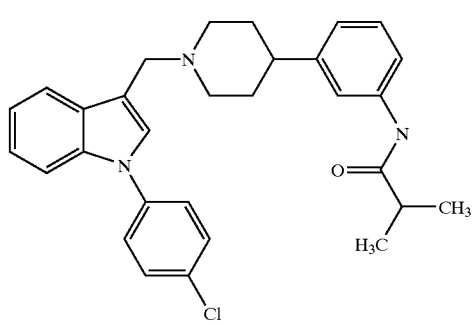 | 10.4 |
| 460 | 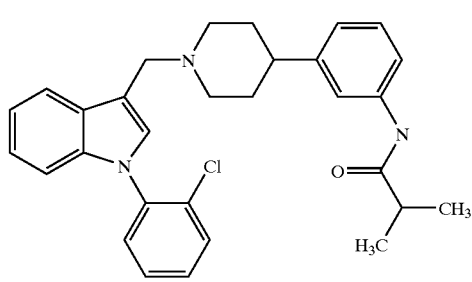 | 9.1 |

-continued
| | | |
|---|---|---|
| 461 | 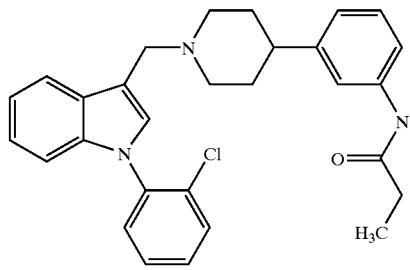 | 35.6 |
| 462 | 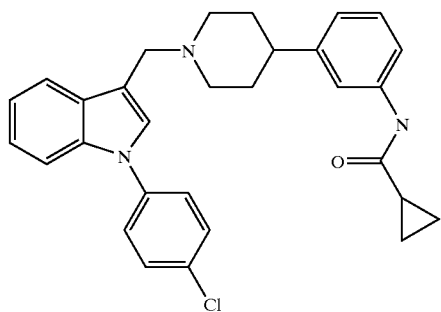 | 12.4 |
| 463 | 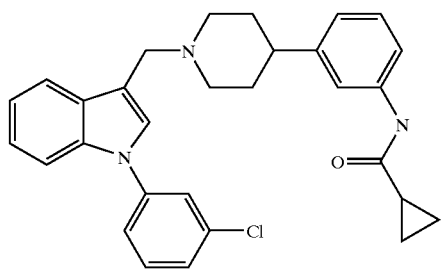 | 17.2 |
| 464 | 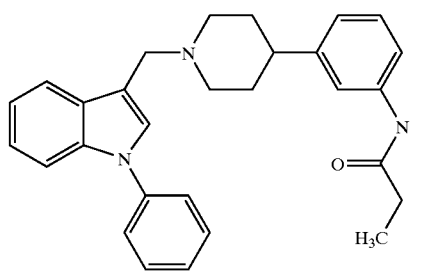 | 84.1 |
| 465 | 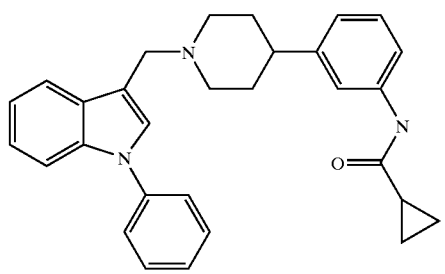 | 10.7 |

-continued
| | | |
|---|---|---|
| 466 | 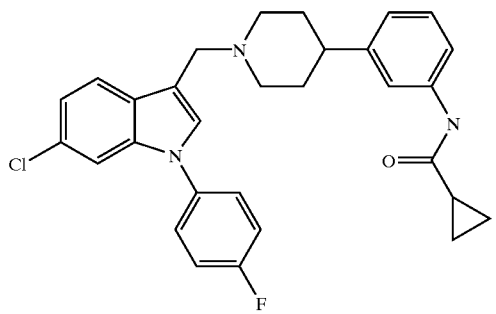 | |
| 467 | 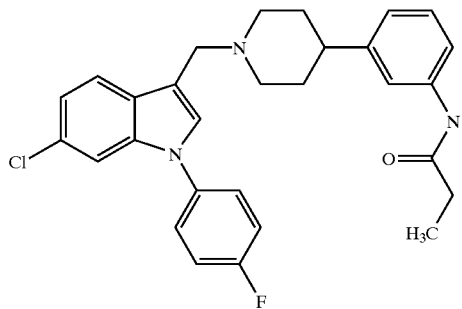 | |
| 468 | 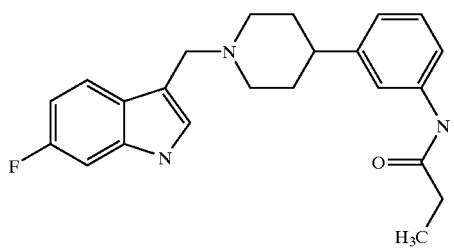 | 912.3 |
| 469 | 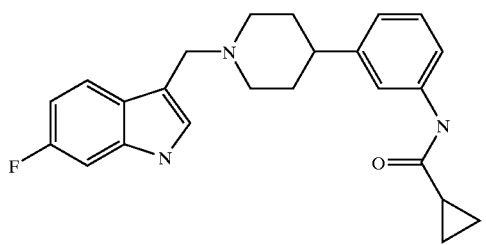 | 479.5 |
| 470 | 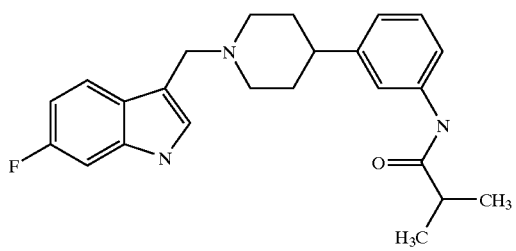 | 654.1 |

-continued
| | | |
|---|---|---|
| 471 | 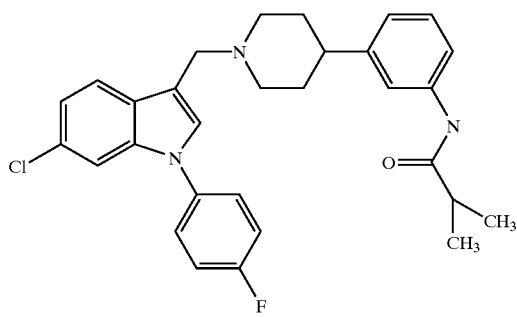 | 4.3 |
| 472 | 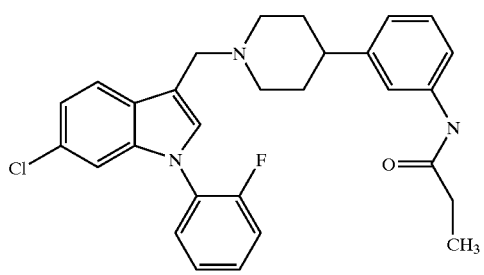 | 12.2 |
| 473 | 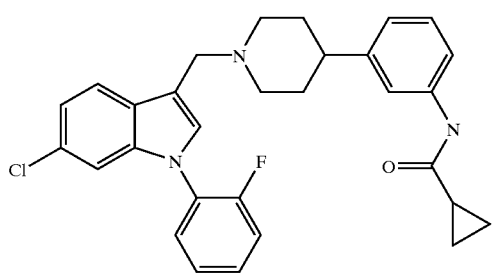 | 11.3 |
| 474 | 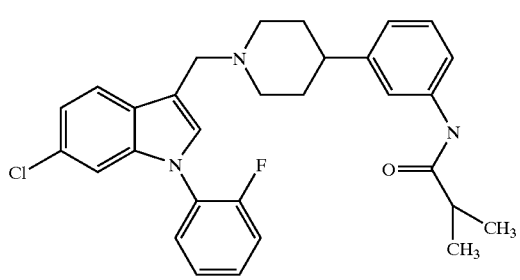 | 13.3 |
| 475 | 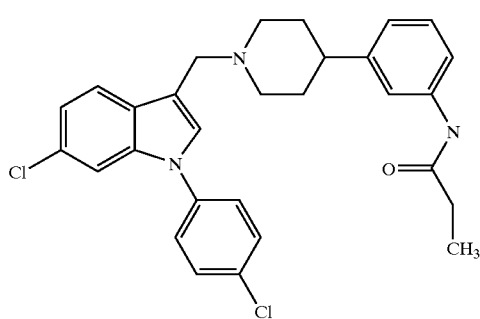 | 12.4 |

-continued
| | | |
|---|---|---|
| 476 | 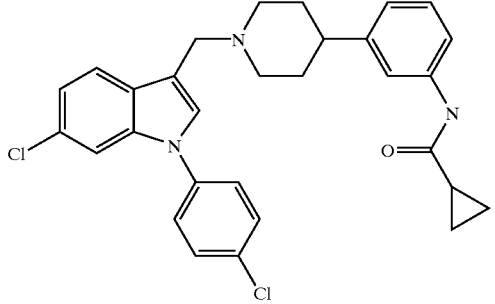 | 12.7 |
| 477 | 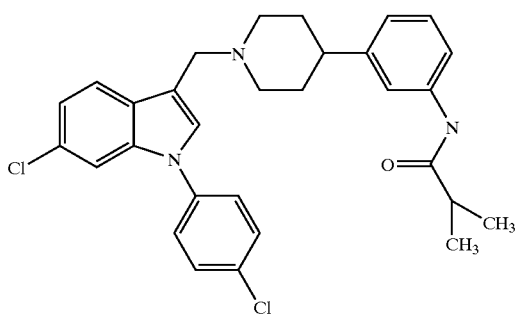 | 14.9 |
| 478 | 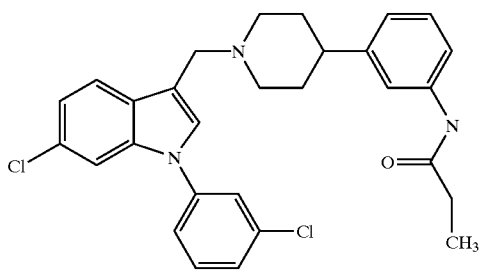 | 11.7 |
| 479 | 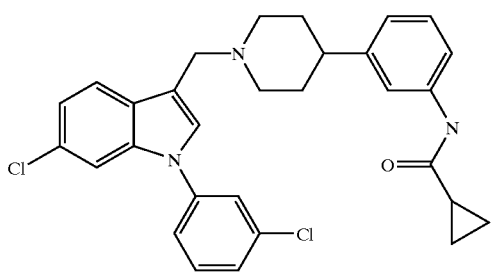 | 8.1 |
| 480 | 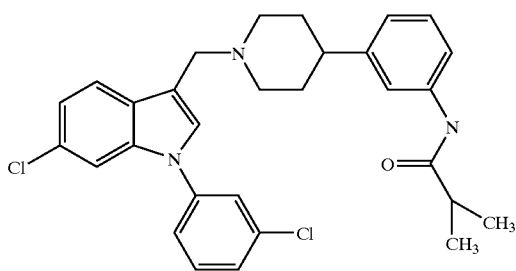 | 9.0 |

-continued
| | | |
|---|---|---|
| 481 | 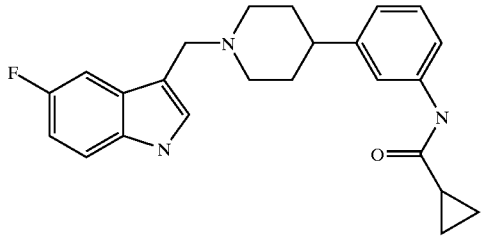 | 664.0 |
| 482 | 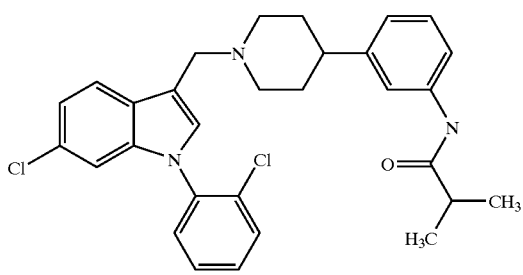 | |
| 483 | 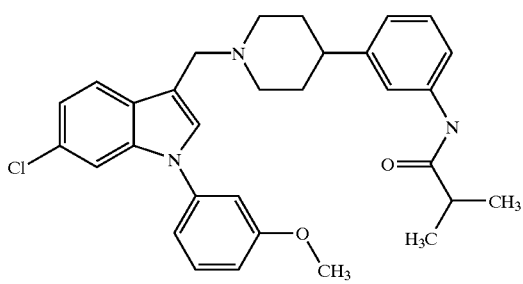 | |
| 484 | 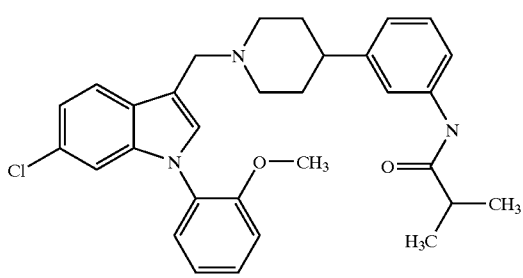 | |
| 485 | 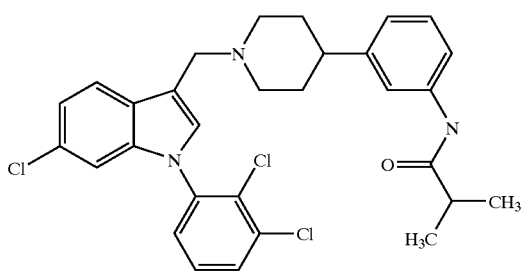 | |

486 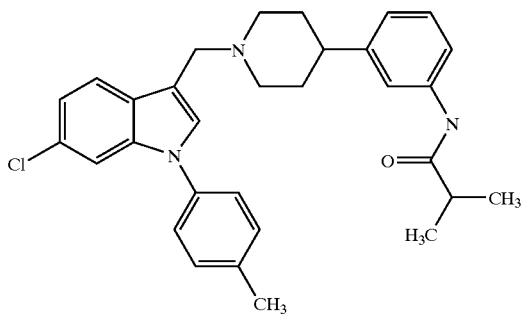
487 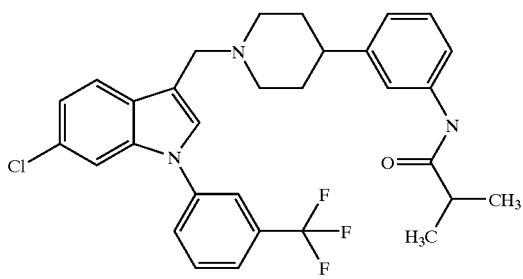
488 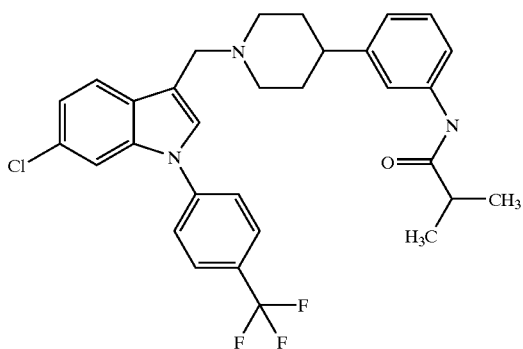
489 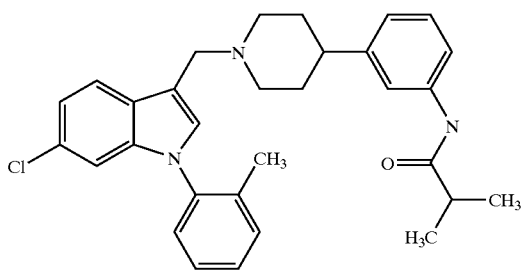
490 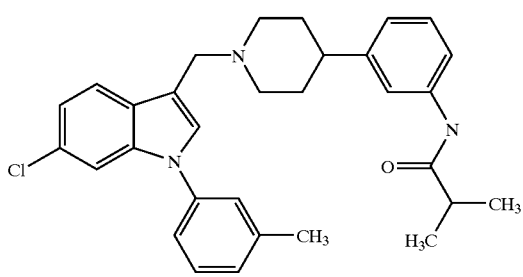

-continued
491 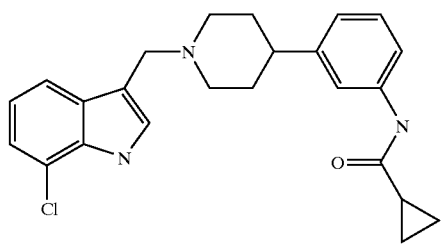
492 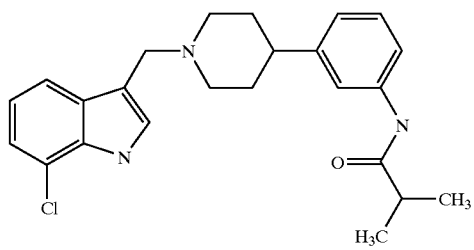
493 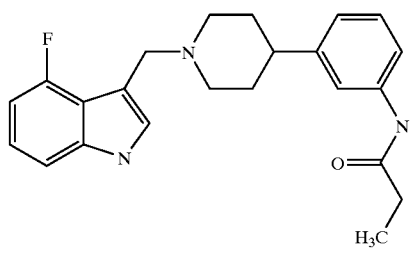
494 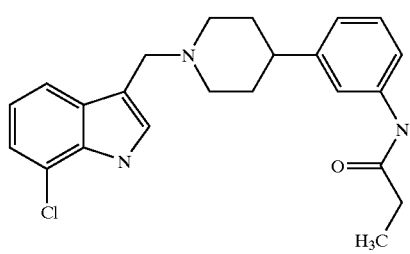
495 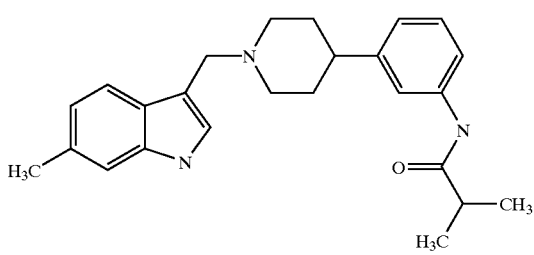   95.1
496 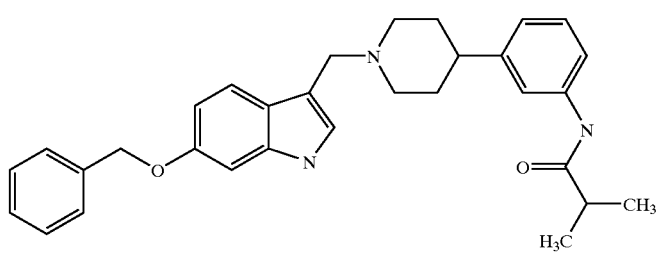   288.0

-continued
| | | |
|---|---|---|
| 497 | 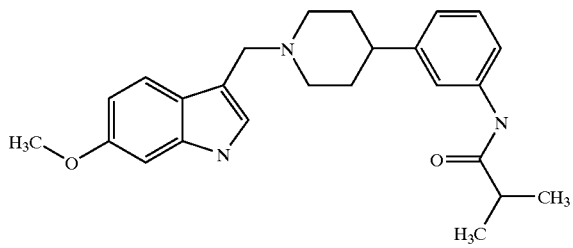 | 97.7 |
| 498 | 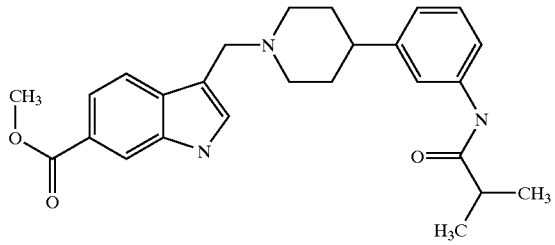 | 52.2 |
| 499 | 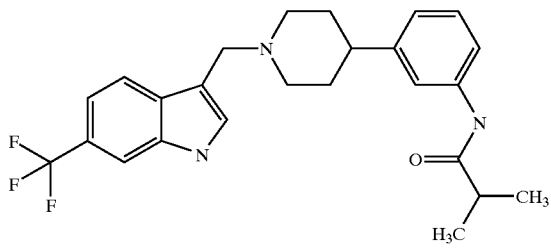 | 11.9 |
| 500 | 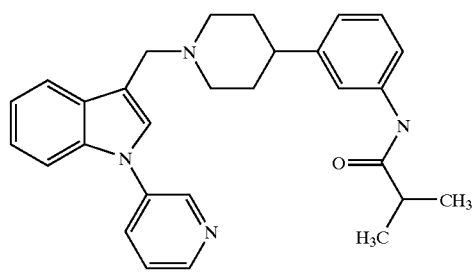 | 29.4 |
| 501 | 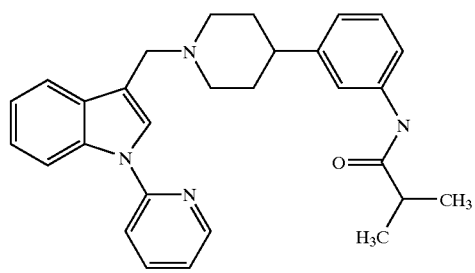 | 22.1 |
| 502 | 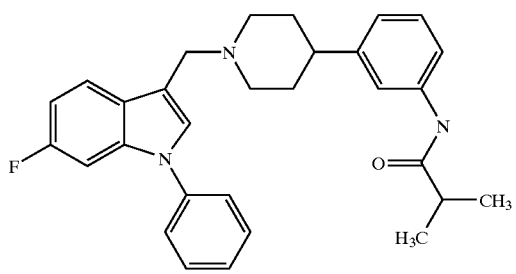 | 4.6 |

-continued
| | | |
|---|---|---|
| 503 | 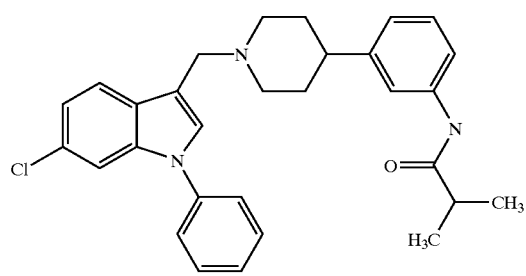 | 6.0 |
| 504 | 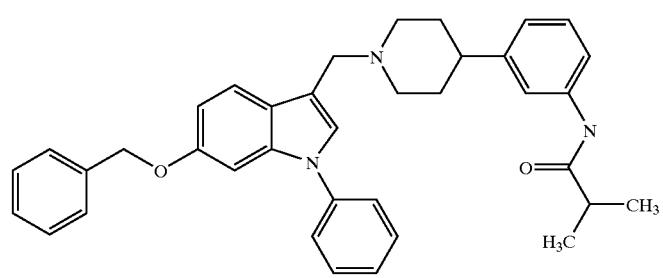 | 22.5 |
| 505 | 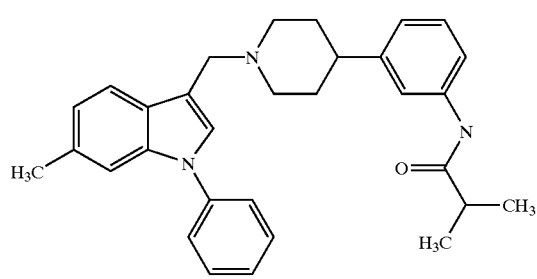 | 6.5 |
| 506 | 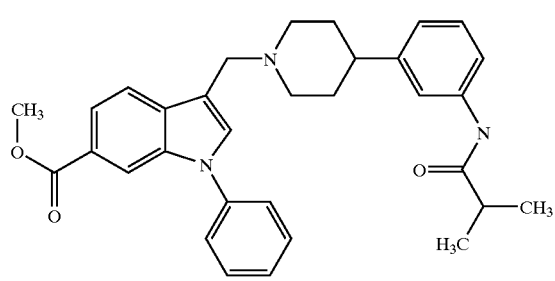 | 2.5 |
| 507 | 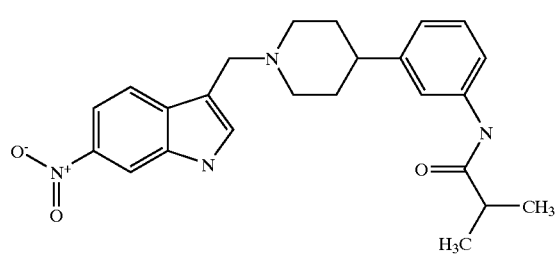 | 57.9 |

-continued
| | | |
|---|---|---|
| 508 | 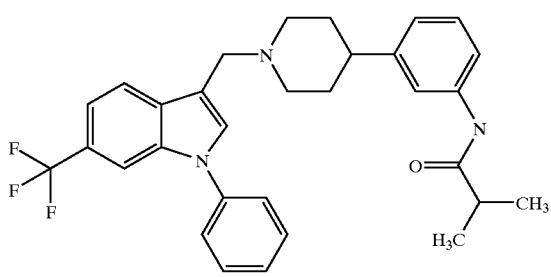 | 8.5 |
| 509 | 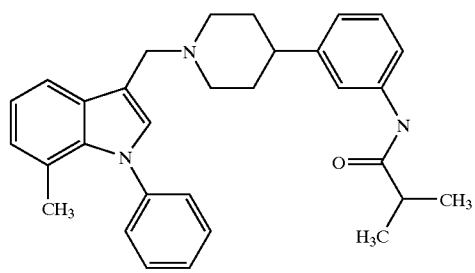 | 24.3 |
| 510 | 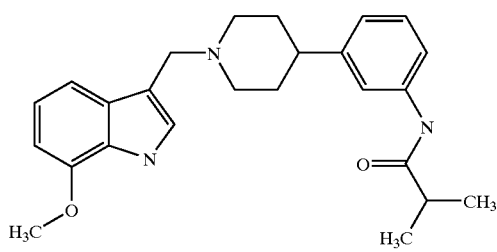 | 304.9 |
| 511 | 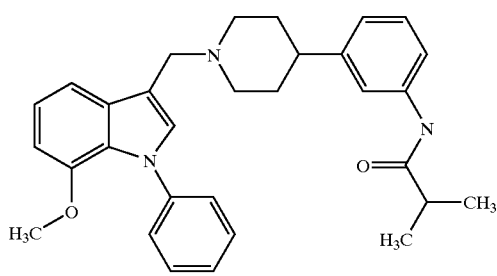 | 6.0 |
| 512 | 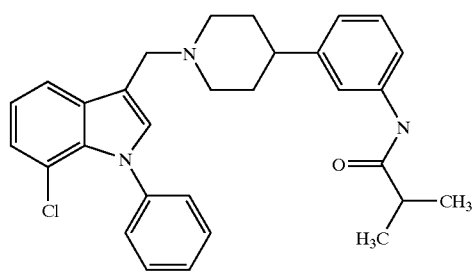 | 42.7 |
| 513 | 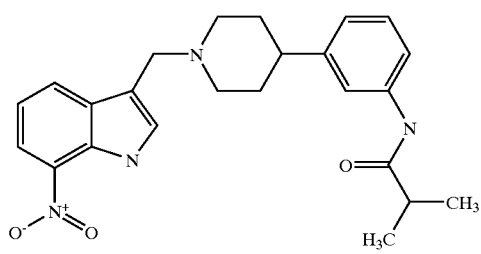 | 178.7 |

-continued
| | | |
|---|---|---|
| 514 | 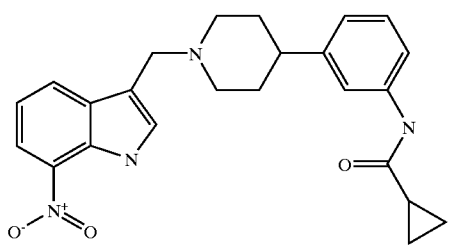 | 151.4 |
| 515 | 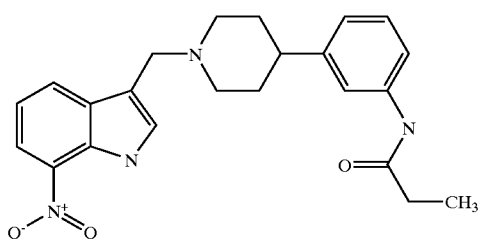 | 296.2 |
| 516 | 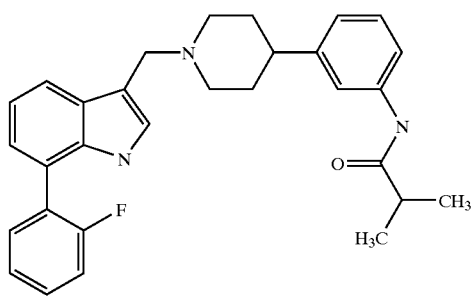 | 90.9 |
| 517 | 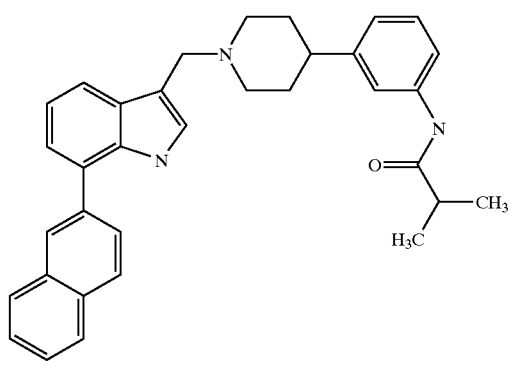 | 286.9 |
| 518 | 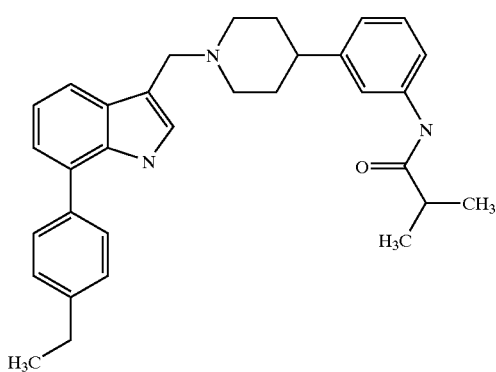 | 226.2 |

-continued
| | | |
|---|---|---|
| 519 | 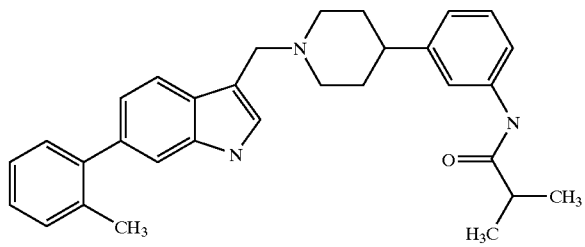 | 80.9 |
| 520 | 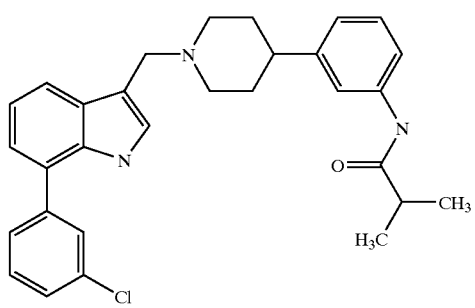 | 135.1 |
| 521 | 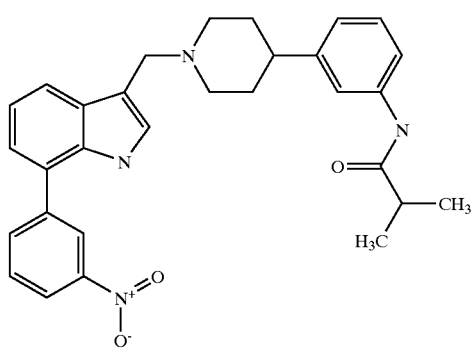 | 27.0 |
| 522 | 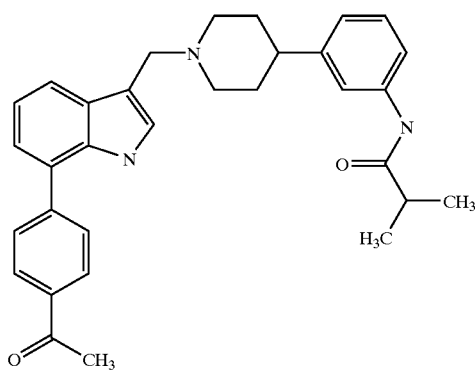 | 247.0 |
| 523 | 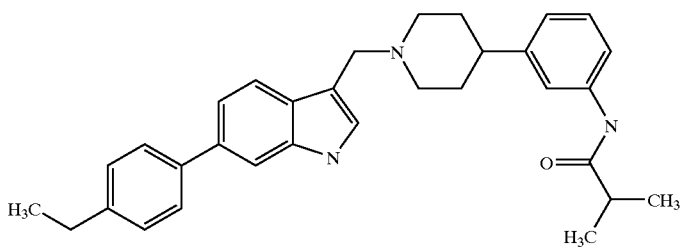 | 54.8 |

-continued
| | | |
|---|---|---|
| 524 | 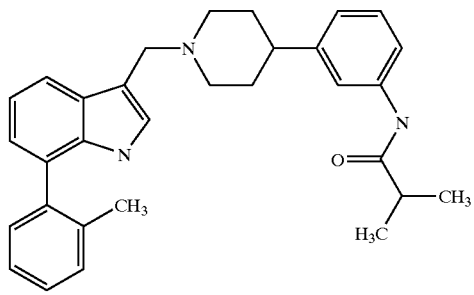 | 198.7 |
| 525 | 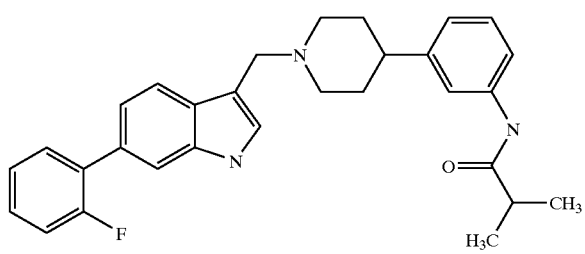 | 91.4 |
| 526 | 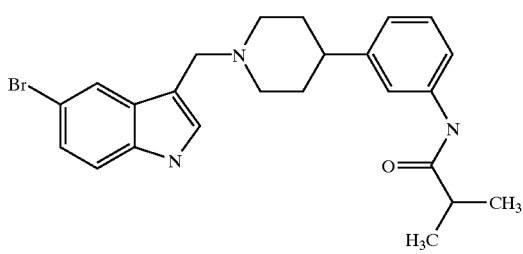 | 410.6 |
| 527 | 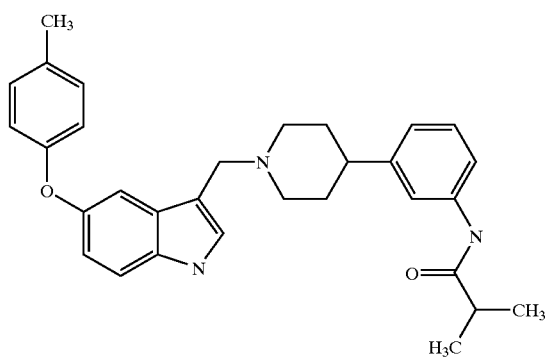 | 226.5 |
| 528 | 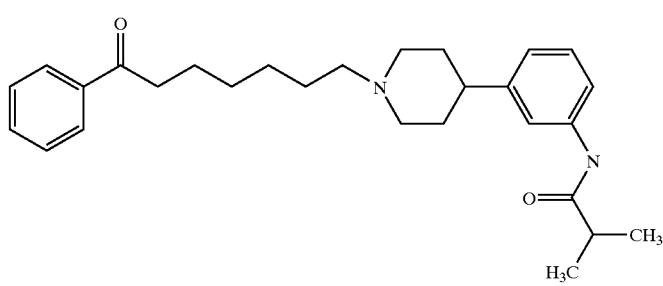 | 115.1 |

-continued
| | | |
|---|---|---|
| 529 | 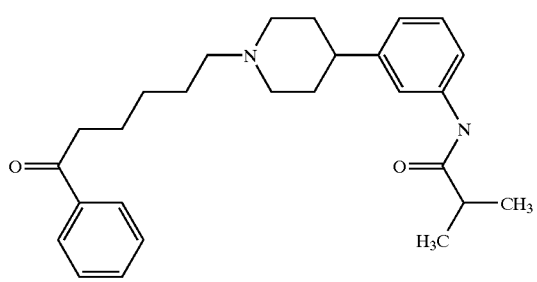 | 42.4 |
| 530 | 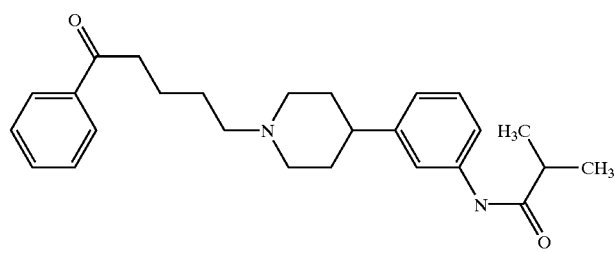 | |
| 531 | 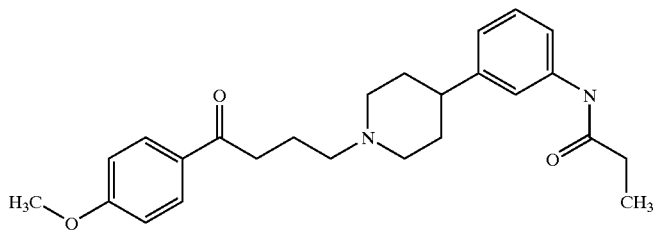 | 105.3 |
| 532 | 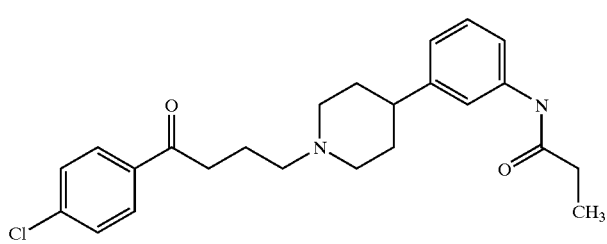 | 8.7 |
| 533 | 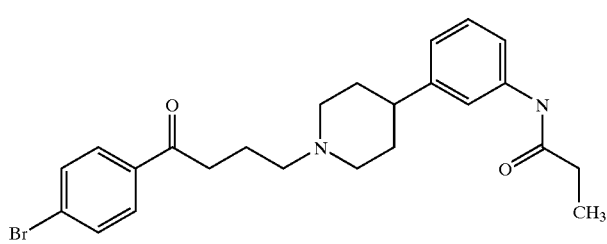 | 10.6 |
| 534 | 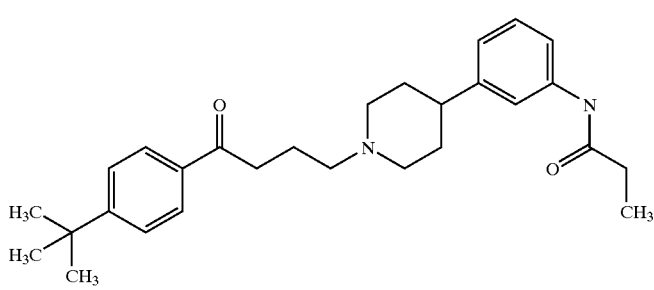 | 154.9 |

-continued
| | |
|---|---|
| 535 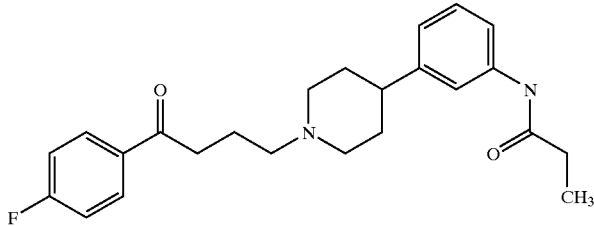 | 28.1 |
| 536 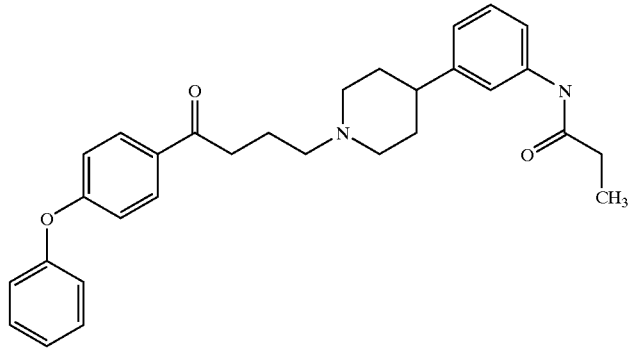 | 150.4 |
| 537 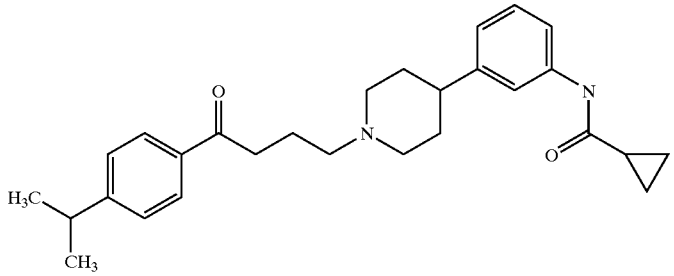 | 67.7 |
| 538 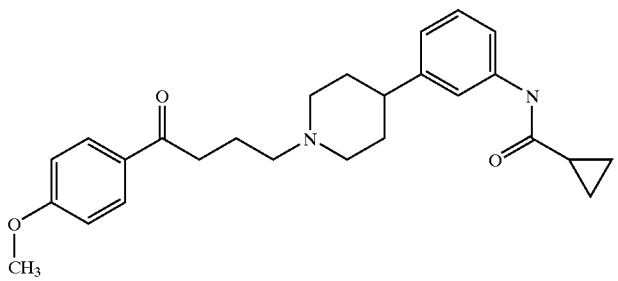 | 36.3 |
| 539 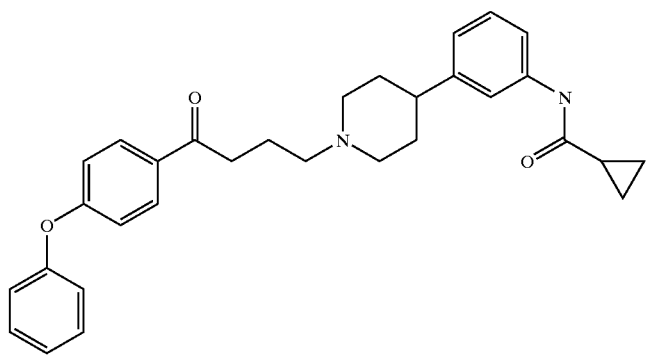 | 268.4 |

-continued
| | | |
|---|---|---|
| 540 | 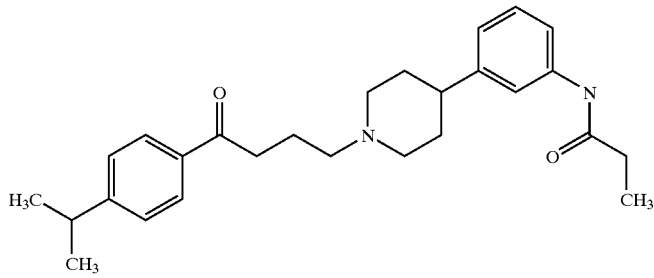 | 172.3 |
| 541 | 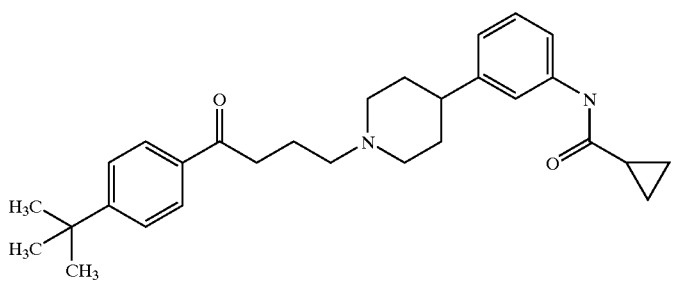 | 318.6 |
| 542 | 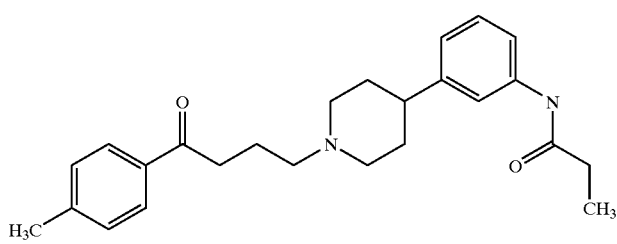 | 31.3 |
| 543 | 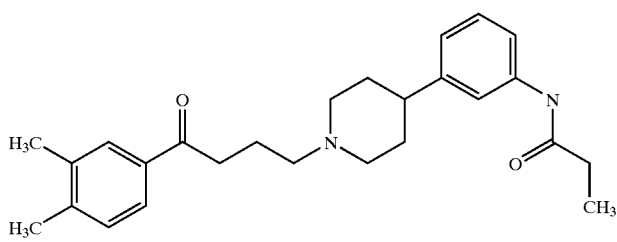 | 27.6 |
| 544 | 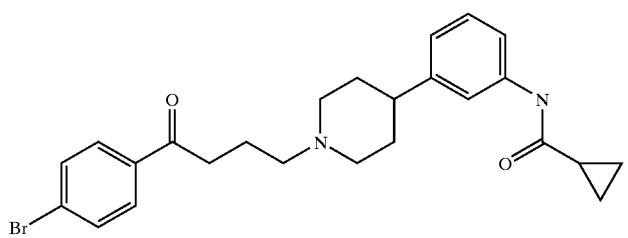 | 16.2 |
| 545 | 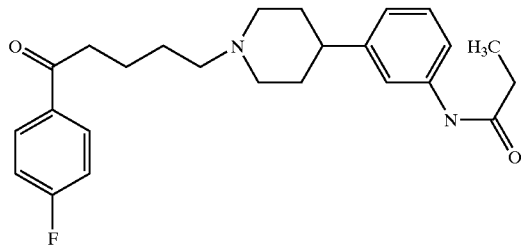 | 52.0 |

-continued
| 546 | 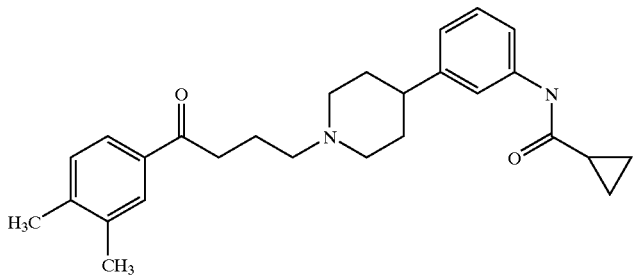 | 87.9 |
| 547 | 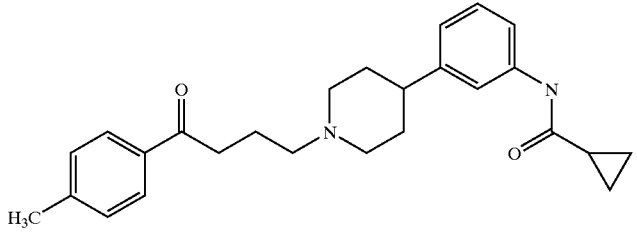 | 75.5 |
| 548 | 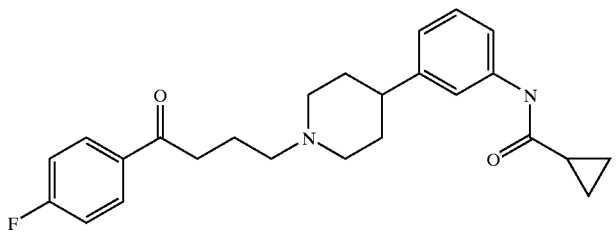 | 125.6 |
| 549 | 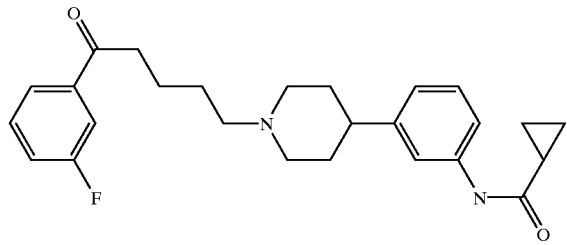 | 39.7 |
| 550 | 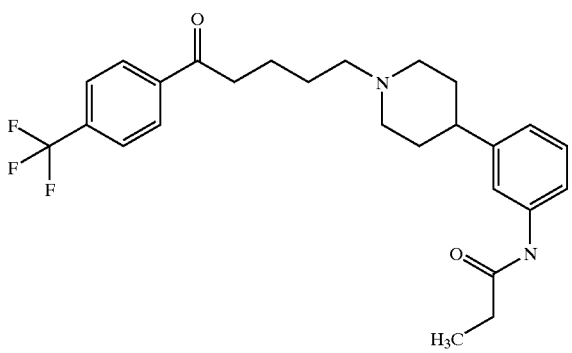 | 60.9 |

-continued
| | | |
|---|---|---|
| 551 | 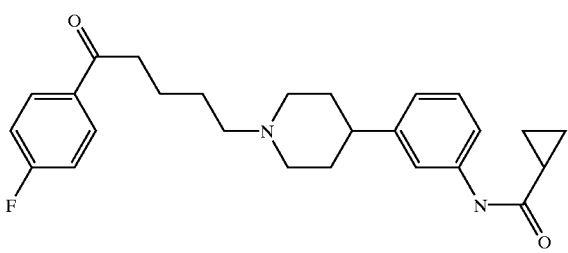 | 21.6 |
| 552 | 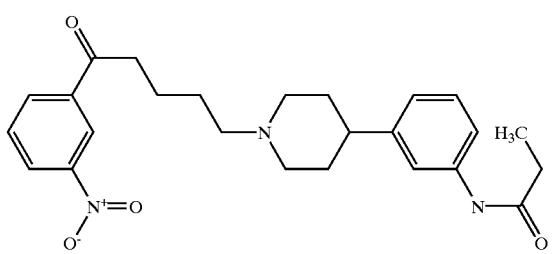 | 24.7 |
| 553 | 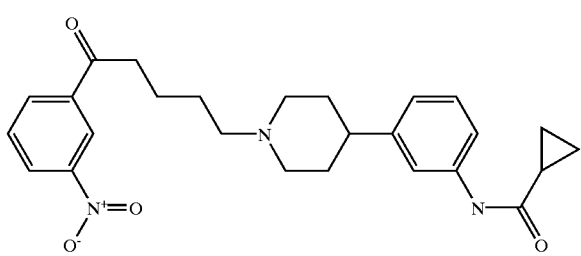 | 27.5 |
| 554 | 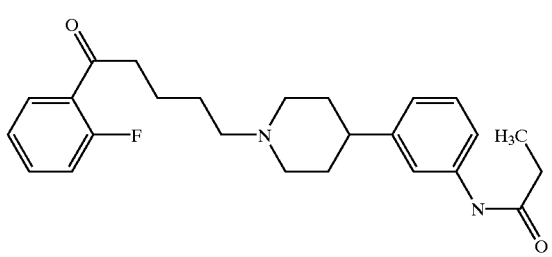 | 70.9 |
| 555 | 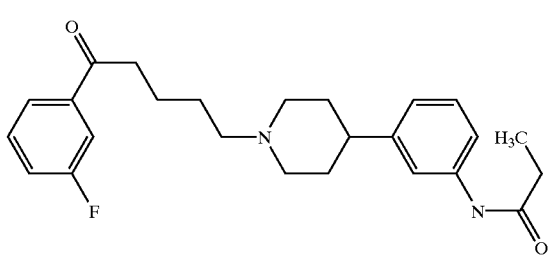 | 50.3 |
| 556 | 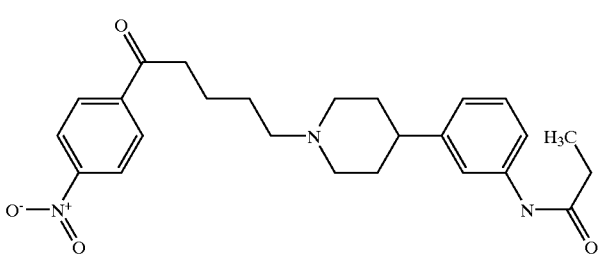 | 35.6 |

-continued
| | | |
|---|---|---|
| 557 | 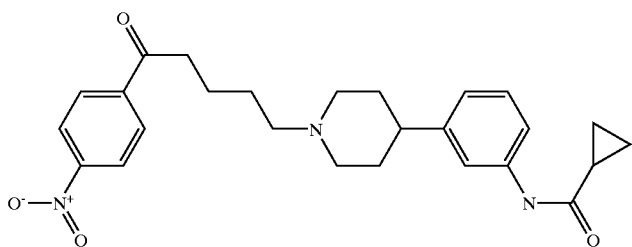 | 25.6 |
| 558 | 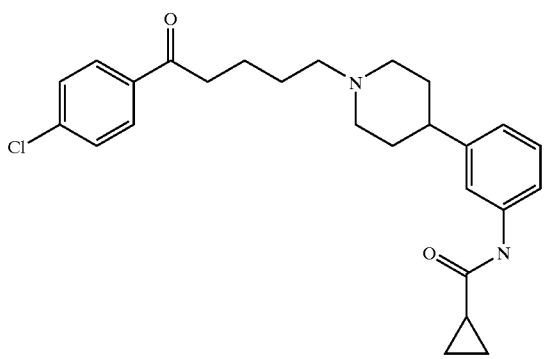 | 20.2 |
| 559 | 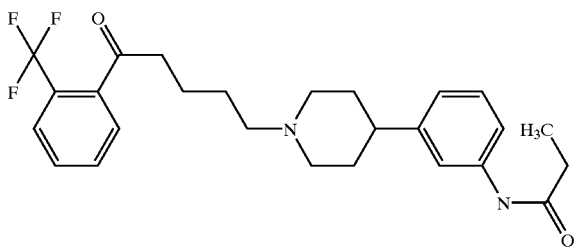 | 62.3 |
| 560 | 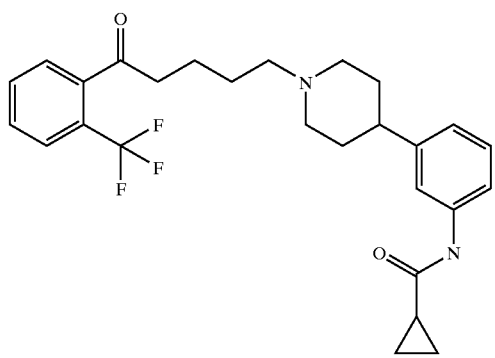 | 55.7 |
| 561 | 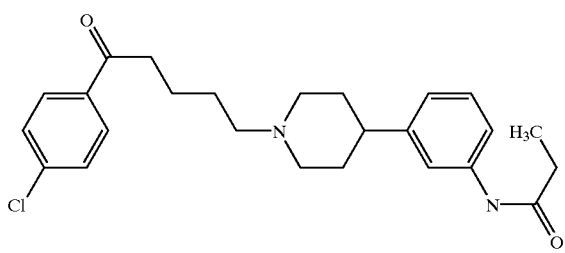 | 92.9 |

-continued
| | | |
|---|---|---|
| 562 | 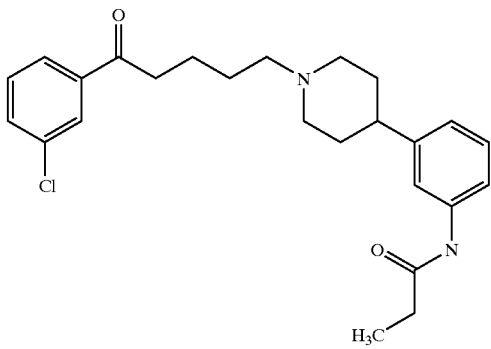 | 48.1 |
| 563 | 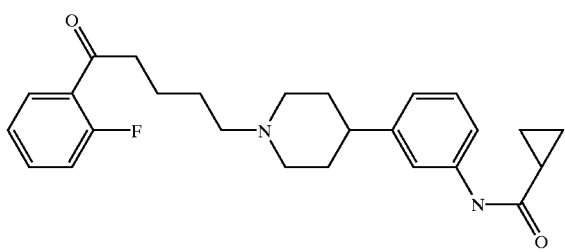 | 50.2 |
| 564 | 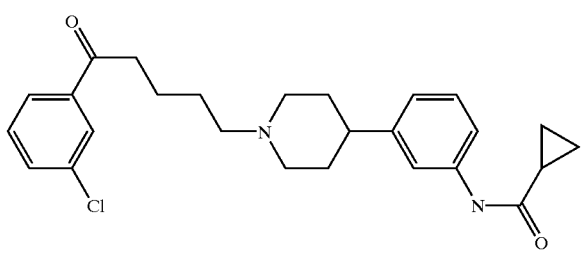 | 28.9 |
| 565 | 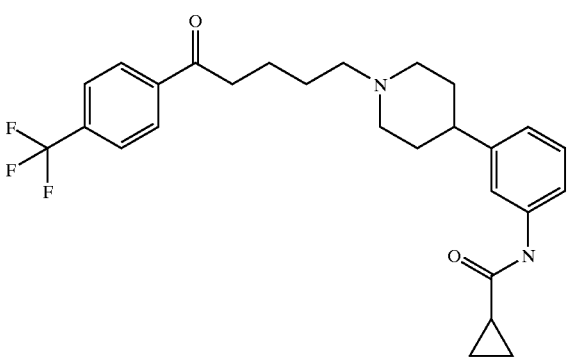 | 49.2 |
| 566 | 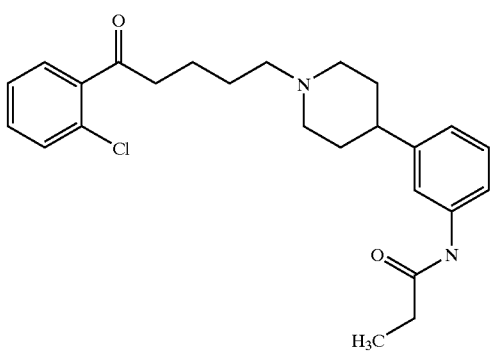 | 77.8 |

| | | |
|---|---|---|
| 567 | 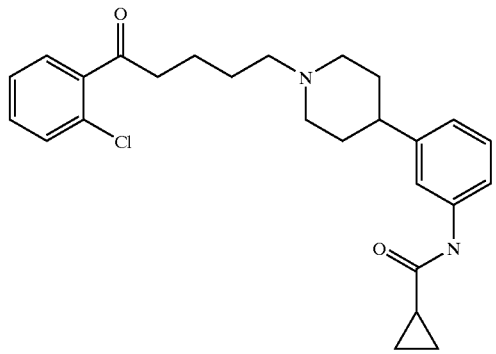 | 92.2 |
| 568 | 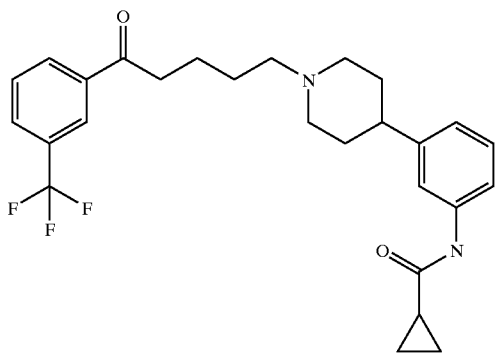 | 68.8 |
| 569 | 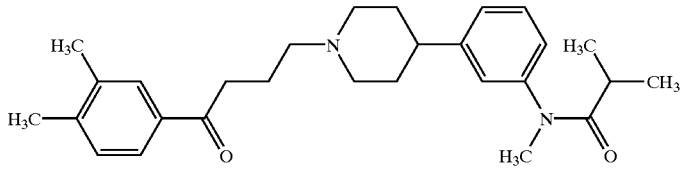 | 549.3 |
| 570 | 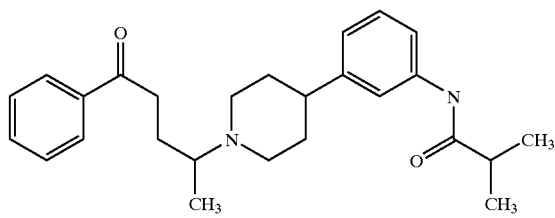 | 136.3 |
| 571 | 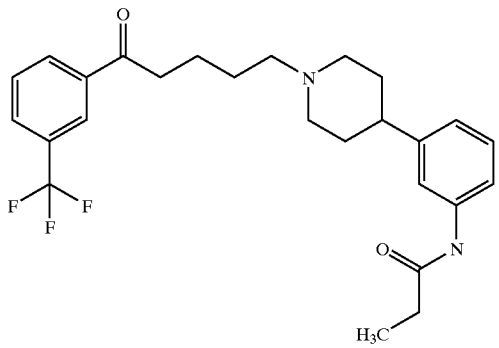 | 88.3 |

-continued
| | | | |
|---|---|---|---|
| 572 | 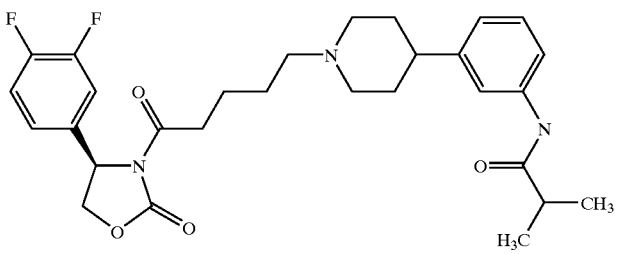 | Chiral | 181.5 |
| 573 | 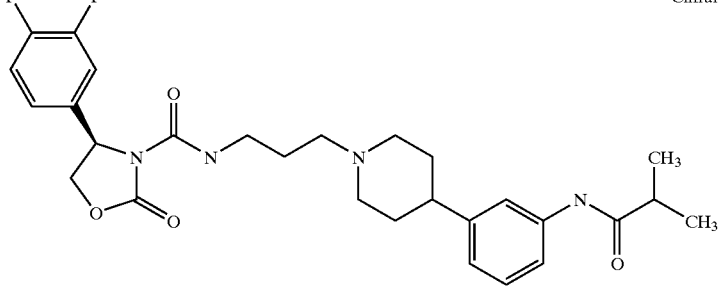 | Chiral | 114.3 |
| 574 | 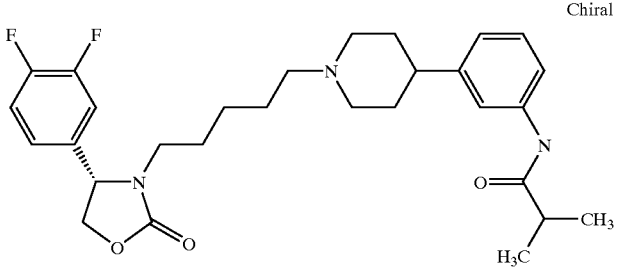 | Chiral | 87.1 |
| 575 | 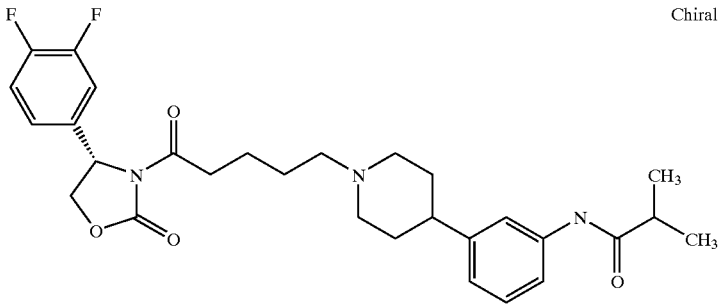 | Chiral | 192.6 |
| 576 | 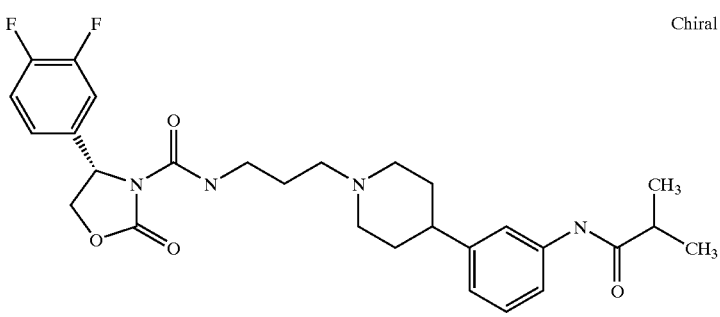 | Chiral | 74.3 |

-continued
| | | | |
|---|---|---|---|
| 577 | 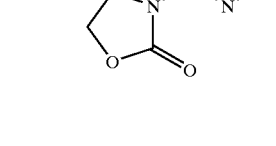 | Chiral | 64.7 |
| 578 | 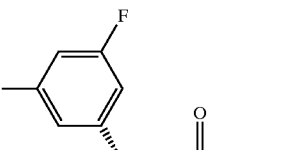 | Chiral | 98.8 |
| 579 | 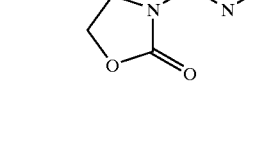 | | 131.1 |
| 580 | 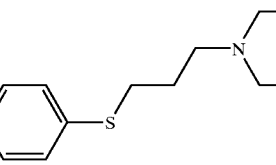 | | 54.0 |
| 581 |  | | 86.4 |
| 582 | 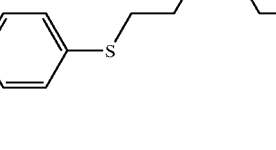 | | 58.3 |

-continued
| | | |
|---|---|---|
| 583 | 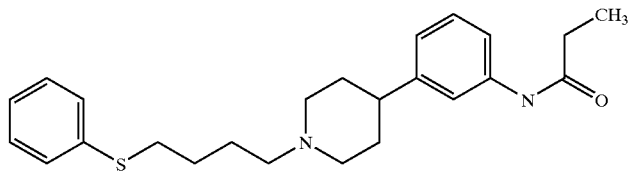 | 55.5 |
| 584 | 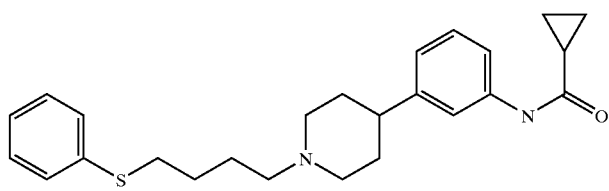 | 51.8 |
| 585 | 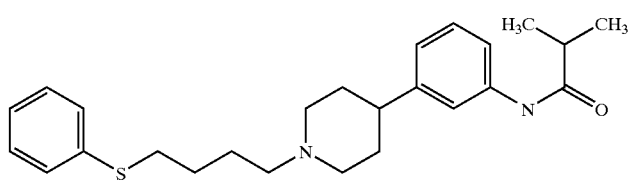 | 37.2 |
| 586 | 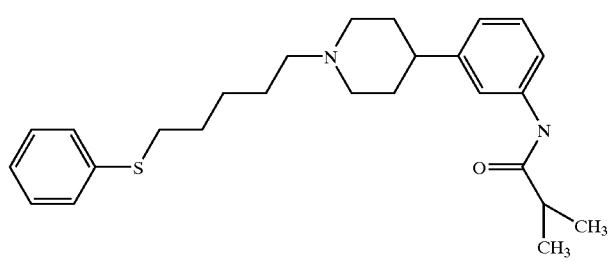 | 42.9 |
| 587 | 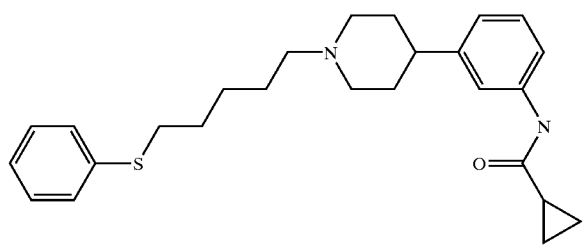 | 46.9 |
| 588 | 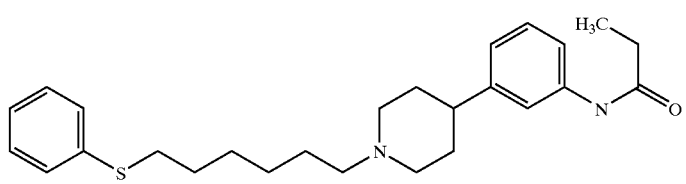 | 283.9 |
| 589 | 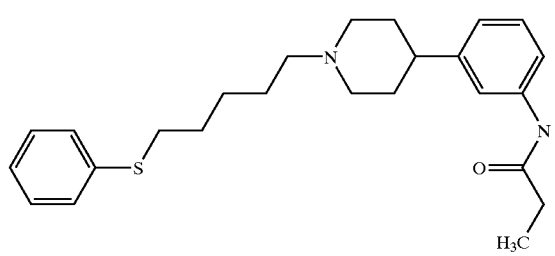 | 66.6 |

-continued
| | | |
|---|---|---|
| 590 | 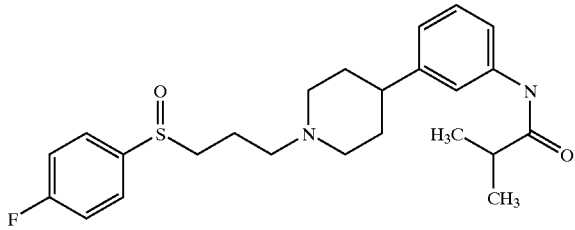 | 157.1 |
| 591 | 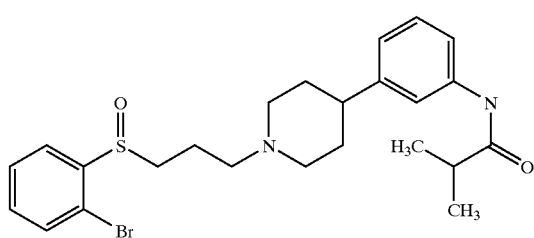 | 137.5 |
| 592 | 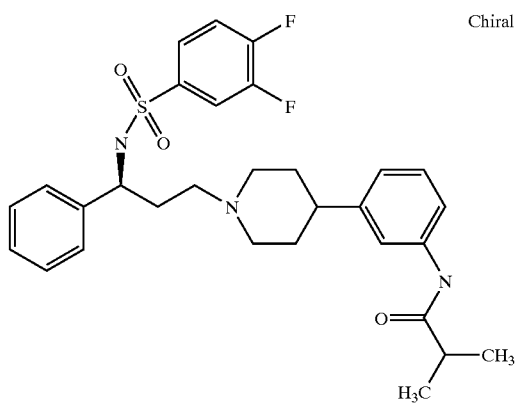 Chiral | 185.6 |
| 593 | 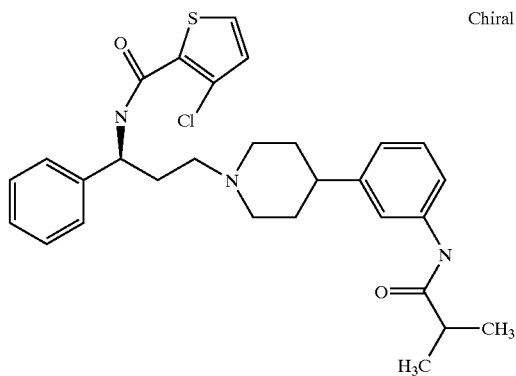 Chiral | 7.6 |

-continued
| | | | |
|---|---|---|---|
| 594 | 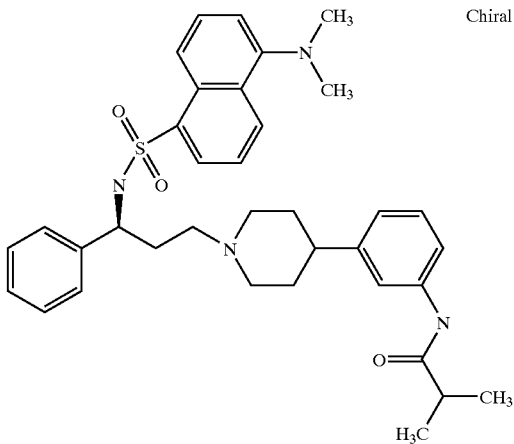 | Chiral | 67.0 |
| 595 | 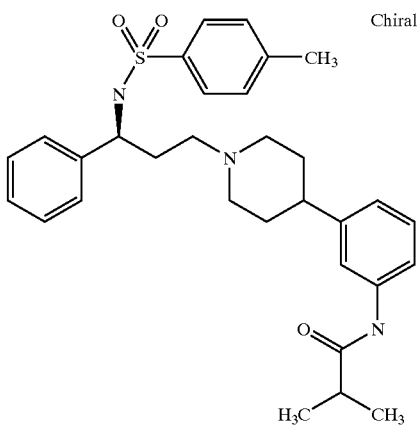 | Chiral | 36.3 |
| 596 | 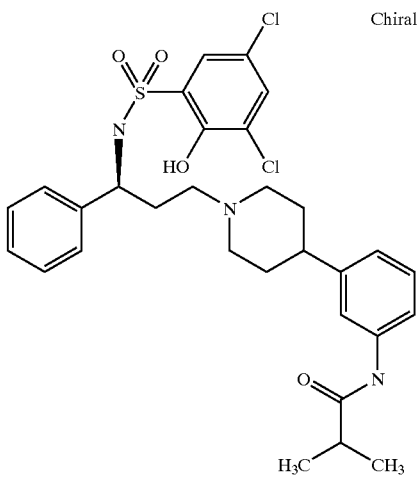 | Chiral | 596.7 |

-continued
| | | | |
|---|---|---|---|
| 597 | 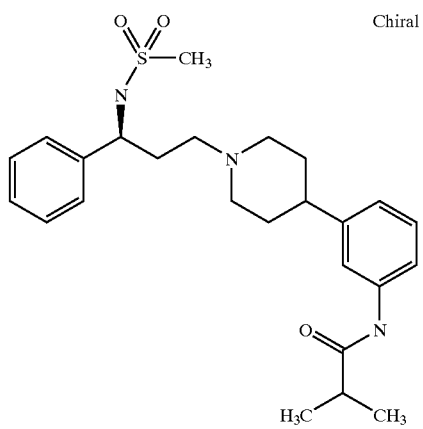 | Chiral | 222.7 |
| 598 | 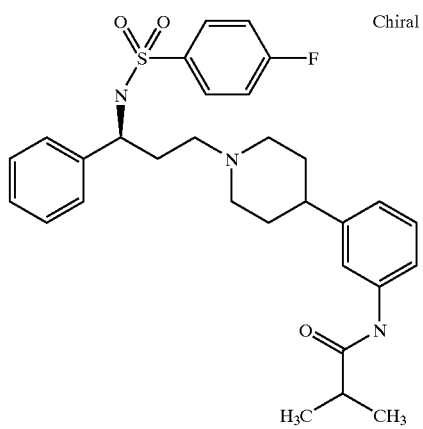 | Chiral | 25.3 |
| 599 | 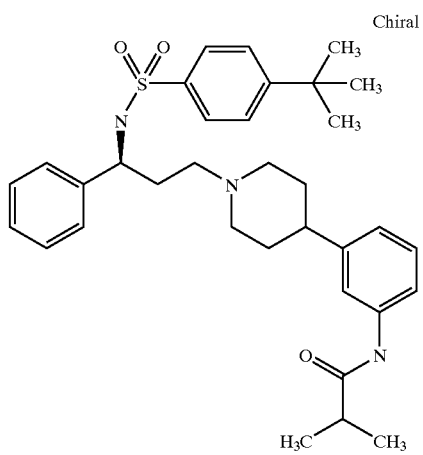 | Chiral | 50.0 |

-continued
| | | | |
|---|---|---|---|
| 600 | 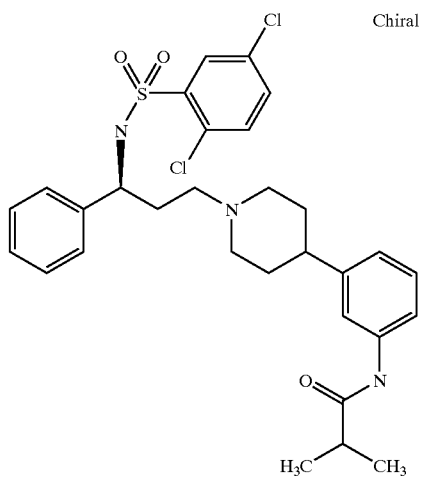 | Chiral | 41.3 |
| 601 | 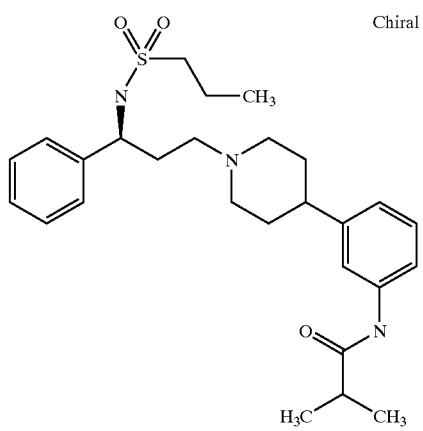 | Chiral | 144.2 |
| 602 | 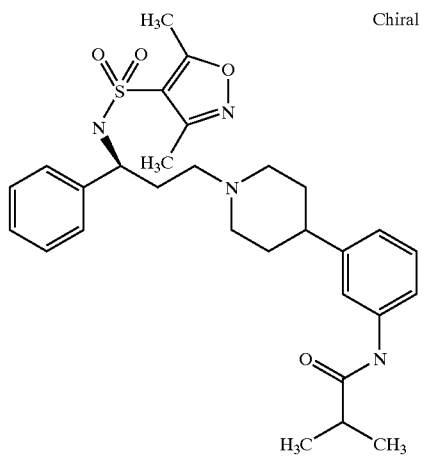 | Chiral | 44.6 |

-continued
| | | |
|---|---|---|
| 603 | 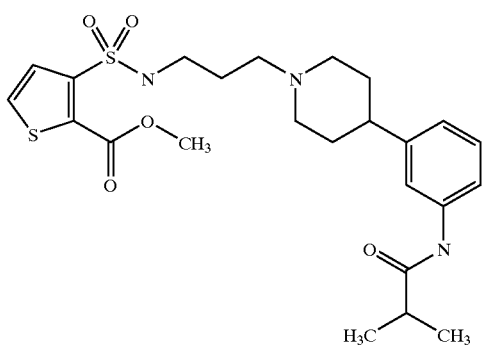 | 286.8 |
| Example | MOLSTRUCTURE | rMCH1 Ki (nM) |
|---|---|---|
| 604 | Chiral<br />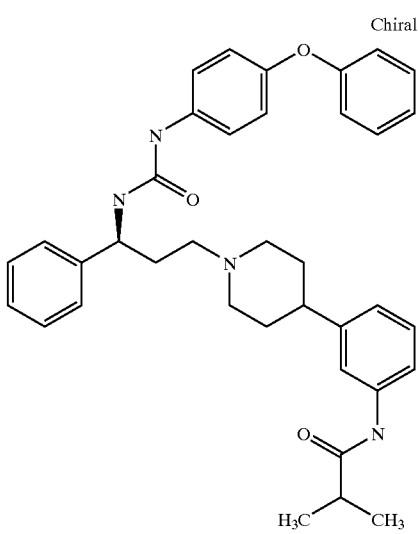 | 36.8 |
| 605 | Chiral<br />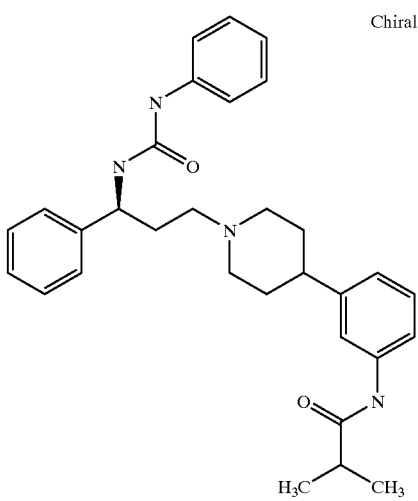 | 94.5 |

-continued
| 606 | 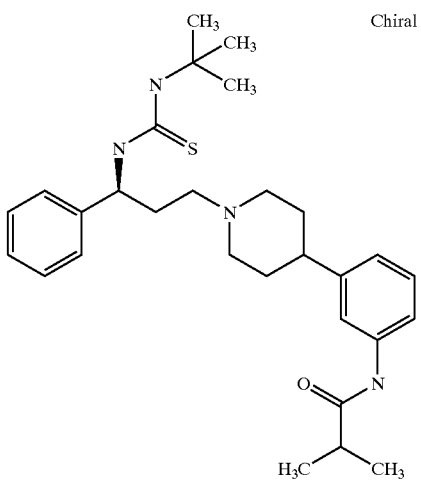 | Chiral | 40.4 |
| 607 | 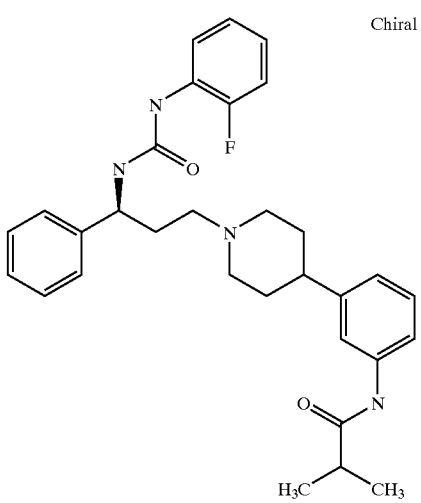 | Chiral | 142.1 |
| 608 | 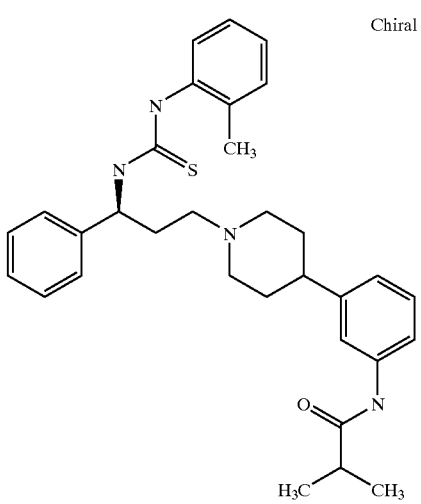 | Chiral | 34.9 |

-continued
| | | | |
|---|---|---|---|
| 609 | 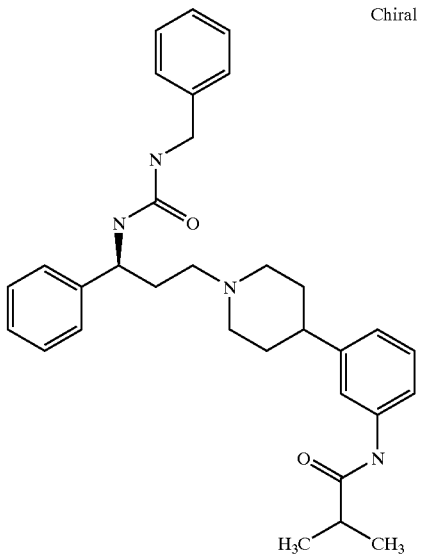 | Chiral | 35.4 |
| 610 | 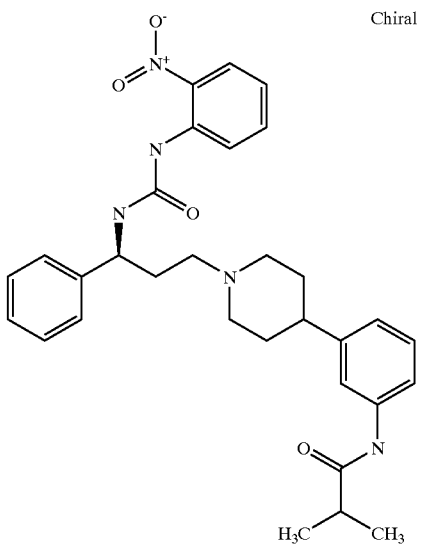 | Chiral | 529.8 |
| 611 | 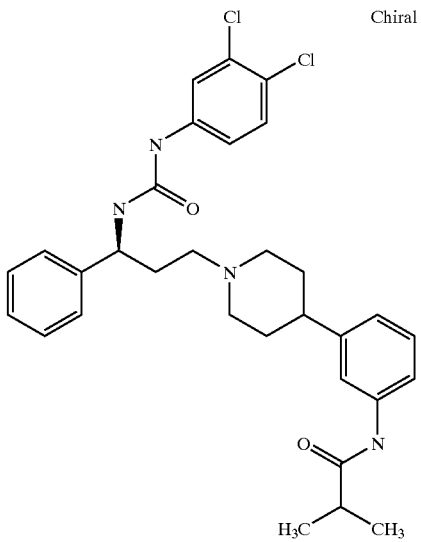 | Chiral | 65.1 |

-continued
| | | | |
|---|---|---|---|
| 612 | 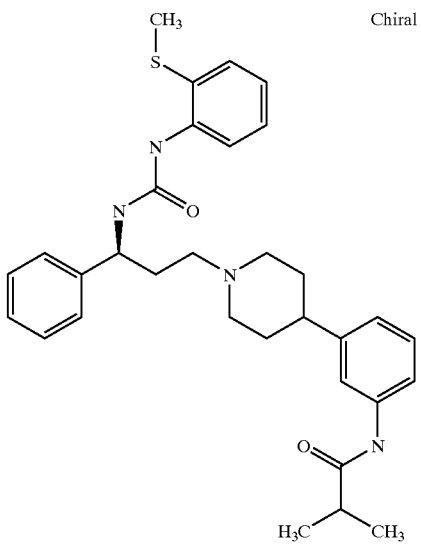 | Chiral | 121.0 |
| 613 | 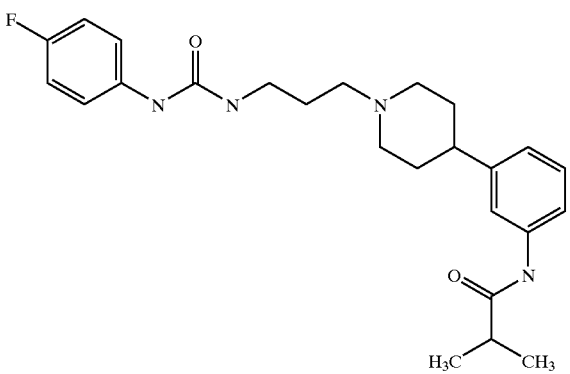 | | 34.9 |
| 614 | 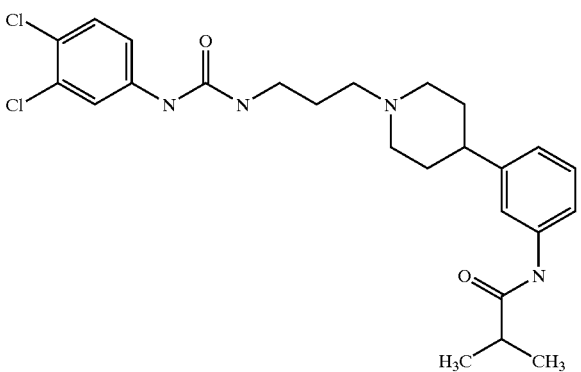 | | 84.8 |

| | | |
|---|---|---|
| 615 | 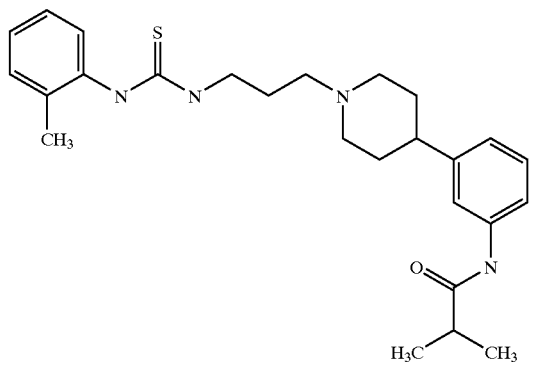 | 210.5 |
| 616 | 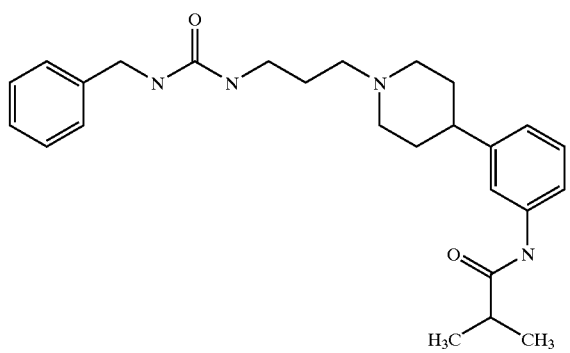 | 405.6 |
| 617 | 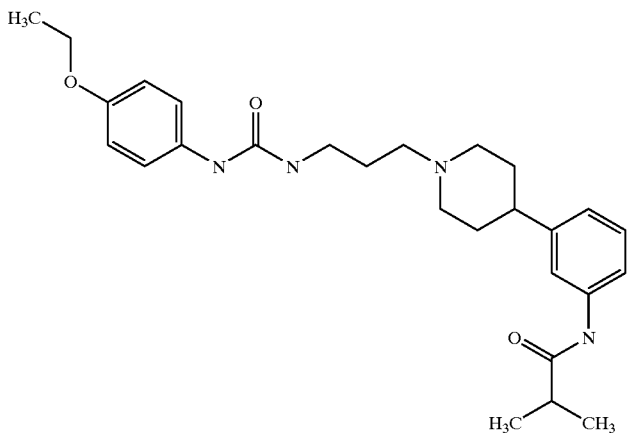 | 608.9 |
| 618 | 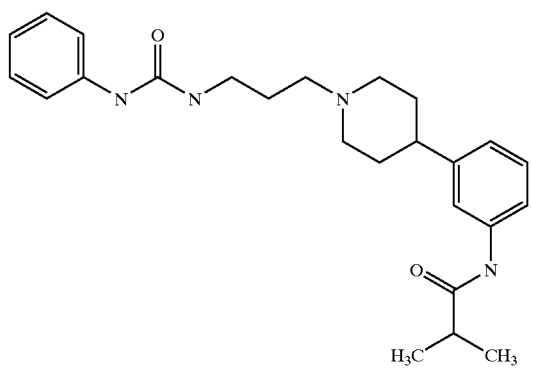 | 399.5 |

-continued
| | | |
|---|---|---|
| 619 | 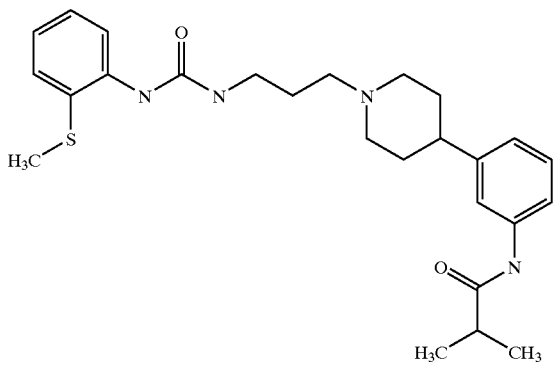 | 177.5 |
| 620 | 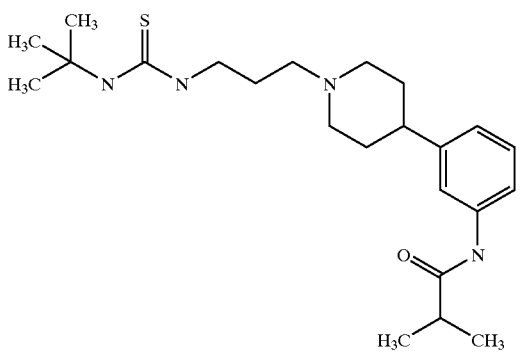 | 223.3 |
| 621 | 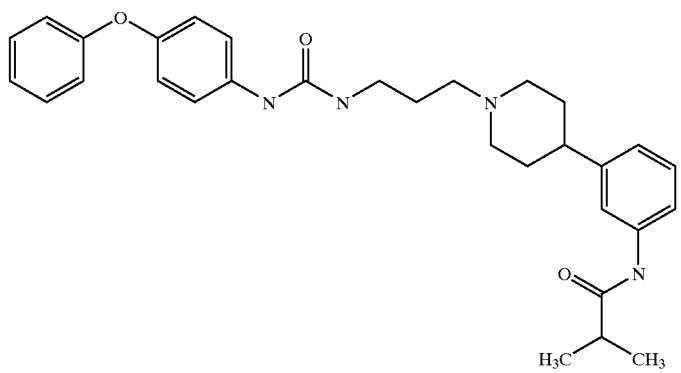 | 204.6 |
| Example | Structure | rMCH1 Ki (nM) |
|---|---|---|
| 622 | 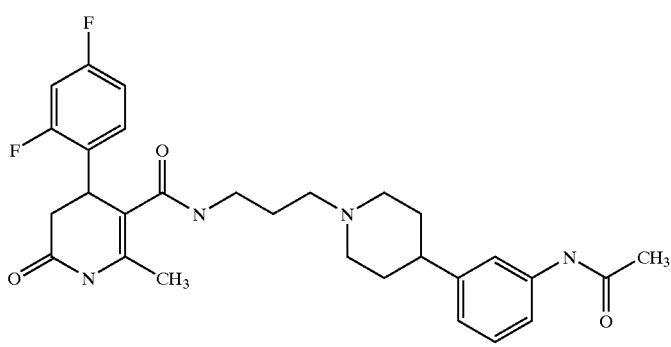 | 162.4 |

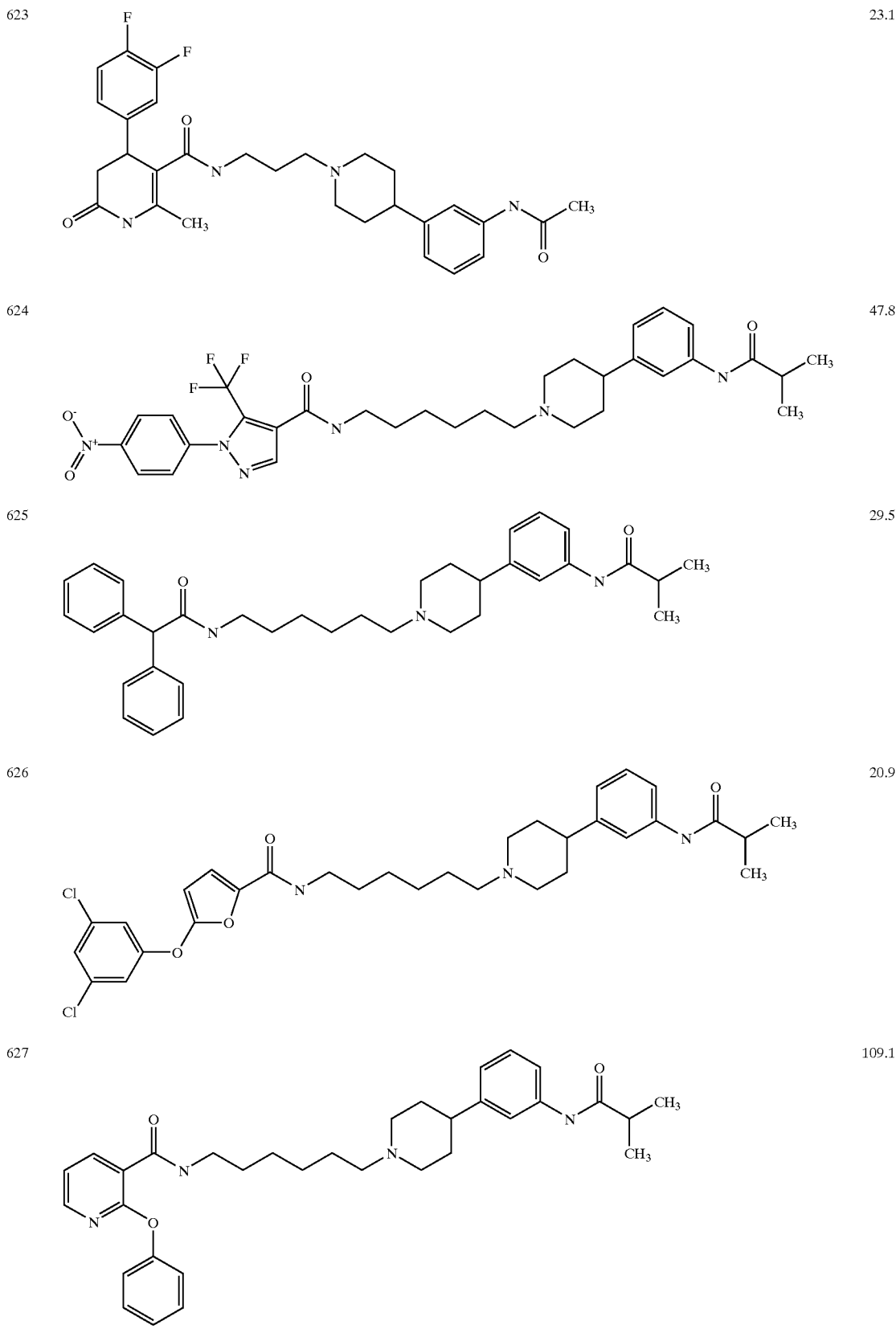

-continued
| 628 | 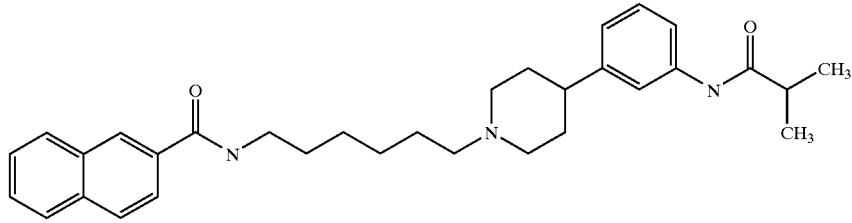 | 160.6 |
| 629 | 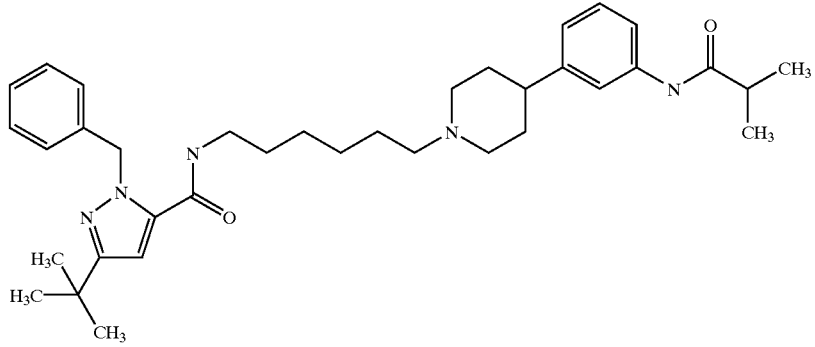 | 42.9 |
| 630 | 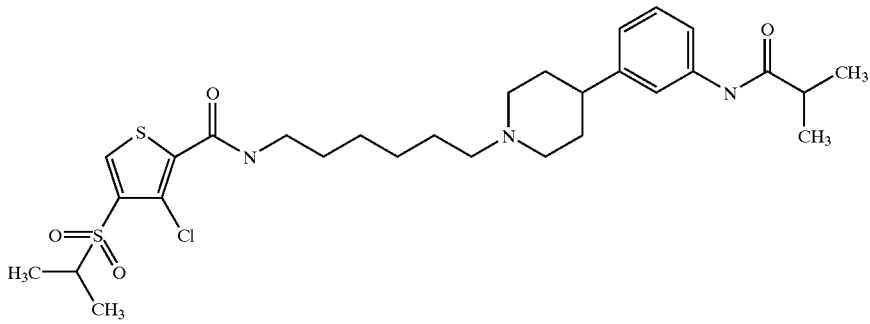 | 201.8 |
| 631 | 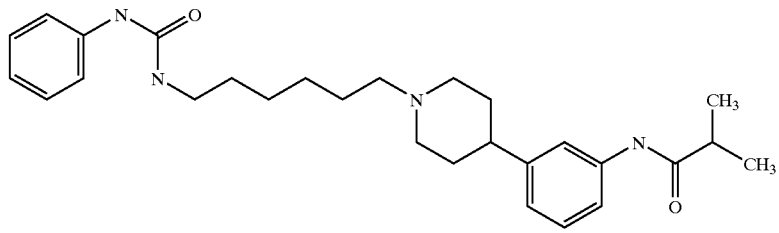 | 258.8 |
| 632 | 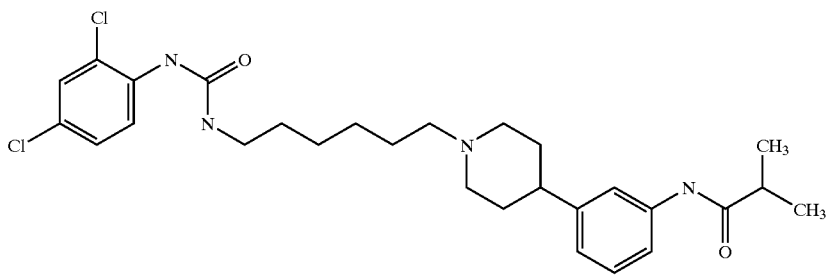 | 76.6 |

| | | |
|---|---|---|
| 633 | 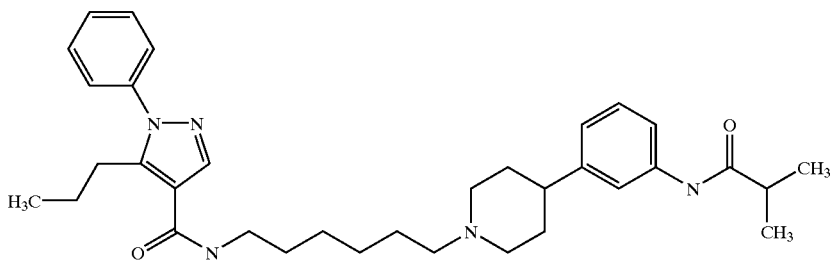 | 107.9 |
| 634 | 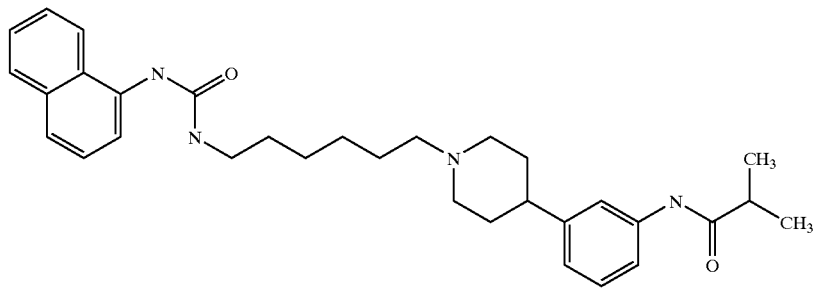 | 116.1 |
| 635 | 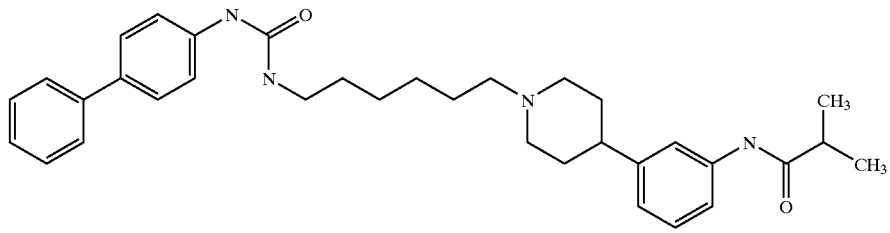 | 73.6 |
| 636 | 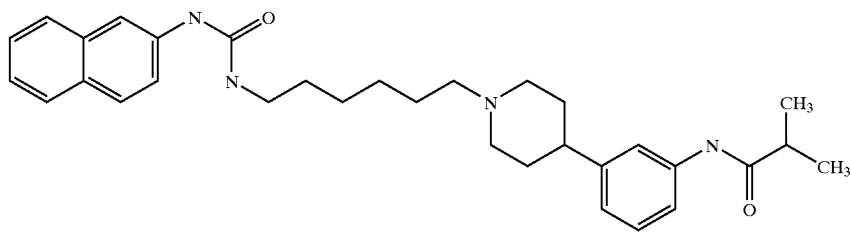 | 40.8 |
| 637 | 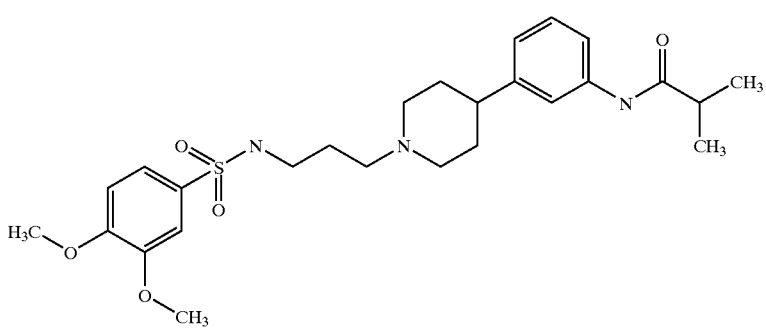 | 105.6 |

-continued
| | | |
|---|---|---|
| 638 | 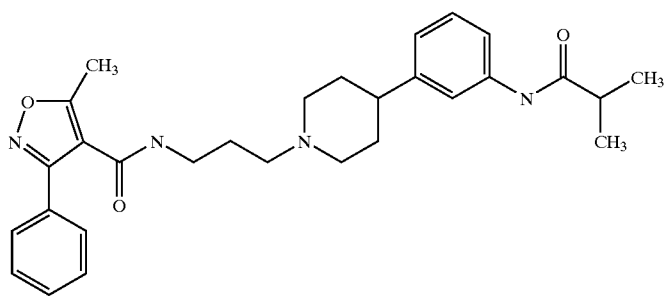 | 29.8 |
| 639 | 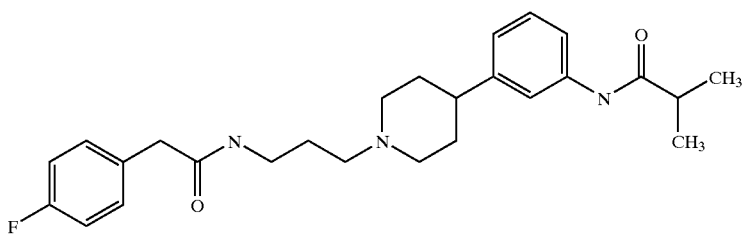 | 36.3 |
| 640 | 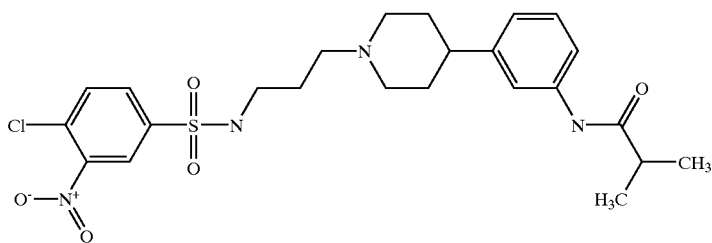 | 11.2 |
| 641 | 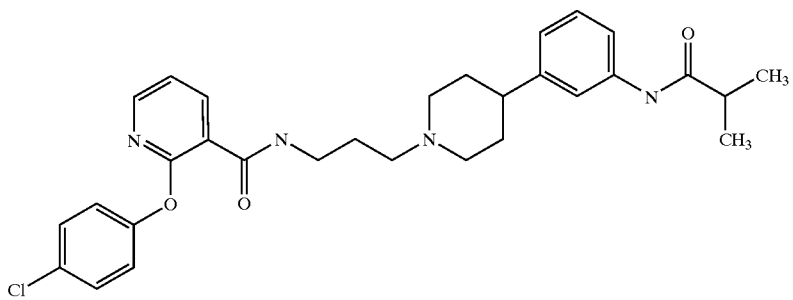 | 14.2 |
| 642 | 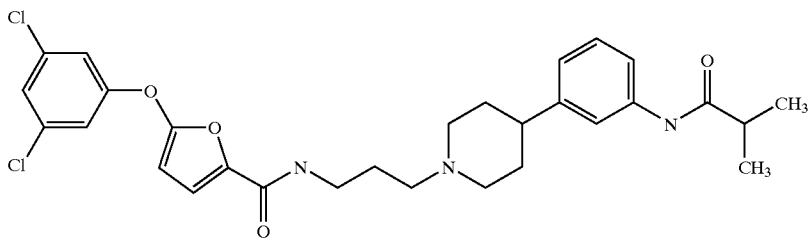 | 8.3 |
| 643 | 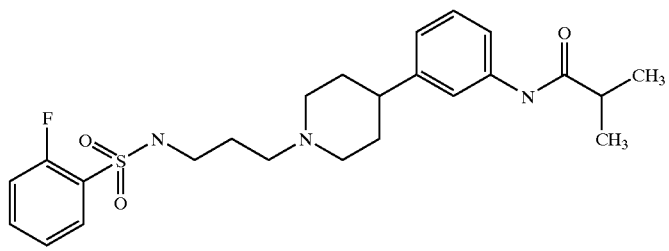 | 129.9 |

-continued
| | | |
|---|---|---|
| 644 | 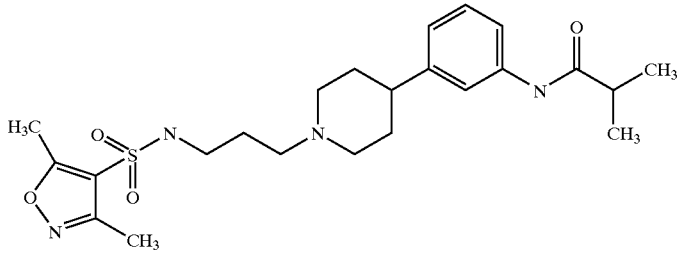 | 196.1 |
| 645 | 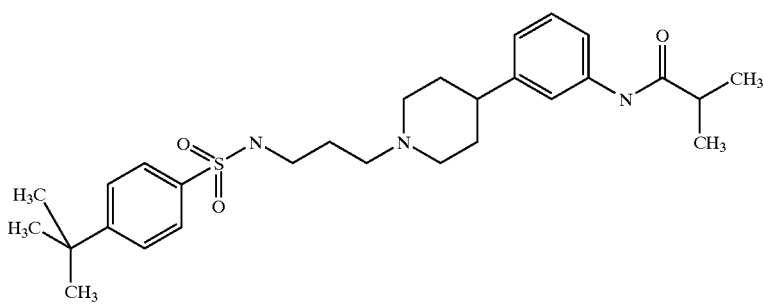 | 85.3 |
| 646 | 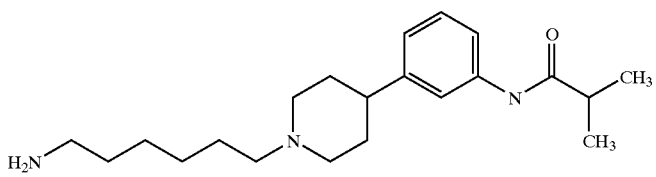 | 235.7 |
| 647 | 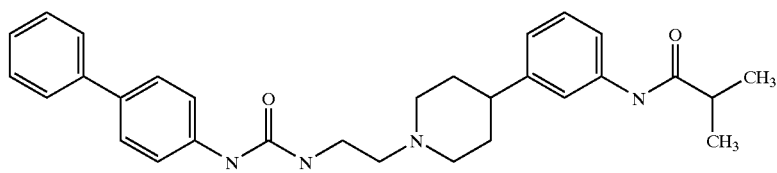 | 81.6 |
| 648 | 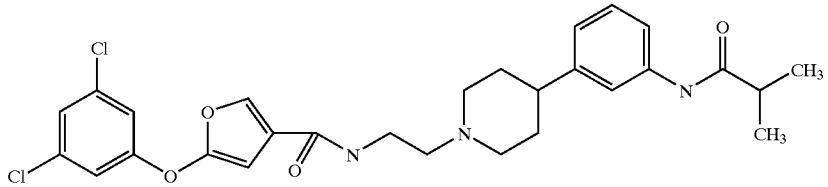 | 13.4 |
| 649 | 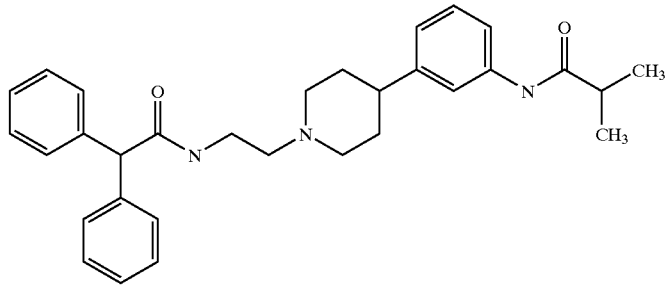 | 1.7 |

-continued
| | | |
|---|---|---|
| 650 | 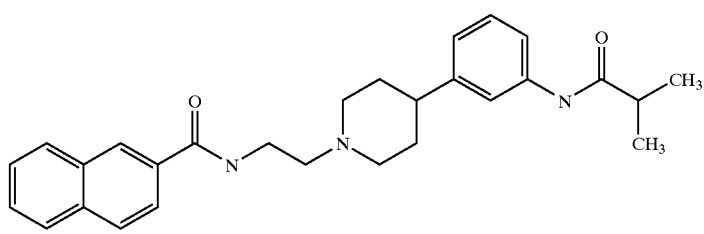 | 21.1 |
| 651 | 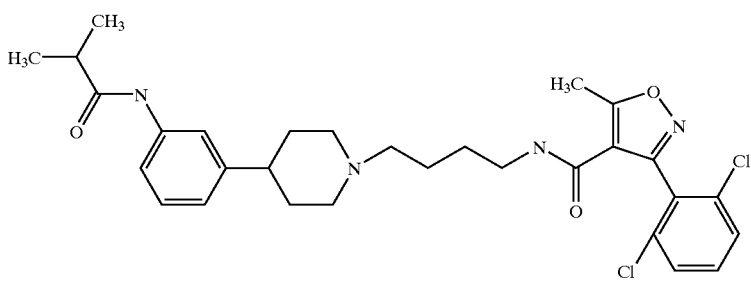 | 16.7 |
| 652 | 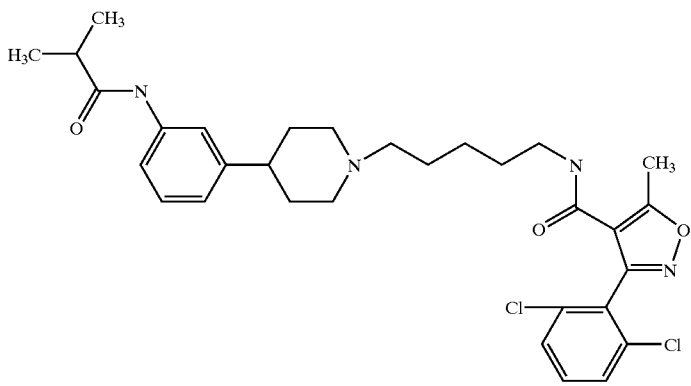 | 7.1 |
| 653 | 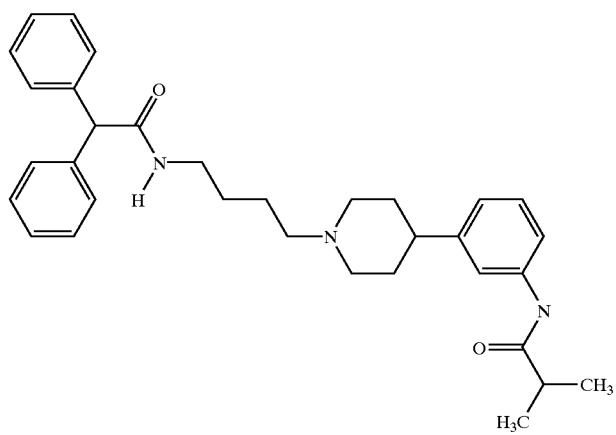 | 48.8 |

| | | |
|---|---|---|
| 654 | 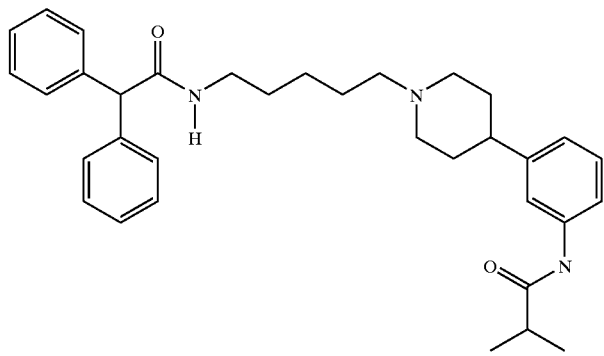 | 43.6 |
| 655 | 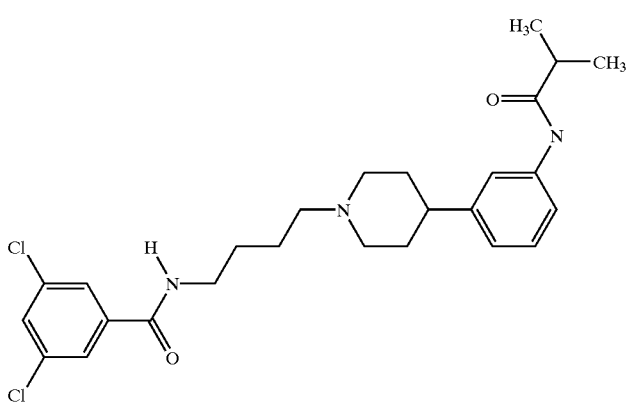 | 31.1 |
| 656 | 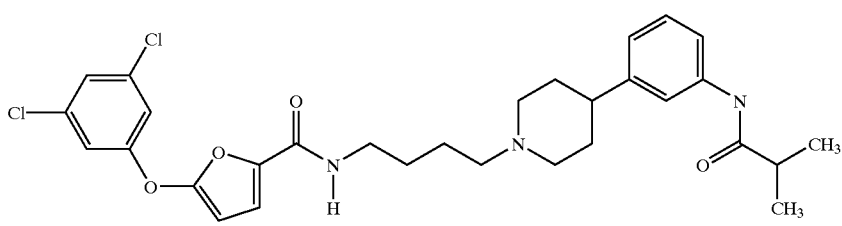 | 49.7 |
| 657 | 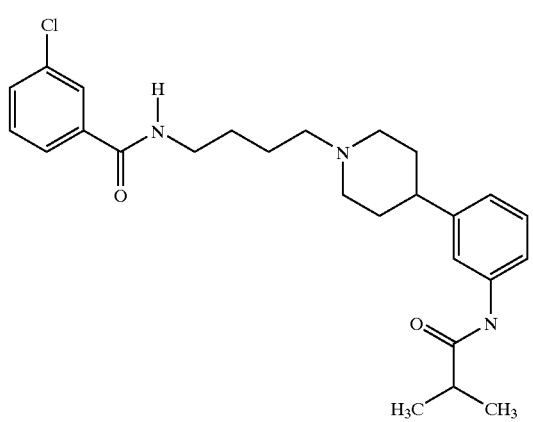 | 77.9 |

| | | |
|---|---|---|
| 658 | 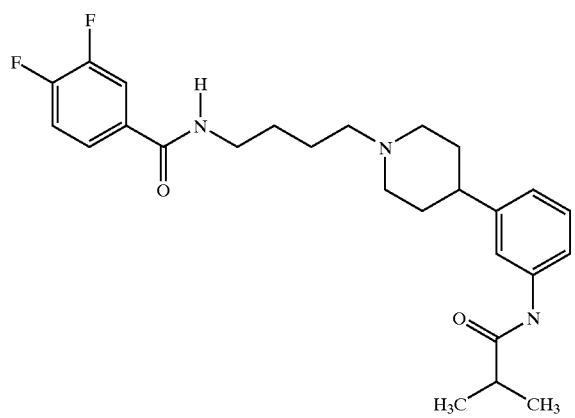 | 12.0 |
| 659 | 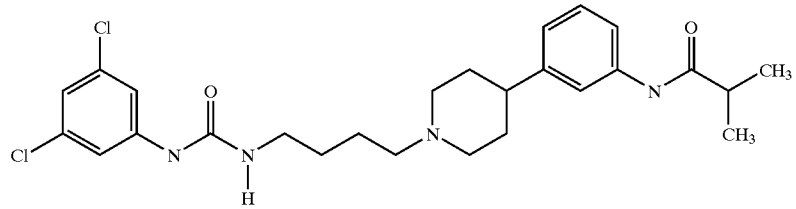 | 40.2 |
| 660 | 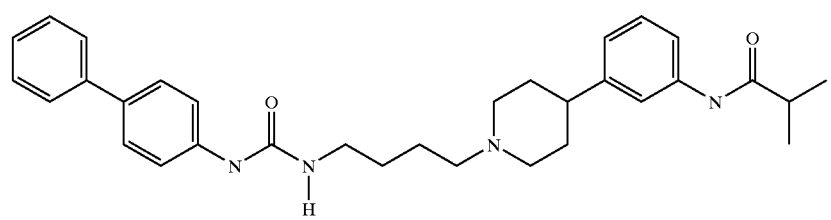 | 128.9 |
| 661 | 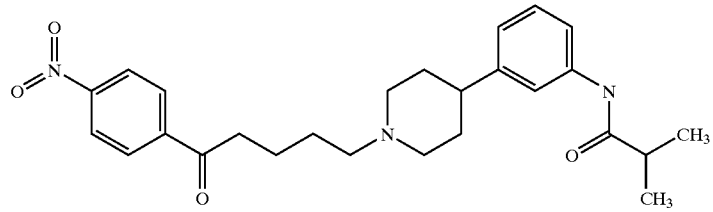 | 33.3 |
| 662 | 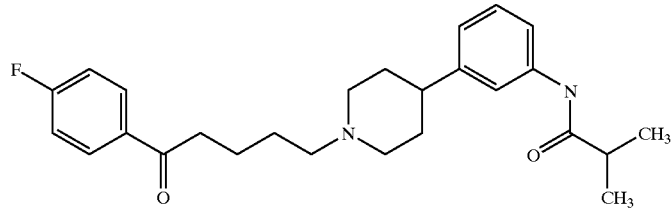 | 50.3 |
| 663 | 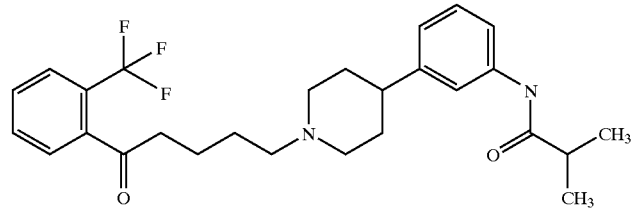 | 73.4 |

-continued
| 664 | 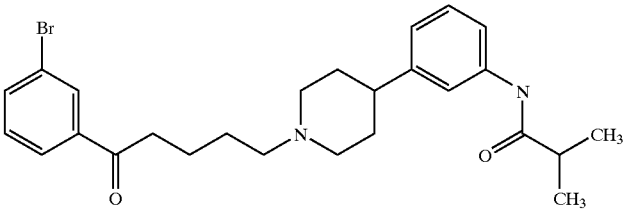 | 21.9 |
| --- | --- | --- |
| 665 | 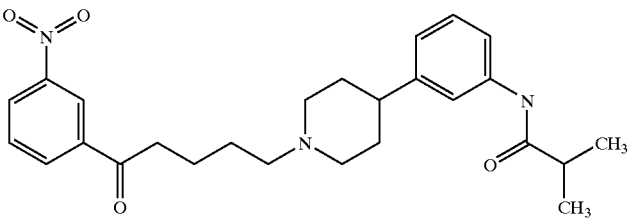 | 38.4 |
| 666 | 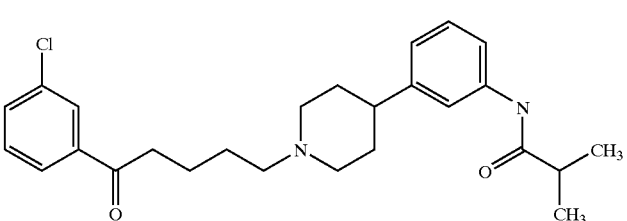 | 21.9 |
| 667 | 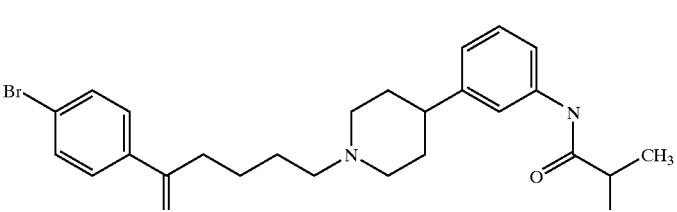 | 43.9 |
| 668 | 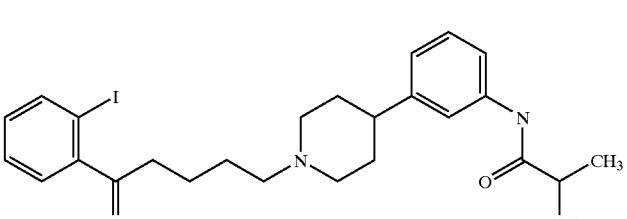 | 25.8 |
| 669 | 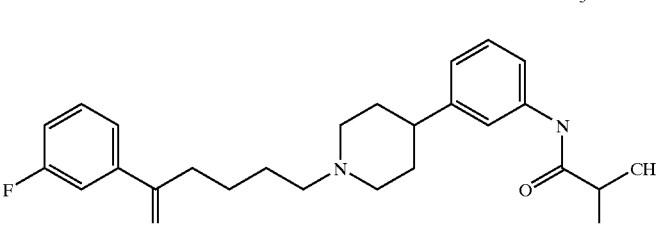 | 42.2 |
| 670 | 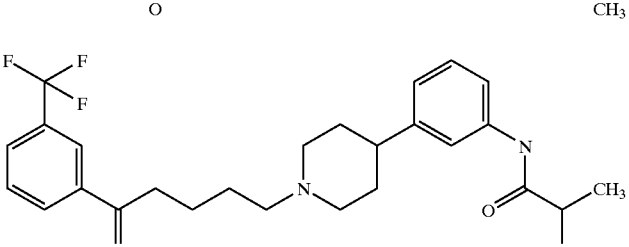 | 57.6 |

-continued
| | | |
|---|---|---|
| 671 | 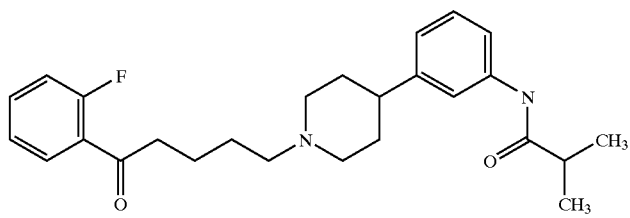 | 88.6 |
| 672 | 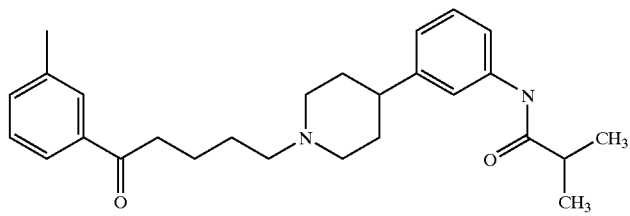 | 19.7 |
| 673 | 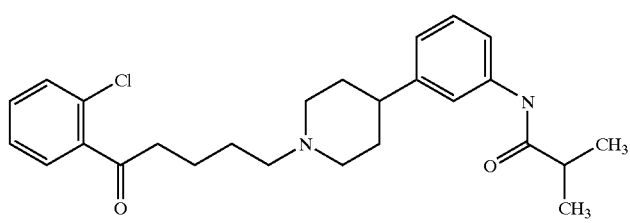 | 32.5 |
| 674 | 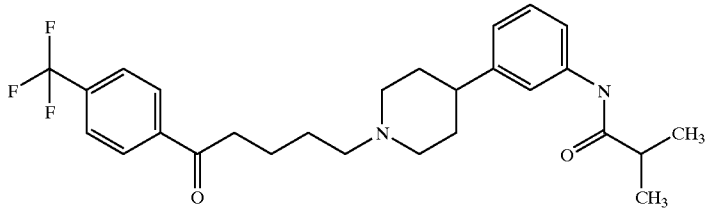 | 39.6 |
| 675 | 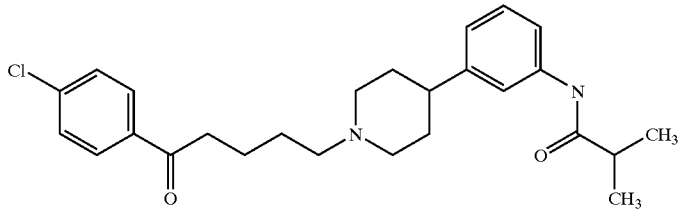 | 32.6 |
| 676 | 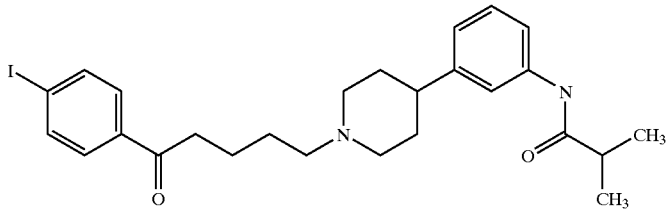 | 21.9 |
| 677 | 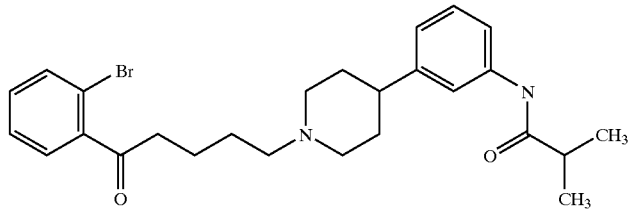 | 52.3 |

-continued
| | | |
|---|---|---|
| 678 | 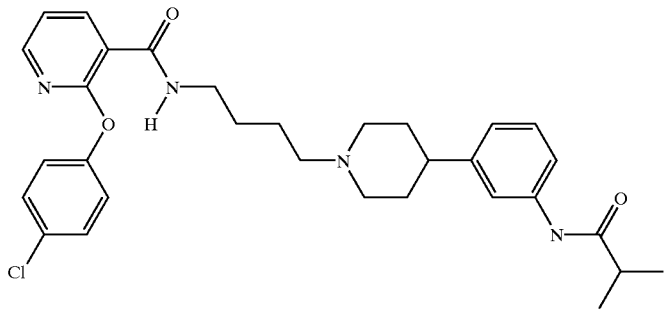 | 14.7 |
| 679 | 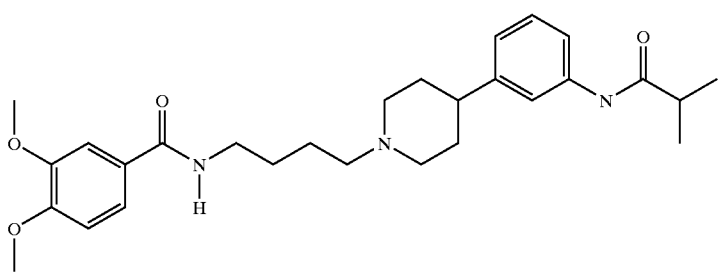 | 97.9 |
| 680 | 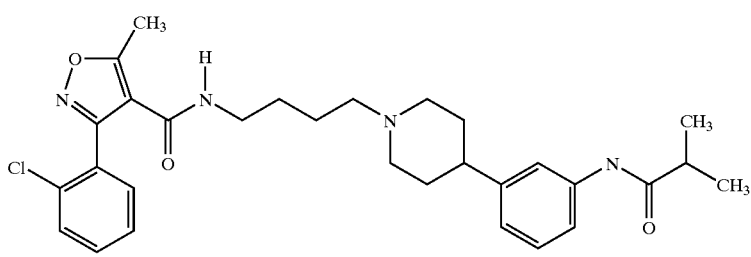 | 28.1 |
| 681 | 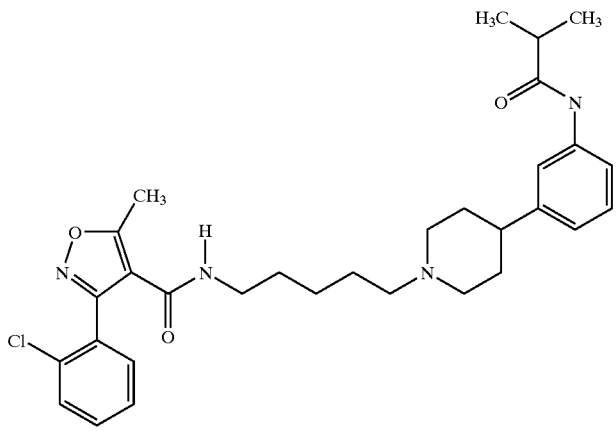 | 23.9 |
| 682 | 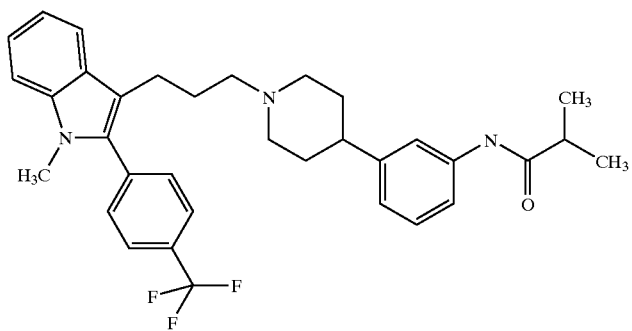 | 7.1 |

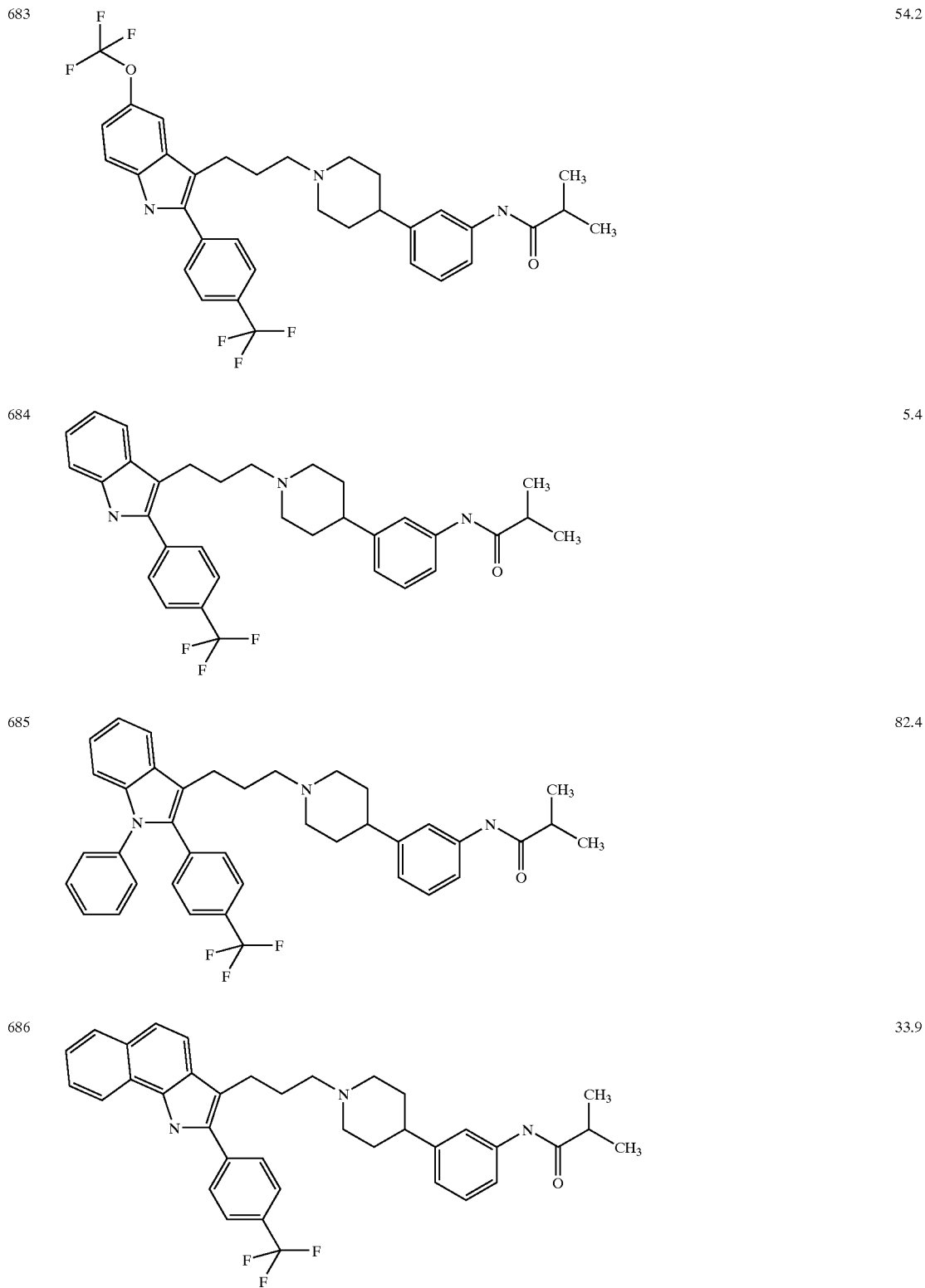

| 687 | 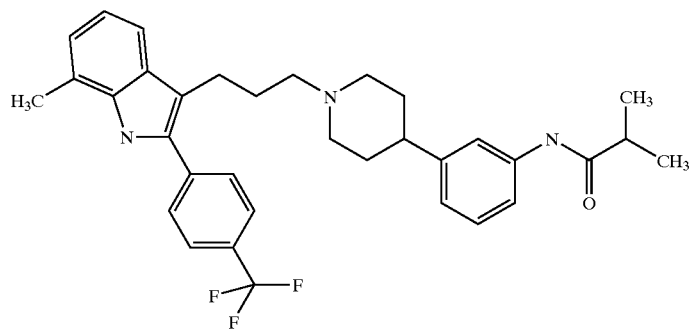 | 20.6 |
| 688 | 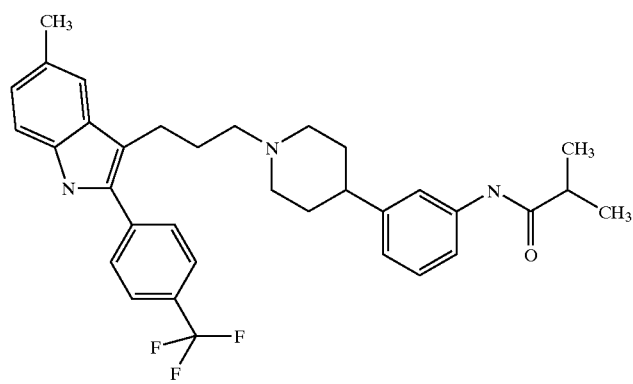 | 41.0 |
| 689 | 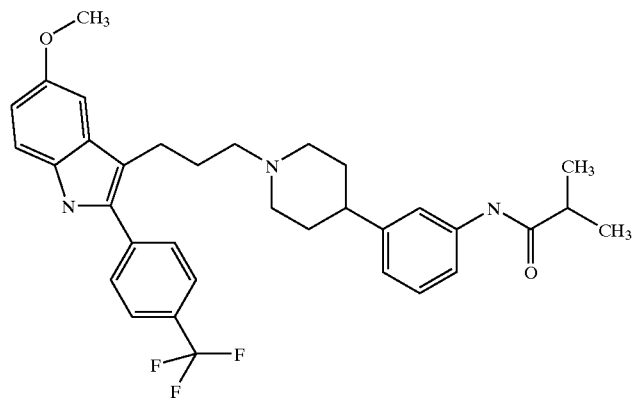 | 11.3 |
| 690 | 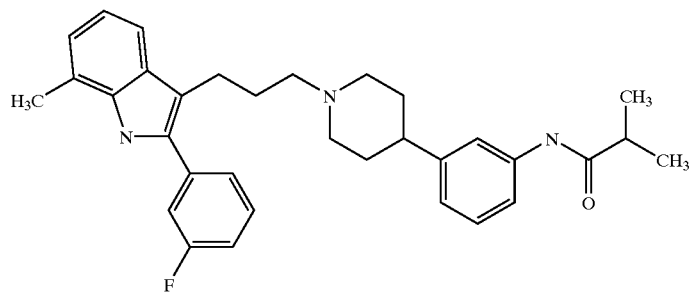 | 5.2 |

-continued
| | | |
|---|---|---|
| 691 | 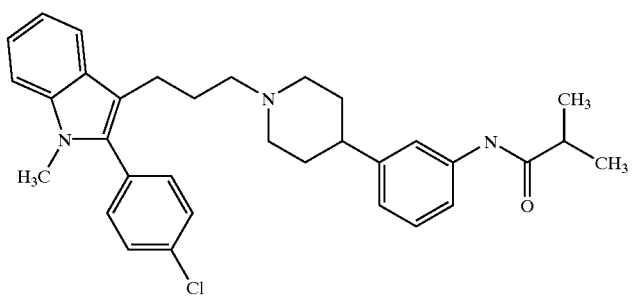 | 16.3 |
| 692 | 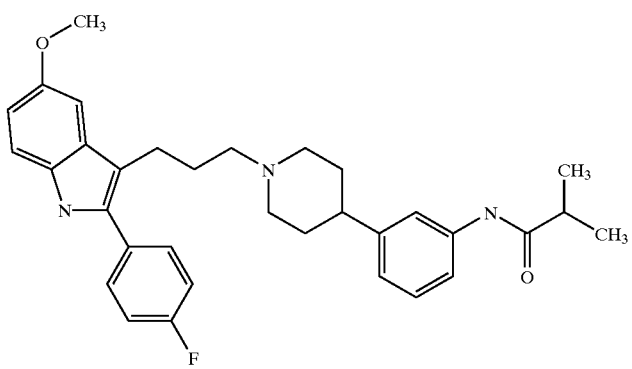 | 2.0 |
| 693 | 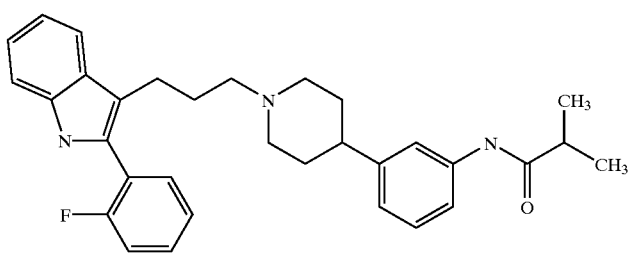 | 0.4 |
| 694 | 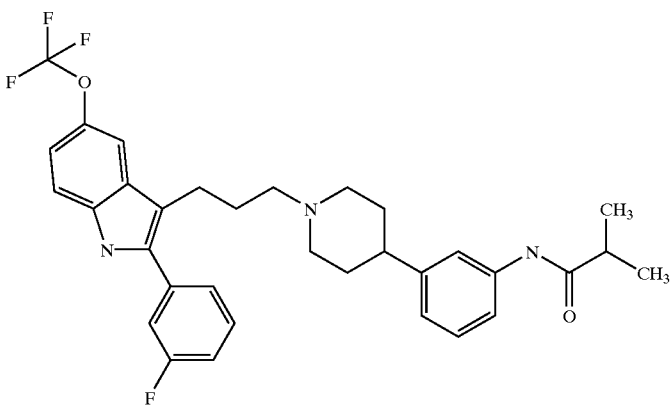 | 6.4 |

-continued

| | | |
|---|---|---|
| 695 | | 2.1 |
| 696 | | 48.3 |
| 697 | | 3.0 |
| 698 | | 3.0 |
| 699 | | 5.4 |

| | | |
|---|---|---|
| 700 | 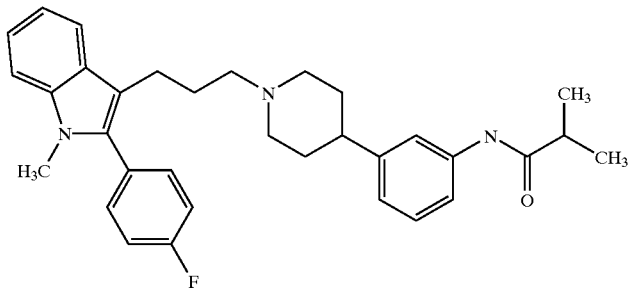 | 2.0 |
| 701 | 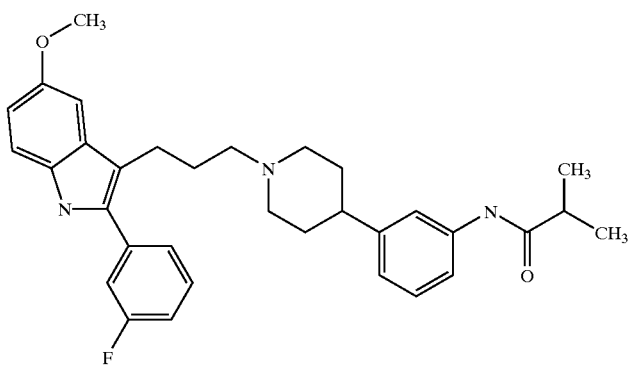 | 2.5 |
| 702 | 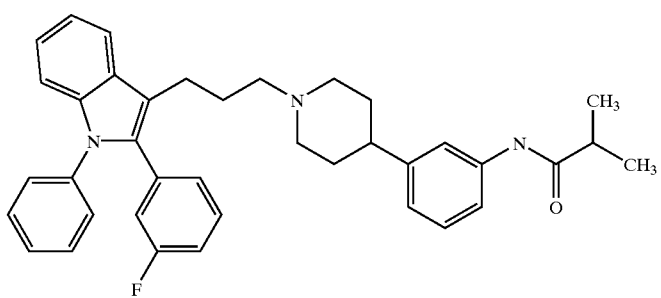 | 27.0 |
| 703 | 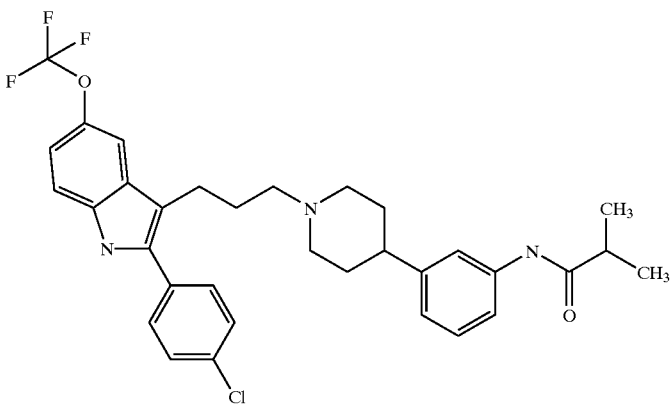 | 16.6 |

-continued
| | | |
|---|---|---|
| 704 | 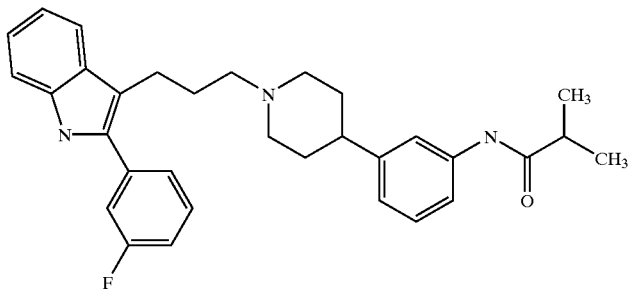 | 1.2 |
| 705 | 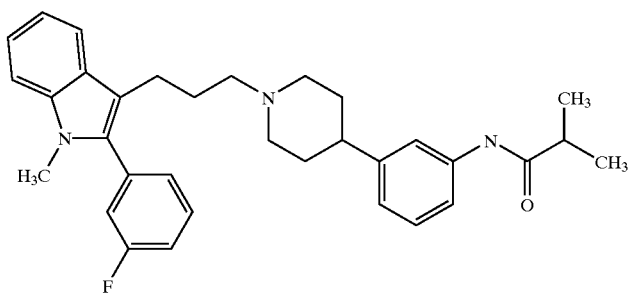 | 8.5 |
| 706 | 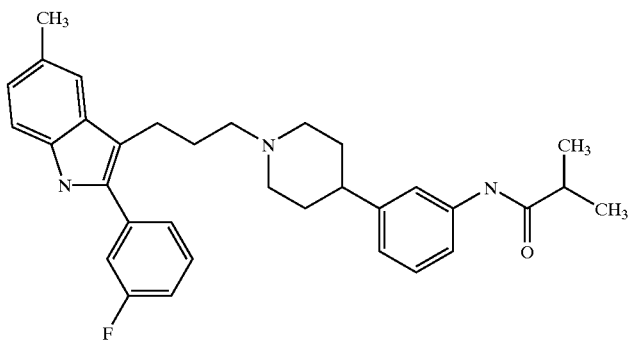 | 4.2 |
| 707 | 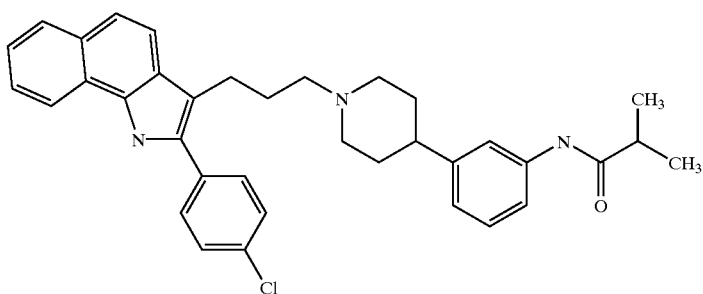 | 19.6 |
| 708 | 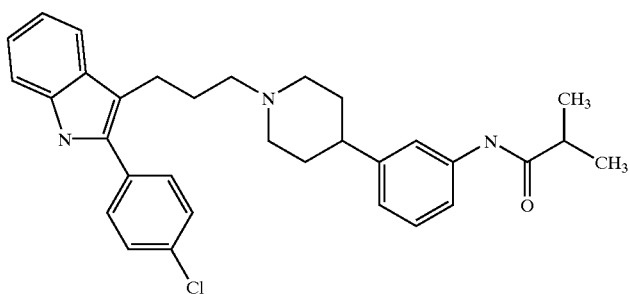 | 3.8 |

-continued
| | | |
|---|---|---|
| 709 | 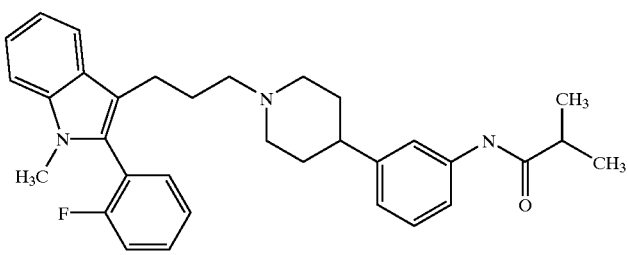 | 1.3 |
| 710 | 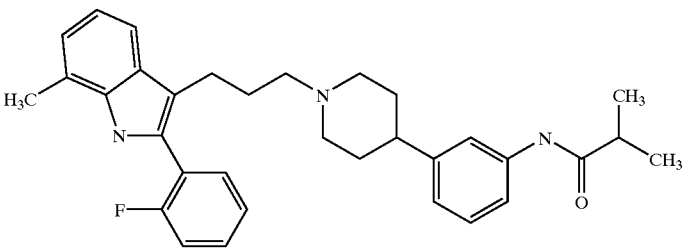 | 6.9 |
| 711 | 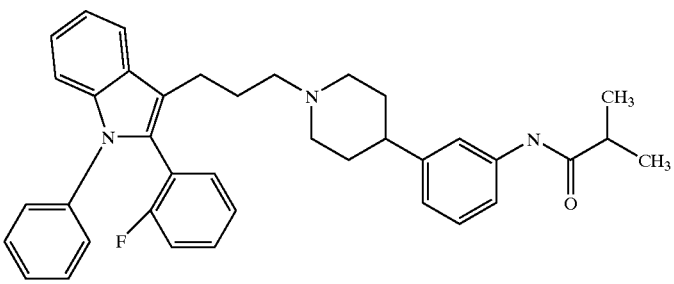 | 90.5 |
| 712 | 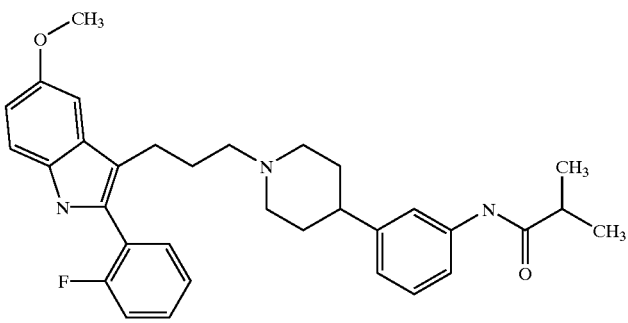 | 8.6 |
| 713 | 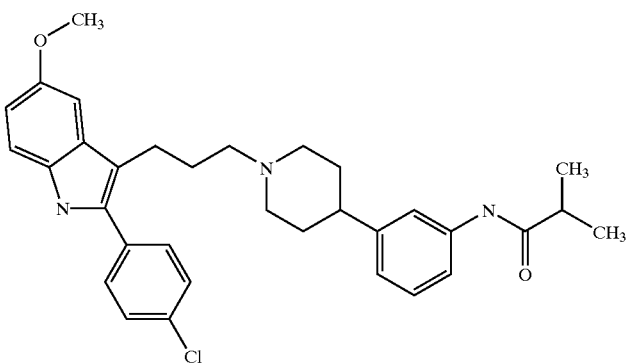 | 7.7 |

-continued
| | | |
|---|---|---|
| 714 | 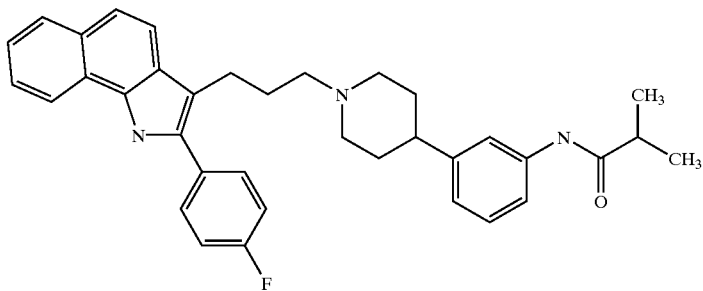 | 4.7 |
| 715 | 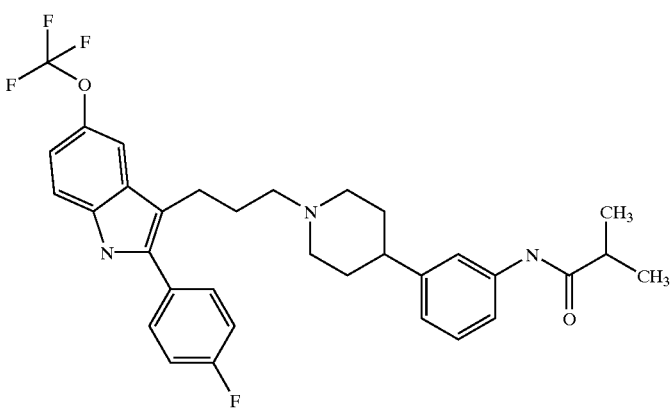 | 4.2 |
| 716 | 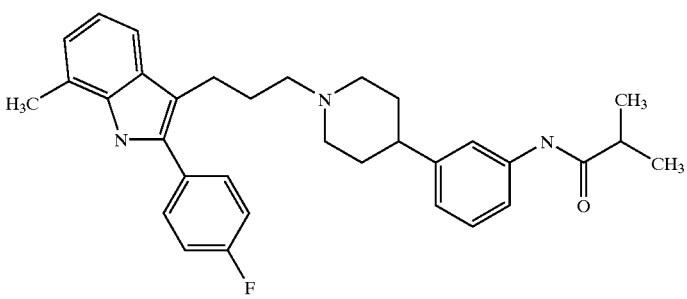 | 4.5 |
| 717 | 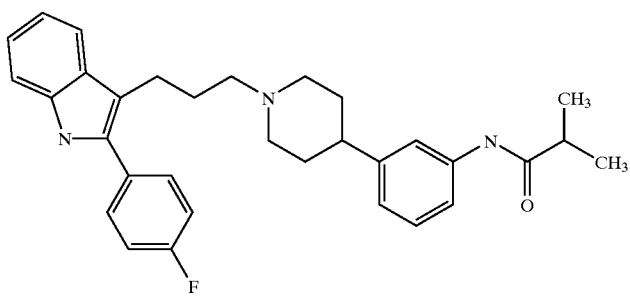 | 1.3 |

-continued
| | | |
|---|---|---|
| 718 | 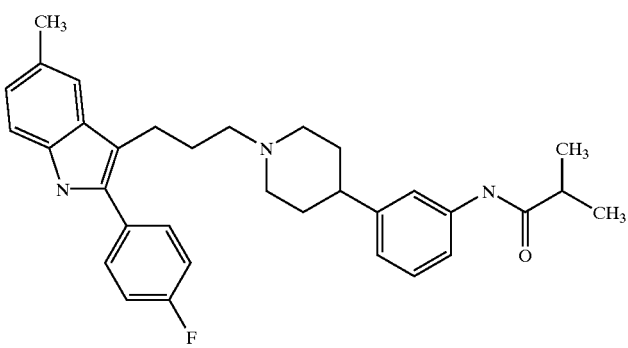 | 3.4 |
| 719 | 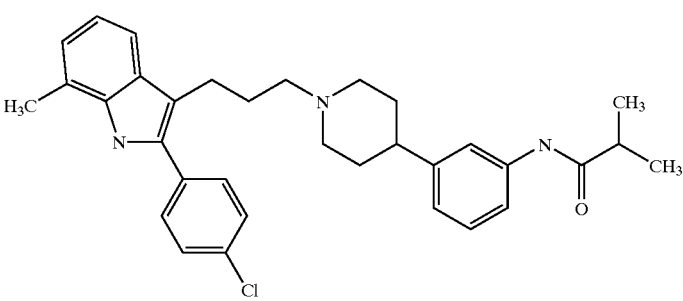 | 14.9 |
| 720 | 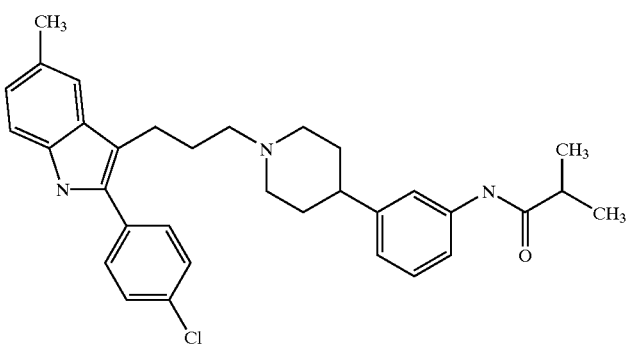 | 12.5 |
| 721 | 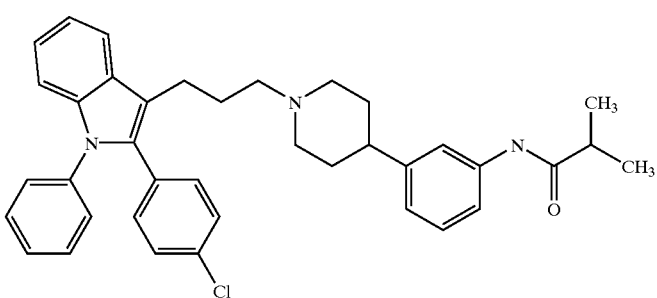 | 75.3 |
| 722 | 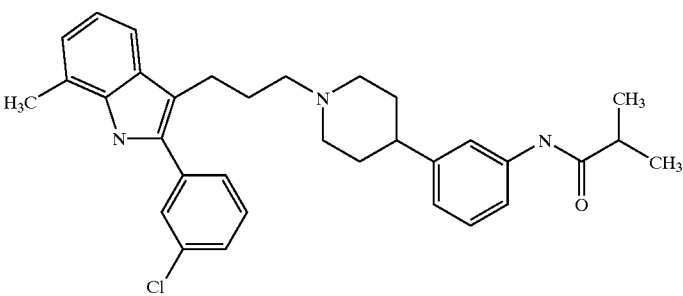 | 6.4 |

-continued
| | | |
|---|---|---|
| 723 | 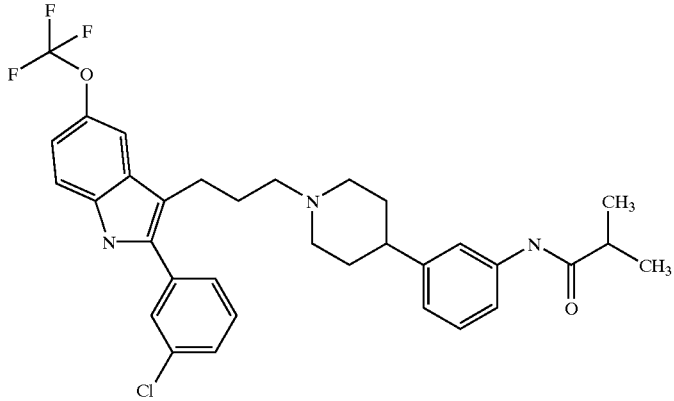 | 9.2 |
| 724 | 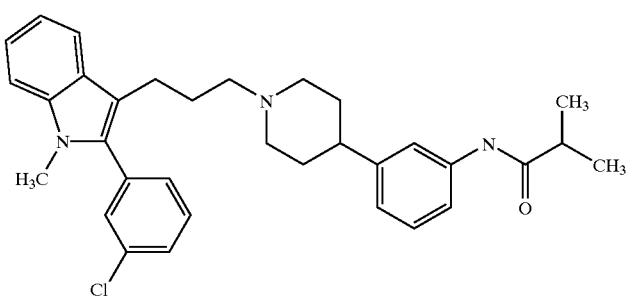 | 5.0 |
| 725 | 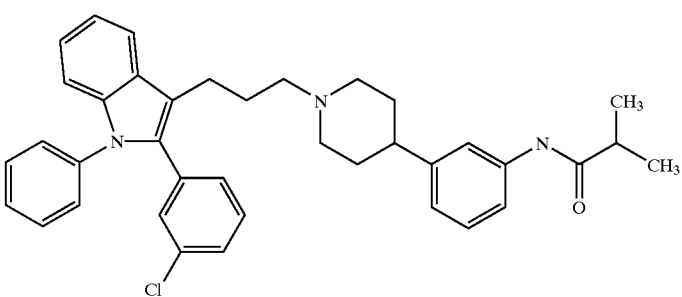 | 151.6 |
| 726 | 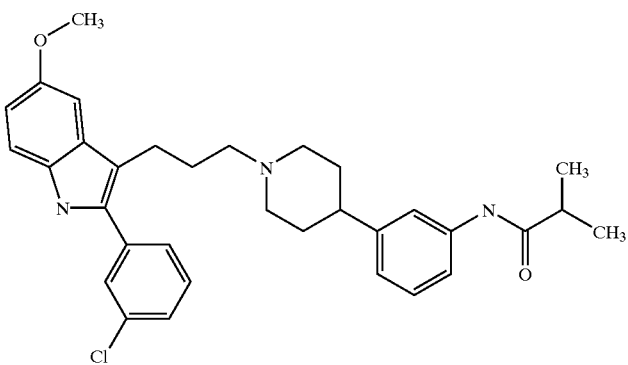 | 5.0 |

-continued
| 727 | 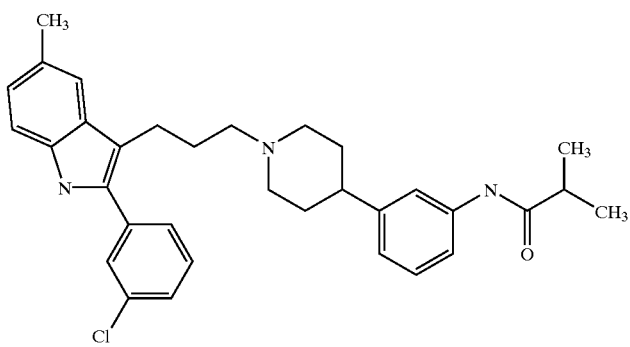 | 3.4 |
| 728 | 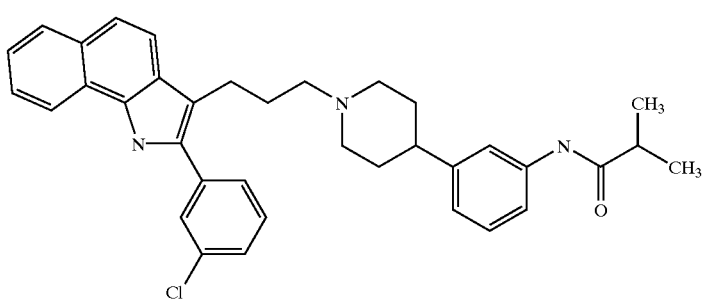 | 16.3 |
| 729 | 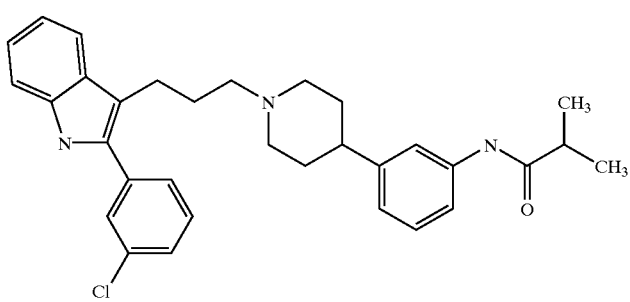 | 1.7 |
| 730 | 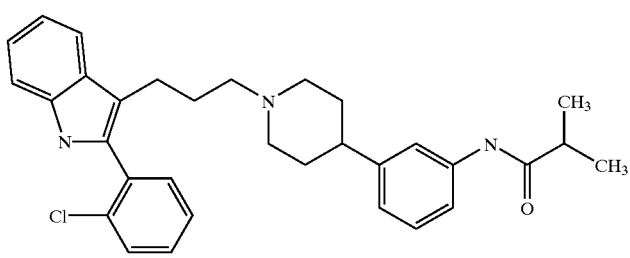 | 0.9 |
| 731 | 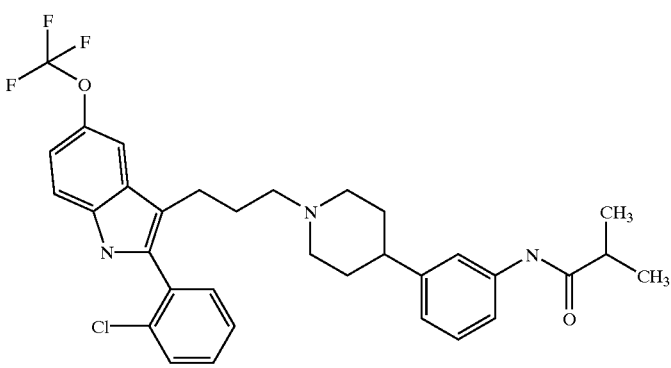 | 9.9 |

-continued
| | | |
|---|---|---|
| 732 | 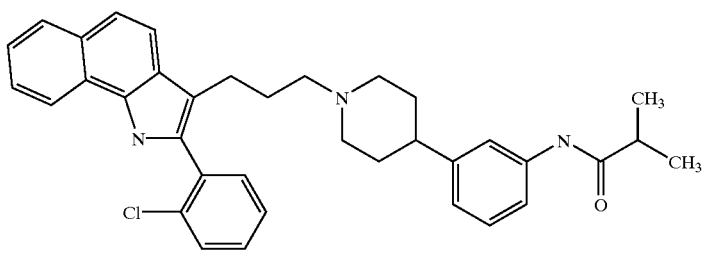 | 5.8 |
| 733 | 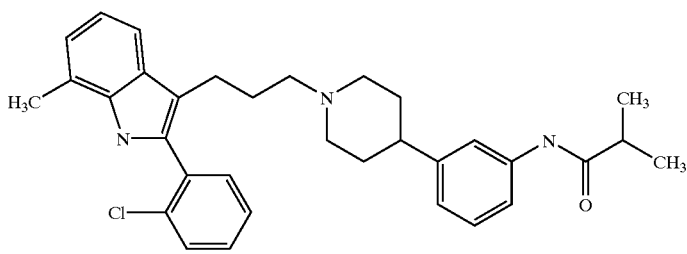 | 10.0 |
| 734 | 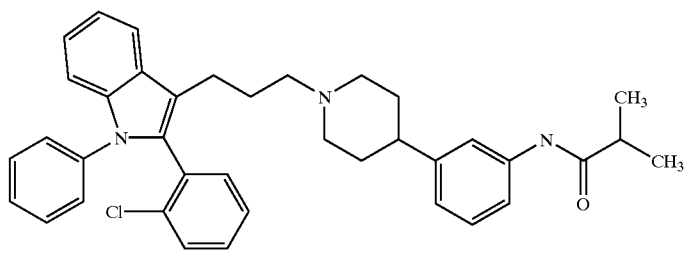 | 28.6 |
| 735 | 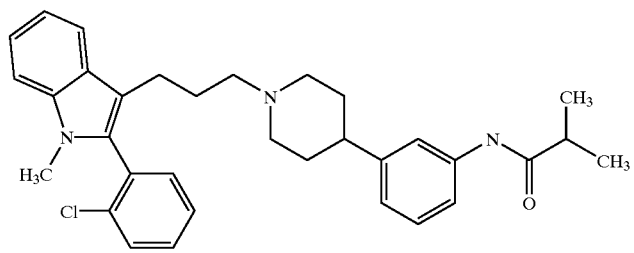 | 1.1 |
| 736 | 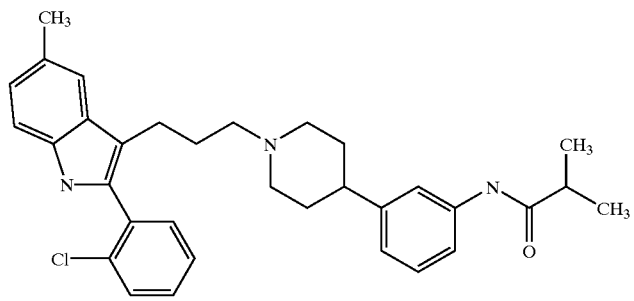 | 5.7 |

-continued
| | | |
|---|---|---|
| 737 | 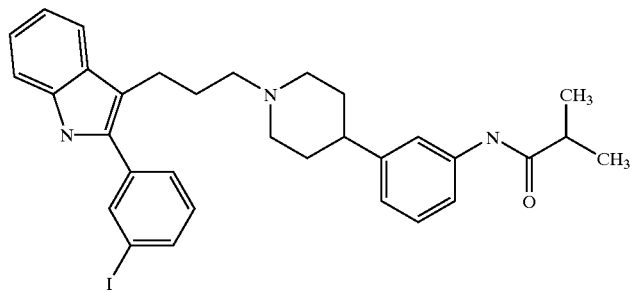 | 1.0 |
| 738 | 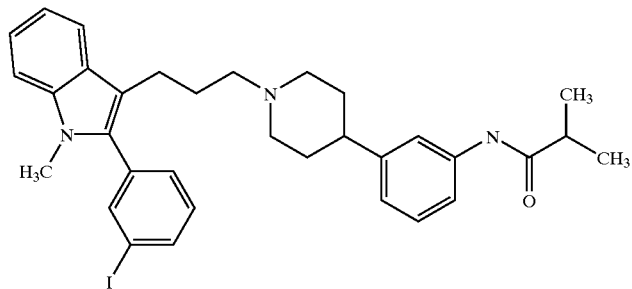 | 10.2 |
| 739 | 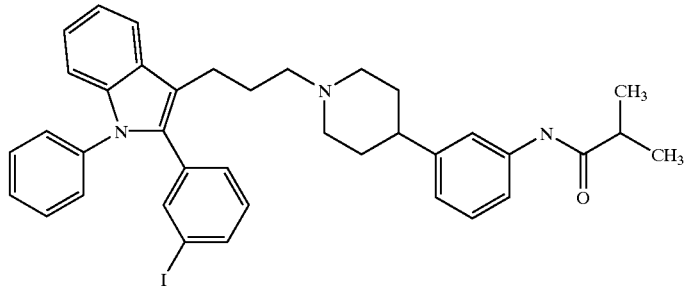 | 213.6 |
| 740 | 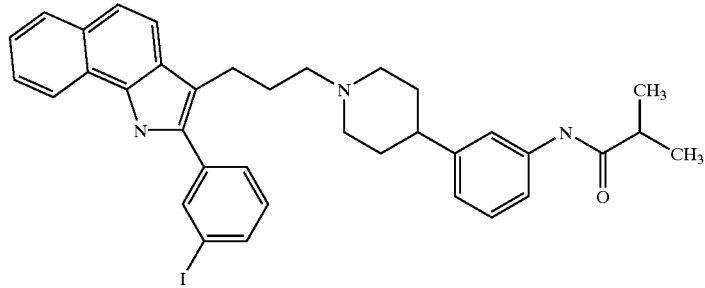 | 12.2 |
| 741 | 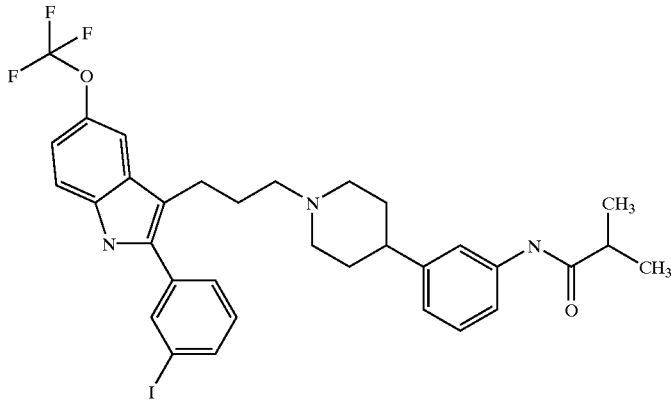 | 2.8 |

| | | |
|---|---|---|
| 742 | 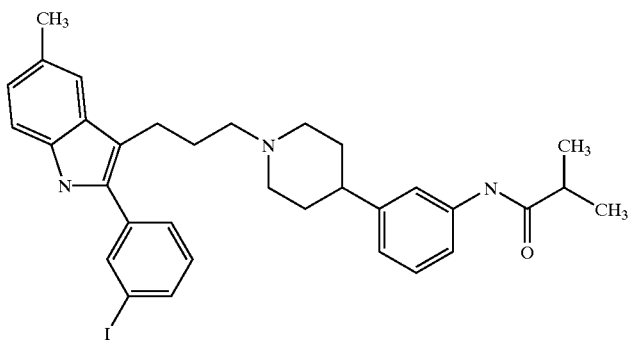 | 1.4 |
| 743 | 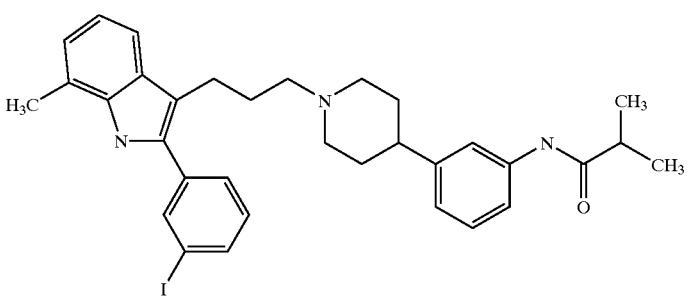 | 4.1 |
| 744 | 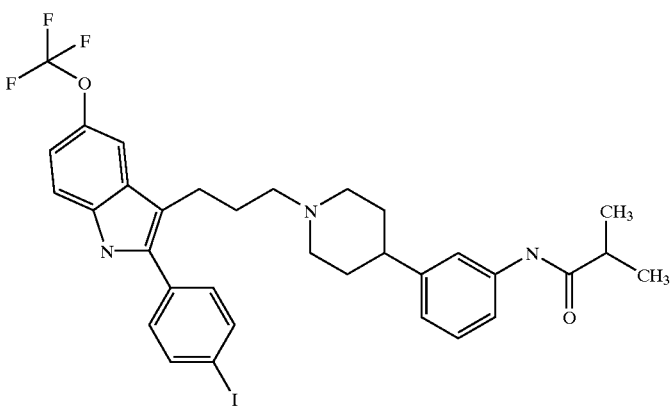 | 47.1 |
| 745 | 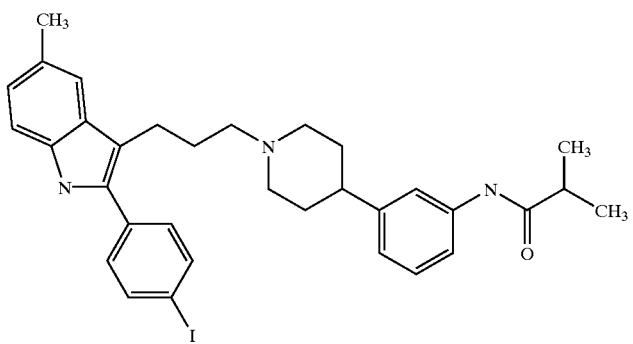 | 15.8 |

| | | |
|---|---|---|
| 746 | 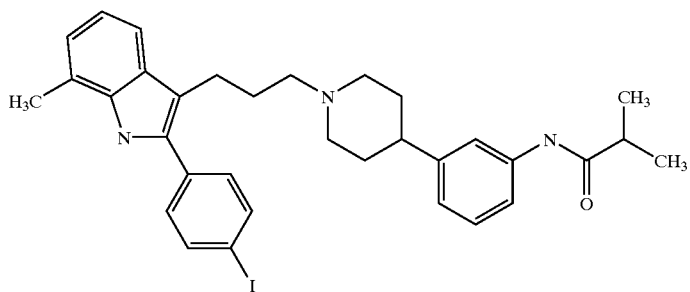 | 8.0 |
| 747 | 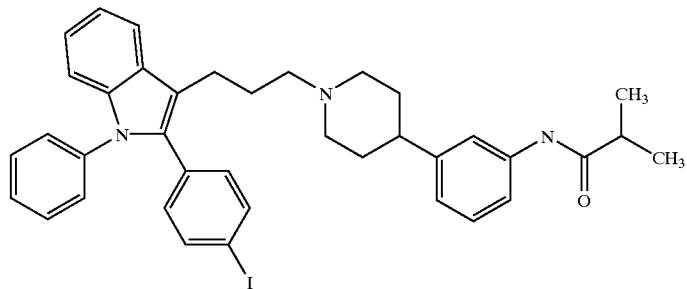 | 160.6 |
| 748 | 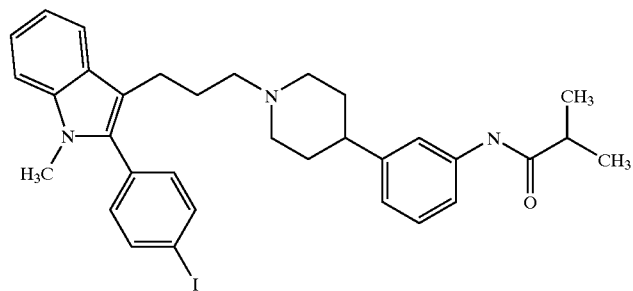 | 3.1 |
| 749 | 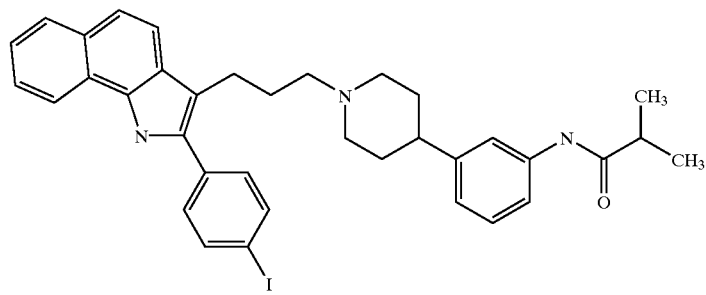 | 23.2 |
| 750 | 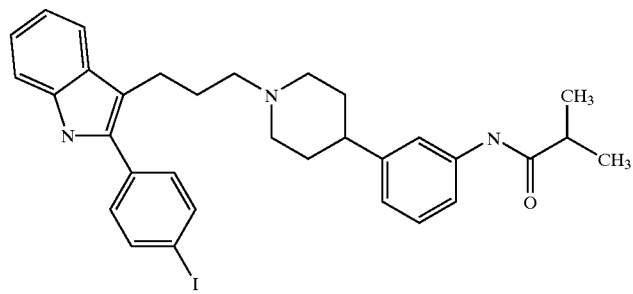 | 2.6 |

-continued
| | | |
|---|---|---|
| 751 | 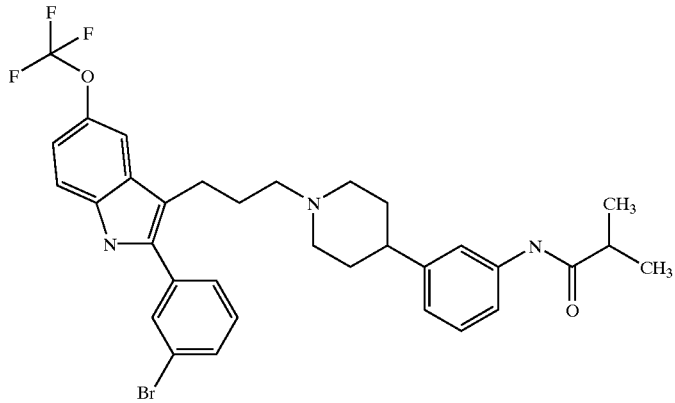 | 12.4 |
| 752 | 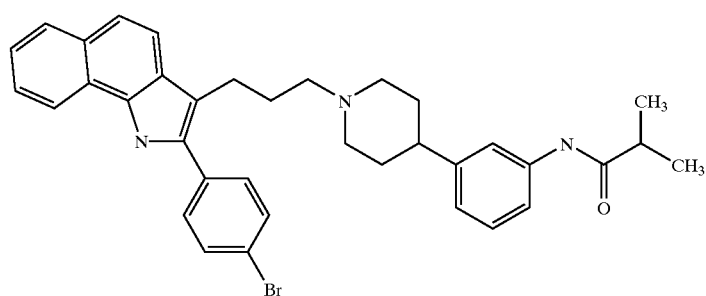 | 21.7 |
| 753 | 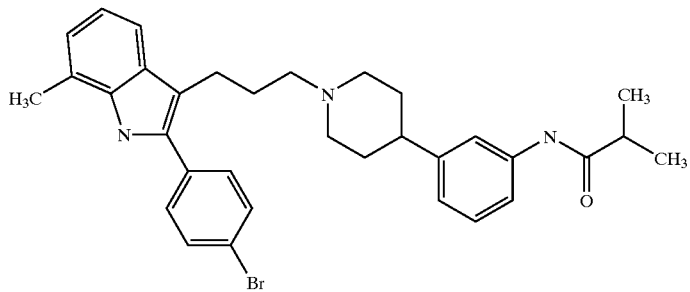 | 16.6 |
| 754 | 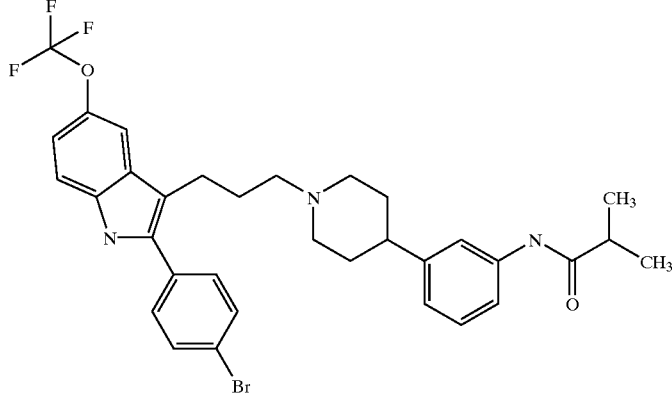 | 49.2 |

-continued
| | | |
|---|---|---|
| 755 | 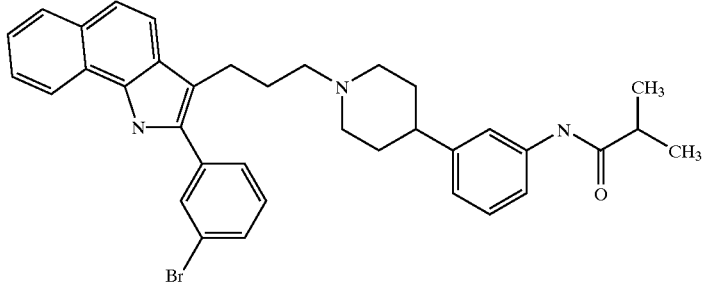 | 23.8 |
| 756 | 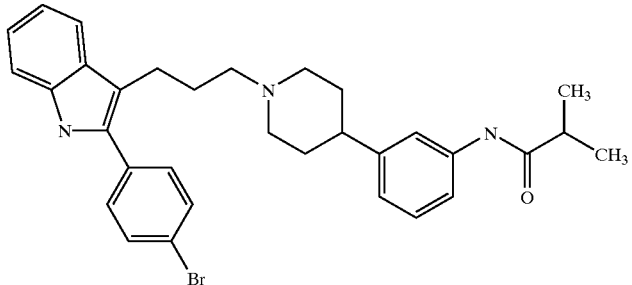 | 4.2 |
| 757 | 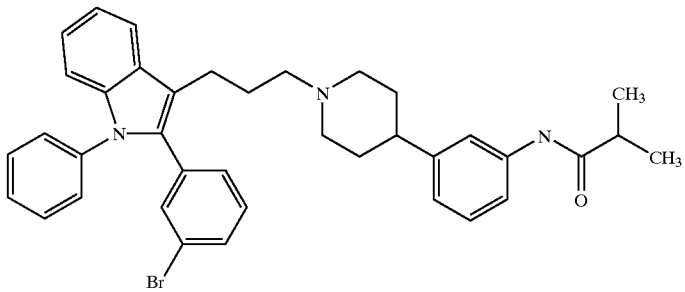 | 6.9 |
| 758 | 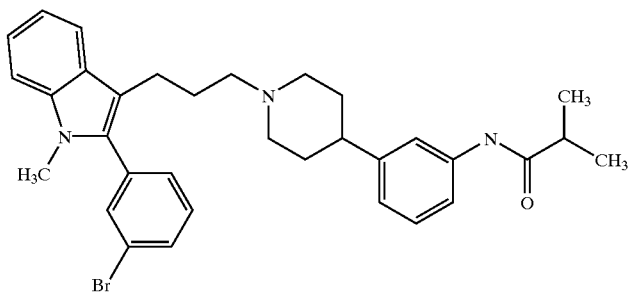 | 110.0 |
| 759 | 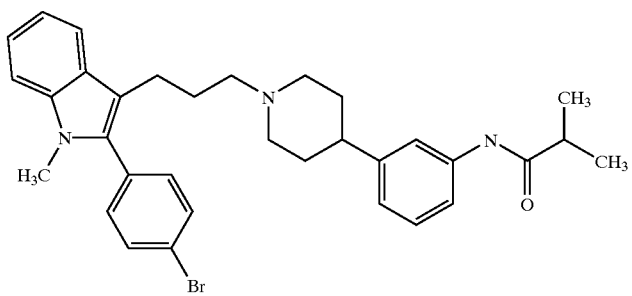 | 9.3 |

-continued
| | | |
|---|---|---|
| 760 | 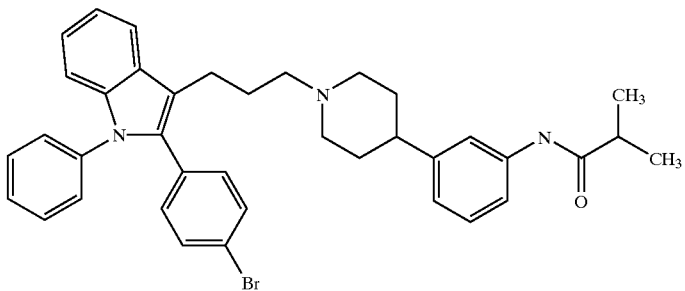 | 92.3 |
| 761 | 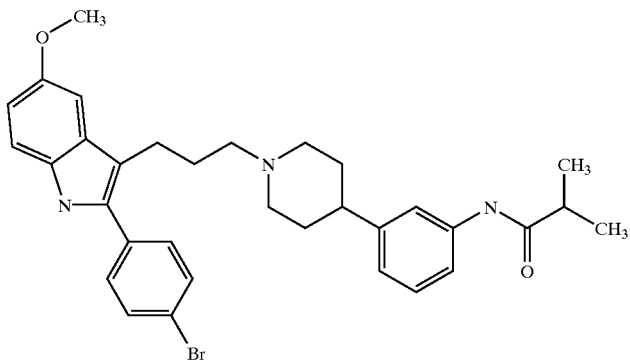 | 15.9 |
| 762 | 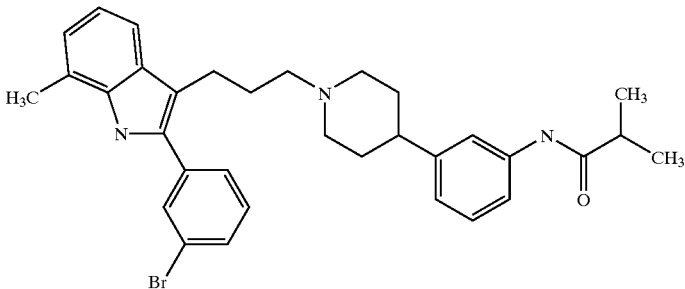 | 6.3 |
| 763 | 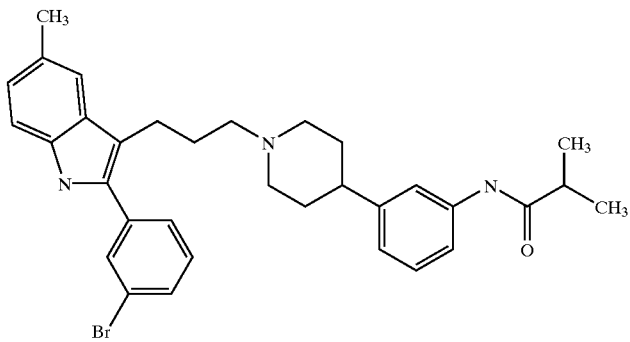 | 1.9 |

| | | |
|---|---|---|
| 764 | 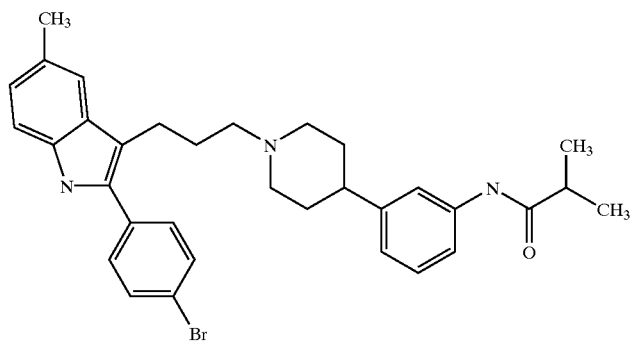 | 14.6 |
| 765 | 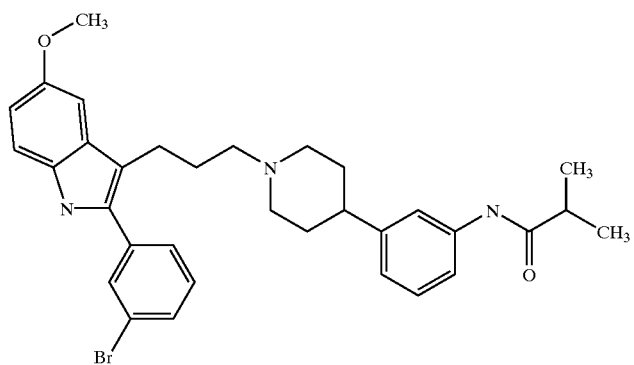 | 6.5 |
| 766 | 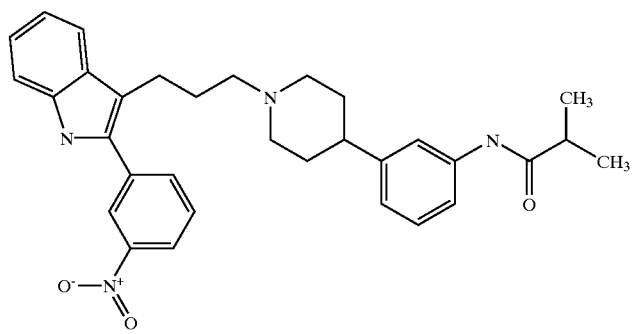 | 7.6 |
| 767 | 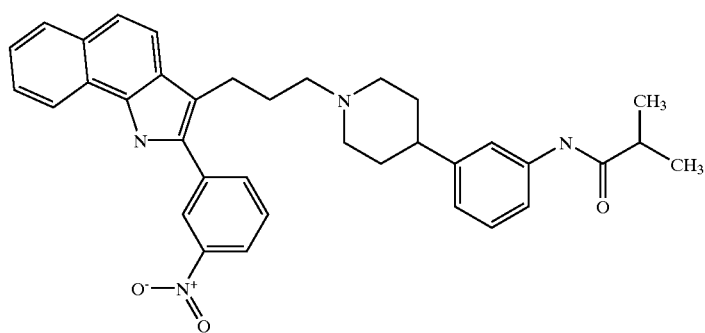 | 34.8 |

-continued
| | | |
|---|---|---|
| 768 | 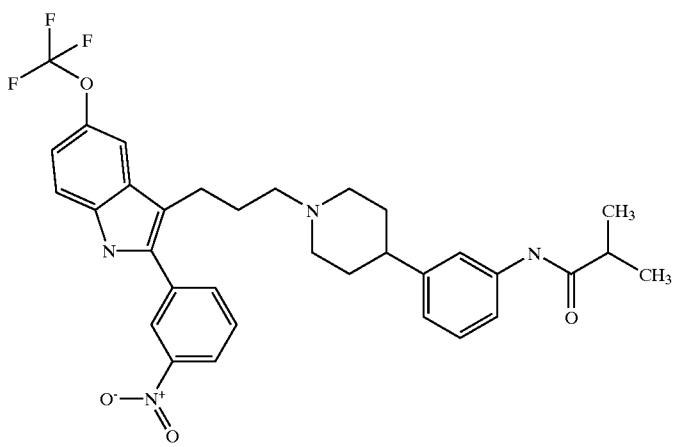 | 17.5 |
| 769 | 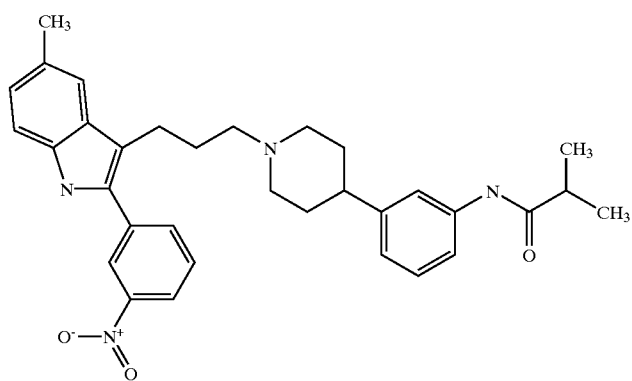 | 12.4 |
| 770 | 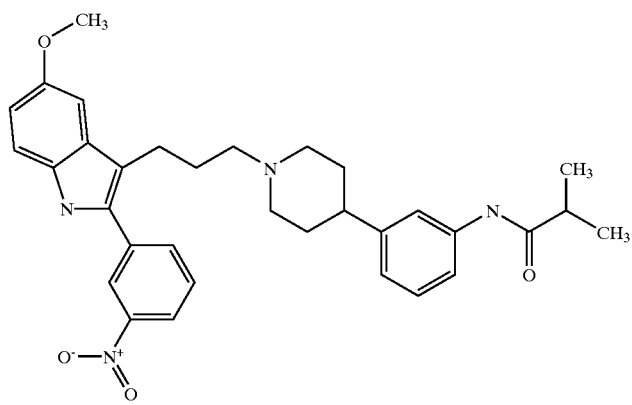 | 12.7 |
| 771 | 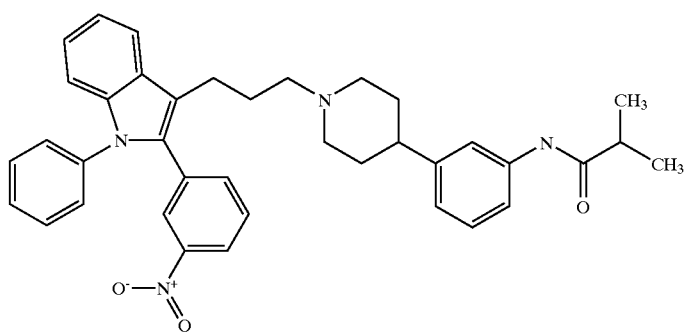 | 189.0 |

-continued
| | | |
|---|---|---|
| 772 | 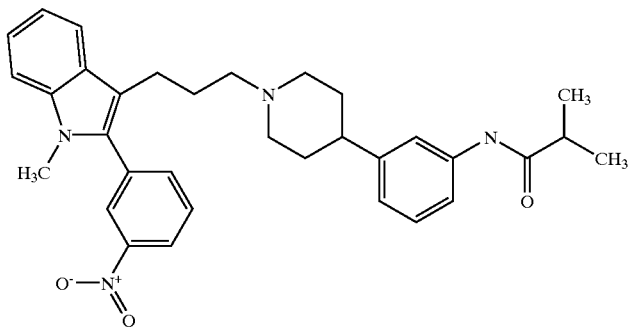 | 14.9 |
| 773 | 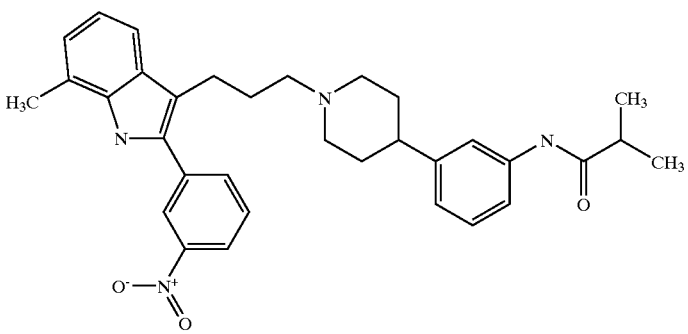 | 23.8 |
| 774 | 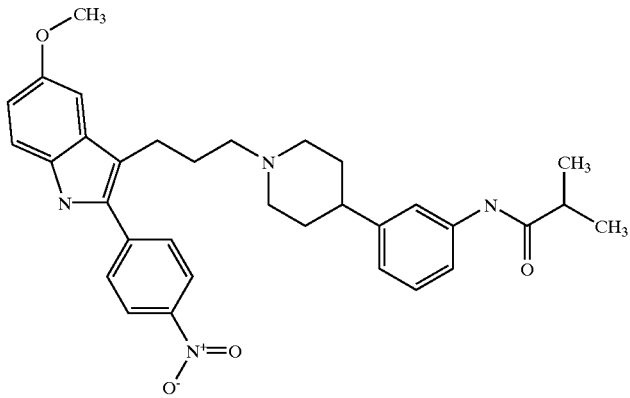 | 7.9 |
| 775 | 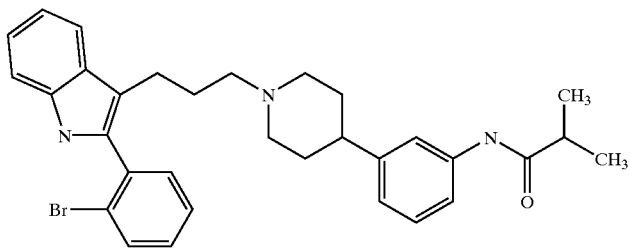 | 4.9 |

-continued
| | | |
|---|---|---|
| 776 | 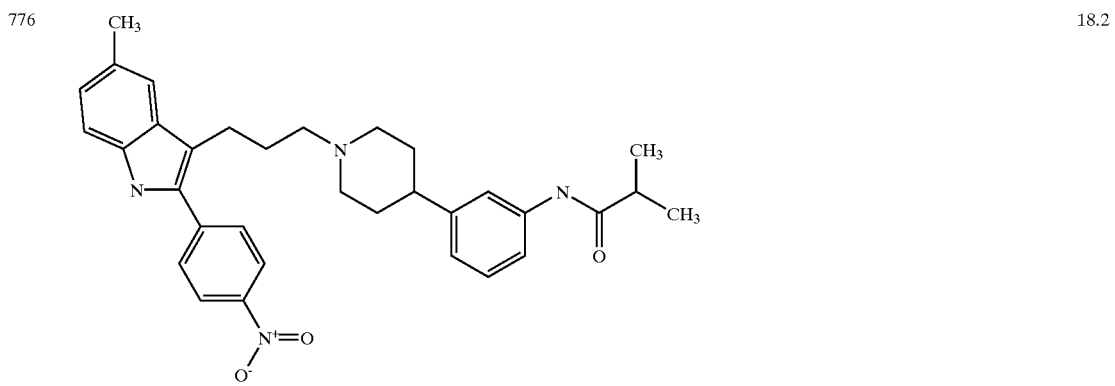 | 18.2 |
| 777 | 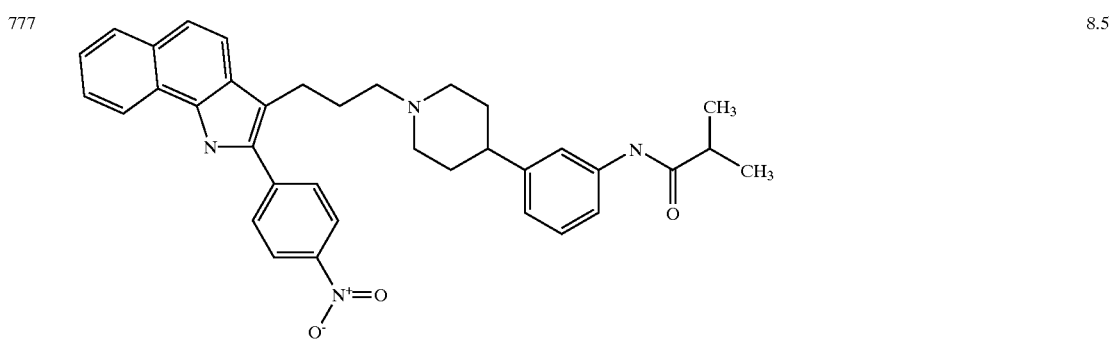 | 8.5 |
| 778 | 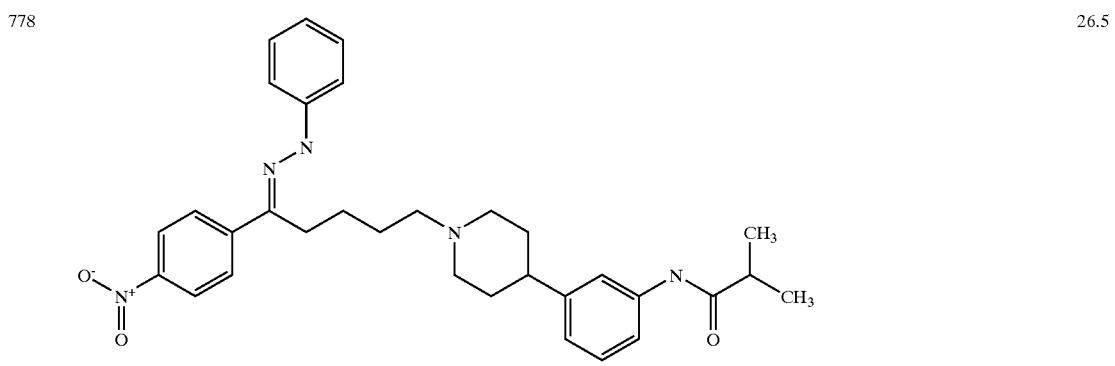 | 26.5 |
| 779 | 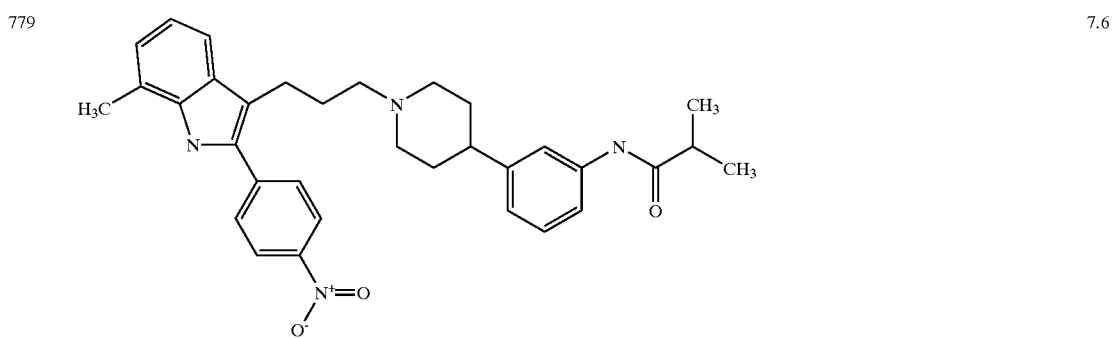 | 7.6 |

-continued
| | | |
|---|---|---|
| 780 | 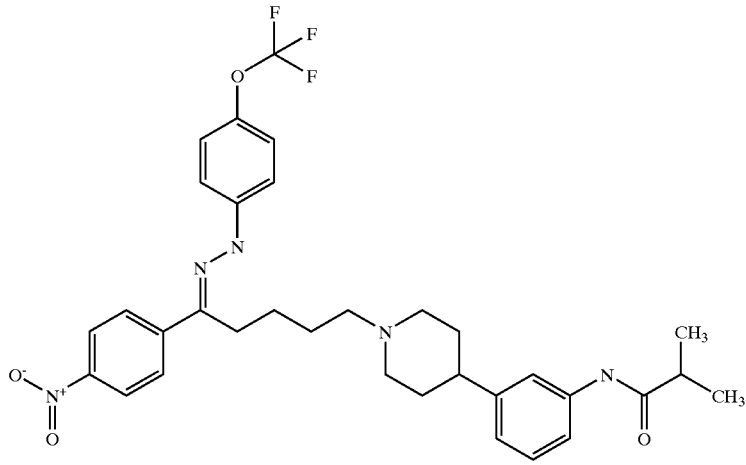 | 64.3 |
| 781 | 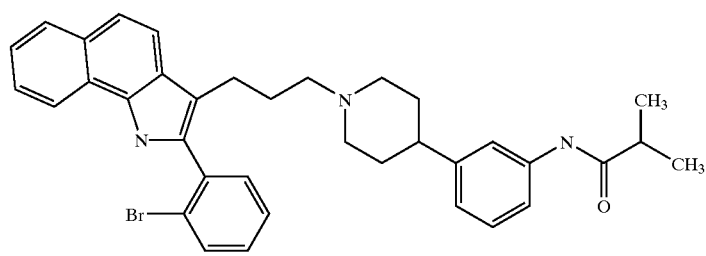 | 7.6 |
| 782 | 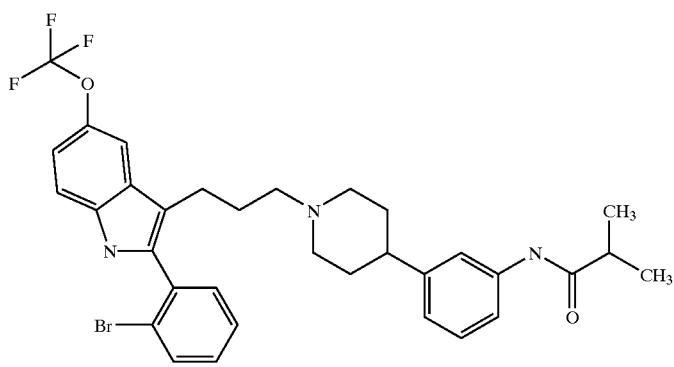 | 18.1 |
| 783 | 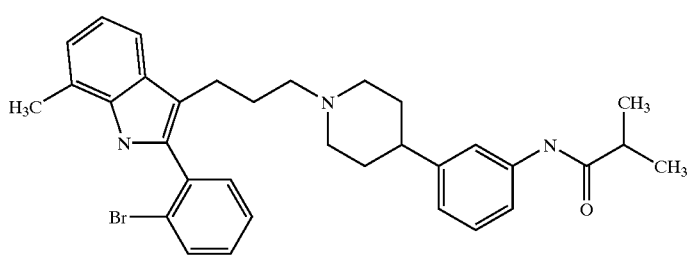 | 18.0 |
| 784 | 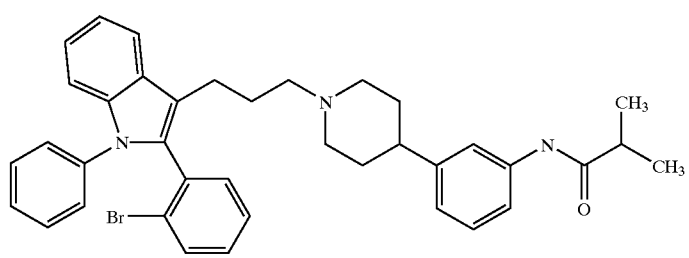 | 121.2 |

-continued
| | | |
|---|---|---|
| 785 | 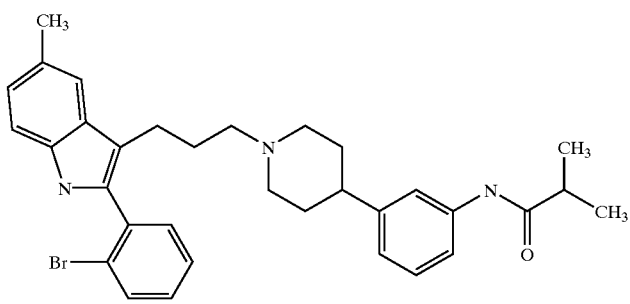 | 22.7 |
| 786 | 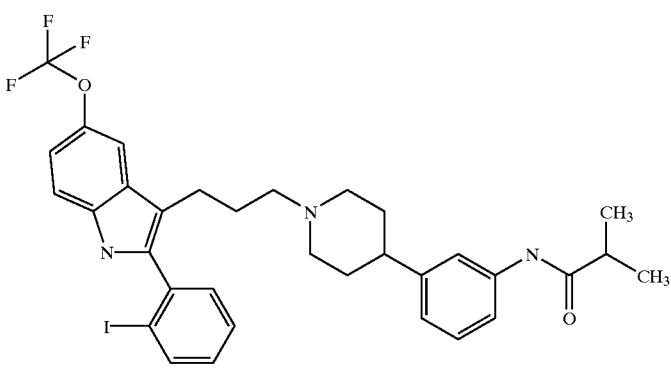 | 19.7 |
| 787 | 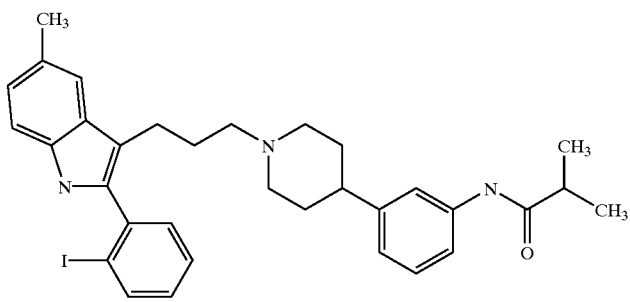 | 21.6 |
| 788 | 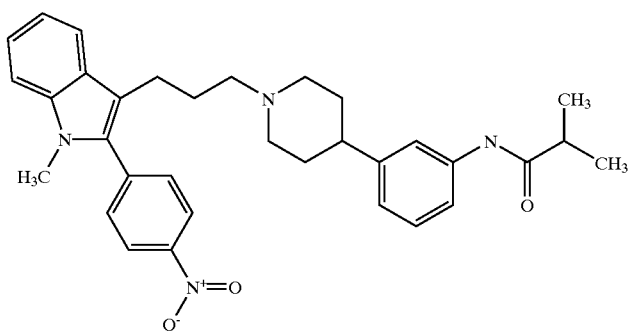 | 11.1 |

-continued
| | | |
|---|---|---|
| 789 | 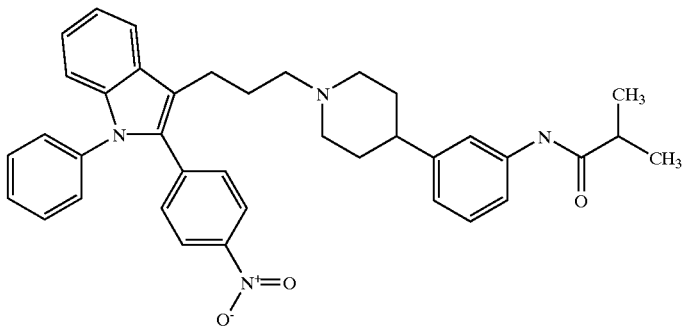 | 36.4 |
| 790 | 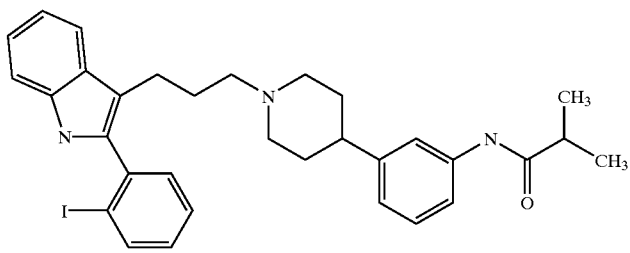 | 4.4 |
| 791 | 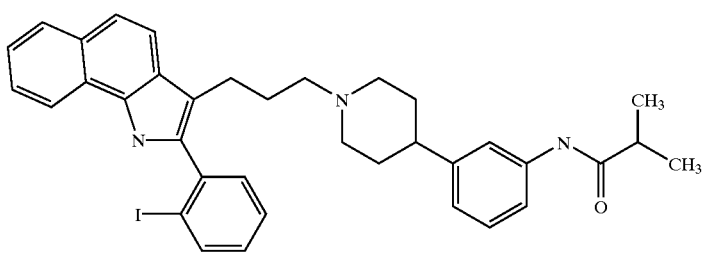 | 12.7 |
| 792 | 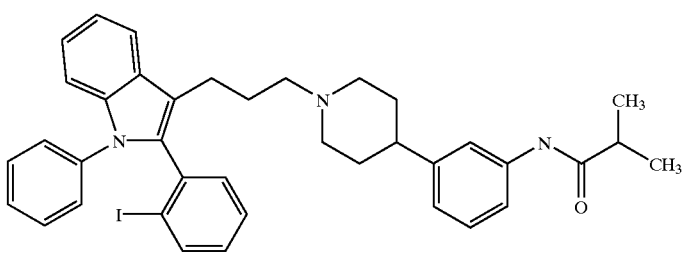 | 122.0 |
| 793 | 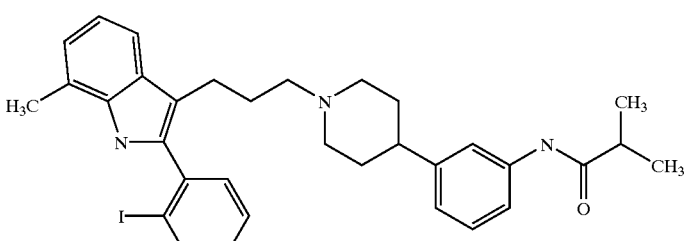 | 16.3 |
| 794 | 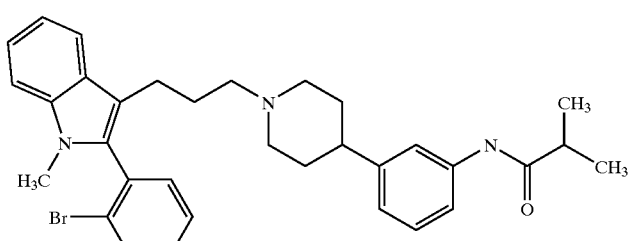 | 4.9 |

| | | |
|---|---|---|
| 795 | 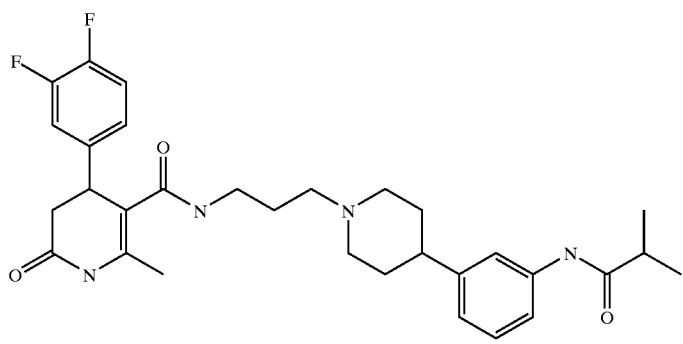 | 51.1 |
| 796 | 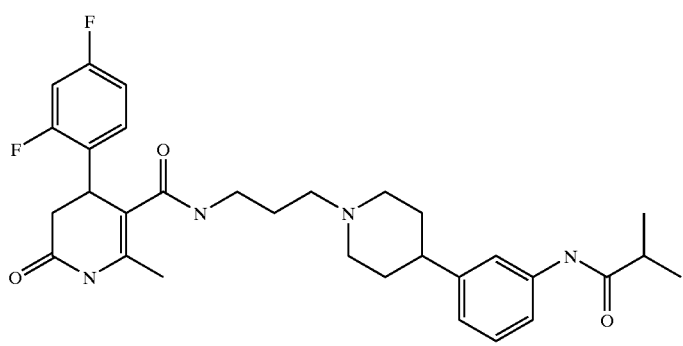 | 43.0 |
| 797 | 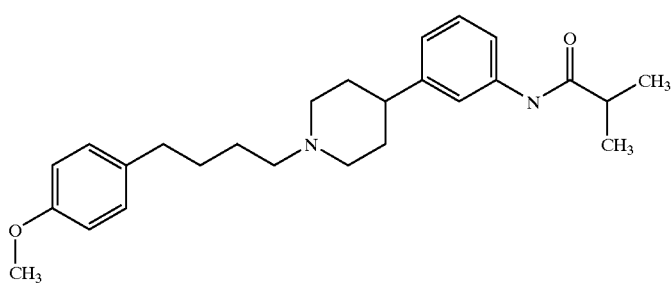 | 42.4 |
| 798 | 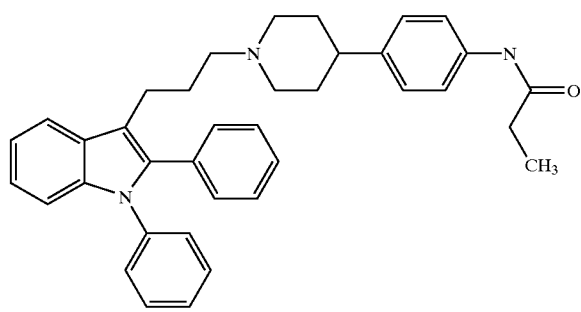 | 474.7 |
| 799 | 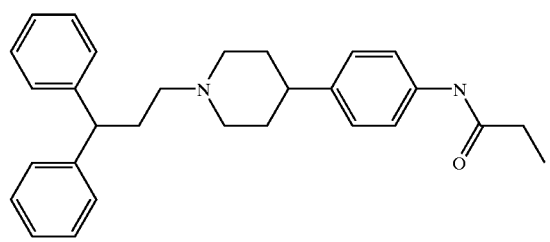 | 370.6 |

-continued
| | | |
|---|---|---|
| 800 | 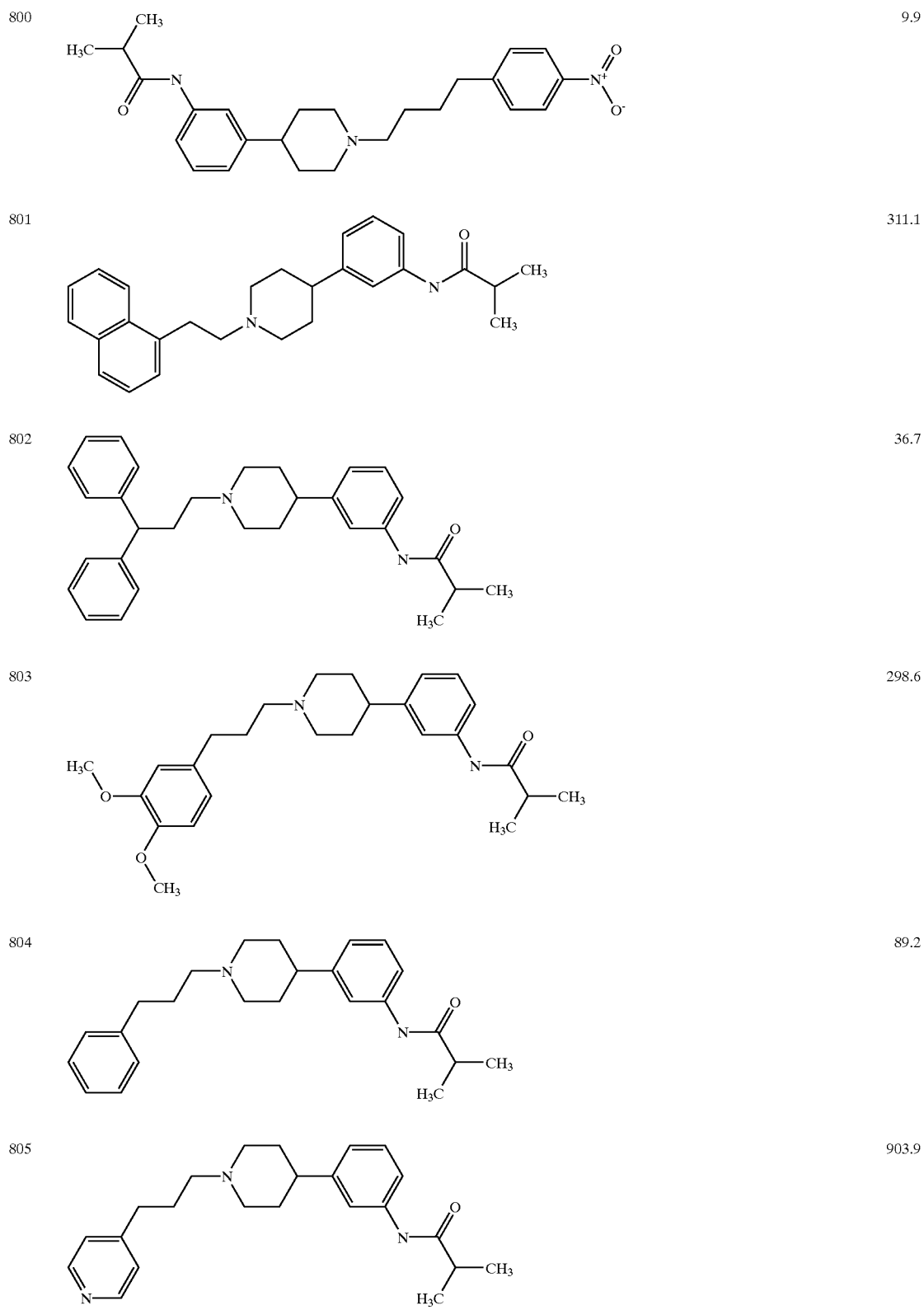 | 9.9 |
| 801 | | 311.1 |
| 802 | | 36.7 |
| 803 | | 298.6 |
| 804 | | 89.2 |
| 805 | | 903.9 |

-continued

| | | |
|---|---|---|
| 806 | [structure] | 14.1 |
| 807 | [structure] | 2.7 |
| 808 | [structure] Chiral | 10.8 |
| 809 | [structure] | 56.8 |
| 810 | [structure] | 191.2 |
| 811 | [structure] | 190.8 |

-continued
| | | |
|---|---|---|
| 812 | 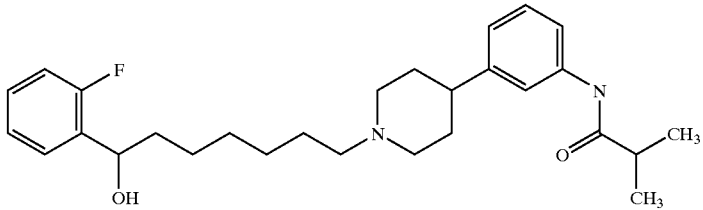 | 244.8 |
| 813 | 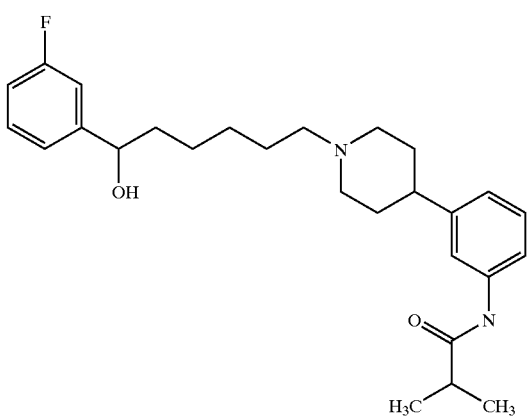 | 57.3 |
| 814 | 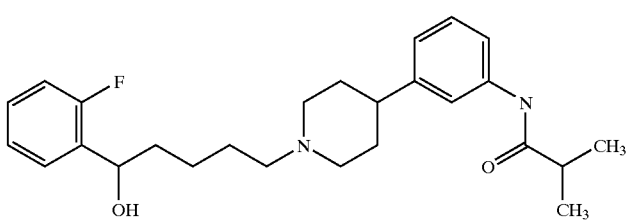 | 159.5 |
| 815 | 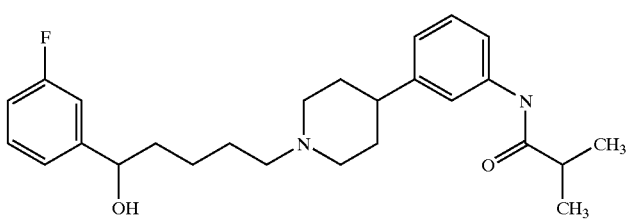 | 126.9 |
| 816 | 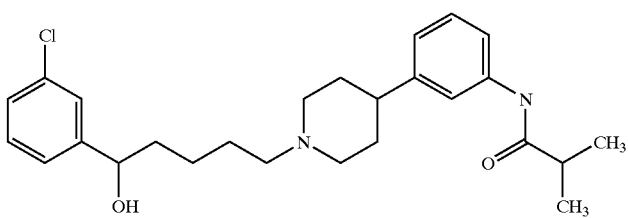 | 89.6 |
| 817 | 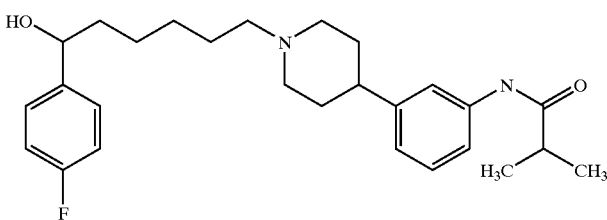 | 34.9 |

-continued
| | | |
|---|---|---|
| 818 | 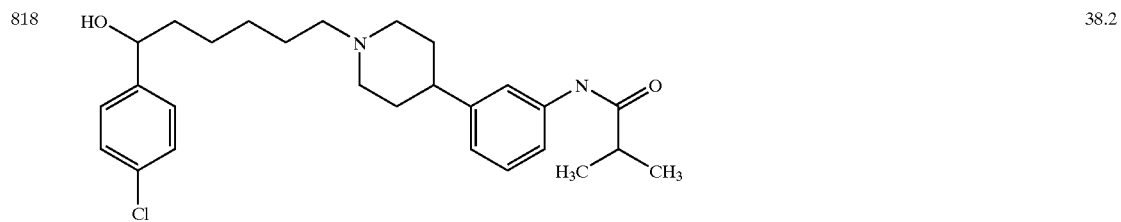 | 38.2 |
| 819 | 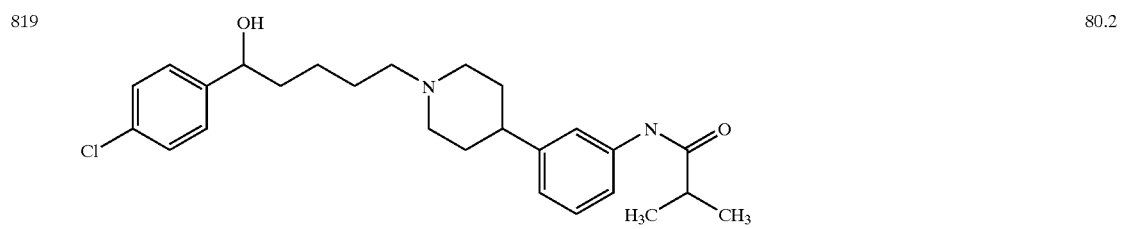 | 80.2 |
| 820 | 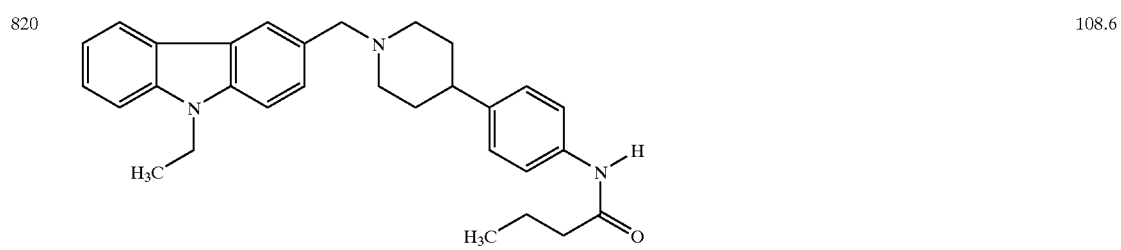 | 108.6 |
| 821 | 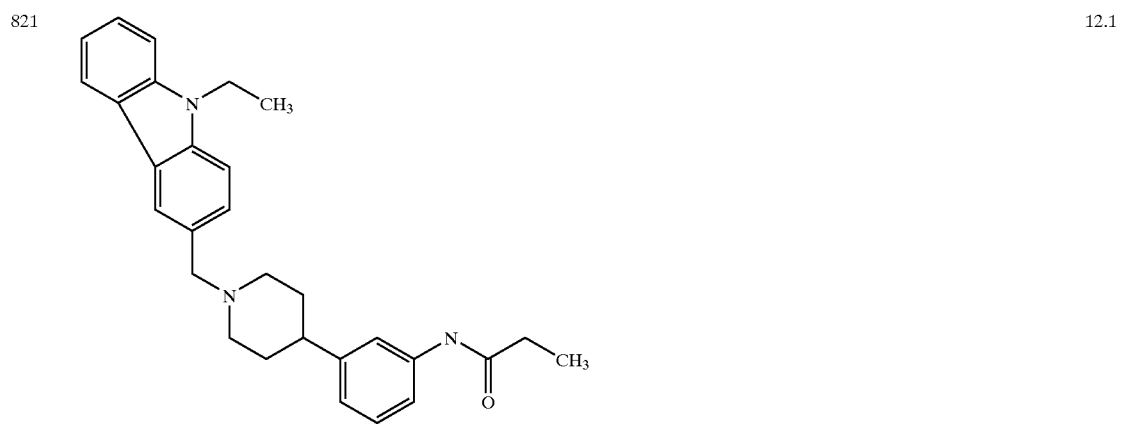 | 12.1 |
| 822 | 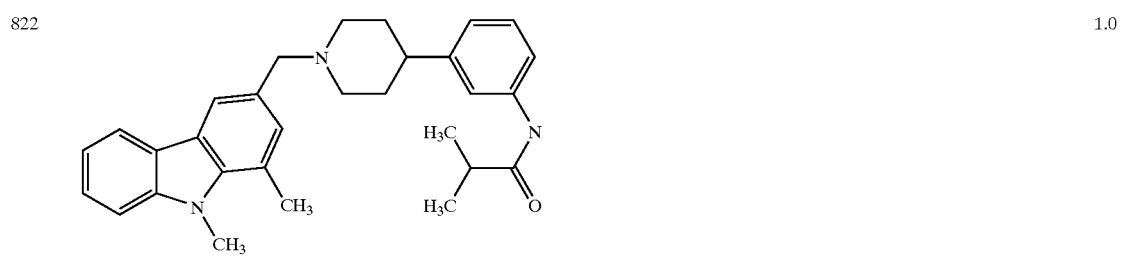 | 1.0 |

-continued
| | | |
|---|---|---|
| 823 | 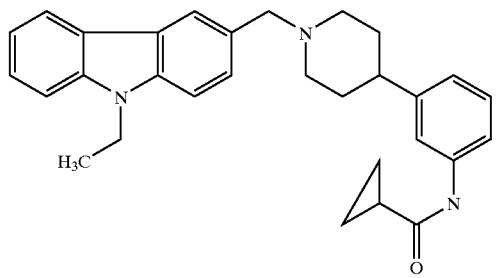 | 2.7 |
| 824 | 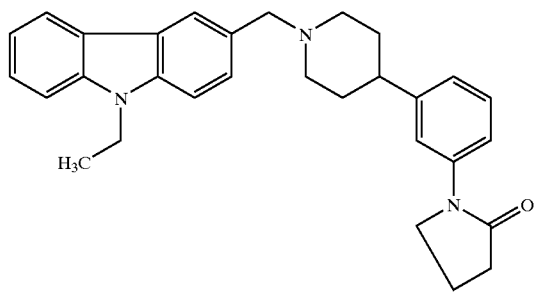 | 36.5 |
| 825 | 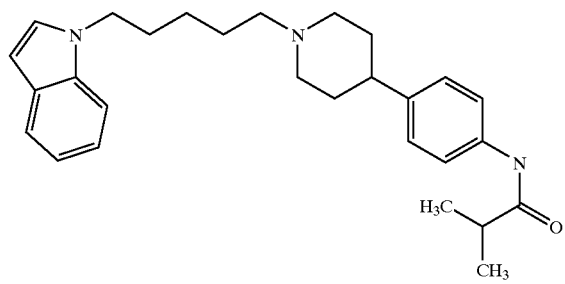 | 600.7 |
| 826 | 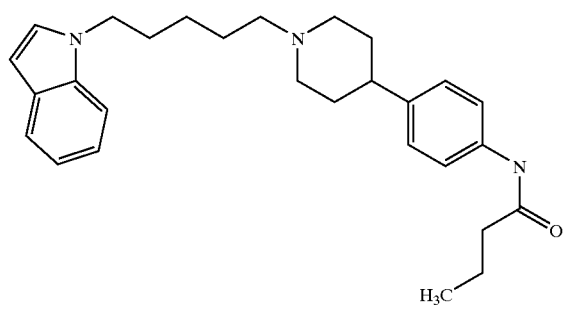 | 785.6 |
| 827 | 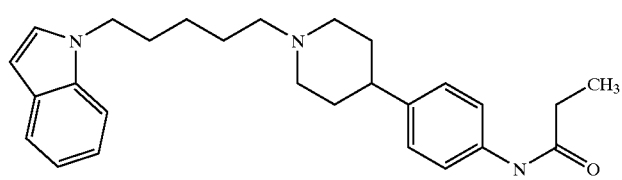 | 215.4 |
| 828 | 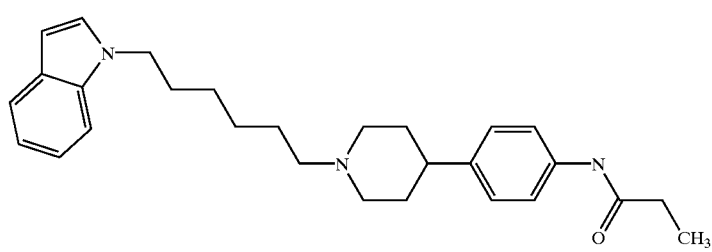 | 515.9 |

-continued
| 829 | 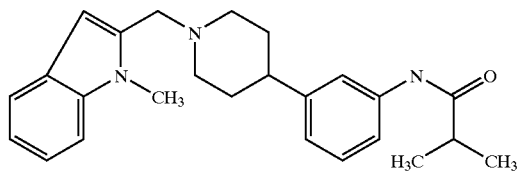 | 228.0 |
| 830 | 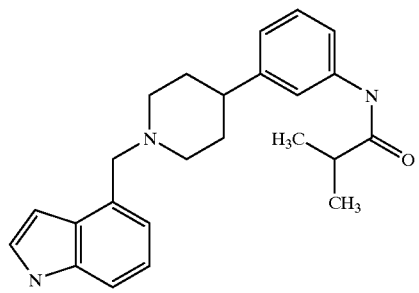 | 468.6 |
| 831 | 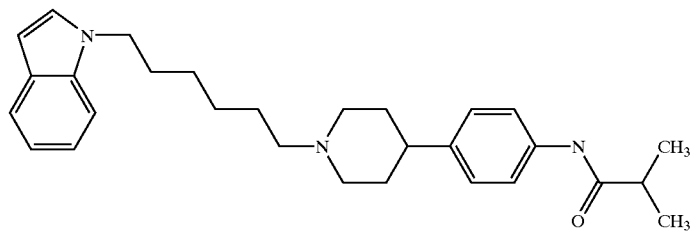 | 569.8 |
| 832 | 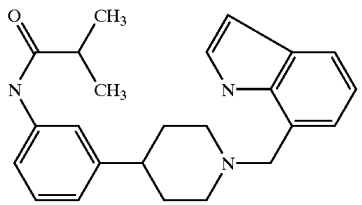 | 614.3 |
| 833 | 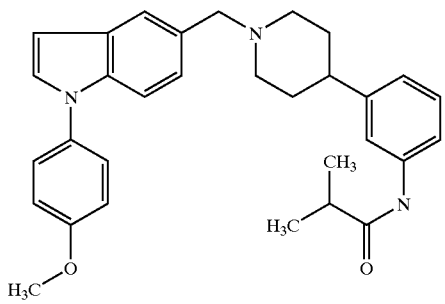 | 27.5 |
| 834 | 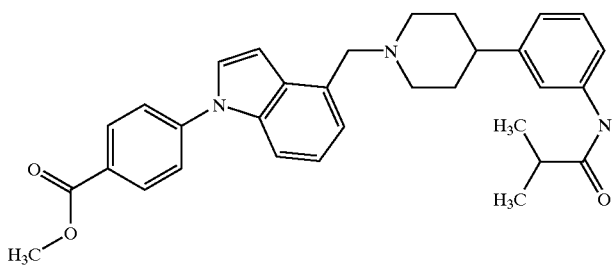 | 38.3 |

-continued
| | | |
|---|---|---|
| 835 | 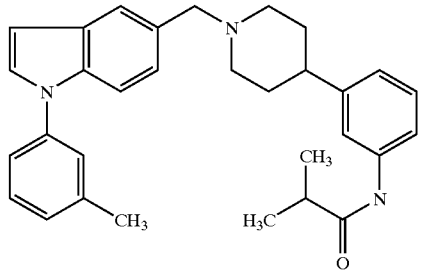 | 21.3 |
| 836 | 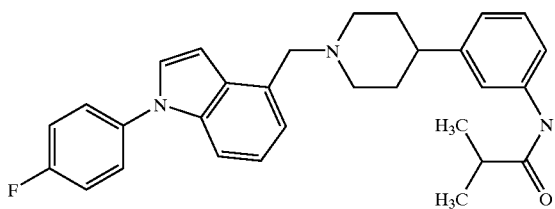 | 7.8 |
| 837 | 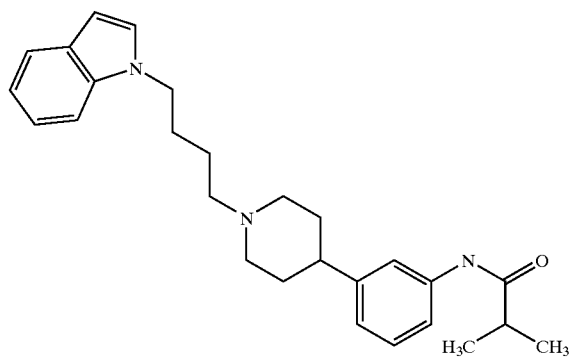 | 35.9 |
| 838 | 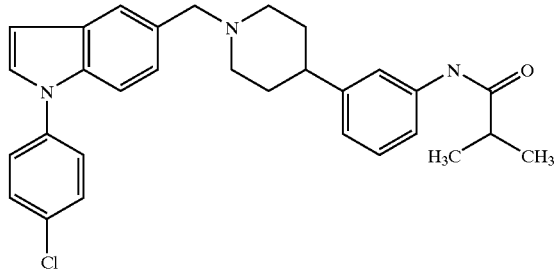 | 11.2 |
| 839 | 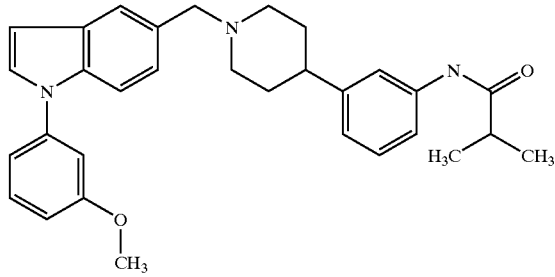 | 62.2 |

-continued
| | | |
|---|---|---|
| 840 | 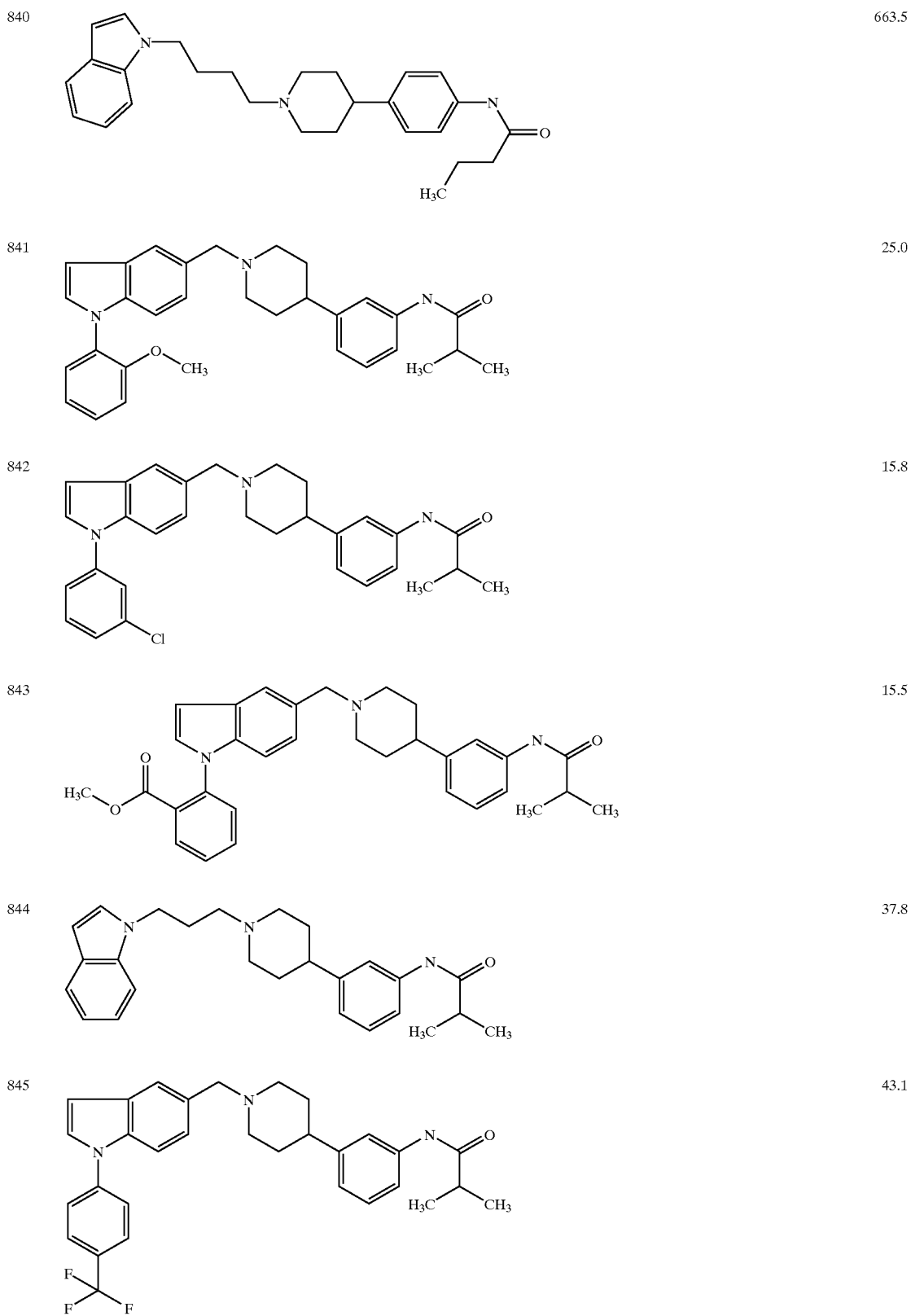 | 663.5 |
| 841 | | 25.0 |
| 842 | | 15.8 |
| 843 | | 15.5 |
| 844 | | 37.8 |
| 845 | | 43.1 |

-continued
| | | |
|---|---|---|
| 846 | 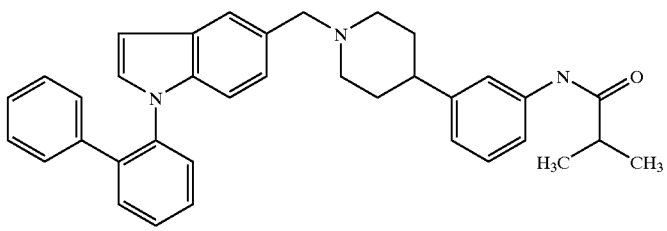 | 18.4 |
| 847 | 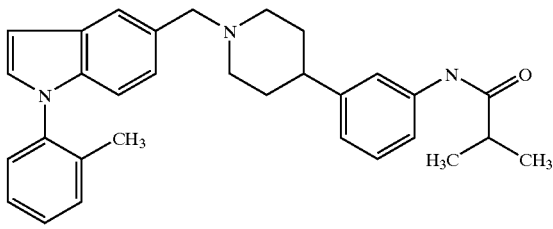 | 10.2 |
| 848 | 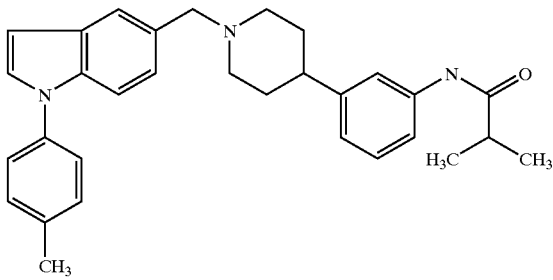 | 19.1 |
| 849 | 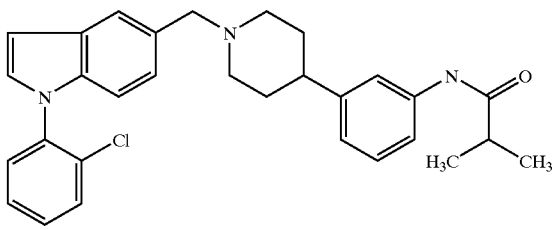 | 9.4 |
| 850 | 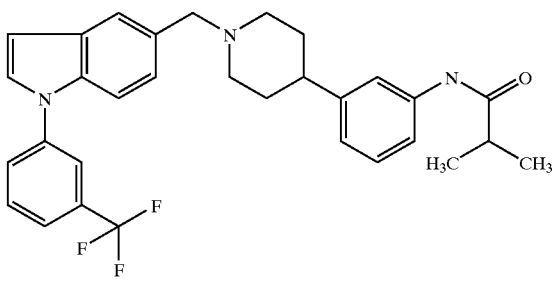 | 9.5 |
| 851 | 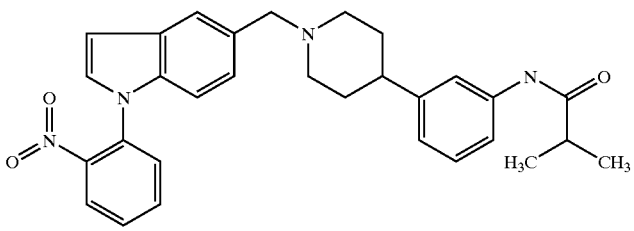 | 27.4 |

-continued
| | | |
|---|---|---|
| 852 | 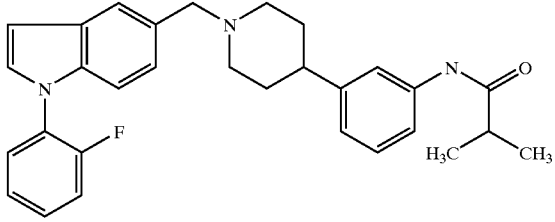 | 14.5 |
| 853 | 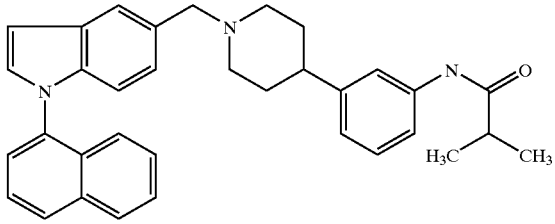 | 48.0 |
| 854 | 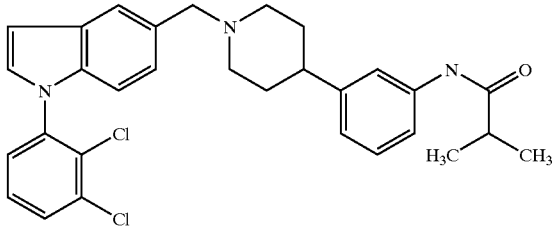 | 13.8 |
| 855 | 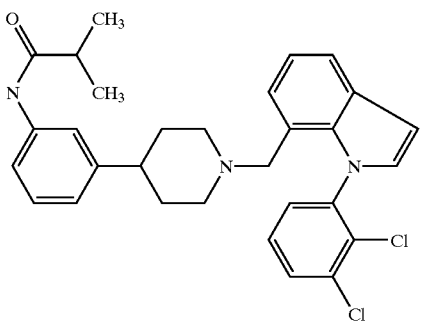 | 256.0 |
| 856 | 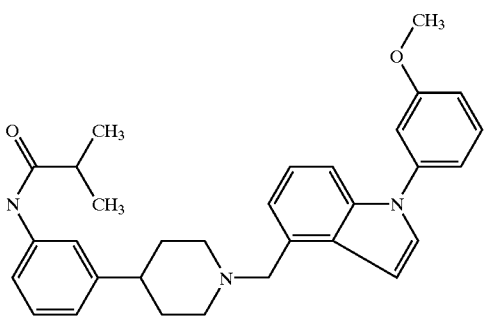 | 122.6 |
| 857 | 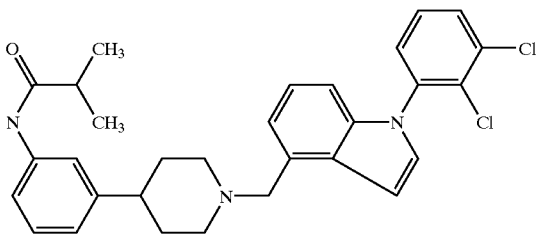 | 89.8 |

-continued
| | | |
|---|---|---|
| 858 | 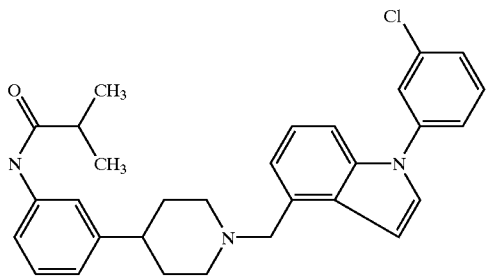 | 44.9 |
| 859 | 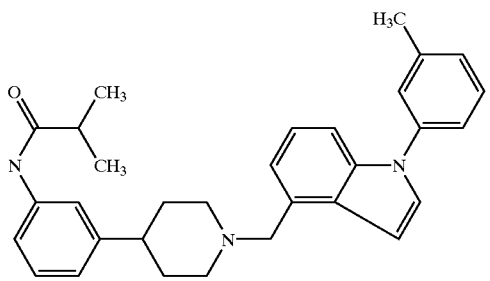 | 320.7 |
| 860 | 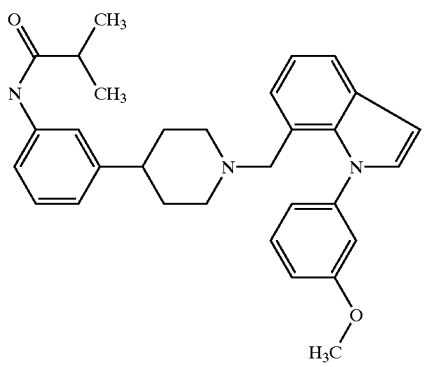 | 40.5 |
| 861 | 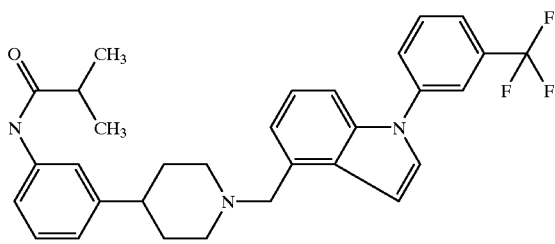 | 94.1 |
| 862 | 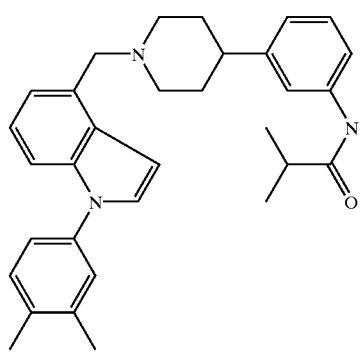 | 437.6 |

| | | |
|---|---|---|
| 863 | 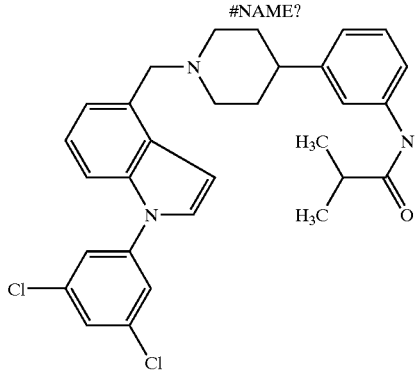 #NAME? | 269.0 |
| 864 | 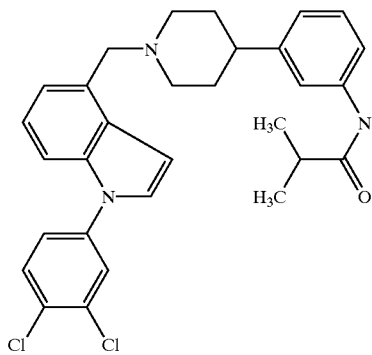 | 292.0 |
| 865 | 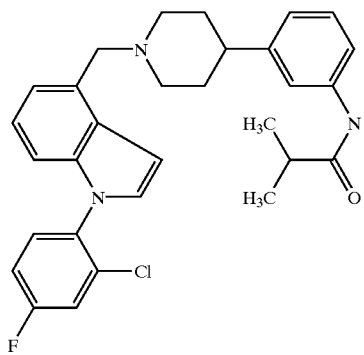 | 94.6 |
| 866 | 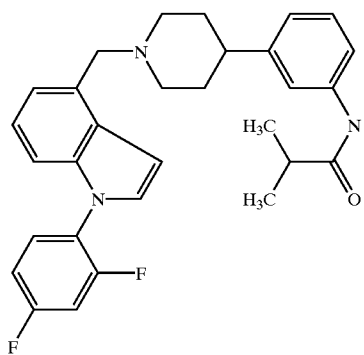 | 169.2 |

-continued
| | | |
|---|---|---|
| 867 | 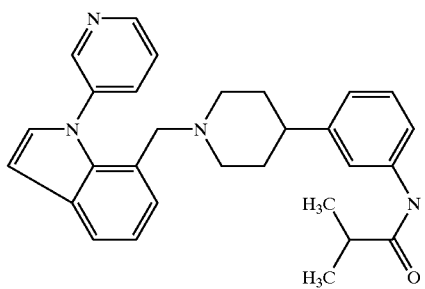 | 891.9 |
| 868 | 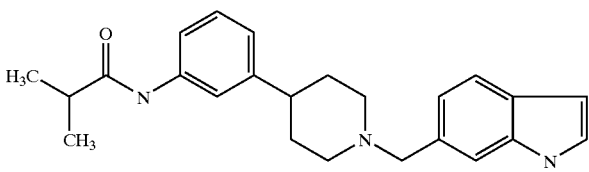 | 403.4 |
| 869 | 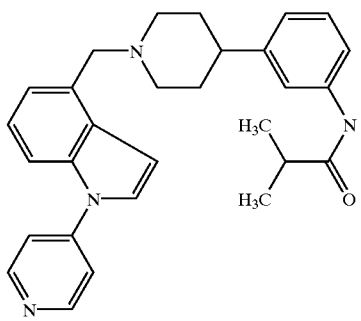 | 430.9 |
| 870 | 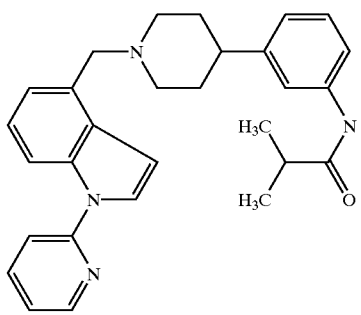 | 166.7 |
| 871 | 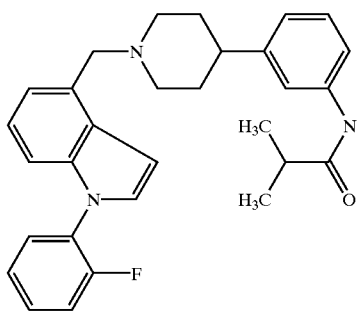 | 251.7 |

-continued
| | | |
|---|---|---|
| 872 | 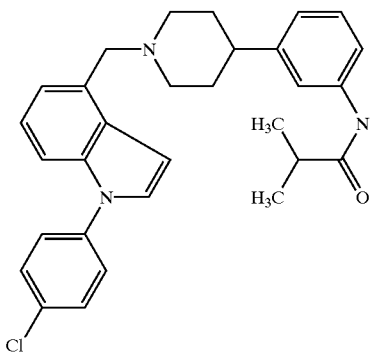 | 306.3 |
| 873 | 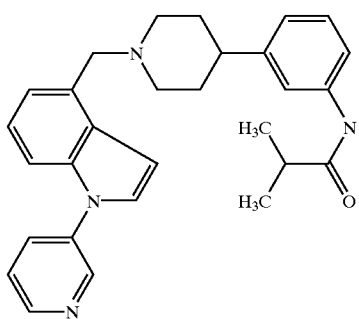 | 345.0 |
| 874 | 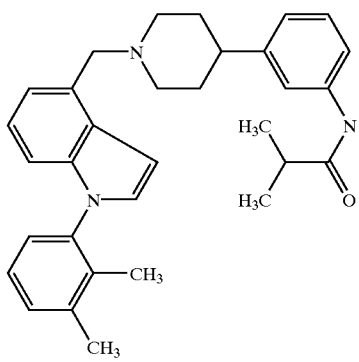 | 247.1 |
| 875 | 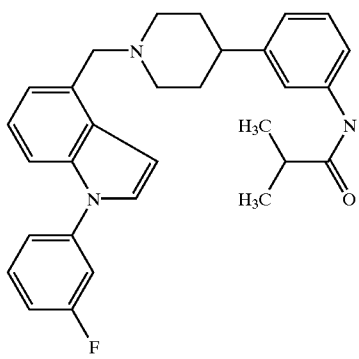 | 130.1 |

-continued
| | | |
|---|---|---|
| 876 | 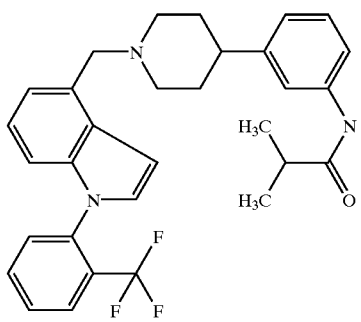 | 758.2 |
| 877 | 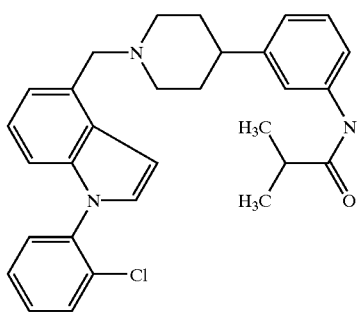 | 245.1 |
| 878 | 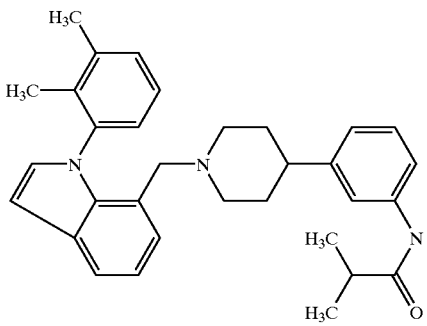 | 168.8 |
| 888 | 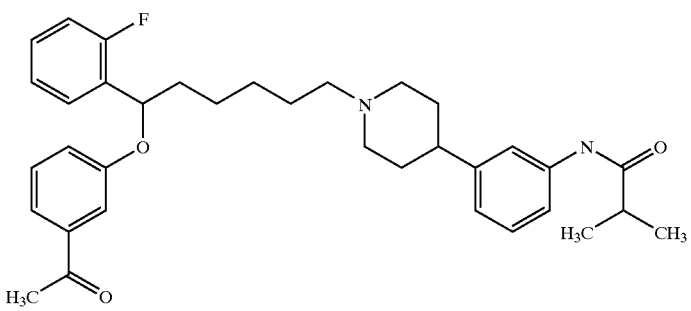 | 19.8 |
| 889 | 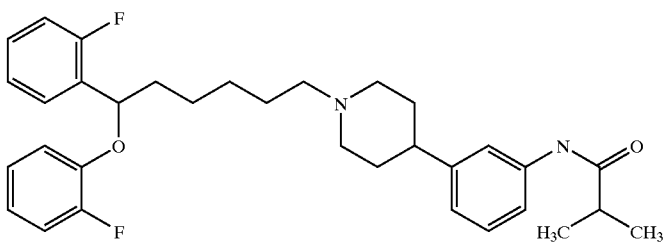 | 8.6 |

-continued
| | | |
|---|---|---|
| 890 | 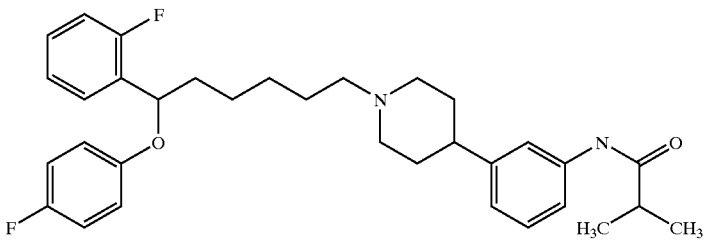 | 11.1 |
| 891 | 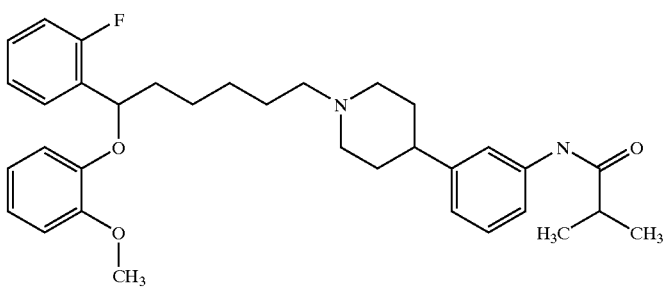 | 6.5 |
| 892 | 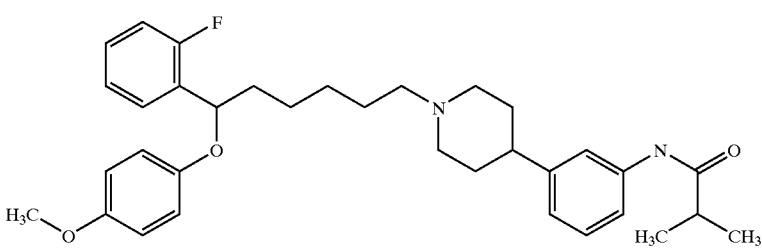 | 17.3 |
| 893 | 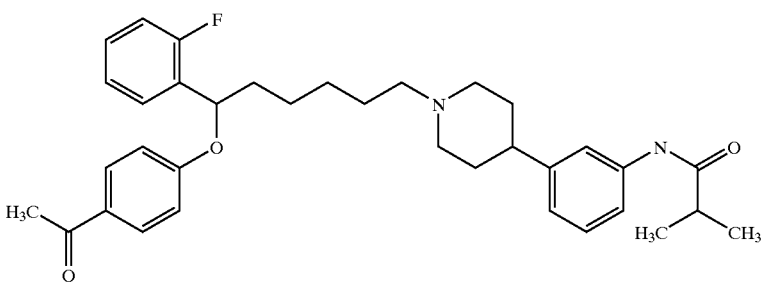 | 23.0 |
| 894 | 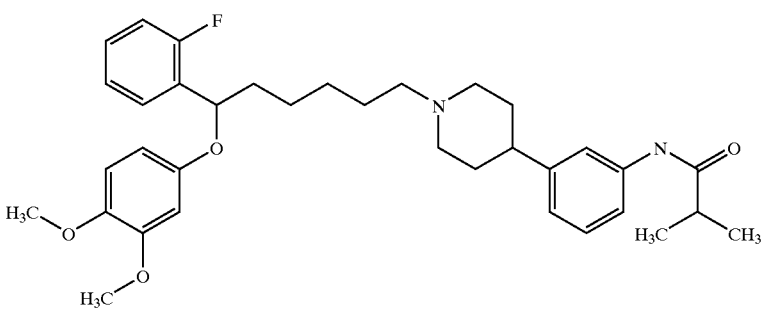 | 41.7 |

-continued
| | | |
|---|---|---|
| 895 | 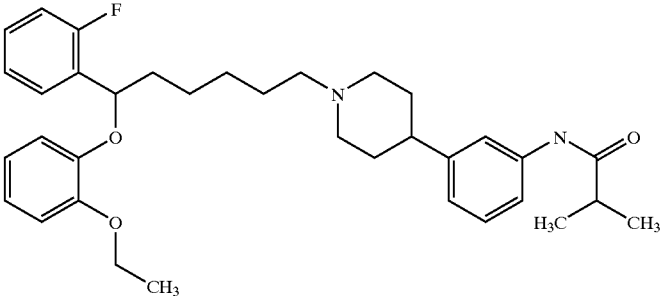 | 6.4 |
| 896 | 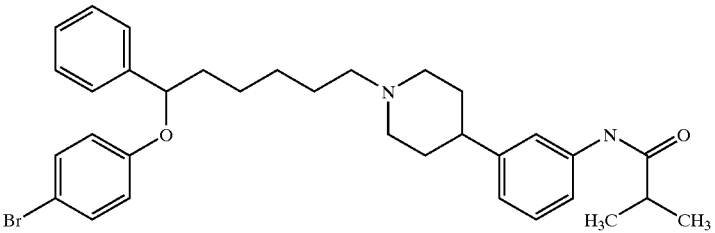 | 30.3 |
| 897 | 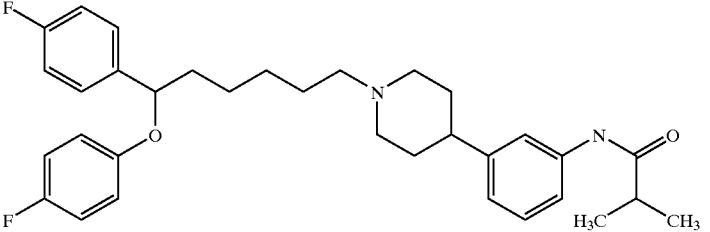 | 6.4 |
| 898 | 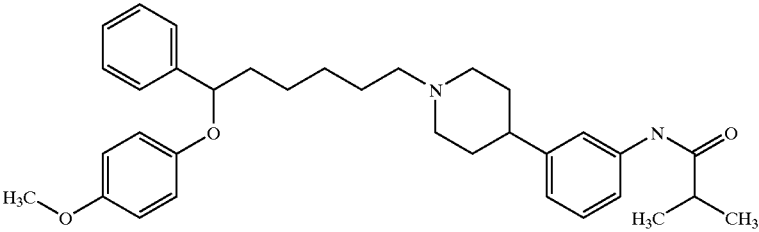 | 33.7 |
| 899 | 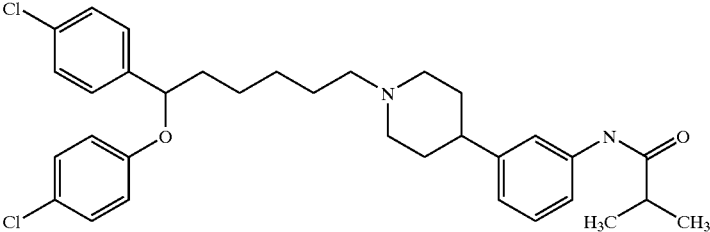 | 18.0 |
| 900 | 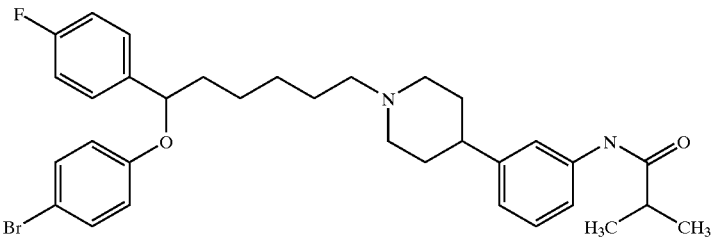 | 11.2 |

-continued
| | | |
|---|---|---|
| 901 | 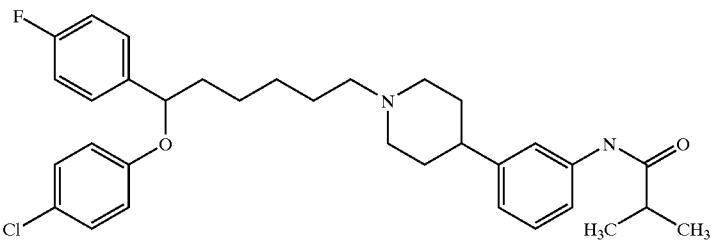 | 8.2 |
| 902 | 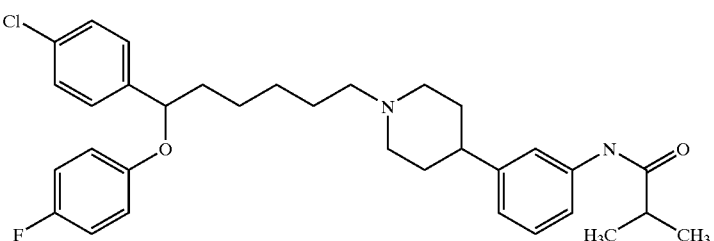 | 11.0 |
| 903 | 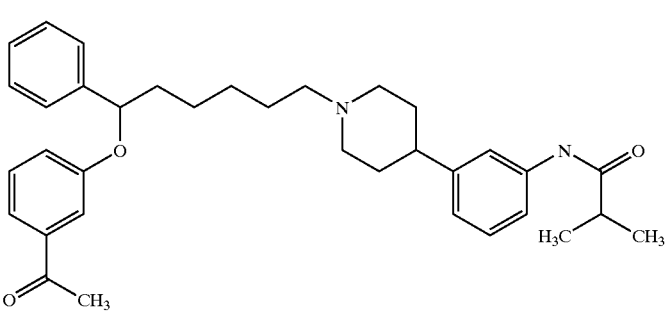 | 12.2 |
| 904 | 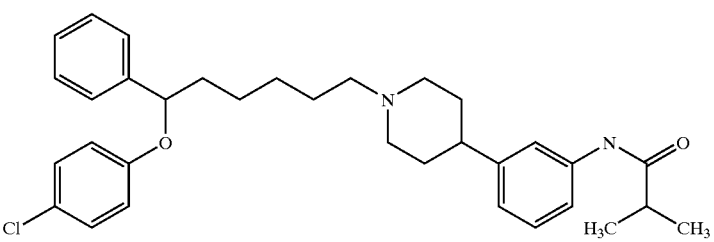 | 14.2 |
| 905 | 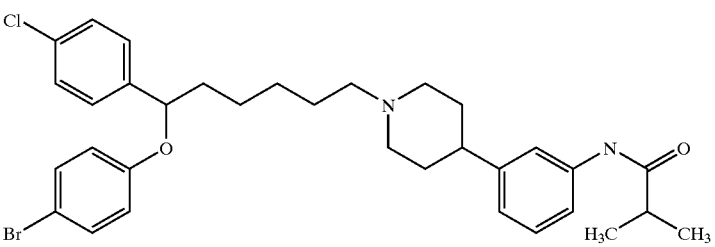 | 5.9 |
| 906 | 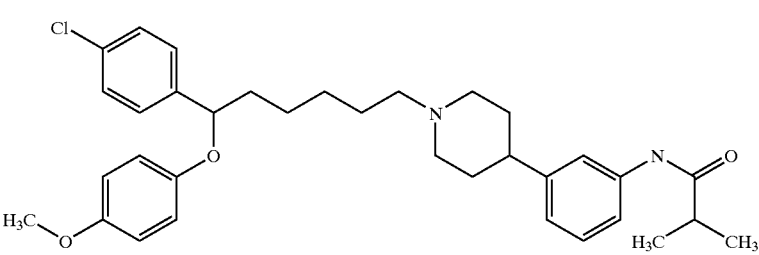 | 5.7 |

| | | |
|---|---|---|
| 907 | 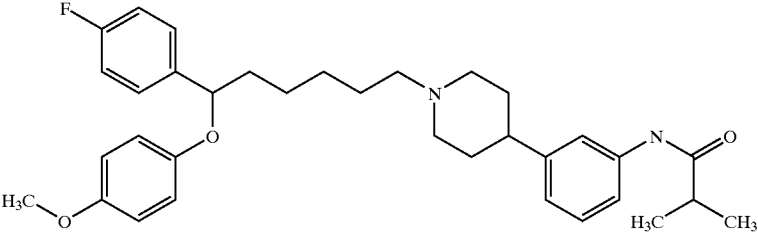 | 3.1 |
| 908 | 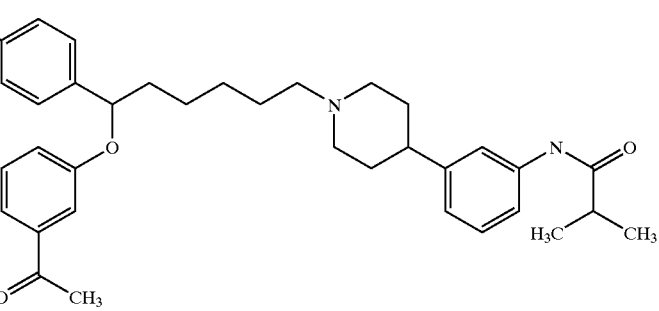 | 3.7 |
| 909 | 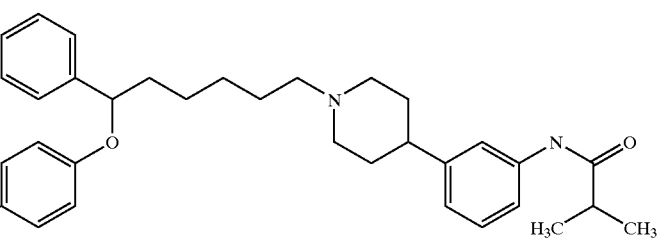 | 10.0 |
| 910 | 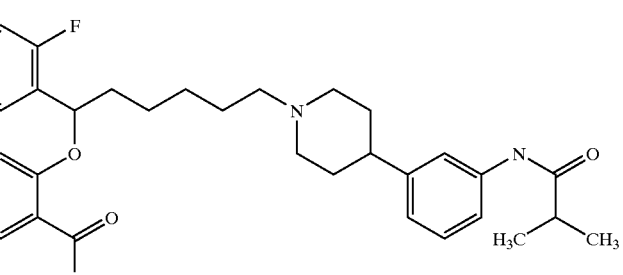 | 10.1 |
| 911 | 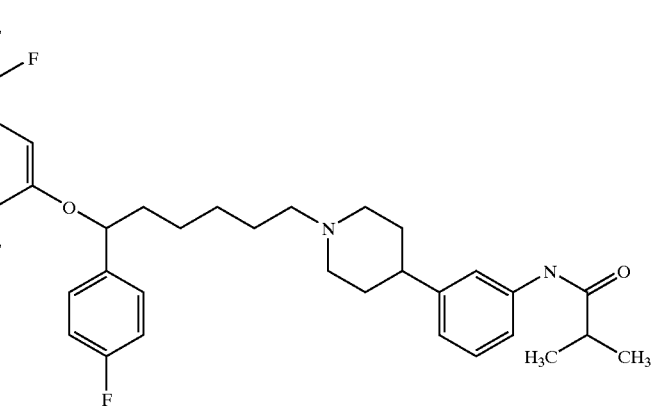 | 7.6 |

-continued
| 912 | 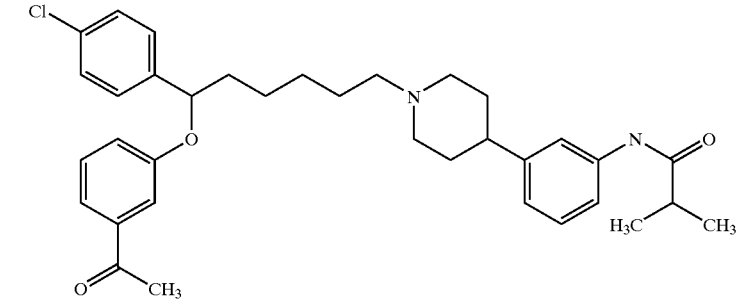 | 5.7 |
| 913 | 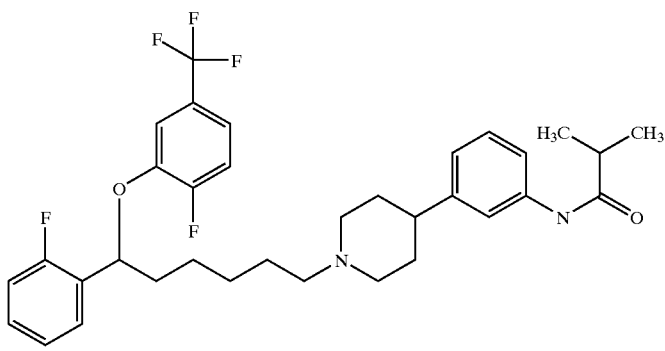 | 12.9 |
| 914 | 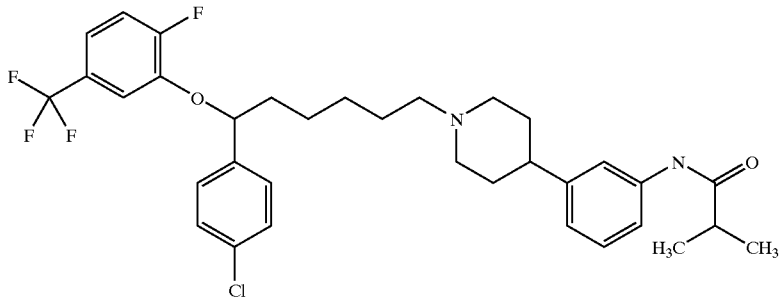 | 17.3 |
| 915 | 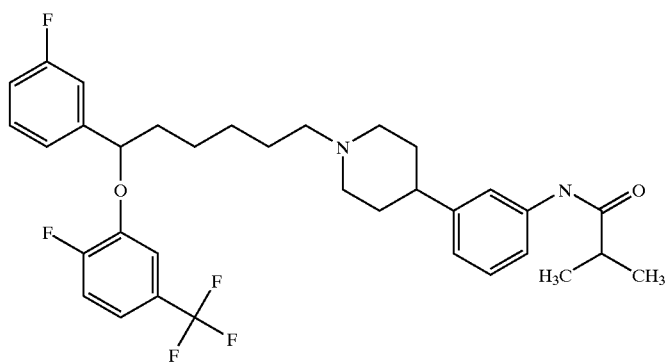 | 22.6 |

-continued
| | | |
|---|---|---|
| 916 | 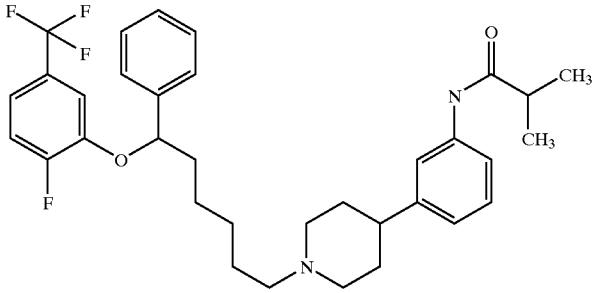 | 20.2 |
| 917 | 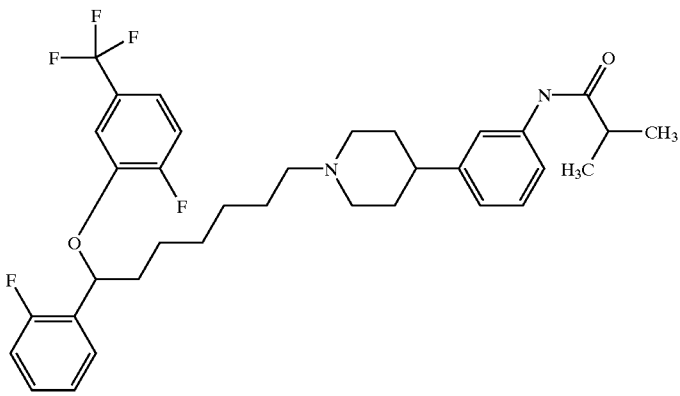 | 78.0 |
| 918 | 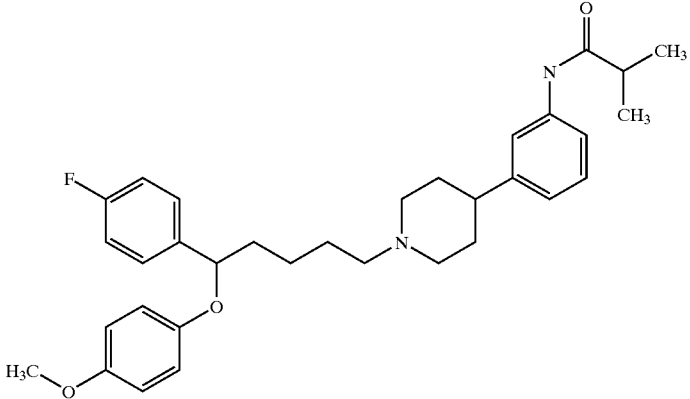 | 29.3 |
| 919 | 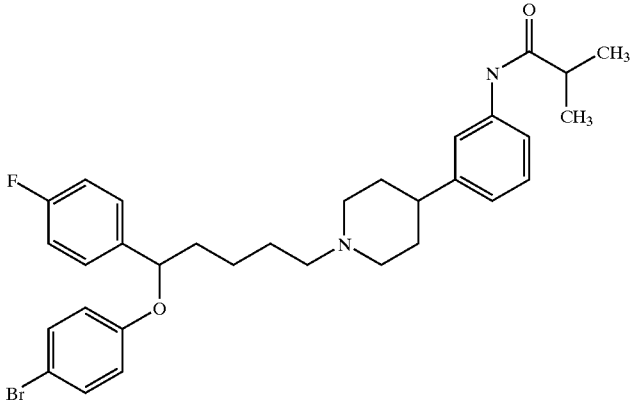 | 14.0 |

-continued
| 920 | 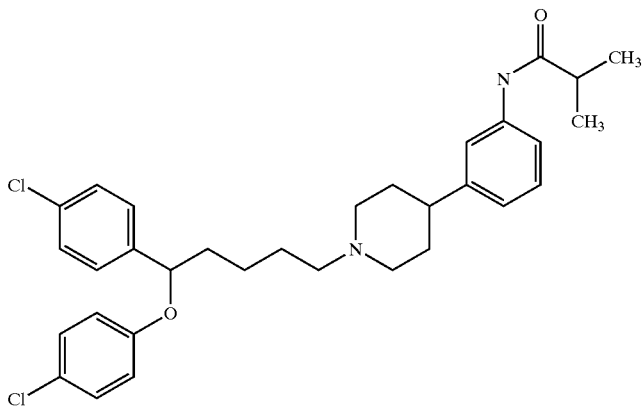 | 6.9 |
| 921 | 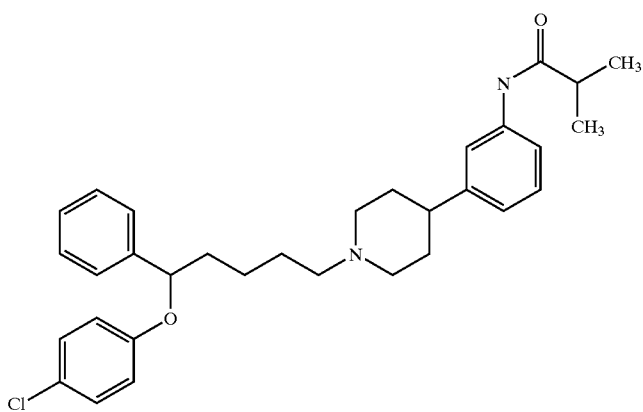 | 6.8 |
| 922 | 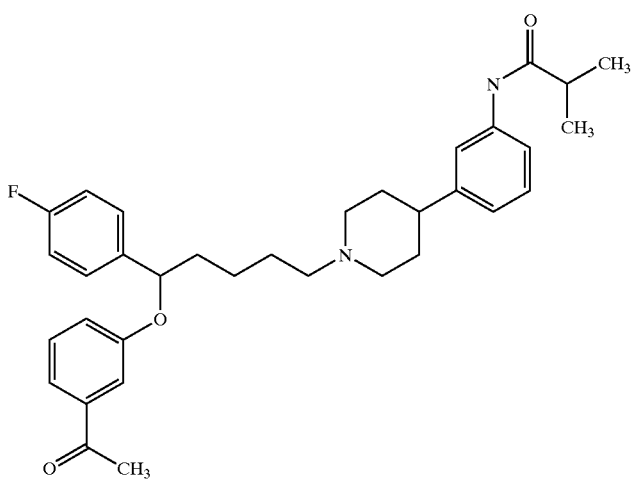 | 25.0 |

| 923 | 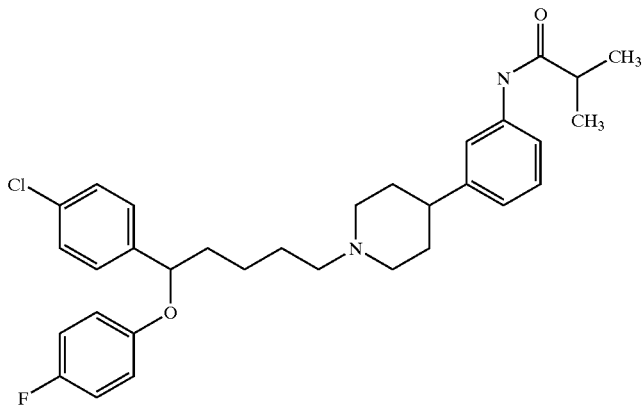 | 1.3 |
| 924 | 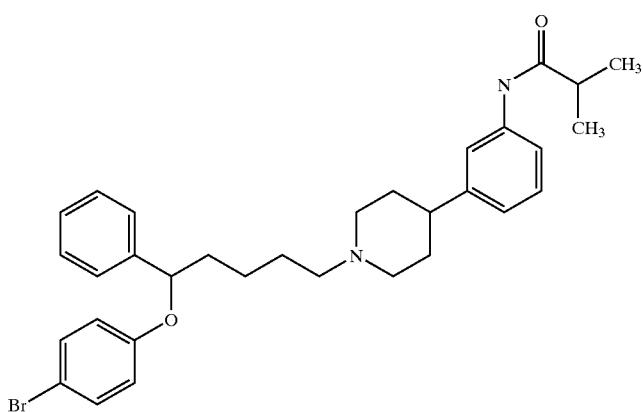 | 13.1 |
| 925 | 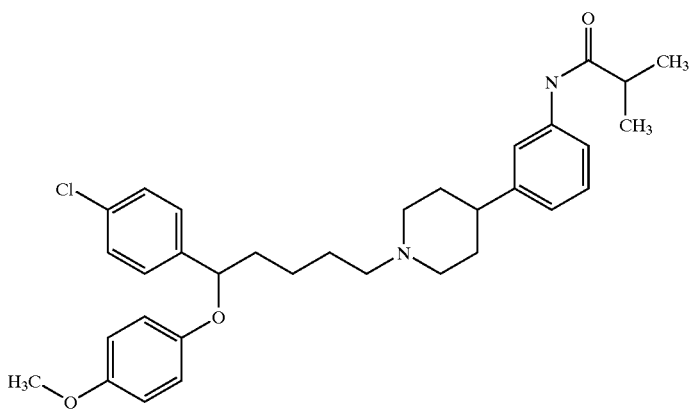 | 13.4 |

| | | |
|---|---|---|
| 926 | 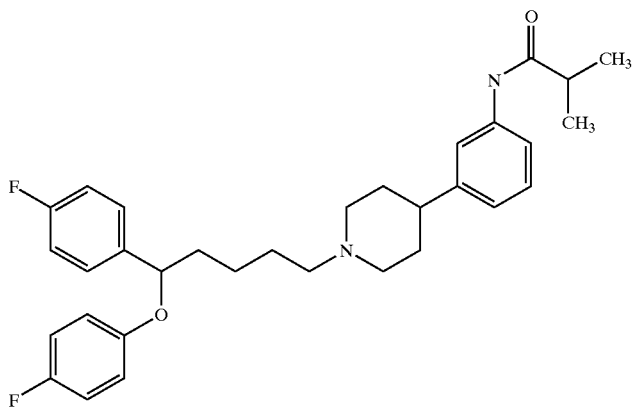 | 1.4 |
| 927 | 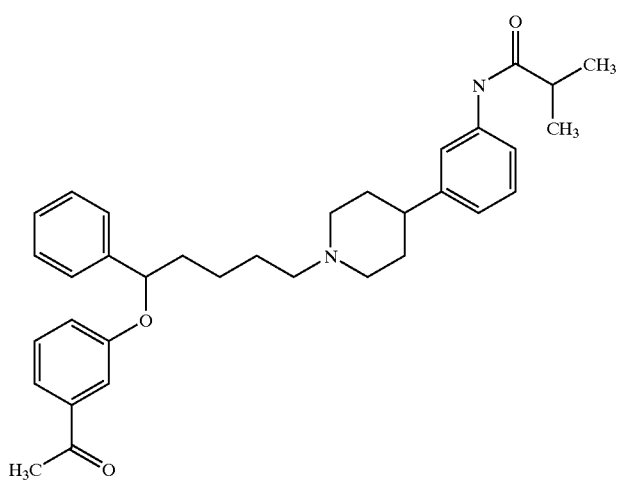 | 60.7 |
| 928 | 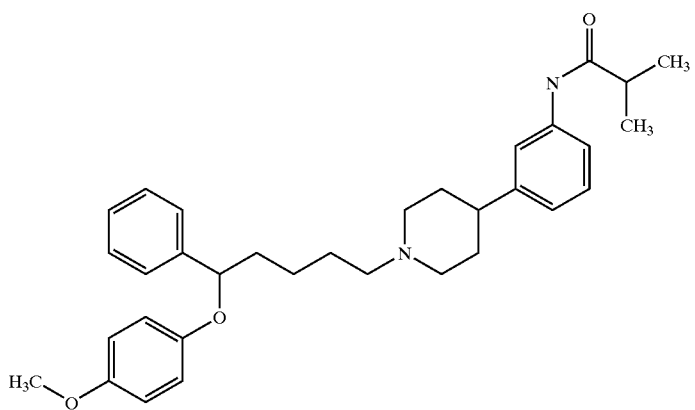 | 14.9 |

| | | |
|---|---|---|
| 929 | 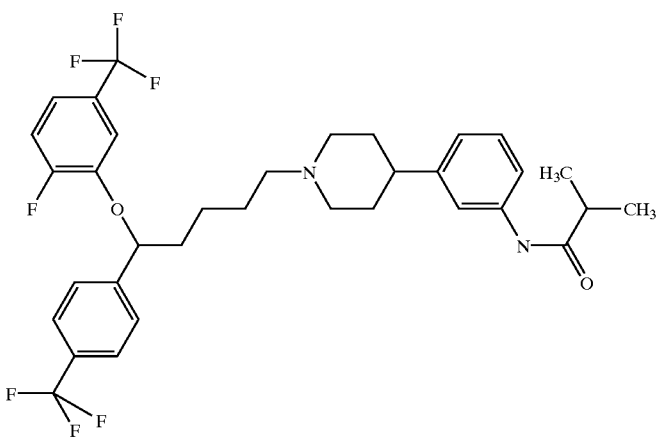 | 29.9 |
| 930 | 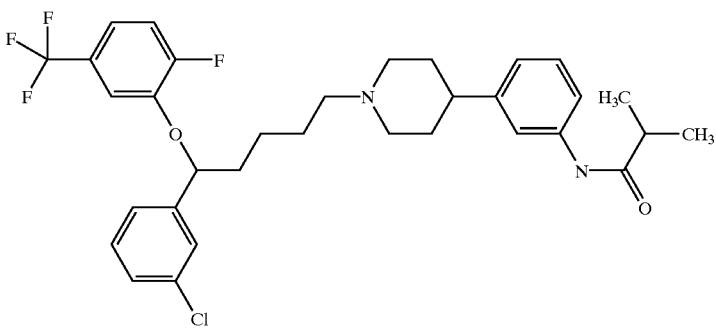 | 14.6 |
| 931 | 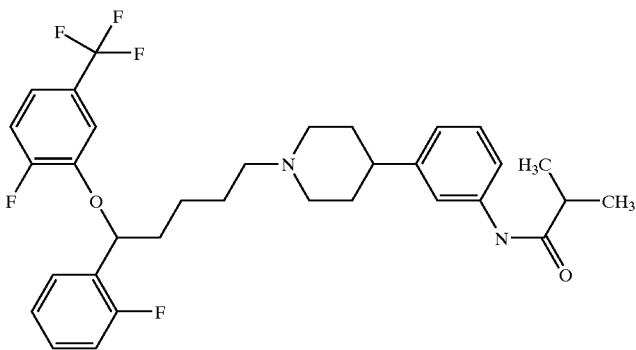 | 9.6 |
| 932 | 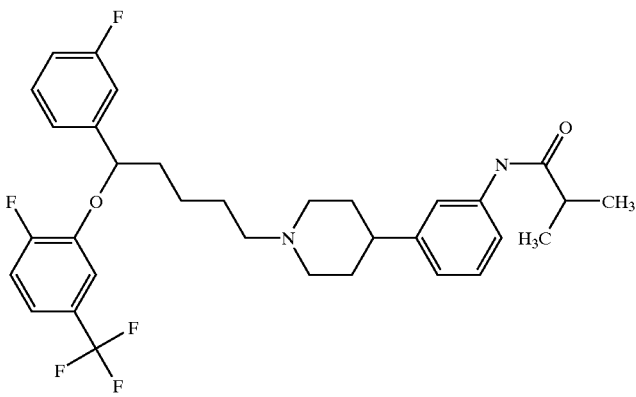 | 9.4 |

| 933 | 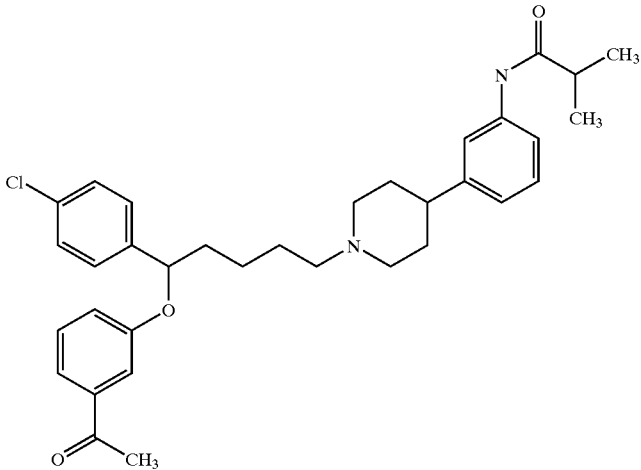 | 10.9 |
| 934 | 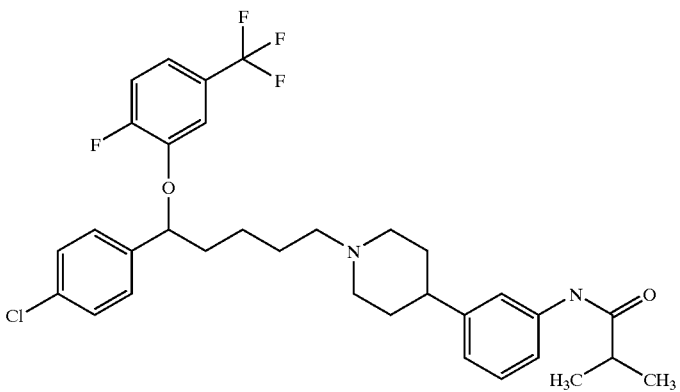 | 12.3 |
| 935 | 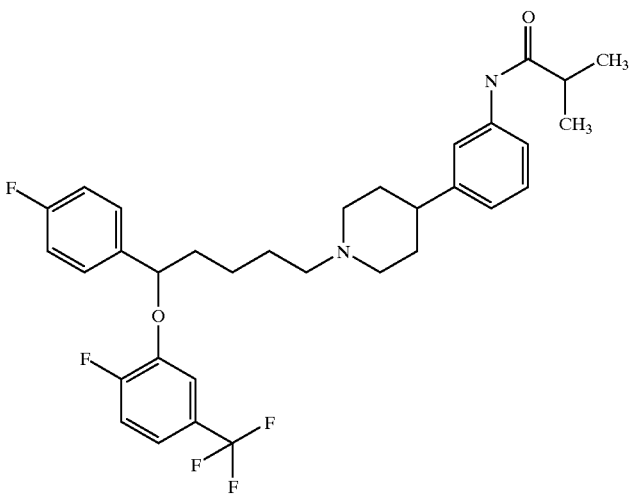 | 19.7 |

| | |
|---|---|
| 936 | 11.6 |
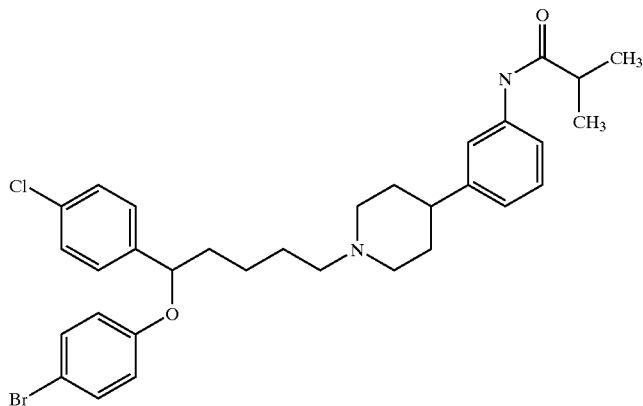
| | |
|---|---|
| 937 | 28.4 |
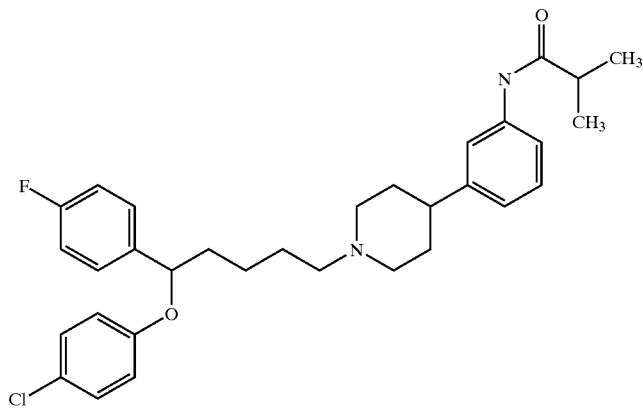
| | |
|---|---|
| 938 | 608.6 |
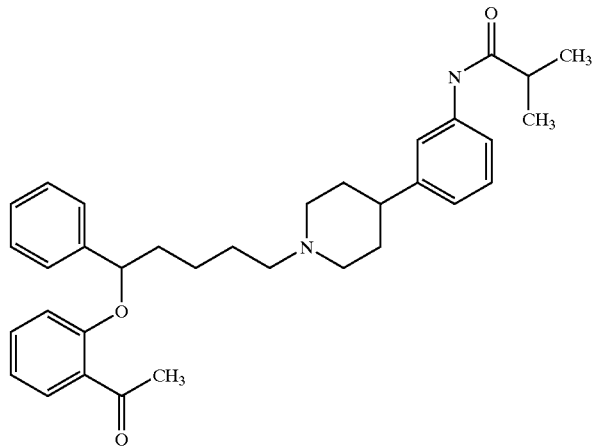

-continued
| | | |
|---|---|---|
| 939 | 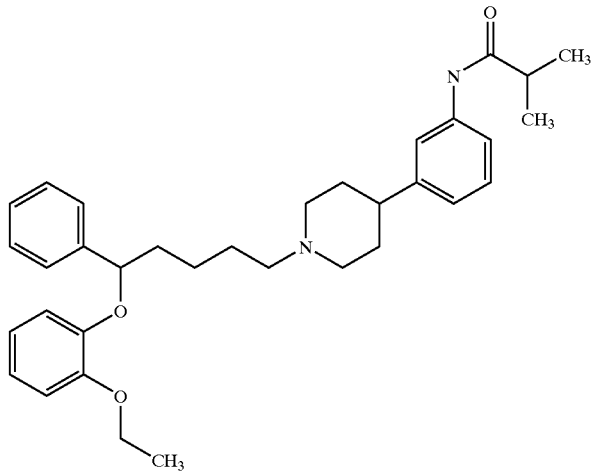 | 62.0 |
| 940 | 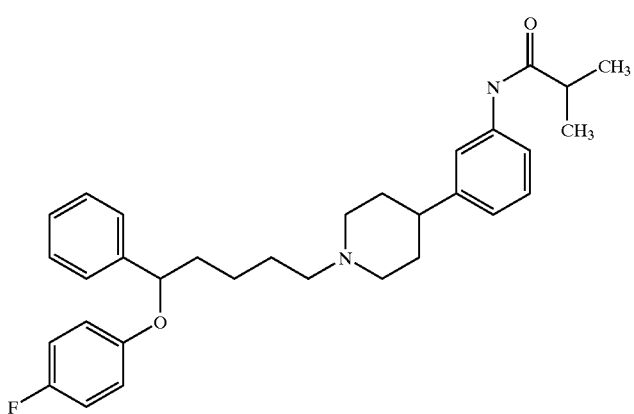 | 1.8 |
| 941 | 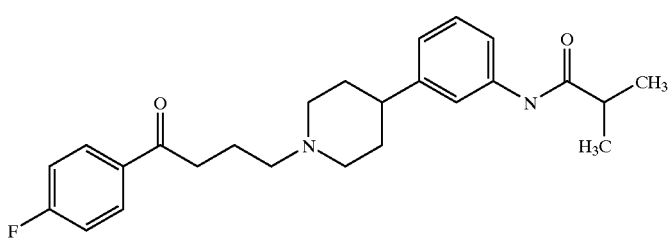 | 15.2 |
| 942 | 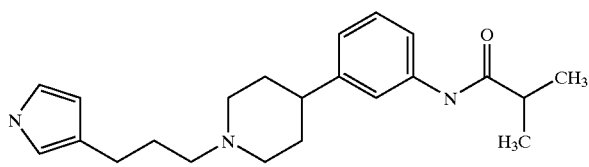 | 187.9 |
| 943 | 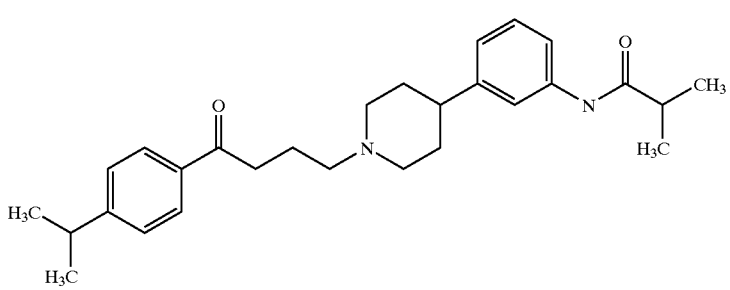 | 101.7 |

-continued
944 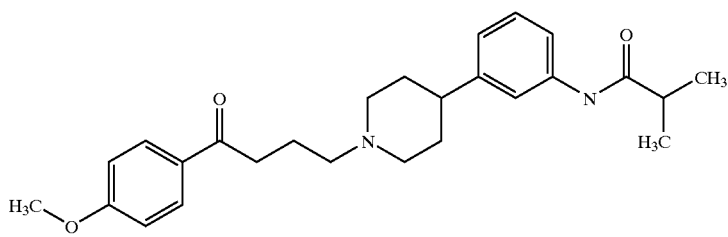 38.8
945 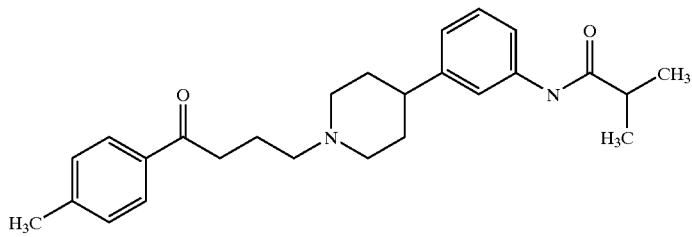 31.2
946 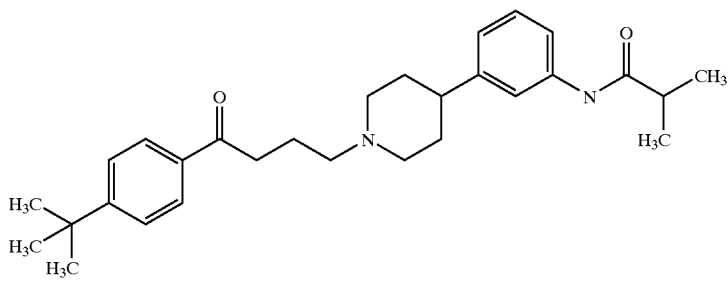 336.6
947 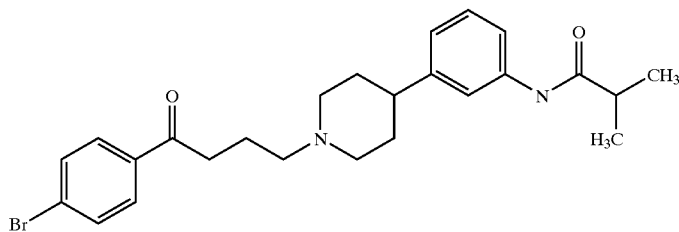 4.3
948 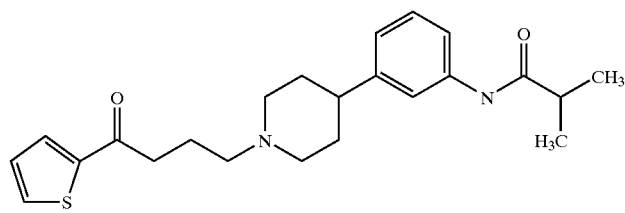 21.2
TABLE 2
Binding affinities (Ki) at the rat MCH1, human Dopamine D2, human Histamine H1 and human Alpha-1a Adrenergic receptors.
| Compound | rMCH1 Ki (nM) | hD2 Ki (nM) | hH1 Ki (nM) | hALPHA-1a Ki (nM) |
|---|---|---|---|---|
| 1 | 90 | 6092 | 823 | 49 |
| 2 | 3.9 | 2839 | 700 | 32.1 |
| 3 | 768 | ND | ND | ND |
| 4 | 357 | ND | ND | ND |
| 5 | 14.2 | 1139 | 1618 | 9.1 |
| 6 | 274 | ND | ND | ND |
| 7 | 1000 | ND | ND | ND |
| 8 | 627 | ND | ND | ND |
| 9 | 69 | 1430 | 1733 | 26.4 |
| 10 | 2.8 | 862 | 461 | 19.4 |
| 11 | 197 | ND | ND | ND |
| 12 | 84 | 771 | 571 | 57 |
| 13 | 11.9 | 551 | ND | 61 |
| 14 | 167 | ND | ND | ND |

TABLE 2-continued

Binding affinities (Ki) at the rat MCH1, human Dopamine D2, human Histamine H1 and human Alpha-1a Adrenergic receptors.

| Compound | rMCH1 Ki (nM) | hD2 Ki (nM) | hH1 Ki (nM) | hALPHA-1a Ki (nM) |
|---|---|---|---|---|
| 15 | 720 | ND | ND | ND |
| 16 | 272 | ND | ND | ND |
| 17 | 342 | ND | ND | ND |
| 18 | 29.5 | 782 | ND | 115 |
| 19 | 506 | ND | ND | ND |
| 20 | 21 | 470 | ND | 41.3 |
| 21 | 630 | ND | ND | ND |
| 22 | 52 | 5181 | 2277 | 284 |
| 23 | 1036 | ND | ND | ND |
| 24 | 67 | 1252 | ND | 127 |
| 25 | 463 | ND | ND | ND |
| 26 | 192 | 1977 | ND | 516 |
| 27 | 91 | 503 | ND | 130 |
| 28 | 511 | ND | ND | ND |
| 29 | 654 | ND | ND | ND |
| 30 | 382 | ND | ND | ND |
| 31 | 362 | ND | ND | ND |
| 32 | 160 | ND | ND | ND |
| 33 | 615 | ND | ND | ND |
| 34 | 651 | ND | ND | ND |
| 35 | 11.5 | 9654 | 2000 | 533 |
| 36 | 62 | 12,026 | 2454 | 1489 |
| 37 | 29.1 | 34,933 | 16,734 | 1087 |
| 38 | 18.2 | >50000 | 6595 | 1592 |
| 39 | 11.8 | >50000 | 6401 | 2937 |
| 40 | 50 | 7451 | 273 | 12.3 |
| 41 | 946 | ND | ND | ND |
| 42 | 118 | ND | ND | ND |
| 43 | 12 | 10,428 | 2560 | 434 |
| 44 | 11.5 | 8673 | 11,092 | 704 |
| 45 | 1.6 | 42.2 | 3.4 | 18 |
| 46 | 187 | ND | ND | ND |
| 47 | 52 | >50000 | 36,907 | >50000 |
| 48 | 6.7 | 735 | 6390 | 452 |
| 49 | 7.1 | 471 | 39.1 | 140 |
| 50 | 3.9 | 1077 | 304 | 161 |
| 51 | 3.1 | 152 | 130 | 33.5 |
| 52 | 3.8 | 244 | 264 | 13.2 |
| 53 | 7.1 | 191 | 1320 | 221 |
| 54 | 4.9 | 83 | 283 | 187 |
| 55 | 5 | 162 | 1100 | 125 |
| 56 | 22.3 | 435 | 32.5 | 55 |
| 57 | 16.6 | 41,994 | 48,658 | 3206 |
| 58 | 20.1 | 390 | 590 | 233 |
| 59 | 12.9 | 262 | 46.9 | 49.1 |
| 60 | 0.923 | 52 | 546 | 22.3 |
| 61 | 13.6 | 281 | 969 | 310 |
| 62 | 12.8 | 319 | 25,320 | 719 |
| 63 | 22.4 | 766 | 25,307 | 1058 |
| 64 | 14.8 | 313 | 6994 | 1142 |
| 65 | 17 | 331 | 9390 | 1720 |
| 66 | 3.3 | 132 | 3473 | 944 |
| 67 | 5.9 | 133 | 2146 | 511 |
| 68 | 9.3 | 66 | 329 | 204 |
| 69 | 32.5 | 46.6 | >50000 | 232 |
| 70 | 50 | 1050 | 7998 | 1521 |
| 71 | 6.6 | 119 | 1710 | 226 |
| 72 | 31.4 | 41,454 | 33,096 | 645 |
| 73 | 22.3 | 41,454 | 6522 | 381 |
| 74 | 48.6 | 39,511 | 1862 | 333 |
| 75 | 11.8 | 19,041 | 2844 | 2469 |
| 76 | 44.6 | 41,454 | 39,710 | 10,965 |
| 77 | 25.7 | 447 | 4178 | 167 |
| 78 | 22.2 | 37.6 | >50000 | 1313 |
| 79 | 19.4 | 244 | 507 | 722 |
| 80 | 14.3 | 833 | 9789 | 620 |
| 81 | 377 | ND | ND | ND |
| 82 | 11.2 | ND | ND | ND |
| 83 | 48.1 | ND | ND | ND |
| 84 | 121 | ND | ND | ND |
| 85 | 3.2 | 2449 | 3816 | 3021 |

V. Synthesis of Compound A

Described below is the synthesis of Compound A. Compound A is the radiolabeled compound that was used in the radioligand binding assays described above.

N-[3-(3,2,3,6-TETRAHYDRO-4-PYRIDINYL) PHENYL]ACETAMIDE: The reaction of saturated of aqueous $Na_2CO_3$ solution (25 mL), tert-butyl 4-{[(trifluoromethyl)sulfonyl]oxy}-1,2,3,6-tetrahydro-1-pyridine-carboxylate (20 mmol), 3-acetamidophenylporonic acid (30 mmol) and tetrakis-triphenylphosphine palladium (0). (1.15 g) in dimethoxyethane (40 mL) at reflux temperature overnight gave tert-butyl 4-[3-(acetylamino)phenyl]-3,6-dihydro-1(2H)-pyridinecarboxylate. Deprotection of the BOC group using HCl in dioxane followed by basification (pH 11–12) gave the desired product.

TERT-BUTYL N-(3-BROMOPROPYL)CARBAMATE: was prepared from 3-bromopropylamine hydrobromide and $BOC_2O$ in the presence of base in dichloromethane.

N-{3-[1-(3-AMINOPROPYL)-1,2,3,6-TETRAHYDRO-4-PYRIDINYL]PHENYL}ACETAMIDE: The reaction of tert-butyl N-(3-bromopropyl)carbamate and N-[3-(1,2,3,6-tetrahydro-4-pyridinyl)phenyl]acetamide in refluxing dioxane with catalytic $Bu_4NI$ and base as described in Scheme A gave tert-butyl 3-(4-[3-(acetylamino)phenyl]-3,6-dihydro-1(2H)-pyridinyl)propylcarbamate. Deprotection of the BOC group using HCl in dioxane followed by basification (pH 11–12) gave the desired product.

METHYL(4S)-3-({[3-(4-[3-(ACETYLAMINO) PHENYL]-3,6-DIHYDRO-1(2H)-PYRIDINYL)PROPYL] AMINO}CARBONYL)-4-(3,4-DIFLUOROPHENYL)-6-(METHOXYMETHYL)-2-OXO-1,2,3,4-TETRAHYDRO-5-PYRIMIDINECARBOXYLATE: Prepared from the reaction of 5-methyl 1-(4-nitrophenyl) (6S)-6-(3,4-difluorophenyl)-4-(methoxymethyl)-2-oxo-3,6-dihydro-1,5 (2H)-pyrimidinedicarboxylate (describe in PCT Publication No. WO 00/37026, published Jun. 29, 2000) and N-{3-[1-(3-aminopropyl)-1,2,3,6-tetrahydro-4-pyridinyl] phenyl}acetamide: $^1$H NMR 5 8.90 (t, 1H, J=3.6 Hz), 7.75 (s, 1H), 7.50–7.00 (m, 8H), 6.68 (s, 1H), 6.03 (br s, 1H), 4.67 (s, 2H), 3.71 (s, 3H), 3.47 (s, 3H), 3.38 (ABm, 2H), 3.16 (m, 2H), 2.71 (t, 2H, J=5.4 Hz), 2.56 (m, 4H), 2.35–1.90 (br, 2H), 2.17 (s, 3H), 1.82 (p, 2H, J=7.2 Hz); ESMS, 612.25 $(M+H)^+$.

TRITIATED METHYL(4S)-3-{[(3-{4-[3-(ACETYLAMINO)PHENYL]-1-PIPERIDINYL}PROPYL)AMINO]CARBONYL}-4-(3,4-DIFLUOROPHENYL)-6-(METHOXYMETHYL)-2-OXO-1,2,3,4-TETRAHYDRO-5-PYRIMIDINECARBOXYLATE ([$^3$H] COMPOUND A): This radiochemical synthesis was carried out by Amersham Pharmacia Biotech, Cardiff, Wales. A methanolic solution of methyl(4S)-3-({[3-(4-[3-(acetylamino)phenyl]-3,6-dihydro-1(2H)-pyridinyl)propyl]amino}carbonyl)-4-(3,4-difluorophenyl)-6-(methoxymethyl)-2-oxo-1,2,3,4-tetrahydro-5-pyrimidinecarboxylate was exposed to tritium gas at 1 atmosphere pressure in the presence of 5% palladium on carbon with stirring overnight to give the tritiated methyl(4S)-3-{[(3-{4-[3-(acetylamino)phenyl]-1-piperidinyl}propyl)amino]carbonyl}-4-(3,4-difluorophenyl)-6-(methoxymethyl)-2-oxo-1,2,3,4-tetrahydro-5-pyrimidinecarboxylate ((+)-isomer). After purification by reverse phase HPLC (Hypersil ODS, 4.6× 100 mm, methanol:$H_2O$:$Et_3N$ 10:90:1 to 100:0:1 in 15 min at 1.0 mL/min, with radiochemical and UV detection), this product was used as a radioligand in the MCH1 binding assays. The same procedure was carried out with $H_2$ gas in place of $^3H_2$ to afford the non-radioactive version of Compound A.

VI. In-vivo Methods

The following in vivo methods were performed to predict the efficacy of MCH1 antagonists for the treatment of obesity (3-day body weight and sweetened condensed milk), depression (forced swim test), anxiety (social interaction test), and urinary disorders (DIRC and CSTI).

Effects of MCH1 Antagonists on Body Weight (3 Day)

Male Long Evans rats (Charles River) weighing 180–200 grams were housed in groups of four on a 12-hour light/dark cycle with free access to food and water. Test compounds were administered twice daily via i.p. injection, 1 hour before the dark cycle and 2 hours after lights on, for three days. All rats were weighed daily after each morning injection. Overall results were expressed as body weight (grams) gained per day (mean±SEM) and were analyzed by two-way ANOVA. Data for each time point were analyzed by one-way ANOVA followed by post hoc Newman-Keuls test. The data were analyzed using the GraphPad Prism (v2.01) (GraphPad Software, Inc., San Diego, Calif.). All data were presented as means±S.E.M.

Effects of MCH1 Antagonists on Consumption of Sweetened Condensed Milk

Male C57BL/6 mice (Charles River) weighing 17–19 grams at the start of experiments were housed in groups of four or five on a 12 hour light/dark cycle with free access to food and water. For 7 days, mice were weighed, placed in individual cages and allowed to drink sweetened condensed milk (Nestle, diluted 1:3 with water) for 1 hour, 2–4 hours into the light cycle. The amount of milk consumed was determined by weighing the milk bottle before and after each drinking bout. On the test day, mice received i.p. injections of Test Compound (3, 10 or 30 mg/kg in 0.01% lactic acid), vehicle (0.01% lactic acid) of d-fenfluramine (10 mg/kg in 0.01% lactic acid) 30 min. prior to exposure to milk. The amount of milk consumed on the test day (in mls milk/kg body weight) was compared to the baseline consumption for each mouse determined on the previous 2 days. Data for each time point were analyzed by one-way ANOVA.

Forced Swim Test (FST) in the Rat

Animals

Male Sprague-Dawley rats (Taconic Farms, N.Y.) were used in all experiments. Rats were housed 5 per cage and maintained on a 12:12-h light-dark cycle. Rats were handled for 1 minutes each day for 4 days prior to behavioral testing.

Drug Administration

Animals were randomly assigned to receive a single i.p. administration of vehicle (2.5% EtOH/2.5% Tween-80), imipramine (positive control; 60 mg/kg), or Test Compound 60 minutes before the start of the 5 minute test period. All injections were given using 1 cc tuberculin syringe with 26 3/8 gauge needles (Becton-Dickinson, VWR Scientific, Bridgeport, N.J.). The volume of injection was 1 ml/kg.

Experimental Design

The procedure used in this study was similar to that previously described (Porsolt, et al., 1978), except the water depth was 31 cm in this procedure. The greater depth in this test prevents the rats from supporting themselves by touching the bottom of the cylinder with their feet. Swim sessions were conducted by placing rats in individual plexiglass cylinders (46 cm tall×20 cm in diameter) containing 23–25° C. water 31 cm deep. Swim tests were conducted always between 900 and 1700 hours and consisted of an initial 15-min conditioning test followed 24 h later by a 5-minute test. Drug treatments were administered 60 minutes before the 5-minute test period. Following all swim sessions, rats were removed from the cylinders, dried with paper towels and placed in a heated cage for 15 minutes and returned to their home cages. All test sessions were videotaped using a color video camera and recorded for scoring later.

Behavioral Scoring

The rat's behavior was rated at 5-second intervals during the 5-minute test by a single individual, who was blind to the treatment condition. Scored behaviors were:

1. Immobility—rat remains floating in the water without struggling and was only making those movements necessary to keep its head above water;
2. Climbing—rat was making active movements with its forepaws in and out of the water, usually directed against the walls;
3. Swimming—rat was making active swimming motions, more than necessary to merely maintain its head above water, e.g. moving around in the cylinder; and
4. Diving—entire body of the rat was submerged.

Data Analysis

The forced swim test data (immobility, swimming, climbing, diving) were subjected to a randomized, one-way ANOVA and post hoc tests conducted using the Newman-Keuls test. The data were analyzed using the GraphPad Prism (v2.01) (GraphPad Software, Inc., San Diego, Calif.). All data were presented as means±S.E.M. All data were presented as means±S.E.M.

Forced Swim Test (FST) in the Mouse

Animals

DBA/2 mice (Taconic Farms, N.Y.) were used in all experiments. Animals were housed 5 per cage in a controlled environment under a 12:12 hour light:dark cycle. Animals were handled 1 min each day for 4 days prior to the experiment. This procedure included a mock gavage with a 1.5 inch feeding tube.

Drug Administration

Animals were randomly assigned to receive a single administration of vehicle (5% EtOH/5% Tween-80), Test Compound, or imipramine (60 mg/kg) by oral gavage 1 hour before the swim test.

Experimental Design

The procedure for the forced swim test in the mouse was similar to that described above for the rat, with some modifications. The cylinder used for the test was a 1-liter beaker (10.5cm diameter×15 cm height) fill to 800 ml (10cm depth) of 23–25° C. water. Only one 5-minute swim test was conducted for each mouse, between 1300 and 1700 hours. Drug treatments were administered 30–60 minutes before the 5-minute test period. Following all swim sessions, mice were removed from the cylinders, dried with paper towels and placed in a heated cage for 15 minutes. All test sessions were videotaped using a Sony color video camera and recorder for scoring later.

Behavioral Scoring

The behavior during minutes 2–5 of the test was played back on a TV monitor and scored by the investigator. The total time spent immobile (animal floating with only minimal movements to remain afloat) and mobile (swimming and movements beyond those required to remain afloat) were recorded.

Data Analysis

The forced swim test data (time exhibiting immobility, mobility; seconds) were subjected to a randomized, one-way ANOVA and post hoc tests conducted using the Newman-Keuls test. The data were analyzed using the GraphPad Prism (v2.01) (GraphPad Software, Inc., San Diego, Calif.). All data were presented as means±S.E.M.

Social Interaction Test (SIT)

Rats are allowed to acclimate to the animal care facility for 5 days and are housed singly for 5 days prior to testing.

Animals are handled for 5 minutes per day. The design and procedure for the Social Interaction Test is carried out as previously described by Kennett, et al. (1997). On the test day, weight matched pairs of rats (±5%), unfamiliar to each other, are given identical treatments and returned to their home cages. Animals are randomly divided into 5 treatment groups, with 5 pairs per group, and are given one of the following i.p. treatments: Test Compound (10, 30 or 100 mg/kg), vehicle (1 ml/kg) or chlordiazepoxide (5 mg/kg). Dosing is 1 hour prior to testing. Rats are subsequently placed in a white perspex test box or arena (54×37×26 cm), whose floor is divided up into 24 equal squares, for 15 minutes. An air conditioner is used to generate background noise and to keep the room at approximately 74° F. All sessions are videotaped using a JVC camcorder (model GR-SZ1, Elmwood Park, N.J.) with either TDK (HG ultimate brand) or Sony 30 minute videocassettes. All sessions are conducted between 1300–1630 hours. Active social interaction, defined as grooming, sniffing, biting, boxing, wrestling, following and crawling over or under, is scored using a stopwatch (Sportsline model no. 226, 1/100 sec. discriminability) The number of episodes of rearing (animal completely raises up its body on its hind limbs), grooming (licking, biting, scratching of body), and face washing (i.e. hands are moved repeatedly over face), and number of squares crossed are scored. Passive social interaction (animals are lying beside or on top of each other) is not scored. All behaviors are assessed later by an observer who is blind as to the treatment of each pair. At the end of each test, the box is thoroughly wiped with moistened paper towels.

Animals

Male albino Sprague-Dawley rats (Taconic Farms, N.Y.) are housed in pairs under a 12 hr light dark cycle (lights on at 0700 hrs.) with free access to food and water.

Drug Administration

Test Compound is dissolved in either 100% DMSO or 5% lactic acid, v/v (Sigma Chemical Co., St. Louis, Mo.). Chlordiazepoxide (Sigma Chemical Co., St. Louis, Mo.) is dissolved in double distilled water. The vehicle consists of 50% DMSO (v/v) or 100% dimethylacetamide (DMA). All drug solutions are made up 10 minutes prior to injection and the solutions are discarded at the end of the test day. The volume of drug solution administered is 1 ml/kg.

Data Analysis

The social interaction data (time interacting, rearing and squares crossed) are subjected to a randomized, one-way ANOVA and post hoc tests conducted using the Student-Newman-Keuls test. The data are subjected to a test of normality (Shapiro-Wilk test). The data are analyzed using the GBSTAT program, version 6.5 (Dynamics Microsystems, Inc., Silver Spring, Md., 1997).

In Vivo Models of the Micturition Reflex

The effects of compounds on the micturition reflex were assessed in the "distension-induced rhythmic contraction" (DIRC), as described in previous publications (e.g. Maggi et al, 1987; Morikawa et al, 1992), and Continuous Slow Transvesicular Infusion (CSTI) models in rats.

DIRC Model

Female Sprague Dawley rats weighing approximately 300 g were anesthetized with subcutaneous urethane (1.2 g/kg). The trachea was cannulated with PE240 tubing to provide a clear airway throughout the experiment. A midline abdominal incision was made and the left and right ureters were isolated. The ureters were ligated distally (to prevent escape of fluids from the bladder) and cannulated proximally with PE10 tubing. The incision was closed using 4-0 silk sutures, leaving the PE10 lines routed to the exterior for the elimination of urine. The bladder was canulated via the transurethral route using PE50 tubing inserted 2.5 cm beyond the urethral opening. This cannula was secured to the tail using tape and connected to a pressure transducer. To prevent leakage from the bladder, the cannula was tied tightly to the exterior urethral opening using 4-0 silk. To initiate the micturition reflex, the bladder was first emptied by applying pressure to the lower abdomen, and then filled with normal saline in 100 increments (maximum=2 ml) until spontaneous bladder contractions occurred (typically 20–40 mmHg at a rate of one contraction every 2 to 3 minutes. Once a regular rhythm was established, vehicle (saline) or Test Compounds were administered i.v. or i.p. to explore their effects on bladder activity. The 5-HT$_{1A}$ antagonist WAY-100635 was given as a positive control. Data were expressed as contraction interval (in seconds) before drug application (basal), or after the application of vehicle or test article.

Continuous Slow Transvesicular Infusion (CSTI) rat Model

Male Sprague Dawley rats weighing approximately 300 g were used for the study. Rats were anaesthetized with pentobarbitone sodium (50 mg/kg, i.p). Through a median abdominal incision, bladder was exposed and a polyethylene cannula (PE 50) was introduced into the bladder through a small cut on the dome of the bladder and the cannula was secured with a purse string suture. The other end of the cannula was exteriorized subcutaneously at the dorsal neck area. Similarly, another cannula (PE 50) was introduced into the stomach through a paramedian abdominal incision with the free end exteriorized subcutaneously to the neck region. The surgical wounds were closed with silk 4-0 suture and the animal was allowed to recover with appropriate post surgical care. On the following day, the animal was placed in a rat restrainer. The open end of the bladder-cannula was connected to a pressure transducer as well as infusion pump through a three-way stopcock. The bladder voiding cycles were initiated by continuous infusion of normal saline at the rate of 100 μl/min. The repetitive voiding contractions were recorded on a Power Lab on-line data acquisition software. After recording the basal voiding pattern for an hour, the test drug or vehicle was administered directly into stomach through the intragastric catheter and the voiding cycles were monitored for 5 hours. Micturition pressure and frequency were calculated before and after the treatment (at every 30 min interval) for each animal. Bladder capacity was calculated from the micturition frequency, based on the constant infusion of 100 ul/min. The effect of the test drug was expressed as a percentage of basal, pre-drug bladder capacity. WAY 100635 was used as positive control for comparison.

In Vivo Results

TABLE 2

Effect of MCH1 antagonist (Example No.) in the following in vivo models: 3-day Body Weight (3D BW), mouse Sweetened Condensed Milk (mSwCM), mouse Forced Swim Test (mFST), rat Forced Swim Test (rFST), DIRC model, or CSTI model

| Example No. | 3D BW | mSwCM | mFST | rFST | DIRC | CSTI |
|---|---|---|---|---|---|---|
| 2 | A | B | C | D | E | F |
|  | Not | Not | C | Not | E | F |
| 10 | Done | Done |  | Done |  |  |
| 39 | A | B | Not Done | D | Not Done | Not Done |

TABLE 2-continued

Effect of MCH1 antagonist (Example No.) in the following in vivo models: 3-day Body Weight (3D BW), mouse Sweetened Condensed Milk (mSwCM), mouse Forced Swim Test (mFST), rat Forced Swim Test (rFST), DIRC model, or CSTI model

| Example No. | 3D BW | mSwCM | mFST | rFST | DIRC | CSTI |
|---|---|---|---|---|---|---|
| 43 | Not Done | B | C | Not Done | Not Done | Not Done |
| 44 | Not Done | Not Done | No effect | Not Done | Not Done | Not Done |
| 89 | Not Done | B | No effect | Not Done | Not Done | Not Done |
| 90 | Not Done | No effect | No effect | Not Done | Not Done | Not Done |
| 91 | Not Done | Not Done | C | Not Done | E | F |
| 93 | Not Done | Not Done | No effect | Not Done | Not Done | Not Done |
| 95 | Not Done | B | No effect | Not Done | Not Done | Not Done |
| 99 | A | Not Done | C | Not Done | E | F |
| 105 | Not Done | B | C | Not Done | Not Done | Not Done |
| 106 | Not Done | B | C | Not Done | E | F |
| 112 | Not Done | Not Done | No effect | Not Done | Not Done | Not Done |
| 116 | A | Not Done | C | Not Done | E | F |

A = Produced a significant reduction in weight gain relative to vehicle-treated controls
B = Produced a significant decrease in consumption of milk relative to vehicle-treated controls
C = Produced a significant decrease in immobility relative to vehicle-treated animals when administered orally.
D = Produced a significant decrease in immobility or a significant increase in swimming activity relative to vehicle-treated animals
E = Produced a significant increase in contraction interval relative to pre-drug interval
F = Produced an increase in bladder capacity in rats relative to baseline capacity.

REFERENCES

American Psychiatric Association (1994a), Diagnostic and Statistical Manual of Mental Disorders. 4th ed. Washington, D.C.: American Psychiatric Association.

American Psychiatric Association (1994b), American DSM-IV Sourcebook. Washington, D.C.: American Psychiatric Association.

Auburger, G., et al., (1992) Assignment of the second (cuban) locus of autosomal dominant cerebellar ataxia to chromosome 12q23-24.1, between flanking markers D12S58 and PLA2. *Cytogenet. Cell. Genet.* 61:252–256.

Bahjaoui-Bouhaddi, M., et al., (1994) Insulin treatment stimulates the rat melanin-concentrating hormone-producing neurons. *Neuropeptides* 24:251–258.

Baker, B. I. (1991) Melanin-concentrating hormone: a general vertebrate neuropeptide. *Int. Rev. Cytol.* 126:1–47.

Baker, B. I. (1994) Melanin-concentrating hormone update: functional consideration. *TEM* 5:120–126.

Bassett, A. S., et al., (1988) Partial trisomy chromosome 5 cosegregating with schizophrenia. *Lancet* 1:799–801.

Bednarek, M. A., et al. "Synthesis and biological evaluation in vitro of a selective, high potency peptide agonist of human melanin-concentrating hormone action at human melanin-concentrating hormone receptor 1" *J Biol Chem* 277(16): 13821–13826 (2002).

Bittencourt, J. C., et al., (1992) The melanin-concentrating hormone system of the rat brain: An immuno- and hybridization histochemical characterization. *J. Comp. Neurol.* 319:218–245.

Bobes, J. (1998) J Clin Psychiatry; 59[suppl 17]:12–16.

Borowsky, B., et al., *Nature Medicine* (in press).

Bradford, M. M. (1976) A rapid and sensitive method for the quantitation of microgram quantities of protein utilizing the principle or protein-dye binding. *Anal. Biochem.* 72: 248–254.

Burgaud, J. L., et al., (1997) Melanin-concentrating hormone binding sites in human SVK14 keratinocytes. *Biochem. Biophys. Res. Commun.* 241(3):622–629.

Chambers, J., et al., "Melanin-concentrating hormone is the cognate ligand for the orphan G-protein-coupled receptor SLC-1" *Nature* 400(6741): 261–6 (1999).

Chen, Y., et al, "Targeted disruption of the melanin-concentrating hormone receptor-1 results in hyperphagia and resistance to diet-induced obesity" *Endocrinology* 143 (7): 2469–2477(2002).

Craddock, N., et al., (1993) The gene for Darier's disease maps to chromosome 12q23-q24.1. *Hum. Mol. Genet.* 2:1941–1943.

Dondoni, A., et al., (1995) *T. Synthesis*, 181.

Drozdz, R. and Eberle, A. N. (1995) Binding sites for melanin-concentrating hormone (MCH) in brain synaptosomes and membranes from peripheral tissues identified with highly tritiated MCH. *J. Recept. Signal. Transduct. Res.* 15(1–4):487–502.

Drozdz, R., et al., (1995) Melanin-concentrating hormone binding to mouse melanoma cells in vitro. *FEBS* 359:199–202.

Drozdz, R., et al., (1998) Characterization of the receptor for melanin-concentrating hormone on melanoma cells by photocrosslinking. *Ann. NY Acad. Sci.* 839(1):210–213.

Gale Group (2001) Gale Encyclopedia of Psychology, 2nd ed. Gale Group.

Gilliam, T. C., et al., (1989) Deletion mapping of DNA markers to a region of chromosome 5 that cosegregates with schizophrenia. *Genomics* 5:940–944.

Goodman W K, Price L H, Rasmussen S A et al. (1989), The Yale-Brown Obsessive Compulsive Scale. Arch Gen Psychiatry 46:1006–1011.

Gonzalez, M. I., et al., (1997) Stimulatory effect of melanin-concentrating hormone on luteinizing hormone release. *Neuroendocrinology* 66(4):254–262.

Gonzalez, M. I., et al., (1996) Behavioral effects of α-melanocyte-stimulating hormone (α-MSH) and melanin-concentrating hormone (MCH) after central administration in female rats. *Peptides* 17:171–177.

Grillon, S., et al., (1997) Exploring the expression of the melanin-concentrating hormone messenger RNA in the rat lateral hypothalamus after goldthioglucose injection. *Neuropeptides* 31(2):131–136.

Herve, C. and Fellmann, D. (1997) Changes in rat melanin-concentrating hormone and dynorphin messenger ribonucleic acids induced by food deprivation. *Neuropeptides* 31(3):237–242.

Hervieu, G., et al., (1996) Development and stage-dependent expression of melanin-concentrating hormone in mammalian germ cells. *Biology of Reproduction* 54:1161–1172.

Kauwachi, H., et al., (1983) Characterization of melanin-concentrating hormone in chum salmon pituitaries. *Nature* 305:321–333.

Knigge, K. M., et al., (1996) Melanotropic peptides in the mammalian brain: The melanin-concentrating hormone. *Peptides* 17:1063–1073.

Knigge, K. M. and Wagner, J. E. (1997) Melanin-concentrating hormone (MCH) involvement in pentylenetetrazole (PTZ)-induced seizure in rat and guinea pig. *Peptides* 18(7):1095–1097.

Lakaye, B., et al., "Cloning of the rat brain cDNA encoding for the SLC-1 G protein-coupled receptor reveals the presence of an intron in the gene" *Biochem Biophys Acta* 1401(2): 216–220 (1998).

Ludwig, D. S., et al., (1998) Melanin-concentrating hormone: a functional melanocortin antagonist in the hypothalamus. *Am. J. Physiol. Endocrinol. Metab.* 274(4) :E627–E633.

MacKenzie, F. J., et al., (1984) Evidence that the dopaminergic incerto-hypothalamic tract has a stimulatory effect on ovulation and gonadotropin release. *Neuroendocrinology* 39:289–295.

Maggi, C. A., et al., "Spinal and supraspinal components of GABAergic inhibition of the micturition reflex in rats." *J Pharmacol Exp Ther* 240: 998–1005 (1987).

Marsh, D. J., et al, "Melanin-concentrating hormone 1 receptor-deficient mice are lean, hyperactive, and hyperphagic and have altered metabolism" *Proc Natl Acad Sci USA* 99(5): 3240–3245 (2002).

Martin, R., et al., (1997) *J. Tetrahedron Letters*, 38, 1633.

McBride, R. B., et al., (1994) The actions of melanin-concentrating hormone (MCH) on passive avoidance in rats: A preliminary study. *Peptides* 15:757–759.

Medical Economics Company (2002), Physicians' Desk Reference, 56th ed., Montvale, N.J.: Medical Economics Company, Inc., pp. 1609–1615, 2751–2756, 3495–3504.

Melki, J., et al., (1990) Gene for chronic proximal spinal muscular atrophies maps to chromosome 5q. *Nature* (London) 344:767–768.

Miller, C. L., et al., (1993) α-MSH and MCH are functional antagonists in a CNS auditory paradigm. *Peptides* 14:1–10.

Morikawa, K., et al., "Inhibitory effect of inaperisone hydrochloride (inaperisone), a new centrally acting muscle relaxant, on the micturition reflex." *Eur J Pharmacol* 213: 409–415 (1992).

Nahon, J-L. (1994) The melanin-concentrating hormone: from the peptide to the gene. *Critical Rev. in Neurobiol* 221:221–262.

Parkes, D. G. (1996) Diuretic and natriuretic actions of melanin concentrating hormone in conscious sheep. *J. Neuroendocrinol.* 8:57–63.

Pedeutour, F., et al., (1994) Assignment of the human pro-melanin-concentrating hormone gene (PMCH) to chromosome 12q23-24 and two variant genes (PMCHL1 and PMCHL2) to chromosome 5p14 and 5q12-q13. *Genomics* 19:31–37.

Porsolt, R. D., et al., "Behavioural despair in rats: a new model sensitive to antidepressant treatments" *Eur J Pharmacol* 47(4): 379–391 (1978).

Presse, F., et al. (1992) Rat melanin-concentrating hormone messenger ribonucleic acid expression: marked changes during development and after stress and glucocorticoid stimuli. *Endocrinology* 131:1241–1250.

Qu, D., et al. (1996) A role for melanin-concentrating hormone in the central regulation of feeding behaviour. *Nature* 380:243–247.

Rossi, M., et al., (1997) Melanin-concentrating hormone acutely stimulates feeding, but chronic administration has no effect on body weight. *Endocrinology* 138:351–355.

Sahu, A. (1998) Evidence suggesting that galanin (GAL), melanin-concentrating hormone (MCH), neurotensin (NT), proopiomelanocortin (POMC) and neuropeptide Y (NPY) are targets of leptin signaling in the hypothalamus. *Endocrinology* 139(2):795–798.

Sakurai, T., et al., (1998) Orexins and orexin receptors: A family of hypothalamic neuropeptides and G protein-coupled receptors that regulate feeding behavior. *Cell* 92:573–585.

Sanchez, M., et al., (1997) Melanin-concentrating hormone (MCH) antagonizes the effects of α-MSH and neuropeptide E-I on grooming and locomotor activities in the rat. *Peptides* 18:393–396.

Saito, Y., et al., "Molecular characterization of the melanin-concentrating-hormone receptor" *Nature* 400 (6741): 265–269 (1999).

Schneier F R, Heckelman L R, Garfinkel R, et al. (1994) J Clin Psychiatry 55:322–331.

Sherrington, R., et al., (1988) Localization of a susceptibility locus for schizophrenia on chromosome 5. *Nature* (London) 336:164–167.

Srebnik, M., et al., (1988) *J. Org. Chem.*, 53, 2916–2920.

Takekawa, S., et al., "T-226296: a novel, orally active and selective melanin-concentrating hormone receptor antagonist" *Eur J Pharmacol* 438(3): 129–35 (2002)

Twells, R., et al., (1992) Chromosomal assignment of the locus causing olivo-ponto-cerebellar atrophy (SCA2) in a cuban founder population. *Cytogenet. Cell. Genet.* 61:262–265.

Westbrook, C. A., et al., (1992) Report of the second international workshop on human chromosome 5 mapping. *Cytogenet. Cell. Genet.* 61:225–231.

What is claimed is:

1. A compound having the structure:

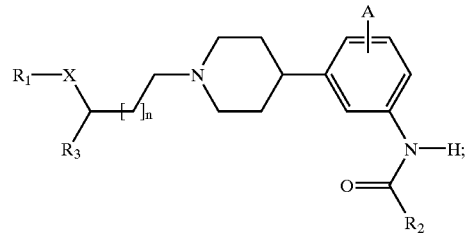

wherein $R_1$ is hydrogen, straight chained or branched $C_1$–$C_7$ alkyl, monofluoroalkyl or polyfluoroalkyl, aryl or heteroaryl, wherein the aryl or heteroaryl is optionally substituted with one or more —F, —Cl, —Br, —I, —CN, —$NO_2$, —$CH_3$, —$CF_3$, —$COCH_3$, —$CO_2R_2$, phenyl, phenoxy or straight chained or branched $C_1$–$C_7$ alkyl;

wherein $R_2$ is straight-chained or branched $C_3$–$C_4$ alkyl or cyclopropyl;

wherein $R_3$ is aryl or heteroaryl, wherein the aryl or heteroaryl is optionally substituted with one or more —F, —Cl, —Br, —I, —CN, —$NO_2$, straight chained or branched $C_1$–$C_7$ alkyl;

wherein A is —H, —F, —Cl, —Br, —CN, —$NO_2$, —$COR_3$, —$CO_2R_3$, straight chained or branched $C_1$–$C_7$ alkyl, monofluoroalkyl or polyfluoroalkyl;

wherein X is O or NH; and wherein n is an integer from 0 to 5 inclusive.

2. The compound of claim 1, wherein $R_1$ is aryl optionally substituted with one or more —F, —Cl, —Br, —I, —CN, —$NO_2$, —$COCH_3$, —$CO_2R_2$, straight chained or branched $C_1$–$C_7$ alkyl;

wherein $R_3$ is phenyl;

wherein A is H; and wherein X is O.

3. The compound of claim 2, wherein $R_2$ is isopropyl.

4. The compound of claim 3, wherein the compound has the structure:

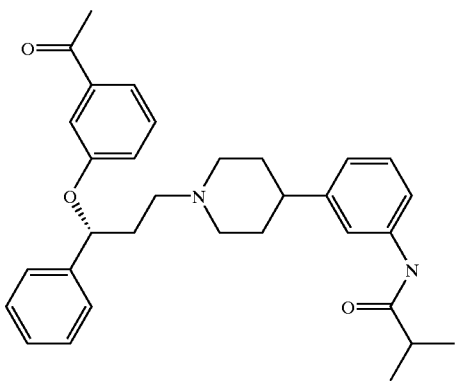

5. The compound of claim 3, wherein the compound has the structure:

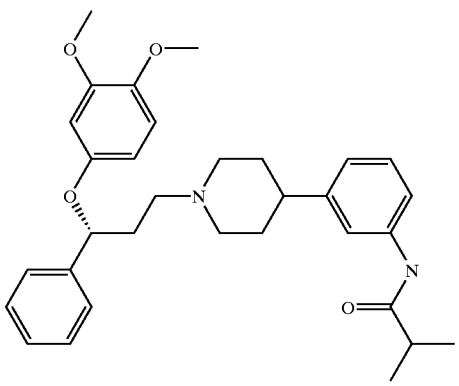

6. The compound of claim 1, wherein $R_1$ is hydrogen, straight chained or branched $C_1$–$C_7$ alkyl; and wherein $R_3$ is aryl.

7. The compound of claim 6, wherein $R_2$ is isopropyl; and A is hydrogen.

8. The compound of claim 7, wherein the compound has the structure:

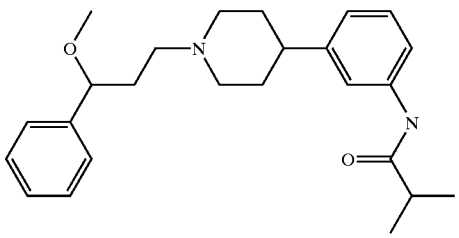

9. The compound of claim 7, wherein the compound has the structure:

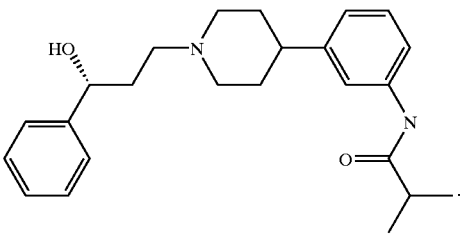

10. A compound having the structure:

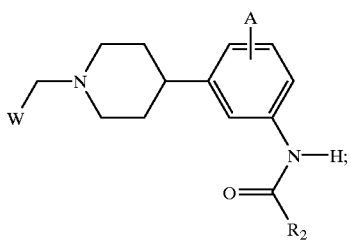

wherein W is

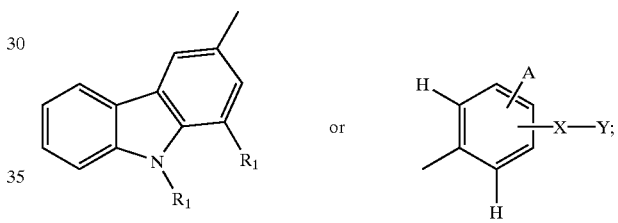

wherein each $R_1$ is independently hydrogen, methyl or ethyl;

wherein $R_2$ is straight-chained or branched $C_3$–$C_4$ alkyl or cyclopropyl;

wherein $R_3$ is hydrogen, aryl or heteroaryl, wherein the aryl or heteroaryl is optionally substituted with one or more —H, —F, —Cl, —Br, —I, —CN, —$NO_2$, straight chained or branched $C_1$–$C_7$ alkyl;

wherein each A is independently —H, —F, —Cl, —Br, —CN, —$NO_2$, —$COR_3$, —$CO_2R_3$, straight chained or branched $C_1$–$C_7$ alkyl, monofluoroalkyl or polyfluoroalkyl;

wherein X is O, $NR_3$, CO or may be absent; and wherein Y is hydrogen, aryl or heteroaryl, wherein the aryl or heteroaryl is optionally substituted with one or more —F, —Cl, —Br, —I, —CN, —$NO_2$, straight chained or branched $C_1$–$C_7$ alkyl.

11. The compound of claim 10, wherein W is

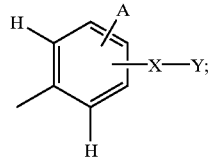

and wherein X is O or may be absent.

12. The compound of claim 11, wherein $R_2$ is isopropyl.

13. The compound of claim 12, wherein the compound has the structure:

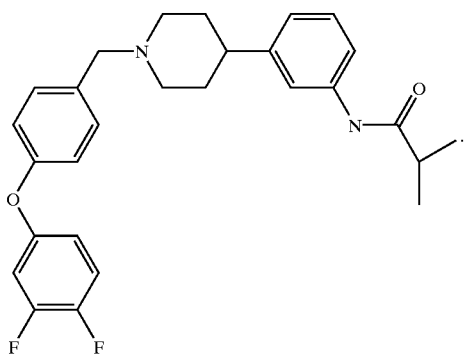

14. The compound of claim 12, wherein the compound has the structure:

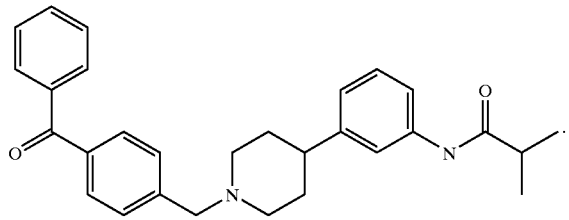

15. The compound of claim 10, wherein W is

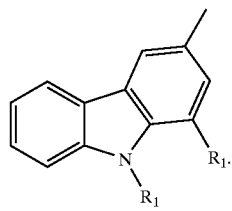

16. The compound of claim 15, wherein A is —H, —F, —Cl, —Br.

17. The compound of claim 16, wherein $R_2$ is isopropyl; and A is hydrogen.

18. The compound of claim 17, wherein the compound has the structure:

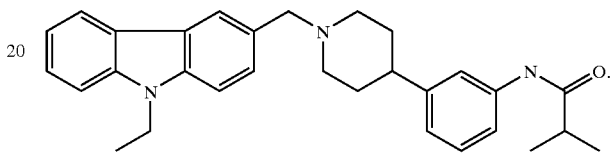

19. A method of reducing the body mass of a subject, which comprises administering to the subject an amount of a compound of claim 1 effective to reduce the body mass of the subject.

20. A method of treating a subject suffering from depression, which comprises administering to the subject an amount of a compound of claim 1 effective to treat the subject's depression.

* * * * *